US008012956B2

(12) United States Patent
Rice et al.

(10) Patent No.: US 8,012,956 B2
(45) Date of Patent: Sep. 6, 2011

(54) TROPANE COMPOUNDS

(75) Inventors: Kenneth D. Rice, San Rafael, CA (US); Naing Aay, San Mateo, CA (US); Neel Kumar Anand, Burlingame, CA (US); Arlyn Arcalas, South San Francisco, CA (US); Tae-Gon Baik, Foster City, CA (US); Charles M. Blazey, San Francisco, CA (US); Owen Joseph Bowles, Pacifica, CA (US); Chris A. Buhr, Redwood City, CA (US); Joerg Bussenius, Foster City, CA (US); Simona Costanzo, Los Altos, CA (US); Jeffrey Kimo Curtis, San Anselmo, CA (US); Steven Charles Defina, Burlingame, CA (US); Larisa Dubenko, San Francisco, CA (US); Abigail R. Kennedy, Oakland, CA (US); Angie Inyoung Kim, San Mateo, CA (US); Katherine Lara, San Mateo, CA (US); Sunghoon Ma, Foster City, CA (US); Jean-Claire Limun Manalo, Daly City, CA (US); Csaba J. Peto, Alameda, CA (US); Tsze H. Tsang, El Cerrito, CA (US); Longcheng Wang, Palo Alto, CA (US)

(73) Assignee: Exelixis, Inc., South San Francisco, CA (US)

( * ) Notice: Subject to any disclaimer, the term of this patent is extended or adjusted under 35 U.S.C. 154(b) by 345 days.

(21) Appl. No.: 12/290,159

(22) Filed: Oct. 27, 2008

(65) Prior Publication Data

US 2009/0163471 A1 Jun. 25, 2009

Related U.S. Application Data

(60) Provisional application No. 61/000,687, filed on Oct. 25, 2007.

(51) Int. Cl.

| | |
|---|---|
| *A61K 31/46* | (2006.01) |
| *A61K 31/5377* | (2006.01) |
| *A61K 31/496* | (2006.01) |
| *A61K 31/497* | (2006.01) |
| *C07D 451/04* | (2006.01) |

(52) U.S. Cl. ........... 514/210.21; 514/233.2; 514/253.04; 514/255.05; 514/304; 546/124; 546/125; 544/127; 544/362; 544/405

(58) Field of Classification Search ............ 514/210.21, 514/233.2, 253.04, 255.05, 304; 546/124, 546/125; 544/127, 362, 405

See application file for complete search history.

(56) References Cited

U.S. PATENT DOCUMENTS

| | | | |
|---|---|---|---|
| 5,958,945 | A | 9/1999 | Imbert et al. |
| 5,985,878 | A | 11/1999 | Stokbroekx et al. |
| 2004/0242622 | A1 | 12/2004 | Mammen et al. |

FOREIGN PATENT DOCUMENTS

| | | | |
|---|---|---|---|
| EP | 0101641 | A2 | 2/1984 |
| WO | 97/10244 | A1 | 3/1997 |
| WO | 97/26258 | A1 | 7/1997 |
| WO | 2004/106333 | A1 | 12/2004 |
| WO | 2004/113334 | A1 | 12/2004 |
| WO | 2005/033107 | A1 | 4/2005 |
| WO | 2005095380 | * | 10/2005 |
| WO | 2006/075004 | A2 | 7/2006 |

OTHER PUBLICATIONS

Xavier Barril et al., "4-Amino derivatives of the Hsp90 inhibitor CCT018159", Bioorganic & Medicinal Chemistry Letters, 16 (2006) 2543-2548.

PCT International Search Report and the Written Opinion of the International Searching Authority for PCT/2008/012221, mailed Feb. 10, 2009.

* cited by examiner

*Primary Examiner* — D M Seaman
*Assistant Examiner* — Niloofar Rahmani
(74) *Attorney, Agent, or Firm* — McDonnell Boehnen Hulbert & Berghoff LLP

(57) ABSTRACT

A compound according to Formula I or II:

I

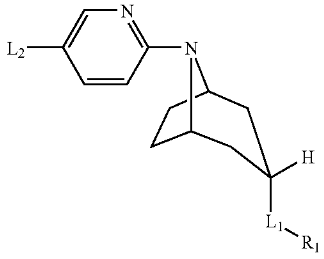

or

II

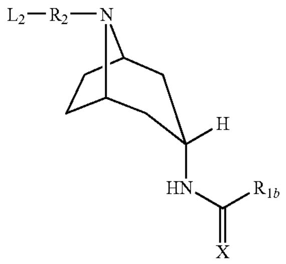

wherein $R_1$, $R_{1b}$, $R_2$, $L_1$, and $L_2$ and $L_{2b}$ are as defined in the specification, pharmaceutical compositions thereof, and methods of use thereof.

18 Claims, No Drawings

TROPANE COMPOUNDS

CROSS REFERENCE TO RELATED APPLICATIONS

This application claims priority to U.S. Provisional Application Ser. No. 61/000,687, filed Oct. 25, 2007, the entire contents of which is incorporated by reference in its entirety.

FIELD OF THE INVENTION

This disclosure relates to certain tropane compounds. In particular, this disclosure relates to certain tropane compounds useful as inhibitors of HSP90.

BACKGROUND OF THE INVENTION

HSP90 (heat shock protein 90) is one of the most abundant cellular proteins. There are at least four HSP90 family members in the human genome: the stress-inducible HSP90 (HSP90α or HSP90AA1), the constitutive cytosolic HSP90β (HSP90AB1), the endoplasmic reticulum-localized GRP94 (HSP90B), and the mitochondrial TRAP1 [2]. HSP90 contains approximately 730 amino acids arranged as 3 major domains: an N-terminal ATP-binding domain, a central domain and a C-terminal dimerization domain. HSP90 acts primarily as molecular chaperone, promoting the folding and stabilization of many labile cellular proteins. In general, HSP90 acts in concert with the HSP70 chaperone machinery, and also recruits multiple co-chaperone proteins to regulate its activity. Over 100 HSP90 substrates ("client proteins") have been described in the art. HSP90 constitutes ~1-2% of total protein in normal cells and this concentration can double under stress conditions, reflecting its importance in maintaining cellular homeostasis.

HSP90 expression and activity is frequently upregulated in tumor cells and is particularly associated with poor prognosis in breast cancer. Furthermore, HSP90 in tumor cells appears to exist in a hyperactivated state with elevated ATPase activity which is highly sensitive to HSP90 inhibition, compared to the largely latent form found in normal cells. This hyperactivated state suggests that HSP90 inhibitors can selectively target tumor cells, with relatively low impact on normal tissues. Many HSP90 client proteins are involved in various aspects of tumor growth and progression. HSP90 promotes the folding and/or stabilization of many oncogenic proteins that confer autonomous growth on cells (eg, EGFR and ErbB2, B-Raf and steroid hormone receptors, and also regulates multiple proteins that promote tumor cell survival (eg, IGF-1 receptor, PDK1 and Akt, RIP, IκBand survivin. HSP90 can also promote aberrant cell cycle progression by stabilizing Cdk4, Cdk6 and cyclin D, Cdk2, and Plk1. Conversely, HSP90 inhibitors can downregulate the cell cycle checkpoint kinase Chk1 and sensitize tumors to various forms of chemotherapy. HSP90 inhibition can also blunt tumor angiogenesis, since hypoxia-inducible factor (HIF-1α) and the vascular endothelial growth factor (VEGF) receptor tyrosine kinases are HSP90 clients. The receptor tyrosine kinase Met, which stimulates cellular motility, migration and invasion, is also downregulated in response to HSP90 inhibition, both directly and via inhibition of HIF-1α. Apart from its role as a cellular chaperone, HSP90α has also been implicated in extracellular matrix degradation and tumor cell invasion, via activation (and possibly stabilization) of the matrix metalloproteinase MMP2. HSP90 depletion or inhibition promotes telomere erosion and apoptosis, and can also enable the evolution of heterogenous, metastatic and drug-resistant phenotypes by allowing propagation of metastable mutations. HSP90 has been implicated in activation of the unfolded protein response (UPR,). Failure of the UPR (for example, via inhibition of HSP90) leads to an ER stress signal and apoptosis. Therefore, HSP90 inhibitors can promote tumor cell death indirectly by disrupting the UPR, as well as by directly targeting pro-survival factors.

Accordingly, there is a need for new compounds that can inhibit HSP90.

SUMMARY OF THE INVENTION

One aspect of the disclosure relates to a compound according to Formula I or II:

I

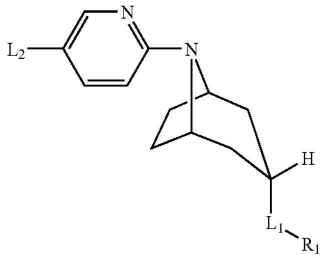

or

II

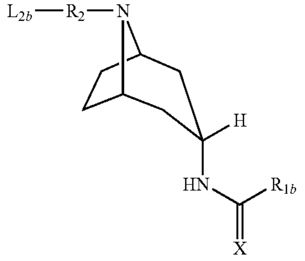

wherein $R_1$, $R_{1b}$, $R_2$, $L_1$, and $L_2$ and $L_{2b}$ are as defined in the specification.

Another aspect of this disclosure relates to a method of inhibiting HSP90 in a cell, comprising contacting the cell, in which inhibition of HSP90 is desired, with a compound according to Formula I or II.

Another aspect of this disclosure relates to a method of inhibiting HSP90 in a cell, comprising contacting a cell in which inhibition of HSP90 is desired with a pharmaceutical composition, comprising the compound according Formula I or II, and a pharmaceutically acceptable carrier, excipient, or diluent.

Another aspect of this disclosure relates to a method of treating one of the diseases or conditions disclosed herein that involves HSP90, comprising administering to an animal, in need of said treatment, the compound according to Formula I or II, optionally in combination with the one or more additional therapeutic agents or therapies disclosed herein.

DETAILED DESCRIPTION OF THE INVENTION

There are many different aspects of the disclosure described hereinbelow, and each aspect is non-limiting in regard to the scope of the disclosure. The terms "aspects" and "embodiments" are meant to be non-limiting regardless of where the terms "aspect" or "embodiment" appears in this specification. The transitional term "comprising" as used herein, which is synonymous with "including," "containing,"

or "characterized by," is inclusive or open-ended and does not exclude additional, unrecited elements or method steps.

One aspect of the disclosure relates to a compound according to Formula I:

I

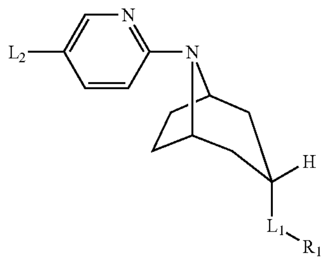

or a pharmaceutically acceptable salt thereof, wherein:

$R_1$ is selected from (C)

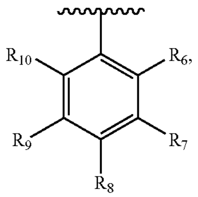

(D)

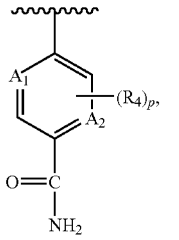

(E)

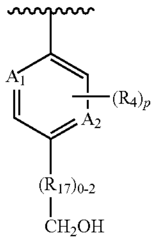

and (Q)

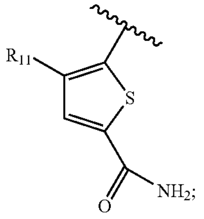

$R_3$ is selected from hydrogen, —$CF_3$, —$NH_2$, —OH, alkyl optionally substituted with 1, 2 or 3 $R_5$, alkoxy, dialkylaminoalkyl, cycloalkyl optionally substituted with arylalkoxy, aryl optionally substituted with 1, 2 or 3 groups selected from halogen, alkyl, alkoxy, dialkylaminoalkoxy and heterocycloalkyl optionally substituted with alkyl or aryl, alkenyl, alkynyl, heterocycloalkyl optionally substituted with a group selected from alkyl, —C(O)O-alkyl and arylalkyl, arylalkyl optionally substituted with alkylheterocycloalkyl at any ring position of the aryl group, and heteroaryl;

$R_4$, $R_7$, $R_8$, $R_9$ and $R_{11}$ are each independently selected from hydrogen, —$OR_{16}$, —$SR_{16}$, —N(H)$R_{16}$, hydroxy, alkenyl, alkynyl, hydroxyalkynyl, halogen, hydroxyalkyl, dihydroxyalkyl, —O—C(O)—$NH_2$, amino(imino)alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl, alkyl optionally substituted with 1-8 halogen, dialkylamino, —N(H)alkylheterocycloalkyl, alkylsulfonylheterocycloalkylamino, cycloalkylalkylamino, cycloalkoxy, —$NH_2$, —O-alkyl-heterocycloalkyl, dialkylaminoalkoxy, alkylsulfonylalkylamino and —N(H)heterocycloalkyl optionally substituted with 1, 2 or 3 groups selected from alkyl, alkoxy and halogen;

$R_5$ is selected from halogen, cycloalkyl, cycloalkylalkylamino, heteroaryl optionally substituted with 1, 2 or 3 groups selected from halogen, alkyl and alkoxy, alkylthio, heterocycloalkyl optionally substituted with 1, 2, or 3 groups selected from alkyl, halogen, phenyl and oxo, aryl optionally substituted with 1, 2 or 3 groups selected from halogen, alkyl, alkoxy, dialkylaminoalkoxy, and heterocycloalkyl optionally substituted with alkyl, alkoxy, dialkylamino, —OH, —C(O)—$NH_2$, —C(O)—O—$CH_3$, —C(O)—N(H)($C_1$-$C_3$) alkyl, heteroarylamino optionally substituted with halogen, and —$OCF_3$;

$R_6$ and $R_{10}$ are each selected from hydrogen, alkyl optionally substituted with 1-8 halogens, alkylthio, alkenyl, alkynyl, hydroxyalkynyl, halogen, hydroxyalkyl, dihydroxyalkyl, amino(imino)alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl, alkylamino optionally substituted with 1-8 halogens, dialkylamino, alkoxyalkylamino, —N(H)alkylheterocycloalkyl, cycloalkylalkylamino, alkylsulfonylheterocycloalkylamino, cycloalkylalkylamino, cycloalkylamino optionally substituted with a group selected form —OH, alkyl, —$CF_3$ and heterocycloalkyl, —N(H)cycloalkyl optionally substituted with —OH or —$NH_2$, —$NH_2$, —N(H)-heteroaryl, —N(H)-aryl optionally substituted with 1, 2 or 3 groups selected from alkoxy, heterocycloalkylalkoxy and dialkylaminoalkoxy, alkylsulfonylalkylamino and —N(H)heterocycloalkyl;

$R_{16}$ is selected from hydrogen, alkyl optionally substituted with 1-8 halogens, cycloalkyl optionally substituted with 1 or 2 groups selected from —OH, —$NH_2$, alkyl, heterocycloalkyl, and —$CF_3$, cycloalkylalkyl, heterocycloalkyl optionally substituted with —OH or —$NH_2$, alkoxyalkyl, aryl optionally substituted with 1, 2 or 3 alkoxy, heterocycloalkylalkyl, heteroaryl, gem-dicycloalkylalkyl and dialkylaminoalkyl;

$R_{17}$, when present, is —$CH_2$— or —CH(OH)—;

each of $A_1$ or $A_2$ is N or C(H), wherein $A_1$ and $A_2$ can be the same or different, provided that $A_1$ can be substituted with $R_4$ only when $A_1$ is C(H), and provided that $A_2$ can be substituted with $R_4$ only when $A_2$ is C(H);

$L_1$ is selected from —C(O)O—, —C(O)NH—, —C(O)$NHSO_2$—, —$(CH_2)_n$C(O)NH—, —$(CH_2)_n$NHC(O)—, —$(CH_2)_m$NH—, —$(CH_2)_n$$SO_2$NH—, —$(CH_2)_n$$NHSO_2$—, —$(CH_2)_m$C(O)—, —$(CH_2)_m$O—, and —$(CH_2)_m$NH—$(CH_2)_n$—;

$L_2$ is —C(O)—NH—$R_3$, —CN, —C(O)—N($CH_3$)—$OCH_3$, or —C(O)—$R_3$;

n is 0 or 1;

m is 0, 1 or 2; and each p is independently 0, 1, 2, 3 or 4.

In another embodiment, the compound of Formula I is a compound of Formula IB:

IB

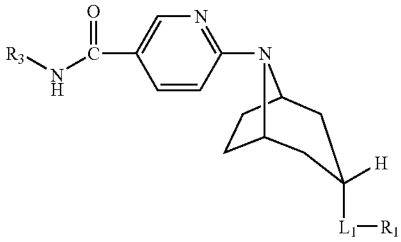

or a pharmaceutically acceptable salt thereof, wherein $L_1$, $R_1$ and $R_3$ are as defined in Formula I.

In another embodiment, the compound of Formula I is a compound of Formula IC:

IC

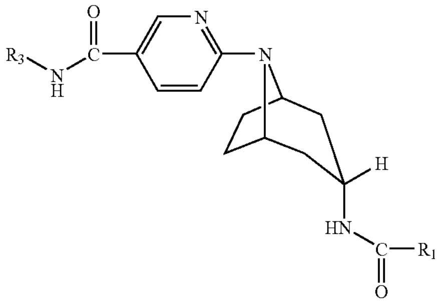

or a pharmaceutically acceptable salt thereof, wherein $R_1$ and $R_3$ are as defined in Formula I.

Another embodiment of Formula I is the compound of Formula ID:

ID

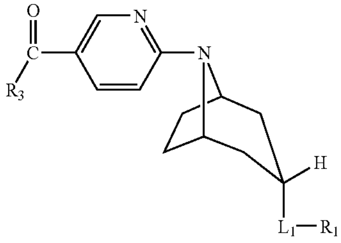

or a pharmaceutically acceptable salt thereof, wherein $R_1$, $R_3$ and $L_1$ are as defined in Formula I.

Another embodiment of Formula I is the compound of Formula IE:

IE

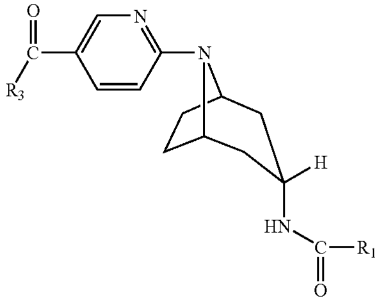

or a pharmaceutically acceptable salt thereof, wherein $R_1$ and $R_3$ are as defined in Formula I.

Another embodiment relates to any one of Formula I, IB, IC, ID or IE as defined above, or a pharmaceutically acceptable salt thereof.

Another embodiment relates to a compound of Formula I, wherein $R_1$ is selected from (C)

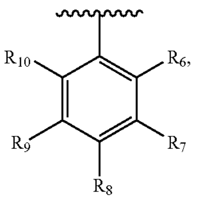

(D)

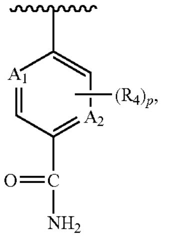

(E)

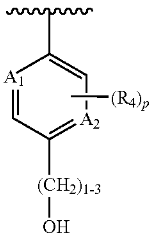

and (Q)

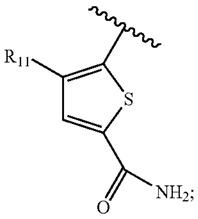

$R_3$ is selected from hydrogen, —$CF_3$, —$NH_2$, —OH, alkyl optionally substituted with 1, 2 or 3 $R_5$, alkoxy, dialkylaminoalkyl, cycloalkyl optionally substituted with arylalkoxy, aryl optionally substituted with 1, 2 or 3 groups selected from halogen, alkyl, alkoxy, dialkylaminoalkoxy and heterocycloalkyl optionally substituted with alkyl or aryl, alkenyl, alkynyl, heterocycloalkyl optionally substituted with a group selected from alkyl, —C(O)O-alkyl and arylalkyl, arylalkyl optionally substituted with alkylheterocycloalkyl at any ring position of the aryl group, and heteroaryl;

$R_4$, $R_7$, $R_8$, $R_9$ and $R_{11}$ are each independently selected from hydrogen, —$OR_{16}$, —$SR_{16}$, —N(H)$R_{16}$, hydroxy, alkenyl, alkynyl, hydroxyalkynyl, alkoxy, halogen, hydroxyalkyl, dihydroxyalkyl, —O—C(O)—$NH_2$, amino(imino) alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl, alkyl optionally substituted with 1-8 halogen, dialkylamino, —N(H)alkylheterocycloalkyl, alkylsulfonylheterocycloalkylamino, cycloalkylalkylamino, cycloalkoxy, —$NH_2$, —O-alkyl-heterocycloalkyl, dialkylaminoalkoxy, alkylsulfonylalkylamino and —N(H)heterocycloalkyl optionally substituted with 1, 2 or 3 groups selected from alkyl, alkoxy and halogen;

$R_5$ is selected from halogen, cycloalkyl, cycloalkylalkylamino, heteroaryl optionally substituted with 1, 2 or 3 groups selected from halogen, alkyl and alkoxy, alkylthio, heterocycloalkyl optionally substituted with 1, 2, or 3 groups selected from alkyl, halogen, phenyl and oxo, aryl optionally substituted with 1, 2 or 3 groups selected from halogen, alkyl, alkoxy, dialkylaminoalkoxy, and heterocycloalkyl (optionally substituted with alkyl), alkoxy, dialkylamino, —OH, —C(O)—$NH_2$, —C(O)—O—$CH_3$, —C(O)—N(H)($C_1$-$C_3$) alkyl, heteroarylamino optionally substituted with halogen, and —$OCF_3$;

$R_6$ and $R_{10}$ are each selected from hydrogen, alkyl optionally substituted with 1-8 halogens, alkylthio, alkenyl, alkynyl, hydroxyalkynyl, halogen, hydroxyalkyl, dihydroxyalkyl, amino(imino)alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl, alkylamino optionally substituted with 1-8 halogens, dialkylamino, alkoxyalkylamino, —N(H)alkylheterocycloalkyl, cycloalkylalkylamino, alkylsulfonylheterocycloalkylamino, cycloalkylalkylamino, cycloalkylamino optionally substituted with a group selected form —OH, alkyl, —$CF_3$ and heterocycloalkyl, —N(H)cycloalkyl optionally substituted with —OH or —$NH_2$), —$NH_2$, —N(H)-heteroaryl, —N(H)-aryl optionally substituted with 1, 2 or 3 groups selected from alkoxy, heterocycloalkylalkoxy and dialkylaminoalkoxy, alkylsulfonylalkylamino and —N(H)heterocycloalkyl;

$R_{16}$ is selected from hydrogen, alkyl optionally substituted with 1-8 halogens, cycloalkyl optionally substituted with 1 or 2 groups selected from —OH, —$NH_2$, alkyl, heterocycloalkyl, and —$CF_3$, cycloalkylalkyl, heterocycloalkyl optionally substituted with —OH or —$NH_2$, alkoxyalkyl, aryl optionally substituted with 1, 2 or 3 alkoxy, heterocycloalkylalkoxy, heteroaryl, gem-dicycloalkylalkyl and dialkylaminoalkoxy;

each of $A_1$ or $A_2$ is —N═ or —CH═, wherein $A_1$ and $A_2$ can be the same or different;

$L_1$ is selected from —NHC(O)—, —$NHSO_2$—, —NHC(O)O—, —C(O)O—, —C(O)NH—, —C(O)$NHSO_2$—, —C(O)—, —$(CH_2)_n$C(O)NH—, —$(CH_2)_n$NHC(O)—, —$(CH_2)_m$NH—, —$(CH_2)_n$$SO_2$NH—, —$(CH_2)_n$$NHSO_2$—, —$(CH_2)_m$C(O)—, —$(CH_2)_m$O—, and —$(CH_2)_m$NH—;

$L_2$ is —C(O)—NH—$R_3$, —CN or —C(O)—$R_3$;

n is 0 or 1;

m is 0, 1 or 2; and each p is independently 0, 1, 2, 3 or 4.

Another embodiment relates to a compound of Formula I, or a pharmaceutically acceptable salt thereof, wherein:

$R_1$ is selected from

C2

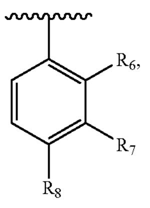

-continued

D2

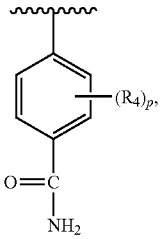

and

E2

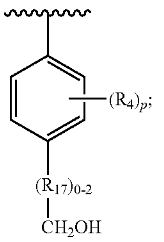

$R_3$ is selected from $CF_3$, cyclopropyl, cyclobutyl, cyclohexyl optionally substituted with hydroxyl, cyclopropylmethyl, N-propyl, 3-methylbutyl, (1S)-2-hydroxy-1-methylethyl, (2S)-2-hydroxypropyl, methoxyethyl, ethoxyethyl, methylphenyl, phenyl, dimethylphenyl, methoxyphenyl, dimethylaminoethyl, dimethylaminopropyl, diethylaminoethyl, diethylaminopropyl, cyclopentyl, halophenyl, phenylmethyl, phenylethyl optionally substituted with hydroxyl at the ethyl position of phenylethyl, phenylpropyl, phenylpiperidinyl, diethylaminoethyloxyphenylmethyl, diethylaminoethyloxyphenylethyl, pyrrolidinylphenylmethyl, diethylaminoethyloxy-2-fluorophenylethyl, phenyl($C_1$-$C_3$)alkyl optionally substituted at the phenyl position of phenyl($C_1$-$C_3$)alkyl with 1-3 groups selected from methoxy, halo and methyl, methylphenyl($C_1$-$C_4$)alkyl wherein the ($C_1$-$C_4$)alkyl portion of methylphenyl($C_1$-$C_4$)alkyl is optionally substituted with —C(O)$NH_2$, —C(O)$NHCH_3$ or —C(O)$NHCH_2CH_3$, thienylmethyl, furanylmethyl, pyridinylethyl, pyridinylmethyl, methylpyrazinylmethyl, methyl, ethyl, methylpropyl, 2-methylpropyl, 2,3-dihydroxypropyl, (1S)-1-methylpropyl, (1S)-1,2-dimethylpropyl, (1R)-1,2-dimethylpropyl, methyloxypropyl, ethyloxypropyl, (1S)-1-methyl-2-(methyloxy) ethyl, 1,3-benzodioxolyl, 1,3-benzodioxolylmethyl, N-prop-2-yn-1-yl, N-[3-(4-methylpiperazin-1-yl)propyl, N-[2-(ethylthio)ethyl], (1S,2S)-2-[(phenylmethyl)oxy] cyclopentyl, 6-chloropyridinylmethyl, 2-chloro-6-fluorophenylmethyl, methylthioethyl, N-butyl, 1-methylethyloxyethyl, 1-methylethyloxypropyl, 4,4-bismethyloxybutyl, methylpyrazinylmethyl, propyloxypropyl, trifluoromethyloxyphenylmethyl, methyloxyphenylethyl, (2,2-dimethyl-1,3-dioxolan-4-yl)methyl, phenylmethylpyrrolidinyl, oxopyrrolidinylpropyl, pyrrolidinylethyl, methylpyrrolidinylethyl, ethylpyrrolidinylmethyl, N-(1R,2R,4S)-bicyclo[2.2.1]hept-2-yl, 3,3-dimethylbutyl, ethyloxyphenylmethyl, phenylmethylpiperidinyl, ethoxycarbonylpiperidinyl, trifluoromethylphenylmethyl, imidazolylpropyl, (3R)-pyrrolidin-3-yl, morpholinylethyl, morpholinylpropyl, piperidinylethyl, pyrrolidinyl, piperidinyl, pyrrolidinylmethyl, 1-methylethylpyrrolidinyl, ethylpyrrolidinyl, methylpyrrolidinyl, methylethylpiperidinyl, methylpiperidinyl, ethylpiperidinyl, ethylazetidinyl, azetidinyl, methylazetidinyl, 1-methylethylazetidinyl, methylpiperazinylphenylmethyl, piperazinylphenylmethyl, methylpiperazinylphenyl, methylpiperidinylphenyl, piperidinylphenyl($C_1$-$C_3$)alkyl optionally substituted with 1-4 halo, methylpiperazinylphenyl(halo)methyl, methylpiperidinylphenylmethyl, methylpiperazinylphenylethyl, 2-methylpropylpiperazinylphenylmethyl, morpholinylphenylmethyl, piperazinylpyridinylethyl, —$CH(CH_3)C(O)$—$NH_2$, dimethylaminoethyloxyphenyl, isopropyl, ($C_1$-$C_5$)alkyl optionally substituted with 1-7 halo, —OH, —$NH_2$, cylcohexyl($C_1$-$C_5$)alkyl optionally substituted with 1-2 hydroxyl groups, phenylaminoethyl optionally substituted with halo, morpholinylethyl, phenylpiperazinylethyl, and methylpiperazinylethyl;

each $R_4$, when present, is independently selected from halo, 1-ethylpropylamino, methyl, ethyl, cyclohexylamino optionally substituted with hydroxyl, cyclobutylamino, 1-methylpropyloxy, methoxyethoxy, —$CF_3$, piperidinyl or amino, mopholinylamino, dimethylaminobutyl, methylethylaminopropyl, methylethylaminopropylamino, cyclopentylamino, piperidinylamino, methylethylamino, ethylamino, 2-methylpropylamino, tetrahydraopyranylamino, ethylpiperidinylamino, 2,2-dimethylpropylamino, pyrrolidinylamino, 1-methylpropylamino, 2-methylpropylamino, amino, 1,1 dimethylethylamino, tetrahydropyranylmethylamino, piperidinylamino optionally substituted with methylsulfonyl, phenylamino optionally substituted with 1-3 groups selected from methoxy and dimethylaminoethyloxy, methylsulfonylethylamino, methoxyethylamino, morpholinylethyloxy, —$N(H)C(O)CH_3$, cyclobutylamino, methoxy, cyclobutyloxy, cyclobutylamino, pyridinylamino, ethylamino, 1-methylcyclopropylethylamino, methylethyloxyethylamino, butylamino, piperidinyl, pentylamino, azetinyl, 1,2-dimethylpropylamino, 1-methylethylpropylamino, propylamino, 1-cyclopropylpropylamino, 1-propylbutylamino, 1-cyclopropylethylamino, dicyclopropylmethylamino, 1,2,2-trimethylpropylamino, tetrahydrofuranylamino, ($C_1$-$C_5$) alkylamino substituted with 1-7 halo, morpholinylethyloxy and cyclopropylmethylamino;

$R_6$ is selected from hydrogen, ($C_1$-$C_4$)alkyl optionally substituted with hydroxy, ($C_1$-$C_3$)alkylamino or dimethylamino, ($C_1$-$C_4$)alkynyl optionally substituted with hydroxyl, and halo;

$R_7$ is selected from hydrogen, —OH, —O($C_1$-$C_3$)alkyl, —S($C_1$-$C_3$)alkyl, —N(H)($C_1$-$C_3$)alkyl, ($C_5$-$C_6$)cycloalkylamino optionally substituted with hydroxyl, ($C_1$-$C_3$)alkyl amino or dimethyl amino, —$C(O)NH_2$, and —O—$C(O)NH_2$;

$R_8$ is selected from hydrogen, —O($C_1$-$C_3$)alkyl, —O—C(O)$NH_2$, and —C(═NH)—$NH_2$;

$L_1$ is —N(H)C(O)—;

$L_2$ is —C(O)—NH—$R_3$ or —C(O)—$R_3$; and each p is independently 0, 1, 2 or 3.

Another embodiment relates to a compound of Formula I, or a pharmaceutically acceptable salt thereof, wherein:

$R_1$ is selected from

C2

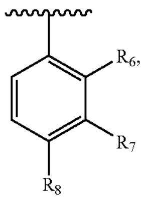

-continued

D2

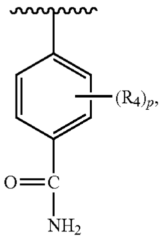

and

E2

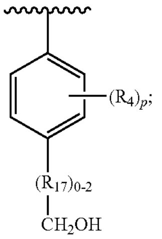

$R_3$ is selected from hydrogen, —$CF_3$, —$NH_2$, —OH, alkyl optionally substituted with 1, 2 or 3 $R_5$, alkoxy, diethylaminoethoxy, ethylmethylaminoethoxy, dimethylaminoethoxy, cylcopentyl optionally substituted with arylalkoxy, cyclobutyl optionally substituted with arylalkoxy, cyclopropyl optionally substituted with arylalkoxy, aryl optionally substituted with 1, 2 or 3 groups selected from halogen, alkyl, alkoxy, dialkylaminoalkoxy, piperazinyl optionally substituted with alkyl or phenyl, morpholinyl optionally substituted with alkyl or phenyl, azetidinyl and piperidinyl optionally substituted with alkyl or phenyl, alkenyl, alkynyl, heterocycloalkyl selected from piperidinyl, pyrrolidinyl, morpholinyl and piperizinyl, wherein the heterocycloalkyl is optionally substituted with a group selected from alkyl, —C(O)O-alkyl and arylalkyl, arylalkyl optionally substituted with alkylheterocycloalkyl at any ring position of the aryl group, and heteroaryl;

$R_6$ is selected from hydrogen, ($C_1$-$C_4$)alkyl optionally substituted with hydroxy, ($C_1$-$C_3$)alkylamino or dimethylamino, ($C_1$-$C_4$)alkynyl optionally substituted with hydroxyl, and halo;

$R_7$ is selected from hydrogen, —OH, —O($C_1$-$C_3$)alkyl, —S($C_1$-$C_3$)alkyl, —N(H)($C_1$-$C_3$)alkyl, ($C_5$-$C_6$)cycloalkylamino optionally substituted with hydroxyl, ($C_1$-$C_3$)alkylamino or dimethylamino, —$C(O)NH_2$, and —O—C(O)$NH_2$;

$R_8$ is selected from hydrogen, —O($C_1$-$C_3$)alkyl, —O—C(O)$NH_2$, and —C(═NH)—$NH_2$;

each $R_4$, when present, is independently selected from methyl, 1-methylethylamino, ethylamino, 1-ethylpropylamino, 2-methylpropylamino, (2,2-dimethylpropyl)amino, (2-aminoethyl)amino, (2,2,3,3,3-pentafluoropropyl)amino, 1-methylpropylamino, (1S)-1-methylpropylamino, (2,2,2-trifluoroethyl)amino, 1-propylbutylamino, propylamino, 1,2-dimethylpropylamino, (3,3,3-trifluoropropyl)amino, (2,2,3,3,4,4,4-heptafluorobutyl)amino, butylamino, 1,2,2-trimethylpropylamino, 1-[(methyloxy)methyl]propylamino, 1-methylethyloxyethylamino, 1-methylpropylamino, pentylamino, (2,2,3,3,3-pentafluoropropyl)amino, butylamino, 2-[(1-methylethyl)oxy]ethylamino, (1S)-1-methylpropylamino, (1R)-1-methylpropylamino, (1S)-1,2-dimethylpropylamino, 1-cyclopropylethylamino, (1R)-1,2-dimethylpropylamino, 1-ethyl-2-methylpropylamino, and 3-[(1-methylethyl)amino]propylamino;

$L_1$ is —N(H)C(O)—;

$L_2$ is —C(O)—NH—$R_3$ or —C(O)—$R_3$; and each p is independently 0, 1, 2 or 3.

Another embodiment relates to a compound of Formula IB or ID, or a pharmaceutically acceptable salt thereof, wherein:

$R_1$ is selected from

C2

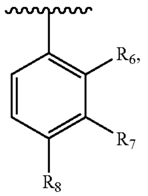

D2

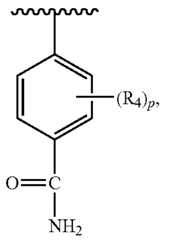

and

E2

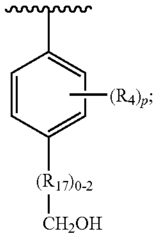

$R_3$ is selected from $CF_3$, cyclopropyl, cyclobutyl, cyclohexyl optionally substituted with hydroxyl, cyclopropylmethyl, N-propyl, 3-methylbutyl, (1S)-2-hydroxy-1-methylethyl, (2S)-2-hydroxypropyl, methoxyethyl, ethoxyethyl, methylphenyl, phenyl, dimethylphenyl, methoxyphenyl, dimethylaminoethyl, dimethylaminopropyl, diethylaminoethyl, diethylaminopropyl, cyclopentyl, halophenyl, phenylmethyl, phenylethyl optionally substituted with hydroxyl at the ethyl position of phenylethyl, phenylpropyl, phenylpiperidinyl, diethylaminoethyloxyphenylmethyl, diethylaminoethyloxyphenylethyl, pyrrolidinylphenylmethyl, diethylaminoethyloxy-2-fluorophenylethyl, phenyl($C_1$-$C_3$)alkyl optionally substituted at the phenyl position of phenyl($C_1$-$C_3$)alkyl with 1-3 groups selected from methoxy, halo and methyl, methylphenyl($C_1$-$C_4$)alkyl wherein the ($C_1$-$C_4$)alkyl portion of methylphenyl($C_1$-$C_4$)alkyl is optionally substituted with —C(O)$NH_2$, —C(O)$NHCH_3$ or —C(O)$NHCH_2CH_3$, thienylmethyl, furanylmethyl, pyridinylethyl, pyridinylmethyl, methylpyrazinylmethyl, methyl, ethyl, methylpropyl, 2-methylpropyl, 2,3-dihydroxypropyl, (1S)-1-methylpropyl, (1S)-1,2-dimethylpropyl, (1R)-1,2-dimethylpropyl, methyloxypropyl, ethyloxypropyl, (1S)-1-methyl-2-(methyloxy)ethyl, 1,3-benzodioxolyl, 1,3-benzodioxolylmethyl, N-prop-2-yn-1-yl, N-[3-(4-methylpiperazin-1-yl)propyl], N-[2-(ethylthio)ethyl], (1S,2S)-2-[(phenylmethyl)oxy]cyclopentyl, 6-chloropyridinylmethyl, 2-chloro-6-fluorophenylmethyl, methylthioethyl, N-butyl, 1-methylethyloxyethyl, 1-methylethyloxypropyl, 4,4-bismethyloxybutyl, methylpyrazinylmethyl, propyloxypropyl, trifluoromethyloxyphenylmethyl, methyloxyphenylethyl, (2,2-dimethyl-1,3-dioxolan-4-yl)methyl, phenylmethylpyrrolidinyl, oxopyrrolidinylpropyl, pyrrolidinylethyl, methylpyrrolidinylethyl, ethylpyrrolidinylmethyl, N-(1R,2R,4S)-bicyclo[2.2.1]hept-2-yl, 3,3-dimethylbutyl, ethyloxyphenylmethyl, phenylmethylpiperidinyl, ethoxycarbonylpiperidinyl, trifluoromethylphenylmethyl, imidazolylpropyl, (3R)-pyrrolidin-3-yl, morpholinylethyl, morpholinylpropyl, piperidinylethyl, pyrrolidinyl, piperidinyl, pyrrolidinylmethyl, 1-methylethylpyrrolidinyl, ethylpyrrolidinyl, methylpyrrolidinyl, methylethylpiperidinyl, methylpiperidinyl, ethylpiperidinyl, ethylazetidinyl, azetidinyl, methylazetidinyl, 1-methylethylazetidinyl, methylpiperazinylphenylmethyl, piperazinylphenylmethyl, methylpiperazinylphenyl, methylpiperidinylphenyl, piperidinylphenyl($C_1$-$C_3$)alkyl optionally substituted with 1-4 halo, methylpiperazinylphenyl(halo)methyl, methylpiperidinylphenylmethyl, methylpiperazinylphenylethyl, 2-methylpropylpiperazinylphenylmethyl, morpholinylphenylmethyl, piperazinylpyridinylethyl, —$CH(CH_3)C(O)$—$NH_2$, dimethylaminoethyloxyphenyl, isopropyl, ($C_1$-$C_5$)alkyl optionally substituted with 1-7 halo, —OH, —$NH_2$, cylcohexyl($C_1$-$C_5$)alkyl optionally substituted with 1-2 hydroxyl groups, phenylaminoethyl optionally substituted with halo, morpholinylethyl, phenylpiperazinylethyl, and methylpiperazinylethyl;

each $R_4$, when present, is independently selected from halo, 1-ethylpropylamino, methyl, ethyl, cyclohexylamino optionally substituted with hydroxyl, cyclobutylamino, 1-methylpropyloxy, methoxyethoxy, —$CF_3$, piperidinyl or amino, mopholinylamino, dimethylaminobutyl, methylethylaminopropyl, methylethylaminopropylamino, cyclopentylamino, piperidinylamino, methylethylamino, ethylamino, 2-methylpropylamino, tetrahydraopyranylamino, ethylpiperidinylamino, 2,2-dimethylpropylamino, pyrrolidinylamino, 1-methylpropylamino, 2-methylpropylamino, amino, 1,1 dimethylethylamino, tetrahydropyranylmethylamino, piperidinylamino optionally substituted with methylsulfonyl, phenylamino optionally substituted with 1-3 groups selected from methoxy and dimethylaminoethyloxy, methylsulfonylethylamino, methoxyethylamino, morpholinylethyloxy, —N(H)C(O)$CH_3$, cyclobutylamino, methoxy, cyclobutyloxy, cyclobutylamino, pyridinylamino, ethylamino, 1-methylcyclopropylethylamino, methylethyloxyethylamino, butylamino, piperidinyl, pentylamino, azetinyl, 1,2-dimethylpropylamino, 1-methylethylpropylamino, propylamino, 1-cyclopropylpropylamino, 1-propylbutylamino, 1-cyclopropylethylamino, dicyclopropylmethylamino, 1,2,2-trimethylpropylamino, tetrahydrofuranylamino, ($C_1$-$C_5$) alkylamino substituted with 1-7 halo, morpholinylethyloxy and cyclopropylmethylamino;

$R_6$ is selected from hydrogen, ($C_1$-$C_4$)alkyl optionally substituted with hydroxy, ($C_1$-$C_3$)alkylamino or dimethylamino, ($C_1$-$C_4$)alkynyl optionally substituted with hydroxyl, and halo;

$R_7$ is selected from hydrogen, —OH, —O($C_1$-$C_3$)alkyl, —S($C_1$-$C_3$)alkyl, —N(H)($C_1$-$C_3$)alkyl, ($C_5$-$C_6$)cycloalkylamino optionally substituted with hydroxyl, ($C_1$-$C_3$)alkylamino or dimethylamino, —C(O)$NH_2$, and —O—C(O)$NH_2$;

$R_8$ is selected from hydrogen, —O($C_1$-$C_3$)alkyl, —O—C(O)$NH_2$, and —C(=NH)—$NH_2$;

$L_1$ is —N(H)C(O)—;

$L_2$ is —C(O)—NH—$R_3$ or —C(O)—$R_3$; and each p is independently 0, 1, 2 or 3.

Another embodiment relates to a compound of Formula IC or IE, or a pharmaceutically acceptable salt thereof, wherein:

$R_1$ is selected from

C2

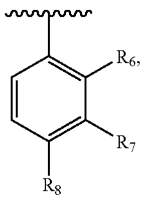

D2

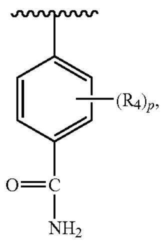

and

E2

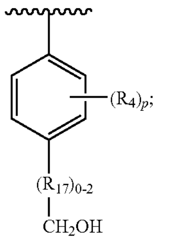

$R_1$ is selected from

C2

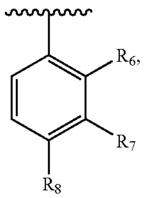

D2

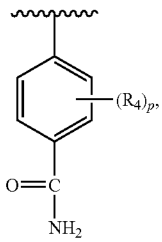

and

E2

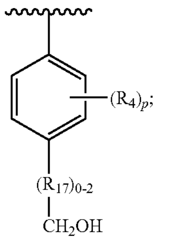

$R_3$ is selected from $CF_3$, cyclopropyl, cyclobutyl, cyclohexyl optionally substituted with hydroxyl, cyclopropylmethyl, N-propyl, 3-methylbutyl, (1S)-2-hydroxy-1-methylethyl, (2S)-2-hydroxypropyl, methoxyethyl, ethoxyethyl, methylphenyl, phenyl, dimethylphenyl, methoxyphenyl, dimethylaminoethyl, dimethylaminopropyl, diethylaminoethyl, diethylaminopropyl, cyclopentyl, halophenyl, phenylmethyl, phenylethyl optionally substituted with hydroxyl at the ethyl position of phenylethyl, phenylpropyl, phenylpiperidinyl, diethylaminoethyloxyphenylmethyl, diethylaminoethyloxyphenylethyl, pyrrolidinylphenylmethyl, diethylaminoethyloxy-2-fluorophenylethyl, phenyl($C_1$-$C_3$)alkyl optionally substituted at the phenyl position of phenyl($C_1$-$C_3$)alkyl with 1-3 groups selected from methoxy, halo and methyl, methylphenyl($C_1$-$C_4$)alkyl wherein the ($C_1$-$C_4$)alkyl portion of methylphenyl($C_1$-$C_4$)alkyl is optionally substituted with $-C(O)NH_2$, $-C(O)NHCH_3$ or $-C(O)NHCH_2CH_3$, thienylmethyl, furanylmethyl, pyridinylethyl, pyridinylmethyl, methylpyrazinylmethyl, methyl, ethyl, methylpropyl, 2-methylpropyl, 2,3-dihydroxypropyl, (1S)-1-methylpropyl, (1S)-1,2-dimethylpropyl, (1R)-1,2-dimethylpropyl, methyloxypropyl, ethyloxypropyl, (1S)-1-methyl-2-(methyloxy)ethyl, 1,3-benzodioxolyl, 1,3-benzodioxolylmethyl, N-prop-2-yn-1-yl, N-[3-(4-methylpiperazin-1-yl)propyl, N-[2-(ethylthio)ethyl], (1S,2S)-2-[(phenylmethyl)oxy]cyclopentyl, 6-chloropyridinylmethyl, 2-chloro-6-fluorophenylmethyl, methylthioethyl, N-butyl, 1-methylethyloxyethyl, 1-methylethyloxypropyl, 4,4-bismethyloxybutyl, methylpyrazinylmethyl, propyloxypropyl, trifluoromethyloxyphenylmethyl, methyloxyphenylethyl, (2,2-dimethyl-1,3-dioxolan-4-yl)methyl, phenylmethylpyrrolidinyl, oxopyrrolidinylpropyl, pyrrolidinylethyl, methylpyrrolidinylethyl, ethylpyrrolidinylmethyl, N-(1R,2R,4S)-bicyclo[2.2.1]hept-2-yl, 3,3-dimethylbutyl, ethyloxyphenylmethyl, phenylmethylpiperidinyl, ethoxycarbonylpiperidinyl, trifluoromethylphenylmethyl, imidazolylpropyl, (3R)-pyrrolidin-3-yl, morpholinylethyl, morpholinylpropyl, piperidinylethyl, pyrrolidinyl, piperidinyl, pyrrolidinylmethyl, 1-methylethylpyrrolidinyl, ethylpyrrolidinyl, methylpyrrolidinyl, methylethylpiperidinyl, methylpiperidinyl, ethylpiperidinyl, ethylazetidinyl, azetidinyl, methylazetidinyl, 1-methylethylazetidinyl, methylpiperazinylphenylmethyl, piperazinylphenylmethyl, methylpiperazinylphenyl, methylpiperidinylphenyl, piperidinylphenyl($C_1$-$C_3$)alkyl optionally substituted with 1-4 halo, methylpiperazinylphenyl(halo)methyl, methylpiperidinylphenylmethyl, methylpiperazinylphenylethyl, 2-methylpropylpiperazinylphenylmethyl, morpholinylphenylmethyl, piperazinylpyridinylethyl, $-CH(CH_3)C(O)-NH_2$, dimethylaminoethyloxyphenyl, isopropyl, ($C_1$-$C_5$)alkyl optionally substituted with 1-7 halo, —OH, $-NH_2$, cylcohexyl($C_1$-$C_5$)alkyl optionally substituted with 1-2 hydroxyl groups, phenylaminoethyl optionally substituted with halo, morpholinylethyl, phenylpiperazinylethyl, and methylpiperazinylethyl;

each $R_4$, when present, is independently selected from halo, 1-ethylpropylamino, methyl, ethyl, cyclohexylamino optionally substituted with hydroxyl, cyclobutylamino, 1-methylpropyloxy, methoxyethoxy, $-CF_3$, piperidinyl or amino, mopholinylamino, dimethylaminobutyl, methylethylaminopropyl, methylethylaminopropylamino, cyclopentylamino, piperidinylamino, methylethylamino, ethylamino, 2-methylpropylamino, tetrahydraopyranylamino, ethylpiperidinylamino, 2,2-dimethylpropylamino, pyrrolidinylamino, 1-methylpropylamino, 2-methylpropylamino, amino, 1,1 dimethylethylamino, tetrahydropyranylmethylamino, piperidinylamino optionally substituted with methylsulfonyl, phenylamino optionally substituted with 1-3 groups selected from methoxy and dimethylaminoethyloxy, methylsulfonylethylamino, methoxyethylamino, morpholinylethyloxy, —N(H)C(O)$CH_3$, cyclobutylamino, methoxy, cyclobutyloxy, cyclobutylamino, pyridinylamino, ethylamino, 1-methylcyclopropylethylamino, methylethyloxyethylamino, butylamino, piperidinyl, pentylamino, azetinyl, 1,2-dimethylpropylamino, 1-methylethylpropylamino, propylamino, 1-cyclopropylpropylamino, 1-propylbutylamino, 1-cyclopropylethylamino, dicyclopropylmethylamino, 1,2,2-trimethylpropylamino, tetrahydrofuranylamino, $(C_1-C_5)$ alkylamino substituted with 1-7 halo, morpholinylethyloxy and cyclopropylmethylamino;

$R_6$ is selected from hydrogen, $(C_1-C_4)$alkyl optionally substituted with hydroxy, $(C_1-C_3)$alkylamino or dimethylamino, $(C_1-C_4)$alkynyl optionally substituted with hydroxyl, and halo;

$R_7$ is selected from hydrogen, —OH, —O$(C_1-C_3)$alkyl, —S$(C_1-C_3)$alkyl, —N(H)$(C_1-C_3)$alkyl, $(C_5-C_6)$cycloalkylamino optionally substituted with hydroxyl, $(C_1-C_3)$alkyl amino or dimethyl amino, —C(O)$NH_2$, and —O—C(O)$NH_2$;

$R_8$ is selected from hydrogen, —O$(C_1-C_3)$alkyl, —O—C(O)$NH_2$, and —C(=NH)—$NH_2$;

$L_1$ is —N(H)C(O)—;

$L_2$ is —C(O)—NH—$R_3$ or —C(O)—$R_3$; and each p is independently 0, 1, 2 or 3.

In other embodiments, $R_1$ of the compound of Formula I, or a pharmaceutically acceptable salt thereof, is aryl optionally substituted with 1, 2 or 3 groups independently selected from (1) —C(O)$NH_2$, (2) methoxy, (3) alkyl, such as methyl as a non-limiting example, (4) alkylamino, such as ethylpropylamino, methylpropylamino or cyclopropylpropylpropylamino as non-limiting examples, (5) cycloalkylamino optionally substituted with OH, such as cyclohexylamino or cyclopentylamino as non-limiting examples, and (6) heterocycloalkylamino, such as furanyl or tetrahydro-2H-pyran as non-limiting examples.

In another embodiment of the compound of Formula I, or a pharmaceutically acceptable salt thereof, $L_1$ is —NHC(O)—.

In another embodiment of the compound of Formula I, or a pharmaceutically acceptable salt thereof, $L_1$ is selected from —NHC(O)—, —$NHSO_2$—, —NHC(O)O—, —C(O)O—, —C(O)NH—, —C(O)$NHSO_2$—, —C(O)—, —$(CH_2)$C(O)NH—, —$(CH_2)$NHC(O)—, —$(CH_2)$NH—, —$(CH_2)_n$$SO_2$NH—, —$(CH_2)$$NHSO_2$—, —$(CH_2)$C(O)—, —$(CH_2)$O—, and —NH—$(CH_2)$—.

In another embodiment of the compound of Formula I, or a pharmaceutically acceptable salt thereof, $L_2$ is —C(O)—NH-cyclopropyl, —C(O)—NH—$CH_3$, —C(O)-cyclopropyl, or —C(O)—$CH_3$.

In another embodiment of the compound of Formula I, or a pharmaceutically acceptable salt thereof, $L_2$ is —C(O)—NH-cyclopropyl or —C(O)—NH—$CH_3$.

In another embodiment of the compound of Formula I, or a pharmaceutically acceptable salt thereof, $L_2$ is —C(O)—NH—$CH_3$.

In another embodiment of the compound of Formula I, or a pharmaceutically acceptable salt thereof, $L_2$ is —C(O)—NH-cyclopropyl In another embodiment of the compound of Formula I, or a pharmaceutically acceptable salt thereof, $L_2$ is —C(O)-cyclopropyl or —C(O)—$CH_3$ In another embodiment of the compound of Formula I, or a pharmaceutically acceptable salt thereof, $L_2$ is —C(O)-cyclopropyl.

In another embodiment of the compound of Formula I, or a pharmaceutically acceptable salt thereof, $L_2$ is —C(O)—$CH_3$.

In another embodiment of the compound of Formula I, IB, IC, ID, and IE, or a pharmaceutically acceptable salt thereof, $R_1$ is selected from:

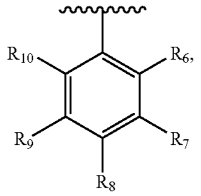

(C)

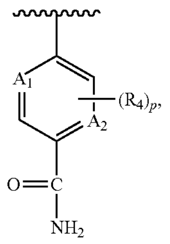

(D)

and

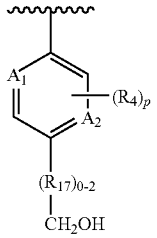

(E)

wherein $A_1$, $A_2$, $R_4$, $R_6$, $R_7$, $R_8$, $R_9$, $R_{10}$, $R_{17}$, and p are as defined above.

In another embodiment of the compound of Formula I, IB, IC, ID, and IE, or a pharmaceutically acceptable salt thereof, $R_1$ is selected from:

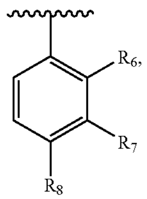

C2

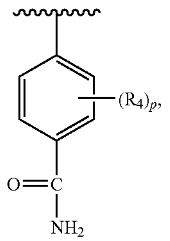

D2 and

-continued

E2

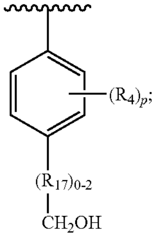

wherein $R_4$, $R_6$, $R_7$, $R_8$, $R_{17}$, and p are as defined above.

In another embodiment of the compound of Formula I, IB, IC, ID, or IE, $R_1$ is selected from one of the following of Group Z:

Group Z (G)

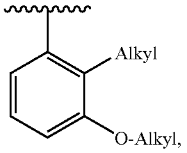

(H)

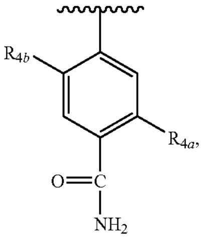

and (I)

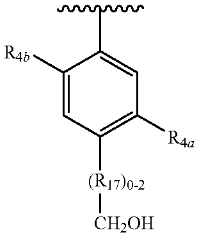

wherein $R_{4a}$ is selected from hydrogen, —$OR_{16}$, —$SR_{16}$, —N(H)$R_{16}$, hydroxy, alkenyl, alkynyl, hydroxyalkynyl, alkoxy, halogen, hydroxyalkyl, dihydroxyalkyl, —O—C(O)—$NH_2$, amino(imino)alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl, alkyl optionally substituted with 1-8 halogens, dialkylamino, —N(H)alkylheterocycloalkyl, alkylsulfonylheterocycloalkylamino, cycloalkylalkylamino, cycloalkoxy, —$NH_2$, —O-alkyl-heterocycloalkyl, dialkylaminoalkoxy, alkylsulfonylalkylamino and —N(H)heterocycloalkyl optionally substituted with 1, 2 or 3 groups selected from alkyl, alkoxy and halogen;

$R_{4b}$ is selected from H, halogen and methyl optionally substituted with 1-3 halogens;

$R_{16}$ is selected from hydrogen, alkyl optionally substituted with 1-8 halogens, cycloalkyl optionally substituted with 1 or 2 groups selected from —OH, —$NH_2$, alkyl, heterocycloalkyl, and —$CF_3$, cycloalkylalkyl, heterocycloalkyl optionally substituted with —OH or —$NH_2$, alkoxyalkyl, aryl optionally substituted with 1, 2 or 3 alkoxy, heterocycloalkylalkyl, heteroaryl, gem-dicycloalkylalkyl and dialkylaminoalkyl; and $R_{17}$, when present, is —$CH_2$— or —CH(OH)—.

Another aspect of the disclosure relates to a compound according to

Formula I:

I

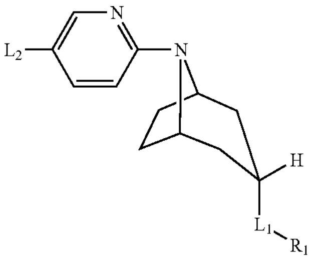

or a pharmaceutically acceptable salt thereof, wherein:

$R_1$ is selected from:

(C)

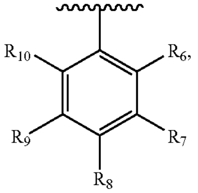

(D)

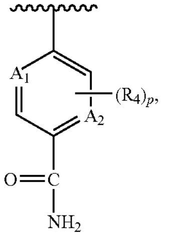

and (E)

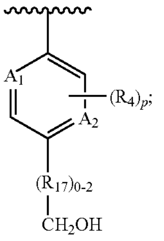

$R_3$ is selected from hydrogen, —$CF_3$, —$NH_2$, —OH, alkyl optionally substituted with 1, 2 or 3 $R_5$, alkoxy, dialkylaminoalkyl, cycloalkyl optionally substituted with arylalkoxy, aryl optionally substituted with 1, 2 or 3 groups selected from halogen, alkyl, alkoxy, dialkylaminoalkoxy and heterocycloalkyl optionally substituted with alkyl or aryl, alkenyl, alkynyl, heterocycloalkyl optionally substituted with a group selected from alkyl, —C(O)O-alkyl and arylalkyl, arylalkyl optionally substituted with alkylheterocycloalkyl at any ring position of the aryl group, and heteroaryl;

$R_4$, $R_7$, $R_8$, $R_9$ and $R_{11}$ are each independently selected from hydrogen, —$OR_{16}$, —$SR_{16}$, —N(H)$R_{16}$, hydroxy, alkenyl, alkynyl, hydroxyalkynyl, alkoxy, halogen, hydroxyalkyl, dihydroxyalkyl, —O—C(O)—$NH_2$, amino(imino) alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl, alkyl optionally substituted with 1-8 halogen, dialkylamino, —N(H)alkylheterocycloalkyl, alkylsulfonylheterocycloalkylamino, cycloalkylalkylamino, cycloalkoxy, —$NH_2$, —O— alkyl-heterocycloalkyl, dialkylaminoalkoxy, alkylsulfonylalkylamino and —N(H)heterocycloalkyl optionally substituted with 1, 2 or 3 groups selected from alkyl, alkoxy and halogen;

$R_5$ is selected from halogen, cycloalkyl, cycloalkylalkylamino, heteroaryl optionally substituted with 1, 2 or 3 groups selected from halogen, alkyl and alkoxy, alkylthio, heterocycloalkyl optionally substituted with 1, 2, or 3 groups selected from alkyl, halogen, phenyl and oxo, aryl optionally substituted with 1, 2 or 3 groups selected from halogen, alkyl, alkoxy, dialkylaminoalkoxy, and heterocycloalkyl optionally substituted with alkyl, alkoxy, dialkylamino, —OH, —C(O)—$NH_2$, —C(O)—O—$CH_3$, —C(O)—N(H)($C_1$-$C_3$) alkyl, heteroarylamino optionally substituted with halogen, and —$OCF_3$;

$R_6$ and $R_{10}$ are each selected from hydrogen, alkyl optionally substituted with 1-8 halogens, alkylthio, alkenyl, alkynyl, hydroxyalkynyl, halogen, hydroxyalkyl, dihydroxyalkyl, amino(imino)alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl, alkylamino optionally substituted with 1-8 halogens, dialkylamino, alkoxyalkylamino, —N(H)alkylheterocycloalkyl, cycloalkylalkylamino, alkylsulfonylheterocycloalkylamino, cycloalkylalkylamino, cycloalkylamino optionally substituted with a group selected form —OH, alkyl, —$CF_3$ and heterocycloalkyl, —N(H)cycloalkyl optionally substituted with —OH or —$NH_2$, —$NH_2$, —N(H)-heteroaryl, —N(H)-aryl optionally substituted with 1, 2 or 3 groups selected from alkoxy, heterocycloalkylalkoxy and dialkylaminoalkoxy, alkylsulfonylalkylamino and —N(H)heterocycloalkyl;

$R_{16}$ is selected from hydrogen, alkyl optionally substituted with 1-8 halogens, cycloalkyl optionally substituted with 1 or 2 groups selected from —OH, —$NH_2$, alkyl, heterocycloalkyl, and —$CF_3$, cycloalkylalkyl, heterocycloalkyl optionally substituted with —OH or —$NH_2$, alkoxyalkyl, aryl optionally substituted with 1, 2 or 3 alkoxy, heterocycloalkylalkyl, heteroaryl, gem-dicycloalkylalkyl and dialkylaminoalkyl;

$R_{17}$, when present, is —$CH_2$— or —CH(OH)—;

each of $A_1$ or $A_2$ is N or C(H), wherein $A_1$ and $A_2$ can be the same or different, provided that $A_1$ can be substituted with $R_4$ only when $A_1$ is C(H), and provided that $A_2$ can be substituted with $R_4$ only when $A_2$ is C(H);

$L_1$ is selected from —NHC(O)—, —$NHSO_2$—, —NHC(O)O—, —C(O)O—, —C(O)NH—, —C(O)$NHSO_2$—, —C(O)—, —($CH_2$)C(O)NH—, —($CH_2$)NHC(O)—, —($CH_2$)NH—, —$(CH_2)_n SO_2$NH—, —($CH_2$)$NHSO_2$—, —($CH_2$)C(O)—, —($CH_2$)O—, and —NH—($CH_2$)—;

$L_2$ is —C(O)—NH-cyclopropyl or —NH—C(O)—$CH_3$;

n is 0 or 1;

m is 0, 1 or 2; and each p is independently 0, 1, 2, 3 or 4.

Another aspect of the disclosure relates to a compound according to Formula I:

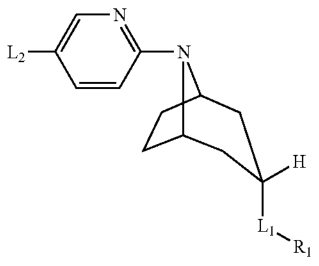

I or a pharmaceutically acceptable salt thereof, wherein:

$R_1$ is selected from:

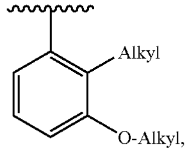

(G)

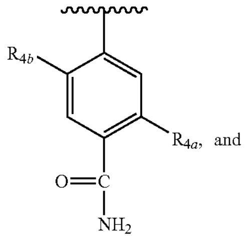

(H)

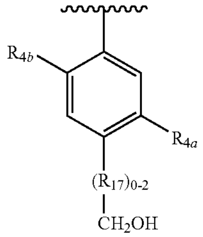

(I)

wherein $R_{4a}$ is selected from hydrogen, —$OR_{16}$, —$SR_{16}$, —N(H)$R_{16}$, hydroxy, alkenyl, alkynyl, hydroxyalkynyl, alkoxy, halogen, hydroxyalkyl, dihydroxyalkyl, —O—C(O)—$NH_2$, amino(imino)alkyl, —C(O)—$NH_2$, —N(H)C(O) alkyl, alkylaminoalkyl, alkylaminoalkylamino, aminoalkylamino, arylalkylamino, heterocycloalkyl, dialkylaminoalkyl, alkyl optionally substituted with 1-8 halogens, dialkylamino, —N(H)alkylheterocycloalkyl, alkylsulfonylheterocycloalkylamino, cycloalkylalkylamino, cycloalkoxy, —$NH_2$, —O-alkyl-heterocycloalkyl, dialkylaminoalkoxy, alkylsulfonylalkylamino and —N(H)heterocycloalkyl optionally substituted with 1, 2 or 3 groups selected from alkyl, alkoxy and halogen;

$R_{4b}$ is selected from H, halogen and methyl optionally substituted with 1-3 halogens;

$R_{16}$ is selected from hydrogen, alkyl optionally substituted with 1-8 halogens, cycloalkyl optionally substituted with 1 or 2 groups selected from —OH, —$NH_2$, alkyl, heterocycloalkyl, and —$CF_3$, cycloalkylalkyl, heterocycloalkyl optionally substituted with —OH or —$NH_2$, alkoxyalkyl, aryl optionally substituted with 1, 2 or 3 alkoxy, heterocycloalkylalkyl, heteroaryl, gem-dicycloalkylalkyl and dialkylaminoalkyl;

$R_{17}$, when present, is —$CH_2$— or —CH(OH)—;

$L_1$ is selected from —NHC(O)—, —$NHSO_2$—, —NHC(O)O—, —C(O)O—, —C(O)NH—, —C(O)$NHSO_2$—, —C(O)—, —($CH_2$)C(O)NH—, —($CH_2$)NHC(O)—, —($CH_2$)NH—, —$(CH_2)_n SO_2$NH—, —($CH_2$)$NHSO_2$—, —($CH_2$)C(O)—, —($CH_2$)O—, and —NH—($CH_2$)—; and $L_2$ is —C(O)—NH-cyclopropyl or —NH—C(O)—$CH_3$.

Another aspect of the disclosure relates to a compound according to Formula I:

I

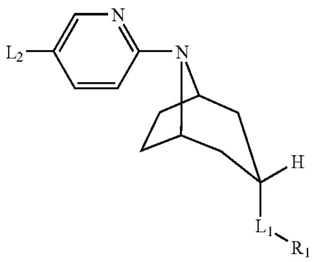

or a pharmaceutically acceptable salt thereof, wherein:

$R_1$ is selected from:

(G)

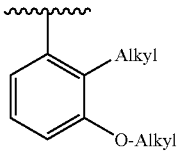

and (H)

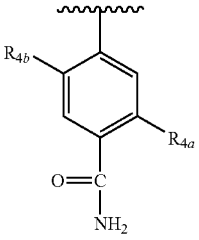

wherein $R_{4a}$ is selected from hydrogen, —$OR_{16}$, —$SR_{16}$, —N(H)$R_{16}$, hydroxy, alkenyl, alkynyl, hydroxyalkynyl, alkoxy, halogen, hydroxyalkyl, dihydroxyalkyl, —O—C(O)—$NH_2$, amino(imino)alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl, alkyl optionally substituted with 1-8 halogens, dialkylamino, —N(H)alkylheterocycloalkyl, alkylsulfonylheterocycloalkylamino, cycloalkylalkylamino, cycloalkoxy, —$NH_2$, —O-alkyl-heterocycloalkyl, dialkylaminoalkoxy, alkylsulfonylalkylamino and —N(H)heterocycloalkyl optionally substituted with 1, 2 or 3 groups selected from alkyl, alkoxy and halogen;

$R_{4b}$ is selected from H, halogen and methyl optionally substituted with 1-3 halogens;

$R_{16}$ is selected from hydrogen, alkyl optionally substituted with 1-8 halogens, cycloalkyl optionally substituted with 1 or 2 groups selected from —OH, —$NH_2$, alkyl, heterocycloalkyl, and —$CF_3$, cycloalkylalkyl, heterocycloalkyl optionally substituted with —OH or —$NH_2$, alkoxyalkyl, aryl optionally substituted with 1, 2 or 3 alkoxy, heterocycloalkylalkyl, heteroaryl, gem-dicycloalkylalkyl and dialkylaminoalkyl;

$L_1$ is selected from —NHC(O)—, —$NHSO_2$—, —NHC(O)O—, —C(O)O—, —C(O)NH—, —C(O)$NHSO_2$—, —C(O)—, —($CH_2$)C(O)NH—, —($CH_2$)NHC(O)—, —($CH_2$)NH—, —$(CH_2)_n SO_2$NH—, —($CH_2$)$NHSO_2$—, —($CH_2$)C(O)—, —($CH_2$)O—, and —NH—($CH_2$)—; and $L_2$ is —C(O)—NH-cyclopropyl or —NH—C(O)—$CH_3$.

For purposes of this specification, the language for the definition of $R_{16}$, as defined in Formula I, is meant to mean that $R_{16}$ can be hydrogen, or $R_{16}$ can be alkyl optionally substituted with 1-8 halogen groups, or $R_{16}$ can be cycloalkyl optionally substituted with 1 or 2 groups selected from —OH, —$NH_2$, alkyl, heterocycloalkyl, and —$CF_3$, or $R_{16}$ can be cycloalkylalkyl, or $R_{16}$ can be heterocycloalkyl optionally substituted with —OH or —NH, or $R_{16}$ can be alkoxyalkyl, or $R_{16}$ can be aryl optionally substituted with 1, 2 or 3 alkoxy, or $R_{16}$ can be heterocycloalkylalkyl, or $R_{16}$ can be heteroaryl, or $R_{16}$ can be gem-dicycloalkylalkyl, or $R_{16}$ can be dialkylaminoalkyl. This interpretation of the language for $R_{16}$ is meant to be exemplary for the interpretation of the language in the definitions for the other variables listed in this specification.

When any of the embodiments in this specification refers to a compound of Formula I, IB, IC, ID or IE, this is meant to mean that this embodiment includes each of Formula I, IB, IC, ID or IE individually or in any combination of each other. For instance, when any of the embodiments in this specification refers to a compound of Formula I, IB, IC, ID or IE, this can be interpreted to include only compounds having Formula I, or only compounds having Formula IB, or only compounds having Formula IC, or only compounds having Formula ID, or only compounds having Formula IE, or a combination of any two of Formula I, IB, IC, ID or IE, (such as, for example, a compound of Formula IB or IC, or a compound of Formula ID or IE, wherein all variables $L_1$, $R_1$ and $R_3$ are as defined in Formula I) or a combination of any three of Formula I, IB, IC, ID or IE, or a combination of any four of Formula I, IB, IC, ID or IE, or all of Formula I, IB, IC, ID and IE.

Unless otherwise specified, the compounds disclosed herein are meant to include pharmaceutically acceptable salts of these compounds, whether this is exlicitely srated or not, as alternative embodiments to the free base forms of the compounds in this disclosure.

In another embodiment of the compound of Formula I, IB, IC, ID, or IE, or a pharmaceutically acceptable salt thereof, $R_{4a}$ is selected from —N(H)$R_{16}$, —$OR_{16}$, and —$SR_{16}$;

$R_{4b}$ is selected from H, alkyl optionally substituted with one or more halogens, and halogen; and $R_{16}$ is selected from hydrogen, alkyl optionally substituted with 1-8 halogens, cycloalkyl optionally substituted with 1 or 2 groups selected from —OH, —$NH_2$, —$CH_3$ and —$CF_3$, cycloalkylalkyl, heterocycloalkyl optionally substituted with alkyl, —OH or —$NH_2$, alkoxyalkyl, aryl optionally substituted with 1, 2 or 3 alkoxy, heterocycloalkylalkyl, heteroaryl, gem-dicycloalkylalkyl and dialkylaminoalkyl.

In another embodiment of the compound of Formula I, IB, IC, ID, or IE, or a pharmaceutically acceptable salt thereof, $R_{4a}$ is cyclohexylamino optionally substituted with —OH.

In another embodiment of the compound of Formula I, IB, IC, ID, or IE, or a pharmaceutically acceptable salt thereof, $R_{4b}$ is alkyl optionally substituted with 1-8 fluoro.

In another embodiment of the compound of Formula I, IB, IC, ID, or IE, or a pharmaceutically acceptable salt thereof, $R_{16}$ is cyclopropyl, cyclopentyl or cyclohexyl, wherein each cyclopropyl, cyclopentyl or cyclohexyl can be optionally substituted with 1 or 2 —OH.

In another embodiment of the compound of Formula I, IB, IC, ID, or IE, or a pharmaceutically acceptable salt thereof, $R_1$ is (K)

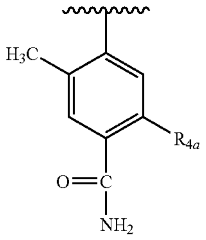

or (L)

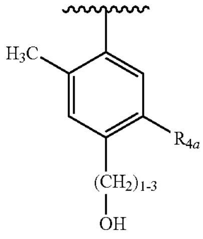

wherein $R_{4a}$ is selected from —N(H)$R_{16}$, —O$R_{16}$, and —S$R_{16}$; and $R_{16}$ is selected from hydrogen, alkyl optionally substituted with 1-8 halogens, cycloalkyl optionally substituted with 1 or 2 groups selected from —OH, —$NH_2$, —$CH_3$ and —$CF_3$, cycloalkylalkyl, heterocycloalkyl optionally substituted with —OH or —$NH_2$, alkoxyalkyl, aryl optionally substituted with 1, 2 or 3 alkoxy, heteroaryl, gem-dicycloalkylalkyl and dialkylaminoalkyl.

In another embodiment of the compound of Formula I, IB, IC, ID, or IE, or a pharmaceutically acceptable salt thereof, $R_1$ is (N)

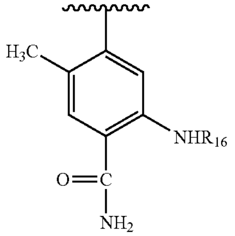

or (P)

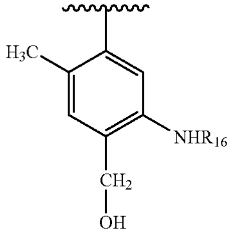

wherein $R_{16}$ is selected from hydrogen, alkyl optionally substituted with 1-8 halogens, cycloalkyl optionally substituted with 1 or 2 groups selected from —OH, —$NH_2$, —$CH_3$ and —$CF_3$, cycloalkylalkyl, heterocycloalkyl optionally substituted with —OH or —$NH_2$, alkoxyalkyl, aryl optionally substituted with 1, 2 or 3 alkoxy, heteroaryl, gem-dicycloalkylalkyl and dialkylaminoalkyl.

In another embodiment of the compound of Formula I, IB, IC, ID, or IE, or a pharmaceutically acceptable salt thereof, $R_1$ is (L)

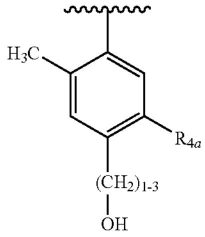

wherein $R_{4a}$ is selected from —N(H)$R_{16}$, —O$R_{16}$, and —S$R_{16}$; and $R_{16}$ is selected from hydrogen, alkyl optionally substituted with 1-8 halogens, cycloalkyl optionally substituted with 1 or 2 groups selected from —OH, —$NH_2$, —$CH_3$ and —$CF_3$, cycloalkylalkyl, heterocycloalkyl optionally substituted with —OH or —$NH_2$, alkoxyalkyl, aryl optionally substituted with 1, 2 or 3 alkoxy, heteroaryl, gem-dicycloalkylalkyl and dialkylaminoalkyl.

In another embodiment of the compound of Formula I, IB, IC, ID, or IE, or a pharmaceutically acceptable salt thereof, $R_1$ is (K)

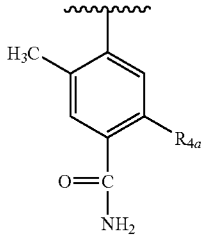

wherein $R_{4a}$ is selected from —N(H)$R_{16}$, —O$R_{16}$, and —S$R_{16}$; and $R_{16}$ is selected from hydrogen, alkyl optionally substituted with 1-8 halogens, cycloalkyl optionally substituted with 1 or 2 groups selected from —OH, —$NH_2$, —$CH_3$ and —$CF_3$, cycloalkylalkyl, heterocycloalkyl optionally substituted with —OH or —$NH_2$, alkoxyalkyl, aryl optionally substituted with 1, 2 or 3 alkoxy, heteroaryl, gem-dicycloalkylalkyl and dialkylaminoalkyl.

In another embodiment of the compound of Formula I, IB, IC, ID, or IE, or a pharmaceutically acceptable salt thereof, $R_1$ is

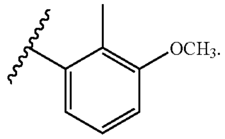

In another embodiment of the compound of Formula I, IB, IC, ID, or IE, or a pharmaceutically acceptable salt thereof, the heterocycloalkyl substituents of aryl in $R_3$ is piperazinyl, morpholinyl, azetidinyl or piperidinyl. In another embodiment, the heterocycloalkyl substituents of aryl in $R_3$ for Formula I, IB, IC, ID and IE is piperazinyl, morpholinyl or piperidinyl, wherein the piperazinyl, morpholinyl or piperidinyl is N-substituted with alkyl or phenyl. In other embodiments, the heterocycloalkyl substituents of aryl in $R_3$ for Formula I, IB, IC, ID or IE is piperazinyl, morpholinyl, azetidinyl or piperidinyl, and $R_1$ is of Formula (G), (H), (I), (K), (L), (N) or (P).

When any of the embodiments in this specification refers to a compound of Formula (G), (H), (I), (K), (L), (N) or (P), this is meant to mean that this embodiment includes each of Formula (G), (H), (I), (K), (L), (N) or (P) individually or in any combination of each other. For instance, when any of the embodiments in this specification refers to a compound of Formula (G), (H), (I), (K), (L), (N) or (P), this can be interpreted to include only compounds having Formula (G), or only compounds having Formula (H), or only compounds having Formula (I), or only compounds having Formula (K), or only compounds having Formula (L), or only compounds having Formula (N), or only compounds having Formula (P), or a combination of any two of Formula (G), (H), (I), (K), (L), (N) or (P), or a combination of any three of Formula (G), (H), (I), (K), (L), (N) or (P), or a combination of any four of Formula (G), (H), (I), (K), (L), (N) or (P), or a combination of any five of Formula (G), (H), (I), (K), (L), (N) or (P), or a combination of any six of Formula (G), (H), (I), (K), (L), (N) or (P), or all of Formula (G), (H), (I), (K), (L), (N) and (P).

Non-limiting examples of the heterocycloalkyl for Formula I, IB, IC, ID or IE, when $R_3$ is heterocycloalkyl, include piperidinyl, pyrrolidinyl, morpholinyl and piperizinyl. In another embodiment, this heterocycloalkyl group is piperidinyl or pyrrolidinyl. In another embodiment, this heterocycloalkyl group is piperidinyl. In another embodiment, this heterocycloalkyl group is pyrrolidinyl. In other embodiments, the heterocycloalkyl for Formula I, IB, IC, ID or IE, when $R_3$ is heterocycloalkyl, include piperidinyl, pyrrolidinyl, morpholinyl and piperizinyl, and $R_1$ is of Formula (G), (H), (I), (K), (L), (N) or (P).

Non-limiting examples of the dialkylaminoalkoxy in $R_3$ for Formula I, IB, IC, ID and IE include diethylaminoethoxy, ethylmethylaminoethoxy and dimethylaminoethoxy.

In other embodiments, the dialkylaminoalkoxy in $R_3$ for Formula I, IB, IC, ID or IE, or a pharmaceutically acceptable salt thereof, is diethylaminoethoxy, ethylmethylaminoethoxy or dimethylaminoethoxy, and $R_1$ is of Formula (G), (H), (I), (K), (L), (N) or (P).

Non-limiting examples of the heterocycloalkyl for Formula I, IB, IC, ID and IE, or a pharmaceutically acceptable salt thereof, when $R_5$ is heterocycloalkyl, include piperidinyl or piperizinyl, In another embodiment, the piperidinyl or piperizinyl is N-substituted with methyl. In other embodiments, the heterocycloalkyl for Formula I, IB, IC, ID or IE, or a pharmaceutically acceptable salt thereof, when $R_5$ is heterocycloalkyl, is piperidinyl or piperizinyl, and $R_1$ is of Formula (G), (H), (I), (K), (L), (N) or (P).

Non-limiting examples of the heterocycloalkyl substituents of aryl in $R_5$ for Formula I, IB, IC, ID and IE, or a pharmaceutically acceptable salt thereof, include piperazinyl, morpholinyl and piperidinyl. In other embodiments, the heterocycloalkyl substituent of aryl in $R_5$ for Formula I, IB, IC, ID and IE, or a pharmaceutically acceptable salt thereof, is piperazinyl, morpholinyl or piperidinyl, and $R_1$ is of Formula (G), (H), (I), (K), (L), (N) or (P).

In other embodiments, $R_3$ for the compound of Formula I, IB, IC, ID or IE or a pharmaceutically acceptable salt thereof, is cycloalkyl, such as cylcopentyl, cyclobutyl or cyclopropyl as non-limiting examples. In other embodiments, $R_3$ for the compound of Formula I, IB, IC, ID or IE is cylcopentyl, cyclobutyl or cyclopropyl, and $R_1$ is of Formula (G), (H), (I), (K), (L), (N) or (P).

In other embodiments, $R_3$ for the compound of Formula I, IB, IC, ID or IE, or a pharmaceutically acceptable salt thereof, is heterocycloalkyl, such as pyrrolidinyl, piperidinyl or azetidinyl as non-limiting examples. In other embodiments, $R_3$ for the compound of Formula I, IB, IC, ID or IE, or a pharmaceutically acceptable salt thereof, is cylcopentyl, cyclobutyl or cyclopropyl, and $R_1$ is of Formula (G), (H), (I), (K), (L), (N) or (P).

In other embodiments, $R_3$ for the compound of Formula I, IB, IC, ID or IE, or a pharmaceutically acceptable salt thereof, is heteroaryl. In other embodiments, $R_3$ for the compound of Formula I, IB, IC, ID or IE, or a pharmaceutically acceptable salt thereof, is heteroaryl, and $R_1$ is of Formula (G), (H), (I), (K), (L), (N) or (P). In other embodiments, $R_3$ for the compound of Formula I, IB, IC, ID or IE, or a pharmaceutically acceptable salt thereof, is H. In other embodiments, $R_3$ for the compound of Formula I, IB, IC, ID or IE, or a pharmaceutically acceptable salt thereof, is H, and $R_1$ is of Formula (G), (H), (I), (K), (L), (N) or (P).

In other embodiments, $R_3$ for the compound of Formula I, IB, IC, ID or IE, or a pharmaceutically acceptable salt thereof, is arylalkyl, such as phenylmethyl as a non-limiting example. In other embodiments, $R_3$ for the compound of Formula I, IB, IC, ID or IE is arylalkyl, and $R_1$ is of Formula (G), (H), (I), (K), (L), (N) or (P).

In other embodiments of the compound of Formula I, IB, IC, ID or IE, or a pharmaceutically acceptable salt thereof, $R_1$ is (H)

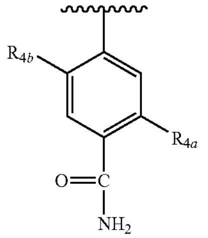

or (I)

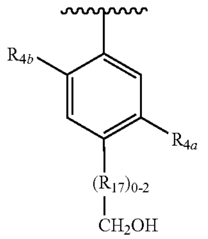

wherein $R_{4a}$ is cycloalkylamino optionally substituted with —OH, alkyl, —$CF_3$, or heterocycloalkyl;

$R_{4b}$ is selected from H, halo and methyl optionally substituted with 1-3 halogens; and $R_{17}$, when present, is —$CH_2$— or —CH(OH)—. In this embodiment, $L_1$ can be —N(H)C(O)—.

Non-limiting examples of $R_{4a}$ for any of the above embodiments include trans-4-hydroxycyclohexylamino, cyclohexylamino, cyclopentylamino, cyclopropylamino, cis-4-hydroxy-4-methylcyclohexylamino, 4-(trifluoromethyl)cyclohexylamino and trans-4-piperidin-1-ylcyclohexylamino.

In other embodiments of the compound of Formula I, IB, IC, ID or IE, or a pharmaceutically acceptable salt thereof, $R_1$ is (H)

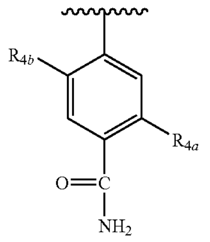

or (I)

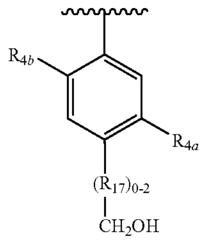

wherein $R_{4a}$ is trans-4-hydroxycyclohexyl amino, cyclohexyl amino, cyclopentylamino, cyclopropylamino, cis-4-hydroxy-4-methylcyclohexylamino, 4-(trifluoromethyl)cyclohexylamino or trans-4-piperidin-1-ylcyclohexylamino;

$R_{4b}$ is selected from H, halo and methyl optionally substituted with 1-3 halogens; and $R_{17}$, when present, is —$CH_2$— or —CH(OH)—.

In other embodiments of the compound of Formula I, IB, IC, ID or IE, or a pharmaceutically acceptable salt thereof, $R_1$ or a pharmaceutically acceptable salt thereof, is (H)

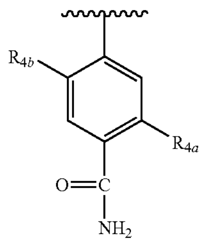

or (I)

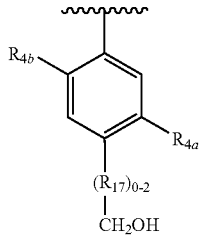

wherein $R_{4a}$ is cycloalkylalkylamino;

$R_{4b}$ is selected from H, halo and methyl optionally substituted with 1-3 halogens. In this embodiment, $L_1$ can be —N(H)C(O)—; and $R_{17}$, when present, is —$CH_2$— or —CH(OH)—.

A non-limiting example of $R_{4a}$ for any of the above embodiments includes cyclopropylmethylamino.

In other embodiments of the compound of Formula I, IB, IC, ID or IE, or a pharmaceutically acceptable salt thereof, $R_1$ is (H)

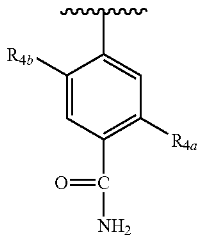

or (I)

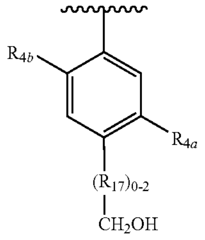

wherein $R_{4a}$ is alkylamino optionally substituted with 1-8 halo;

$R_{4b}$ is selected from H, halo and methyl optionally substituted with 1-3 halogens; and $R_{17}$, when present, is —$CH_2$— or —CH(OH)—. In this embodiment, $L_1$ can be —N(H)C(O)—.

Non-limiting examples of $R_{4a}$ for any of the above embodiments include 1-methylethylamino, ethylamino, 1-ethylpropylamino, 2-methylpropylamino, (2,2-dimethylpropyl)amino, (2-aminoethyl)amino, (2,2,3,3,3-pentafluoropropyl)amino, 1-methylpropylamino, (1S)-1-methylpropylamino, (2,2,2-trifluoroethyl)amino, 1-propylbutylamino, propylamino, 1,2-dimethylpropylamino, (3,3,3-trifluoropropyl)amino, (2,2,3,3,4,4,4-heptafluorobutyl)amino, butyl amino, 1,2,2-trimethylpropylamino, 1-[(methyloxy)methyl]propylamino, 1-methylethyloxyethylamino, 1-methylpropylamino, pentylamino, (2,2,3,3,3-pentafluoropropyl)amino, butylamino, 2-[(1-methylethyl)oxy]ethylamino, (1S)-1-methylpropylamino, (1R)-1-methylpropylamino, (1S)-1,2-dimethylpropylamino, 1-cyclopropylethylamino, (1R)-1,2-dimethylpropylamino, 1-ethyl-2-methylpropylamino, and 3-[(1-methylethyl)amino]propylamino.

In other embodiments of the compound of Formula I, IB, IC, ID or IE, or a pharmaceutically acceptable salt thereof, $R_1$ is (H)

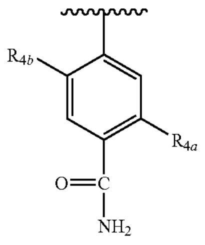

or

-continued (I)

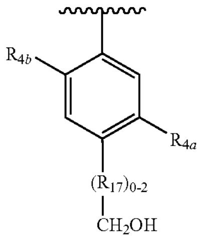

wherein $R_{4a}$ is heterocycloalkylamino optionally substituted with alkyl; $R_{4b}$ is selected from H, halogen and methyl optionally substituted with 1-3 halogens; and $R_{17}$, when present, is —$CH_2$— or —CH(OH)—. In this embodiment, $L_1$ can be —N(H)C(O)—.

Non-limiting examples of $R_{4a}$ for any of the above embodiments include tetrahydrofuran-3-ylamino, piperidin-4-ylamino, tetrahydro-2H-pyran-4-ylamino, (1-ethylpiperidin-4-yl)amino, (tetrahydrofuran-2-ylmethyl)amino, pyrrolidin-3-ylamino, (piperidin-3-ylmethyl)amino, (pyrrolidin-3-ylmethyl)amino, (3S)-tetrahydrofuran-3-ylamino, (3R)-tetrahydrofuran-3-ylamino, azetidin-1-yl, piperidin-1-ylamino, and (3S)-tetrahydrofuran-3-ylamino.

In other embodiments of the compound of Formula I, IB, IC, ID or IE, $R_1$ is (H)

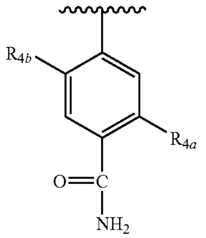

or (I)

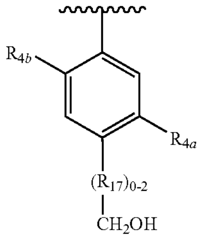

wherein $R_{4a}$ is —N(H)-aryl optionally substituted with 1, 2 or 3 alkoxy, heterocycloalkylalkoxy or dialkylaminoalkoxy;

$R_{4b}$ is selected from H, halogen and methyl optionally substituted with 1-3 halogens; and $R_{17}$, when present, is —$CH_2$— or —CH(OH)—.

In this embodiment, $L_1$ can be —N(H)C(O)—.

Non-limiting examples of $R_{4a}$ for any of the above embodiments include phenylamino, (phenylmethyl)amino, (3-{[2-(dimethylamino)ethyl]oxy}phenyl)amino, 3-{[2-(dimethylamino)-4-(methyloxy)ethyl]oxy}phenyl)amino and {4-(methyloxy)-3-[(2-morpholin-4-ylethyl)oxy]phenyl}amino.

In another embodiment, $R_1$ in Formula I, IB, IC, ID, or IE, or a pharmaceutically acceptable salt thereof, is selected from one of Group Z; $R_{4a}$ is (2,2,3,3,3-pentafluoropropyl)amino, butylamino, 2-[(1-methylethyl)oxy]ethylamino, (1S)-1-methylpropyl]amino, (1-methylpropyl)amino, (1R)-1-methylpropyl]amino, 2-(propylamino), (1S)-1,2-dimethylpropyl]amino, (1-cyclopropylethyl)amino, (1R)-1,2-dimethylpropyl]amino or 2,2-dimethylpropylamino; and $R_{4b}$ is H.

In another embodiment, $R_1$ in Formula I, IB, IC, ID, or IE, or a pharmaceutically acceptable salt thereof, is selected from one of Group Z; $R_{4a}$ is 1-ethylpropylamino; and $R_{4b}$ is chloro, fluoro, bromo, or methyl.

In other embodiments, $R_1$ in Formula I, IB, IC, ID, or IE, or a pharmaceutically acceptable salt thereof, s selected from one of Group Z; $R_{4a}$ is 1-ethyl-2-methylpropyl)amino, (1R)-1-methylpropylamino, 1-cyclopropylethylamino, 1-cyclopropylpropylamino, (1R)-1,2,2-trimethylpropylamino, (1R)-1,2-dimethylpropylamino, 3,3,3-trifluoro-1-methylpropylamino, 2-methyl-1-trifluoromethylpropylamino, 2-methyl-1-(1-methylethyl)propylamino, 1-methylethylamino, dicyclopropylmethylamino, cyclopentylamino, trifluoromethylpropylamino, 2-methylpropylamino, cyclopentylmethylamino, cyclobutylamino, (1S)-1-methylpropylamino, 3,3,3-trifluoropropylamino, propylamino or 2-fluoro-1-(fluoromethyl)ethylamino; and $R_{4b}$ is methyl.

In other embodiments, $R_1$ in Formula I, IB, IC, ID, or IE, or a pharmaceutically acceptable salt thereof, is selected from one of Group Z; $R_{4a}$ is 1-ethylpropylamino or (1R)-1-methylpropylamino; and $R_{4b}$ is $CF_3$.

In other embodiments, $R_1$ in Formula I, IB, IC, ID, or IE, or a pharmaceutically acceptable salt thereof, is selected from one of Group Z; $R_{4a}$ is (1R)-1-methylpropylamino, 1-methylethylamino, cyclopentylamino, 2-methylpropylamino, 2,2-dimethylpropylamino, (1R)-1,2-dimethylpropylamino, propylamino, (3,3,3-trifluoropropyl)amino or cyclobutylamino; and $R_{4b}$ is Br.

In other embodiments, $R_1$ in Formula I, IB, IC, ID, or IE, or a pharmaceutically acceptable salt thereof, is selected from one of Group Z; $R_{4a}$ is (cyclopropylmethyl)amino, (1-ethylpropyl)amino, (cis-4-hydroxy-4-methylcyclohexyl)amino or (trans-4-piperidin-1-ylcyclohexyl)amino; and $R_{4b}$ is H.

In other embodiments, $R_1$ in Formula I, IB, IC, ID, or IE is selected from one of Group Z; $R_{4a}$ is cyclopropylmethylamino or 1-(1-methylcyclopropyl)ethylamino; and $R_{4b}$ is methyl.

In other embodiments, $R_1$ in Formula I, IB, IC, ID, or IE, or a pharmaceutically acceptable salt thereof, is selected from one of Group Z; $R_{4a}$ is pyridin-4-ylamino; and $R_{4b}$ is H.

In another embodiment, $R_1$ in Formula I, IB, IC, ID, or IE, or a pharmaceutically acceptable salt thereof, is selected from one of Group Z; $R_{4a}$ is (3S)-tetrahydrofuran-3-ylamino; and $R_{4b}$ is methyl.

In another embodiment, the compound of Formula I is selected from one of the following compounds from Table I, or a pharmaceutically acceptable salt of any of the compounds in Table I:

TABLE I

| STRUCTURE | NAME & ACTIVITY |
|---|---|
| 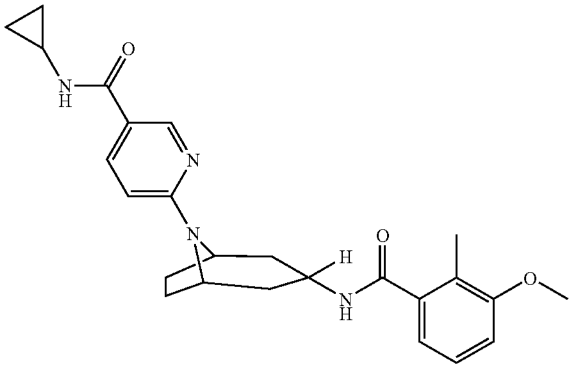 | N-cyclopropyl-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 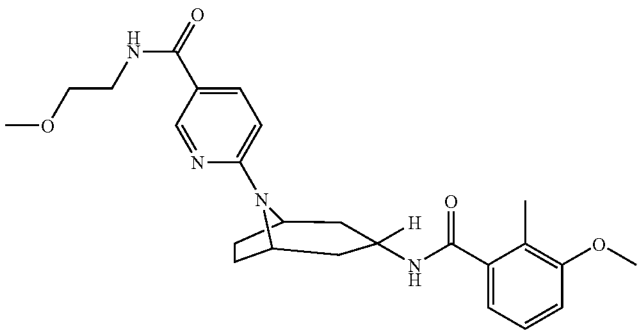 | 6-[3-endo-({[2-methyl-3-(methyloxy)phenyl]carbonyl}amino)-8-azabicyclo[3.2.1]oct-8-yl]-N-[2-(methyloxy)ethyl]pyridine-3-carboxamide<br>ACTIVITY = D |
| 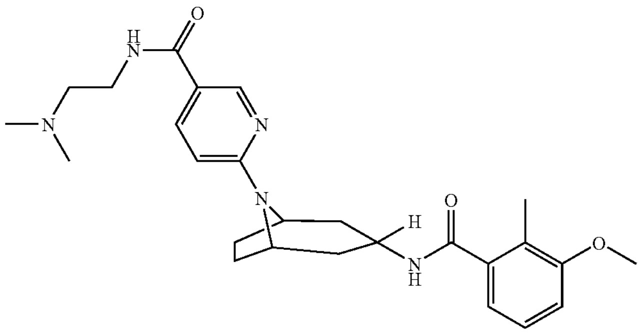 | N-[2-(dimethylamino)ethyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 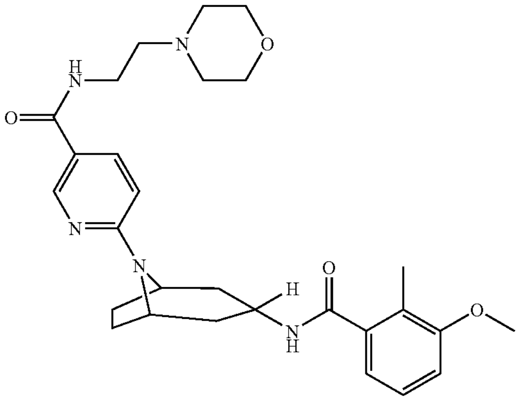 | 6-[3-endo-({[2-methyl-3-(methyloxy)phenyl]carbonyl}amino)-8-azabicyclo[3.2.1]oct-8-yl]-N-(2-morpholin-4-ylethyl)pyridine-3-carboxamide<br>ACTIVITY = C |

TABLE I-continued

| STRUCTURE | NAME & ACTIVITY |
|---|---|
| 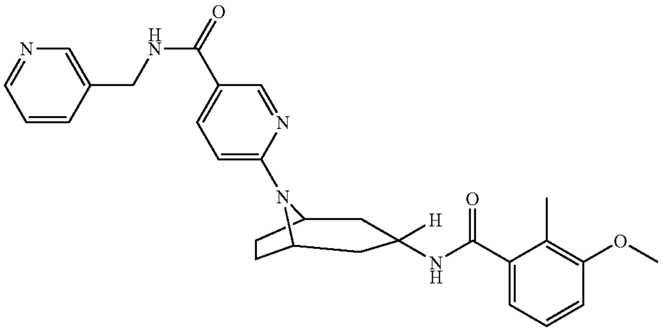 | 6-[3-endo-({[2-methyl-3-(methyloxy)phenyl]carbonyl}amino)-8-azabicyclo[3.2.1]oct-8-yl]-N-(pyridin-3-ylmethyl)pyridine-3-carboxamide<br>ACTIVITY = A |
| 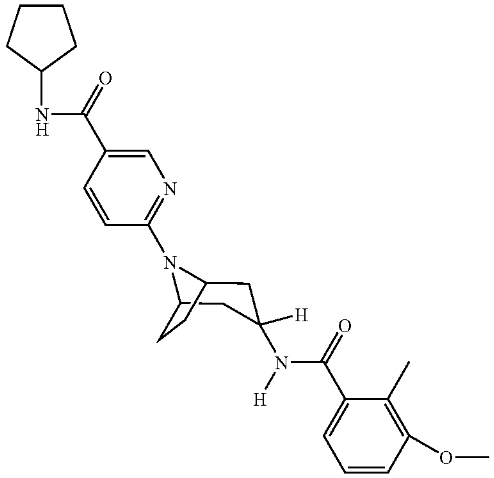 | N-cyclopentyl-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 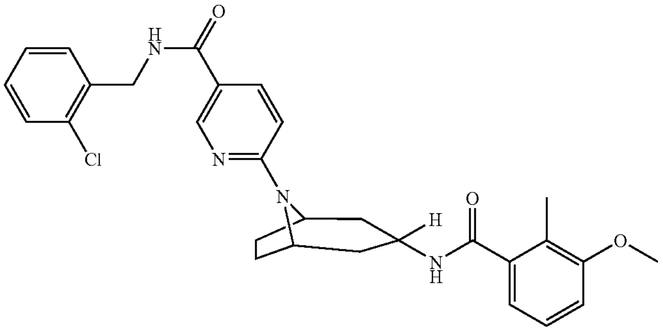 | N-[(2-chlorophenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 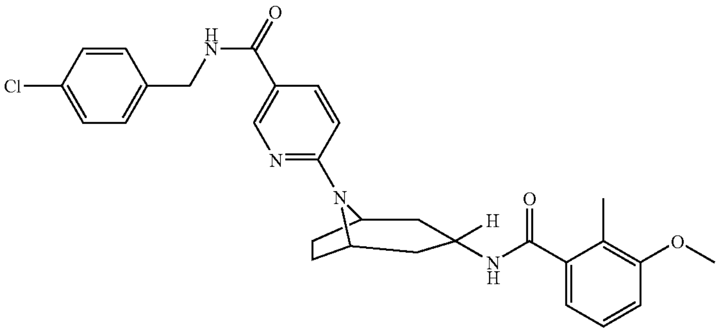 | N-[(4-chlorophenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = B |

TABLE I-continued

| STRUCTURE | NAME & ACTIVITY |
| --- | --- |
| 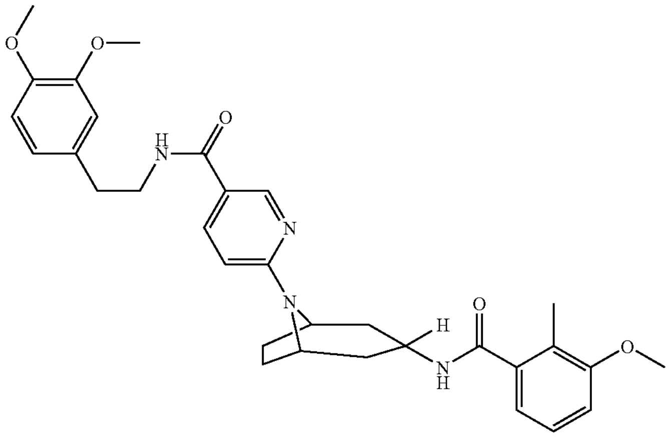 | N-{2-[3,4-bis(methyloxy)phenyl]ethyl}-6-[3-endo-({[2-methyl-3-(methyloxy)phenyl]carbonyl}amino)-8-azabicyclo[3.2.1]oct-8-yl]pyridine-3-carboxamide ACTIVITY = D |
| 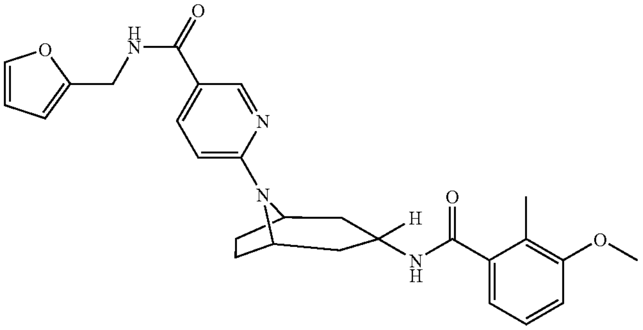 | N-(furan-2-ylmethyl)-6-[3-endo-({[2-methyl-3-(methyloxy)phenyl]carbonyl}amino)-8-azabicyclo[3.2.1]oct-8-yl]pyridine-3-carboxamide ACTIVITY = A |
| 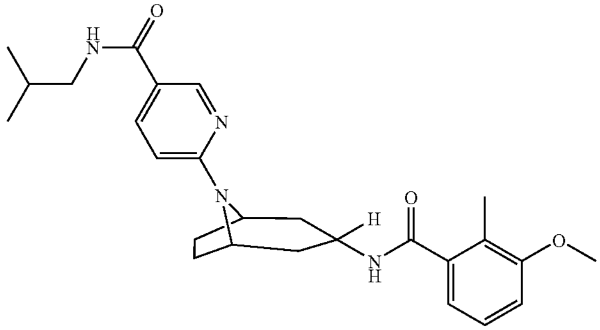 | 6-[3-endo-({[2-methyl-3-(methyloxy)phenyl]carbonyl}amino)-8-azabicyclo[3.2.1]oct-8-yl]-N-(2-methylpropyl)pyridine-3-carboxamide ACTIVITY = C |
| 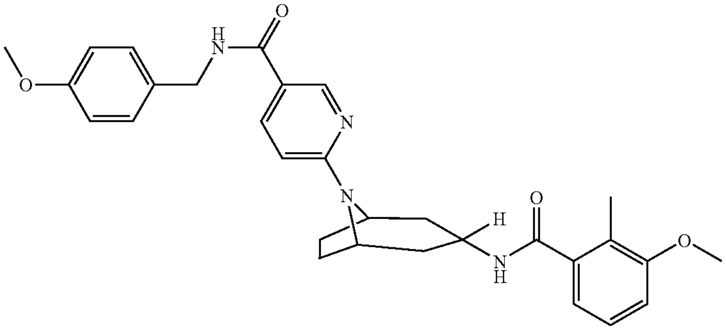 | 6-[3-endo-({[2-methyl-3-(methyloxy)phenyl]carbonyl}amino)-8-azabicyclo[3.2.1]oct-8-yl]-N-{[4-(methyloxy)phenyl]methyl}pyridine-3-carboxamide ACTIVITY = A |

TABLE I-continued

| STRUCTURE | NAME & ACTIVITY |
| --- | --- |
| 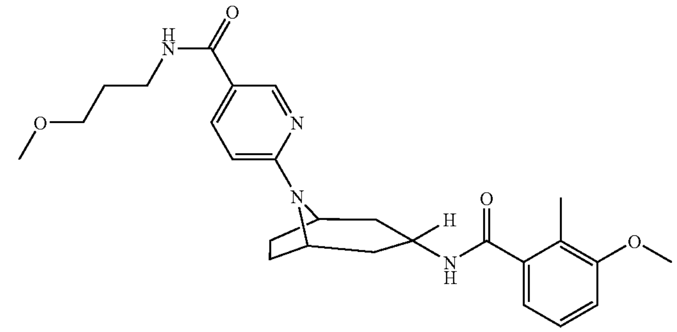 | 6-[3-endo-({[2-methyl-3-(methyloxy)phenyl]carbonyl}amino)-8-azabicyclo[3.2.1]oct-8-yl]-N-[3-(methyloxy)propyl]pyridine-3-carboxamide<br>ACTIVITY = B |
| 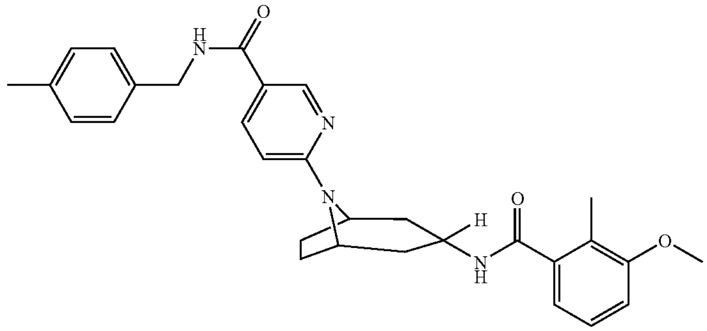 | 6-[3-endo-({(2-methyl-3-(methyloxy)phenyl]carbonyl}amino)-8-azabicyclo[3.2.1]oct-8-yl]-N-[(4-methylphenyl)methyl]pyridine-3-carboxamide<br>ACTIVITY = A |
| 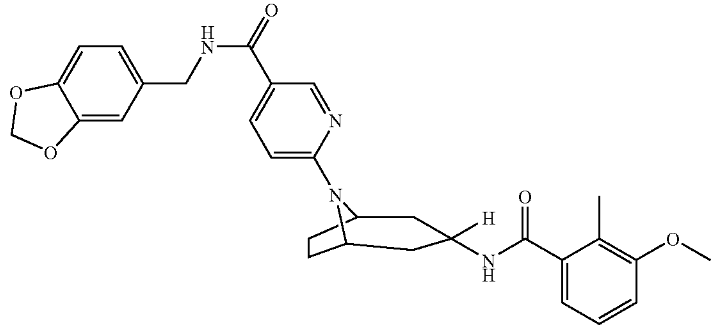 | N-(1,3-benzodioxol-5-ylmethyl)-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 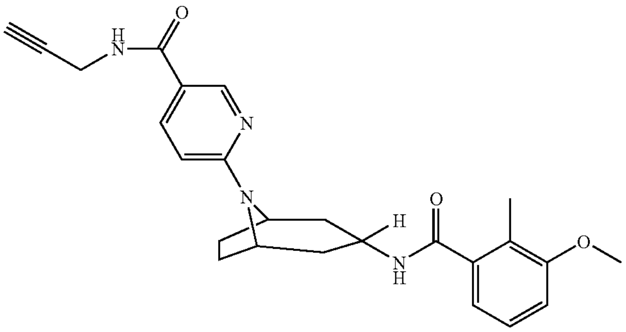 | 6-[3-endo-({[2-methyl-3-(methyloxy)phenyl)carbonyl}amino)-8-azabicyclo(3.2.1]oct-8-yl]-N-prop-2-yn-1-ylpyridine-3-carboxamide<br>ACTIVITY = C |

TABLE I-continued

| STRUCTURE | NAME & ACTIVITY |
|---|---|
| 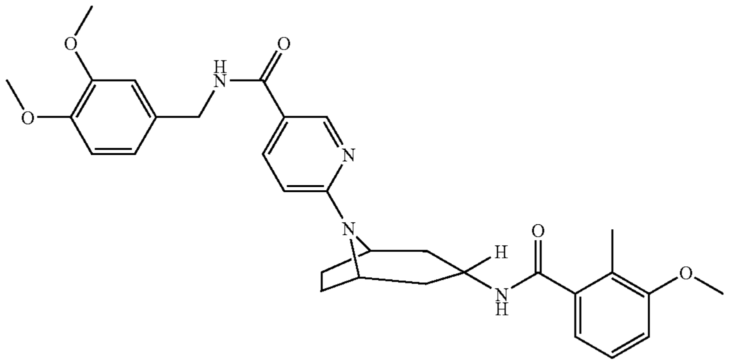 | N {[3,4-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 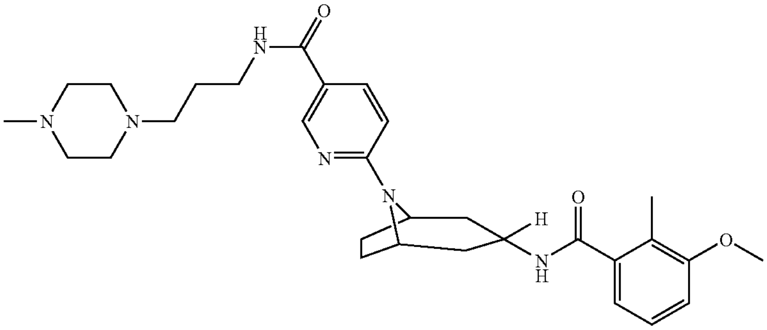 | 6-[3-endo-({[2-methyl-3-(methyloxy)phenyl]carbonyl}amino)-8-azabicyclo[3.2.1]oct-8-yl]-N-[3-(4-methylpiperazin-1-yl)propyl]pyridine-3-carboxamide<br>ACTIVITY = B |
| 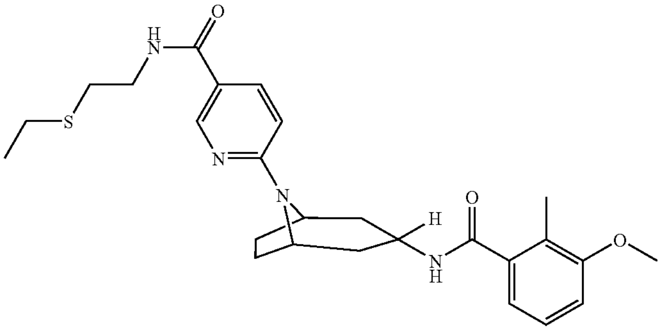 | N-[2-(ethylthio)ethyl]-6-[3-endo-({[2-methyl-3-(methyloxy)phenyl]carbonyl}amino)-8-azabicyclo[3.2.1]oct-8-yl]pyridine-3-carboxamide |
| 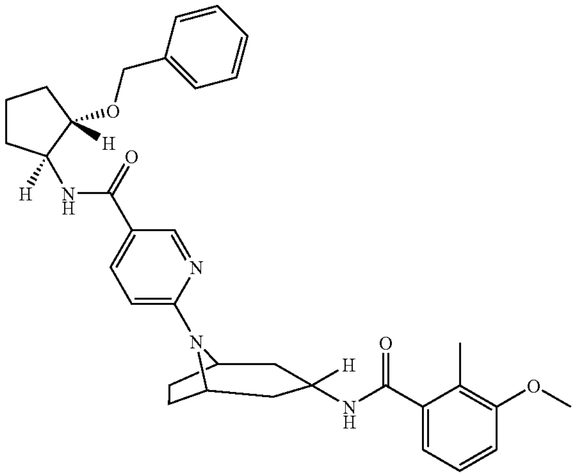 | 6-[3-endo-({[2-methyl-3-(methyloxy)phenyl]carbonyl}amino)-8-azabicyclo[3.2.1]oct-8-yl]-N-{(1S,2S)-2-[(phenylmethyl)oxy]cyclopentyl}pyridine-3-carboxamide<br>ACTIVITY = D |

TABLE I-continued

| STRUCTURE | NAME & ACTIVITY |
|---|---|
| 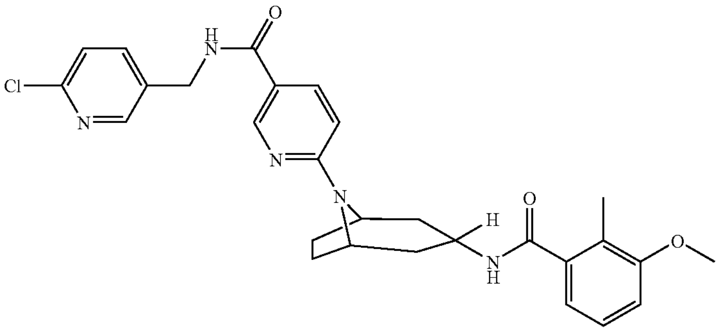 | N-[(6-chloropyridin-3-yl)methyl]-6-[3-endo-({[2-methyl-3-(methyloxy)phenyl]carbonyl}amino)-8-azabicycio[3.2.1]oct-8-yl]pyridine-3-carboxamide ACTIVITY = A |
| 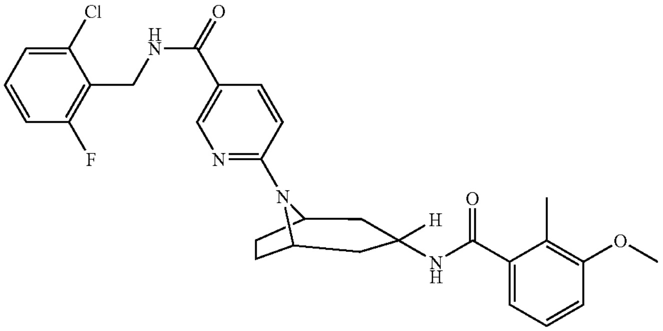 | N-[(2-chloro-6-fluorophenyl)methyl]-6-[3-endo-({[2-methyl-3-(methyloxy)phenyl]carbonyl}amino)-8-azabicyclo[3.2.1]oct-8-yl]pyridine-3-carboxamide ACTIVITY = A |
| 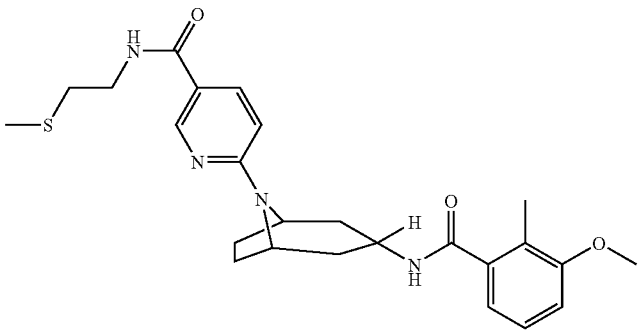 | 6-[3-endo-({[2-methyl-3-(methyloxy)phenyl]carbonyl}amino)-8-azabicyclo[3.2.1]oct-8-yl]-N-[2-(methylthio)ethyl]pyridine-3-carboxamide ACTIVITY = C |
| 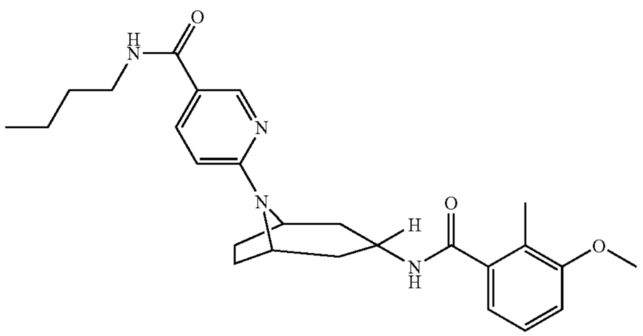 | N-butyl-6-[3-endo-({[2-methyl-3-(methyloxy)phenyl]carbonyl}amino)-8-azabicyclo[3.2.1]oct-8-yl]pyridine-3-carboxamide ACTIVITY = B |

TABLE I-continued

| STRUCTURE | NAME & ACTIVITY |
|---|---|
| 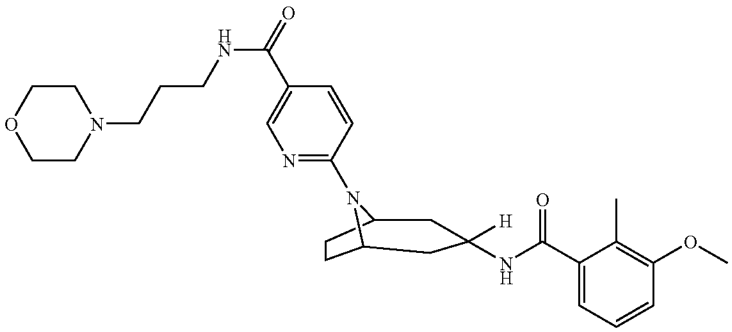 | 6-[3-endo-({[2-methyl-3-(methyloxy)phenyl]carbonyl}amino)-8-azabicyclo[3.2.1]oct-8-yl]-N-(3-morpholin-4-ylpropyl)pyridine-3-carboxamide<br>ACTIVITY = B |
| 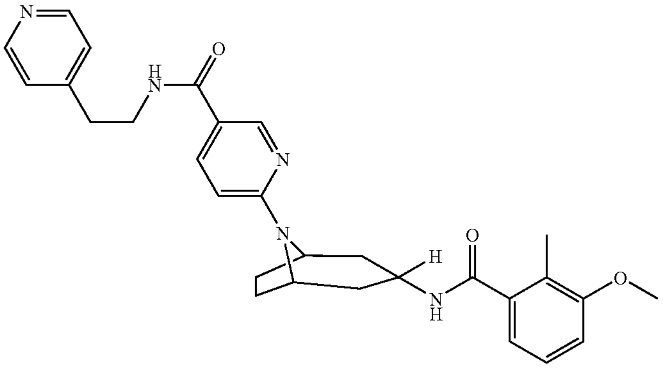 | 6-[3-endo-({[2-methyl-3-(methyloxy)phenyl]carbonyl}amino)-8-azabicyclo[3.2.1]oct-8-yl]-N-(2-pyridin-4-ylethyl)pyridine-3-carboxamide<br>ACTIVITY = C |
| 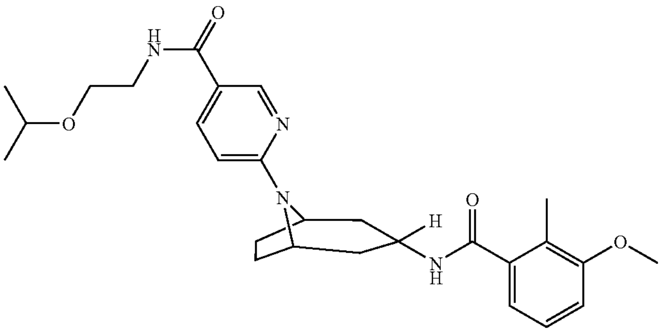 | N-{2-[(1-methylethyl)oxy]ethyl}-6-(3-endo-({[2-methyl-3-(methyloxy)phenyl]carbonyl}amino)-8-azabicyclo[3.2.1]oct-8-yl]pyridine-3-carboxamide<br>ACTIVITY = D |
| 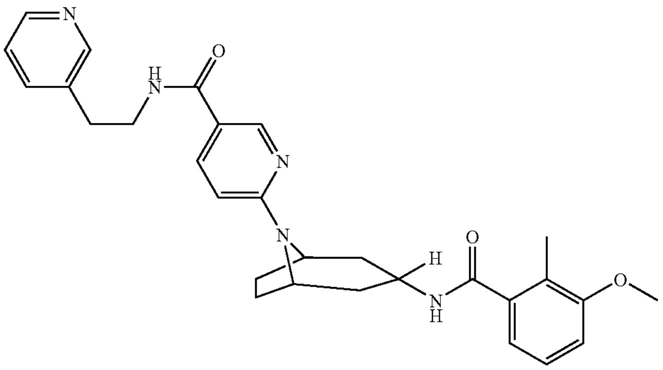 | 6-[3-endo-({[2-methyl-3-(methyloxy)phenyl]carbonyl}amino)-8-azabicyclo[3.2.1]oct-8-yl]-N-(2-pyridin-3-ylethyl)pyridine-3-carboxamide<br>ACTIVITY = C |

TABLE I-continued

| STRUCTURE | NAME & ACTIVITY |
| --- | --- |
| 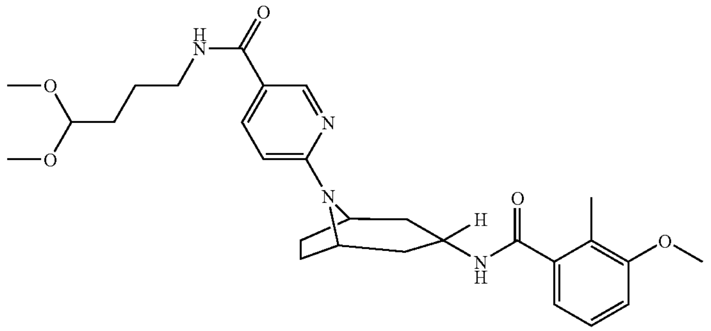 | N-[4,4-bis(methyloxy)butyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 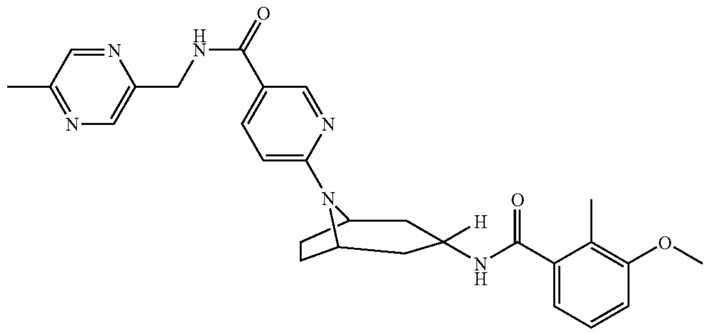 | 6-[3-endo-({[2-methyl-3-(methyloxy)phenyl]carbonyl}amino)-8-azabicyclo[3.2.1]oct-8-yl]-N-[(5-methylpyrazin-2-yl)methyl]pyridine-3-carboxamide<br>ACTIVITY = A |
| 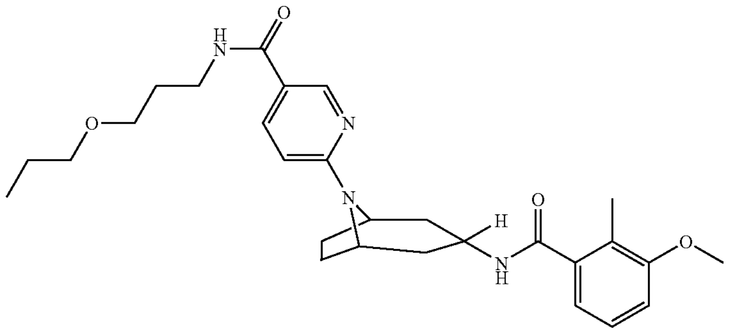 | 6-[3-endo-({[2-methyl-3-(methyloxy)phenyl]carbonyl}amino)-8-azabicyclo[3.2.1]oct-8-yl]-N-[3-endo-(propyloxy)propyl]pyridine-3-carboxamide<br>ACTIVITY = B |
| 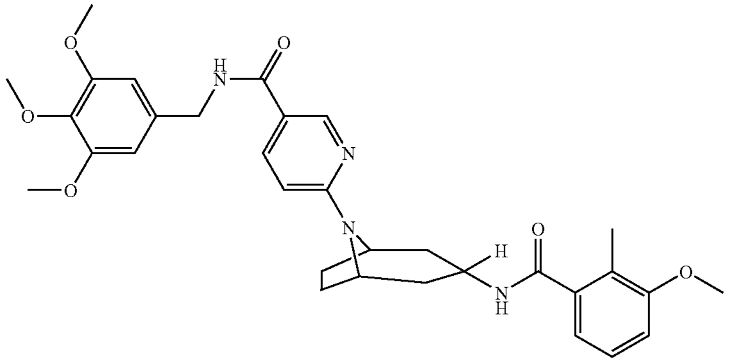 | 6-[3-endo-({[2-methyl-3-(methyloxy)phenyl]carbonyl}amino)-8-azabicyclo[3.2.1]oct-8-yl]-N-{[3,4,5-tris(methyloxy)phenyl]methyl}pyridine-3-carboxamide<br>ACTIVITY = C |

TABLE I-continued

| STRUCTURE | NAME & ACTIVITY |
| --- | --- |
| 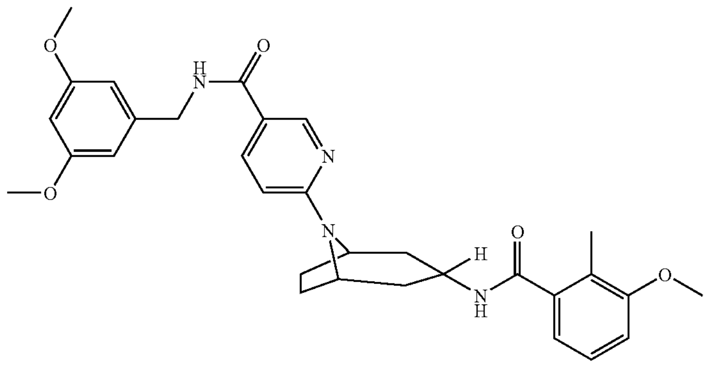 | N-{[3,5-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 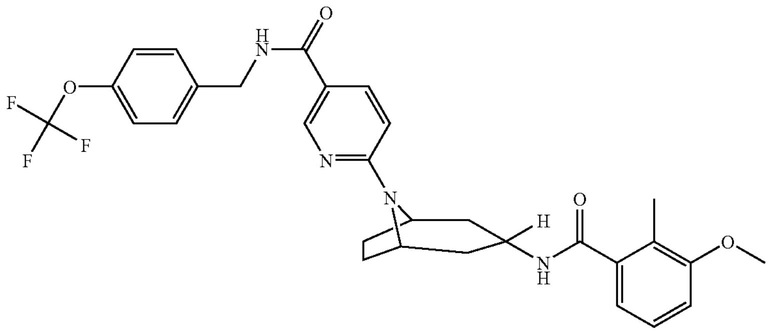 | 6-[3-endo-({[2-methyl-3-(methyloxy)phenyl]carbonyl}amino)-8-azabicyclo[3.2.1]oct-8-yl]-N-({4-[(trifluoromethyl)oxy]phenyl}methyl)pyridine-3-carboxamide<br>ACTIVITY = D |
| 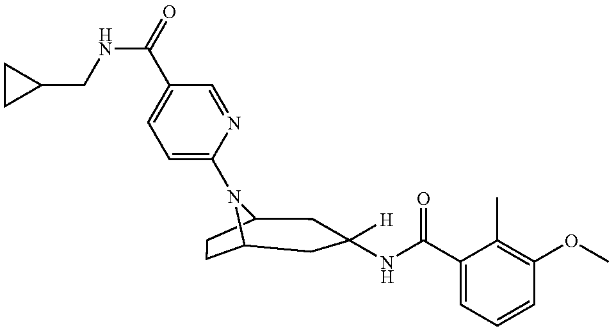 | N-(cyclopropylmethyl)-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 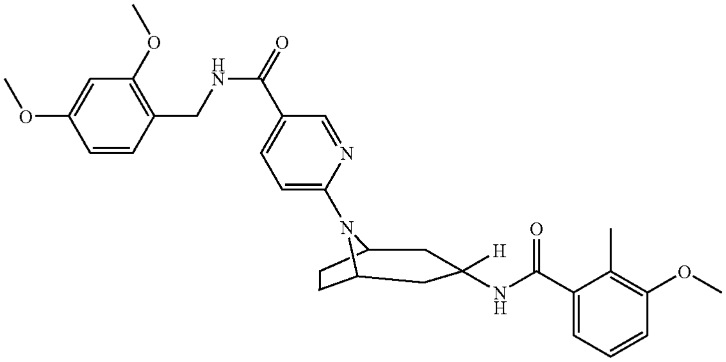 | N-{[2,4-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = B |

TABLE I-continued

| STRUCTURE | NAME & ACTIVITY |
|---|---|
| 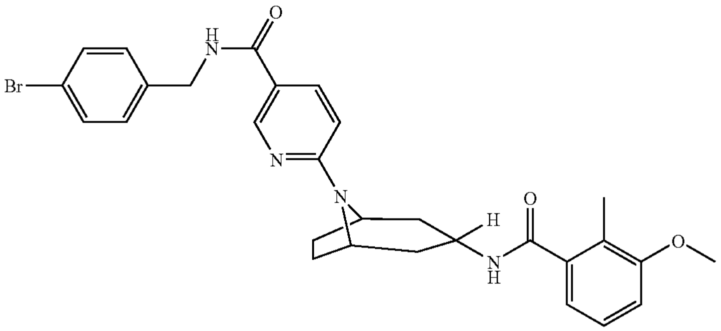 | N-[(4-bromophenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 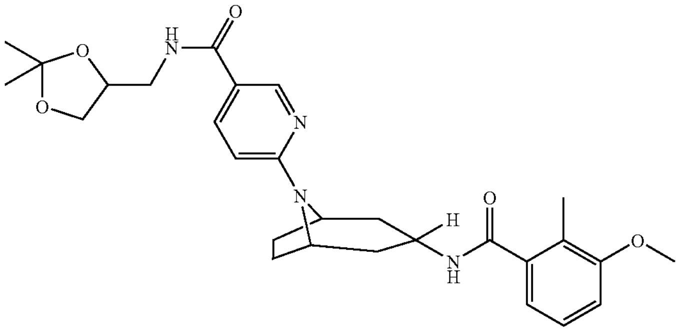 | N-[(2,2-dimethyl-1,3-dioxolan-4-yl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = D |
| 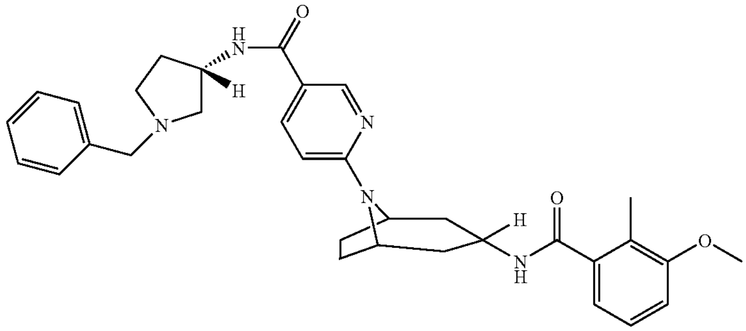 | 6-[3-endo-({[2-methyl-3-(methyloxy)phenyl]carbonyl}amino)-8-azabicyclo[3.2.1]oct-8-yl]-N-[(3S)-1-(phenylmethyl)pyrrolidin-3-yl]pyridine-3-carboxamide<br>ACTIVITY = B |
| 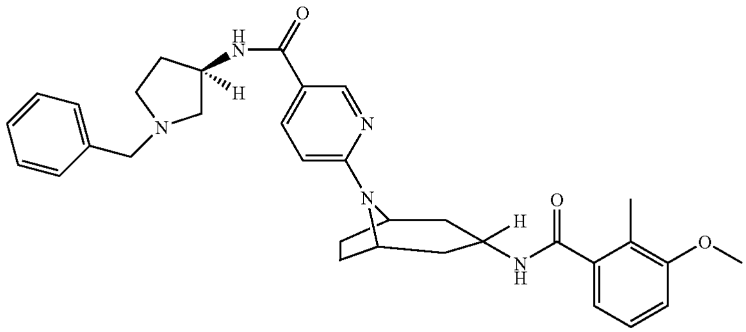 | 6-[3-endo-({[2-methyl-3-(methyloxy)phenyl]carbonyl}amino)-8-azabicyclo[3.2.1]oct-8-yl]-N-[(3R)-1-(phenylmethyl)pyrrolidin-3-yl]pyridine-3-carboxamide<br>ACTIVITY = A |

TABLE I-continued

| STRUCTURE | NAME & ACTIVITY |
| --- | --- |
| 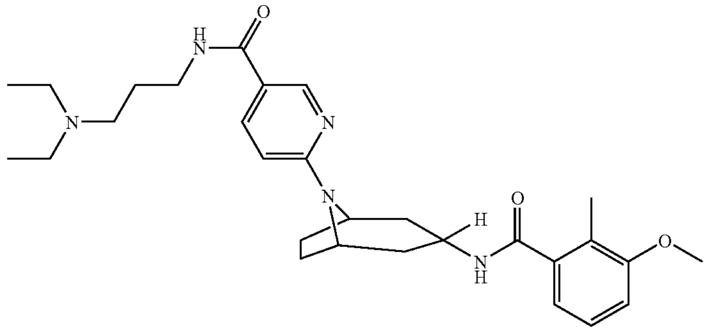 | N-[3-(diethylamino)propyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 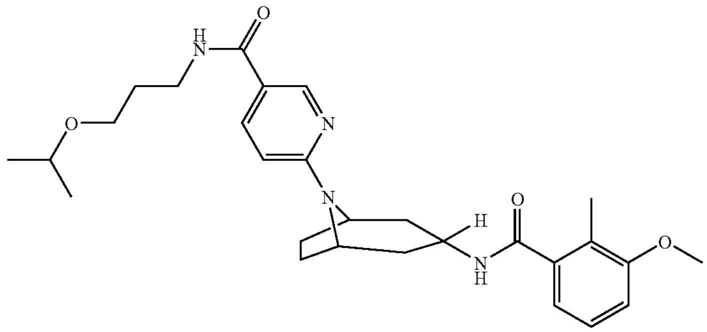 | N-{3-[(1-methylethyl)oxy]propyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 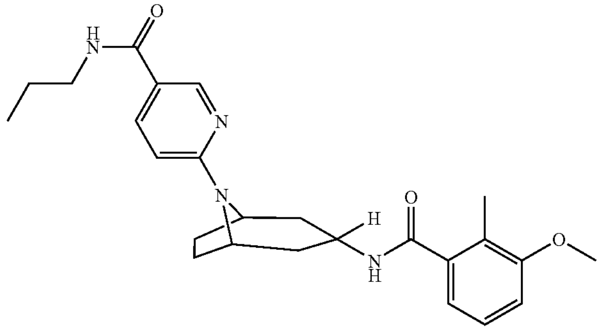 | 6-[3-endo-({[2-methyl-3-(methyloxy)phenyl]carbonyl}amino)-8-azabicyclo[3.2.1]oct-8-yl]-N-propylpyridine-3-carboxamide<br>ACTIVITY = C |
| 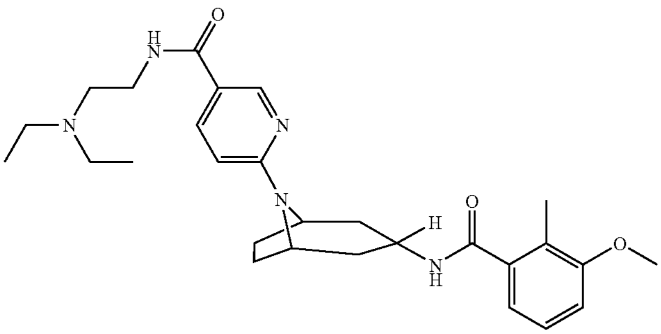 | N-[2-(diethylamino)ethyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = B |

TABLE I-continued

| STRUCTURE | NAME & ACTIVITY |
| --- | --- |
| 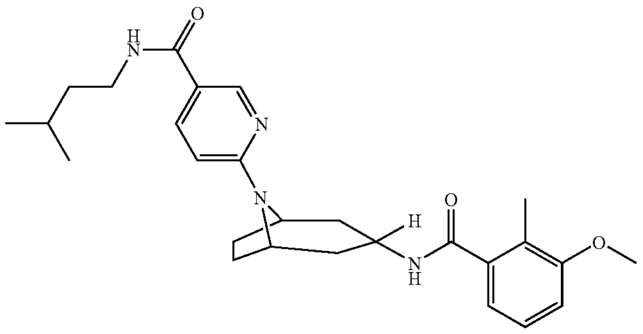 | N-(3-methylbutyl)-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 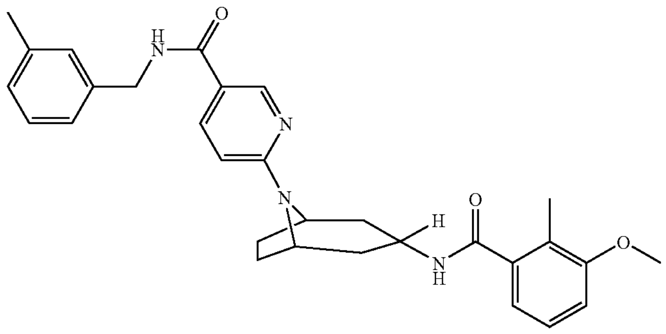 | 6-[3-endo-({[2-methyl-3-(methyloxy)phenyl]carbonyl}amino)-8-azabicyclo[3.2.1]oct-8-yl]-N-[(3-methylphenyl)methyl]pyridine-3-carboxamide<br>ACTIVITY = D |
| 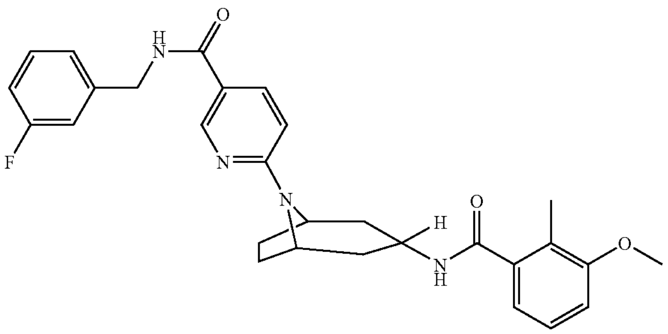 | N-[(3-fluorophenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 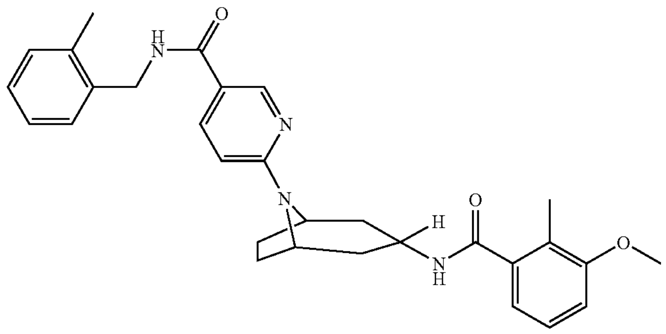 | 6-[3-endo-({[2-methyl-3-(methyloxy)phenyl]carbonyl}amino)-8-azabicyclo[3.2.1]oct-8-yl]-N-[(2-methylphenyl)methyl]pyridine-3-carboxamide<br>ACTIVITY = A |

TABLE I-continued

| STRUCTURE | NAME & ACTIVITY |
| --- | --- |
| 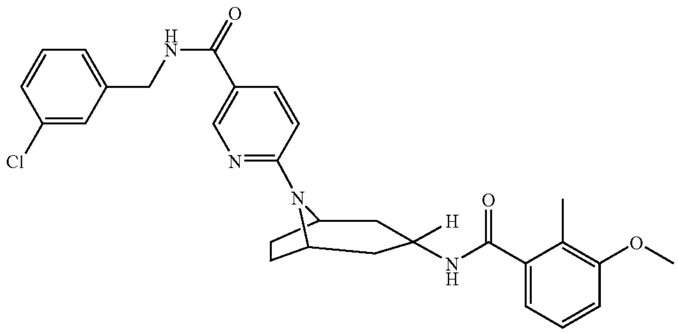 | N-[(3-chlorophenyl)methyl]-6-[3-endo-({[2-methyl-3-(methyloxy)phenyl]carbonyl}amino) 8-azabicyclo[3.2.1]oct-8-yl]pyridine-3-carboxamide ACTIVITY = D |
| 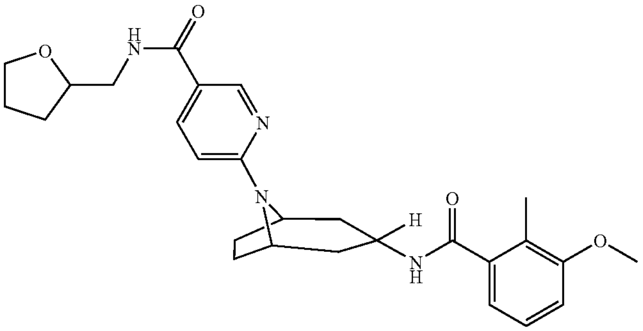 | 6-[3-endo-({[2-methyl-3-(methyloxy)phenyl]carbonyl}amino)-8-azabicyclo[3.2.1]oct-8-yl]-N-(tetrahydrofuran-2-ylmethyl)pyridine-3-carboxamide ACTIVITY = D |
| 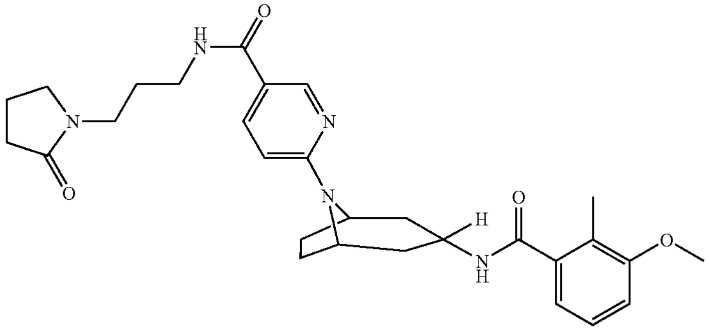 | 6-[3-endo-({[2-methyl-3-(methyloxy)phenyl]carbonyl}amino)-8-azabicyclo[3.2.1]oct-8-yl]-N-[3-(2-oxopyrrolidin-1-yl)propyl]pyridine-3-carboxamide ACTIVITY = B |
| 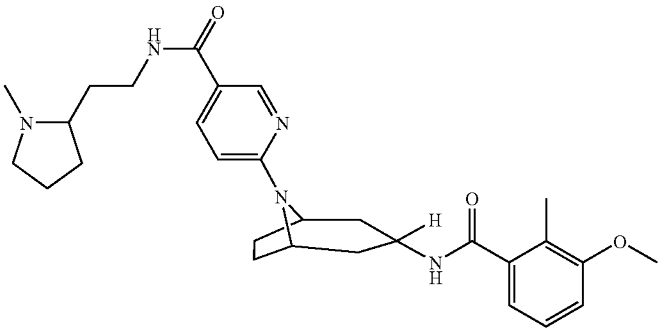 | 6-[3-endo-({[2-methyl-3-(methyloxy)phenyl]carbonyl}amino)-8-azabicyclo[3.2.1]oct-8-yl]-N-[2-(1-methylpyrrolidin-2-yl)ethyl]pyridine-3-carboxamide ACTIVITY = B |

TABLE I-continued

| STRUCTURE | NAME & ACTIVITY |
|---|---|
| 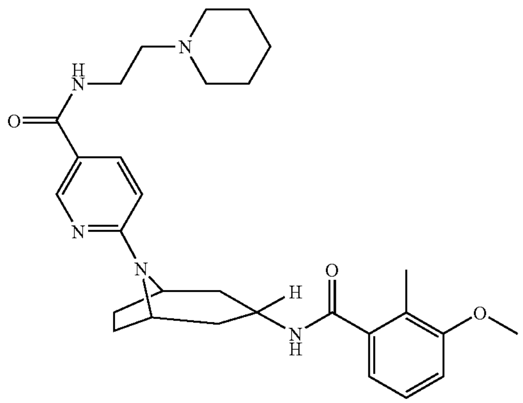 | 6-[3-endo-({[2-methyl-3-(methyloxy)phenyl]carbonyl}amino)-8-azabicyclo[3.2.1]oct-8-yl]-N-(2-piperidin-1-ylethyl)pyridine-3-carboxamide<br>ACTIVITY = C |
| 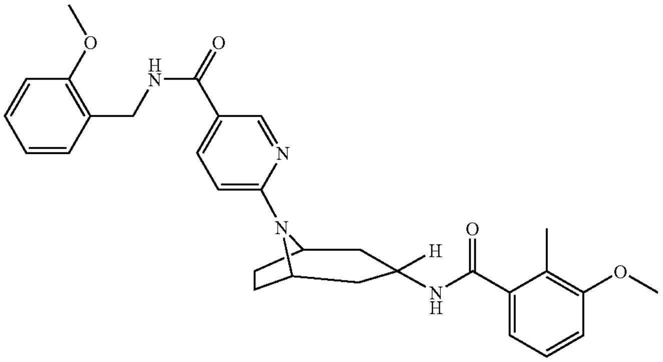 | 6-[3-endo-({[2-methyl-3-(methyloxy)phenyl]carbonyl}amino)-8-azabicyclo[3.2.1]oct-8-yl]-N-{[2-(methyloxy)phenyl]methyl}pyridine-3-carboxamide<br>ACTIVITY = C |
| 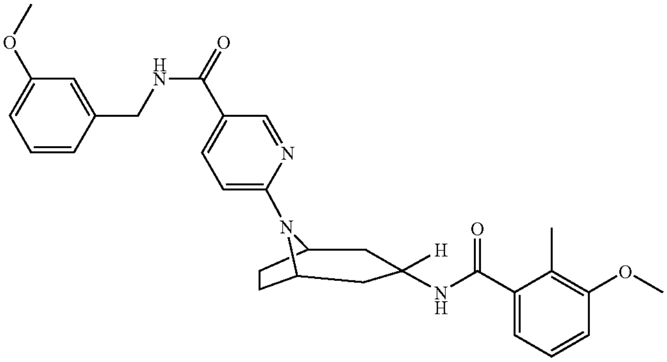 | 6-[3-endo-({[2-methyl-3-(methyloxy)phenyl]carbonyl}amino)-8-azabicyclo[3.2.1]oct-8-yl]-N-{[3-(methyloxy)phenyl]methyl}pyridine-3-carboxamide<br>ACTIVITY = D |
| 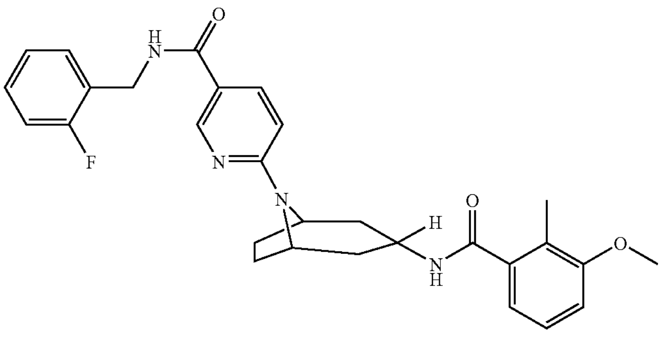 | N-[(2-fluorophenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |

TABLE I-continued

| STRUCTURE | NAME & ACTIVITY |
| --- | --- |
| 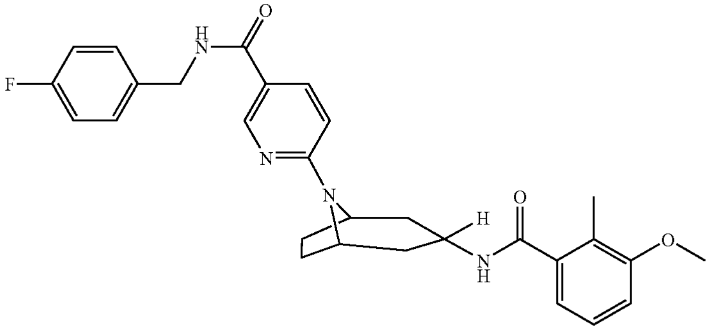 | N-[(4-fluorophenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 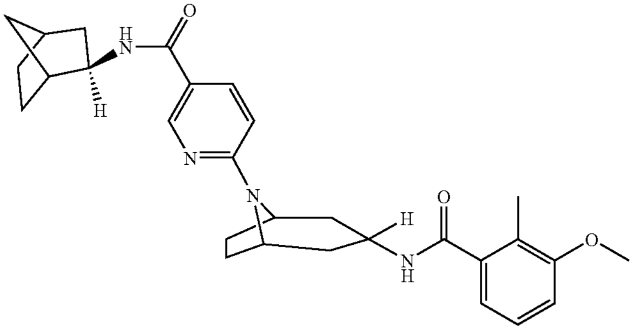 | N-[(1R,2R,4S)-bicyclo[2.2.1]hept-2-yl]-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 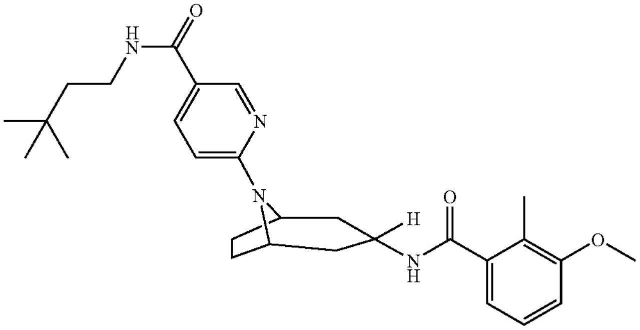 | N-(3,3-dimethylbutyl)-6-[3-endo-({[2-methyl-3-(methyloxy)phenyl]carbonyl}amino)-8-azabicyclo[3.2.1]oct-8-yl]pyridine-3-carboxamide<br>ACTIVITY = D |
| 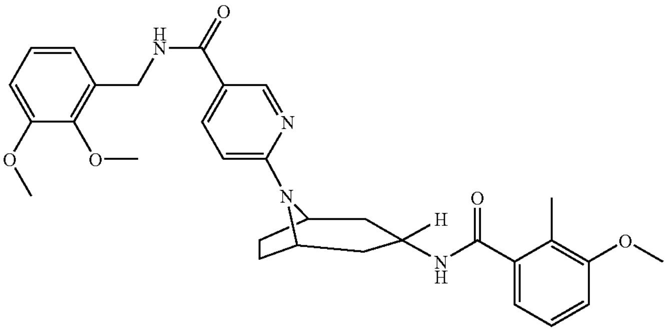 | N-{[2,3-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = D |

TABLE I-continued

| STRUCTURE | NAME & ACTIVITY |
| --- | --- |
| 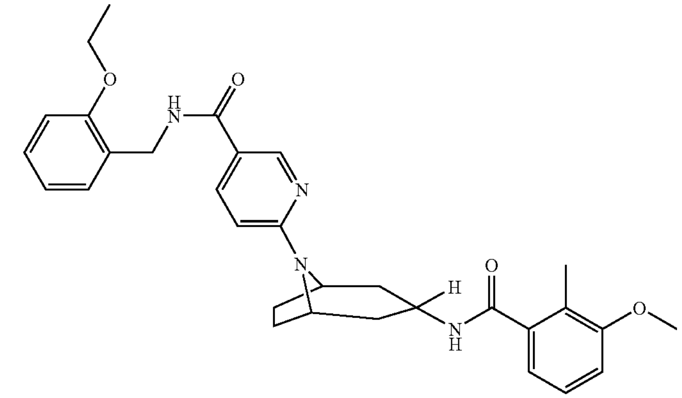 | N-{[2-(ethyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 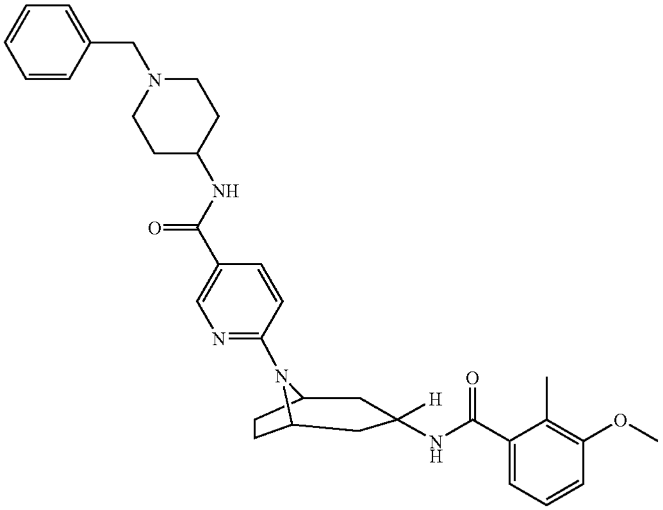 | 6-[3-endo-({[2-methyl-3-(methyloxy)phenyl]carbonyl}amino)-8-azabicyclo[3.2.1]oct-8-yl]-N-[1-(phenylmethyl)piperidin-4-yl]pyridine-3-carboxamide<br>ACTIVITY = A |
| 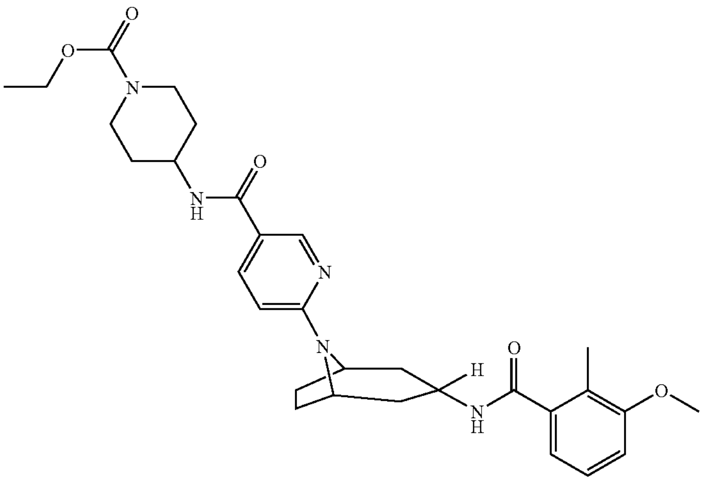 | ethyl 4-[({6-[3-endo-({[2-methyl-3-(methyloxy)phenyl]carbonyl}amino)-8-azabicyclo[3.2.1]oct-8-yl]pyridin-3-yl}carbonyl)amino]piperidine-1-carboxylate<br>ACTIVITY =A |

TABLE I-continued

| STRUCTURE | NAME & ACTIVITY |
|---|---|
| 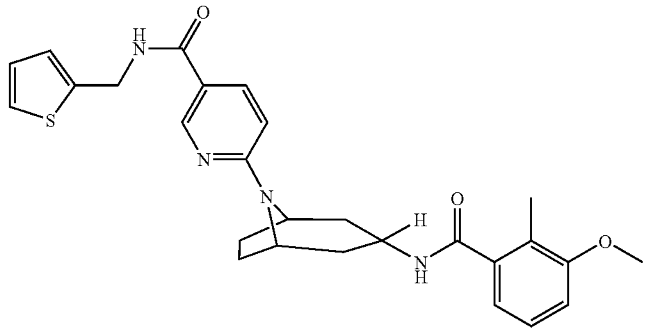 | 6-[3-endo({[2-methyl-3-(methyloxy)phenyl]carbonyl}amino)-8-azabicyclo[3.2.1]oct-8-yl]-N-(2-thienylmethyl)pyridine-3-carboxamide ACTIVITY = A |
| 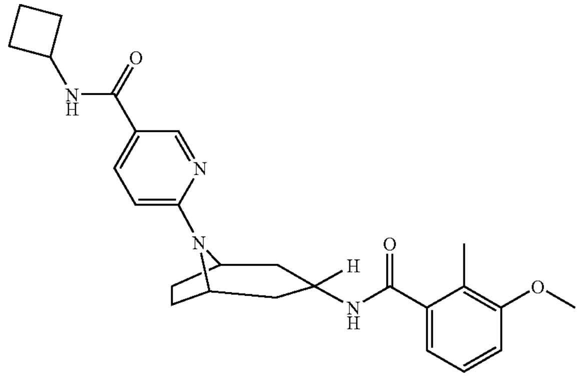 | N-cyclobutyl-6-[3-endo-({[2-methyl-3-(methyloxy)phenyl]carbonyl}amino)-8-azabicyclo[3.2.1]oct-8-yl]pyridine-3-carboxamide ACTIVITY = B |
| 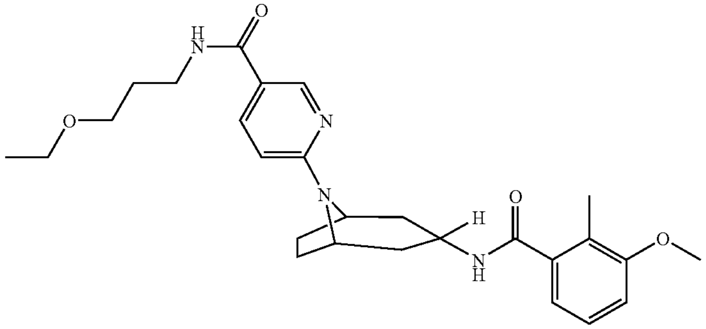 | N-[3-(ethyloxy)propyl]-6-[3-endo-({[2-methyl-3-(methyloxy)phenyl]carbonyl}amino)-8-azabicyclo[3.2.1]oct-8-yl]pyridine-3-carboxamide ACTIVITY = C |
| 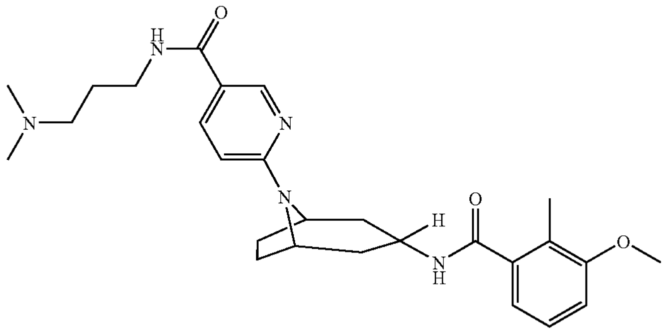 | N-[3-(dimethylamino)propyl]-6-[3-endo-({[2-methyl-3-(methyloxy)phenyl]carbonyl}amino)-8-azabicyclo[3.2.1]oct-8-yl]pyridine-3-carboxamide ACTIVITY = B |

TABLE I-continued

| STRUCTURE | NAME & ACTIVITY |
| --- | --- |
| 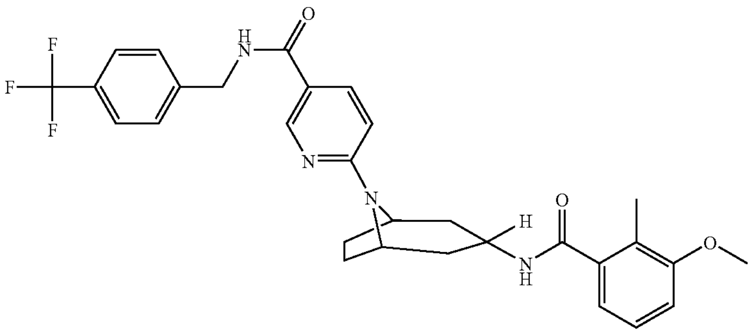 | 6-[3-endo-({[2-methyl-3-(methyloxy)phenyl]carbonyl}amino)-8-azabicyclo[3.2.1]oct-8-yl]-N-{[4-(trifluoromethyl)phenyl]methyl}pyridine-3-carboxamide<br>ACTIVITY = C |
| 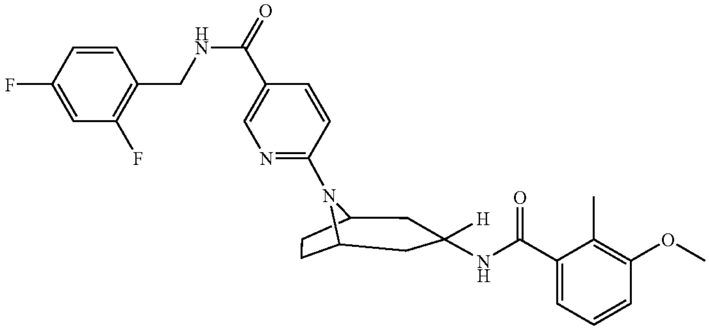 | N-[(2,4-difluorophenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 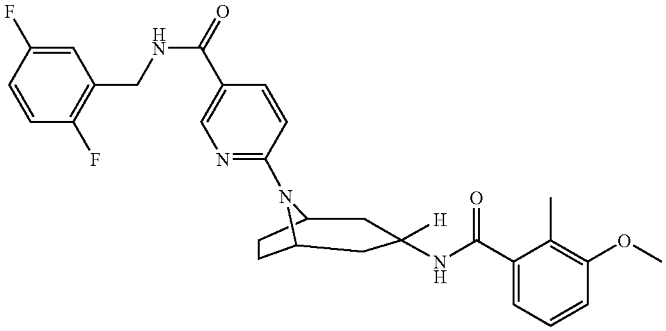 | N-[(2,5-difluorophenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 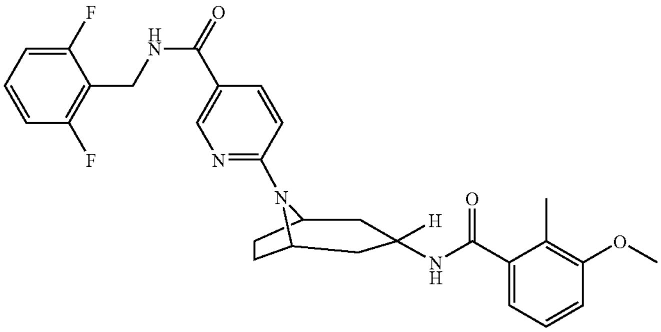 | N-[(2,6-difluorophenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |

TABLE I-continued

| STRUCTURE | NAME & ACTIVITY |
|---|---|
| 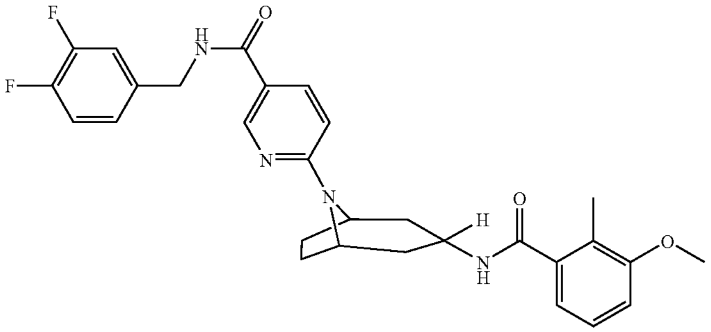 | N-[(3,4-difluorophenyl)methyl]-6-[3-endo-({(2-methyl-3-(methyloxy)phenyl]carbonyl}amino)-8-azablcyclo[3.2.1]oct-8-yl]pyridine-3-carboxamide<br>ACTIVITY = A |
| 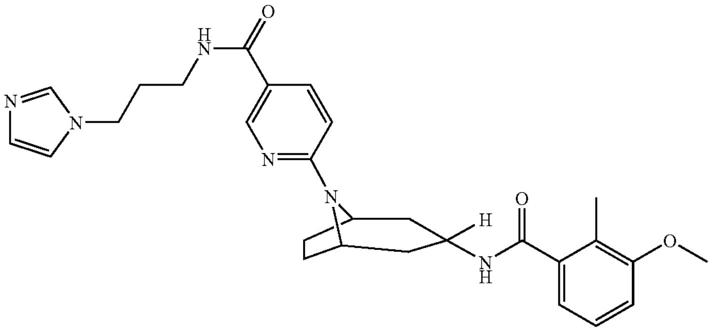 | N-[3-(1H-imidazol-1-yl)propyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 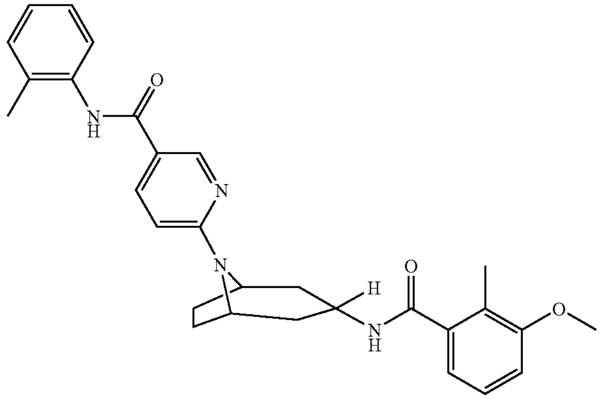 | 6-[3-endo-({[2-methyl-3-(methyloxy)phenyl]carbonyl}amino)-8-azabicyclo[3.2.1]oct-8-yl]-N-(2-methylphenyl)pyridine-3-carboxamide<br>ACTIVITY = D |
| 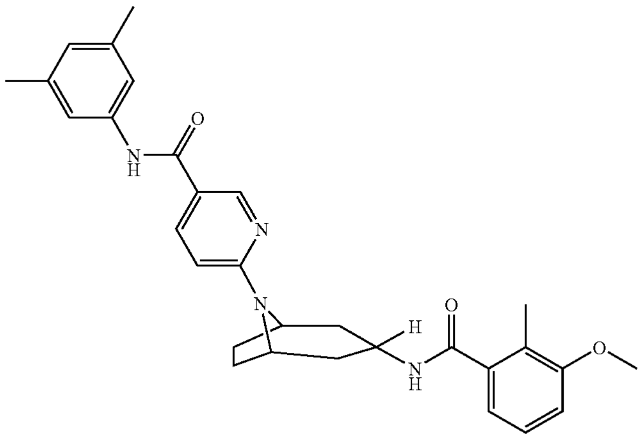 | N-(3,5-dimethylphenyl)-6-[3-endo-({[2-methyl-3-(methyloxy)phenyl]carbonyl}amino)-8-azabicyclo[3.2.1]oct-8-yl]pyridine-3-carboxamide<br>ACTIVITY = D |

TABLE I-continued

| STRUCTURE | NAME & ACTIVITY |
|---|---|
| 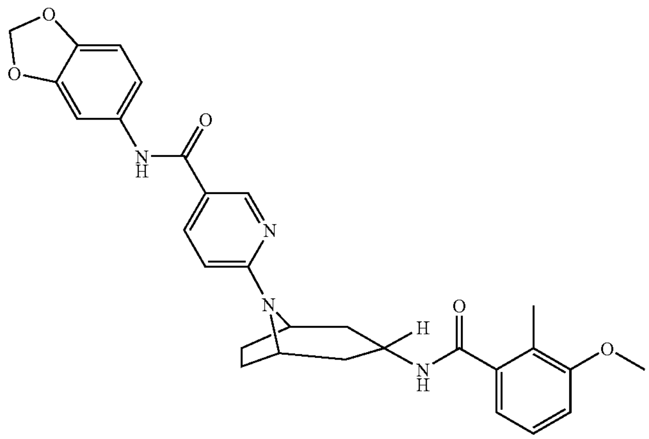 | N-1,3-benzodioxol-5-yl-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 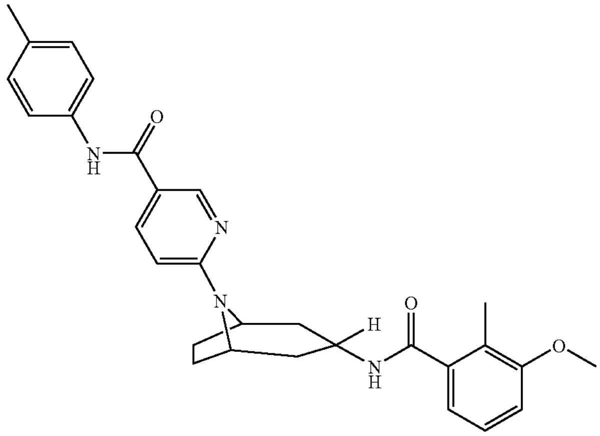 | 6-[3-endo-({[2-methyl-3-(methyloxy)phenyl]carbonyl}amino)-8-azabicyclo[3.2.1]oct-8-yl]-N-(4-methylphenyl)pyridine-3-carboxamide<br>ACTIVITY = C |
| 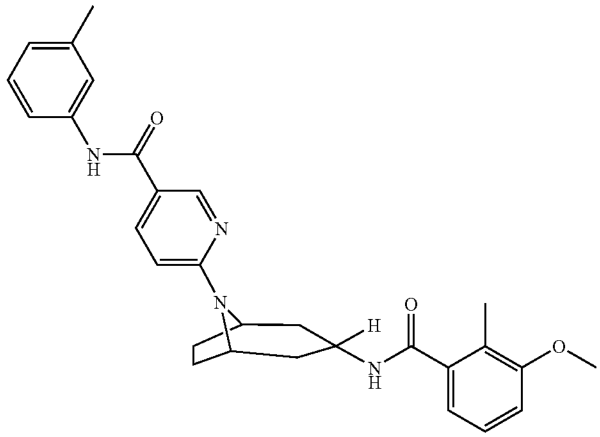 | 6-[3-endo-({[2-methyl-3-(methyloxy)phenyl]carbonyl}amino)-8-azabicyclo[3.2.1]oct-8-yl]-N-(3-methylphenyl)pyridine-3-carboxamide<br>ACTIVITY = D |

TABLE I-continued

| STRUCTURE | NAME & ACTIVITY |
|---|---|
| 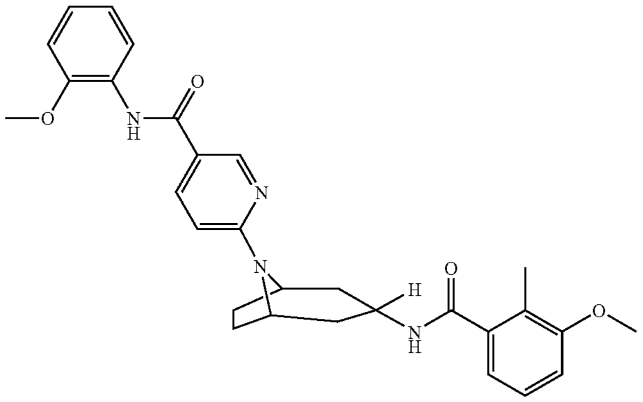 | 6-[3-endo-({[2-methyl-3-(methyloxy)phenyl]carbonyl}amino)-8-azabicyclo[3.2.1]oct-8-yl]-N-[2-(methyloxy)phenyl]pyridine-3-carboxamide<br>ACTIVITY = D |
| 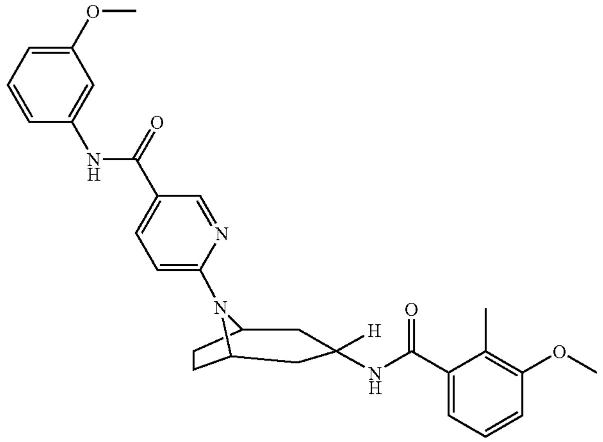 | 6-[3-endo-({[2-methyl-3-(methyloxy)phenyl]carbonyl}amino)-8-azabicyclo[3.2.1]oct-8-yl]-N-[3-(methyloxy)phenyl]pyridine-3-carboxamide<br>ACTIVITY = D |
| 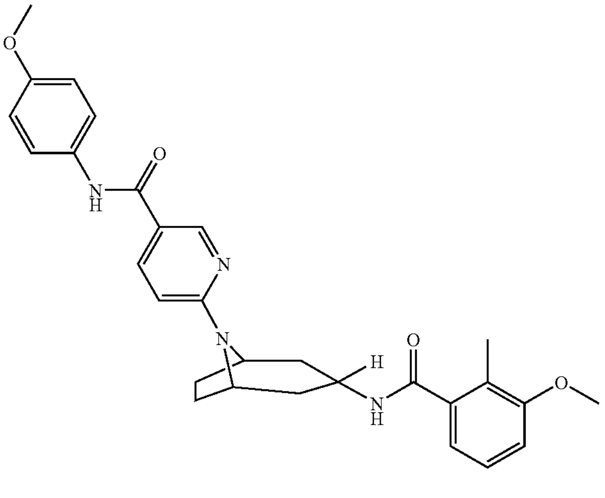 | 6-[3-endo-({[2-methyl-3-(methyloxy)phenyl]carbonyl}amino)-8-azabicyclo[3.2.1]oct-8-yl]-N-[4-(methyloxy)phenyl]pyridine-3-carboxamide<br>ACTIVITY = B |

TABLE I-continued

| STRUCTURE | NAME & ACTIVITY |
|---|---|
| 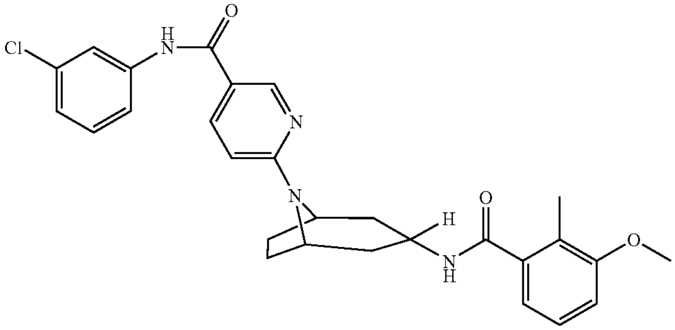 | N-(3-chlorophenyl)-6-[3-endo-({[2-methyl-3-(methyloxy)phenyl]carbonyl)amino)-8-azabicyclo[3.2.1]oct-8-yl]pyridine-3-carboxamide<br>ACTIVITY = D |
| 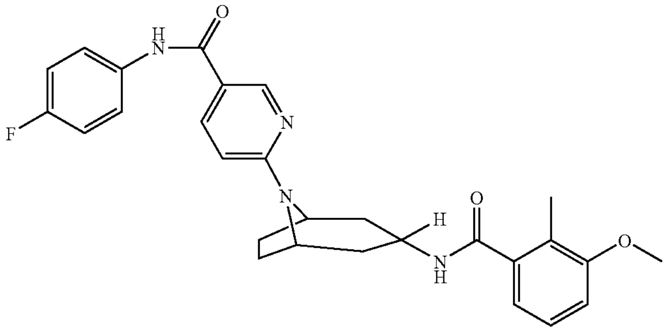 | N-(4-fluorophenyl)-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 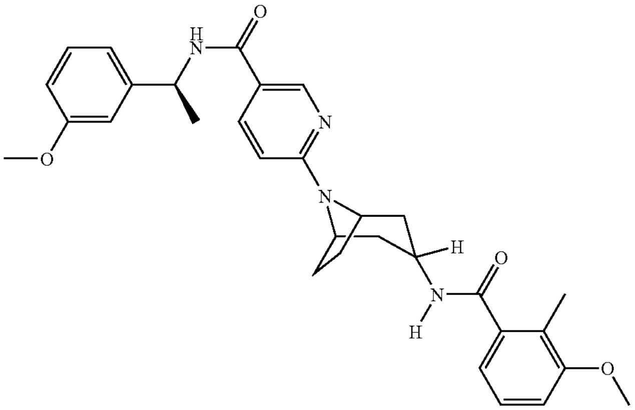 | 6-[3-endo-({[2-methyl-3-(methyloxy)phenyl]carbonyl}amino)-8-azabicyclo[3.2.1]oct-8-yl]-N-{(1S)-1-[3-(methyloxy)phenyl]ethyl}pyridine-3-carboxamide<br>ACTIVITY = A |
| 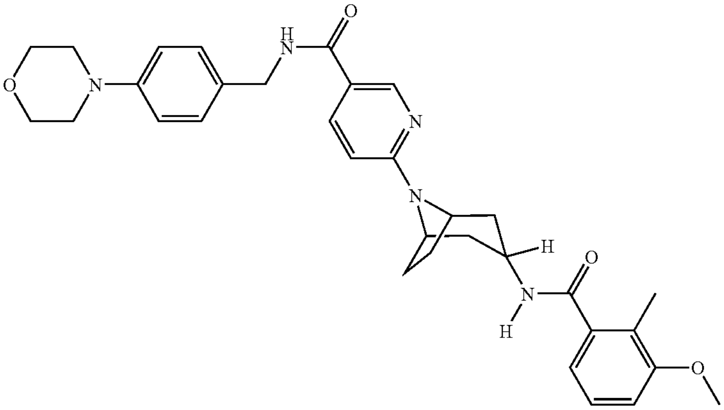 | 6-[3-endo-({[2-methyl-3-(methyloxy)phenyl]carbonyl}amino)-8-azabicyclo[3.2.1]oct-8-yl]-N-[(4-morpholin-4-ylphenyl)methyl]pyridine-3-carboxamide<br>ACTIVITY = A |

TABLE I-continued
| STRUCTURE | NAME & ACTIVITY |
| --- | --- |
| 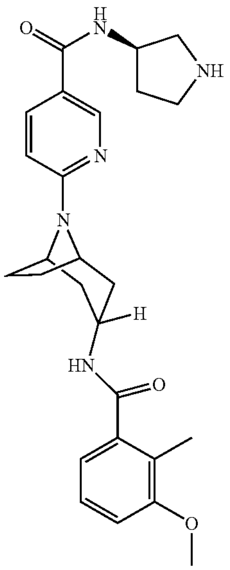 | 6-[3-endo-({[2-methyl-3-(methyloxy)phenyl]carbonyl}amino)-8-azabicyclo[3.2.1]oct-8-yl]-N-[(3R)-pyrrolidin-3-yl]pyridine-3-carboxamide<br>ACTIVITY = B |
| 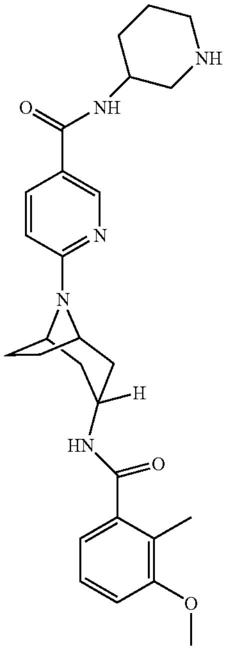 | 6-[3-endo-({[2-methyl-3-(methyloxy)phenyl]carbonyl}amino)-8-azabicyclo[3.2.1]oct-8-yl]-N-piperidin-3-ylpyridine-3-carboxamide<br>ACTIVITY = B |

TABLE I-continued
| STRUCTURE | NAME & ACTIVITY |
|---|---|
| 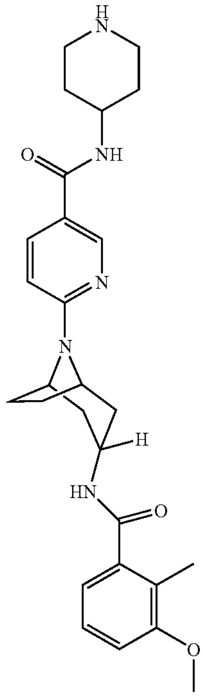 | 6-[3-endo-({[2-methyl-3-(methyloxy)phenyl]carbonyl}amino)-8-azabicyclo[3.2.1]oct-8-yl]-N-piperidin-4-ylpyridine-3-carboxamide<br>ACTIVITY = A |
| 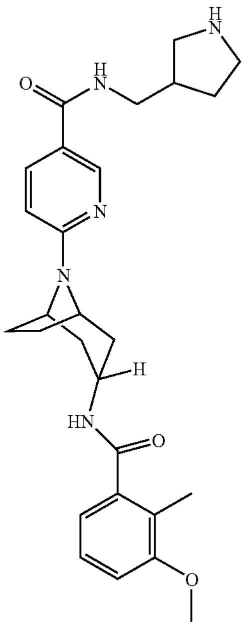 | 6-[3-endo-({[2-methyl-3-(methyloxy)phenyl]carbonyl}amino)-8-azabicyclo[3.2.1]oct-8-yl-N-(pyrrolidin-3-ylmethyl)pyridine-3-carboxamide<br>ACTIVITY = A |

TABLE I-continued

| STRUCTURE | NAME & ACTIVITY |
| --- | --- |
| 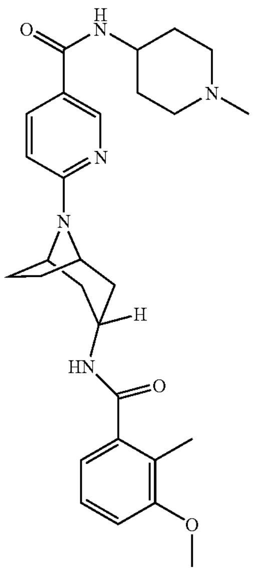 | 6-[3-endo-({[2-methyl-3-(methyloxy)phenyl]carbonyl}amino)-8-azabicyclo[3.2.1]oct-8-yl]-N-(1-methylpiperidin-4-yl)pyridine-3-carboxamide<br>ACTIVITY = B |
| 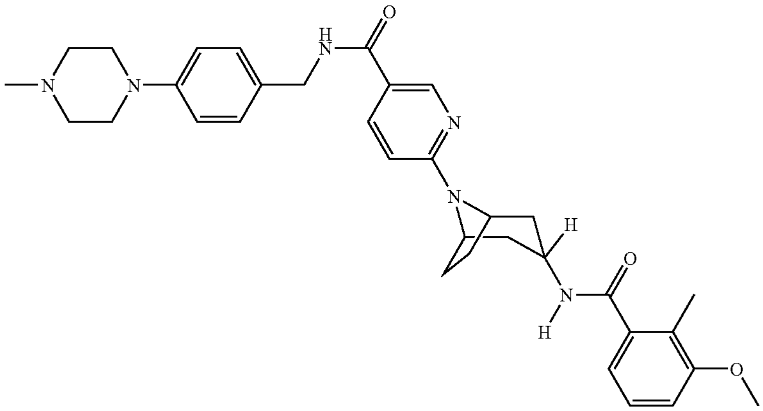 | 6-[3-endo-({[2-methyl-3-(methyloxy)phenyl]carbonyl}amino)-8-azabicyclo[3.2.1]oct-8-yll-N-{[4-(4-methylpiperazin-1-yl)phenyl]methyl}pyridine-3-carboxamide<br>ACTIVITY = A |
| 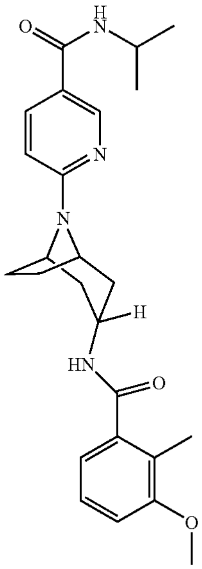 | N-(1-methylethyl)-6-[3-endo-({[2-methyl-3-(methyloxy)phenyl]carbonyl}amino)-8-azabicyclo[3.2.1]oct-8-yl]pyridine-3-carboxamide<br>ACTIVITY = C |

TABLE I-continued
| STRUCTURE | NAME & ACTIVITY |
|---|---|
| 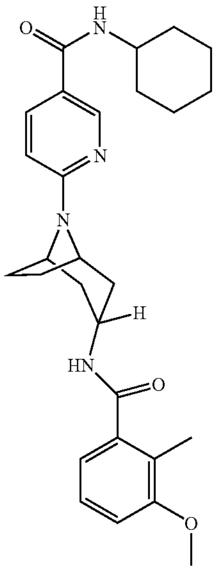 | N-cyclohexyl-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 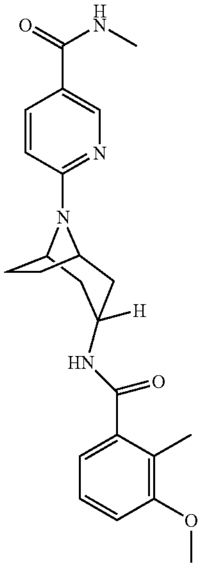 | N-methyl-6-[3-endo-({[2-methyl-3-(methyloxy)phenyl]carbonyl}amino)-8-azabicyclo[3.2.1]oct-8-yl]pyridine-3-carboxamide<br>ACTIVITY = C |

TABLE I-continued

| STRUCTURE | NAME & ACTIVITY |
|---|---|
| 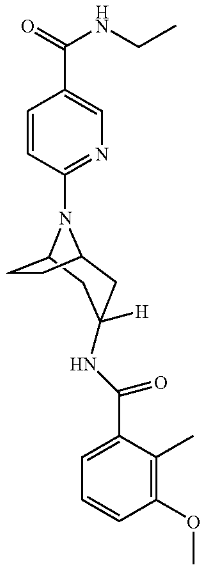 | N-ethyl-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 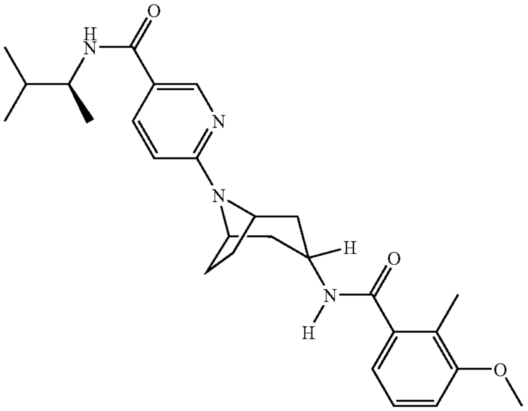 | N-[(1S)-1,2-dimethylpropyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 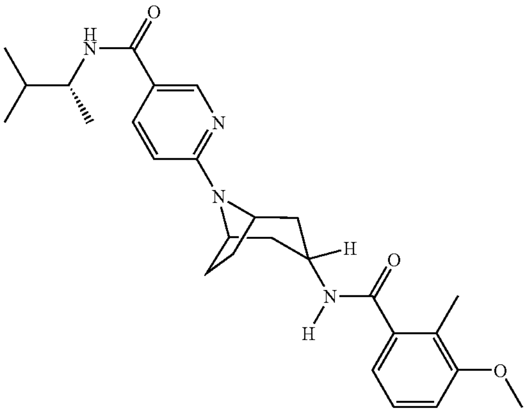 | N-[(1R)-1,2-dimethylpropyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = D |

TABLE I-continued

| STRUCTURE | NAME & ACTIVITY |
| --- | --- |
| 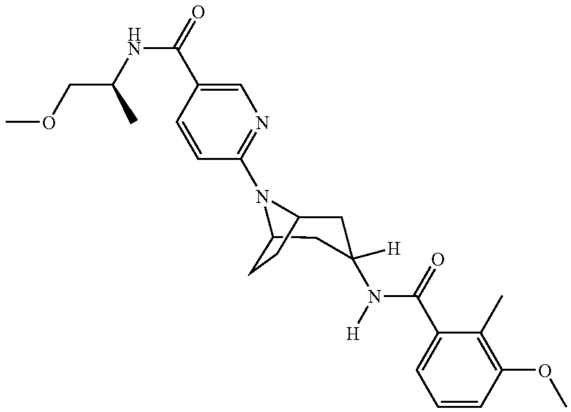 | N-[(1S)-1-methyl-2-(methyloxy)ethyl]-6-[3-endo-({[2-methyl-3-(methyloxy)phenyl]carbonyl}amino)-8-azabicyclo[3.2.1]oct-8-yl]pyridine-3-carboxamide ACTIVITY= C |
| 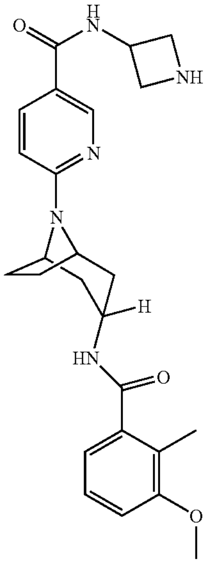 | N-azetidin-3-yl-6-[3-endo-({[2-methyl-3-(methyloxy)phenyl]carbonyl}amino)-8-azabicyclo[3.2.1]oct-8-yl]pyridine-3-carboxamide ACTIVITY = B |
| 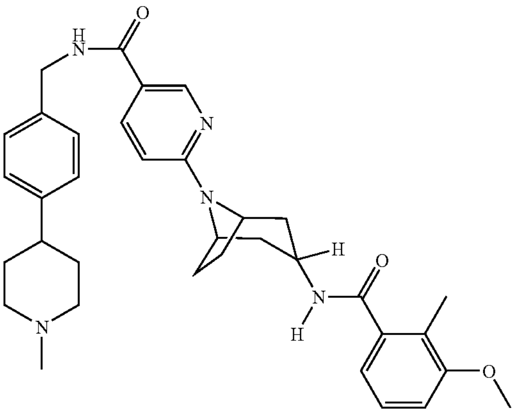 | 6-[3-endo-({[2-methyl-3-(methyloxy)phenyl]carbonyl}amino)-8-azabicyclo[3.2.1]oct-8-yl]-N-{[4-(1-methylpiperidin-4-yl)phenyl]methyl}pyridine-3-carboxamide ACTIVITY = A |

TABLE I-continued

| STRUCTURE | NAME & ACTIVITY |
| --- | --- |
| 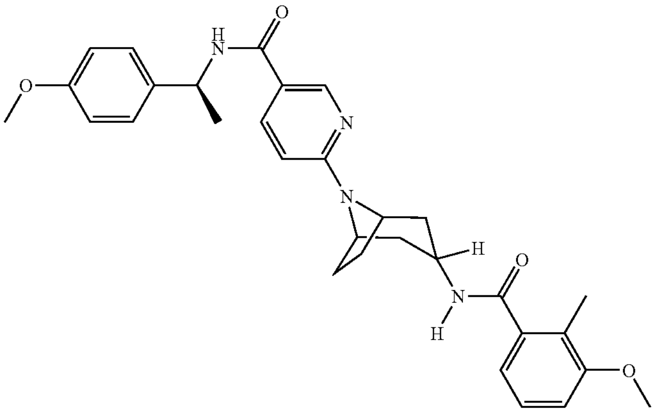 | 6-[3-endo-({[2-methyl-3-(methyloxy)phenyl]carbonyl}amino)-8-azabicyclo[3.2.1]oct-8-yl]-N-{(1S)-(methyloxy)phenyl]ethyl}pyridine-3-carboxamide<br>ACTIVITY= A |
| 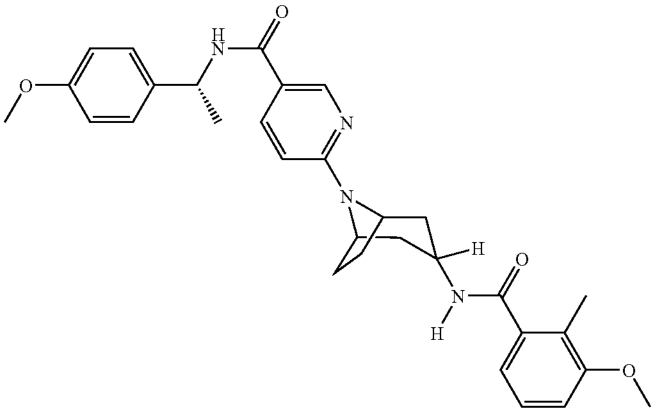 | 6-[3-endo-({[2-methyl-3-(methyloxy)phenyl]carbonyl}amino)-8-azabicyclo[3.2.1]oct-8-yl]-N-{(1R)-1-[4-(methyloxy)phenyl]ethyl}pyridine-3-carboxamide<br>ACTIVITY = D |
| 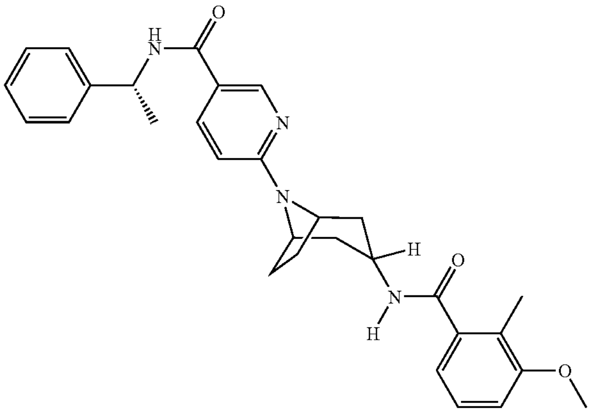 | 6-[3-endo-({[2-methyl-3-(methyloxy)phenyl]carbonyl}amino)-8-azabicyclo[3.2.1]oct-8-yl]-N-[(1R)-1-phenylethyl]pyridine-3-carboxamide<br>ACTIVITY = D |

TABLE I-continued

| STRUCTURE | NAME & ACTIVITY |
|---|---|
| 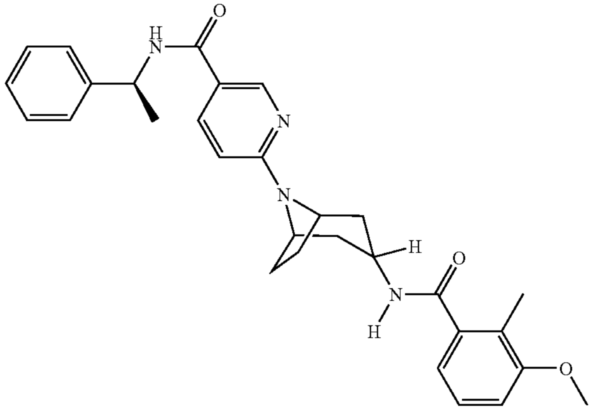 | 6-[3-endo-({[2-methyl-3-(methyloxy)phenyl]carbonyl}amino)-8-azabicyclo[3.2.1]oct-8-yl]-N-[(1S)-1-phenylethyl]pyridine-3-carboxamide<br>ACTIVITY = A |
| 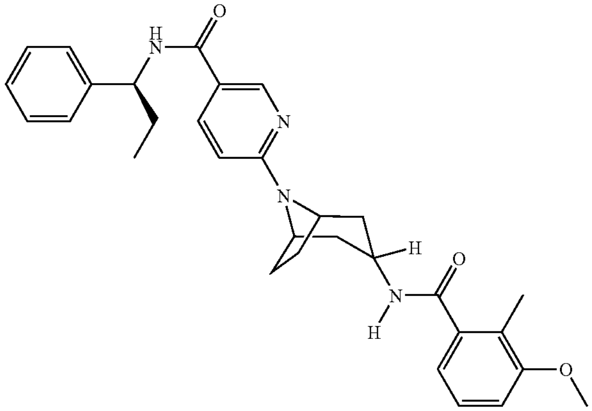 | 6-[3-endo-({[2-methyl-3-(methyloxy)phenyl]carbonyl}amino)-8-azabicyclo[3.2.1]oct-8-yl]-N-[(1S)-1-phenylpropyl]pyridine-3-carboxamide<br>ACTIVITY = B |
| 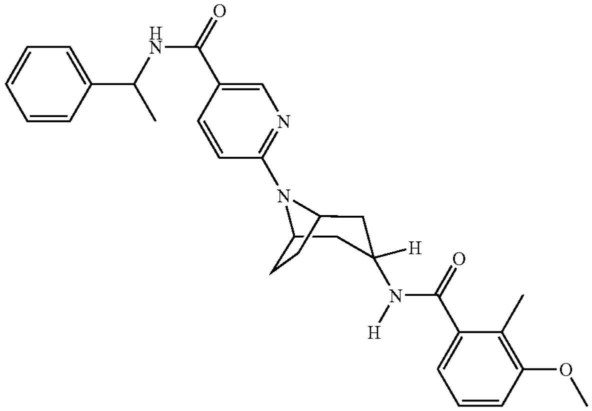 | 6-[3-endo-({[2-methyl-3-(methyloxy)phenyl]carbonyl}amino)-8-azabicyclo[3.2.1]oct-8-yl]-N-((1-phenylethyl)pyridine-3-carboxamide<br>ACTIVITY = A |

TABLE I-continued

| STRUCTURE | NAME & ACTIVITY |
|---|---|
| 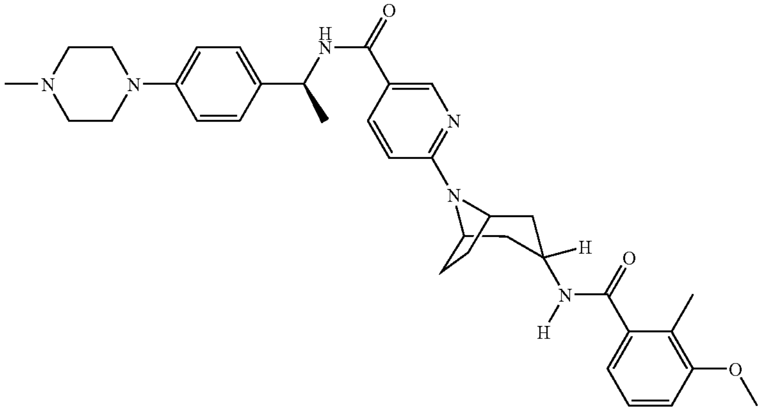 | 6-[3-endo-({[2-methyl-3-(methyloxy)phenyl]carbonyl}amino)-8-azabicyclo[3.2.1]oct-8-yl]-N-{(1S)-1-[4-(4-methylpiperazin-1-yl)phenyl]ethyl}pyridine-3-carboxamide ACTIVITY = A |
| 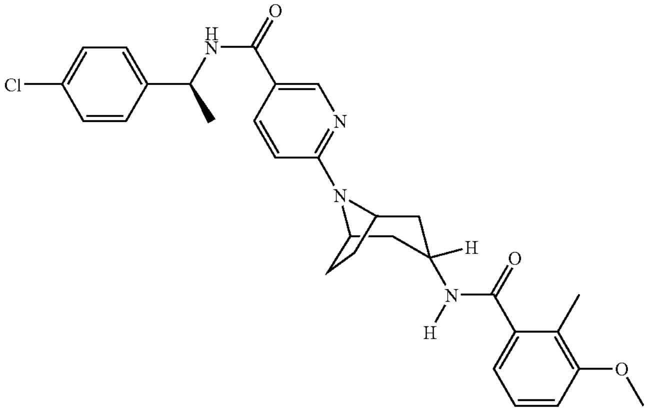 | N-[(1S)-1-(4-chlorophenyl)ethyl]-6-[3-endo-({[2-methyl-3-(methyloxy)phenyl]carbonyl}amino)-8-azabicyclo[3.2.1]oct-8-yl]pyridine-3-carboxamide ACTIVITY = A |
| 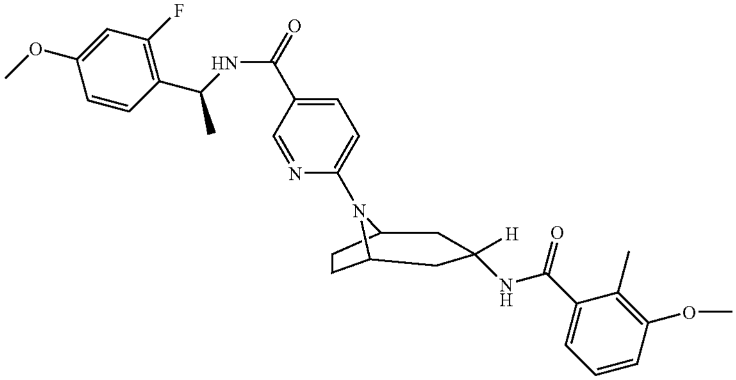 | N-{(1S)-1-[2-fluoro-4-(methyloxy)phenyl]ethyl}-6-[3-endo-({[2-methyl-3-(methyloxy)phenyl]carbonyl}amino)-8-azabicyclo[3.2.1]oct-8-yl]pyridine-3-carboxamide ACTIVITY = A |

TABLE I-continued

| STRUCTURE | NAME & ACTIVITY |
|---|---|
| 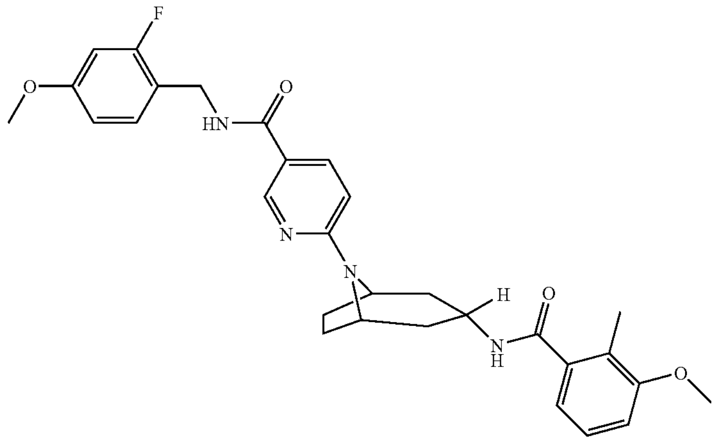 | N-{[2-fluoro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 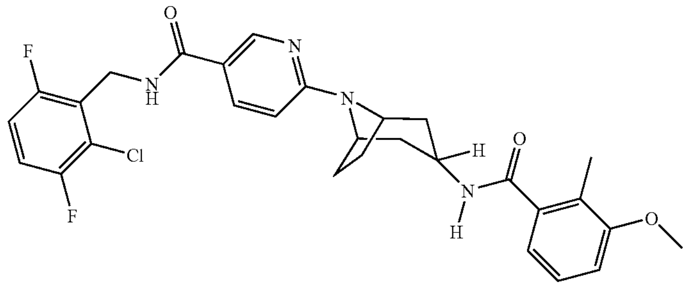 | N-[(2-chloro-3,6-difluorophenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 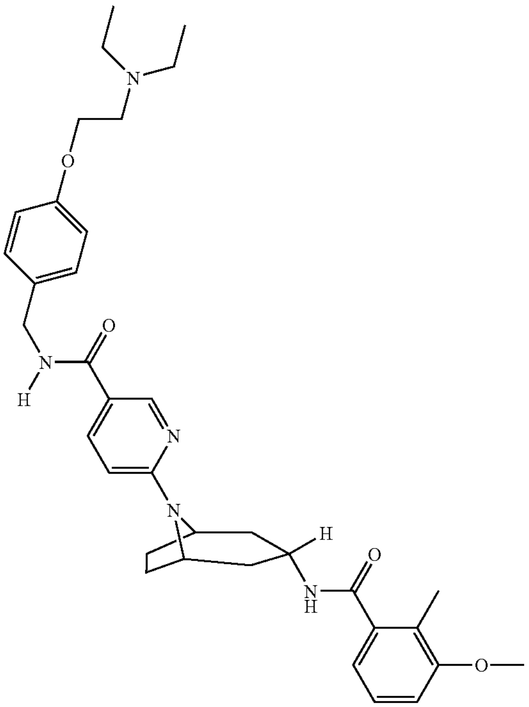 | N-[(4-{[2-(diethylamino)ethyl]oxy}phenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |

TABLE I-continued

| STRUCTURE | NAME & ACTIVITY |
|---|---|
| 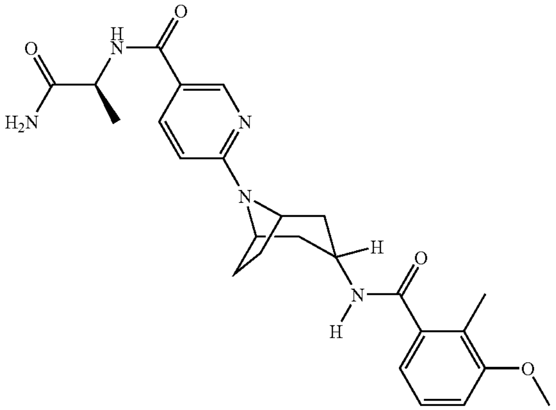 | N-[(1S)-2-amino-1-methyl-2-oxoethyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 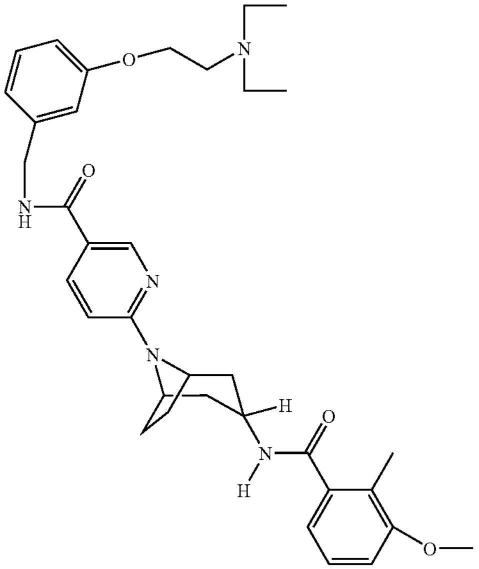 | N-[(3-{[2-(diethylamino)ethyl]oxy}pheny)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 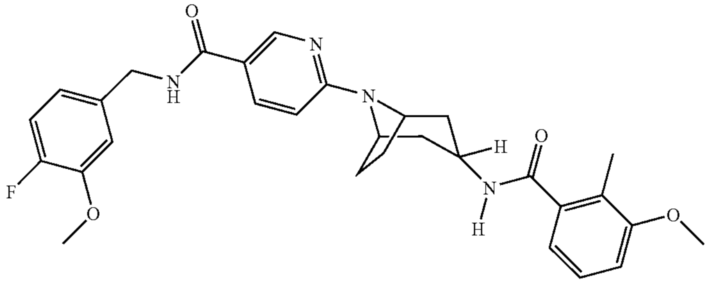 | N-{[4-fluoro-3-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 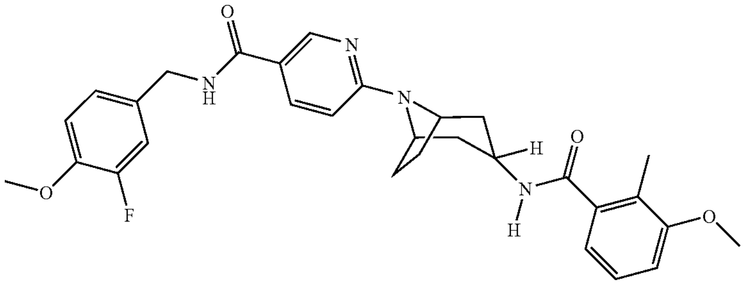 | N-{[3-fluoro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = A |

TABLE I-continued

| STRUCTURE | NAME & ACTIVITY |
|---|---|
| 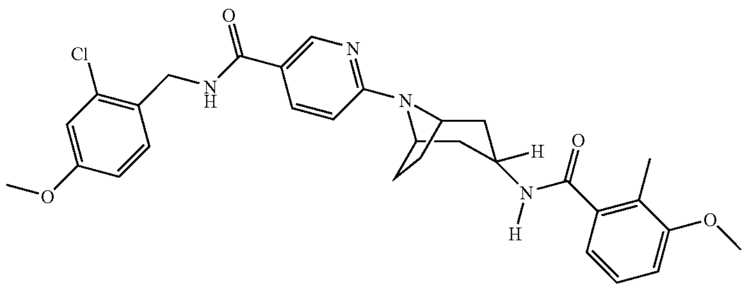 | N-{[2-chloro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide ACTIVITY = A |
| 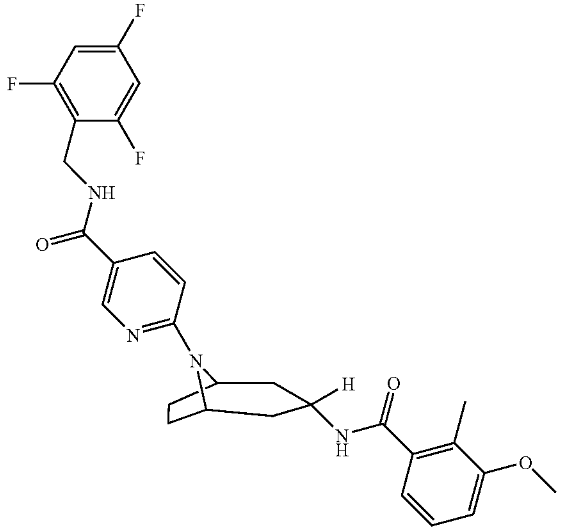 | 6-[3-endo-({[2-methyl-3-(methyloxy)phenyl]carbonyl}amino)-8-azabicyclo[3.2.1]oct-8-yl]-N-[(2,4,6-trifluorophenyl)methyl]pyridine-3-carboxamide ACTIVITY = A |
| 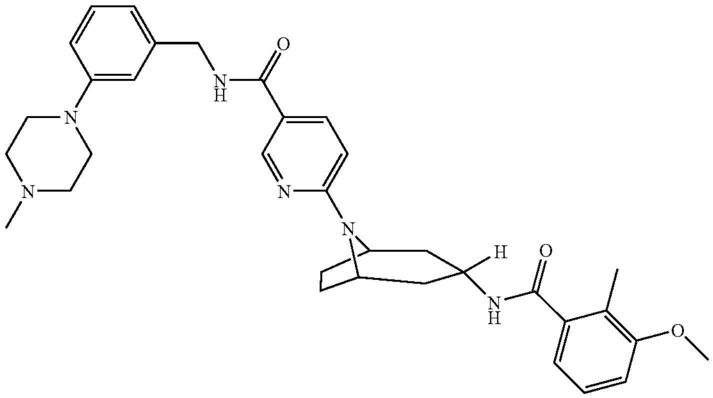 | 6-[3-endo-({[2-methyl-3-(methyloxy)phenyl]carbony}amino)-8-azabicyclo[3.2.1]oct-8-yl]-N-{[3-(4-methylpiperazin-1-yl)phenyl]methyl}pyridine-3-carboxamide ACTIVITY = A |
| 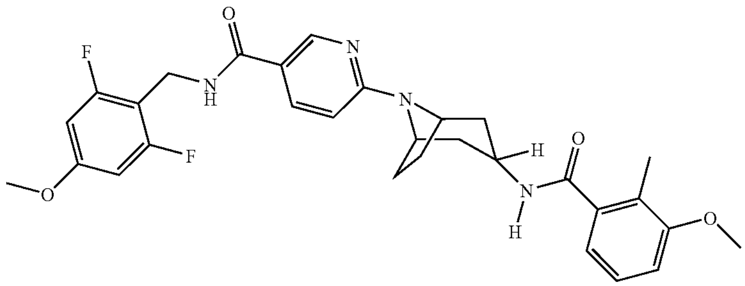 | N-{[2,6-difluoro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide ACTIVITY = A |

TABLE I-continued

| STRUCTURE | NAME & ACTIVITY |
|---|---|
| 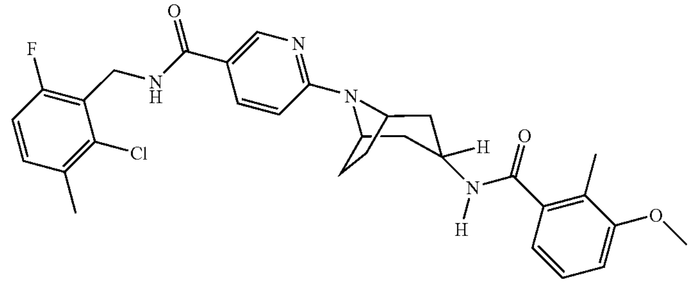 | N-[(2-chloro-6-fluoro-3-methylphenyl)methyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 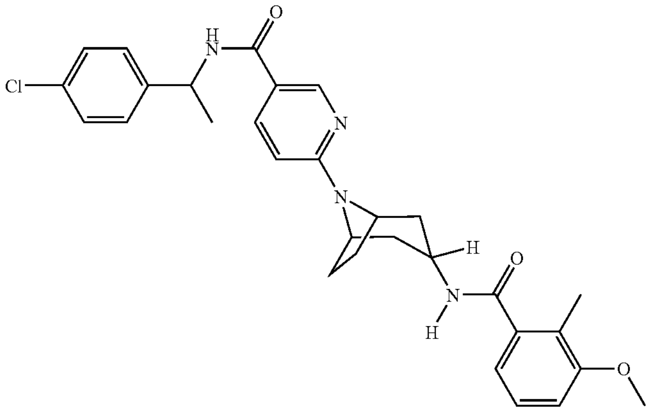 | N-[1-(4-chlorophenyl)ethyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 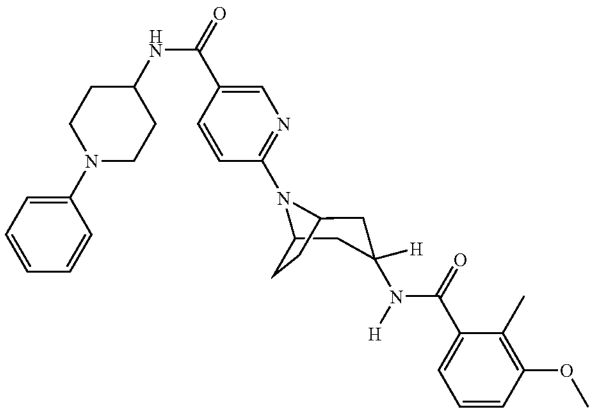 | 6-[3-endo-({[2-methyl-3-(methyboxy)phenyl]carbonyl}amino)-8-azabicyclo[3.2.1]oct-8-yl]-N-(1-phenylpiperidin-4-yl)pyridine-3-carboxamide<br>ACTIVITY = D |
| 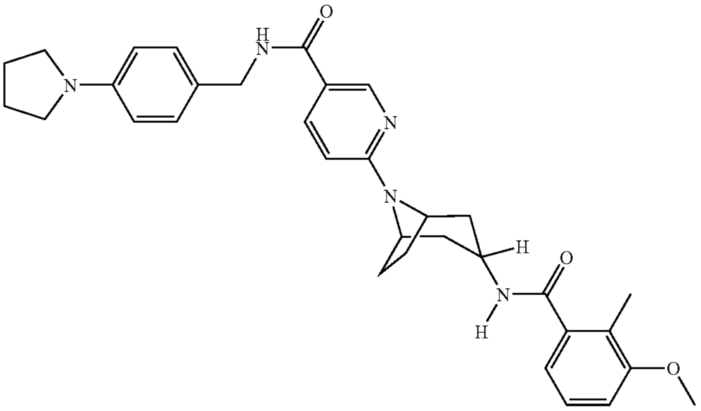 | 6-[3-endo-({[2-methyl-3-(methyloxy)phenyl]carbonyl}amino)-8-azabicyclo[3.2.1]oct-8-yl]-N-[(4-pyrrolidin-1-ylphenyl)methyl]pyridine-3-carboxamide<br>ACTIVITY = B |

TABLE I-continued

| STRUCTURE | NAME & ACTIVITY |
|---|---|
| 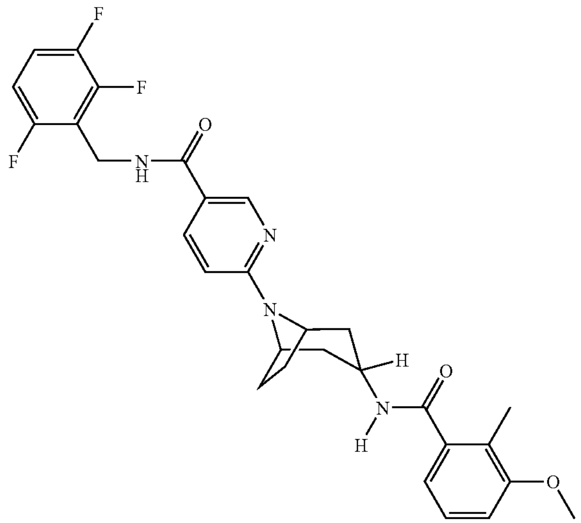 | 6-[3-endo-({[2-methyl-3-(methyloxy)phenyl]carbonyl}amino)-8-azabicyclo[3.2.1]oct-8-yl]-N-[(2,3,6-trifluorophenyl)methyl]pyridine-3-carboxamide<br>ACTIVITY = B |
| 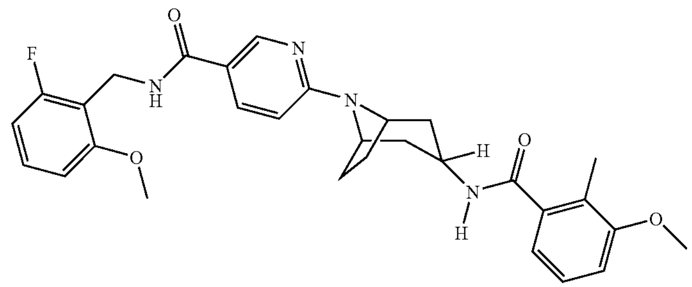 | N-{[2-fluoro-6-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 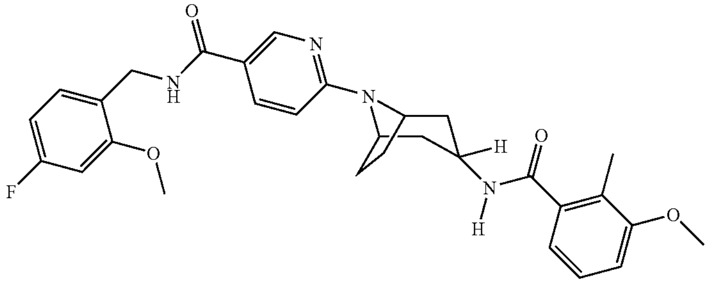 | N-{[4-fluoro-2-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = C |

TABLE I-continued

| STRUCTURE | NAME & ACTIVITY |
| --- | --- |
| 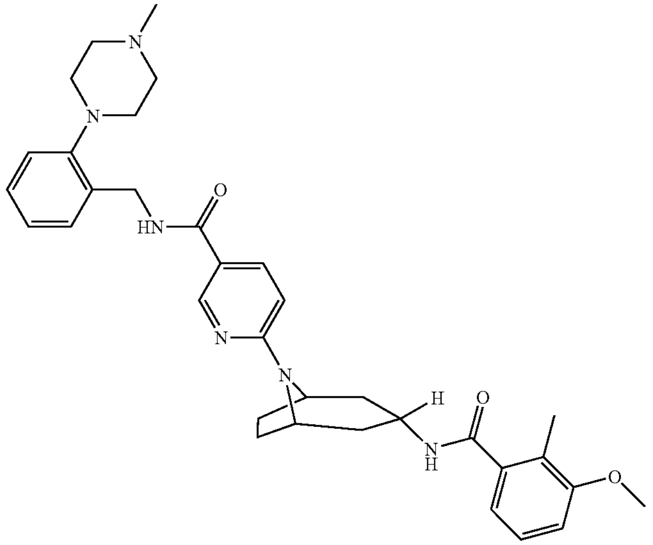 | 6-[3-endo-({[2-methyl-3-(methyloxy)phenyl]carbonyl}amino)-8-azabicyclo[3.2.1]oct-8-yl]-N-{[2-(4-methylpiperazin-1-yl)phenyl]methyl}pyridine-3-carboxamide<br>ACTIVITY = C |
| 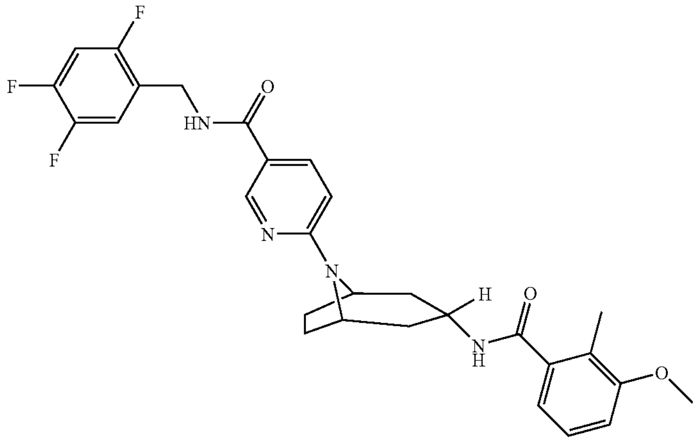 | 6-[3-endo-({[2-methyl-3-(methyloxy)phenyl]carbonyl}amino)-8-azabicyclo[3.2.1]oct-8-yl]-N-[(2,4,5-trifluorophenyl)methyl]pyridine-3-carboxamide<br>ACTIVITY = B |
| 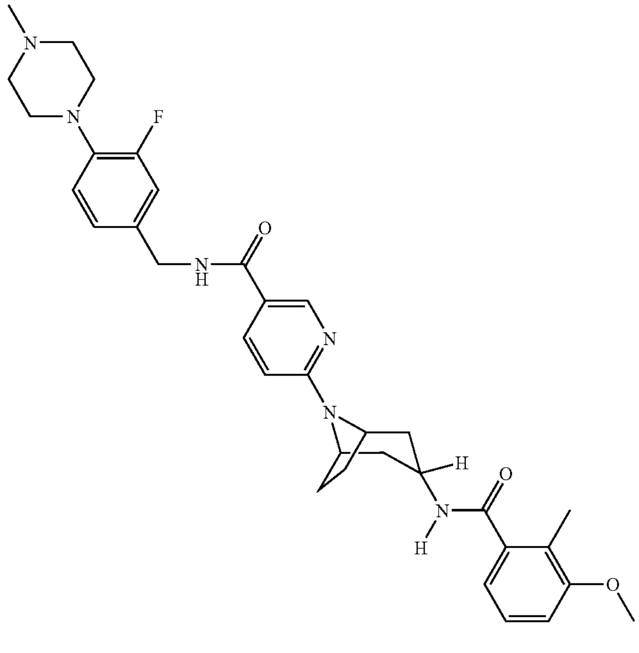 | N-{[3-fluoro-4-(4-methylpiperazin-1-yl)phenyl]methyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = A |

TABLE I-continued
| STRUCTURE | NAME & ACTIVITY |
|---|---|
| 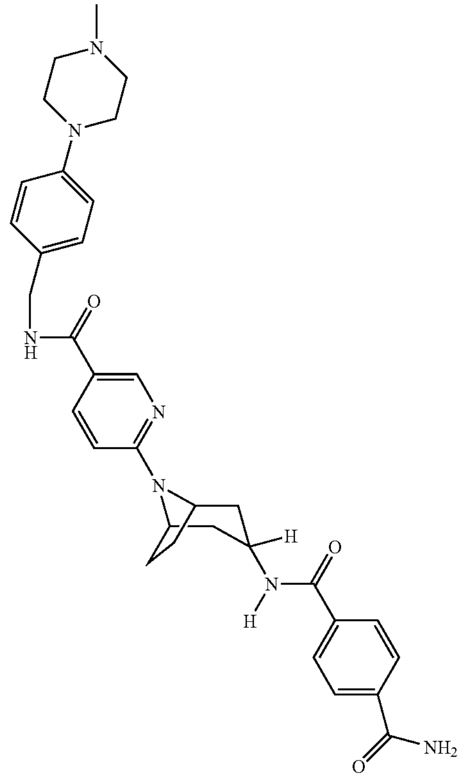 | N-(8-{5-[({[4-(4-methylpiperazin-1-yl)phenyl]methyl}amino)carbonyl]pyridin-2-yl}-8-azabicyclo[3.2.1]oct-3-endo-yl)benzene-1,4-dicarboxamide ACTIVITY = A |
| 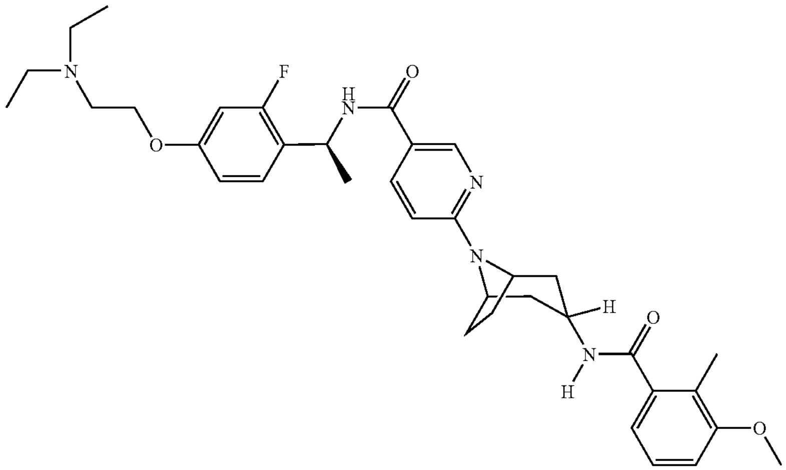 | N-[(1S)-1-(4-{[2-(diethylamino)ethyl]oxy}-2-fluorophenyl)ethyl]-6-[3-endo-({[2-methyl-3-(methyloxy)phenyl]carbonyl}amino)-8-azabicyclo[3.2.1]oct-8-yl]pyridine-3-carboxamide ACTIVITY = A |

TABLE I-continued
| STRUCTURE | NAME & ACTIVITY |
| --- | --- |
| 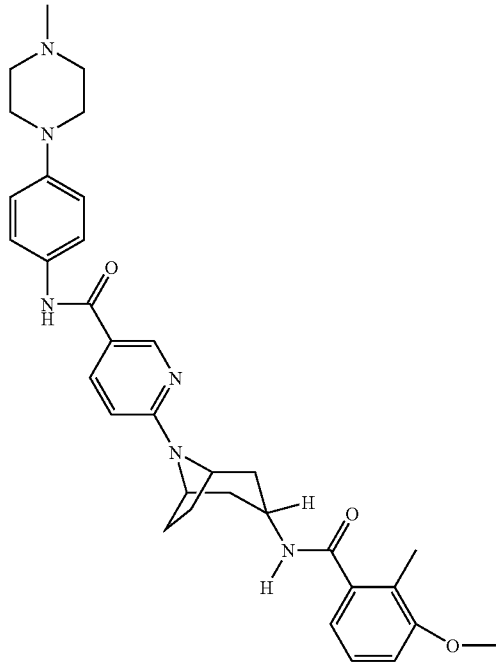 | 6-[3-endo-({[2-methyl-3-(methyloxy)phenyl]carbonyl}amino)-8-azabicyclo[3.2.1]oct-8-yl]-N-[4-(4-methylpiperazin-1-yl)phenyl]pyridine-3-carboxamide ACTIVITY = A |
| 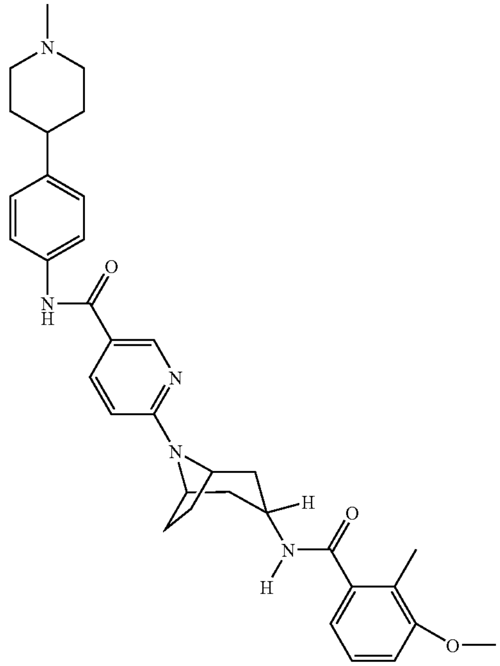 | 6-[3-endo-({[2-methyl-3-(methyloxy)phenyl]carbonyl}amino)-8-azabicyclo[3.2.1]oct-8-yl]-N-[4-(1-methylpiperidin-4-yl)phenyl]pyridine-3-carboxamide ACTIVITY = C |

TABLE I-continued

| STRUCTURE | NAME & ACTIVITY |
|---|---|
| 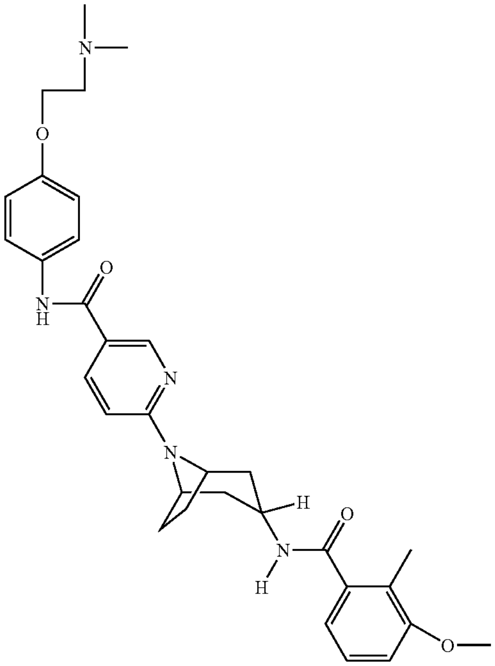 | N-(4-{[2-(dimethylamino)ethyl]oxy}phenyl)-6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 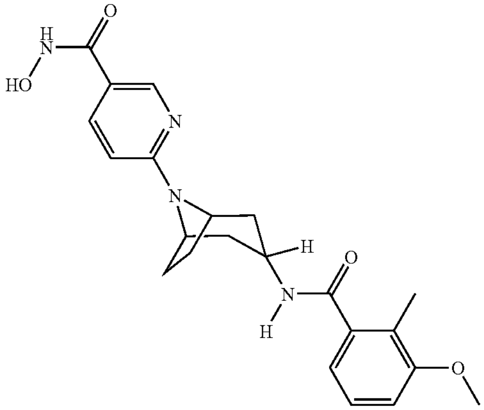 | N-hydroxy-6-[3-endo-({[2-methyl-3-(methyloxy)phenyl]carbonyl}amino)-8-azabicyclo[3.2.1]oct-8-yl]pyridine-3-carboxamide<br>ACTIVITY = D |
| 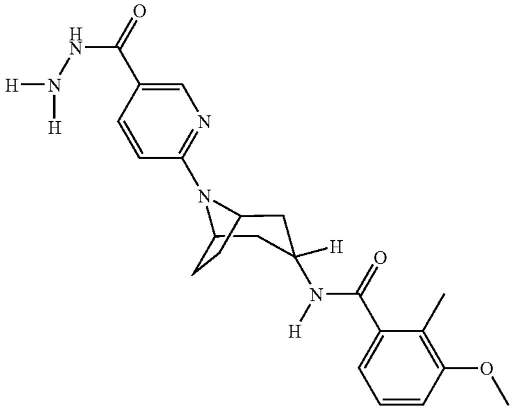 | N-{8-[5-(hydrazinocarbonyl)pyridin-2-yl]-8-azabicyclo[3.2.1]oct-3-endo-yl}-2-methyl-3-(methyloxy)benzamide<br>ACTIVITY = D |

TABLE I-continued

| STRUCTURE | NAME & ACTIVITY |
| --- | --- |
| 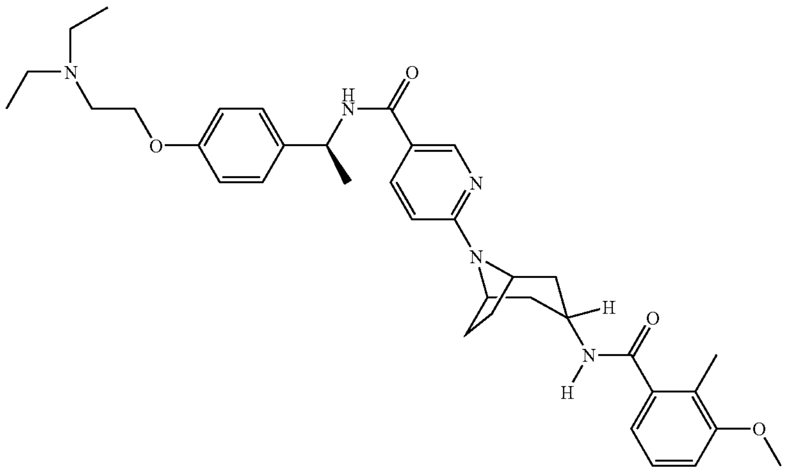 | N-[(1S)-1-(4-{[2-(diethylamino)ethyl]oxy}phenyl)ethyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 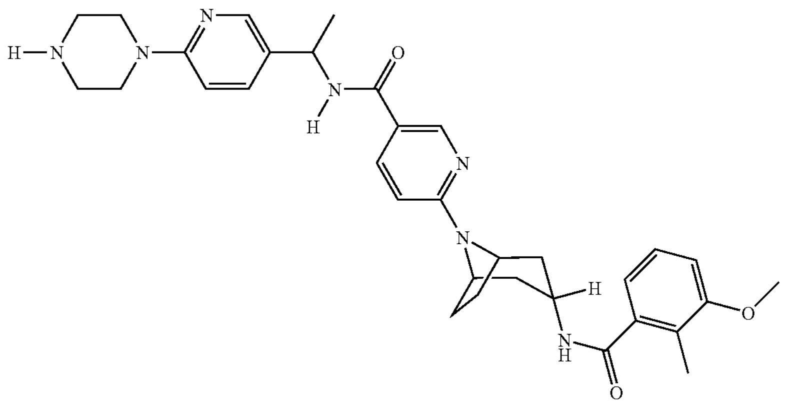 | 6-[3-endo-({[2-methyl-3-(methyloxy)phenyl]carbonyl}amino)-8-azabicyclo[3.2.1]oct-8-yl]-N-[1-(6-piperazin-1-ylpyridin-3-yl)ethyl]pyridine-3-carboxamide<br>ACTIVITY = A |
| 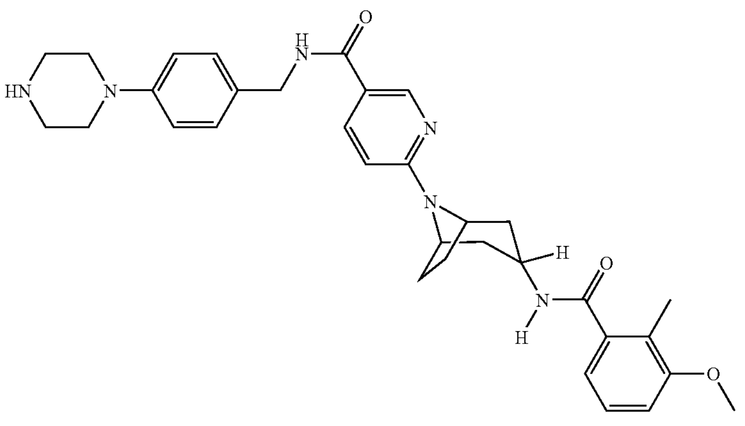 | 6-[3-endo-({[2-methyl-3-(methyloxy)phenyl]carbonyl}amino)-8-azabicyclo[3.2.1]oct-8-yl]-N-[(4-piperazin-1-ylphenyl)methyl]pyridine-3-carboxamide<br>ACTIVITY = A |

TABLE I-continued

| STRUCTURE | NAME & ACTIVITY |
| --- | --- |
| 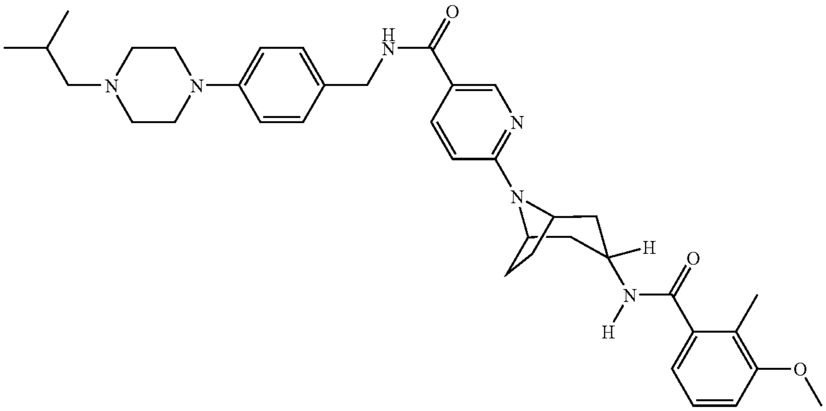 | 6-[3-endo-({[2-methyl-3-(methyloxy)phenyl]carbonyl}amino)-8-azabicyclo[3.2.1]oct-8-yl]-N-({4-[4-(2-methylpropyl)piperazin-1-yl]phenyl}methyl)pyridine-3-carboxamide<br>ACTIVITY = A |
| 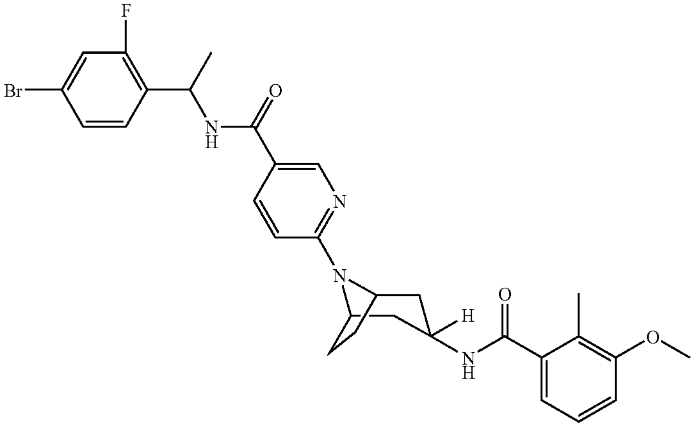 | N-[1-(4-bromo-2-fluorophenyl)ethyl]-6-[3-endo-({[2-methyl-3-(methyloxy)phenyl]carbonyl}amino)-8-azabicyclo[3.2.1]oct-8-yl]pyridine-3-carboxamide<br>ACTIVITY= D |
| 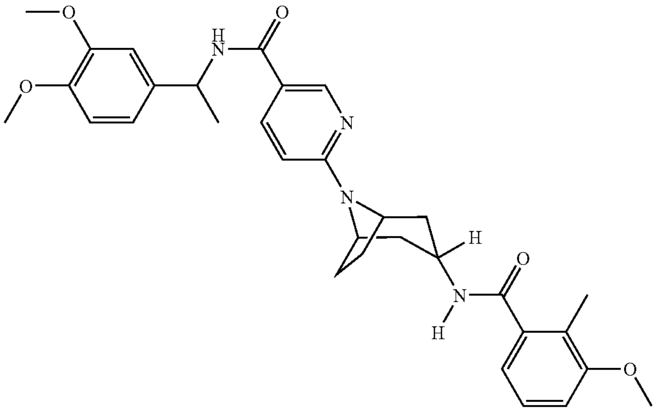 | N-{1-[3,4-bis(methyloxy)phenyl]ethyl}-6-[3-endo-({[2-methyl-3-(methyloxy)phenyl]carbonyl}amino)-8-azabicyclo[3.2.1]oct-8-yl]pyridine-3-carboxamide<br>ACTIVITY = B |

TABLE I-continued

| STRUCTURE | NAME & ACTIVITY |
|---|---|
| 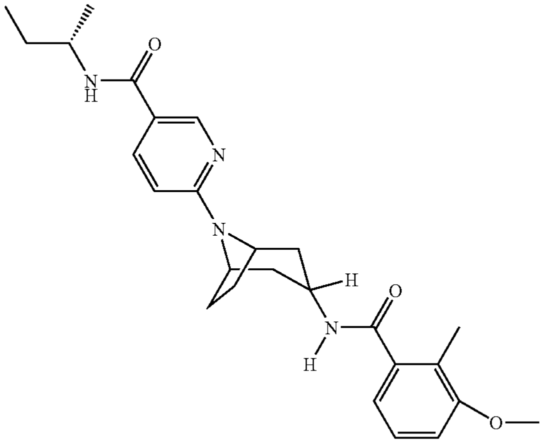 | 6-[3-endo-({[2-methyl-3-(methyloxy)phenyl]carbonyl}amino)-8-azabicyclo[3.2.1]oct-8-yl]-N-[(1S)-1-methylpropyl]pyridine-3-carboxamide<br>ACTIVITY = D |
| 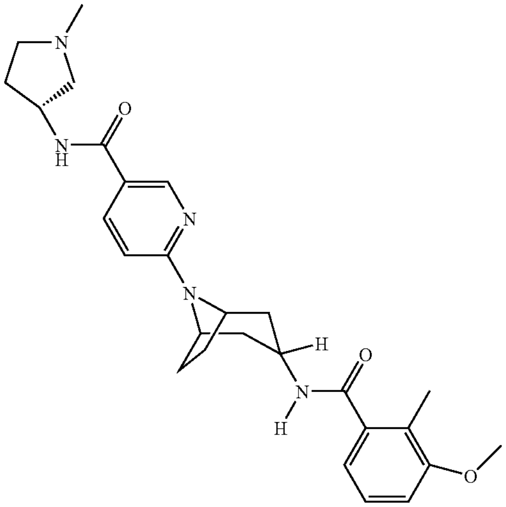 | 6-[3-endo-({[2-methyl-3-(methyloxy)phenyl]carbonyl}amino)-8-azabicyclo[3.2.1]oct-8-yl]-N-[(3R)-1-methylpyrrolidin-3-yl]pyridine-3-carboxamide<br>ACTIVITY = A |
| 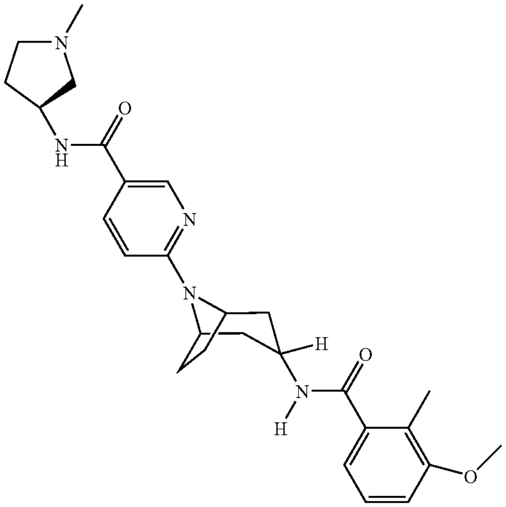 | 6-[3-endo-({[2-methyl-3-(methyloxy)phenyl]carbonyl}amino)-8-azabicyclo[3.2.1]oct-8-yl]-N-[(3S)-1-methylpyrrolidin-3-yl]pyridine-3-carboxamide<br>ACTIVITY = C |

TABLE I-continued
| STRUCTURE | NAME & ACTIVITY |
| --- | --- |
| 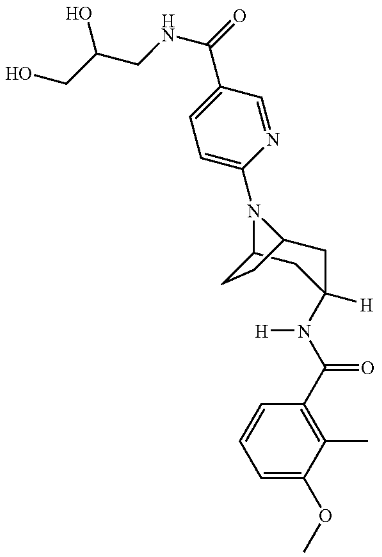 | N-(2,3-dihydroxypropyl)-6-[3-endo-({[2-methyl-3-(methyloxy)phenyl]carbonyl}amino)-8-azabicyclo[3.2.1]oct-8-yl]pyridine-3-carboxamide<br>ACTIVITY = C |
| 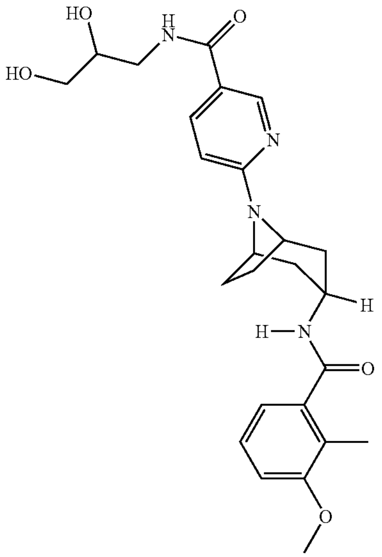 | N-[(1S,2S)-2-hydroxycyclopentyl]-6-[3-endo-({[2-methyl-3-(methyloxy)phenyl]oarbonyl}amino)-8-azabicyclo[3.2.1]oct-8-yl]pyridine-3-carboxamide<br>ACTIVITY = B |

TABLE I-continued
| STRUCTURE | NAME & ACTIVITY |
| --- | --- |
| 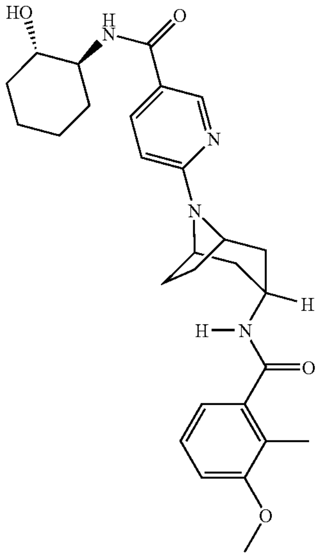 | N-[(1S,2S)-2-hydroxycyclohexyl]-6-[3-endo-({[2-methyl-3-(methyloxy)phenyl]carbonyl}amino)-8-azabicyclo[3.2.1]oct-8-yl]pyridlne-3-carboxamide<br>ACTIVITY = D |
| 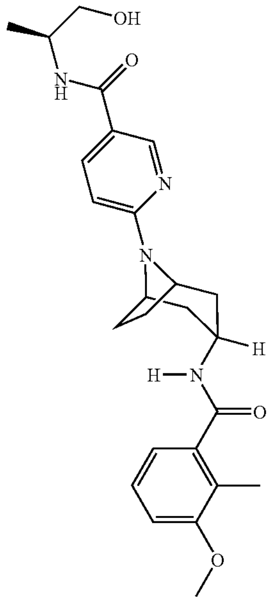 | N-[(1S)-2-hydroxy-1-methylethyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = C |

TABLE I-continued

| STRUCTURE | NAME & ACTIVITY |
| --- | --- |
| 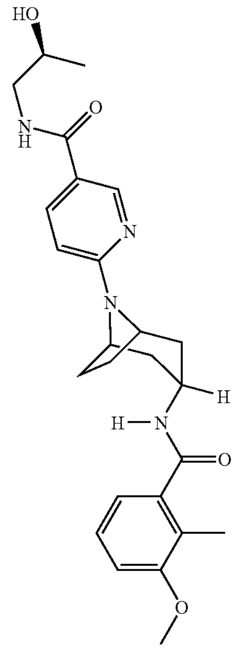 | N-[(2S)-2.hydroxypropyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = D |
| 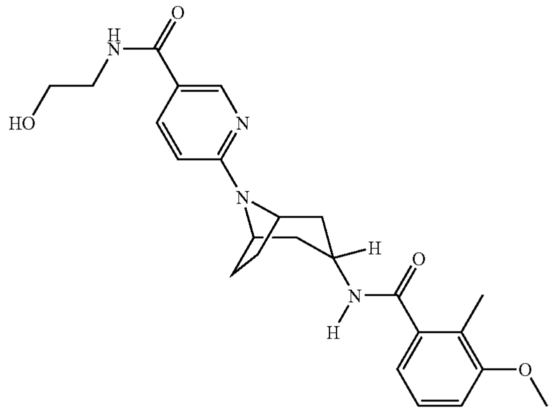 | N-(2-hydroxyethyl)-6-[3-endo-({[2-methyl-3-(methyloxy)phenyl]carbonyl}amino)-8-azabicyclo[3.2.1]oct-8-yl]pyridine-3-carboxamide<br>ACTIVITY = D |
| 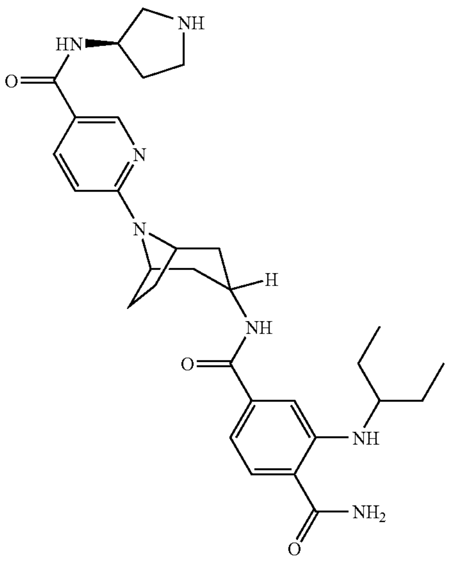 | 2-[(1-ethylpropyl)amino]-N4-[8-(5-{[(3R)-pyrrolidin-3-ylamino]carbonyl}pyridin-2-yl)-8-azabicyclo[3.2.1]oct-3-endo-yl]benzene-1,4-dicarboxamide<br>ACTIVITY = A |

TABLE I-continued
| STRUCTURE | NAME & ACTIVITY |
|---|---|
| 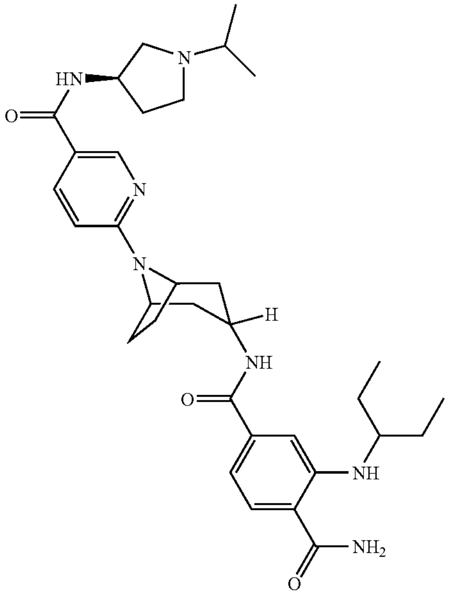 | 2-[(1-ethylpropyl)amino]-N4-{8-[5-({[(3R)-1-(1-methylethyl)pyrrolidin-3-yl]amino}carbonyl)pyridin-2-yl]-8-azabicyclo[3.2.1]oct-3-endo-yl}benzene-1,4-dicarboxamide ACTIVITY = A |
| 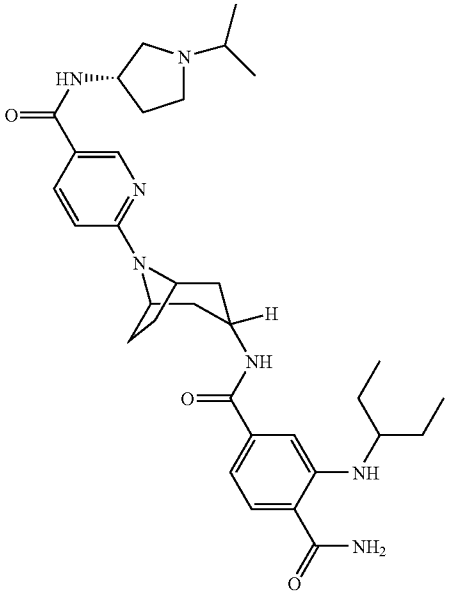 | 2-[(1-ethylpropyl)amino]-N4-{8-[5-({[(3S)-1-(1-methylethyl)pyrrolidin-3-yl]amino}carbonyl)pyridin-2-yl]-8-azabicyclo[3.2.1]oct-3-endo-yl}benzene-1,4-dicarboxamide ACTIVITY= A |

TABLE I-continued
| STRUCTURE | NAME & ACTIVITY |
|---|---|
| 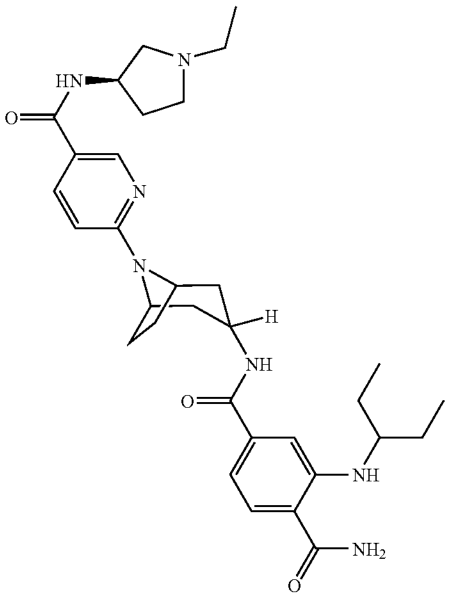 | 2-[(1-ethylpropyl)amino]-N4-{8-[5-({[(3R)-1-ethylpyrrolidin-3-yl]amino}carbonyl)pyridin-2-yl]-8-azabicyclo[3.2.1]oct-3-endo-yl}benzene-1,4-dicarboxamide ACTIVITY = A |
| 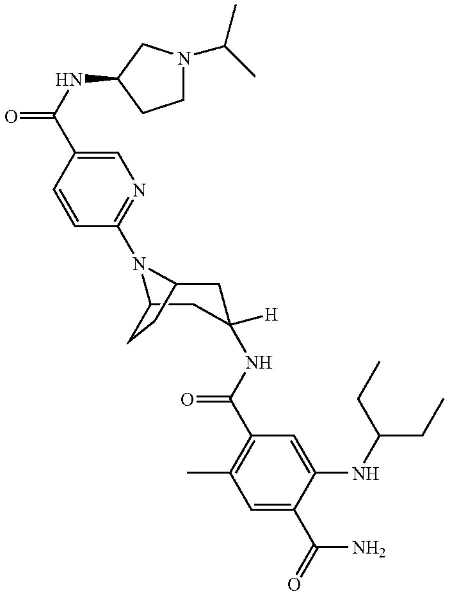 | 5-[(1-ethylpropyl)amino]-2-methyl-N-{8-[5-({[(3R)-1-(1-methylethyl)pyrrolidin-3-yl]amino}carbonyl)pyridin-2-yl]-8-azabicyclo[3.2.1]oct-3-endo-yl}benzene-1,4-dicarboxamide ACTIVITY = A |

TABLE I-continued

| STRUCTURE | NAME & ACTIVITY |
|---|---|
| 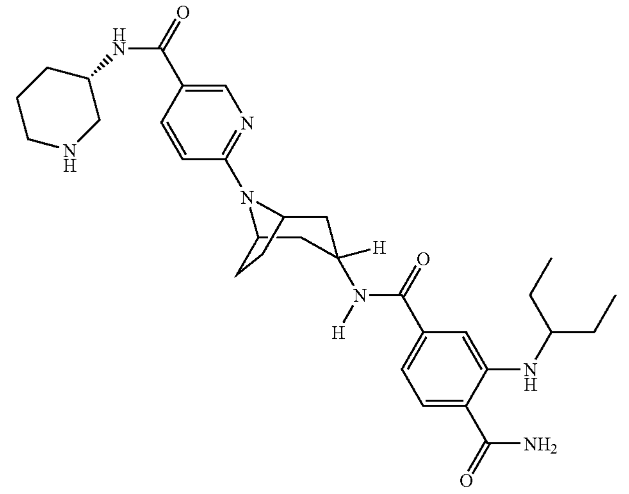 | 2-[(1-ethylpropyl)amino]-N4-[8-(5-{[(3S)-piperidin-3-ylamino]carbonyl}pyridin-2-yl)-8-azabicyclo[3.2.1]oct-3-endo-yl]benzene-1,4-dicarboxamide ACTIVITY = A |
| 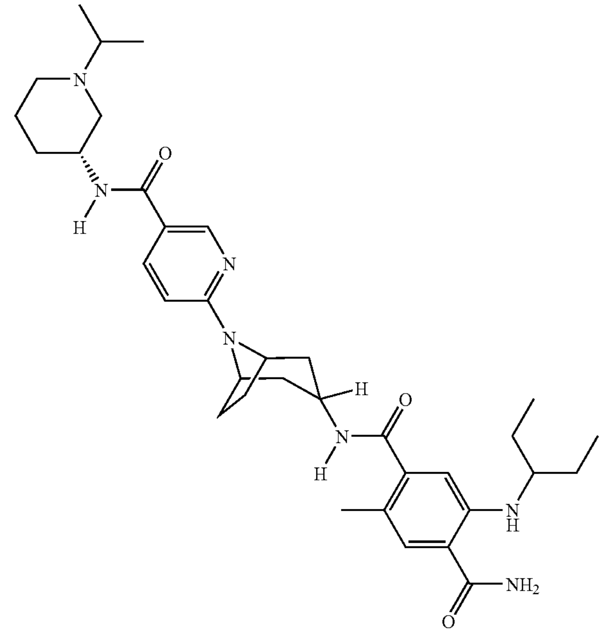 | 5-[(1-ethylpropyl)amino]-2-methyl-N-{8-[5-({[(3R)-1-(1-methylethyl)piperidin-3-yl]amino}carbonyi)pyridin-2-yl]-8-azabicyclo[3.2.1]oct-3-endo-yl}benzene-1,4-dicarboxamide ACTIVITY = A |
| 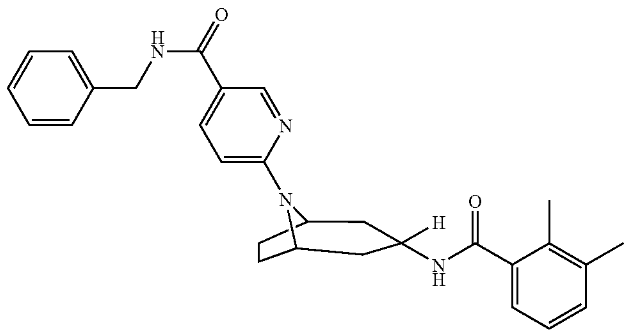 | 6-(3-endo-{[(2,3-dimethylphenyl)carbonyl]amino}-8-azabicyclo[3.2.1]oct-8-yl)-N-(phenylmethyl)pyridine-3-carboxamide ACTIVITY = D |

TABLE I-continued

| STRUCTURE | NAME & ACTIVITY |
| --- | --- |
| 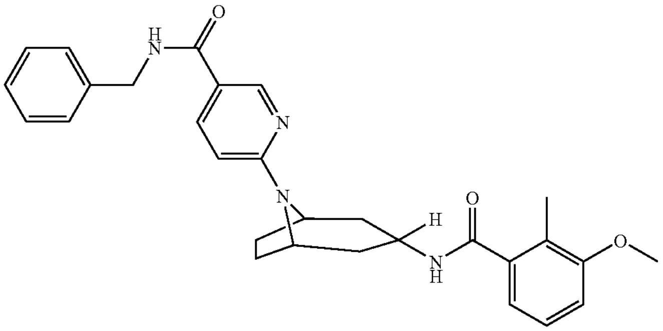 | 6-[3-endo-({[2-methyl-3-(methyloxy)phenyl]carbonyl}amino)-8-azabicyclo[3.2.1]oct-8-yl]-N-(phenylmethyl)pyridine-3-carboxamide<br>ACTIVITY = A |
| 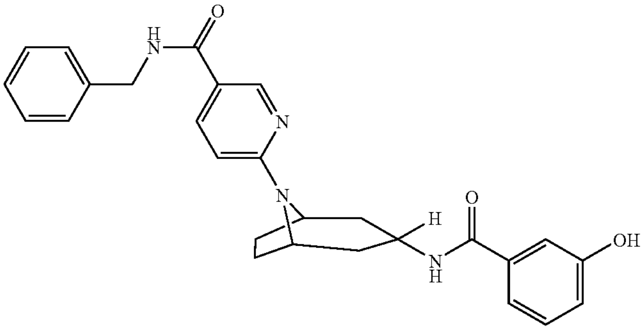 | 6-(3-endo-{[(3-hydroxy-2-methylphenyl)carbonyl]amino}-8-azabicyclo[3.2.1]oct-8-yl)-N-(phenylmethyl)pyridine-3-carboxamide<br>ACTIVITY = C |
| 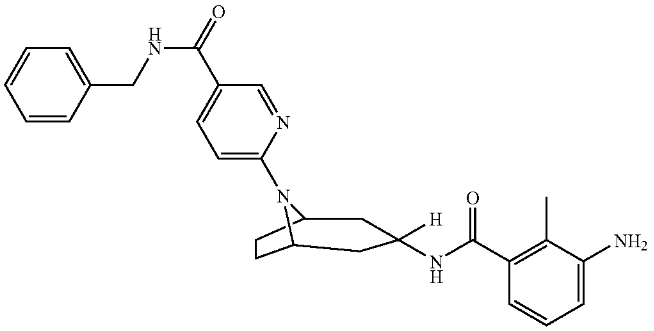 | 6-(3-endo-{[(3-amino-2-methylphenyl)carbonyl]amino}-8-azabicyclo[3.2.1]oct-8-yl)-N-(phenylmethyl)pyridine-3-carboxamide<br>ACTIVITY = D |
| 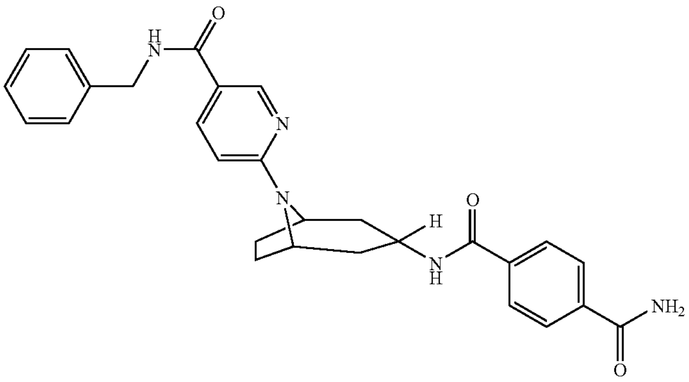 | N-[8-(5-{[(phenylmethyl)amino]carbonyl}pyridin-2-yl)-8-azabicyclo[3.2.1]oct-3-endo-yl]benzene-1,4-dicarboxamide<br>ACTIVITY = A |

TABLE I-continued

| STRUCTURE | NAME & ACTIVITY |
|---|---|
| 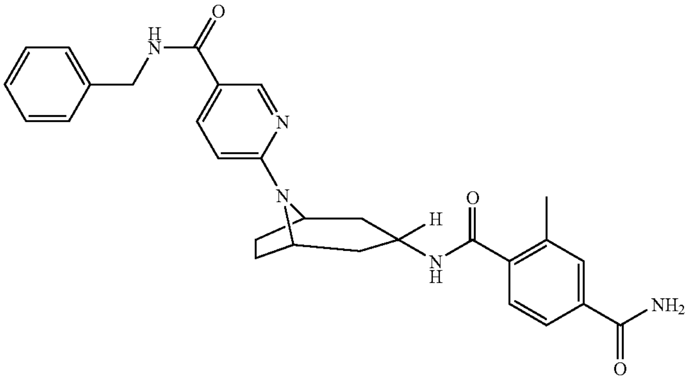 | 2-methyl-N 1-[8-(5-{[(phenylmethyl)amino]carbonyl}pyridin-2-yl)-8-azabicyclo[3.2.1]oct-3-endo-yl]benzene-1,4-dicarboxamide ACTIVITY = B |
| 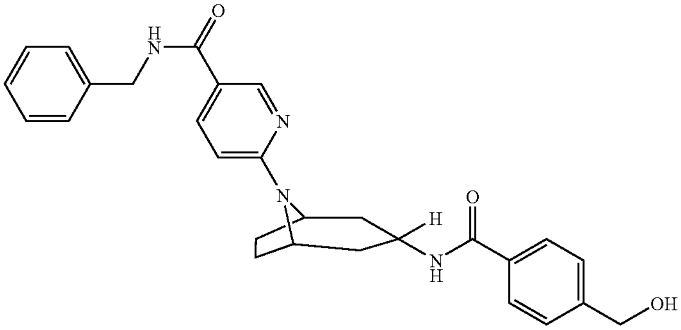 | 6-[3-endo-({[4-(hydroxymethyl)phenyl]carbonyl}amino)-8-azabicyclo[3.2.1]oct-8-yl]-N-(phenylmethyl)pyridine-3-carboxamide ACTIVITY = A |
| 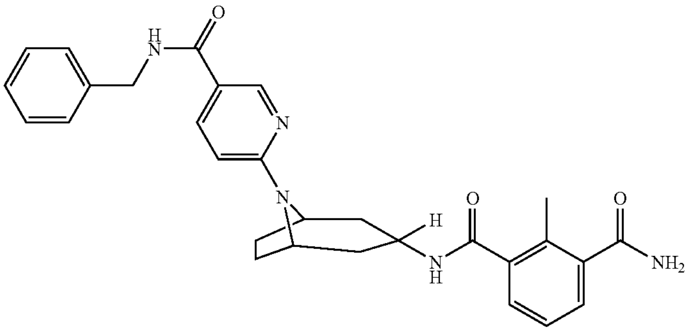 | 2-methyl-N-[8-(5-{[(phenylmethyl)amino]carbonyl}pyridin-2-yl)-8-azabicyclo[3.2.1]oct-3-endo-yl]benzene-1,3-dicarboxamide ACTIVITY = D |

TABLE I-continued
| STRUCTURE | NAME & ACTIVITY |
|---|---|
| 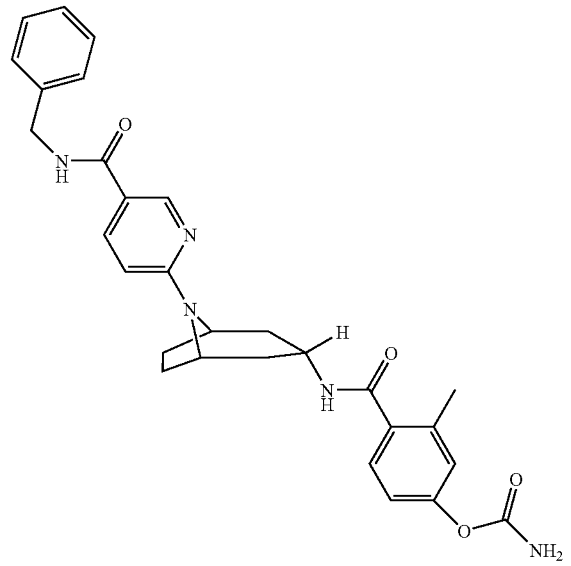 | 3-methyl-4-({[8-(5-{[(phenylmethyl)amino]carbonyl}pyridin-2-yl)-8-azabicyclo[3.2.1]oct-3-endo-yl]amino}carbonyl)phenyl carbamate<br>ACTIVITY = D |
| 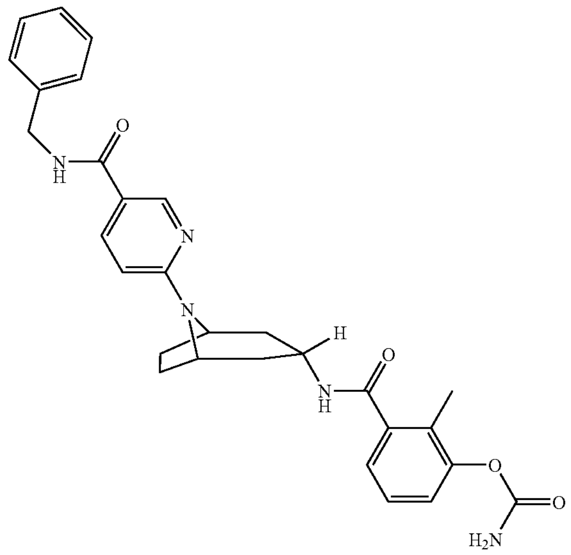 | 2-methyl-3-({[8-(5-{[(phenylmethyl)amino]carbonyl}pyridin-2-yl)-8-azabicyclo[3.2.1]oct-3-endo-yl]amino}carbonyl)phenyl carbamate<br>ACTIVITY = D |

TABLE I-continued
| STRUCTURE | NAME & ACTIVITY |
| --- | --- |
| 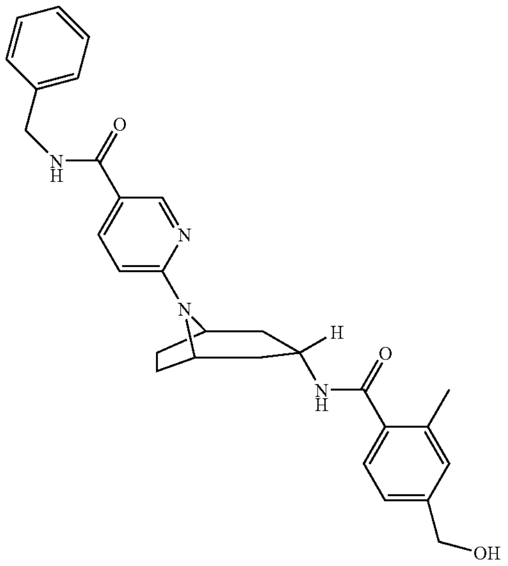 | 6-[3-endo-({[4-(hydroxymethyl)-2-methylphenyl]carbonyl}amino)-8-azabicyclo[3.2.1]oct-8-yl]-N-(phenylmethyl)pyridine-3-carboxamide ACTIVITY = A |
| 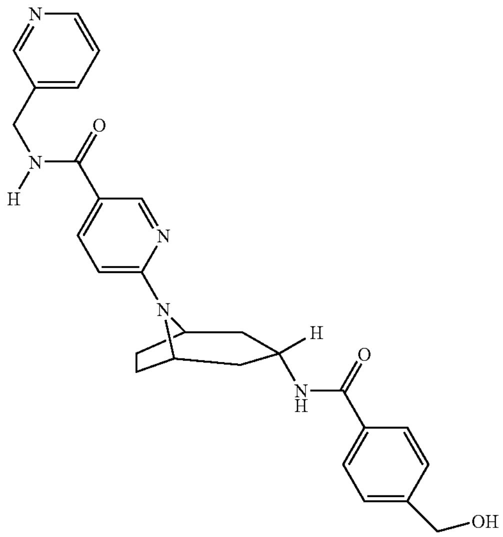 | 6-[3-endo-({[4-(hydroxymethyl)phenyl]carbonyl}amino)-8-azabicyclo[3.2.1]oct-8-yl]-N-(pyridin-3-ylmethyl)pyridine-3-carboxamide ACTIVITY = A |

TABLE I-continued
| STRUCTURE | NAME & ACTIVITY |
| --- | --- |
| 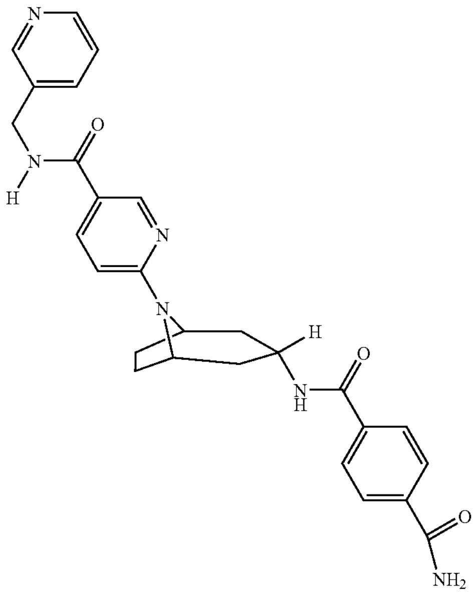 | N-[8-(5-{[(pyridin-3-ylmethyl)amino]carbonyl}pyridin-2-yl)-8-azabicyclo[3.2.1]oct-3-endo-yl]benzene-1,4-dicarboxamide ACTIVITY = A |
| 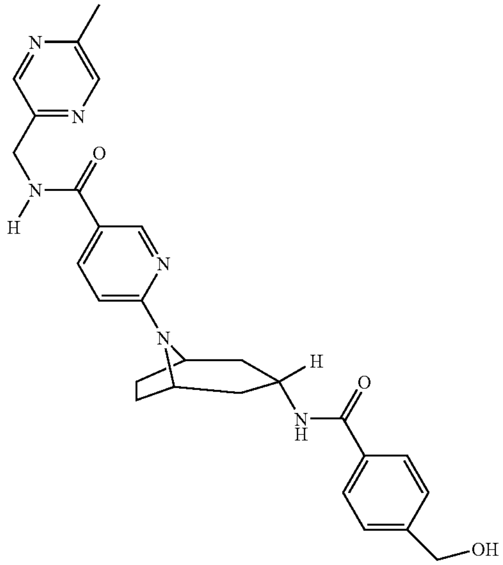 | 6-[3-endo-({[4-(hydroxymethyl)phenyl]carbonyl}amino)-8-azabicyclo[3.2.1]oct-8-yl]-N-[(5-methylpyrazin-2-yl)methyl]pyridine-3-carboxamide ACTIVITY = A |

TABLE I-continued
| STRUCTURE | NAME & ACTIVITY |
| --- | --- |
| 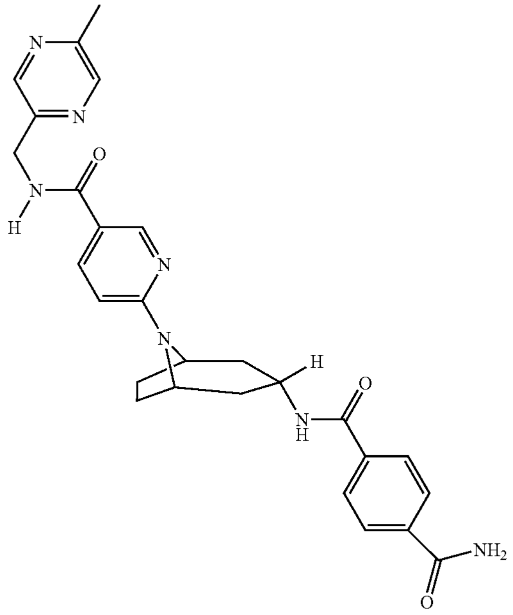 | N-{8-[5-({[(5-methylpyrazin-2-yl)methyl]amino}carbonyl)pyridin-2-yl]-8-azabicyclo[3.2.1]oct-3-endo-yl}benzene-1,4-dicarboxamide<br>ACTIVITY = C |
| 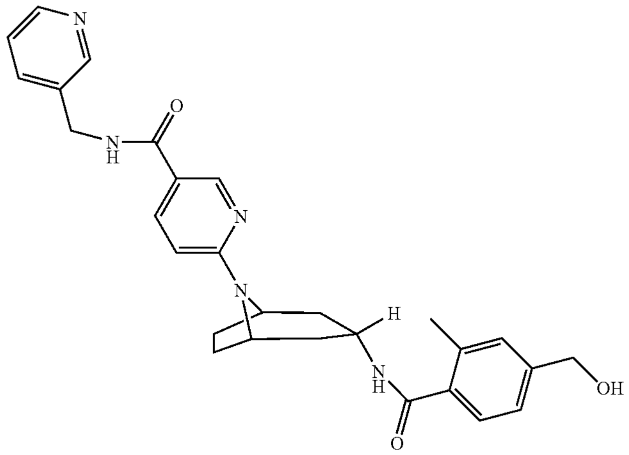 | 6-[3-endo-({[4-(hydroxymethyl)-2-methylphenyl]carbonyl}amino)-8-azabicyclo[3.2.1]oct-8-yl]-N-(pyridin-3-ylmethyl)pyridine-3-carboxamide<br>ACTIVITY = A |

TABLE I-continued
| STRUCTURE | NAME & ACTIVITY |
| --- | --- |
| 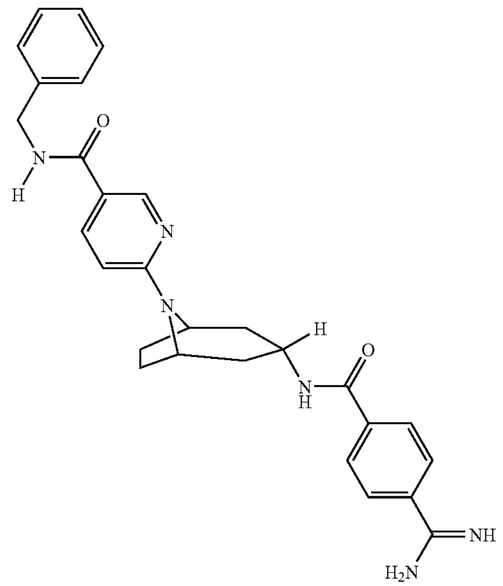 | 6-{3-endo-[({4-[amino(imino)methyl]phenyl}carbonyl)amino]-8-azabicyclo[3.2.1]oct-8-yl}-N-(phenylmethyl)pyridine-3-carboxamide ACTIVITY = D |
| 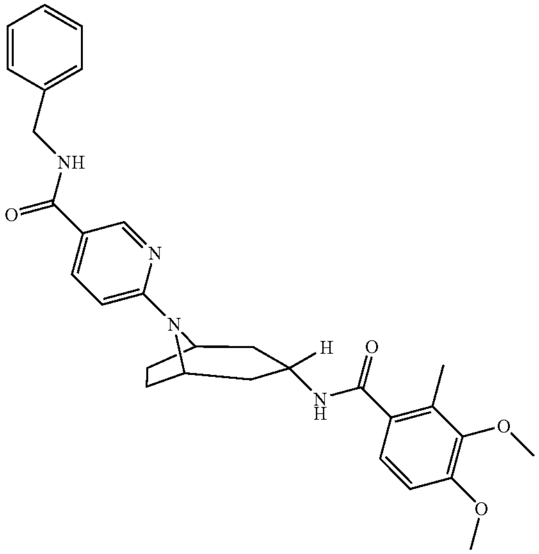 | 6-[3-endo-({[2-methyl-3,4-bis(methyloxy)phenyl]carbonyl}amino)-8-azabicyclo[3.2.1]oct-8-yl]-N-(phenylmethyl)pyridine-3-carboxamide ACTIVITY = D |

TABLE I-continued

| STRUCTURE | NAME & ACTIVITY |
|---|---|
| 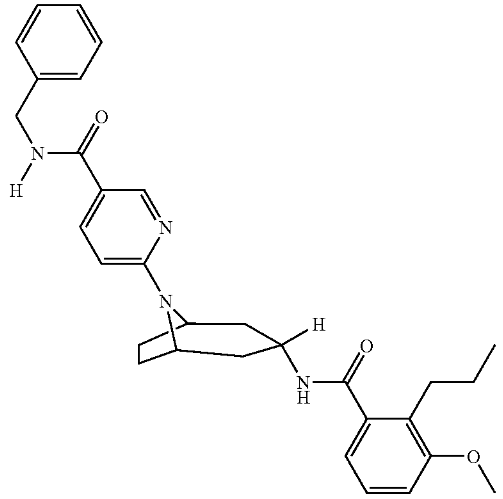 | 6-[3-endo-({[3-(methyloxy)-2-propylphenyl]carbonyl}amino)-8-azabicyclo[3.2.1]oct-8-yl]-N-(phenylmethyl)pyridine-3-carboxamide<br>ACTIVITY = D |
| 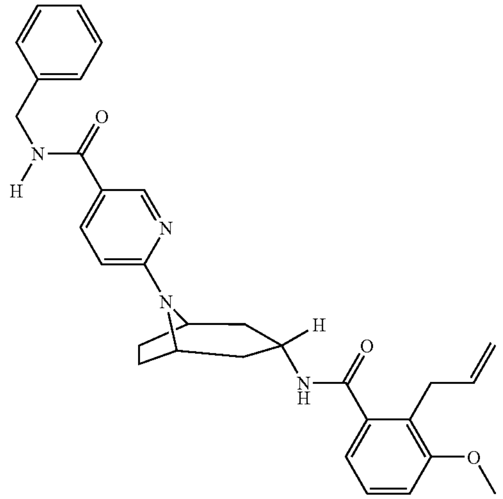 | 6-[3-endo-({[3-(methyloxy)-2-prop-2-en-1-ylphenyl]carbonyl}amino)-8-azabicyclo[3.2.1]oct-8-yl]-N-(phenylmethyl)pyridine-3-carboxamide<br>ACTIVITY = B |
| 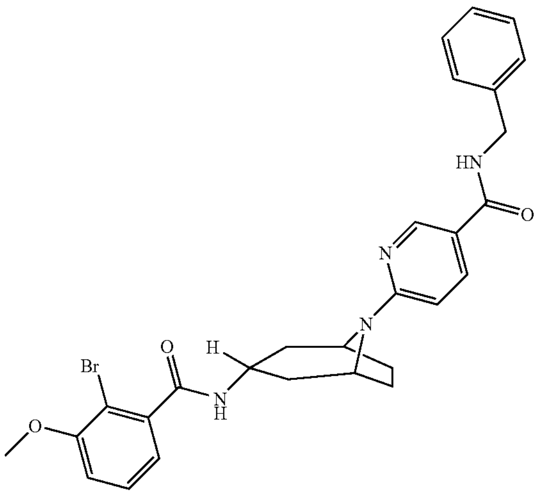 | 6-[3-endo-({[2-bromo-3-(methyloxy)phenyl]carbonyl}amino)-8-azabicyclo[3.2.1]oct-8-yl]-N-(phenylmethyl)pyridine-3-carboxamide<br>ACTIVITY = C |

TABLE I-continued
| STRUCTURE | NAME & ACTIVITY |
| --- | --- |
| 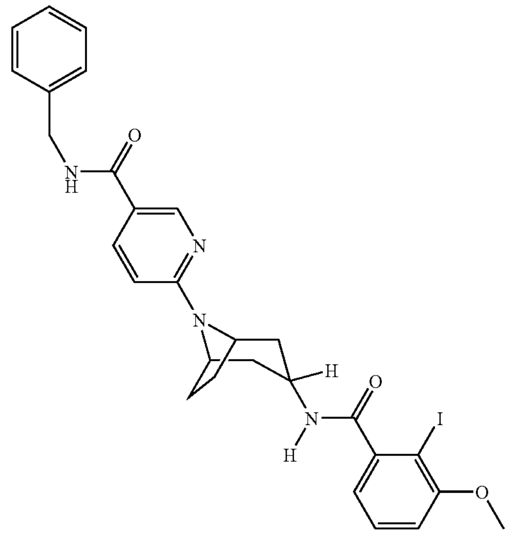 | 6-[3-endo-({[2-iodo-3-(methyloxy)phenyl]carbonyl}amino)-8-azabicyclo[3.2.1]oct-8-yl]-N-(phenylmethyl)pyridine-3-carboxamide<br>ACTIVITY = D |
| 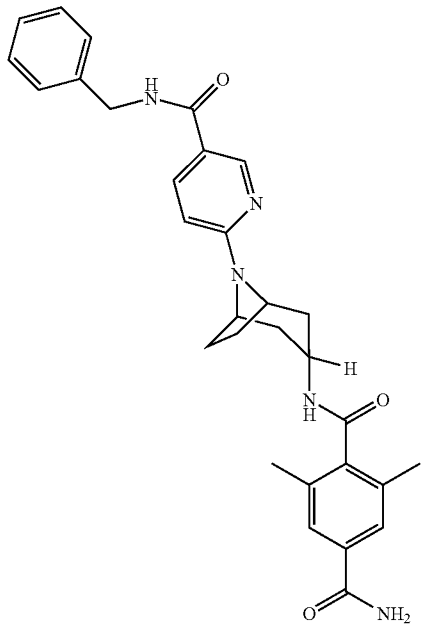 | 2,6-dimethyl-N1-[8-(5-{[(phenylmethyl)amino]carbonyl}pyridin-2-yl)-8-azabicyclo[3.2.1]oct-3-endo-yl]benzene-1,4-dicarboxamide<br>ACTIVITY = B |

TABLE I-continued
| STRUCTURE | NAME & ACTIVITY |
|---|---|
| 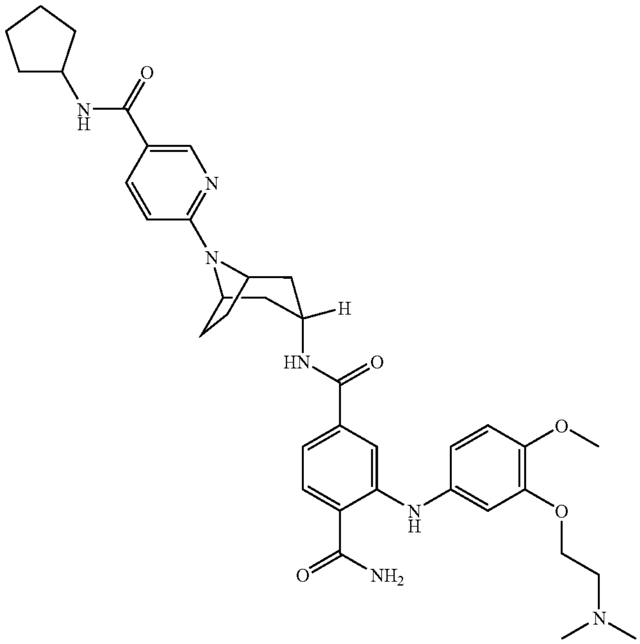 | N4-(8-[5-[(cyclopentylamino)carbonyl]pyridin-2-yl}-8-azabicyclo[3.2.1]oct-3-endo-(dimethylamino)ethyl]oxy}-4-(methyloxy)phenyl]amino}benzene-1,4-dicarboxamide<br>ACTIVITY = A |
| 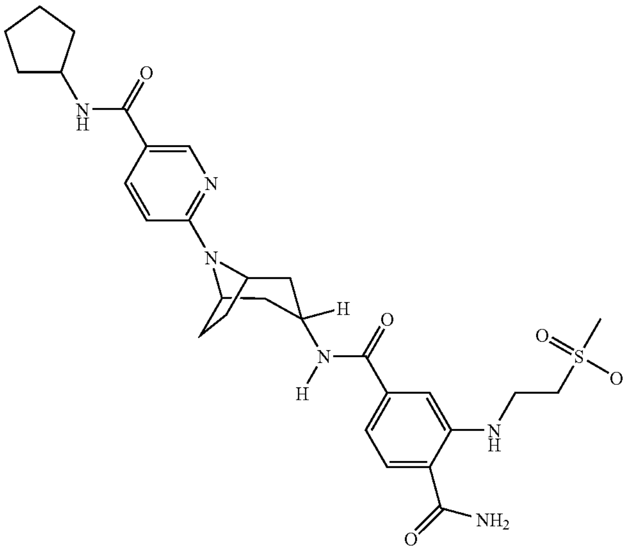 | N4-(8-{5-[(cyclopentylamino)carbonyl]pyridin-2-yl}-8-azabicyclo[3.2.1]oct-3-endo-yl)-2-{[2-(methylsulfonyl)ethyl]amino}benzene-1,4-dicarboxamide<br>ACTIVITY = A |

TABLE I-continued

| STRUCTURE | NAME & ACTIVITY |
| --- | --- |
| 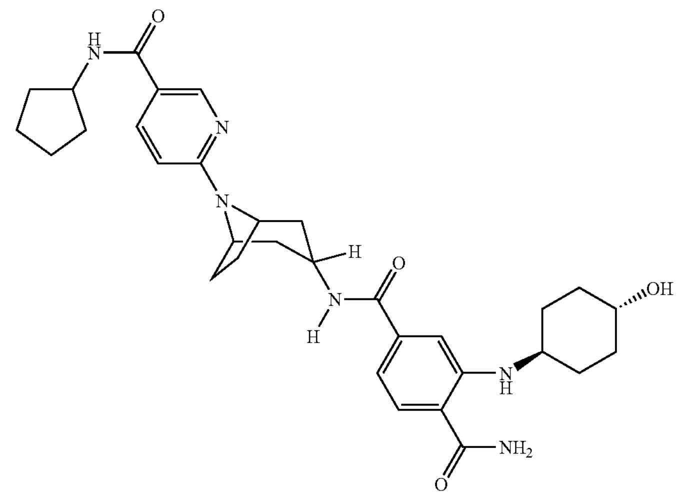 | N4-(8-{5-((cyclopentylamino)carbonyl]pyridin-2-yl}-8-azabicyclo[3.2.1]oct-3-endo-yl)-2-[(4-trans-hydroxycyclohexyl)amino]benzene-1,4-dicarboxamide<br>ACTIVITY = A |
| 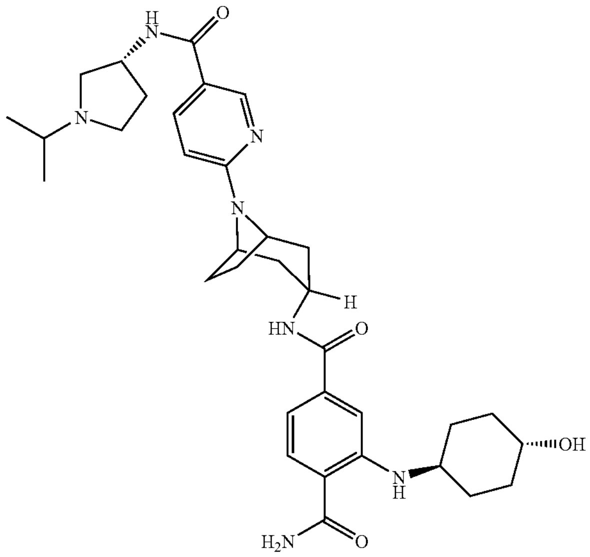 | 2-[(4-trans-hydroxycyclohexyl)amino]-N4-{8-[5-({[1-(1-methylethyl)pyrrolidin-3-yl]amino}carbonyl)pyridin-2-yl]-8-azabicyclo[3.2.1]oct-3-endo-yl}benzene-1,4-dicarboxamide<br>ACTIVITY = A |
| 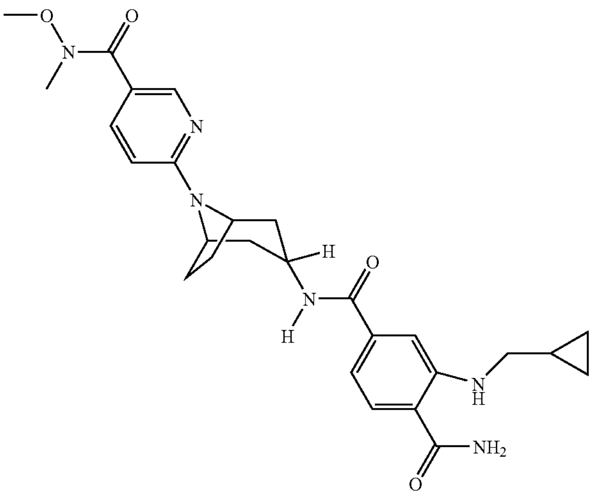 | 2-[(cyclopropylmethyl)amino]-N4-[8-(5-{[methyl(methyloxy)amino]carbonyl}pyridin-2-yl)-8-azabicyclo[3.2.1]oct-3-endo-yl]benzene-1,4-dicarboxamide<br>ACTIVITY = C |

TABLE I-continued

| STRUCTURE | NAME & ACTIVITY |
|---|---|
| 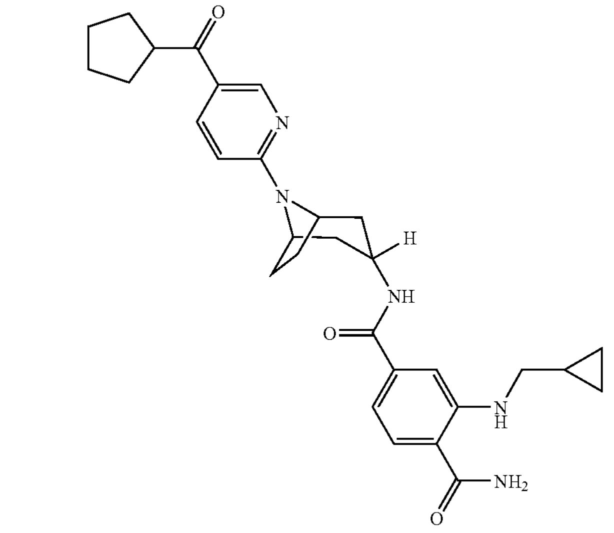 | N4-(8-{5-[(cyclopentylamino)carbonyl]pyridin-2-yl}-8-azabicyclo[3.2.1]oct-3-endo-yl)-2-[(cyclopropylmethyl)amino]benzene-1,4-dicarboxamide ACTIVITY = A |
| 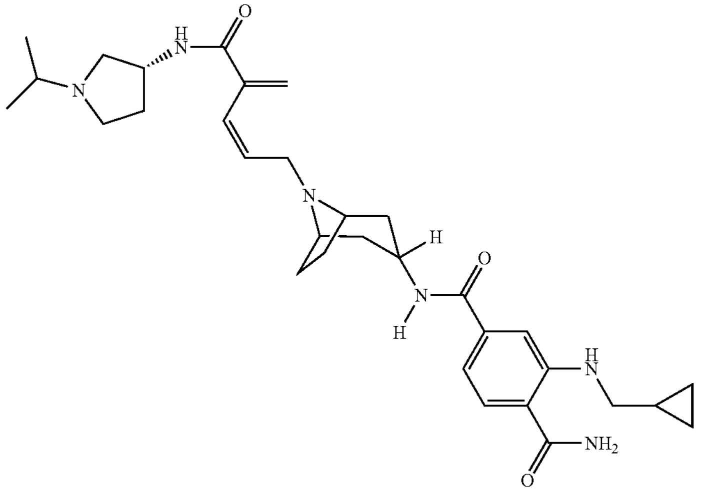 | 2-((cyclopropylmethyl)amino]-N4-{8-[5-({[(3R)-1-(1-methylethyl)pyrrolidin-3-yl]amino}carbonyl)pyridin-2-yl]-8-azabicyclo[3.2.1]oct-3-endo-yl}benzene-1,4-dicarboxamide ACTIVITY = A |
| 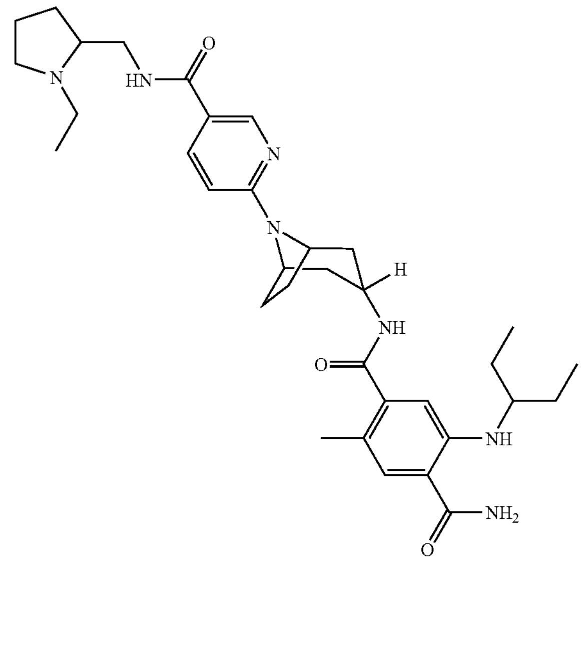 | 5-[(1-ethylpropyl)amino]-N-{8-[5-({[(1-ethylpyrrolidin-2-yl)methyl]amino}carbonyl)pyridin-2-yl]-8-azabicyclo[3.2.1]oct-3-endo-yl}-2-methylbenzene-1,4-dicarboxamide ACTIVITY = A |

TABLE I-continued

| STRUCTURE | NAME & ACTIVITY |
| --- | --- |
| 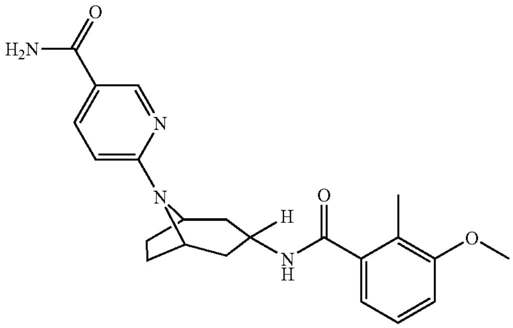 | 6-[3-endo-({[2-methyl-3-(methyloxy)phenyl]carbonyl}amino)-8-azabicyclo[3.2.1]oct-8-yl]pyridine-3-carboxamide<br>ACTIVITY = B |
| 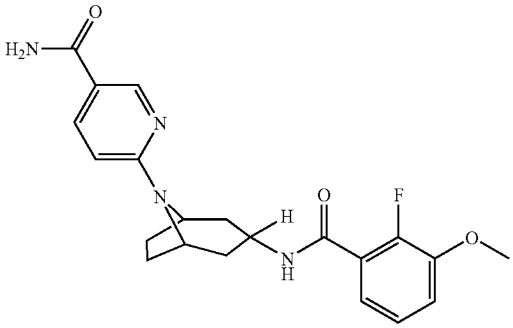 | 6-[3-endo-({[2-fluoro-3-(methyloxy)phenyl]carbonyl}amino)-8-azabicyclo[3.2.1]oct-8-yl]pyridine-3-carboxamide<br>ACTIVITY = D |
| 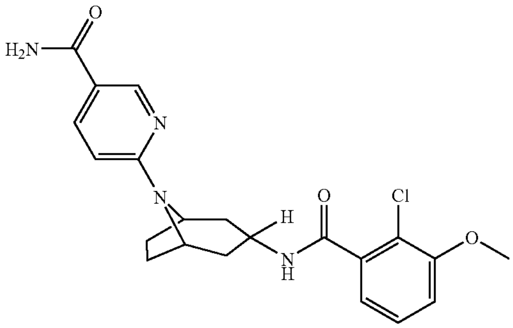 | 6-[3-endo-({[2-chloro-3-(methyloxy)phenyl]carbonyl}amino)-8-azabicyclo[3.2.1]oct-8-yl]pyridine-3-carboxamide<br>ACTIVITY = D |
| 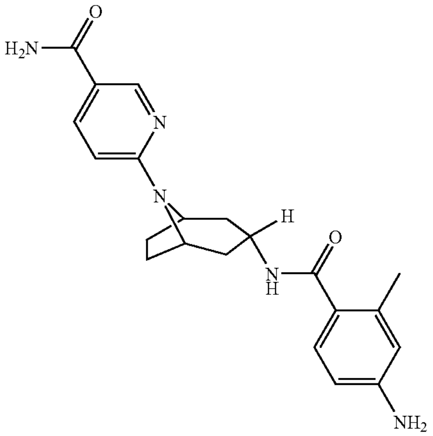 | 6-(3-endo-{[(4-amino-2-methylphenyl)carbonyl]amino}-8-azabicyclo[3.2.1]oct-8-yl)pyridine-3-carboxamide<br>ACTIVITY = D |

TABLE I-continued
| STRUCTURE | NAME & ACTIVITY |
| --- | --- |
| 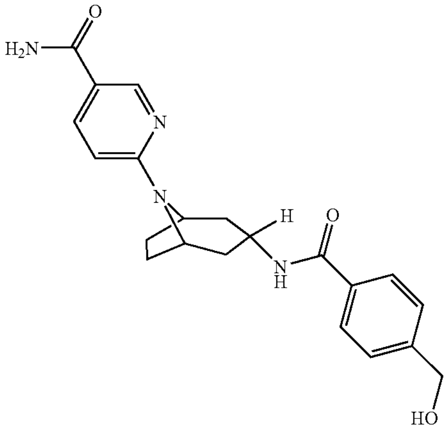 | 6-[3-endo-({[4-(hydroxymethyl)phenyl]carbonyl}amino)-8-azabicyclo[3.2.1]oct-8-yl]pyridine-3-carboxamide<br>ACTIVITY = A |
| 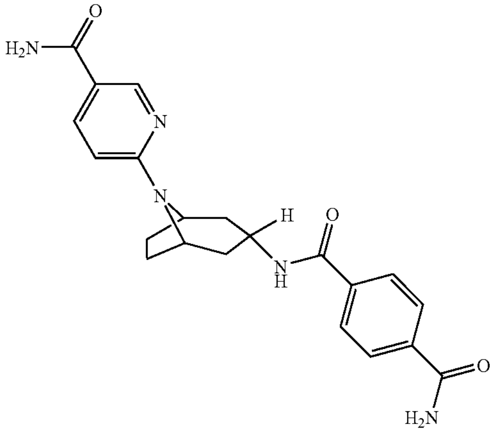 | N-{8-[5-(aminocarbonyl)pyridin-2-yl]-8-azabicyclo[3.2.1]oct-3-endo-yl}benzene-1,4-dicarboxamide<br>ACTIVITY = C |
| 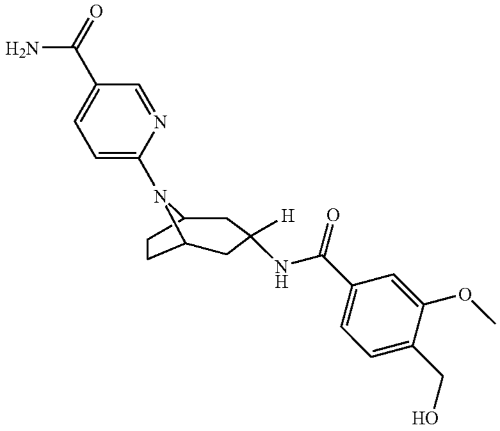 | 6-[3-endo-({[4-(hydroxymethyl)-3-(methyloxy)phenyl]carbonyl}amino)-8-azabicyclo[3.2.1]oct-8-yl]pyridine-3-carboxamide<br>ACTIVITY = B |

TABLE I-continued

| STRUCTURE | NAME & ACTIVITY |
| --- | --- |
| 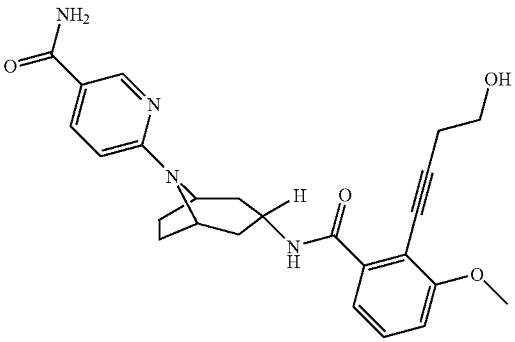 | 6-[3-endo-({[2-(4-hydroxybut-1-yn-1-yl)-3-(methyloxy)phenyl]carbonyl}amino)-8-azabicyclo[3.2.1]oct-8-yl]pyridine-3-carboxamide<br>ACTIVITY = D |
| 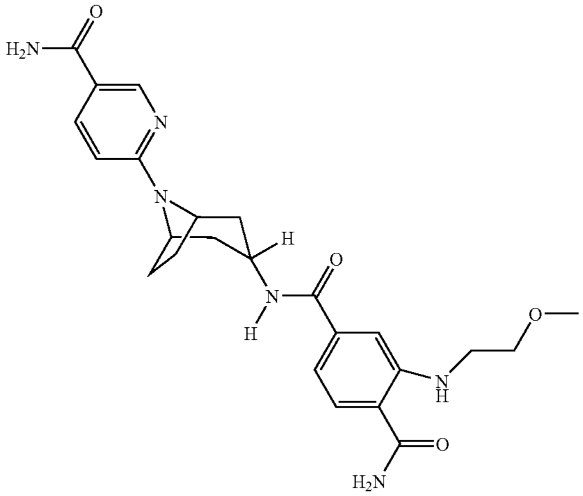 | N4-{8-[5-(aminocarbonyl)pyridin-2-yl]-8-azabicyclo[3.2.1]oct-3-endo-yl}-2-{[2-(methyloxy)ethyl]amino}benzene-1,4-dicarboxamide<br>ACTIVITY = A |
| 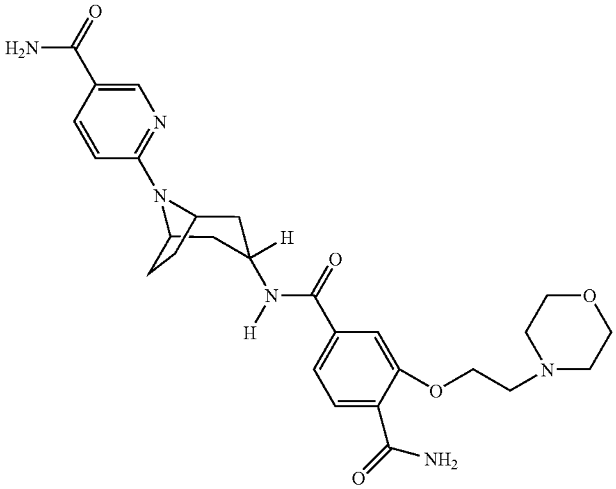 | N4-{8-[5-(aminocarbonyl)pyridin-2-yl]-8-azabicyclo[3.2.1]oct-3-endo-yl}-2-[(2-morpholin-4-ylethyl)oxybenzene-1,4-dicarboxylate<br>ACTIVITY = C |

TABLE I-continued

| STRUCTURE | NAME & ACTIVITY |
|---|---|
| 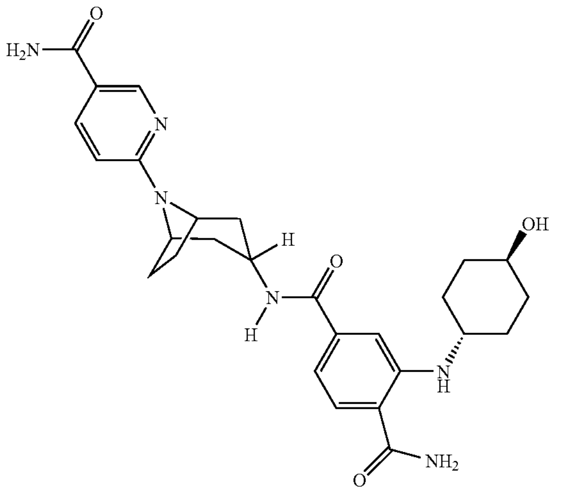 | N4-{8-[5-(aminocarbonyl)pyridin-2-yl]-8-azabicyclo[3.2.1]oct-3-endo-yl}-2-[(4-hydroxycyclohexyl)amino]benzene-1,4-dicarboxamide<br>ACTIVITY = A |
| 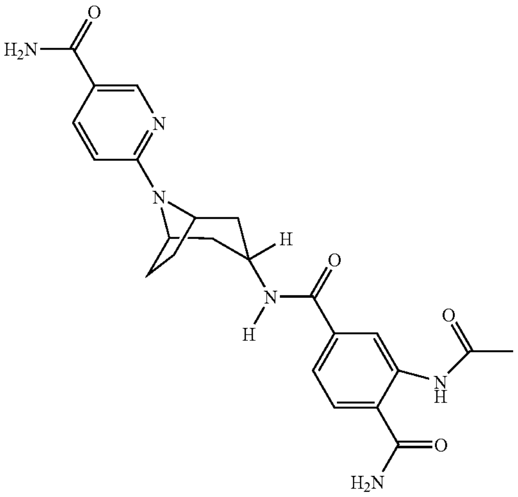 | 2-(acetylamino)-N4-{8-[5-(aminocarbonyl)pyridin-2-yl]-8-azabicyclo[3.2.1]oct-3-endo-yl}benzene-1,4-dicarboxamide<br>ACTIVITY = C |
| 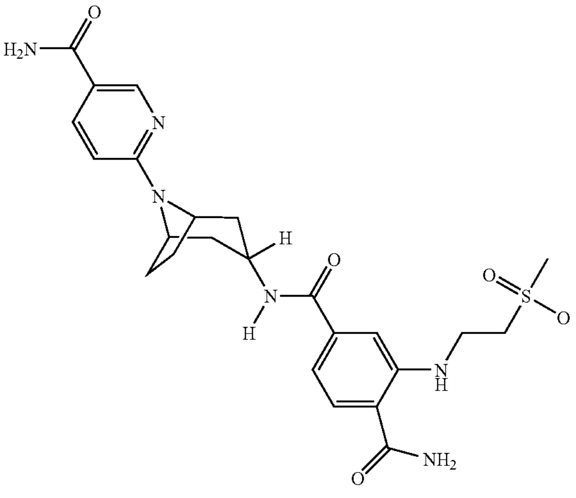 | N4-{8-[5-(aminocarbonyl)pyridin-2-yl]-8-azabicyclo[3.2.1]oct-3-endo-yl}-2-{[2-(methylsulfonyl)ethyl]amino}benzene-1,4-dicarboxamide<br>ACTIVITY = A |

TABLE I-continued

| STRUCTURE | NAME & ACTIVITY |
| --- | --- |
| 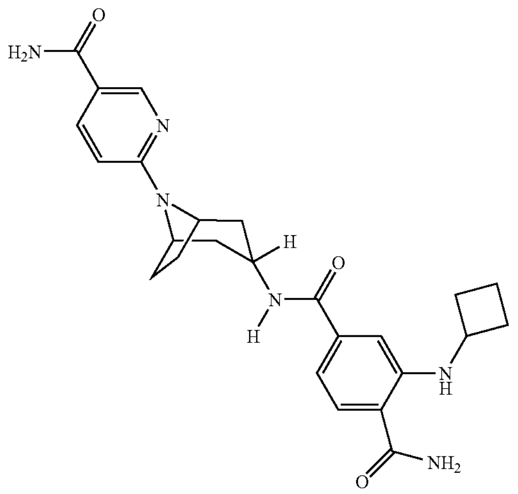 | N4-{8-[5-(aminocarbonyl)pyridin-2-yl]-8-azabicyclo[3.2.1]oct-3-endo-yl}-2-(cyclobutylamino)benzene-1,4-dicarboxamide<br>ACTIVITY = A |
| 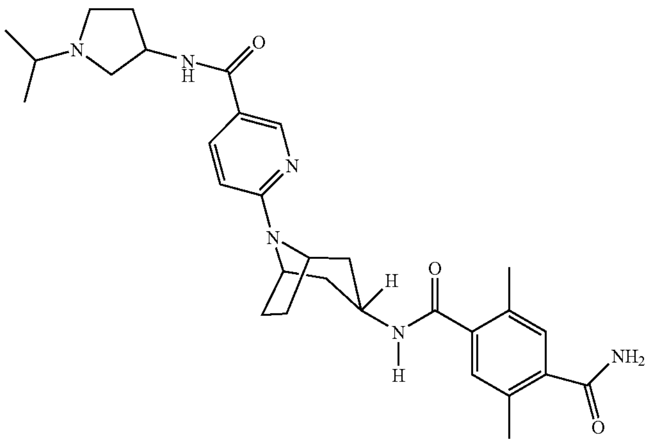 | 2,5-dimethyl-N-{8-[5-({[(3S)-1-(1-methylethyl)pyrrolidin-3-yl]amino}carbonyl)pyridin-2-yl]-8-azabicyclo[3.2.1]oct-3-endo-yl}benzene-1,4-dicarboxamide<br>ACTIVITY = A |
| 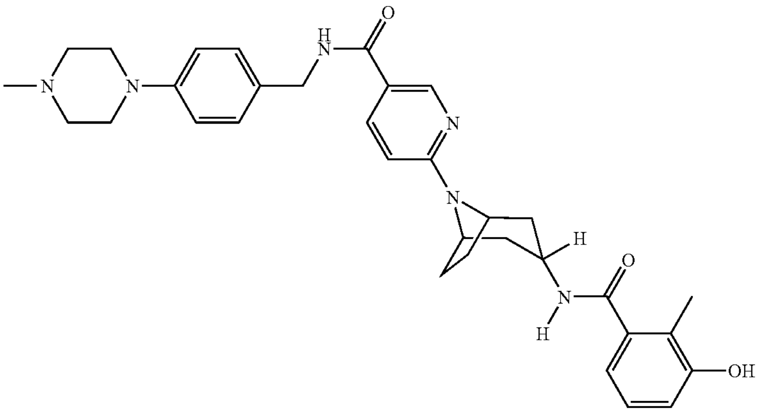 | 6-(3-endo-{[(3-hydroxy-2-methylphenyl)carbonyl]amino}-8-azabicyclo[3.2.1]oct-8-yl)-N-{(1S)-1-[4-(4-methylpiperazin-1-yl)phenyl]ethyl}pyridine-3-carboxamide<br>ACTIVITY= A |

TABLE I-continued
| STRUCTURE | NAME & ACTIVITY |
| --- | --- |
| 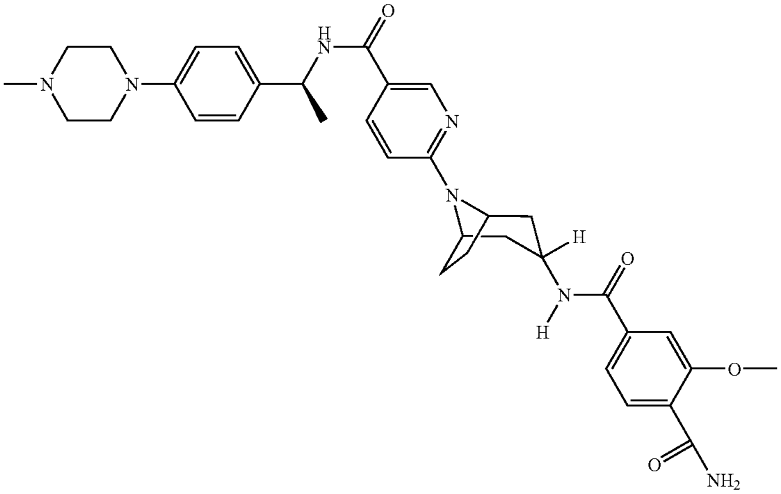 | 2-(methyloxy)-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide ACTIVITY = A |
| 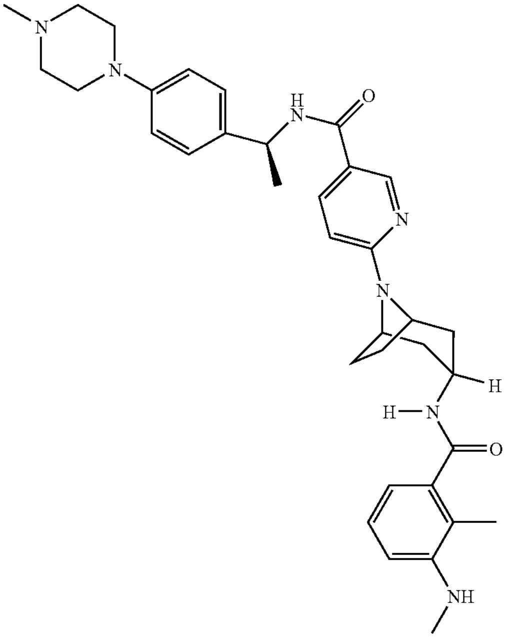 | 6-[3-endo-({[2-methyl-3-(methylamino)phenyl]carbonyl}amino)-8-azabicyclo[3.2.1]oct-8-yl]-N-{(1S)-1-[4-(4-methylpiperazin-1-yl)phenyl]ethyl}pyridine-3-carboxamide ACTIVITY = A |

TABLE I-continued

| STRUCTURE | NAME & ACTIVITY |
| --- | --- |
| 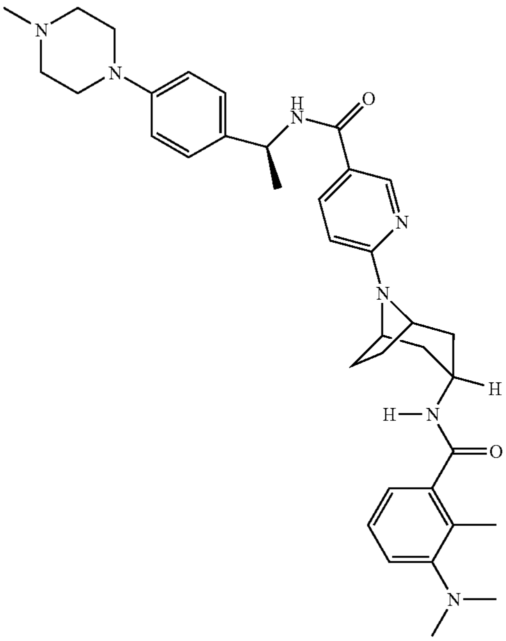 | 6-[3-endo-({[3-(dimethylamino)-2-methylphenyl]carbonyl}amino)-8-azabicyclo[3.2.1]oct-8-yl]-N-{(1S)-1-[4-(4-methylpiperazin-1-yl)phenyl]ethyl}pyridine-3-carboxamide ACTIVITY = D |
| 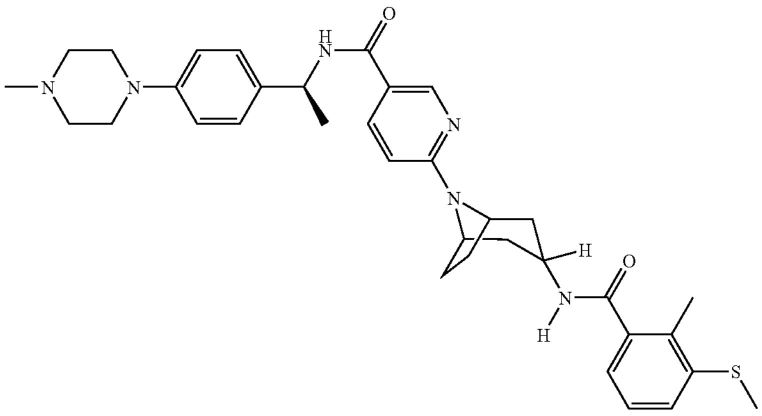 | 6-[3-endo-({[2-methyl-3-(methylthio)phenyl]carbonyl}amino)-8-azabicyclo[3.2.1]oct-8-yl]-N-{(1S)-1-[4-(4-methylpiperazin-1-yl)phenyl]ethyl}pyridine-3-carboxamide ACTIVITY = B |
| 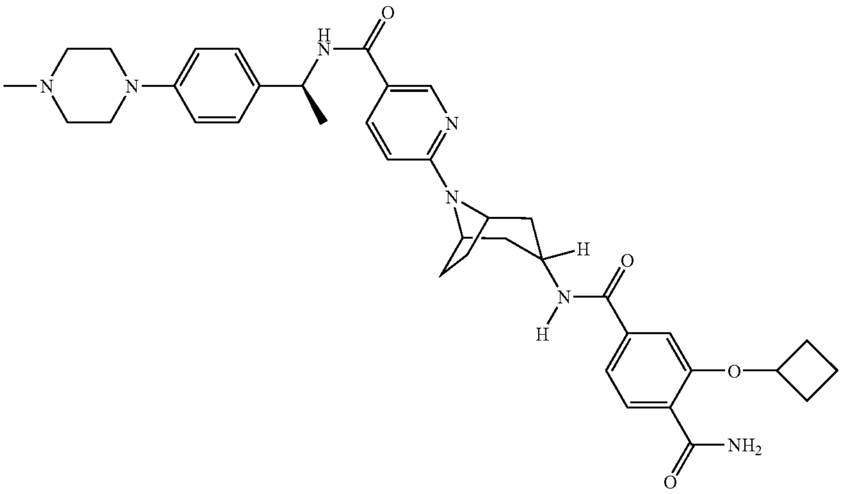 | 2-(cyclobutyloxy)-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide ACTIVITY = B |

TABLE I-continued

| STRUCTURE | NAME & ACTIVITY |
|---|---|
| 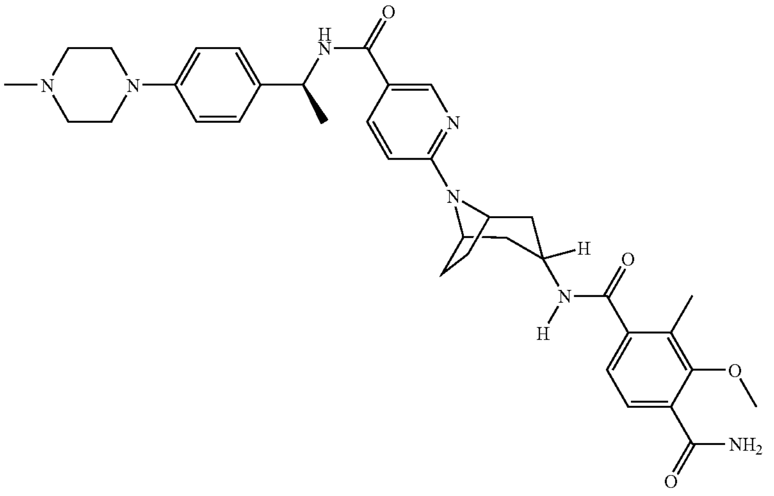 | 2-methyl-3-(methyloxy)-N-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide ACTIVITY = A |
| 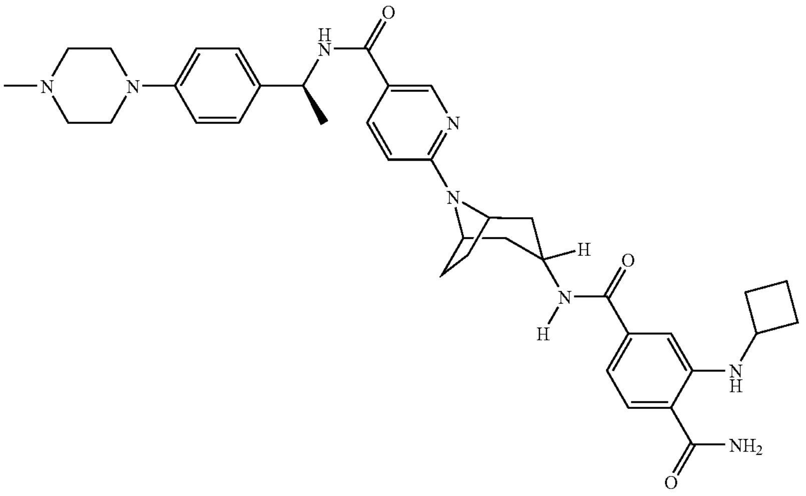 | 2-(cyclobutylamino)-N4-(8-{5-[({(1S) 1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide ACTIVITY = A |
| 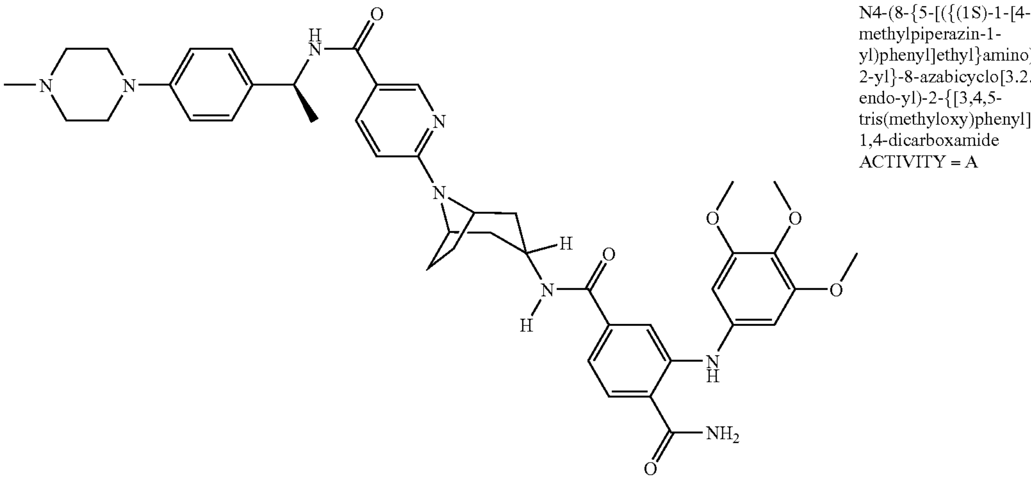 | N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-{[3,4,5-tris(methyloxy)phenyl]amino}benzene-1,4-dicarboxamide ACTIVITY = A |

TABLE I-continued

| STRUCTURE | NAME & ACTIVITY |
|---|---|
| 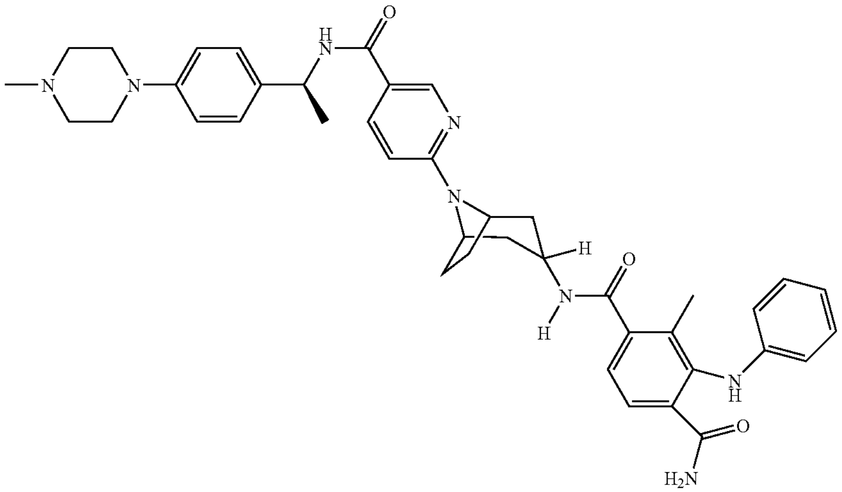 | N4-(8-{5-[({(1S)- 1-[4-(4-methylpiperazin-1-yl)phenyl]ethyl}amino)carbonyl]pyridin-2-yl}-8-azabicyclo[3.2.1]oct-3-endo-yl)-2-(phenylamino)benzene-1,4-dicarboxamide<br>ACTIVITY = A |
| 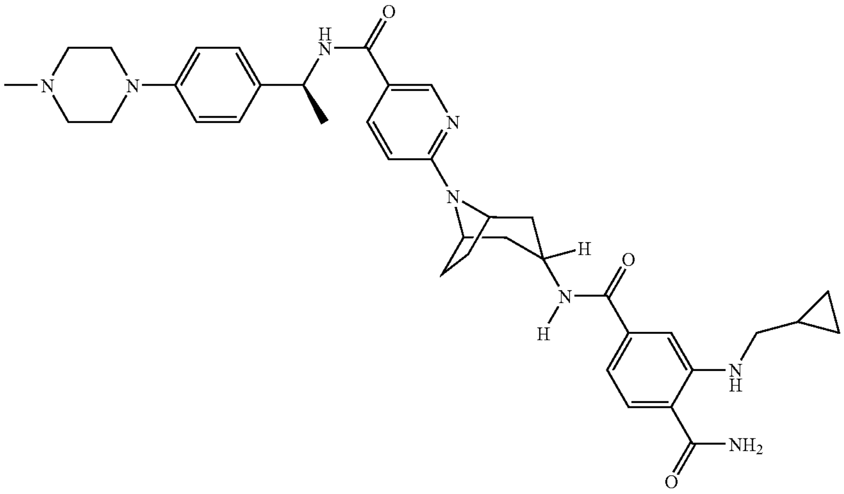 | 2-[(cyclopropylmethyl)amino]-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide<br>ACTIVITY = A |
| 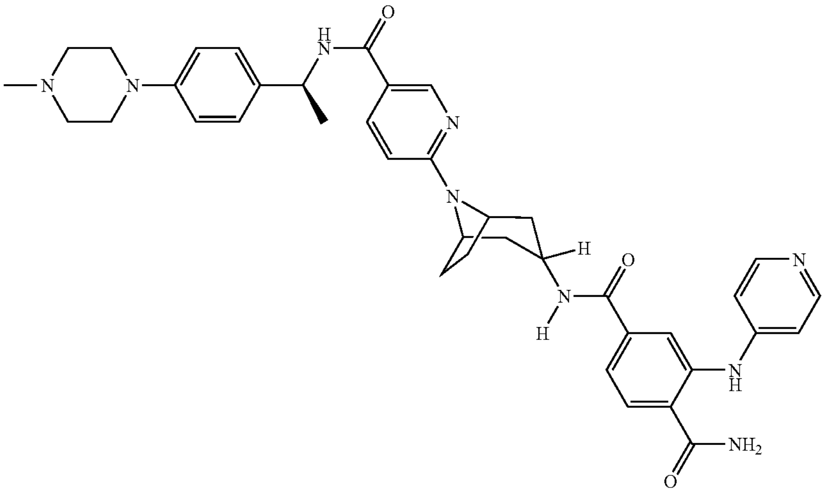 | N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-(pyridin-4-ylamino)benzene-1,4-dicarboxylate<br>ACTIVITY = A |

TABLE I-continued

| STRUCTURE | NAME & ACTIVITY |
|---|---|
| 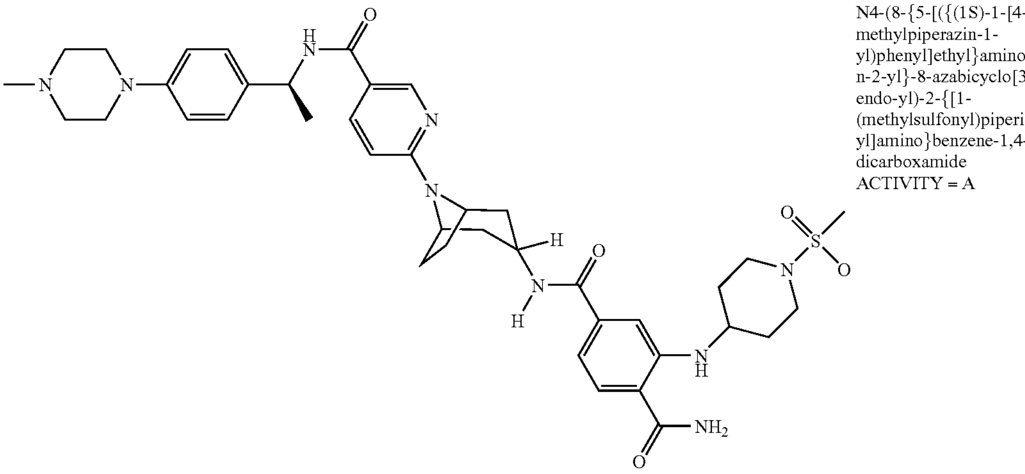 | N4-(8-{5-[({(1S)-1-[4-(4-methylpiperazin-1-yl)phenyl]ethyl}amino)carbonyl]pyridin-n-2-yl}-8-azabicyclo[3.2.1]oct-3-endo-yl)-2-{[1-(methylsulfonyl)piperidin-4-yl]amino}benzene-1,4-dicarboxamide<br>ACTIVITY = A |
| 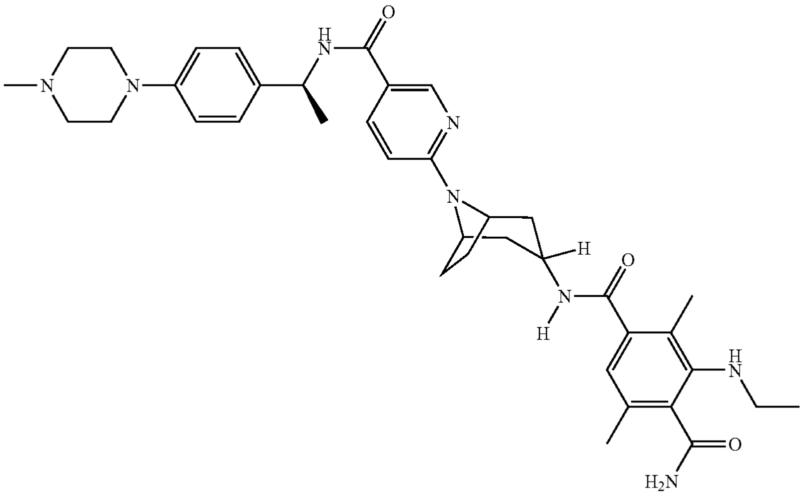 | 3-(ethylamino)-2,5-dimethyl-N1-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide<br>ACTIVITY = D |
| 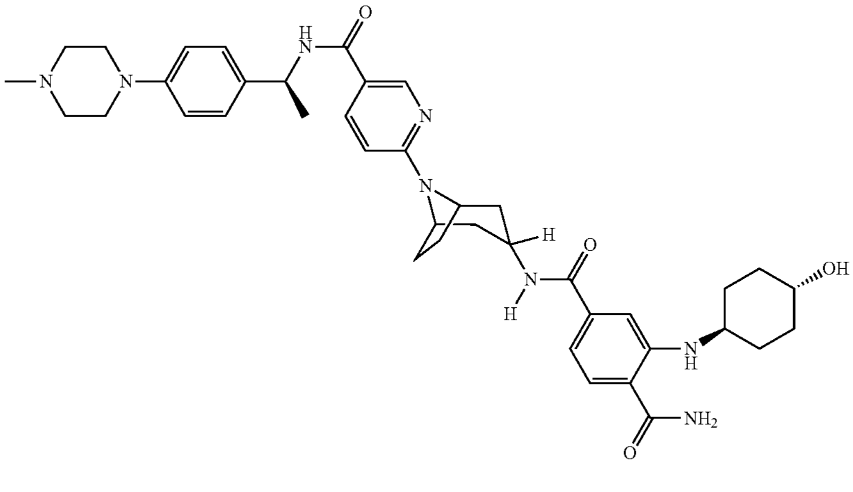 | 2-[(4-hydroxycyclohexyl)amino]-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide<br>ACTIVITY = A |

TABLE I-continued

| STRUCTURE | NAME & ACTIVITY |
|---|---|
| 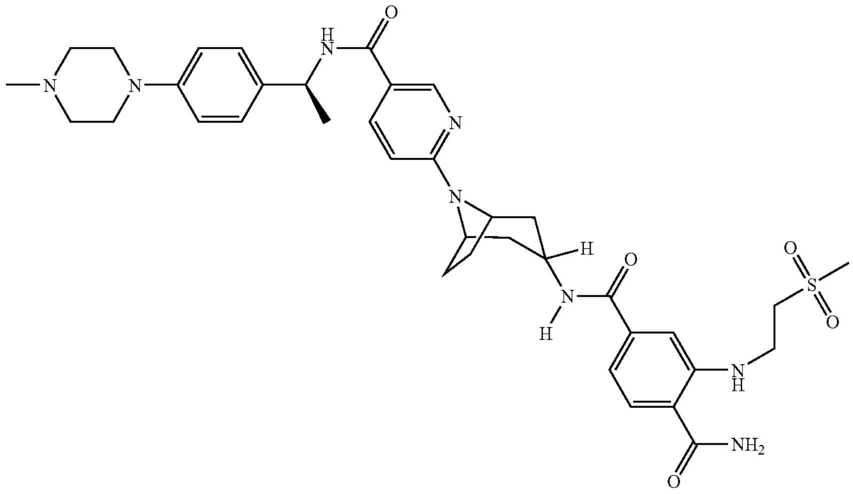 | N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-{[2-(methylsulfonyl)ethyl]amino}benzene-1,4-dicarboxamide ACTIVITY = A |
| 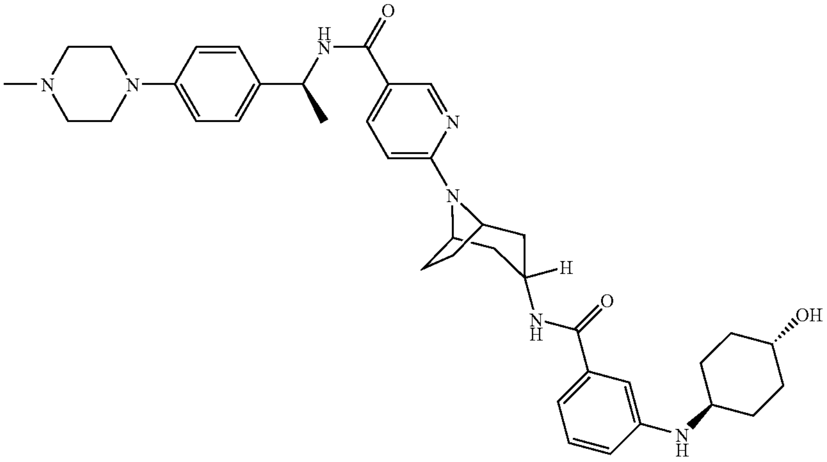 | 6-{3-endo-[({3-[(4-hydroxycyclohexyl)amino] phenyl}carbonyl) amino]-8-azabicyclo[3.2.1]oct-8-yl}-N-{(1S)-1-[4-(4-methylpiperazin-1-yl)phenyl]ethyl}pyridine-3-carboxamide ACTIVITY = D |
| 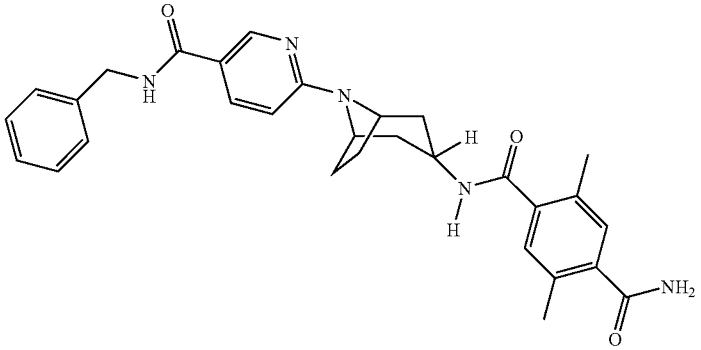 | 2,5-dimethyl-N-[8-(5-{[(phenylmethyl)amino]carbonyl}pyridin-2-yl)-8-azabicyclo[3.2.1]oct-3-endo-yl]benzene-1,4-dicarboxamide ACTIVITY = A |

TABLE I-continued
| STRUCTURE | NAME & ACTIVITY |
| --- | --- |
| 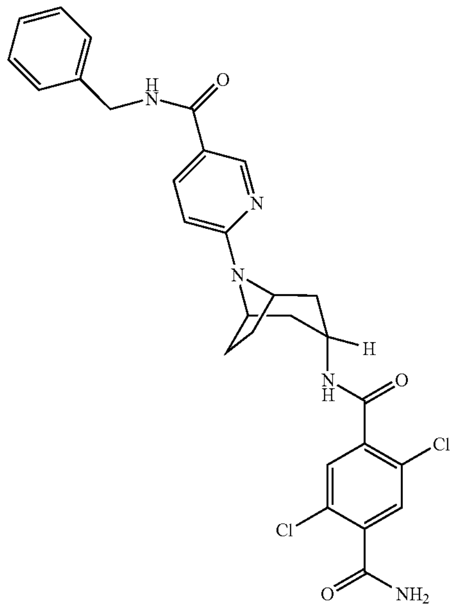 | 2,5-dichloro-N-[8-(5-{[(phenylmethyl)amino]carbonyl}pyridin-2-yl)-8-azabicyclo[3.2.1]oct-3-endo-yl]benzene-1,4-dicarboxamide ACTIVITY = A |
| 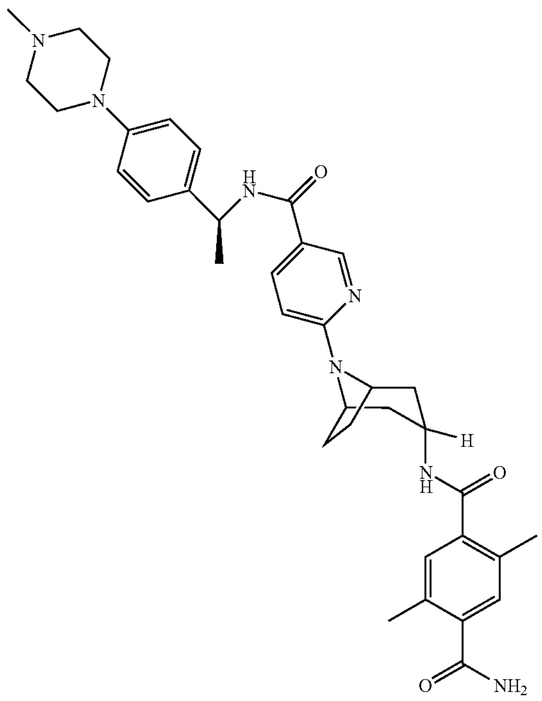 | 2,5-dimethyl-N-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide ACTIVITY = A |

TABLE I-continued

| STRUCTURE | NAME & ACTIVITY |
| --- | --- |
| 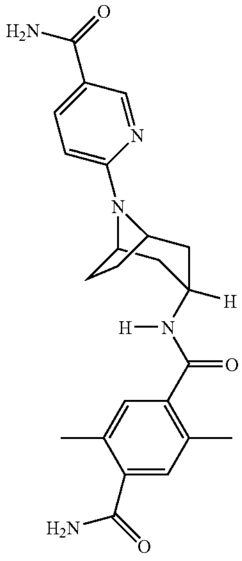 | N-{8-[5-(aminocarbonyl)pyridin-2-yl]-8-azabicyclo[3.2.1]oct-3-endo-yl}-2,5-dimethylbenzene-1,4-dicarboxamide<br>ACTIVITY = A |
| 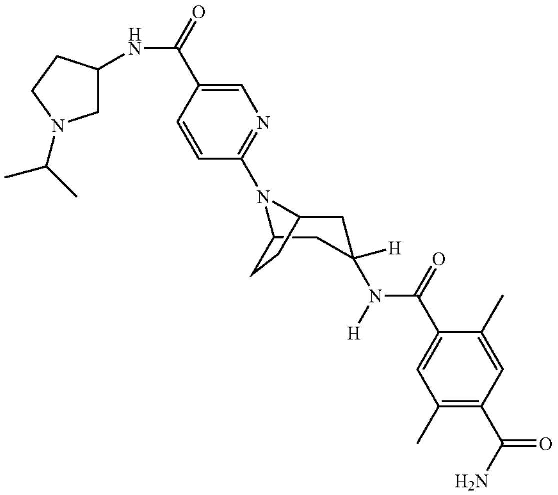 | 2,5-dimethyl-N-{8-[5-({[(3R)-1-(1-methylethyl)pyrrolidin-3-yl]amino}carbonyl)pyridin-2-yl]-8-azabicyclo[3.2.1]oct-3-endo-yl}benzene-1,4-dicarboxamide<br>ACTIVITY = A |
| 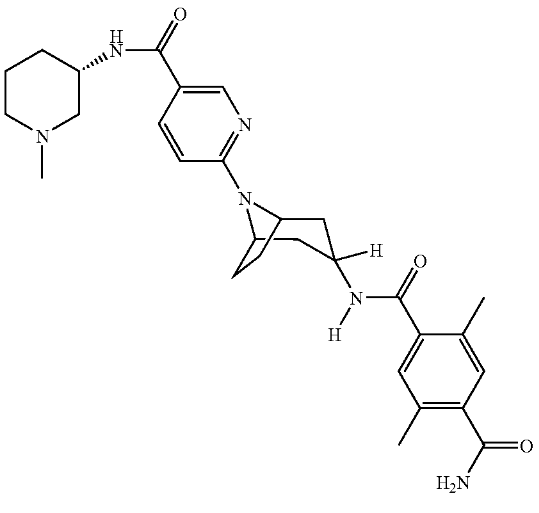 | 2,5-dimethyl-N-{8-[5-({[(3S)-1-methylpiperidin-3-yl]amino}carbonyl)pyridin-2-yl]-8-azabicyclo[3.2.1]oct-3-endo-yl}benzene-1,4-dicarboxamide<br>ACTIVITY = A |

TABLE I-continued

| STRUCTURE | NAME & ACTIVITY |
| --- | --- |
| 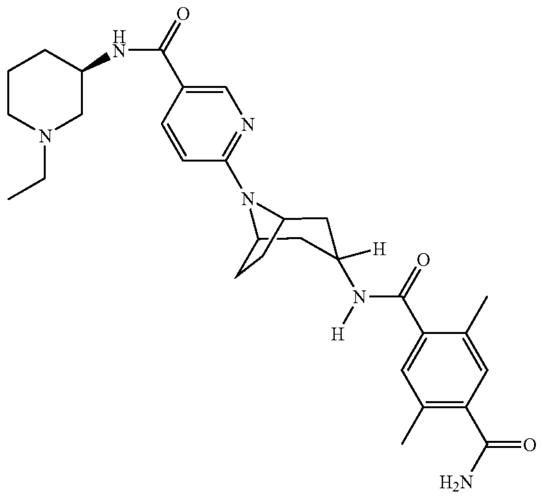 | N-{8-[5-({[(3R)-1-ethylpiperidin-3-yl]amino}carbonyl)pyridin-2-yl]-8-azabicyclo[3.2.1]oct-3-endo-yl}-2,5-dimethylbenzene-1,4-dicarboxamide ACTIVITY = A |
| 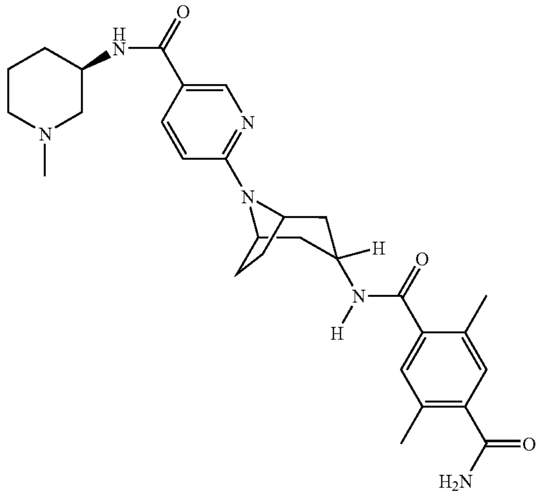 | 2,5-dimethyl-N-{8-[5-({[(3R)-1-methylpiperidin-3-yl]amino}carbonyl)pyridin-2-yl]-8-azabicyclo[3.2.1]oct-3-endo-yl}benzene-1,4-dicarboxamide ACTIVITY = A |
| 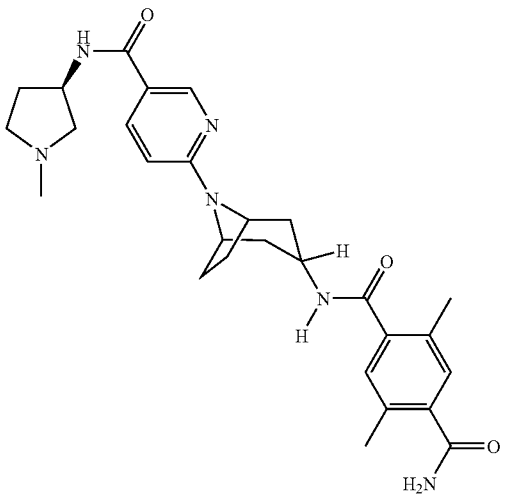 | 2,5-dimethyl-N-{8-[5-({[(3R)-1-methylpyrrolidin-3-yl]amino}carbonyl)pyridin-2-yl]-8-azabicyclo[3.2.1]oct-3-endo-yl}benzene-1,4-dicarboxamide ACTIVITY = B |

TABLE I-continued

| STRUCTURE | NAME & ACTIVITY |
|---|---|
| 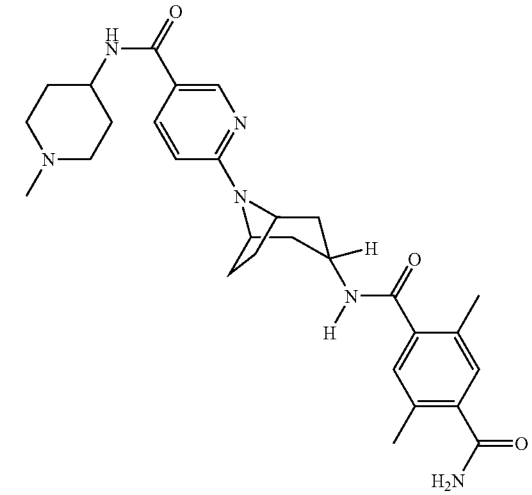 | 2,5-dimethyl-N-[8-(5-{[(1-methylpiperidin-4-yl)amino]carbonyl}pyridin-2-yl)-8-azabicyclo[3.2.1]oct-3-endo-yl]benzene-1,4-dicarboxamide ACTIVITY = B |
| 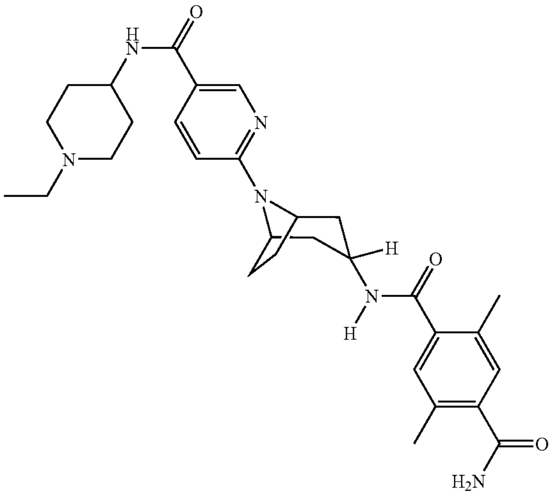 | N-[8-(5-{[(1-ethylpiperidin-4-yl)amino]carbonyl}pyridin-2-yl)-8-azabicyclo[3.2.1]oct-3-endo-yl]-2,5-dimethylbenzene-1,4-dicarboxamide ACTIVITY = B |
| 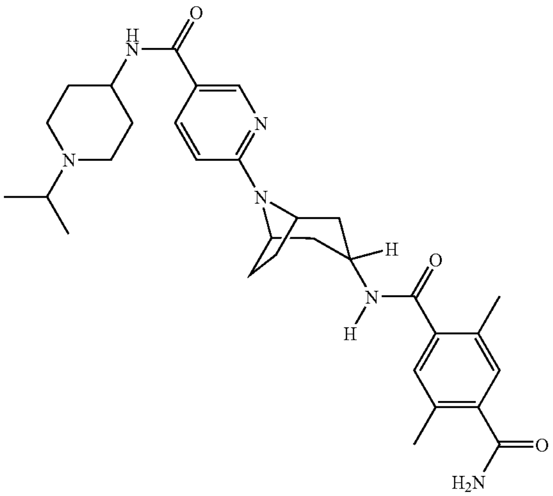 | 2,5-dimethy~-N-{8-[5-({[1-(1 methylethyl)piperidin-4-yl]amino}carbonyl)pyridin-2-yl]-8-azabicyclo[3.2.1]oct-3-endo-yl}benzene-1,4-dicarboxamide ACTIVITY = B |

TABLE I-continued

| STRUCTURE | NAME & ACTIVITY |
|---|---|
| 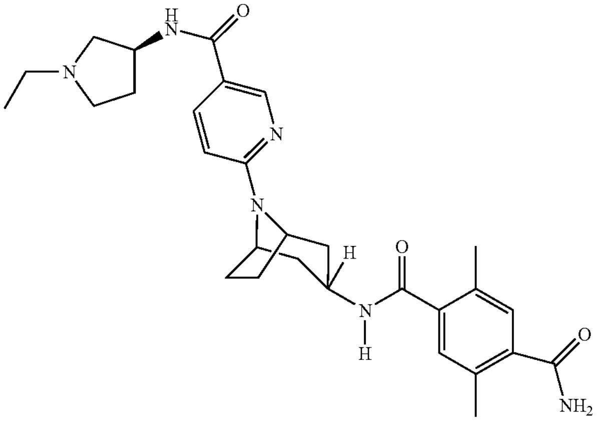 | N-{8-[5-({[(3S)-1-ethylpyrrolidin-3-yl]amino}carbonyl)pyridin-2-yl]-8-azabicyclo[3.2.1]oct-3-endo-yl}-2,5-dimethylbenzene-1,4-dicarboxamide ACTIVITY = A |
| 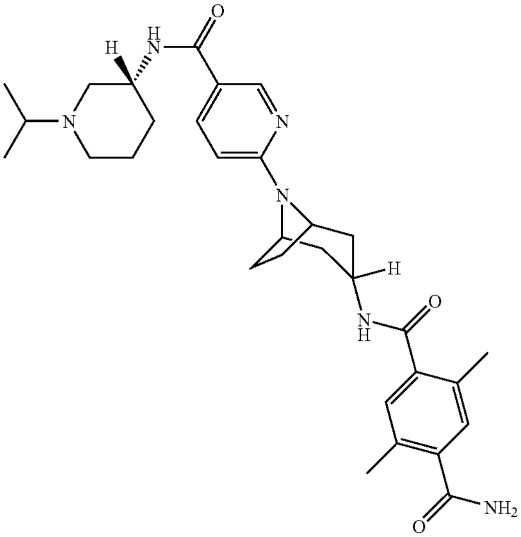 | 2,5-dimethyl-N-{8-[5-({[(3R)-1-(1-methylethyl)piperidin-3-yl]amino}carbonyl)pyridin-2-yl]-8-azabicyclo[3.2.1]oct-3-endo-yl}benzene-1,4-dicarboxamide ACTIVITY = A |
| 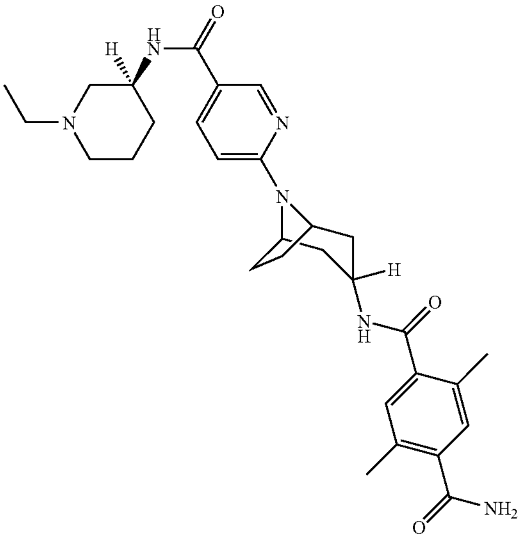 | N-{8-[5-({[(3S)-1-ethylpiperidin-3-yl]amino}carbonyl)pyridin-2-yl]-8-azabicyclo[3.2.1]oct-3-endo-yl}-2 5-dimethylbenzene-1,4-dicarboxamide ACTIVITY = B |

TABLE I-continued

| STRUCTURE | NAME & ACTIVITY |
|---|---|
| 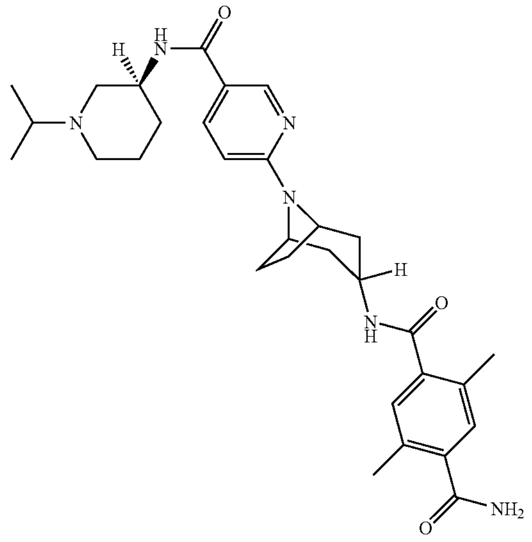 | 2,5-dimethyl-N-{8-[5-({[(3S)-1-(1-methylethyl)piperidin-3-yl]amino}carbonyl)pyridin-2-yl]-8-azabacyclo[3.2.1]oct-3-endo-yl}benzene-1,4-dicarboxamide ACTIVITY = B |
| 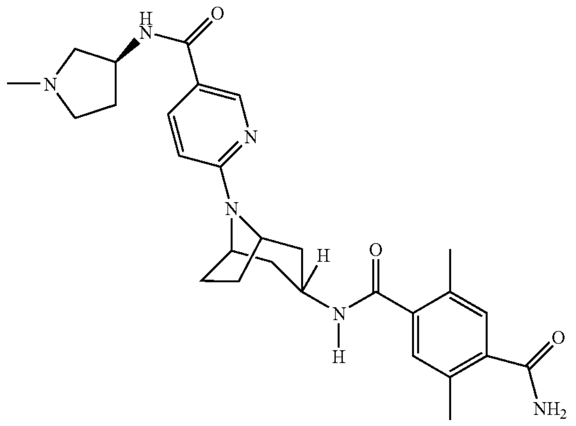 | 2,5-dimethyl-N-{8-[5-({[(3S)-1-methylpyrrolidin-3-yl]amino}carbonyl)pyridin-2-yl]-8-azabicyclo[3.2.1]oct-3-endo-yl}benzene-1,4-dicarboxamide ACTIVITY = A |
| 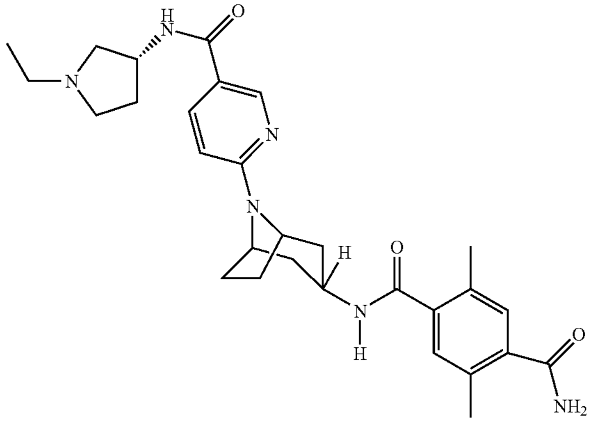 | N-{8-[5-({[(3R)-1-ethylpyrrolidin-3-yl]amino}carbonyl)pyridin-2-yl]-8-azabicyclo[3.2.1]oct-3-endo-yl}-2,5-dimethylbenzene-1,4-dicarboxamide ACTIVITY = A |

TABLE I-continued
| STRUCTURE | NAME & ACTIVITY |
|---|---|
| 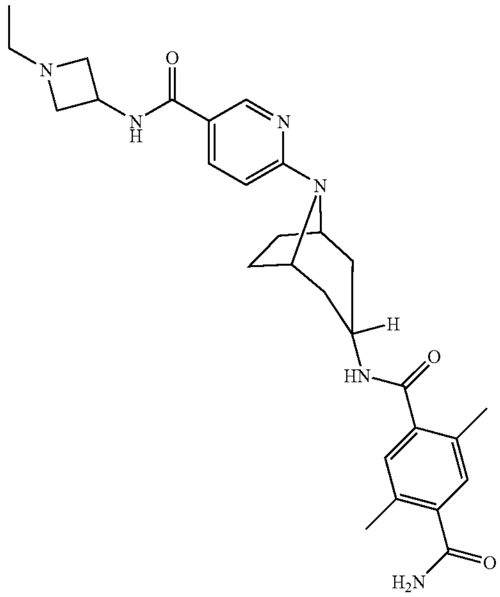 | N-[8-(5-{[(1-ethylazetidin-3-yl)amino]carbonyl}pyridin-2-yl)-8-azabicyclo[3.2.1]oct-3-endo-yl]-2,5-dimethylbenzene-1,4-dicarboxamide ACTIVITY = A |
| 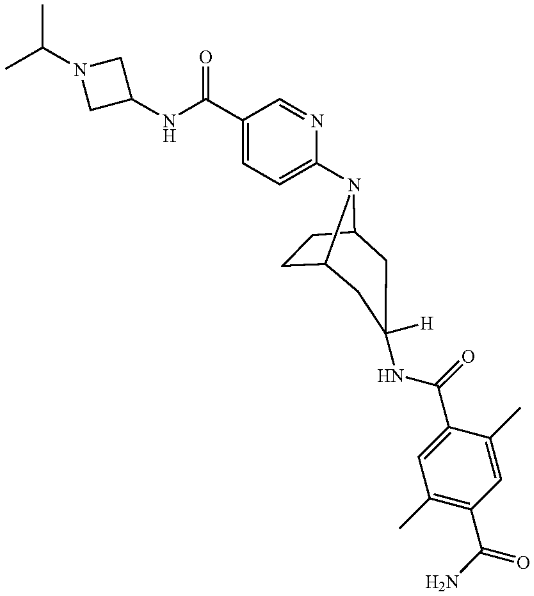 | 2,5-dimethyl-N-{8-[5-({[1-(1-methylethyl)azetidin-3-yl]amino}carbonyl)pyridin-2-yl]-8-azabicyclo[3.2.1]oct-3-endo-yl}benzene-1,4-dicarboxamide ACTIVITY = A |

TABLE I-continued

| STRUCTURE | NAME & ACTIVITY |
| --- | --- |
| 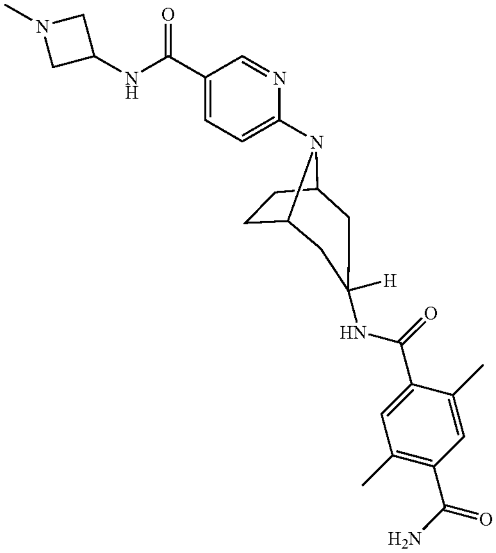 | 2,5-dimethyl-N-[8-(5-{[(1-methylazetidin-3-yl)amino]carbonyl}pyridin-2-yl)-8-azabicyclo[3.2.1]oct-3-endo-yl]benzene-1,4-dicarboxamide ACTIVITY = A |
| 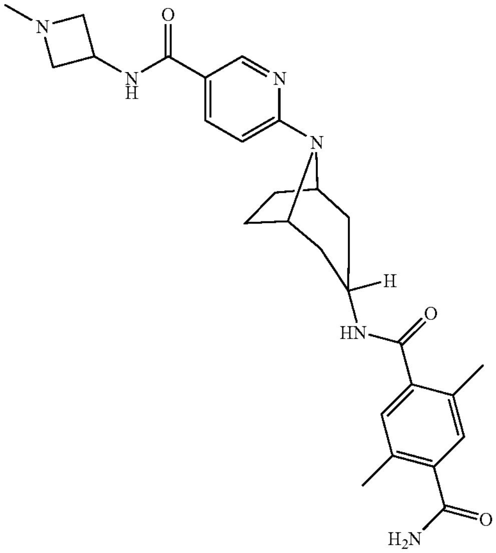 | methyl (2S)-[({6-3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoate ACTIVITY = C |
| 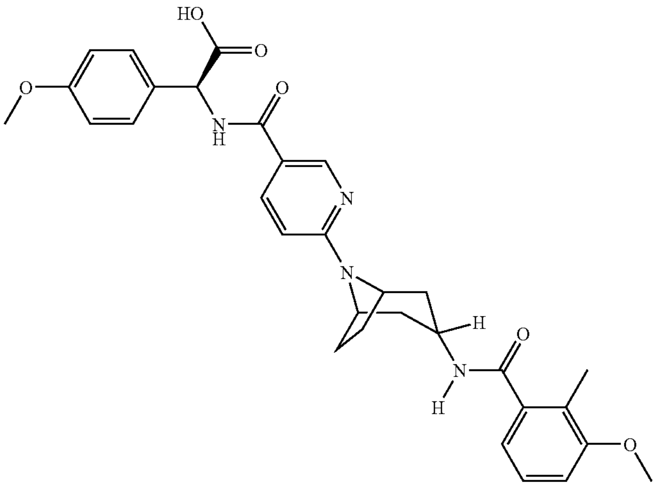 | (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoic acid ACTIVITY = C |

TABLE I-continued

| STRUCTURE | NAME & ACTIVITY |
|---|---|
| 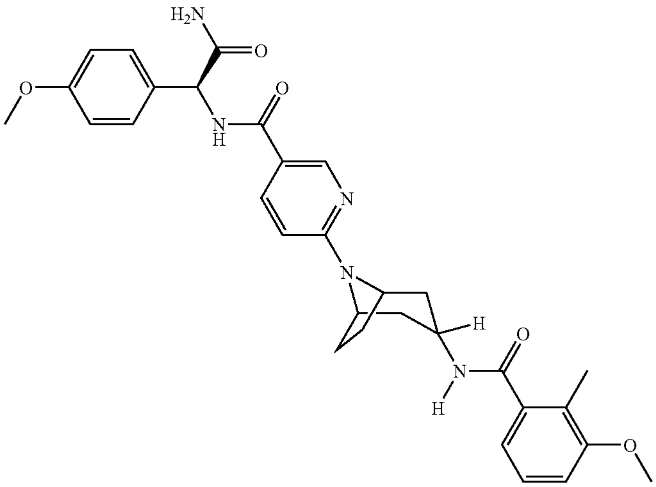 | N-{(1S)-2-amino-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide ACTIVITY = B |
| 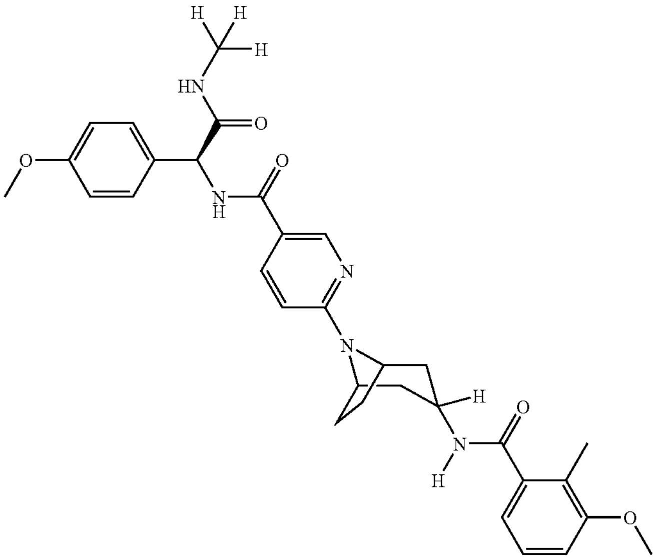 | N-{(1S)-2-(methylamino)-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide ACTIVITY = B |
| 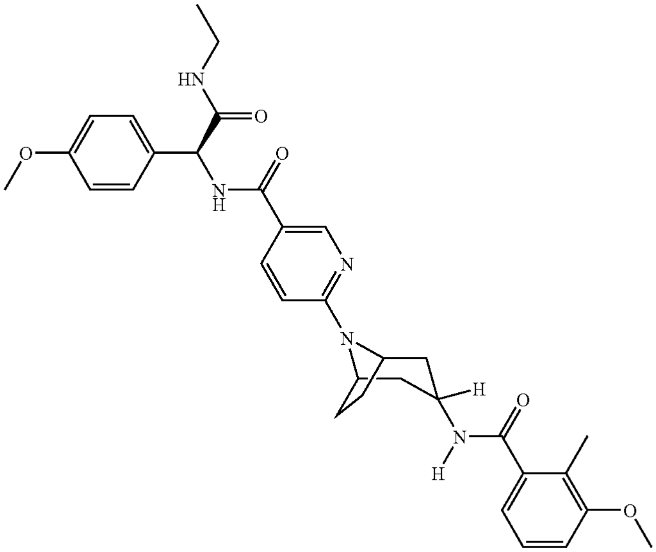 | N-{(1S)-2-(ethylamino)-1-{4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide ACTIVITY = B |

TABLE I-continued
| STRUCTURE | NAME & ACTIVITY |
| --- | --- |
| 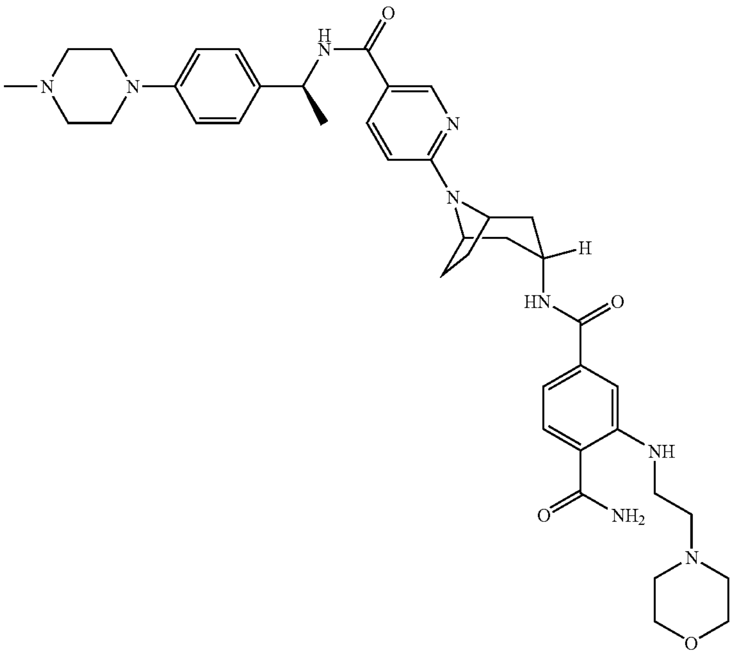 | N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-[(2-morpholin-4-ylethyl)amino]benzene-1,4-dicarboxamide ACTIVITY = A |
| 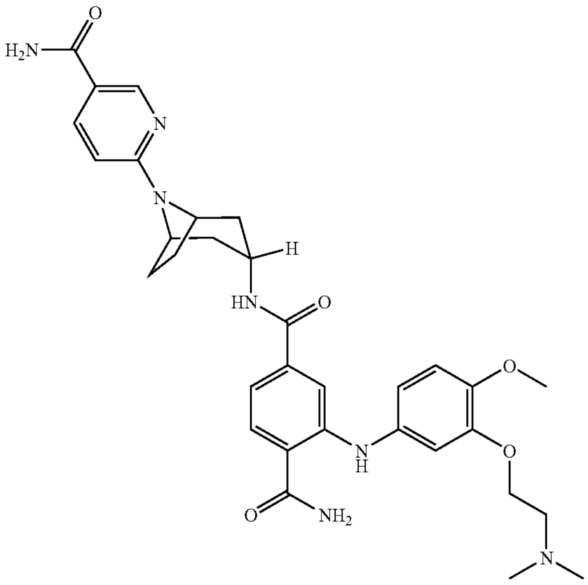 | N4-{8-[5-(aminocarbonyl)pyridin-2-yl]-8-azabicyclo[3.2.1]oct-3-endo-yl}-2-{[3-{[2-(dimethylamino)ethyl]oxy}-4-(methyloxy)phenyl]amino}benzene-1,4-dicarboxamide ACTIVITY = A |

TABLE I-continued

| STRUCTURE | NAME & ACTIVITY |
|---|---|
| 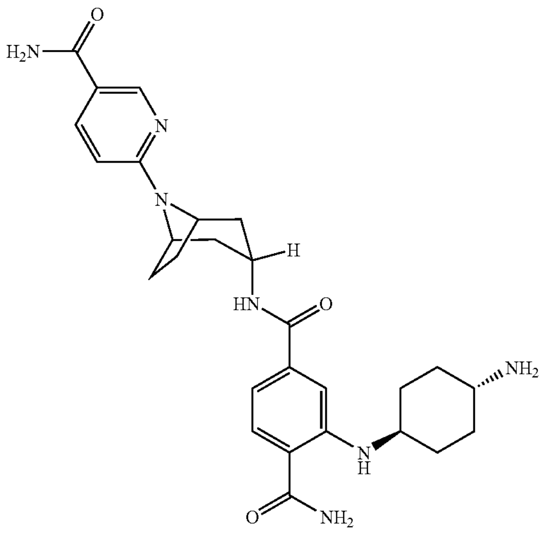 | N4-{8-[5-(aminocarbonyl)pyridin-2-yl]-8-azabicyclo[3.2.1]oct-3-endo-yl}-2-[(trans-4-aminocyclohexyl)amino]benzene-1,4-dicarboxamide<br>ACTIVITY = A |
| 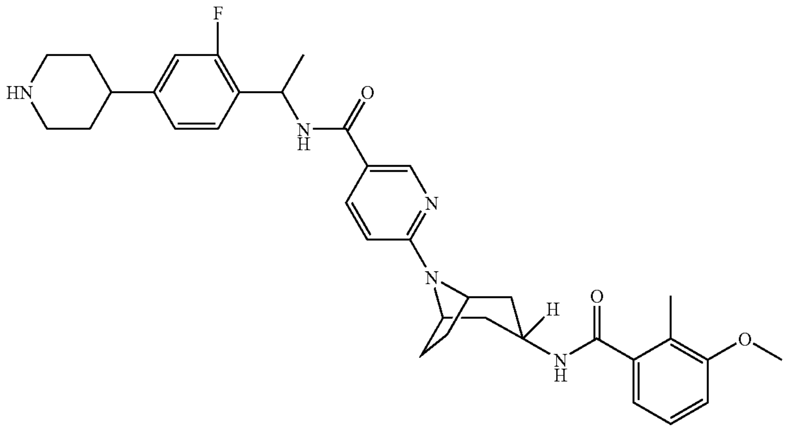 | N-[1-(2-fluoro-4-piperidin-4-ylphenyl)ethyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = A |
| 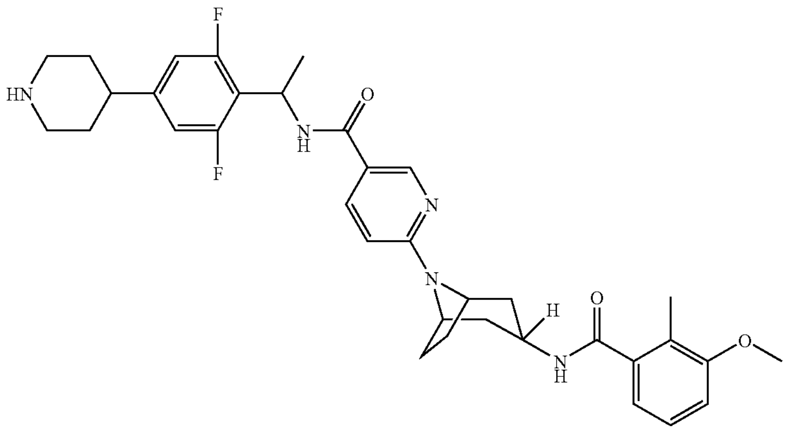 | N-[1-(2,6-difluoro-4-piperidin-4-ylphenyl)ethyl]-6-[3-endo-({[2-methyl-3-(methyloxy)phenyl]carbonyl}amino)-8-azabicyclo[3.2.1]oct-8-yl]pyridine-3-carboxamide<br>ACTIVITY = D |

TABLE I-continued

| STRUCTURE | NAME & ACTIVITY |
|---|---|
| 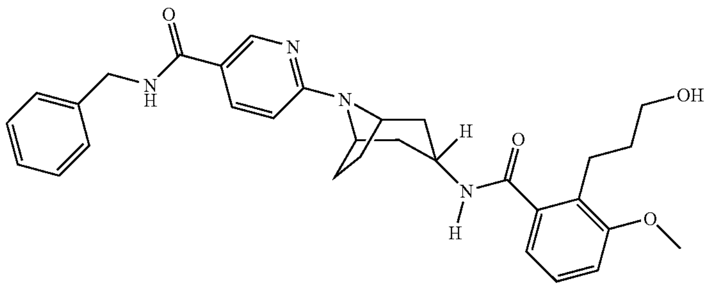 | 6-[3-endo-({[2-(3-hydroxypropyl)-3-(methyloxy)phenyl]carbonyl}amino)-8-azabicyclo[3.2.1]oct-8-yl]-N-(phenylmethyl)pyridine-3-carboxamide<br>ACTIVITY = A |
| 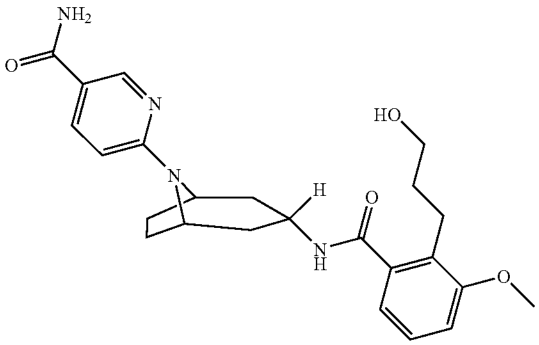 | 6-[3-endo-({[2-(3-hydroxypropyl)-3-(methyloxy)phenyl]carbonyl}amino)-8-azabicyclo[3.2.1]oct-8-yl]pyridine-3-carboxamide<br>ACTIVITY = C |
| 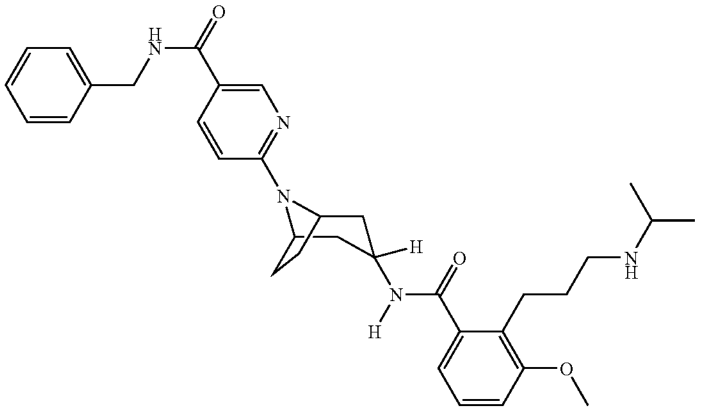 | 6-[3-endo-({[2-{3-[(1-methylethyl)amino]propyl}-3-(methyloxy)phenyl]carbonyl}amino)-8-azabicyclo[3.2.1]oct-8-yl]-N-(phenylmethyl)pyridine-3-carboxamide<br>ACTIVITY = C |
| 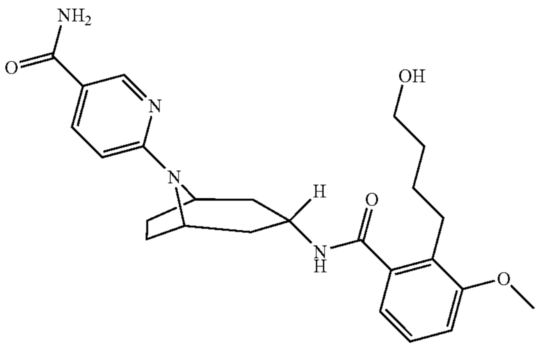 | 6-[3-endo-({[2-(4-hydroxybutyl)-3-(methyloxy)phenyl]carbonyl}amino)-8-azabicyclo[3.2.1]oct-8-yl]pyridine-3-carboxamide<br>ACTIVITY = B |

TABLE I-continued

| STRUCTURE | NAME & ACTIVITY |
| --- | --- |
| 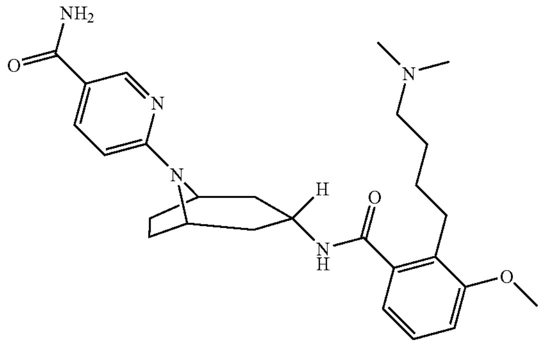 | 6-(3-endo[({2-[4-(dimethylamino)butyl]-3-(methyloxy)phenyl}carbonyl)amino]-8-azabicyclo[3.2.1]oct-8-yl}pyridine-3-carboxamide<br>ACTIVITY = C |
| 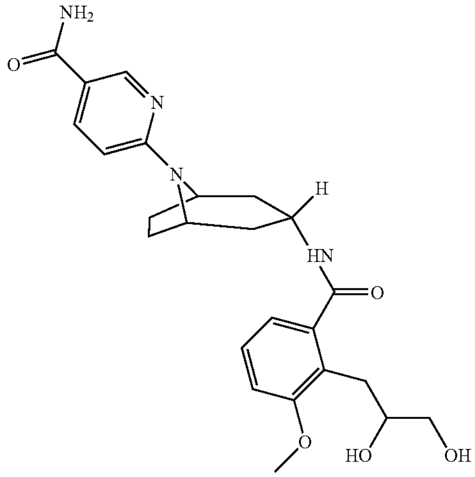 | 6-[3-endo-({[2-(2,3-dihydroxypropyl)-3-(methyloxy)phenyl]carbonyl}amino)-8-azabicyclo[3.2.1]oct-8-yl]pyridine-3-carboxamide<br>ACTIVITY = D |
| 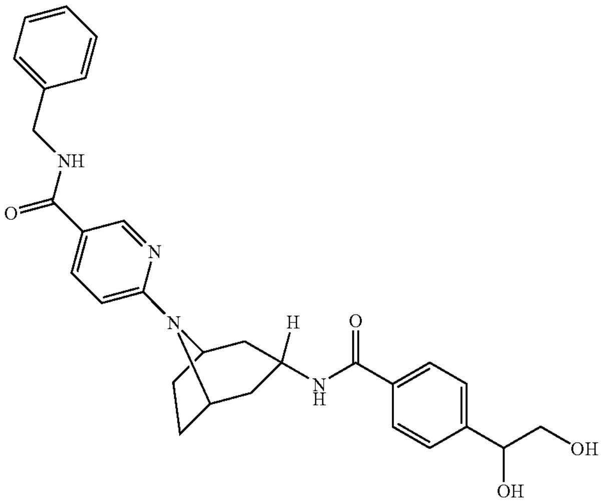 | 6-[3-endo-({(4-(1,2-dihydroxyethyl)phenyl]carbonyl}amino)-8-azabicyclo[3.2.1]oct-8-yl]-N-(phenylmethyl)pyridine-3-carboxamide<br>ACTIVITY = C |

TABLE I-continued
| STRUCTURE | NAME & ACTIVITY |
| --- | --- |
| 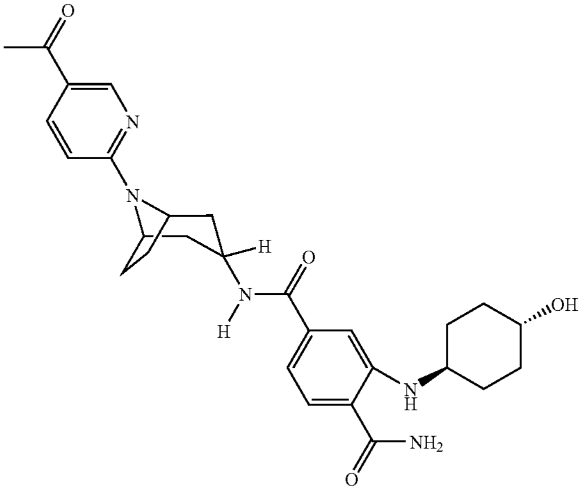 | N4-[8-(5-acetylpyridin-2-yl)-8-azabicyclo[3.2.1]oct-3-endo-yl]-2-[(trans-4-hydroxycyclohexyl)amino]benzene-1,4-dicarboxamide<br>ACTIVITY = A |
| 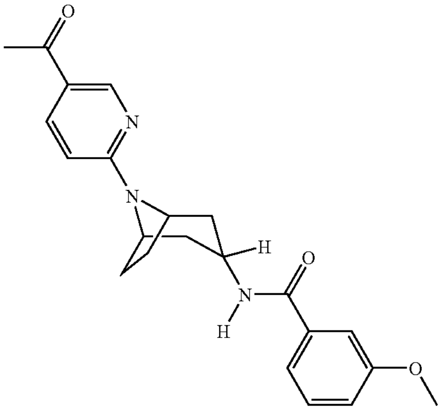 | N-[8-(5-acetylpyradin-2-yl)-8-azabicyclo[3.2.1]oct-3-endo-yl]-2-methyl-3-(methyloxy)benzamide<br>ACTIVITY = B |
| 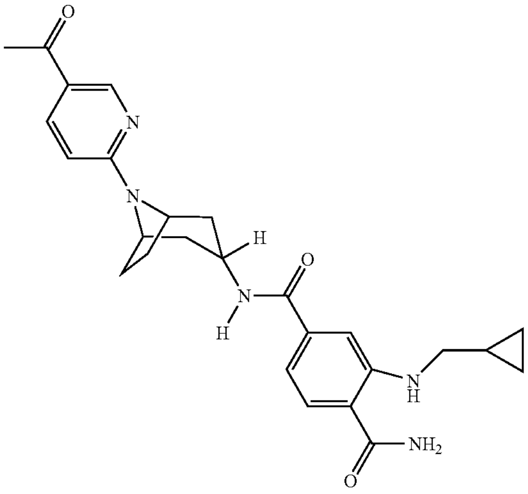 | N4-[8-(5-acetylpyridin-2-yl)-8-azabicyclo[3.2.1]oct-3-endo-yl]-2-[(cyclopropylmethyl)amino]benzene-1,4-dicarboxamide<br>ACTIVITY = A |

TABLE I-continued
| STRUCTURE | NAME & ACTIVITY |
| --- | --- |
| 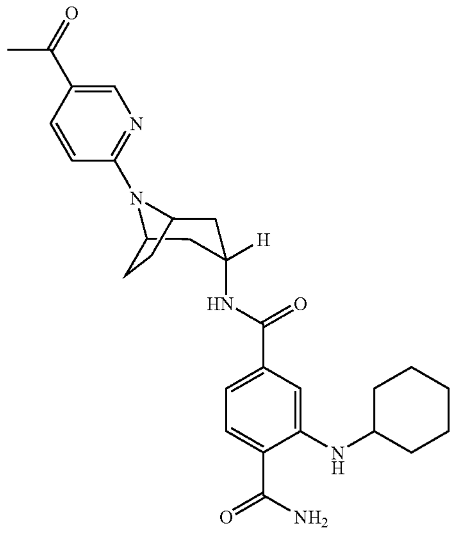 | N4-[8-(5-acetylpyridin-2-yl)-8-azabicyclo[3.2.1]oct-3-endo-yl]-2-(cyctohexylamino)benzene-1,4-dicarboxamide<br>ACTIVITY = A |
| 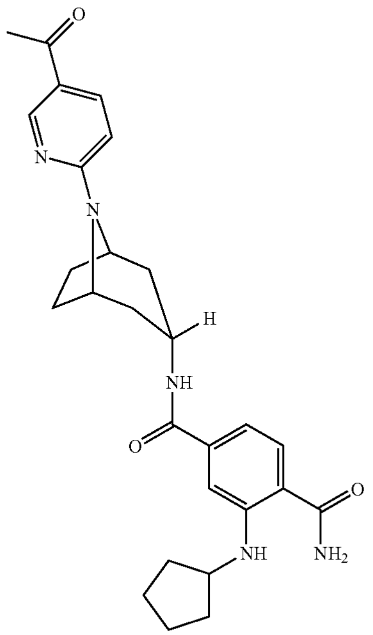 | N4-[8-(5-acetylpyridin-2-yl)-8-azabicyclo[3.2.1]oct-3-endo-yl]-2-(cyclopentylamino)benzene-1,4-dicarboxamide<br>ACTIVITY = A |

TABLE I-continued
| STRUCTURE | NAME & ACTIVITY |
| --- | --- |
| 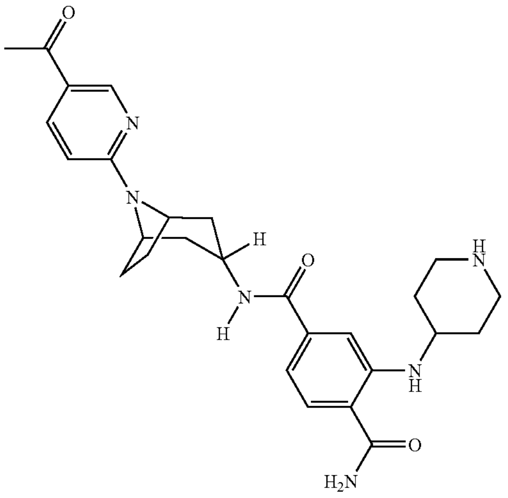 | N4-[8-(5-acetylpyridin-2-yl)-8-azabicyclo[3.2.1]oct-3-endo-yl]-2-(piperidin-4-ylamino)benzene-1,4-dicarboxamide ACTIVITY = A |
| 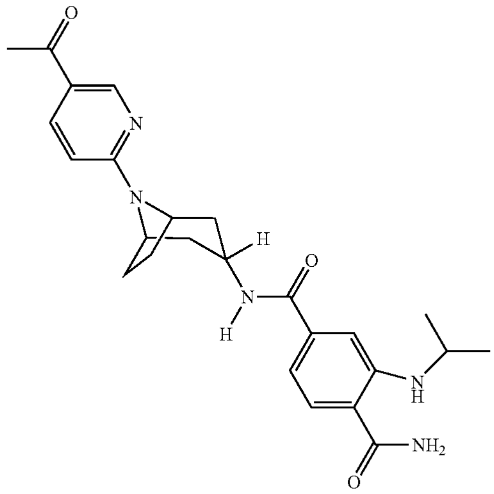 | N4-[8-(5-acetylpyridin-2-yl)-8-azabicyclo[3.2.1]oct-3-endo-yl]-2-[(1-methylethyl)amino]benzene-1,4-dicarboxamide ACTIVITY = A |
| 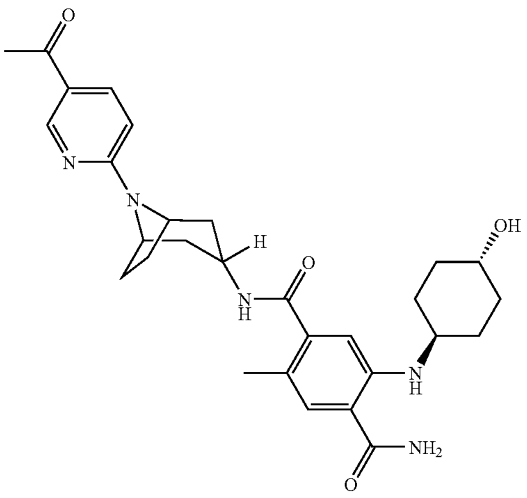 | N-[8-(5-acetylpyridin-2-yl)-8-azabicyclo[3.2.1]oct-3-endo-yl]-5-[(trans-4-hydroxycyclohexyl)amino]-2-methylbenzene-1,4-dicarboxamide ACTIVITY = A |

TABLE I-continued
| STRUCTURE | NAME & ACTIVITY |
|---|---|
| 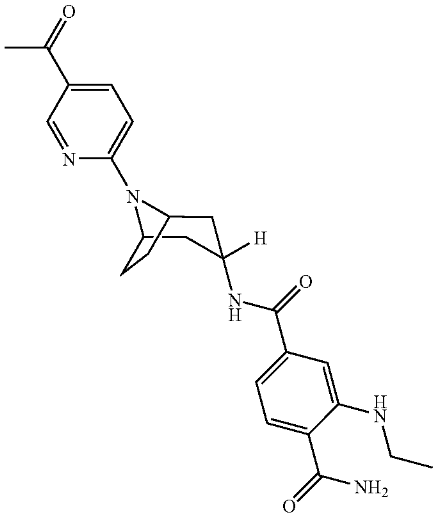 | N4-[8-(5-acetylpyridin-2-yl)-8-azabicyclo[3.2.1]oct-3-endo-yl]-2-(ethylamino)benzene-1,4-dicarboxamide<br>ACTIVITY = A |
| 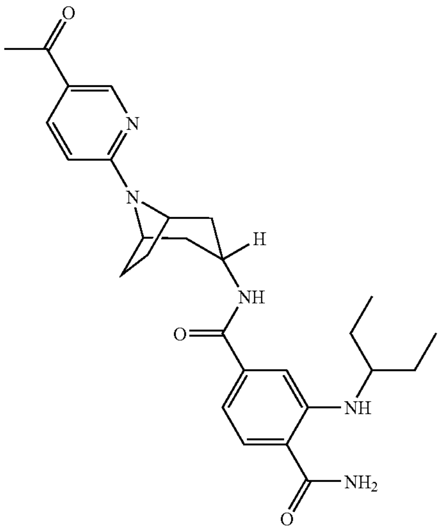 | N4-[8-(5-acetylpyridin-2-yl)-8-azabicyclo[3.2.1]oct-3-endo-yl]-2-[(1-ethylpropyl)amino]benzene-1,4-dicarboxamide<br>ACTIVITY = A |
| 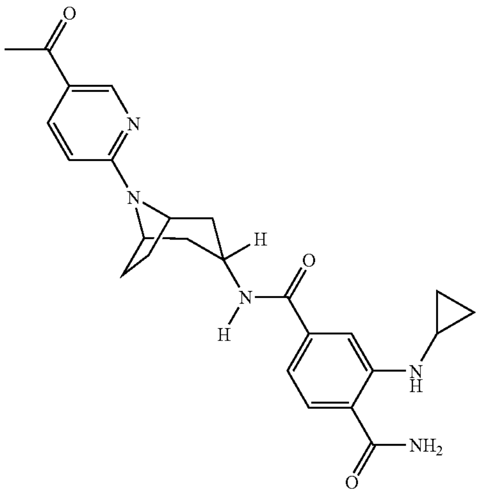 | N4-[8-(5-acetylpyridin-2-yl)-8-azabicyclo[3.2.1]oct-3-endo-yl]-2-(cyclopropylamino)benzene-1,4-dicarboxamide<br>ACTIVITY = A |

TABLE I-continued
| STRUCTURE | NAME & ACTIVITY |
|---|---|
| 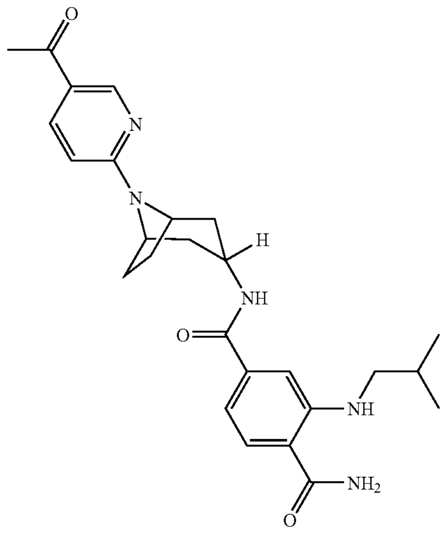 | N4-[8-(5-acetylpyridin-2-yl)-8-azabicyclo[3.2.1]oct-3-endo-yl]-2-[(2-methylpropyl)amino]benzefle-1,4-dicarboxamide<br>ACTIVITY = A |
| 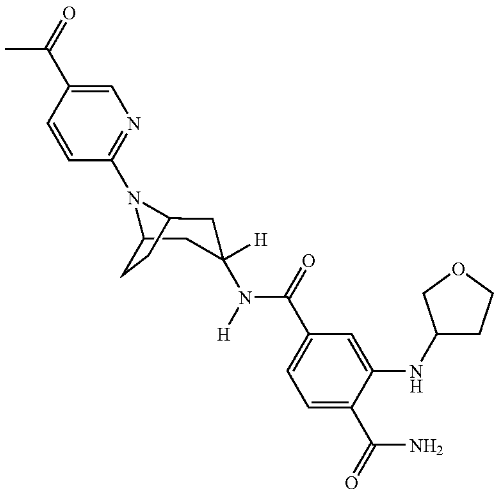 | N4-[8-(5-acetylpyridin-2-yl)-8-azabicyclo[3.2.1]oct-3-endo-yl]-2-(tetrahydrofuran-3-ylamino)benzene-1,4-dicarboxamide<br>ACTIVITY = A |

TABLE I-continued

| STRUCTURE | NAME & ACTIVITY |
| --- | --- |
| 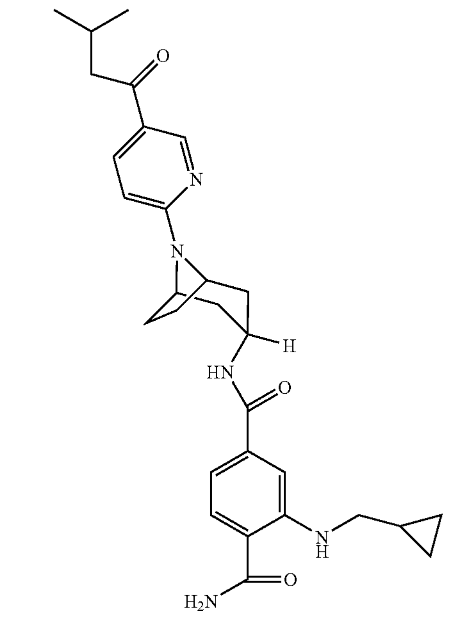 | 2-[(cyclopropylmethyl)amino]-N4-{8-[5-(3-methylbutanoyl)pyridin-2-yl]-8-azabicyclo[3.2.1]oct-3-endo-yl}benzene-1,4-dicarboxamide ACTIVITY = C |
| 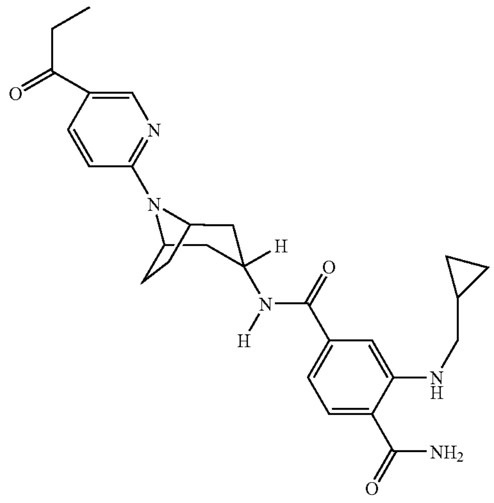 | 2-[(cyclopropylmethyl)amino]-N4-[8-(5-propanoylpyridin-2-yl)-8-azabicyclo[3.2.1]oct-3-endo-yl]benzene-1,4-dicarboxamide ACTIVITY = A |
| 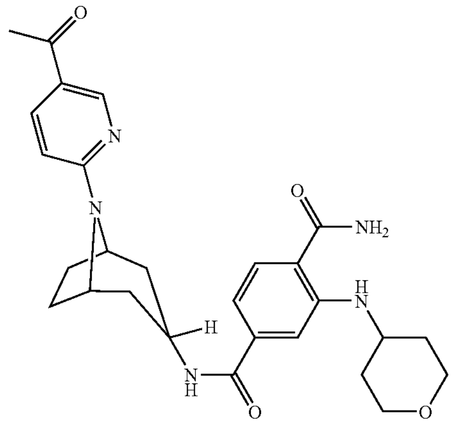 | N4-[8-(5-acetylpyridin-2-yl)-8-azabicyclo[3.2.1]oct-3-endo-yl]-2-(tetrahydro-2H-pyran-4-ylamino)benzene-1,4-dicarboxamide ACTIVITY = A |

TABLE I-continued

| STRUCTURE | NAME & ACTIVITY |
|---|---|
| 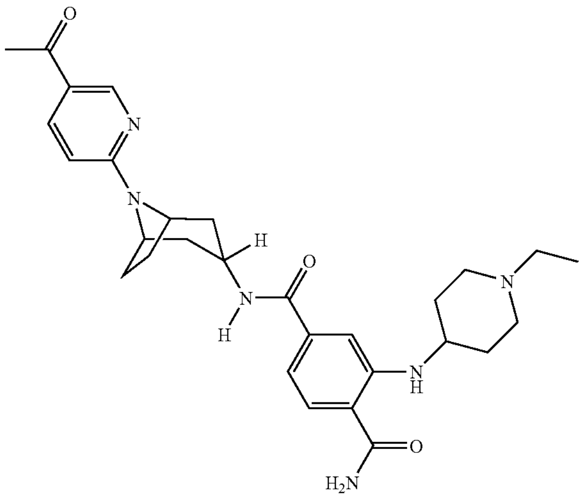 | N4-[8-(5-acetylpyridin-2-yl)-8-azabicyclo[3.2.1]oct-3-endo-yl]-2-[(1-ethylpiperidin-4-yl)amino]benzene-1,4-dicarboxamide<br>ACTIVITY = B |
| 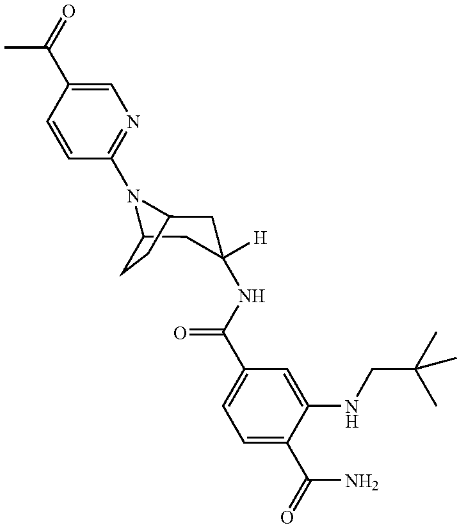 | N4-[8-(5-acetylpyridin-2-y)-8-azabicyclo[3.2.1]oct-3-endo-yl]-2-[(2,2-dimethylpropyl)amino]benzene-1,4-dicarboxamide<br>ACTIVITY = A |
| 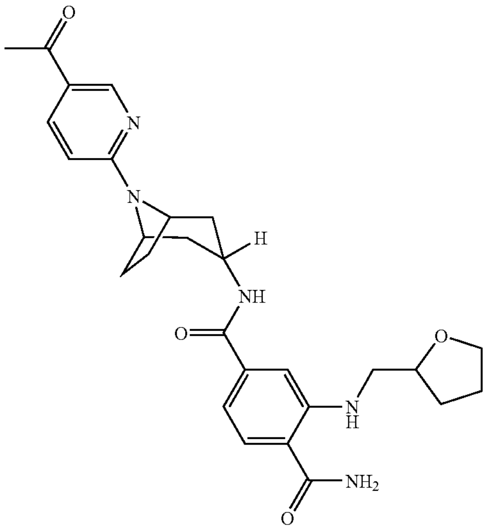 | N4-[8-(5-acetylpyridin-2-yl)-8-azabicyclo[3.2.1]oct-3-endo-yl]-2-[(tetrahydrofuran-2-ylmethyl)amino]benzene-1,4-dicarboxamide<br>ACTIVITY = A |

TABLE I-continued

| STRUCTURE | NAME & ACTIVITY |
| --- | --- |
| 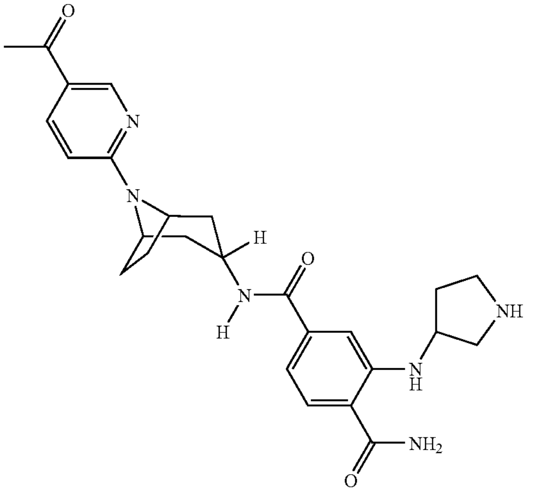 | N4-[8-(5-acetylpyridin-2-yl)-8-azabicyclo[3.2.1]oct.3-endo-yl]-2-(pyrrolidin-3-ylamino)benzene-1,4-dicarboxamide<br>ACTIVITY = A |
| 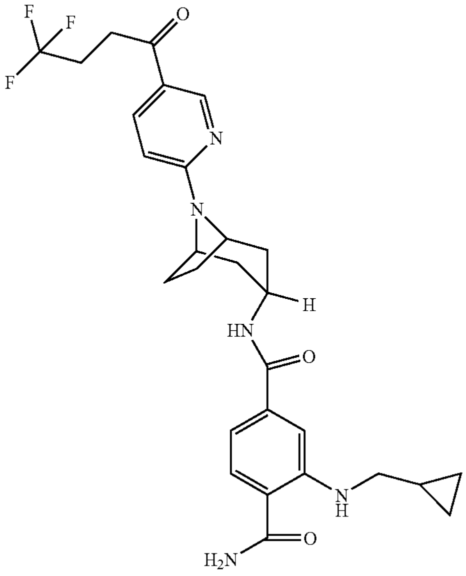 | 2-[(cyclopropylmethyl)amino]-N4-{8-[5-(4,4,4-trifluorobutanoyl)pyridin-2-yl]-8-azabicyclo[3.2.1]oct-3-endo-yl}benzene-1,4-dicarboxamide<br>ACTIVITY = D |
| 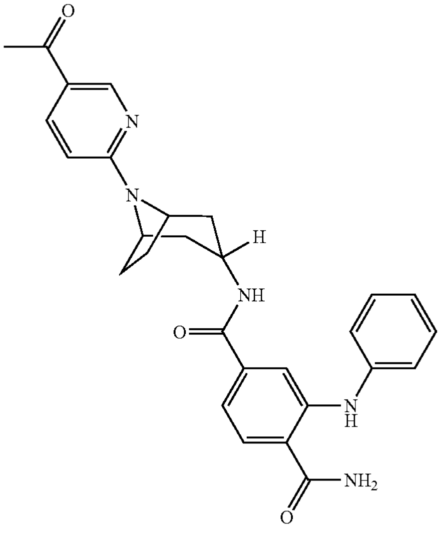 | N4-[8-(5-acetylpyridin-2-yl)-8-azabicyclo[3.2.1]oct.3-endo-yl]-2-(phenylamino)benzene-1,4-dicarboxamide<br>ACTIVITY = A |

TABLE I-continued

| STRUCTURE | NAME & ACTIVITY |
|---|---|
| 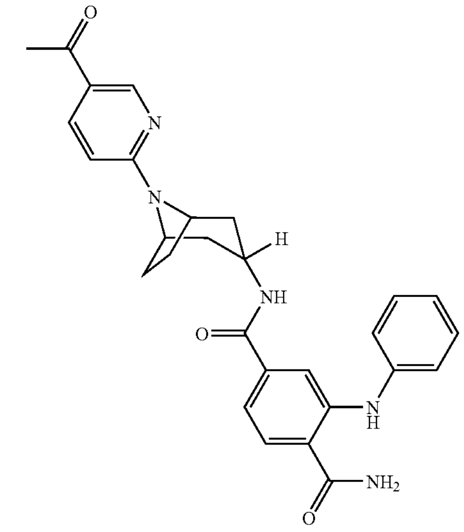 | N4-[8-(5-acetylpyridin-2-yl)-8-azabicyclo[3.2.1]oct-3-endo-yl]-2-[(2-aminoethyl)amino]benzene-1,4-dicarboxamide<br>ACTIVITY = A |
| 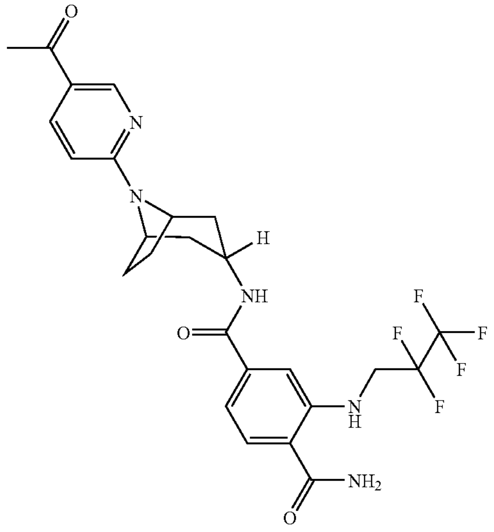 | N4-[8-(5-acetylpyridin-2-yl)-8-azabicyclo[3.2.1]oct-3-endo-yl]-2-[(2,2,3,3,3-pentafluoropropyl)amino]benzene-1,4-dicarboxamide<br>ACTIVITY = A |
| 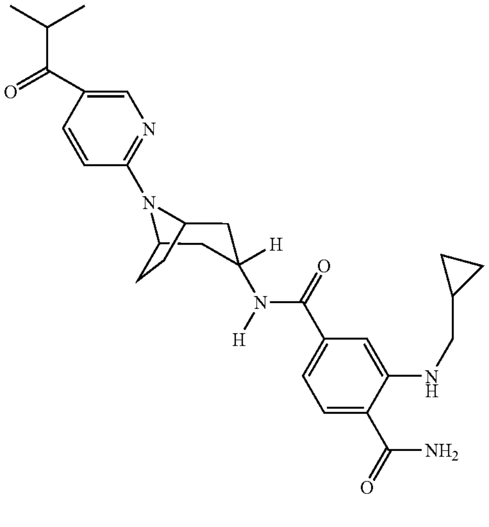 | 2-[(cyclopropylmethyl)aminol-N4-{8-[5-(2-methylpropanoyl)pyridin-2-yl]-8-azabicyclo[3.2.1]oct-3-endo-yl}benzene-1,4-dicarboxamide<br>ACTIVITY = C |

TABLE I-continued

| STRUCTURE | NAME & ACTIVITY |
| --- | --- |
| 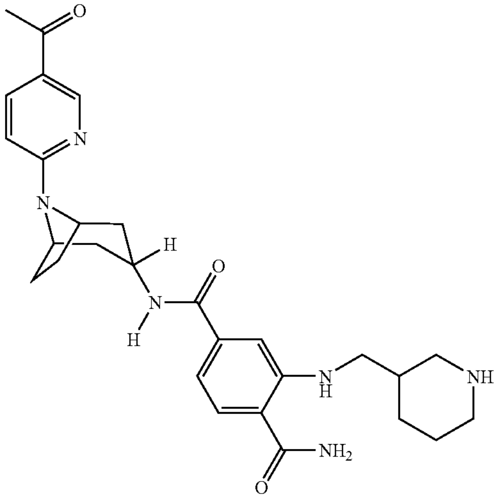 | N4-(8-(5-acetylpyridin-2-yl)-8-azabicyclo[3.2.1]oct-3-endo-yl]-2-[(piperidin-3-ylmethyl)amino]benzene-1,4-dicarboxamide ACTIVITY = A |
| 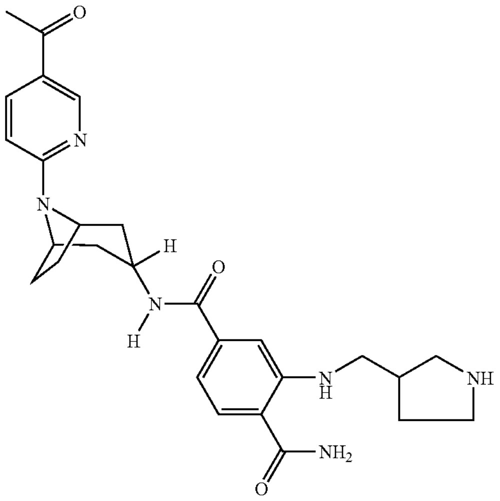 | N4-[8-(5-acetylpyridin-2-yl)-8-azabicyclo[3.2.1]oct-3-endo-yl]-2-[(pyrrolidin-3-ylmethyl)amino]benzene-1,4-dicarboxamide ACTIVITY = A |
| 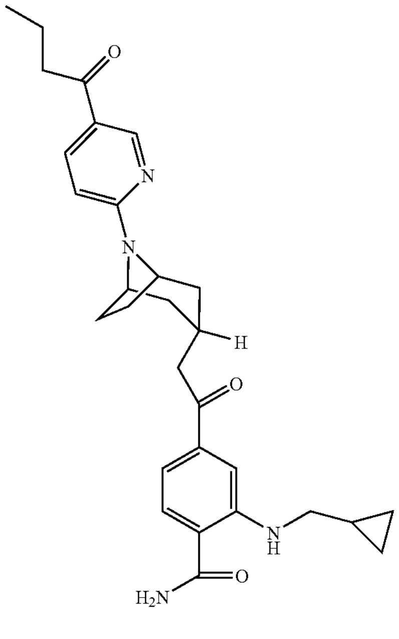 | N4-[8-(5-butanoylpyridin-2-yl)-8-azabicyclo[3.2.1]oct-3-endo-yl]-2-[(cyclopropylmethyl)amino]benzene-1,4-dicarboxamide ACTIVITY = B |

TABLE I-continued
| STRUCTURE | NAME & ACTIVITY |
| --- | --- |
| 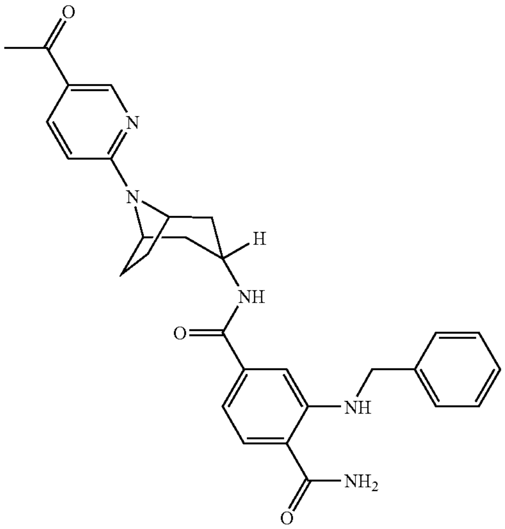 | N4-[8-(5-acetylpyridin-2-yl)-8-azabicyclo[3.2.1]oct-3-endo-yl]-2-[(phenylmethyl)amino]benzene-1,4-dicarboxamide<br>ACTIVITY = B |
| 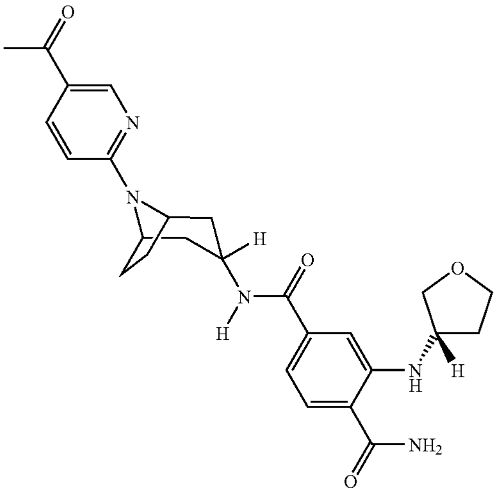 | N4-[8-(5-acetylpyridin-2-yl)-8-azabicyclo[3.2.1]oct-3-endo-yl]-2-[(3S)-tetrahydrofuran-3-ylamino]benzene-1,4-dicarboxamide<br>ACTIVITY = A |
| 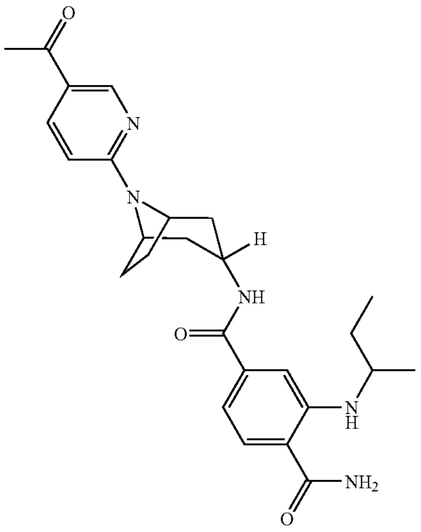 | N4-[8-(5-acetylpyridin-2-yl)-8-azabicyclo[3.2.1]oct-3-endo-yl]-2-((1-methylpropyl)amino]benzene-1,4-dicarboxamide<br>ACTIVITY = A |

TABLE I-continued
| STRUCTURE | NAME & ACTIVITY |
| --- | --- |
| 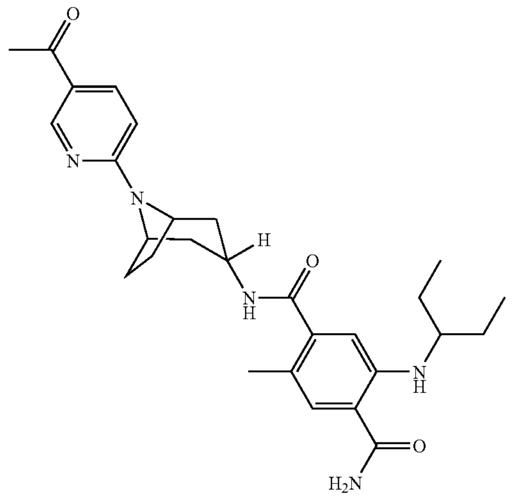 | N-[8-(5-acetylpyridin-2-yl)-8-azabicyclo[3.2.1]oct-3-endo-yl-5-[(1-ethylpropyl)amino]-2-methylbenzene-1,4-dicarboxamide ACTIVITY = A |
| 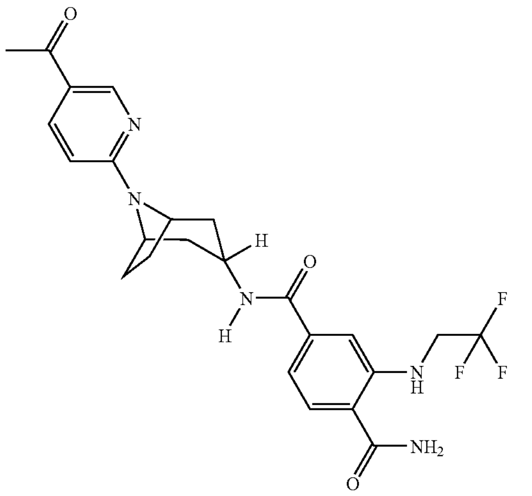 | N4-[8-(5-acetylpyridin-2-yl)-8-azabicyclo[3.2.1]oct-3-endo-yl]-2-[(2,2,2-trifluoroethyl)amino]benzene-1,4-dicarboxamide ACTIVITY = A |
| 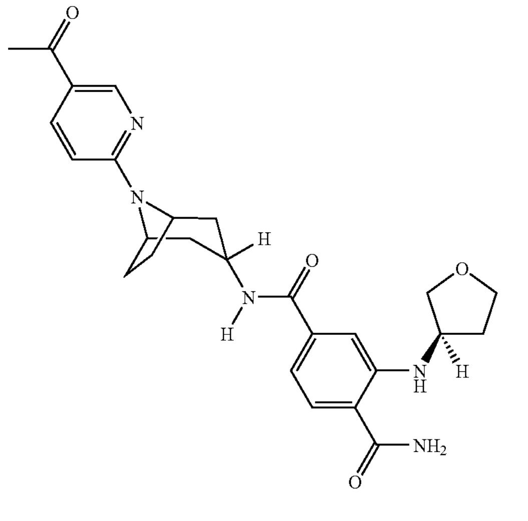 | N4-[8-(5-acetylpyridin-2-yl)-8-azabicyclo[3.2.1]oct-3-endo-yl]-2-[(3R)-tetrahydrofuran-3-ylamino]benzene-1,4-dioarboxamide ACTIVITY = A |

TABLE I-continued

| STRUCTURE | NAME & ACTIVITY |
|---|---|
| 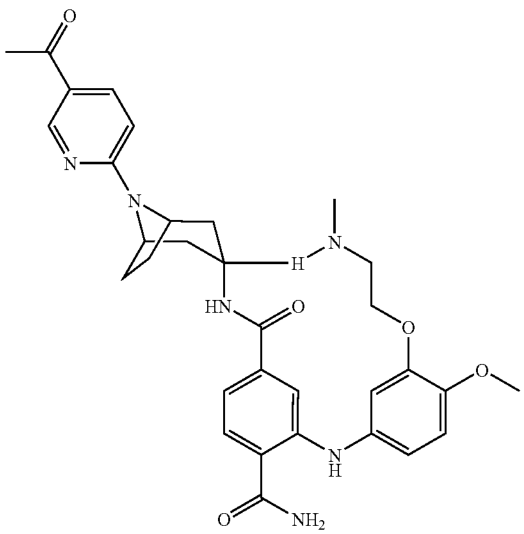 | N4-[8-(5-acetylpyridin-2-yl)-8-azabicyclo[3.2.1]oct-3-endo-yl]-2-{[3-{[2-(dimethylamino)ethyl]oxy}-4-(methyloxy)phenyl]amino}benzene-1,4-dicarboxamide<br>ACTIVITY = A |
| 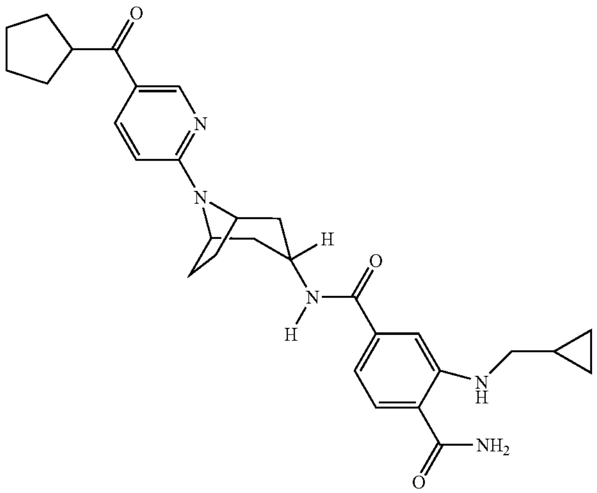 | N4-{8-[5-(cyclopentylcarbonyl)pyridin-2-yl]-8-azabicyclo[3.2.1]oct-3-endo-yl}-2-[(cyclopropylmethyl)amino]benzene-1,4-dicarboxamide<br>ACTIVITY = D |
| 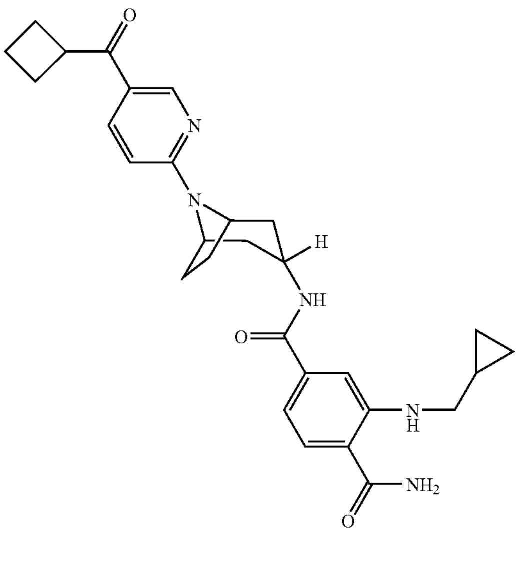 | N4-{8-[5-(cyclobutylcarbonyl )pyridin-2-yl]-8-azabicyclo[3.2.1]oct-3-endo-yl}-2-[(cyclopropylmethyl)amino]benzene-1,4-dicarboxamide<br>ACTIVITY = C |

TABLE I-continued
| STRUCTURE | NAME & ACTIVITY |
|---|---|
| 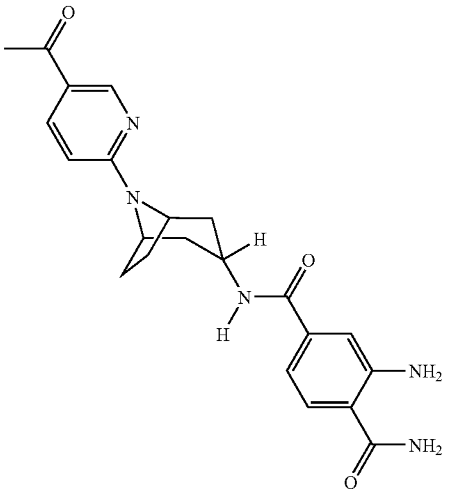 | N4-[8-(5-acetylpyridin-2-yl)-8-azabicyclo[3.2.1]oct-3-endo-yl]-2-aminobenzene-1,4-dicarboxamide ACTIVITY = B |
| 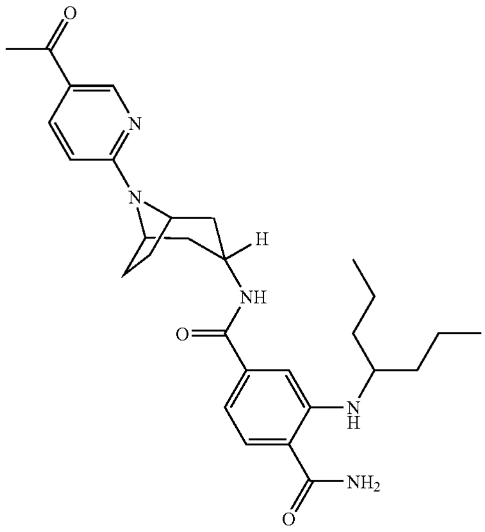 | N4-[8-(5-acetylpyridin-2-yl)-8-azabicyclo[3.2.1]oct-3-endo-yl]-2-[(1-propylbutyl)amino]benzene-1,4-dicarboxamide ACTIVITY = A |
| 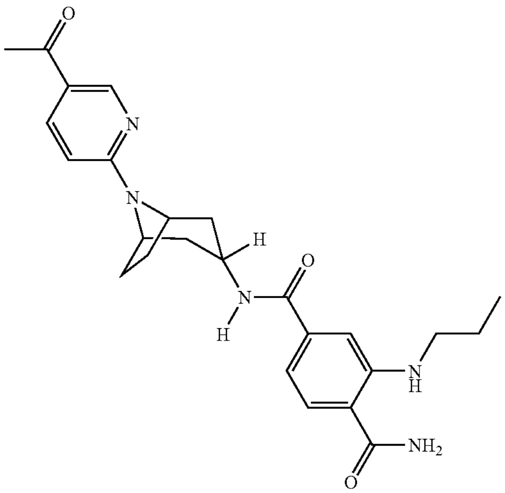 | N4-[8-(5-acetylpyridin-2-yl)-8-azabicyclo[3.2.1]oct-3-endo-yl]-2-(propylamino)benzene-1,4-dicarboxamide ACTIVITY = A |

TABLE I-continued
| STRUCTURE | NAME & ACTIVITY |
| --- | --- |
| 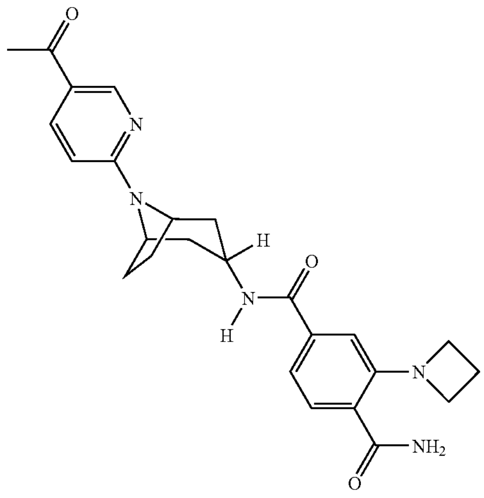 | N4-[8-(5-acetylpyridin-2-yl)-8-azabicyclo[3.2.1]oct-3-endo-yl]-2-azetidin-1-ylbenzene-1,4-dicarboxamide<br>ACTIVITY = D |
| 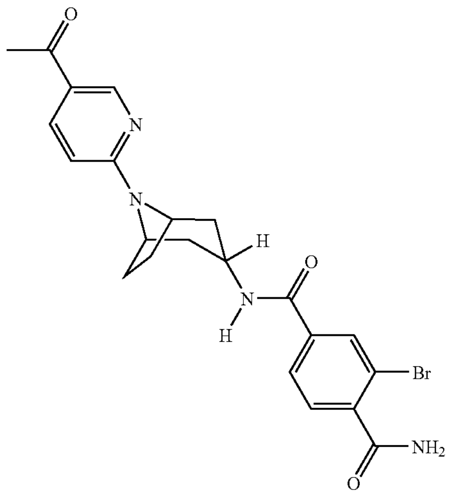 | N4-[8-(5-acetylpyridin-2-yl)-8-azabicyclo[3.2.1]oct-3-endo-yl]-2-bromobenzene-1,4-dicarboxamide<br>ACTIVITY = A |
| 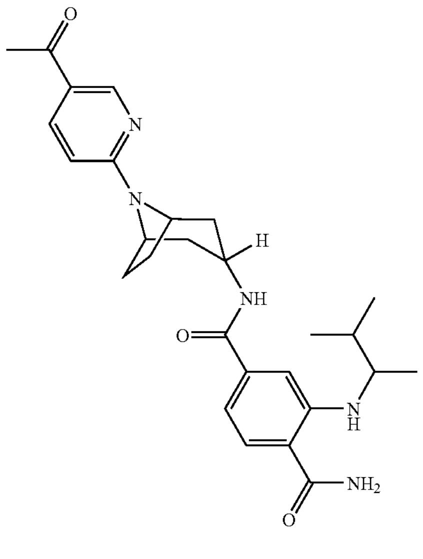 | N4-[8-(5-acetylpyridin-2-yl)-8-azabicyclo[3.2.1]oct-3-endo-yl]-2-[(1,2-dimethylpropyl)amino]benzene-1,4-dicarboxamide<br>ACTIVITY = A |

TABLE I-continued

| STRUCTURE | NAME & ACTIVITY |
|---|---|
| 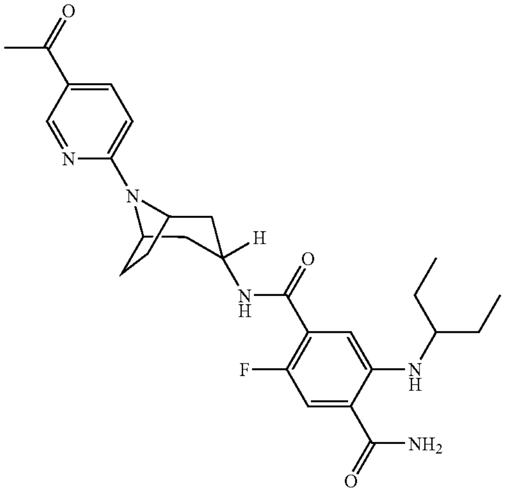 | N-[8-(5-acetylpyridin-2-yl)-8-azabicyclo[3.2.1]oct-3-endo-yl]-5-[(1-ethylpropyl)amino]-2-fluorobenzene-1,4-dicarboxamide ACTIVITY = A |
| 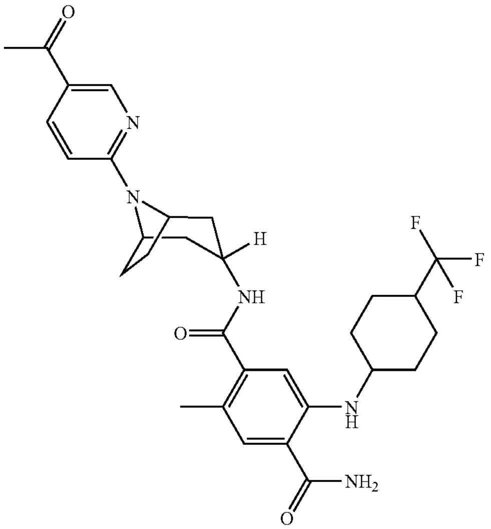 | N-[8-(5-acetylpyridin-2-yl)-8-azabicyclo[3.2.1]oct-3-endo-yl]-2-methyl-5-{[4-(trifluoromethyl)cyclohexyl]amino}benzene-1,4-dicarboxamide ACTIVITY = A |
| 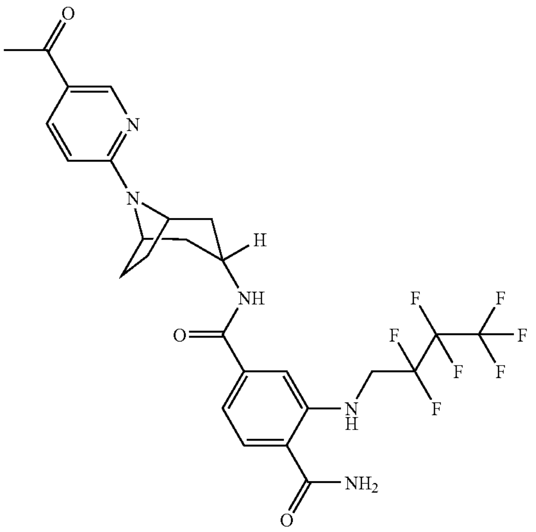 | N4-[8-(5-acetylpyridin-2-yl)-8-azabicyclo[3.2.1]oct-3-endo-yl]-2-[(2,2,3,3,4,4,4-heptafluorobutyl)amino]benzene-1,4-dicarboxamide ACTIVITY = B |

TABLE I-continued

| STRUCTURE | NAME & ACTIVITY |
|---|---|
| 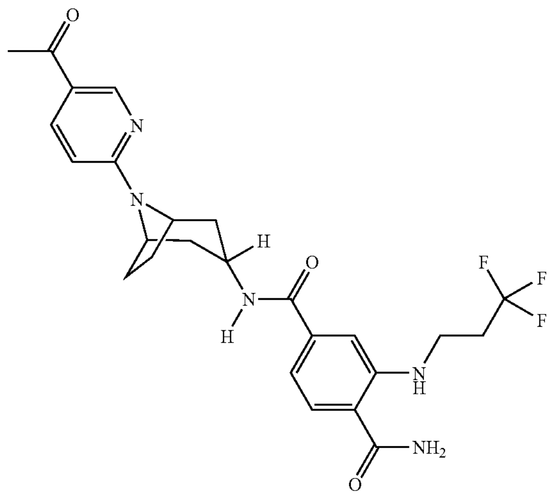 | N4-[8-(5-acetylpyridin-2-yl)-8-azabicyclo[3.2.1]oct-3-endo-yl]-2-[(3,3,3-trifluoropropyl)amino]benzene-1,4-dicarboxamide<br>ACTIVITY = A |
| 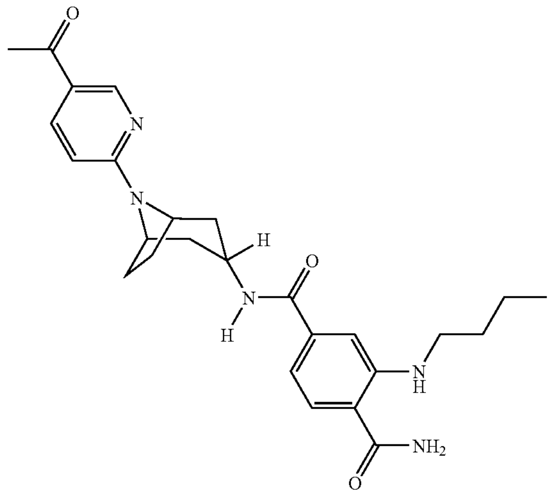 | N4-[8-(5-acetylpyridin-2-yl)-8-azabicyclo[3.2.1]oct-3-endo-yl]-2-(butylamino)benzene-1,4-dicarboxamide<br>ACTIVITY = A |
| 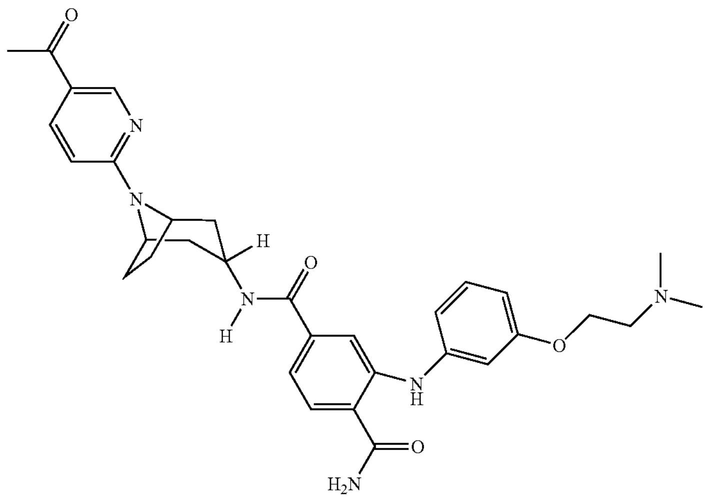 | N4-[8-(5-acetylpyridin-2-yl)-8-azabicyclo[3.2.1]oct-3-endo-yl]-2-[(3-{[2-(dimethylamino)ethyl]oxy}phenyl)amino]benzene-1,4-dicarboxamide<br>ACTIVITY = A |

TABLE I-continued
| STRUCTURE | NAME & ACTIVITY |
|---|---|
| 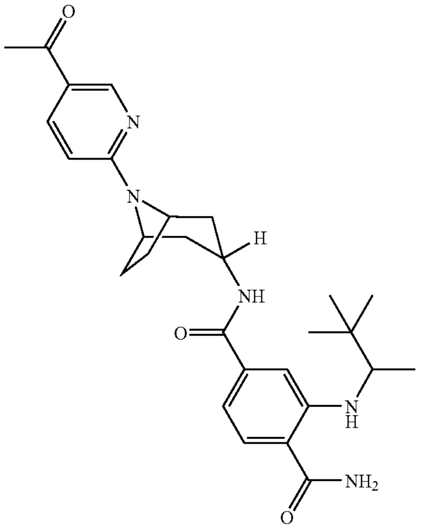 | N4-[8-(5-acetylpyridin-2-yl)-8-azabicyclo[3.2.1]oct-3-endo-yl]-2-[(1,2,2-trimethylpropyl)amino]benzene-1,4-dicarboxamide ACTIVITY = A |
| 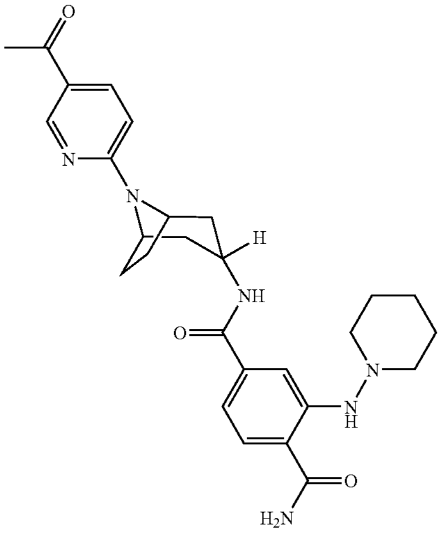 | N4-[8-(5-acetylpyridin-2-yl)-8-azabicyclo[3.2.1]oct-3-endo-yl]-2-(piperidin-1-ylamino)benzene-1,4-dicarboxamide ACTIVITY = A |
| 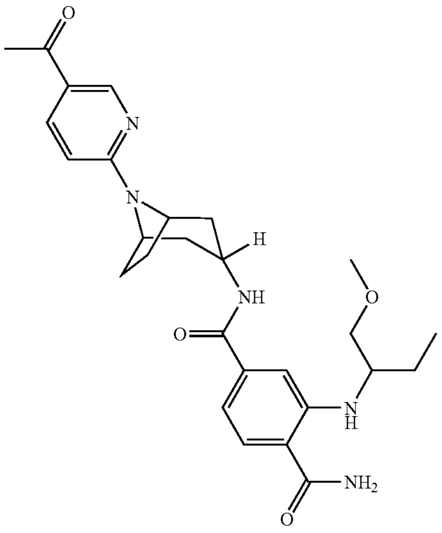 | N4-(8-(5-acetylpyridin-2-yl)-8-azabicyclo[3.2.1]oct-3-endo-yl]-2-({1-[(methyloxy)methyl]propyl}amino) benzene-1,4-dicarboxamide ACTIVITY = A |

TABLE I-continued

| STRUCTURE | NAME & ACTIVITY |
| --- | --- |
| 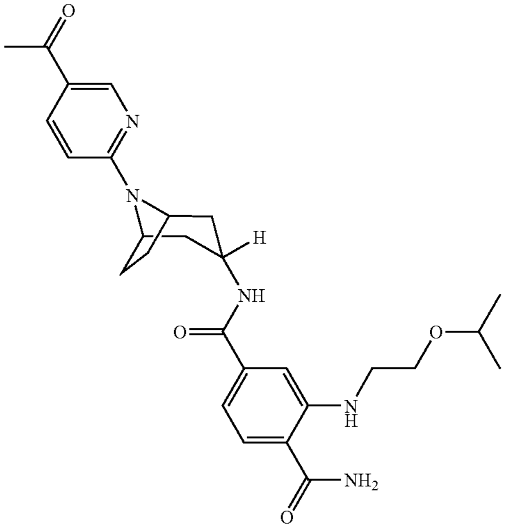 | N4-[8-(5-acetylpyridin-2-yl)-8-azabicyclo[3.2.1]oct-3-endo-yl]-2-({2-[(1-methylethyl)oxy]ethyl}amino)benzene-1,4-dicarboxamide<br>ACTIVITY = A |
| 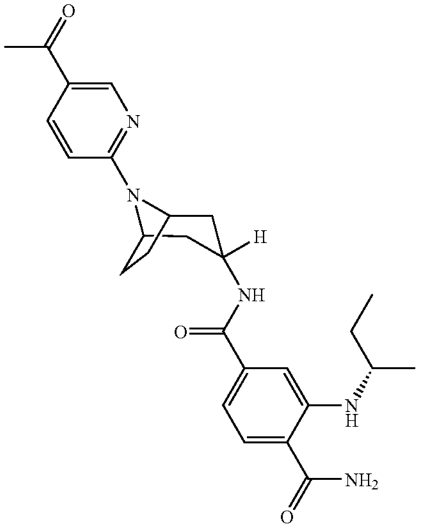 | N4-[8-(5-acetylpyridin-2-yl)-8-azabicyclo[3.2.1]oct-3-endo-yl]-2-{[(1S)-1-methylpropyl]amino}benzene-1,4-dicarboxamide<br>ACTIVITY = A |
| 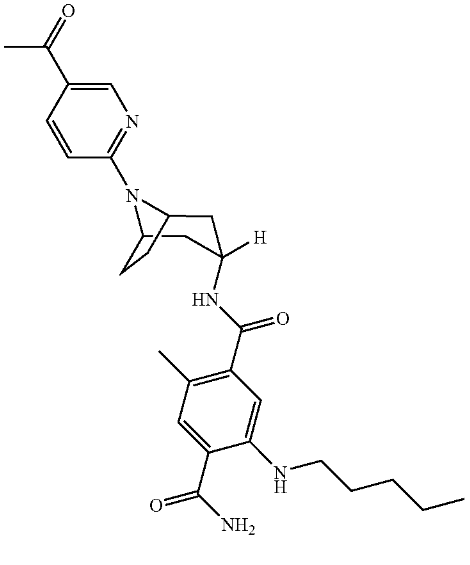 | N-[8-(5-acetylpyridin-2-yl)-8-azabicyclo[3.2.1]oct-3-endo-yl]-2-methyl-5-(pentylamino)benzene-1,4-dicarboxamide<br>ACTIVITY = A |

TABLE I-continued

| STRUCTURE | NAME & ACTIVITY |
| --- | --- |
| 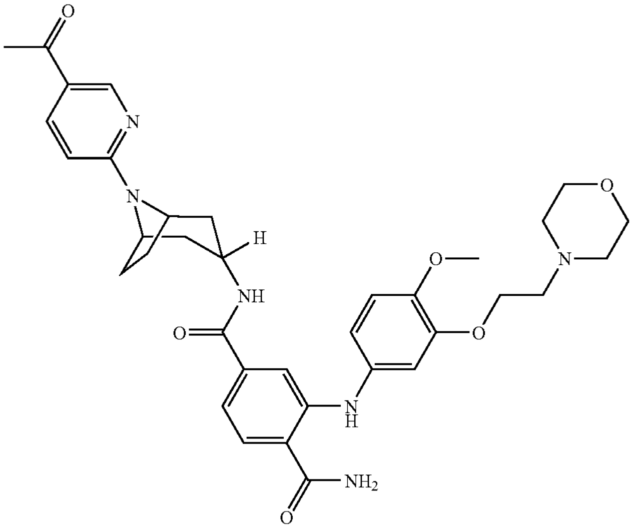 | N4-[8-(5-acetylpyridin-2-yl)-8-azabicyclo[3.2.1]oct-3-endo-yl]-2-({4-(methyloxy)-3-[(2-morpholin-4-ylethyl)oxy]phenyl}amino)benzene-1,4-dicarboxamide<br>ACTIVITY = A |
| 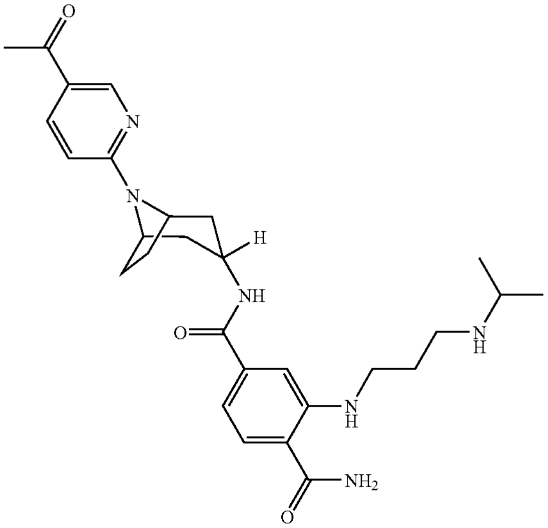 | N4-[8-(5-acetylpyridin-2-yl)-8-azabicyclo[3.2.1]oct-3-endo-yl]-2-({3-[(1-methylethyl)amino]propyl}amino) benzene-1,4-dicarboxamide<br>ACTIVITY = B |
| 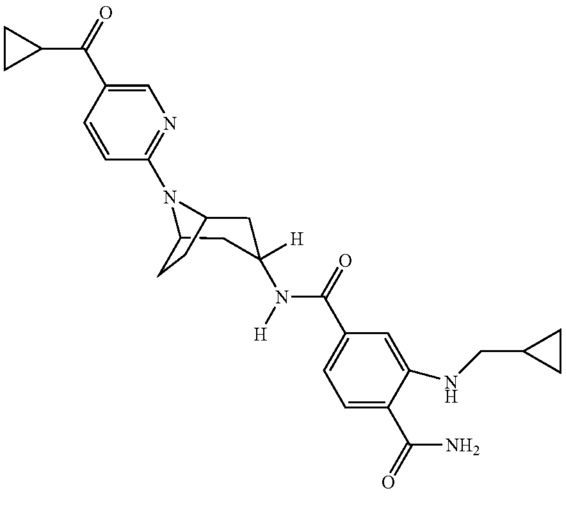 | N4-{8-[5-(cyclopropylcarbonyl)pyridin-2-yl]-8-azabicyclo[3.2.1]oct-3-endo-yl}-2-[(cyclopropylmethyl)amino]benzene-1,4-dicarboxamide<br>ACTIVITY = A |

TABLE I-continued

| STRUCTURE | NAME & ACTIVITY |
|---|---|
| 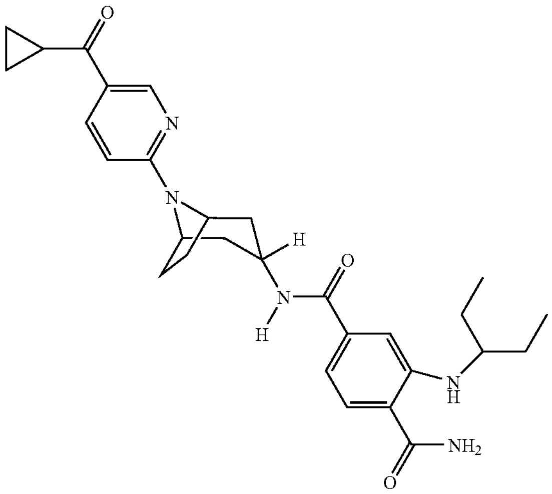 | N4-{8-[5-(cyclopropylcarbonyl)pyridin-2-yl]-8-azabicyclo[3.2.1]oct-3-endo-yl}-2-[(1-ethylpropyl)amino]benzene-1,4-dicarboxamide<br>ACTIVITY = A |
| 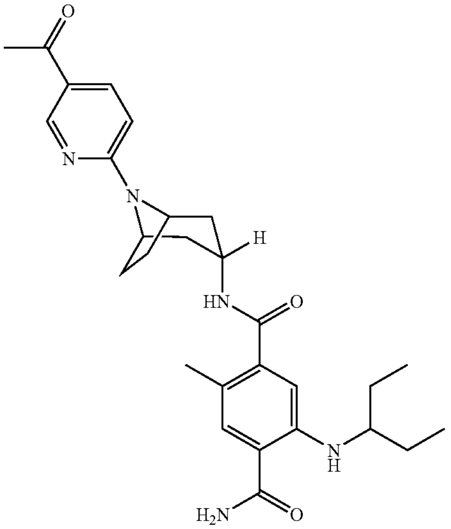 | N-{8-[5-(cyclopropylcarbonyl)pyridin-2-yl]-8-azabicyclo[3.2.1]oct-3-endo-yl}-5-[(1-ethylpropyl)amino]-2-methylbenzene-1,4-dicarboxamide<br>ACTIVITY = A |
| 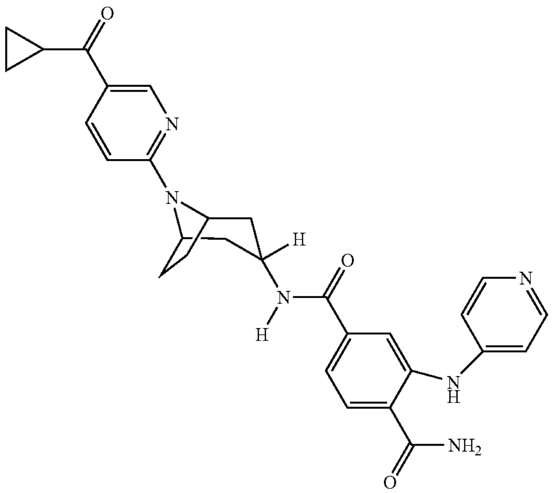 | N4-{8-[5-(cyclopropylcarbonyl)pyridin-2-yl]-8-azabicyclo[3.2.1]oct-3-endo-yl}-2-(pyridin-4-ylamino)benzene-1,4-dicarboxamide<br>ACTIVITY = A |

TABLE I-continued
| STRUCTURE | NAME & ACTIVITY |
|---|---|
| 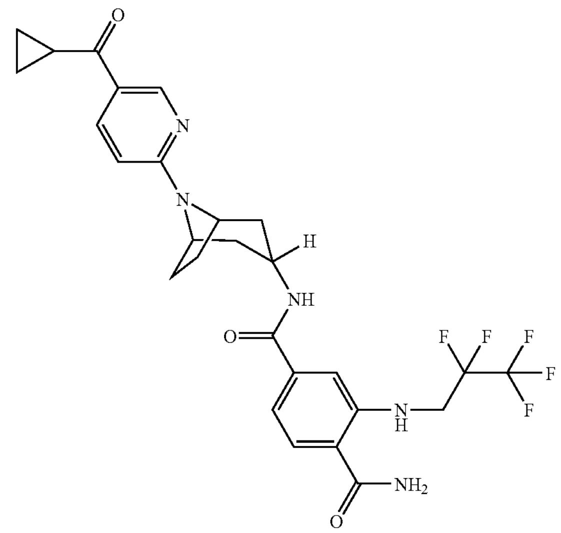 | N4-{8-[5-(cyclopropylcarbonyl)pyridln-2-yl]-8-azabicyclo[3.2.1]oct-3-endo-yl}-2-[(2,2,3,3,3-pentafluoropropyl)amino]benzene-1,4-dicarboxamide ACTIVITY = A |
| 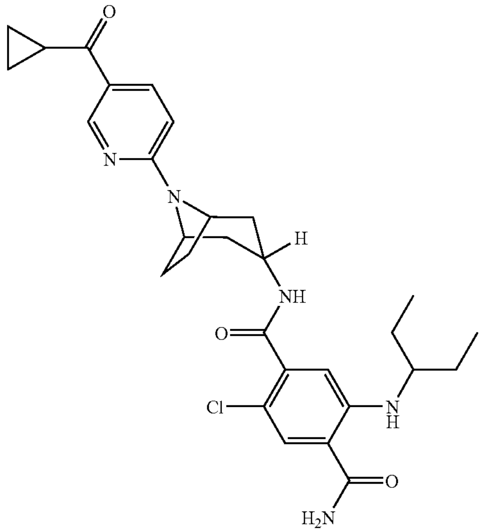 | 2-chloro-N-{8-[5-(cyclopropylcarbonyl)pyridin-2-yl]-8-azabicyclo[3.2.1]oct-3-endo-yl}-5-[(1-ethylpropyl)amino]benzene-1,4-dicarboxamide ACTIVITY = A |

TABLE I-continued
| STRUCTURE | NAME & ACTIVITY |
| --- | --- |
| 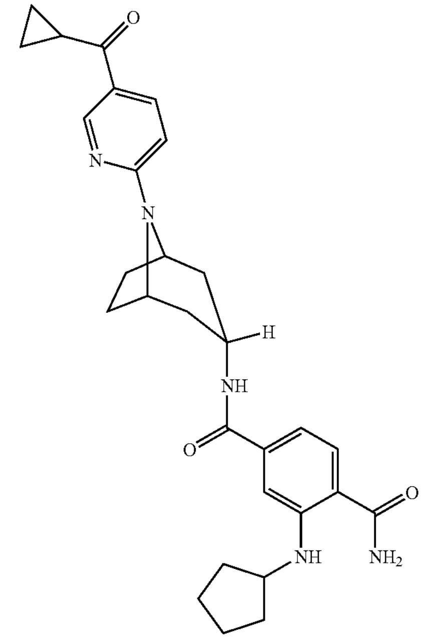 | 2-(cyclopentylamino)-N4-{8-[5-cyclopropylcarbonyl)pyridin-2-yl]-8-azabicyclo[3.2.1]oct-3-endo-yl}benzene-1,4-dicarboxamide<br>ACTIVITY = A |
| 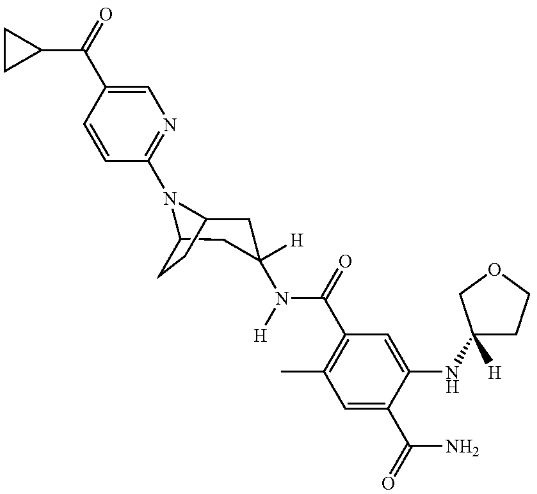 | N-{8-[5-(cyclopropylcarbonyl)pyridin-2-yl]-8-azabicyclo[3.2.1]oct-3-endo-yl}-2-methyl-5-[(3S)-tetrahydrofuran-3-ylamino]benzene-1,4-dicarboxamide<br>ACTIVITY = A |

TABLE I-continued

| STRUCTURE | NAME & ACTIVITY |
|---|---|
| 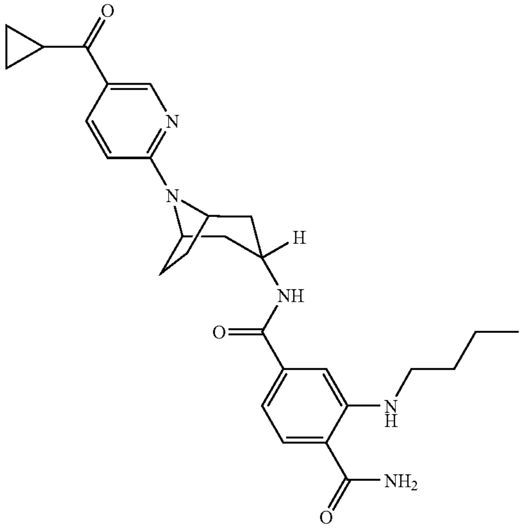 | 2-(butylamino)-N4-{8-[5-(cyclopropylcarbonyl)pyridin-2-yl]-8-azabicyclo[3.2.1]oct-3-endo-yl}benzene-1,4-dicarboxamide<br>ACTIVITY = A |
| 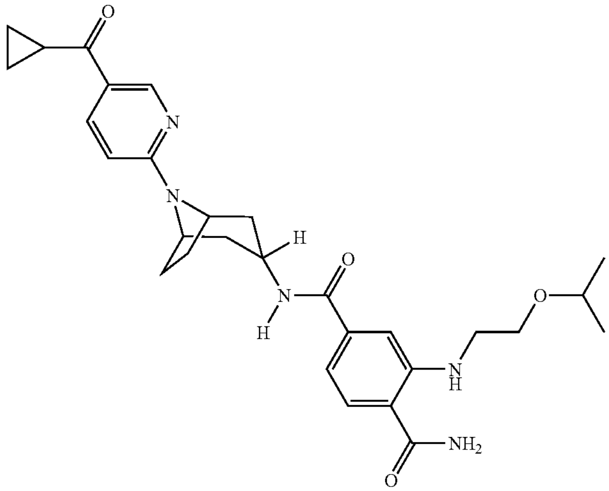 | N4-{8-[5-(cyclopropylcarbonyl)pyridin-2-yl]-8-azabicyclo[3.2.1]oct-3-endo-yl}-2-({2-[(1-methylethyl)oxy]ethyl}amino)benzene-1,4-dicarboxamide<br>ACTIVITY = A |
| 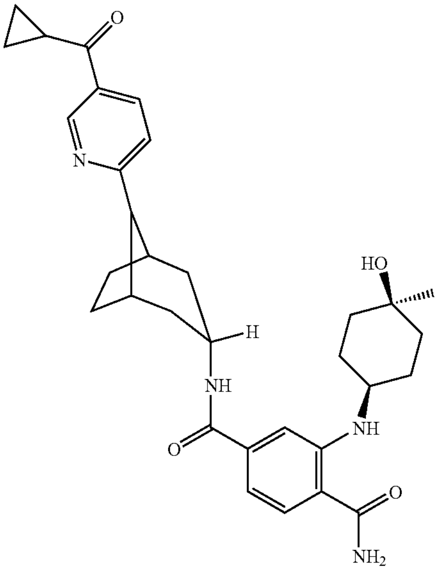 | N4-{8-[5-(cyclopropylcarbonyl)pyridin-2-yl]-8-azabicyclo[3.2.1]oct-3-endo-yl}-2-[(cis-4-hydroxy-4-methylcyclohexyl)amino]benzene-1,4-dicarboxamide<br>ACTIVITY = A |

TABLE I-continued

| STRUCTURE | NAME & ACTIVITY |
| --- | --- |
| 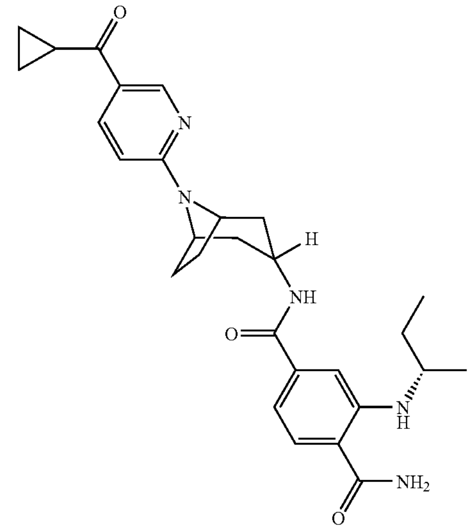 | N4-{8-[5-(cyclopropylcarbonyl)pyridin-2-yl]-8-azabicyclo[3.2.1]oct-3-endo-yl}-2-{[(1S)-1-methylpropyl]amino}benzene-1,4-dicarboxamide ACTIVITY = A |
| 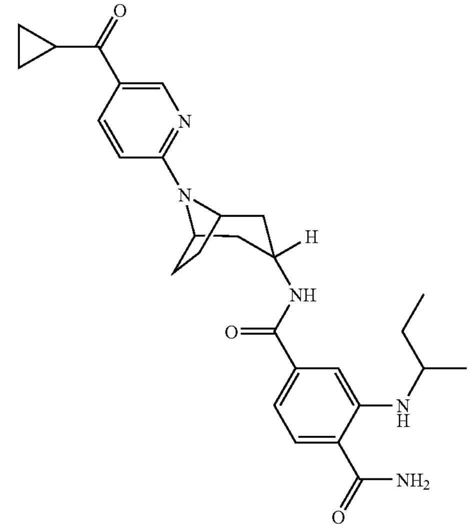 | N4-{8-[5-(cyclopropylcarbonyl)pyridin-2-yl]-8-azabicyclo[3.2.1]oct-3-endo-yl}-2-[(1-methylpropyl)amino]benzene-1,4-dicarboxamide ACTIVITY = A |
| 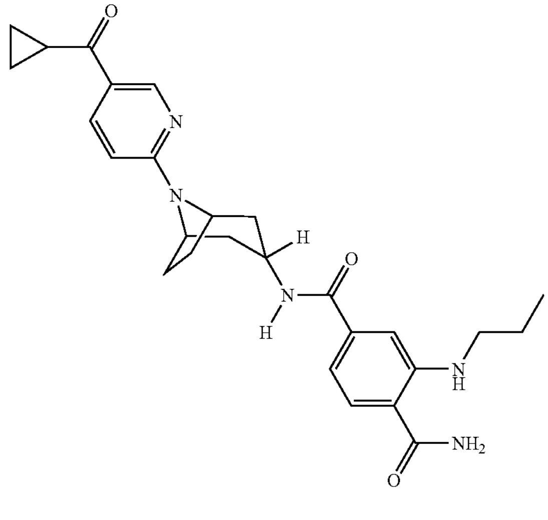 | N4-{8-[5-(cyclopropylcarbonyl)pyridin-2-yl]-8-azabicyclo[3.2.1]oct-3-endo-yl}-2-(propylamino)benzene-1,4-dicarboxamide ACTIVITY = A |

TABLE I-continued
| STRUCTURE | NAME & ACTIVITY |
|---|---|
| 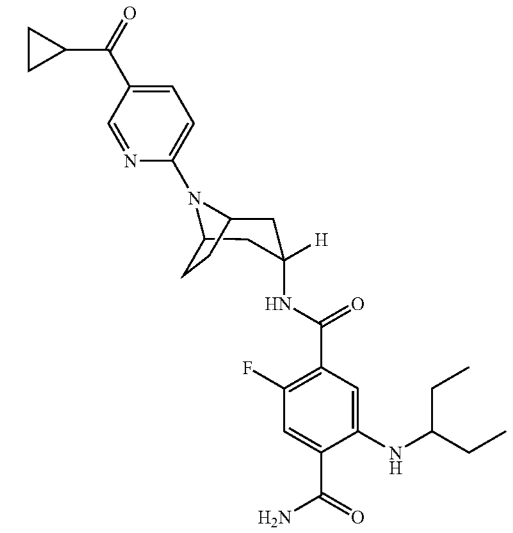 | N-{8-[5-(cyclopropylcarbonyl)pyridin-2-yl]-8-azabicyclo[3.2.1]oct-3-endo-yl}-5-[(1-ethylpropyl)amino]-2-fluorobenzene-1,4-dicarboxamide<br>ACTIVITY = A |
| 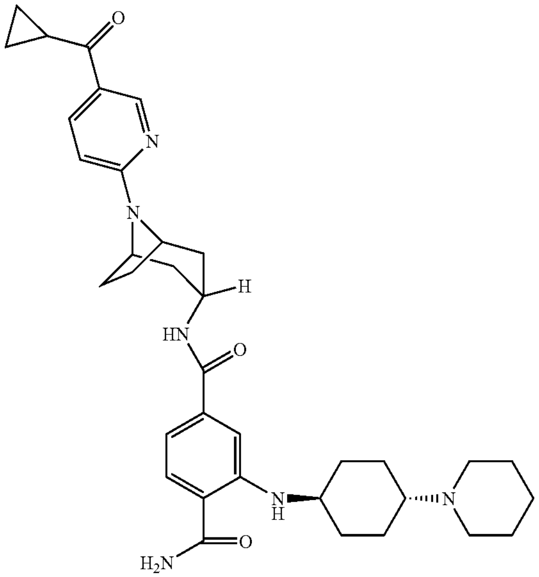 | N4-{8-[5-(cyclopropylcarbonyl)pyridin-2-yl]-8-azabicyclo[3.2.1]oct-3-endo-yl}-2-[(trans-4-piperidin-1-ylcyclohexyl)amino]benzene-1,4-dicarboxamide<br>ACTIVITY = A |

TABLE I-continued
| STRUCTURE | NAME & ACTIVITY |
|---|---|
| 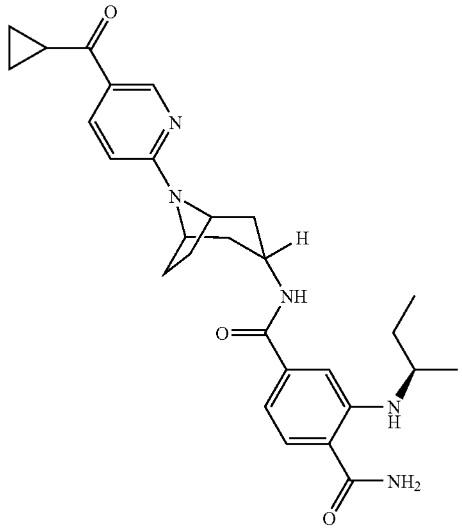 | N4-{8-[5-(cyclopropylcarbonyl)pyridin-2-yl]-8-azabicyclo[3.2.1]oct-3-endo-yl}-2-{[(1R)-1-methylpropyl]amino}benzene-1,4-dicarboxamide ACTIVITY = A |
| 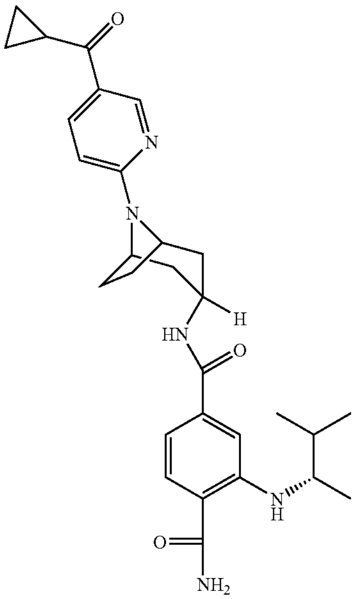 | N4-{8-[5-(cyclopropylcarbonyl)pyridin-2-yl]-8-azabicyclo[3.2.1]oct-3-endo-yl}-2-{[(1S)-1,2-dimethylpropyl]amino}benzene-1,4-dicarboxamide ACTIVITY = A |

TABLE I-continued
| STRUCTURE | NAME & ACTIVITY |
| --- | --- |
| 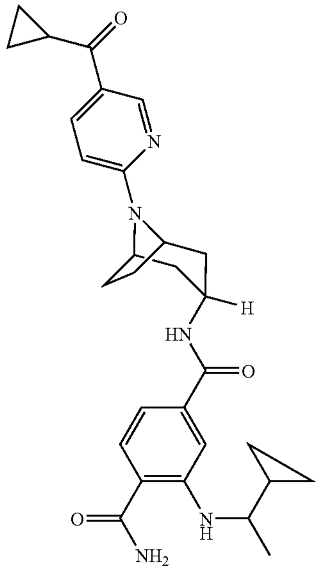 | N4-{8-[5-(cyclopropylcarbonyl)pyridin-2-yl]-8-azabicyclo[3.2.1]oct-3-endo-yl}-2-[(1-cyclopropylethyl)amino]benzene-1,4-dicarboxamide<br>ACTIVITY = A |
| 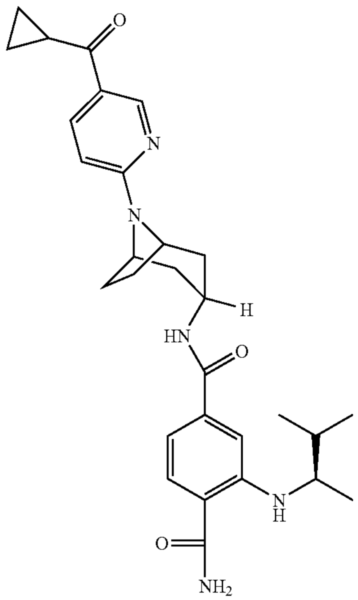 | N4-(8-[5-(cyclopropylcarbonyl)pyridin-2-yl]-8-azabicyclo[3.2.1]oct-3-endo-yl)-2-{[(1R)-1,2-dimethylpropyl]amino}benzene-1,4-dicarboxamide<br>ACTIVITY = A |

TABLE I-continued

| STRUCTURE | NAME & ACTIVITY |
| --- | --- |
| 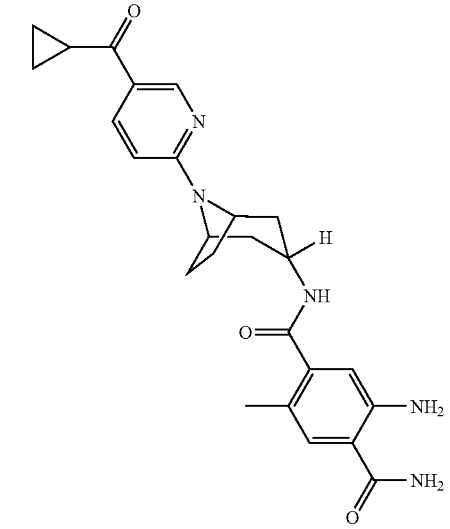 | 5-amino-N-{8-[5-(cyclopropylcarbonyl)pyridin-2-yl]-8-azabicyclo[3.2.1]oct-3-endo-yl}-2-methylbenzene-1,4-dicarboxamide ACTIVITY = A |
| 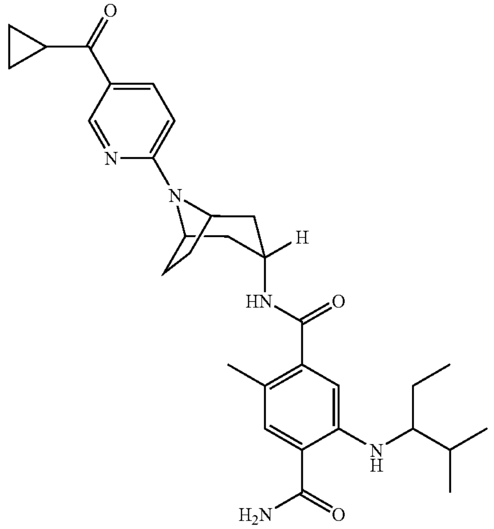 | N-{8-[5-(cyclopropylcarbonyl)pyridin-2-yl]-8-azabicyclo[3.2.1]oct-3-endo-yl}-5-[(1-ethyl-2-methylpropyl)amino]-2-methylbenzene-1,4-dicarboxamide ACTIVITY = A |
| 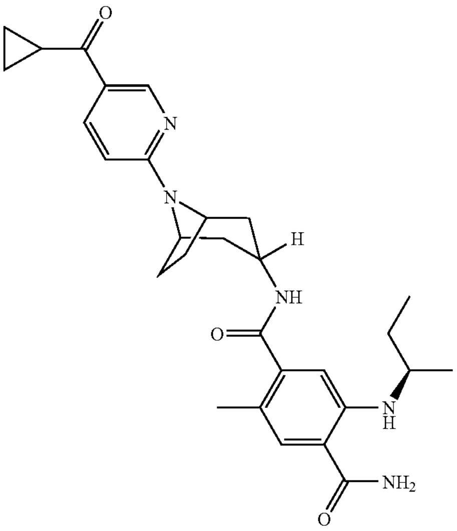 | N-{8-[5-(cyclopropylcarbonyl)pyridin-2-yl]-8-azabicyclo[3.2.1]oct-3-endo-yl}-2-methyl-5-{[(1R)-1-methylpropyl]amino}benzene-1,4-dicarboxamide ACTIVITY = A |

TABLE I-continued

| STRUCTURE | NAME & ACTIVITY |
|---|---|
| 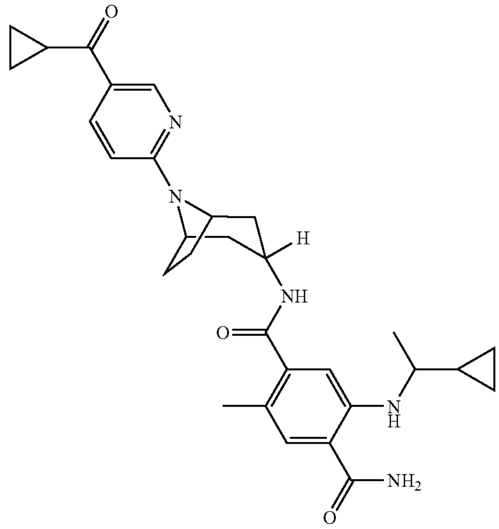 | N-{8-[5-(cyclopropylcarbonyl)pyridin-2-yl]-8-azabicycbo[3.2.1]oct-3-endo-yl}-5-[(l -cyclopropylethyl)amino]-2-methylbenzene-1,4-dicarboxamide ACTIVITY = A |
| 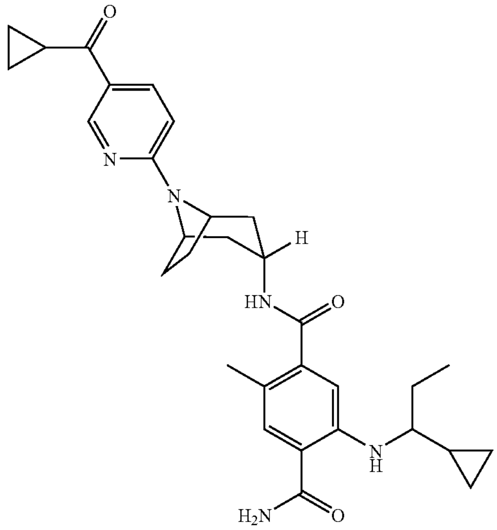 | N-{8-(5-(cyclopropylcarbonyl)pyridin-2-yl]-8-azabicyclo[3.2.1]oct-3-endo-yl}-5-[(1-cyclopropylpropyl)amino]-2-methylbenzene-1,4-dicarboxamide ACTIVITY = A |
| 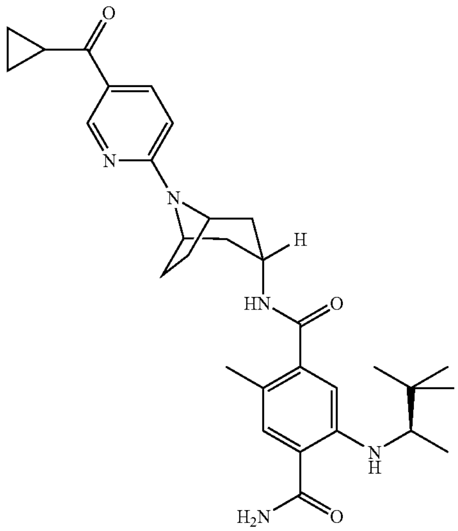 | N-{8-[5-(cyclopropylcarbonyl)pyridin-2-yl]-8-azabicyclo[3.2.1]oct-3-endo-yl}-2-methyl-5-{[(1R)-1,2,2-trimethylpropyl]amino}benzene-1,4-dicarboxamide ACTIVITY = A |

TABLE I-continued

| STRUCTURE | NAME & ACTIVITY |
|---|---|
| 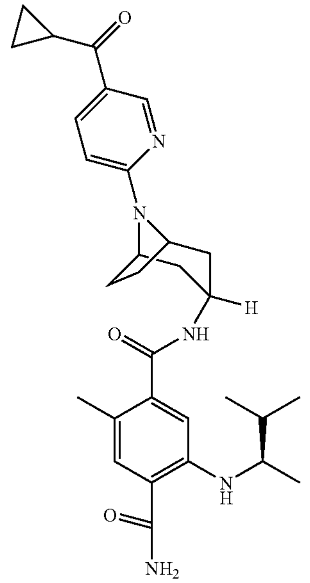 | N-{8-[5-(cyclopropylcarbonyl)pyridin-2-yl]-8-azabicyclo[3.2.1]oct-3-endo-yl}-5-{[(1R)-1,2-dimethylpropyl]amino}-2-methylbenzene-1,4-dicarboxamide ACTIVITY = A |
| 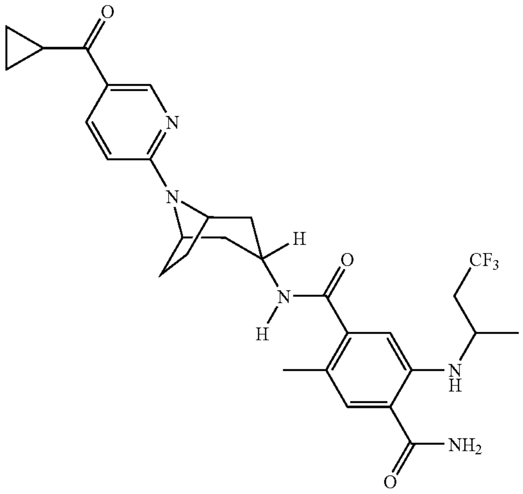 | N-{8-[5-(cyclopropylcarbonyl)pyridin-2-yl]-8-azabicyclo[3.2.1]oct-3-endo-yl}-2-methyl-5-[(3,3,3-trifluoro-1-methylpropyl)amino]benzene-1,4-dicarboxamide ACTIVITY = A |
| 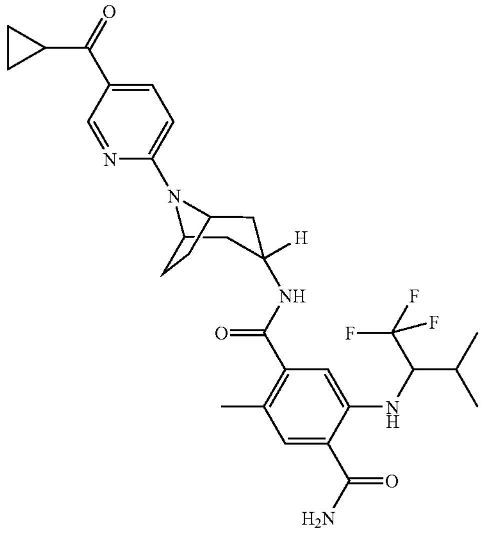 | N-{8-[5-(cyclopropylcarbonyl)pyridin-2-yl]-8-azabicyclo[3.2.1]oct-3-endo-yl}-2-methyl-5-{[2-methyl-1-(trifluoromethyl)propyl]amino}benzene-1,4-dicarboxamide ACTIVITY = A |

TABLE I-continued
| STRUCTURE | NAME & ACTIVITY |
|---|---|
| 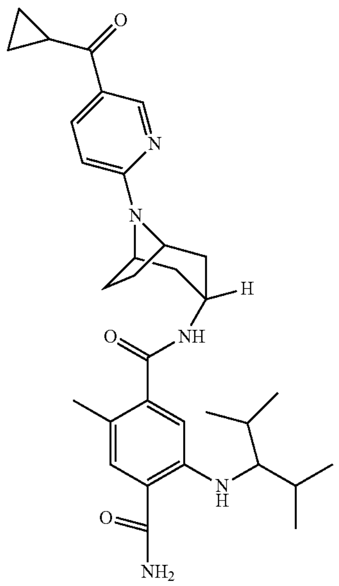 | N-{8-[5-(cyclopropylcarbonyl)pyridin-2-yl]-8-azabicyclo[3.2.1]oct-3-endo-yl}-2-methyl-5-{[2-methyl-1-(1-methylethyl)propyl]amino}benzene-1,4-dicarboxamide<br>ACTIVITY = A |
| 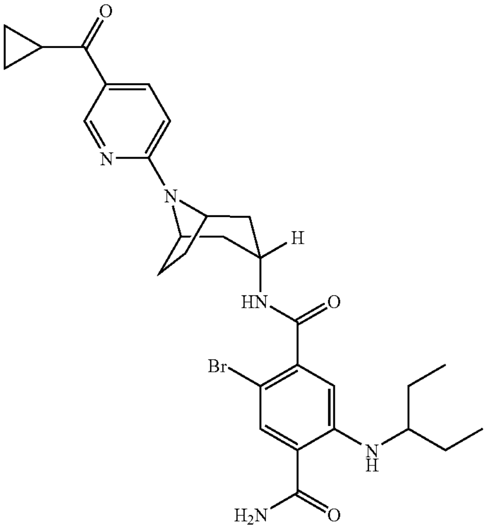 | 2-bromo-N-{8-[5-(cyclopropylcarbonyl)pyridin-2-yl]-8-azabicyclo[3.2.1]oct-3-endo-yl}-5-[(1-ethylpropyl)amino]benzene-1,4-dicarboxamide<br>ACTIVITY = A |

TABLE I-continued
| STRUCTURE | NAME & ACTIVITY |
| --- | --- |
| 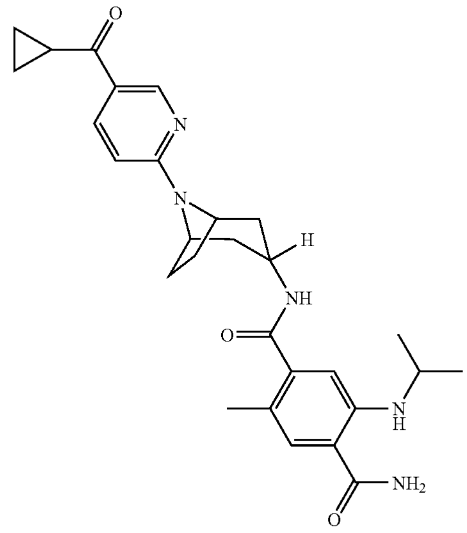 | N-{8-[5-(cyclopropylcarbonyl)pyridin-2-yl]-8-azabicyclo[3.2.1]oct-3-endo-yl}-2-methyl-5-[(1-methylethyl)amino]benzene-1,4-dicarboxamide<br>ACTIVITY = A |
| 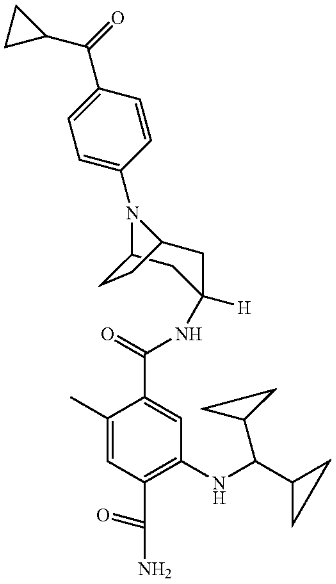 | N-{8-[5-(cyclopropylcarbonyl)pyridin-2-yl]-8-azabicyclo[3.2.1]oct-3-endo-yl}-5-[(dicyclopropylmethyl)amino]-2-methylbenzene-1,4-dicarboxamide<br>ACTIVITY = A |

TABLE I-continued

| STRUCTURE | NAME & ACTIVITY |
| --- | --- |
| 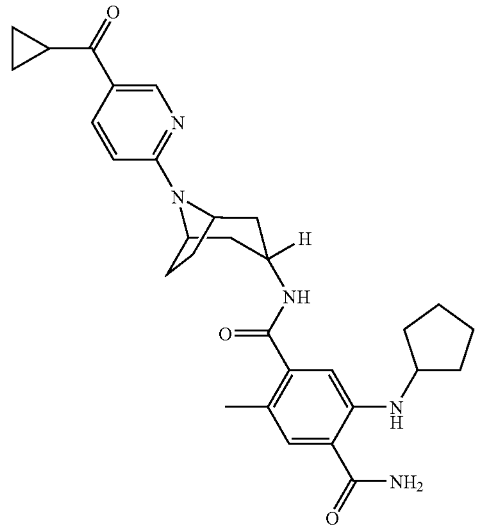 | 5-(cyclopentylamino)-N-{8-[5-(cyclopropylcarbonyl)pyridin-2-yl]-8-azabicyclo[3.2.1]oct-3-endo-yl}-2-methylbenzene-1,4-dicarboxamide<br>ACTIVITY = A |
| 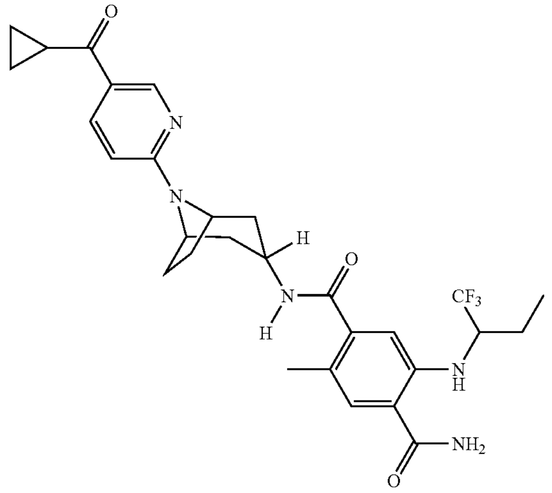 | N-{8-[5-(cyclopropylcarbonyl)pyridine-2-yl]-8-azabicyclo[3.2.1]oct-3-endo-yl}-2-methyl-5-{[1-(trifluoromethyl)propyl]amino}benzene-1,4-dicarboxamide<br>ACTIVITY = A |
| 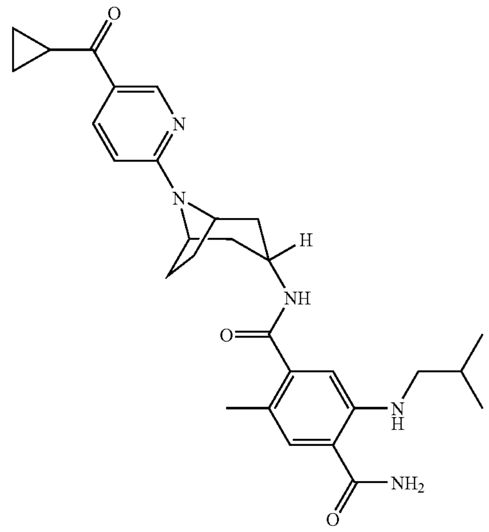 | N-{8-[5-(cyclopropylcarbonyl)pyridine-2-yl]-8-azabicyclo[3.2.1]oct-3-endo-yl}-2-methyl-5-[(2-methylpropyl)amino]benzene-1,4-dicarboxamide<br>ACTIVITY = A |

TABLE I-continued

| STRUCTURE | NAME & ACTIVITY |
|---|---|
| 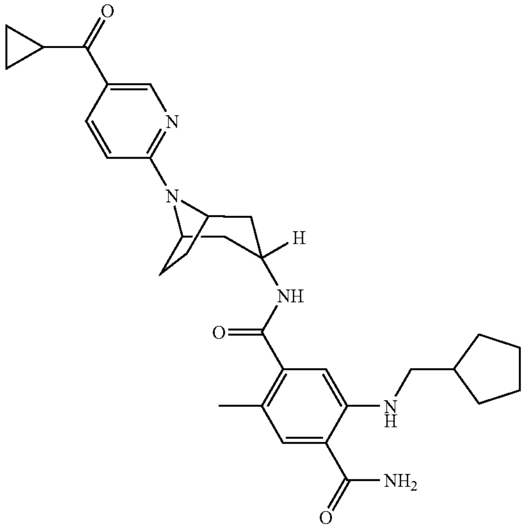 | 5-[(cyclopentylmethyl)amino]-N-{8-[5-(cyclopropylcarbonyl)pyridin-2-yl]-8-azabicyclo[3.2.1]oct-3-endo-yl}-2-methylbenzene-1,4-dicarboxamide<br>ACTIVITY = A |
| 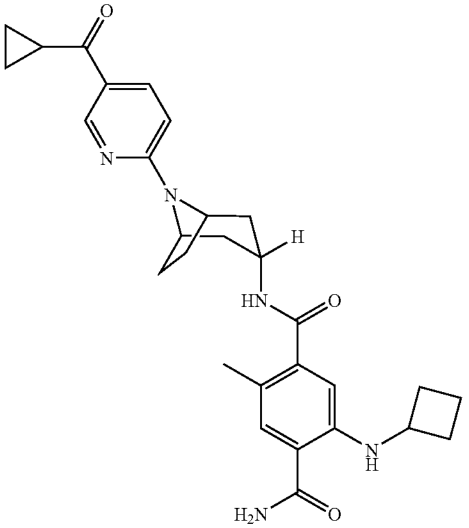 | 5-(cyclobutylamino)-N-{8-[5-(cyclopropylcarbonyl)pyridin-2-yl]-8-azabicyclo[3.2.1]oct-3-endo-yl}-2-methylbenzene-1,4-dicarboxamide<br>ACTIVITY = A |
| 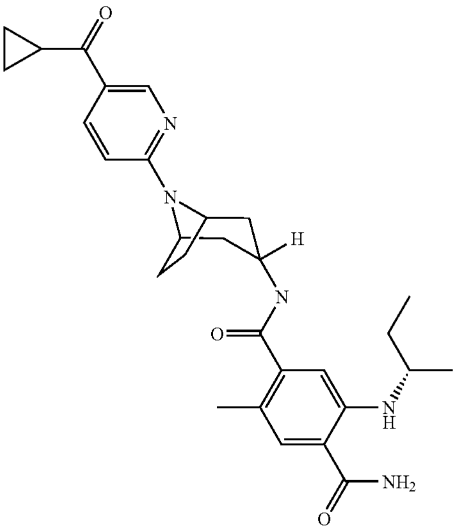 | N-{8-[5-(cyclopropylcarbonyl)pyridine-2-yl]-8-azabicyclo[3.2.1]oct-3-endo-yl}-2-methyl-5-{[(1S)-1-methylpropyl]amino}benzene-1,4-dicarboxamide<br>ACTIVITY = A |

TABLE I-continued

| STRUCTURE | NAME & ACTIVITY |
|---|---|
| 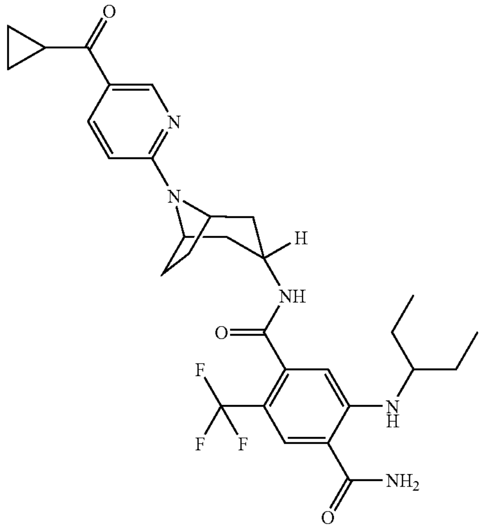 | N-{8-[5-(cyclopropylcarbonyl)pyridine-2-yl]-8-azabicyclo[3.2.1]oct-3-endo-yl}-5-[(1-ethylpropyl)amino]-2-(trifluoromethyl)benzene-1,4-dicarboxamide<br>ACTIVITY = A |
| 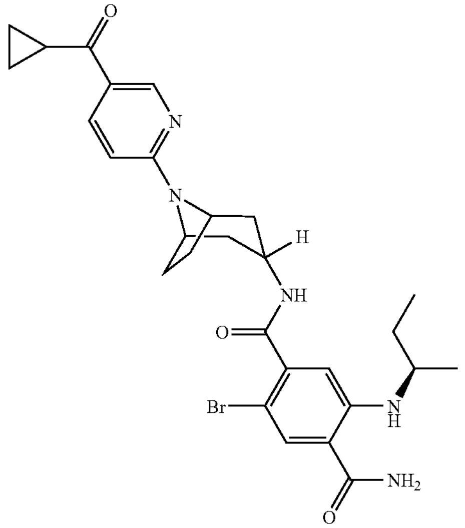 | 2-bromo-N-{8-[5-(cyclopropylcarbonyl)pyridin-2-yl]-8-azabicyclo[3.2.1]oct-3-endo-yl}-5-{[(1R)-1-methylpropyl]amino}benzene-1,4-dicarboxamide<br>ACTIVITY = A |
| 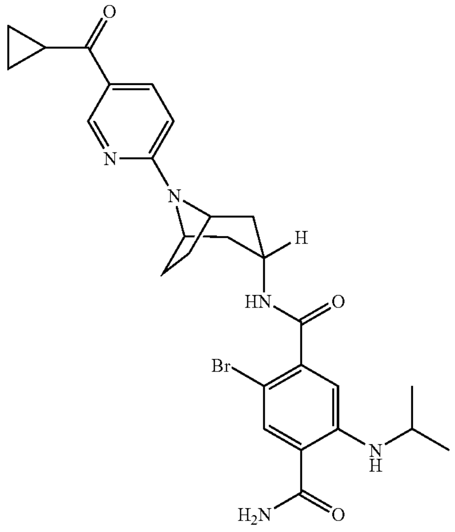 | 2-bromo-N-{8-(5-(cyclopropylcarbonyl)pyridin-2-yl]-8-azabicyclo[3.2.1]oct-3-endo-yl}-5-[(1-methylethyl)amino]benzene-1,4-dicarboxamide<br>ACTIVITY = A |

TABLE I-continued

| STRUCTURE | NAME & ACTIVITY |
| --- | --- |
| 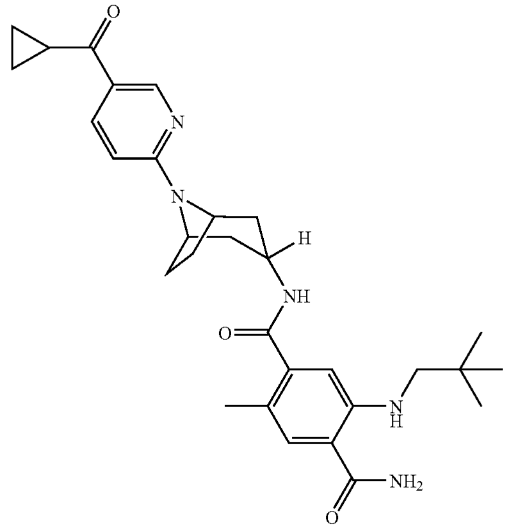 | N-{8-[5-(cyclopropylcarbonyl)pyridin-2-yl]-8-azabicyclo[3.2.1]oct-3-endo-yl)-5-[(2,2-dimethylpropyl)amino]-2-methylbenzene-1,4-dicarboxamide ACTIVITY = A |
| 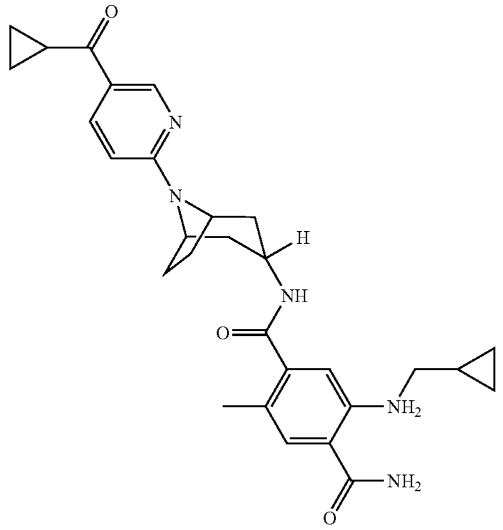 | N-{8-[5-(cyclopropylcarbonyl)pyridin-2-yl]-8-azabicyclo[3.2.1]oct-3-endo-yl)-5-[(cyclopropylmethyl)amino]-2-methylbenzene-1,4-dicarboxamide ACTIVITY = A |
| 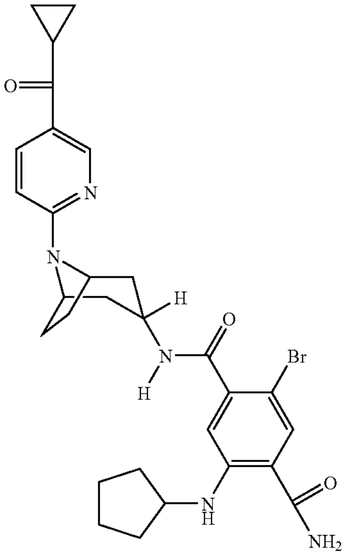 | 2-bromo-5-(cyclopentylamino)-N-{8-[5-(cyclopropylcarbonyl)pyridin-2-yl]-8-azabicyclo[3.2.1]oct-3-endo-yl}benzene-1,4-dicarboxamide ACTIVITY = A |

TABLE I-continued
| STRUCTURE | NAME & ACTIVITY |
|---|---|
| 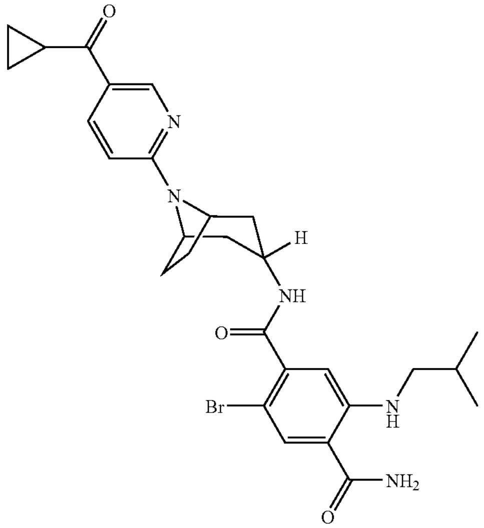 | 2-bromo-N-{8-[5-(cyclopropylcarbonyl)pyridin-2-yl]-8-azabicyclo[3.2.1]oct-3-endo-yl}-5-[(2-methylpropyl)amino]benzene-1,4-dicarboxamide<br>ACTIVITY = A |
| 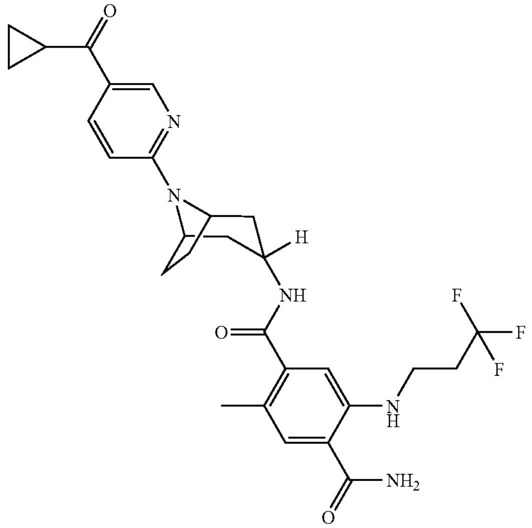 | N-{8-[5-(cyclopropylcarbonyl)pyridin-2-yl]-8-azabicyclo[3.2.1]oct-3-endo-yl}-2-methyl-5-[(3,3,3-trifluoropropyl)amino]benzene-1,4-dicarboxamide<br>ACTIVITY = A |

TABLE I-continued
| STRUCTURE | NAME & ACTIVITY |
| --- | --- |
| 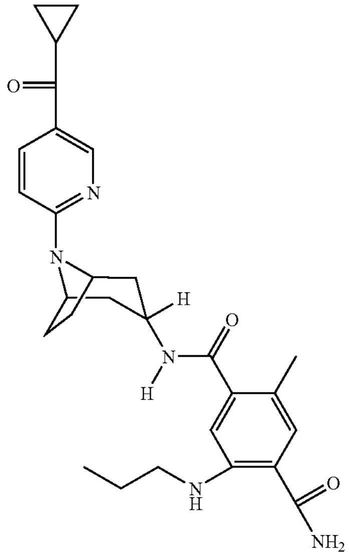 | N-{8-[5-(cyclopropylcarbonyl)pyridin-2-yl]-8-azabicyclo[3.2.1]oct-3-endo-yl}-2-methyl-5-(propylamino)benzene-1,4-dicarboxamide<br>ACTIVITY = A |
| 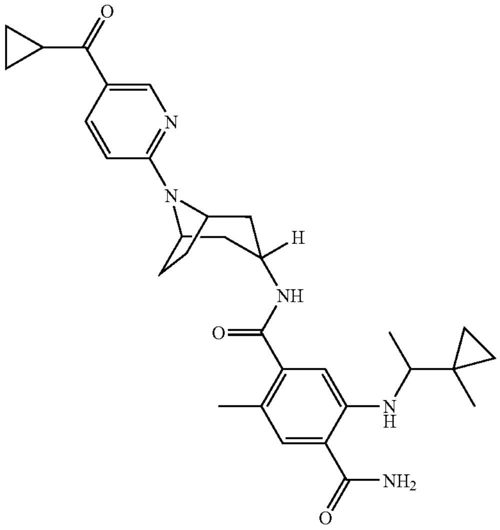 | N-{8-[5-(cyclopropylcarbonyl)pyridin-2-yl]-8-azabicyclo[3.2.1]oct-3-endo-yl}-2-methyl-5-{[1-(1-methylcyclopropyl)ethyl]amino}benzene-1,4-dicarboxamide<br>ACTIVITY = A |

TABLE I-continued

| STRUCTURE | NAME & ACTIVITY |
| --- | --- |
| 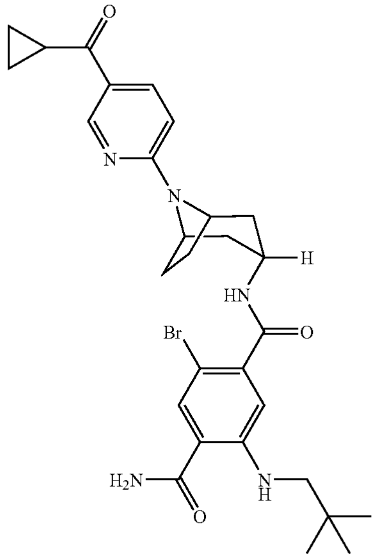 | 2-bromo-N-{8-[5-(cyclopropylcarbonyl)pyridin-2-yl]-8-azabicyclo[3.2.1]oct-3-endo-yl}-5-[(2,2-dimethylpropyl)amino]benzene-1,4-dicarboxamide<br>ACTIVITY = A |
| 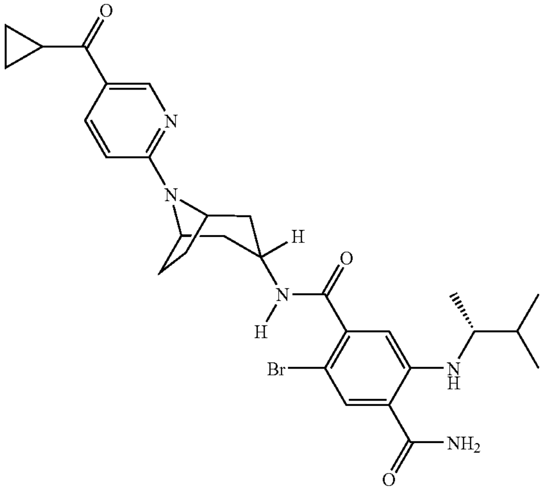 | 2-bromo-N-{8-[5-(cyclopropylcarbonyl)pyridin-2-yl]-8-azabicyclo[3.2.1]oct-3-endo-yl}-5-{[(1R)-1 2-dimethylpropyl]amino}benzene-1,4-dicarboxamide<br>ACTIVITY = A |
| 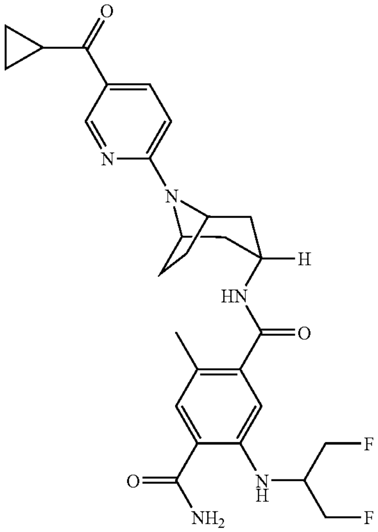 | N-{8-[5-(cyclopropylcarbonyl)pyridin-2-yl]-8-azabicyclo[3.2.1]oct-3-endo-yl}-5-{[2-fluoro-1-(fluoromethyl)ethyl]amino}-2-methylbenzene-1,4-dicarboxamide<br>ACTIVITY = A |

TABLE I-continued
| STRUCTURE | NAME & ACTIVITY |
|---|---|
| 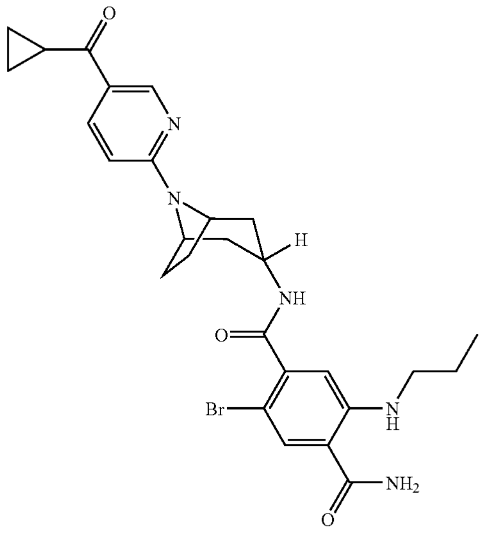 | 2-bromo-N-{8-[5-(cyclopropylcarbonyl)pyridin-2-yl]-8-azabicyclo[3.2.1]oct-3-endo-yl}-5-(propylamino)benzene-1,4-dicarboxamide<br>ACTIVITY = A |
| 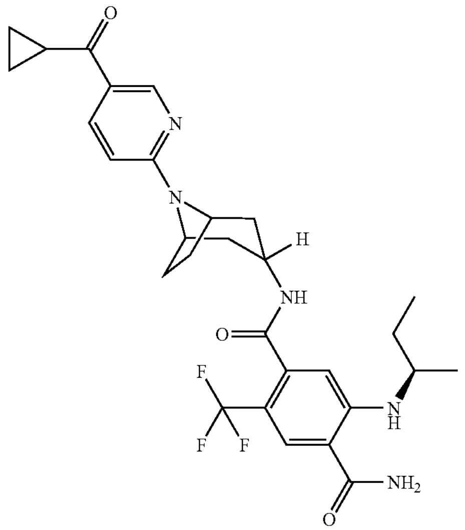 | N-{8-[5-(cyclopropylcarbonyl)pyridin-2-yl]-8-azabicyclo[3.2.1]oct-3-endo-yl}-5-{[(1R)-1-methylpropyl]amino}-2-(trifluoromethyl)benzene-1,4-dicarboxamide<br>ACTIVITY = A |

TABLE I-continued
| STRUCTURE | NAME & ACTIVITY |
| --- | --- |
| 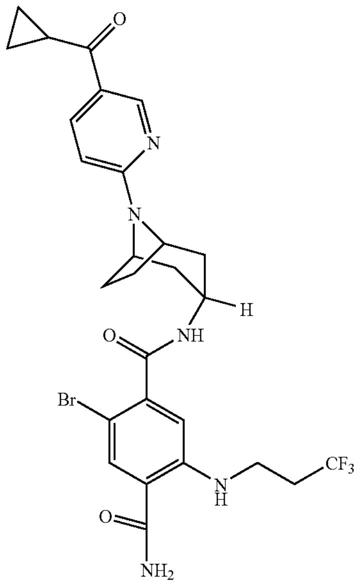 | 2-bromo-N-{8-[5-(cyclopropylcarbonyl)pyridin-2-yl]-8-azabicyclo[3.2.1]oct-3-endo-yl}-5-[(3,3,3-trifluoropropyl)amino]benzene-1,4-dicarboxamide<br>ACTIVITY = A |
| 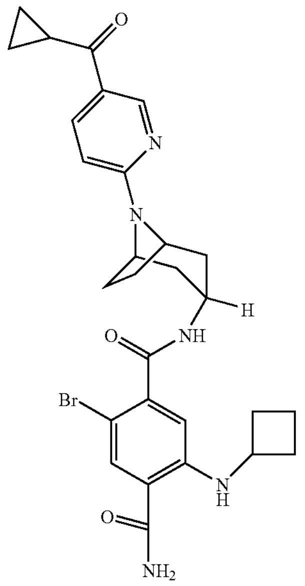 | 2-bromo-5-(cyclobutylamino)-N-{8-[5-(cyclopropylcarbonyl)pyridin-2-yl]-8-azabicyclo[3.2.1]oct-3-endo-yl}benzene-1,4-dicarboxamide<br>ACTIVITY = A |

TABLE I-continued
| STRUCTURE | NAME & ACTIVITY |
|---|---|
| 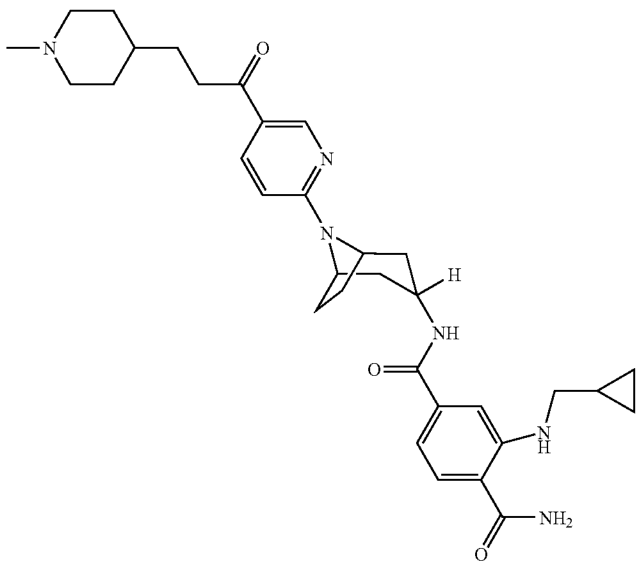 | 2-[(cyclopropylmethyl)amino]-N4-(8-{5-[3-(1-methylpiperidin-4-yl)propanoyl]pyridin-2-yl}-8-azabicyclo[3.2.1]oct-3-endo-yl)benzene-1,4-dicarboxamide ACTIVITY = A |
| 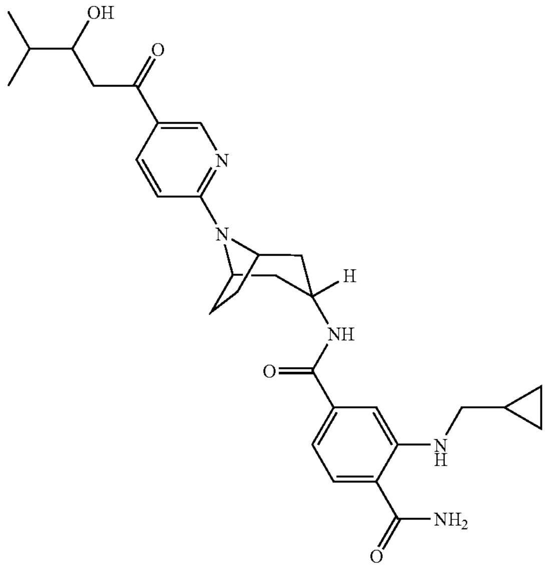 | 2-[(cyclopropylmethyl)amino]-N4-{8-[5-(3-hydroxy-4-methylpentanoyl)pyridin-2-yl]-8-azabicyclo[3.2.1]oct-3-endo-yl}benzene-1,4-dicarboxamide ACTIVITY = A |

TABLE I-continued
| STRUCTURE | NAME & ACTIVITY |
| --- | --- |
| 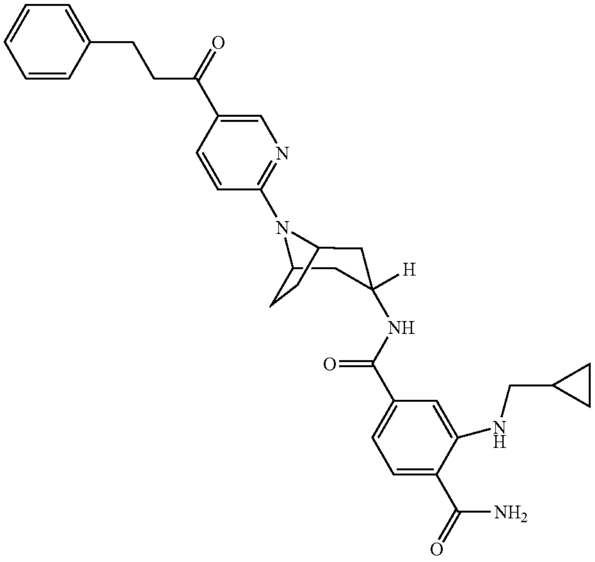 | 2-[(cyclopropylmethyl)amino]-N4-{8-[5-(3-phenylpropanoyl)pyridin-2-yl]-8-azabicyclo[3.2.1]oct-3-endo-yl}benzene-1,4-dicarboxamide ACTIVITY = D |
| 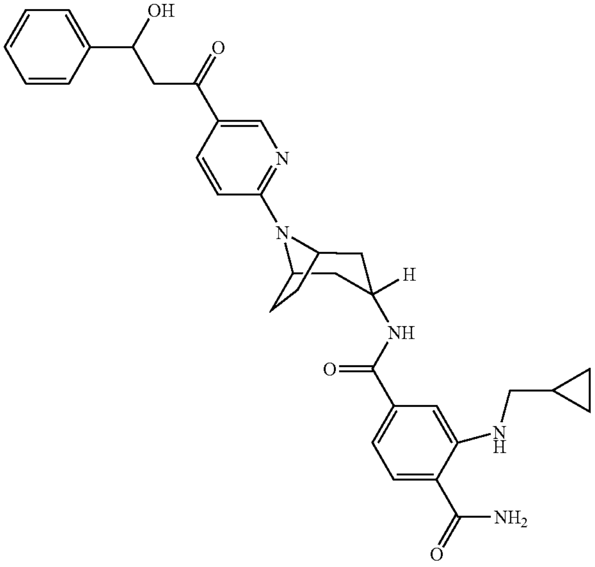 | 2-[(cyclopropylmethyl)amino]-N4-{8-[5-(3-hydroxy-3-phenylpropanoyl)pyridin-2-yl]-8-azabicyclo[3.2.1]oct-3-endo-yl}benzene-1,4-dicarboxamide ACTIVITY = B |

TABLE I-continued
| STRUCTURE | NAME & ACTIVITY |
| --- | --- |
| 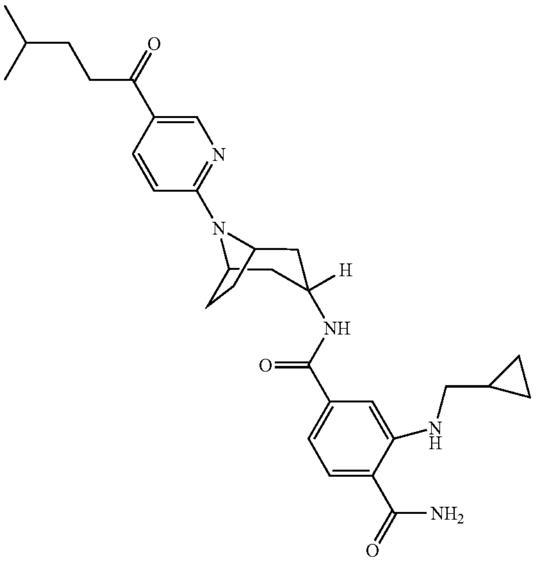 | 2-[(cyclopropylmethyl)amino]-N4-{8-[5-(4-methylpentanoyl)pyridin-2-yl]-8-azabicyclo[3.2.1]oct-3-endo-yl}benzene-1,4-dicarboxamide ACTIVITY = A |
| 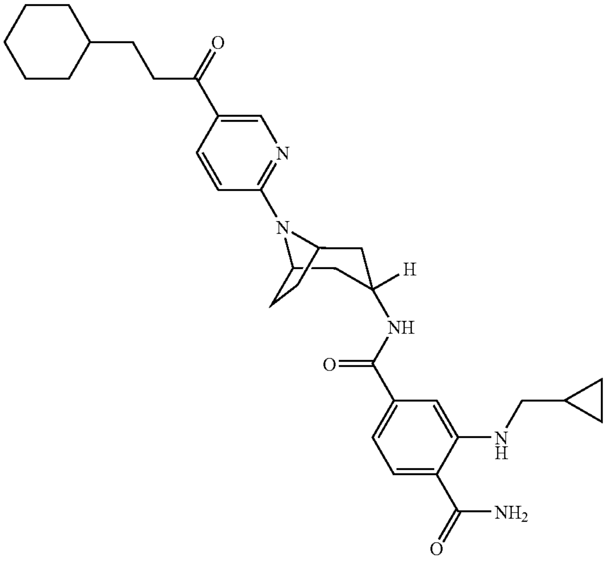 | N4-{8-[5-(3-cyclohexylpropanoyl)pyridin-2-yl]-8-azabicyclo[3.2.1]oct-3-endo-yl}-2-[(cyclopropylmethyl)amino]benzene-1,4-dicarboxamide ACTIVITY = C |

TABLE I-continued

| STRUCTURE | NAME & ACTIVITY |
| --- | --- |
| 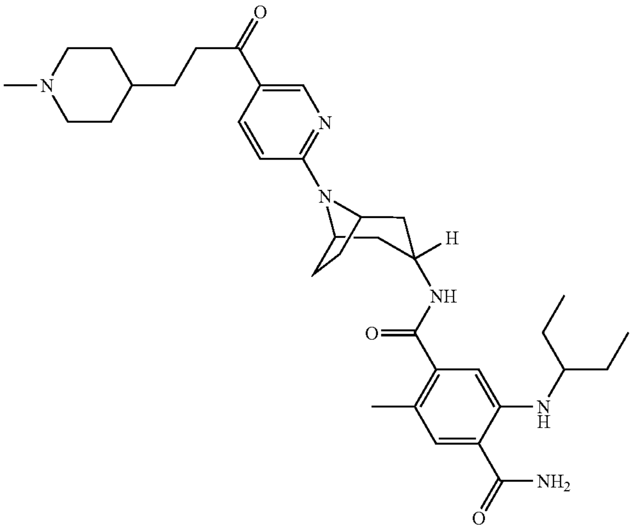 | 5-[(1-ethylpropyl)amino]-2-methyl-N-(8-{5-[3-(1-methylpiperidin-4-yl)propanoyl]pyridin-2-yl}-8-azabicyclo[3.2.1]oct-3-endo-yl)benzene-1,4-dicarboxamide ACTIVITY = A |
| 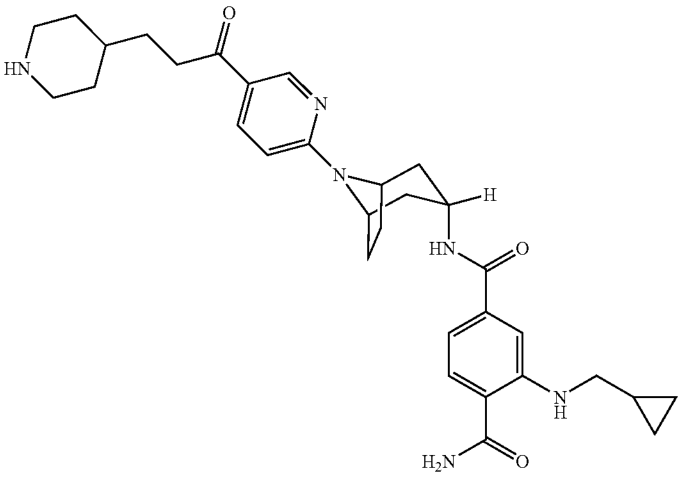 | 2-[(cyclopropylmethyl)amino]-N4-{8-[5-(3-piperidin-4-ylpropanoyl)pyridin-2-yl]-8-azabicyclo[3.2.1]oct-3-endo-yl}benzene-1,4-dicarboxamide ACTIVITY = A |
| 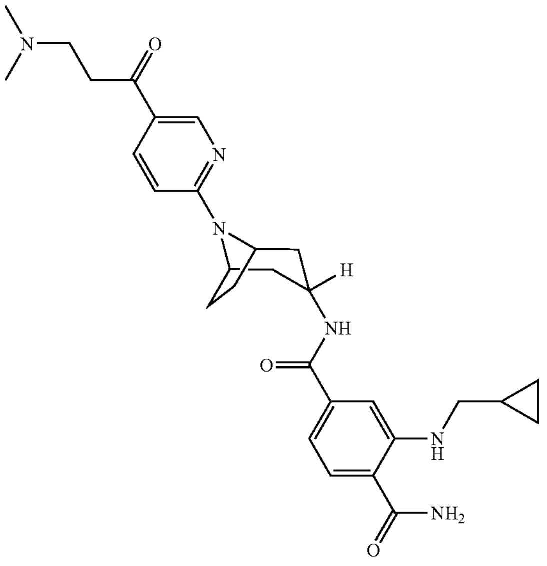 | 2-[(cyclopropylmethyl)amino]-N4-{8-[5-(N,N-dimethyl-beta-alanyl)pyridin-2-yl]-8-azabicyclo[3.2.1]oct-3-endo-yl}benzene-1,4-dicarboxamide ACTIVITY = A |

TABLE I-continued
| STRUCTURE | NAME & ACTIVITY |
|---|---|
| 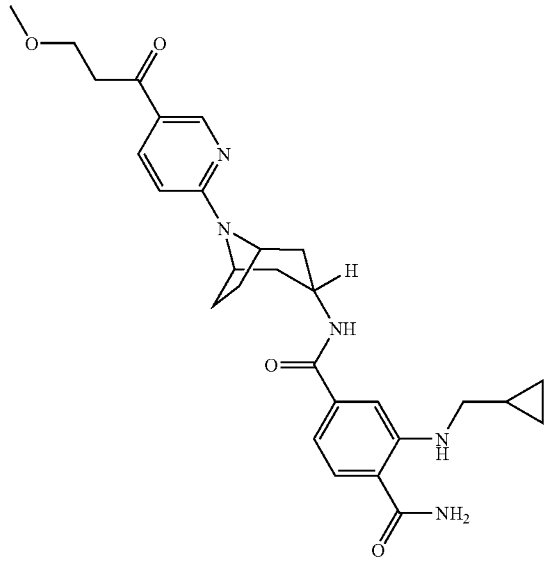 | 2-[(cyclopropylmethyl)amino]-N4-(8-{5-[3-(methyloxy)propanoyl]pyridin-2-yl}-8-azabicyclo[3.2.1]oct-3-endo-yl)benzene-1,4-dicarboxamide ACTIVITY = A |
| 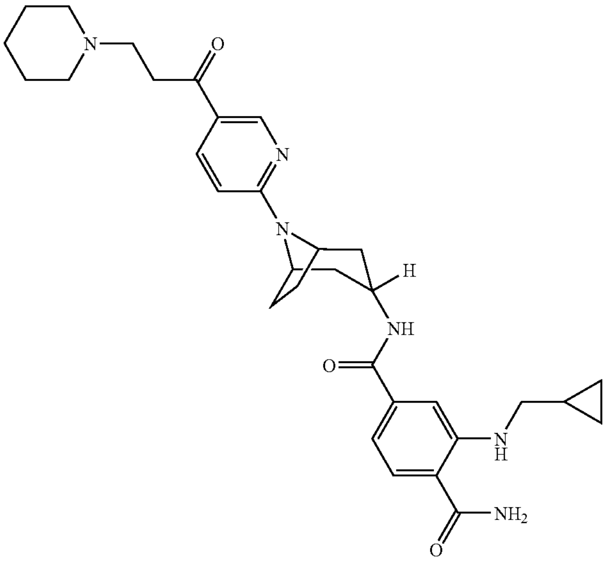 | 2-[(cyclopropylmethyl)amino]-N4-{8-(5-(3-piperidin-1-ylpropanoyl)pyridin-2-yl]-8-azabicyclo[3.2.1]oct-3-endo-yl}benzene-1,4-dicarboxamide ACTIVITY = A |

TABLE I-continued
| STRUCTURE | NAME & ACTIVITY |
|---|---|
| 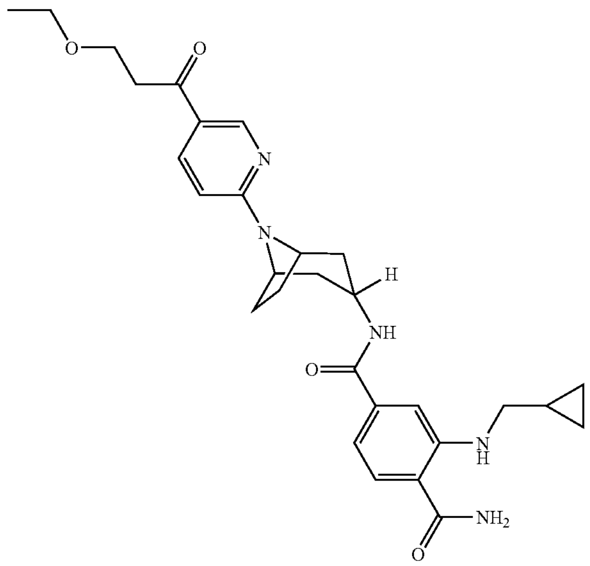 | 2-[(cyclopropylmethyl)amino]-N4-(8-{5-[3-(ethyloxy)propanoyl]pyridin-2-yl}-8-azabicyclo[3.2.1]oct-3-endo-yl)benzene-1,4-dicarboxamide ACTIVITY = A |
| 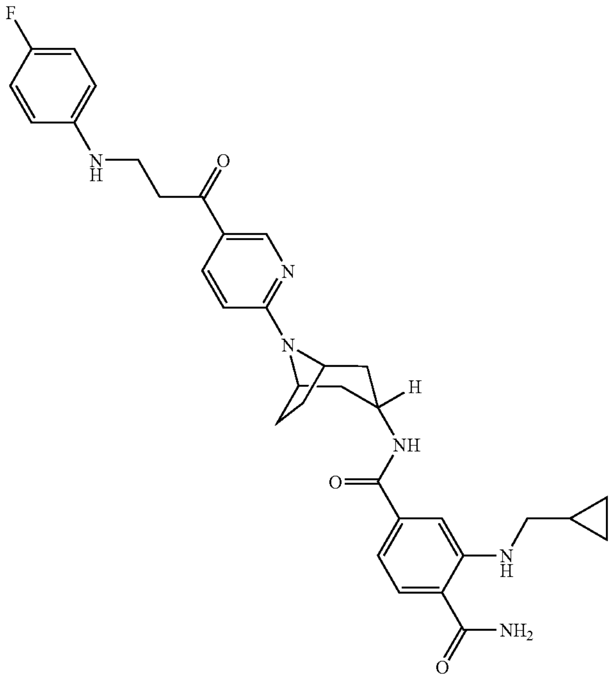 | 2-[(cyclopropylmethyl)amino]-N4-(8-{5-(N-(4-fluorophenyl)-beta-alanyl]pyridin-2-yl}-8-azabicyclo[3.2.1]oct-3-endo-yl)benzene-1,4-dicarboxamide ACTIVITY = D |

TABLE I-continued
| STRUCTURE | NAME & ACTIVITY |
| --- | --- |
| 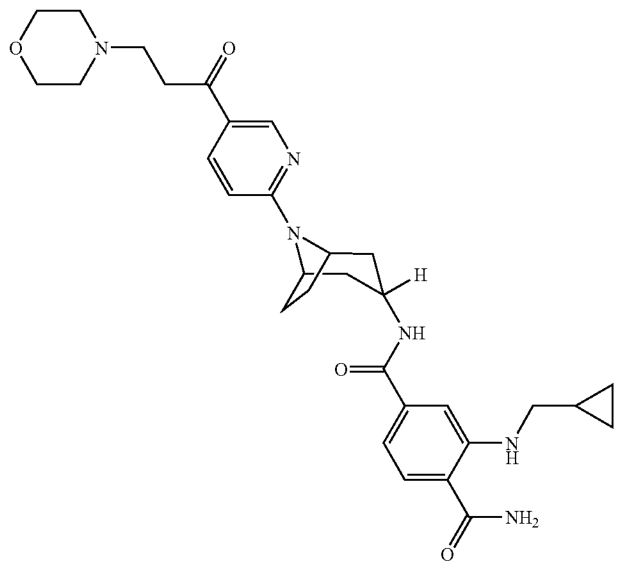 | 2-[(cyclopropylmethyl)amino]-N4-{8-[5-(3-morpholin-4-ylpropanoyl)pyridin-2-yl]-8-azabicyclo[3.2.1]oct-3-endo-yl}benzene-1,4-dicarboxamide ACTIVITY = A |
| 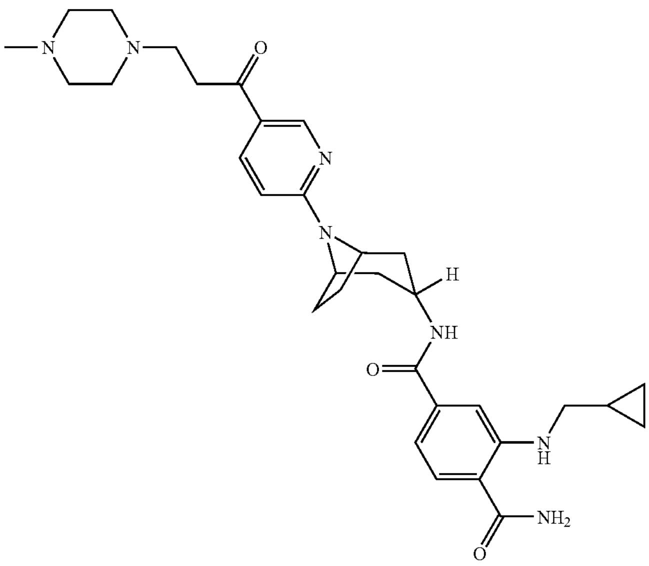 | 2-[(cyclopropylmethyl)amino]-N4-(8-{5-[3-(4-methylpiperazin-1-yl)propanoyl]pyridin-2-yl}-8-azabicyclo[3.2.1]oct-3-endo-yl)benzene-1,4-dicarboxamide ACTIVITY = A |

TABLE I-continued
| STRUCTURE | NAME & ACTIVITY |
|---|---|
| 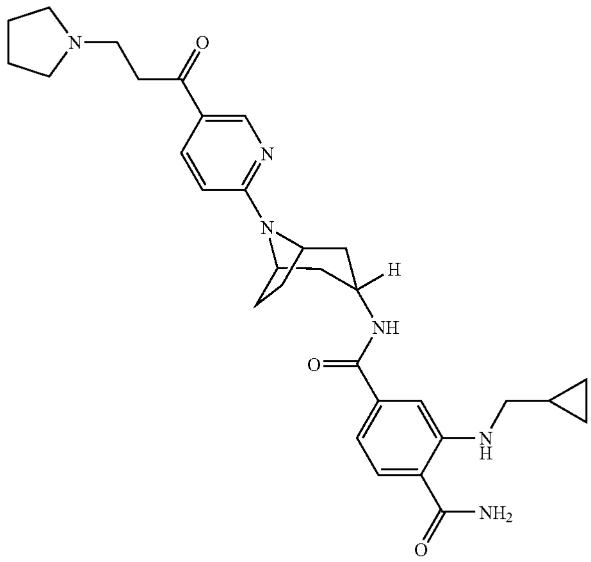 | 2-[(cyclopropylmethyl)amino]-N4-{8-[5-(3-pyrrolidin-1-ylpropanoyl)pyridin-2-yl]-8-azabicyclo[3.2.1]oct-3-endo-yl}benzene-1,4-dicarboxamide ACTIVITY = A |
| 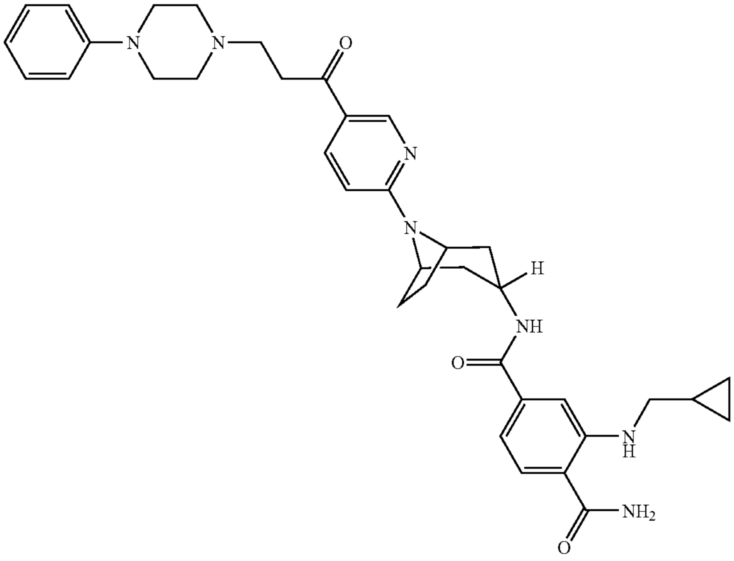 | 2-[(cyclopropylmethyl)amino]-N4-(8-{5-[3-(4-phenylpiperazin-1-yl)propanoyl]pyridin-2-yl}-8-azabicyclo[3.2.1]oct-3-endo-yl)benzene-1,4-dicarboxamide ACTIVITY = B |

TABLE I-continued
| STRUCTURE | NAME & ACTIVITY |
|---|---|
| 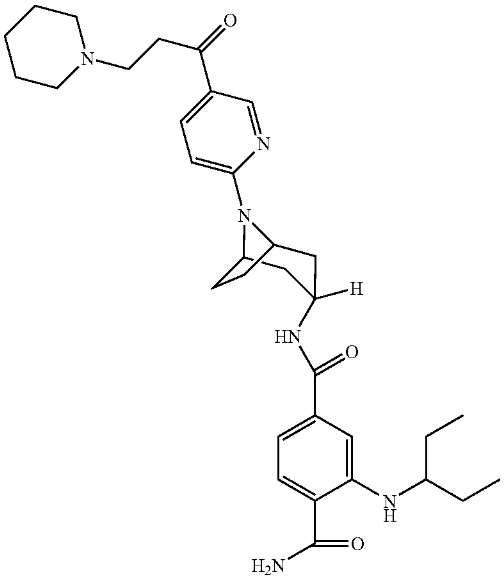 | 2-[(1-ethylpropyl)amino]-N4-{8-[5-(3-piperidin-1-ylpropanoyl)pyridin-2-yl]-8-azabicyclo[3.2.1]oct-3-endo-yl}benzene-1,4-dicarboxamide ACTIVITY = A |
| 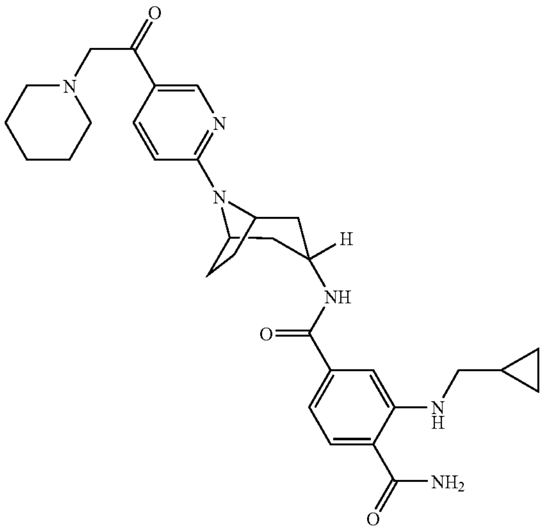 | 2-[(cyclopropylmethyl )amino]-N4-{8-[5-(piperidin-1-ylacetyl)pyridin-2-yl]-8-azabicyclo[3.2.1]oct-3-endo-yl}benzene-1,4-dicarboxamide ACTIVITY = D |

TABLE I-continued

| STRUCTURE | NAME & ACTIVITY |
|---|---|
| 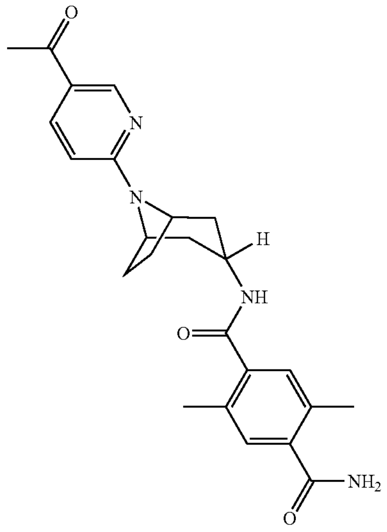 | N-[8-(5-acetylpyridin-2-yl)-8-azabicyclo[3.2.1]oct-3-endo-yl]-2,5-dimethylbenzene-1,4-dicarboxamide ACTIVITY = A |
| 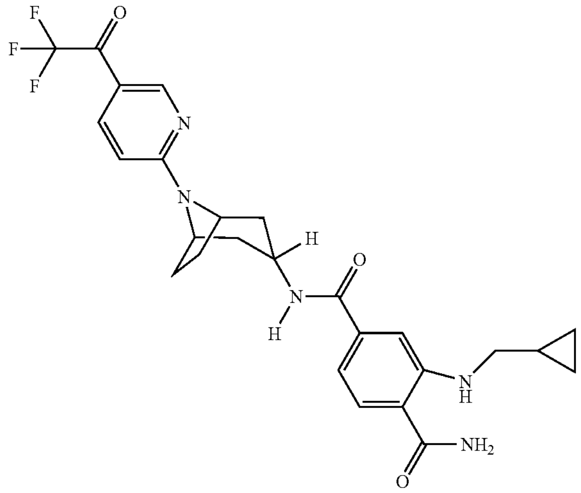 | 2-[(cyclopropylmethyl)amino]-N4-{8-[5-(trifluoroacetyl)pyridin-2-yl]-8-azabicyclo[3.2.1]oct-3-endo-yl}benzene-1,4-dicarboxamide ACTIVITY = D |
| 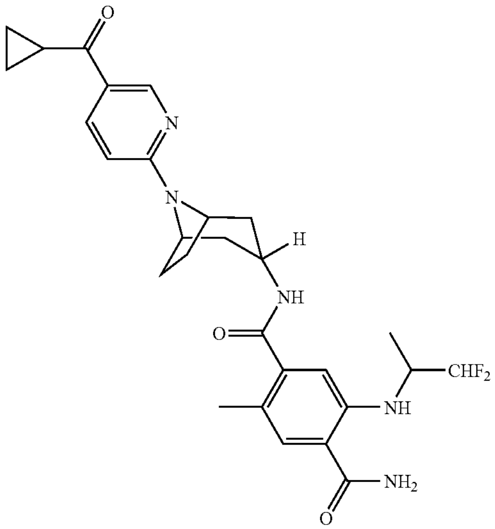 | N-{8-[5-(cyclopropylcarbonyl)pyridin-2-yl]-8-azabicyclo[3.2.1]oct-3-endo-yl}-5-[(2,2-difluoro-1-methylethyl)amino]-2-methylbenzene-1,4-dicarboxamide ACTIVITY = A |

TABLE I-continued

| STRUCTURE | NAME & ACTIVITY |
| --- | --- |
| 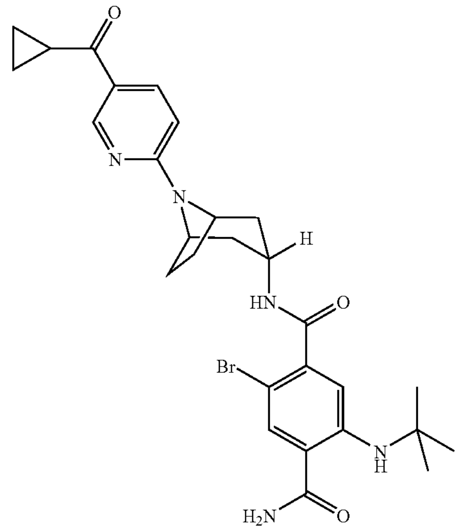 | 2-bromo-N-{8-[5-(cyclopropylcarbonyl)pyridin-2-yl]-8-azabicyclo[3.2.1]oct-3-endo-yl}-5-[(1,1-dimethylethyl)amino]benzene-1,4-dicarboxamide<br>ACTIVITY = A |
| 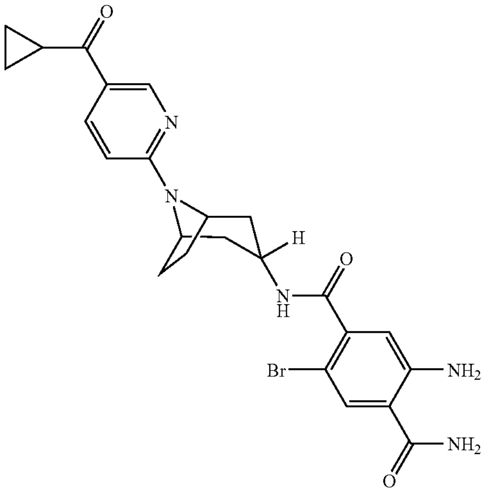 | 5-amino-2-bromo-N-{8-[5-(cyclopropylcarbonyl)pyridin-2-yl]-8-azabicyclo[3.2.1]oct-3-endo-yl}benzene-1,4-dicarboxamide<br>ACTIVITY = A |
| 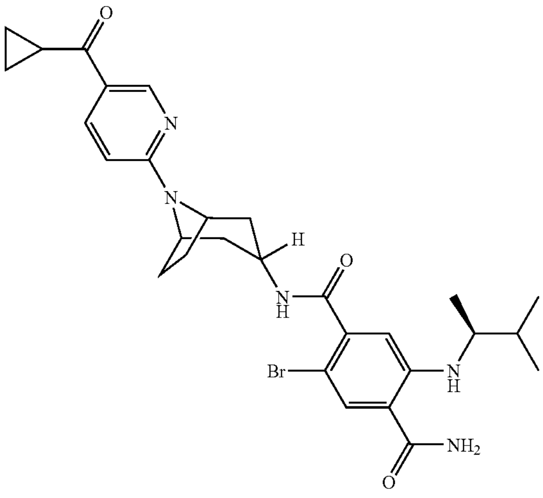 | 2-bromo-N-{8-[5-(cyclopropylcarbonyl)pyridin-2-yl]-8-azabicyclo[3.2.1]oct-3-endo-yl}-5-{[(1S)-1,2-dimethylpropyl]amino}benzene-1,4-dicarboxamide<br>ACTIVITY = A |

TABLE I-continued
| STRUCTURE | NAME & ACTIVITY |
| --- | --- |
| 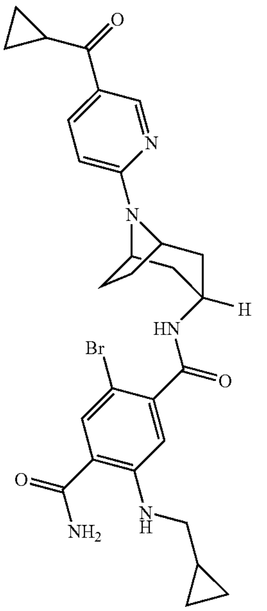 | 2-bromo-N-{8-[5-(cyclopropylcarbonyl)pyridin-2-yl]-8-azabicyclo[3.2.1]oct-3-endo-yl}-5-[(cyclopropylmethyl)amino]benzene-1,4-dicarboxamide<br>ACTIVITY = A |
| 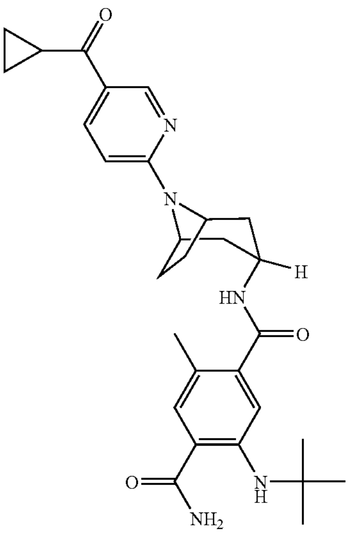 | N-{8-[5-(cyclopropylcarbonyl)pyridin-2-yl]-8-azabicyclo[3.2.1]oct-3-endo-yl}-5-[(1,1-dimethylethyl)amino]-2-methylbenzene-1,4-dicarboxamide<br>ACTIVITY = A |

TABLE I-continued

| STRUCTURE | NAME & ACTIVITY |
| --- | --- |
| 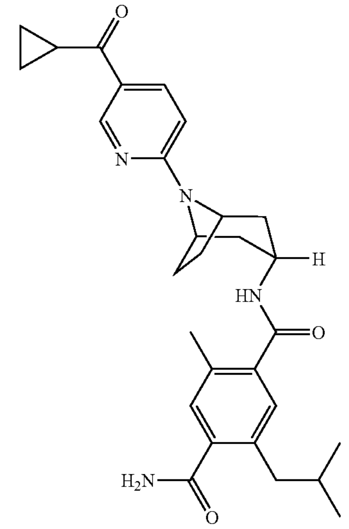 | N-{8-(5-(cyclopropylcarbonyl)pyridin-2-yl]-8-azabicyclo[3.2.1]oct-3-endo-yl}-2-methyl-5-(2-methylpropyl)benzene-1,4-dicarboxamide ACTIVITY = A |
| 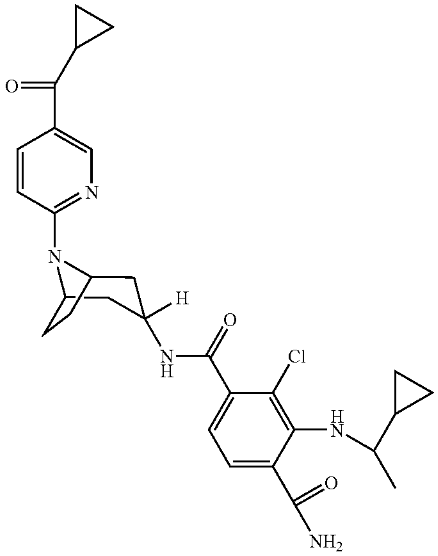 | 2-chloro-N-{8-[5-(cyclopropylcarbonyl)pyridin-2-yl]-8-azabicyclo[3.2.1]oct-3-endo-yl}-3-[(1-cyclopropylethyl)amino]benzene-1,4-dicarboxamide ACTIVITY = A |
| 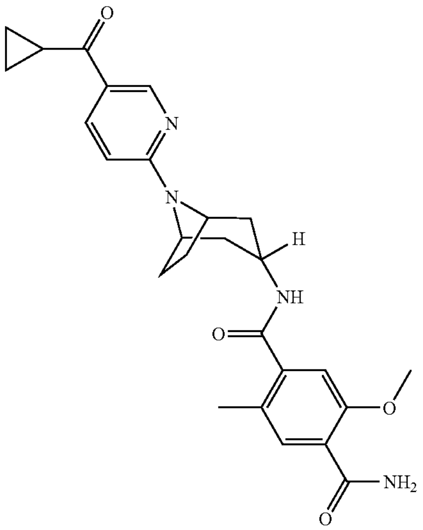 | N-{8-[5-(cyclopropylcarbonyl)pyridin-2-yl]-8-azabicyclo[3.2.1]oct-3-endo-yl}-2-methyl-5-(methyloxy)benzene-1,4-dicarboxamide ACTIVITY = A |

TABLE I-continued
| STRUCTURE | NAME & ACTIVITY |
| --- | --- |
| 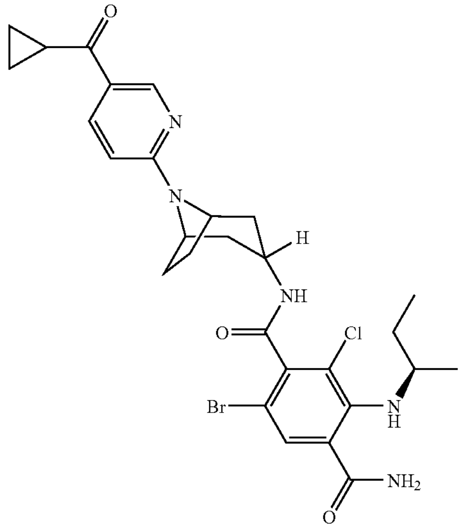 | 5-bromo-3-chloro-N4-{8-[5-(cyclopropylcarbonyl)pyridin-2-yl]-8-azabicyclo[3.2.1]oct-3-endo-yl}-2-{[(1R)-1-methylpropyl]amino}benzene-1,4-dicarboxamide<br>ACTIVITY = A |
| 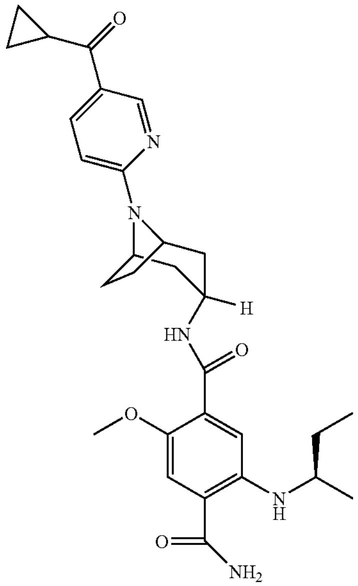 | N-{8-[5-(cyclopropylcarbonyl)pyridin-2-yl]-8-azabicyclo[3.2.1]oct-3-endo-yl}-2-(methyloxy)-5-{[(1R)-1-methylpropyl]amino}benzene-1,4-dicarboxamide<br>ACTIVITY = A |

TABLE I-continued

| STRUCTURE | NAME & ACTIVITY |
|---|---|
| 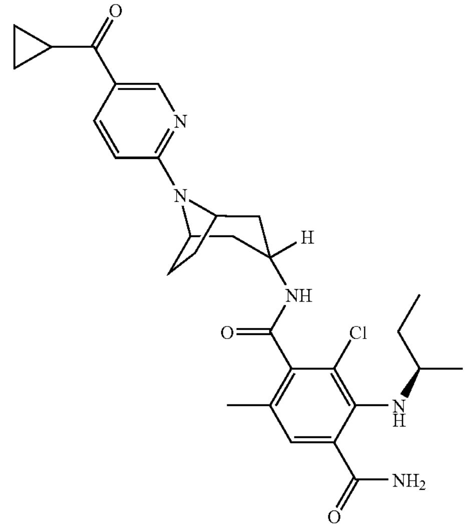 | 3-chloro-N4-{8-[5-(cyclopropylcarbonyl)pyridin-2-yl]-8-azabicyclo[3.2.1]oct-3-endo-yl}-5-methyl-2-{[(1R)-1-methylpropyl]amino}benzene-1,4-dicarboxamide<br>ACTIVITY = A |
| 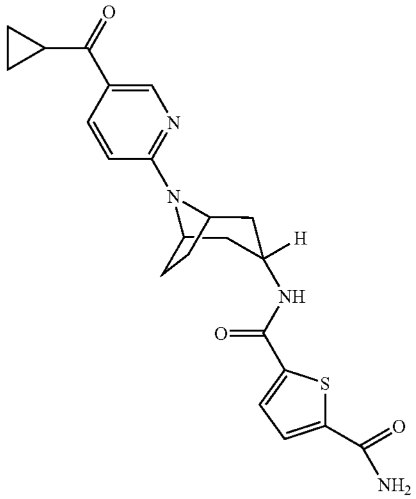 | N-{8-[5-(cyclopropylcarbonyl)pyridin-2-yl]-8-azabicyclo[3.2.1]oct-3-endo-yl}thiophene-2.5-dicarboxamide<br>ACTIVITY = C |
| 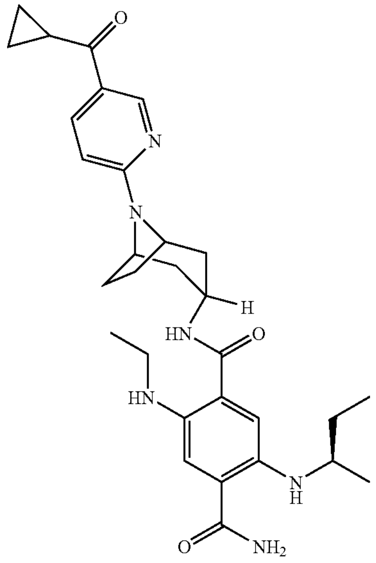 | N-{8-[5-(cyclopropylcarbonyl)pyridin-2-yl]-8-azabicyclo[3.2.1]oct-3-endo-yl}-2-(ethylamino)-5-{[(1R)-1-methylpropyl]amino}benzene-1,4-dicarboxamide<br>ACTIVITY = D |

TABLE I-continued

| STRUCTURE | NAME & ACTIVITY |
|---|---|
| 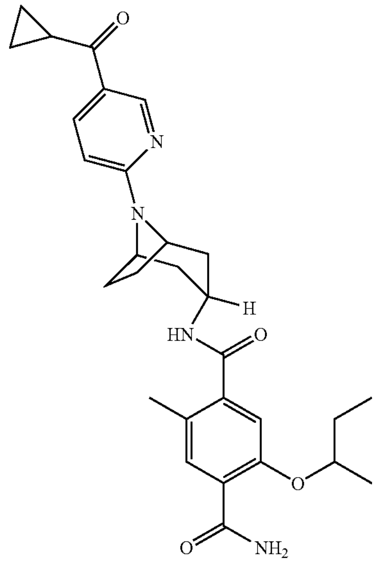 | N-{8-[5-(cyclopropylcarbonyl)pyridin-2-yl-8-azabicyclo[3.2.1]oct-3-endo-yl}-2-methyl-5-[(1-methylpropyl)oxy]benzene-1,4-dicarboxamide<br>ACTIVITY = A |
| 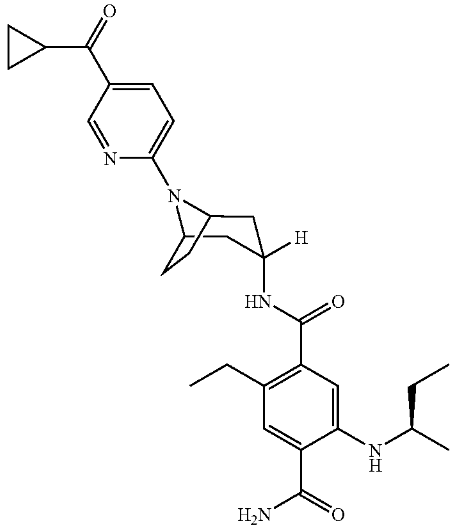 | N-{8-[5-(cyclopropylcarbonyl)pyridin-2-yl]-8-azabicyclo[3.2.1]oct-3-endo-yl}-2-ethyl-5-{[(1R)-1-methylpropyl]amino}benzene-1,4-dicarboxamide<br>ACTIVITY = A |
| 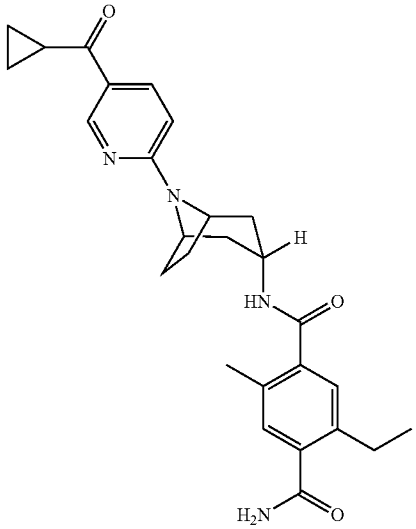 | N-{8-[5-(cyclopropylcarbonyl)pyridin-2-yl]-8-azabicyclo[3.2.1]oct-3-endo-yl}-5-ethyl-2-methylbenzene-1,4-dicarboxamide<br>ACTIVITY = A |

TABLE I-continued

| STRUCTURE | NAME & ACTIVITY |
| --- | --- |
| 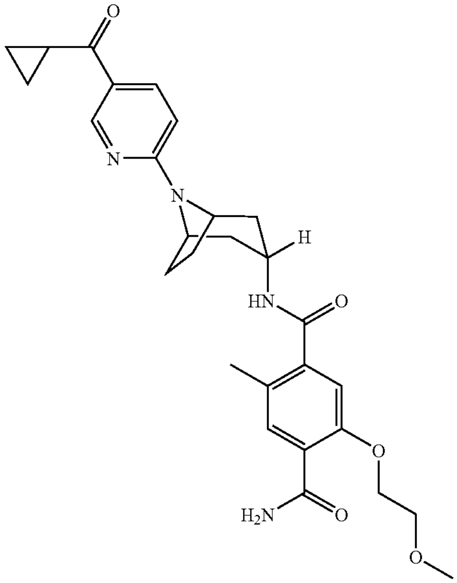 | N-{8-[5-(cyclopropylcarbonyl)pyridin-2-yl]-8-azabicyclo[3.2.1]oct-3-endo-yl}-2-methyl-5-{[2-(methyloxy)ethyl]oxy}benzene-1,4-dicarboxamide ACTIVITY = B |

Another aspect of the disclosure relates to a compound according to Formula II:

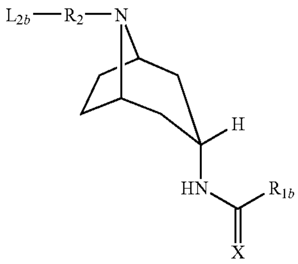

II or a pharmaceutically acceptable salt thereof, wherein:

$R_{1b}$ is selected from heteroaryl optionally substituted with 1, 2 or 3 groups selected from —$NH_2$, halogen, phenyl and alkyl;

$R_2$ is a phenyl or a heteroaryl that can contain 1, 2 or 3 heteroatoms, wherein the aryl or heteroaryl can be substituted with 1, 2 or 3 groups selected from alkyl, —OH, alkoxy, and halogen;

$R_{3b}$ is selected from hydrogen, —$CF_3$, —$NH_2$, —OH, alkyl optionally substituted with 1, 2 or 3 $R_{5b}$, alkoxy, dialkylaminoalkyl, cycloalkyl optionally substituted with arylalkoxy, aryl optionally substituted with 1, 2 or 3 groups selected from halogen, alkyl, alkoxy, dialkylaminoalkoxy and heterocycloalkyl optionally substituted with alkyl or aryl, alkenyl, alkynyl, heterocycloalkyl optionally substituted with a group selected from alkyl, —C(O)O-alkyl and arylalkyl, arylalkyl optionally substituted with alkylheterocycloalkyl at any ring position of the aryl group, and heteroaryl;

$R_{5b}$ is selected from halogen, cycloalkyl, heteroaryl optionally substituted with 1, 2 or 3 groups selected from halogen, alkyl and alkoxy, alkylthio, heterocycloalkyl optionally substituted with 1, 2, or 3 groups selected from alkyl, halogen, phenyl and oxo, aryl optionally substituted with 1, 2 or 3 groups selected from halogen, alkyl, alkoxy, dialkylaminoalkoxy and heterocycloalkyl optionally substituted with alkyl, alkoxy, dialkylamino, —OH, —C(O)—$NH_2$, —C(O)—O—$CH_3$, —C(O)—N(H)($C_1$-$C_3$)alkyl, heteroarylamino optionally substituted with halogen and —$OCF_3$;

$L_{2b}$ is —C(O)—NH—$R_{3b}$, —CN or —C(O)—$R_{3b}$; and

X is O or S.

Another embodiment of the compound of Formula II is a compound according to Formula IIB or IIC:

IIB

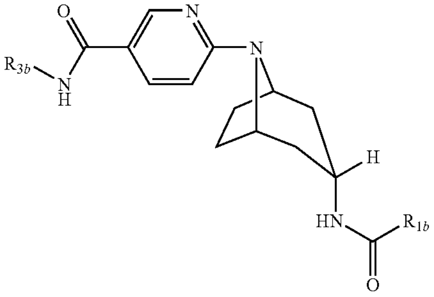

IIC

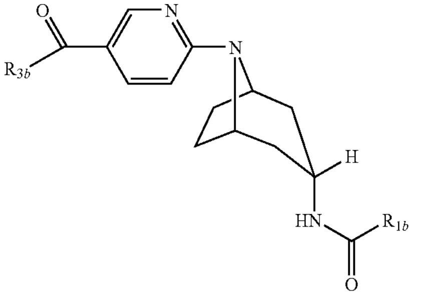

wherein $R_{1b}$ is as defined in the compound of Formula II; and $R_{3b}$ is selected from alkyl optionally substituted with 1, 2 or 3 halogens, cycloalkyl and hydrogen.

In another embodiment of the compound of Formula II, $R_{3b}$ is selected from H, cycloalkyl, and $(C_1-C_6)$alkyl optionally substituted with one or more halogens.

In another embodiment of Formula II, IIB or IIC, $R_{3b}$ is methyl.

In another embodiment of Formula II, IIB or IIC, $R_{3b}$ is cyclopropyl.

In another embodiment of the compound of Formula II, IIB or IIC, $R_{3b}$ is $-CH_2CF_3$.

In another embodiment of the compound of Formula II, IIB or IIC, $R_{3b}$ is 1-methylethyl.

In another embodiment of the compound of Formula II, IIB or IIC, $R_{1b}$ is (O)

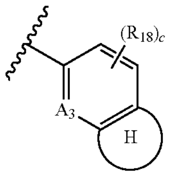

wherein:

$A_3$ is =N— or =CH—;

each $R_{18}$ is independently selected from $-NH_2$, halogen and alkyl;

the (H) ring is a 5 or 6 membered heterocyclic ring fused to the two carbon atoms to which the (H) ring is attached, wherein the (H) ring contains 1, 2 or 3 heteroatoms selected from N, O or S; and c is 0, 1 or 2.

In other embodiments of the compound of Formula II, IIB or IIC, $R_{1b}$ is of Formula (O) and is selected from 1H-benzimidazole optionally substituted with 1 or 2 methyl groups, 1H-indole optionally substituted with 1 or 2 methyl groups, benzofuran, 3,4-dihydro-2H-chromenyl optionally substituted with 1 or 2 methyl groups, 2,3-dihydrobenzofuranyl optionally substituted with 1 or 2 methyl groups, 2,3-dihydro-1,4-benzodioxin-6-yl optionally substituted with 1 or 2 methyl groups, 1H-1,2,3-benzotriazole optionally substituted with 1, 2 or 3 methyl groups, 9H-purin-9-yl optionally substituted with 1 or 2 groups selected from halogen and amino, 1,3-benzothiazole optionally substituted with 1 or 2 methyl groups, and 2,3-dihydro-1-benzofuran optionally substituted with 1 or 2 methyl groups.

In other embodiments of the compound of Formula II, IIB or IIC, $R_{1b}$ is

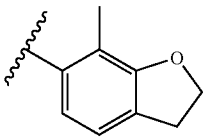

or

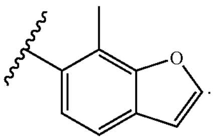

.

In another embodiment, the compound of Formula II is selected from one of the following compounds from Table II, or a pharmaceutically acceptable salt of any of the compounds in Table II:

TABLE II

| STRUCTURE | NAME |
| --- | --- |
| 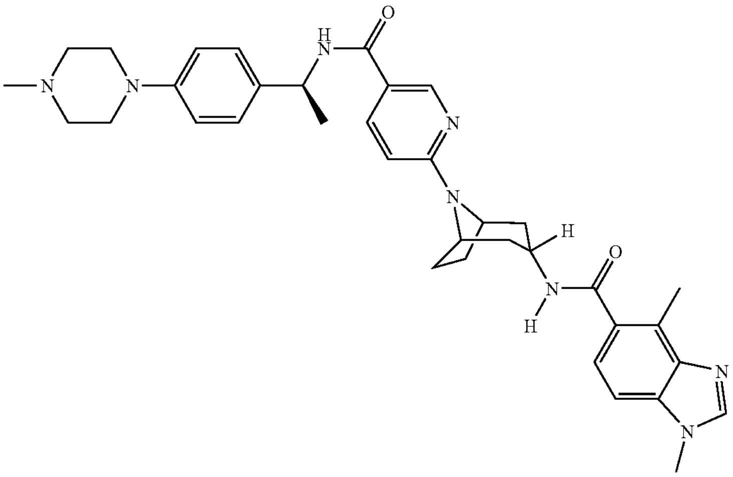 | 1,4-dimethyl-N-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-1H-benzimidazole-5-carboxamide |

TABLE II-continued

| STRUCTURE | NAME |
|---|---|
| 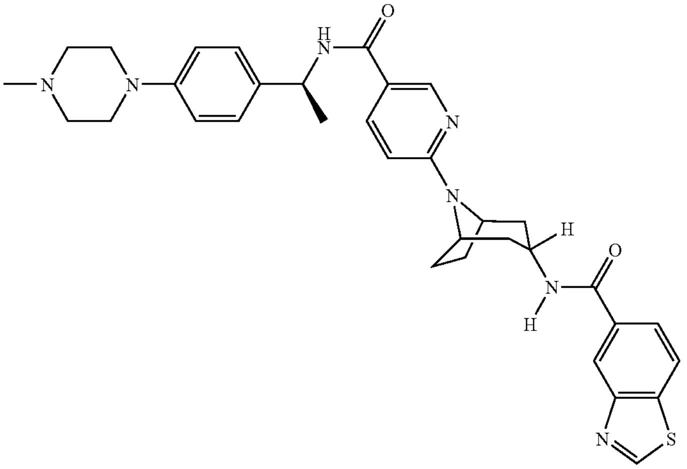 | N-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-1,3-benzothiazole-5-carboxamide |
| 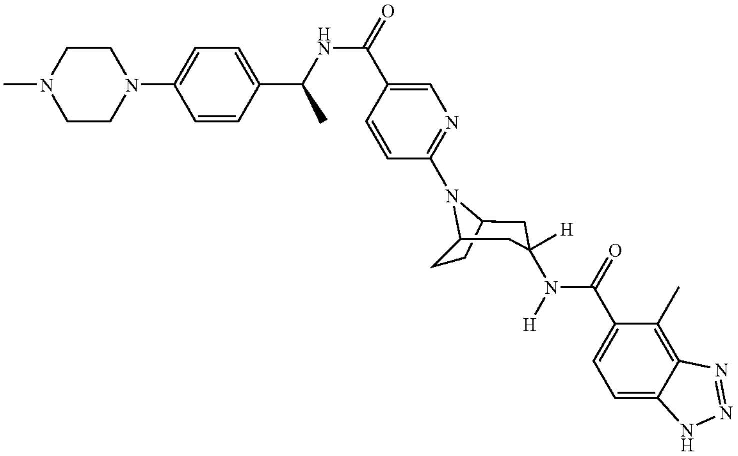 | 4-methyl-N-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-1H-1,2,3-benzotriazole-5-carboxamide |
| 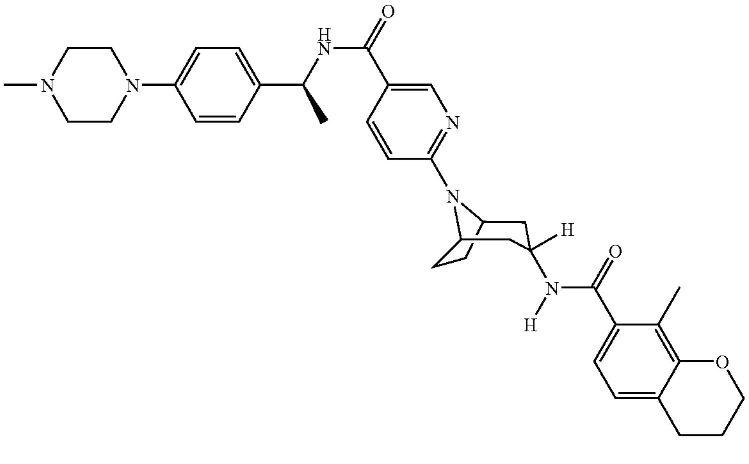 | 6-(3-endo-{[(8-methyl-3,4-dihydro-2H-chromen-7-yl)carbonyl]amino}-8-azabicyclo[3.2.1]oct-8-yl)-N-{(1S)-1-[4-(4-methylpiperazin-1-yl)phenyl]ethyl}pyridine-3-carboxamide |

TABLE II-continued
| STRUCTURE | NAME |
|---|---|
| 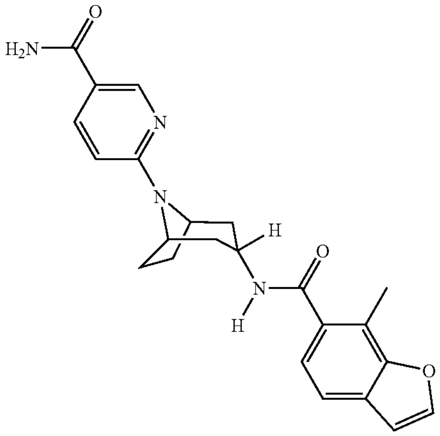 | 6-(3-endo-{[(7-methyl-1-benzofuran-6-yl)carbonyl]amino}-8-azabicyclo[3.2.1]oct-8-yl)pyridine-3-carboxamide |
| 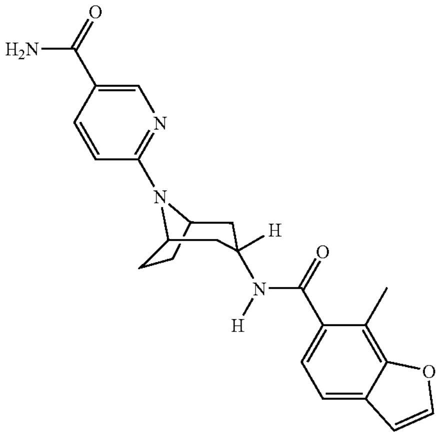 | 6-(3-endo-{[(7-methyl-1-benzofuran-6-yl)carbonyl]amino}-8-azabicyclo[3.2.1]oct-8-yl)-N-{(1S)-1-[4-(4-methylpiperazin-1-yl)phenyl]ethyl}pyridine-3-carboxamide |
| 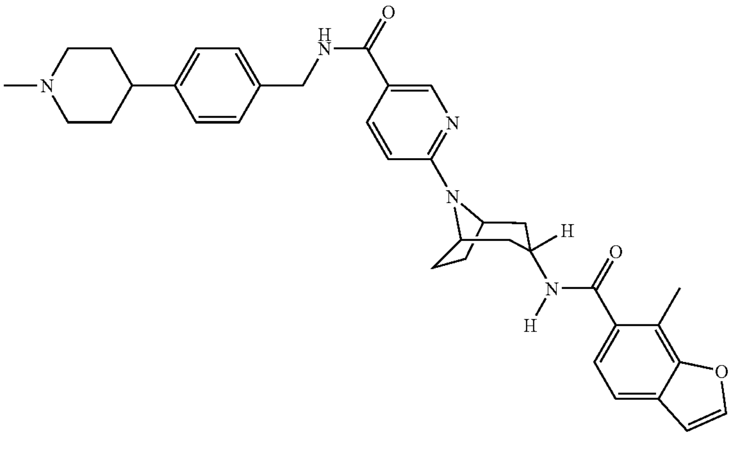 | 6-(3-endo-{[(7-methyl-1-benzofuran-6-yl)carbonyl]amino}-8-azabicyclo[3.2.1]oct-8-yl)-N-{[4-(1-methylpiperidin-4-yl)phenyl]methyl}pyridine-3-carboxamide |

TABLE II-continued

| STRUCTURE | NAME |
|---|---|
| 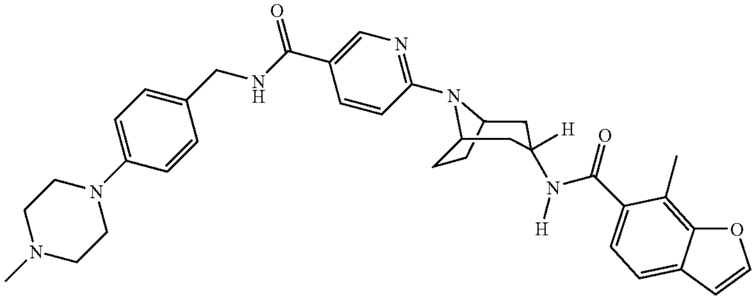 | 6-(3-endo-{[(7-methyl-1-benzofuran-6-yl)carbonyl]amino}-8-azabicyclo[3.2.1]oct-8-yl)-N-{[4-(4-methylpiperazin-1-yl)phenyl]methyl}pyridine-3-carboxamide |
| 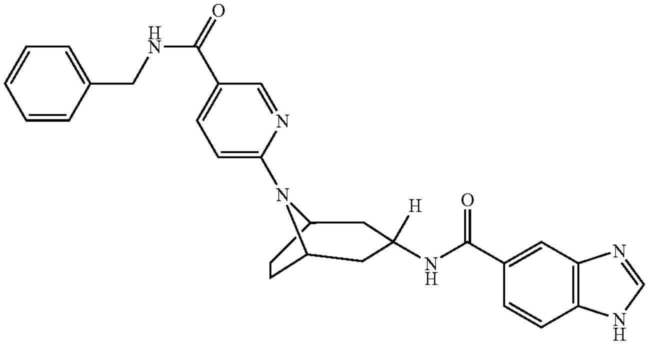 | N-[8-(5-{[(phenylmethyl)amino]carbonyl}pyridin-2-yl)-8-azabicyclo[3.2.1]oct-3-endo-yl]-1H-benzimidazole-5-carboxamide |
| 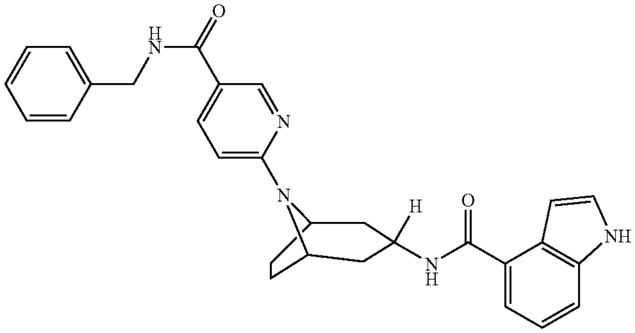 | N-[8-(5-{[(phenylmethyl)amino]carbonyl}pyridin-2-yl)-8-azabicyclo[3.2.1]oct-3-endo-yl]-1H-indole-4-carboxamide |
| 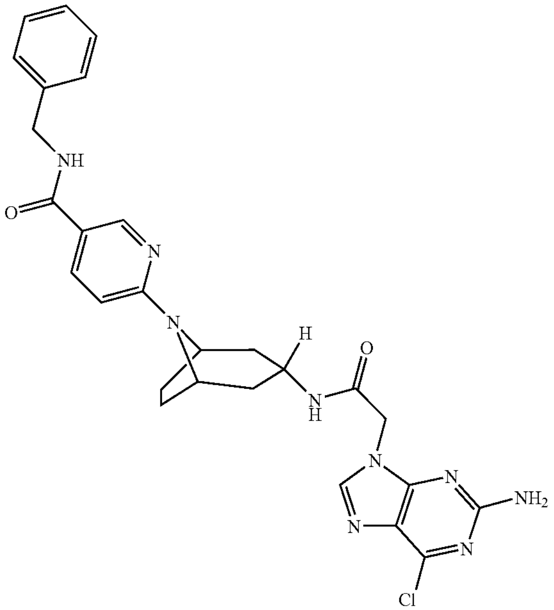 | 6-(3-endo-{[(2-amino-6-chloro-9H-purin-9-yl)acetyl]amino}-8-azabicyclo[3.2.1]oct-8-yl)-N-(phenylmethyl)pyridine-3-carboxamide |

TABLE II-continued

| STRUCTURE | NAME |
|---|---|
| 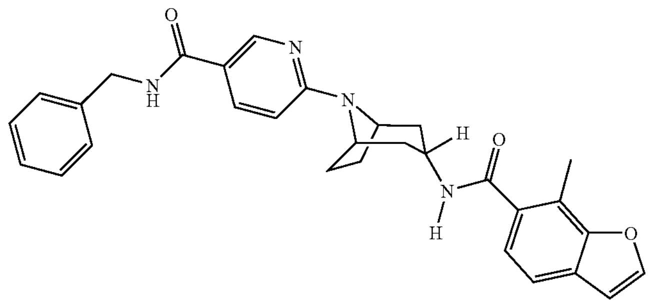 | 6-(3-endo-{[(7-methyl-1-benzofuran-6-yl)carbonyl]amino}-8-azabicyclo[3.2.1]oct-8-yl)-N-(phenylmethyl)pyridine-3-carboxamide |
| 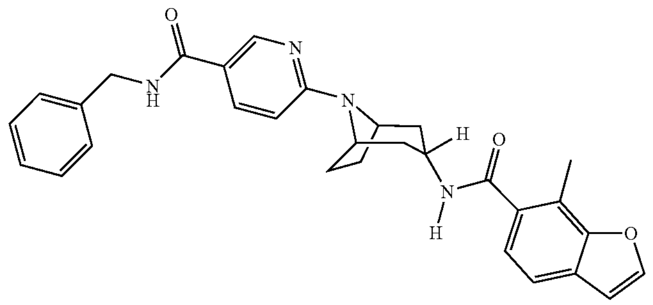 | 6-(3-endo-{[(7-methyl-2,3-dihydro-1-benzofuran-6-yl)carbonyl]amino}-8-azabicyclo[3.2.1]oct-8-yl)-N-(phenylmethyl)pyridine-3-carboxamide |
| 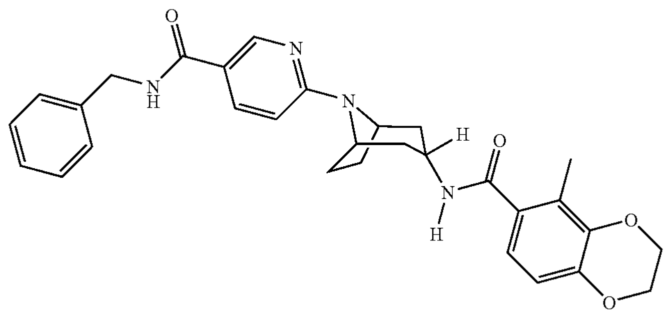 | 6-(3-endo-{[(5-methyl-2,3-dihydro-1,4-benzodioxin-6-yl)carbonyl]amino}-8-azabicyclo[3.2.1]oct-8-yl)-N-(phenylmethyl)pyridine-3-carboxamide |
| 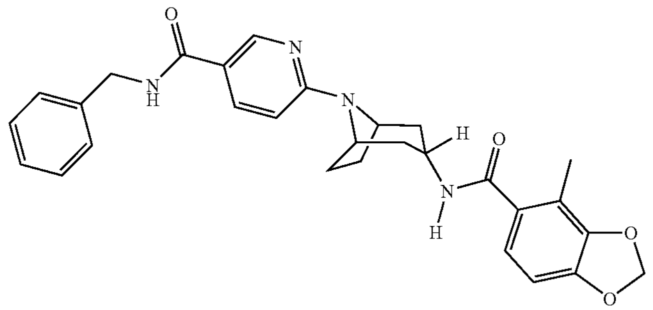 | 6-(3-endo-{[(4-methyl-1,3-benzodioxol-5-yl)carbonyl]amino}-8-azabicyclo[3.2.1]oct-8-yl)-N-(phenylmethyl)pyridine-3-carboxamide |
| 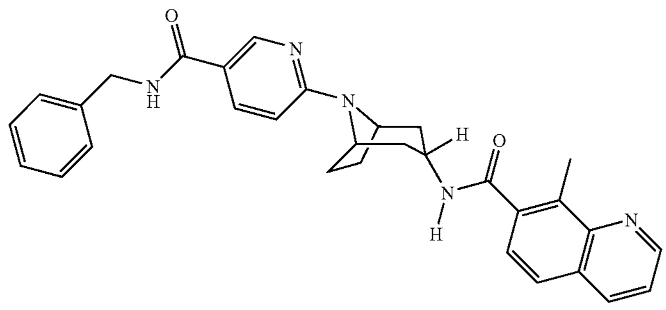 | 8-methyl-N-[8-(5-{[(phenylmethyl)amino]carbonyl}pyridin-2-yl)-8-azabicyclo[3.2.1]oct-3-endo-yl]quinoline-7-carboxamide |

TABLE II-continued

| STRUCTURE | NAME |
|---|---|
| 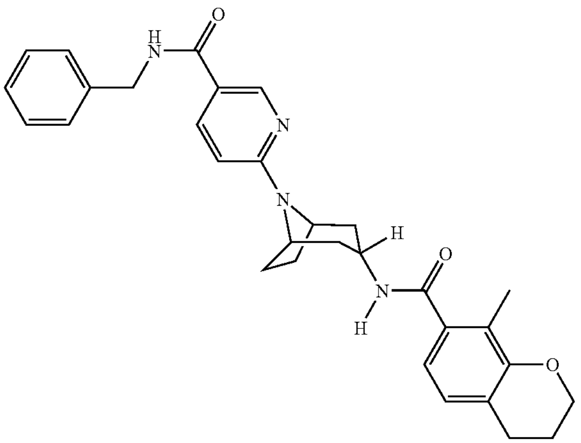 | 6-(3-endo-{[(8-methyl-3,4-dihydro-2H-chromen-7-yl)carbonyl]amino}-8-azabicyclo[3.2.1]oct-8-yl)-N-(phenylmethyl)pyridine-3-carboxamide |
| 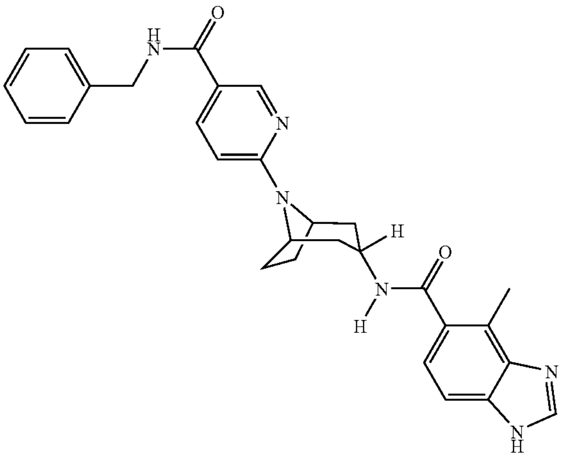 | 4-methyl-N-[8-(5-{[(phenylmethyl)amino]carbonyl}pyridin-2-yl)-8-azabicyclo[3.2.1]oct-3-endo-yl]-1H-benzimidazole-5-carboxamide |
| 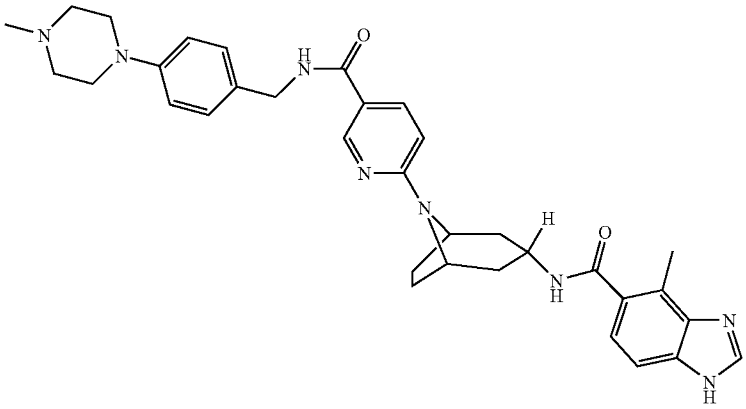 | 4-methyl-N-(8-{5-[({[4-(4-methylpiperazin-1-yl)phenyl]methyl}amino)carbonyl]pyridin-2-yl}-8-azabicyclo[3.2.1]oct-3-endo-yl)-1H-benzimidazole-5-carboxamide |
| 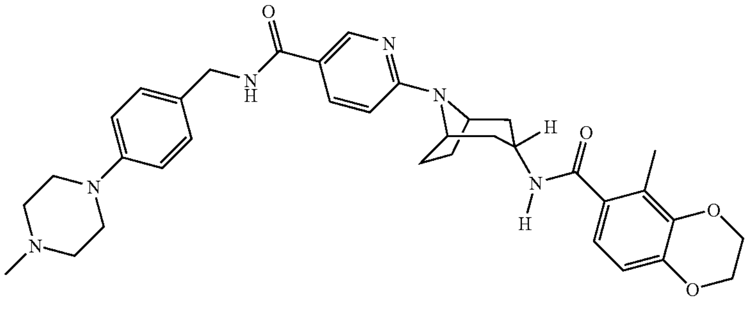 | 6-(3-endo-{[(5-methyl-2,3-dihydro-1,4-benzodioxin-6-yl)carbonyl]amino}-8-azabicyclo[3.2.1]oct-8-yl)-N-{[4-(4-methylpiperazin-1-yl)phenyl]methyl}pyridine-3-carboxamide |

TABLE II-continued
| STRUCTURE | NAME |
| --- | --- |
| 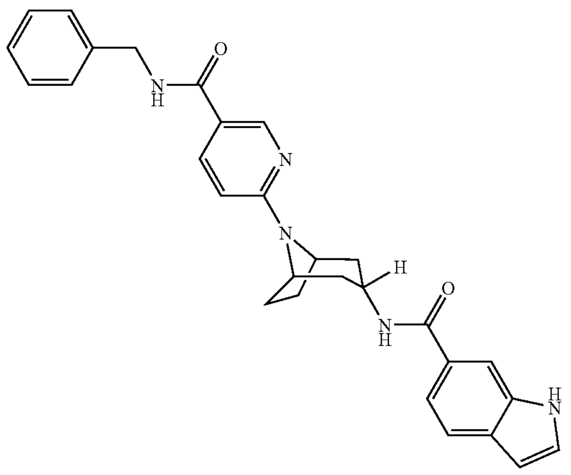 | N-[8-(5-{[(phenylmethyl)amino]carbonyl}pyridin-2-yl)-8-azabicyclo[3.2.1]oct-3-endo-yl]-1H-indole-6-carboxamide |
| 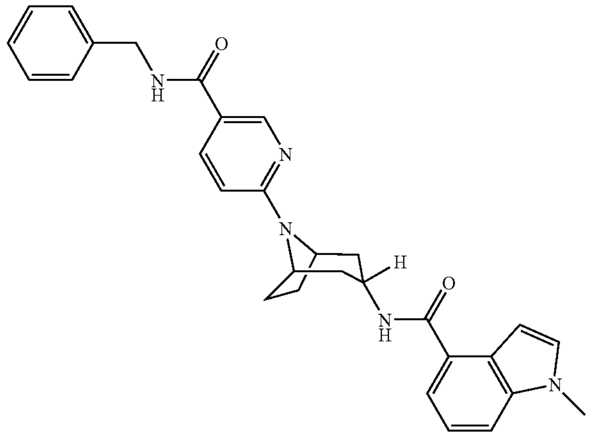 | 1-methyl-N-[8-(5-{[(phenylmethyl)amino]carbonyl}pyridin-2-yl)-8-azabicyclo[3.2.1]oct-3-endo-yl]-1H-indole-4-carboxamide |
| 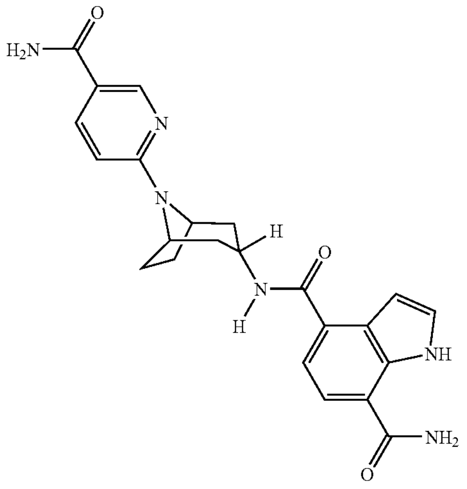 | N4-{8-[5-(aminocarbonyl)pyridin-2-yl]-8-azabicyclo[3.2.1]oct-3-endo-yl}-1H-indole-4,7-dicarboxamide |

TABLE II-continued

| STRUCTURE | NAME |
|---|---|
| 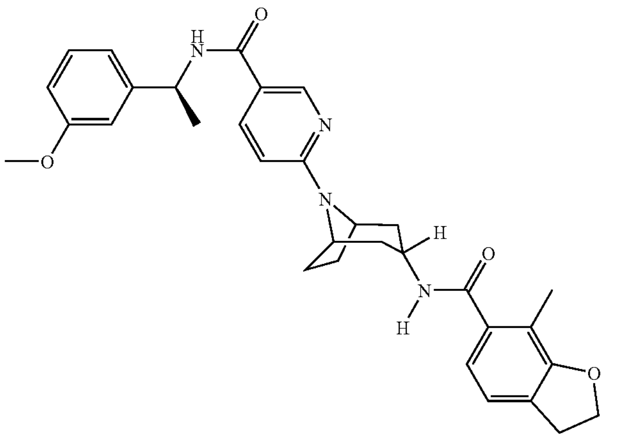 | 6-(3-endo-{[(7-methyl-2,3-dihydro-1-benzofuran-6-yl)carbonyl]amino}-8-azabicyclo[3.2.1]oct-8-yl)-N-{(1S)-1-[3-(methyloxy)phenyl]ethyl}pyridine-3-carboxamide |
| 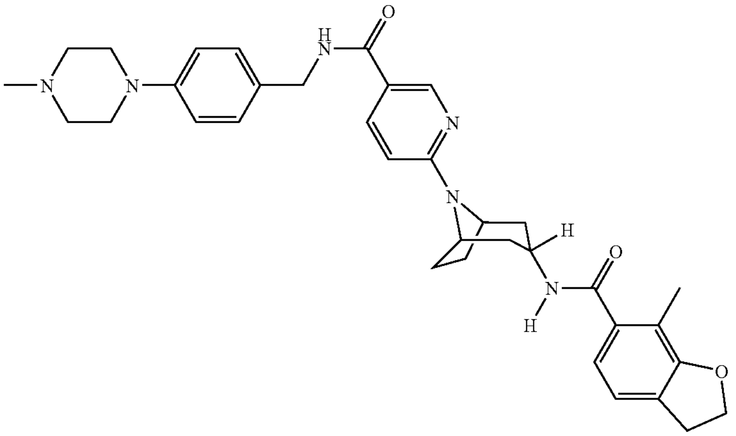 | 6-(3-endo-{[(7-methyl-2,3-dihydro-1-benzofuran-6-yl)carbonyl]amino}-8-azabicyclo[3.2.1]oct-8-yl)-N-{[4-(4-methylpiperazin-1-yl)phenyl]methyl}pyridine-3-carboxamide |
| 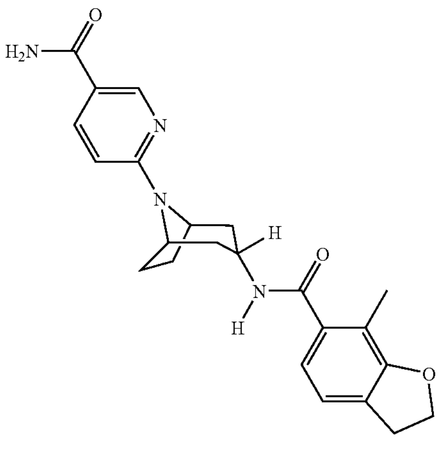 | 6-(3-endo-{[(7-methyl-2,3-dihydro-1-benzofuran-6-yl)carbonyl]amino}-8-azabicyclo[3.2.1]oct-8-yl)pyridine-3-carboxamide |

TABLE II-continued

| STRUCTURE | NAME |
|---|---|
| 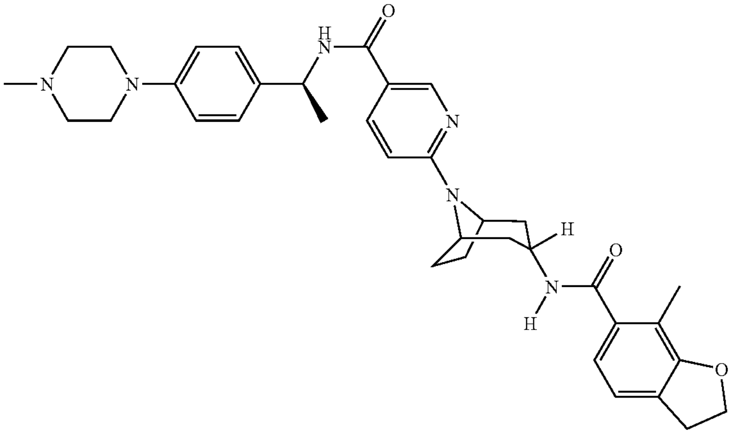 | 6-(3-endo-{[(7-methyl-2,3-dihydro-1-benzofuran-6-yl)carbonyl]amino}-8-azabicyclo[3.2.1]oct-8-yl)-N-{(1S)-1-[4-(4-methylpiperazin-1-yl)phenyl]ethyl}pyridine-3-carboxamide |
| 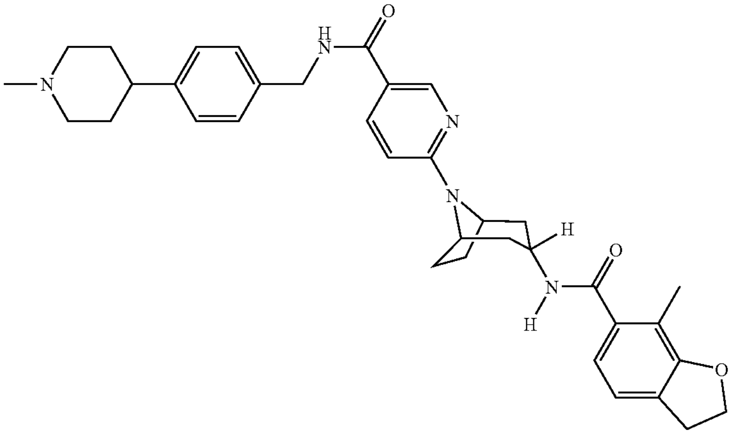 | 6-(3-endo-{[(7-methyl-2,3-dihydro-1-benzofuran-6-yl)carbonyl]amino}-8-azabicyclo[3.2.1]oct-8-yl)-N-{[4-(1-methylpiperidin-4-yl)phenyl]methyl}pyridine-3-carboxamide |
| 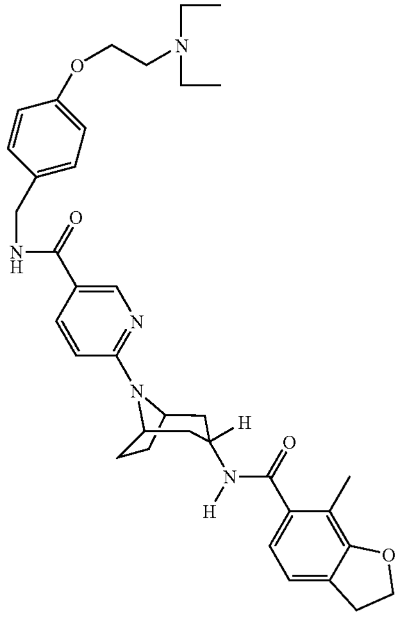 | N-[(4-{[2-(diethylamino)ethyl]oxy}phenyl)methyl]-6-(3-endo-{[(7-methyl-2,3-dihydro-1-benzofuran-6-yl)carbonyl]amino}-8-azabicyclo[3.2.1]oct-8-yl)pyridine-3-carboxamide |

TABLE II-continued

| STRUCTURE | NAME |
| --- | --- |
| 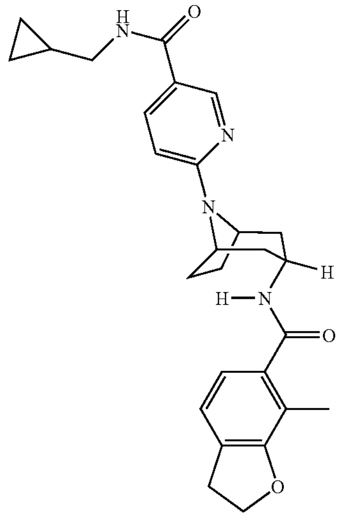 | N-(cyclopropylmethyl)-6-(3-endo-{[(7-methyl-2,3-dihydro-1-benzofuran-6-yl)carbonyl]amino}-8-azabicyclo[3.2.1]oct-8-yl)pyridine-3-carboxamide |
| 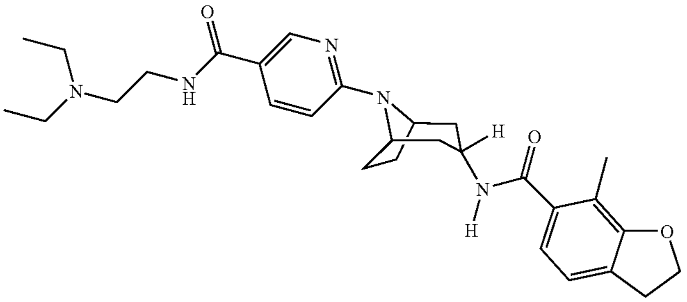 | N-[2-(diethylamino)ethyl]-6-(3-endo-{[(7-methyl-2,3-dihydro-1-benzofuran-6-yl)carbonyl]amino}-8-azabicyclo[3.2.1]oct-8-yl)pyridine-3-carboxamide |
| 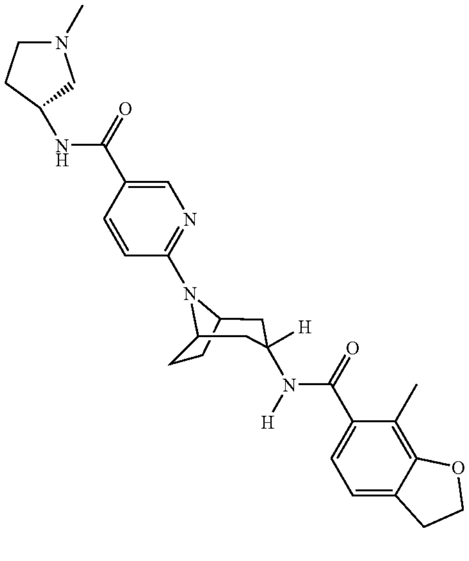 | 6-(3-endo-{[(7-methyl-2,3-dihydro-1-benzofuran-6-yl)carbonyl]amino}-8-azabicyclo[3.2.1]oct-8-yl)-N-[(3R)-1-methylpyrrolidin-3-yl]pyridine-3-carboxamide |

TABLE II-continued

| STRUCTURE | NAME |
|---|---|
| 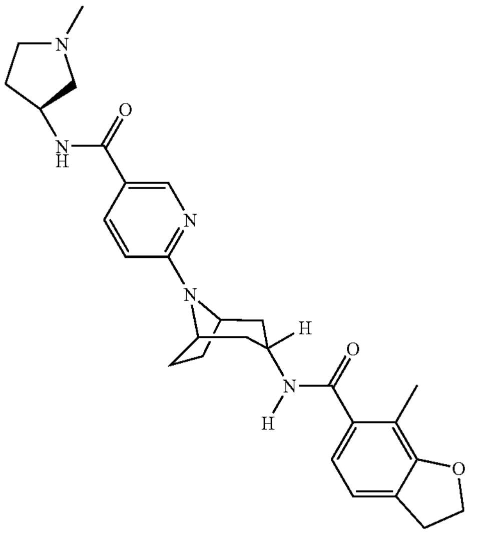 | 6-(3-endo-{[(7-methyl-2,3-dihydro-1-benzofuran-6-yl)carbonyl]amino}-8-azabicyclo[3.2.1]oct-8-yl)-N-[(3S)-1-methylpyrrolidin-3-yl]pyridine-3-carboxamide |
| 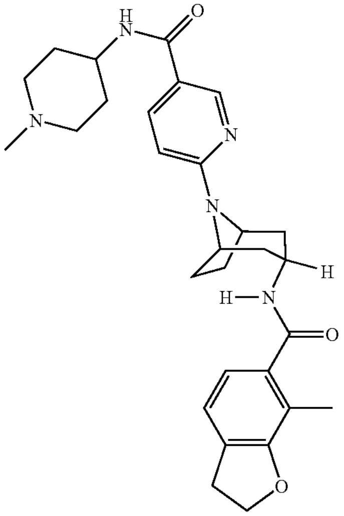 | 6-(3-endo-{[(7-methyl-2,3-dihydro-1-benzofuran-6-yl)carbonyl]amino}-8-azabicyclo[3.2.1]oct-8-yl)-N-(1-methylpiperidin-4-yl)pyridine-3-carboxamide |
| 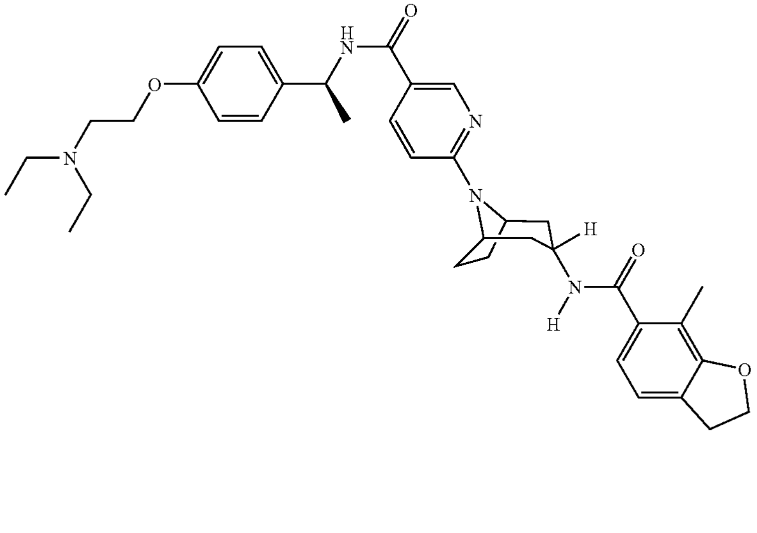 | N-[(1S)-1-(4-{[2-(diethylamino)ethyl]oxy}phenyl)ethyl]-6-(3-endo-{[(7-methyl-2,3-dihydro-1-benzofuran-6-yl)carbonyl]amino}-8-azabicyclo[3.2.1]oct-8-yl)pyridine-3-carboxamide |

TABLE II-continued

| STRUCTURE | NAME |
|---|---|
| 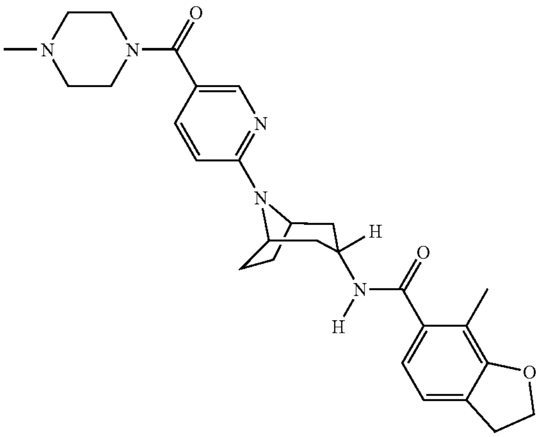 | 7-methyl-N-(8-{5-[(4-methylpiperazin-1-yl)carbonyl]pyridin-2-yl}-8-azabicyclo[3.2.1]oct-3-endo-yl)-2,3-dihydro-1-benzofuran-6-carboxamide |
| 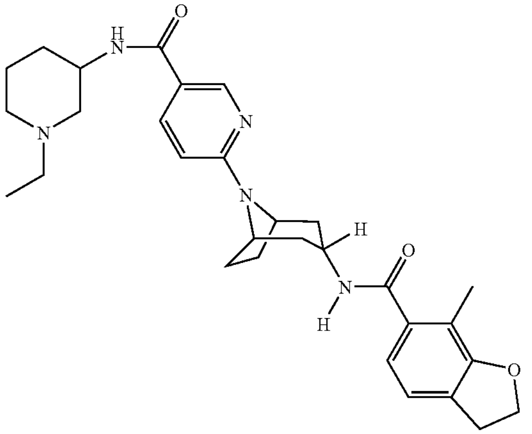 | N-(1-ethylpiperidin-3-yl)-6-(3-endo-{[(7-methyl-2,3-dihydro-1-benzofuran-6-yl)carbonyl]amino}-8-azabicyclo[3.2.1]oct-8-yl)pyridine-3-carboxamide |
| 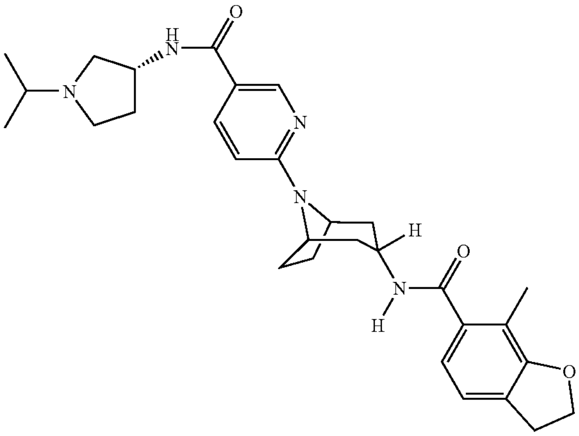 | 6-(3-endo-{[(7-methyl-2,3-dihydro-1-benzofuran-6-yl)carbonyl]amino}-8-azabicyclo[3.2.1]oct-8-yl)-N-[(3R)-1-(1-methylethyl)pyrrolidin-3-yl]pyridine-3-carboxamide |

TABLE II-continued

| STRUCTURE | NAME |
|---|---|
| 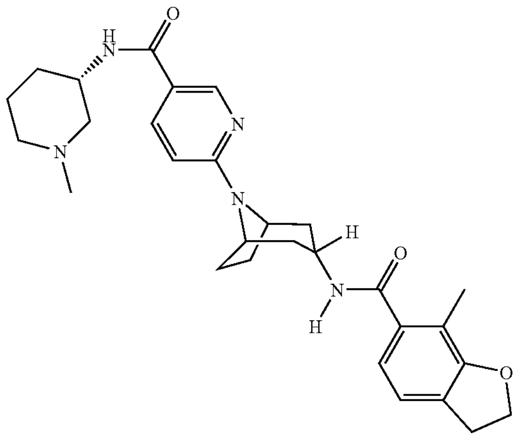 | 6-(3-endo-{[(7-methyl-2,3-dihydro-1-benzofuran-6-yl)carbonyl]amino}-8-azabicyclo[3.2.1]oct-8-yl)-N-[(3S)-1-methylpiperidin-3-yl]pyridine-3-carboxamide |
| 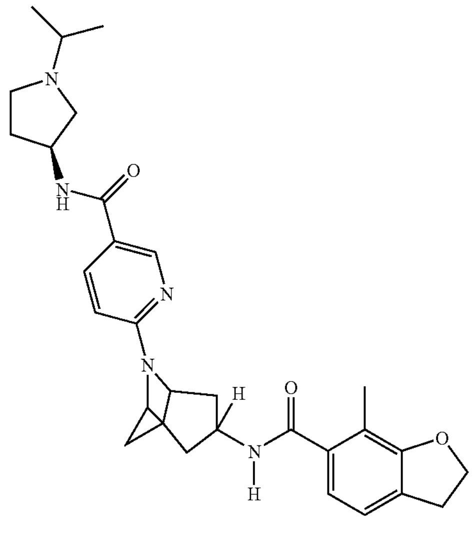 | 6-(3-endo-{[(7-methyl-2,3-dihydro-1-benzofuran-6-yl)carbonyl]amino}-8-azabicyclo[3.2.1]oct-8-yl)-N-[(3S)-1-(1-methylethyl)pyrrolidin-3-yl]pyridine-3-carboxamide |
| 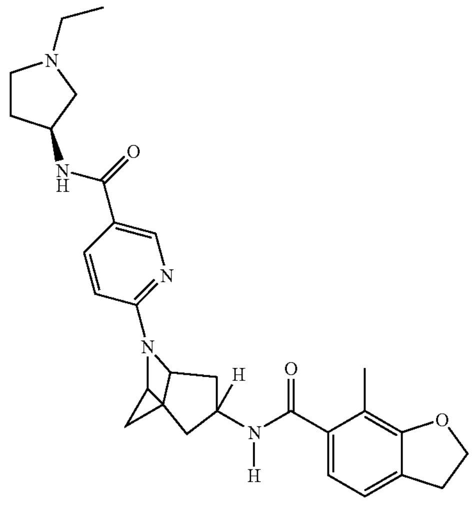 | N-[(3S)-1-ethylpyrrolidin-3-yl]-6-(3-endo-{[(7-methyl-2,3-dihydro-1-benzofuran-6-yl)carbonyl]amino}-8-azabicyclo[3.2.1]oct-8-yl)pyridine-3-carboxamide |

TABLE II-continued

| STRUCTURE | NAME |
| --- | --- |
| 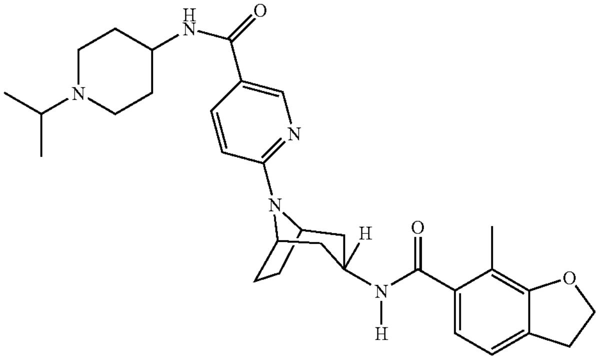 | 6-(3-endo-{[(7-methyl-2,3-dihydro-1-benzofuran-6-yl)carbonyl]amino)-8-azabicyclo[3.2.1]oct-8-yl)-N-[1-(1-methylethyl)piperidin-4-yl]pyridine-3-carboxamide |
| 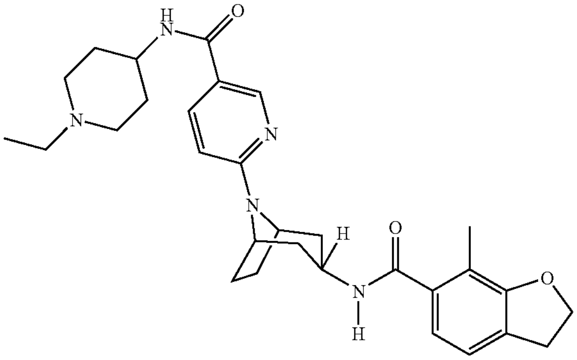 | N-(1-ethylpiperidin-4-yl)-6-(3-endo-{[(7-methyl-2,3-dihydro-1-benzofuran-6-yl)carbonyl]amino}-8-azabicyclo[3.2.1]oct-8-yl)pyridine-3-carboxamide |
| 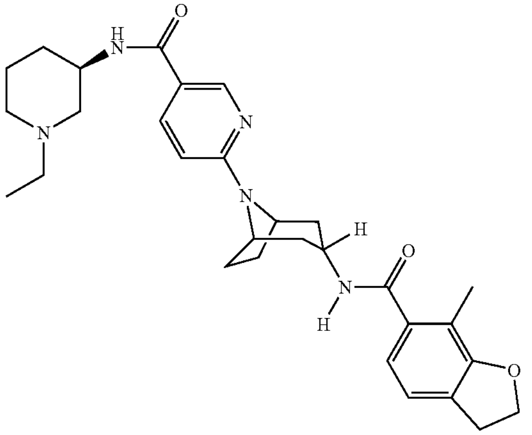 | N-[(3R)-1-ethylpiperidin-3-yl]-6-(3-endo-{[(7-methyl-2,3-dihydro-1-benzofuran-6-yl)carbonyl]amino}-8-azabicyclo[3.2.1]oct-8-yl)pyridine-3-carboxamide |

TABLE II-continued
| STRUCTURE | NAME |
| --- | --- |
| 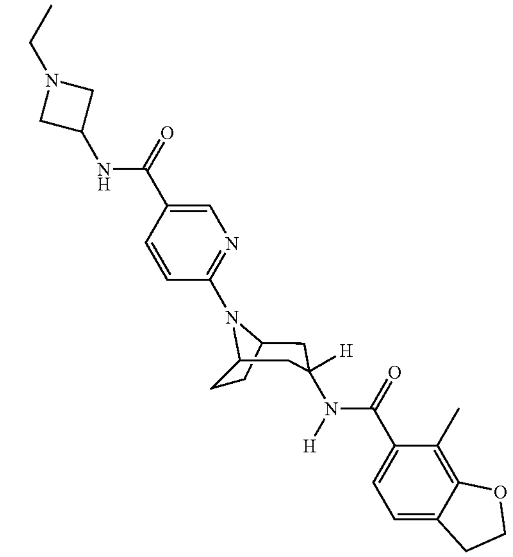 | N-(1-ethylazetidin-3-yl)-6-(3-endo-{[(7-methyl-2,3-dihydro-1-benzofuran-6-yl)carbonyl]amino}-8-azabicyclo[3.2.1]oct-8-yl)pyridine-3-carboxamide |
| 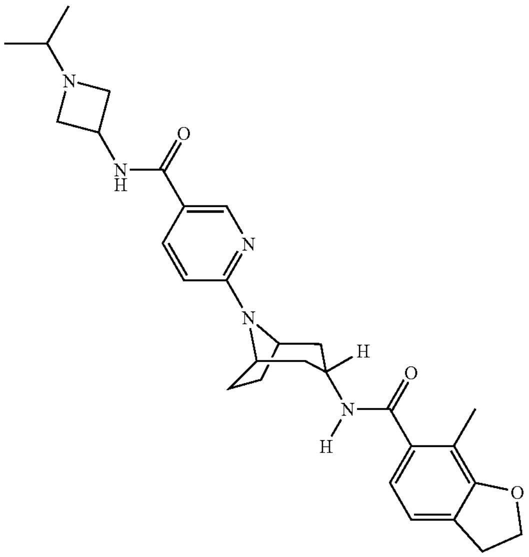 | 6-(3-endo-{[(7-methyl-2,3-dihydro-1-benzofuran-6-yl)carbonyl]amino}-8-azabicyclo[3.2.1]oct-8-yl)-N-[1-(1-methylethyl)azetidin-3-yl]pyridine-3-carboxamide |

TABLE II-continued

| STRUCTURE | NAME |
|---|---|
| 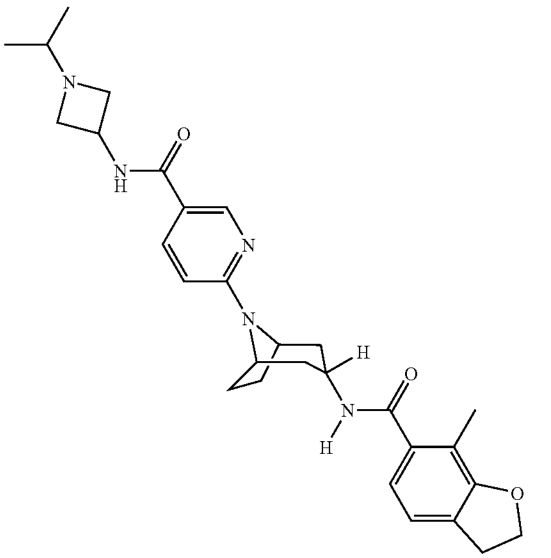 | N-(1-methylazetidin-3-yl)-6-(3-endo-{[(7-methyl-2,3-dihydro-1-benzofuran-6-yl)carbonyl]amino}-8-azabicyclo[3.2.1]oct-8-yl)pyridine-3-carboxamide |
| 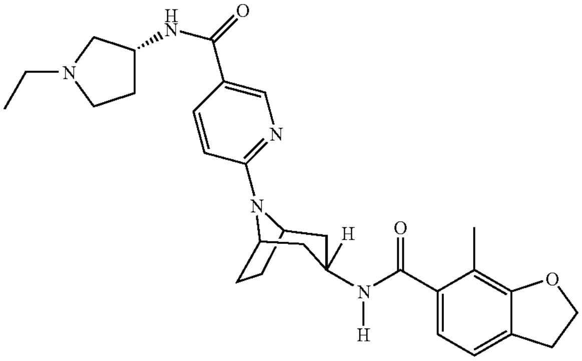 | N-[(3R)-1-ethylpyrrolidin-3-yl]-6-(3-endo-{[(7-methyl-2,3-dihydro-1-benzofuran-6-yl)carbonyl]amino}-8-azabicyclo[3.2.1]oct-8-yl)pyridine-3-carboxamide |
| 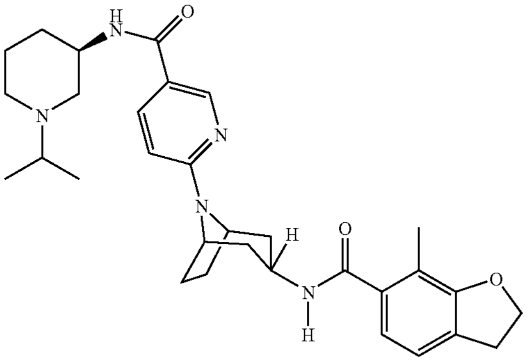 | 6-(3-endo-{[(7-methyl-2,3-dihydro-1-benzofuran-6-yl)carbonyl]amino}-8-azabicyclo[3.2.1]oct-8-yl)-N-[(3R)-1-(1-methylethyl)piperidin-3-yl]pyridine-3-carboxamide |

TABLE II-continued

| STRUCTURE | NAME |
|---|---|
| 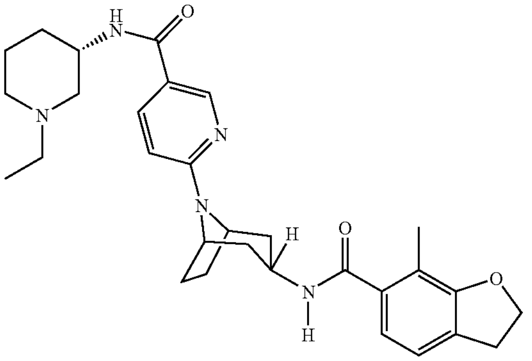 | N-[(3S)-1-ethylpiperidin-3-yl]-6-(3-endo-{[(7-methyl-2,3-dihydro-1-benzofuran-6-yl)carbonyl]amino}-8-azabicyclo[3.2.1]oct-8-yl)pyridine-3-carboxamide |
| 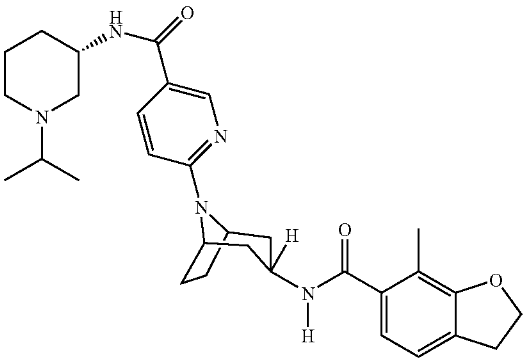 | 6-(3-endo-{[(7-methyl-2,3-dihydro-1-benzofuran-6-yl)carbonyl]amino}-8-azabicyclo[3.2.1]oct-8-yl)-N-[(3S)-1-(1-methylethyl)piperidin-3-yl]pyridine-3-carboxamide |
| 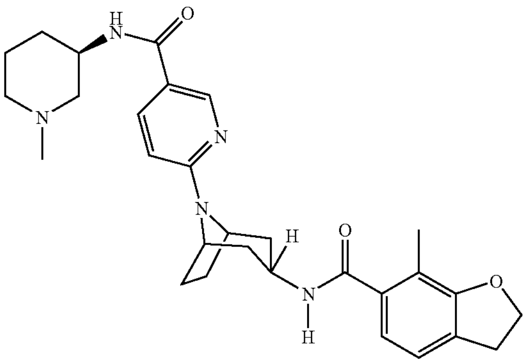 | 6-(3-endo-{[(7-methyl-2,3-dihydro-1-benzofuran-6-yl)carbonyl]amino}-8-azabicyclo[3.2.1]oct-8-yl)-N-[(3R)-1-methylpiperidin-3-yl]pyridine-3-carboxamide |

Compounds in Tables I and II are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Names were generated using ACD/Labs naming software 8.00 release, product version 8.08.

The activity for each of the compounds in Table I is represented by the letters A, B, C and D. These letters are listed next to each of the compounds in Table I in the same row as each of the compounds. The activity that is associated with each of these letters is defined below:

A stands for HSP90 $IC_{50}$ values less than 500 nM.

B stands for HSP90 $IC_{50}$ values ranging from 500 nM to 999 nM.

C stands for HSP90 $IC_{50}$ values ranging from 1000 nM to 1999 nM.

D stands for HSP90 $IC_{50}$ values of ranging from 2000 nM to 10,000 nM.

HSP90 expression and activity is frequently upregulated in tumor cells [5-8] and is particularly associated with poor prognosis in breast cancer [9,10]. Furthermore, HSP90 in tumor cells appears to exist in a hyperactivated state with elevated ATPase activity which is highly sensitive to HSP90 inhibition, compared to the largely latent form found in normal cells [11]. This hyperactivated state suggests that HSP90 inhibitors can selectively target tumor cells, with relatively low impact on normal tissues. Many HSP90 client proteins are involved in various aspects of tumor growth and progression [6, 7, 12, 13]. HSP90 promotes the folding and/or stabilization of many oncogenic proteins that confer autonomous growth on cells (eg, EGFR and ErbB2 [14-17], B-Raf [18,19] and steroid hormone receptors [20]) and also regulates multiple proteins that promote tumor cell survival (eg, IGF 1 receptor [21], PDK1 and Akt [22,23], RIP [24], IκB [24,25] and survivin [26]). HSP90 can also promote aberrant cell cycle progression by stabilizing Cdk4, Cdk6 and cyclin D

[27], Cdk2, and Plk1 [28,29]. Conversely, HSP90 inhibitors can downregulate the cell cycle checkpoint kinase Chk1 and sensitize tumors to various forms of chemotherapy [30,31]. HSP90 inhibition can also blunt tumor angiogenesis, since hypoxia-inducible factor (HIF-1α) and the vascular endothelial growth factor (VEGF) receptor tyrosine kinases are HSP90 clients [32]. The receptor tyrosine kinase Met, which stimulates cellular motility, migration and invasion, is also downregulated in response to HSP90 inhibition, both directly and via inhibition of HIF-1α [33,34]. Apart from its role as a cellular chaperone, HSP90α has also been implicated in extracellular matrix degradation and tumor cell invasion, via activation (and possibly stabilization) of the matrix metalloproteinase MMP2 [35, 36]. HSP90 depletion or inhibition promotes telomere erosion and apoptosis [37], and can also enable the evolution of heterogenous, metastatic and drug-resistant phenotypes by allowing propagation of metastable mutations [38,39]. HSP90 has been implicated in activation of the unfolded protein response (UPR, [40,41]). Failure of the UPR (for example, via inhibition of HSP90) leads to an ER stress signal and apoptosis. Therefore, HSP90 inhibitors can promote tumor cell death indirectly by disrupting the UPR, as well as by directly targeting pro-survival factors.

In addition to cancer, several other diseases can be amenable to treatment using HSP90 inhibitors. There is substantial data supporting a role for HSP90 inhibitors in treating neurodegenerative and infectious diseases. Other possible HSP90 non-oncology indications include inflammatory diseases, autoimmune disorders, stroke, ischemia, cardiac disorders, sepsis, fibrogenetic disorders (for example, scleroderma, polymyositis, systemic lupus, rheumatoid arthritis, liver cirrhosis, keloid formation, interstitial nephritis, cystic fibrosis and pulmonary fibrosis) and metabolic diseases.

Several neurodegenerative diseases ("tauopathies"), including Alzheimer's disease (AD) and frontotemporal lobal dementia, are characterized by accumulation of hyperphosphorylated or mutated forms of the microtubule-associated protein Tau [42]. HSP90 inhibitors can be able to degrade aberrant Tau proteins via two complementary mechanisms. First, HSP90 appears to stabilize p35 (a neuronal protein involved in aberrant Tau phosphorylation) and mutant (but not wild-type) Tau protein [43]. Second, HSP90 inhibition induces expression of HSP70, which can promote productive folding of Tau [44] and/or selective degradation of aberrant Tau proteins [45]. Moreover, HSP90 isolated from brain tissue affected by AD showed markedly higher affinity for an HSP90 inhibitor compared with HSP90 from normal brain tissue [45], concordant with a similar observation in tumor cells [11].

HSP90 expression in the host organism has been implicated in mediating both infection and replication of a broad range of viral pathogens, including negative, strand RNA viruses and influenza virus [46-48], hepatitis B [49], hepatitis C [50,51] and herpes simplex virus type 1 [52]. Importantly, pharmacological inhibition of HSP90 was found to impair the replication of RNA without selecting for the emergence of drug-resistant mutants [53]. HSP90 also promotes the growth and survival of pathogenic yeast, though in this case the endogenous fungal enzyme is involved. Geldanamycin increases the susceptibility of *Candida* and *Aspergillus* species to other antibiotics [54], and an antibody directed against yeast HSP90 (Mycograb) was recently shown to significantly enhance the activity of amphotericin B in a randomized, double blind clinical study [55]. Fungal HSP90 can also help to promote drug resistance [54]. HSP90 inhibition was also recently shown to ameliorate pulmonary damage and inflammation in a mouse model of acute sepsis [56], suggesting a broader role for HSP90 inhibitors in treating infectious and inflammatory diseases.

The benzoquinone ansamycin geldanamycin was identified as an inhibitor of HSP90 [57], and several geldanamycin analogs have been evaluated as anticancer agents in clinical trials, with some evidence of activity. However, formulation and administration of these agents remains challenging. An orally available inhibitor of HSP90 would have broad utility in the treatment of a wide range of malignancies and potentially other diseases.

HSP90 inhibitors have been reported to show synergistic effects on tumor cell growth and survival when combined with various chemotherapeutics. Examples include HSP90 inhibitors in combination with proteosome inhibitors (eg bortezomib) in multiple myeloma, EGFR (eg Iressa) or PI3K (eg LY294002) inhibitors in malignant glioma, DNA damaging agents (eg etoposide or cisplatin) in leukemia and pediatric tumors, and radiation in various tumors including cervical, prostate, glioma and pancreatic. While observed synergy can be hypothesized to be due to loss of stability of specific HSP90 client proteins, it may also be due to loss of general stress buffering capacity of the cell.

Additionally, several drug-resistant mutant proteins have been shown to be dependent on HSP90 for their stabilization and activity, paving the way for in vivo proof of concept studies and clinical trial design for use of HSP90 inhibitors against certain drug-resistant tumors. Examples include imatinib-resistant c-KIT mutations in GIST (gastrointestinal stromal tumor), gefitinib and erlotinib-resistant EGFR (L858R/T790M) mutants in NSCL, and imatinib-resistant BCR-ABL(T3151) mutant in CML. In fact, the 17-AAG related HSP90 inhibitor IPI-504 was recently granted orphan drug status for GIST after a high rate of response was observed in Gleevec-resistant GIST patients enrolled in a Phase I trial.

Additionally, inhibition of HSP90 may be in part responsible for the anti-tumor activity of the recently FDA-approved histone deacetylase inhibitor Vorinostat (suberoylanilide hydroxamic acid, or SAHA). HSP90 activity has been reported to be negatively regulated through direct acetylation of the chaperone, and HDAC inhibitors are shown to result in the accumulation of inactive, acetylated HSP90 protein and increased degradation of HSP90 client proteins, implicating HDAC function in the positive control of HSP90 function. Hence, the clinical mechanism of action of HDAC inhibitors alone or in combination may in certain instances be due to inhibition of HSP90 function.

HSP90 expression in the host organism has been implicated in mediating both infection and replication of a broad range of viral pathogens. The HSP90 inhibitors geldanamycin and radicicol impair the replication of negative strand RNA viruses and influenza virus by destabilizing the viral RNA polymerase, and geldanamycin can also inhibit replication of hepatitis C virus. HSP90 also directs the folding and intracellular localization of the DNA polymerase from herpes simplex virus type 1 and is required for hepatitis B reverse transcriptase activity. Pharmacological inhibition of HSP90 was found to impair the replication of RNA viruses in cell culture and infected animals, without selecting for the emergence of drug-resistant mutants. Indeed, HSP90 may be broadly implicated in the development of drug resistance in microorganisms, as discussed below.

HSP90 also promotes the growth and survival of pathogenic yeast, though in this case the endogenous fungal enzyme is involved. Geldanamycin increases the susceptibility of *Candida* and *Aspergillus* species to other antibiotics, and an antibody directed against yeast HSP90 (Mycograb) was recently shown to significantly enhance the activity of amphotericin B in a randomized, double blind clinical study. As in the case of tumor cells HSP90 may act via multiple mechanisms, but perhaps most striking is the potential for fungal HSP90 to promote drug resistance. Endogenous HSP90 may support the expression of mutant proteins that confer drug resistance, and HSP90 inhibitors appear to inhibit drug resistance under acute selection conditions, but have less effect on resistance that is acquired by more gradual selection in the presence of antibiotics. Thus, HSP90 inhibitors may have utility early in treatment of fungal infections, before resistance mutations have a chance to emerge. Intriguingly the drug resistance-inducing effects of HSP90 are mediated by calcineurin, which is also implicated in both cyclosporine A resistance and geldanamycin activity in the malarial parasite *Plasmodium falciparum.*

HSP90 inhibition was also recently shown to ameliorate pulmonary damage and inflammation in a mouse model of acute sepsis, suggesting a broader role for HSP90 inhibitors in treating infectious and inflammatory diseases.

In addition to cancer, several other diseases may be amenable to treatment using HSP90 inhibitors. These include neurodegenerative disorders and infectious diseases. Several neurodegenerative diseases, including Alzheimer's disease (AD) and frontotemporal lobal dementia, are characterized by accumulation of hyperphosphorylated or mutated forms of the microtubule-associated protein Tau. These pathogenic Tau proteins form intracellular aggregates known as neurofibrillary tangles, which have been proposed to have a causative role in disease but may alternatively represent a cellular protective mechanism against the toxic, soluble form of Tau. Selective degradation of aberrant Tau proteins may therefore represent a novel therapeutic strategy. HSP90 inhibitors may achieve this degradation via two complementary mechanisms. First, HSP90 appears to stabilize p35 (a neuronal protein involved in aberrant Tau phosphorylation) and mutant (but not wild-type) Tau protein: the activity of these pathogenic proteins would therefore be reduced by HSP90 inhibition. Second, HSP90 inhibition induces expression of HSP70, which may promote productive folding of Tau and/or selective degradation of aberrant Tau proteins. Moreover, HSP90 isolated from brain tissue affected by AD showed markedly higher affinity for an HSP90 inhibitor compared with HSP90 from normal brain tissue, concordant with a similar observation in tumor cells.

REFERENCES

1. Lai, B. T., et al. (1984) Quantitation and intracellular localization of the 85K heat shock protein by using monoclonal and polyclonal antibodies. Mol Cell Biol 4, 2802-2810
2. Chen, B., et al. (2005) The HSP90 family of genes in the human genome: insights into their divergence and evolution. Genomics 86, 627-637
3. Bracher, A., and Hartl, F. U. (2005) Towards a complete structure of Hsp90. Structure 13, 501-502
4. Wegele, H., et al. (2004) Hsp70 and Hsp90—a relay team for protein folding. Rev Physiol Biochem Pharmacol 151, 1-44
5. Neckers, L. (2007) Heat shock protein 90: the cancer chaperone. J Biosci 32, 517-530
6. Powers, M. V., and Workman, P. (2006) Targeting of multiple signalling pathways by heat shock protein 90 molecular chaperone inhibitors. Endocr Relat Cancer 13 Suppl 1, S125-135
7. Whitesell, L., and Lindquist, S. L. (2005) HSP90 and the chaperoning of cancer. Nat Rev Cancer 5, 761-772
8. Sreedhar, A. S., et al. (2004) Hsp9β isoforms: functions, expression and clinical importance. FEBS Lett 562, 11-15
9. Conroy, S. E., et al. (1998) Autoantibodies to the 90 kDa heat shock protein and poor survival in breast cancer patients. Eur J Cancer 34, 942-943
10. Pick, E., et al. (2007) High HSP90 expression is associated with decreased survival in breast cancer. Cancer Res 67, 2932-2937
11. Kamal, A., et al. (2003) A high-affinity conformation of Hsp90 confers tumour selectivity on Hsp90 inhibitors. Nature 425, 407-410
12. Xu, W., and Neckers, L. (2007) Targeting the molecular chaperone heat shock protein 90 provides a multifaceted effect on diverse cell signaling pathways of cancer cells. Clin Cancer Res 13, 1625-1629
13. Bagatell, R., and Whitesell, L. (2004) Altered Hsp90 function in cancer: a unique therapeutic opportunity. Mol Cancer Ther 3, 1021-1030
14. Citri, A., et al. (2004) The achilles heel of ErbB-2/$HER_2$: regulation by the Hsp90 chaperone machine and potential for pharmacological intervention. Cell Cycle 3, 51-60
15. Shimamura, T., et al. (2005) Epidermal growth factor receptors harboring kinase domain mutations associate with the heat shock protein 90 chaperone and are destabilized following exposure to geldanamycins. Cancer Res 65, 6401-6408
16. Yang, S., et al. (2006) Association with HSP90 inhibits Cbl-mediated down-regulation of mutant epidermal growth factor receptors. Cancer Res 66, 6990-6997
17. Xu, W., et al. (2007) Sensitivity of epidermal growth factor receptor and ErbB2 exon 20 insertion mutants to Hsp90 inhibition. Br J Cancer
18. da Rocha Dias, S., et al. (2005) Activated B-RAF is an Hsp90 client protein that is targeted by the anticancer drug 17-allylamino-17-demethoxygeldanamycin. Cancer Res 65, 10686-10691
19. Grbovic, O. M., et al. (2006) V600E B-Raf requires the Hsp90 chaperone for stability and is degraded in response to Hsp90 inhibitors. Proc Natl Acad Sci USA 103, 57-62
20. Fang, Y., et al. (1996) Hsp90 regulates androgen receptor hormone binding affinity in vivo. J Biol Chem 271, 28697-28702
21. Nielsen, T. O., et al. (2004) Expression of the insulin-like growth factor I receptor and urokinase plasminogen activator in breast cancer is associated with poor survival: potential for intervention with 17-allylamino geldanamycin. Cancer Res 64, 286-291
22. Basso, A. D., et al. (2002) Akt forms an intracellular complex with heat shock protein 90 (Hsp90) and Cdc37 and is destabilized by inhibitors of Hsp90 function. J Biol Chem 277, 39858-39866
23. Solit, D. B., et al. (2003) Inhibition of heat shock protein 90 function down-regulates Akt kinase and sensitizes tumors to Taxol. Cancer Res 63, 2139-2144
24. Lewis, J., et al. (2000) Disruption of hsp90 function results in degradation of the death domain kinase, receptor-interacting protein (RIP), and blockage of tumor necrosis factor-induced nuclear factor-kappaB activation. J Biol Chem 275, 10519-10526
25. Wang, X., et al. (2006) 17-allylamino-17-demethoxygeldanamycin synergistically potentiates tumor necrosis factor-induced lung cancer cell death by blocking the nuclear factor-kappaB pathway. Cancer Res 66, 1089-1095

26. Fortugno, P., et al. (2003) Regulation of survivin function by Hsp90. Proc Natl Acad Sci USA 100, 13791-13796
27. Srethapakdi, M., et al. (2000) Inhibition of Hsp90 function by ansamycins causes retinoblastoma gene product-dependent GI arrest. Cancer Res 60, 3940-3946
28. de Carcer, G. (2004) Heat shock protein 90 regulates the metaphase-anaphase transition in a polo-like kinase-dependent manner. Cancer Res 64, 5106-5112
29. Prince, T., et al. (2005) Cdk2: a genuine protein kinase client of Hsp90 and Cdc37. Biochemistry 44, 15287-15295
30. Arlander, S. J., et al. (2003) Hsp90 inhibition depletes Chk1 and sensitizes tumor cells to replication stress. J Biol Chem 278, 52572-52577
31. Mesa, R. A., et al. (2005) Heat shock protein 90 inhibition sensitizes acute myelogenous leukemia cells to cytarabine. Blood 106, 318-327
32. Sanderson, S., et al. (2006) Benzoquinone ansamycin heat shock protein 90 inhibitors modulate multiple functions required for tumor angiogenesis. Mol Cancer Ther 5, 522-532
33. Koga, F., et al. (2007) Low dose geldanamycin inhibits hepatocyte growth factor and hypoxia-stimulated invasion of cancer cells. Cell Cycle 6, 1393-1402
34. Webb, C. P., et al. (2000) The geldanamycins are potent inhibitors of the hepatocyte growth factor/scatter factor-met-urokinase plasminogen activator-plasmin proteolytic network. Cancer Res 60, 342-349
35. Eustace, B. K., et al. (2004) Functional proteomic screens reveal an essential extracellular role for hsp90 alpha in cancer cell invasiveness. Nat Cell Biol 6, 507-514
36. Tsutsumi, S., and Neckers, L. (2007) Extracellular heat shock protein 90: A role for a molecular chaperone in cell motility and cancer metastasis. Cancer Sci 98, 1536-1539
37. Compton, S. A., et al. (2006) Induction of nitric oxide synthase-dependent telomere shortening after functional inhibition of Hsp90 in human tumor cells. Mol Cell Biol 26, 1452-1462
38. Queitsch, C., et al. (2002) Hsp90 as a capacitor of phenotypic variation. Nature 417, 618-624
39. Rutherford, S. L., and Lindquist, S. (1998) Hsp90 as a capacitor for morphological evolution. Nature 396, 336-342
40. Marcu, M. G., et al. (2002) Heat shock protein 90 modulates the unfolded protein response by stabilizing IRE1alpha. Mol Cell Biol 22, 8506-8513
41. Davenport, E. L., et al. (2007) Heat shock protein inhibition is associated with activation of the unfolded protein response (UPR) pathway in myeloma plasma cells. Blood
42. Dermaut, B., et al. (2005) Tau is central in the genetic Alzheimer-frontotemporal dementia spectrum. Trends Genet. 21, 664-672
43. Luo, W., et al. (2007) Roles of heat-shock protein 90 in maintaining and facilitating the neurodegenerative phenotype in tauopathies. Proc Natl Acad Sci USA 104, 9511-9516
44. Dou, F., et al. (2003) Chaperones increase association of tau protein with microtubules. Proc Natl Acad Sci USA 100, 721-726
45. Dickey, C. A., et al. (2007) The high-affinity HSP90-CHIP complex recognizes and selectively degrades phosphorylated tau client proteins. J Clin Invest 117, 648-658
46. Connor, J. H., et al. (2007) Antiviral activity and RNA polymerase degradation following Hsp90 inhibition in a range of negative strand viruses. Virology 362, 109-119
47. Naito, T., et al. (2007) Involvement of Hsp90 in assembly and nuclear import of influenza virus RNA polymerase subunits. J Virol 81, 1339-1349
48. Momose, F., et al. (2002) Identification of Hsp90 as a stimulatory host factor involved in influenza virus RNA synthesis. J Biol Chem 277, 45306-45314
49. Hu, J., et al. (2004) Requirement of heat shock protein 90 for human hepatitis B virus reverse transcriptase function. J Virol 78, 13122-13131
50. Okamoto, T., et al. (2006) Hepatitis C virus RNA replication is regulated by FKBP8 and Hsp90. Embo J 25, 5015-5025
51. Nakagawa, S., et al. (2007) Hsp90 inhibitors suppress HCV replication in replicon cells and humanized liver mice. Biochem Biophys Res Commun 353, 882-888
52. Burch, A. D., and Weller, S. K. (2005) Herpes simplex virus type 1 DNA polymerase requires the mammalian chaperone hsp90 for proper localization to the nucleus. J Virol 79, 10740-10749
53. Geller, R., et al. (2007) Evolutionary constraints on chaperone-mediated folding provide an antiviral approach refractory to development of drug resistance. Genes Dev 21, 195-205
54. Cowen, L. E., and Lindquist, S. (2005) Hsp90 potentiates the rapid evolution of new traits: drug resistance in diverse fungi. Science 309, 2185-2189
55. Pachl, J., et al. (2006) A randomized, blinded, multicenter trial of lipid-associated amphotericin B alone versus in combination with an antibody-based inhibitor of heat shock protein 90 in patients with invasive candidiasis. Clin Infect Dis 42, 1404-1413
56. Chatterjee, A., et al. (2007) Hsp90 Inhibitors Prolong Survival, Attenuate Inflammation and Reduce Lung Injury in Murine Sepsis. Am J Respir Crit. Care Med
57. Whitesell, L., et al. (1994) Inhibition of heat shock protein HSP90-pp60v-src heteroprotein complex formation by benzoquinone ansamycins: essential role for stress proteins in oncogenic transformation. Proc Natl Acad Sci USA 91, 8324-8328
58. Solit, D. B., and Rosen, N. (2006) Hsp90: a novel target for cancer therapy. Curr Top Med Chem 6, 1205-1214

Another embodiment of the disclosure relates to a pharmaceutical composition comprising the compound of Formula I, IB, IC, ID, IE, or a pharmaceutically acceptable salt thereof, and a pharmaceutically acceptable carrier, excipient, or diluent.

Another embodiment of the disclosure relates to a method of inhibiting HSP90 in a cell, comprising contacting the cell, in which inhibition of HSP90 is desired, with the compound of Formula I, IB, IC, ID or IE, or a pharmaceutically acceptable salt thereof.

Another embodiment of the disclosure relates to a method of inhibiting HSP90 in a cell, comprising contacting a cell in which inhibition of HSP90 is desired with a pharmaceutical composition, comprising the compound of Formula I, IB, IC, ID or IE, or a pharmaceutically acceptable salt thereof, and a pharmaceutically acceptable carrier, excipient, or diluent.

Another embodiment of the disclosure relates to a method of treating a disease or condition that involves HSP90, comprising administering to an animal, in need of said treatment, the compound of Formula I, IB, IC, ID or IE, or a pharmaceutically acceptable salt thereof.

Another embodiment of the disclosure relates to a method of treating a disease or condition that involves HSP90, comprising administering to an animal, in need of said treatment, a pharmaceutical composition comprising the compound of Formula I, IB, IC, ID or IE, or a pharmaceutically acceptable salt thereof, and a pharmaceutically acceptable carrier, excipient, or diluent. In a further embodiment, the disease or condition being treated is cancer.

In another embodiment, it is contemplated that the HSP90 inhibiting compounds of Formula I, IB, IC, ID or IE, or a pharmaceutically acceptable salt thereof, can be used to treat one or more diseases or conditions selected from breast cancer, CML, colorectal carcinoma, glioma, melanoma, multiple myeloma, non-small cell lung cancer, ovarian cancer, prostate cancer, renal cell carcinoma, small cell lung carcinoma, and UPR (unfolded protein response).

In another embodiment, it is contemplated that the HSP90 inhibiting compounds of Formula I, IB, IC, ID or IE, or a pharmaceutically acceptable salt thereof, can be used to treat one or more diseases or conditions selected from neurodegenerative diseases, infectious diseases, inflammatory diseases, autoimmune disorders, stroke, ischemia, cardiac disorders, sepsis, fibrogenetic disorders (for example, scleroderma, polymyositis, systemic lupus, rheumatoid arthritis, liver cirrhosis, keloid formation, interstitial nephritis, cystic fibrosis and pulmonary fibrosis) and metabolic diseases.

Another embodiment of the disclosure relates to a pharmaceutical composition comprising one or more compounds from Table I, or a pharmaceutically acceptable salt thereof, and a pharmaceutically acceptable carrier, excipient, or diluent.

Another embodiment of the disclosure relates to a method of inhibiting HSP90 in a cell, comprising contacting the cell, in which inhibition of HSP90 is desired, with one or more compounds from Table I, or a pharmaceutically acceptable salt thereof.

Another embodiment of the disclosure relates to a method of inhibiting HSP90 in a cell, comprising contacting a cell in which inhibition of HSP90 is desired with a pharmaceutical composition, comprising one or more compounds from Table I, or a pharmaceutically acceptable salt thereof, and a pharmaceutically acceptable carrier, excipient, or diluent.

Another embodiment of the disclosure relates to a method of treating a disease or condition that involves HSP90, comprising administering to an animal, in need of said treatment, one or more compounds from Table I, or a pharmaceutically acceptable salt thereof.

Another embodiment of the disclosure relates to a method of treating a disease or condition that involves HSP90, comprising administering to an animal, in need of said treatment, a pharmaceutical composition comprising one or more compounds from Table I, or a pharmaceutically acceptable salt thereof, and a pharmaceutically acceptable carrier, excipient, or diluent. In a further embodiment, the disease or condition being treated is cancer.

In another embodiment, it is contemplated that the HSP90 inhibiting compounds from Table I, or a pharmaceutically acceptable salt thereof, can treat one or more indications selected from breast cancer, CML, colorectal carcinoma, glioma, melanoma, multiple myeloma, non-small cell lung cancer, ovarian cancer, prostate cancer, renal cell carcinoma, small cell lung carcinoma, and UPR (unfolded protein response).

The HSP90 inhibiting compounds of one or more compounds from Table I, or a pharmaceutically acceptable salt thereof, are also contemplated to be useful as being able to treat one or more diseases or conditions selected from neurodegenerative diseases, infectious diseases, inflammatory diseases, autoimmune disorders, stroke, ischemia, cardiac disorders, sepsis, fibrogenetic disorders (for example, scleroderma, polymyositis, systemic lupus, rheumatoid arthritis, liver cirrhosis, keloid formation, interstitial nephritis, cystic fibrosis and pulmonary fibrosis) and metabolic diseases.

Several neurodegenerative diseases ("tauopathies"), including Alzheimer's disease (AD) and frontotemporal lobal dementia, are characterized by accumulation of hyperphosphorylated or mutated forms of the microtubule-associated protein Tau. It is contemplated that the HSP90 inhibiting compounds disclosed herein can degrade aberrant Tau proteins via two complementary mechanisms. First, HSP90 appears to stabilize p35 (a neuronal protein involved in aberrant Tau phosphorylation) and mutant (but not wild-type) Tau protein. Second, HSP90 inhibition induces expression of HSP70, which can promote productive folding of Tau and/or selective degradation of aberrant Tau proteins.

It is also completed that the HSP90 inhibiting compounds disclosed herein can mediate and treat infection from a broad range of viral pathogens, including negative strand RNA viruses and influenza virus, hepatitis B, hepatitis C and herpes simplex virus type 1.

In another embodiment, it is contemplated that the HSP90 inhibiting compounds of Formula I, IB, IC, ID or IE, or a pharmaceutically acceptable salt thereof, can be used to treat a neurodegenerative disease characterized by accumulation of hyperphosphorylated or mutated forms of the microtubule-associated protein Tau.

In another embodiment, it is contemplated that the HSP90 inhibiting compounds of Formula I, IB, IC, ID, IE, or a pharmaceutically acceptable salt thereof, can be used in a method of degrading aberrant Tau proteins in an animal, comprising administering a compound according to claim 1 to said animal.

In another embodiment, it is contemplated that one or more of the HSP90 inhibiting compounds from Table I, or a pharmaceutically acceptable salt thereof, can be used to treat a neurodegenerative disease characterized by accumulation of hyperphosphorylated or mutated forms of the microtubule-associated protein Tau.

In another embodiment, it is contemplated that one or more of the HSP90 inhibiting compounds from Table I, or a pharmaceutically acceptable salt thereof, can be used in a method of degrading aberrant Tau proteins in an animal, comprising administering a compound according to claim 1 to said animal.

In other embodiments, any of the above methods of treating any of the diseases or conditions described herein further comprises administering radiation treatment or one or more therapeutic agents selected from Camptothecin, Topotecan, 9-Nitrocamptothecin, 9-Aminocamptothecin, Karenitecin, Irinotecan, Etoposide, Etoposide Phosphate, Teniposide, Amsacrine, Razoxane, Dexrazoxane, Mechlorethamine, Cyclophosphamide, Ifosfamide, Chlorambucil, Melphalan, Thiotepa, Trenimon, Triethylenemelamine, Dianhydrogalactitol, Dibromodulcitol, Busulfan, dimethylsulfate, Chloroethylnitrosourea, Carmustine, Lomustine, Methyl-Lomustine, Streptozotocin, Chlorozotocin, Prednimustine, Estramustine, Procarbazine, Dacarbazine, Hexamethylmelamine, Pentamethylmelamine, Temozolomide, Cisplatin, Carboplatin, Oxaliplatin, Bleomycin, Dactinomycin, Mithramycin, Rapamycin, Mitomycin C, Daunorubicin, Doxorubicin, Epirubicin, Idarubicin, Methotrexate, Edatrexate, Trimethoprim, Nolatrexed, Raltitrexed, Hydroxyurea, 5-fluorouracil, Ftorafur, Capecitabine, Furtulon, Eniluracil, ara-C, 5-azacytidine, Gemcitabine, Mercaptopurine, Thioguanine, Pentostatin, antisense DNA, antisense RNA, an antisense DNA/RNA hybrid, a ribozyme, ultraviolet radiation, Vincristine, Vinblastine, Paclitaxel, Docetaxel, L-Asparaginase, a kinase inhibitor, Imatinib, Mitotane, Aminoglutethimide, Diethylstilbestrol, Ethinyl estradiol, Tamoxifen, Anastrozole, Testosterone propionate, Fluoxymesterone, Flutamide, Leuprolide, Prednisone, Hydroxyprogesterone caproate, Medroxyprogesterone acetate, Megestrol acetate, Interferon-alfa, and Interleukin.

ABBREVIATIONS AND DEFINITIONS

The following abbreviations and terms have the indicated meanings throughout:

| Abbreviation | Meaning |
|---|---|
| Ac | Acetyl |
| Br | Broad |
| ° C. | degrees Celsius |
| c- | Cyclo |
| CBZ | CarboBenZoxy = benzyloxycarbonyl |
| D | Doublet |
| Dd | doublet of doublet |
| Dt | doublet of triplet |
| DIPEA | N,N-diisopropylethylamine |
| DMF | N,N-dimethylformamide |
| DMSO | dimethyl sulfoxide |
| EI | Electron Impact ionization |
| Et | Ethyl |
| G | gram(s) |
| GC | gas chromatography |
| h or hr | hour(s) |
| HOAc | acetic acid |
| HOBt | Hydroxybenzotriazole |
| HPLC | high pressure liquid chromatography |
| L | liter(s) |
| M | molar or molarity |
| M | Multiplet |
| Me | Methyl |
| Mesyl | Methanesulfonyl |
| Mg | milligram(s) |
| MHz | megahertz (frequency) |
| Min | minute(s) |
| mL | milliliter(s) |
| mM | Millimolar |
| Mmol | millimole(s) |
| Mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | Nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | Phenyl |
| PhOH | Phenol |
| PfP | Pentafluorophenol |
| PfPy | Pentafluoropyridine |
| PPTS | Pyridinium p-toluenesulfonate |
| Py | Pyridine |
| PyBroP | bromo-tris-pyrrolidino-phosphonium hexafluorophosphate |
| Q | Quartet |
| RT | Room temperature |
| Sat'd | Saturated |
| S | Singlet |
| s- | Secondary |
| t- | Tertiary |
| t or tr | Triplet |
| TBDMS | t-butyldimethylsilyl |
| TES | Triethylsilyl |
| TFA | trifluoroacetic acid |
| THF | Tetrahydrofuran |
| TMOF | trimethyl orthoformate |
| TMS | Trimethylsilyl |
| Tosyl | p-toluenesulfonyl |
| Trt | triphenylmethyl |
| uL | microliter(s) |
| uM | Micromole(s) or micromolar |

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond, "- - - -" means a single or double bond. When a group is depicted removed from its parent formula, the "∿∿" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, $—CH_2CH_2—$. It is understood by one of ordinary skill in the art that the aforementioned descriptive techniques are common in the chemical arts to provide brevity and simplicity to description of otherwise complex structures.

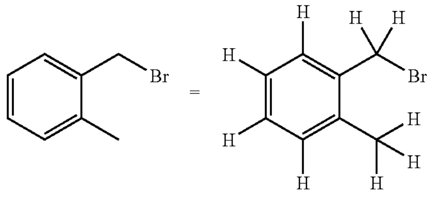

If a group "R" is depicted as "floating" on a ring system, as for example in the formula:

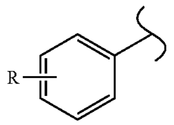

then, unless otherwise defined, a substituent "R" can reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

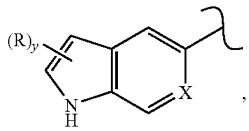

, or

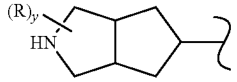

, or

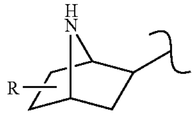

then, unless otherwise defined, a substituent "R" can reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group can reside on either the 5-membered or the 6-membered ring of the fused ring system. In the formula depicted above, when y is 2 for example, then the two "R's" can reside on any two atoms of the ring system, again assuming each replaces a depicted, implied, or expressly defined hydrogen on the ring.

When a group "R" is depicted as existing on a ring system containing saturated carbons, as for example in the formula:

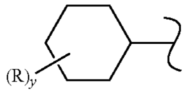

where, in this example, "y" can be more than one, assuming each replaces a currently depicted, implied, or expressly defined hydrogen on the ring; then, unless otherwise defined, where the resulting structure is stable, two "R's" can reside on the same carbon. A simple example is when R is a methyl group; there can exist a geminal dimethyl on a carbon of the depicted ring (an "annular" carbon). In another example, two R's on the same carbon, including that carbon, can form a ring, thus creating a spirocyclic ring (a "spirocyclyl" group) structure with the depicted ring as for example in the formula:

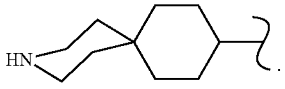

"Administration" and variants thereof (e.g., "administering" a compound) in reference to a compound of this disclosure (i.e., a compound of formula I, II or III as described herein) means introducing the compound or a prodrug of the compound into the system of the animal in need of treatment. When a compound of this disclosure or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkyl" is intended to include molecules having 1-12 carbons in size (C—$C_{12}$)alkyl, which can be straight chained or branched. For example, alkyl can refer to an n-hexyl, isohexyl, cyclobutylethyl, and the like. Alkyl is intended to include lower alkyl groups of from 1-6 carbons in size, such as methyl, ethyl, propyl, isopropyl, butyl, s-butyl, t-butyl, isobutyl, pentyl, hexyl and the like. An alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl; and for example, "propyl" or "$C_3$ alkyl" each include n-propyl and isopropyl.

—($C_1$-$C_6$)alkyl is a subset of alkyl groups that are from one to six carbon atoms in length, and can be straight chained or branched.

—($C_1$-$C_3$)alkyl is a subset of alkyl groups that are from one to three carbon atoms in length, and can be straight chained or branched.

"Cycloalkyl" means a non-aromatic mono- or multicyclic ring system comprising about 3 to about 14 carbon atoms, including 5 to 10 carbon atoms, or 5 to 7 carbon ring atoms. Non-limiting examples of monocyclic cycloalkyls include cyclopropyl, cyclopentyl, cyclohexyl, cycloheptyl and the like. Non-limiting examples of multicyclic cycloalkyls include 1-decalin, norbornyl, adamantyl and the like. Cycloalkyls can be fused or bridge ring systems or spirocyclic systems.

"Cycloalkylalkyl" means a "cycloalkyl" group, as defined herein, attached to an "alkyl" group, as defined herein, wherein the alkyl group is attached to the parent moiety.

"Alkyl substituted with one or more halo and hydroxy" means an alkyl group substituted with 1, 2, or 3 hydroxy or 1, 2 or 3 halo.

"Alkylene" refers to straight or branched chain divalent group consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkenylene" refers to a straight or branched chain unsaturated divalent group consisting solely of carbon and hydrogen atoms, having from two to ten carbon atoms. Alkenylene is a subset of alkyl, referring to the same residues as alkyl, but having two points of attachment and, specifically, double bond unsaturation. The unsaturation present includes at least one double bond.

"Alkynylene" refers to a straight or branched chain unsaturated divalent group consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above groups, "alkylene," "alkenylene" and "alkynylene," when optionally substituted, can contain alkyl substitution which itself contains unsaturation. For example, 2-(2-phenylethynyl-but-3-enyl)-naphthalene (IUPAC name) contains an n-butylid-3-ynyl group with a vinyl substituent at the 2-position of said group.

"Alkoxy" or "alkoxyl" both refer to the group —O-alkyl, wherein the term "alkyl" is as defined hereinabove. Examples include methoxy, ethoxy, propoxy, isopropoxy, and the like.

"Aryl" means a monovalent six- to fourteen-membered mono- or multicyclic ring, wherein the monocyclic ring is aromatic and at least one of the rings in the multicyclic ring is aromatic. A multicyclic ring that contains only one aryl ring is intended to be included within the definition of aryl. An aryl can also be six- to ten membered, or six membered. Representative non-limiting examples of aryl include phenyl, naphthyl, and the like.

"Arylalkyl" means a residue in which an aryl moiety, as defined above, is attached to a parent structure via one of an alkyl (i.e, alkylene, alkenylene, or alkynylene). Examples include benzyl, phenethyl, phenylvinyl, phenylallyl and the like. The "alkyl" portion of the group can be one to ten carbons, and in another embodiment, one to six carbons; the latter can also be referred to as $C_{1-6}$ arylalkyl. When a group is referred to as or "—($C_1$-$C_6$)alkylaryl," an aryl moiety is attached to a parent structure via an alkylene group. Examples include benzyl, phenethyl, and the like.

In some examples, as appreciated by one of ordinary skill in the art, two adjacent groups on an aromatic system can be fused together to form a ring structure. The fused ring structure can contain heteroatoms and can be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems includes non-aromatic and aromatic systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the compounds disclosed herein can themselves have spiro rings attached thereto via a single ring atom of the fused-polycyclic.

"Halogen" or "halo" both refer to fluorine, chlorine, bromine or iodine.

"Haloalkyl" (which includes alkyl optionally substituted with up to 8 halogens) and "haloaryl" refer generically to alkyl and aryl groups that are substituted with one or more halogens, respectively. Non-limiting examples of "haloalkyl" include 3,3,3-trifluoro-1-methylpropyl, 2-methyl-1-(trifluoromethyl)propyl, —$CH_2F$, —$CHCl_2$ and —$CF_3$.

"Heteroatom" refers to O, S, N, or P. In another example, the heteroatom is O or N. In another example, the heteroatom is O. In another example, the heteroatom is N.

"Heterocyclyl" refers to a stable three- to fifteen-membered ring substituent that consists of carbon atoms and from one to five heteroatoms selected from the group consisting of nitrogen, phosphorus, oxygen and sulfur. For purposes of this disclosure, the heterocyclyl substituent can be a monocyclic, bicyclic or tricyclic ring system, which can include fused or bridged ring systems as well as spirocyclic systems. The terms "heterocycloalkyl" and "heteroaryl" are groups that are encompassed by the broader term "heterocyclyl." The nitrogen, phosphorus, carbon or sulfur atoms in the heterocyclyl group can be optionally oxidized to various oxidation states. In a specific example, the group —$S(O)_{0-2}$—, refers to —S- (sulfide), —S(O)— (sulfoxide), and —$SO_2$— (sulfone) respectively. For convenience, nitrogens, particularly but not exclusively, those defined as annular aromatic nitrogens, are meant to include their corresponding N-oxide form, although not explicitly defined as such in a particular example. Thus, for a compound of this disclosure having, for example, a pyridyl ring; the corresponding pyridyl-N-oxide is meant to be included as another compound of the disclosure. In addition, annular nitrogen atoms can be optionally quaternized; and the ring substituent can be partially or fully saturated or aromatic. Examples of heterocyclyl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, tetrahydrofuranyl, tetrahydroisoquinolinyl, and tetrahydroquinolinyl.

"Heterocycloalkyl" refers to a stable 4-12 membered monocyclic or multicyclic ring, wherein at least one of the rings contain at least one heteroatom and wherein there are no aromatic rings. Heterocycloalkyl is meant to include multicyclic rings wherein one ring contains a heteroatom and another ring does not contain a heteroatom.

"Heterocycloalkylalkyl" refers to a heterocycloalkyl, as defined herein, attached to the parent moiety through an "alkyl," as defined herein. One non-limiting example of heterocycloalkyl includes piperadinyl. Another non-limiting example of heterocycloalkyl includes piperazinyl. Another non-limiting example of heterocycloalkyl includes furanyl. Another non-limiting example of heterocycloalkyl includes pyrrolidinyl. Another non-limiting example of heterocycloalkyl includes morpholinyl.

"Amino" refers to —$NH_2$.

"Alkylamino" refers to —NH(alkyl), wherein "alkyl" is as defined above, and wherein the parent moiety is attached to the nitrogen atom. In one example, alkylamino is (1R)-1,2-dimethylpropylamino. In another example, alkylamino is (1S)-1,2-dimethylpropylamino. In another example, alkylamino is propylamino. In another example, alkylamino is (1R)-1-methylpropyl]amino. In another example, alkylamino is (1S)-1-methylpropyl]amino. In another example, alkylamino is (1R)-1,2,2-trimethylpropylamino. In another example, alkylamino is (1S)-1,2,2-trimethylpropylamino. In another example, alkylamino is 2-methyl-1-(1-methylethyl)propylamino.

"Gem-dicycloalkylalkl" refers to a group wherein two cycloalkyl groups are attached to the same carbon atom on an alkyl group, and the alkyl group is attached to the parent moiety. One non-limiting example gem-dicycloalkyl is dicyclopropylmethyl having the following structure:

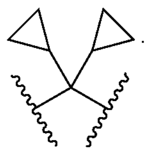

"Dialkylamino" refers to —$N(alkyl)_2$, wherein "alkyl" is as defined above, and wherein the parent moiety is attached to the nitrogen atom.

"Dialkylaminoalkyl" refers to -(alkyl)$N(alkyl)_2$, wherein "alkyl" is as defined above. One such non-limiting example of "dialkylaminoalkyl" includes —$CH_2C(CH_3)_2CH_2N(CH_3)_2$.

"Aminoalkyl" refers to -(alkyl)$NH_2$, wherein "alkyl" is as defined above, and wherein the parent moiety is attached to the alkyl group. The amino group can be attached at any point along the alkyl group. Non-limiting examples of aminoalkyl include —$CH(NH_2)CH_3$.

"Heteroaryl" means a 5- to 12-membered, monocyclic aromatic heterocyclyl (where heterocyclyl is defined herein) or bicyclic heterocyclyl ring system (where at least one of the rings in the bicyclic system is aromatic) where the monocyclic ring and at least one of the rings in the bicyclic ring system contains one, two, three, four, or five heteroatom(s) selected from nitrogen, oxygen, phosphorous, and sulfur. The ring containing the heteroatom can be aromatic or non-aromatic. Representative examples include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzdioxolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Fused, bridged, and spiro moieties are also included within the scope of this definition.

"Carbonyl" refers to the group "—C(O)—", which is bivalent.

"Aminocarbonyl" refers to the group "—C(O)—$NH_2$," wherein the parent moiety is attached to the carbonyl group.

"Alkoxycarbonyl" refers to the group "—C(O)alkoxy," wherein alkoxy is as defined above, and the parent moiety is attached to the carbonyl. A non-limiting example includes —C(O)—$OC(CH_3)_3$.

"Hydroxyalkynyl" refers to a group wherein the parent moiety is attached to the alkynyl group, and a hydroxyl group is attached to the alkynyl. A non-limiting example includes 4-hydroxybut-1-yn-1-yl.

"Hydroxyalkyl" refers to a group wherein the parent moiety is attached to the alkyl group, and a hydroxyl group is attached to the alkyl, and wherein the alkyl portion is as defined herein.

"Amino(imino)alkyl" refers to a group represented by -alkyl-C(═NH)—$NH_2$, wherein alkyl is as defined above. A non-limiting example includes amino(imino)methyl.

"Dihydroxyalkyl" refers to a group wherein the parent moiety is attached to the alkyl group, and a two hydroxyl groups are attached to the alkyl, and wherein the alkyl portion is as defined herein.

"Alkylaminoalkyl" refers to -(alkyl)NH(alkyl), wherein the "alkyl" portions are as defined above.

"Alkylaminoalkylamino" refers to —N(H)(alkyl)NH (alkyl), wherein "alkyl" is as defined above.

"Aminoalkylamino" refers to —N(H)(alkyl)$NH_2$, wherein "alkyl" is as defined above.

"Arylalkylamino" refers to —N(H)(alkyl)aryl, wherein "alkyl" and aryl are as defined above.

"Alkylsulfonylheterocycloalkylamino" refers to —N(H)— alkylheterocycloalkyl-$S(O)_2$-alkyl, wherein the amino is attached to the parent moiety.

"Cycloalkylalkylamino" refers to —N(H)-alkylcycloalkyl, wherein the amino is attached to the parent moiety.

"Cycloalkoxy" refers to —O-cycloalkyl, wherein cycloalkyl is as defined above and the oxygen is attached to the parent moiety.

"Dialkylaminoalkoxy" refers to -(alkoxy)$N(alkyl)_2$, wherein "alkoxy" and "alkyl" are both defined above. One such non-limiting example of "dialkylaminoalkoxy" includes dimethylaminoethyloxy represented by —O—$(CH_2)_2N(CH_3)_2$.

"Alkylsulfonylalkylamino" refers to —$NH_2$—$S(O)_2$-alkyl, wherein the amino portion of this group is attached to the parent moiety, and wherein "alkyl" is as defined above. A non-limiting example includes methylsulfonylethylamino.

When a portion of term (such as the "alkyl" portion of "arylalkyl") is referred to as being defined above or defined herein, this means that this portion has the same meaning as the definition of this term within this specification.

The phrases "the compounds in this disclosure," the compounds in the disclosure, the compounds disclosed herein, compounds of this disclosure, and similar phrases that contain both of the words "compounds" and "disclosure" are meant to mean compounds of Formula I, II or III, and all of the embodiments for each of these three compounds.

In the case where there is a point of attachment for a monovalent substituent, such as —$CH_3$, —$NH_2$, or —OH, the indication of where the point of attachment is not necessary. That is, —$CH_3$ has the same meaning as $CH_3$, —$NH_2$ has the same meaning as $NH_2$, and —OH has the same meaning as OH.

In Tables 1 and II, where there appears to be an empty valence for oxygen or nitrogen for any of the compounds listed in this table, where the name of the structure requires that the empty valence is filled with hydrogen, it is assumed that the missing valence is filled with hydrogen for each of these cases.

When a group is referred to as "—($C_1$-$C_6$)alkyl heterocyclyl" the heterocyclyl is attached to a parent structure via an alkyl group.

"Hydroxyalkyl" means -alkyl-OH, wherein alkyl is as defined hereinabove.

"Optional" or "optionally" means that the subsequently described event or circumstance can or can not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted arylalkyl," both the "alkyl" portion and the "aryl" portion of the molecule can or can not be substituted.

Unless otherwise specified, the term "optionally substituted" applies to the chemical moiety immediately preceding it. For instance, if a variable group (such as R) is defined as aryl, optionally substituted alkyl, or cycloalkyl, then only the alkyl group is optionally substituted.

"Saturated bridged ring system" refers to a bicyclic or polycyclic ring system that is not aromatic. Such a system can contain isolated or conjugated unsaturation, but not aromatic or heteroaromatic rings in its core structure (but can have aromatic substitution thereon). For example, hexahydro-furo [3,2-b]furan, 2,3,3a,4,7,7a-hexahydro-1H-indene, 7-aza-bicyclo[2.2.1]-heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

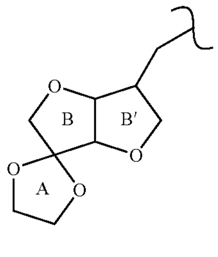

Some of the compounds of the disclosure can have imino, amino, oxo or hydroxy substituents off aromatic heterocyclyl systems. For purposes of this disclosure, it is understood that such imino, amino, oxo or hydroxy substituents can exist in their corresponding tautomeric form, i.e., amino, imino, hydroxy or oxo, respectively.

"Animal" for the purposes of this disclosure includes humans (including patients receiving treatment) and other animals, particularly mammals, and other organisms. Thus, the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of this disclosure, while modulating kinase activity as described herein, can also modulate, either directly or indirectly, phosphatase activity. This additional modulation, if present, can be synergistic (or not) to activity of compounds of this disclosure toward a related or otherwise interdependent kinase or kinase family. In any case, as stated previously, the compounds of this disclosure are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of this disclosure, that when administered to a patient, ameliorates a symptom of the disease. The amount of a compound of this disclosure which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" as referred to in the specification and in the claims refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostrate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defomians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences,* $17^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this disclosure include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this disclosure include, but are not limited to, primary amides, and secondary and tertiary alkyl amides (for example with between about one and about six carbons). Amides and esters of the compounds of this disclosure can be prepared according to conventional methods. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of this disclosure or its salt can be the biologically active form of the compound in the body. In one example, a prodrug can be used such that the biologically active form, a metabolite, is released in vivo. In another example, a biologically active metabolite is discovered serendipitously, that is, no prodrug design per se was undertaken. An assay for activity of a metabolite of a compound of this disclosure is known to one of skill in the art in light of the present disclosure.

The compounds of this disclosure also include N-oxide derivatives and protected derivatives of compounds of Formula I, II or III. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that can be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition can be necessary, and will be ascertainable with routine experimentation by one of ordinary skill in the art.

One of ordinary skill in the art would understand that certain crystallized, protein-ligand complexes, in particular HSP90-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of this disclosure as their ligand component, are an aspect of this disclosure.

As well, one of ordinary skill in the art would appreciate that such suitable x-ray quality crystals can be used as part of a method of identifying a candidate agent capable of binding to and modulating the activity of kinases. Such methods can be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for kinase modulation, and determining whether said candidate agent modulates kinase activity in the assay. Such methods can also include administering the candidate agent, determined to modulate kinase activity, to a mammal suffering from a condition treatable by kinase modulation, such as those described above.

Also, one skilled in the art would appreciate that compounds disclosed herein can be used in a method of evaluating the ability of a test agent to associate with a molecule or molecular complex comprising a ligand binding domain of a kinase. Such a method can be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

In certain other preferred embodiments, administration can preferably be by the oral route. Administration of the compounds of this disclosure, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of this disclosure as the/an active agent, and, in addition, can include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It can also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the compounds in this disclosure can also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid dosage forms, as described above, can be prepared with coatings and shells, such as enteric coatings and others well known in the art. They can contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of this disclosure, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, can contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of this disclosure with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this disclosure include ointments, powders, sprays, and inhalants. The active component is admixed under sterile conditions with a physiologically acceptable carrier and any preservatives, buffers, or propellants as can be required. Ophthalmic formulations, eye ointments, powders, and solutions are also contemplated for the compounds in this disclosure.

Compressed gases can be used to disperse a compound of this disclosure in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of this disclosure, or a pharmaceutically acceptable salt thereof, and 99% to 1% by weight of a suitable pharmaceutical excipient. In one example, the composition will be between about 5% and about 75% by weight of a compound(s) of this disclosure, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of this disclosure, or a pharmaceutically acceptable salt thereof, for treatment of a disease-state in accordance with the teachings of this disclosure.

The compounds of this disclosure, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of this disclosure can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

The compositions will include a conventional pharmaceutical carrier or excipient and a compound of this disclosure as the/an active agent, and, in addition, can include other medicinal agents and pharmaceutical agents. Compositions of the compounds in this disclosure can be used in combination with anticancer and/or other agents that are generally administered to a patient being treated for cancer, e.g. surgery, radiation and/or chemotherapeutic agent(s). Chemotherapeutic agents that can be useful for administration in combination with compounds of Formula I in treating cancer include alkylating agents, platinum containing agents.

If formulated as a fixed dose, such combination products employ the compounds of this disclosure within the dosage range described above and the other pharmaceutically active agent(s) within its approved dosage range. Compounds of this disclosure can alternatively be used sequentially with known pharmaceutically acceptable agent(s) when a combination formulation is inappropriate.

Representative pharmaceutical formulations containing the compounds disclosed herein are described below.

Synthetic Procedures

The compounds disclosed herein, or their pharmaceutically acceptable salts, can have asymmetric carbon atoms, oxidized sulfur atoms or quaternized nitrogen atoms in their structure.

The compounds disclosed herein and their pharmaceutically acceptable salts can exist as single stereoisomers, racemates, and as mixtures of enantiomers and diastereomers. The compounds disclosed herein can also exist as geometric isomers. All such single stereoisomers, racemates and mixtures thereof, and geometric isomers are intended to be within the scope of the compounds disclosed herein.

It is assumed that when considering generic descriptions of compounds of the disclosed herein for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

Methods for the preparation and/or separation and isolation of single stereoisomers from racemic mixtures or non-racemic mixtures of stereoisomers are well known in the art. For example, optically active (R)- and (S)-isomers can be prepared using chiral synthons or chiral reagents, or resolved using conventional techniques. Enantiomers (R- and S-isomers) can be resolved by methods known to one of ordinary skill in the art, for example by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step can be required to liberate the desired enantiomeric form. Alternatively, specific enantiomer can be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer can be further enriched (with concomitant loss in yield) by recrystallization.

In addition, the compounds of this disclosure can exist in unsolvated as well as solvated forms with pharmaceutically acceptable solvents such as water, ethanol, and the like. In general, the solvated forms are considered equivalent to the unsolvated forms for the purposes of the compounds of this disclosure.

In addition, it is intended that the present disclosure cover compounds made either using standard organic synthetic techniques, including combinatorial chemistry or by biological methods, such as bacterial digestion, metabolism, enzymatic conversion, and the like.

The examples and scheme below depict the general synthetic procedure for the compounds disclosed herein. Synthesis of the compounds disclosed herein is not limited by these examples and schemes. One skilled in the art will know that other procedures can be used to synthesize the compounds disclosed herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure.

such as HCl, to remove BOC and arrive at compound (D). To compound (D), $R_1COOH$ is added under appropriate reaction conditions and with a suitable coupling reagent, such as HATU, to condense and form the amide bond in compound (E). The carboxylate of compound (E) is then hydrolyzed under basic conditions to yield the carboxylic acid of compound (F). $R_3NH_2$ is then added to compound F under appropriate reaction conditions and with a suitable coupling reagent, such as HATU, to condense and form the amide bond in compound (G).

Example 1

6-[3-endo-({[2-methyl-3-(methyloxy)phenyl]carbonyl}amino)-8-azabicyclo[3.2.1]oct-8-yl]-N-({4-[4-(2-methylpropyl)piperazin-1-yl]phenyl}methyl)pyridine-3-carboxamide STEP 1: 1,1-Dimethylethyl 8-azabicyclo[3.2.1]oct-3-endo-ylcarbamate hydrochloride (synthesized according to the method of reagent preparation 1) (10.44 g, 40 mmol), ethyl 6-chloronicotinate (7.4 g, 40 mmol) and triethylamine (22.4 mL, 160 mmol) were added to 1,2-dimethoxyethane (40 mL) and the resulting suspension was heated at 125° C. for 24 hours in a sealed tube vessel. On cooling to room temperature, the mixture was diluted with ethyl acetate (200 mL) then washed with water (200 mL). The organic layer was washed twice with 10% aqueous citric acid (2×100 mL), brine then

SYNTHETIC SCHEME1:

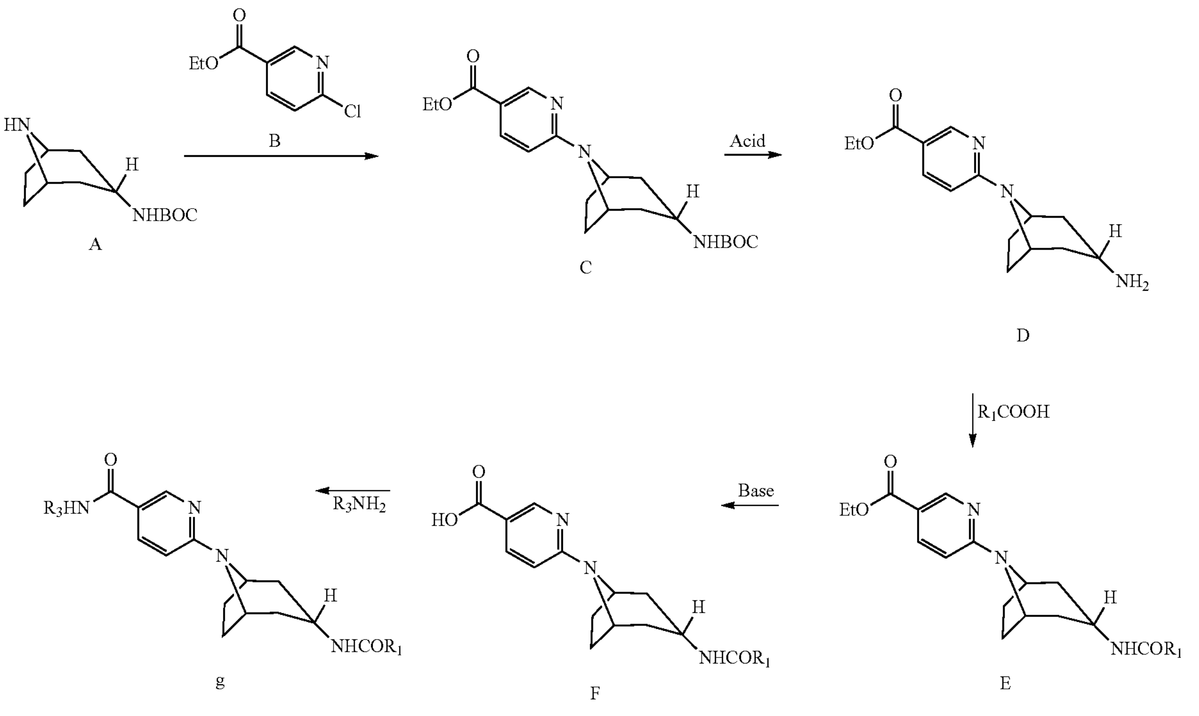

A
C
D
E
F
g

Scheme 1 describes the synthesis of all of the compound(s) listed in Example 1 wherein $R_1$ and $R_3$ are as defined in the specification.

In Scheme 1, compound (B) is added to compound (A) under appropriate reaction conditions to undergo an aromatic nucleophilic substitution reaction to arrive at compound (C). Compound (C) is then deprotected under acidic conditions, dried over anhydrous sodium sulfate. Filtration and concentration afforded a solid residue that was then suspended in ethyl ether. The solid was collected by filtration then washed with additional ethyl ether to give ethyl 6-[3-endo-({[(1,1-dimethylethyl)oxy]carbonyl}amino)-8-azabicyclo[3.2.1]oct-8-yl]pyridine-3-carboxylate (6.78 g, 45% yield). $^1H$ NMR (400 MHz, $d_6$-DMSO): 8.63 (s, 1H), 7.90 (d, 1H), 6.90

(br s, 1H), 6.73 (d, 1H), 4.53 (br s, 2H), 4.24 (q, 2H), 3.43 (br s, 1H), 2.14-2.10 (m, 2H), 2.00-1.90 (m, 4H), 1.75 (br d, 2H), 1.39 (s, 9H), 1.28 (tr, 3H).

STEP 2: To a solution of ethyl 6-[3-endo-({[(1,1-dimethylethyl)oxy]carbonyl}amino)-8-azabicyclo[3.2.1]oct-8-yl] pyridine-3-carboxylate (2.83 g, 7.54 mmol) in ethanol (20 mL) was added a solution of 4N hydrochloric acid in dioxane (20 mL), and the reaction mixture was refluxed for 2 min. After cooling to room temperature the mixture was diluted with ethyl acetate (100 mL), and saturated aqueous sodium carbonate was added until the aqueous layer reached pH 10. The layers were separated, the aqueous layer was further extracted with ethyl acetate (2×50 mL), the combined organic layers were washed with brine (20 mL), dried over sodium sulfate, and concentrated to give ethyl 6-(3-endo-amino-8-azabicyclo[3.2.1]oct-8-yl)pyridine-3-carboxylate (1.88 g, 90% yield). $^1$H NMR (400 MHz, methanol-$d_4$): 8.65 (d, 1H), 7.98 (dd, 1H), 6.69 (d, 1H), 5.59 (br s, 2H), 4.30 (q, 2H), 3.00 (m, 1H), 2.30-2.05 (m, 6H), 1.58 (d, 2H), 1.35 (t, 3H); MS (EI) for $C_{15}H_{21}N_3O_2$: 276 ($MH^+$).

STEP 3: A solution of ethyl 6-(3-endo-amino-8-azabicyclo [3.2.1]oct-8-yl)pyridine-3-carboxylate (2.63 g, 9.55 mmol), 3-methoxy-2-methylbenzoic acid (1.59 g, 9.55 mmol), HATU (3.63 g, 9.55 mmol), and diisopropylethylamine (3.70 g, 28.65 mmol) in dimethylformamide (20 mL) was stirred at room temperature for 4 days. The reaction mixture was diluted with ethyl acetate (150 mL), washed with saturated sodium bicarbonate (50 mL), 5% aqueous lithium chloride (2×50 mL), and brine (50 mL), dried over sodium sulfate, and dried to provide crude ethyl 6-[3-endo-({[2-methyl-3-methyloxy)phenyl]carbonyl}amino)-8-azabicyclo[3.2.1]oct-8-yl] pyridine-3-carboxylate (4.73 g). MS (EI) for $C_{24}H_{29}N_3O_4$: 424 ($MH^+$).

STEP 4: A suspension of crude ethyl 6-[3-endo-({[2-methyl-3-methyloxy)phenyl]carbonyl}amino)-8-azabicyclo [3.2.1]oct-8-yl]pyridine-3-carboxylate (4.72 g, max. 9.55 mmol) and potassium hydroxide (1.07 g, 19.10 mmol) in methanol (90 mL) and water (30 mL) was stirred at 60° C. for 2 hours. After cooling to room temperature, some of the methanol was evaporated, water was added to the resulting mixture, and the pH adjusted to 5 with 1N aqueous hydrochloric acid. The precipitate was filtered, washed with water, and dried to afford 6-[3-endo-({[2-methyl-3-methyloxy)phenyl]carbonyl}amino)-8-azabicyclo[3.2.1]oct-8-yl]pyridine-3-carboxylic acid (3.14 g, 83% yield over two steps). $^1$H NMR (400 MHz, DMSO-$d_6$): 12.45 (s, 1H), 6.83 (br s, 1H), 8.64 (d, 1H), 8.24 (d, 1H), 7.91 (dd, 1H), 7.23 (t, 1H), 7.02 (d, 1H), 6.86 (d, 1H), 6.75 (d, 1H), 4.60 (br s, 2H), 3.86 (m, 1H), 3.80 (s, 3H), 2.21 (m, 2H), 2.14 (s, 3H), 2.07 (m, 2H), 1.97 (m, 2H), 1.87 (d, 2H); MS (EI) for $C_{22}H_{25}N_3O_4$: 396 ($MH^+$).

STEP 5: A solution of tert-butyl 4-[4-(aminomethyl)phenyl]piperazine-1-carboxylate (223 mg, 0.77 mmol), 6-[3-endo-({[2-methyl-3-methyloxy)phenyl]-carbonyl}amino)-8-azabicyclo[3.2.1]oct-8-yl]pyridine-3-carboxylic acid (324 mg, 0.77 mmol), HATU (291 mg, 0.77 mmol), and diisopropylethylamine (302 mg, 2.34 mmol) in dimethylformamide (5 mL) was stirred at room temperature for 24 hours. The reaction mixture was diluted with ethyl acetate (50 mL), washed with saturated sodium bicarbonate (25 mL), 5% aqueous lithium chloride (2×25 mL), and brine (25 mL), dried over sodium sulfate, and dried to provide 1,1-dimethylethyl 4-(4-{[({6-[3-endo-({[2-methyl-3-(methyloxy)phenyl] carbonyl}amino)-8-azabicyclo[3.2.1]oct-8-yl]pyridine-3-yl}carbonyl)amino]methyl}phenyl)piperazine-1-carboxylate (498 mg, 97% yield). $^1$H NMR (400 MHz, $CDCl_3$): 8.58 (d, 1H), 7.90 (dd, 1H), 7.28 (m, 1H), 7.21 (t, 1H), 6.92 (m, 4H), 6.53 (d, 1H), 6.19 (d, 1H), 6.13 (t, 1H), 4.61 (br s, 2H), 4.55 (d, 2H), 4.25 (m, 1H), 3.85 (s, 3H), 3.57 (m, 4H), 3.12 (m, 4H), 2.34 (m, 2H), 2.29 (s, 3H), 2.21 (m, 2H), 2.00 (m, 2H), 1.82 (d, 2H), 1.48 (s, 9H); MS (EI) for $C_{38}H_{48}N_6O_5$: 669 ($MH^+$).

STEP 6: To a solution of 1,1-dimethylethyl 4-(4-{[({6-[3-endo-({[2-methyl-3-(methyloxy)phenyl]carbonyl}amino)-8-azabicyclo[3.2.1]oct-8-yl]pyridine-3-yl}carbonyl)amino] methyl}phenyl)piperazine-1-carboxylate (495 mg, 0.74 mmol) in methanol (5 mL) was added a solution of 4N hydrochloric acid in dioxane (5 mL), and the reaction mixture was refluxed for 2 min. Concentration and purification by preparatory HPLC (0.1% aqueous ammonium acetate-acetonitrile) provided 6-[3-endo-({[2-methyl-3-(methyloxy)phenyl] carbonyl}amino)-8-azabicyclo[3.2.1]oct-8-yl]-N-[(4-piperazin-1-ylphenyl)methyl]pyridine-3-carboxamide acetate salt (45 mg, 9% yield). $^1$H NMR (400 MHz, methanol-$d_4$): 8.60 (d, 1H), 7.97 (dd, 1H), 7.27 (d, 2H), 7.23 (t, 1H), 6.99 (m, 3H), 6.90 (d, 1H), 6.75 (d, 1H), 4.60 (br s, 2H), 4.47 (s, 3H), 3.99 (m, 1H), 3.84 (s, 3H), 3.25 (m, 4H), 2.29 (m, 2H), 2.21 (s, 3H), 2.19 (m, 2H), 1.92 (s, 6H), 1.90 (m, 2H); MS (EI) for $C_{33}H_{40}N_6O_3$: 569 ($MH^+$).

STEP 7: A mixture of 6-[3-endo-({[2-methyl-3-(methyloxy)phenyl]-carbonyl}amino)-8-azabicyclo[3.2.1]oct-8-yl]-N-[(4-piperazin-1-ylphenyl)methyl]-pyridine-3-carboxamide (276 mg, 0.30 mmol), 1-iodo-2-methylpropane (62 mg, 0.34 mmol), and cesium carbonate (500 mg, 1.50 mmol) in dimethylformamide (4 mL) was stirred at room temperature for 18 hours. Purification by preparatory HPLC (0.1% aqueous ammonium acetate-acetonitrile) provided 6-[3-endo-({[2-methyl-3-(methyloxy)phenyl]carbonyl}amino)-8-azabicyclo[3.2.1]oct-8-yl]-N-({4-[4-(2-methylpropyl)piperazin-1-yl]phenyl}methyl)pyridine-3-carboxamide acetate salt (17 mg, 8% yield). $^1$H NMR (400 MHz, methanol-$d_4$): 8.60 (d, 1H), 7.97 (dd, 1H), 7.23 (m, 3H), 7.00 (d, 1H), 6.95 (m, 1H), 6.90 (d, 1H), 6.75 (d, 1H), 4.59 (br s, 2H), 4.46 (s, 2H), 3.99 (m, 1H), 3.84 (s, 3H), 3.17 (m, 4H), 2.62 (m, 4H), 2.29 (m, 2H), 2.23 (m, 5H), 2.12 (m, 2H), 1.90 (m, 4H), 0.94 (d, 6H); MS (EI) for $C_{37}H_{48}N_6O_3$: 625 ($MH^+$).

Using analogous synthetic techniques and substituting with alternative starting reagents, the following compounds [1(A)-1(FC)] were prepared. Alternative starting materials were obtained commercially unless otherwise indicated.

1(B): N-cyclopropyl-6-[3-endo-({[2-methyl-3-(methyloxy)phenyl]carbonyl}amino)-8-azabicyclo[3.2.1]oct-8-yl] pyridine-3-carboxamide. Prepared according to the method of example 1 by using cyclopropylamine in step 5, then omission of steps 6 and 7. MS (EI) for $C_{25}H_{30}N_4O_3$: 435 ($MH^+$).

1(C): 6-[3-endo-({[2-methyl-3-(methyloxy)phenyl] carbonyl}amino)-8-azabicyclo[3.2.1]oct-8-yl]-N-[2-(methyloxy)ethyl]pyridine-3-carboxamide. Prepared according to the method of example 1 by using 2-methoxyethylamine in step 5, then omission of steps 6 and 7. MS (EI) for $C_{25}H_{32}N_4O_4$: 453 ($MH^+$).

1(D): N-[2-(dimethylamino)ethyl]-6-[3-endo-({[2-methyl-3-(methyloxy)phenyl]carbonyl}amino)-8-azabicyclo [3.2.1]oct-8-yl]pyridine-3-carboxamide. Prepared according to the method of example 1 by using 2-(dimethylamino) ethylamine in step 5, then omission of steps 6 and 7. MS (EI) for $C_{26}H_{35}N_5O_3$: 466 ($MH^+$).

1(E): 6-[3-endo-({[2-methyl-3-(methyloxy)phenyl] carbonyl}amino)-8-azabicyclo[3.2.1]oct-8-yl]-N-(2-morpholin-4-ylethyl)pyridine-3-carboxamide. Prepared according to the method of example 1 by using 2-(morpholin-4-yl) ethylamine in step 5, then omission of steps 6 and 7. MS (EI) for $C_{28}H_{37}N_5O_4$: 507.99 ($MH^+$).

1(F): 6-[3-endo-({[2-methyl-3-(methyloxy)phenyl]carbonyl}amino)-8-azabicyclo[3.2.1]oct-8-yl]-N-(pyridin-3-ylmethyl)pyridine-3-carboxamide. Prepared according to the method of example 1 by using 3-aminomethylpyridine in step 5, then omission of steps 6 and 7. MS (EI) for $C_{28}H_{31}N_5O_3$: 485.97 ($MH^+$).

1(G): N-cyclopentyl-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using cyclopentylamine in step 5, then omission of steps 6 and 7. MS (EI) for $C_{27}H_{34}N_4O_3$: 463.02 ($MH^+$).

1(H): N-[(2-chlorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2-chlorobenzylamine in step 5, then omission of steps 6 and 7. MS (EI) for $C_{29}H_{31}ClN_4O_3$: 519.99 ($MH^+$).

1(I): N-[(4-chlorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 4-chlorobenzylamine in step 5, then omission of steps 6 and 7. MS (EI) for $C_{29}H_{31}ClN_4O_3$: 519.93 ($MH^+$).

1(J): N-{2-[3,4-bis(methyloxy)phenyl]ethyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3,4-dimethoxyphenethylamine in step 5, then omission of steps 6 and 7. MS (EI) for $C_{32}H_{38}N_4O_5$: 558.94 ($MH^+$).

1(K): N-(furan-2-ylmethyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using furfurylamine in step 5, then omission of steps 6 and 7. MS (EI) for $C_{27}H_{30}N_4O_4$: 474.97 ($MH^+$).

1(L): 6-[3-endo-({[2-methyl-3-(methyloxy)phenyl]carbonyl}amino)-8-azabicyclo[3.2.1]oct-8-yl]-N-(2-methylpropyl)pyridine-3-carboxamide. Prepared according to the method of example 1 by using isobutylamine in step 5, then omission of steps 6 and 7. MS (EI) for $C_{26}H_{34}N_4O_3$: 451.01 ($MH^+$).

1(M): 6-[3-endo-({[2-methyl-3-(methyloxy)phenyl]carbonyl}amino)-8-azabicyclo[3.2.1]oct-8-yl]-N-{[4-(methyloxy)phenyl]methyl}pyridine-3-carboxamide. Prepared according to the method of example 1 by using 4-methoxybenzylamine in step 5, then omission of steps 6 and 7. MS (EI) for $C_{30}H_{34}N_4O_4$: 514.97 ($MH^+$).

1(N): 6-[3-endo-({[2-methyl-3-(methyloxy)phenyl]carbonyl}amino)-8-azabicyclo[3.2.1]oct-8-yl]-N-[3-(methyloxy)propyl]pyridine-3-carboxamide. Prepared according to the method of example 1 by using 3-methoxypropylamine in step 5, then omission of steps 6 and 7. MS (EI) for $C_{26}H_{34}N_4O_4$: 497.00 ($MH^+$).

1(O): 6-[3-endo-({[2-methyl-3-(methyloxy)phenyl]carbonyl}amino)-8-azabicyclo[3.2.1]oct-8-yl]-N-[(4-methylphenyl)methyl]pyridine-3-carboxamide. Prepared according to the method of example 1 by using 4-methylbenzylamine in step 5, then omission of steps 6 and 7. MS (EI) for $C_{30}H_{34}N_4O_3$: 498.98 ($MH^+$).

1(P): N-(1,3-benzodioxol-5-ylmethyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using piperonylamine in step 5, then omission of steps 6 and 7. MS (EI) for $C_{30}H_{32}N_4O_5$: 528.94 ($MH^+$).

1(Q): 6-[3-endo-({[2-methyl-3-(methyloxy)phenyl]carbonyl}amino)-8-azabicyclo[3.2.1]oct-8-yl]-N-prop-2-yn-1-ylpyridine-3-carboxamide. Prepared according to the method of example 1 by using propargylamine in step 5, then omission of steps 6 and 7. MS (EI) for $C_{25}H_{28}N_4O_3$: 432.98 ($MH^+$).

1(R): N-{[3,4-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3,4-dimethoxybenzylamine in step 5, then omission of steps 6 and 7. MS (EI) for $C_{31}H_{36}N_4O_5$: 544.96 ($MH^+$).

1(S): 6-[3-endo-({[2-methyl-3-(methyloxy)phenyl]carbonyl}amino)-8-azabicyclo[3.2.1]oct-8-yl]-N-[3-(4-methylpiperazin-1-yl)propyl]pyridine-3-carboxamide. Prepared according to the method of example 1 by using 3-(4-methylpiperazin-1-yl)propylamine in step 5, then omission of steps 6 and 7. MS (EI) for $C_{30}H_{42}N_6O_3$: 535.03 ($MH^+$).

1(T): N-[2-(ethylthio)ethyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2-(ethylthio)ethylamine in step 5, then omission of steps 6 and 7. MS (EI) for $C_{26}H_{34}N_4O_3S$: 482.97 ($MH^+$).

1(U): 6-[3-endo-({[2-methyl-3-(methyloxy)phenyl]carbonyl}amino)-8-azabicyclo[3.2.1]oct-8-yl]-N-{(1S,2S)-2-[(phenylmethyl)oxy]cyclopentyl}pyridine-3-carboxamide. Prepared according to the method of example 1 by using (1S,2S)-2-(benzyloxy)cyclopentylamine in step 5, then omission of steps 6 and 7. MS (EI) for $C_{34}H_{40}N_4O_4$: 568.98 ($MH^+$).

1(V): N-[(6-chloropyridin-3-yl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using (6-chloropyridin-3-yl)methylamine in step 5, then omission of steps 6 and 7. MS (EI) for $C_{28}H_{30}ClN_5O_3$: 520.92 ($MH^+$).

1(W): N-[(2-chloro-6-fluorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2-chloro-6-fluorobenzylamine in step 5, then omission of steps 6 and 7. MS (EI) for $C_{29}H_{30}ClFN_4O_3$: 537.90 ($MH^+$).

1(X): 6-[3-endo-({[2-methyl-3-(methyloxy)phenyl]carbonyl}amino)-8-azabicyclo[3.2.1]oct-8-yl]-N-[2-(methylthio)ethyl]pyridine-3-carboxamide. Prepared according to the method of example 1 by using 2-(methylthio)ethylamine in step 5, then omission of steps 6 and 7. MS (EI) for $C_{25}H_{32}N_5O_3S$: 469.45 ($MH^+$).

1(Y): N-butyl-6-[3-endo-({[2-methyl-3-(methyloxy)phenyl]-carbonyl}amino)-8-azabicyclo[3.2.1]oct-8-yl]pyridine-3-carboxamide. Prepared according to the method of example 1 by using butylamine in step 5, then omission of steps 6 and 7. MS (EI) for $C_{26}H_{34}N_4O_3$: 451.08 ($MH^+$).

1(Z): 6-[3-endo-({[2-methyl-3-(methyloxy)phenyl]carbonyl}amino)-8-azabicyclo[3.2.1]oct-8-yl]-N-(3-morpholin-4-ylpropyl)pyridine-3-carboxamide. Prepared according to the method of example 1 by using 3-(morpholin-4-yl)propylamine in step 5, then omission of steps 6 and 7. MS (EI) for $C_{29}H_{39}N_5O_4$: 522.08 ($MH^+$).

1(AA): 6-[3-endo-({[2-methyl-3-(methyloxy)phenyl]carbonyl}amino)-8-azabicyclo[3.2.1]oct-8-yl]-N-(2-pyridin-4-ylethyl)pyridine-3-carboxamide. Prepared according to the method of example 1 by using 2-(pyridin-4-yl)ethylamine in step 5, then omission of steps 6 and 7. MS (EI) for $C_{29}H_{33}N_5O_3$: 500.45 ($MH^+$).

1(AB): N-{2-[(1-methylethyl)oxy]ethyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2-[(1-methylethyl)oxy]ethylamine in step 5, then omission of steps 6 and 7. MS (EI) for $C_{27}H_{36}N_4O_4$: 481.07 ($MH^+$).

1(AC): 6-[3-endo-({[2-methyl-3-(methyloxy)phenyl]carbonyl}amino)-8-azabicyclo[3.2.1]oct-8-yl]-N-(2-pyridin-3-ylethyl)pyridine-3-carboxamide. Prepared according to the method of example 1 by using 2-(pyridin-3-yl)ethylamine in step 5, then omission of steps 6 and 7. MS (EI) for $C_{29}H_{33}N_5O_3$: 499.99 ($MH^+$).

1(AD): N-[4,4-bis(methyloxy)butyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 4,4-bis(methyloxy)butylamine in step 5, then omission of steps 6 and 7. MS (EI) for $C_{28}H_{38}N_4O_5$: 511.04 ($MH^+$).

1(AE): 6-[3-endo-({[2-methyl-3-(methyloxy)phenyl]carbonyl}amino)-8-azabicyclo[3.2.1]oct-8-yl]-N-[(5-methylpyrazin-2-yl)methyl]pyridine-3-carboxamide. Prepared according to the method of example 1 by using (5-methylpyrazin-2-yl)methylamine in step 5, then omission of steps 6 and 7. MS (EI) for $C_{28}H_{32}N_6O_3$: 501.57 ($MH^+$).

1(AF): 6-[3-endo-({[2-methyl-3-(methyloxy)phenyl]carbonyl}amino)-8-azabicyclo[3.2.1]oct-8-yl]-N-[3-(propyloxy)propyl]pyridine-3-carboxamide. Prepared according to the method of example 1 by using 3-(propyloxy)propylamine in step 5, then omission of steps 6 and 7. MS (EI) for $C_{28}H_{38}N_4O_4$: 495.05 ($MH^+$).

1(AG): 6-[3-endo-({[2-methyl-3-(methyloxy)phenyl]carbonyl}amino)-8-azabicyclo[3.2.1]oct-8-yl]-N-{[3,4,5-tris(methyloxy)phenyl]methyl}pyridine-3-carboxamide. Prepared according to the method of example 1 by using 3,4,5-tris(methyloxy)benzylamine in step 5, then omission of steps 6 and 7. MS (EI) for $C_{32}H_{38}N_4O_6$: 575.32 ($MH^+$).

1(AH): N-{[3,5-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3,5-bis(methyloxy)benzylamine in step 5, then omission of steps 6 and 7. MS (EI) for $C_{31}H_{36}N_4O_5$: 544.97 ($MH^+$).

1(AI): N-[(1S)-1-(4-{[2-(diethylamino)ethyl]oxy}phenyl)ethyl]-6-[3-endo-({[2-methyl-3-(methyloxy)phenyl]carbonyl}amino)-8-azabicyclo[3.2.1]oct-8-yl]pyridine-3-carboxamide. Prepared as the acetate salt according to the method of example 1 by using 2-({4-[(1S)-1-aminoethyl]phenyl}oxy)-N,N-diethylethanamine (synthesized according to reagent preparation 4) in step 5, then omission of steps 6 and 7. $^1$H NMR (400 MHz, methanol-$d_4$): 8.59 (d, 1H), 7.97 (dd, 1H), 7.31 (m, 2H), 7.23 (t, 1H), 6.99 (d, 1H), 6.90 (m, 3H), 6.74 (d, 1H), 5.18 (q, 1H), 4.59 (br s, 2H), 4.08 (t, 2H), 3.99 (m, 1H), 3.84 (s, 3H), 2.90 (t, 2H), 2.67 (q, 4H), 2.29 (m, 2H), 2.21 (s, 3H), 2.19 (m, 2H), 2.12 (m, 2H), 1.90 (d, 2H), 1.53 (d, 3H), 1.09 (t, 6H); MS (EI) for $C_{36}H_{47}N_5O_4$: 614 ($MH^+$).

1(AJ): 6-[3-endo-({[2-methyl-3-(methyloxy)phenyl]carbonyl}amino)-8-azabicyclo[3.2.1]oct-8-yl]-N-({4-[(trifluoromethyl)oxy]phenyl}methyl)pyridine-3-carboxamide. Prepared according to the method of example 1 by using 4-trifluoromethoxybenzylamine in step 5, then omission of steps 6 and 7. MS (EI) for $C_{30}H_{31}F_3N_4O_4$: 569.59 ($MH^+$).

1(AK): N-(cyclopropylmethyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using cyclopropylmethylamine in step 5, then omission of steps 6 and 7. MS (EI) for $C_{26}H_{32}N_4O_3$: 499.39 ($MH^+$).

1(AL): N-{[2,4-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2,4-bis(methyloxy)benzylamine in step 5, then omission of steps 6 and 7. MS (EI) for $C_{31}H_{36}N_4O_5$: 545.66 ($MH^+$).

1(AM): N-[(4-bromophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 4-bromobenzylamine in step 5, then omission of steps 6 and 7. MS (EI) for $C_{29}H_{31}BrN_4O_3$: 564 ($MH^+$).

1(AN): N-[(2,2-dimethyl-1,3-dioxolan-4-yl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using (2,2-dimethyl-1,3-dioxolan-4-yl)methylamine in step 5, then omission of steps 6 and 7. MS (EI) for $C_{28}H_{36}N_4O_5$: 509 ($MH^+$).

1(AO): 6-[3-endo-({[2-methyl-3-(methyloxy)phenyl]carbonyl}amino)-8-azabicyclo[3.2.1]oct-8-yl]-N-[(3S)-1-(phenylmethyl)pyrrolidin-3-yl]pyridine-3-carboxamide. Prepared according to the method of example 1 by using (S)-1-benzylpyrrolidin-3-amine in step 5, then omission of steps 6 and 7. MS (EI) for $C_{33}H_{39}N_5O_3$: 554 ($MH^+$).

1(AP): 6-[3-endo-({[2-methyl-3-(methyloxy)phenyl]carbonyl}amino)-8-azabicyclo[3.2.1]oct-8-yl]-N-[(3R)-1-(phenylmethyl)pyrrolidin-3-yl]pyridine-3-carboxamide. Prepared according to the method of example 1 by using (R)-1-benzylpyrrolidin-3-amine in step 5, then omission of steps 6 and 7. MS (EI) for $C_{33}H_{39}N_5O_3$: 554 ($MH^+$).

1(AQ): N-[3-(diethylamino)propyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-(diethylamino)propylamine in step 5, then omission of steps 6 and 7. MS (EI) for $C_{29}H_{41}N_5O_3$: 508 ($MH^+$).

1(AR): N-{3-[(1-methylethyl)oxy]propyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-(1-methylethyloxy)propylamine in step 5, then omission of steps 6 and 7. MS (EI) for $C_{28}H_{38}N_4O_4$: 495 ($MH^+$).

1(AS): 6-[3-endo-({[2-methyl-3-(methyloxy)phenyl]carbonyl}amino)-8-azabicyclo[3.2.1]oct-8-yl]-N-propylpyridine-3-carboxamide. Prepared according to the method of example 1 by using propylamine in step 5, then omission of steps 6 and 7. MS (EI) for $C_{25}H_{32}N_4O_3$: 437 ($MH^+$).

1(AT): N-[2-(diethylamino)ethyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2-(diethylamino)ethylamine in step 5, then omission of steps 6 and 7. MS (EI) for $C_{28}H_{39}N_5O_3$: 494 ($MH^+$).

1(AU): N-(3-methylbutyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-methylbutylamine in step 5, then omission of steps 6 and 7. MS (EI) for $C_{27}H_{36}N_4O_3$: 465 ($MH^+$).

1(AV): 6-[3-endo-({[2-methyl-3-(methyloxy)phenyl]carbonyl}amino)-8-azabicyclo[3.2.1]oct-8-yl]-N-[(3-methylphenyl)methyl]pyridine-3-carboxamide. Prepared according to the method of example 1 by using 3-methylbenzylamine in step 5, then omission of steps 6 and 7. MS (EI) for $C_{30}H_{34}N_4O_3$: 499 ($MH^+$).

1(AW): N-[(3-fluorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-fluorobenzylamine in step 5, then omission of steps 6 and 7. MS (EI) for $C_{29}H_{31}FN_4O_3$: 503 ($MH^+$).

1(AX): 6-[3-endo-({[2-methyl-3-(methyl oxy)phenyl]carbonyl}amino)-8-azabicyclo[3.2.1]oct-8-yl]-N-[(2-methylphenyl)methyl]pyridine-3-carboxamide. Prepared according to the method of example 1 by using 2-methylbenzylamine in step 5, then omission of steps 6 and 7. MS (EI) for $C_{30}H_{34}N_4O_3$: 499 ($MH^+$).

1(AY): N-[(3-chlorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-chlorobenzylamine in step 5, then omission of steps 6 and 7. MS (EI) for $C_{29}H_{31}ClN_4O_3$: 520 ($MH^+$).

1(AZ): 6-[3-endo-({[2-methyl-3-(methyloxy)phenyl]carbonyl}amino)-8-azabicyclo[3.2.1]oct-8-yl]-N-(tetrahydrofuran-2-ylmethyl)pyridine-3-carboxamide. Prepared according to the method of example 1 by using tetrahydrofurfurylamine in step 5, then omission of steps 6 and 7. MS (EI) for $C_{27}H_{34}N_4O_4$: 479 ($MH^+$).

1(BA): 6-[3-endo-({[2-methyl-3-(methyloxy)phenyl]carbonyl}amino)-8-azabicyclo[3.2.1]oct-8-yl]-N-[3-(2-oxopyrrolidin-1-yl)propyl]pyridine-3-carboxamide. Prepared according to the method of example 1 by using 3-(2-oxopyrrolidin-1-yl)propylamine in step 5, then omission of steps 6 and 7. MS (EI) for $C_{29}H_{37}N_5O_4$: 520 ($MH^+$).

1(BB): 6-[3-endo-({[2-methyl-3-(methyloxy)phenyl]carbonyl}amino)-8-azabicyclo[3.2.1]oct-8-yl]-N-[2-(1-methylpyrrolidin-2-yl)ethyl]pyridine-3-carboxamide. Prepared according to the method of example 1 by using 2-(1-methylpyrrolidin-2-yl)ethylamine in step 5, then omission of steps 6 and 7. MS (EI) for $C_{29}H_{39}N_5O_3$: 506 ($MH^+$).

1(BC): 6-[3-endo-({[2-methyl-3-(methyloxy)phenyl]carbonyl}amino)-8-azabicyclo[3.2.1]oct-8-yl]-N-(2-piperidin-1-ylethyl)pyridine-3-carboxamide. Prepared according to the method of example 1 by using 2-(piperidin-1-yl)ethylamine in step 5, then omission of steps 6 and 7. MS (EI) for $C_{29}H_{39}N_5O_3$: 506 ($MH^+$).

1(BD): 6-[3-endo-({[2-methyl-3-(methyloxy)phenyl]carbonyl}amino)-8-azabicyclo[3.2.1]oct-8-yl]-N-{[2-(methyloxy)phenyl]methyl}pyridine-3-carboxamide. Prepared according to the method of example 1 by using 2-methoxybenzylamine in step 5, then omission of steps 6 and 7. MS (EI) for $C_{30}H_{34}N_4O_4$: 515 ($MH^+$).

1(BE): 6-[3-endo-({[2-methyl-3-(methyloxy)phenyl]carbonyl}amino)-8-azabicyclo[3.2.1]oct-8-yl]-N-{[3-(methyloxy)phenyl]methyl}pyridine-3-carboxamide. Prepared according to the method of example 1 by using 3-methoxybenzylamine in step 5, then omission of steps 6 and 7. MS (EI) for $C_{30}H_{34}N_4O_4$: 515 ($MH^+$).

1(BF): N-[(2-fluorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2-fluorobenzylamine in step 5, then omission of steps 6 and 7. MS (EI) for $C_{29}H_{31}FN_4O_3$: 503 ($MH^+$).

1(BG): N-[(4-fluorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 4-fluorobenzylamine in step 5, then omission of steps 6 and 7. MS (EI) for $C_{29}H_{31}FN_4O_3$: 503 ($MH^+$).

1(BH): N-[(1R,2R,4S)-bicyclo[2.2.1]hept-2-yl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2-amino-(1R,2R,4S)-bicyclo[2.2.1]heptane in step 5, then omission of steps 6 and 7. MS (EI) for $C_{29}H_{36}N_4O_3$: 489 ($MH^+$).

1(BI): N-(3,3-dimethylbutyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3,3-dimethylbutylamine in step 5, then omission of steps 6 and 7. MS (EI) for $C_{28}H_{38}N_4O_3$: 479 ($MH^+$).

1(BJ): N-{[2,3-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2,3-dimethoxybenzylamine in step 5, then omission of steps 6 and 7. MS (EI) for $C_{31}H_{36}N_4O_5$: 545 ($MH^+$).

1(BK): N-{[2-(ethyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2-ethoxybenzylamine in step 5, then omission of steps 6 and 7. MS (EI) for $C_{31}H_{36}N_4O_4$: 529 ($MH^+$).

1(BL): 6-[3-endo-({[2-methyl-3-(methyloxy)phenyl]carbonyl}amino)-8-azabicyclo[3.2.1]oct-8-yl]-N-[1-(phenylmethyl)piperidin-4-yl]pyridine-3-carboxamide. Prepared according to the method of example 1 by using 1-benzyl-4-aminopiperidine in step 5, then omission of steps 6 and 7. MS (EI) for $C_{34}H_{41}N_5O_3$: 463 ($MH^+$).

1(BM): ethyl 4-[({6-[3-endo-({[2-methyl-3-(methyloxy)phenyl]carbonyl}amino)-8-azabicyclo[3.2.1]oct-8-yl]pyridin-3-yl}carbonyl)amino]piperidine-1-carboxylate. Prepared according to the method of example 1 by using ethyl 4-aminopiperidine-1-carboxylate in step 5, then omission of steps 6 and 7. MS (EI) for $C_{30}H_{39}N_5O_5$: 550 ($MH^+$).

1(BN): 6-[3-endo-({[2-methyl-3-(methyloxy)phenyl]carbonyl}amino)-8-azabicyclo[3.2.1]oct-8-yl]-N-(2-thienylmethyl)pyridine-3-carboxamide. Prepared according to the method of example 1 by using 2-aminomethylthiophene in step 5, then omission of steps 6 and 7. MS (EI) for $C_{27}H_{30}N_4O_3S$: 491 ($MH^+$).

1(BO): N-cyclobutyl-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using cyclobutylamine in step 5, then omission of steps 6 and 7. MS (EI) for $C_{26}H_{32}N_4O_3$: 449 ($MH^+$).

1(BP): N-[3-(ethyloxy)propyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-(ethyloxy)propylamine in step 5, then omission of steps 6 and 7. MS (EI) for $C_{27}H_{36}N_4O_4$: 481 ($MH^+$).

1(BQ): N-[3-(dimethylamino)propyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-(dimethylamino)propylamine in step 5, then omission of steps 6 and 7. MS (EI) for $C_{27}H_{37}N_5O_3$: 480 ($MH^+$).

1(BR): 6-[3-endo-({[2-methyl-3-(methyloxy)phenyl]carbonyl}amino)-8-azabicyclo[3.2.1]oct-8-yl]-N-{[4-(trifluoromethyl)phenyl]methyl}pyridine-3-carboxamide. Prepared according to the method of example 1 by using 4-trifluoromethylbenzylamine in step 5, then omission of steps 6 and 7. MS (EI) for $C_{30}H_{31}F_3N_4O_3$: 553 ($MH^+$).

1(BS): N-[(2,4-difluorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2,4-difluorobenzylamine in step 5, then omission of steps 6 and 7. MS (EI) for $C_{29}H_{30}F_2N_4O_3$: 521 ($MH^+$).

1(BT): N-[(2,5-difluorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2,5-difluorobenzylamine in step 5, then omission of steps 6 and 7. MS (EI) for $C_{29}H_{30}F_2N_4O_3$: 521 ($MH^+$).

1(BU): N-[(2,6-difluorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 2,6-difluorobenzylamine in step 5, then omission of steps 6 and 7. MS (EI) for $C_{29}H_{30}F_2N_4O_3$: 521 ($MH^+$).

1(BV): N-[(3,4-difluorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3,4-difluorobenzylamine in step 5, then omission of steps 6 and 7. MS (EI) for $C_{29}H_{30}F_2N_4O_3$: 521 ($MH^+$).

1(BW): N-[3-(1H-imidazol-1-yl)propyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-(1H-imidazol-1-yl)propylamine in step 5, then omission of steps 6 and 7. MS (EI) for $C_{28}H_{34}N_6O_3$: 503 ($MH^+$).

1(BX): 6-[3-endo-({[2-methyl-3-(methyloxy)phenyl]carbonyl}amino)-8-azabicyclo[3.2.1]oct-8-yl]-N-(2-methylphenyl)pyridine-3-carboxamide. Prepared according to the method of example 1 by using 2-methylaniline in step 5, then omission of steps 6 and 7. $^1H$ NMR (400 MHz, d6-DMSO): 9.61 (s, 1H), 8.75 (s, 1H), 8.25 (s, 1H), 8.05 (dd, 1H), 7.32 (d, 1H), 7.21 (m, 3H), 7.02 (d, 1H), 6.86 (d, 1H), 6.81 (d, 1H), 4.58 (s, 2H), 3.87 (s, 1H), 3.81 (s, 3H), 3.32 (s, 1H), 2.23 (s, 3H), 2.21 (m, 1H), 2.14 (s, 3H), 2.10 (m, 1H), 1.99 (m, 2H), 1.86 (d, 2H). MS (EI) for $C_{29}H_{32}N_4O_3$: 485.6 ($MH^+$).

1(BY): N-(3,5-dimethylphenyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3,5-dimethylaniline in step 5, then omission of steps 6 and 7. $^1H$ NMR (400 MHz, d6-DMSO): 9.83 (s, 1H), 8.72 (s, 1H), 8.25 (s, 1H), 8.04 (dd, 1H), 7.38 (s, 1H), 7.24 (t, 1H), 7.02 (d, 1H), 6.87 (d, 1H), 6.80 (d, 1H), 6.72 (s, 1H), 4.59 (s, br, 1H), 3.86 (m, 1H), 3.81 (s, 3H), 2.26 (s, 6H), 2.21 (m, 2H), 2.15 (s, 3H), 2.10 (m, 2H), 1.99 (m, 2H), 1.86 (d, 2H). MS (EI) for $C_{30}H_{34}N_4O_3$: 499.4 ($MH^+$).

1(BZ): N-1,3-benzodioxol-5-yl-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using benzo[d][1,3]dioxol-5-amine in step 5, then omission of steps 6 and 7. $^1H$ NMR (400 MHz, d6-DMSO): 9.90 (s, 1H), 8.70 (s, 1H), 8.25 (s, 1H), 8.02 (dd, 1H), 7.42 (, s, 1H), 7.24 (t, 1H), 7.14 (dd, 1H), 7.02 (d, 1H), 6.88 (t, 2H), 6.80 (d, 1H), 6.00 (s, 2H), 4.59 (s, br, 2H), 3.87 (m, 1H), 3.81 (s, 3H), 2.21 (m, 2H), 2.14 (s, 3H), 2.11 (m, 2H), 1.99 (m, 2H), 1.87 (d, 2H). MS (EI) for $C_{29}H_{30}N_4O_5$: 515.5 ($MH^+$).

1(CA): 6-[3-endo-({[2-methyl-3-(methyloxy)phenyl]carbonyl}amino)-8-azabicyclo[3.2.1]oct-8-yl]-N-(4-methylphenyl)pyridine-3-carboxamide. Prepared according to the method of example 1 by using 4-methylaniline in step 5, then omission of steps 6 and 7. $^1H$ NMR (400 MHz, d6-DMSO): 9.90 (s, 1H), 8.72 (s, 1 h), 8.25 (s, 1H), 8.04 (dd, 1H), 7.63 (m, 2H), 7.23 (t, 1H), 7.13 (d, 2H), 7.02 (d, 1H), 6.86 (d, 1H), 6.80 (d, 1H), 4.58 (s, 2H), 3.87 (m, 1H), 3.81 (s, 3H), 2.27 (m, 5H), 2.12 (m, 5H), 1.99 (m, 2H), 1.87 (d, 2H). MS (EI) for $C_{29}H_{32}N_4O_3$: 485.8 ($MH^+$).

1(CB): 6-[3-endo-({[2-methyl-3-(methyloxy)phenyl]carbonyl}amino)-8-azabicyclo[3.2.1]oct-8-yl]-N-[(3-methylphenyl)methyl]pyridine-3-carboxamide. Prepared according to the method of example 1 by using 3-methylaniline in step 5, then omission of steps 6 and 7. MS (EI) for $C_{30}H_{34}N_4O_3$: 499 ($MH^+$).

1(CC): 6-[3-endo-({[2-methyl-3-(methyloxy)phenyl]carbonyl}amino)-8-azabicyclo[3.2.1]oct-8-yl]-N-[2-(methyloxy)phenyl]pyridine-3-carboxamide. Prepared according to the method of example 1 by using 2-methoxyaniline in step 5, then omission of steps 6 and 7. $^1H$ NMR (400 MHz, d6-DMSO): 9.22 (s, 1H), 8.72 (s, 1H), 8.25 (s, 1H), 8.03 (dd, 1H), 7.75 (dd, 1H), 7.23 (t, 1H), 7.15 (t, 1H), 7.08 (d, 1H), 7.02 (d, 1H), 6.95 (t, 1H), 6.87 (d, 1H), 6.80 (d, 1H), 4.57 (s, br, 2H), 3.83 (m, 4H), 3.81 (s, 3H), 2.17 (m, 2H), 2.15 (m, 3H), 2.11 (m, 1H), 1.99 (m, 2H), 1.87 (m, 3H). MS (EI) for $C_{29}H_{32}N_4O_4$: 501 ($MH^+$).

1(CD): 6-[3-endo-({[2-methyl-3-(methyloxy)phenyl]carbonyl}amino)-8-azabicyclo[3.2.1]oct-8-yl]-N-[3-(methyloxy)phenyl]pyridine-3-carboxamide. Prepared according to the method of example 1 by using 3-methoxyaniline in step 5, then omission of steps 6 and 7. $^1H$ NMR (400 MHz, d6-DMSO): 9.93 (s, 1H), 8.70 (s, 1H), 8.23 (s, 1H), 8.03 (dd, 1H), 7.44 (s, 1H), 7.31 (s, 1H), 7.21 (m, 2H), 7.00 (d, 1H), 6.85 (d, 1H), 6.79 (d, 1H), 6.64 (dd, 1H), 4.57 (s, br, 2H), 3.85 (m, 1H), 3.79 (s, 3H), 3.72 (s, 3H), 2.20 (m, 2H), 2.13 (s, 3H), 2.08 (m, 2H), 1.98 (m, 2H), 1.85 (d, 2H). MS (EI) for $C_{29}H_{32}N_4O_4$: 501 ($MH^+$).

1(CE): 6-[3-endo-({[2-methyl-3-(methyloxy)phenyl]carbonyl}amino)-8-azabicyclo[3.2.1]oct-8-yl]-N-[4-(methyloxy)phenyl]pyridine-3-carboxamide. Prepared according to the method of example 1 by using 4-methoxyaniline in step 5, then omission of steps 6 and 7. $^1H$ NMR (400 MHz, d6-DMSO): 9.87 (s, 1H), 8.71 (s, 1H), 8.05 (dd, 1H), 7.63 (m, 2H), 7.23 (t, 1H), 7.02 (d, 1H), 6.89 (m, 3H), 6.80 (d, 1H), 4.58 (s, br, 2H), 3.86 (m, 1H), 3.81 (s, 3H), 3.74 (s, 3H), 2.24 (m, 2H), 2.11 (m, 5H), 1.99 (m, 2H), 1.86 (d, 2H). MS (EI) for $C_{29}H_{32}N_4O_4$: 501 ($MH^+$).

1(CF): N-(3-chlorophenyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-chloroaniline in step 5, then omission of steps 6 and 7. $^1H$ NMR (400 MHz, d6-DMSO): 10.14 (s, 1H), 8.73 (s, 1H), 8.25 (s, 1H), 8.05 (dd, 1H), 7.95 (s, 1H), 7.67 (d, 1H), 7.37 (t, 1H), 7.24 (t, 1H), 7.13 (d, 1H), 7.02 (1H), 6.85 (m, 2H), 4.60 (s, br, 2H), 3.86 (m, 1H), 3.81 (s, 3H), 2.22 (m, 2H), 2.15 (s, 3H), 2.11 (m, 2H), 1.99 (m, 2H), 1.87 (d, 2H). MS (EI) for $C_{28}H_{29}ClN_4O_3$: 506 ($MH^+$).

1(CG): N-(4-fluorophenyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 4-fluoroaniline in step 5, then omission of steps 6 and 7. $^1H$ NMR (400 MHz, d6-DMSO): 10.04 (s, 1H), 8.72 (s, 1H), 8.25 (s, 1H), 8.05 (dd, 1H), 7.75 (m, 2H), 7.18 (m, 3H), 7.02 (d, 1H), 6.83 (m, 2H), 4.59 (s, br, 2H), 3.83 (m 1H), 3.80 (s, 3H), 2.21 (m, 2H), 2.14 (m, 5H), 1.99 (m, 2H), 1.87 (d, 2H). MS (EI) for $C_{28}H_{29}FN_4O_3$: 489 ($MH^+$).

1(CH): 6-[3-endo-({[2-methyl-3-(methyloxy)phenyl]carbonyl}amino)-8-azabicyclo[3.2.1]oct-8-yl]-N-[1-(6-piperazin-1-ylpyridin-3-yl)ethyl]pyridine-3-carboxamide. $^1$H NMR (400 MHz, d6-DMSO): 9.76 (br s, 2H), 9.46 (d, 1H), 8.60 (s, 1H), 8.42 (d, 1H), 8.36 (s, 1H), 8.18 (d, 1H), 8.08 (s, 1H), 7.44-7.38 (m, 2H), 7.24 (tr, 1H), 7.03 (d, 1H), 6.88 (d, 1H), 5.20-5.10 (br m, 1H), 4.01 (br, 4H), 3.92 (br, 2H), 3.81 (s, 2H), 3.58 (s, 3H), 3.24 (br, 4H), 2.35-2.28 (br m, 2H), 2.20-2.00 (br m, 6H), 2.15 (s, 3H), 1.52 (d, 3H). Prepared according to the method of example 1 by using tert-butyl 4-(5-(1-aminoethyl)pyridin-2-yl)piperazine-1-carboxylate in step 5 (synthesized according to reagent preparation 7), then omission of step 6.

1(CI): N-[1-(4-bromo-2-fluorophenyl)ethyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 1-(4-bromo-2-fluorophenyl)ethanamine (synthesized according to reagent preparation 8) in step 5, then omission of steps 6 and 7. $^1$HNMR (400 MHz, $CDCl_3$): 8.59 (d, 1H), 7.88 (dd, 1H), 7.24-7.19 (m, 4H), 6.92 (dd, 1H), 6.52 (d, 1H), 6.41 (d, 1H), 6.20 (d, 1H), 5.38 (m, 1H), 4.61 (br, 2H), 4.25 (q, 1H), 3.86 (s, 3H), 2.36-2.31 (m, 2H), 2.29 (s, 3H), 2.21, (m, 2H), 2.01 (m, 2H), 1.84 (d, 2H), 1.64 (br, 1H), 1.57 (d, 3H); MS (EI) for $C_{30}H_{32}BrFN_4O_3$: 696 ($MH^+$).

1(CJ): 6-[3-endo-({[2-methyl-3-(methyloxy)phenyl]carbonyl}amino)-8-azabicyclo[3.2.1]oct-8-yl]-N-{[4-(1-methylpiperidin-4-yl)phenyl]methyl}pyridine-3-carboxamide. Prepared according to the method of example 1 by using 4-(1-methylpiperidin-4-yl)benzylamine (synthesized according to reagent preparation 2) in step 5, then omission of steps 6 and 7. $^1$H NMR (400 MHz, $d_6$-DMSO): 8.81 (dd, 1H), 8.63 (d, 1H), 8.22 (d, 1H), 7.96 (dd, 1H), 7.21 (m, 3H), 7.01 (d, 2H), 6.86 (d, 1H), 6.74 (d, 1H), 4.61 (m, 4H), 4.23 (d, 1H), 3.83 (s, 3H), 3.47 (q, 2H), 3.08 (d, 2H), 2.51 (m, 1H), 2.42 (m, 8H), 2.19 (m, 4H), 1.99 (d, 2H), 1.92-1.80 (br m, 6H), 1.21 (m, 4H). MS (EI) for $C_{35}H_{43}N_5O_3$: 582 ($MH^+$).

1(CK): 6-[3-endo-({[2-methyl-3-(methyloxy)phenyl]carbonyl}amino)-8-azabicyclo[3.2.1]oct-8-yl]-N-[(3R)-pyrrolidin-3-yl]pyridine-3-carboxamide. Prepared according to the method of example 1 by using 1,1-dimethylethyl (3R)-pyrrolidin-3-ylcarbamate in step 5, then omission of step 7. $^1$H NMR (400 MHz, $d_6$-DMSO): 9.48 (s, 1H), 9.36 (s, 1H), 9.09 (s, 1H), 8.60 (s, 1H), 8.33-8.38 (m, 2H), 7.29 (d, 1H), 7.24 (t, 1H), 7.03 (d, 1H), 6.88 (d, 1H), 4.86 (br s, 2H), 4.52-4.57 (m, 2H), 3.91 (s, 1H), 3.81 (s, 3H), 3.34-3.42 (m, 2H), 3.19-3.29 (m, 2H), 2.30 (d, 2H), 2.16-2.23 (m, 2H), 2.15 (s, 3H), 1.98-2.06 (m, 4H). MS (EI) for $C_{26}H_{33}N_5O_3$: 464 ($MH^+$).

1(CL): 6-[3-endo-({[2-methyl-3-(methyloxy)phenyl]carbonyl}amino)-8-azabicyclo[3.2.1]oct-8-yl]-N-piperidin-3-ylpyridine-3-carboxamide. Prepared according to the method of example 1 by using 1,1-dimethylethyl-3-aminopiperidine-1-carboxylate in step 5, then omission of step 7. $^1$H NMR (400 MHz, $d_6$-DMSO): 9.43 (s, 1H), 9.17 (s, 1H), 8.98 (s, 1H), 8.78 (s, 1H), 8.61 (d, 1H), 8.39 (d, 1H), 8.34 (d, 1H), 7.31 (s, 1H), 7.24 (t, 2H), 7.03 (d, 1H), 6.88 (d, 1H), 4.88 (br s, 2H), 4.19-4.27 (m, 1H), 3.88-3.93 (s, 1H), 3.81 (s, 1H), 3.27 (d, 1H), 3.12 (d, 1H), 2.87-2.96 (m, 2H), 2.30 (d, 2H), 2.15 (s, 4H), 1.98-2.06 (m, 3H), 1.87-1.92 (m, 2H), 1.61-1.76 (m, 2H). MS (EI) for $C_{27}H_{35}N_5O_3$: 478 ($MH^+$).

1(CM): 6-[3-endo-({[2-methyl-3-(methyloxy)phenyl]carbonyl}amino)-8-azabicyclo[3.2.1]oct-8-yl]-N-piperidin-4-ylpyridine-3-carboxamide. Prepared according to the method of example 1 by using 1,1-dimethylethyl-4-aminopiperidine-1-carboxylate in step 5, then omission of step 7. $^1$H NMR (400 MHz, $d_6$-DMSO): 9.02 (s, 2H), 8.82 (s, 1H), 8.55 (s, 1H), 8.35 (s, 2H), 7.30 (s, 1H), 7.24 (t, 1H), 7.03 (d, 1H), 6.88 (d, 1H), 4.89 (br s, 1H), 4.04-4.09 (m, 1H), 3.91 (s, 1H), 3.81 (s, 3H), 3.65-3.74 (m, 1H), 3.47-3.52 (m, 1H), 3.31 (d, 2H), 3.00 (s, 2H), 2.30 (d, 2H), 2.15 (s, 4H), 1.94-2.10 (m, 5H), 1.80 (q, 2H). MS (EI) for $C_{27}H_{35}N_5O_3$: 478 ($MH^+$).

1(CN): 6-[3-endo-({[2-methyl-3-(methyloxy)phenyl]carbonyl}amino)-8-azabicyclo[3.2.1]oct-8-yl]-N-(pyrrolidin-3-ylmethyl)pyridine-3-carboxamide. Prepared according to the method of example 1 by using 1,1-dimethylethyl-3-(aminomethyl)pyrrolidine-1-carboxylate in step 5, then omission of step 7. $^1$H NMR (400 MHz, $d_6$-DMSO): 9.31 (t, 2H), 9.14 (t, 1H), 8.77 (br s, 1H), 8.54 (d, 1H), 8.35-8.40 (m, 2H), 7.96 (s, 1H), 7.38 (d, 1H), 7.24 (t, 1H), 7.03 (d, 1H), 6.88 (s, 1H), 3.92 (s, 1H), 3.81 (s, 2H), 3.65-3.74 (m, 2H), 3.45-3.52 (m, 2H), 3.32-3.37 (m, 2H), 3.18-3.28 (m, 2H), 3.07-3.13 (m, 1H), 2.89 (s, 4H), 2.73 (s, 3H), 2.31 (d, 2H), 2.15 (s, 4H), 1.98-2.05 (m, 4H0, 1.63-1.70 (m, 1H). MS (EI) for $C_{27}H_{35}N_5O_3$: 478 ($MH^+$).

1(CO): N-cyclohexyl-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using cyclohexylamine in step 5, then omission of steps 6 and 7. $^1$H NMR (400 MHz, $d_6$-DMSO): 8.59 (d, 1H), 8.21 (d, 1H), 7.94 (d, 1H), 7.92 (d, 1H), 7.23 (t, 1H), 7.02 (d, 1H), 6.86 (d, 1H), 6.73 (d, 1H), 4.54 (s, 2H), 3.80 (s, 4H), 3.73 (s, 1H), 3.34 (s, 3H), 2.19 (d, 2H0, 2.14 (s, 2H), 2.06-2.12 (m, 2H), 1.96-1.99 (m, 2H), 1.72-1.85 (m, 5H), 1.60 (d, 1H), 1.29 (t, 3H), 1.01-1.19 (m, 1H). MS (EI) for $C_{28}H_{36}N_4O_3$: 477 ($MH^+$).

1(CP): N-methyl-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using methylamine in step 5, then omission of steps 6 and 7. $^1$H NMR (400 MHz, $d_6$-DMSO): 8.47 (d, 1H), 8.41 (d, 1H), 8.28 (d, 1H), 8.10 (d, 1H), 7.23 (t, 1H), 7.08 (d, 1H), 7.03 (d, 1H), 6.87 (d, 1H), 4.64 (s, 2H), 3.86-3.92 (m, 1H), 3.81 (s, 3H), 2.78 (d, 2H), 2.23-2.28 (m, 2H), 2.11-2.16 (m, 5HO, 1.99-2.02 (m, 2H), 1.97 (s, 1H), 1.93 (s, 1H). MS (EI) for $C_{23}H_{28}N_4O_3$: 409 ($MH^+$).

1(CQ): N-ethyl-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using ethylamine in step 5, then omission of steps 6 and 7. $^1$H NMR (400 MHz, $d_6$-DMSO): 8.59 (d, 1H), 8.21 (t, 2H), 7.92 (dd, 1H), 7.23 (t, 1H), 7.01 (d, 1H), 6.86 (d, 1H), 6.74 (d, 1H), 4.54 (s, 2H), 3.82 (s, 1H), 3.80 (s, 3H), 3.34 (s, 3H), 3.22-3.29 (m, 2H), 2.17-2.22 (m, 1H), 2.14 (s, 3H), 2.07-2.12 (m, 2H), 1.96-1.99 (m, 2H), 1.86 (s, 1H), 1.82 (s, 1H), 1.10 (t, 3H). MS (EI) for $C_{24}H_{30}N_4O_3$: 423 ($MH^+$).

1(CR): 6-[3-endo-({[2-methyl-3-(methyloxy)phenyl]carbonyl}amino)-8-azabicyclo[3.2.1]oct-8-yl]-N-[(1R)-1-phenylethyl]pyridine-3-carboxamide. Prepared according to the method of example 1 by using (1R)-1-phenylethanamine in step 5, then omission of steps 6 and 7. $^1$H NMR (400 MHz, $d_6$-DMSO): 8.72 (d, 1H), 8.57 (d, 1H), 8.27 (d, 1H), 8.14 (d, 1H), 7.31-7.39 (m, 4H), 7.20-7.25 (m, 2H), 7.00-7.04 (m, 2H), 6.87 (d, 1H), 5.12-5.19 (m, 1H), 4.63 (s, 2H), 3.85-3.90 (m, 1H), 3.81 (s, 3H), 2.24 (d, 2H), 2.14 (s, 4H), 2.11 (s, 1H), 2.00-2.03 (m, 2H), 1.94 (s, 1H), 1.91 (s, 1H), 1.47 (d, 3H). MS (EI) for $C_{30}H_{34}N_4O_3$: 499 ($MH^+$).

1(CS): 6-[3-endo-({[2-methyl-3-(methyloxy)phenyl]carbonyl}amino)-8-azabicyclo[3.2.1]oct-8-yl]-N-[(1S)-1-phenylethyl]pyridine-3-carboxamide. Prepared according to the method of example 1 by using (1S)-1-phenylethanamine in step 5, then omission of steps 6 and 7. $^1$H NMR (400 MHz, $d_6$-DMSO): 8.74 (d, 1H), 8.55 (d, 1H), 8.28 (d, 1H), 8.16 (d, 1H), 7.31-7.38 (m, 4H), 7.21-7.25 (m, 2H), 7.02-7.05 (m, 2H), 6.87 (d, 1H), 5.12-5.19 (m, 1H), 4.63 (s, 2H), 3.84-3.91 (m, 1H), 3.81 (s, 3H), 2.25 (d, 2H), 2.14 (s, 4H), 2.11 (s, 1H), 2.00-2.03 (m, 2H), 1.96 (s, 1H), 1.92 (s, 1H), 1.47 (d, 3H). MS (EI) for $C_{30}H_{34}N_4O_3$: 499 ($MH^+$).

1(CT): 6-[3-endo-({[2-methyl-3-(methyloxy)phenyl] carbonyl}amino)-8-azabicyclo[3.2.1]oct-8-yl]-N-[(1S)-1-phenylpropyl]pyridine-3-carboxamide. Prepared according to the method of example 1 by using (1R)-1-phenylpropan-1-amine in step 5, then omission of steps 6 and 7. $^1H$ NMR (400 MHz, $d_6$-DMSO): 8.61 (d, 1H), 8.57 (s, 1H), 8.26 (d, 1H), 8.11 (d, 1H), 7.38 (d, 2H), 7.32 (t, 2H), 7.20-7.25 (m, 2H), 7.02 (d, 1H), 6.96 (s, 1H), 6.87 (d, 1H), 4.86-4.92 (m, 1H), 4.61 (s, 2H), 3.86 (s, 1H), 3.81 (s, 3H), 2.24 (d, 2H), 2.14 (s, 4H), 2.10 (s, 1H), 1.97-2.02 (m, 2H), 1.93 (s, 1H), 1.89 (s, 1H), 1.75-1.86 (m, 2H), 0.90 (t, 3H). MS (EI) for $C_{31}H_{36}N_4O_3$: 513 ($MH^+$).

1(CU): N-[(1S)-1-(4-chlorophenyl)ethyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using (1R)-1-(4-chlorophenyl)ethanamine in step 5, then omission of steps 6 and 7. $^1H$ NMR (400 MHz, $d_6$-DMSO): 8.71 (d, 1H), 8.57 (d, 1H), 8.25 (d, 1H), 8.10 (d, 1H), 7.39 (s, 4H), 7.23 (t, 1H), 7.02 (d, 1H), 6.97 (d, 1H), 6.87 (d, 1H), 5.09-5.17 (m, 1H), 4.62 (s, 2H), 3.85-3.90 (m, 1H), 3.81 (s, 3H), 2.22-2.27 (m, 2H), 2.14 (s, 2H), 2.08-2.12 (m, 2H), 2.00-2.02 (m, 2H), 1.94 (s, 1H), 1.90 (s, 1H), 1.46 (d, 3H). MS (EI) for $C_{30}H_{33}ClN_4O_3$: 533 ($MH^+$).

1(CV): N-[(1S)-2-amino-1-methyl-2-oxoethyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using L-alaninamide hydrochloride in step 5, then omission of steps 6 and 7. $^1H$ NMR (400 MHz, $d_6$-DMSO): 8.56 (d, 1H), 8.44 (d, 1H), 8.28 (d, 1H), 8.16 (d, 1H), 7.40 (s, 1H), 7.23 (t, 1H), 7.04-7.07 (m, 1H), 7.01 (d, 1H), 6.87 (d, 1H), 4.65 (s, 2H), 4.37-4.44 (m, 1H), 3.87-3.91 (m, 1H), 3.81 (s, 3H), 2.89 (s, 1H), 2.73 (s, 1H), 2.24-2.29 (m, 2H), 2.15 (s, 4H), 2.09-2.13 (m, 1H), 2.01-2.04 (m, 2H), 1.96 (s, 1H), 1.93 (s, 1H), 1.32 (d, 3H). MS (EI) for $C_{25}H_{31}N_5O_4$: 466 ($MH^+$).

1(CW): N-hydroxy-6-[3-endo-({[2-methyl-3-(methyloxy)phenyl]carbonyl}amino)-8-azabicyclo[3.2.1]oct-8-yl] pyridine-3-carboxamide. Prepared according to the method of example 1 by using hydroxylamine hydrochloride in step 5, then omission of steps 6 and 7. $^1H$ NMR (400 MHz, $d_6$-DMSO): 10.18 (s, 1H), 8.60 (d, 1H), 8.23 (d, 1H), 7.92 (dd, 1H), 7.23 (t, 1H), 7.02 (d, 1H), 6.86 (d, 1H), 6.76 (d, 1H), 4.56 (br s, 2H), 3.85 (s, 1H), 3.80 (s, 3H), 3.34 (s, 6H), 2.20 (d, 1H), 2.14 (s, 1H), 2.07-2.11 (m, 1H), 1.98 (s, 2H), 1.84-1.87 (m, 2H). MS (EI) for $C_{22}H_{26}N_4O_4$: 410 ($MH^+$).

1(CX): N-{8-[5-(hydrazinocarbonyl)pyridin-2-yl]-8-azabicyclo[3.2.1]oct-3-endo-yl}-2-methyl-3-(methyloxy) benzamide. Prepared according to the method of example 1 by using hydrazine hydrochloride in step 5, then omission of steps 6 and 7. $^1H$ NMR (400 MHz, $d_6$-DMSO): 11.11 (br s, 1H), 8.42 (d, 1H), 8.26 (d, 1H), 7.95 (d, 1H), 7.23 (t, 1H), 7.02 (d, 1H), 6.96 (d, 1H), 6.87 (d, 1H), 4.60 (s, 2H), 3.87 (s, 1H), 3.81 (s, 3H), 2.21-2.26 (m, 2H), 2.14 (s, 3H), 2.07-2.12 (m, 1H), 1.98-2.00 (m, 2H), 1.93 (s, 1H), 1.89 (s, 1H). MS (EI) for $C_{22}H_{27}N_5O_3$: 411 ($MH^+$).

1(CY): 6-[3-endo-({[2-methyl-3-(methyloxy)phenyl] carbonyl}amino)-8-azabicyclo[3.2.1]oct-8-yl]-N-(1-methylpiperidin-4-yl)pyridine-3-carboxamide. Prepared according to the method of example 1 by using 1-methylpiperidin-4-amine in step 5, then omission of steps 6 and 7. $^1H$ NMR (400 MHz, $d_6$-DMSO): 10.47 (br s, 1H), 8.71 (d, 1H), 8.54 (d, 1H), 8.32 (d, 1H), 8.25 (d, 1H), 7.20-7.26 (m, 2H), 1.03 (d, 1H), 6.88 (d, 1H), 4.81 (br s, 2H), 3.86-3.94 (m, 1H), 3.81 (s, 3H), 3.43 (d, 2H), 3.30-3.36 (m, 1H), 2.98-3.11 (m, 3H), 2.76 (t, 1H), 2.71-2.74 (m, 3H), 2.28 (d, 2H), 2.15 (s, 4H), 1.84-2.05 (m, 6H). MS (EI) for $C_{28}H_{37}N_5O_3$: 492 ($MH^+$).

1(CZ): N-(1-methylethyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using propan-2-amine in step 5, then omission of steps 6 and 7. $^1H$ NMR (400 MHz, $d_6$-DMSO): 8.59 (d, 1H), 8.22 (d, 1H), 7.95 (t, 1H), 7.93 (d, 1H), 7.23 (t, 1H), 7.02 (d, 1H), 6.86 (d, 1H), 6.73 (d, 1H), 4.54 (s, 2H), 4.05-4.10 (m, 1H), 3.84 (s, 1H), 3.80 (s, 3H), 3.34 (s, 4H), 2.17-2.22 (m, 2H), 2.14 (s, 2H), 2.06-2.12 (m, 1H), 1.96-1.99 (m, 2H), 1.85 (s, 1H), 1.82 (s, 1H), 1.14 (d, 6H). MS (EI) for $C_{25}H_{32}N_4O_3$: 437 ($MH^+$).

1(DA): 2-[(1-ethylpropyl)amino]-N4-[8-(5-{[3R]-pyrrolidin-3-ylaminocarbonyl}pyridine-2-yl)-8-azabicyclo[3.2.1] oct-3-endo-yl]benzene-1,4-dicarboxamide. Prepared according to the method of example 1 by using 4-(aminocarbonyl)-3-[(1-ethylpropyl)amino]benzoic acid (synthesized according to reagent preparation 39) in step 3 and 1,1-dimethylethyl (3R)-3-aminopyrrolidine-1-carboxylate in step 5, then omission of step 7. MS (EI) for $C_{30}H_{41}N_7O_3$: 548.4 ($MH^+$).

1(DB): 2-[(1-ethylpropyl)amino]-N4-{8-[5-({[(3R)-1-(1-methylethyl)pyrrolidin-3-yl]amino}carbonyl)pyridine-2-yl]-8-azabicyclo[3.2.1]oct-3-endo-yl}benzene-1,4-dicarboxamide. Prepared according to the method of example 1 by using 4-(aminocarbonyl)-3-[(1-ethylpropyl)amino]benzoic acid in step 3 (synthesized according to reagent preparation 39) and (3R)-1-(1-methylethyl)pyrrolidine-3-amine hydrochloride (synthesized according to reagent preparation 9) in step 5, then omission of steps 6 and 7. MS (EI) for $C_{33}H_{47}N_7O_3$: 590.4 ($MH^+$).

1(DC): 2-[(1-ethylpropyl)amino]-N4-{8-[5-({[(3S)-1-(1-methylethyl)pyrrolidin-3-yl]amino}carbonyl)pyridine-2-yl]-8-azabicyclo[3.2.1]oct-3-endo-yl}benzene-1,4-dicarboxamide. Prepared according to the method of example 1 by using 4-(aminocarbonyl)-3-[(1-ethylpropyl)amino]benzoic acid (synthesized according to reagent preparation 39) in step 3 and (3S)-1-(1-methylethyl)pyrrolidine-3-amine hydrochloride (synthesized according to reagent preparation 9) in step 5, then omission of steps 6 and 7. MS (EI) for $C_{33}H_{47}N_7O_3$: 590.4 ($MH^+$).

1(DD): 2-[(1-ethylpropyl)amino]-N4-{8-[5-({[(3R)-1-ethylpyrrolidin-3-yl]amino}carbonyl)pyridine-2-yl]-8-azabicyclo[3.2.1]oct-3-endo-yl}benzene-1,4-dicarboxamide. Prepared according to the method of example 1 by using 4-(aminocarbonyl)-3-[(1-ethylpropyl)amino]benzoic acid (synthesized according to reagent preparation 39) in step 3 and (3R)-1-ethylpyrrolidine-3-amine (synthesized according to reagent preparation 9) in step 5, then omission of steps 6 and 7. MS (EI) for $C_{33}H_{47}N_7O_3$: 590.4 ($MH^+$).

1(DE): 2-[(1-ethylpropyl)amino]-2-methyl-N4-{8-[5-({[(3R)-1-(1-methylethyl)pyrrolidin-3-yl]amino}carbonyl) pyridine-2-yl]-8-azabicyclo[3.2.1]oct-3-endo-yl}benzene-1,4-dicarboxamide. Prepared according to the method of example 1 by using 4-(aminocarbonyl)-5-[(1-ethylpropyl) amino]-2-methyl benzoic acid (synthesized according to reagent preparation 42) in step 3 and (3R)-1-(1-methylethyl) pyrrolidine-3-amine hydrochloride (synthesized according to reagent preparation 9) in step 5, then omission of steps 6 and 7. MS (EI) for $C_{34}H_{49}N_7O_3$: 604.4 ($MH^+$).

1(DF): 2-[(1-ethylpropyl)amino]-N4-{8-(5-{[(3S)-pyrrolidin-3-ylamino]carbonyl}pyridine-2-yl)-8-azabicyclo [3.2.1]oct-3-endo-yl}benzene-1,4-dicarboxamide. Prepared according to the method of example 1 by using 4-(aminocarbonyl)-5-[(1-ethylpropyl)amino]-2-methyl benzoic acid in step 3 (synthesized according to reagent preparation 42) and 1,1-dimethylethyl (3S)-3-aminopiperidine-1-carboxylate in step 5, then omission of step 7. MS (EI) for $C_{34}H_{49}N_7O_3$: 562.2 ($MH^+$).

1(DG): 5-[(1-ethylpropyl)amino]-2-methyl-N4-{8-(5-({[(3R)-1-(1-methylethyl)piperidin-3-yl]amino}carbonyl) pyridine-2-yl)-8-azabicyclo[3.2.1]oct-3-endo-yl}benzene-1, 4-dicarboxamide. Prepared according to the method of example 1 by using 4-(aminocarbonyl)-5-[(1-ethylpropyl) amino]-2-methyl benzoic acid (synthesized according to reagent preparation 42) in step 3 and (3R)-1-(1-methylethyl) piperidine-3-amine (synthesized according to reagent preparation 9) in step 5, then omission of steps 6 and 7. MS (EI) for $C_{35}H_{51}N_7O_3$: 618.3 ($MH^+$).

1(DH): N-[(4-{[2-(diethylamino)ethyl]oxy}phenyl)methyl]-6-[3-endo-({[2-methyl-3-(methyloxy)phenyl] carbonyl}amino)-8-azabicyclo[3.2.1]oct-8-yl]pyridine-3-carboxamide. Prepared according to the method of example 1 by using 2-{4-(aminomethyl)phenyl]oxy}-N,N-diethylethanamine (synthesized according to reagent preparation 4) in step 5, then omission of steps 6 and 7. $^1$H-NMR ($CD_3OD$): 8.50 (d, 1H), 8.35 (d, 1H), 7.35 (s, 1H), 7.35-7.33 (m, 1H), 7.32 (s, 1H), 7.23 (t, 1H), 7.02-6.98 (m, 3H), 6.89 (d, 1H), 4.83 (s, 2H), 4.51 (s, 2H), 4.33 (t, 3H), 4.21-418(m, 1H), 3.85 (s, 3H), 3.61 (t, 2H), 3.38-3.36 (m, 2H), 3.30-3.29 (m, 4H), 2.10 (s, 3H), 2.03 (s, 2H), 2.00 (s, 2H), 1.36 (t, 6H). MS (EI) for $C_{35}H_{45}N_5O_4$: 601 ($MH^+$).

1(DI): N-[(3-{[2-(diethylamino)ethyl]oxy}phenyl)methyl]-6-[3-endo-({[2-methyl-3-(methyloxy)phenyl] carbonyl}amino)-8-azabicyclo[3.2.1]oct-8-yl]pyridine-3-carboxamide. Prepared according to the method of example 1 by using 2-{3-(aminomethyl)phenyl]oxy}-N,N-diethylethanamine (synthesized according to reagent preparation 4) in step 5, then omission of steps 6 and 7. $^1$H-NMR ($CD_3OD$): 8.50 (s, 1H), 8.49 (s, 1H), 8.21 (dd, 1H), 7.32 (t, 1H), 7.26 (t, 1H), 7.16 (d, 1H), 7.01-6.94 (m, 3H), 6.93-6.90 (m, 2H), 4.68 (s, 2H), 4.55 (s, 2H), 4.34 (t, 2H), 4.06-4.05 (m, 1H), 3.84 (s, 3H), 3.59 (t, 2H), 3.37-3.35 (m, 2H), 3.35-2.33 (m, 4H), 2.31 (s, 3H), 2.28 (s, 2H), 2.21 (s, 2H), 1.38 (t, 6H). MS (EI) for $C_{35}H_{45}N_5O_4$: 601 ($MH^+$).

1(DJ): N-(8-{5-[({[4-(4-methylpiperazin-1-yl)phenyl] methyl}amino)-carbonyl]pyridin-2-yl}-8-azabicyclo[3.2.1] oct-3-endo-yl)benzene-1,4-dicarboxamide. Prepared according to the method of example 1 by using terephthalic acid monoamide in step 3 and 4-(4-methylpiperazin-1-yl) benzylamine in step 5, then omission of steps 6 and 7.

$^1$H-NMR ($CD_3OD$): 8.60 (s, 1H), 8.00-7.95 (m, 3H), 7.83 (d, 2H), 7.25 (d, 2H), 6.95 (d, 2H), 6.75 (s, 1H), 4.62 (s, 2H), 4.47 (s, 2H), 4.00-4.01 (m, 1H), 3.28-3.21 (m, 4H), 2.87-2.82 (m, 4), 2.51 (s, 3H), 2.31-2.16 (m, 8H). MS (EI) for $C_{33}H_{39}N_7O_3$: 583 ($MH^+$).

1(DK): 6-[3-endo-({[2-methyl-3-(methyloxy)phenyl] carbonyl}amino)-8-azabicyclo[3.2.1]oct-8-yl]-N-[4-(4-methylpiperazin-1-yl)phenyl]pyridine-3-carboxamide. Prepared according to the method of example 1 by using 4-(4-methylpiperazin-1-yl)aniline in step 5, then omission of steps 6 and 7. $^1$H-NMR (DMSO-$d_6$): 9.79 (s, 1H), 8.71 (d, 1H), 8.23 (d, 1H), 8.03 (d, 1H), 7.58 (d, 2H), 7.23 (t, 1H), 7.02 (d, 1H), 6.92-6.90 (m, 2H), 6.80 (d, 1H), 4.58 (s, 2H), 3.82 (s, 1H), 3.81 (s, 3H), 3.09-2.98 (m, 4H), 2.46-2.23 (m, 4H), 2.25 (s, 3H), 2.20 (s, 2H), 2.15 (s, 3H), 2.11-1.98 (m, 4H), 1.86 (d, 2H). MS (EI) for $C_{33}H_{40}N_6O_3$: 569 ($MH^+$).

1(DL): 6-[3-endo-({[2-methyl-3-(methyloxy)phenyl] carbonyl}amino)-8-azabicyclo[3.2.1]oct-8-yl]-N-[4-(1-methylpiperidin-4-yl)phenyl]pyridine-3-carboxamide. Prepared according to the method of example 1 by using 4-(1-methylpiperidin-4-yl)aniline in step 5, then omission of steps 6 and 7. $^1$H-NMR ($CD_3OD$): 8.59 (s, 1H), 8.45 (d, 1H), 8.35 (dd, 1H), 7.64 (d, 2H), 7.28-7.23 (m, 3H), 7.02 (d, 1H), 6.91 (d, 1H), 4.73 (s, 2H), 3.85-3.82 (m, 1H), 3.62 (s, 3H), 3.31 (s, 1H), 3.30 (s, 1H), 3.15 (t, 2H), 2.99 (s, 1H), 2.92 (s, 3H), 2.85 (s, 1H), 2.36-2.34 (m, 4H), 2.26 (s, 3H), 2.15-2.09 (m, 2H), 1.96-1.93 (m, 2H). MS (EI) for $C_{34}H_{41}N_5O_3$: 569 ($MH^+$).

1(DM): N-(4-{[2-(dimethylamino)ethyl]oxy}phenyl)-6-[3-endo-({[2-methyl-3-(methyloxy)phenyl] carbonyl}amino)-8-azabicyclo[3.2.1]oct-8-yl]pyridine-3-carboxamide. Prepared according to the method of example 1 by using 4-[2-(diethylamino)ethoxy]aniline in step 5, then omission of steps 6 and 7. $^1$H-NMR ($CD_3OD$): 8.57 (d, 1H), 8.46 (d, 1H), 8.34 (d, 1H), 7.64 (s, 1H), 7.62 (s, 1H), 7.24 (t, 2H), 7.07-7.03 (m, 3H), 6.91 (d, 2H), 4.73 (s, 2H), 4.36 (t, 2H), 4.04-4.02 (m, 1H), 3.85 (s, 3H), 3.60 (t, 2H), 2.99 (s, 6H), 2.35-2.33 (m, 4H), 2.22 (s, 3H), 2.13-2.12 (m, 4H). MS (EI) for $C_{32}H_{39}N_5O_4$: 559 ($MH^+$).

1(DN): 6-[3-endo-({[2-methyl-3-(methyloxy)phenyl] carbonyl}amino)-8-azabicyclo[3.2.1]oct-8-yl]-N-[(1S)-1-methylpropyl]pyridine-3-carboxamide. Prepared according to the method of example 1 by using (S)-(+)-2-butylamine in step 5, then omission of steps 6 and 7.

$^1$H-NMR (DMSO-$d_6$): 8.49 (s, 1H), 8.31 (d, 1H), 8.27-8.24 (m, 1H), 7.22 (t, 2H), 7.04 (d, 1H), 6.88 (d, 1H), 4.72 (s, 2H), 3.92-3.91 (m, 1H), 3.81 (s, 3H), 2.27-2.15 (m, 4H), 2.06 (s, 3H), 2.01-1.99 (m, 4H), 1.52-147(m, 2H), 1.14 (d, 2H), 0.88 (t, 2H). MS (EI) for $C_{26}H_{34}N_4O_3$: 451 ($MH^+$).

1(DO): 6-[3-endo-({[2-methyl-3-(methyloxy)phenyl] carbonyl}amino)-8-azabicyclo[3.2.1]oct-8-yl]-N-[(3R)-1-methylpyrrolidin-3-yl]pyridine-3-carboxamide. Prepared according to the method of example 1 by using (3R)-1-methylpyrrolidin-3-amine in step 5, then omission of steps 6 and 7. $^1$H-NMR ($CD_3OD$): 8.51-8.50 (m, 1H), 8.39 (d, 1H), 7.39 (d, 1H), 7.24 (t, 1H), 7.03 (d, 1H), 6.91 (d, 1H), 4.77 (s, 2H), 4.70 (s, 1H), 4.11-4.07 (m, 1H), 3.92-3.90 (m, 1H0, 3.85 (s, 3H), 3.81-3.78 (m, 1H), 3.51-3.49 (m, 2H), 3.21-3.19 (m, 1H), 3.04 (s, 2H), 2.98 (s, 3H), 2.42-2.40 (m, 1H), 2.37-2.34 (m, 4H), 2.22 (s, 3H), 2.19-2.15 (m, 4H). MS (EI) for $C_{27}H_{35}N_5O_3$: 479 ($MH^+$).

1(DP): 6-[3-endo-({[2-methyl-3-(methyloxy)phenyl] carbonyl}amino)-8-azabicyclo[3.2.1]oct-8-yl]-N-[(3S)-1-methylpyrrolidin-3-yl]pyridine-3-carboxamide. Prepared according to the method of example 1 by using (3S)-1-methylpyrrolidin-3-amine in step 5, then omission of steps 6 and 7. $^1$H-NMR ($CD_3OD$): 8.47 (s, 1H), 8.38 (d, 1H), 7.39 (d, 1H), 7.25 (t, 1H), 7.03 (d, 1H), 6.91 (d, 1H), 4.75 (s, 2H), 4.65-4.60 (m, 1H), 4.11-4.01 (m, 2H), 3.84 (s, 3H), 3.81-3.78 (m, 1H), 3.45-3.40 (m, 1H), 3.22-3.20 (m, 1H), 3.11 (s, 2H), 2.28 (s, 3H), 2.65-2.60 (m, 1H), 2.44-2.40 (m, 4H), 2.21 (s, 3H), 2.18-2.16 (m, 4H). MS (EI) for $C_{27}H_{35}N_5O_3$: 479 ($MH^+$).

1(DQ): N-[(2-chloro-3,6-difluorophenyl)methyl]-6-[3-endo-({[2-methyl-3-(methyloxy)phenyl]carbonyl}amino)-8-azabicyclo[3.2.1]oct-8-yl]pyridine-3-carboxamide. Prepared as the trifluoroacetate salt according to the method of example 1 by using 2-chloro-3,6-difluorobenzylamine in step 5, then omission of steps 6 and 7. $^1$H NMR (400 MHz, $d_6$-DMSO): 8.71 (br s, 1H), 8.51 (s, 1H), 8.25 (d, 1H), 8.04 (d, 1H), 7.50-7.42 (m, 1H), 7.35-7.29 (m, 2H), 7.03-6.85 (m, 3H), 4.62-4.56 (m, 4H), 3.89-3.83 (m, 1H), 3.80 (s, 3H), 2.26-2.20 (m, 2H), 2.15-1.86 (m, 9H). MS (EI) for $C_{29}H_{29}ClF_2N_4O_3$: 556 ($MH^+$).

1 (DR): 6-[3-endo-({[2-methyl-3-(methyloxy)phenyl] carbonyl}amino)-8-azabicyclo[3.2.1]oct-8-yl]-N-{(1S)-1-[4-(4-methylpiperazin-1-yl)phenyl]ethyl}pyridine-3-carboxamide. Prepared as the hydrochloride salt according to the method of example 1 by using (1S)-1-[4-(4-methylpiperazine-1-yl)phenyl]ethanamine dihydrochloride (synthesized according to reagent preparation 3) in step 5, then omission of steps 6 and 7. $^{1}$H NMR (400 MHz, $d_6$-DMSO): 10.99 (br s, 1H), 9.11 (d, 1H), 8.56 (s, 1H), 8.38-8.33 (m, 2H), 7.38-7.22 (m, 4H), 7.04-6.87 (m, 4H), 5.13-5.05 (m, 1H), 3.94-3.89 (m, 1H), 3.82-3.73 (m, 5H), 3.49-3.43 (m, 2H), 3.16-3.04 (m, 4H), 2.79 (d, 3H), 2.34-1.98 (m, 8H), 1.45 (d, 3H). MS (EI) for $C_{35}H_{44}N_6O_3$: 597 ($MH^+$).

1(DS): N-{[4-fluoro-3-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared as the trifluoroacetate salt according to the method of example 1 by using 4-fluoro-3-methoxybenzylamine (synthesized according to reagent preparation 6) in step 5, then omission of steps 6 and 7. $^{1}$H NMR (400 MHz, $d_6$-DMSO): 8.95 (br s, 1H), 8.55 (s, 1H), 8.27 (d, 1H), 8.13 (d, 1H), 7.25-7.11 (m, 3H), 7.08-7.01 (m, 2H), 6.89-6.83 (m, 2H), 4.63 (br s, 2H), 4.44 (d, 2H), 3.91-3.86 (m, 1H), 3.83-3.79 (m, 6H), 2.28-2.22 (m, 2H), 2.17-2.09 (m, 5H), 2.05-1.90 (m, 4H). MS (EI) for $C_{30}H_{33}FN_4O_4$: 533 ($MH^+$).

1(DT): N-{[3-fluoro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared as the trifluoroacetate salt according to the method of example 1 by using 3-fluoro-4-methoxybenzylamine (synthesized according to reagent preparation 6) in step 5, then omission of steps 6 and 7. $^{1}$H NMR (400 MHz, $d_6$-DMSO): 8.93 (br s, 1H), 8.55 (s, 1H), 8.27 (d, 1H), 8.11 (d, 1H), 7.26-7.21 (m, 1H), 7.17-7.00 (m, 5H), 6.87 (d, 1H), 4.61 (br s, 2H), 4.40 (d, 2H), 3.91-3.85 (m, 1H), 3.82-3.78 (m, 6H), 2.28-2.20 (m, 2H), 2.17-1.89 (m, 9H). MS (EI) for $C_{30}H_{33}FN_4O_4$: 533 ($MH^+$).

1(DU): N-{[2-chloro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared as the trifluoroacetate salt according to the method of example 1 by using 2-chloro-4-methoxybenzylamine (synthesized according to reagent preparation 6) in step 5, then omission of steps 6 and 7. $^{1}$H NMR (400 MHz, $d_6$-DMSO): 8.89 (br s, 1H), 8.56 (s, 1H), 8.27 (d, 1H), 8.14 (d, 1H), 7.30-7.21 (m, 2H), 7.06-7.00 (m, 3H), 6.93-6.85 (m, 2H), 4.63 (br s, 2H), 4.47 (d, 2H), 3.92-3.85 (m, 1H), 3.81 (s, 3H), 3.76 (s, 3H), 2.28-2.25 (m, 2H), 2.17-2.09 (m, 5H), 2.04-1.90 (m, 4H). MS (EI) for $C_{30}H_{33}ClN_4O_4$: 549 ($MH^+$).

1(DV): N-{[2,6-difluoro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared as the trifluoroacetate salt according to the method of example 1 by using 2,6-Difluoro-4-methoxybenzylamine (synthesized according to reagent preparation 6) in step 5, then omission of steps 6 and 7. $^{1}$H NMR (400 MHz, $d_6$-DMSO): 8.78 (br s, 1H), 8.49 (s, 1H), 8.28 (d, 1H), 8.13 (d, 1H), 7.26-7.21 (m, 1H), 7.10-7.01 (m, 2H), 6.87 (d, 1H), 6.77-6.71 (m, 2H), 4.64 (br s, 2H), 4.42 (d, 2H), 3.92-3.85 (m, 1H), 3.81 (s, 3H), 3.78 (s, 3H), 2.28-2.22 (m, 2H), 2.17-2.08 (m, 5H), 2.04-1.91 (m, 4H). MS (EI) for $C_{30}H_{32}F_2N_4O_4$: 551 ($MH^+$).

1(DW): N-{[2-fluoro-6-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared as the trifluoroacetate salt according to the method of example 1 by using 2-fluoro-6-methoxybenzylamine (synthesized according to reagent preparation 6) in step 5, then omission of steps 6 and 7. $^{1}$H NMR (400 MHz, $d_6$-DMSO): 8.52 (br s, 1H), 8.47 (s, 1H), 8.27 (d, 1H), 8.15 (d, 1H), 7.36-7.21 (m, 2H), 7.10-7.00 (m, 2H), 6.90-6.78 (m, 3H), 4.64 (br s, 2H), 4.46 (d, 2H), 3.91-3.85 (m, 1H), 3.83 (s, 3H), 3.81 (s, 3H), 2.28-2.20 (m, 2H), 2.16-2.08 (m, 5H), 2.04-1.90 (m, 4H). MS (EI) for $C_{30}H_{33}FN_4O_4$: 533 ($MH^+$).

1(DX): N-{[4-fluoro-2-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared as the trifluoroacetate salt according to the method of example 1 by using 4-fluoro-2-methoxybenzylamine (synthesized according to reagent preparation 6) in step 5, then omission of steps 6 and 7. $^{1}$H NMR (400 MHz, $d_6$-DMSO): 8.82 (br s, 1H), 8.54 (s, 1H), 8.28 (d, 1H), 8.17 (d, 1H), 7.26-7.17 (m, 2H), 7.11-7.01 (m, 2H), 6.94-6.86 (m, 2H), 6.76-6.70 (m, 1H), 4.65 (br s, 2H), 4.38 (d, 2H), 3.92-3.87 (m, 1H), 3.84 (s, 3H), 3.81 (s, 3H), 2.28-2.23 (m, 2H), 2.17-2.10 (m, 5H), 2.05-1.92 (m, 4H). MS (EI) for $C_{30}H_{33}FN_4O_4$: 533 ($MH^+$).

1(DY): N-[(2-chloro-6-fluoro-3-methylphenyl)methyl]-6-[3-endo-({[2-methyl-3-(methyloxy)phenyl]carbonyl}amino)-8-azabicyclo[3.2.1]oct-8-yl]pyridine-3-carboxamide. Prepared as the trifluoroacetate salt according to the method of example 1 by using 1-(2-chloro-6-fluoro-3-methylphenyl)methanamine (synthesized according to reagent preparation 6) in step 5, then omission of steps 6 and 7. $^{1}$H NMR (400 MHz, $d_6$-DMSO): 8.68 (br s, 1H), 8.49 (d, 1H), 8.27 (d, 1H), 8.11 (d, 1H), 7.40-7.35 (m, 1H), 7.25-7.14 (m, 2H), 7.03-7.00 (m, 2H), 6.86 (d, 1H), 4.62 (br s, 2H), 4.57 (d, 2H), 3.90-3.84 (m, 1H), 3.80 (s, 3H), 2.32 (s, 3H), 2.28-2.21 (m, 2H), 2.15-2.08 (m, 5H), 2.04-1.90 (m, 4H). MS (EI) for $C_{30}H_{32}ClFN_4O_3$: 551 ($MH^+$).

1(DZ): 6-[3-endo-({[2-methyl-3-(methyloxy)phenyl]carbonyl}amino)-8-azabicyclo[3.2.1]oct-8-yl]-N-[(2,3,6-trifluorophenyl)methyl]pyridine-3-carboxamide. Prepared according to the method of example 1 by using 2,3,6-trifluorobenzylamine in step 5, then omission of steps 6 and 7. $^{1}$H NMR (400 MHz, d6-DMSO): 8.73-8.67 (m, 1H), 8.58 (s, 1H), 8.22 (s, 1H), 7.95-7.90 (d, 1H), 7.50-7.40 (m, 1H), 7.25-7.19 (m, 1H), 7.17-7.09 (m, 1H), 7.03-6.99 (d, 1H), 6.88-6.84 (d, 1H), 6.75-6.71 (d, 1H), 4.57-4.47 (m, 4H), 3.87-3.77 (m, 4H), 2.23-2.16 (d, 2H), 2.14 (s, 3H), 2.11-2.03 (m, 2H), 2.01-1.93 (m, 2H), 1.88-1.79 (d, 2H). MS (EI) for $C_{29}H_{29}F_3N_4O_3$: 539 ($MH^+$).

1(EA): N-{[3-fluoro-4-(4-methylpiperazin-1-yl)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-fluoro-4-(4-methylpiperazin-1-yl)benzylamine (synthesized according to the method of reagent preparation 5) in step 5, then omission of steps 6 and 7. $^{1}$H NMR (400 MHz, d6-DMSO): 8.79-8.73 (m, 1H), 8.64 (s, 1H), 8.24-8.20 (m, 1H), 7.99-7.90 (m, 2H), 7.26-7.20 (m, 1H), 7.10-6.98 (m, 3H), 6.88-6.84 (d, 1H), 6.78-6.72 (d, 1H), 4.61-4.50 (m, 2H), 4.40-4.35 (d, 2H), 3.88-3.78 (m, 4H), 3.32-3.30 (m, 4H), 3.11-2.96 (br. s, 4H), 2.59 (s, 3H), 2.24-2.16 (m, 2H), 2.14 (s, 3H), 2.13-2.04 (m, 2H), 2.01-1.94 (m, 2H), 1.89-1.79 (d, 2H). MS (EI) for $C_{34}H_{41}FN_6O_3$: 601 ($MH^+$).

1(EB): N-(2,3-dihydroxypropyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 3-aminopropane-1,2-diol in step 5, then omission of steps 6 and 7. $^{1}$H NMR (400 MHz, d6-DMSO): 8.61 (s, 1H), 8.23-8.18 (m, 2H), 7.97-7.92 (d, 1H), 7.26-7.20 (m, 1H), 7.04-6.99 (d, 1H), 6.88-6.84 (d, 1H), 6.76-6.72 (d, 1H), 4.84-4.81 (d, 2H), 4.60-4.50 (m, 4H), 3.88-3.78 (m, 4H), 3.63-3.57 (m, 1H), 3.21-3.11 (m, 2H), 2.24-2.16 (m, 2H), 2.14 (s, 3H), 2.10-2.04 (m, 2H), 2.01-1.94 (m, 2H), 1.89-1.79 (d, 2H). MS (EI) for $C_{25}H_{32}N_4O_5$: 469 ($MH^+$).

1(EC): N-[(1S,2S)-2-hydroxycyclopentyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using (1S, 2S)-2-aminocyclopentanol in step 5, then omission of steps 6 and 7. $^1$H NMR (400 MHz, d6-DMSO): 8.60 (s, 1H), 8.24-8.20 (d, 1H), 8.00-7.90 (m, 2H), 7.27-7.19 (m, 1H), 7.04-6.99 (d, 1H), 6.88-6.84 (d, 1H), 6.77-6.71 (d, 1H), 4.80-4.76 (d, 2H), 4.60-4.50 (br. s, 2H), 4.01-3.90 (m, 2H), 3.87-3.78 (m, 4H), 2.24-2.16 (m, 2H), 2.14 (s, 3H), 2.10-2.04 (m, 2H), 2.01-1.94 (m, 2H), 1.89-1.79 (d, 2H), 1.70-1.60 (m, 4H), 1.51-1.40 (m, 2H). MS (EI) for $C_{27}H_{34}N_4O_4$: 479 (MH$^+$).

1(ED): N-[(1S,2S)-2-hydroxycyclohexyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using (1S, 2S)-2-aminocyclohexanol in step 5, then omission of steps 6 and 7. $^1$H NMR (400 MHz, d6-DMSO): 8.60 (s, 1H), 8.24-8.20 (d, 1H), 7.98-7.93 (d, 1H), 7.88-7.84 (d, 1H), 7.26-7.20 (m, 1H), 7.04-6.99 (d, 1H), 6.88-6.84 (d, 1H), 6.77-6.71 (d, 1H), 4.64-4.59 (m, 1H), 4.58-4.50 (br. s, 2H), 3.87-3.78 (m, 4H), 3.66-3.54 (m, 1H), 2.24-2.16 (m, 2H), 2.14 (s, 3H), 2.10-2.04 (m, 2H), 2.01-1.94 (m, 2H), 1.90-1.78 (m, 3H), 1.69-1.59 (m, 4H), 1.27-1.16 (m, 4H). MS (EI) for $C_{28}H_{36}N_4O_4$: 493 (MH$^+$).

1(EE): N-azetidin-3-yl-6-[3-endo-({[2-methyl-3-(methyloxy)phenyl]carbonyl}amino)-8-azabicyclo[3.2.1]oct-8-yl] pyridine-3-carboxamide. Prepared according to the method of example 1 by using 1,1-dimethylethyl-3-aminoazetidine-1-carboxylate in step 5, then omission of step 7. $^1$H NMR (400 MHz, d$_6$-DMSO): 9.25 (s, 1H), 8.98 (s, 2H), 8.61 (d, 1H), 8.29 (d, 1H), 8.12 (d, 1H), 7.24 (t, 1H), 7.05 (s, 1H), 7.03 (d, 1H), 6.87 (d, 1H), 4.75-4.84 (m, 2H), 4.70 (s, 2H), 4.07-4.19 (m, 4H), 3.87 (s, 1H), 3.81 (s, 3H), 2.25 (d, 2H), 2.08-2.14 (m, 4H), 2.00-2.03 (m, 2H), 1.95 (s, 1H), 1.92 (s, 1H). MS (EI) for $C_{25}H_{31}N_5O_3$: 450 (MH$^+$).

1(EF): N-[(1S)-2-hydroxy-1-methylethyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using (S)-2-aminopropan-1-ol in step 5, then omission of steps 6 and 7. $^1$H NMR (400 MHz, d6-DMSO): 8.60 (s, 1H), 8.25-8.20 (d, 1H), 7.97-7.92 (d, 1H), 7.87-7.81 (d, 1H), 7.26-7.20 (m, 1H), 7.04-6.99 (d, 1H), 6.88-6.84 (d, 1H), 6.76-6.72 (d, 1H), 4.75-4.67 (m, 1H), 4.60-4.50 (br. s, 2H), 4.05-3.94 (m, 2H), 3.87-3.78 (m, 4H), 3.48-3.40 (m, 1H), 2.24-2.16 (m, 2H), 2.14 (s, 3H), 2.10-2.04 (m, 2H), 2.01-1.94 (m, 2H), 1.89-1.79 (d, 2H), 1.14-1.08 (d, 3H). MS (EI) for $C_{25}H_{32}N_4O_4$: 453 (MH$^+$).

1(EG): N-[(2S)-2-hydroxypropyl]-6-[3-endo-({[2-methyl-3-(methyloxy)phenyl]carbonyl}amino)-8-azabicyclo [3.2.1]oct-8-yl]pyridine-3-carboxamide. Prepared according to the method of example 1 by using (S)-1-aminopropan-2-ol in step 5, then omission of steps 6 and 7. $^1$H NMR (400 MHz, d6-DMSO): 8.60 (s, 1H), 8.24-8.16 (m, 2H), 7.97-7.92 (d, 1H), 7.26-7.20 (m, 1H), 7.04-6.99 (d, 1H), 6.88-6.84 (d, 1H), 6.76-6.72 (d, 1H), 4.76-4.73 (d, 1H), 4.57-4.52 (br. s, 2H), 3.87-3.79 (m, 4H), 3.78-3.72 (m, 1H), 3.21-3.13 (m, 2H), 2.24-2.16 (m, 2H), 2.14 (s, 3H), 2.10-2.04 (m, 2H), 2.01-1.94 (m, 2H), 1.89-1.79 (d, 2H), 1.07-1.03 (d, 3H). MS (EI) for $C_{25}H_{32}N_4O_4$: 453 (MH$^+$).

1(EH): 6-[3-endo-({[2-methyl-3-(methyloxy)phenyl] carbonyl}amino)-8-azabicyclo[3.2.1]oct-8-yl]-N-{(1S)-1-[3-(methyloxy)phenyl]ethyl}pyridine-3-carboxamide. Prepared according to the method of example 1 by using (S)-1-(3-methoxyphenyl)ethanamine in step 5, then omission of steps 6 and 7. $^1$H NMR (400 MHz, DMSO-d$_6$): 8.64 (d, 1H), 8.52 (d, 1H), 8.23 (d, 1H), 7.98 (dd, 1H), 7.22 (t, 2H), 7.02 (d, 1H), 6.94 (m, 2H), 6.86 (d, 1H), 6.80 (m, 1H), 6.76 (d, 1H), 5.12 (m, 1H), 4.54 (bs, 2H), 3.85 (m, 1H), 3.82 (s, 3H), 3.74 (s, 3H), 2.20 (m, 2H), 2.15 (s, 3H), 2.08 (m, 2H), 1.98 (m, 2H), 1.84 (m, 2H), 1.44 (d, 3H). MS (EI) for $C_{31}H_{36}N_4O_4$: 529 (MH$^+$).

1(EI): 6-[3-endo-({[2-methyl-3-(methyloxy)phenyl] carbonyl}amino)-8-azabicyclo[3.2.1]oct-8-yl]-N-[(4-morpholin-4-ylphenyl)methyl]pyridine-3-carboxamide. Prepared according to the method of example 1 by using (4-morpholinophenyl)methanamine in step 5, then omission of steps 6 and 7. $^1$H NMR (400 MHz, DMSO-d$_6$): 8.70 (t, 1H), 8.63 (d, 1H), 8.22 (d, 1H), 7.96 (dd, 1H), 7.22 (t, 1H), 7.18 (d, 2H), 7.02 (d, 1H), 6.89 (d, 2H), 6.86 (d, 1H), 6.74 (d, 1H), 4.54 (bs, 2H), 4.32 (d, 2H), 3.83 (m, 1H), 3.80 (s, 3H), 3.72 (m, 4H), 3.02 (m, 4H), 2.20 (m, 2H), 2.15 (s, 3H), 2.08 (m, 2H), 1.96 (m, 2H), 1.84 (d, 2H). MS (EI) for $C_{33}H_{39}N_5O_4$: 570 (MH$^+$).

1(EJ): N-[(1S)-1,2-dimethylpropyl]-6-[3-endo-({[2-methyl-3-(methyloxy)phenyl]carbonyl}amino)-8-azabicyclo [3.2.1]oct-8-yl]pyridine-3-carboxamide. Prepared according to the method of example 1 by using (S)-3-methylbutan-2-amine in step 5, then omission of steps 6 and 7. $^1$H NMR (400 MHz, DMSO-d$_6$): 8.61 (d, 1H), 8.21 (d, 1H), 7.94 (dd, 1H), 7.84 (d, 1H), 7.22 (t, 1H), 7.02 (d, 1H), 6.86 (d, 2H), 6.74 (d, 1H), 4.52 (bs, 2H), 3.82 (m, 2H), 3.80 (s, 3H), 2.20 (m, 2H), 2.14 (s, 3H), 2.09 (m, 2H), 1.96 (m, 2H), 1.84 (d, 2H), 1.74 (m, 1H), 1.08 (d, 3H), 0.88 (d, 3H), 0.86 (d, 3H). MS (EI) for $C_{27}H_{36}N_4O_3$: 465 (MH$^+$).

1(EK): N-[(1R)-1,2-dimethylpropyl]-6-[3-endo-({[2-methyl-3-(methyloxy)phenyl]carbonyl}amino)-8-azabicyclo [3.2.1]oct-8-yl]pyridine-3-carboxamide. Prepared according to the method of example 1 by using (R)-3-methylbutan-2-amine in step 5, then omission of steps 6 and 7. $^1$H NMR (400 MHz, DMSO-d$_6$): 8.60 (d, 1H), 8.21 (d, 1H), 7.94 (dd, 1H), 7.85 (d, 1H), 7.23 (t, 1H), 7.02 (d, 1H), 6.86 (d, 2H), 6.74 (d, 1H), 4.53 (bs, 2H), 3.82 (m, 2H), 3.80 (s, 3H), 2.20 (m, 2H), 2.15 (s, 3H), 2.10 (m, 2H), 1.97 (m, 2H), 1.84 (d, 2H), 1.74 (m, 1H), 1.08 (d, 3H), 0.88 (d, 3H), 0.86 (d, 3H). MS (EI) for $C_{27}H_{36}N_4O_3$: 465 (MH$^+$).

1(EL): N-[(1S)-1-methyl-2-(methyloxy)ethyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using (S)-1-methoxypropan-2-amine in step 5, then omission of steps 6 and 7. $^1$H NMR (400 MHz, DMSO-d$_6$): 8.59 (d, 1H), 8.21 (d, 1H), 7.94 (m, 2H), 7.22 (t, 1H), 7.02 (d, 1H), 6.86 (d, 2H), 6.74 (d, 1H), 4.54 (bs, 2H), 4.17 (m, 1H), 3.84 (m, 1H), 3.80 (s, 3H), 3.39 (d, 0.5H), 3.37 (d, 0.5H), 3.26 (d, 0.5H), 3.26 (s, 3H), 3.24 (d, 0.5H), 2.19 (m, 2H), 2.14 (s, 3H), 2.09 (m, 2H), 1.97 (m, 2H), 1.84 (d, 2H), 1.07 (d, 3H). MS (EI) for $C_{26}H_{34}N_4O_4$: 467 (MH$^+$).

1(EM): 6-[3-endo-({[2-methyl-3-(methyloxy)phenyl] carbonyl}amino)-8-azabicyclo[3.2.1]oct-8-yl]-N-{(1S)-1-[4-(methyloxy)phenyl]ethyl}pyridine-3-carboxamide. Prepared according to the method of example 1 by using (S)-1-(4-methoxyphenyl)ethanamine in step 5, then omission of steps 6 and 7. $^1$H NMR (400 MHz, DMSO-d$_6$): 8.63 (d, 1H), 8.45 (d, 1H), 8.21 (d, 1H), 7.96 (dd, 1H), 7.29 (d, 2H), 7.23 (t, 1H), 7.02 (d, 1H), 6.87 (m, 3H), 6.74 (d, 1H), 5.10 (m, 1H), 4.52 (bs, 2H), 3.80 (s, 3H), 3.71 (s, 3H), 3.81 (m, 1H), 2.20 (m, 2H), 2.14 (s, 3H), 2.06 (m, 2H), 1.97 (m, 2H), 1.83 (d, 2H), 1.42 (d, 3H). MS (EI) for $C_{31}H_{36}N_4O_4$: 528 (M).

1(EN): 6-[3-endo-({[2-methyl-3-(methyloxy)phenyl] carbonyl}amino)-8-azabicyclo[3.2.1]oct-8-yl]-N-{(1R)-1-[4-(methyloxy)phenyl]ethyl)}pyridine-3-carboxamide. Prepared according to the method of example 1 by using (R)-1-(4-methoxyphenyl)ethanamine in step 5, then omission of steps 6 and 7. $^{1}$H NMR (400 MHz, DMSO-$d_6$): 8.63 (d, 1H), 8.45 (d, 1H), 8.21 (d, 1H), 7.96 (dd, 1H), 7.29 (d, 2H), 7.23 (t, 1H), 7.01 (d, 1H), 6.86 (m, 3H), 6.74 (d, 1H), 5.10 (m, 1H), 4.53 (bs, 2H), 3.82 (m, 1H), 3.80 (s, 3H), 3.71 (s, 3H), 2.19 (m, 2H), 2.14 (s, 3H), 2.08 (m, 2H), 1.97 (m, 2H), 1.83 (d, 2H), 1.43 (d, 3H). MS (EI) for $C_{31}H_{36}N_4O_4$: 529 ($MH^+$).

1(EO): 6-[3-endo-({[2-methyl-3-(methyloxy)phenyl]carbonyl}amino)-8-azabicyclo[3.2.1]oct-8-yl]-N-((1-phenylethyl)pyridine-3-carboxamide. Prepared according to the method of example 1 by using 1-phenylethanamine in step 5, then omission of steps 6 and 7. $^{1}$H NMR (400 MHz, DMSO-$d_6$): 8.65 (d, 1H), 8.53 (d, 1H), 8.21 (d, 1H), 7.98 (dd, 1H), 7.38 (m, 2H), 7.32 (m, 2H), 7.22 (m, 2H), 7.02 (d, 1H), 6.86 (d, 1H), 6.75 (d, 1H), 5.12 (m, 1H), 4.54 (bs, 2H), 3.82 (m, 1H), 3.80 (s, 3H), 2.20 (m, 2H), 2.14 (s, 3H), 2.08 (m, 2H), 1.97 (m, 2H), 1.84 (d, 2H), 1.45 (d, 3H). MS (EI) for $C_{30}H_{34}N_4O_3$: 499 ($MH^+$).

1(EP): N-[1-(4-chlorophenyl)ethyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using 1-(4-chlorophenyl)ethanamine in step 5, then omission of steps 6 and 7. $^{1}$H NMR (400 MHz, DMSO-$d_6$): 8.63 (d, 1H), 8.55 (d, 1H), 8.21 (d, 1H), 7.96 (dd, 1H), 7.39 (m, 4H), 7.23 (t, 1H), 7.02 (d, 1H), 6.86 (d, 1H), 6.75 (d, 1H), 5.12 (m, 1H), 4.54 (bs, 2H), 3.84 (m, 1H), 3.80 (s, 3H), 2.20 (m, 2H), 2.13 (s, 3H), 2.08 (m, 2H), 1.96 (m, 2H), 1.84 (d, 2H), 1.44 (d, 3H). MS (EI) for $C_{30}H_{33}ClN_4O_3$: 535 ($MH^+$).

1(EQ): 6-[3-endo-({[2-methyl-3-(methyloxy)phenyl]carbonyl}amino)-8-azabicyclo[3.2.1]oct-8-yl]-N-(1-phenylpiperidin-4-yl)pyridine-3-carboxamide. Prepared according to the method of example 1 by using 1-phenylpiperidin-4-amine in step 5, then omission of steps 6 and 7. $^{1}$H NMR (400 MHz, DMSO-$d_6$): 8.61 (d, 1H), 8.21 (d, 1H), 8.03 (d, 1H), 7.94 (dd, 1H), 7.21 (m, 3H), 7.02 (d, 1H), 6.96 (m, 2H), 6.86 (d, 1H), 6.74 (m, 2H), 4.54 (bs, 2H), 3.94 (m, 1H), 3.83 (m, 1H), 3.80 (s, 3H), 3.72 (m, 2H), 2.80 (m, 2H), 2.19 (m, 2H), 2.14 (s, 3H), 2.08 (m, 2H), 1.96 (m, 2H), 1.84 (d, 4H), 1.64 (m, 2H). MS (EI) for $C_{33}H_{39}N_5O_3$: 554 ($MH^+$).

1(ER): 6-[3-endo-({[2-methyl-3-(methyloxy)phenyl]carbonyl}amino)-8-azabicyclo[3.2.1]oct-8-yl]-N-[(4-pyrrolidin-1-ylphenyl)methyl]pyridine-3-carboxamide. Prepared according to the method of example 1 by using (4-(pyrrolidin-1-yl)phenyl)methanamine in step 5, then omission of steps 6 and 7. $^{1}$H NMR (400 MHz, DMSO-$d_6$): 8.62 (m, 2H), 8.21 (d, 1H), 7.95 (dd, 1H), 7.22 (t, 1H), 7.11 (m, 2H), 7.01 (d, 1H), 6.85 (d, 1H), 6.73 (d, 1H), 6.47 (m, 2H), 4.52 (bs, 2H), 4.32 (d, 2H), 3.83 (m, 1H), 3.79 (s, 3H), 3.17 (m, 4H), 2.19 (m, 2H), 2.13 (s, 3H), 2.08 (m, 2H), 1.92-1.98 (m, 6H), 1.84 (d, 2H). MS (EI) for $C_{33}H_{39}N_5O_3$: 553 (M).

1(ES): N-[(1S)-1-(4-{[2-(diethylamino)ethyl]oxy}-2-fluorophenyl)ethyl]-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using (S)-2-(4-(1-aminoethyl)-3-fluorophenoxy)-N,N-diethylethanamine (synthesized according to reagent preparation 4) in step 5, then omission of steps 6 and 7. $^{1}$H NMR (400 MHz, DMSO-$d_6$): 8.64 (d, 1H), 8.52 (d, 1H), 8.21 (d, 1H), 7.97 (dd, 1H), 7.34 (t, 1H), 7.23 (t, 1H), 7.01 (d, 1H), 6.86 (d, 1H), 6.73-6.79 (m, 3H), 5.30 (m, 1H), 4.54 (bs, 2H), 4.00 (t, 2H), 3.83 (m, 1H), 3.80 (s, 3H), 2.74 (t, 2H), 2.52 (dd, 4H), 2.20 (m, 2H), 2.13 (s, 3H), 2.08 (m, 2H), 1.96 (m, 2H), 1.84 (d, 2H) 1.41 (d, 3H), 0.96 (t, 6H). MS (EI) for $C_{36}H_{46}FN_5O_3$: 633 ($MH^+$).

1(ET): N-{1-[3,4-bis(methyloxy)phenyl]ethyl}-6-[3-endo-({[2-methyl-3-(methyloxy)phenyl]carbonyl}amino)-8-azabicyclo[3.2.1]oct-8-yl]pyridine-3-carboxamide. 6-[3-endo-({[2-methyl-3-(methyloxy)phenyl]carbonyl}amino)-8-azabicyclo[3.2.1]oct-8-yl]-N-{[4-(4-methylpiperazin-1-yl)phenyl]methyl}pyridine-3-carboxamide. Prepared according to the method of example 1 by using 1-(3,4-dimethoxyphenyl)ethanamine in step 5, then omission of steps 6 and 7. $^{1}$H NMR (400 MHz, DMSO-$d_6$): 8.63 (d, 1H), 8.44 (d, 1H), 8.21 (d, 1H), 7.94 (dd, 1H), 7.23 (t, 1H), 7.02 (d, s, 2H), 6.86 (m, 3H), 6.74 (d, 1H), 5.10 (m, 1H), 4.54 (bs, 2H), 3.83 (m, 1H), 3.80 (s, 3H), 3.75 (s, 3H), 3.71 (s, 3H), 2.19 (m, 2H), 2.13 (s, 3H), 2.08 (m, 2H), 1.97 (m, 2H), 1.84 (d, 2H), 1.43 (d, 3H). MS (EI) for $C_{32}H_{38}N_4O_5$: 559 ($MH^+$).

1(EU): 6-[3-endo-({[2-methyl-3-(methyloxy)phenyl]carbonyl}amino)-8-azabicyclo[3.2.1]oct-8-yl]-N-{[4-(4-methylpiperazin-1-yl)phenyl]methyl}pyridine-3-carboxamide. Prepared according to the method of example 1 by using (4-(4-methylpiperazin-1-yl)phenyl)methanamine in step 5 then omission of steps 6 and 7. $^{1}$H NMR (400 MHz, DMSO-$d_6$): 8.68 (t, 1H), 8.63 (d, 1H), 8.21 (d, 1H), 7.96 (dd, 1H), 7.22 (t, 1H), 7.15 (m, 2H), 7.02 (d, 1H), 6.87 (m, 3H), 6.74 (d, 1H), 4.53 (bs, 2H), 4.33 (d, 2H), 3.82 (m, 1H), 3.79 (s, 3H), 3.06 (m, 4H), 2.42 (m, 4H), 2.20 (s, m, 5H), 2.14 (s, 3H), 2.08 (m, 2H), 1.96 (m, 2H), 1.84 (d, 2H). MS (EI) for $C_{34}H_{42}N_6O_3$: 583 ($MH^+$).

1(EV): N-{(1S)-1-[2-fluoro-4-(methyloxy)phenyl]ethyl}-6-[3-endo-({[2-methyl-3-(methyloxy)phenyl]carbonyl}amino)-8-azabicyclo[3.2.1]oct-8-yl]pyridine-3-carboxamide. Prepared as the hydrochloride salt according to the method of example 1 by using (1S)-1-(2-fluoro-4-methoxyphenyl)ethanamine hydrochloride in step 5, and then omission of steps 6 and 7. $^{1}$H NMR (400 MHz, Methanol-$d_4$): 8.60 (d, 1H), 7.97 (dd, 1H), 7.31 (t, 1H), 7.23 (t, 1H), 6.99 (d, 1H), 6.90 (d, 1H), 6.77-6.64 (m, 3H), 5.43-5.35 (m, 1H), 4.60 (br s, 2H), 4.03-3.96 (m, 1H), 3.84 (s, 3H), 3.77 (s, 3H), 2.35-2.06 (m, 9H), 1.90 (d, 2H), 1.52 (d, 3H); MS (EI) for $C_{31}H_{35}FN_4O_4$: 547 ($MH^+$).

1(EW): N-{[2-fluoro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using (2-fluoro-4-methoxyphenyl)methanamine in step 5, then omission of steps 6 and 7. $^{1}$H NMR (400 MHz, Methanol-$d_4$): 8.60 (d, 1H), 7.96 (dd, 1H), 7.29 (t, 1H), 7.22 (t, 1H), 6.99 (d, 1H), 6.90 (d, 1H), 6.77-6.66 (m, 3H), 4.60 (br s, 2H), 4.52 (s, 2H), 4.04-3.95 (m, 1H), 3.84 (s, 3H), 3.77 (s, 3H), 2.35-2.07 (m, 9H), 1.91 (d, 2H); MS (EI) for $C_{30}H_{33}FN_4O_4$: 533 ($MH^+$).

1(EX): 6-[3-endo-({[2-methyl-3-(methyloxy)phenyl]carbonyl}amino)-8-azabicyclo[3.2.1]oct-8-yl]-N-[(2,4,6-trifluorophenyl)methyl]pyridine-3-carboxamide. Prepared according to the method of example 1 by using (2,4,6-trifluorophenyl)methanamine in step 5, then omission of steps 6 and 7. $^{1}$H NMR (400 MHz, DMSO-$d_6$): 8.60 (t, 1H), 8.56 (d, 1H), 8.19 (d, 1H), 7.90 (dd, 1H), 7.23-7.11 (m, 3H), 6.99 (d, 1H), 6.83 (d, 1H), 6.70 (d, 1H), 4.51 (br s, 2H), 4.41 (d, 2H), 3.85-3.74 (m, 4H), 2.23-1.99 (m, 7H), 1.98-1.88 (m, 2H), 1.81 (d, 2H); MS (EI) for $C_{29}H_{29}F_3N_4O_3$: 537 (M−H).

1(EY): 6-[3-endo-({[2-methyl-3-(methyloxy)phenyl]carbonyl}amino)-8-azabicyclo[3.2.1]oct-8-yl]-N-{[3-(4-methylpiperazin-1-yl)phenyl]methyl}pyridine-3-carboxamide. Prepared as the acetate salt according to the method of example 1 by using 1-[3-(4-methylpiperazin-1-yl)phenyl]methanamine in step 5, then omission of steps 6 and 7. $^{1}$H NMR (400 MHz, Methanol-$d_4$): 8.61 (d, 1H), 7.98 (dd, 1H), 7.26-7.20 (m, 2H), 7.02-6.97 (m, 2H), 6.93-6.85 (m, 3H), 6.76 (d, 1H), 4.60 (br s, 2H), 4.51 (s, 2H), 4.04-3.96 (m, 1H), 3.84 (s, 3H), 3.39-3.22 (m, 4H), 2.89-2.81 (m, 4H), 2.54-2.51

(m, 3H), 2.34-2.25 (m, 2H), 2.23-2.08 (m, 7H), 1.96 (s, 3H), 1.90 (d, 2H); MS (EI) for $C_{34}H_{42}N_6O_3$: 583 ($MH^+$).

1(EZ): 6-[3-endo-({[2-methyl-3-(methyloxy)phenyl]carbonyl}amino)-8-azabicyclo[3.2.1]oct-8-yl]-N-{[2-(4-methylpiperazin-1-yl)phenyl]methyl}pyridine-3-carboxamide. Prepared according to the method of example 1 by using 1-[2-(4-methylpiperazin-1-yl)phenyl]methanamine in step 5, then omission of steps 6 and 7. $^1H$ NMR (400 MHz, DMSO-$d_6$): 8.65-8.58 (m, 2H), 8.16 (d, 1H), 7.92 (dd, 1H), 7.19-7.12 (m, 3H), 7.07-6.93 (m, 3H), 6.79 (d, 1H), 6.69 (d, 1H), 4.53-4.41 (m, 4H), 3.82-3.75 (m, 1H), 3.73 (s, 3H), 2.89-2.81 (m, 4H), 2.68-2.56 (m, 4H), 2.31 (br s, 3H), 2.18-1.98 (m, 7H), 1.95-1.86 (m, 2H), 1.78 (d, 2H); MS (EI) for $C_{34}H_{42}N_6O_3$: 583 ($MH^+$).

1(FA): 6-[3-endo-({[2-methyl-3-(methyloxy)phenyl]carbonyl}amino)-8-azabicyclo[3.2.1]oct-8-yl]-N-[(2,4,5-trifluorophenyl)methyl]pyridine-3-carboxamide. Prepared according to the method of example 1 by using 2,4,5-trifluorobenzylamine in step 5, then omission of steps 6 and 7. $^1H$ NMR (400 MHz, DMSO-$d_6$): 8.77 (t, 1H), 8.62 (d, 1H), 8.21 (d, 1H), 7.94 (dd, 1H), 7.57-7.48 (m, 1H), 7.44-7.34 (m, 1H), 7.20 (t, 1H), 6.99 (d, 1H), 6.84 (d, 1H), 6.74 (d, 1H), 4.53 (br s, 2H), 4.41 (d, 2H), 3.87-3.74 (m, 4H), 2.25-1.75 (m, 1H); MS (EI) for $C_{29}H_{29}F_3N_4O_3$: 537 (M−H).

1(FB): N-(2-hydroxyethyl)-6-[3-endo-({[2-methyl-3-(methyloxy)phenyl]carbonyl}amino)-8-azabicyclo[3.2.1]oct-8-yl]pyridine-3-carboxamide. Prepared according to the method of example 1 by using ethanolamine in step 5, then omission of steps 6 and 7. $^1H$ NMR (400 MHz, Methanol-$d_4$): 8.46 (d, 1H), 8.41 (d, 1H), 8.31 (dd, 1H), 7.32 (d, 1H), 7.24 (t, 1H), 7.01 (d, 1H), 6.91 (d, 1H), 4.71 (br s, 2H), 4.13-4.07 (m, 1H), 3.85 (s, 3H), 3.71 (t, 2H), 3.50 (t, 2H), 32.41-2.18 (m, 9H), 2.14 (d, 2H); MS (EI) for $C_{24}H_{30}N_4O_4$: 439 ($MH^+$).

1(FC): 6-[3-endo-({[2-methyl-3-(methyloxy)phenyl]carbonyl}amino)-8-azabicyclo[3.2.1]oct-8-yl]-N-[(4-piperazin-1-ylphenyl)methyl]pyridine-3-carboxamide. Prepared as the acetate salt in example 1 step 5. $^1H$ NMR (400 MHz, methanol-$d_4$): 8.60 (d, 1H), 7.97 (dd, 1H), 7.27 (d, 2H), 7.23 (t, 1H), 6.99 (m, 3H), 6.90 (d, 1H), 6.75 (d, 1H), 4.60 (br s, 2H), 4.47 (s, 3H), 3.99 (m, 1H), 3.84 (s, 3H), 3.25 (m, 4H), 2.29 (m, 2H), 2.21 (s, 3H), 2.19 (m, 2H), 1.92 (s, 6H), 1.90 (m, 2H); MS (EI) for $C_{33}H_{40}N_6O_3$: 569 ($MH^+$).

SYNTHETIC SCHEME 2:

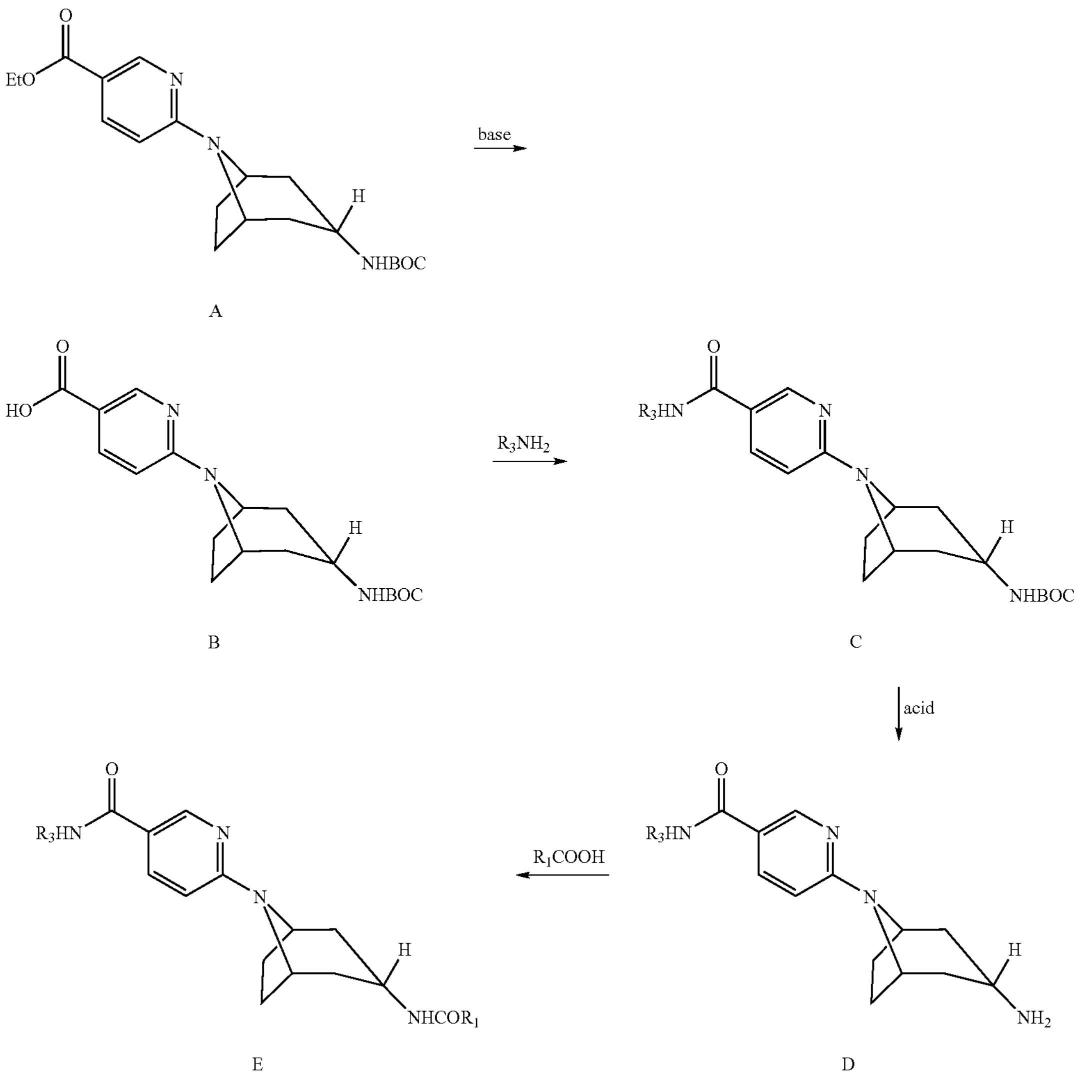

Scheme 2 generally describes the synthesis of all of the compound(s) listed in Example 2, wherein $R_1$ and $R_3$ are as defined in the specification.

In Scheme 2, the carboxylate of compound (A) is hydrolyzed to form compound (B) under acidic conditions, such as with the use of KOH. $R_3NH_2$ is then added to compound (B) under appropriate reaction conditions and with a suitable coupling reagent, such as HATU, to condense and form the amide bond in compound (C). Compound (C) is then deprotected under acid conditions, such as with the use of HCl, to remove BOC and form compound (D). To compound (D) is added $R_1COOH$ under appropriate reaction conditions and with a suitable coupling reagent, such as HATU, to condense and form the amide bond in compound (E).

Example 2

6-[3-endo-({[2-methyl-3-(methyloxy)phenyl]carbonyl}-amino)-8-azabicyclo[3.2.1]oct-8-yl]-N-(phenylmethyl)pyridine-3-carboxamide STEP 1: A mixture of ethyl 6-[3-endo-({[(1,1-dimethylethyl)oxy]carbonyl}-amino)-8-azabicyclo[3.2.1]oct-8-yl] pyridine-3-carboxylate (prepared in example 1) (13.56 g, 36.12 mmol) and potassium hydroxide (4.05 g, 72.23 mmol) in methanol (120 mL) and water (40 mL) was stirred at 70° C. for 1 h. The reaction mixture was concentrated and then acidified to pH5 with 1N aqueous hydrochloric acid. The precipitate was collected by filtration, washed with water and dried to give 6-[3-endo-({[(1,1-dimethylethyl)oxy] carbonyl}amino)-8-azabicyclo[3.2.1]oct-8-yl]pyridine-3-carboxylic acid (11.69 g, 93% yield). $^1$H NMR (400 MHz, $d_6$-DMSO): δ 12.46 (br s, 1H), 8.61 (d, 1H), 7.89 (dd, 1H), 6.90 (br s, 1H), 6.71 (d, 1H), 4.52 (br s, 2H), 3.44 (m, 1H), 2.12 (m, 2H), 1.94 (m, 4H), 1.75 (d, 2H), 1.39 (s, 9H); MS (EI) for $C_{18}H_{25}N_3O_4$: 348 ($MH^+$).

STEP 2: A mixture of 6-[3-endo-({[(1,1-dimethylethyl) oxy]carbonyl}amino)-8-azabicyclo[3.2.1]oct-8-yl]pyridine-3-carboxylic acid (643 mg, 1.85 mmol), benzylamine (198 mg, 1.85 mmol), HATU (704 mg, 1.85 mmol), and diisopropylethylamine (598 mg, 4.63 mmol) in DMF (10 mL) was stirred at room temperature for 18 h. The reaction mixture was diluted with ethyl acetate (100 mL), washed with water (50 mL), 5% lithium chloride (2×50 mL), and brine (50 mL), dried over sodium sulfate then filtered and concentrated. The resulting solid was triturated with ethyl acetate (10 mL) then dried to afford 1,1-dimethylethyl [8-(5-{[(phenylmethyl) amino]carbonyl}pyridine-2-yl)-8-azabicyclo[3.2.1]oct-3-endo-yl]carbamate (612 mg, 76% yield). $^1$H NMR (400 MHz, $d_6$-DMSO): δ 8.79 (t, 1H), 8.63 (d, 1H), 7.96 (dd, 1H), 7.31 (m, 5H), 7.23 (m, 1H), 6.87 (br s, 1H), 6.72 (d, 1H), 4.49 (br s, 2H), 4.45 (d, 2H), 3.42 (m, 1H), 2.11 (m, 2H), 1.95 (m, 4H), 1.72 (d, 2H), 1.39 (s, 9H); MS (EI) for $C_{25}H_{32}N_4O_3$: 437 ($MH^+$).

STEP 3: A solution of 1,1-dimethylethyl [8-(5-{[(phenylmethyl)amino]carbonyl}pyridine-2-yl)-8-azabicyclo[3.2.1] oct-3-endo-yl]carbamate (13.49 g, 30.90 mmol) in methanol (75 mL) and 4M HCl in dioxane (75 mL) was refluxed for 2 min. The reaction mixture was concentrated, and water (500 mL) was added. The aqueous solution was washed with ethyl acetate (2×150 mL), and then basified to pH 11 with 50% sodium hydroxide. The aqueous layer was extracted with ethyl acetate (3×250 mL), and the organic extracts were washed with brine (50 mL). The organic solution was dried over sodium sulfate, filtered and concentrated to give 6-(3-endo-amino-8-azabicyclo[3.2.1]oct-8-yl)-N-(phenylmethyl) pyridine-3-carboxamide (9.40 g, 90% yield). $^1$H NMR (400 MHz, $d_6$-DMSO): δ 8.76 (t, 1H), 8.62 (d, 1H), 7.94 (dd, 1H), 7.30 (m, 5H), 7.23 (m, 1H), 6.63 (d, 1H), 4.49 (br s, 2H), 4.45 (d, 2H), 3.14 (m, 1H), 2.34 (m, 2H), 1.92 (m, 4H), 1.57 (br s, 2H), 1.42 (d, 2H).

STEP 4: A mixture of 3-(methyloxy)-2-methylbenzoic acid (22 mg, 0.13 mmol), 6-(3-endo-amino-8-azabicyclo [3.2.1]oct-8-yl)-N-(phenylmethyl)pyridine-3-carboxamide (44 mg, 0.13 mmol), HATU (50 mg, 0.13 mmol), and diisopropylethylamine (52 mg, 0.40 mmol) in DMF (2 mL) was stirred at room temperature for 5 h. The reaction mixture was diluted with ethyl acetate (50 mL), washed with saturated sodium bicarbonate (2×30 mL), 5% lithium chloride (20 mL), and brine (20 mL), dried over sodium sulfate then filtered and concentrated. The resulting solid was suspended in acetonitrile and the insoluble product collected by filtration then washed with methanol (3×) to afford the title compound (19 mg, 22% yield). $^1$H NMR (400 MHz, $d_6$-DMSO): δ 8.80 (t, 1H), 8.65 (s, 1H), 8.23 (d, 1H), 7.98 (m, 1H), 7.31 (m, 4H), 7.23 (m, 2H), 7.02 (d, 1H), 6.86 (d, 1H), 6.76 (d, 1H), 4.55 (br s, 2H), 4.46 (d, 2H), 3.84 (m, 1H), 3.80 (s, 3H), 2.26 (m, 2H), 2.14 (s, 3H), 2.09 (m, 2H), 1.97 (m, 2H), 1.85 (d, 2H); MS (EI) for $C_{29}H_{32}N_4O_3$: 485 ($MH^+$).

Using analogous synthetic techniques and substituting with alternative starting reagents, the following compounds [2(A)-2(AU)] were prepared. Alternative starting materials were obtained commercially unless otherwise indicated.

(2B): N-[8-(5-{[(phenylmethyl)amino]carbonyl}pyridin-2-yl)-8-azabicyclo[3.2.1]oct-3-endo-yl]-1H-indole-4-carboxamide. Prepared according to the method of example 2 by using indole-4-carboxylic acid in step 4. $^1$H-NMR (400 MHz, DMSO-$d_6$): 11.31 (s, 1H), 8.87 (s, 1H), 8.64 (s, 1H), 8.12-8.03 (m, 2H), 7.54 (d, 2H), 7.45 (t, 1H), 7.35-7.30 (m, 4H), 7.24-7.19 (m, 1H), 7.15 (t, 1H), 6.85 (br s, 1H), 6.78 (t, 1H), 4.62 (br s, 2H), 4.47 (d, 2H), 3.94 (br s, 1H), 2.33-2.31 (m, 2H), 2.08-1.96 (m, 6H). MS (EI) for $C_{29}H_{29}N_5O_2$: 478 ($M^-$).

(2C): 6-(3-endo-{[(3-hydroxy-2-methylphenyl)carbonyl] amino}-8-azabicyclo[3.2.1]oct-8-yl)-N-(phenylmethyl)pyridine-3-carboxamide. Prepared according to the method of example 2 by using 3-hydroxy-2-methylbenzoic acid in step 4. $^1$H-NMR (400 MHz, DMSO-$d_6$): 9.50 (br s, 1H), 8.95 (br s, 1H), 8.57 (s, 1H), 8.22 (d, 1H), 8.10 (s, 1H), 7.35-7.26 (m, 2H), 7.25-7.07 (m, 1H), 7.01 (t, 1H), 6.84 (d, 1H), 6.72 (d, 1H), 4.62 (br s, 2H), 4.47 (d, 2H), 3.86 (br s, 1H), 2.26-2.24 (m, 2H), 2.11 (s, 3H), 2.08-1.99 (m, 2H), 1.94-1.90 (m, 4H). MS (EI) for $C_{28}H_{30}N_4O_3$: 471 ($MH^+$).

(2D): 6-(3-endo-{[(3-amino-2-methylphenyl)carbonyl] amino}-8-azabicyclo[3.2.1]oct-8-yl)-N-(phenylmethyl)pyridine-3-carboxamide. Prepared according to the method of example 2 by using 3-amino-2-methylbenzoic acid in step 4. $^1$H-NMR (400 MHz, DMSO-$d_6$): 8.80 (t, 1H), 8.65 (br s, 1H), 8.09 (d, 1H), 7.99-7.96 (m, 1H), 7.33-7.31 (m, 3H), 7.25-7.24 (m, 1H), 6.91 (t, 1H), 6.75 (d, 1H), 6.67 (d, 1H), 6.48 (d, 1H), 4.97 (br s, 2H), 4.55 (s, 1H), 4.46 (d, 2H), 3.82 (s, 1H), 2.21-2.08 (m, 2H), 2.07-1.98 (m, 7H), 1.97-1.84 (m, 2H). MS (EI) for $C_{28}H_{31}N_5O_2$: 468 ($M^-$).

(2E): N-[8-(5-{[(phenylmethyl)amino]carbonyl}pyridin-2-yl)-8-azabicyclo[3.2.1]oct-3-endo-yl]benzene-1,4-dicarboxamide. Prepared according to the method of example 2 by using terephthalic acid monoamide in step 4. $^1$H-NMR (400 MHz, DMSO-$d_6$): 8.80 (t, 1H), 8.66 (s, 1H), 8.32 (d, 1H), 8.10 (s, 1H), 8.00-7.95 (m, 2H), 7.84-7.82 (m, 2H), 7.53 (s, 1H), 7.33-7.31 (m, 2H), 6.78 (d, 1H), 4.58 (s, 2H), 4.46 (d, 2H), 3.86 (s, 1H), 2.23-2.21 (m, 2H), 2.11-1.90 (m, 6H). MS (EI) for $C_{28}H_{29}N_5O_3$: 484 ($MH^+$).

(2F): 2-methyl-N1-[8-(5-{[(phenylmethyl)amino] carbonyl}pyridin-2-yl)-8-azabicyclo[3.2.1]oct-3-endo-yl] benzene-1,4-dicarboxamide. Prepared according to the method of example 2 by using 4-(aminocarbonyl)-2-methylbenzoic acid (synthesized according to reagent preparation 11) in step 4. $^1$H-NMR (400 MHz, DMSO-$d_6$): 8.82 (t, 1H), 8.66 (s, 1H), 8.34 (d, 1H), 8.01-7.98 (m, 2H), 7.75-7.72 (m, 2H), 7.43 (s, 1H), 7.43-7.31 (m, 3H), 7.29-7.14 (m, 2H), 6.77 (d, 1H), 6.59 (s, 1H), 4.56 (s, 2H), 4.46 (d, 2H), 3.87 (s, 1H), 2.37 (s, 3H), 2.22-2.20 (m, 2H), 2.12-2.08 (m, 2H), 1.99-1.87 (m, 4H). MS (EI) for $C_{29}H_{31}N_5O_3$: 496 ($M^-$).

(2G): 2-methyl-N-[8-(5-{[(phenylmethyl)amino]carbonyl}pyridin-2-yl)-8-azabicyclo[3.2.1]oct-3-endo-yl]benzene-1,3-dicarboxamide. Prepared according to the method of example 2 by using 3-(aminocarbonyl)-2-methylbenzoic acid (synthesized according to reagent preparation 10) in step 4. $^1$H-NMR (400 MHz, DMSO-$d_6$): 8.87 (t, 1H), 8.62 (d, 1H), 8.35 (d, 1H), 8.03 (dd, 1H), 7.76 (s, 1HO, 7.46 (s, 2H), 7.32-7.30 (m, 4H), 7.27 (s, 2H), 7.12 (s, 2H), 6.99 (d, 1H), 4.58 (s, 2H0, 4.46 (d, 2H), 3.87 (s, 1H), 2.32 (s, 3H), 2.23-2.20 (m, 2H), 2.11-1.99 (m, 4H), 1.97-1.86 (m, 2H). MS (EI) for $C_{29}H_{31}N_5O_3$: 498 ($MH^+$).

(2H): 6-[3-endo-({[4-(hydroxymethyl)phenyl]carbonyl}amino)-8-azabicyclo[3.2.1]oct-8-yl]-N-(pyridin-3-ylmethyl)pyridine-3-carboxamide. Prepared according to the method of example 2 by using 3-(aminomethyl)pyridine in step 2 and 4-(hydroxymethyl)benzoic acid in step 4. $^1$H-NMR (400 MHz, $CD_3OD$): 8.61 (s, 1H), 8.58 (s, 1H), 8.47 (s, 1H), 8.21 (d, 1H), 8.02 (d, 1H), 7.99 (d, 1H), 7.93-7.91 (m, 2H), 7.50-7.45 (m, 3H), 6.81 (d, 1H), 4.67 (s, 2H), 4.64 (s, 2H), 4.60 (s, 2H), 4.02 (s, 1H), 2.30-2.18 (m, 6H), 2.00-1.96 (m, 2H). MS (EI) for $C_{27}H_{29}N_5O_3$: 472 ($MH^+$).

(2I): N-[8-(5-{[(pyridin-3-ylmethyl)amino]carbonyl}pyridin-2-yl)-8-azabicyclo[3.2.1]oct-3-endo-yl]benzene-1,4-dicarboxamide. Prepared according to the method of example 2 by using 3-(aminomethyl)pyridine in step 2 and terephthalic acid monoamide in step 4. $^1$H-NMR (400 MHz, $CD_3OD$): 8.53 (d, 1H), 8.46 (s, 1H), 8.35 (d, 1H), 8.27 (d, 1H), 7.91-7.86 (m, 3H), 7.77-7.75 (m, 2H), 7.32 (t, 1H), 6.71 (d, 1H), 4.54 (brs, 2H), 4.49 (s, 2H), 3.92 (br s, 1H), 2.19-2.2.10 (m, 6H), 1.89-1.83 (m, 2H). MS (EI) for $C_{27}H_{28}N_6O_3$: 485 ($MH^+$).

(2J): 6-[3-endo-({[4-(hydroxymethyl)phenyl]carbonyl}amino)-8-azabicyclo[3.2.1]oct-8-yl]-N-[(5-methylpyrazin-2-yl)methyl]pyridine-3-carboxamide. Prepared according the method of example 2 by using 2-(aminomethyl)-5-methylpyrazine in step 2 and 4-(hydroxymethyl)benzoic acid in step 4. $^1$H-NMR (400 MHz, $CD_3OD$): 8.55 (s, 1H), 8.40-8.39 (m, 2H), 7.91 (dd, 1H), 7.68-7.65 (m, 2H), 7.37 (d, 2H), 6.68 (d, 1H), 4.58 (s, 2H), 4.57 (s, 2H), 4.54 (s, 2H), 3.92 (br s, 1H), 2.45 (s, 3H), 2.21-2.17 (m, 6H), 189-1.83 (m, 2H). MS (EI) for $C_{27}H_{30}N_6O_3$: 487 ($MH^+$).

(2K): N-{8-[5-({[(5-methylpyrazin-2-yl)methyl]amino}carbonyl)pyridin-2-yl]-8-azabicyclo[3.2.1]oct-3-endo-yl}benzene-1,4-dicarboxamide. Prepared according the method of example 2 by using 2-(aminomethyl)-5-methylpyrazine in step 2 and terephthalic acid monoamide in step 4. $^1$H-NMR (400 MHz, $CD_3OD$): 8.51-8.45 (m, 4H), 8.25 (d, 1H), 7.98-7.96 (m, 2H), 7.88-7.85 (m, 2H), 7.18 (d, 1H), 4.72 (s, 2H), 4.68 (s, 2H), 4.10 (br s, 1H), 2.54 (s, 3H), 2.38-2.24 (m, 6H), 2.16-2.12 (m, 2H). MS (EI) for $C_{27}H_{29}N_7O_3$: 500 ($MH^+$).

(2L): 6-(3-endo-{[(5-methyl-2,3-dihydro-1,4-benzodioxin-6-yl)carbonyl]amino}-8-azabicyclo[3.2.1]oct-8-yl)-N-(phenylmethyl)pyridine-3-carboxamide. Prepared according to the method of example 2 by using 5-methyl-2,3-dihydro-1,4-benzodioxine-6-carboxylic acid (see: J. Med. Chem. 1997, 40, 18-23) in step 5. $^1$H NMR (400 MHz, $d_6$-DMSO): 8.82-8.77 (m, 1H), 8.65 (s, 1H), 8.08 (d, 1H), 7.98 (dd, 1H), 7.35-7.28 (m, 4H), 7.26-7.21 (m, 1H), 6.81-6.74 (m, 3H), 4.54 (br s, 2H), 4.45 (d, 2H), 4.30-4.22 (m, 4H), 3.84-3.78 (m, 1H), 3.34 (s, 3H), 2.22-1.94 (m, 9H), 1.87-1.80 (m, 2H). MS (EI) for $C_{30}H_{32}N_4O_4$: 513 ($MH^+$).

(2M): 6-(3-endo-{[(4-methyl-1,3-benzodioxol-5-yl)carbonyl]amino}-8-azabicyclo[3.2.1]oct-8-yl)-N-(phenylmethyl)pyridine-3-carboxamide. Prepared according to the method of example 2 by using 4-methyl-1,3-benzodioxole-5-carboxylic acid (see: J. Med. Chem. 1997, 40, 18-23. Prepared using bromochloromethane in place of dibromoethane) in step 5. $^1$H NMR (400 MHz, $d_6$-DMSO): 8.82-8.77 (m, 1H), 8.65 (d, 1H), 8.12 (d, 1H), 7.98 (dd, 1H), 7.35-7.28 (m, 4H), 7.26-7.21 (m, 1H), 6.89 (d, 1H), 6.82 (d, 1H), 6.76 (d, 1H), 6.05 (s, 2H), 4.54 (br s, 2H), 4.45 (d, 2H), 3.84-3.78 (m, 1H), 3.34 (s, 3H), 2.24-2.17 (m, 5H), 2.11-1.95 (m, 4H), 1.88-1.81 (m, 2H). MS (EI) for $C_{29}H_{30}N_4O_4$: 499 ($MH^+$).

(2N): 6-(3-endo-{[(5-methyl-2,3-dihydro-1,4-benzodioxin-6-yl)carbonyl]amino}-8-azabicyclo[3.2.1]oct-8-yl)-N-{[4-(4-methylpiperazin-1-yl)phenyl]methyl}pyridine-3-carboxamide. Prepared as the acetate salt according to the method of example 2 by using 4-(4-methylpiperazin-1-yl)benzyl amine in step 2 and 5-methyl-2,3-dihydro-1,4-benzodioxine-6-carboxylic acid (J. Med. Chem. 1997, 40, pp 18-23) in step 5. $^1$H NMR (400 MHz, $d_6$-DMSO): 8.72-8.66 (m, 1H), 8.63 (d, 1H), 8.09 (d, 1H), 7.96 (dd, 1H), 7.15 (d, 2H), 6.88 (d, 2H), 6.81-6.72 (m, 3H), 4.54 (br s, 2H), 4.37-4.21 (m, 6H), 3.84-3.78 (m, 1H), 3.10-3.06 (m, 4H), 2.45-2.41 (m, 4H), 2.23-2.13 (m, 8H), 2.10-1.94 (m, 4H), 1.90-1.80 (m, 7H). MS (EI) for $C_{35}H_{42}N_6O_4$: 611 ($MH^+$).

(2O): 6-(3-endo-{[(7-methyl-1-benzofuran-6-yl)carbonyl]amino}-8-azabicyclo[3.2.1]oct-8-yl)-N-(phenylmethyl)pyridine-3-carboxamide. Prepared according to the method of example 2 by using 7-methyl-1-benzofuran-6-carboxylic acid (synthesized according to reagent preparation 15) in step 5. $^1$H NMR (400 MHz, $d_6$-DMSO): 8.82-8.78 (m, 1H), 8.66 (s, 1H), 8.26-8.24 (m, 1H), 8.10 (s, 1H), 8.00-7.97 (m, 1H), 7.56-7.53 (m, 1H), 7.35-7.22 (m, 5H), 7.00 (s, 1H), 6.79-6.75 (m, 1H), 4.57 (br s, 2H), 4.46 (d, 2H), 3.98 (m, 1H), 2.52 (s, 3H), 2.65-2.20 (m, 2H), 2.15-2.07 (m, 2H), 2.03-1.98 (m, 2H), 1.91-1.85 (m, 2H). MS (EI) for $C_{30}H_{30}N_4O_3$: 495 ($MH^+$).

(2P): 8-methyl-N-[8-(5-{[(phenylmethyl)amino]carbonyl}pyridin-2-yl)-8-azabicyclo[3.2.1]oct-3-endo-yl]quinoline-7-carboxamide. Prepared according to the method of example 2 by using 8-methylquinoline-7-carboxylic acid (see: US2006069144) in step 5. $^1$H NMR (400 MHz, $d_6$-DMSO): 8.99 (dd, 1H), 8.85-8.80 (m, 1H), 8.66 (d, 1H), 8.43 (d, 1H), 8.38 (dd, 1H), 8.00 (dd, 1H), 7.88 (d, 1H), 7.61-7.57 (m, 1H), 7.47 (d, 1H), 7.35-7.30 (m, 4H), 7.26-7.21 (m, 1H), 6.82-6.77 (m, 1H), 4.59 (br s, 2H), 4.46 (d, 2H), 3.99-3.93 (m, 1H), 2.76 (s, 3H), 2.28-2.13 (m, 4H), 2.03-1.98 (m, 2H), 1.92-1.86 (m, 2H). MS (EI) for $C_{31}H_{31}N_5O_2$: 506 ($MH^+$).

(2Q): 3-methyl-4-({[8-(5-{[(phenylmethyl)amino]carbonyl}pyridin-2-yl)-8-azabicyclo[3.2.1]oct-3-endo-yl]amino}carbonyl)phenyl carbamate. Synthesized as the trifluoroacetate salt according to the method of example 2 using 4-[(aminocarbonyl)oxy]-2-methylbenzoic acid (synthesized according to reagent preparation 12) in step 4. $^1$H NMR (400 MHz, DMSO): 9.00-8.93 (br s, 1H), 8.59-8.56 (s, 1H), 8.33-8.29 (s, 1H), 8.15-8.10 (d, 1H), 7.37-7.21 (m, 6H), 7.05-6.90 (m, 3H), 4.67-4.59 (br s, 2H), 4.50-4.45 (d, 2H), 4.40-4.00 (br s, 2H), 3.91-3.84 (br s, 2H), 2.36-2.32 (s, 3H), 2.31-2.23 (m, 2H), 2.18-2.08 (m, 2H), 2.05-1.99 (m, 2H), 1.97-1.89 (d, 2H). MS (EI) for $C_{29}H_31N_5O_4.C_2H_1O_2F_3$: 514 ($MH^+$).

(2R): 2-methyl-3-({[8-(5-{[(phenylmethyl)amino]carbonyl}pyridin-2-yl)-8-azabicyclo[3.2.1]oct-3-endo-yl]amino}carbonyl)phenyl carbamate. Synthesized as the trifluoroacetate salt according to the method of example 2 using 3-[(aminocarbonyl)oxy]-2-methylbenzoic acid (synthesized according to reagent preparation 12) in step 4. $^1$H NMR (400 MHz, $CD_3OD$): 8.51-8.48 (d, 1H), 8.48-8.46 (s, 1H), 8.28-8.23 (d, 1H), 7.38-7.12 (m, 8H), 4.72-4.67 (br s, 2H), 4.58-4.56 (s, 2H), 2.39-2.05 (m, 1H). MS (EI) for $C_{29}H_{31}N_5O_4.C_2H_1O_2F_3$: 514 ($MH^+$).

(2S): 6-[3-endo-({[4-(hydroxymethyl)-2-methylphenyl]carbonyl}amino)-8-azabicyclo[3.2.1]oct-8-yl]-N-(phenylmethyl)pyridine-3-carboxamide. Synthesized as the trifluoroacetate salt according to the method of example 2 using 4-(hydroxymethyl)-2-methylbenzoic acid (synthesized according to reagent preparation 13) in step 4.

$^1$H NMR (400 MHz, $CD_3OD$): 8.37-8.33 (d, 2H), 8.25-8.20 (d, 1H), 7.28-7.13 (m, 8H), 4.64-4.60 (br s, 2H), 4.52.4.50 (s, 2H), 4.49-4.47 (s, 2H), 4.03-3.97 (m, 1H), 2.33-2.30 (s, 3H), 2.29-2.00 (m, 8H). MS (EI) for $C_{29}H_{31}N_5O_4.C_2H_1O_2F_3$: 485 ($MH^+$).

(2T): 6-[3-endo-({[4-(hydroxymethyl)-2-methylphenyl]carbonyl}amino)-8-azabicyclo[3.2.1]oct-8-yl]-N-(pyridin-3-ylmethyl)pyridine-3-carboxamide. Synthesized as the trifluoroacetate salt according to the method of example 2 using (piperidin-3-yl)methylamine in step 2 and 4-(hydroxymethyl)-2-methylbenzoic acid (synthesized according to reagent preparation 13) in step 4. $^1$H NMR (400 MHz, $CD_3OD$): 8.86-8.81 (d, 1H), 8.76-8.70 (d, 1H), 8.52-8.47 (m, 2H), 8.29-8.23 (d, 1H), 7.99-7.93 (m, 1H), 7.36-7.30 (d, 2H), 7.27-7.21 (m, 3H), 4.76-4.69 (br s, 4H), 4.62-4.59 (s, 2H), 4.49-4.47 (s, 2H), 4.12-4.04 (m, 1H), 2.83-2.80 (s, 3H), 2.45-2.07 (m, 8H). MS (EI) for $C_{28}H_{31}N_5O_3.C_2H_1O_2F_3$: 486 ($MH^+$).

(2U): 6-{3-endo-[({4-[amino(imino)methyl]phenyl}carbonyl)amino]-8-azabicyclo[3.2.1]oct-8-yl}-N-(phenylmethyl)pyridine-3-carboxamide. Prepared as the trifluoroacetate salt according to the method of example 2 by using 4-amidinobenzoic acid hydrochloride in step 4. $^1$H NMR (400 MHz, methanol-$d_4$): 8.53 (d, 1H), 8.50 (d, 1H), 8.22 (dd, 1H), 8.00 (d, 2H), 7.90 (d, 2H), 7.33 (m, 5H), 7.26 (m, 1H), 7.13 (d, 1H), 4.71 (br s, 2H), 4.57 (s, 2H), 4.10 (m, 1H), 2.30 (m, 6H), 2.11 (d, 2H); MS (EI) for $C_{28}H_{30}N_6O_2$: 407 ($MH^+$).

(2V): 6-[3-endo-({[3-(methyloxy)-2-propylphenyl]carbonyl}amino)-8-azabicyclo[3.2.1]oct-8-yl]-N-(phenylmethyl)pyridine-3-carboxamide. Prepared as the trifluoroacetate salt according to the method of example 2 by using 3-methoxy-2-propylbenzoic acid (synthesized according to reagent preparation 18) in step 4. $^1$H NMR (400 MHz, methanol-$d_4$): 8.47 (d, 1H), 8.39 (d, 1H), 8.25 (dd, 1H), 7.33 (d, 1H), 7.27-7.16 (m, 3H), 7.02 (d, 1H), 6.90 (d, 1H), 4.68 (br s, 2H), 4.57 (s, 2H), 4.06 (m, 1H), 3.83 (s, 3H), 2.67 (m, 2H), 2.33 (m, 4H), 2.20 (m, 2H), 2.06 (d, 2H), 1.57 (m, 2H), 0.92 (t, 3H); MS (EI) for $C_{31}H_{36}N_4O_3$: 513 ($MH^+$).

(2W): 6-[3-endo-({[3-(methyloxy)-2-prop-2-en-1-ylphenyl]carbonyl}amino)-8-azabicyclo[3.2.1]oct-8-yl]-N-(phenylmethyl)pyridine-3-carboxamide. Prepared according to the method of example 2 by using 3-(methyloxy)-2-prop-2-en-1-ylbenzoic acid (synthesized according to reagent preparation 19) in step 4. $^1$H NMR (400 MHz, methanol-$d_4$): 8.46 (d, 1H), 8.31 (d, 1H), 8.26 (dd, 1H), 7.37-7.23 (m, 6H), 7.19 (d, 1H), 7.05 (d, 1H), 6.94 (d, 1H), 5.90 (m, 1H), 4.94 (m, 2H), 4.68 (br s, 2H), 4.57 (s, 2H), 4.05 (m, 1H), 3.84 (s, 3H), 3.51 (d, 2H), 2.31 (m, 4H), 2.18 (m, 2H), 2.07 (d, 2H); MS (EI) for $C_{31}H_{34}N_4O_3$: 511 ($MH^+$).

(2X): N4-(8-{5-[(cyclopentylamino)carbonyl]pyridin-2-yl}-8-azabicyclo[3.2.1]oct-3-endo-yl)-2-{[2-(methylsulfonyl)ethyl]amino}benzene-1,4-dicarboxamide. Prepared according to the method of example 2 by using cyclopentylamine in step 2 and 4-(aminocarbonyl)-3-{[2-(methylsulfonyl)ethyl]amino}benzoic acid (synthesized according to reagent preparation 39) in step 4. $^1$H NMR (400 MHz, methanol-$d_4$): 8.57 (d, 1H), 8.14 (d, 1H), 7.95 (dd, 1H), 7.67 (d, 1H), 7.13 (d, 1H), 7.01 (dd, 1H), 6.75 (d, 1H), 4.62 (br s, 2H), 4.30 (m, 1H), 4.00 (m, 1H), 3.81 (t, 2H), 3.47 (t, 2H), 3.01 (s, 3H), 2.24 (m, 6H), 1.97 (m, 4H), 1.78 (m, 2H), 1.60 (m, 4H); MS (EI) for $C_{29}H_{38}N_6O_5S$: 538 ($MH^+$).

(2Y): N4-(8-{5-[(cyclopentylamino)carbonyl]pyridin-2-yl}-8-azabicyclo[3.2.1]oct-3-endo-yl)-2-[(4-trans-hydroxycyclohexyl)amino]benzene-1,4-dicarboxamide. Prepared according to the method of example 2 by using cyclopentylamine in step 2 and 4-(aminocarbonyl)-3-[(trans-4-hydroxycyclohexyl)amino]benzoic acid (synthesized according to reagent preparation 39) in step 4. $^1$H NMR (400 MHz, methanol-$d_4$): 8.57 (d, 1H), 7.96 (dd, 1H), 7.62 (d, 1H), 7.07 (d, 1H), 6.89 (dd, 1H), 6.75 (d, 1H), 4.63 (br s, 2H), 4.30 (m, 1H), 4.00 (m, 1H), 3.63 (m, 1H), 3.41 (m, 1H), 2.20 (m, 8H), 1.99 (m, 6H), 1.78 (m, 2H), 1.60 (m, 4H), 1.38 (m, 4H); MS (EI) for $C_{32}H_{42}N_6O_4$: 575 ($MH^+$).

(2Z): N-[8-(5-{[(phenylmethyl)amino]carbonyl}pyridin-2-yl)-8-azabicyclo[3.2.1]oct-3-endo-yl]-1H-indole-6-carboxamide. Prepared according to the method of example 2 by using 1H-indole-6-carboxylic acid in step 4. $^1$H NMR (400 MHz, DMSO-$d_6$): 11.39 (s, 1H), 8.81 (t, 1H), 8.67 (d, 1H), 8.12 (d, 1H), 7.99 (dd, 1H), 7.88 (s, 1H), 7.59 (d, 1H), 7.50 (dd, 1H), 7.45 (dd, 1H), 7.32 (m, 4.5H), 7.24 (m, 0.5H), 6.78 (d, 1H), 6.49 (m, 1H), 4.60 (bs, 2H), 4.46 (d, 2H), 3.84 (m, 1H), 2.30 (m, 2H), 2.06 (m, 4H), 1.94 (d, 2H). MS (EI) for $C_{29}H_{29}N_5O_2$: 480 ($MH^+$).

(2AA): 1-methyl-N-[8-(5-{[(phenylmethyl)amino]carbonyl}pyridin-2-yl)-8-azabicyclo[3.2.1]oct-3-endo-yl]-1H-indole-4-carboxamide. Prepared according to the method of example 2 by using 1-methyl-1H-indole-4-carboxylic acid in step 4. $^1$H NMR (400 MHz, DMSO-$d_6$): 8.81 (t, 1H), 8.66 (d, 1H), 8.10 (d, 1H), 7.99 (dd, 1H), 7.61 (d, 1H) 7.42 (d, 1H), 7.38 (d, 1H), 7.32 (m, 4H), 7.24 (m, 2H), 6.78 (m, 2H), 4.60 (bs, 2H), 4.46 (d, 2H), 3.86 (m, 1H), 3.81 (s, 3H), 2.28 (m, 2H), 2.06 (m, 4H), 1.94 (d, 2H). MS (EI) for $C_{30}H_{31}N_5O_2$: 494 ($MH^+$).

(2AB): 6-(3-endo-{[(7-methyl-2,3-dihydro-1-benzofuran-6-yl)carbonyl]amino}-8-azabicyclo[3.2.1]oct-8-yl)-N-(phenylmethyl)pyridine-3-carboxamide. Isolated in trifluoroacetate salt form according to the method of example 2 by using 7-methyl-2,3-dihydro-1-benzofuran-6-carboxylic acid (synthesized according to reagent preparation 16) in step 3. $^1$H NMR (400 MHz, $d_6$-DMSO): 9.02 (m, 1H), 8.55 (d, 1H), 8.18 (m, 2H), 7.32 (m, 4H), 7.25 (m, 1H), 7.10 (m, 2H), 6.81 (d, 1H), 4.65 (broad s, 2H), 4.53 (t, 2H), 4.47 (d, 2H), 3.87 (m, 1H), 3.20 (t, 2H), 2.27 (m, 2H), 2.14 (s, 3H), 2.11 (m, 2H), 2.02 (m, 2H), 1.97 (d, 2H). MS (EI) for $C_{30}H_{32}N_4O_3$: 497 ($MH^+$).

(2AC): 6-(3-endo-{[(8-methyl-3,4-dihydro-2H-chromen-7-yl)carbonyl]amino}-8-azabicyclo[3.2.1]oct-8-yl)-N-(phenylmethyl)pyridine-3-carboxamide. Prepared according to the method of example 2 by using 8-methyl-3,4-dihydro-2H-chromene-7-carboxylic acid (Sawada, Y. et al, *Pest Management Science,* 2003, 59(1), 36-48.) in step 3. $^1$H NMR (400 MHz, $d_6$-DMSO): 8.79 (t, 1H), 8.63 (d, 1H), 8.10 (d, 1H), 7.91 (dd, 1H), 7.28 (m, 4H), 7.21 (m, 1H), 6.92 (d, 1H), 6.72 (t, 2H), 4.52 (broad s, 2H), 4.44 (d, 2H), 4.16 (t, 2H), 3.81 (m, 1H), 2.72 (t, 2H), 2.18 (m, 2H), 2.07 (s, 3H), 2.04 (m, 2H), 1.96 (m, 2H), 1.92 (m, 2H), 1.84 (d, 2H). MS (EI) for $C_{31}H_{34}N_4O_3$: 511 ($MH^+$).

(2AD): 4-methyl-N-[8-(5-{[(phenylmethyl)amino]carbonyl}pyridin-2-yl)-8-azabicyclo[3.2.1]oct-3-endo-yl]-1H-benzimidazole-5-carboxamide. Prepared according to the method of example 2 by using 7-methyl-1H-benzimidazole-6-carboxylic acid (synthesized according to reagent preparation 23) in step 3. $^1$H NMR (400 MHz, $d_6$-DMSO): 8.81 (m, 1H), 8.66 (dd, 1H), 8.23 (m, 1H), 8.14 (broad s, 1H), 7.98 (m, 1H), 7.31 (m, 4H), 7.23 (m, 1H), 6.76 (dd, 1H), 4.57 (broad s, 2H), 4.46 (t, 2H), 3.88 (m, 1H), 2.62 (m, 2H), 2.27 (m, 1H), 2.14 (m, 2H), 2.07 (m, 2H), 1.90 (m, 2H), 1.64 (d, 2H). MS (EI) for $C_{29}H_{30}N_6O_2$: 495 ($MH^+$).

(2AE): N-[8-(5-{[(phenylmethyl)amino]carbonyl}pyridin-2-yl)-8-azabicyclo[3.2.1]oct-3-endo-yl]-1H-benzimidazole-5-carboxamide. Isolated as the trifluoroacetate salt according to the method of example 2 by using 1H-benzimidazole-5-carboxylic acid in step 3. $^1$H NMR (400 MHz, $d_6$-DMSO): 9.07 (m, 1H), 8.60 (m, 1H), 8.21 (m, 2H), 7.96 (m, 2H), 7.34 (m, 4H), 7.26 (m, 1H), 7.15 (m, 1H), 4.71 (broad s, 2H), 4.49 (d, 2H), 3.95 (m, 1H), 2.79 (m, 2H), 2.35 (m, 1H), 2.15 (m, 1H), 2.08 (m, 4H). MS (EI) for $C_{28}H_{28}N_6O_2$: 481 ($MH^+$).

(2AF): 2-[(cyclopropylmethyl)amino]-N4-{8-[5-({[(3R)-1-(1-methylethyl)pyrrolidin-3-yl]amino}carbonyl)pyridin-2-yl]-8-azabicyclo[3.2.1]oct-3-endo-yl}benzene-1,4-dicarboxamide. Prepared according to the method of example 2 by using (R)-1-isopropylpyrrolidin-3-amine (synthesized according to reagent preparation 9) in step 2 and 4-(aminocarbonyl)-3-[(cyclopropylmethy)amino]benzoic acid (synthesized according to reagent preparation 39) in step 4. $^1$H NMR (400 MHz, $d_6$-DMSO): 8.62 (d, 1H), 8.32-8.24 (m, 2H), 8.17 (d, 1H), 7.96 (dd, 1H), 7.93 (br s, 1H), 7.67 (d, 1H), 7.30 (br s, 1H), 6.98 (d, 1H), 6.89 (dd, 1H), 6.78 (d, 1H), 4.58 (br s, 2H), 4.48-4.35 (m, 1H), 3.85-3.78 (m, 1H), 3.65-2.55 (m, 7H), 3.03 (dd, 2H), 2.25-2.12 (m, 2H), 2.12-1.97 (m, 4H), 1.95-1.86 (m, 2H), 1.29-1.04 (m, 7H), 0.54-0.49 (m, 2H), 0.27-0.22 (m, 2H); MS (EI) for $C_{32}H_{43}F_3N_7O_3$: 574 ($MH^+$).

(2AG): 5-[(1-ethylpropyl)amino]-N-{8-[5-({[(1-ethylpyrrolidin-2-yl)methyl]amino}carbonyl)pyridin-2-yl]-8-azabicyclo[3.2.1]oct-3-endo-yl}-2-methylbenzene-1,4-dicarboxamide. Prepared according to the method of example 2 by using 1-(ethylpyrrolidin-2-yl)methanamine in step 2 and 4-(aminocarbonyl)-2-methyl-5-[(1-ethylpropyl)amino]benzoic acid (synthesized according to reagent preparation 42) in step 4. $^1$H NMR (400 MHz, $d_6$-DMSO): 8.58 (d, 1H), 8.28 (d, 1H), 8.16 (t, 1H), 8.04 (d, 1H), 7.92 (dd, 1H), 7.84 (br s, 1H), 7.48 (s, 1H), 7.16 (br s, 1H), 6.74 (d, 1H), 6.56 (s, 1H), 4.54 (br s, 2H), 3.82 (br s, 1H), 3.28-3.18 (m, 1H), 3.06-2.96 (m, 2H), 2.88-2.77 (m, 1H), 2.58-2.50 (m, 1H), 2.30-2.20 (m, 3H), 2.18 (s, 3H), 2.16-1.94 (m, 5H), 1.92-1.83 (m, 3H), 1.82-1.72 (m, 1H), 1.68-1.42 (m, 7H), 1.04 (t, 3H), 0.88 (t, 6H); MS (EI) for $C_{34}H_{49}N_7O_3$: 604 ($MH^+$).

(2AH): N4-(8-{5-[(cyclopentylamino)carbonyl]pyridin-2-yl}-8-azabicyclo[3.2.1]oct-3-endo-yl)-2-{[3-{[2-(dimethylamino)ethyl]oxy}-4-(methyloxy)phenyl]amino}benzene-1,4-dicarboxamide. Prepared according to the method of example 2 by using cyclopentylamine in step 2 and 4-(aminocarbonyl)-3-{[3-{[2-(dimethylamino)ethyl]oxy}-4-(methyloxy)phenyl]amino}benzoic acid (prepared according to the methods in reagent preparation 40) in step 4. $^1$H NMR (400 MHz, $CD_3OD$): 8.56 (d, 1H), 7.94 (dd, 1H), 7.72 (d, 1H), 7.43 (d, 1H), 7.05-7.02 (m, 2H), 6.98-6.93 (m, 2H), 6.72 (d, 1H), 4.57 (br s, 2H), 4.36 (m, 3H), 3.93 (m, 1H), 3.86 (s, 3H), 3.42 (m, 2H), 2.89 (s, 6H), 2.21 (m, 2H), 2.09 (br s, 2H), 2.00 (m, 2H), 1.94 (s, 3H), 1.88 (d, 2H), 1.77 (m, 2H), 1.67-1.52 (m, 4H); MS (EI) for $C_{37}H_{47}N_7O_5$: 670 ($MH^+$).

(2AI): 6-[3-endo-({[2-iodo-3-(methyloxy)phenyl]carbonyl}amino)-8-azabicyclo[3.2.1]oct-8-yl]-N-(phenylmethyl)pyridine-3-carboxamide. Prepared according to the method of example 2 by using 2-iodo-3-methoxybenzoic acid (synthesized according to reagent preparation 21) in step 4. $^1$H NMR (400 MHz, d6-DMSO): 8.95 (br. s, 1H), 8.57 (s, 1H), 8.38-8.34 (d, 1H), 8.16-8.09 (d, 1H), 7.42-7.22 (m, 4H), 7.05-6.97 (m, 2H), 6.88-6.84 (d, 2H), 4.66-4.59 (m, 2H), 4.50-4.45 (d, 2H), 3.92-3.83 (m, 4H), 2.36-2.28 (m, 2H), 2.19-2.10 (m, 2H), 2.02-1.89 (m, 4H). MS (EI) for $C_{28}H_{29}IN_4O_3$: 597 ($MH^+$).

(2AJ): 2,6-dimethyl-N1-[8-(5-{[(phenylmethyl)amino]carbonyl}pyridin-2-yl)-8-azabicyclo[3.2.1]oct-3-endo-yl]benzene-1,4-dicarboxamide. Prepared according to the method of example 2 by using 4-(aminocarbonyl)-2,6-dimethylbenzoic acid in step 4. $^1$H NMR (400 MHz, d6-DMSO): 8.83-8.77 (m, 1H), 8.66 (s, 1H), 8.41-8.37 (d, 1H), 8.01-7.96 (d, 1H), 7.92 (s, 1H), 7.56 (s, 2H), 7.36-7.21 (m, 6H), 6.78-6.74 (d, 1H), 4.59-4.53 (m, 2H), 4.48-4.44 (d, 2H), 3.96-3.91 (m, 1H), 2.26 (s, 6H), 2.21-2.11 (m, 4H), 2.00-1.91 (m, 2H), 1.83-1.75 (m, 2H). MS (EI) for $C_{30}H_{33}N_5O_3$: 512 ($MH^+$).

(2AK): 2-[(4-trans-hydroxycyclohexyl)amino]-N4-{8-[5-({[1-(1-methylethyl)pyrrolidin-3-yl]amino}carbonyl)pyridin-2-yl]-8-azabicyclo[3.2.1]oct-3-endo-yl}benzene-1,4-dicarboxamide. Prepared according to the method of example 2 by using (3R)-1-(1-methylethyl)pyrrolidin-3-amine in step 2 (synthesized according to reagent preparation 9) and 4-(aminocarbonyl)-3-[(trans-4-hydroxycyclohexyl)amino]-benzoic acid (synthesized according to reagent preparation 39) in step 4. $^1$H NMR (400 MHz, d6-DMSO): 8.63-8.60 (d, 1H), 8.24-8.16 (m, 3H), 8.00-7.87 (m, 2H), 7.68-7.63 (d, 1H), 7.31-7.25 (br. s, 1H), 6.96 (s, 1H), 6.85-6.80 (d, 1H), 6.78-6.73 (d, 1H), 4.64-4.51 (m, 3H), 4.39-4.29 (m, 2H), 3.86-3.80 (m, 1H), 2.84-2.87 (m, 2H), 2.70-2.61 (m, 2H), 2.47-2.40 (m, 2H), 2.38-2.30 (m, 2H), 2.28-2.20 (m, 2H), 2.12-1.92 (m, 4H), 1.79-1.69 (m, 2H), 1.37-1.17 (m, 6H), 1.06-0.99 (m, 6H), 0.97-0.93 (m, 2H). MS (EI) for $C_{34}H_{47}N_7O_4$: 618 ($MH^+$).

(2AL): 6-[3-endo-({[4-(hydroxymethyl)phenyl]carbonyl}amino)-8-azabicyclo[3.2.1]oct-8-yl]-N-(phenylmethyl)pyridine-3-carboxamide. Prepared according to the method of example 2 by using 4-(hydroxymethyl)benzoic acid in step 4. $^1$H NMR (400 MHz, Methanol-$d_4$): 8.62 (d, 1H), 7.99 (dd, 1H), 7.79-7.74 (m, 2H), 7.48-7.44 (m, 2H), 7.37-7.28 (m, 4H), 7.27-7.20 (m, 1H), 6.77 (d, 1H), 4.67 (s, 2H), 4.62 (br s, 2H), 4.55 (s, 2H), 4.05-3.97 (m, 1H), 2.35-2.09 (m, 6H), 1.96 (d, 2H); MS (EI) for $C_{28}H_{30}N_4O_3$: 471 ($MH^+$).

(2AO): 6-(3-endo-{[(2-amino-6-chloro-9H-purin-9-yl)acetyl]amino}-8-azabicyclo[3.2.1]oct-8-yl)-N-(phenylmethyl)pyridine-3-carboxamide. Prepared as the trifluoroacetate salt according to the method of example 2 by using 2-amino-6-chloro-9H-purine-9-acetic acid in step 4. $^1$H NMR (400 MHz, Methanol-$d_4$): 8.45 (d, 1H), 8.39 (d, 1H), 8.25 (dd, 1H), 8.07 (s, 1H), 7.18 (d, 1H), 4.67 (br s, 2H), 3.99-3.91 (m, 1H), 3.33-3.28 (s, 2H), 2.38-2.16 (m, 6H), 1.99 (d, 2H); MS (EI) for $C_{27}H_{28}ClN_9O_2$: 456 ($MH^+$).

(2AP): 6-[3-endo-({[2-methyl-3,4-bis(methyloxy)phenyl]carbonyl}amino)-8-azabicyclo[3.2.1]oct-8-yl]-N-(phenylmethyl)pyridine-3-carboxamide. Prepared as the trifluoroacetate salt according to the method of example 2 by using 3,4-dimethoxy-2-methylbenzoic acid (synthesized according to reagent preparation 17) in step 4. $^1$H NMR (400 MHz, Methanol-$d_4$): 8.42 (d, 1H), 8.36-8.29 (m, 2H), 7.38-7.23 (m, 5H), 6.94 (s, 1H), 6.84 (s, 1H), 4.72 (br s, 2H), 4.57 (s, 2H), 4.12-4.05 (m, 1H), 3.85-3.83 (m, 6H), 2.45-2.20 (m, 9H), 2.14 (d, 2H); MS (EI) for $C_{30}H_{34}N_4O_4$: 515 ($MH^+$).

(2AQ): 6-[3-endo-({[2-bromo-3-(methyloxy)phenyl]carbonyl}amino)-8-azabicyclo[3.2.1]oct-8-yl]-N-(phenylmethyl)pyridine-3-carboxamide. Prepared according to the method of example 2 by using 2-bromo-3-methoxybenzoic acid (synthesized according to reagent preparation 20) in step 4. $^1$H NMR (400 MHz, DMSO-$d_6$): 8.80 (t, 1H), 8.65 (d, 1H), 8.38 (d, 1H), 7.98 (dd, 1H), 7.39 (t, 1H), 7.36-7.28 (m, 4H), 7.27-7.20 (m, 1H), 7.14 (dd, 1H), 6.91 (dd, 1H), 6.76 (d, 1H), 4.54 (br s, 2H), 4.46 (d, 2H), 3.90-3.80 (m, 4H), 2.30-2.20 (m, 2H), 2.15-2.04 (m, 2H), 2.00-1.89 (m, 2H), 1.83 (d, 2H); MS (EI) for $C_{28}H_{29}BrN_4O_3$: 547 (M−H).

(2AR): 4-methyl-N-(8-{5-[({[4-(4-methylpiperazin-1-yl) phenyl]methyl}amino)carbonyl]pyridin-2-yl}-8-azabicyclo [3.2.1]oct-3-endo-yl)-1H-benzimidazole-5-carboxamide. Prepared as the trifluoroacetate salt according to the method of example 2 by using 7-methyl-1H-benzimidazole-6-carboxylic acid (synthesized according to reagent preparation 23) in step 4. $^1$H NMR (400 MHz, Methanol-$d_4$): 9.38 (s, 1H), 8.58 (d, 1H), 8.49 (d, 1H), 8.22 (dd, 1H), 7.72 (d, 1H), 7.59 (d, 1H), 7.32-7.28 (m, 2H), 7.16 (d, 1H), 7.02-6.98 (m, 2H), 4.71 (br s, 2H), 4.49 (s, 2H), 4.20-4.09 (m, 1H), 3.87-3.78 (m, 2H), 3.64-3.55 (m, 2H), 3.29-3.20 (m, 2H), 3.07-2.94 (m, 5H), 2.69 (s, 3H), 2.43-2.16 (m, 6H), 2.09 (d, 2H); MS (EI) for $C_{34}H_{40}N_8O_2$: 593 ($MH^+$).

(2AS): N4-(8-{5-[(cyclopentylamino)carbonyl]pyridin-2-yl}-8-azabicyclo[3.2.1]oct-3-endo-yl)-2-[(cyclopropylmethyl)amino]benzene-1,4-dicarboxamide. Prepared according to the method of example 2 by using 4-aminocarbonyl-3-(cyclopropylmethyl)benzoic acid (synthesized according to reagent preparation 39) in step 4.1H NMR (400 MHz, DMSO-$d_6$): 8.59 (d, 1H), 8.25 (t, 1H), 8.15 (d, 1H), 8.01 (d, 1H), 7.96-7.90 (m, 2H), 7.67 (d, 1H), 7.28 (br s, 1H), 6.98 (s, 1H), 6.88 (dd, 1H), 6.75 (d, 1H), 4.55 (br s, 2H), 4.23-4.16 (m, 1H), 3.85-3.78 (m, 1H), 3.04 (t, 2H), 2.25-1.79 (m, 10H), 1.76-1.43 (m, 6H), 1.17-1.05 (m, 1H), 0.54-0.48 (m, 2H), 0.27-0.22 (m, 2H); MS (EI) for $C_{30}H_{38}N_6O_3$: 531 ($MH^+$).

2(AT): 6-(3-endo-{[(2,3-dimethylphenyl)carbonyl] amino}-8-azabicyclo[3.2.1]oct-8-yl)-N-(phenylmethyl)pyridine-3-carboxamide. Prepared according to the method of example 2 by using 2,3-dimethylbenzoic acid in step 4. $^1$H NMR (400 MHz, DMSO-$d_6$): 8.81-8.79 (m, 1H), 8.65 (d, 1H), 8.23 (d, 1H), 7.97 (dd, 1H), 7.33-7.24 (m, 3H), 7.23-7.07 (m, 3H), 6.76 (d, 1H), 4.55 (br s, 2H), 4.47 (s, 2H), 3.85 (br s, 1H), 2.22 (s, 3H), 2.20 (s, 2H), 2.11 (s, 3H), 2.09-2.08 (m, 2H), 1.98-1.97 (m, 2H), 1.87-1.84 (m, 2H). MS (EI) for $C_{29}H_{32}N_4O_2$: 469 ($MH^+$).

2(AU): 2-[(cyclopropylmethyl)amino]-N4-[8-(5-{[methyl (methyloxy)amino]carbonyl}pyridin-2-yl)-8-azabicyclo [3.2.1]oct-3-endo-yl]benzene-1,4-dicarboxamide. Prepared according to the method of example 2 by using N,O-dimethylhydroxylamine hydrochloride in step 2 and 4-(aminocarbonyl)-3-[(cyclopropylmethyl)amino]benzoic acid (synthesized according to reagent preparation 39) in step 4. $^1$H NMR (400 MHz, methanol-$d_4$): 8.55 (d, 1H), 7.93 (dd, 1H), 7.63 (d, 1H), 7.05 (d, 1H), 6.91 (dd, 1H), 6.75 (d, 1H), 4.63 (br s, 2H), 4.00 (m, 1H), 3.64 (s, 3H), 3.35 (s, 3H), 3.08 (d, 2H), 2.24 (m, 6H), 1.97 (d, 2H), 1.15 (m, 1H), 0.58 (m, 2H), 0.29 (m, 2H); MS (EI) for $C_{27}H_{34}N_6O_4$: 507 ($MH^+$).

SYNTHETIC SCHEME 3:

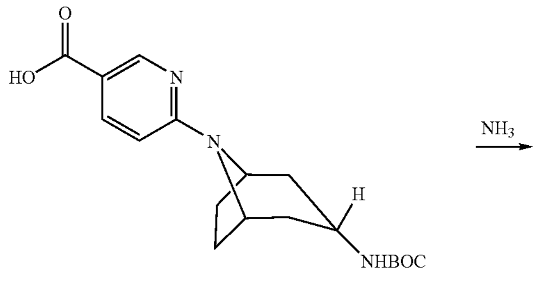

A

-continued

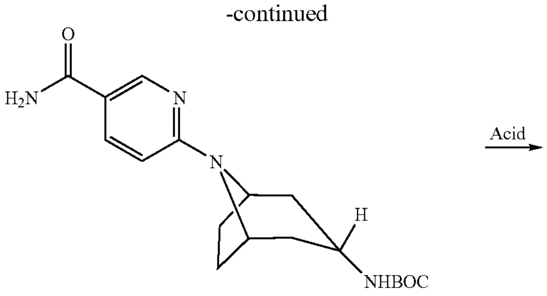

B

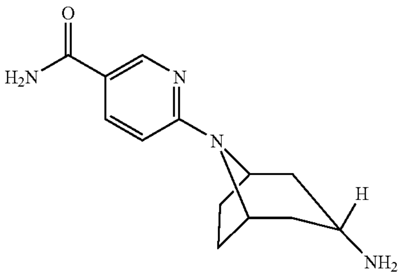

C

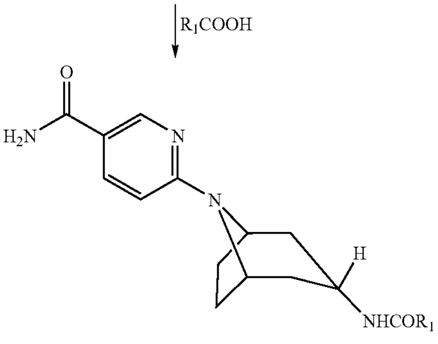

D

Scheme 3 generally describes the synthesis of all of the compound(s) listed in Example 3, wherein $R_1$ is as defined in the specification.

In Scheme 3, ammonia is added to compound (A) under suitable reaction conditions to form compound (B). Compound B is then deprotected under acidic conditions, such as with the use of HCl, to remove BOC and form compound (C). To compound (C) is added $R_1COOH$ under appropriate reaction conditions and with a suitable coupling reagent, such as HATU, to condense and form the amide bond in compound (D).

Example 3

6-[3-endo-({[2-fluoro-3-(methyloxy)phenyl] carbonyl}amino)-8-azabicyclo[3.2.1]oct-8-yl]pyridine-3-carboxamide STEP 1: To 6-(3-endo-(tert-butoxycarbonylamino)-8-azabicyclo[3.2.1]octan-8-yl)nicotinic acid (prepared in example 2) (4.43 g, 12.8 mmol) in THF (100 ml) was added triethylamine (2.69 ml, 19.2 mmol) and isobutyl chloroformate (1.67 ml, 13.4 mmol). The mixture was stirred at 0° C. for 1 hour, at which time a 28% solution of concentrated aqueous ammonia (20 ml) was added. The reaction mixture was stirred for 3 hours then the volume was reduced in vacuo. The resultant mixture was diluted with water and extracted with ethyl acetate. The organic layer was dried over anhydrous sodium sulfate, filtered, concentrated in vacuo to afford (1.85 g, 42% yield) of tert-butyl 8-(5-carbamoylpyridin-2-yl)-8-azabicyclo[3.2.1]octan-3-endo-ylcarbamate, which was used without further purification. $^1$H NMR (400 MHz, DMSO-$d_6$): 8.60 (s, 1H), 7.94-7.88 (d, 1H), 7.71 (s, 1H), 7.09 (s, 1H), 6.86 (s, 1H), 6.72-6.67 (d, 1H), 4.52-4.40 (m, 2H), 3.45-3.39 (m, 1H), 2.15-2.07 (m, 2H), 2.02-1.87 (m, 2H), 1.86-1.87 (m, 2H), 1.75-1.66 (m, 2H), 1.39 (s, 9H). MS (EI) for $C_{18}H_{26}N_4O_3$: 347 (MH$^+$).

STEP 2: To tert-butyl 8-(5-carbamoylpyridin-2-yl)-8-azabicyclo[3.2.1]octan-3-endo-ylcarbamate (1.85 g, 5.3 mmol) in methanol (20 ml) was added a solution of 4N hydrogen chloride in dioxane (2.65 ml) and the reaction mixture refluxed for five minutes. After cooling to room temperature, the reaction mixture was concentrated and dried to afford 6-(3-endo-amino-8-azabicyclo[3.2.1]octan-8-yl)nicotinamide as the hydrochloride salt (1.31 g, 100% yield). MS (EI) for $C_{13}H_{18}N_4O$: 247 (MH$^+$).

STEP 3: A mixture of tert-butyl 8-(5-carbamoylpyridin-2-yl)-8-azabicyclo[3.2.1]octan-3-endo-ylcarbamate hydrochloride salt (0.050 g, 0.157 mmol), 2-fluoro-3-methoxybenzoic acid (0.027 g, 0.157 mmol), HOAt (0.314 ml, 0.5 M solution in dimethylformamide, 0.157 mmol), HATU (0.060 g, 0.157 mmol), and N-methylmorpholine (0.069 ml, 0.628 mmol) in dimethylformamide (0.5 mL) was stirred at room temperature for 16 h. The reaction mixture was poured into water (2 ml) and the resulting precipitate was collected by filtration. The filter cake was washed with water (2×1 mL), and dried to give 6-[3-endo-({[2-fluoro-3-(methyloxy)phenyl]carbonyl}amino)-8-azabicyclo[3.2.1]oct-8-yl]pyridine-3-carboxamide (0.038 g, 61% yield). $^1$H NMR (400 MHz, $d_6$-DMSO): 8.62 (d, 1H), 8.41 (d, 1H), 7.94 (dd, 1H), 7.74 (br s, 1H), 7.36 (t, 1H), 7.20 (dd, 1H), 7.12 (br s, 1H), 6.95 (dd, 1H), 6.73 (d, 1H), 4.54 (br s, 2H), 3.90-3.82 (m, 4H), 2.28-2.18 (m, 2H), 2.14-2.03 (m, 2H), 2.00-1.88 (m, 2H), 1.83 (d, 2H); MS (EI) for $C_{21}H_{23}ClN_4O_3$: 415 (MH$^+$).

Using analogous synthetic techniques and substituting with alternative starting reagents, the following compounds [(3B)-(3Q)] were prepared. Alternative starting materials were obtained commercially unless otherwise indicated.

(3B): 6-[3-endo-({[2-methyl-3-(methyloxy)phenyl]carbonyl}amino)-8-azabicyclo[3.2.1]oct-8-yl]pyridine-3-carboxamide. Prepared according to the method of example 3 by using 2-methyl-3-methoxybenzoic acid in step 3. $^1$H NMR (400 MHz, DMSO-$d_6$): 8.62 (d, 1H), 8.22 (d, 1H), 7.94 (dd, 1H), 7.74 (br s, 1H), 7.23 (t, 1H), 7.12 (br s, 1H), 7.02 (d, 1H), 6.86 (d, 1H), 6.73 (d, 1H), 4.54 (br s, 2H), 3.84 (m, 1H), 3.80 (s, 3H), 2.20 (m, 2H), 2.14 (s, 3H), 2.08 (m, 2H), 1.96 (m, 2H), 1.84 (d, 2H); MS (EI) for $C_{22}H_{26}N_4O_3$: 395 (MH$^+$).

(3C): 6-[3-endo-({[2-chloro-3-(methyloxy)phenyl]carbonyl}amino)-8-azabicyclo[3.2.1]oct-8-yl]pyridine-3-carboxamide. Prepared according to the method of example 3 by using 2-chloro-3-methoxybenzoic acid in step 3. $^1$H NMR (400 MHz, $d_6$-DMSO): 8.62 (d, 1H), 8.38-8.34 (m, 1H), 7.94 (dd, 1H), 7.74 (br s, 1H), 7.31-7.25 (m, 1H), 7.23-7.16 (m, 1H), 7.12 (br s, 1H), 7.09-7.03 (m, 1H), 6.73 (d, 1H), 4.55 (br s, 2H), 3.87 (s, 3H), 2.28-2.17 (m, 2H), 2.12-1.90 (m, 4H), 1.84 (d, 2H); MS (EI) for $C_{21}H_{23}FN_4O_3$: 399 (MH$^+$).

(3D): 6-(3-endo-{[(4-amino-2-methylphenyl)carbonyl]amino}-8-azabicyclo[3.2.1]oct-8-yl)pyridine-3-carboxamide. Prepared as the acetate salt according to the method of example 3 by using 4-amino-2-methylbenzoic acid in step 3. $^1$H NMR (400 MHz, $CD_3OD$): 8.62 (s, 1H), 8.01-7.96 (d, 1H), 7.18-7.14 (d, 1H), 6.77-6.73 (d, 1H), 6.55-6.50 (m, 2H), 4.64-4.58 (br. s, 2H), 4.00-3.93 (m, 1H), 2.32 (s, 3H), 2.31-2.11 (m, 6H), 1.91 (s, 3H), 1.90-1.88 (m, 2H). MS (EI) for $C_{21}H_{25}N_5O_2$: 380 (MH$^+$).

(3E): 6-[3-endo-({[4-(hydroxymethyl)phenyl]carbonyl}amino)-8-azabicyclo[3.2.1]oct-8-yl]pyridine-3-carboxamide. Prepared according to the method of example 3 by using 4-(hydroxymethyl)benzoic acid in step 3. $^1$H NMR (400 MHz, $d_6$-DMSO): 8.62 (d, 1H), 8.15 (d, 1H), 7.95 (dd, 1H), 7.79-7.70 (m, 3H), 7.41 (d, 2H), 7.12 (br s, 1H), 6.75 (d, 1H), 5.32 (t, 1H), 4.62-4.52 (m, 4H), 3.88-3.82 (m, 1H), 2.26-2.16 (m, 2H), 2.13-1.86 (m, 6H); MS (EI) for $C_{21}H_{24}N_4O_3$: 379 (M−H).

(3F): N-{8-[5-(aminocarbonyl)pyridin-2-yl]-8-azabicyclo[3.2.1]oct-3-endo-yl}benzene-1,4-dicarboxamide. Prepared according to the method of example 3 by using terephthalic acid monoamide in step 3. $^1$H NMR (400 MHz, $d_6$-DMSO): 8.54 (br s, 1H), 8.16 (d, 1H), 8.12-8.04 (m, 1H), 7.90 (br s, 1H), 7.47 (d, 2H), 7.41 (d, 2H), 7.38-7.26 (m, 2H), 6.99 (br s, 1H), 4.64 (br s, 2H), 4.53 (s, 2H), 3.92-3.85 (m, 1H), 3.83 (s, 3H), 2.30-2.20 (m, 2H), 2.18-1.92 (m, 6H); MS (EI) for $C_{22}H_{26}N_4O_4$: 409 (M−H).

(3G): 6-[3-endo-({[4-(hydroxymethyl)-3-(methyloxy)phenyl]carbonyl}-amino)-8-azabicyclo[3.2.1]oct-8-yl]pyridine-3-carboxamide. Prepared as the trifluoroacetate salt according to the method of example 3 by using 4-(hydroxymethyl)-3-methoxybenzoic acid (synthesized according to reagent preparation 24) in step 3. $^1$H NMR (400 MHz, $d_6$-DMSO): 8.62 (d, 1H), 8.32 (d, 1H), 8.10 (br s, 1H), 7.98-7.92 (m, 3H), 7.86-7.80 (m, 2H), 7.75 (br s, 1H), 7.53 (br s, 1H), 7.13 (br s, 1H), 6.75 (d, 1H), 4.57 (br s, 2H), 3.91-3.83 (m, 1H), 2.28-2.17 (m, 2H), 2.14-1.96 (m, 4H), 1.91 (d, 2H); MS (EI) for $C_{22}H_{23}N_5O_3$: 392 (M−H).

(3J): 6-[3-endo-({[2-(4-hydroxybut-1-yn-1-yl)-3-(methyloxy)phenyl]-carbonyl}amino)-8-azabicyclo[3.2.1]oct-8-yl]pyridine-3-carboxamide. Prepared according to the method of example 3 by using 2-(4-hydroxybut-1-ynyl)-3-methoxybenzoic acid (synthesized according to reagent preparation 28) in step 3. $^1$H NMR (400 MHz, $d_6$-DMSO: 8.61 (d, 1H), 8.21 (d, 1H), 7.95 (dd, 1H), 7.74 (br s, 1H), 7.33 (t, 1H), 7.15-7.06 (m, 2H), 6.94 (d, 1H), 6.73 (d, 1H), 4.83 (br s, 1H), 4.55 (br s, 2H), 3.89-3.84 (m, 1H), 3.82 (s, 3H), 3.58-3.52 (m, 2H), 2.55 (t, 2H), 2.26-2.20 (m, 2H), 2.15-2.05 (m, 2H), 1.97-1.92 (m, 2H), 1.83 (d, 2H); MS (EI) for $C_{25}H_{28}N_4O_4$: 449 (MH$^+$).

(3K): N4-{8-[5-(aminocarbonyl)pyridin-2-yl]-8-azabicyclo[3.2.1]oct-3-endo-yl}-2-{[2-(methyloxy)ethyl]amino}benzene-1,4-dicarboxamide. Prepared according to the method of example 3 by using 4-aminocarbonyl-3-(2-methoxyethylamino)benzoic acid (synthesized according to reagent preparation 39) in step 3. $^1$H NMR (400 MHz, $d_4$-MeOH): 8.53 (d, 1H), 7.89 (dd, 1H), 7.54 (d, 1H), 7.80 (d, 1H), 6.84 (dd, 1H), 6.66 (d, 1H), 4.54 (br, 2H), 3.91 (tr, 1H), 2.55 (tr, 2H), 3.30 (tr, 2H), 3.29 (s, 3H), 2.20-2.09 (m, 7H), 1.89 (m, 2H); MS (EI) for $C_{24}H_{30}N_6O_4$: 467 (MH$^+$).

(3L): N4-{8-[5-(aminocarbonyl)pyridin-2-yl]-8-azabicyclo[3.2.1]oct-3-endo-yl}-2-[(2-morpholin-4-ylethyl)oxy-benzene-1,4-dicarboxylate. Prepared according to the method of example 3 by using 4-aminocarbonyl-3-(2-morpholinoethoxy)benzoic acid (synthesized according to reagent preparation 27) in step 3. $^1$HNMR (400 MHz, $d_4$-MeOH): 8.50 (d, 1H), 8.40 (d, 1H), 8.23 (dd, 1H), 7.68 (d, 1H), 7.62 (s, 1H), 7.55 (d, 1H), 7.15 (d, 1H), 4.72 (s, 2H), 4.61 (s, 2H), 4.09-3.99 (m, 4H), 3.62-3.60 (m, 4H), 2.37-2.26 (m, 6H), 2.15 (d, 2H). MS (EI) for $C_{27}H_{34}N_6O_5$: 523 (MH$^+$).

(3M): N4-{8-[5-(aminocarbonyl)pyridin-2-yl]-8-azabicyclo[3.2.1]oct-3-endo-yl}-2-[(4-hydroxycyclohexyl)amino]benzene-1,4-dicarboxamide. Prepared according to the method of example 3 by using 4-(aminocarbonyl)-3-[(trans-4-hydroxycyclohexyl)amino]benzoic acid (synthesized according to reagent preparation 39) in step 3. $^{1}H$ NMR (400 MHz, DMSO-$d_6$): 8.62 (d, 1H), 8.20 (m, 2H), 7.95 (dd, 1H), 7.91 (br s, 1H), 7.75 (br s, 1H), 7.66 (d, 1H), 7.27 (br s, 1H), 7.12 (br s, 1H), 7.06 (br s, 1H), 6.96 (s, 1H), 6.83 (d, 1H), 6.75 (d, 1H), 4.60 (d, 1H), 4.57 (br s, 2H), 3.83 (m, 1H), 3.48 (m, 1H), 2.24 (m, 2H), 2.10-1.81 (m, 10H), 1.25 (m, 4H); MS (EI) for $C_{27}H_{34}N_6O_4$: 507 ($MH^+$).

(3N): 2-(acetylamino)-N4-{8-[5-(aminocarbonyl)pyridin-2-yl]-8-azabicyclo[3.2.1]oct-3-endo-yl}benzene-1,4-dicarboxamide. Prepared according to the method of example 3 by using 3-(acetylamino)-4-(aminocarbonyl)benzoic acid (synthesized according to reagent preparation 29) in step 3. $^{1}H$ NMR (400 MHz, $d_4$-MeOH): 8.68 (d, 1H), 8.53 (d, 1H), 7.89 (dd, 1H), 7.73 (d, 1H), 7.42 (dd, 1H) 6.67 (d, 1H), 4.54 (br, 2H), 3.93 (tr, 1H), 2.18 (m, 5H), 2.10 (s, 3H), 2.08 (m, 3H), 1.86 (m, 2H); MS (EI) for $C_{23}H_{26}N_6O_4$: 451 ($MH^+$).

(3O): N4-{8-[5-(aminocarbonyl)pyridin-2-yl]-8-azabicyclo[3.2.1]oct-3-endo-yl}-1H-indole-4,7-dicarboxamide. Prepared according to the method of example 3 by using 7-carbamoyl-1H-indole-4-carboxylic acid (synthesized according to reagent preparation 30) in step 3. $^{1}H$ NMR (400 MHz, DMSO-$d_6$): 11.28 (s, 1H), 8.64 (s, 1H), 8.59 (d, 1H), 8.22 (d, 1H), 8.18 (bs, 1H), 8.00 (dd, 1H), 7.74 (d, 1H), 7.52 (bs, 1H), 7.42 (s, 1H), 7.32 (m, 2H), 6.78 (bs, 1H), 6.76 (d, 1H), 4.54 (bs, 2H), 3.84 (m, 1H), 2.28 (m, 2H), 2.08 (m, 4H), 1.96 (m, 2H). MS (EI) for $C_{23}H_{24}N_6O_3$: 432 ($MH^+$).

(3P): N4-{8-[5-(aminocarbonyl)pyridin-2-yl]-8-azabicyclo[3.2.1]oct-3-endo-yl}-2-{[2-(methylsulfonyl)ethyl]amino}benzene-1,4-dicarboxamide. Prepared according to the method of example 3 by using 4-(aminocarbonyl)-3-{[2-(methylsulfonyl)ethyl]amino}benzoic acid (synthesized according to reagent preparation 39) in step 3. $^{1}H$ NMR (400 MHz, DMSO-$d_6$): 8.64 (d, 1H), 8.32 (t, 1H), 8.19 (d, 1H), 7.95 (m, 2H), 7.75 (br s, 1H), 7.69 (d, 1H), 7.36 (br s, 1H), 7.12 (br s, 1H), 7.01 (s, 1H), 7.01 (s, 1H), 6.95 (d, 1H), 6.75 (d, 1H), 4.57 (br s, 2H), 3.84 (m, 1H), 3.66 (m, 2H), 3.46 (t, 2H), 3.03 (s, 3H), 2.21 (m, 2H), 2.08 (m, 2H), 2.00 (m, 2H), 1.90 (d, 2H); MS (EI) for $C_{24}H_{30}N_6O_5S$: 515 ($MH^+$).

(3Q): N4-{8-[5-(aminocarbonyl)pyridin-2-yl]-8-azabicyclo[3.2.1]oct-3-endo-yl}-2-(cyclobutylamino)benzene-1,4-dicarboxamide. Prepared according to the method of example 3 by using 4-(aminocarbonyl)-3-[(cyclobutyl)amino]benzoic acid (synthesized according to reagent preparation 39) in step 3. $^{1}H$ NMR (400 MHz, $d_6$-DMSO: 8.62 (d, 1H), 8.31 (d, 1H), 8.18 (d, 1H), 7.98-7.92 (m, 2H), 7.74 (br s, 1H), 7.67 (d, 1H), 7.32 (br s, 1H), 7.12 (br s, 1H), 6.89 (d, 1H), 6.85 (s, 1H), 6.75 (d, 1H), 4.57 (br s, 2H), 4.01-3.91 (m, 1H), 3.86-3.79 (m, 1H), 2.44-2.33 (m, 2H), 2.26-2.16 (m, 2H), 2.13-1.70 (m, 10H); MS (EI) for $C_{25}H_{30}N_6O_3$: 463 ($MH^+$).

SYNTHETIC SCHEME 4:

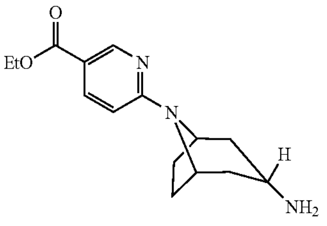

A

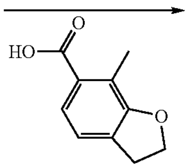

B

-continued

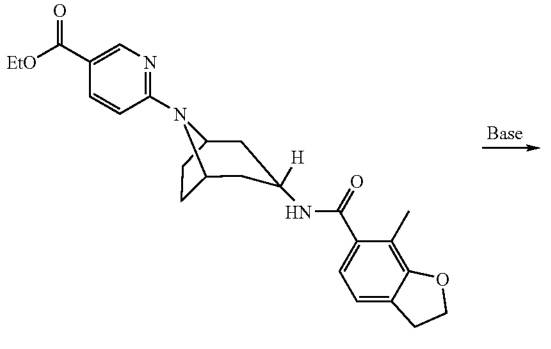

C

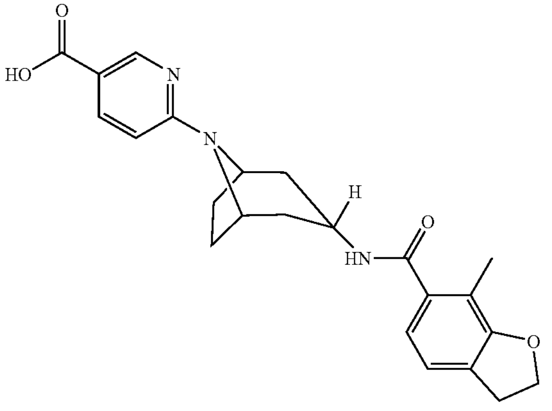

D

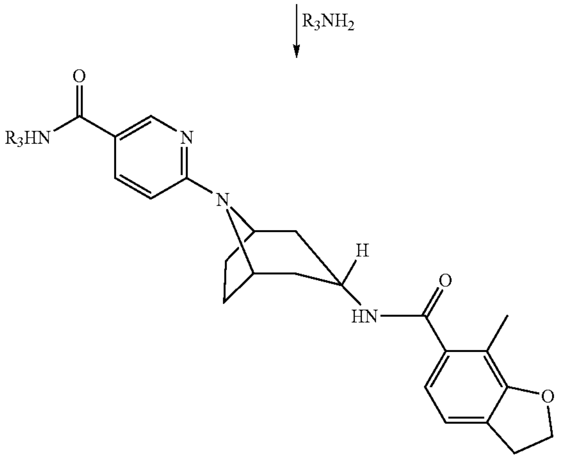

E

Scheme 4 generally describes the synthesis of all of the compound(s) listed in Example 4, wherein $R_3$ is as defined in the specification.

In Scheme 4, compound (B) is added to compound (A) under appropriate reaction conditions and with a suitable coupling reagent, such as HATU, to condense and form the amide bond in compound (C). The carboxylate of compound C is hydrolyzed with a base, such as LiOH, to form compound (D). To compound (D) is added $R_3NH_2$ under appropriate reaction conditions and with a suitable coupling reagent, such as HOBT and EDCI, to condense and form the amide bond in compound (E).

Example 4

N-(1-ethylazetidin-3-yl)-6-(3-endo-{[(7-methyl-2,3-dihydro-1-benzofuran-6-yl)carbonyl]amino}-8-azabicyclo[3.2.1]oct-8-yl)pyridine-3-carboxamide STEP 1: To a solution of 7-methyl-2,3-dihydro-1-benzofuran-6-carboxylic acid (synthesized in reagent preparation 16) (1.72 g, 9.63 mmol), HATU (3.66 g, 9.63 mmol), and DIEA (6.70 ml, 38.5 mmol) in DMF (25 mL) was added ethyl 6-(3-endo-amino-8-azabicyclo[3.2.1]oct-8-yl)pyridine-3-carboxylate (synthesized in example 1) (2.68 g, 9.63 mmol). The mixture was stirred at 30° C. for 22 hours, at which time it was partitioned between ethyl acetate and saturated sodium bicarbonate. The organic layer was separated and washed with lithium chloride and then brine. The organic layer was dried over anhydrous sodium sulfate, filtered then concentrated in vacuo to afford (5.39 g, 129%) of ethyl 6-(3-endo-{[(7-methyl-2,3-dihydro-1-benzofuran-6-yl)carbonyl]amino}-8-azabicyclo[3.2.1]oct-8-yl)pyridine-3-carboxylate which was used without further purification. $^1$H NMR (400 MHz, DMSO-$d_6$): 8.67-8.64 (s, 1H), 8.18-8.13 (s, 1H), 7.98-7.89 (d, 1H), 7.13-7.07 (d, 1H), 6.83-6.73 (m, 2H), 4.64-4.50 (m, 4H), 4.29-4.21 (m, 2H), 3.88-3.81 (m, 1H), 3.25-3.15 (m, 2H), 2.26-2.18 (d, 2H), 2.16-2.12 (s, 3H), 2.10-1.85 (m, 6H), 1.32-1.26 (m, 3H). MS (EI) for $C_{25}H_{29}N_3O_4$: 436 (MH$^+$).

STEP 2: To a solution of ethyl 6-(3-endo-{[(7-methyl-2,3-dihydro-1-benzofuran-6-yl)carbonyl]amino}-8-azabicyclo[3.2.1]oct-8-yl)pyridine-3-carboxylate (4.19 g, 9.63 mmol) in methanol (100 ml) was added 2M lithium hydroxide (24.0 ml, 48.0 mmol). The mixture was stirred at 50° C. for 24 hours, at which time the volume was reduced in vacuo, the pH adjusted to 5 with 1 N hydrochloric acid, and extracted with ethyl acetate. The organic layer was dried over anhydrous sodium sulfate, filtered, concentrated in vacuo to afford (3.27 g, 83%) of 6-(3-endo-{[(7-methyl-2,3-dihydro-1-benzofuran-6-yl)carbonyl]amino}-8-azabicyclo[3.2.1]oct-8-yl)pyridine-3-carboxylic acid, which was used without further purification. $^1$H NMR (400 MHz, DMSO-$d_6$): 12.65-12.34 (br. s, 1H), 8.64-8.61 (s, 1H), 8.16-8.12 (d, 1H), 7.93-7.89 (d, 1H), 7.13-7.07 (d, 1H), 6.82-6.79 (d, 1H), 6.76-6.72 (d, 1H), 4.62-4.50 (m, 4H), 3.88-3.81 (m, 1H), 3.25-3.15 (m, 2H), 2.26-2.18 (d, 2H), 2.15-2.12 (s, 3H), 2.10-1.85 (m, 6H). MS (EI) for $C_{23}H_{25}N_3O_4$: 408 (MH$^+$).

STEP 3: To a solution of 6-(3-endo-{[(7-methyl-2,3-dihydro-1-benzofuran-6-yl)carbonyl]amino}-8-azabicyclo[3.2.1]oct-8-yl)pyridine-3-carboxylic acid (236 mg, 0.580 mmol), HOBT (94 mg, 0.696 mmol), N-methylmorpholine (127 μL, 1.16 mmol) and EDCI (133 mg, 0.696 mmol) in DMF (3 mL) was added tert-butyl 3-aminoazetidine-1-carboxylate (120 mg, 0.696 mmol). The reaction mixture was stirred at room temperature for 5 h, at which time it was concentrated in vacuo then purified by flash chromatography (5% methanol in dichloromethane eluent) to afford 1,1-dimethylethyl 3-({[6-(3-endo-{[(7-methyl-2,3-dihydro-1-benzofuran-6-yl)carbonyl]amino}-8-azabicyclo[3.2.1]oct-8-yl)pyridin-3-yl]carbonyl}amino)azetidine-1-carboxylate (270 mg, 83%) as a white powder. MS (EI) for $C_{31}H_{39}N_5O_5$: 560 (M−H).

STEP 4: To a solution of 1,1-dimethylethyl 3-({[6-(3-endo-{[(7-methyl-2,3-dihydro-1-benzofuran-6-yl)carbonyl]amino}-8-azabicyclo[3.2.1]oct-8-yl)pyridin-3-yl]carbonyl}amino)azetidine-1-carboxylate (270 mg, 0.480 mmol) in acetonitrile (5 mL) was added a solution of hydrogen chloride (4.0M in dioxane, 500 μL) at room temperature and stirred for 15 h. The white suspension was filtered and the product washed with diethyl ether to give N-azetidin-3-yl-6-(3-endo-{[(7-methyl-2,3-dihydro-1-benzofuran-6-yl)carbonyl]amino}-8-azabicyclo[3.2.1]oct-8-yl)pyridine-3-carboxamide hydrochloride salt (233 mg, 97%). MS (EI) for $C_{26}H_{31}N_5O_3$: 462 (MH$^+$).

STEP 5: To a solution of N-azetidin-3-yl-6-(3-endo-{[(7-methyl-2,3-dihydro-1-benzofuran-6-yl)carbonyl]amino}-8-azabicyclo[3.2.1]oct-8-yl)pyridine-3-carboxamide hydrochloride salt (50 mg, 0.100 mmol) in methanol (1 mL) and tetrahydrofuran (1 mL) at 0° C. was added acetaldehyde (11 μL, 0.200 mmol). The reaction mixture was stirred at 0° C. for 20 min, at which time sodium cyanoborohydride (13 mg, 0.200 mmol) was added then stirred at room temperature for 5 h. The reaction mixture was quenched with 1N aqueous hydrochloric acid then diluted with water. The solution was purified by preparatory HPLC (0.1% aqueous ammonium acetate-acetonitrile) to afford the title compound (11.7 mg) as a white powder. $^1$H NMR (400 MHz, DMSO-$d_6$): 8.59 (d, 1H), 8.47 (d, 1H), 8.12 (d, 1H), 7.94 (dd, 1H), 7.10 (d, 1H), 6.80 (d, 1H), 6.74 (d, 1H), 4.55-4.51 (m, 4H), 4.45-4.40 (m, 1H), 3.85-3.79 (br m, 1H), 3.51 (t, 2H), 3.20 (t, 2H), 2.87 (t, 2H), 2.42-2.37 (m, 2H), 2.22-2.17 (m, 2H), 2.13 (s, 3H), 2.10-2.04 (m, 2H), 1.99-1.96 (m, 2H), 1.86-1.83 (m, 2H), 0.87 (t, 3H). MS (EI) for $C_{28}H_{35}N_5O_3$: 490 (MH$^+$).

Using analogous synthetic techniques and substituting with alternative starting reagents, the following compounds [(4A)-(4AC)] were prepared. Alternative starting reagents were obtained commercially unless otherwise indicated.

(4B): 6-(3-endo-{[(7-methyl-2,3-dihydro-1-benzofuran-6-yl)carbonyl]amino}-8-azabicyclo[3.2.1]oct-8-yl)-N-{(1S)-1-[3-(methyloxy)phenyl]ethyl}pyridine-3-carboxamide. Prepared according to the method of example 4 by using (S)-1-(3-methoxyphenyl)ethanamine in step 4, then omission of steps 5 and 6. $^1$H NMR (400 MHz, DMSO-$d_6$): 8.72 (m, 1H), 8.60 (d, 1H), 8.18 (d, 1H), 8.13 (m, 1H), 7.22 (t, 1H), 7.11 (d, 1H), 6.98 (m, 1H), 6.94 (m, 2H), 6.80 (m, 2H), 5.12 (m, 1H), 4.66 (bs, 2H), 4.52 (m, 2H), 3.86 (m, 1H), 3.74 (s, 3H), 3.20 (m, 2H), 2.24 (m, 2H), 2.16 (s, 3H), 2.09 (m, 2H), 2.02 (m, 2H), 1.94 (m, 2H), 1.46 (d, 3H). MS (EI) for $C_{32}H_{36}N_4O_4$: 541 (MH$^+$).

(4C): 6-(3-endo-{[(7-methyl-2,3-dihydro-1-benzofuran-6-yl)carbonyl]amino}-8-azabicyclo[3.2.1]oct-8-yl)-N-{[4-(4-methylpiperazin-1-yl)phenyl]methyl}pyridine-3-carboxamide. Prepared according to the method of example 4 by using (4-(4-methylpiperazin-1-yl)phenyl)methanamine in step 4, then omission of steps 5 and 6. $^1$H NMR (400 MHz, DMSO-$d_6$): 8.70 (t, 1H), 8.63 (d, 1H), 8.13 (d, 1H), 7.96 (dd, 1H), 7.15 (d, 2H), 7.11 (d, 1H), 6.88 (m, 2H), 6.80 (d, 1H), 6.74 (d, 1H), 4.58 (m, 4H), 4.34 (d, 2H), 3.82 (m, 1H), 3.20 (m, 2H), 3.08 (m, 4H), 2.43 (m, 4H), 2.21 (s, 3H), 2.20 (m, 2H), 2.13 (s, 3H), 2.07 (m, 2H), 1.97 (m, 2H), 1.84 (d, 2H). MS (EI) for $C_{35}H_{42}N_6O_3$: 595 (MH$^+$).

(4D): 6-(3-endo-{[(7-methyl-2,3-dihydro-1-benzofuran-6-yl)carbonyl]amino}-8-azabicyclo[3.2.1]oct-8-yl)pyridine-3-carboxamide. Isolated as hydrochloride salt. Prepared according to the method of example 4 by using ammonia in step 4, then omission of steps 5 and 6. $^1$H NMR (400 MHz, $CD_3OD$): 8.44 (d, 1H), 8.36 (d, 1H), 8.32 (dd, 1H), 7.29 (d, 1H), 7.10 (d, 1H), 6.85 (d, 1H), 4.71 (br s, 2H), 4.56 (t, 2H), 4.07 (m, 1H), 3.23 (t, 2H), 2.34 (m, 4H), 2.23 (m, 2H), 2.21 (s, 3H), 2.13 (d, 2H); MS (EI) for $C_{23}H_{26}N_4O_3$: 407 (MH$^+$).

(4E): 6-(3-endo-{[(7-methyl-2,3-dihydro-1-benzofuran-6-yl)carbonyl]amino}-8-azabicyclo[3.2.1]oct-8-yl)-N-{(1S)-1-[4-(4-methylpiperazin-1-yl)phenyl]ethyl}pyridine-3-carboxamide. Prepared according to the method of example 4 by using (S)-1-(4-(4-methylpiperazin-1-yl)phenyl)ethanamine (synthesized according to reagent preparation 3) in step 4, then omission of steps 5 and 6. $^1$H NMR (400 MHz, $CDCl_3$ w/ 10% $CD_3OD$): 8.59 (d, 1H), 7.88 (dd, 1H), 7.27 (d, 1H), 7.06 (d, 1H), 6.83 (dd, 4H), 6.57 (d, 1H), 5.18 (m, 1H), 4.57 (t, 3H), 4.06 (m, 1H), 3.26 (t, 2H), 3.12 (dd, 4H), 2.70 (s, 4H), 2.55 (dd, 4H), 2.35-2.20 (br m, 8H), 2.19-2.04 (br m, 4H), 1.83 (br d, 2H), 1.51 (d, 3H), 1.41 (s, 2H). MS (EI) for $C_{36}H_{44}N_6O_3$: 609 ($MH^+$).

(4F): 6-(3-endo-{[(7-methyl-2,3-dihydro-1-benzofuran-6-yl)carbonyl]amino}-8-azabicyclo[3.2.1]oct-8-yl)-N-{4-(4-methylpiperazin-1-yl)phenylmethyl}pyridine-3-carboxamide. Prepared according to the method of example 4 by using 4-(1-methylpiperidin-4-yl)benzylamine (synthesized according to reagent preparation 2) in step 4, then omission of steps 5 and 6. $^1H$ NMR (400 MHz, $CD_3OD$): 8.41 (d, 1H), 8.37 (dd, 1H), 7.38 (d, 1H), 7.31 (dd, 4H), 7.10 (d, 1H), 6.85 (d, 1H), 4.75 (br s, 2H), 4.57 (t, 2H), 4.55 (s, 2H), 4.09 (t, 1H), 3.60 (br d, 2H), 3.21 (br m, 6H), 2.91 (s, 4H), 2.88 (s, 2H), 2.40-1.85 (br m, 1H).). MS (EI) for $C_{36}H_{43}N_5O_3$: 593 ($MH^+$).

(4G): N-[(4-{[2-(diethylamino)ethyl]oxy}phenyl)methyl]-6-(3-endo-{[(7-methyl-2,3-dihydro-1-benzofuran-6-yl)carbonyl]amino}-8-azabicyclo[3.2.1]oct-8-yl)pyridine-3-carboxamide. Prepared according to the method of example 4 by using 2-[4-(aminomethyl)phenoxy]-N,N-diethylethylamine (synthesized according to reagent preparation 4) in step 4, then omission of steps 5 and 6. $^1H$ NMR (400 MHz, $CD_3OD$): 8.40 (d, 1H), 8.39 (dd, 1H), 7.39-7.33 (m, 3H), 7.11 (d, 1H), 7.01-6.99 (m, 2H), 6.86 (d, 1H), 4.59 (s, 2H), 4.56-4.36 (m, 4H), 4.34-4.33 (m, 2H), 4.09 (t, 1H), 3.60 (q, 2H), 3.32-3.31 (m, 3H), 3.23 (t, 2H), 2.38-2.33 (m, 4H), 2.32-2.24 (m, 8H), 1.38 (s, 2H), 1.37 (s, 2H), 1.35 (s, 2H); MS (EI) for $C_{36}H_{45}N_5O_4$: 612 ($MH^+$).

(4H): N-(cyclopropylmethyl)-6-(3-endo-{[(7-methyl-2,3-dihydro-1-benzofuran-6-yl)carbonyl]amino}-8-azabicyclo [3.2.1]oct-8-yl)pyridine-3-carboxamide hydrochloride. Prepared according to the method of example 4 by using cyclopropylmethanamine in step 4, then omission of steps 5 and 6. $^1H$ NMR (400 MHz, DMSO-$d_6$): 8.70-8.60 (br. s, 1H), 8.52-8.47 (s, 1H), 8.27-8.16 (d, 2H), 7.22-7.09 (m, 2H), 6.84-6.79 (d, 1H), 4.78-4.65 (br. s, 2H), 4.59-4.49 (m, 2H), 3.93-3.88 (m, 1H), 3.25-3.10 (m, 4H), 2.32-2.24 (d, 2H), 2.18-1.97 (m, 9H), 1.07-0.97 (m, 1H), 0.47-0.40 (m, 2H), 0.26-0.19 (m, 2H). MS (EI) for $C_{27}H_{32}N_4O_3$: 461 ($MH^+$).

(4I): N-[2-(diethylamino)ethyl]-6-(3-endo-{[(7-methyl-2,3-dihydro-1-benzofuran-6-yl)carbonyl]amino}-8-azabicyclo[3.2.1]oct-8-yl)pyridine-3-carboxamide. Isolated as hydrochloride salt. Prepared according to the method of example 4 by using N,N-diethylethane-1,2-diamine in step 4, then omission of steps 5 and 6. $^1H$ NMR (400 MHz, DMSO-$d_6$): 9.08 (br s, 1H), 8.60 (s, 1H), 8.30-8.20 (m, 2H), 7.25-7.10 (m, 2H), 6.81 (d, 1H), 4.77 (br s, 2H), 4.54 (t, 2H), 3.87 (br s, 1H), 3.66-3.61 (m, 2H), 3.25-3.15 (m, 8H), 2.30-1.95 (m, 1H), 1.25-1.21 (t, 6H). MS (EI) for $C_{29}H_{39}N_5O_3$: 506 ($MH^+$).

(4J): 6-(3-endo-{[(7-methyl-2,3-dihydro-1-benzofuran-6-yl)carbonyl]amino}-8-azabicyclo[3.2.1]oct-8-yl)-N-[(3R)-1-methylpyrrolidin-3-yl]pyridine-3-carboxamide. Prepared according to the method of example 4 by using (R)-1-methylpyrrolidin-3-amine in step 4, then omission of steps 5 and 6. $^1H$ NMR (400 MHz, $CD_3OD$): 8.50 (s, 1H), 8.40 (s, 1H), 7.38 (d, 1H), 7.11 (d, 1H), 6.08 (d, 1H), 4.80 (s, 2H), 4.65 (s, 1H), 4.55 (t, 2H), 4.08-4.03 (m, 2H), 3.98-3.88 (m, 1H), 3.77-3.75 (m, 2H), 3.49-3.41 (m, 2H), 3.34 (t, 4H), 3.05 (s, 1H), 2.98 (s, 2H), 2.72-2.61 (m, 1H), 2.38-2.19 (m, 8H), 2.18 (s, 3H); MS (EI) for $C_{28}H_{35}N_5O_3$: 490 ($MH^+$).

(4K): 6-(3-endo-{[(7-methyl-2,3-dihydro-1-benzofuran-6-yl)carbonyl]amino}-8-azabicyclo[3.2.1]oct-8-yl)-N-[(3S)-1-methylpyrrolidin-3-yl]pyridine-3-carboxamide. Prepared according to the method of example 4 by using (S)-1-methylpyrrolidin-3-amine in step 4, then omission of steps 5 and 6. $^1H$ NMR (400 MHz, $CD_3OD$): 8.50 (s, 1H), 8.40 (s, 1H), 7.38 (d, 1H), 7.10 (d, 1H), 6.85 (d, 1H), 4.76 (s, 2H), 4.66-4.60 (m, 1H), 4.57 (t, 3H), 4.10-4.08 (m, 2H), 3.80-3.77 (m, 2H), 3.46-3.40 (m, 1H), 3.23 (t, 3H), 3.18 (s, 2H), 3.05 (s, 2H), 2.70-2.60 (m, 1H), 2.38-2.19 (m, 8H), 2.26 (s, 3H); MS (EI) for $C_{28}H_{35}N_5O_3$: 490 ($MH^+$).

(4L): 6-(3-endo-{[(7-methyl-2,3-dihydro-1-benzofuran-6-yl)carbonyl]amino}-8-azabicyclo[3.2.1]oct-8-yl)-N-(1-methylpiperidin-4-yl)pyridine-3-carboxamide. Prepared according to the method of example 4 by using 1-methylpiperidin-4-amine in step 4, then omission of steps 5 and 6. $^1H$ NMR (400 MHz, DMSO-$d_6$): 8.62-8.58 (s, 1H), 8.15-8.11 (d, 1H), 8.05-8.00 (d, 1H), 7.95-7.90 (d, 1H), 7.13-7.09 (d, 1H), 6.82-6.78 (d, 1H), 6.76-6.72 (d, 1H), 4.58-4.48 (m, 4H), 3.87-3.78 (m, 1H), 3.24-3.15 (m, 2H), 3.00-2.91 (m, 1H), 2.39-2.30 (br. s, 4H), 2.25-2.17 (d, 2H), 2.15-2.12 (s, 3H), 2.11-2.03 (m, 2H), 2.01-1.95 (m, 2H), 1.93-1.90 (s, 3H), 1.87-1.77 (m, 4H), 1.68-1.55 (m, 2H). MS (EI) for $C_{27}H_{37}N_5O_3$: 504 ($MH^+$).

(4M): N-[(1S)-1-(4-{[2-(diethylamino)ethyl]oxy}phenyl)ethyl]-6-(3-endo-{[(7-methyl-2,3-dihydro-1-benzofuran-6-yl)carbonyl]amino}-8-azabicyclo[3.2.1]oct-8-yl)pyridine-3-carboxamide. Prepared according to the method of example 4 by using (S)-2-[4-(1-aminoethyl)phenoxy]-N,N-diethylethylamine (synthesized according to reagent preparation 4) in step 4, then omission of steps 5 and 6. $^1H$ NMR (400 MHz, $CD_3OD$): 8.59 (d, 1H), 7.97 (dd, 1H), 7.35 (d, 2H), 7.09 (d, 1H), 6.97 (d, 2H), 6.84 (d, 1H), 6.75 (d, 1H), 5.22-5.14 (m, 1H), 4.64-4.52 (m, 4H), 4.30-4.26 (m, 2H), 4.01-3.94 (m, 1H), 3.51-3.43 (m, 2H), 3.27-3.15 (m, 6H), 2.33-2.09 (m, 9H), 1.89 (d, 2H), 1.53 (d, 3H), 1.31 (t, 6H); MS (EI) for $C_{37}H_{47}N_5O_4$: 626 ($MH^+$).

(4N): 7-methyl-N-(8-{5-[(4-methylpiperazin-1-yl)carbonyl]pyridin-2-yl}-8-azabicyclo[3.2.1]oct-3-endo-yl)-2,3-dihydro-1-benzofuran-6-carboxamide. Prepared according to the method of example 4 by using 1-methylpiperazine in step 4, then omission of steps 5 and 6. $^1H$ NMR (400 MHz, $CDCl_3$): 8.29 (d, 1H), 7.61 (dd, 1H), 7.05 (d, 1H), 6.81 (d, 1H), 6.54 (d, 1H), 6.22 (d, 1H), 4.60 (m, 4H), 4.24 (q, 1H), 3.39 (br s, 3H), 3.24 (t, 2H), 2.45 (br s, 3H), 2.37-2.12 (br m, 7H), 2.05-1.95 (br m, 3H), 1.81 (br d, 2H), 1.25 (s, 3H). MS (EI) for $C_{28}H_{35}N_5O_3$: 490 ($MH^+$).

(4O): N-(1-ethylpiperidin-3-yl)-6-(3-endo-{[(7-methyl-2,3-dihydro-1-benzofuran-6-yl)carbonyl]amino}-8-azabicyclo[3.2.1]oct-8-yl)pyridine-3-carboxamide. Prepared according to the method of example 4 by using 1-ethylpiperidin-3-amine in step 4, then omission of steps 5 and 6. $^1H$ NMR (400 MHz, $CDCl_3$): 8.64 (br s, 1H), 7.96 (br s, 1H), 7.05 (d, 1H) 6.87 (d, 1H), 6.54 (d, 1H), 6.23 (d, 1H), 4.58 (m, 2H), 4.36-4.22 (br m, 2H), 3.24 (t, 2H), 2.75-2.15 (br m, 1H), 2.07-1.95 (br m, 2H), 1.80 (br d, 4H), 1.60 (br s, 2H), 1.25 (s, 1H), 1.09 (br s, 2H)). MS (EI) for $C_{30}H_{39}N_5O_3$: 518 ($MH^+$).

(4P): 6-(3-endo-{[(7-methyl-2,3-dihydro-1-benzofuran-6-yl)carbonyl]amino}-8-azabicyclo[3.2.1]oct-8-yl)-N-[(3R)-1-(1-methylethyl)pyrrolidin-3-yl]pyridine-3-carboxamide. Prepared according to the method of example 4 by using (R)-1-isopropylpyrrolidin-3-amine (synthesized according to reagent preparation 9) in step 4, then omission of steps 5 and 6. $^1H$ NMR (400 MHz, DMSO-$d_6$): 8.61 (d, 1H), 8.27 (br s, 1H), 8.13 (d, 1H), 7.95 (dd, 1H), 7.11 (d, 1H), 6.80 (d, 1H), 6.76 (d, 1H), 4.56-4.51 (m, 4H), 4.41 (br m, 1H), 3.82 (br m, 1H), 3.20 (t, 2H), 2.23-2.17 (m, 2H), 2.13 (s, 3H), 2.11-2.04 (m, 2H), 2.01-1.96 (m, 2H), 1.87-1.82 (m, 2H), 1.13 (br m, 6H). MS (EI) for $C_{30}H_{39}N_5O_3$: 518 ($MH^+$).

(4Q): 6-(3-endo-{[(7-methyl-2,3-dihydro-1-benzofuran-6-yl)carbonyl]amino}-8-azabicyclo[3.2.1]oct-8-yl)-N-[(3S)-1-methylpiperidin-3-yl]pyridine-3-carboxamide. Prepared according to the method of example 4 by using (S)-1-methylpiperidin-3-amine (synthesized according to reagent preparation 9) in step 4, then omission of steps 5 and 6. $^1$H NMR (400 MHz, DMSO-$d_6$): 8.60 (s, 1H), 8.13 (d, 1H), 7.93 (dd, 1H), 7.11 (d, 1H), 6.80 (d, 1H), 6.76 (d, 1H), 4.56-4.51 (m, 4H), 3.84-3.79 (br m, 2H), 3.20 (t, 4H), 2.22-2.17 (m, 2H), 2.13 (s, 3H), 2.10-2.04 (m, 2H), 2.01-1.96 (m, 2H), 1.87-1.81 (m, 4H). MS (EI) for $C_{29}H_{37}N_5O_3$: 504 (MH$^+$).

(4R): 6-(3-endo-{[(7-methyl-2,3-dihydro-1-benzofuran-6-yl)carbonyl]amino}-8-azabicyclo[3.2.1]oct-8-yl)-N-[(3S)-1-(1-methylethyl)pyrrolidin-3-yl]pyridine-3-carboxamide. Prepared according to the method of example 4 by using (S)-1-isopropylpyrrolidin-3-amine (synthesized according to reagent preparation 9) in step 4, then omission of steps 5 and 6. $^1$H NMR (400 MHz, $CDCl_3$): 8.64 (d, 1H), 7.95 (dd, 1H), 7.05 (d, 1H), 6.80 (d, 1H), 6.52 (d, 1H), 6.23 (d, 1H), 4.74 (br s, 1H), 4.60 (br s, 1H), 4.59 (t, 3H), 4.23 (q, 1H), 3.24 (t, 2H), 3.18 (br s, 1H), 2.98 (br d, 1H), 2.73 (dd, 1H), 2.59 m, 1H), 2.47-2.32 (br m, 3H), 2.24 (s, 3H), 2.25-2.19 (br m, 2H), 2.01 (q, 2H), 1.82 (d, 3H), 1.19 (t, 6H). MS (EI) for $C_{30}H_{39}N_5O_3$: 518 (MH$^+$).

(4S): N-[(3S)-1-ethylpyrrolidin-3-yl]-6-(3-endo-{[(7-methyl-2,3-dihydro-1-benzofuran-6-yl)carbonyl]amino}-8-azabicyclo[3.2.1]oct-8-yl)pyridine-3-carboxamide. Prepared according to the method of example 4 by using (S)-1-ethylpyrrolidin-3-amine (synthesized according to reagent preparation 9) in step 4, then omission of steps 5 and 6. $^1$H NMR (400 MHz, $CDCl_3$): 8.60 (d, 1H), 7.92 (d, 1H), 7.08 (d, 1H), 6.87 (d, 1H), 6.53 (d, 1H), 6.40 (d, 1H), 6.24 (d, 1H), 4.62 (m, 4H), 4.23 (q, 1H), 3.24 (t, 2H), 2.97 (m, 1H), 2.76 (br m, 1H), 2.55-2.45 (br m, 3H), 2.43-2.26 (br m, 6H), 2.25-2.18 (br m, 2H), 2.02 (m, 3H), 1.82 br d, 2H), 1.72 (m, 1H), 1.12 (t, 3H). MS (EI) for $C_{29}H_{37}N_5O_3$: 504 (MH$^+$).

(4T): 6-(3-endo-{[(7-methyl-2,3-dihydro-1-benzofuran-6-yl)carbonyl]-amino}-8-azabicyclo[3.2.1]oct-8-yl)-N-[1-(1-methylethyl)piperidin-4-yl]pyridine-3-carboxamide. Prepared according to the method of example 4 by using 1-(1-methylethyl)piperidin-4-amine (synthesized according to reagent preparation 9) in step 4, then omission of steps 5 and 6. $^1$H NMR (400 MHz, $CDCl_3$): 8.53 (d, 1H), 7.91 (d, 1H), 7.05 (d, 1H), 6.87 (d, 1H), 6.53 (d, 1H), 6.21 (d, 1H), 5.77 (d, d, 1H), 4.60 (m, 4H), 4.22 (q, 1H), 3.98 (m, 1H), 3.24 (t, 2H), 2.81 (d, 2H), 2.74 (m, 1H), 2.32 (m, 8H), 2.22 (m, 2H), 2.11-1.98 (br m, 4H), 1.82 (br m, 4H), 1.67 (br s, 2H), 1.52 (m, 2H), 1.05 (d, 6H). MS (EI) for $C_{31}H_{41}N_5O_3$: 532 (MH$^+$).

(4U): N-[1-ethylpiperidin-4-yl]-6-(3-endo-{[(7-methyl-2,3-dihydro-1-benzofuran-6-yl)carbonyl]amino}-8-azabicyclo[3.2.1]oct-8-yl)pyridine-3-carboxamide. Prepared according to the method of example 4 by using 1-ethylpiperidin-4-amine (synthesized according to reagent preparation 9) in step 4, then omission of steps 5 and 6. $^1$H NMR (400 MHz, $CDCl_3$): 8.56 (d, 1H), 7.91 (d, 1H), 7.04 (d, 1H), 6.86 (d, 1H), 6.53 (d, 1H), 6.22 (d, 1H), 5.86 (d, 1H), 4.60 (m, 4H), 4.22 (q, 1H), 4.01 (m, 1H), 3.24 (t, 2H), 2.93 (br d, 2H), 2.47 (q, 2H), 2.37-2.28 (br m, 5H), 2.27-1.96 (br m, 6H), 1.81 (br d, 2H), 1.61 (m, 2H), 1.11 (t, 3H). MS (EI) for $C_{30}H_{39}N_5O_3$: 518 (MH$^+$).

(4V): N-[(3R)-1-ethylpiperidin-3-yl]-6-(3-endo-{[(7-methyl-2,3-dihydro-1-benzofuran-6-yl)carbonyl]amino}-8-azabicyclo[3.2.1]oct-8-yl)pyridine-3-carboxamide. Prepared according to the method of example 4 by using (R)-1-methylpiperidin-3-amine (synthesized according to reagent preparation 9) in step 4, then omission of steps 5 and 6. $^1$H NMR (400 MHz, DMSO-$d_6$): 8.60 (s, 1H), 8.13 (d, 1H), 7.93 (dd, 1H), 7.11 (d, 1H), 6.80 (d, 1H), 6.75 (d, 1H), 4.56-4.51 (m, 4H), 3.82 (br m, 1H), 3.20 (t, 2H), 2.22-2.17 (m, 2H), 2.14 (s, 3H), 2.10-2.04 (m, 2H), 2.00-1.96 (m, 2H), 1.87-1.81 (m, 4H), 1.07 (br m, 3H). MS (EI) for $C_{30}H_{39}N_5O_3$: 516 (M−H).

(4W): 6-(3-endo-{[(7-methyl-2,3-dihydro-1-benzofuran-6-yl)carbonyl]amino}-8-azabicyclo[3.2.1]oct-8-yl)-N-[1-(1-methylethyl)azetidin-3-yl]pyridine-3-carboxamide. Prepared according to the method of example 4 by using acetone in step 6. $^1$H NMR (400 MHz, DMSO-$d_6$): 8.60 (d, 1H), 8.50 (br s, 1H), 8.13 (d, 1H), 7.94 (dd, 1H), 7.11 (d, 1H), 6.80 (d, 1H), 6.75 (d, 1H), 4.56-4.51 (m, 4H), 4.40 (br m, 1H), 3.82 (br m, 1H), 3.61 (br s, 1H), 3.22-3.18 (m, 2H), 2.21-2.19 (m, 2H), 2.14 (s, 3H), 2.11-2.04 (m, 2H), 2.00-1.96 (m, 2H), 1.87-1.82 (m, 2H), 0.91 (d, 6H). MS (EI) for $C_{29}H_{37}N_5O_3$: 504 (MH$^+$).

(4X): N-(1-methylazetidin-3-yl)-6-(3-endo-{[(7-methyl-2,3-dihydro-1-benzofuran-6-yl)carbonyl]amino}-8-azabicyclo[3.2.1]oct-8-yl)pyridine-3-carboxamide. Prepared according to the method of example 4 by using 1-methylazetidin-3-amine (synthesized according to reagent preparation 9) in step 4, then omission of steps 5 and 6. $^1$H NMR (400 MHz, DMSO-$d_6$): 8.60 (d, 1H), 8.48 (d, 1H), 8.13 (d, 1H), 7.94 (dd, 1H), 7.11 (d, 1H), 6.80 (d, 1H), 6.74 (d, 1H), 4.56-4.51 (m, 4H), 4.43-4.38 (m, 1H), 3.82 (br m, 1H), 3.56-3.52 (m, 2H), 3.22-3.18 (m, 4H), 2.94-2.91 (m, 2H), 2.34-2.32 (m, 1H), 2.24 (s, 3H), 2.14 (s, 3H), 2.10-2.05 (m, 2H), 1.99-1.95 (m, 2H). MS (EI) for $C_{27}H_{33}N_5O_3$: 476 (MH$^+$).

(4Y): N-[(3R)-1-ethylpyrrolidin-3-yl]-6-(3-endo-{[(7-methyl-2,3-dihydro-1-benzofuran-6-yl)carbonyl]amino-}8-azabicyclo[3.2.1]oct-8-yl)pyridine-3-carboxamide. Prepared according to the method of example 4 by using (R)-1-ethylpyrrolidin-3-amine (synthesized according to reagent preparation 9) in step 4, then omission of steps 5 and 6. MS (EI) for $C_{29}H_{37}N_5O_3$: 504 (MH$^+$).

(4Z): 6-(3-endo-{[(7-methyl-2,3-dihydro-1-benzofuran-6-yl)carbonyl]amino}-8-azabicyclo[3.2.1]oct-8-yl)-N-[(3R)-1-(1-methylethyl)piperidin-3-yl]pyridine-3-carboxamide. Prepared according to the method of example 4 by using (R)-1-isopropylpiperidin-3-amine (synthesized according to reagent preparation 9) in step 4, then omission of steps 5 and 6. $^1$H NMR (400 MHz, DMSO-$d_6$): 8.60 (s, 1H), 7.93 (d, 1H), 7.04 (d, 1H), 6.86 (d, 1H), 6.54 (d, 1H), 6.31 (d, 1H), 4.59 (m, 4H), 4.21 (m, 2H), 3.23 (t, 2H), 2.75 (m, 1H), 2.70-2.50 (br m, 3H), 2.40-1.45 (br m, 8H), 1.01 (dd, 6H). MS (EI) for $C_{31}H_{41}N_5O_3$: 532 (MH$^+$).

(4AA): N-[(3S)-1-ethylpiperidin-3-yl]-6-(3-endo-{[(7-methyl-2,3-dihydro-1-benzofuran-6-yl)carbonyl]amino}-8-azabicyclo[3.2.1]oct-8-yl)pyridine-3-carboxamide. Prepared according to the method of example 4 by using (S)-1-ethylpiperidin-3-amine (synthesized according to reagent preparation 9) in step 4, then omission of steps 5 and 6. MS (EI) for $C_{30}H_{39}N_5O_3$: 518 (MH$^+$).

(4AB): 6-(3-endo-{[(7-methyl-2,3-dihydro-1-benzofuran-6-yl)carbonyl]amino}-8-azabicyclo[3.2.1]oct-8-yl)-N-[(3S)-1-(1-methylethyl)piperidin-3-yl]pyridine-3-carboxamide. Prepared according to the method of example 4 by using (S)-1-isopropylpiperidin-3-amine (synthesized according to reagent preparation 9) in step 4, then omission of steps 5 and 6. $^1$H NMR (400 MHz, $CDCl_3$): 8.60 (d, 1H), 7.93 (d, 1H), 7.04 (d, 1H), 6.88 (d, 1H), 6.54 (d, 1H), 6.30 (d, 1H), 4.59 (m, 4H), 4.21 (m, 2H), 3.23 (t, 2H), 2.79-2.42 (br m, 4H), 2.39-2.30 (br m, 6H), 2.28-2.11 (br m, 2H), 2.03 (m, 2H), 1.92-1.44 (br m, 6H), 1.01 (dd, 6H). MS (EI) for $C_{31}H_{41}N_5O_3$: 532 (MH$^+$).

(4AC): 6-(3-endo-{[(7-methyl-2,3-dihydro-1-benzofuran-6-yl)carbonyl]-amino}-8-azabicyclo[3.2.1]oct-8-yl)-N-[(3R)-1-methylpiperidin-3-yl]pyridine-3-carboxamide. Prepared according to the method of example 4 by using (R)-1-methylpiperidin-3-amine (synthesized according to reagent preparation 9) in step 4, then omission of steps 5 and 6. MS (EI) for $C_{29}H_{37}N_5O_3$: 504 (MH$^+$).

SYNTHETIC SCHEME 5:

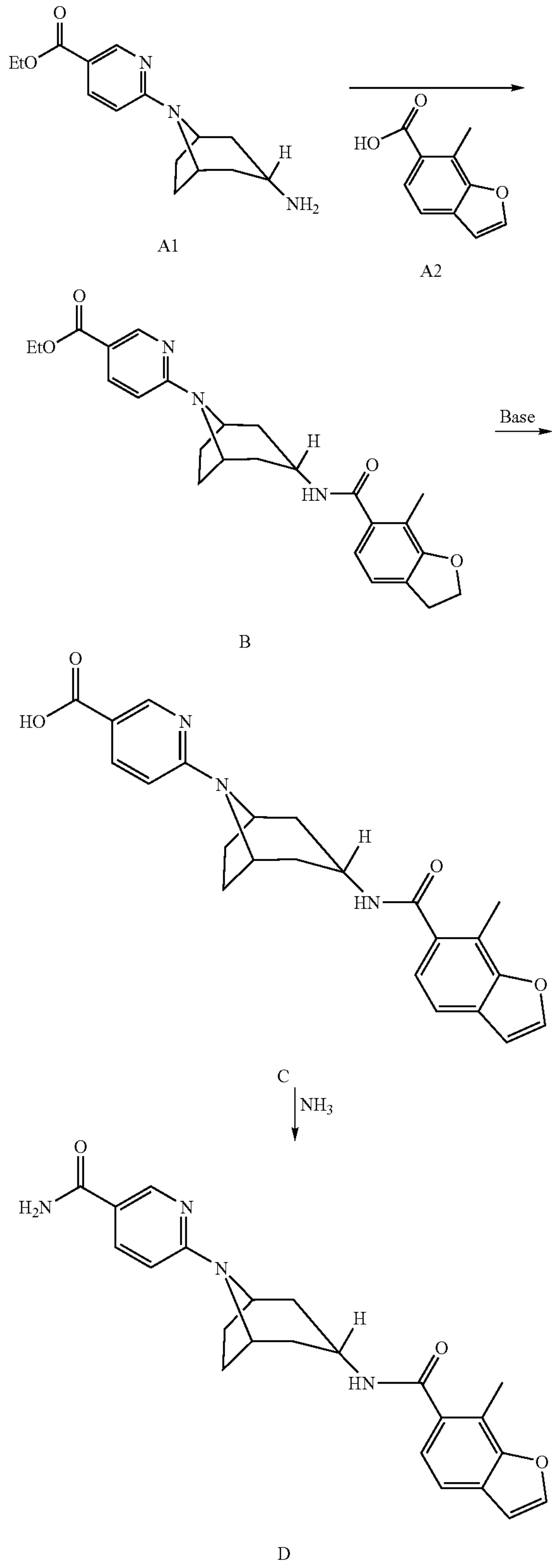

Scheme 5 generally describes the synthesis of all of the compound(s) listed in Example 5.

In Scheme 5, compound (A2) is added to compound (A1) under appropriate reaction conditions and with a suitable coupling reagent, such as HATU, to condense and form the amide bond in compound (B). The carboxylate of compound B is hydrolyzed with a base, such as KOH, to form compound (C). To compound (C) is added $NH_3$ under appropriate reaction conditions to form compound (D).

Example 5

6-(3-endo-{[(7-methyl-1-benzofuran-6-yl)carbonyl]amino}-8-azabicyclo[3.2.1]oct-8-yl)pyridine-3-carboxamide STEP 1: A solution of ethyl 6-(3-endo-amino-8-azabicyclo[3.2.1]oct-8-yl)pyridine-3-carboxylate (191 mg, 0.69 mmol, synthesized in example 1, step 2,7-methyl-1-benzofuran-6-carboxylic acid (synthesized in reagent preparation 15) (122 mg, 0.69 mmol), HATU (262 mg, 0.69 mmol), and diisopropylethylamine (267 mg, 2.07 mmol) in DMF (5 mL) was stirred at room temperature for 23 h. The reaction mixture was diluted with ethyl acetate (100 mL), washed with saturated sodium bicarbonate (50 mL), 5% aqueous lithium chloride (2×20 mL), and brine (20 mL), dried over sodium sulfate, filtered and dried to give ethyl 6-(3-endo-{[(7-methyl-1-benzofuran-6-yl)carbonyl]amino}-8-azabicyclo[3.2.1]oct-8-yl)pyridine-3-carboxylate (329 mg). $^1$H NMR (400 MHz, DMSO-$d_6$): 8.66 (d, 1H), 8.26 (d, 1H), 8.09 (d, 1H), 7.93 (dd, 1H), 7.54 (d, 1H), 7.25 (d, 1H), 6.99 (d, 1H), 6.78 (d, 1H), 4.61 (br s, 2H), 4.25 (q, 2H), 3.91 (m, 1H), 2.53 (s, 3H), 2.26 (m, 2H), 2.10 (m, 2H), 2.01 (m, 2H), 1.91 (d, 2H), 1.29 (t, 3H); MS (EI) for $C_{25}H_{27}N_3O_4$: 434 ($MH^+$).

STEP 2: A suspension of ethyl 6-(3-endo-{[(7-methyl-1-benzofuran-6-yl)carbonyl]amino}-8-azabicyclo[3.2.1]oct-8-yl)pyridine-3-carboxylate (324 mg, 0.75 mmol) and potassium hydroxide (84 mg, 1.50 mmol) in methanol (9 mL) and water (3 mL) was stirred at 60° C. for 3 h. After cooling to room temperature some of the methanol was evaporated, water was added to the resulting mixture, and the pH adjusted to 5 with 1N aqueous hydrochloric acid. The precipitate was collected by filtration, washed with water, and dried to afford 6-(3-endo-{[(7-methyl-1-benzofuran-6-yl)carbonyl]amino}-8-azabicyclo[3.2.1]oct-8-yl)pyridine-3-carboxylic acid (204 mg, 67% yield). $^1$H NMR (400 MHz, DMSO-$d_6$): 12.47 (br s, 1H), 8.64 (d, 1H), 8.26 (d, 1H), 8.09 (d, 1H), 7.92 (dd, 1H), 7.55 (d, 1H), 7.25 (d, 1H), 7.00 (d, 1H), 6.77 (d, 1H), 4.60 (br s, 2H), 3.91 (m, 1H), 2.25 (m, 2H), 2.10 (m, 2H), 2.01 (m, 2H), 1.90 (d, 2H); MS (EI) for $C_{23}H_{23}N_3O_4$: 406 ($MH^+$).

STEP 3: Ammonia was bubbled through a solution of 6-(3-endo-{[(7-methyl-1-benzofuran-6-yl)carbonyl]amino}-8-azabicyclo[3.2.1]oct-8-yl)pyridine-3-carboxylic acid (70 mg, 0.17 mmol) and HATU (66 mg, 0.17 mmol) in DMF (3 mL) for 15 min, and the reaction mixture was stirred for 80 min at room temperature. Ammonia introduction was then repeated for another 15 min, and stirring at room temperature was continued for 22 h. The mixture was poured into water, the precipitated product was collected by filtration then further purified by preparatory reverse phase HPLC (0.1% aqueous trifluoroacetic acid-acetonitrile eluent). Pure fractions were concentrated and the residue lyophilized from 1N aqueous hydrochloric acid to provide 6-(3-endo-{[(7-methyl-1-benzofuran-6-yl)carbonyl]-amino}-8-azabicyclo[3.2.1]oct-8-yl)pyridine-3-carboxamide hydrochloride (28 mg, 37% yield). $^1$H NMR (400 MHz, methanol-$d_4$): 8.47 (d, 1H), 8.44 (d, 1H), 8.35 (dd, 1H), 7.86 (d, 1H), 7.53 (d, 1H), 7.35 (d, 1H), 7.27 (d, 1H), 6.87 (d, 1H), 4.75 (br s, 2H), 4.15 (m, 1H), 2.59 (s, 3H), 2.38 (m, 4H), 2.26 (m, 2H), 2.19 (d, 2H); MS (EI) for $C_{23}H_{24}N_4O_3$: 405 ($MH^+$).

Using analogous synthetic techniques and substituting with alternative starting reagents, the following compounds [(5B)-(5D)] were prepared. Alternative starting reagents were obtained commercially unless otherwise indicated.

(5B): 6-(3-endo-{[(7-methyl-1-benzofuran-6-yl)carbonyl]amino}-8-azabicyclo[3.2.1]oct-8-yl)-N-{(1S)-1-[4-(4-methylpiperazin-1-yl)phenyl]ethyl}pyridine-3-carboxamide. Prepared according to the method of example 5 by using (1S)-1-[4-(4-methylpiperazin-1-yl)phenyl]ethanamine (synthesized according to reagent preparation 3) in step 3. $^1$H NMR (400 MHz, $CDCl_3$): 8.56 (d, 1H), 7.86 (d, 1H), 7.71 (d, 1H), 7.45 (d, 1H), 7.27 (m, 1H), 6.90 (d, 2H), 6.78 (d, 1H), 6.51 (d, 1HH), 6.32 (d, 1H), 6.14 (1H), 5.25 (m, 1H), 4.61 (br s, 2H), 4.25 (q, 1H), 3.47 (s, 2H), 3.21 (m, 4H), 2.41-2.29 (br m, 5H), 2.27-2.18 (br m, 2H), 2.09-1.98 (br m, 2H), 1.56 (d, 3H). MS (EI) for $C_{36}H_{42}N_6O_3$: 606 ($MH^+$).

(5C): 6-(3-endo-{[(7-methyl-1-benzofuran-6-yl)carbonyl]amino}-8-azabicyclo[3.2.1]oct-8-yl)-N-{[4-(1-methylpiperidin-4-yl)phenyl]methyl}pyridine-3-carboxamide. Prepared according to the method of example 5 by using 4-(1-methylpiperidin-4-yl)benzylamine (synthesized according to reagent preparation 2) in step 3. $^1$H NMR (400 MHz, $d_6$-DMSO): 10.25 (d, 1H), 8.82 (t, 1H), 8.65 (d, 1H), 8.25 (d, 1H), 8.09 (d, 1H), 7.98 (d, 1H), 7.54 (m, 1H), 7.54 (d, 1H), 7.38-7.17 (br m, 5H), 7.00 (d, 1H), 6.76 (d, 1H), 4.56 (s, 2H), 4.42 (d, 2H), 4.11 (br s, 1H), 3.88 (br s, 1H), 3.47 (d, 2H), 3.17 (s, 3H), 3.04 (br s, 2H), 2.52 (s, 3H), 2.25 (d, 1H), 2.16-1.81 (br m, 6H). MS (EI) for $C_{36}H_{41}N_5O_3$: 592 ($MH^+$).

(5D): 6-(3-endo-{[(7-methyl-1-benzofuran-6-yl)carbonyl]amino}-8-azabicyclo[3.2.1]oct-8-yl)-N-{[4-(4-methylpiperazin-1-yl)phenyl]methyl}pyridine-3-carboxamide. Prepared as the hydrochloride salt according to the method of example 5 by using 4-(4-methylpiperazin-1-yl)benzylamine in step 3. $^1$H NMR (400 MHz, $d_6$-DMSO): 10.95 (br s, 1H), 9.32 (br s, 1H), 8.53 (s, 1H), 8.38-8.32 (m, 2H), 8.10 (s, 1H), 7.55 (d, 2H), 7.36 (d, 1H), 7.27-7.21 (m, 3H), 7.00-6.95 (m, 3H), 4.56 (br s, 2H), 3.96 (br s, 1H), 3.77 (d, 2H), 3.45 (d, 2H), 3.17-3.02 (m, 4H), 2.79 (s, 3H), 2.53 (2, 3H), 2.36-2.32 (m, 2H), 2.24-2.01 (m, 6H). MS (EI) for $C_{35}H_{40}N_6O_3$: 593 ($MH^+$).

SYNTHETIC SCHEME 6:

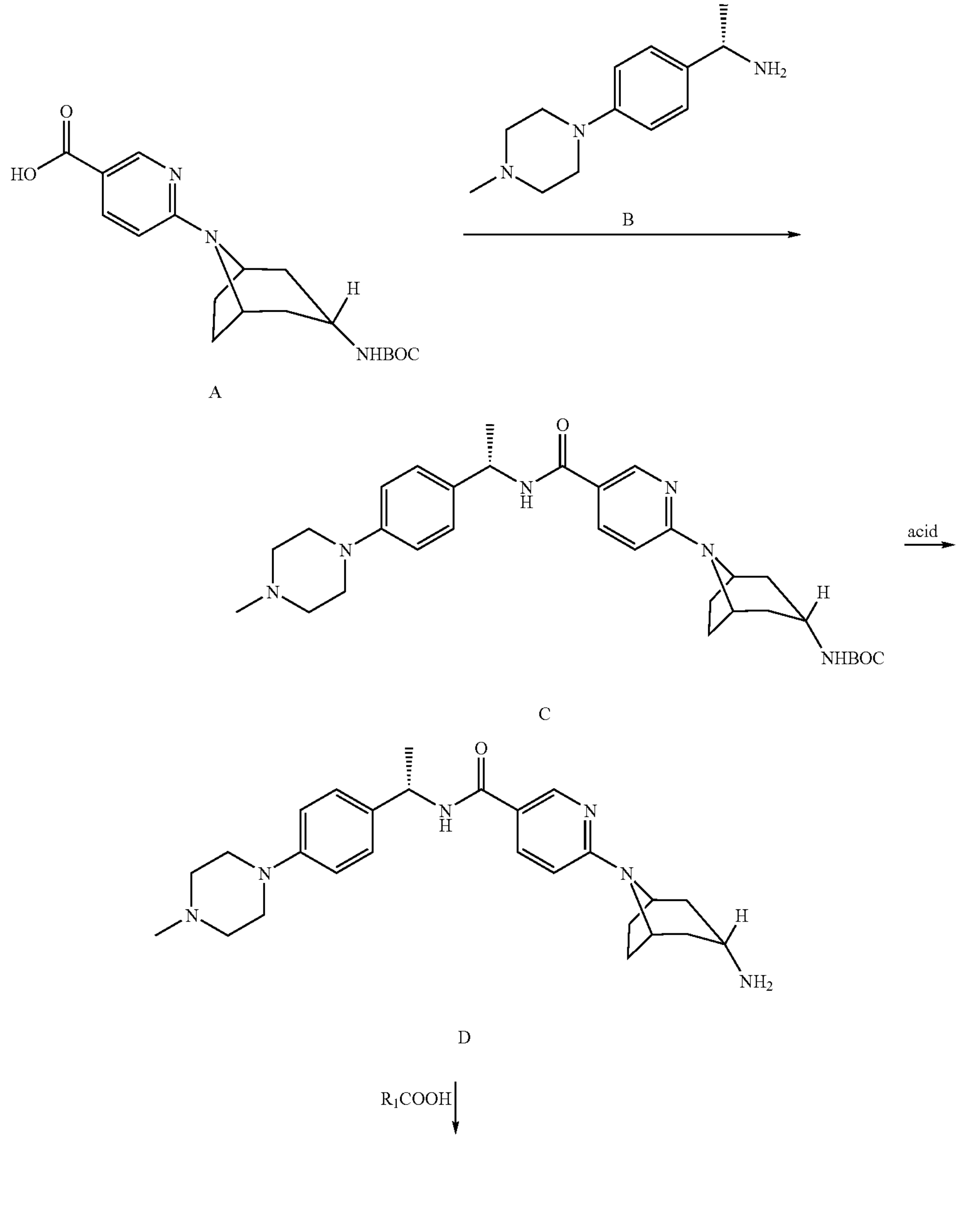

A

C

D

-continued

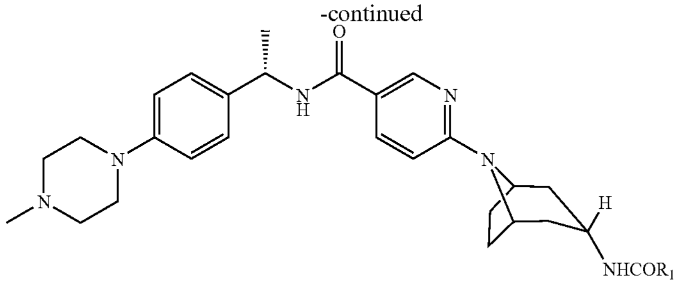

E

Scheme 6 generally describes the synthesis of all of the compound(s) listed in Example 6, wherein $R_1$ is as defined in the specification.

To compound (A) is added compound (B) under appropriate reaction conditions and with a suitable coupling reagent, such as HATU, to condense and form the amide bond in compound (C). Compound (C) is deprotected to form compound (D) under acidic conditions, such as with the use of HCl. To compound (D) is added $R_1COOH$ under appropriate reaction conditions and with a suitable coupling reagent, such as HATU, to condense and form the amide bond in compound (E).

Example 6

6-(3-endo-{[(3-hydroxy-2-methylphenyl)carbonyl]amino}-8-azabicyclo[3.2.1]oct-8-yl)-N-{(1S)-1-[4-(4-methylpiperazin-1-yl)phenyl]ethyl}pyridine-3-carboxamide STEP 1: A solution of 6-[3-endo-({[(1,1-dimethylethyl)oxy]carbonyl}-amino)-8-azabicyclo[3.2.1]oct-8-yl]pyridine-3-carboxylic acid (prepared in example 2) (164 mg, 0.47 mmol), (1S)-1-[4-(4-methylpiperazine-1-yl)phenyl]ethanamine dihydrochloride (synthesized according to reagent preparation 3) (140 mg, 0.47 mmol), HATU (180 mg, 0.47 mmol) and N-methylmorpholine (516 μL, 4.7 mmol) in dimethylformamide (3 mL) was heated at 40° C. for 15 hours. On cooling to room temperature the solution was diluted with ethyl acetate, then washed with 5% aqueous lithium chloride, 0.5N aqueous sodium hydroxide, brine, and then dried over anhydrous sodium sulfate. Filtration and concentration afforded an orange residue which was purified by silica gel column chromatography eluting with 5-10% methanol in dichloromethane. Pure fractions were pooled and concentrated to afford 192 mg, 0.35 mmol (74%) of 1,1-dimethylethyl (8-{5-[({(1S)-1-[4-(4-methylpiperazine-1-yl)phenyl]ethyl}amino)carbonyl]pyridin-2-yl}-8-azabicyclo[3.2.1]oct-3-endo-yl)carbamate as a yellow foam. MS (EI) for $C_{31}H_{44}N_6O_3$: 549 ($MH^+$).

STEP 2: To a solution of 1,1-dimethylethyl (8-{5-[({(1S)-1-[4-(4-methylpiperazine-1-yl)phenyl]ethyl}amino)carbonyl]pyridin-2-yl}-8-azabicyclo[3.2.1]oct-3-endo-yl)carbamate (192 mg, 0.35 mmol) in methanol (5 mL) was added a solution of 4N hydrogen chloride in dioxane (2 mL), and the reaction mixture was refluxed for 2 min. After cooling to room temperature the mixture was diluted with ethyl acetate and basified using 1N aqueous sodium hydroxide until the pH reached 10. The layers were separated, and the aqueous layer was further extracted using ethyl acetate. The combined organic layers were washed with brine then dried over anhydrous sodium sulfate. Filtration and concentration afforded a colorless residue which was purified by silica gel column chromatography eluting with 5-10% of a (10% concentrated aqueous ammonia solution in methanol) in chloroform. Pure fractions were pooled and concentrated to give 6-(3-endo-[amino]-8-azabicyclo[3.2.1]oct-8-yl)-N-{(1S)-1-[4-(4-methylpiperazin-1-yl)phenyl]ethyl}pyridine-3-carboxamide as a white foam. $^1H$ NMR (400 MHz, $CDCl_3$): 8.53 (d, 1H), 7.84 (dd, 1H), 7.29 (s, 1H), 6.90 (d, 2H), 6.47 (d, 1H), 6.01 (d, 1H), 5.28-5.21 (m, 1H), 4.51 (br s, 2H), 3.26-3.18 (m, 5H), 2.58-2.55 (m, 4H), 2.35 (s, 3H), 2.33-2.28 (m, 2H), 2.19-2.13 (m, 2H), 2.09-2.04 (m, 2H), 1.56 (d, 3H), 1.48-1.44 (m, 2H). MS (EI) for $C_{26}H_{36}N_6O_1$: 449 ($MH^+$).

STEP 3: A solution of 6-(3-endo-[amino]-8-azabicyclo[3.2.1]oct-8-yl)-N-{(1S)-1-[4-(4-methylpiperazin-1-yl)phenyl]ethyl}pyridine-3-carboxamide, 3-Hydroxy-2-methylbenzoic acid (8.5 mg, 0.06 mmol), HATU (22 mg, 0.06 mmol), and N-methylmorpholine (18 μl, 0.17 mmol) in dimethylformamide (1 mL) was stirred at 40° C. for 15 hours. The reaction mixture was purified by preparative reverse phase HPLC (ammonium acetate buffered aqueous acetonile eluent) to afford 17 mg, 0.03 mmol (50%) of 6-(3-endo-{[(3-hydroxy-2-methylphenyl)carbonyl]amino}-8-azabicyclo[3.2.1]oct-8-yl)-N-{(1S)-1-[4-(4-methylpiperazin-1-yl)phenyl]ethyl}pyridine-3-carboxamide acetate salt. $^1H$ NMR (400 MHz, $d_6$-DMSO): 9.48 (s, 1H), 8.62 (s, 1H), 8.43 (d, 1H), 8.16 (d, 1H), 7.96 (dd 1H), 7.22 (d, 2H), 7.06-7.02 (m, 1H), 6.91-6.83 (m, 3H), 6.75-6.70 (m, 2H), 5.11-5.04 (m, 1H), 4.53 (br s, 2H), 4.53 (d, 2H), 3.81 (br s, 1H), 3.71-3.10 (m, 4H), 2.67-2.56 (m, 2H), 2.37-2.31 (m, 2H), 2.25-2.17 (m, 2H), 2.11-1.82 (m, 12H), 1.42 (d, 3H). MS (EI) for $C_{34}H_{42}N_6O_3$: 583 ($MH^+$).

Using analogous synthetic techniques and substituting with alternative starting reagents, the following compounds [(6B-6U)] were prepared. Alternative starting materials were obtained commercially unless otherwise indicated.

(6B): N-(8-{5-[({(1S)-1-[4-(4-methylpiperazin-1-yl)phenyl]ethyl}amino)-carbonyl]pyridin-2-yl}-8-azabicyclo[3.2.1]oct-3-endo-yl)-1,3-benzothiazole-5-carboxamide. Prepared as the acetate salt according to the method of example 6 by using benzothiazole-5-carboxylic acid in step 3. $^1H$ NMR (400 MHz, $d_6$-DMSO): 9.51 (s, 1H), 8.64 (d, 1H), 8.52 (d, 1H), 8.44 (d, 1H), 8.41 (d, 1H), 8.28 (d, 1H), 7.99 (dd, 1H), 7.91 (dd, 1H), 7.22 (d, 2H), 6.88 (d, 2H), 6.77 (d, 1H), 5.05-5.12 (m, 1H), 4.59 (br s, 2H), 3.90 (br s, 1H), 3.08 (t, 4H), 2.43 (t, 4H), 2.24-2.29 (m, 2H), 2.21 (s, 3H), 2.10-2.15 (m, 2H), 2.03-2.05 (m, 2H), 1.98 (s, 1H), 1.94 (s, 1H), 1.43 (d, 3H). MS (EI) for $C_{34}H_{39}N_7O_2S$: 610 ($MH^+$).

(6C): 6-(3-endo-{[(8-methyl-3,4-dihydro-2H-chromen-7-yl)carbonyl]amino}-8-azabicyclo[3.2.1]oct-8-yl)-N-{(1S)-1-[4-(4-methylpiperazin-1-yl)phenyl]ethyl}pyridine-3-carboxamide. Prepared as the acetate salt according to the method of example 6 by using 8-methyl-3,4-dihydro-2H-chromene-7-carboxylic acid (Sawada, Y. et al, Pest Management Science, 2003, 59(J), 36-48.) in step 3. $^1H$ NMR (400 MHz, $d_6$-DMSO): 8.62 (d, 1H), 8.42 (d, 1H), 8.11 (d, 1H), 7.96 (dd, 1H), 7.20 (d, 2H), 6.94-6.86 (m, 1H), 6.73 (d, 2H), 5.10-5.04 (m, 1H), 4.53 (br s, 2H), 4.20-4.16 (m, 2H), 3.80 (br s, 1H), 3.10-3.06 (m, 4H), 2.76-2.73 (m, 2H), 2.44-2.41 (m, 4H), 2.20-2.02 (m, 10H), 2.00-1.81 (m, 9H), 1.41 (d, 3H). MS (EI) for $C_{37}H_{46}N_6O_3$: 623 (MH$^+$).

(6D): 6-[3-endo-({[2-methyl-3-(methylthio)phenyl]carbonyl}amino)-8-azabicyclo[3.2.1]oct-8-yl]-N-{(1S)-1-[4-(4-methylpiperazin-1-yl)phenyl]ethyl}pyridine-3-carboxamide. Prepared as the trifluoracetate salt according to the method of example 6 by using 2-methyl-3-(methylthio)benzoic acid (synthesized according to reagent preparation 33) in step 3. $^1$H NMR (400 MHz, CDCl$_3$): 8.56 (d, 1H), 7.87 (dd, 1H), 7.32-7.27 (m, 3H), 7.22-7.18 (m, 1H), 7.13-7.11 (m, 1H), 6.93 (d, 2H), 6.52 (d, 1H), 6.18 (d, 1H), 6.06 (d, 1H), 5.30-5.22 (m, 1H), 4.60 (br s, 2H), 4.27-4.22 (m, 1H), 3.22-2.96 (m, 4H), 2.66 (s, 3H), 2.60-2.55 (m, 4H), 2.42 (s, 3H), 2.35-2.30 (m, 5H), 2.24-2.18 (m, 2H), 2.02-1.94 (m, 2H), 1.84-1.78 (m, 2H), 1.56 (d, 3H). MS (EI) for $C_{35}H_{44}N_6O_2S$: 613 (MH$^+$).

(6E): 2-methyl-3-(methyloxy)-N-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide. Prepared as the trifluoroacetate salt according to the method of example 6 by using 4-(aminocarbonyl)-2-methyl-3-(methyloxy)benzoic acid (synthesized according to reagent preparation 34) in step 3. $^1$H NMR (400 MHz, CD$_3$OD): 8.71 (d, 1H), 8.56-8.48 (m, 2H), 8.17 (d, 1H), 7.69 (d, 1H), 7.33 (d, 2H), 7.19 (d, 1H), 7.08-7.00 (m, 3H), 5.19-5.13 (m, 1H), 4.66 (br s, 2H), 4.10-4.03 (m, 1H), 3.87-3.78 (m, 4H), 3.63-3.55 (m, 2H), 3.04-2.94 (m, 4H), 2.38-2.15 (m, 8H), 2.06-1.99 (m, 2H), 1.54 (d, 3H), 1.34-1.26 (m, 2H). MS (EI) for $C_{36}H_{45}N_7O_4$: 640 (MH$^+$).

(6F): 6-{3-endo-[({3-[(4-hydroxycyclohexyl)amino]phenyl}-carbonyl)amino]-8-azabicyclo[3.2.1]oct-8-yl}-N-{(1S)-1-[4-(4-methylpiperazin-1-yl)phenyl]ethyl}pyridine-3-carboxamide. Prepared according to the method of example 6 by using 3-[(trans-4-hydroxycyclohexyl)amino]benzoic acid (synthesized according to reagent preparation 37) in step 3. $^1$H NMR (400 MHz, d$_6$-DMSO): 8.63 (d, 1H), 8.43 (d, 1H), 8.02 (d, 1H), 7.97 (dd, 1H), 7.21 (d, 2H), 7.13 (t, 1H), 6.84-6.89 (m, 4H), 6.75 (d, 1H), 6.67-6.70 (m, 1H), 5.64 (d, 1H), 5.04-5.11 (m, 1H), 4.56 (br s, 2H), 3.81 (br s, 1H), 3.34 (s, 5H), 3.08 (t, 4H), 2.49-2.51 (m, 6H), 2.21 (s, 5H), 1.82-2.02 (m, 6H), 1.62 (s, 1H), 1.42 (d, 3H), 1.12-1.31 (m, 3H). MS (EI) for $C_{39}H_{51}N_7O_3$: 666 (MH$^+$).

(6G): N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-(phenylamino)benzene-1,4-dicarboxamide. Prepared according to the method of example 6 by using 4-(aminocarbonyl)-3-(phenylamino)benzoic acid (synthesized according to reagent preparation 39) in step 3. MS (EI) for $C_{14}H_{12}N_2O_3$: 257 (MH$^+$); $^1$HNMR (400 MHz, d$_4$-methanol): 8.49, (d, 1H), 7.85 (dd, 1H), 7.63 (dd, 1H), 7.55 (d, 1H), 7.25-7.15 (m, 6H), 6.97 (m, 2H), 6.86 (d, 2H), 6.61 (d, 1H), 5.06 (q, 1H), 4.47 (br, 2H), 3.85 (tr, 1H), 3.14 (br, 4H), 2.73 (br, 4H), 2.41 (s, 3H), 2.13-1.97 (m, 6H), 1.81 (d, 2H), 1.42 (d, 3H); MS (EI) for $C_{40}H_{46}N_8O_3$: 689 (MH$^+$).

(6H): 1,4-dimethyl-N-(8-{5-[({(1S)-1-[4-(4-methylpiperazin-1-yl)phenyl]ethyl}amino)carbonyl]pyridin-2-yl}-8-azabicyclo[3.2.1]oct-3-yl)-1H-benzimidazole-5-carboxamide. Prepared as the acetate salt according to the method of example 6 by using 1,4-dimethyl-1H-benzimidazole-5-carboxylic acid (synthesized according to reagent preparation 35) in step 3. $^1$HNMR (400 MHz, d$_4$-methanol): 8.60 (d, 1H), 8.18 (s, 1H), 7.96 (dd, 1H), 7.45 (d, 1H), 7.35 (d, 1H), 7.29 (d, 2H), 6.95 (d, 2H), 6.74 (d, 1H), 5.17 (q, 1H), 4.61 (br, 2H), 4.04 (tr, 1H), 3.90 (s, 3H), 3.22 (br, 4H), 2.78 (br, 4H), 2.68 (s, 3H), 2.47 (s, 3H), 2.35-2.10 (m, 5H), 1.95 (br, 1H), 1.93 (s, 3H), 1.92 (br, 1H), 1.52 (d, 3H); MS (EI) for $C_{36}H_{44}N_8O_2$: 621 (MH$^+$).

(6I): 4-methyl-N-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-1H-1,2,3-benzotriazole-5-carboxamide. Prepared according to the method of example 6 by using 4-methyl-1H-benzotriazole-5-carboxylic acid (synthesized according to reagent preparation 22) in step 3. $^1$H NMR (400 MHz, d$_6$-DMSO): 8.63 (d, 1H), 8.43 (d, 1H), 8.26 (d, 1H), 7.97 (dd, 1H), 7.71 (d, 1H), 7.31 (d, 1H), 7.21 (d, 2H), 6.88 (d, 2H), 6.75 (d, 1H), 5.08 (m, 1H), 4.56 (broad s, 2H), 3.90 (m, 1H), 3.08 (m, 4H), 2.69 (s, 3H), 2.43 (m, 4H), 2.24 (d, 2H), 2.21 (s, 3H), 2.13 (m, 2H), 2.01 (m, 2H), 1.84 (m, 6H), 1.42 (d, 3H). MS (EI) for $C_{34}H_{41}N_9O_2$: 608 (MH$^+$).

(6J): 2-(methyloxy)-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide. Prepared according to the method of example 6 by using 4-(aminocarbonyl)-3-(methyloxy)benzoic acid (synthesized according to reagent preparation 26) in step 3. $^1$H NMR (CD$_3$OD): 8.60 (s, 1H), 8.46 (d, 1H), 8.03-7.96 (m, 2H), 7.52 (s, 1H), 7.44 (d, 1H), 7.40 (d, 1H), 6.99-6.97 (m, 2H), 6.78 (d, 1H), 5.18-5.16 (m, 1H), 4.04 (s, 2H), 4.03-4.00 (m, 4H), 3.05 (s, 3H), 2.31-2.16 (m, 6H), 1.97-1.93 (m, 2H), 1.53 (d, 3H). MS (EI) for $C_{35}H_{43}N_7O_4$: 626 (MH$^+$).

(6K): 2-(cyclobutyloxy)-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide. Prepared as the trifluoroacetate salt according to the method of example 6 by using 4-(aminocarbonyl)-3-(cyclobutyloxy)benzoic acid (synthesized according to reagent preparation 25) in step 3. $^1$H NMR (CD$_3$OD): 8.46 (d, 1H), 8.23 (d, 1H), 8.28 (d, 1H), 8.04 (d, 1H), 7.43 (d, 1H), 7.34-7.32 (m, 3H), 7.23 (d, 1H), 7.01-6.99 (m, 1H), 5.18-5.17 (m, 1H), 4.73 (s, 2H), 4.08 (s, 1H), 3.84 (d, 2H), 3.58 (d, 2H), 3.29-3.25 (m, 4H), 3.06-2.98 (m, 4H), 2.58-2.54 (m, 2H), 2.37-2.26 (m, 4H), 2.17 (d, 2H), 1.95-1.93 (m, 1H), 1.92-1.81 (m, 1H), 1.78-1.53 (m, 3H). MS (EI) for $C_{38}H_{47}N_7O_4$: 666 (MH$^+$).

(6L): 6-[3-endo-({[2-methyl-3-(methylamino)phenyl]carbonyl}amino)-8-azabicyclo[3.2.1]oct-8-yl]-N-{(1S)-1-[4-(4-methylpiperazin-1-yl)phenyl]ethyl}pyridine-3-carboxamide. Prepared as the acetate salt according to the method of example 6 by using 2-methyl-3-(methylamino)benzoic acid (synthesized according to reagent preparation 31) in step 3. $^1$H NMR (400 MHz, d$_6$-DMSO): 8.63 (s, 1H), 8.44-8.40 (d, 1H), 8.10 (s, 1H), 7.99-7.94 (d, 1H), 7.24-7.18 (d, 2H), 7.09-7.04 (m, 1H), 6.91-6.85 (d, 2H), 6.76-6.71 (d, 1H), 6.55-6.49 (m, 2H), 5.19-5.16 (br. s, 1H), 5.11-5.02 (m, 1H), 4.58-4.50 (br. s, 2H), 3.85-3.77 (m, 1H), 3.16 (s, 3H), 3.11-3.05 (m, 4H), 2.75-2.71 (m, 2H), 2.46-2.40 (m, 2H), 2.23-2.16 (m, 5H), 2.12-2.00 (m, 5H), 1.99-1.94 (m, 2H), 1.89-1.81 (m, 5H), 1.44-1.39 (d, 3H). MS (EI) for $C_{35}H_{45}N_7O_2$: 596 (MH$^+$).

(6M): 6-[3-endo-({[3-(dimethylamino)-2-methylphenyl]carbonyl}amino)-8-azabicyclo[3.2.1]oct-8-yl]-N-{(1S)-1-[4-(4-methylpiperazin-1-yl)phenyl]ethyl}pyridine-3-carboxamide. Prepared as the acetate salt according to the method of example 6 by using 3-(dimethylamino)-2-methylbenzoic acid (synthesized according to reagent preparation 32) in step 3. $^1$H NMR (400 MHz, d$_6$-DMSO): 8.63 (s, 1H), 8.44-8.40 (d, 1H), 8.21 (s, 1H), 7.99-7.94 (d, 1H), 7.25-7.17 (m, 3H), 7.13-7.09 (d, 1H), 6.95-6.91 (d, 1H), 6.91-6.85 (d, 2H), 6.76-6.71 (d, 1H), 5.11-5.02 (m, 1H), 4.58-4.50 (br. s, 2H), 3.87-3.80 (m, 1H), 3.16 (s, 3H), 3.11-3.05 (m, 4H), 2.63 (s, 6H), 2.46-2.40 (m, 4H), 2.26-2.18 (m, 5H), 2.15-2.05 (m, 2H), 2.02-1.93 (m, 2H), 1.89-1.81 (m, 5H), 1.44-1.39 (d, 3H). MS (EI) for $C_{36}H_{47}N_7O_2$: 610 (MH$^+$).

(6N): N4-(8-{5-[({(1S)-1-[4-(4-methylpiperazin-1-yl)phenyl]ethyl}-amino)carbonyl]pyridin-2-yl}-8-azabicyclo[3.2.1]oct-3-endo-yl)-2-(pyridin-4-ylamino)benzene-1,4-dicarboxylate. Prepared as the trifluoroacetate salt according to the method of example 6 by using 4-aminocarbonyl-3-(pyridine-4-ylamino)benzoic acid (synthesized according to reagent preparation 39) in step 3. $^1$H NMR (400 MHz, d$_4$-methanol): 8.42 (d, 1H), 8.38 (d, 1H), 8.18-8.10 (m, 3H), 7.81-7.71 (m, 3H), 7.26-7.22 (m, 2H), 7.11-7.06 (m, 3H), 6.94-6.88 (m, 2H), 5.11-5.04 (m, 1H), 4.64 (br s, 2H), 4.00 (br s, 2H), 3.77-3.68 (m, 2H), 3.55-3.46 (m, 2H), 3.21-3.12 (m, 2H), 2.99-2.85 (m, 5H), 2.31-1.98 (m, 8H), 1.45 (d, 3H); MS (EI) for $C_{39}H_{45}N_9O_3$: 688 ($MH^+$).

(6O): N4-(8-{5-[({(1S)-1-[4-(4-methylpiperazin-1-yl)phenyl]ethyl}-amino)carbonyl]pyridin-2-yl}-8-azabicyclo[3.2.1]oct-3-endo-yl)-2-{[1-(methylsulfonyl)piperidin-4-yl]amino}benzene-1,4-dicarboxamide. Prepared according to the method of example 6 by using 4-aminocarbonyl-3-(1-methylsulfonyl)piperidin-4-ylamino)benzoic acid (synthesized according to reagent preparation 39) in step 3. $^1H$ NMR (400 MHz, $d_4$-methanol): 8.50 (d, 1H), 7.88 (dd, 1H), 7.57 (d, 1H), 7.22-7.17 (m, 2H), 7.02 (br s, 1H), 6.89-6.82 (m, 3H), 6.66 (d, 1H), 5.11-5.04 (m, 1H), 4.53 (br s, 2H), 3.93-3.86 (m, 1H), 3.61-3.47 (m, 2H), 3.16-3.09 (m, 4H), 3.02-2.92 (m, 2H), 2.76 (s, 3H), 2.70-2.63 (m, 4H), 2.36 (s, 3H), 2.25-1.99 (m, 8H), 1.91-1.79 (m, 3H), 1.63-1.46 (m, 2H), 1.43 (d, 3H); MS (EI) for $C_{40}H_{53}N_9O_5S$: 772 ($MH^+$).

(6P): 2-(cyclobutylamino)-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide. Prepared as the trifluoroacetate salt according to the method of example 6 by using 4-aminocarbonyl-3-(cyclobutylamino)benzoic acid (synthesized according to reagent preparation 39) in step 3. $^1H$ NMR (400 MHz, $d_4$-methanol): 8.45 (d, 1H), 8.34-8.28 (m, 2H), 7.64 (d, 1H), 7.35-7.31 (m, 2H), 7.28-7.23 (m, 1H), 7.03-6.98 (m, 2H), 6.96-6.93 (m, 1H), 6.92-6.90 (m, 1H), 5.20-5.14 (m, 1H), 4.73 (br s, 2H), 4.11-3.98 (m, 2H), 3.86-3.78 (m, 2H), 3.64-3.54 (m, 2H), 3.29-3.21 (m, 2H), 3.07-2.94 (m, 5H), 2.54-2.11 (m, 8H), 2.00-1.80 (m, 4H), 1.54 (d, 3H); MS (EI) for $C_{38}H_{48}N_8O_3$: 665 ($MH^+$).

(6Q): N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-{[3,4,5-tris(methyloxy)phenyl]amino}benzene-1,4-dicarboxamide. Prepared as the acetate salt according to the method of example 6 by using 4-aminocarbonyl-3-(3,4,5-trimethoxyphenylamino)benzoic acid (synthesized according to reagent preparation 39) in step 3. $^1H$ NMR (400 MHz, $d_4$-methanol): 8.58 (d, 1H), 7.95 (dd, 2H), 7.72 (d, 1H), 7.54 (d, 2H), 7.31-7.27 (m, 1H), 7.08 (dd, 2H), 6.98-6.93 (m, 2H), 6.72 (d, 1H), 6.55 (s, 2H), 5.19-5.12 (m, 1H), 4.57 (br s, 2H), 3.97-3.90 (m, 1H), 3.81 (s, 6H), 3.74 (s, 3H), 3.27-3.21 (m, 4H), 2.89-2.82 (m, 4H), 2.52 (s, 3H), 2.26-2.16 (m, 2H), 2.09 (br s, 4H), 1.96 (s, 3H), 1.89 (d, 2H), 1.52 (d, 3H); MS (EI) for $C_{43}H_{52}N_8O_6$: 777 ($MH^+$).

(6R): 3-(ethylamino)-2,5-dimethyl-N1-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide. Prepared as the acetate salt according to the method of example 6 by using 4-(aminocarbonyl)-3-(ethylamino)-2,5-dimethylbenzoic acid (synthesized according to reagent preparation 36) in step 3. $^1H$ NMR (400 MHz, $CD_3OD$): 8.59 (d, 1H), 7.97 (dd, 1H), 7.29 (d, 2H), 6.96 (d, 2H), 6.76 (s, 1H), 6.75 (d, 1H), 5.17 (q, 1H), 4.60 (br, 2H), 3.99 (t, 1H), 3.28-3.19 (m, 4H), 3.11 (q, 2H), 2.79-2.74 (m, 4H), 2.45 (s, 3H), 2.34-2.26 (m, 2H), 2.32 (s, 3H), 2.23-2.09 (m, 4H), 2.22 (s, 3H), 1.93-1.86 (m, 2H), 1.52 (d, 3H), 1.17 (t, 3H); MS (EI) for $C_{38}H_{50}N_8O_3$: 667 ($MH^+$).

(6S): 2-[(4-hydroxycyclohexyl)amino]-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide. Prepared according to the method of example 6 by using 4-(aminocarbonyl)-3-[(trans-4-hydroxycyclohexyl)amino]benzoic acid (synthesized according to reagent preparation 39) in step 3. $^1H$ NMR (400 MHz, $d_4$-methanol): 8.60 (d, 1H), 7.97 (dd, 1H), 7.62 (d, 1H), 7.31 (d, 2H), 7.07 (s, 1H), 6.98 (d, 2H), 6.89 (dd, 2H), 6.75 (d, 1H), 5.16 (m, 1H), 4.63 (br s, 2H), 3.99 (m, 1H), 3.63 (m, 1H), 3.41 (m, 1H), 3.03 (m, 4H), 2.70 (s, 3H), 2.30-2.12 (m, 8H), 1.98 (m, 4H), 1.53 (d, 3H), 1.50-1.26 (m, 4H); MS (EI) for $C_{40}H_{52}N_8O_4$: 709 ($MH^+$).

(6T): N4-(8-{5-[({(1S)-1-[4-(4-methylpiperazin-1-yl)phenyl]ethyl}-amino)carbonyl]pyridin-2-yl}-8-azabicyclo[3.2.1]oct-3-endo-yl)-2-{[2-(methylsulfonyl)ethyl]amino}benzene-1,4-dicarboxamide. Prepared as the acetate salt according to the method of example 6 by using 4-(aminocarbonyl)-3-{[2-(methylsulfonyl)ethyl]amino}benzoic acid (synthesized according to reagent preparation 39) in step 3. $^1H$ NMR (400 MHz, DMSO-$d_6$): 8.63 (d, 1H), 8.43 (d, 1H), 8.32 (m, 1H), 8.19 (d, 1H), 7.98 (m, 2H), 7.69 (d, 1H), 7.36 (br s, 1H), 7.21 (d, 2H), 7.01 (s, 1H), 6.95 (d, 1H), 6.88 (d, 2H), 6.76 (d, 1H), 5.08 (m, 1H), 4.57 (br s, 2H), 3.83 (br s, 1H), 3.66 (m, 2H), 3.46 (t, 2H), 3.07 (m, 4H), 3.03 (s, 3H), 2.43 (m, 4H), 2.22 (m, 2H), 2.20 (s, 3H), 2.08 (m, 2H), 2.01 (m, 2H), 1.91 (s, 3H), 1.87 (m, 2H), 1.42 (d, 3H); MS (EI) for $C_{37}H_{48}N_8O_5S$: 717 ($MH^+$).

(6U): 2-[(cyclopropylmethyl)amino]-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide. Prepared as the acetate salt according to the method of example 6 by using 4-(aminocarbonyl)-3-[(cyclopropylmethyl)amino]benzoic acid (synthesized according to reagent preparation 39) in step 3. $^1H$NMR (400 MHz, $d_4$-methanol): 8.59, (d, 1H), 7.96 (dd, 1H), 7.62 (dd, 1H), 7.29 (d, 2H), 7.05 (br s, 1H), 6.98-6.89 (m, 3H), 6.75 (d, 1H), 5.20-5.14 (m, 1H), 4.62 (br s, 2H), 4.01-3.95 (m, 1H), 3.28-3.22 (m, 4H), 3.08 (d, 2H), 2.92-2.87 (m, 4H), 2.56 (s, 3H), 2.30-2.14 (m, 6H), 1.98-1.92 (m, 3H), 1.52 (d, 3H), 1.20-1.11 (m, 1H), 0.60-0.055 (m, 2H), 0.31-0.26 (m, 2H); MS (EI) for $C_{38}H_{48}N_8O_3$: 665 ($MH^+$).

SYNTHETIC SCHEME 7:

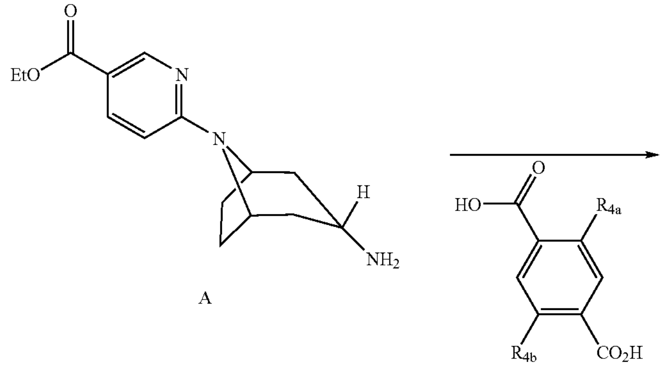

A

B

-continued

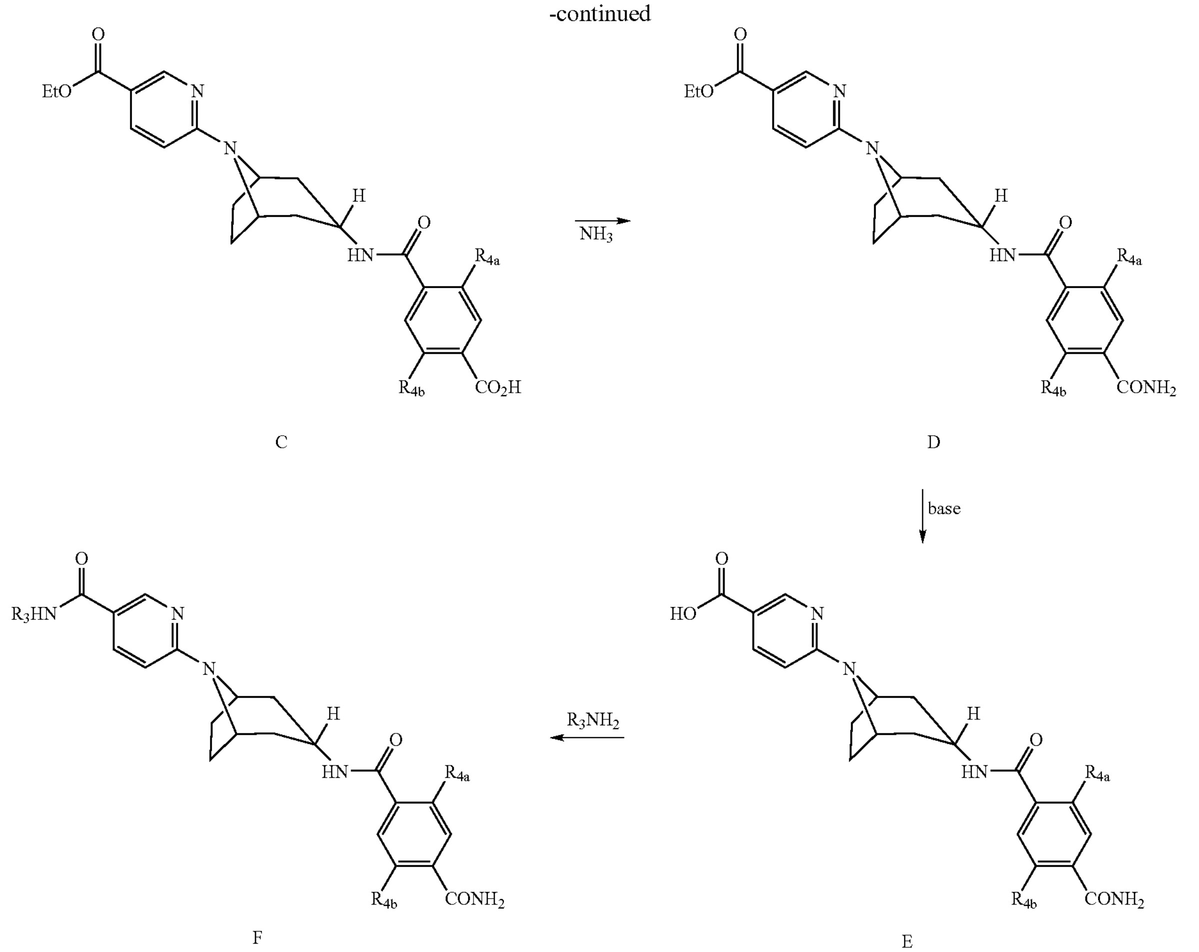

C D E F

Scheme 7 generally describes the synthesis of all of the compound(s) listed in Example 7, wherein $R_3$, $R_{4a}$, and $R_{4b}$ are as defined in the specification. This scheme is applicable when $R_{4a}$ and $R_{4b}$ are the same.

In Scheme 7, to compound (A) is added compound (B) under appropriate reaction conditions and with a suitable coupling reagent, such as HATU, to condense and form the amide bond in compound (C). To compound (C) is added $NH_3$ under appropriate reaction conditions to form compound (D). The carboxylate of compound (D) is then hydrolyzed with a base, such as LiOH, to form compound (E). To compound (E) is added $R_3NH_2$ and a suitable coupling agent, such as HOBT and EDCI, under appropriate reaction conditions to form compound (F).

Example 7

2,5-dimethyl-N-{8-[5-({[(3R)-1-(1-methylethyl) pyrrolidin-3-yl]amino}carbonyl)pyridin-2-yl]-8-azabicyclo[3.2.1]oct-3-endo-yl}benzene-1,4-dicarboxamide STEP 1: A solution of 2,5-Dimethylbenzene-1,4-dicarboxylic acid (1.14 g, 5.86 mmol), 2-(7-aza-1H-benzotriazole-1-yl)-1,1,3,3-tetramethyluronium hexafluorophosphate (2.23 g, 5.86 mmol) and N,N-diisopropylethylamine (4.7 mL, 27 mmol) in N,N-dimethylformamide (20 mL) was stirred at room temperature for 30 minutes. Then ethyl 6-(3-endo-amino-8-azabicyclo[3.2.1]oct-8-yl)pyridine-3-carboxylate hydrochloride (prepared in example 1) (1.66 g, 5.32 mmol) was added and the resultant solution was stirred at 50° C. for 12 hours. On cooling to room temperature, the solution was concentrated in vacuo. The residue was split into two portions and both portions were taken up in 10 mL N,N-dimethylformamide, and 2-(7-aza-1H-benzotriazole-1-yl)-1,1,3,3-tetramethyluronium hexafluorophosphate (1.11 g, 2.93 mmol) and N,N-diisopropylethylamine (2.3 mL, 13 mmol) were added to each. The solutions were warmed to 50° C. and ammonia (gas) was bubbled through the solutions for 20 minutes. The solutions were combined, then the solvent was removed in vacuo. The crude material was partitioned between water and 10% methanol in dichloromethane. The layers were separated and the aqueous layer was extracted (2×100 mL dichloromethane). The combined organic layers were dried (magnesium sulfate), filtered and concentrated. The crude solid was triturated with methanol/hexanes/ethyl acetate and the solid collected by filtration to give ethyl 6-[3-endo-({[4-(aminocarbonyl)-2,5-dimethylphenyl] carbonyl}amino)-8-azabicyclo[3.2.1]oct-8-yl]pyridine-3-carboxylate (1.79 g, 75% yield). $^1H$ NMR (400 MHz, $d_6$-DMSO): 8.58 (d, 1H), 8.28 (d, 1H), 8.01 (dd, 1H), 7.70 (br s, 1H), 7.40 (br s, 1H), 7.24 (s, 1H), 7.13 (s, 1H), 6.93 (d, 1H), 4.64 (broad s, 2H), 4.27 (q, 2H), 3.88 (m, 1H), 2.32 (s, 3H), 2.30 (s, 3H), 2.24 (m, 2H), 2.13 (m, 2H), 2.01 (m, 2H), 1.93 (d, 2H), 1.30 (t, 3H). MS (EI) for $C_{25}H_{38}N_4O_4$: 451 ($MH^+$).

STEP 2: To a solution of ethyl 6-[3-endo-({[4-(aminocarbonyl)-2,5-dimethylphenyl]carbonyl}amino)-8-azabicyclo [3.2.1]oct-8-yl]pyridine-3-carboxylate (1.00 g, 2.21 mmol)

in methanol (6.0 mL) and tetrahydrofuran (6.0 mL) was added 3.0 mL of 2.0 M lithium hydroxide (aqueous) and the resultant solution was warmed to 50° C. for one hour. The organic solvents were removed in vacuo, and the remaining aqueous solution was brought to pH 2 using concentrated aqueous hydrochloric acid. The solid thus formed was collected by filtration and dried in vacuo to give 1.18 g (70% yield) of the desired 6-[3-endo-({[4-(aminocarbonyl)-2,5-dimethylphenyl]carbonyl}amino)-8-azabicyclo[3.2.1]oct-8-yl]pyridine-3-carboxylic acid, which was used without further purification in step 3.

STEP 3: A solution of 6-[3-endo-({[4-(aminocarbonyl)-2,5-dimethylphenyl]carbonyl}amino)-8-azabicyclo[3.2.1]oct-8-yl]pyridine-3-carboxylic acid (0.050 g, 0.12 mmol), (3R)-1-(1-methylethyl)pyrrolidin-3-amine hydrochloride (synthesized in reagent preparation 9) (0.14 mmol), 1-hydroxybenzotriazole (0.019 g, 0.14 mmol), 1-(3-dimethylaminopropyl)-3-ethylcarbodiimide hydrochloride (0.027 g, 0.14 mmol), and 4-methylmorpholine (0.05 mL, 0.5 mmol) in N,N-dimethylformamide (2.0 mL) was stirred at room temperature for 12 hours. The solution was then diluted with water and purified by HPLC (reverse-phase, acetonitrile/water with 0.1% ammonium acetate). Concentration in vacuo and lyophilization from water gave 0.034 g (54% yield) of the desired 2,5-dimethyl-N-{8-[5-({[(3R)-1-(1-methylethyl)pyrrolidin-3-yl]amino}carbonyl)pyridin-2-yl]-8-azabicyclo[3.2.1]oct-3-endo-yl}benzene-1,4-dicarboxamide as the acetate salt. $^1$H NMR (400 MHz, $d_6$-DMSO): 8.61 (d, 1H), 8.22 (dd, 1H), 7.98 (dd, 1H), 7.70 (broad s, 1H), 7.40 (broad s, 1H), 7.24 (s, 1H), 7.12 (s, 1H), 6.74 (d, 1H), 4.55 (broad s, 2H), 4.35 (m, 1H), 3.84 (m, 1H), 2.81 (t, 1H), 2.67 (t, 1H), 2.44 (m, 1H), 2.34 (s, 3H), 2.30 (s, 3H), 2.19 (m, 2H), 2.10 (m, 4H), 1.98 (m, 2H), 1.91 (s, 3H), 1.83 (m, 2H), 1.73 (m, 2H), 1.02 (t, 6H). MS (EI) for $C_{30}H_{40}N_6O_3$: 533 (MH$^+$).

Using analogous synthetic techniques and substituting with alternative starting reagents, the following compounds [(7B)-(7S)] were prepared. Alternative starting reagents were obtained commercially unless otherwise indicated.

(7B): 2,5-dimethyl-N-[8-(5-{[(phenylmethyl)amino]carbonyl}pyridin-2-yl)-8-azabicyclo[3.2.1]oct-3-endo-yl]benzene-1,4-dicarboxamide. Prepared according to the method of example 7 by using 6-(3-endo-amino-8-azabicyclo[3.2.1]oct-8-yl)-N-(phenylmethyl)pyridine-3-carboxamide (synthesized in example 2) in step 1 and omitting steps 2 and 3. $^1$H NMR (400 MHz, $d_6$-DMSO): 8.90 (s, 1H), 8.71 (s, 1H), 8.31 (d, 1H), 8.07 (d, 1H), 7.76 (s, 1H), 7.46 (s, 1H), 7.41-7.28 (m, 6H), 7.19 (s, 1H), 6.86 (d, 1H), 4.64 (br s, 2H), 4.53 (d, 2H), 3.92 (br s, 1H), 2.41 (s, 3H), 2.36 (s, 3H), 2.30-1.90 (m, 8H). MS (EI) for $C_{30}H_{33}N_5O_3$: 512 (MH$^+$).

(7C): 2,5-dichloro-N-[8-(5-{[(phenylmethyl)amino]carbonyl}pyridin-2-yl)-8-azabicyclo[3.2.1]oct-3-endo-yl]benzene-1,4-dicarboxamide. Prepared according to the method of example 7 as an acetate salt by using 2,5-dichloroterephthalic acid and 6-(3-endo-amino-8-azabicyclo[3.2.1]oct-8-yl)-N-(phenylmethyl)pyridine-3-carboxamide (synthesized in example 2) in step 1 and omitting steps 2 and 3. $^1$H NMR (400 MHz, $d_6$-DMSO): 8.83-8.78 (m, 1H), 8.67-8.64 (d, 1H), 8.57-8.54 (d, 1H), 8.03-7.96 (m, 2H), 7.80-7.77 (s, 1H), 7.59 (s, 1H), 7.53 (s, 1H), 7.36-7.29 (m, 4H), 7.26-7.21 (m, 1H), 6.26-6.21 (m, 1H), 4.59-4.53 (br. s, 2H), 4.48-4.44 (d, 2H), 3.92-3.84 (m, 1H), 2.26-2.18 (m, 2H), 2.15-2.07 (m, 2H), 2.01-1.93 (m, 2H), 1.86-1.78 (d, 2H). MS (EI) for $C_{28}H_{27}Cl_2N_5O_3$: 553 (MH$^+$).

(7D): 2,5-dimethyl-N-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide. Prepared according to the method of example 7 as an acetate salt by using 6-(3-endo-amino-8-azabicyclo[3.2.1]oct-8-yl)-N-{(1S)-1-[4-(4-methylpiperazin-1-yl)phenyl]ethyl)}pyridine-3-carboxamide (synthesized in example 6) in step 1 and omitting steps 2 and 3. $^1$H NMR (400 MHz, $d_6$-DMSO): 8.66-8.61 (s, 1H), 8.47-8.41 (d, 1H), 8.25 (s, 1H), 8.01-7.94 (d, 1H), 7.70 (s, 1H), 7.40 (s, 1H), 7.27-7.21 (m, 3H), 7.12 (s, 1H), 6.95-6.88 (d, 2H), 6.79-6.71 (d, 1H), 5.13-5.03 (m, 1H), 4.59-4.53 (br. s, 2H), 3.86-3.79 (m, 1H), 3.27-3.15 (br. s, 4H), 2.93-2.81 (br. s, 4H), 2.52 (s, 3H), 2.35 (s, 3H), 2.30 (s, 3H), 2.24-2.16 (d, 2H), 2.15-2.07 (m, 2H), 2.02-1.95 (m, 2H), 1.87-1.80 (d, 2H), 1.46-1.39 (d, 3H). MS (EI) for $C_{36}H_{45}N_7O_3$: 624 (MH$^+$).

(7E): N-{8-[5-(aminocarbonyl)pyridin-2-yl]-8-azabicyclo[3.2.1]oct-3-endo-yl}-2,5-dimethylbenzene-1,4-dicarboxamide. Prepared according to the method of example 7 as an acetate salt by using 6-(3-endo-amino-8-azabicyclo[3.2.1]oct-8-yl)pyridine-3-carboxamide (synthesized in example 3) in step 1 and omitting steps 2 and 3. $^1$H NMR (400 MHz, $d_6$-DMSO): 8.51 (s, 1H), 8.26 (s, 1H), 8.06 (d, 1H), 7.90-7.83 (br. s, 1H), 7.68 (s, 1H), 7.38 (s, 1H), 7.33-7.26 (br. s, 1H), 7.25-7.17 (d, 1H), 7.13-7.04 (d, 1H), 6.93 (s, 1H), 4.66-4.55 (br. s, 2H), 3.89-3.82 (m, 1H), 2.33 (s, 3H), 2.28 (s, 3H), 2.26-2.19 (m, 2H), 2.15-2.07 (m, 2H), 2.03-1.96 (m, 2H), 1.93-1.86 (d, 2H). MS (EI) for $C_{28}H_{27}N_5O_3$: 422 (MH$^+$).

(7F): 2,5-dimethyl-N-{8-[5-({[(3S)-1-methylpiperidin-3-yl]amino}carbonyl)pyridin-2-yl]-8-azabicyclo[3.2.1]oct-3-endo-yl}benzene-1,4-dicarboxamide. Prepared as the acetate salt according to the method of example 7 by using (3S)-1-methylpiperidin-3-amine hydrochloride (synthesized according to reagent preparation 9) in step 3. $^1$H NMR (400 MHz, $d_6$-DMSO): 8.59 (d, 1H), 8.24 (d, 1H), 7.93 (m, 2H), 7.70 (broad s, 1H), 7.40 (broad s, 1H), 7.24 (s, 1H), 7.12 (s, 1H), 6.74 (d, 1H), 4.55 (broad s, 2H), 3.90 (m, 2H), 2.82 (m, 1H), 2.68 (m, 1H), 2.34 (s, 3H), 2.30 (s, 3H), 2.19 (m, 4H), 2.12 (m, 2H), 1.99 (m, 2H), 1.91 (s, 3H), 1.83 (m, 4H), 1.78 (m, 2H), 1.71 (m, 2H), 1.53 (m, 1H), 1.27 (m, 2H). MS (EI) for $C_{30}H_{40}N_6O_3$: 519 (MH$^+$).

(7G): N-{8-[5-({[(3R)-1-ethylpiperidin-3-yl]amino}carbonyl)pyridin-2-yl]-8-azabicyclo[3.2.1]oct-3-endo-yl}-2,5-dimethylbenzene-1,4-dicarboxamide. Prepared as the acetate salt according to the method of example 7 by using (3R)-1-ethylpiperidin-3-amine hydrochloride (synthesized according to reagent preparation 9) in step 3. $^1$H NMR (400 MHz, $d_6$-DMSO): 8.60 (d, 1H), 8.23 (d, 1H), 7.92 (m, 2H), 7.70 (broad s, 1H), 7.40 (broad s, 1H), 7.24 (s, 1H), 7.12 (s, 1H), 6.74 (d, 1H), 4.55 (broad s, 2H), 3.88 (m, 3H), 2.88 (m, 1H), 2.76 (m, 1H), 2.35 (s, 3H), 2.30 (s, 3H), 2.19 (m, 2H), 2.10 (m, 2H), 1.99 (m, 1H), 1.91 (s, 3H), 1.80 (m, 4H), 1.68 (m, 2H), 1.49 (m, 2H), 1.32 (m, 2H), 1.01 (t, 3H). MS (EI) for $C_{30}H_{40}N_6O_3$: 533 (MH$^+$).

(7H): 2,5-dimethyl-N-{8-[5-({[(3R)-1-methylpiperidin-3-yl]amino}carbonyl)pyridin-2-yl]-8-azabicyclo[3.2.1]oct-3-endo-yl}benzene-1,4-dicarboxamide. Prepared as the acetate salt according to the method of example 7 by using (3R)-1-methylpiperidin-3-amine hydrochloride (synthesized according to reagent preparation 9) in step 3. $^1$H NMR (400 MHz, $d_6$-DMSO): 8.59 (d, 1H), 8.24 (d, 1H), 7.93 (m, 2H), 7.70 (broad s, 1H), 7.40 (broad s, 1H), 7.24 (s, 1H), 7.12 (s, 1H), 6.74 (d, 1H), 4.55 (broad s, 2H), 3.89 (m, 3H), 2.79 (m, 1H), 2.64 (m, 1H), 2.35 (s, 3H), 2.30 (s, 3H), 2.18 (m, 2H), 2.10 (m, 2H), 1.99 (m, 2H), 1.91 (s, 3H), 1.80 (m, 4H), 1.68 (m, 2H), 1.50 (m, 2H), 1.27 (m, 2H). MS (EI) for $C_{29}H_{38}N_6O_3$: 519 (MH$^+$).

(7I): 2,5-dimethyl-N-{8-[5-({[(3R)-1-methylpyrrolidin-3-yl]amino}carbonyl)pyridin-2-yl]-8-azabicyclo[3.2.1]oct-3-endo-yl}benzene-1,4-dicarboxamide. Prepared as the acetate salt according to the method of example 7 by using (3R)-1- methylpyrrolidin-3-amine in step 3. $^1$H NMR (400 MHz, $d_6$-DMSO): 8.60 (d, 1H), 8.23 (dd, 1H), 7.96 (d, 1H), 7.70 (broad s, 1H), 7.40 (broad s, 1H), 7.24 (s, 1H), 7.12 (s, 1H), 6.73 (d, 1H), 4.54 (broad s, 2H), 4.37 (m, 1H), 3.83 (m, 1H), 2.68 (m, 1H), 2.57 (m, 1H), 2.39 (m, 2H), 2.35 (s, 3H), 2.30 (s, 3H), 2.25 (s, 3H), 2.21 (m, 2H), 2.12 (m, 4H), 1.98 (m, 2H), 1.91 (s, 3H), 1.83 (m, 2H), 1.72 (m, 1H). MS (EI) for $C_{28}H_{36}N_6O_3$: 505 ($MH^+$).

(7J): 2,5-dimethyl-N-[8-(5-{[(1-methylpiperidin-4-yl)amino]carbonyl)}pyridin-2-yl)-8-azabicyclo[3.2.1]oct-3-endo-yl]benzene-1,4-dicarboxamide. Prepared as the acetate salt according to the method of example 7 by using 1-methylpiperidin-4-amine in step 3. $^1$H NMR (400 MHz, $d_6$-DMSO): 8.59 (d, 1H), 8.24 (d, 1H), 7.94 (m, 2H), 7.69 (broad s, 1H), 7.39 (broad s, 1H), 7.24 (s, 1H), 7.12 (s, 1H), 6.74 (d, 1H), 4.55 (broad s, 2H), 3.85 (m, 1H), 3.70 (m, 1H), 2.76 (m, 2H), 2.35 (s, 3H), 2.29 (s, 3H), 2.19 (m, 2H), 2.10 (m, 2H), 2.00 (m, 2H), 1.92 (m, 4H), 1.91 (s, 3H), 1.72 (m, 2H), 1.54 (m, 2H). MS (EI) for $C_{29}H_{38}N_6O_3$: 519 ($MH^+$).

(7K): N-[8-(5-{[(1-ethylpiperidin-4-yl)amino]carbonyl}pyridin-2-yl)-8-azabicyclo[3.2.1]oct-3-endo-yl]-2,5-dimethylbenzene-1,4-dicarboxamide. Prepared as the acetate salt according to the method of example 7 by using 1-ethylpiperidin-4-amine (synthesized according to reagent preparation 9) in step 3. $^1$H NMR (400 MHz, $d_6$-DMSO): 8.59 (d, 1H), 8.24 (d, 1H), 7.94 (m, 2H), 7.70 (broad s, 1H), 7.40 (broad s, 1H), 7.24 (s, 1H), 7.12 (s, 1H), 6.74 (d, 1H), 4.55 (broad s, 2H), 3.83 (m, 1H), 3.71 (m, 1H), 2.86 (m, 2H), 2.35 (s, 3H), 2.30 (s, 3H), 2.19 (m, 2H), 2.10 (m, 2H), 1.99 (m, 2H), 1.91 (s, 3H), 1.90 (m, 4H), 1.75 (m, 2H), 1.52 (m, 2H), 1.00 (t, 3H). MS (EI) for $C_{30}H_{40}N_6O_3$: 533 ($MH^+$).

(7L): 2,5-dimethyl-N-{8-[5-({[1-(1-methylethyl)piperidin-4-yl]amino}carbonyl)pyridin-2-yl]-8-azabicyclo[3.2.1]oct-3-endo-yl}benzene-1,4-dicarboxamide. Prepared as the acetate salt according to the method of example 7 by using 1-(1-methylethyl)piperidin-4-amine hydrochloride (synthesized according to reagent preparation 9) in step 3. $^1$H NMR (400 MHz, $d_6$-DMSO): 8.59 (d, 1H), 8.24 (d, 1H), 7.93 (m, 2H), 7.70 (broad s, 1H), 7.40 (broad s, 1H), 7.24 (s, 1H), 7.12 (s, 1H), 6.74 (d, 1H), 4.54 (broad s, 2H), 3.84 (m, 1H), 3.67 (m, 1H), 2.79 (m, 2H), 2.69 (m, 1H), 2.34 (s, 3H), 2.30 (s, 3H), 2.13 (m, 6H), 2.00 (m, 2H), 1.91 (s, 3H), 1.82 (m, 2H), 1.49 (m, 2H), 0.96 (d, 6H). MS (EI) for $C_{31}H_{42}N_6O_3$: 547 ($MH^+$).

(7M): N-{8-[5-({[(3S)-1-ethylpyrrolidin-3-yl]amino}carbonyl)pyridin-2-yl]-8-azabicyclo[3.2.1]oct-3-endo-yl}-2,5-dimethylbenzene-1,4-dicarboxamide. Prepared according to the method of example 7 as hydrochloride salt by using (3S)-1-ethylpyrrolidin-3-amine hydrochloride (synthesized according to reagent preparation 9) in step 3. $^1$H NMR (400 MHz, $CDCl_3$ w/10% $CD_3OD$): 8.68 (d, 1H), 8.00 (dd, 1H), 7.28 (s, 1H), 7.16 (s, 1H), 6.58 (d, 1H), 4.84 (br s, 1H), 4.61 (br s, 1H), 3.66 (br s, 1H), 3.51 d, 1H), 3.12-2.94 (m, 3H), 2.85 (q, 1H), 2.53-2.42 (m, 1H), 2.43 (s, 3H), 2.43 (s, 3H), 2.35-2.24 (m, 2H), 2.22-2.07 (m, 4H), 1.91 (br d, 2H), 1.33 (t, 3H). MS (EI) for $C_{29}H_{38}N_6O_4$: 519 ($MH^+$).

(7N): 2,5-dimethyl-N-{8-[5-({[(3R)-1-(1-methylethyl)piperidin-3-yl]amino}carbonyl)pyridin-2-yl]-8-azabicyclo[3.2.1]oct-3-endo-yl}benzene-1,4-dicarboxamide. Prepared according to the method of example 7 as an acetate salt by using (3R)-1-(1-methylethyl)piperidin-3-amine hydrochloride (synthesized according to reagent preparation 9) in step 3. $^1$H NMR (400 MHz, $d_6$-DMSO): 8.59 (d, 1H), 8.24 (d, 1H), 7.94 (dd, 1H), 7.89 (d, 1H), 7.70 (s, 1H), 7.40 (s, 1H), 7.24 (s, 1H), 7.12 (s, 1H), 6.74 (d, 1H), 4.55 (br s, 2H), 3.84 (br s, 2H), 2.81 (dd, 1H), 2.65-2.75 (m, 2H), 2.35 (s, 3H), 2.30 (s, 3H), 2.17-2.22 (m, 2H), 1.97-2.13 (m, 7H), 1.76-1.82 (m, 2H), 1.66-1.69 (m, 1H), 1.41-1.51 (m, 1H), 1.24-1.34 (m, 1H), 0.96 (d, 6H). MS (EI) for $C_{31}H_{42}N_6O_3$: 547 ($MH^+$).

(7O): N-{8-[5-({[(3S)-1-ethylpiperidin-3-yl]amino}carbonyl)pyridin-2-yl]-8-azabicyclo[3.2.1]oct-3-endo-yl}-2,5-dimethylbenzene-1,4-dicarboxamide. Prepared according to the method of example 7 as an acetate salt by using (3S)-1-ethylpiperidine-3-amine hydrochloride (synthesized according to reagent preparation 9) in step 3. $^1$H NMR (400 MHz, $d_6$-DMSO): 8.59 (d, 1H), 8.24 (d, 1H), 7.90-7.95 (m, 2H), 7.70 (s, 1H), 7.40 (s, 1H), 7.24 (s, 1H), 7.12 (S, 1H), 6.74 (d, 1H), 4.55 (br s, 2H), 3.83-3.92 (m, 2H), 2.87 (dd, 1H), 2.75 (dd, 1H), 2.35 (s, 4H), 2.32 (d, 1H), 2.30 (s, 4H), 2.17-2.22 (m, 2H), 2.08-2.13 (m, 2H), 1.98-2.00 (m, 2H), 1.76-1.82 (m, 5H), 1.66-1.70 (m, 1H), 1.44-1.53 (m, 1H), 1.25-1.35 (m, 1H), 0.99 (t, 3H). MS (EI) for $C_{30}H_{40}N_6O_3$: 533 ($MH^+$).

(7P): 2,5-dimethyl-N-{8-[5-({[(3S)-1-(1-methylethyl)piperidin-3-yl]amino}carbonyl)pyridin-2-yl]-8-azabicyclo[3.2.1]oct-3-endo-yl}benzene-1,4-dicarboxamide. Prepared according to the method of example 7 as an acetate salt by using (3S)-1-(1-methylethyl)piperidin-3-amine hydrochloride (synthesized according to reagent preparation 9) in step 3. $^1$H NMR (400 MHz, $d_6$-DMSO): 8.59 (d, 1H), 8.24 (d, 1H), 7.94 (dd, 1H), 7.89 (d, 1H), 7.70 (s, 1H), 7.40 (s, 1H), 7.24 (s, 1H), 7.12 (s, 1H), 6.74 (d, 1H), 4.55 (br s, 2H), 3.84 (br s, 2H), 2.81 (d, 1H), 2.65-2.75 (m, 2H), 2.35 (s, 3H), 2.30 (s, 3H), 2.17-2.22 (m, 2H), 2.07-2.13 (m, 3H), 1.97-2.04 (m, 3H), 1.76-1.82 (m, 2H), 1.66-1.70 (m, 1H), 1.41-1.50 (m, 1H), 1.24-1.34 (m, 1H), 0.96 (d, 6H). MS (EI) for $C_{31}H_{42}N_6O_3$: 547 ($MH^+$).

(7Q): 2,5-dimethyl-N-{8-[5-({[(3S)-1-(1-methylethyl)pyrrolidin-3-yl]amino}carbonyl)pyridin-2-yl]-8-azabicyclo[3.2.1]oct-3-endo-yl}benzene-1,4-dicarboxamide. Prepared according to the method of example 7 as a hydrochloride salt by using (S)-1-isopropylpyrrolidin-3-amine (synthesized according to reagent preparation 9) in step 3. $^1$H NMR (400 MHz, $CDCl_3$ w/ 10% $CD_3OD$): 8.64 (d, 1H), 7.97 (d, 1H), 7.29 (s, 1H), 7.17 (s, 1H), 6.61 (d, 1H), 4.69-6.60 (br m, 3H), 4.13 (m, 1H), 3.13 (d, 1H), 3.15 (m, 2H), 2.92 (d, 1HO, 2.68 (t, 2H), 2.58-2.03 (br m, 10H), 1.92 (d, 2H), 1.09 (dd, 6H). MS (EI) for $C_{30}H_{40}N_6O_3$: 533 ($MH^+$).

(7R): 2,5-dimethyl-N-{8-[5-({[(3S)-1-methylpyrrolidin-3-yl]amino}carbonyl)pyridin-2-yl]-8-azabicyclo[3.2.1]oct-3-endo-yl}benzene-1,4-dicarboxamide. Prepared according to the method of example 7 as a hydrochloride salt by using (3S)-1-methylpyrrolidin-3-amine in step 3. $^1$H NMR (400 MHz, $d_6$-DMSO): 8.63 (s, 1H), 7.95 (dd, 1H), 7.46 (d, 1H), 9.29 (s, 1H), 7.17 (s, 1H), 6.60 (d, 1H), 4.75 (m, 1H), 3.36 (m, 3H), 3.15 (q, 1H), 2.85 (br d, 1H), 2.66 (m, 1H), 2.49-2.27 (br m, 12H), 2.25-2.05 (br m, 3H), 1.93-1.75 (br m, 3H), 1.72 (m, 1H), 1.11 (t, 1H). MS (EI) for $C_{28}H_{36}N_6O_3$: 505 ($MH^+$).

(7S): N-{8-[5-({[(3R)-1-ethylpyrrolidin-3-yl]amino}carbonyl)pyridin-2-yl]-8-azabicyclo[3.2.1]oct-3-endo-yl}-2,5-dimethylbenzene-1,4-dicarboxamide. Prepared according to the method of example 7 as a hydrochloride salt by using (3R)-1-ethylpyrrolidin-3-amine hydrochloride (synthesized according to reagent preparation 9) in step 3. $^1$H NMR (400 MHz, $d_6$-DMSO): 11.60 (br d, 1H), 8.63 (dd, 1H), 8.32 (d, 1H), 7.70 (s, 1H), 7.40 (s, 1H), 7.25 (s, 1H), 7.13 (s, 1H), 4.78 (br s, 1H), 4.65 (br s, 1H), 3.95-3.05 (br m, 9H), 2.45-1.90 (br m, 14H), 1.25 (dt, 3H). MS (EI) for $C_{29}H_{38}N_6O_3$: 519 ($MH^+$).

SYNTHETIC SCHEME 9:

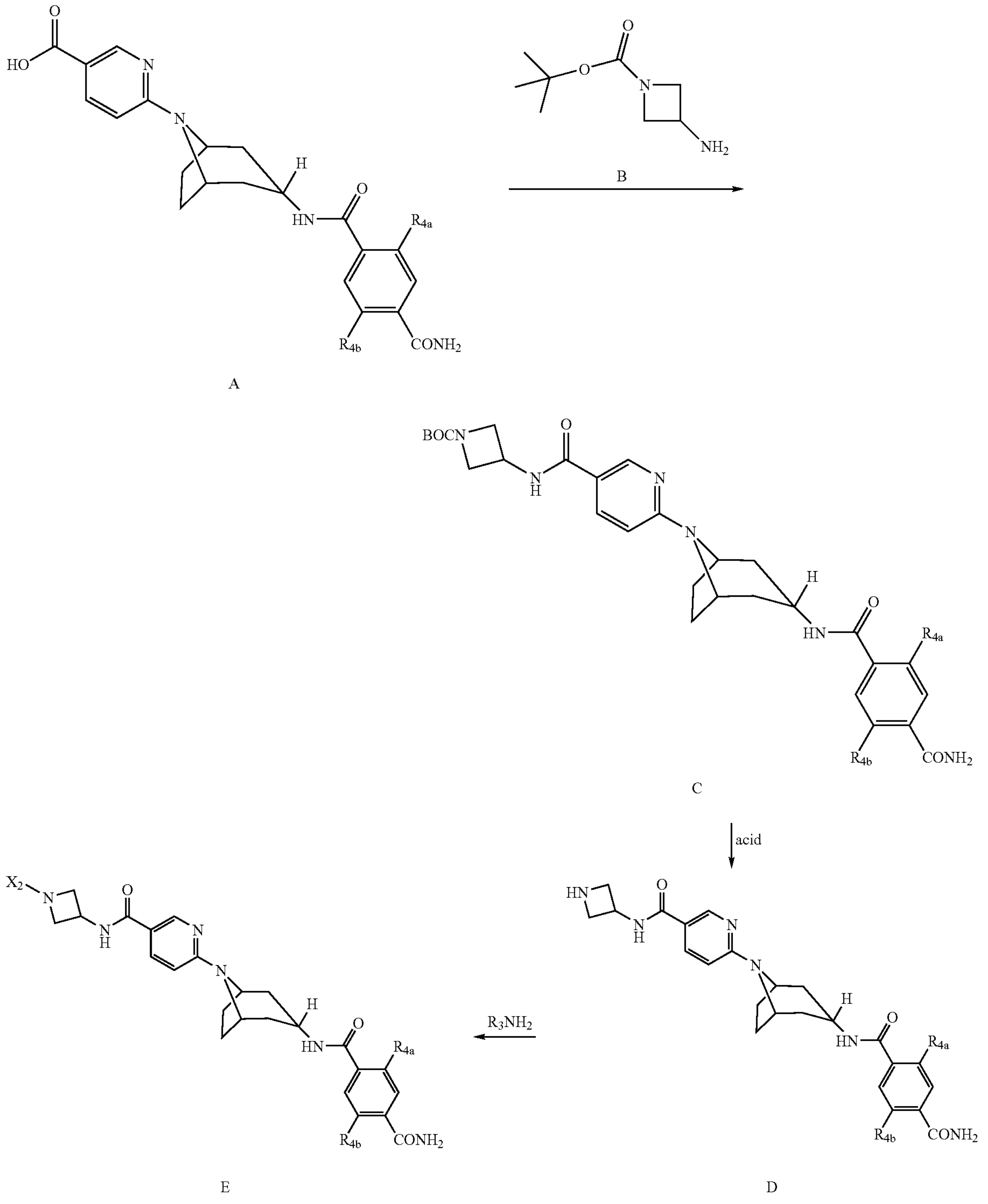

Scheme 9 generally describes the synthesis of all of the compound(s) listed in Example 9, wherein $X_2$, $R_{4a}$, and $R_{4b}$ are as defined in the specification.

In Scheme 9, compound (B) is added to compound (A) under appropriate reaction conditions and suitable solvents to condense and form the amide bond in compound (C). Compound (C) is then deprotected with an acid, such as HCl, to remove BOC and form compound (D). Compound (D) is then converted to (E) by treatment with $X_2$ under reductive alkylation conditions, wherein $X_2$ is either an aldehyde or ketone reagent allowed to react with (D) in the presence of a suitable reducing agent such as sodium cyanoborohydride, and wherein $X_2$ becomes either a methyl group, or is otherwise an alkyl group attached to the azetidinyl group by way of a methylene linker.

Example 10

N-{(1S)-2-amino-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide STEP 1: A solution of (S)-methyl 2-amino-2-(4-methoxyphenyl)acetate trifluoroacetate salt (synthesized according to reagent preparation 38) (0.30 g, 1.00 mmol), 6-[3-endo-({[2-methyl-3-methyloxy)phenyl]carbonyl}amino)-8-azabicyclo[3.2.1]oct-8-yl]pyridine-3-carboxylic acid (prepared in example 1, STEP 4) (0.43 g, 1.00 mmol), HOBt (0.16 g, 1.20 mmol), EDCI (0.23 g, 1.20 mmol) and 4-methylmorpholine (0.88 mL, 8.00 mmol) in dimethylformamide (5 mL) was stirred at room temperature for 18 hours. The reaction mixture was partitioned between ethyl acetate (100 mL) and brine (50 mL). The organic layer was separated and washed with brine (50 mL), dried over sodium sulfate, filtered and the solvent was concentrated. The residue was subjected to column chromatography (hexane:ethyl acetate 4:1 to 3:2) to give methyl (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoate, (0.51 g, 89% yield). MS (EI) for $C_{32}H_{36}N_4O_6$: 573 ($MH^+$).

STEP 2: A solution of methyl (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoate (0.48 g, 0.84 mmol) and an aqueous solution of 4M potassium hydroxide (0.42 mL, 1.68 mmol) in methanol (10 mL), tetrahydrofuran (5 mL) and water (5 mL) was stirred at 50° C. for 30 minutes. After cooling to room temperature the solvent was evaporated and the pH was adjusted to 2 with concentrated aqueous hydrochloric acid. The precipitate was collected by filtration, washed with water, and dried to afford (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoic acid (0.42 g, 89%). MS (EI) for $C_{31}H_{34}N_4O_6$: 557 (M−H).

STEP 3: A solution of (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoic acid (0.10 g, 0.18 mmol), a 2M solution of ammonia in methanol (0.18 mL, 0.36 mmol), HOBt (0.027 g, 0.20 mmol), EDCI (0.042 g, 0.22 mmol) and 4-methylmorpholine (0.10 mL, 0.90 mmol) in dimethylformamide (3 mL) was stirred at room temperature for 18 hours. The solvent was concentrated in vacuo and the residue was purified by preparatory reverse phase HPLC (0.1% ammonium acetate in aqueous acetonitrile mobile phase) to give N-{(1S)-2-amino-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide (17 mg, 11% yield). MS (EI) for $C_{31}H_{35}N_5O_5$: 558 ($MH^+$).

Using analogous synthetic techniques and substituting with alternative starting reagents, the following compounds [(9B)-(9E)] were prepared. Alternative starting materials were obtained commercially unless otherwise indicated.

(9B): methyl (2S)-[({6-[3-endo-({[2-methyl-3-(methyloxy)phenyl]carbonyl}-amino)-8-azabicyclo[3.2.1]oct-8-yl]pyridin-3-yl}carbonyl)amino][4-(methyloxy)phenyl]-ethanoate. Prepared in example 10 step 1. MS (EI) for $C_{32}H_{36}N_4O_6$: 573 ($MH^+$).

(9C): (2S)-[({6-[3-endo-({[2-methyl-3-(methyloxy)phenyl]carbonyl}-amino)-8-azabicyclo[3.2.1]oct-8-yl]pyridin-3-yl}carbonyl)amino][4-(methyloxy)phenyl]-ethanoic acid. Prepared in example 10 step 2. MS (EI) for $C_{31}H_{34}N_4O_6$: 557 (M−H).

(9D): N-{(1S)-2-(methylamino)-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 10 by using methylamine in step 3. $^1$H NMR (400 MHz, DMSO-$d_6$): 8.65 (d, 1H), 8.51 (d, 1H), 8.22 (d, 1H), 8.11 (m, 1H), 8.01 (dd, 1H), 7.38 (m, 2H), 7.22 (t, 1H), 7.01 (d, 1H), 6.90 (m, 2H), 6.86 (d, 1H), 6.73 (d, 1H), 5.54 (d, 1H), 4.54 (bs, 2H), 3.82 (m, 1H), 3.79 (s, 3H), 3.72 (s, 3H), 2.60 (d, 3H), 2.20 (m, 2H), 2.14 (s, 3H), 2.08 (m, 2H), 1.96 (m, 2H), 1.84 (d, 2H). MS (EI) for $C_{32}H_{37}N_5O_5$: 572 ($MH^+$).

(9E): N-{(1S)-2-(ethylamino)-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 10 by using ethylamine in step 3. MS (EI) for $C_{33}H_{39}N_5O_5$: 586 ($MH^+$).

SYNTHETIC SCHEME 10:

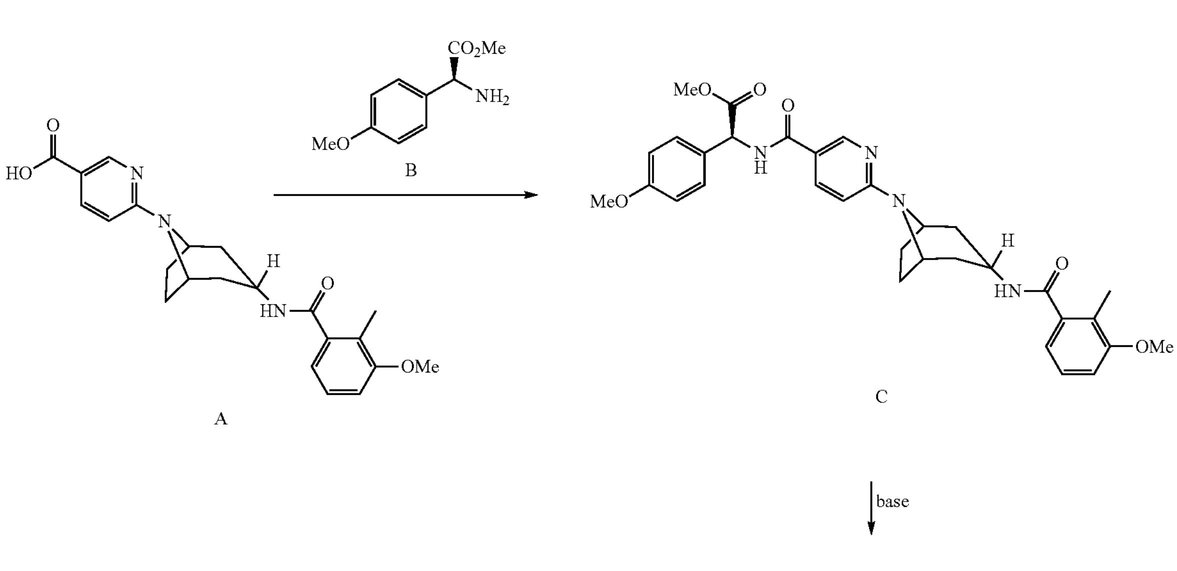

A

C

-continued

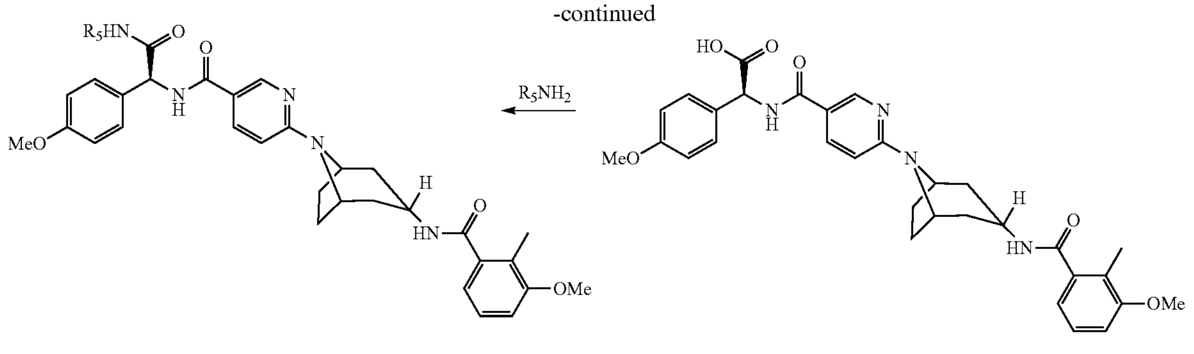

E D

Scheme 10 generally describes the synthesis of all of the compounds listed in Example 10, wherein $R_5$ is as defined in the specification.

In Scheme 10, compound (B) is added to compound (A) under appropriate reaction conditions and with a suitable coupling reagent, such as EDCI and HOBT, to condense and form the amide bond in compound (C). The ester in compound (C) is then hydrolyzed with a base, such as KOH, to form compound (D). To compound (D) is added $R_5NH_2$ under appropriate reaction conditions and with a suitable coupling reagent, such as EDCI and HOBT, to condense and form the amide bond in compound (E).

Example 10

N-{(1S)-2-amino-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide STEP 1: A solution of (S)-methyl 2-amino-2-(4-methoxyphenyl)acetate trifluoroacetate salt (synthesized according to reagent preparation 38) (0.30 g, 1.00 mmol), 6-[3-endo-({[2-methyl-3-methyloxy)phenyl]carbonyl}amino)-8-azabicyclo[3.2.1]oct-8-yl]pyridine-3-carboxylic acid (prepared in example 1, STEP 4) (0.43 g, 1.00 mmol), HOBt (0.16 g, 1.20 mmol), EDCI (0.23 g, 1.20 mmol) and 4-methylmorpholine (0.88 mL, 8.00 mmol) in dimethylformamide (5 mL) was stirred at room temperature for 18 hours. The reaction mixture was partitioned between ethyl acetate (100 mL) and brine (50 mL). The organic layer was separated and washed with brine (50 mL), dried over sodium sulfate, filtered and the solvent was concentrated. The residue was subjected to column chromatography (hexane:ethyl acetate 4:1 to 3:2) to give methyl (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoate, (0.51 g, 89% yield). MS (EI) for $C_{32}H_{36}N_4O_6$: 573 ($MH^+$).

STEP 2: A solution of methyl (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoate (0.48 g, 0.84 mmol) and an aqueous solution of 4M potassium hydroxide (0.42 mL, 1.68 mmol) in methanol (10 mL), tetrahydrofuran (5 mL) and water (5 mL) was stirred at 50° C. for 30 minutes. After cooling to room temperature, the solvent was evaporated and the pH was adjusted to 2 with concentrated aqueous hydrochloric acid. The precipitate was collected by filtration, washed with water, and dried to afford (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoic acid (0.42 g, 89%). MS (EI) for $C_{31}H_{34}N_4O_6$: 557 (M−H).

STEP 3: A solution of (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoic acid (0.10 g, 0.18 mmol), a 2M solution of ammonia in methanol (0.18 mL, 0.36 mmol), HOBt (0.027 g, 0.20 mmol), EDCI (0.042 g, 0.22 mmol) and 4-methylmorpholine (0.10 mL, 0.90 mmol) in dimethylformamide (3 mL) was stirred at room temperature for 18 hours. The solvent was concentrated in vacuo and the residue was purified by preparatory reverse phase HPLC (0.1% ammonium acetate in aqueous acetonitrile mobile phase) to give N-{(1S)-2-amino-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide (17 mg, 11% yield). MS (EI) for $C_{31}H_{35}N_5O_5$: 558 ($MH^+$).

Using analogous synthetic techniques and substituting with alternative starting reagents the following compounds [(10B)-(10E)] were prepared. Alternative starting materials were obtained commercially unless otherwise indicated.

(10B): methyl (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoate. Prepared in example 10 step 1. MS (EI) for $C_{32}H_{36}N_4O_6$: 573 ($MH^+$).

(10C): (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoic acid. Prepared in example 10 step 2. MS (EI) for $C_{31}H_{34}N_4O_6$: 557 (M−H).

(10D): N-{(1S)-2-(methylamino)-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 10 by using methylamine in step 3. $^1H$ NMR (400 MHz, DMSO-$d_6$): 8.65 (d, 1H), 8.51 (d, 1H), 8.22 (d, 1H), 8.11 (m, 1H), 8.01 (dd, 1H), 7.38 (m, 2H), 7.22 (t, 1H), 7.01 (d, 1H), 6.90 (m, 2H), 6.86 (d, 1H), 6.73 (d, 1H), 5.54 (d, 1H), 4.54 (bs, 2H), 3.82 (m, 1H), 3.79 (s, 3H), 3.72 (s, 3H), 2.60 (d, 3H), 2.20 (m, 2H), 2.14 (s, 3H), 2.08 (m, 2H), 1.96 (m, 2H), 1.84 (d, 2H). MS (EI) for $C_{32}H_{37}N_5O_5$: 572 ($MH^+$).

(10E): N-{(1S)-2-(ethylamino)-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide. Prepared according to the method of example 10 by using ethylamine in step 3. MS (EI) for $C_{33}H_{39}N_5O_5$: 586 ($MH^+$).

SYNTHETIC SCHEME 11:

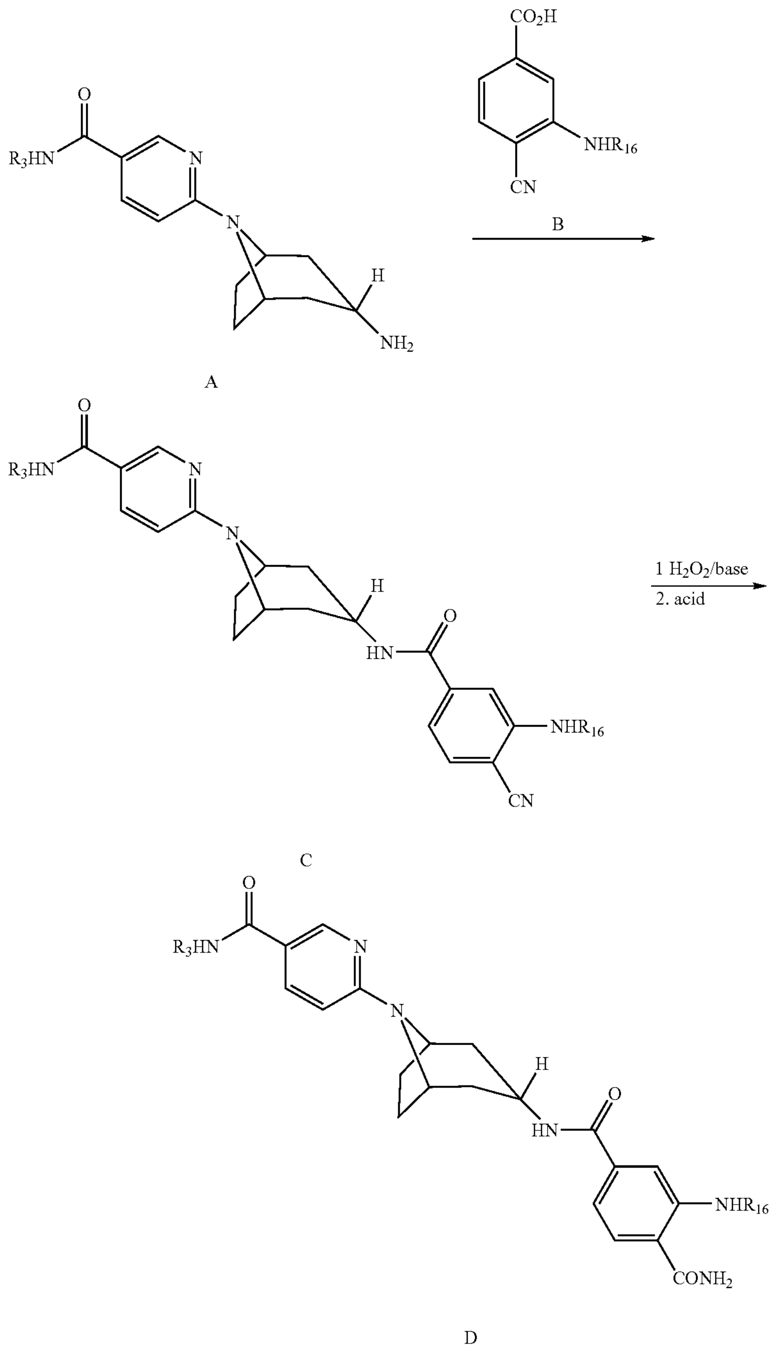

Scheme 11 generally describes the synthesis of all of the compound(s) listed in Example 11, wherein $R_3$ and $R_{16}$ are as defined in the specification.

In Scheme 11, compound (B) is added to compound (A) under appropriate reaction conditions and with a suitable coupling reagent, such as HOBT, to condense and form the amide bond in compound (C). Compound (C) is then converted to compound (D) by hydrolysis of the aromatic nitrile by treatment with a base, such as potassium carbonate, in the presence of a suitable oxidant, such as hydrogen peroxide, to arrive at the aromatic carboxamide (D).

Example 11

N4-{8-[5-(aminocarbonyl)pyridin-2-yl]-8-azabicyclo[3.2.1]oct-3-endo-yl}-2-[(trans-4-aminocyclohexyl)amino]benzene-1,4-dicarboxamide STEP 1: To a solution of methyl 3-bromo-4-cyanobenzoate (200 mg, 0.83 mmol) in dichloromethane (1.5 mL) and methanol (1.5) was added 1.0 N aqueous sodium hydroxide (1.7 mL, 1.7 mmol). The mixture was stirred vigorously for 2 h at room temperature. The volatile solvents were then removed in vacuo. The aqueous residue was acidified with 1 N aqueous hydrochloric acid and was then extracted with ethyl acetate. The organic layer was dried over magnesium sulfate, filtered, and concentrated to provide 3-bromo-4-cyanobenzoic acid (190 mg, 0.83 mmol, quantitative yield). $^1$H NMR (400 MHz, $CDCl_3$): 8.42 (d, 1H), 8.15 (dd, 1H), 7.80 (d, 1H).

STEP 2: To a solution of 3-bromo-4-cyanobenzoic acid (1.51 g, 6.69 mmol) in acetone (30 mL) was added cesium carbonate (4.4 g, 13.4 mmol) and benzyl bromide (790 uL, 6.69 mmol). The mixture was stirred at reflux for 15 hours at which point additional benzyl bromide was added (200 uL, 1.68 mmol). The mixture was stirred at reflux for a further 2 h and was then cooled to room temperature. Water and ethyl acetate were added and the layers were separated. The aqueous phase was then saturated with lithium chloride and extracted with ethyl acetate. The organic extracts were combined, dried over magnesium sulfate, filtered, and concentrated. The residue was purified by column chromatography (4:1 hexanes:ethyl acetate) to provide phenylmethyl 3-bromo-4-cyanobenzoate (957 mg, 3.03 mmol, 45% yield) as a yellow orange oil that slowly solidified. $^1$H NMR (400 MHz, $CDCl_3$): 8.35 (d, 1H), 8.09 (dd, 1H), 7.73 (d, 1H), 7.46-7.35 (m, 5H), 5.35 (s, 2H).

STEP 3: A pressure vessel containing a magnetic stirbar was charged with phenylmethyl 3-bromo-4-cyanobenzoate (100 mg, 0.32 mmol), 1,1-dimethylethyl(trans-4-aminocyclohexyl)carbamate (69 mg, 0.32 mmol), cesium carbonate (125 mg, 0.38 mmol), XANTPHOS (19 mg, 0.032 mmol), tris(dibenzylideneacetone)dipalladium(0) (15 mg, 0.016 mmol) and dioxane (1.5 mL). The vessel was then sealed and heated to 95° C. The suspension was stirred for approximately 24 h at that temperature and was then allowed to cool to room temperature. The suspension was poured into water, and the resulting aqueous mixture was extracted twice with ethyl acetate. The organic extracts were combined, dried over magnesium sulfate, filtered, and concentrated in vacuo. The residue was then purified by column chromatography (4:1 hexanes:ethyl acetate) to provide impure phenylmethyl 4-cyano-3-{[trans-4-({[(1,1-dimethylethyl)oxy]carbonyl}-amino)cyclohexyl]amino}benzoate (71.8 mg, 0.16 mmol) as a yellow powder. This material was carried into the subsequent step without further purification. $^1$H NMR (400 MHz, $CDCl_3$): 7.45-7.28 (m, 8H), 5.37 (s, 2H), 4.47 (m, 1H), 3.40 (m, 1H), 2.12 (m, 4H), 1.46 (s, 9H), 1.31 (m, 4H).

STEP 4: Palladium on carbon 10% by weight Degussa type (50 mg) was added to a solution of phenylmethyl 4-cyano-3-{[trans-4-({[(1,1-dimethylethyl)oxy]carbonyl}amino)cyclohexyl]amino}benzoate (71.8 mg, 0.16 mmol) in ethyl acetate (3 mL) and methanol (400 uL). The mixture was subjected to 1 atm of hydrogen for 70 min. The catalyst was then removed by filtration through celite. The resulting filtrate was concentrated to provide 4-cyano-3-{[trans-4-({[(1,1-dimethylethyl)oxy]carbonyl}amino)cyclohexyl]amino}benzoic acid (55.8 mg, 0.16 mmol) which was carried into the subsequent step without further purification. $^1$H NMR (400 MHz, $CD_3OD$): 7.47 (d, 1H), 7.37 (s, 1H), 7.24 (d, 1H), 3.47-3.21 (m, 2H), 2.09 (m, 2H), 1.98 (m, 2H), 1.88 (m, 2H), 1.43 (s, 9H), 1.24 (m, 2H); MS (EI) for $C_{19}H_{25}N_3O_4$: 304 ($MH^+$-tert-butyl).

STEP 5: To a solution of 4-cyano-3-{[trans-4-({[(1,1-dimethylethyl)oxy]carbonyl}amino)cyclohexyl]amino}benzoic acid (55.8 mg, 0.16 mmol) was added HATU (59 mg, 0.16 mmol). The resulting mixture was stirred at room temperature for 2.5 h. More HATU (60 mg, 0.16 mmol) was then added, and the mixture was stirred for a further 40 min at room temperature. At that point 6-(3-endo-amino-8-azabicyclo[3.2.1]oct-8-yl)pyridine-3-carboxamide (synthesized in example 3) (45 mg, 0.16 mmol) was added followed by diisopropylethylamine (167 uL, 0.96 mmol). The solution was stirred 45 min at room temperature after which water was added. The aqueous mixture was then extracted twice with ethyl acetate. The organic extracts were combined, washed with 10% aqueous lithium chloride solution, dried over magnesium sulfate, filtered, and concentrated. The residue was subject to column chromatography (5% methanol in dichloromethane) to provide 1,1-dimethylethyl [trans-4-({5-[({8-[5-(aminocarbonyl)pyridin-2-yl]-8-azabicyclo[3.2.1]oct-3-endo-yl}amino)carbonyl]-2-cyanophenyl}amino)cyclohexyl]carbamate (50.8 mg, 0.061 mmol). $^1$H NMR (400 MHz, $CDCl_3$): 8.62 (d, 1H), 7.94 (dd, 1H), 7.44 (d, 1H), 7.15 (s, 1H), 6.80 (d, 1H), 6.62 (d, 1H), 6.56 (d, 1H), 4.65 (br s, 2H), 4.53 (d, 1H), 4.47 (br d, 1H), 4.22 (m, 1H), 3.55-3.36 (m, 2H), 2.39-2.25 (m, 4H), 2.18-2.02 (m, 6H), 1.86 (d, 2H), 1.45 (s, 9H), 1.37-1.22 (m, 4H); MS (EI) for $C_{32}H_{41}N_7O_4$: 588 ($MH^+$).

STEP 6: To a solution of 1,1-dimethylethyl [trans-4-({5-[({8-[5-(aminocarbonyl)pyridin-2-yl]-8-azabicyclo[3.2.1]oct-3-endo-yl}amino)carbonyl]-2-cyanophenyl}amino)cyclohexyl]carbamate (40.7 mg, 0.069 mmol) in DMSO (1 mL) was added potassium carbonate (19 mg, 0.138 mmol) followed by aqueous hydrogen peroxide (30%, 2 drops). The mixture was stirred at room temperature for 1 h. Additional hydrogen peroxide (4 drops) was then added, and the mixture was stirred a further 35 min at 45° C. After cooling to room temperature, the solution was diluted to 2 mL total volume with acetonitrile:water (2.5:1), and the mixture was purified by preparative reverse phase HPLC to provide 1,1-dimethylethyl [trans-4-({2-(aminocarbonyl)-5-[({8-[5-(aminocarbonyl)pyridin-2-yl]-8-azabicyclo[3.2.1]oct-3-endo-yl}amino)carbonyl]phenyl}amino)cyclohexyl]carbamate (17.6 mg, 0.029 mmol, 42% yield). $^1$H NMR (400 MHz, $CD_3OD$): 8.64 (d, 1H), 7.99 (dd, 1H), 7.63 (d, 1H), 7.06 (s, 1H), 6.88 (dd, 1H), 6.76 (d, 1H), 4.64 (br s, 2H), 4.00 (m, 1H), 3.37 (m, 2H), 2.30-2.12 (m, 8H), 2.02-1.93 (m, 4H), 1.43 (s, 9H), 1.35 (m, 4H).

STEP 7: To a flask containing 1,1-dimethylethyl [trans-4-({2-(aminocarbonyl)-5-[({8-[5-(aminocarbonyl)pyridin-2-yl]-8-azabicyclo[3.2.1]oct-3-endo-yl}amino)carbonyl]phenyl}amino)cyclohexyl]carbamate (17.6 mg, 0.029 mmol) was added 2.0 M aqueous hydrochloric acid (2 mL, 4 mmol). The mixture was stirred for 1 h at room temperature then the resulting solution was lyophilized to give N4-{8-[5-(aminocarbonyl)pyridin-2-yl]-8-azabicyclo[3.2.1]oct-3-endo-yl}-2-[(trans-4-aminocyclohexyl)amino]benzene-1,4-dicarboxamide as the hydrochloride salt. $^1$H NMR (400 MHz, $CD_3OD$): 8.45 (d, 1H), 8.38 (dd, 1H), 8.13 (d, 1H), 8.03 (d, 1H), 7.96 (dd, 1H), 7.40 (d, 1H), 4.82 (br s, 2H), 4.15 (br s, 1H), 3.77 (m, 1H), 3.20 (m, 1H), 2.49 (m, 2H), 2.43-2.24 (m, 6H), 2.17 (m, 4H), 1.71 (m, 2H), 1.56 (m, 2H); MS (EI) for $C_{27}H_{35}N_7O_3$: 506 ($MH^+$).

Using analogous synthetic techniques and substituting with alternative starting reagents, the following compounds [(11B)-(11C)] were prepared. Alternative starting materials were obtained commercially unless otherwise indicated.

(11B): N4-{8-[5-(aminocarbonyl)pyridin-2-yl]-8-azabicyclo[3.2.1]oct-3-endo-yl}-2-{[3-{[2-(dimethylamino)ethyl]oxy}-4-(methyloxy)phenyl]amino}benzene-1,4-dicarboxamide. Prepared according to the method of example 11 by using 3-{[2-(dimethylamino)ethyl]oxy}-4-(methyloxy)aniline (Gaster et al. *J. Med. Chem.* 1998, 41, 1218-1235) in step 3 then omission of step 7. $^1$H NMR (400 MHz, $CD_3OD$): 8.42 (d, 1H), 8.37 (dd, 1H), 7.74 (d, 1H), 7.48 (d, 1H), 7.36 (d, 1H), 7.08-6.99 (m, 3H), 6.95 (d, 1H), 4.75 (br s, 2H), 4.34 (m, 2H), 4.06 (m, 1H), 3.88 (s, 3H), 3.58 (m, 2H), 3.02 (s, 6H), 2.33-2.15 (m, 8H); MS (EI) for $C_{32}H_{39}N_7O_5$: 602 ($MH^+$).

(11C): N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-[(2-morpholin-4-ylethyl)amino]benzene-1,4-dicarboxamide. Prepared according to the method of example 11 by proceeding directly to step 5 using 6-(3-endo-amino-8-azabicyclo[3.2.1]oct-8-yl)-N-{(1S)-1-[4-(4-methylpiperazin-1-yl)phenyl]ethyl}pyridine-3-carboxamide (synthesized in example 6) and 3-bromo-4-cyanobenzoic acid (synthesized in step 1 above) then conducting step 3 using 2-morpholin-4-ylethanamine and step 6. $^1H$ NMR (400 MHz, $CD_3OD$): 8.60 (d, 1H), 7.97 (dd, 1H), 7.63 (d, 1H), 7.29 (d, 2H), 7.08 (s, 1H), 6.96 (d, 2H), 6.93 (d, 1H), 6.75 (d, 1H), 5.17 (q, 1H), 4.62 (br s, 2H), 3.98 (m, 1H), 3.73 (m, 4H), 3.35 (t, 2H), 3.24 (m, 4H), 2.84 (m, 4H), 2.68 (t, 2H), 2.54 (m, 4H), 2.51 (s, 3H), 2.30-2.12 (m, 6H), 1.97 (m, 2H), 1.94 (s, 6H), 1.52 (d, 3H); (EI) for $C_{40}H_{53}N_9O_4$: 724.6 ($MH^+$).

SYNTHETIC SCHEME 12:
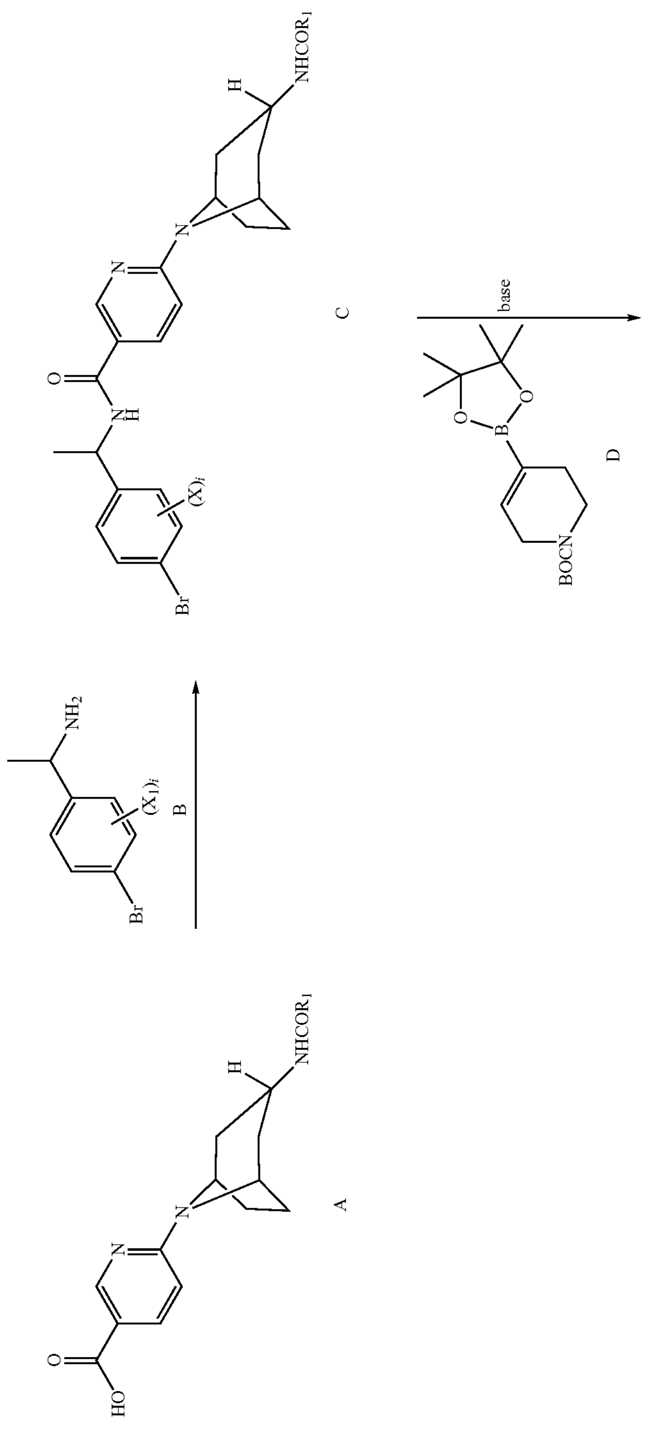

-continued
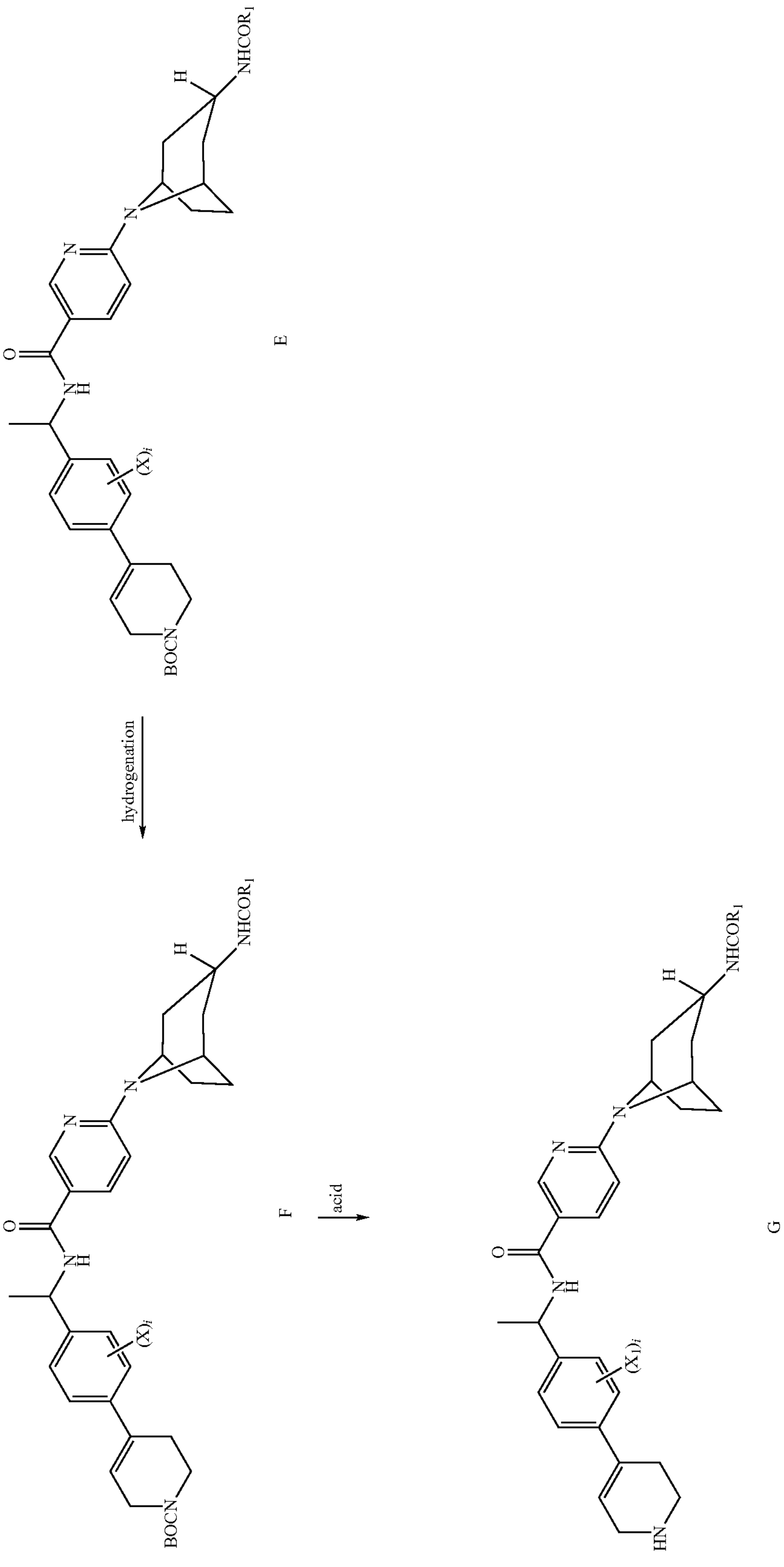
E
F
G

Scheme 12 generally describes the synthesis of all of the compound(s) listed in Example 12, wherein $X_1$, $R_1$ and (i) are as defined in the specification.

In Scheme 12, compound (B) is added to compound (A) under appropriate reaction conditions and with a suitable coupling reagent, such as EDCI and HOBT, to condense and form the amide bond in compound (C). Aryl bromide (C) is then treated with a boronate ester (D) under suitable reaction conditions in the presence of an appropriate palladium catalyst to arrive at compound (E). Compound (E) is reduced with a reducing agent, such as 10% palladium on charcoal, to arrive at compound (F). Compound (F) is then deprotected in the presence of an acid, such as HCl, to remove BOC and arrive at compound (G).

Example 12

N-[1-(2,6-difluoro-4-piperidin-4-ylphenyl)ethyl]-6-[3-endo-({[2-methyl-3-(methyloxy)phenyl]carbonyl}amino)-8-azabicyclo[3.2.1]oct-8-yl]pyridine-3-carboxamide STEP 1: To a mixture of 1-(4-bromo-2,6-difluorophenyl) ethanone (450 mg, 0.91 mmol), titanium isopropoxide (1.14 mL, 4.61 mmol) in ethanol (10 mL) was added a solution of 2M ammonia in ethanol (4.8 mL, 9.6 mmol), and the resulting mixture was stirred at room temperature. After 18 hours, sodium borohydride (115 mg, 3.48 mmol) was added and stirring was continued at room temperature for three hours. The reaction mixture was poured into a 2M aqueous ammonium hydroxide solution (100 mL) then filtered. The filtrate was extracted with ethyl acetate (3×50 mL), and the combined extract was washed with water (100 mL), then brine (100 mL), dried over sodium sulfate, filtered and concentrated to give 1-(4-bromo-2,6-difluorophenyl)ethanamine (236 mg, 62% yield), MS (EI) for $C_8H_8BrF_2N$: 237 ($MH^+$).

STEP 2: A mixture of 6-[3-endo-({[2-methyl-3-(methyloxy)phenyl]-carbonyl}amino)-8-azabicyclo[3.2.1]oct-8-yl] pyridine-3-carboxylic acid (synthesized in example 1)(276 mg, 0.70 mmol), EDCI (95 mg, 0.70 mmol), 1-hydroxybenzotriazole (95 mg, 0.70 mmol), and N,N-diisopropylethylamine (0.37 mL, 2.1 mmol) in N,N-dimethylformamide (3 mL) was stirred at room temperature for 15 minutes. To this mixture was added a solution of 1-(4-bromo-2,6-difluorophenyl)ethanamine (165 mg, 0.70 mmol) in N,N-dimethylformamide (0.5 mL) and stirring was continued for 18 hours. The reaction mixture was diluted with ethyl acetate (30 mL), washed with 5% aqueous lithium chloride solution (2×10 mL), saturated sodium bicarbonate solution (10 mL), dried over sodium sulfate, filtered and concentrated. The crude product was purified by flash chromatography (65-95% ethyl acetate-hexanes) to give the N-[1-(4-bromo-2,6-difluorophenyl)ethyl]-6-[3-endo-({[2-methyl-3-(methyloxy)phenyl]carbonyl}amino)-8-azabicyclo[3.2.1]oct-8-yl]pyridine-3-carboxamide (348 mg, 81% yield). $^1$HNMR (400 MHz, $CDCl_3$): 8.58 (d, 1H), 7.86 (dd, 1H), 7.20-7.17 (dd, 1H), 7.08 (s, 1H), 7.06 (s, 1H), 6.95 (dd, 2H), 6.70 (br, 1H), 6.36-6.35 (br, 1H), 6.69-6.67 (m, 1H), 4.50 (br, 2H), 4.22-4.20 (m, 1H), 3.86 (s, 3H), 2.29-2.27 (m, 2H), 2.28 (s, 3H), 2.20-2.17 (m, 2H), 2.00 (d, 2H), 1.85-1.81 (d, 2H), 1.58-1.57 (d, 3H); MS (EI) for $C_{30}H_{31}BrF_2N_4O_3$: 614 ($MH^+$).

STEP 3: A mixture of N-[1-(4-bromo-2,6-difluorophenyl) ethyl]-6-[3-endo-({[2-methyl-3-(methyloxy)phenyl]carbonyl}amino)-8-azabicyclo[3.2.1]oct-8-yl]pyridine-3-carboxamide (348 mg, 0.57 mmol), 3,6-dihydro-2H-pyridine-1-tert-butoxycarbonyl-4-boronic acid pinacol ester (228 mg, 0.74 mmol), [1,1'-bis(diphenylphosphino)ferrocene]dichloropalladium(II) complex with dichloromethane (28 mg, 5 mol %), potassium carbonate (234 mg, 1.7 mmol), and N,N-dimethylformamide (4.5 mL) was first degassed with nitrogen for 10 minutes then stirred at 80° C. for 18 hours. The reaction mixture was cooled to room temperature, diluted with ethyl acetate (45 mL), washed with 5% aqueous lithium chloride solution (2×20 mL), dried over sodium sulfate, filtered and concentrated. The crude product was purified by flash chromatography (65-95% ethyl acetate in hexanes) to give 1,1-dimethylethyl 4-(3,5-difluoro-4-{1-[({6-[3-endo-({[2-methyl-3-(methyloxy)phenyl]carbonyl}amino)-8-azabicyclo[3.2.1]oct-8-yl]pyridin-3-yl}carbonyl)amino]ethyl}phenyl)-3,6-dihydropyridine-1(2H)-carboxylate (290 mg, 71% yield). $^1$HNMR (400 MHz, $CDCl_3$): 8.59 (d, 1H), 7.90 (dd, 1H), 7.21 (dd, 1H), 6.94-6.88 (m, 4H), 6.60 (d, 1H), 6.53 (d, 1H), 6.20 (d, 1H), 6.06 (br, 1H), 5.78-5.74 (m, 1H), 4.61 (br, 2H), 4.27 (q, 1H), 4.07 (br, 2H), 3.85 (s, 3H), 3.62 (tr, 2H), 2.42 (br, 2H), 2.36-2.31 (m, 2H), 2.29 (s, 3H), 2.22-2.20 (m, 2H), 2.03-1.97 (m, 2H), 1.85 (br, 1H), 1.81 (br, 1H), 1.62 (d, 3H), 1.49 (s 9H); MS (EI) for $C_{40}H_{47}F_2N_5O_5$: 716 ($MH^+$).

STEP 4: A mixture of 1,1-dimethylethyl 4-(3,5-difluoro-4-{1-[({6-[3-endo-({[2-methyl-3-(methyloxy)phenyl]carbonyl}amino)-8-azabicyclo[3.2.1]oct-8-yl]pyridin-3-yl}carbonyl)amino]ethyl}phenyl)-3,6-dihydropyridine-1(2H)-carboxylate (133 mg, 0.19 mmol), 10% palladium on charcoal (Degussa type, 100 mg), acetic acid (100 uL, 1.0 mmol), and methanol (20 mL) was shaken in a Parr hydrogenation apparatus at 30 psi for 6 hours. The reaction mixture was filtered, concentrated, re-dissolved in a 1:1 mixture (6 mL) of methanol and 4M hydrogen chloride in dioxane, and stirred at room temperature overnight. The reaction mixture was basified with 2M ammonia in methanol, concentrated, and purified by preparatory reverse phase HPLC (ammonium acetate buffered aqueous acetonitrile eluent). The product containing fractions were combined, and lyophillized to give a solid (58 mg, 0.094 mmol) which dissolved in methanol (4 mL) containing and 4M hydrogen chloride in dioxane (49 uL, 0.20 mmol), then evaporated to dryness which gave N-[1-(2,6-difluoro-4-piperidin-4-ylphenyl)ethyl]-6-[3-endo-({[2-methyl-3-(methyloxy)phenyl]carbonyl}amino)-8-azabicyclo[3.2.1]oct-8-yl]pyridine-3-carboxamide hydrochloride. (65 mg, 51% yield). $^1$HNMR (400 MHz, $d_4$-methanol): 8.40 (d, 1H), 8.34 (dd, 1H), 7.37 (d, 1H), 7.23 (dd, H), 7.01 (d, 1H), 6.94-6.90 (m, 3H), 5.48 (q, 1H), 4.80 (br, 2H), (4.10 (tr, 1H), 3.84 (s, 3H), 3.47 (br, 2H), 3.16 (m, 2H), 3.93 (m, 2H), 2.37-2.33 (m, 4H), 2.24-2.15 (m, 2H), 2.20 (s, 3H), 2.06 (d, 2H), 1.94-1.89 (m, 2H), 1.65 (d, 2H); MS (EI) for $C_{35}H_{41}F_2N_5O_3$: 618 ($MH^+$).

Using analogous synthetic techniques and substituting with alternative starting reagents, compound (12B) was prepared. Alternative starting materials were obtained commercially unless otherwise indicated.

(12B): N-[1-(2-fluoro-4-piperidin-4-ylphenyl)ethyl]-6-[3-endo-({[2-methyl-3-(methyloxy)phenyl]carbonyl}amino)-8-azabicyclo[3.2.1]oct-8-yl]pyridine-3-carboxamide. Prepared as the hydrochloride salt according to the method of example 12 by starting with 4-bromo-2-fluoroacetophenone in step 1. $^1$H-NMR (400 MHz, $d_4$-methanol): 8.44 (s, 1H), 8.38 (d, 1H), 7.40 (m, 2H), 7.24 (dd, 1H), 7.19 (d, 1H), 7.02 (dd, 2H), 6.91 (d, 1H), 5.41 (q, 1H), 4.79 (br, 2H), 4.11 (tr, 1H), 3.84 (s, 3H), 3.48 (d, 2H) 3.14 (m, 2H), 2.90 (m, 2H), 2.38-2.35 (m, 4H), 2.24-2.15 (m, 4H), 2.21 (s, 3H), 2.10-2.20 (m, 2H), 1.92-1.87 (m, 2H), 1.57 (d, 3H); MS (EI) for $C_{35}H_{42}FN_5O_3$: 600 ($MH^+$).

SYNTHETIC SCHEME 13:
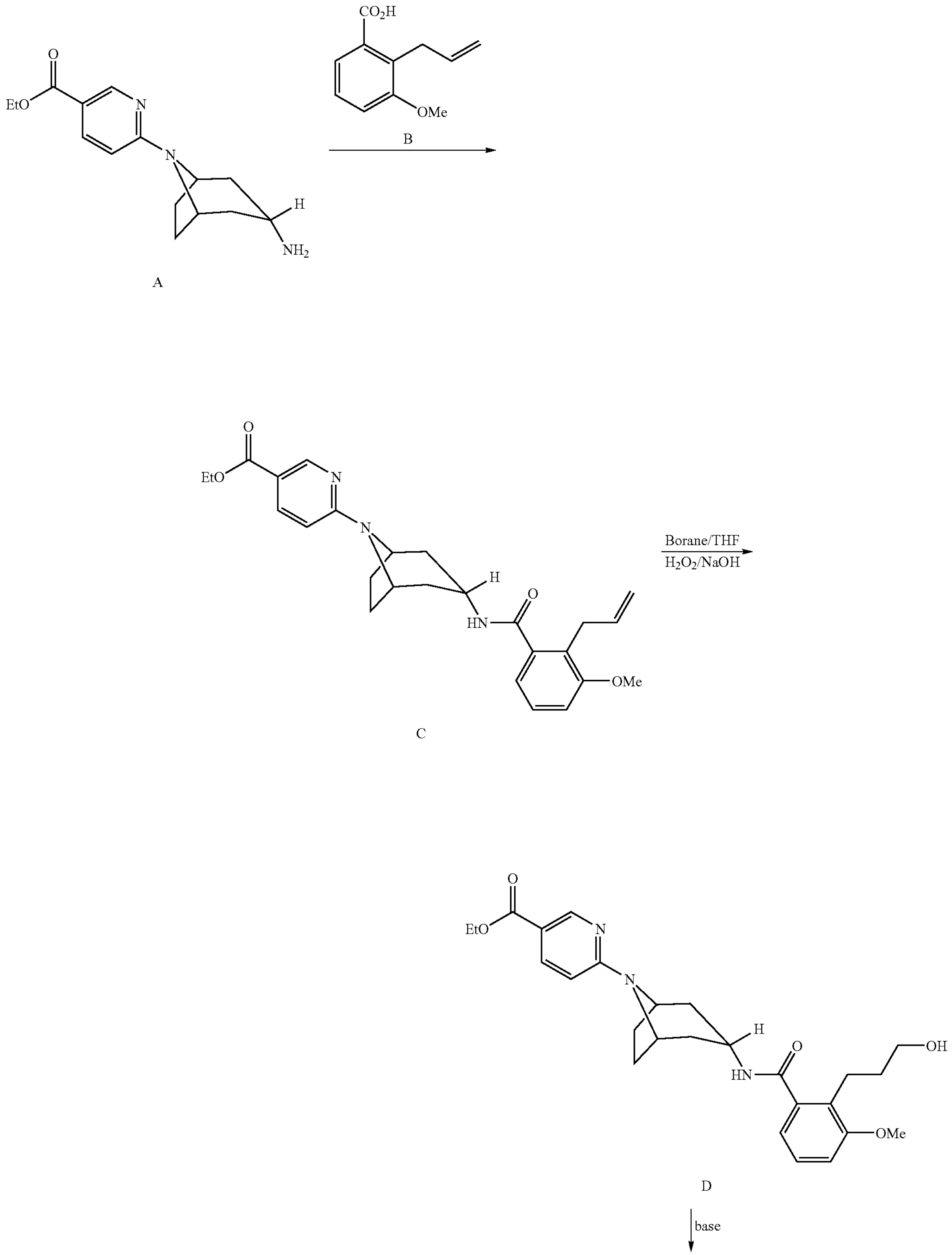

-continued

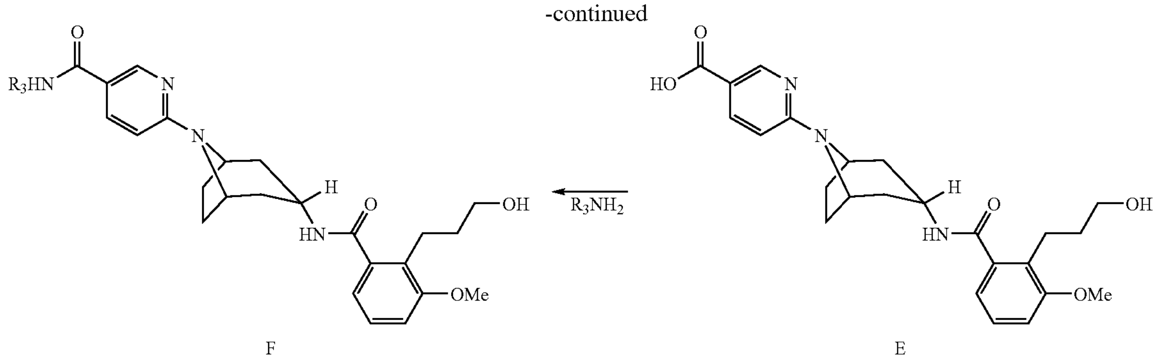

Scheme 13 generally describes the synthesis of all of the compound(s) listed in Example 13, wherein $R_3$ is as defined in the specification.

In Scheme 13, compound (B) is added to compound (A) under appropriate reaction conditions and with a suitable coupling reagent, such as HATU, to condense and form the amide bond in compound (C). Compound (C) is then converted to intermediate (D) by hydroboration. Thus, (C) is first treated with borane in THF followed by reaction with hydrogen peroxide in the presence of a suitable base such as sodium hydroxide. The carboxylate of compound (D) is then hydrolyzed by a base, such as KOH, to arrive at compound (E). $R_3NH_2$ is then added to compound (E) under appropriate reaction conditions and with a suitable coupling reagent, such as HATU, to condense and form the amide bond in compound (F).

Example 13

6-[3-endo-({[2-(3-hydroxypropyl)-3-(methyloxy) phenyl]-carbonyl}amino)-8-azabicyclo[3.2.1]oct-8-yl]-N-(phenylmethyl)pyridine-3-carboxamide STEP 1: A solution of ethyl 6-(3-endo-amino-8-azabicyclo[3.2.1]oct-8-yl)pyridine-3-carboxylate hydrochloride (synthesized in example 1) (2.60 g, 6.69 mmol), 3-(methyloxy)-2-prop-2-en-1-ylbenzoic acid (synthesized in reagent preparation 19) (1.28 g, 6.69 mmol), HATU (2.54 g, 6.69 mmol), and diisopropylethylamine (3.46 g, 26.76 mmol) in DMF (10 mL) was stirred at room temperature for 18 h. The reaction mixture was diluted with ethyl acetate (250 mL), washed with saturated sodium bicarbonate (100 mL), 5% lithium chloride (2×100 mL), and brine (100 mL), dried over sodium sulfate, filtered and concentrated to give crude ethyl 6-[3-endo-({[3-(methyloxy)-2-prop-2-en-1-ylphenyl] carbonyl}amino)-8-azabicyclo[3.2.1]oct-8-yl]pyridine-3-carboxylate (3.52 g) as a brown oil. MS (EI) for $C_{26}H_{31}N_3O_4$: 450 ($MH^+$).

STEP 2: To a solution of ethyl 6-[3-endo-({[3-(methyloxy)-2-prop-2-en-1-ylphenyl]carbonyl}amino)-8-azabicyclo[3.2.1]oct-8-yl]pyridine-3-carboxylate (213 mg, 0.40 mmol) in THF (5 mL) was added a 1.0 M solution of borane THF complex in THF (0.40 mL, 0.40 mmol) at 0° C. After removing the ice bath, the mixture was stirred at room temperature for 4 h. Additional 1.0 M solution of borane THF complex in THF (0.40 mL, 0.40 mmol) was added and stirring was continued for 18 h. Another 1.0 M solution of borane THF complex in THF (0.40 mL, 0.40 mmol) was added and the mixture was stirred for an additional 24 h. Then water (1.0 mL) was added followed by 10% sodium hydroxide (1.0 mL), and 30% hydrogen peroxide (2.2 mL). The reaction mixture was stirred at room temperature for another 90 min, then cooled to 0° C., and sodium thiosulfate (3.40 g, 21.5 mmol) was added carefully. The ice bath was removed and the mixture was stirred at room temperature for 30 min. The mixture was acidified to pH3 with 1N hydrochloric acid, and extracted with ethyl acetate (3×40 mL). The organic layers were washed with brine (20 mL), dried over sodium sulfate, filtered and concentrated to afford crude ethyl 6-[3-endo-({[2-(3-hydroxypropyl)-3-(methyloxy)phenyl]carbonyl}amino)-8-azabicyclo[3.2.1]oct-8-yl]pyridine-3-carboxylate (258 mg). MS (EI) for $C_{26}H_{33}N_3O_5$: 468 ($MH^+$).

STEP 3: A suspension of ethyl 6-[3-endo-({[2-(3-hydroxypropyl)-3-(methyloxy)phenyl]carbonyl}amino)-8-azabicyclo[3.2.1]oct-8-yl]pyridine-3-carboxylate (240 mg, 0.51 mmol) and potassium hydroxide (58 mg, 1.02 mmol) in methanol (6 mL) and water (2 mL) was stirred at 60° C. for 2 h. After cooling to room temperature, water was added to the resulting mixture, and the pH adjusted to 5 with 1N aqueous hydrochloric acid. Extraction with ethyl acetate (3×30 mL), drying over sodium sulfate then filtration and concentration provided crude 6-[3-endo-({[2-(3-hydroxypropyl)-3-(methyloxy)phenyl]carbonyl}amino)-8-azabicyclo[3.2.1]oct-8-yl]pyridine-3-carboxylic acid (120 mg, 53% yield). MS (EI) for $C_{24}H_{29}N_3O_5$: 440 ($MH^+$).

STEP 4: A solution of 6-[3-endo-({[2-(3-hydroxypropyl)-3-(methyloxy)-phenyl]carbonyl}amino)-8-azabicyclo[3.2.1]oct-8-yl]pyridine-3-carboxylic acid (35 mg, 0.08 mmol), N-methylmorpholine (26 µl, 0.24 mmol), benzylamine (10 µl, 0.08 mmol) and HATU (30 mg, 0.08 mmol) in dimethylformamide (1 mL) was stirred at 40° C. for 15 h. The mixture was cooled to room temperature and diluted with ethyl acetate. The organic portion was washed with 5% aqueous lithium chloride, 20% aqueous citric acid, brine, dried over sodium sulfate then filtered and concentrated. Purification by preparatory reverse phase HPLC (0.1% trifluoroacetic acid buffered aqueous acetonitrile eluent) afforded 6-[3-endo-({[2-(3-hydroxypropyl)-3-(methyl-oxy)phenyl]carbonyl}-amino)-8-azabicyclo[3.2.1]oct-8-yl]-N-(phenylmethyl)-pyridine-3-carboxamide as the trifluoroacetate salt (17 mg, 38% yield). $^1$H NMR (400 MHz, $d_6$-DMSO): 8.98 (br s, 1H), 8.56 (s, 1H), 8.30 (d, 1H), 8.14 (d, 1H), 7.35-7.31 (m, 5H), 7.26-7.21 (m, 2H), 7.05-7.02 (m, 2H), 6.85 (d, 1H), 4.63 (br s, 2H), 4.47 (d, 2H), 3.90-3.83 (m, 1H), 3.80 (s, 3H), 3.35 (t, 2H), 2.64-2.59 (m, 2H), 2.28-1.90 (m, 8H), 1.68-1.60 (m, 2H). MS (EI) for $C_{31}H_{36}N_4O_4$: 529 ($MH^+$).

Using analogous synthetic techniques and substituting with alternative starting reagents, compound (13B) was prepared. Alternative starting materials were obtained commercially unless otherwise indicated.

(13B): 6-[3-endo-({[2-(3-hydroxypropyl)-3-(methyloxy) phenyl]carbonyl}amino)-8-azabicyclo[3.2.1]oct-8-yl]pyridine-3-carboxamide. Prepared according to the method of example 13 by using ammonia in step 4. $^1$H NMR (400 MHz, $d_4$-MeOH): 8.62 (d, 1H), 8.34-8.31 (m, 1H), 7.99 (dd, 1H), 7.25 (t, 1H), 7.03 (d, 1H), 6.91 (d, 1H), 6.76 (d, 1H), 4.61 (br s, 2H), 4.04-3.97 (m, 1H), 3.84 (s, 3H), 3.51 (t, 2H), 2.75 (t, 2H), 2.35-2.07 (m, 6H), 1.92 (d, 2H), 1.85-1.76 (m, 2H); MS (EI) for $C_{24}H_{30}N_4O_4$: 439 ($MH^+$).

SYNTHETIC SCHEME 14:
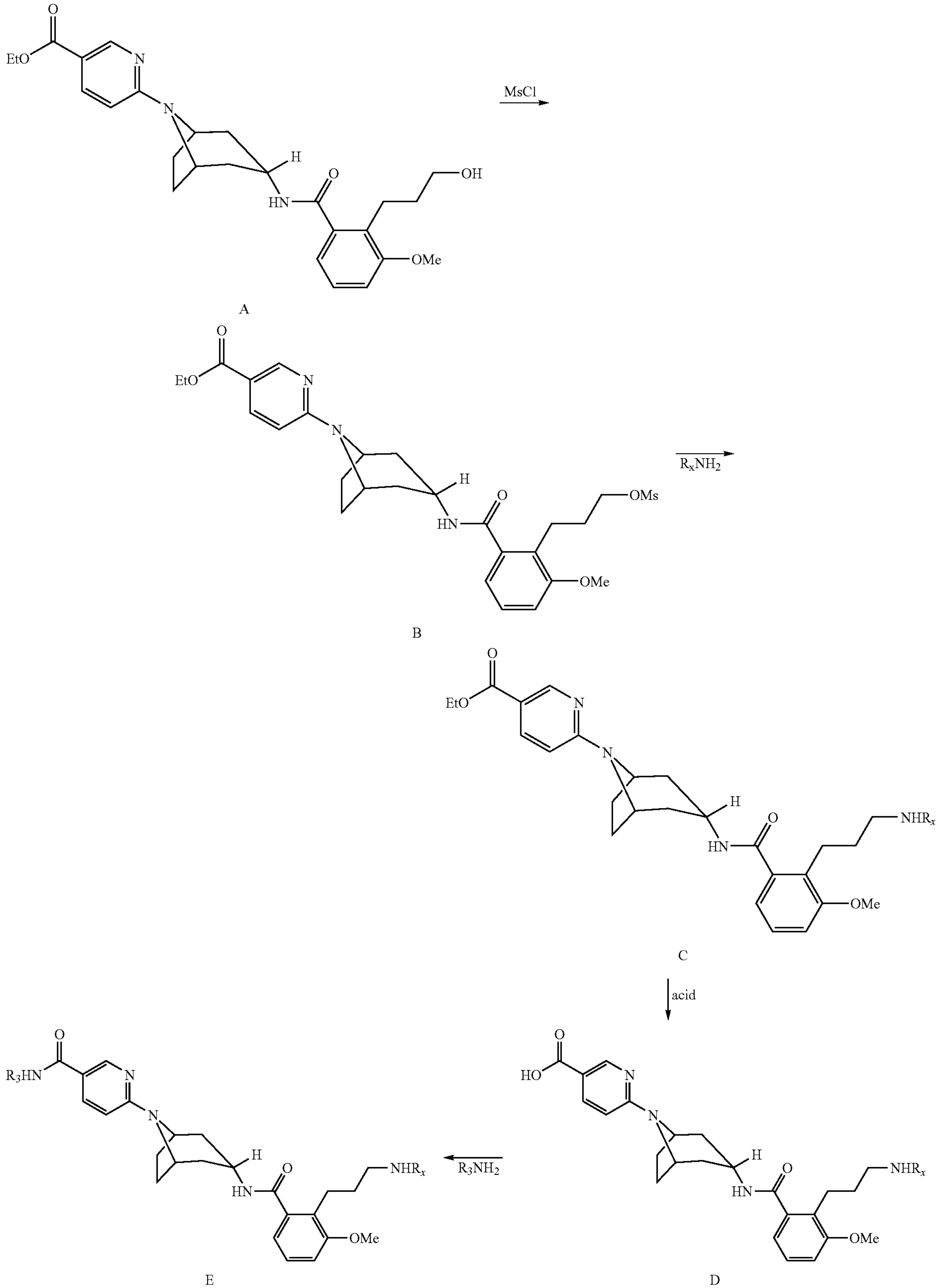
A
B
C
D
E

Scheme 14 generally describes the synthesis of all of the compound(s) listed in Example 14, wherein $R_3$ is as defined in the specification and $R_x$ is alkyl.

In Scheme 14, MsCl is added to compound (A) under appropriate reaction conditions to arrive at compound (B). To compound (B) is added $R_xNH_2$ under appropriate reaction conditions to arrive at compound (C). The carboxylate of compound (C) is then hydrolyzed with a base to arrive at compound (D). To compound (D) is added $R_3NH_2$ under appropriate reaction conditions and with a suitable coupling reagent, such as HATU, to condense and form the amide bond in compound (E).

Example 14

6-[3-endo-({[2-{3-[(1-methylethyl)amino]propyl}-3-(methyloxy)phenyl]carbonyl}amino)-8-azabicyclo[3.2.1]oct-8-yl]-N-(phenylmethyl)pyridine-3-carboxamide STEP 1: A solution of ethyl 6-[3-endo-({[2-(3-hydroxypropyl)-3-(methyloxy)phenyl]carbonyl}amino)-8-azabicyclo[3.2.1]oct-8-yl]pyridine-3-carboxylate (synthesized in example 13) (90 mg, 0.19 mmol, example 13, step 2), triethylamine (51 mg, 0.50 mmol), and mesyl chloride (29 mg, 0.26 mmol) in dichloromethane (5 mL) was stirred at room temperature for 2.5 h. The reaction mixture was concentrated and isopropylamine (5 mL) was added. The resulting mixture was stirred at 50° C. for 17 h and then concentrated. The residue was partitioned between ethyl acetate (50 mL) and saturated sodium bicarbonate (50 mL). The layers were separated and the organic layer was washed with brine (20 mL), dried over sodium sulfate, then filtered and concentrated to give crude ethyl 6-[3-endo-({[2-{3-[(1-methylethyl)amino]propyl}-3-(methyloxy)phenyl]carbonyl}amino)-8-azabicyclo[3.2.1]oct-8-yl]pyridine-3-carboxylate (87 mg, 89% yield) as a yellow oil. MS (EI) for $C_{29}H_{40}N_4O_4$: 509 ($MH^+$).

STEP 2: A suspension of ethyl 6-[3-endo-({[2-{3-[(1-methylethyl)amino]-propyl}-3-(methyloxy)phenyl]carbonyl}amino)-8-azabicyclo[3.2.1]oct-8-yl]pyridine-3-carboxylate (83 mg, 0.16 mmol) and potassium hydroxide (18 mg, 0.32 mmol) in methanol (3 mL) and water (1 mL) was stirred at 60° C. for 1 h. After cooling to room temperature, some of the methanol was evaporated, water was added to the resulting mixture and the pH adjusted to 7 with 1N aqueous hydrochloric acid. The resulting mixture was concentrated and purified by preparatory HPLC (0.1% trifluoroacetic acid-aqueous acetonitrile) to afford 6-[3-endo-({[2-{3-[(1-methylethyl)amino]propyl}-3-(methyloxy)phenyl]carbonyl}amino)-8-azabicyclo[3.2.1]oct-8-yl]pyridine-3-carboxylic acid trifluoroacetate salt (39 mg, 41% yield) as a colorless oil. MS (EI) for $C_{27}H_{36}N_4O_4$: 481 ($MH^+$).

STEP 3: A solution of 6-[3-endo-({[2-{3-[(1-methylethyl)amino]propyl}-3-(methyloxy)phenyl]carbonyl}amino)-8-azabicyclo[3.2.1]oct-8-yl]pyridine-3-carboxylic acid trifluoroacetate salt (39 mg, 0.08 mmol), benzylamine (10 mg, 0.09 mmol), HATU (31 mg, 0.08 mmol), and diisopropylethylamine (26 mg, 0.20 mmol) in DMF (2 mL) was stirred at room temperature for 5 h. The reaction mixture was purified by preparatory reverse phase HPLC (0.1% trifluoroacetic acid-aqueous acetonitrile) to provide 6-[3-endo-({[2-{3-[(1-methylethyl)amino]propyl}-3-(methyloxy)phenyl]carbonyl}amino)-8-azabicyclo[3.2.1]oct-8-yl]-N-(phenylmethyl)pyridine-3-carboxamide trifluoroacetate salt (25 mg, 45% yield). $^1H$ NMR (400 MHz, methanol-$d_4$): 8.57 (d, 1H), 8.46 (d, 1H), 8.26 (dd, 1H), 7.35 (m, 5H), 7.26 (m, 1H), 7.19 (d, 1H), 7.14 (d, 1H), 7.02 (d, 1H), 4.70 (br s, 2H), 4.57 (s, 2H), 4.10 (m, 1H), 3.88 (s, 3H), 3.25 (m, 1H), 2.88 (t, 2H), 2.81 (t, 2H), 2.39-2.20 (m, 6H), 2.10 (m, 2H), 1.26 (d, 6H); MS (EI) for $C_{34}H_{43}N_5O_3$: 570 ($MH^+$).

SYNTHETIC SCHEME 15:

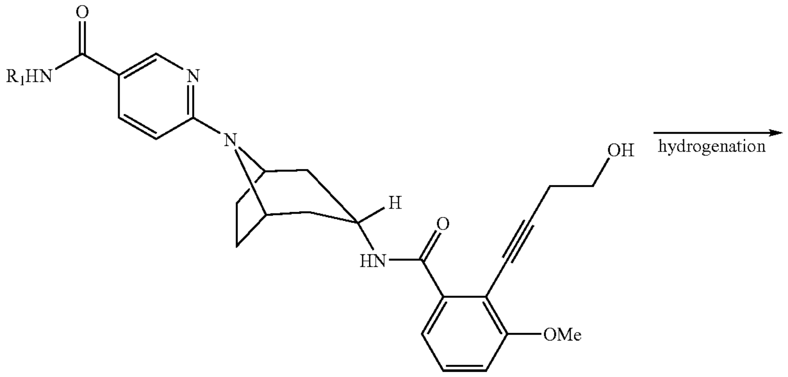

A

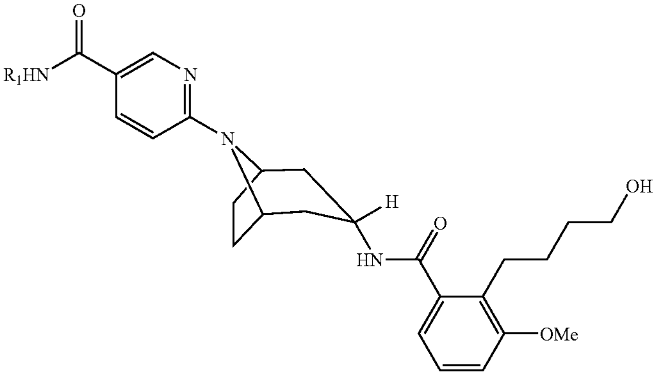

B

Scheme 15 generally describes the synthesis of all of the compound(s) listed in Example 15, wherein $R_1$ is as defined in the specification.

In Scheme 15, compound (A) is hydrogenated, such as being placed under a hydrogen balloon or in a pressure vessel under a hydrogen atmosphere in the presence of a suitable catalyst such as palladium on carbon, to arrive at compound (B).

Example 15

6-[3-endo-({[2-(4-hydroxybutyl)-3-(methyloxy)phenyl]carbonyl}amino)-8-azabicyclo[3.2.1]oct-8-yl]pyridine-3-carboxamide STEP 1: 6-[3-endo-({[2-(4-hydroxybut-1-yn-1-yl)-3-(methyloxy)phenyl]carbonyl}amino)-8-azabicyclo[3.2.1]oct-8-yl]pyridine-3-carboxamide (synthesized in example 3) (0.069 g, 0.152 mmol) in methanol (20 ml) was stirred under a hydrogen balloon overnight at room temperature. The mixture was filtered through Celite and the filter cake rinsed with ethyl acetate (2×10 ml). The filtrate was dried over anhydrous sodium sulfate, filtered and the solution was concentrated. The solid residue was purified by preparatory reverse phase HPLC (0.1% ammonium acetate buffered aqueous acetonitrile mobile phase) and the combined pure fractions were lyophilized to yield 6-[3-endo-({[2-(4-hydroxybutyl)-3-(methyloxy)phenyl]carbonyl}-amino)-8-azabicyclo[3.2.1]oct-8-yl]pyridine-3-carboxamide as a white powder (0.047 g; 68% yield). $^1$H NMR (400 MHz, $d_4$-MeOH): 8.56 (d, 1H), 8.34 (d, 1H), 8.10 (dd, 1H), 7.24 (t, 1H), 7.02 (d, 1H), 6.96-6.88 (m, 2H), 4.65 (br s, 2H), 4.06-3.99 (m, 1H), 3.53 (t, 2H), 2.73 (t, 2H), 2.37-2.10 (m, 6H), 1.98 (d, 2H), 1.66-1.50 (m, 4H); MS (EI) for $C_{25}H_{32}N_4O_4$: 453 ($MH^+$).

SYNTHETIC SCHEME 16:

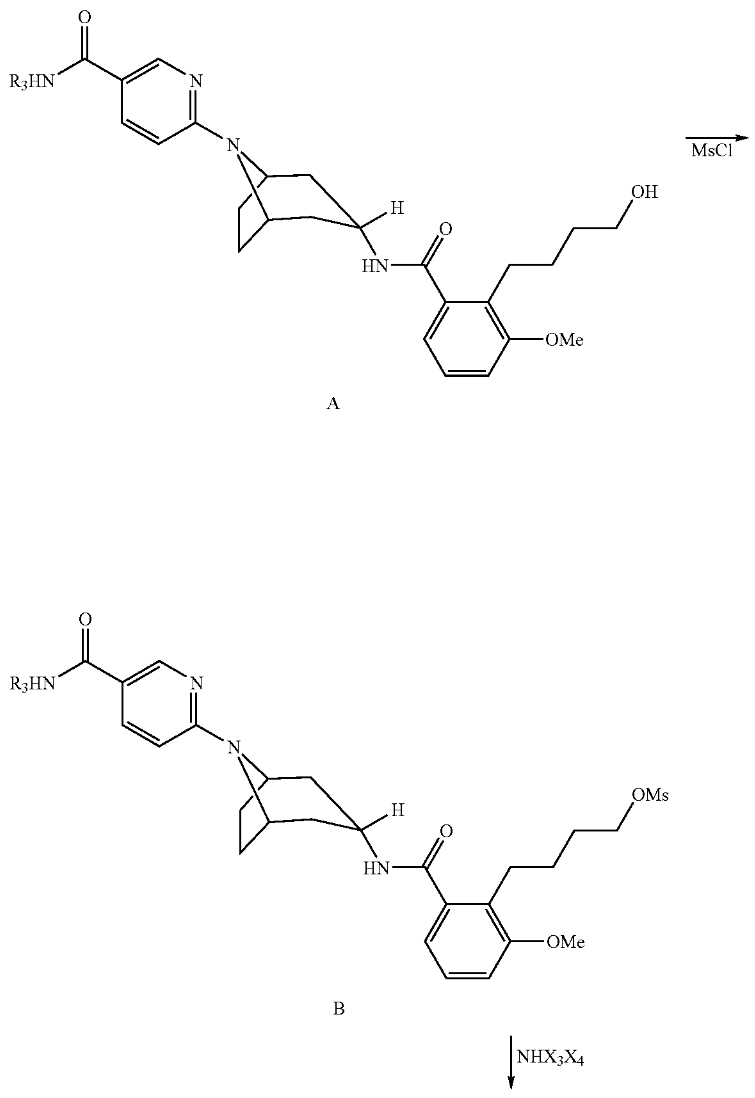

-continued

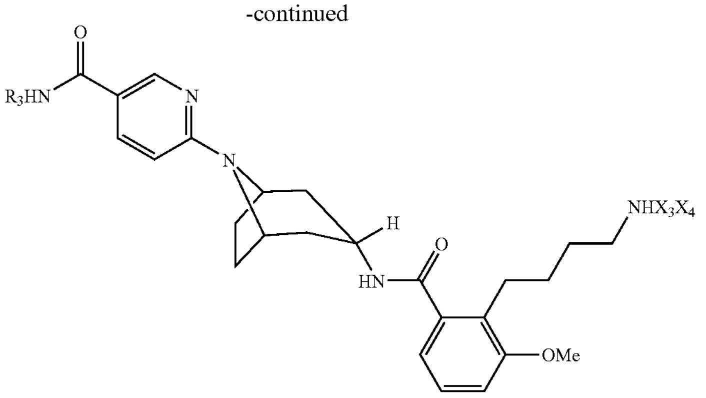

C

Scheme 16 generally describes the synthesis of all of the compound(s) listed in Example 16, wherein $R_3$ is as defined in the specification and $X_3$ and $X_4$ are each independently H or alkyl.

In Scheme 16, MsCl is added to compound (A) under appropriate reaction conditions to arrive at compound (B). To compound (B) is added $NHX_3X_4$ under appropriate reaction conditions to arrive at compound (C).

Example 16

6-{3-endo-[({2-[4-(dimethylamino)butyl]-3-(methyloxy)phenyl}carbonyl)amino]-8-azabicyclo[3.2.1]oct-8-yl}pyridine-3-carboxamide STEP 1: To a stirred solution of 6-[3-endo-({[2-(4-hydroxybutyl)-3-(methyloxy)phenyl]carbonyl}amino)-8-azabicyclo[3.2.1]oct-8-yl]pyridine-3-carboxamide (synthesized in example 15) (0.038 g, 0.0823 mmol) in dichloromethane (3 ml) was added triethylamine (0.034 ml, 0.250 mmol) followed by methanesulfonyl chloride (0.008 ml; 0.110 mmol) and the reaction mixture was stirred at room temperature overnight. More triethylamine (0.034 ml, 0.250 mmol) and methanesulfonyl chloride (0.008 ml; 0.110 mmol) were added to the solution and the mixture was stirred at room temperature for two additional hours. The mixture was rotary evaporated and to the residue was added dimethylamine (4 ml, 2 M solution in tetrahydrofuran, 2 mmol). The resulting solution was stirred in a sealed tube vessel at 60° C. for 2 h, cooled to room temperature and concentrated. The residue was purified by preparatory reverse phase HPLC (0.1% ammonium acetate in aqueous acetonitrile mobile phase) and the combined pure fractions were lyophilized to yield 6-{3-endo-[({2-[4-(dimethylamino)butyl]-3-(methyloxy)phenyl}carbonyl)amino]-8-azabicyclo[3.2.1]oct-8-yl}pyridine-3-carboxamide (0.006 g; 15% yield). $^1H$ NMR (400 MHz, $d_4$-MeOH): 8.62 (d, 1H), 8.01 (dd, 1H), 7.28 (t, 1H), 7.05 (d, 1H), 6.94 (d, 1H), 6.78 (d, 1H), 4.62 (br s, 2H), 4.05-3.95 (m, 1H), 3.24-3.17 (m, 2H), 3.11 (t, 2H), 2.85 (s, 6H), 2.37-2.08 (m, 6H), 1.91 (d, 2H), 1.80-1.60 (m, 4H); MS (EI) for $C_{27}H_{37}N_5O_3$: 480 ($MH^+$).

SYNTHETIC SCHEME 17:

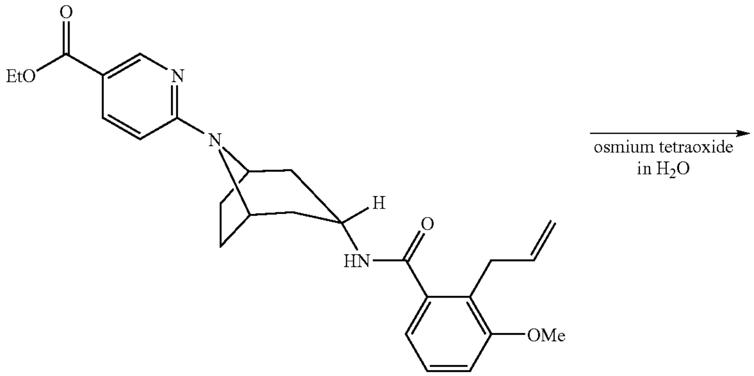

A

-continued

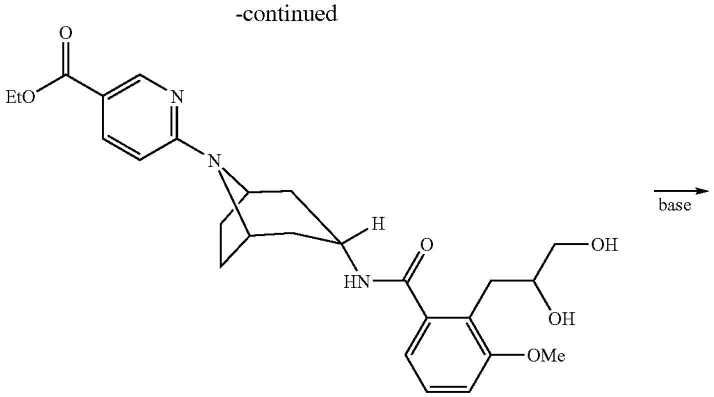

B

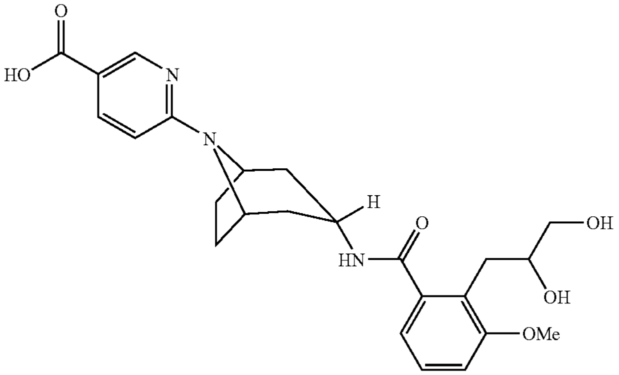

C $NR_3NH_2$

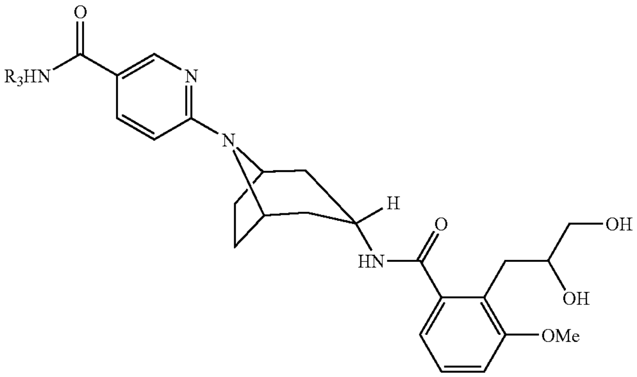

D

Scheme 17 generally describes the synthesis of all of the compound(s) listed in Example 17, wherein $R_3$ is as defined in the specification.

In Scheme 17, compound (A) is hydroxylated with an oxidizing agent, such as osmium tetroxide, under appropriate reaction conditions to form compound (B). The carboxylate of compound (B) is then hydrolyzed with a base, such as KOH, to form compound (C). The carboxylic acid thus formed is converted to carboxamide (D) by treatment with an amine $R_3NH_2$, or ammonia in the case of $R_3$ selected to be hydrogen, in the presence of a suitable coupling agent such as HATU.

Example 17

6-[3-endo-({[2-(2,3-dihydroxypropyl)-3-(methyloxy)phenyl]carbonyl}amino)-8-azabicyclo[3.2.1]oct-8-yl]pyridine-3-carboxamide STEP 1: To a stirred solution of ethyl 6-[3-endo-({[3-(methyloxy)-2-prop-2-en-1-ylphenyl]carbonyl}amino)-8-azabicyclo[3.2.1]oct-8-yl]pyridine-3-carboxylate (synthesized in example 13) (0.210 g, 0.470 mmol) and 4-methylmorpholine N-oxide (0.137 g; 1.17 mmol) in a mixture of acetone (0.8 ml) and water (0.2 ml) was added a catalytic amount of osmium tetroxide (0.020 ml, 4 wt % solution in water). The reaction mixture was stirred at 40° C. for 5 h and then quenched by addition of a 10% aqueous solution of sodium bisulfite (0.5 ml). The water phase was extracted with ethyl acetate (2×2 ml) and the organic layer was dried over anhydrous sodium sulfate and concentrated under vacuum to give ethyl 6-[3-endo({[2-(2,3-dihydroxypropyl)-3-(methyloxy)phenyl]carbonyl}amino)-8-azabicyclo[3.2.1]oct-8-yl]pyridine-3-carboxylate (0.191 g; 85% yield). MS (EI) for $C_{26}H_{33}N_3O_6$: 484 ($MH^+$).

STEP 2: To a stirred solution of ethyl 6-[3-endo({[2-(2,3-dihydroxypropyl)-3-(methyloxy)phenyl]carbonyl}amino)-8-azabicyclo[3.2.1]oct-8-yl]pyridine-3-carboxylate (0.191 g, 0.395 mmol) in methanol (4.5 ml) was added potassium hydroxide (0.044 g; 0.79 mmol) in water (1.5 ml) and the reaction mixture was stirred at 60° C. for 3 h. The solvent was partially evaporated and the solution was acidified to pH 4 by addition of 1.5 M aqueous hydrochloric acid. The water phase was extracted with ethyl acetate (2×5 ml) and the combined organic layers were dried over anhydrous sodium sulfate, filtered and concentrated to give 6-[3-({[2-(2,3-dihydroxypropyl)-3-(methyloxy)phenyl]carbonyl}amino)-8-azabicyclo[3.2.1]oct-8-yl]pyridine-3-carboxylic acid (0.117 g; 65% yield). MS (EI) for $C_{24}H_{29}N_3O_6$: 454 (M–H).

STEP 3: A stirred solution of 6-[3-({[2-(2,3-dihydroxypropyl)-3-(methyloxy)phenyl]carbonyl}amino)-8-azabicyclo [3.2.1]oct-8-yl]pyridine-3-carboxylic acid (0.117 g, 0.257 mmol) and HATU in dimethylformamide was saturated with $NH_3$(g) for 0.5 h, and the reaction mixture was stirred in a sealed tube at room temperature overnight. The crude mixture was purified by preparatory reverse phase HPLC (0.1% ammonium acetate buffered aqueous acetonitrile eluent) and the combined pure fractions were lyophilized to yield 6-[3-endo-({[2-(2,3-dihydroxypropyl)-3-(methyloxy)phenyl] carbonyl}amino)-8-azabicyclo[3.2.1]oct-8-yl]pyridine-3-carboxamide (0.047 g, 40% yield). $^1$H NMR (400 MHz, $d_4$-MeOH): 8.89-8.85 (m, 1H), 8.62 (d, 1H), 7.98 (dd, 1H), 7.30 (t, 1H), 7.07 (d, 1H), 7.03 (d, 1H), 6.74 (d, 1H), 4.60 (br s, 2H), 4.07-3.94 (m, 2H), 3.87 (s, 3H), 3.56-3.52 (m, 2H), 3.03 (dd, 1H), 2.71-2.63 (m, 1H), 2.36-1.92 (m, 8H); MS (EI) for $C_{24}H_{30}N_4O_5$: 454 ($MH^+$).

SYNTHETIC SCHEME 18:

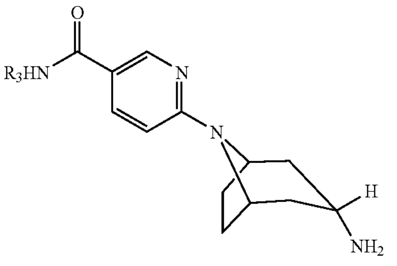

A

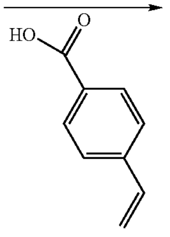

B

-continued

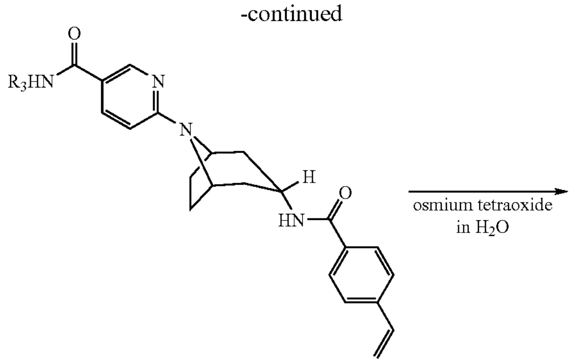

C

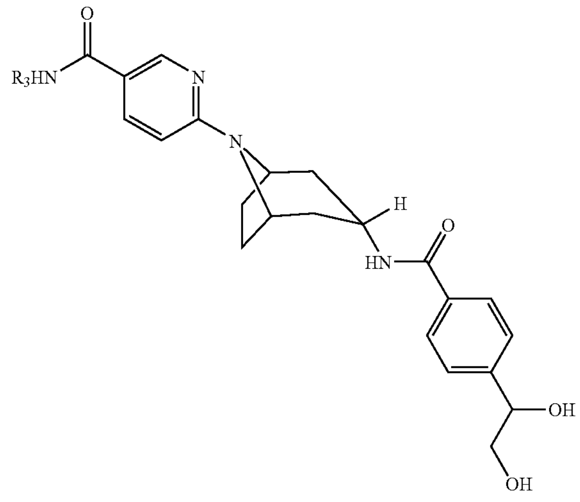

D

Scheme 18 generally describes the synthesis of all of the compound(s) listed in Example 18, wherein $R_3$ is as defined in the specification.

In Scheme 18, compound (B) is added to compound (A) under appropriate reaction conditions and with a suitable coupling reagent, such as HATU, to condense and form the amide bond in compound (C). Compound (C) is then hydroxylated with an oxidizing agent, such as osmium tetroxide, under appropriate reaction conditions to form compound (D).

Example 18

6-[3-endo-({[4-(1,2-dihydroxyethyl)phenyl]carbonyl}-amino)-8-azabicyclo[3.2.1]oct-8-yl]-N-(phenylmethyl)pyridine-3-carboxamide STEP 1: To a stirred solution of 4-vinylbenzoic acid (0.036 mg; 0.244 mmol) and N-methylmorpholine (0.098 g, 0.976 mmol) in dimethylformamide (1 ml) was added HOAt (0.490 ml; 0.5 M solution in dimethylformamide, 0.244 mmol), HATU (0.093 g, 0.244 mmol) and 6-(3-endo-amino-8-azabicyclo[3.2.1]oct-8-yl)-N-(phenylmethyl)pyridine-3-carboxamide (synthesized in example 2) (0.100 g, 0.244 mmol). The reaction mixture was stirred at room temperature overnight followed by addition of water (3 ml) and the resulting solid was collected by filtration and dried under vacuum to give 6-(3-endo{[(4-ethenylphenyl)carbonyl]amino}-8-azabicyclo[3.2.1]oct-8-yl)-N-(phenylmethyl)pyridine-3-carboxamide (0.081; 71% yield). MS (EI) for $C_{29}H_{30}N_4O_2$: 467 ($MH^+$).

STEP 2: To a stirred solution of 6-(3-endo {[(4-ethenylphenyl)carbonyl]-amino}-8-azabicyclo[3.2.1]oct-8-yl)-N-(phenylmethyl)pyridine-3-carboxamide (0.081 g, 0.174 mmol) and 4-methylmorpholine N-oxide (0.053 g; 0.452 mmol) in a mixture of acetone (0.5 ml) and water (0.13 ml) was added a catalytic amount of osmium tetroxide (0.010 ml, 4 wt % solution in water). The reaction mixture was stirred at 40° C. overnight and then quenched by addition of a 10% aqueous solution of sodium bisulfite (0.5 ml). The water phase was extracted with ethyl acetate (2×2 ml) and the organic layer was dried over anhydrous sodium sulfate then filtered and concentrated. The residue was purified by preparatory reverse phase HPLC (0.05% trifluoroacetic acid buffered aqueous acetonitrile mobile phase) and the combined pure fractions were lyophilized to yield 6-[3-endo-({[4-(1,2-dihydroxyethyl)phenyl]carbonyl}amino)-8-azabicyclo[3.2.1]oct-8-yl]-N-(phenylmethyl)pyridine-3-carboxamide (0.052 g; 49% yield) as the trifluoroacetate salt. MS (EI) for $C_{29}H_{32}N_4O_4$: 499 (M−H).

To compound (B) is added $R_3MgX$, (a Grignard reagent), wherein X represents a halogen, under appropriate reaction conditions to arrive at compound (C). Compound (C) is then deprotected with an acid, such as HCl, to remove the BOC and arrive at compound (D). To compound (D) is added $R_1COOH$ under appropriate reaction conditions and with a suitable coupling reagent, such as HATU, to condense and form the amide bond in compound (E).

Example 19

N4-[8-(5-acetylpyridin-2-yl)-8-azabicyclo[3.2.1]oct-3-endo-yl]-2-[(1-ethylpiperidin-4-yl)amino]benzene-1,4-dicarboxamide STEP 1: A mixture of 6-[3-endo-({[(1,1-dimethylethyl)oxy]carbonyl}-amino)-8-azabicyclo[3.2.1]oct-8-yl]pyridine-3-carboxylic acid (7.96 g, 22.91 mmol, example 2, step

SYNTHETIC SCHEME 19:

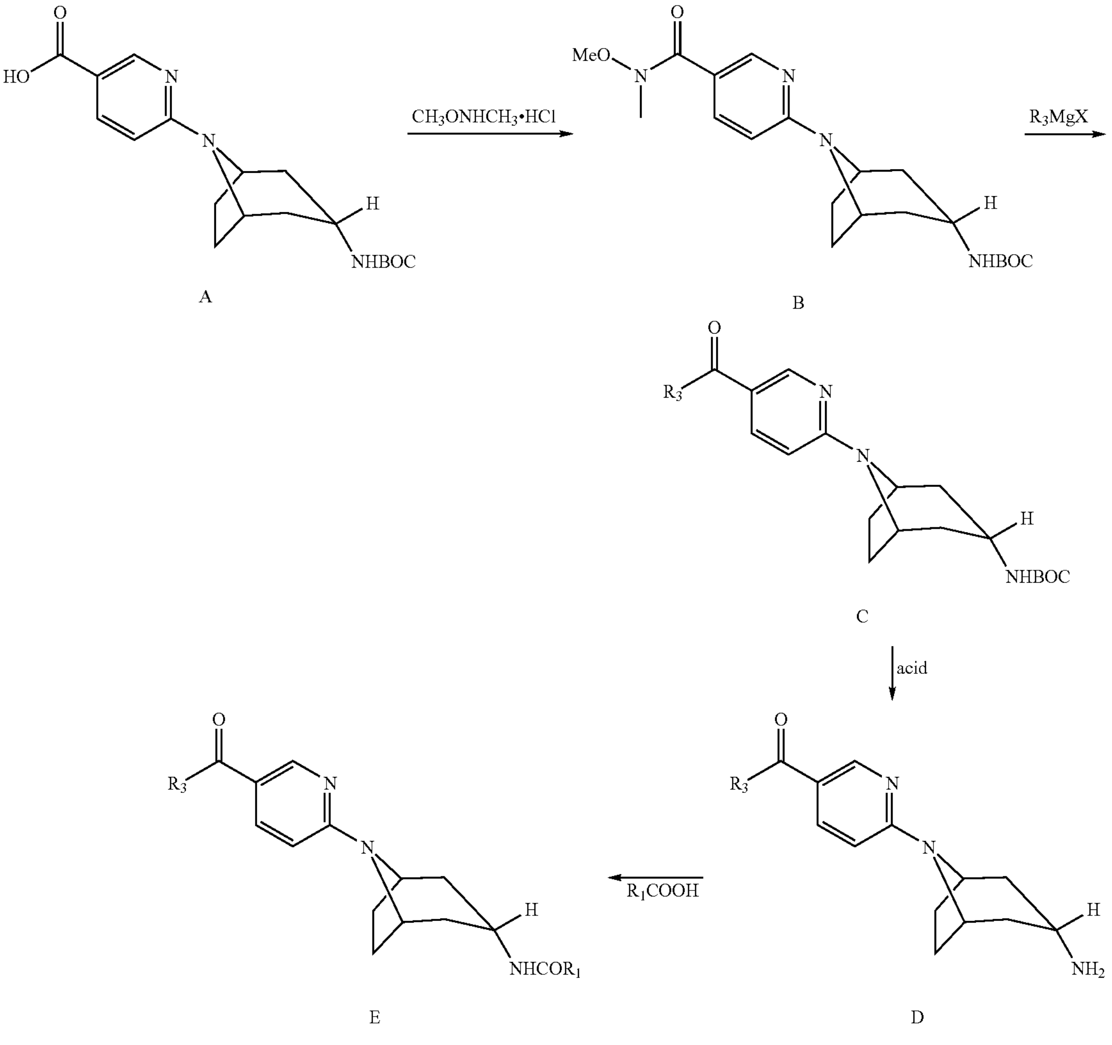

Scheme 19 generally describes the synthesis of all of the compound(s) listed in Example 19, wherein $R_3$ and $R_1$ are as defined in the specification.

In Scheme 19, $CH_3ONHCH_3$.HCl N,O-dimethylhydroxylamine hydrochloride is added to compound (A) under appropriate reaction conditions and with a suitable coupling reagent, such as HATU, to condense and form compound (B).

1), N,O-dimethylhydroxylamine hydrochloride (2.23 g, 22.91 mmol), HATU (8.71 g, 22.91 mmol), and diisopropylethylamine (11.84 g, 91.64 mmol) in DMF (50 mL) was stirred at room temperature for 3 h. The reaction mixture was poured into water (250 mL), filtered and the filter cake was washed with water (2×100 mL) then dried to give 1,1-dim ethylethyl [8-(5-{[methyl(methyloxy)amino]carbonyl}pyridine-2-yl)-8-azabicyclo[3.2.1]oct-3-endo-yl]carbamate (8.55 g, 96% yield). $^1$H NMR (400 MHz, DMSO-$d_6$): 8.46 (d, 1H), 7.79 (dd, 1H), 6.88 (br s, 1H), 6.69 (d, 1H), 4.49 (br s, 2H), 3.60 (s, 3H), 3.44 (m, 1H), 3.22 (s, 3H), 2.12 (m, 2H), 1.98 (m, 2H), 1.90 (m, 2H), 1.74 (d, 2H), 1.39 (s, 9H). MS (EI) for $C_{20}H_{30}N_4O_4$: 391 ($MH^+$).

STEP 2: To a suspension of 1,1-dimethylethyl [8-(5-{[methyl(methyloxy)amino]carbonyl}pyridine-2-yl)-8-azabicyclo[3.2.1]oct-3-endo-yl]carbamate (3.97 g, 10.17 mmol) in THF (70 mL) was added dropwise a 3M solution of methylmagnesium bromide in ether (17 mL, 51.00 mmol) at 0° C. The ice bath was removed and the solution was stirred for 1 h. The solution was poured into saturated ammonium chloride (200 mL), extracted with ethyl acetate (3×100 mL) and the organic layers were washed with brine (100 mL), dried over sodium sulfate then filtered and concentrated. Column chromatography on silica (hexanes:ethyl acetate 1:1) afforded 1,1-dimethylethyl [8-(5-acetylpyridine-2-yl)-8-azabicyclo[3.2.1]oct-3-endo-yl]carbamate (2.55 g, 73% yield). $^1$H NMR (400 MHz, methanol-$d_4$): 8.71 (d, 1H), 8.03 (dd, 1H), 6.71 (d, 1H), 4.60 (br s, 2H), 3.59 (m, 1H), 2.49 (s, 3H), 2.20-2.04 (m, 6H), 1.81 (d, 2H), 1.44 (s, 9H).

STEP 3: To a solution of 1,1-dimethylethyl [8-(5-acetylpyridine-2-yl)-8-azabicyclo[3.2.1]oct-3-endo-yl]carbamate (2.00 g, 5.79 mmol) in methanol (5 mL) was added a solution of 4N hydrochloric acid in dioxane (5 mL) and the reaction mixture was refluxed for 2 min. After cooling to room temperature the mixture was concentrated, neutralized with saturated aqueous sodium bicarbonate, extracted with ethyl acetate (7×50 mL), dried over sodium sulfate, then filtered and concentrated to provide 1-[6-(3-endo-amino-8-azabicyclo[3.2.1]oct-8-yl)pyridine-3-yl]ethanone (1.11 g, 78% yield). $^1$H NMR (400 MHz, methanol-$d_4$): 8.70 (d, 1H), 8.01 (dd, 1H), 6.70 (d, 1H), 4.62 (br s, 2H), 3.01 (m, 1H), 2.48 (s, 3H), 2.29-2.06 (m, 6H), 1.60 (d, 2H). MS (EI) for $C_{14}H_{19}N_3O$: 246 ($MH^+$).

STEP 4: To a solution of 1-[6-(3-endo-amino-8-azabicyclo[3.2.1]oct-8-yl)pyridine-3-yl]ethanone (135 mg, 0.55 mmol) and 4-(aminocarbonyl)-3-[(1-{[(1,1-dimethylethyl)oxy]carbonyl}piperidin-4-yl)amino]benzoic acid (200 mg, 0.55 mmol) in DMF (5 mL) were added HATU (418 mg, 1.1 mmol) and diisopropylethylamine (142 mg, 1.1 mmol) at room temperature. The reaction mixture was stirred at room temperature for 30 min. The solution was poured into saturated aqueous sodium chloride solution (30 mL), extracted with ethyl acetate (3×30 mL), dried over sodium sulfate then filtered and concentrated to provide 1,1-dimethylethyl (4-{[5-({[8-(5-acetylpyridin-2-yl)-8-azabicyclo[3.2.1]oct-3-endo-yl]aminocarbonyl)-2-(aminocarbonyl)phenyl]amino}-piperidine-1-carboxylate (285 mg, 87% yield). $^1$H NMR (400 MHz, methanol-$d_4$): 8.70 (d, 1H), 8.01 (d, 1H), 7.96 (s, 3H), 7.65 (d, 1H), 7.1 (s, 1H), 6.9 (d, 1H), 6.70 (d, 1H), 4.65 (s, 1H), 4.0 (m, 3H), 3.65 (m, 1H), 3.1 (br s, 2H), 2.48 (s, 3H), 2.39-2.0 (m, 10H), 1.50 (s, 9H). MS (EI) for $C_{32}H_{42}N_6O_5$: 591 ($MH^+$).

STEP 5: To a solution of 1,1-dimethylethyl (4-{[5-({[8-(5-acetylpyridin-2-yl)-8-azabicyclo[3.2.1]oct-3-endo-yl]aminocarbonyl)-2-(aminocarbonyl)phenyl]amino}piperidine-1-carboxylate (285 mg, 0.483 mmol) in methanol (2 mL) was added hydrogen chloride in dioxane solution (2M, 0.6 mL) at room temperature. The reaction mixture was stirred at 45° C. for 2 h. After cooling to room temperature the mixture was concentrated. The residue was triturated with ethyl acetate then dried to give N4-[8-(5-acetylpyridin-2-yl)-8-azabicyclo[3.2.1]oct-3-endo-yl]-2-(piperidin-4-ylamino)benzene-1,4-dicarboxamide as the hydrochloride salt. $^1$H NMR (400 MHz, methanol-$d_4$): 8.55 (s, 1H), 8.30 (m, 2H), 7.70 (d, 2H), 7.65 (d, 1H), 7.22 (d, 1H), 7.18 (s, 1H), 7.00 (d, 1H), 4.06 (s, 1H), 3.92 (s, 1H), 3.48 (m, 2H), 3.24 (m, 2H), 2.39-2.18 (m, 12H), 1.70 (m, 2H); MS (EI) for $C_{27}H_{34}N_6O_3$: 491 ($MH^+$).

STEP 6: To a solution of N4-[8-(5-acetylpyridin-2-yl)-8-azabicyclo[3.2.1]oct-3-endo-yl]-2-(piperidin-4-ylamino)benzene-1,4-dicarboxamide (130 mg, 0.28 mmol) in methanol were added acetaldehyde (12 mg, 0.28 mmol), sodium cyanoborohydride (18 mg, 0.28 mmol) and acetic acid (17 mg, 0.28 mmol) at room temperature. The reaction mixture was stirred at room temperature for 2 h. Then the reaction mixture was poured into water (250 mL), extracted with ethyl acetate (2×50 mL), dried over sodium sulfate, filtered and concentrated to a volume of 10 mL. The precipitate thus formed was collected by filtration to give N4-[8-(5-acetylpyridin-2-yl)-8-azabicyclo[3.2.1]oct-3-endo-yl]-2-[(1-ethylpiperidin-4-yl)amino]benzene-1,4-dicarboxamide (16 mg, 12% yield). $^1$H NMR (400 MHz, methanol-$d_4$): 8.70 (s, 1H), 8.06 (d, J=9.2 Hz, 1H), 7.69 (d, J=8.2 Hz, 1H), 7.14 (s, 1H), 6.98 (d, J=8.2 Hz, 1H), 6.77 (d, J=9.2 Hz, 1H), 4.70 (br, s, 2H), 4.02 (m, 1H), 3.82-3.45 (m, 2H), 3.20-3.05 (m, 6H), 3.00 (s, 6H), 2.53 (s, 3H), 2.40-2.1 (m, 10H), 2.05 (m, 2H), 1.34 (t, J=7.2 Hz, 3H). MS (EI) for $C_{29}H_{38}N_6O_3$: 519 ($MH^+$).

Using analogous synthetic techniques and substituting with alternative starting reagents, the following compounds [(19B)-(1 9(BE)] were prepared. Alternative starting materials were obtained commercially unless otherwise indicated.

(19B): N4-[8-(5-acetylpyridin-2-yl)-8-azabicyclo[3.2.1]oct-3-endo-yl]-2-(piperidin-4-ylamino)benzene-1,4-dicarboxamide. Prepared in example 19 step 5. $^1$H NMR (400 MHz, methanol-$d_4$): 8.55 (s, 1H), 8.30 (m, 2H), 7.70 (d, 2H), 7.65 (d, 1H), 7.22 (d, 1H), 7.18 (s, 1H), 7.00 (d, 1H), 4.06 (s, 1H), 3.92 (s, 1H), 3.48 (m, 2H), 3.24 (m, 2H), 2.39-2.18 (m, 12H), 1.70 (m, 2H). MS (EI) for $C_{27}H_{34}N_6O_3$: 491 ($MH^+$).

(19C): N4-[8-(5-acetylpyridin-2-yl)-8-azabicyclo[3.2.1]oct-3-endo-yl]-2-({2-[(1-methylethyl)oxy]ethyl}amino)benzene-1,4-dicarboxamide. Prepared as the hydrochloride salt according to the method of example 19 by using 4-(aminocarbonyl)-3-({2-[(1-methylethyl)oxy]ethyl}amino)benzoic acid (synthesized according to reagent prep 39) in step 4, then omission of steps 5 and 6. $^1$H NMR (400 MHz, DMSO-$d_6$) 8.73 (d, 1H), 8.32 (t, 1H), 8.20 (d, 1H), 7.95 (dd, 1H), 7.91 (br s, 1H), 7.68 (d, 1H), 7.32 (br s, 1H), 7.01 (s, 1H), 6.91 (d, 1H), 6.76 (d, 1H), 4.65 (br s, 2H), 3.82 (br s 1H), 3.58 (m, 3H), 3.25 (m, 2H), 2.43 (s, 3H), 2.20 (m, 2H), (2.18 (m, 6H), 1.08 (d, 6H). MS (EI) for $C_{27}H_{35}N_5O_4$: 494 ($MH^+$).

(19D): N4-[8-(5-acetylpyridin-2-yl)-8-azabicyclo[3.2.1]oct-3-endo-yl]-2-[(1-methylethyl)amino]benzene-1,4-dicarboxamide. Prepared according to the method of example 19 by using 4-(aminocarbonyl)-3-[(1-methylethyl)amino]benzoic acid (synthesized according to reagent prep 39) in step 4, then omission of steps 5 and 6. $^1$H NMR (400 MHz, DMSO-$d_6$): 8.75 (s, 1H), 8.20 (dd, 1H), 8.14 (dd, 1H), 7.98 (dd, 1H), 7.92 (bs, 1H), 7.67 (d, 1H), 7.27 (s, 1H), 7.00 (s, 1H), 6.86 (dd, 1H), 6.79 (dd, 1H), 4.64 (bs, 2H), 3.85 (bs, 1H), 3.69 (m, 1H), 2.46 (s, 3H), 2.23 (d, 2H), 2.09-1.95 (m, 6H), 1.20 (d, 6H). MS (EI) for $C_{25}H_{31}N_5O_3$: 450 ($MH^+$).

(19E): N4-[8-(5-acetylpyridin-2-yl)-8-azabicyclo[3.2.1]oct-3-endo-yl]-2-[(1-ethylpropyl)amino]benzene-1,4-dicarboxamide. Prepared according to the method of example 19 by using 4-(aminocarbonyl)-3-[(1-ethylpropyl)amino]benzoic acid (synthesized according to reagent prep 39) in step 4, then omission of steps 5 and 6. $^1$H NMR (400 MHz, DMSO-$d_6$): 8.74 (d, 1H), 8.26 (d, 1H), 8.23 (d, 1H), 7.96 (dd, 1H), 7.92 (bs, 1H), 7.66 (d, 1H), 7.26 (bs, 1H), 6.95 (s, 1H), 6.81 (dd, 2H), 4.63 (bs, 1H), 3.85 (bs, 1H), 3.32 (m, 1H), 2.44 (s, 3H), 2.25 (dd, 2H), 2.04 (m, 6H), 1.97 (m, 1H), 1.54 (m, 4H), 0.90 (t, 6H). MS (EI) for $C_{27}H_{35}N_5O_3$: 478 ($MH^+$).

(19F): N4-[8-(5-acetylpyridin-2-yl)-8-azabicyclo[3.2.1]oct-3-endo-yl]-2-[(2-methylpropyl)amino]benzene-1,4-dicarboxamide. Prepared according to the method of example 19 by using 4-(aminocarbonyl)-3-[(2-methylpropyl)amino]benzoic acid (synthesized according to reagent prep 39) in step 4, then omission of steps 5 and 6. $^1$H NMR (400 MHz, DMSO-$d_6$): 8.74 (d, 1H), 8.39 (t, 1H), 8.21 (d, 1H), 7.96 (dd, 1H), 7.95 (bs, 1H), 7.65 (dd, 1H), 7.30 (bs, 1H), 6.96 (s, 1H), 6.87 (d, 1H), 6.79 (d, 1H), 4.64 (bs, 1H), 3.85 (bs, 1H), 2.99 (t, 2H), 2.46 (s, 3H), 2.25 (d, 2H), 2.04 (m, 4H), 1.97 (m, 4H), 0.95 (d, 6H). MS (EI) for $C_{26}H_{33}N_5O_3$: 464 ($MH^+$).

(19G): N4-[8-(5-acetylpyridin-2-yl)-8-azabicyclo[3.2.1]oct-3-endo-yl]-2-[(2,2-dimethylpropyl)amino]benzene-1,4-dicarboxamide. Prepared according to the method of example 19 by using 4-(aminocarbonyl)-3-[(2,2-dimethylpropyl)-amino]benzoic acid (synthesized according to reagent prep 39) in step 4, then omission of steps 5 and 6. $^1$H NMR (400 MHz, DMSO-$d_6$): 8.73 (s, 1H), 8.51 (bs, 1H), 8.19 (d, 1H), 7.98 (m, 2H), 7.69 (dd, 1H), 7.31 (bs, 1H), 7.02 (s, 1H), 6.87 (dd, 1H), 6.83 (dd, 1H), 4.65 (bs, 2H), 3.84 (bs, 1H), 2.95 (s, 2H), 2.46 (s, 3H), 2.23 (d, 2H), 2.02 (m, 6H), 0.98 (s, 9H). MS (EI) for $C_{27}H_{35}N_5O_3$: 478 ($MH^+$).

(19H): N4-[8-(5-acetylpyridin-2-yl)-8-azabicyclo[3.2.1]oct-3-endo-yl]-2-[(tetrahydrofuran-2-ylmethyl)amino]benzene-1,4-dicarboxamide. Prepared as the hydrochloride salt according to the method of example 19 by using 4-(aminocarbonyl)-3-[(tetrahydrofuran-2-ylmethyl)amino]benzoic acid (synthesized according to reagent prep 39) in step 4, then omission of steps 5 and 6. $^1$H NMR (400 MHz, DMSO-$d_6$): 8.49 (s, 1H), 8.30 (d, 1H), 8.24 (d, 1H), 7.95 (bs, 1H), 7.70 (dd, 1H), 7.46 (s, 1H), 7.32 (s, 2H), 7.20 (s, 1H), 7.05 (s, 1H), 6.92 (d, 1H), 4.06 (m, 1H), 3.91 (bs, 1H), 3.79 (m, 1H), 3.71 (m, 1H), 3.66 (m, 1H), 3.49 (m, 1H), 3.30 (m, 1H), 3.18 (m, 1H), 2.55 (s, 3H), 2.34 (d, 2H), 2.13 (m, 6H), 1.99 (m, 1H), 1.85 (m, 2H), 1.65 (m, 1H). MS (EI) for $C_{27}H_{33}N_5O_4$: 492 ($MH^+$).

(19I): N4-[8-(5-acetylpyridin-2-yl)-8-azabicyclo[3.2.1]oct-3-endo-yl]-2-[(2-aminoethyl)amino]benzene-1,4-dicarboxamide. Prepared as the HCl salt according to the method of example 19 by using 4-(aminocarbonyl)-3-{[2-({[(1,1-dimethylethyl)oxy]carbonyl}amino)ethyl]amino}benzoic acid (synthesized according to reagent prep 39) in step 4, then omission of step 6. $^1$H NMR (400 MHz, DMSO-$d_6$): 8.74 (d, 1H), 8.23 (m, 2H), 7.96 (dd, 2H), 7.68 (dd, 1H), 7.32 (bs, 1H), 7.02 (s, 1H), 6.91 (dd, 1H), 6.80 (dd, 1H), 4.65 (bs, 2H), 3.90 (bs, 1H), 3.20 (m, 2H), 2.85 (t, 2H), 2.45 (s, 3H), 2.22 (d, 2H), 2.05 (m, 4H), 1.96 (m, 2H). MS (EI) for $C_{24}H_{30}N_6O_3$: 451 ($MH^+$).

(19J): N4-[8-(5-acetylpyridin-2-yl)-8-azabicyclo[3.2.1]oct-3-endo-yl]-2-[(1-methylpropyl)amino]benzene-1,4-dicarboxamide. Prepared according to the method of example 19 by using 4-(aminocarbonyl)-3-[(1-methylpropyl)amino]benzoic acid (synthesized according to reagent prep 39) in step 4, then omission of steps 5 and 6. $^1$H NMR (400 MHz, DMSO-$d_6$): 8.74 (d, 1H), 8.21 (m, 2H), 7.97 (dd, 1H), 7.92 (bs, 1H), 7.66 (d, 1H), 7.27 (bs, 1H), 6.97 (s, 1H), 6.84 (dd, 1H), 6.79 (dd, 1H), 4.64 (bs, 2H), 3.85 (bs, 1H), 3.50 (m, 1H), 2.45 (s, 3H), 2.25 (d, 2H), 2.04 (m, 4H), 1.96 (m, 2H), 1.54 (m, 2H), 1.16 (d, 3 h), 0.98 (t, 3H). MS (EI) for $C_{26}H_{33}N_5O_3$: 464 ($MH^+$).

(19K): N4-[8-(5-acetylpyridin-2-yl)-8-azabicyclo[3.2.1]oct-3-endo-yl]-2-[(1-propylbutyl)amino]benzene-1,4-dicarboxamide. Prepared as the HCl salt according to the method of example 19 by using 4-(aminocarbonyl)-3-[(1-propylbutyl)amino]benzoic acid (synthesized according to reagent prep 39) in step 4, then omission of steps 5 and 6. $^1$H NMR (400 MHz, methanol-$d_4$): 8.48 (d, 1 h), 8.40 (d, 1H), 7.88 (d, 1H), 7.52 (s, 1H), 7.40 (m, 2H), 4.81 (bs, 2H), 4.13 (m, 1H), 3.62 (q, 1H), 2.57 (s, 3H), 2.43 (m, 2H), 2.31 (m, 6H), 1.60 (m, 4H), 1.43 (m, 4H), 0.94 (t, 6H); MS (EI) for $C_{29}H_{39}N_5O_3$: 506 ($MH^+$).

(19L): N4-[8-(5-acetylpyridin-2-yl)-8-azabicyclo[3.2.1]oct-3-endo-yl]-2-[(1,2-dimethylpropyl)amino]benzene-1,4-dicarboxamide. Prepared as the HCl salt according to the method of example 19 by using 4-(aminocarbonyl)-3-[(1,2-dimethylpropyl)amino]benzoic acid (synthesized according to reagent prep 39) in step 4, then omission of steps 5 and 6. $^1$H NMR (400 MHz, methanol-$d_4$): 8.51 (d, 1H), 8.39 (dd, 1H), 8.08 (d, 1H), 7.90 (s, 1H), 7.81 (dd, 1H), 7.39 (d, 1H), 4.14 (m, 1H), 3.74 (m, 1H), 2.57 (s, 3H), 2.44 (m, 2H), 2.37 (m, 2H), 2.31 (m, 4H), 2.21 (m, 1H), 1.11 (m, 9H); MS (EI) for $C_{27}H_{35}N_5O_3$: 478 ($MH^+$).

(19M): N4-[8-(5-acetylpyridin-2-yl)-8-azabicyclo[3.2.1]oct-3-endo-yl]-2-[(1,2,2-trimethylpropyl)amino]benzene-1,4-dicarboxamide. Prepared according to the method of example 19 by using 4-(aminocarbonyl)-3-[(1,2,2-trimethylpropyl)-amino]benzoic acid (synthesized according to reagent prep 39) in step 4, then omission of steps 5 and 6. $^1$H NMR (400 MHz, methanol-$d_4$): 8.74 (d, 1H), 8.06 (dd, 1H), 7.64 (d, 1H), 7.12 (s, 1H), 6.84 (d, 1H), 6.76 (d, 1H), 4.70 (bs, 2H), 4.01 (t, 1H), 3.45 (quar, 1H), 2.51 (s, 3H), 2.26 (m, 4H), 2.19 (m, 2H), 2.01 (d, 2H), 1.15 (d, 3H), 1.00 (s, 9H). MS (EI) for $C_{28}H_{37}N_5O_3$: 492 ($MH^+$).

(19N): N4-[8-(5-acetylpyridin-2-yl)-8-azabicyclo[3.2.1]oct-3-endo-yl]-2-({1-[(methyloxy)methyl]propyl}amino)benzene-1,4-dicarboxamide. Prepared according to the method of example 19 by using 4-(aminocarbonyl)-3-({1-[(methyloxy)methyl]propyl}amino)benzoic acid (synthesized according to reagent prep 39) in step 4, then omission of steps 5 and 6. $^1$H NMR (400 MHz, methanol-$d_4$): 8.74 (d, 1H), 8.06 (dd, 1H), 7.63 (d, 1H), 7.11 (s, 1H), 6.90 (d, 1H), 6.76 (d, 1H), 4.70 (bs, 2H), 4.01 (t, 1H), 3.61 (m, 1H), 3.52 (dd, 1H), 3.42 (dd, 1H), 3.36 (s, 3H), 2.51 (s, 3H), 2.26 (m, 4H), 2.18 (m, 2H), 2.01 (m, 2H), 1.76 (m, 1H), 1.59 (m, 1H), 1.00 (t, 3H). MS (EI) for $C_{27}H_{35}N_5O_4$: 494 ($MH^+$).

(19O): N4-[8-(5-acetylpyridin-2-yl)-8-azabicyclo[3.2.1]oct-3-endo-yl]-2-{[(1S)-1-methylpropyl]amino}benzene-1,4-dicarboxamide. Prepared according to the method of example 19 by using 4-(aminocarbonyl)-3-{[(1S)-1-methylpropyl]amino}benzoic acid (synthesized according to reagent prep 39) in step 4, then omission of steps 5 and 6. $^1$H NMR (400 MHz, methanol-$d_4$): 8.74 (d, 1H), 8.24 (d, 1H), 8.06 (dd, 1H), 7.63 (d, 1H), 7.06 (s, 1H), 6.88 (dd, 1H), 6.76 (d, 1H), 4.69 (bs, 2H), 4.01 (m, 1H), 3.56 (m, 1H), 2.50 (s, 3H), 2.26 (m, 4H), 2.19 (m, 2H), 2.00 (m, 2H), 1.61 (m, 2H), 1.22 (m, 3H), 0.98 (t, 3H). MS (EI) for $C_{26}H_{33}N_5O_3$: 464 ($MH^+$).

(19P): N4-[8-(5-acetylpyridin-2-yl)-8-azabicyclo[3.2.1]oct-3-endo-yl]-2-({3-[(1-methylethyl)amino]propyl}amino)benzene-1,4-dicarboxamide. Prepared as the acetate salt according to the method of example 19 by using 4-(aminocarbonyl)-3-({3-[(1-methylethyl)amino]propyl}amino)benzoic acid (synthesized according to reagent prep 39) in step 4, then omission of steps 5 and 6. $^1$H NMR (400 MHz, methanol-$d_4$): 8.74 (d, 1H), 8.06 (dd, 1 h), 7.67 (d, 1H), 7.12 (s, 1H), 6.97 (d, 1H), 6.77 (d, 1H), 4.70 (bs, 2H), 4.01 (m, 1H), 3.38 (t, 2H), 3.08 (t, 2H), 2.51 (s, 3H), 2.23 (m, 6H0, 1.99 (m, 4H), 1.89 (s, 3H), 1.31 (d, 6H); MS (EI) for $C_{28}H_{38}N_6O_3$: 507 ($MH^+$).

(19Q): N4-[8-(5-acetylpyridin-2-yl)-8-azabicyclo[3.2.1]oct-3-endo-yl]-2-[(trans-4-hydroxycyclohexyl)amino]benzene-1,4-dicarboxamide. Prepared according to the method of example 19 by using 4-(aminocarbonyl)-3-[(trans-4-hydroxycyclohexyl)amino]benzoic acid (synthesized according to reagent prep 39) in step 4, then omission of steps 5 and 6. $^1$H NMR (400 MHz, DMSO-d$_6$): 8.74 (d, 1H), 8.27 (m, 2H), 7.97 (dd, 1H), 7.91 (br s, 1H), 7.66 (d, 1H), 7.27 (br s, 1H), 6.96 (s, 1H), 6.83 (d, 1H), 6.79 (d, 1H), 4.64 (br s, 2H), 4.60 (d, 1H), 3.85 (br s, 1H), 3.48 (m, 1H), 2.45 (s, 3H), 2.26 (m, 2H), 2.02 (m, 9H), 1.84 (m, 2H), 1.25 (m, 4H). MS (EI) for $C_{28}H_{35}N_5O_4$: 506 (MH$^+$).

(19R): N-[8-(5-acetylpyridin-2-yl)-8-azabicyclo[3.2.1]oct-3-endo-yl]-2-methyl-3-(methyloxy)benzamide. Prepared according to the method of example 19 by using 2-methyl-3-methoxybenzoic acid in step 4, then omission of steps 5 and 6. $^1$H NMR (400 MHz, DMSO-d$_6$): 8.74 (d, 1H), 8.25 (d, 1H), 7.96 (dd, 1H), 7.23 (t, 1H), 7.02 (d, 1H), 6.86 (d, 1H), 6.78 (d, 1H), 4.62 (br s, 2H), 3.86 (m, 1H), 3.80 (s, 3H), 2.45 (s, 3H), 2.22 (m, 2H), 2.14 (s, 3H), 2.08 (m, 2H), 1.98 (m, 2H), 1.89 (d, 2H). MS (EI) for $C_{23}H_{27}N_3O_3$: 394 (MH$^+$).

(19S): N4-[8-(5-acetylpyridin-2-yl)-8-azabicyclo[3.2.1]oct-3-endo-yl]-2-[(cyclopropylmethyl)amino]benzene-1,4-dicarboxamide. Prepared according to the method of example 19 by using 4-(aminocarbonyl)-3-[(cyclopropylmethyl)amino]-benzoic acid (synthesized according to reagent prep 39) in step 4, then omission of steps 5 and 6. $^1$H NMR (400 MHz, DMSO-d$_6$): 8.74 (d, 1H), 8.26 (t, 1H), 8.18 (d, 1H), 7.96 (dd, 1H), 7.93 (br s, 1H), 7.67 (d, 1H), 7.29 (br s, 1H), 6.99 (d, 1H), 6.89 (dd, 1H), 6.79 (d, 1H), 4.64 (br s, 2H), 3.84 (m, 1H), 3.03 (m, 2H), 2.45 (s, 3H), 2.22 (m, 2H), 2.11-1.92 (m, 6H), 1.11 (m, 1H), 0.52 (m, 2H), 0.24 (m, 2H). MS (EI) for $C_{26}H_{31}N_5O_3$: 462 (MH$^+$).

(19T): N4-{8-[5-(cyclopentylcarbonyl)pyridin-2-yl]-8-azabicyclo[3.2.1]oct-3-endo-yl}-2-[(cyclopropylmethyl)amino]benzene-1,4-dicarboxamide. Prepared according to the method of example 19 by using cyclopentylmagnesium chloride in step 2 and 4-(aminocarbonyl)-3-[(cyclopropylmethyl)amino]benzoic acid (synthesized according to reagent prep 39) in step 4, then omission of steps 5 and 6. $^1$H NMR (400 MHz, DMSO-d$_6$): 8.77 (d, 1H), 8.26 (t, 1H), 8.13 (d, 1H), 8.00 (dd, 1H), 7.94 (br s, 1H), 7.67 (d, 1H), 7.30 (br s, 1H), 6.99 (d, 1H), 6.89 (dd, 1H), 6.79 (d, 1H), 4.64 (br s, 2H), 3.85 (m, 1H), 3.70 (m, 1H), 3.03 (m, 2H), 2.22 (m, 2H), 2.12-1.92 (m, 6H), 1.85 (m, 2H), 1.72 (m, 2H), 1.60 (m, 4H), 1.11 (m, 1H), 0.51 (m, 2H), 0.24 (m, 2H). MS (EI) for $C_{30}H_{37}N_5O_3$: 516 (MH$^+$).

(19U): N4-[8-(5-acetylpyridin-2-yl)-8-azabicyclo[3.2.1]oct-3-endo-yl]-2-(butylamino)benzene-1,4-dicarboxamide. Prepared according to the method of example 19 by using 3-(butylamino)-4-(aminocarbonyl)benzoic acid (synthesized according to reagent preparation 39) in step 4, then omission of steps 5 and 6. $^1$H NMR (400 MHz, d$_6$-DMSO): 8.74 (s, 1H), 8.27-8.20 (m, 2H), 7.97 (dd, 1H), 7.94 (br s, 1H), 7.67 (d, 1H), 7.30 (d, 1H), 6.97 (d, 1H), 6.87 (dd, 1H), 6.79 (d, 1H), 4.63 (br s, 2H), 3.87-3.81 (m, 1H), 3.16 (q, 2H), 2.45 (s, 3H), 2.27-2.20 (m, 2H), 2.10-1.92 (m, 6H), 1.62-1.54 (m, 2H), 1.44-1.33 (m, 2H), 0.93 (t, 3H). MS (EI) for $C_{26}H_{33}N_5O_3$: 464 (MH$^+$).

(19V): N4-[8-(5-acetylpyridin-2-yl)-8-azabicyclo[3.2.1]oct-3-endo-yl]-2-({4-(methyloxy)-3-[(2-morpholin-4-ylethyl)oxy]phenyl}amino)benzene-1,4-dicarboxamide. Prepared according to the method of example 19 by using 4-(aminocarbonyl)-3-({4-(methyloxy)-3-[(2-morpholin-4-ylethyl)oxy]phenyl}-amino)benzoic acid (synthesized according to reagent preparation 40) in step 4, then omission of steps 5 and 6. $^1$H NMR (400 MHz, d$_6$-DMSO): 9.93 (s, 1H), 8.73 (d, 1H), 8.20 (d, 1H), 8.13 (br s, 1H), 7.95 (dd, 1H), 7.76 (d, 1H), 7.56 (br s, 1H), 7.41 (d, 1H), 7.00 (dd, 1H), 6.92 (d, 1H), 6.85-6.81 (m, 2H), 6.76 (d, 1H), 4.59 (br s, 2H), 4.06 (t, 2H), 3.83-3.77 (mm, 1H), 3.74 (s, 3H), 3.56 (t, 4H), 3.50 (s, 1H), 2.68 (t, 2H), 2.44 (s, 3H), 2.34-2.31 (m, 1H), 2.14-2.07 (m, 2H), 2.04-1.85 (m, 7H), 1.23 (br s, 1H). MS (EI) for $C_{35}H_{42}N_6O_6$: 643 (MH$^+$).

(19W): 2-[(cyclopropylmethyl)amino]-N4-{8-[5-(3-methylbutanoyl)pyridin-2-yl]-8-azabicyclo[3.2.1]oct-3-endo-yl}benzene-1,4-dicarboxamide. Prepared according to the method of example 19 by using isobutyl magnesium bromide in step 2 and 4-(aminocarbonyl)-3-(cyclopropylmethylamino)benzoic acid (synthesized according to reagent prep 39) in step 4, then omission of steps 5 and 6. $^1$H NMR (400 MHz, d$_6$-DMSO): 8.75 (s, 1H), 8.29-8.24 (m, 1H), 8.19 (s, 1H), 8.01-7.91 (m, 2H), 7.70-7.65 (d, 1H), 7.35-7.26 (br. s, 1H), 6.99 (s, 1H), 6.92-6.86 (d, 1H), 6.81-6.76 (d, 1H), 4.71-4.53 (br. s, 2H), 3.88-3.81 (m, 1H), 3.06-3.00 (m, 2H), 2.77-2.71 (d, 2H), 2.26-2.19 (m, 2H), 2.17-1.91 (m, 7H), 1.15-1.06 (m, 1H), 0.95-0.90 (d, 6H), 0.55-0.48 (m, 2H), 0.28-0.21 (m, 2H). MS (EI) for $C_{29}H_{37}N_5O_3$: 504 (MH$^+$).

(19X): 2-[(cyclopropylmethyl)amino]-N4-{8-[5-(4,4,4-trifluorobutanoyl)pyridin-2-yl]-8-azabicyclo[3.2.1]oct-3-endo-yl}benzene-1,4-dicarboxamide. Prepared according to the method of example 19 by using trifluoropropylmagnesium bromide in step 2 and 4-(aminocarbonyl)-3-(cyclopropylmethylamino)benzoic acid (synthesized according to reagent prep 39) in step 4, then omission of steps 5 and 6. $^1$H NMR (400 MHz, d$_6$-DMSO): 8.78 (s, 1H), 8.29-8.24 (m, 1H), 8.19 (s, 1H), 8.04-8.00 (d, 1H), 7.94 (s, 1H), 7.69-7.65 (d, 1H), 7.29 (s, 1H), 6.99 (s, 1H), 6.91-6.87 (d, 1H), 6.82-6.78 (d, 1H), 4.73-4.55 (br. s, 2H), 3.88-3.81 (m, 1H), 3.23-3.16 (m, 2H), 3.06-3.01 (m, 2H), 2.68-2.55 (m, 2H), 2.27-2.19 (m, 2H), 2.11-1.93 (m, 6H), 1.15-1.06 (m, 1H), 0.55-0.48 (m, 2H), 0.27-0.21 (m, 2H). MS (EI) for $C_{28}H_{32}F_3N_5O_3$: 544 (MH$^+$).

(19Y): N4-[8-(5-butanoylpyridin-2-yl)-8-azabicyclo[3.2.1]oct-3-endo-yl]-2-[(cyclopropylmethyl)amino]benzene-1,4-dicarboxamide. Prepared as the hydrochloride salt according to the method of example 19 by using propylmagnesium bromide in step 2 and 4-(aminocarbonyl)-3-(cyclopropylmethylamino)benzoic acid (synthesized according to reagent prep 39) in step 4, then omission of steps 5 and 6. $^1$H NMR (400 MHz, d$_6$-DMSO): 8.53 (s, 1H), 8.29-8.24 (m, 1H), 7.74-7.70 (d, 1H), 7.33-7.27 (d, 1H), 7.09 (s, 1H), 7.02-6.97 (d, 1H), 4.86-4.75 (br. s, 2H), 3.98-3.92 (m, 1H), 3.09-3.06 (d, 2H), 2.97-2.92 (m, 2H), 2.39-2.32 (m, 2H), 2.24-2.09 (m, 6H), 1.71-1.61 (m, 2H), 1.18-1.06 (m, 1H), 0.99-0.92 (m, 3H), 0.58-0.51 (m, 2H), 0.31-0.24 (m, 2H). MS (EI) for $C_{28}H_{35}N_5O_3$: 490 (MH$^+$).

(19Z): N4-{8-[5-(cyclobutylcarbonyl)pyridin-2-yl]-8-azabicyclo[3.2.1]oct-3-endo-yl}-2-[(cyclopropylmethyl)amino]benzene-1,4-dicarboxamide. Prepared as the hydrochloride salt according to the method of example 19 by using cyclobutylmagnesium bromide in step 2 and 4-(aminocarbonyl)-3-(cyclopropylmethylamino)benzoic acid (synthesized according to reagent prep 39) in step 4, then omission of steps 5 and 6. $^1$H NMR (400 MHz, d$_6$-DMSO): 8.64 (s, 1H), 8.28-8.23 (m, 1H), 8.18 (s, 1H), 7.95-7.81 (m, 2H), 7.70-7.65 (d, 1H), 7.33-7.26 (br. s, 1H), 6.98 (s, 1H), 6.90-6.87 (d, 1H), 6.81-6.76 (d, 1H), 4.70-4.55 (br. s, 2H), 4.05-3.95 (m, 1H), 3.89-3.81 (m, 1H), 3.06-3.00 (m, 2H), 2.27-2.15 (m, 6H), 2.12-1.91 (m, 6H), 1.83-1.73 (m, 2H), 1.14-1.06 (m, 1H), 0.55-0.48 (m, 2H), 0.28-0.21 (m, 2H); MS (EI) for $C_{29}H_{35}N_5O_3$: 502 (MH$^+$).

(19AA): N4-[8-(5-acetylpyridin-2-yl)-8-azabicyclo[3.2.1]oct-3-endo-yl]-2-(cyclohexylamino)benzene-1,4-dicarboxamide. Prepared according to the method of example 19 by using 4-(aminocarbonyl)-3-(cyclohexylamino)benzoic acid (synthesized according to reagent prep 40) in step 4, then omission of steps 5 and 6. $^1$H NMR (400 MHz, methanol-d$_4$):

8.74 (d, 1H), 8.05 (dd, 1H), 7.62 (d, 1H), 7.07 (d, 1H), 6.87 (dd, 1H), 6.75 (d, 1H), 4.69 (br s, 2H), 4.01 (m, 1H), 3.44 (m, 1H), 2.50 (s, 3H), 2.30-2.14 (m, 6H), 2.09-1.96 (m, 1H), 1.82-1.75 (m, 2H), 1.68-1.61 (m, 1H), 1.50-1.26 (m, 5H). MS (EI) for $C_{28}H_{35}N_5O_3$: 490 ($MH^+$).

(19AB): N4-[8-(5-acetylpyridin-2-yl)-8-azabicyclo[3.2.1]oct-3-endo-yl]-2-(cyclopentylamino)benzene-1,4-dicarboxamide. Prepared according to the method of example 19 by using 4-(aminocarbonyl)-3-(cyclopentylamino)benzoic acid (synthesized according to reagent prep 39) in step 4, then omission of steps 5 and 6. $^1$H NMR (400 MHz, methanol-$d_4$): 8.74 (d, 1H), 8.06 (dd, 1H), 7.63 (d, 1H), 7.09 (d, 1H), 6.89 (dd, 1H), 6.76 (d, 1H), 4.69 (br s, 2H), 4.01 (m, 1H), 3.91 (m, 1H), 2.51 (s, 3H), 2.30-2.15 (m, 6H), 2.10-1.96 (m, 4H), 1.81-1.52 (m, 6H). MS (EI) for $C_{27}H_{33}N_5O_3$: 476 ($MH^+$).

(19AC): N4-[8-(5-acetylpyridin-2-yl)-8-azabicyclo[3.2.1]oct-3-endo-yl]-2-(ethylamino)benzene-1,4-dicarboxamide. Prepared according to the method of example 19 by using 4-(aminocarbonyl)-3-(ethylamino)benzoic acid (synthesized according to reagent prep 40) in step 4, then omission of steps 5 and 6. $^1$H NMR (400 MHz, $d_6$-DMSO): 8.74 (d, 1H), 8.17 (d, 1H), 8.09 (t, 1H), 7.96 (dd, 1H), 7.91 (br s, 1H), 7.67 (d, 1H), 7.28 (br s, 1H), 6.98 (d, 1H), 6.89 (dd, 1H), 6.79 (d, 1H), 4.64 (br s, 2H), 3.85 (m, 1H), 3.18 (m, 2H), 2.45 (s, 3H), 2.25-2.20 (m, 2H), 2.11-1.94 (m, 6H), 1.21 (t, 3H). MS (EI) for $C_{24}H_{29}N_5O_3$: 436 ($MH^+$).

(19AD): N-[8-(5-acetylpyridin-2-yl)-8-azabicyclo[3.2.1]oct-3-endo-yl]-5-[(1-ethylpropyl)amino]-2-methylbenzene-1,4-dicarboxamide. Prepared according to the method of example 19 by using 4-(aminocarbonyl)-2-methyl-5-(pentan-3-ylamino)benzoic acid (synthesized according to reagent prep 42) in step 4, then omission of steps 5 and 6. $^1$H NMR (400 MHz, $d_6$-DMSO): 8.57 (br s, 1H), 8.37 (d, 1H), 8.16 (d, 1H), 7.88 (br s, 1H), 7.51 (s, 1H), 7.18 (m, 2H), 6.59 (s, 1H), 4.42 (m, 2H), 3.89 (m, 1H), 3.23 (m, 1H), 2.52 (m, 2H), 2.36-2.31 (m, 2H), 2.19 (s, 3H), 2.15-2.01 (m, 4H), 2.08 (s, 3H), 1.52 (m, 4H), 0.88 (t, 6H). MS (EI) for $C_{28}H_{37}N_5O_3$: 492 ($MH^+$).

(19AE): N4-[8-(5-acetylpyridin-2-yl)-8-azabicyclo[3.2.1]oct-3-endo-yl]-2-{[3-{[2-(dimethylamino)ethyl]oxy}-4-(methyloxy)phenyl]amino}benzene-1,4-dicarboxamide. Prepared according to the method of example 19 by using 4-(aminocarbonyl)-3-{[3-{[2-(dimethylamino)ethyl]oxy}-4-(methyloxy)phenyl]amino}-benzoic acid (synthesized according to reagent prep 40) in step 4, then omission of steps 5 and 6. $^1$H NMR (400 MHz, methanol-$d_4$): 8.49 (d, 0.5H), 8.37 (dd, 0.5H), 7.97 (dd, 0.5H), 7.87 (d, 0.5H), 7.74 (d, 1H), 7.45 (s, 1H), 7.34 (dd, 1H), 7.09-6.96 (m, 4H), 4.81 (br s, 1H), 4.70 (br s, 1H), 4.34 (m, 2H), 4.05 (m, 1H), 3.88 (s, 3H), 3.58 (m, 3H), 3.02 (s, 6H), 2.56 (s, 1.5H), 2.32-2.12 (m, 8H), 1.54 (s, 1.5H). MS (EI) for $C_{33}H_{40}N_6O_5$: 601 ($MH^+$).

(19AF): N-[8-(5-acetylpyridin-2-yl)-8-azabicyclo[3.2.1]oct-3-endo-yl]-5-[(1-ethylpropyl)amino]-2-fluorobenzene-1,4-dicarboxamide. Prepared according to the method of example 19 by using 4-(aminocarbonyl)-2-fluoro-5-(pentan-3-ylamino)benzoic acid (synthesized according to reagent prep 45) in step 4, then omission of steps 5 and 6. $^1$H NMR (400 MHz, methanol-$d_4$): 8.54 (m, 1H), 8.47 (d, 1H), 8.39 (dd, 1H), 7.59 (d, 1H), 7.37 (d, 1H), 7.15 (d, 1H), 4.79 (br s, 2H), 4.18 (m, 1H), 3.37 (m, 1H), 2.57 (s, 3H), 2.46-2.18 (m, 8H), 1.72-1.51 (m, 4H), 0.95 (t, 6H). MS (EI) for $C_{27}H_{34}FN_5O_3$: 496 ($MH^+$).

(19AG): N4-[8-(5-acetylpyridin-2-yl)-8-azabicyclo[3.2.1]oct-3-endo-yl]-2-(piperidin-1-ylamino)benzene-1,4-dicarboxamide. Prepared according to the method of example 19 by using 4-(aminocarbonyl)-3-(piperidin-1-ylamino)benzoic acid (synthesized according to reagent prep 39) in step 4, then omission of steps 5 and 6. $^1$H NMR (400 MHz, $CDCl_3$): 8.79 (d, 1H), 8.33 (d, 1H), 8.05 (dd, 1H), 7.80 (d, 1H), 7.42 (d, 1H), 6.99 (dd, 1H), 6.72 (d, 1H), 6.55 (d, 1H), 4.71 (br s, 2H), 4.28 (q, 1H), 2.74 (br s, 4H), 2.52 (s, 3H), 2.38-2.25 (m, 4H), 2.22-2.15 (m, 2H), 1.95-1.87 (m, 2H), 1.73-1.63 (m, 6H). MS (EI) for $C_{27}H_{34}N_6O_3$: 491 ($MH^+$).

(19AH): N-[8-(5-acetylpyridin-2-yl)-8-azabicyclo[3.2.1]oct-3-endo-yl]-2-methyl-5-(pentylamino)benzene-1,4-dicarboxamide. Prepared according to the method of example 19 by using 4-(aminocarbonyl)-2-methyl-5-(pentylamino)benzoic acid (synthesized according to reagent prep 39) in step 4, then omission of steps 5 and 6. $^1$H NMR (400 MHz, methanol-$d_4$): 8.64 (d, 1H), 8.49 (d, 1H), 8.39 (dd, 1H), 7.74 (s, 1H), 7.36 (d, 1H), 7.16 (s, 1H), 4.79 (br s, 2H), 4.15 (q, 1H), 3.30 (m, 2H masked by solvent), 2.57 (s, 3H), 2.43-2.33 (m, 7H), 2.30-2.17 (m, 4H), 1.77-1.70 (m, 2H), 1.46-1.36 (m, 4H), 0.95 (t, 3H); MS (EI) for $C_{28}H_{37}N_5O_3$: 492 ($MH^+$).

(19AI): N4-[8-(5-acetylpyridin-2-yl)-8-azabicyclo[3.2.1]oct-3-yl]-2-(pyrrolidin-3-ylamino)benzene-1,4-dicarboxamide. Prepared as the acetate salt according to the method of example 19 by using 4-(aminocarbonyl)-3-[(1-{[(1,1-dimethylethyl)oxy]carbonyl}pyrrolidin-3-yl)amino]benzoic acid (synthesized according to reagent prep 39) in step 4, then omission of step 6. $^1$H NMR (400 MHz, methanol-$d_4$): 8.74 (d, J=2.0 Hz, 1H), 8.06 (dd, J=2.0, 9.2 Hz, 1H), 7.71 (d, J=8.0 Hz, 1H), 7.08 (s, 1H), 7.05 (dd, J=1.2, 8.0 Hz, 1H), 6.77 (d, J=9.2 Hz, 1H), 4.70 (s, 1H), 4.33 (m, 1H), 4.02 (s, 1H), 3.58-3.40 (m, 4H), 2.51 (s, 3H), 2.40 (m, 1H), 2.12-2.36 (m, 4H), 2.10-1.98 (m, 2H). MS (EI) for $C_{26}H_{32}N_6O_3$: 479 ($MH^+$).

(19AJ): N4-[8-(5-acetylpyridin-2-yl)-8-azabicyclo[3.2.1]oct-3-yl]-2-[(piperidin-3-ylmethyl)amino]benzene-1,4-dicarboxamide. Prepared as the HCl salt according to the method of example 19 by using 4-(aminocarbonyl)-3-{[(1-{[(1,1-dimethylethyl)oxy]carbonyl}piperidin-3-yl)methyl]amino}benzoic acid (synthesized according to reagent prep 39) in step 4, then omission of step 6. $^1$H NMR (400 MHz, methanol-$d_4$): 8.50 (s, 1H), 8.39 (d, J=9.2 Hz, 1H), 7.69 (d, J=8.4 Hz, 1H), 7.37 (d, J=9.2 Hz, 1H), 7.14 (s, 1H), 7.00 (m, 1H), 4.80 (br, s, 1H), 4.10 (br, s, 1H), 3.72 (m, 2H), 3.50-3.10 (m, 6H), 2.99-2.76 (m, 4H), 2.43-2.0 (m, 4H). MS (EI) for $C_{28}H_{36}N_6O_3$: 505 ($MH^+$).

(19AK): N4-[8-(5-acetylpyridin-2-yl)-8-azabicyclo[3.2.1]oct-3-yl]-2-[(pyrrolidin-3-ylmethyl)amino]benzene-1,4-dicarboxamide. Prepared as the HCl salt according to the method of example 19 by using 4-(aminocarbonyl)-3-{[(1-{[(1,1-dimethylethyl)oxy]carbonyl}pyrrolidin-3-yl)methyl]amino}benzoic acid (synthesized according to reagent prep 39) in step 4, then omission of step 6. $^1$H NMR (400 MHz, methanol-$d_4$): 8.50 (s, 1H), 8.39 (d, J=9.2 Hz, 1H), 7.69 (d, J=8.4 Hz, 1H), 7.38 (d, J=9.2 Hz, 1H), 7.19 (s, 1H), 7.00 (m, 1H), 4.82 (br, s, 1H), 4.07 (br, s, 1H), 3.72 (m, 1H), 3.50-3.30 (m, 6H), 3.05 (m, 1H), 2.78 (m, 1H), 2.60 (s, 3H), 2.42-2.20 (m, 8H), 1.85 (m, 1H), 1.40 (m, 2H). MS (EI) for $C_{27}H_{34}N_6O_3$: 491 ($MH^+$).

(19AL): N4-[8-(5-acetylpyridin-2-yl)-8-azabicyclo[3.2.1]oct-3-yl]-2-[(3-{[2-(dimethylamino)ethyl]oxy}phenyl)amino]benzene-1,4-dicarboxamide. Prepared as the acetate salt according to the method of example 19 by using 4-(aminocarbonyl)-3-[(3-{[(2-dimethylamino)ethyl]oxy}phenyl)amino]benzoic acid (synthesized according to reagent prep 39) in step 4, then omission of steps 5 and 6. $^1$H NMR (400 MHz, methanol-$d_4$): 8.70 (s, 1H), 8.29 (s, 1H), 8.11 (d, J=6.0 Hz, 1H), 7.73 (m, 2H), 7.38-6.6 (m, 6H), 4.70 (br, s, 2H), 4.46 (br, s, 1H), 4.07 (m, 1H), 3.82-3.45 (m, 3H), 3.05 (m, 2H), 3.00 (s, 6H), 2.86 (m, 2H), 2.53 (s, 3H), 2.20 (m, 4H), 2.05 (m, 2H). MS (EI) for $C_{32}H_{38}N_6O_4$: 571 ($MH^+$).

(19AM): 2-[(cyclopropylmethyl)amino]-N4-[8-(5-propanoylpyridin-2-yl)-8-azabicyclo[3.2.1]oct-3-endo-yl]benzene-1,4-dicarboxamide. Prepared according to the method of example 19 by using ethylmagnesium chloride in step 2 and 4-(aminocarbonyl)-3-(cyclopropylmethylamino)benzoic acid (synthesized according to reagent preparation 39) in step 4, then omission of steps 5 and 6. $^1$HNMR (400 MHz, DMSO-$d_6$): 8.76 (s, 1H), 8.27-8.18 (m, 1H), 7.99-7.93 (m, 1H), 7.68-7.66 (d, 1H), 7.23 (s, 1H), 6.98 (s, 1H), 6.89 (d, 1H), 6.78 (d, 1H), 4.64 (s, 2H), 3.84 (s, 1H), 3.05 (t, 2H), 2.92 (t, 2H), 2.22-2.21 (m, 2H), 2.08-1.97 (m, 6H), 1.11-1.04 (m, 5H), 0.53-0.49 (m, 2H), 0.26-0.24 (m, 2H). MS (EI) for $C_{27}H_{33}N_5O_3$: 476 ($MH^+$).

(19AN): 2-[(cyclopropylmethyl)amino]-N4-{8-[5-(2-methylpropanoyl)pyridin-2-yl]-8-azabicyclo[3.2.1]oct-3-endo-yl}benzene-1,4-dicarboxamide. Prepared as the HCl salt according to the method of example 19 by using isopropylmagnesium chloride in step 2 and 4-(aminocarbonyl)-3-(cyclopropylmethylamino)benzoic acid (synthesized according to reagent preparation 39) in step 4, then omission of steps 5 and 6. $^1$HNMR (400 MHz, DMSO-$d_6$): 8.63 (s, 1H), 8.25 (d, 1H), 8.16 (d, 1H), 7.96 (s, 1H), 7.70-7.68 (m, 1H), 7.32-7.30 (m, 1H), 7.12-7.10 (m, 1H), 6.93 (s, 1H), 6.90 (d, 1H), 4.77 (s, 2H), 3.89 (s, 1H), 3.16-3.01 (m, 2H), 2.28 (s, 6H), 2.11-2.07 (m, 2H), 2.05-2.04 (m, 6H), 1.12 (s, 1H), 1.08-1.06 (m, 4H), 0.53-0.5 (m, 2H), 0.27-0.24 (m, 2H). MS (EI) for $C_{28}H_{35}N_5O_3$: 490 ($MH^+$).

(19AO): N4-[8-(5-acetylpyridin-2-yl)-8-azabicyclo[3.2.1]oct-3-endo-yl]-2-(ethylamino)benzene-1,4-dicarboxamide. Prepared according to the method of example 19 using 4-cyano-5-[(trans-4-hydroxycyclohexyl)amino]-2-methylbenzoic acid (synthesized according to reagent prep 41) in step 3 followed by nitrile hydrolysis as described in example 11 step 6. $^1$HNMR (400 MHz, $d_6$-DMSO): 8.74 (d, 1H), 8.28 (d, 1H), 7.98-7.95 (m, 2H), 7.83 (br s, 1H), 7.47 (s, 1H), 7.16 (br s, 1H), 6.78 (d, 1H), 6.61 (s, 1H), 4.64 (br s, 2H), 4.57 (d, 1H), 3.87-3.82 (m, 1H), 3.51-3.42 (m, 1H), 3.26-3.17 (m, 1H), 2.45 (s, 3H), 2.32-2.26 (m, 2H), 2.19 (s, 3H), 2.08-1.91 (m, 8H), 1.86-1.80 (m, 2H), 1.32-1.15 (m, 4H). MS (EI) for $C_{29}H_{37}N_5O_4$: 520 ($MH^+$).

(19AP): N4-[8-(5-Acetylpyridin-2-yl)-8-azabicyclo[3.2.1]oct-3-endo-yl]-2-(cyclopropylamino)benzene-1,4-dicarboxamide. Prepared according to the method of example 19 by using 4-(aminocarbonyl)-3-(cyclopropylamino)benzoic acid (synthesized according to reagent preparation 40) in step 4, then omission of steps 5 and 6. $^1$H NMR (400 MHz, $d_6$-DMSO): 8.74 (d, 1H), 8.32 (br, 1H), 8.25 (d, 1H), 7.97 (dd, 2H), 7.68 (d, 1H), 7.41 (d, 1H), 7.34 (br, 1H), 6.93 (dd, 1H), 6.79 (d, 1H), 4.64 (br, 2H), 3.87 (br, 1H), 2.45 (s, 3H), 2.32-2.23 (m, 2H), 2.12-1.92 (m, 7H), 0.79-0.73 (m, 2H), 0.50-0.43 (m, 2H). MS (EI) for $C_{25}H_{29}N_5O_3$: 448 ($MH^+$).

(19AQ): N4-[8-(5-Acetylpyridin-2-yl)-8-azabicyclo[3.2.1]oct-3-endo-yl]-2-(tetrahydrofuran-3-ylamino)benzene-1,4-dicarboxamide. Prepared according to the method of example 19 by using 4-(aminocarbonyl)-3-(tetrahydrofuran-3-ylamino)benzoic acid (synthesized according to reagent preparation 39) in step 4, then omission of steps 5 and 6. $^1$HNMR (400 MHz, $d_6$-DMSO): 8.75 (d, 1H), 8.38 (d, 1H), 8.23 (d, 1H), 8.01-7.94 (m, 2H), 7.70 (d, 1H), 7.36 (br s, 1H), 6.97 (s, 1H), 6.92 (dd, 1H), 6.80 (d, 1H), 4.64 (br s, 2H), 4.18-4.10 (m, 1H), 3.94-3.72 (m, 4H), 3.56 (dd, 1H), 2.45 (s, 3H), 2.30-2.19 (m, 3H), 2.12-1.92 (m, 6H), 1.82-1.72 (m, 1H). MS (EI) for $C_{26}H_{31}N_5O_4$: 478 ($MH^+$).

(19AR): N4-[8-(5-Acetylpyridin-2-yl)-8-azabicyclo[3.2.1]oct-3-endo-yl]-2-[(2,2,3,3,3-pentafluoropropyl)amino]benzene-1,4-dicarboxamide. Prepared as the hydrochloride salt according to the method of example 19 by using 4-(aminocarbonyl)-3-(2,2,3,3,3-pentafluoropropylamino)benzoic acid (synthesized according to reagent preparation 39) in step 4, then omission of steps 5 and 6. $^1$H NMR (400 MHz, $d_6$-DMSO): 8.72-8.60 (m, 2H), 8.28 (d, 1H), 8.14-8.07 (m, 2H), 7.74 (d, 1H), 7.51 (br s, 1H), 7.20 (s, 1H), 7.12-7.03 (m, 1H), 7.03 (dd, 1H), 4.78 (br s, 2H), 4.28 (br t, 2H), 3.90 (br s, 1H), 2.51 (s, 3H), 2.35-2.24 (m, 2H), 2.18-1.97 (m, 6H). MS (EI) for $C_{25}H_{26}F_5N_5O_3$: 540 ($MH^+$).

(19AS): N-[8-(5-Acetylpyridin-2-yl)-8-azabicyclo[3.2.1]oct-3-endo-yl]-2-methyl-5-{[4-(trifluoromethyl)cyclohexyl]amino}benzene-1,4-dicarboxamide. Prepared according to the method of example 19 by using 4-(aminocarbonyl)-2-methyl-5-(4-(trifluoromethyl)cyclohexylamino)benzoic acid (synthesized according to reagent preparation 42) in step 4, then omission of steps 5 and 6. $^1$H NMR (400 MHz, $d_6$-DMSO): 8.74 (d, 1H), 8.54 (d, 1H), 8.29 (d, 1H), 7.96 (dd, 1H), 7.90 (br s, 1H), 7.52 (s, 1H), 7.25 (br s, 1H), 6.78 (d, 1H), 6.60 (s, 1H), 4.62 (br s, 2H), 3.88-3.81 (m, 1H), 3.77-3.70 (m, 1H), 2.45 (s, 3H), 2.40-2.30 (m, 1H), 2.29-2.21 (m, 2H), 2.19 (s, 3H), 2.12-1.95 (m, 4H), 1.95-1.85 (m, 4H), 1.77-1.57 (m, 4H), 1.54-1.40 (m, 2H). MS (EI) for $C_{30}H_{36}F_3N_5O_3$: 572 ($MH^+$).

(19AT): N4-[8-(5-Acetylpyridin-2-yl)-8-azabicyclo[3.2.1]oct-3-endo-yl]-2-[(2,2,3,3,4,4,4-heptafluorobutyl)amino]benzene-1,4-dicarboxamide. Prepared according to the method of example 19 by using 4-(aminocarbonyl)-3-(2,2,3,3,4,4,4-heptafluorobutylamino)benzoic acid (synthesized according to reagent preparation 39) in step 4, then omission of steps 5 and 6. $^1$H NMR (400 MHz, $d_6$-DMSO): 8.74 (d, 1H), 8.67 (t, 1H), 8.24 (d, 1H), 8.09 (br s, 1H), 7.97 (dd, 1H), 7.74 (d, 1H), 7.51 (s, 1H), 7.19 (s, 1H), 7.03 (dd, 1H), 6.79 (d, 1H), 4.65 (br s, 2H), 4.32 (td, 2H), 3.87 (br s, 1H), 2.46 (s, 3H), 2.29-2.20 (m, 2H), 2.13-1.90 (m, 6H). MS (EI) for $C_{26}H_{26}F_7N_5O_3$: 588 ($MH^+$).

(19AU): N4-[8-(5-acetylpyridin-2-yl)-8-azabicyclo[3.2.1]oct-3-endo-yl]-2-aminobenzene-1,4-dicarboxamide. Prepared according to the method of example 19 by using 4-(aminocarbonyl)-3-aminobenzoic acid (synthesized according to reagent preparation 43) in step 4, then omission of steps 5 and 6. $^1$H NMR (400 MHz, $d_6$-DMSO): 8.74 (d, 1H), 8.16 (d, 1H), 7.96 (dd, 1H), 7.84 (br s, 1H), 7.60 (d, 1H), 7.22 (br s, 1H), 7.07 (d, 1H), 6.80 (m, 4H), 4.63 (br s, 2H), 3.84 (s, 1H), 2.45 (s, 3H), 2.24 (m, 2H), 2.09-1.91 (m, 6H). MS (EI) for $C_{22}H_{25}N_5O_3$: 408 ($MH^+$).

(19AV): N4-[8-(5-acetylpyridin-2-yl)-8-azabicyclo[3.2.1]oct-3-endo-yl]-2-(tetrahydro-2H-pyran-4-ylamino)benzene-1,4-dicarboxamide. Prepared according to the method of example 19 by using 4-(aminocarbonyl)-3-(tetrahydro-2H-pyran-4-ylamino)benzoic acid (synthesized according to reagent preparation 39) in step 4, then omission of steps 5 and 6. $^1$HNMR (400 MHz, $d_6$-DMSO): 8.74 (d, 1H), 8.31 (d, 1H), 8.23 (d, 1H), 7.98-7.95 (m, 2H), 7.69 (d, 1H), 7.32 (br s, 1H), 7.00 (s, 1H), 6.87 (dd, 1H), 6.79 (d, 1H), 4.63 (br s, 2H), 3.88-3.86 (m, 3H), 3.66-3.56 (m, 1H), 3.45 (t, 2H), 2.46 (s, 3H), 2.24 (d, 2H), 2.07-1.92 (m, 8H), 1.46-1.36 (m, 2H). MS (EI) for $C_{27}H_{33}N_5O$: 492 ($MH^+$).

(19AW): N4-[8-(5-acetylpyridin-2-yl)-8-azabicyclo[3.2.1]oct-3-endo-yl]-2-(phenylamino)benzene-1,4-dicarboxamide. Prepared as the hydrochloride salt according to the method of example 19 by using 4-(aminocarbonyl)-3-(phenylamino)benzoic acid (synthesized according to reagent preparation 39) in step 4, then omission of steps 5 and 6. $^1$H NMR (400 MHz, $d_6$-DMSO): 10.13 (br s, 1H), 8.64 (s, 1H), 8.31 (d, 1H), 8.19 (s, 1H), 8.07 (d, 1H), 7.80 (d, 1H), 7.65 (s, 1H), 7.64 (s, 1H), 7.35-7.31 (m, 2H), 7.25 (d, 2H), 7.11 (dd, 1H), 7.04-7.00 (m, 2H), 4.71 (br s, 2H), 3.84 (br s, 1H), 2.49 (s, 3H), 2.22 (d, 2H), 2.09-2.00 (m, 6H). MS (EI) for $C_{28}H_{29}N_5O_3$: 484 ($MH^+$).

(19AX): N4-[8-(5-acetylpyridin-2-yl)-8-azabicyclo[3.2.1]oct-3-endo-yl]-2-[(phenylmethyl)amino]benzene-1,4-dicarboxamide. Prepared according to the method of example 19 by using 3-(phenylmethyl)-4-(aminocarbonyl)benzoic acid (synthesized according to reagent preparation 39) in step 4, then omission of steps 5 and 6. $^1H$ NMR (400 MHz, $d_6$-DMSO): 10.13 (br s, 1H), 8.72-8.68 (m, 2H), 8.13 (br s, 1H), 7.99-7.94 (m, 2H), 7.69 (d, 1H), 7.37 (br s, 1H), 7.32 (br s, 4H), 7.24 (br s, 1H), 6.91-6.88 (m, 2H), 6.77 (d, 1H), 4.59 (br s, 2H), 4.48 (d, 2H), 3.79 (br s, 1H), 2.44 (s, 3H), 2.09 (d, 2H), 2.02-1.88 (m, 6H). MS (EI) for $C_{29}H_{31}N_5O_3$: 498 ($MH^+$).

(19AY): N4-[8-(5-acetylpyridin-2-yl)-8-azabicyclo[3.2.1]oct-3-endo-yl]-2-[(3S)-tetrahydrofuran-3-ylamino]benzene-1,4-dicarboxamide. Prepared as the hydrochloride salt according to the method of example 19 by using (S)-4-(aminocarbonyl)-3-(tetrahydrofuran-3-ylamino)benzoic acid (synthesized according to reagent preparation 39) in step 4, then omission of steps 5 and 6. $^1H$ NMR (400 MHz, $d_6$-DMSO): 8.59 (s, 1H), 8.29 (s, 1H), 8.14 (d, 1H), 8.00 (br s, 1H), 7.72 (d, 1H), 7.37 (br s, 1H), 7.13 (d, 1H), 6.97 (s, 1H), 6.93 (d, 1H), 4.81 (br s, 2H), 4.16 (br s, 1H), 3.90-3.75 (m, 4H), 3.57 (d, 1H), 2.52 (s, 3H), 2.35-2.19 (m, 4H), 2.09 (br s, 6H), 1.76 (m, 1H). MS (EI) for $C_{26}H_{31}N_5O_4$: 478 ($MH^+$).

(19AZ): N4-[8-(5-acetylpyridin-2-yl)-8-azabicyclo[3.2.1]oct-3-endo-yl]-2-[(2,2,2-trifluoroethyl)amino]benzene-1,4-dicarboxamide. Prepared as the hydrochloride salt according to the method of example 19 by using 4-(aminocarbonyl)-3-(2,2,2-trifluoroethylamino)benzoic acid (synthesized according to reagent preparation 39) in step 4, then omission of steps 5 and 6. $^1H$ NMR (400 MHz, $d_6$-DMSO): 8.64 (s, 2H), 8.24 (d, 1H), 8.12-8.05 (m, 2H), 7.73 (d, 1H), 7.51 (br s, 1H), 7.23 (s, 1H), 7.04 (d, 2H), 4.74 (br s, 2H), 4.26-4.15 (m, 2H), 3.89 (br s, 1H), 2.51 (s, 3H), 2.31-2.22 (m, 2H), 2.16-1.99 (m, 6H). MS (EI) for $C_{27}H_{33}N_5O$: 490 ($MH^+$).

(19BA): N4-[8-(5-acetylpyridin-2-yl)-8-azabicyclo[3.2.1]oct-3-endo-yl]-2-[(3R)-tetrahydrofuran-3-ylamino]benzene-1,4-dicarboxamide. Prepared as the hydrochloride salt according to the method of example 19 by using (R)-4-(aminocarbonyl)-3-(tetrahydrofuran-3-ylamino)benzoic acid (synthesized according to reagent preparation 39) in step 4, then omission of steps 5 and 6. $^1H$ NMR (400 MHz, $d_6$-DMSO): 8.50 (s, 1H), 8.34 (d, 1H), 8.23 (d, 1H), 8.02 (br s, 1H), 7.72 (d, 1H), 7.36 (br s, 1H), 7.33 (d, 1H), 6.98 (s, 1H), 6.94 (d, 1H), 4.87 (br s, 2H), 4.19-4.13 (m, 1H), 3.92-3.87 (m, 2H), 3.86-3.73 (m, 2H), 3.59 (dd, 1H), 2.55 (s, 3H), 2.38-2.21 (m, 4H), 2.18-2.07 (m, 6H), 1.82-1.73 (m, 1H). MS (EI) for $C_{26}H_{31}N_5O_4$: 478 ($MH^+$).

(19BB): N4-[8-(5-acetylpyridin-2-yl)-8-azabicyclo[3.2.1]oct-3-endo-yl]-2-(propylamino)benzene-1,4-dicarboxamide. Prepared as the hydrochloride salt according to the method of example 19 by using 4-(aminocarbonyl)-3-(propylamino)benzoic acid (synthesized according to reagent preparation 39) in step 4, then omission of steps 5 and 6. $^1H$ NMR (400 MHz, $d_6$-DMSO): 8.62 (s, 1H), 8.39 (s, 1H), 8.22-8.15 (m, 1H), 7.98 (br s, 1H), 7.74-7.67 (m, 1H), 7.34 (br s, 1H), 7.25 (br s, 1H), 7.01 (s, 1H), 6.94-6.88 (m, 1H), 4.54 (br s, 2H), 3.90 (s, 1H), 3.18-3.10 (m, 2H), 2.54 (s, 3H), 2.35-2.27 (m, 2H), 2.15-2.06 (m, 6H), 1.65-1.56 (m, 2H), 0.99-0.92 (m, 3H). MS (EI) for $C_{25}H_{31}N_5O_3$: 450 ($MH^+$).

(19BC): N4-[8-(5-acetylpyridin-2-yl)-8-azabicyclo[3.2.1]oct-3-endo-yl]-2-azetidin-1-ylbenzene-1,4-dicarboxamide. Prepared according to the method of example 19 by using 3-(azetidin-1-yl)-4-(aminocarbonyl)benzoic acid (synthesized according to reagent preparation 39) in step 4, then omission of steps 5 and 6. $^1H$ NMR (400 MHz, $d_6$-DMSO): 8.62 (s, 1H), 8.39 (s, 1H), 8.22-8.15 (m, 1H), 7.98 (br s, 1H), 7.74-7.67 (m, 1H), 7.34 (br s, 1H), 7.25 (br s, 1H), 7.01 (s, 1H), 6.94-6.88 (m, 1H), 4.54 (br s, 2H), 3.90 (s, 1H), 3.18-3.10 (m, 2H), 2.54 (s, 3H), 2.35-2.27 (m, 2H), 2.15-2.06 (m, 6H), 1.65-1.56 (m, 2H), 0.99-0.92 (m, 3H). MS (EI) for $C_{25}H_{29}N_5O_3$: 448 ($MH^+$).

(19BD): N4-[8-(5-acetylpyridin-2-yl)-8-azabicyclo[3.2.1]oct-3-endo-yl]-2-bromobenzene-1,4-dicarboxamide. Prepared according to the method of example 19 by using 3-bromo-4-(aminocarbonyl)benzoic acid (synthesized according to reagent preparation 44) in step 4, then omission of steps 5 and 6. $^1H$ NMR (400 MHz, $d_6$-DMSO): 8.74 (d, 1H), 8.37 (d, 1H), 8.02 (d, 1H), 7.98-7.95 (m, 2H), 7.82 (dd, 1H), 7.70 (br s, 1H), 7.50 (d, 1H), 6.80 (d, 1H), 4.65 (br s, 2H), 3.89-3.83 (m, 1H), 2.46 (s, 3H), 2.20-2.19 (m, 2H), 2.14-1.92 (m, 6H). MS (EI) for $C_{22}H_{23}BrN_4O_3$: 471, 473 ($MH^+$).

(19BE): N4-[8-(5-acetylpyridin-2-yl)-8-azabicyclo[3.2.1]oct-3-endo-yl]-2-[(3,3,3-trifluoropropyl)amino]benzene-1,4-dicarboxamide. Prepared according to the method of example 19 by using 4-(aminocarbonyl)-3-(3,3,3-trifluoropropylamino)benzoic acid (synthesized according to reagent preparation 39) in step 4, then omission of steps 5 and 6. $^1H$ NMR (400 MHz, $d_6$-DMSO): 8.74 (d, 1H), 8.38-8.34 (m, 1H), 8.26 (d, 1H), 7.99-7.95 (m, 2H), 7.70 (d, 1H), 7.36 (br s, 1H), 6.97 (s, 1H), 6.93 (dd, 1H), 6.89 (d, 1H), 4.64 (br s, 2H), 3.89-3.83 (m, 1H), 3.48 (q, 2H), 2.68-2.58 (m, 2H), 2.45 (s, 3H), 2.28-2.21 (m, 2H), 2.11-1.91 (m, 6H). MS (EI) for $C_{25}H_{28}F_3N_5O_3$: 504 ($MH^+$).

SYNTHETIC SCHEME 20:

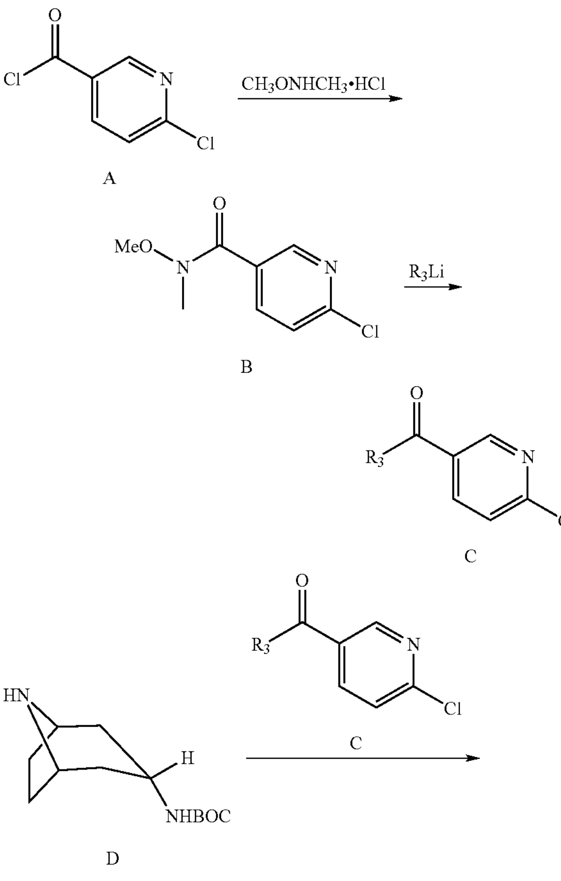

-continued

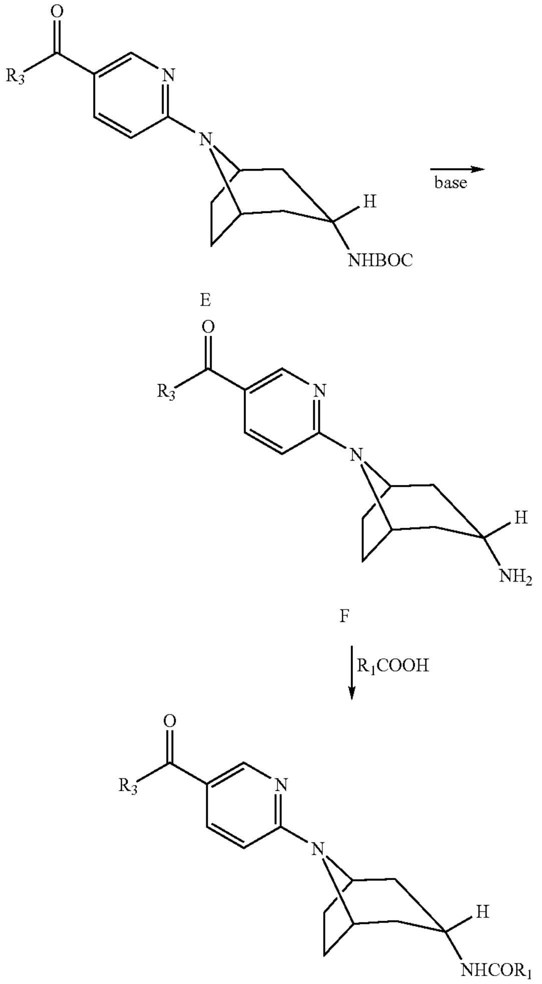

E

F

G

Scheme 20 generally describes the synthesis of all of the compound(s) listed in Example 20, wherein $R_3$ and $R_1$ are as defined in the specification.

In Scheme 20, $CH_3ONHCH_3$.HCl N,O-dimethylhydroxylamine hydrochloride is added to compound (A) under appropriate reaction conditions and with a suitable coupling reagent, such as HATU, to condense and form compound (B). To compound B is added $R_3Li$ under appropriate reaction conditions to arrive at compound (C). To compound (D) is added compound (C) in the presence of a weak base, such as tribasic potassium phosphate, and appropriate reaction conditions to undergo an aromatic nucleophilic substitution reaction and arrive at compound (E). Compound (E) is then deprotected with an acid, such as HCl, to remove the BOC and arrive at compound (F). To compound (F) is added $R_1COOH$ under appropriate reaction conditions and with a suitable coupling reagent, such as HATU, to condense and form the amide bond in compound (G).

Example 20

N-{8-[5-(cyclopropylcarbonyl)pyridin-2-yl]-8-azabicyclo[3.2.1]oct-3-endo-yl}-2-methyl-5-{[(1R)-1-methylpropyl]amino}benzene-1,4-dicarboxamide STEP 1: To a solution of 6-chloronicotinoyl chloride (2 g, 11.4 mmol) and diethylisopropylamine (5 mL, 28.5 mmol) in dichloromethane (100 mL) was added N,O-dimethylhyroxylamine hydrochloride (1.22 g, 12.5 mmol) at 0° C. The solution was allowed to warm to room temperature then was stirred for 48 hours. The mixture was washed with 20% aqueous citric acid (2×100 mL), 1N aqueous sodium hydroxide (2×100 mL), brine (100 mL), dried over anhydrous sodium sulfate, filtered and concentrated to afford 6-chloro-N-methyl-N-(methyloxy)pyridine-3-carboxamide (2.05 g, 92% yield) as a yellow oil. $^1$H NMR (400 MHz, $d_6$-DMSO): 8.65 (d, 1H), 8.08 (dd, 1H), 7.63 (d, 1H), 3.67 (s, 3H), 3.30 (s, 3H); MS (EI) for $C_8H_9ClN_2O_2$: 201 ($MH^+$).

STEP 2: To a solution of cyclopropylbromide (1.24 g, 10.24 mmol) in THF (10 mL) was added dropwise a 2.5M solution of n-butyllithium in hexanes (4.0 mL, 10.00 mmol) at −78° C. and the reaction mixture was stirred for 1 h at this temperature. Then a solution of 6-chloro-N-methyl-N-(methyloxy)pyridine-3-carboxamide (1.00 g, 4.98 mmol) in THF (5 mL) was added quickly at −78° C., and the cooling bath was removed. Stirring was continued for 1 h, then the solution was poured into saturated ammonium chloride (100 mL), extracted with ethyl acetate (3×50 mL) and the organic layers were washed with brine (50 mL), dried over sodium sulfate then filtered and concentrated. Column chromatography on silica (hexanes:ethyl acetate 9:1 to 8:2) afforded (6-chloropyridin-3-yl)(cyclopropyl)-methanone (0.62 g, 68% yield). $^1$H NMR (400 MHz, $CDCl_3$): 9.04 (d, 1H), 8.22 (dd, 1H), 7.46 (d, 1H), 2.61 (m, 1H), 1.32 (m, 2H), 1.15 (m, 2H).

STEP 3: To a solution of 1,1-dimethylethyl 8-azabicyclo[3.2.1]oct-3-endo-ylcarbamate hydrochloride (synthesized in reagent preparation 1) (795 mg, 3.03 mmol) and (6-chloropyridin-3-yl)(cyclopropyl)methanone (500 mg, 2.75 mmol) in diethylene glycol dimethyl ether (5 mL) was added an aqueous solution of potassium phosphate tribasic (1.75 g, 8.25 mmol in 5 mL of water). The biphasic mixture was stirred at 125° C. for 60 h. The mixture was cooled to room temperature and was diluted with water (25 mL). The precipitate thus formed was filtered, washed several times with water followed by hot hexane, and dried to afford 1,1-dimethylethyl{8-[5-(cyclopropylcarbonyl)pyridine-2-yl]-8-azabicyclo[3.2.1]oct-3-endo-yl}carbamate (943 mg, 96% yield). $^1$H NMR (400 MHz, $d_6$-DMSO): 8.85 (d, 1H), 8.00 (dd, 1H), 6.89 (br s, 1H), 6.73 (d, 1H), 4.53 (br s, 2H), 3.44-3.40 (m, 1H), 2.80-2.73 (m, 1H), 2.15-2.08 (m, 2H), 2.00-1.87 (m, 4H), 1.78-1.71 (m, 2H), 1.37 (s, 9H), 0.94-0.88 (m, 4H); MS (EI) for $C_{21}H_{29}N_3O_3$: 372 ($MH^+$).

STEP 4: To a solution of 1,1-dimethylethyl{8-[5-(cyclopropylcarbonyl)pyridine-2-yl]-8-azabicyclo[3.2.1]oct-3-endo-yl}carbamate (1.00 g, 2.69 mmol) in dioxane (18 mL) was added concentrated sulfuric acid (2.0 mL) and the mixture was stirred at room temperature for 30 min. The mixture was carefully poured into saturated aqueous sodium bicarbonate (300 mL), and extracted with 10% methanol in chloroform (3×100 mL). The combined organic layers were washed with water (50 mL), dried over sodium sulfate then filtered and concentrated to give [6-(3-endo-amino-8-azabicyclo[3.2.1]oct-8-yl)pyridin-3-yl](cyclopropyl)-methanone (0.71 g, 97% yield). $^1$H NMR (400 MHz, $d_4$-methanol): 8.80 (d, 1H), 8.07 (dd, 1H), 6.72 (d, 1H), 4.63 (br s, 2H), 3.02 (m, 1H), 2.70 (m, 1H), 2.30-2.06 (m, 7H), 1.60 (d, 2H), 1.08 (m, 2H), 1.02 (m, 2H).

STEP 5: A solution of [6-(3-endo-amino-8-azabicyclo[3.2.1]oct-8-yl)pyridin-3-yl](cyclopropyl)methanone (100 mg, 0.37 mmol), HATU (210 mg, 0.55 mmol), 4-(aminocarbonyl)-2-methyl-5-{[(1R)-1-methylpropyl]amino}benzoic acid (synthesized in reagent preparation 41) (138 mg, 0.55 mmol), and diisopropylethyl-amine (256 μl, 1.47 mmol) in DMF (3 mL) was stirred at room temperature for 2 h. Concentration and column chromatography on silica (dichloromethane:methanol 100:0 then 95:5) followed by trituration of the residue obtained on concentration of the combined pure fractions with ethyl acetate afforded N-{8-[5-(cyclopropylcarbonyl)pyridin-2-yl]-8-azabicyclo[3.2.1]oct-3-endo-yl}-2-methyl-5-{[(1R)-1-methylpropyl]amino}benzene-1,4-dicarboxamide (179 mg, 96% yield) as a pale yellow powder. $^1$H NMR (400 MHz, methanol-$d_4$): 8.84 (d, 1H), 8.11 (dd, 1H), 7.45 (s, 1H), 6.78 (d, 1H), 6.68 (s, 1H), 4.68 (br s, 2H), 4.02 (t, 2H), 3.77-3.67 (m, 1H), 3.25-3.19 (m, 2H), 2.76-2.70 (m, 1H), 2.32-2.25 (m, 7H), 2.18-2.14 (m, 2H), 1.97 (br s, 1H), 1.70-1.59 (m, 1H), 1.60-1.50 (m, 1H), 1.25-1.18 (m, 4H), 1.12-1.09 (m, 2H), 1.06-1.01 (m, 2H), 0.97 (t, 3H); MS (EI) for $C_{29}H_{37}N_5O_3$: 504 ($MH^+$).

Using analogous synthetic techniques and substituting with alternative starting reagents, the following compounds [(20B)-(20BF)] were prepared. Alternative starting materials were obtained commercially unless otherwise indicated.

(20B): N4-{8-[5-(cyclopropylcarbonyl)pyridin-2-yl]-8-azabicyclo[3.2.1]oct-3-endo-yl}-2-[(cyclopropylmethyl)amino]benzene-1,4-dicarboxamide. Prepared according to the method of example 20 by using 4-(aminocarbonyl)-3-[(cyclopropylmethyl)amino]benzoic acid (synthesized according to reagent prep 39) in step 5. $^1$H NMR (400 MHz, DMSO-$d_6$): 8.89 (d, 1H), 8.26 (t, 1H), 8.18 (d, 1H), 8.05 (dd, 1H), 7.93 (br s, 1H), 7.67 (d, 1H), 7.29 (br s, 1H), 6.99 (d, 1H), 6.89 (dd, 1H), 6.81 (d, 1H), 4.64 (br s, 2H), 3.85 (m, 1H), 3.03 (m, 2H), 2.80 (m, 1H), 2.22 (m, 2H), 2.12-1.93 (m, 6H), 1.11 (m, 1H), 0.95 (m, 4H), 0.51 (m, 2H), 0.24 (m, 2H); MS (EI) for $C_{28}H_{33}N_5O_3$: 588 ($MH^+$).

(20C): N4-{8-[5-(cyclopropylcarbonyl)pyridin-2-yl]-8-azabicyclo[3.2.1]oct-3-endo-yl}-2-[(1-ethylpropyl)amino]benzene-1,4-dicarboxamide. Prepared as the hydrochloride salt according to the method of example 20 by using 4-(aminocarbonyl)-3-[(1-ethylpropyl)amino]benzoic acid (synthesized according to reagent preparation 39) in step 5. $^1$H NMR (400 MHz, methanol-$d_4$): 8.61 (d, 1H), 8.45 (dd, 1H), 8.42 (d, 1H), 7.73 (d, 1H), 7.39 (d, 1H), 7.23 (s, 1H), 7.06 (d, 1H), 4.81 (br s, 2H), 4.12 (m, 1H), 3.44 (m, 1H), 2.74 (m, 1H), 2.46-2.23 (m, 8H), 1.74-1.53 (m, 4H), 1.16 (m, 4H), 0.97 (t, 6H); MS (EI) for $C_{29}H_{37}N_5O_3$: 504 ($MH^+$).

(20D): N4-{8-[5-(cyclopropylcarbonyl)pyridin-2-yl]-8-azabicyclo[3.2.1]oct-3-endo-yl}-2-(pyridin-4-ylamino)benzene-1,4-dicarboxamide. Prepared as the hydrochloride salt according to the method of example 20 by using 4-(aminocarbonyl)-3-(pyridin-4-ylamino)benzoic acid (synthesized according to reagent preparation 39) in step 5. $^1$H NMR (400 MHz, methanol-$d_4$): 8.64 (d, 1H), 8.55 (d, 1H), 8.42 (dd, 1H), 8.22 (d, 2H), 7.88 (m, 3H), 7.32 (d, 1H), 7.18 (d, 2H), 4.81 (br s, 2H), 4.14 (m, 1H), 2.74 (m, 1H), 2.43-2.20 (m, 8H), 1.15 (m, 4H); MS (EI) for $C_{29}H_{30}N_6O_3$: 511 ($MH^+$).

(20E): 2-(cyclopentylamino)-N4-{8-[5-(cyclopropylcarbonyl)pyridin-2-yl]-8-azabicyclo[3.2.1]oct-3-endo-yl}benzene-1,4-dicarboxamide. Prepared as the hydrochloride salt according to the method of example 20 by using 4-(aminocarbonyl)-3-(cyclopentylamino)benzoic acid (synthesized according to reagent preparation 39) in step 5. $^1$H NMR (400 MHz, DMSO-$d_6$): 8.76 (s, 1H), 8.29 (d, 1H), 8.22 (d, 1H), 7.96 (br s, 1H), 7.69 (d, 1H), 7.31 (br s, 1H), 7.15 (br d, 1H), 7.02 (s, 1H), 6.87 (d, 1H), 4.80 (br s, 2H), 3.90 (m, 1H), 3.85 (m, 1H), 2.86 (m, 1H), 2.31 (m, 2H), 2.09 (m, 6H), 1.98 (m, 2H), 1.65 (m, 4H), 1.46 (m, 2H), 1.02 (d, 4H); MS (EI) for $C_{29}H_{35}N_5O_3$: 502 ($MH^+$).

(20F): N4-{8-[5-(cyclopropylcarbonyl)pyridin-2-yl]-8-azabicyclo[3.2.1]oct-3-endo-yl}-2-[(cis-4-hydroxy-4-methylcyclohexyl)amino]benzene-1,4-dicarboxamide. Prepared according to the method of example 20 by using 4-(aminocarbonyl)-3-[(cis-4-hydroxy-4-methyl-cyclohexyl)amino]benzoic acid (synthesized according to reagent preparation 39) in step 5. $^1$H NMR (400 MHz, DMSO-$d_6$): 8.88 (d, 1H), 8.23 (d, 2H), 8.06 (dd, 1H), 7.92 (br s, 1H), 7.67 (d, 1H), 7.29 (br s, 1H), 6.97 (s, 1H), 6.83 (d, 2H), 4.66 (br s, 2H), 3.85 (br s, 1H), 2.80 (m, 1H), 2.26 (m, 2H), 2.03 (m, 7H), 1.77 (m, 2H), 1.57 (m, 4H), 1.39 (m, 2H), 1.13 (s, 3H), 0.96 (m, 4H); MS (EI) for $C_{31}H_{39}N_5O_4$: 546 ($MH^+$).

(20G): N4-{8-[5-(cyclopropylcarbonyl)pyridin-2-yl]-8-azabicyclo[3.2.1]oct-3-endo-yl}-2-{[(1R)-1,2-dimethylpropyl]amino}benzene-1,4-dicarboxamide. Prepared according to the method of example 20 by using 4-(aminocarbonyl)-3-{[(1R)-1,2-dimethylpropyl]amino}benzoic acid (synthesized according to reagent preparation 39) in step 5. $^1$H NMR (400 MHz, methanol-$d_4$): 8.85 (d, 1H), 8.11 (dd, 1H), 7.97 (d, 1H), 7.64 (d, 1H), 7.07 (s, 1H), 6.86 (d, 1H), 6.78 (d, 1H), 4.70 (br s, 2H), 4.02 (m, 1H), 3.53 (m, 1H), 2.73 (m, 1H), 2.31-2.16 (m, 6H), 2.02 (m, 2H), 1.90 (m, 1H), 1.16 (d, 3H), 1.10 (m, 2H), 1.04 (m, 2H), 1.01 (d, 3H), 0.96 (d, 3H); MS (EI) for $C_{29}H_{37}N_5O_3$: 504 ($MH^+$).

(20H): N4-{8-[5-(cyclopropylcarbonyl)pyridin-2-yl]-8-azabicyclo[3.2.1]oct-3-endo-yl}-2-({2-[(1-methylethyl)oxy]ethyl}amino)benzene-1,4-dicarboxamide. Prepared according to the method of example 20 by using 4-(aminocarbonyl)-3-({2-[(1-methylethyl)oxy]ethyl}amino)benzoic acid (synthesized according to reagent preparation 39) in step 5. MS (EI) for $C_{29}H_{37}N_5O_4$: 520.6 ($MH^+$).

(20I): N-{8-[5-(cyclopropylcarbonyl)pyridin-2-yl]-8-azabicyclo[3.2.1]oct-3-endo-yl}-2-methyl-5-{[1-(trifluoromethyl)propyl]amino}benzene-1,4-dicarboxamide. Prepared according to the method of example 20 by using 4-(aminocarbonyl)-2-methyl-5-{[1-(trifluoromethyl)propyl]amino}benzoic acid (synthesized according to reagent preparation 39) in step 5. MS (EI) for $C_{29}H_{34}F_3N_5O_3$: 558 ($MH^+$).

(20J): N-{8-[5-(cyclopropylcarbonyl)pyridin-2-yl]-8-azabicyclo[3.2.1]oct-3-endo-yl}-2-methyl-5-[(3,3,3-trifluoro-1-methylpropyl)amino]benzene-1,4-dicarboxamide. Prepared according to the method of example 20 by using 4-(aminocarbonyl)-2-methyl-5-[(3,3,3-trifluoro-1-methylpropyl)amino]benzoic acid (synthesized according to reagent preparation 42) in step 5. MS (EI) for $C_{29}H_{34}F_3N_5O_3$: 558 ($MH^+$).

(20K): 2-bromo-N-{8-[5-(cyclopropylcarbonyl)pyridin-2-yl]-8-azabicyclo[3.2.1]oct-3-endo-yl}-5-[(2-methylpropyl)amino]benzene-1,4-dicarboxamide. Prepared according to the method of example 20 by using 4-(aminocarbonyl)-2-bromo-5-[(2-methylpropyl)amino]benzoic acid (synthesized according to reagent preparation 50) in step 5. MS (EI) for $C_{28}H_{34}BrN_5O_3$: 568 ($MH^+$).

(20L): 5-(cyclobutylamino)-N-{8-[5-(cyclopropylcarbonyl)pyridin-2-yl]-8-azabicyclo[3.2.1]oct-3-endo-yl}-2-methylbenzene-1,4-dicarboxamide. Prepared according to the method of example 20 by using 4-(aminocarbonyl)-5-[(cyclobutylamino)-2-methylbenzoic acid (synthesized according to reagent preparation 41) in step 5. $^1$H NMR (400 MHz, DMSO-$d_6$): 8.90 (s, 1H), 8.32 (s, 1H), 8.05 (m, 1H), 8.04 (m, 1H), 7.84 (br, s, 1H), 7.50 (s, 1H), 7.22 (s, 1H), 6.80 (d, J=9.2 Hz, 1H), 6.46 (s, 1H), 4.64 (br s, 2H), 3.89 (m, 2H), 2.80 (m, 1H), 2.30 (m, 4H), 2.10-1.90 (m, 10H); MS (EI) for $C_{29}H_{35}N_5O_3$: 502 ($MH^+$).

(20M): N5-{8-[5-(cyclopropylcarbonyl)pyridin-2-yl]-8-azabicyclo[3.2.1]oct-3-endo-yl}-3-[(1-ethylpropyl)amino]-6-methylpyridine-2,5-dicarboxamide. Prepared according to the method of example 20 by using 6-(aminocarbonyl)-5-[(1-ethylpropyl)amino]-2-methylpyridine-3-carboxylic acid (synthesized according to reagent preparation 49) in step 5. $^1$H NMR (400 MHz, methanol-$d_4$): 8.84 (s, 1H), 8.11 (d, J=8.80 Hz), 7.97 (s, 2H), 7.09 (s, 1H), 6.78 (d, J=8.80 Hz, 1H), 4.69 (br, s, 2H), 4.04 (br, s, 1H), 3.32 (m, 1H), 2.73 (m, 1H), 2.43 (s, 3H), 2.30-2.06 (m, 6H), 2.03-1.98 (m, 2H), 1.80-1.50 (m, 4H), 1.30 (m, 2H), 1.12-1.01 (m, 4H), 0.96 (t, J=7.2 Hz, 6H); MS (EI) for $C_{29}H_{38}N_6O_3$: 519 ($MH^+$).

(20N): N4-{8-[5-(cyclopropylcarbonyl)pyridin-2-yl]-8-azabicyclo[3.2.1]oct-3-endo-yl}-2-{[(1R)-1-methylpropyl]amino}benzene-1,4-dicarboxamide. Prepared according to the method of example 20 by using 4-(aminocarbonyl)-3-{[(1S)-1-methylpropyl]amino}benzoic acid (synthesized according to reagent preparation 39) in step 5. $^1$H NMR (400 MHz, methanol-$d_4$): 8.84 (d, 1H), 8.11 (dd, 1H), 7.63 (d, 1H), 7.06 (s, 1H), 6.87 (dd, 1H), 6.78 (d, 1H), 4.69 (bs, 2H), 4.02 (t, 1H), 3.55 (q, 1H), 2.73 (m, 1H), 2.27 (m, 4H), 2.20 (m, 2H), 2.01 (m, 2H), 1.62 (m, 2H), 1.23 (d, 3H), 1.10 (m, 2H), 1.04 (m, 2H), 0.99 (t, 3H); MS (EI) for $C_{28}H_{35}N_5O_3$: 490 ($MH^+$).

(20O): N4-{8-[5-(cyclopropylcarbonyl)pyridin-2-yl]-8-azabicyclo[3.2.1]oct-3-endo-yl}-2-[(1-methylpropyl)amino]benzene-1,4-dicarboxamide. Prepared according to the method of example 20 by using 4-(aminocarbonyl)-3-[(1-methylpropyl)amino]benzoic acid (synthesized according to reagent preparation 39) in step 5. $^1$H NMR (400 MHz, methanol-$d_4$): 8.84 (d, 1H), 8.11 (dd, 1H), 7.63 (d, 1H), 7.06 (s, 1H), 6.87 (dd, 1H), 6.78 (d, 1H), 4.71 (bs, 2H), 4.03 (t, 1H), 3.56 (q, 1H), 2.72 (m, 1H), 2.27 (m, 4H), 2.20 (m, 2H), 2.01 (m, 2H), 1.62 (m, 2H), 1.23 (d, 3H), 1.10 (m, 2H), 1.04 (m, 2H), 0.99 (t, 3H); MS (EI) for $C_{28}H_{35}N_5O_3$: 490 ($MH^+$).

(20P): N4-{8-[5-(cyclopropylcarbonyl)pyridin-2-yl]-8-azabicyclo[3.2.1]oct-3-endo-yl}-2-{[(1R)-1-methylpropyl]amino}benzene-1,4-dicarboxamide. Prepared according to the method of example 20 by using 4-(aminocarbonyl)-3-{[(1R)-1-methylpropyl]amino}benzoic acid (synthesized according to reagent preparation 39) in step 5. $^1$H NMR (400 MHz, methanol-$d_4$): 8.84 (d, 1H), 8.11 (dd, 1H), 7.63 (d, 1H), 7.06 (s, 1H), 6.84 (dd, 1H), 6.78 (d, 1H), 4.71 (bs, 2H), 4.02 (m, 1H), 3.56 (m, 1H), 2.73 (m, 1H), 2.27 (m, 4H), 2.20 (m, 2H), 2.00 (m, 2H), 1.62 (m, 2H), 1.23 (d, 3H), 1.10 (m, 2H), 1.04 (m, 2H), 0.99 (t, 3H); MS (EI) for $C_{28}H_{35}N_5O_3$: 490 ($MH^+$).

(20Q): N-{8-[5-(cyclopropylcarbonyl)pyridin-2-yl]-8-azabicyclo[3.2.1]oct-3-endo-yl}-2-methyl-5-[(2-methylpropyl)amino]benzene-1,4-dicarboxamide. Prepared according to the method of example 20 by using 4-(aminocarbonyl)-2-methyl-5-[(2-methylpropyl)amino]benzoic acid (synthesized according to reagent preparation 42) in step 5. $^1$H NMR (400 MHz, DMSO-$d_6$): 8.89 (s, 1H), 8.27 (d, 1H), 8.19 (t, 1H), 8.04 (dd, 1H), 7.86 (bs, 1H), 7.49 (s, 1H), 7.19 (bs, 1H), 6.79 (d, 1H), 6.57 (s, 1H), 4.63 (bs, 2H), 3.85 (m, 1H), 3.32 (m, 1H), 2.93 (t, 2H), 2.80 (m, 1H), 2.27 (m, 2H), 2.19 (s, 3H), 2.04 (m, 4H), 1.93 (m, 2H), 0.94 (m, 10H); MS (EI) for $C_{29}H_{37}N_5O_3$: 504 ($MH^+$).

(20R): 5-[(cyclopentylmethyl)amino]-N-{8-[5-(cyclopropylcarbonyl)pyridin-2-yl]-8-azabicyclo[3.2.1]oct-3-endo-yl}-2-methylbenzene-1,4-dicarboxamide. Prepared according to the method of example 20 by using 4-(aminocarbonyl)-5-[(cyclopentylmethyl)amino]-2-methylbenzoic acid (synthesized according to reagent preparation 42) in step 5. $^1$H NMR (400 MHz, DMSO-$d_6$): 8.89 (d, 1H), 8.26 (d, 1H), 8.12 (t, 1H), 8.04 (dd, 1H), 7.84 (bs, 1H), 7.48 (s, 1H), 7.17 (bs, 1H), 6.79 (d, 1H), 6.58 (s, 1H), 4.64 (bs, 2H), 3.85 (m, 1H), 3.32 (m, 1H), 3.02 (m, 2H), 2.26 (m, 2H), 2.19 (s, 3H), 2.04 (m, 4H), 1.92 (m, 2H), 1.73 (m, 2H), 1.60 (m, 2H), 1.52 (m, 2H), 1.24 (m, 2H), 0.95 (m, 4H); MS (EI) for $C_{31}H_{39}N_5O_3$: 530 ($MH^+$).

(20S): N-{8-[5-(cyclopropylcarbonyl)pyridin-2-yl]-8-azabicyclo[3.2.1]oct-3-endo-yl}-2-methyl-5-{[1-(1-methylcyclopropyl)ethyl]amino}benzene-1,4-dicarboxamide. Prepared according to the method of example 20 by using 4-(aminocarbonyl)-2-methyl-5-{[1-(1-methylcyclopropyl)ethyl]amino}benzoic acid (synthesized according to reagent preparation 42) in step 5. $^1$H NMR (400 MHz, DMSO-$d_6$): 8.89 (d, 1H), 8.27 (d, 1H), 8.17 (d, 1H), 8.04 (dd, 1H), 7.85 (s, 1H), 7.47 (s, 1H), 7.17 (bs, 1H), 6.79 (d, 1H), 6.56 (s, 1H), 4.63 (bs, 1H), 3.85 (m, 1H), 3.09 (t, 1H), 2.81 (m, 1H), 2.27 (m, 2H), 2.18 (s, 3H), 2.03 (m, 4H), 1.93 (m, 2H), 1.15 (d, 3H), 1.07 (s, 3H), 0.95 (m, 4H), 0.37 (m, 2H), 0.26 (m, 2H); MS (EI) for $C_{31}H_{39}N_5O_3$: 530 ($MH^+$).

(20T): 2-chloro-N-{8-[5-(cyclopropylcarbonyl)pyridin-2-yl]-8-azabicyclo[3.2.1]oct-3-endo-yl}-5-[(1-ethylpropyl)amino]benzene-1,4-dicarboxamide. Prepared according to the method of example 20 by using 4-(aminocarbonyl)-2-chloro-5-[(1-ethylpropyl)amino]benzoic acid (synthesized according to reagent preparation 46) in step 5. $^1$H NMR (400 MHz, methanol-$d_4$): 8.71 (d, 1H), 8.59 (d, 1H), 8.45 (dd, 1H), 7.68 (s, 1H), 7.38 (d, 1H), 6.76 (s, 1H), 4.77 (br s, 2H), 4.17-4.12 (m, 1H), 2.77-2.71 (m, 1H), 2.50-2.17 (m, 8H), 1.70-1.48 (m, 4H), 1.21-1.10 (m, 4H), 0.94 (t, 6H); MS (EI) for $C_{29}H_{36}ClN_5O_3$: 538 ($MH^+$).

(20U): 2-bromo-N-{8-[5-(cyclopropylcarbonyl)pyridin-2-yl]-8-azabicyclo[3.2.1]oct-3-endo-yl}-5-(propylamino)benzene-1,4-dicarboxamide. Prepared according to the method of example 20 by using 4-(aminocarbonyl)-2-bromo-5-(propylamino)benzoic acid (synthesized according to reagent preparation 50) in step 5. $^1$H NMR (400 MHz, $d_6$-DMSO): 8.89 (d, 1H), 8.42 (d, 1H), 8.33-8.28 (m, 1H), 8.04 (dd, 2H), 7.84 (s, 1H), 7.35 (br s, 1H), 6.79 (d, 1H), 6.59 (s, 1H), 4.63 (br s, 2H), 3.90-3.83 (m, 1H), 3.12-3.05 (m, 2H), 2.84-2.76 (m, 1H), 2.34-2.26 (m, 2H), 2.15-2.05 (m, 2H), 2.02-1.87 (m, 4H), 1.64-1.52 (m, 2H), 1.00-0.90 (m, 2H); MS (EI) for $C_{29}H_{34}F_3N_5O_3$: 554, 556 ($MH^+$).

(20V): 2-(butylamino)-N4-{8-[5-(cyclopropylcarbonyl)pyridin-2-yl]-8-azabicyclo[3.2.1]oct-3-endo-yl}benzene-1,4-dicarboxamide. Prepared according to the method of example 20 by using 4-(aminocarbonyl)-3-(butylamino)benzoic acid (synthesized according to reagent preparation 39) in step 5. $^1$H NMR (400 MHz, $d_6$-DMSO): 8.89 (d, 1H), 8.25-8.20 (m, 2H), 8.05 (dd, 1H), 7.94 (br s, 1H), 7.68 (d, 1H), 7.30 (br s, 1H), 6.97 (d, 1H), 6.87 (dd, 1H), 6.81 (d, 1H), 4.65 (br s, 2H), 3.86 (br s, 1H), 3.17 (q, 2H), 2.85-2.76 (m, 1H), 2.28-2.20 (m, 2H), 2.13-1.92 (m, 6H), 1.63-1.53 (m, 2H), 1.45-1.34 (m, 2H), 0.99-0.90 (m, 7H); MS (EI) for $C_{28}H_{35}N_5O_3$: 490 ($MH^+$).

(20W): N-{8-[5-(cyclopropylcarbonyl)pyridin-2-yl]-8-azabicyclo[3.2.1]oct-3-endo-yl}-2-methyl-5-{[2-methyl-1-(trifluoromethyl)propyl]amino}benzene-1,4-dicarboxamide. Prepared according to the method of example 20 by using 4-(aminocarbonyl)-2-methyl-5-{[2-methyl-1-(trifluoromethyl)propyl]amino}benzoic acid (synthesized according to reagent preparation 41) in step 5. $^1$H NMR (400 MHz, methanol-$d_4$): 8.84 (d, 1H), 8.30 (d, 1H), 8.11 (dd, 1H), 7.53 (s, 1H), 6.87 (s, 1H), 6.78 (d, 1H), 4.69 (br s, 2H), 4.14-4.00 (m, 2H), 2.76-2.69 (m, 1H), 2.34-2.12 (m, 9H), 2.01-1.93 (m, 2H), 1.12-1.01 (m, 10H); MS (EI) for $C_{30}H_{36}F_3N_5O_3$: 572 ($MH^+$).

(20X): 2-bromo-N-{8-[5-(cyclopropylcarbonyl)pyridin-2-yl]-8-azabicyclo[3.2.1]oct-3-endo-yl}-5-[(2,2-dimethylpropyl)amino]benzene-1,4-dicarboxamide. Prepared according to the method of example 20 by using 4-(aminocarbonyl)-2-bromo-5-[(2,2-dimethylpropyl)amino]benzoic acid (synthesized according to reagent preparation 50 in step 5. $^1$H NMR (400 MHz, $d_6$-DMSO): 8.90 (d, 1H), 8.58 (t, 1H), 8.40 (d, 1H), 8.04 (m, 2H), 7.85 (s, 1H), 7.35 (s, 1H), 6.79 (d, 1H), 6.63 (s, 1H), 4.62 (br s, 2H), 3.89-3.84 (m, 1H), 3.17 (d, 1H), 2.90 (d, 1H), 2.84-2.77 (m, 1H), 2.34-2.28 (m, 2H), 2.14-1.87 (m, 6H), 0.99-0.92 (m, 13H); MS (EI) for $C_{29}H_{36}BrN_5O_3$: 582, 584 ($MH^+$).

(20Y): N-{8-[5-(cyclopropylcarbonyl)pyridin-2-yl]-8-azabicyclo[3.2.1]oct-3-endo-yl}-5-{[2-fluoro-1-(fluoromethyl)ethyl]amino}-2-methylbenzene-1,4-dicarboxamide. Prepared according to the method of example 20 by using 4-(aminocarbonyl)-5-{[2-fluoro-1-(fluoromethyl)ethyl]amino}-2-methylbenzoic acid (synthesized according to reagent preparation 42) in step 5. $^1$H NMR (400 MHz, $d_6$-DMSO): 8.90 (d, 1H), 8.37 (d, 1H), 8.28 (d, 1H), 8.04 (dd, 1H), 7.94 (s, 1H), 7.53 (s, 1H), 6.80 (d, 1H), 6.73 (s, 1H), 4.69-4.48 (m, 6H), 4.15-3.99 (m, 1H), 3.90-3.84 (m, 1H), 2.83-2.77 (m, 1H), 2.30-2.19 (m, 5H), 2.14-1.87 (m, 6H); MS (EI) for $C_{28}H_{33}F_2N_5O_3$: 526 ($MH^+$).

(20Z): N4-{8-[5-(cyclopropylcarbonyl)pyridin-2-yl]-8-azabicyclo[3.2.1]oct-3-endo-yl}-2-[(trans-4-piperidin-1-ylcyclohexyl)amino]benzene-1,4-dicarboxamide. Prepared according to the method of example 20 by using 4-(aminocarbonyl)-3-[(trans-4-(piperidin-1-ylcyclohexyl)amino]benzoic acid (synthesized according to reagent preparation 47) in step 5. $^1$H NMR (400 MHz, methanol-$d_4$): 8.78 (s, 1H), 8.28 (s, 1H), 8.24-8.20 (d, 1H), 7.69-7.65 (d, 1H), 7.13 (s, 1H), 7.00-6.91 (m, 1H), 4.77-4.70 (br. s, 2H), 4.10-4.02 (m, 1H), 3.54-3.44 (m, 4H), 3.27-3.24 (m, 1H), 3.09-3.01 (m, 1H), 2.76-2.69 (m, 1H), 2.37-2.26 (m, 4H), 2.26-2.14 (m, 2H), 2.14-2.04 (d, 2H), 2.03-1.96 (d, 2H), 1.88-1.66 (m, 4H), 1.58-1.47 (m, 2H), 1.44-1.32 (m, 4H), 1.17-1.10 (m, 4H), 1.09-1.03 (m, 2H); MS (EI) for $C_{35}H_{46}N_6O_3$: 599 ($MH^+$).

(20AA): N4-{8-[5-(cyclopropylcarbonyl)pyridin-2-yl]-8-azabicyclo[3.2.1]oct-3-endo-yl}-2-{[(1S)-1,2-dimethylpropyl]amino}benzene-1,4-dicarboxamide. Prepared according to the method of example 20 by using 4-(aminocarbonyl)-3-{[(1S)-1,2-dimethylpropyl]amino}benzoic acid (synthesized according to reagent preparation 39) in step 5. $^1$H NMR (400 MHz, $d_6$-DMSO): 8.90 (s, 1H), 8.40-8.34 (d, 1H), 8.23 (s, 1H), 8.07-8.02 (d, 1H), 7.96-7.89 (s, 1H), 7.70-7.63 (d, 1H), 7.31-7.24 (br. s, 1H), 6.97 (s, 1H), 6.85-6.78 (m, 2H), 4.72-4.53 (br. s, 2H), 3.88-3.81 (m, 1H), 3.52-3.43 (m, 1H), 2.85-2.77 (m, 1H), 2.31-2.19 (m, 4H), 2.12-1.92 (m, 6H), 1.91-1.82 (m, 1H), 1.12-1.05 (d, 3H), 0.99-0.92 (m, 5H), 0.91-0.85 (d, 2H); MS (EI) for $C_{29}H_{37}N_5O_3$: 504 ($MH^+$).

(20AB): N4-{8-[5-(cyclopropylcarbonyl)pyridin-2-yl]-8-azabicyclo[3.2.1]oct-3-endo-yl}-2-[(1-cyclopropylethyl)amino]benzene-1,4-dicarboxamide. Prepared according to the method of example 20 by using 4-(aminocarbonyl)-3-(1-cyclopropylethylamino)benzoic acid (synthesized according to reagent preparation 39) in step 5. $^1$H NMR (400 MHz, methanol-$d_4$): 8.84 (s, 1H), 8.14-8.09 (d, 1H), 7.65-7.60 (d, 1H), 7.08 (s, 1H), 6.92-6.86 (d, 1H), 6.81-6.75 (d, 1H), 4.76-4.64 (br. s, 2H), 4.05-3.98 (m, 1H), 3.28-3.20 (m, 1H), 2.77-2.68 (m, 1H), 2.33-2.15 (m, 6H), 2.05-1.96 (d, 2H), 1.30-1.26 (d, 3H), 1.14-1.07 (m, 2H), 1.06-0.95 (m, 3H), 0.55-0.45 (m, 2H), 0.37-0.22 (m, 2H); MS (EI) for $C_{29}H_{35}N_5O_3$: 502 ($MH^+$).

(20AC): N4-{8-[5-(cyclopropylcarbonyl)pyridin-2-yl]-8-azabicyclo[3.2.1]oct-3-endo-yl}-2-{[(1R)-1,2-dimethylpropyl]amino}benzene-1,4-dicarboxamide. Prepared according to the method of example 20 by using 4-(aminocarbonyl)-3-{[(1R)-1,2-dimethylpropyl]amino}benzoic acid (synthesized according to reagent preparation 39) in step 5. $^1$H NMR (400 MHz, methanol-$d_4$): 8.84 (s, 1H), 8.14-8.09 (d, 1H), 7.45 (s, 1H), 6.80-6.75 (d, 1H), 6.68 (d, 1H), 6.81-6.75 (d, 1H), 4.75-4.63 (br. s, 2H), 4.05-3.98 (m, 1H), 3.47-3.40 (m, 1H), 2.77-2.68 (m, 1H), 2.34-2.21 (m, 7H), 2.20-2.11 (m, 2H), 2.04-1.86 (m, 3), 1.17-1.12 (d, 3H), 1.11-1.08 (m, 2H), 1.06-1.02 (m, 2H), 1.01-0.98 (d, 3H), 0.96-0.92 (d, 2H); MS (EI) for $C_{30}H_{39}N_5O_3$: 518 ($MH^+$).

(20AD): N-{8-[5-(cyclopropylcarbonyl)pyridin-2-yl]-8-azabicyclo[3.2.1]oct-3-endo-yl}-2-methyl-5-{[2-methyl-1-(1-methylethyl)propyl]amino}benzene-1,4-dicarboxamide. Prepared according to the method of example 20 by using 4-(aminocarbonyl)-2-methyl-5-{[2-methyl-1-(1-methylethyl)propyl]amino}benzoic acid (synthesized according to reagent preparation 42) in step 5. $^1$H NMR (400 MHz, methanol-$d_4$): 8.84 (s, 1H), 8.15-8.07 (d, 1H), 7.45 (s, 1H), 6.82-6.73 (m, 2H), 4.75-4.63 (br. s, 2H), 4.05-3.98 (m, 1H), 3.38-3.34 (m, 3H), 3.12-3.05 (m, 1H), 2.74-2.67 (m, 1H), 2.35-2.11 (m, 6H), 2.04-1.86 (m, 2), 1.14-1.00 (m, 7H), 0.99-0.85 (m, 12H); MS (EI) for $C_{32}H_{45}N_5O_3$: 546 ($MH^+$).

(20AE): N-{8-[5-(cyclopropylcarbonyl)pyridin-2-yl]-8-azabicyclo[3.2.1]oct-3-endo-yl}-5-[(dicyclopropylmethyl)amino]-2-methylbenzene-1,4-dicarboxamide. Prepared according to the method of example 20 by using 4-(aminocarbonyl)-5-(dicyclopropylmethylamino)-2-methylbenzoic acid (synthesized according to reagent preparation 42) in step 5. $^1$H NMR (400 MHz, $d_6$-DMSO): 8.90 (s, 1H), 8.31-8.26 (d, 1H), 8.09-7.95 (m, 2H), 7.84 (s, 1H), 7.48 (s, 1H), 7.19 (s, 1H), 6.82-6.76 (d, 1H), 6.57 (s, 1H), 5.54-5.44 (m, 1H), 5.13-5.03 (m, 1H), 4.73-4.53 (m, 2H), 3.89-3.81 (m, 1H), 3.14-3.08 (m, 1H), 2.85-2.77 (m, 1H), 2.31-2.23 (m, 4H), 2.19 (s, 3H), 2.13-1.98 (m, 6H), 1.96-1.88 (m, 2H), 1.40-1.31 (m, 1H), 0.99-0.92 (m, 4H), 0.66-0.59 (m, 2H), 0.35-0.28 (m, 2H); MS (EI) for $C_{32}H_{39}N_5O_3$: 542 ($MH^+$).

(20AF): 2-bromo-N-{8-[5-(cyclopropylcarbonyl)pyridin-2-yl]-8-azabicyclo[3.2.1]oct-3-endo-yl}-5-[(3,3,3-trifluoropropyl)amino]benzene-1,4-dicarboxamide. Prepared according to the method of example 20 by using 4-(aminocarbonyl)-2-bromo-5-(3,3,3-trifluoropropylamino)benzoic acid (synthesized according to reagent preparation 50) in step 5. $^1$H NMR (400 MHz, methanol-$d_4$): 8.84 (s, 1H), 8.15-8.07 (d, 1H), 7.84 (s, 1H), 6.82-6.75 (d, 2H), 6.73 (s, 1H), 4.74-4.61 (br. s, 2H), 4.08-4.00 (m, 1H), 3.53-3.46 (m, 2H), 2.76-2.68 (m, 1H), 2.61-2.47 (m, 2H), 2.37-2.25 (m, 4H), 2.17-2.07 (m, 2H), 2.03-1.94 (d, 2H), 1.14-1.07 (m, 2H), 1.06-0.99 (m, 2H); MS (EI) for $C_{27}H_{29}BrN_5O_3$: 609 ($MH^+$).

(20AG): 2-bromo-5-(cyclobutylamino)-N-{8-[5-(cyclopropylcarbonyl)pyridin-2-yl]-8-azabicyclo[3.2.1]oct-3-endo-yl}benzene-1,4-dicarboxamide. Prepared according to the method of example 20 by using 4-(aminocarbonyl)-2-bromo-5-(cyclobutylamino)benzoic acid (synthesized according to reagent preparation 50) in step 5. $^1$H NMR (400 MHz, $d_6$-DMSO): 8.90 (s, 1H), 8.46-8.43 (d, 1H), 8.40-8.36 (d, 1H), 8.07-8.02 (d, 2H), 7.85 (s, 1H), 7.42-7.37 (br. s, 1H), 6.82-6.77 (d, 1H), 6.47 (s, 1H), 4.72-4.54 (br. s, 2H), 3.95-3.83 (m, 2H), 2.84-2.76 (m, 1H), 2.43-2.26 (m, 4H), 2.13-2.04 (m, 2H), 2.03-1.96 (m, 2H), 1.93-1.87 (d, 2H), 1.85-1.71 (m, 4H), 1.00-0.91 (m, 4H); MS (EI) for $C_{28}H_{32}BrN_5O_3$: 567 ($MH^+$).

(20AH): N-{8-[5-(cyclopropylcarbonyl)pyridin-2-yl]-8-azabicyclo[3.2.1]oct-3-endo-yl}-2-methyl-5-{[(1R)-1,2,2-trimethylpropyl]amino}benzene-1,4-dicarboxamide. Prepared according to the method of example 20 by using 4-(aminocarbonyl)-2-methyl-5-{[(1R)-1,2,2-trimethylpropyl]amino}benzoic acid (synthesized according to reagent preparation 41) in step 5. $^1$H NMR (400 MHz, DMSO-$d_6$): 8.90 (d, 1H), 8.32 (s, 1H), 8.30 (t, 1H), 8.04 (dd, 1H), 7.85 (s, 1H), 7.48 (s, 1H), 7.16 (s, 1H), 6.80 (d, 1H), 6.61 (s, 1H), 4.63 (br s, 1H), 3.82-3.88 (m, 1H), 3.35 (s, 3H), 3.22-3.28 (m, 1H), 2.77-2.84 (m, 1H), 2.28 (d, 2H), 2.19 (t, 3H), 2.00-2.10 (m, 4H), 1.90-1.95 (m, 2H), 1.05 (d, 3H), 0.94 (s, 12H); MS (EI) for $C_{31}H_{41}N_5O_3$: 532 ($MH^+$).

(20AI): 2-bromo-N-{8-[5-(cyclopropylcarbonyl)pyridin-2-yl]-8-azabicyclo[3.2.1]oct-3-endo-yl}-5-[(1-methylethyl)amino]benzene-1,4-dicarboxamide. Prepared according to the method of example 20 by using 4-(aminocarbonyl)-2-bromo-5-[(1-methylethyl)amino]benzoic acid (synthesized according to reagent preparation 50) in step 5. $^1$H NMR (400 MHz, DMSO-$d_6$): 8.90 (d, 1H), 8.44 (d, 1H), 8.19 (d, 1H), 8.04 (dd, 2H), 7.83 (s, 1H), 7.35 (s, 1H), 6.79 (d, 1H), 6.61 (s, 1H), 3.85-3.88 (m, 1H), 3.60-3.64 (m, 2H), 2.78-2.82 (m, 1H), 2.31 (d, 2H), 1.88-2.11 (m, 6H), 1.12-1.18 (m, 7H), 0.93-0.97 (m, 4H); MS (EI) for $C_{27}H_{32}BrN_5O_3$: 555 (MH$^+$).

(20AJ): 2-bromo-N-{8-[5-(cyclopropylcarbonyl)pyridin-2-yl]-8-azabicyclo[3.2.1]oct-3-endo-yl}-5-[(1-ethylpropyl)amino]benzene-1,4-dicarboxamide. Prepared according to the method of example 20 by using 4-(aminocarbonyl)-2-bromo-5-[(1-ethylpropyl)amino]benzoic acid (synthesized according to reagent preparation 50) in step 5. $^1$H NMR (400 MHz, DMSO-$d_6$): 8.89 (d, 1H), 8.45 (d, 1H), 8.31 (d, 1H), 8.04 (dd, 2H), 7.83 (s, 1H), 7.33 (broad s, 1H), 6.79 (d, 1H), 6.60 (s, 1H), 4.60 (broad s, 2H), 3.85 (m, 1H), 3.28 (m, 1H), 2.80 (m, 1H), 2.30 (m, 2H), 2.10 (m, 2H), 1.99 (m, 2H), 1.93 (d, 2H), 1.50 (m, 4H), 0.95 (m, 4H), 0.89 (t, 6H); MS (EI) for $C_{29}H_{36}N_5O_3Br$: 584 (MH$^+$).

(20AK): 2-bromo-N-{8-[5-(cyclopropylcarbonyl)pyridin-2-yl]-8-azabicyclo[3.2.1]oct-3-endo-yl}-5-{[(1R)-1-methylpropyl]amino}benzene-1,4-dicarboxamide. Prepared according to the method of example 20 by using 4-(aminocarbonyl)-2-bromo-5-{[(1R)-1-methylpropyl]amino}benzoic acid (synthesized according to reagent preparation 50) in step 5. $^1$H NMR (400 MHz, DMSO-$d_6$): 8.90 (d, 1H), 8.44 (d, 1H), 8.26 (d, 1H), 8.04 (dd, 2H), 7.83 (s, 1H), 7.34 (broad s, 1H), 6.79 (d, 1H), 6.60 (s, 1H), 4.60 (broad s, 2H), 3.87 (m, 1H), 3.45 (m, 1H), 2.81 (m, 1H), 2.32 (m, 2H), 2.10 (m, 2H), 1.99 (m, 2H), 1.93 (d, 2H), 1.50 (m, 2H), 1.12 (d, 3H), 0.89 (m, 7H); MS (EI) for $C_{28}H_{34}N_5O_3$: 570 (MH$^+$).

(20AL): 2-bromo-N-{8-[5-(cyclopropylcarbonyl)pyridin-2-yl]-8-azabicyclo[3.2.1]oct-3-endo-yl}-5-{[(1R)-1,2-dimethylpropyl]amino}benzene-1,4-dicarboxamide. Prepared according to the method of example 20 by using 4-(aminocarbonyl)-2-bromo-5-{[(1R)-1,2-dimethylpropyl]amino}benzoic acid (synthesized according to reagent preparation 50) in step 5. $^1$H NMR (400 MHz, DMSO-$d_6$): 8.85 (d, 1H), 8.42 (m, 2H), 8.06 (d, 1H), 8.02 (d, 1H), 7.83 (s, 1H), 7.31 (bs, 1H), 6.78 (d, 1H), 6.62 (s, 1H), 4.62 (bs, 2H), 3.86 (m, 1H), 3.40 (m, 1H), 2.81 (m, 1H), 2.32 (m, 2H), 2.08 (m, 2H), 1.98 (m, 2H), 1.90 (m, 2H), 1.83 (m, 1H), 1.06 (d, 3H), 0.94 (m, 7H), 0.87 (m, 3H); MS (EI) for $C_{29}H_{36}BrN_5O_3$: 584 (MH$^+$).

(20AM): N-{8-[5-(cyclopropylcarbonyl)pyridin-2-yl]-8-azabicyclo[3.2.1]oct-3-endo-yl}-5-[(1-ethylpropyl)amino]-2-methylbenzene-1,4-dicarboxamide. Prepared according to the method of example 20 by using 4-aminocarbonyl-2-methyl-5-[(1-ethylpropyl)amino]benzoic acid (synthesized according to reagent preparation 42) in step 5. $^1$H NMR (400 MHz, DMSO-$d_6$): 8.89 (d, 1H), 8.31 (d, 1H), 8.07-8.02 (m, 2H), 7.85 (br s, 1H), 7.48 (s, 1H), 7.17 (br s, 1H), 6.79 (d, 1H), 6.57 (s, 1H), 4.62 (br s, 2H), 3.88-3.82 (m, 1H), 3.27-3.18 (m, 1H), 2.84-2.76 (m, 1H), 2.32-2.23 (m, 2H), 2.18 (s, 3H), 2.13-1.88 (m, 6H), 1.62-1.41 (m, 4H), 0.99-0.92 (m, 4H), 0.88 (t, 6H); MS (EI) for $C_{30}H_{39}N_5O_3$: 518 (MH$^+$).

(20AN): N4-{8-[5-(cyclopropylcarbonyl)pyridin-2-yl]-8-azabicyclo[3.2.1]oct-3-endo-yl}-2-[(2,2,3,3,3-pentafluoropropyl)amino]benzene-1,4-dicarboxamide. Prepared as the hydrochloride salt according to the method of example 20 by using 4-(aminocarbonyl)-3-(2,2,3,3,3-pentafluoropropylamino)benzoic acid (synthesized according to reagent preparation 39) in step 5. $^1$H NMR (400 MHz, methanol-$d_4$): 8.65 (br s, 1H), 8.41-8.34 (m, 2H), 7.72 (d, 1H), 7.28 (br s., 1H), 7.25 (br s, 1H), 7.10 (dd, 1H), 4.78 (br s, 2H), 4.19-4.08 (m, 3H), 2.78-2.70 (m, 1H), 2.44-2.16 (m, 8H), 1.20-1.08 (m, 4H); MS (EI) for $C_{27}H_{28}F_5N_5O_3$: 566 (MH$^+$).

(20AO): N-{8-[5-(cyclopropylcarbonyl)pyridin-2-yl]-8-azabicyclo[3.2.1]oct-3-endo-yl}-5-[(1-ethylpropyl)amino]-2-fluorobenzene-1,4-dicarboxamide. Prepared according to the method of example 20 by using 4-aminocarbonyl-2-fluoro-5-[(1-ethylpropyl)amino]benzoic acid (synthesized according to reagent preparation 45) in step 5. $^1$H NMR (400 MHz, DMSO-$d_6$): 8.89 (d, 1H), 8.37 (d, 1H), 8.07-8.01 (m, 2H), 7.98 (br s, 1H), 7.56 (d, 1H), 7.40 (br s, 1H), 6.80 (d, 1H), 6.72 (d, 1H), 4.63 (br s, 2H), 3.93-3.86 (m, 1H), 3.29-3.20 (m, 1H), 2.84-2.76 (m, 1H), 2.30-2.21 (m, 2H), 2.12-1.86 (m, 6H), 1.61-1.37 (m, 4H), 0.99-0.91 (m, 4H), 0.87 (t, 6H); MS (EI) for $C_{29}H_{36}FN_5O_3$: 522 (MH$^+$).

(20AP): 5-amino-N-{8-[5-(cyclopropylcarbonyl)pyridin-2-yl]-8-azabicyclo[3.2.1]oct-3-endo-yl}-2-methylbenzene-1,4-dicarboxamide. Prepared according to the method of example 20 by using 5-amino-4-(aminocarbonyl)-2-methylbenzoic acid (synthesized according to reagent preparation 43) in step 5. $^1$H NMR (400 MHz, DMSO-$d_6$): 8.87 (d, 1H), 8.28 (d, 1H), 8.07 (dd, 1H), 7.79 (br s, 1H), 7.43 (s, 1H), 7.16 (br s, 1H), 6.85 (d, 1H), 6.67 (s, 1H), 4.65 (br s, 2H), 3.88-3.81 (m, 1H), 2.85-2.77 (m, 1H), 2.29-2.22 (m, 2H), 2.17 (s, 3H), 2.14-1.86 (m, 6H), 0.99-0.93 (m, 4H); MS (EI) for $C_{25}H_{29}N_5O_3$: 448 (MH$^+$).

(20AQ): N-{8-[5-(cyclopropylcarbonyl)pyridin-2-yl]-8-azabicyclo[3.2.1]oct-3-endo-yl}-2-methyl-5-{[(1S)-1-methylpropyl]amino}benzene-1,4-dicarboxamide. Prepared according to the method of example 20 by using 4-(aminocarbonyl)-2-methyl-3-{[(1S)-1-methylpropyl]amino}benzoic acid (synthesized according to reagent preparation 41) in step 5. $^1$H NMR (400 MHz, methanol-$d_4$): 8.85 (d, 1H), 8.12 (dd, 1H), 7.45 (s, 1H), 6.78 (d, 1H), 6.69 (s, 1H), 4.69 (br s, 2H), 4.02 (t, 1H), 3.51-3.43 (m, 1H), 2.76-2.70 (m, 1H), 2.33-2.25 (m, 7H), 2.19-2.14 (m, 2H), 2.01-1.95 (m, 3H), 1.69-1.62 (m, 1H), 1.59-1.52 (m, 1H), 1.22 (d, 3H), 1.13-1.09 (m, 2H), 1.06-1.02 (m, 2H), 0.98 (t, 3H); MS (EI) for $C_{29}H_{37}N_5O_3$: 504 (MH$^+$).

(20AR): N-{8-[5-(cyclopropylcarbonyl)pyridin-2-yl]-8-azabicyclo[3.2.1]oct-3-endo-yl}-5-[(1-cyclopropylethyl)amino]-2-methylbenzene-1,4-dicarboxamide. Prepared according to the method of example 20 by using 4-(aminocarbonyl)-5-(1-cyclopropylethylamino)-2-methylbenzoic acid (synthesized according to reagent preparation 41) in step 5. $^1$H NMR (400 MHz, methanol-$d_4$): 8.85 (d, 1H), 8.12 (dd, 1H), 7.45 (s, 1H), 6.79 (d, 1H), 6.69 (s, 1H), 4.69 (brs, 2H), 4.02 (t, 1H), 3.20-3.13 (m, 1H), 2.77-2.70 (m, 1H), 2.33-2.13 (m, 9H), 2.01-1.95 (m, 3H), 1.27 (d, 3H), 1.12-0.95 (m, 5H), 0.52-0.47 (m, 2H), 0.33-0.24 (m, 2H); MS (EI) for $C_{30}H_{37}N_5O_3$: 515 (MH$^+$).

(20AS): 2-bromo-5-(cyclopentylamino)-N-{8-[5-(cyclopropylcarbonyl)pyridin-2-yl]-8-azabicyclo[3.2.1]oct-3-endo-yl}benzene-1,4-dicarboxamide. Prepared according to the method of example 20 by using 4-(aminocarbonyl)-2-bromo-5-(cyclopentylamino)benzoic acid (synthesized according to reagent preparation 50) in step 5. $^1$H NMR (DMSO-$d_6$): 8.89 (s, 1H), 8.44 (d, 1H), 8.33 (d, 1H), 8.06-8.05 (m, 2H), 7.83 (s, 1H), 7.34 (s, 1H), 6.79 (s, 1H), 6.63 (s, 1H), 4.63 (s, 2H), 3.88 (s, 1H), 3.88-3.77 (m, 1H), 2.95-2.93 (m, 1H), 2.41 (d, 2H), 2.21-1.98 (m, 8H), 1.66-1.59 (m, 4H), 1.46-1.41 (m, 2H), 0.95-0.93 (m, 4H); MS (EI) for $C_{29}H_{34}BrN_5O_3$: 581 (MH$^+$).

(20AT): N-{8-[5-(cyclopropylcarbonyl)pyridin-2-yl]-8-azabicyclo[3.2.1]oct-3-endo-yl}-2-methyl-5-(propylamino)benzene-1,4-dicarboxamide. Prepared according to the method of example 20 by using 4-(aminocarbonyl)-2-methyl-5-(propylamino)benzoic acid (synthesized according to reagent preparation 41) in step 5. $^1$H NMR (DMSO-$d_6$): 8.89 (s, 1H), 8.30 (d, 1H), 8.07 (t, 2H), 7.87 (s, 1H), 7.49 (s, 1H), 7.21 (s, 1H), 6.82 (d, 1H), 6.58 (s, 1H), 4.64 (s, 2H), 3.86-3.85 (m, 1H), 3.09 (t, 2H), 2.83-2.82 (m, 1H), 2.20-2.18 (m, 2H), 2.16 (s, 3H), 2.09-1.94 (m, 6H), 1.62-1.57 (m, 2H), 0.98-0.91 (m, 7H); MS (EI) for $C_{28}H_{35}N_5O_3$: 490 ($MH^+$).

(20AU): N-{8-[5-(cyclopropylcarbonyl)pyridin-2-yl]-8-azabicyclo[3.2.1]oct-3-endo-yl}-5-[(1-ethylpropyl)amino]-2-(trifluoromethyl)benzene-1,4-dicarboxamide. Prepared according to the method of example 20 by using 4-(aminocarbonyl)-5-[(1-ethylpropyl)amino]-2-(trifluoro-methyl)benzoic acid (synthesized according to reagent preparation 51) in step 5. $^1$H NMR (400 MHz, $d_6$-DMSO): 8.90 (d, 1H), 8.82 (d, 1H), 8.50 (d, 1H), 8.20 (br s, 1H), 8.04 (dd, 1H), 7.96 (d, 1H), 7.40 (br s, 1H), 6.79 (d, 1H), 6.64 (s, 1H), 4.63 (br s, 2H), 3.89-3.81 (m, 1H), 3.45-3.33 (m, 1H), 2.84-2.76 (m, 1H), 2.30-2.20 (m, 2H), 2.14-1.92 (m, 4H), 1.88 (d, 2H), 1.66-1.43 (m, 4H), 0.99-0.92 (m, 4H), 0.89 (t, 6H); MS (EI) for $C_{30}H_{36}F_3N_5O_3$: 572 ($MH^+$).

(20AV): N-{8-[5-(cyclopropylcarbonyl)pyridin-2-yl]-8-azabicyclo[3.2.1]oct-3-endo-yl}-2-methyl-5-[(3,3,3-trifluoropropyl)amino]benzene-1,4-dicarboxamide. Prepared according to the method of example 20 by using 4-(aminocarbonyl)-2-methyl-5-(3,3,3-trifluoropropylamino)benzoic acid (synthesized according to reagent preparation 41) in step 5. $^1$H NMR (400 MHz, $d_6$-DMSO): 8.90 (d, 1H), 8.32 (d, 1H), 8.16 (t, 1H), 8.04 (dd, 1H), 7.89 (br s, 1H), 7.52 (s, 1H), 7.26 (br s, 1H), 6.80 (d, 1H), 6.60 (s, 1H), 4.62 (br s, 2H), 3.91-3.83 (m, 1H), 3.43 (q, 2H), 2.85-2.76 (m, 1H), 2.69-2.53 (m, 2H), 2.32-2.23 (m, 2H), 2.21 (s, 3H), 2.15-1.96 (m, 4H), 1.91 (d, 2H), 1.00-0.91 (m, 4H); MS (EI) for $C_{28}H_{32}F_3N_5O_3$: 544 ($MH^+$).

(20AW): N-{8-[5-(cyclopropylcarbonyl)pyridin-2-yl]-8-azabicyclo[3.2.1]oct-3-endo-yl}-5-{[(1R)-1-methylpropyl]amino}-2-(trifluoromethyl)benzene-1,4-dicarboxamide. Prepared according to the method of example 20 by using 4-(aminocarbonyl)-5-{[(1R)-1-methylpropyl]amino}-2-(trifluoromethyl)benzoic acid (synthesized according to reagent preparation 52) in step 5. $^1$H NMR (400 MHz, $d_6$-DMSO): 8.90 (d, 1H), 8.78 (d, 1H), 8.49 (d, 1H), 8.19 (br s, 1H), 8.04 (dd, 1H), 7.96 (s, 1H), 7.41 (br s, 1H), 6.80 (d, 1H), 6.65 (s, 1H), 4.63 (br s, 2H), 3.89-3.82 (m, 1H), 3.58-3.49 (m, 1H), 2.85-2.76 (m, 1H), 2.28-2.20 (m, 2H), 2.14-2.03 (m, 2H), 2.03-1.95 (m, 2H), 1.88 (d, 2H), 1.63-1.47 (m, 2H), 1.17 (d, 3H), 0.99-0.88 (m, 7H); MS (EI) for $C_{29}H_{34}F_3N_5O_3$: 558 ($MH^+$).

(20AX): N-{8-[5-(cyclopropylcarbonyl)pyridin-2-yl]-8-azabicyclo[3.2.1]oct-3-endo-yl}-5-[(1-ethyl-2-methylpropyl)amino]-2-methylbenzene-1,4-dicarboxamide. Prepared according to the method of example 20 by using 4-(aminocarbonyl)-5-[(1-ethyl-2-methylpropyl)amino]-2-methylbenzoic acid (synthesized according to reagent preparation 42) in step 5. $^1$H NMR (400 MHz, $CDCl_3$ w/20% methanol-$d_4$): 8.87 (d, 1H), 8.09 (dd, 1H), 7.34 (s, 1H), 7.21 (m, 1H) 6.66 (d, 1H), 6.62 (d, 1H), 4.67 (br s, 2H), 4.15 (m, 1H), 3.16 (m, 1H), 2.61 (m, 1H), 2.40-2.10 (br m, 8H), 1.92 (br d, 2H), 1.63 (m, 1H), 1.45 (m, 1H), 1.21 (m, 2H), 1.06 (m, 2H), 0.95 (m, 9H); MS (EI) for $C_{31}H_{41}N_5O_3$: 554 (M+Na).

(20AY): N-{8-[5-(cyclopropylcarbonyl)pyridin-2-yl]-8-azabicyclo[3.2.1]oct-3-endo-yl}-5-[(1-cyclopropylpropyl)amino]-2-methylbenzene-1,4-dicarboxamide. Prepared according to the method of example 20 by using 4-(aminocarbonyl)-5-[(1-cyclopropylpropyl)amino]-2-methylbenzoic acid (synthesized according to reagent preparation 42) in step 5. $^1$H NMR (400 MHz, $d_6$-DMSO): 8.89 (d, 1H), 8.28 (d, 1H), 8.04 (m, 2H), 7.83 (br s, 1H), 7.47 (s, 1H), 7.30 (br s, 1H), 6.80 d, 1H), 6.56 (s, 1H), 4.63 (br s, 2H), 3.88 (s, 1H), 2.94 (m, 1H), 2.81 (m, 1H), 22.228 (d, 2), 2.13-1.97 (br m, 4H), 1.92 (br d, 2H), 1.60 (m, 2H), 0.98-0.85 (br m, 5H), 0.44-0.35 (br m, 2H), 0.20 (m, 2H); MS (EI) for $C_{31}H_{39}N_5O_3$: 530 ($MH^+$).

(20AZ): N-{8-[5-(cyclopropylcarbonyl)pyridin-2-yl]-8-azabicyclo[3.2.1]oct-3-endo-yl}-2-methyl-5-[(3S)-tetrahydrofuran-3-ylamino]benzene-1,4-dicarboxamide. Prepared as the hydrochloride salt according to the method of example 20 by using 4-(aminocarbonyl)-2-methyl-5-[(3S)-tetrahydrofuran-3-ylamino]benzoic acid (synthesized according to reagent preparation 41) in step 5. $^1$H NMR of Free Base (400 MHz, $d_6$-DMSO): 8.89 (d, 1H), 8.30 (d, 1H), 8.15 (d, 1H), 8.04 (dd, 1H), 7.90 (br s, 1H), 7.51 (s, 1H), 7.25 (br s, 1H), 6.80 (d, 1H), 6.57 (s, 1H), 4.63 (br s, 2H), 4.09-4.02 (m, 1H), 3.89-3.71 (m, 4H), 3.58 (dd, 1H), 2.84-2.77 (m, 1H), 2.30-2.15 (m, 6H), 2.12-1.98 (m, 4H), 1.96-1.88 (m, 2H), 1.83-1.74 (m, 1H), 0.99-0.91 (m, 4H); MS (EI) for $C_{29}H_{35}N_5O_4$: 518 ($MH^+$).

(20BA): N4-{8-[5-(cyclopropylcarbonyl)pyridin-2-yl]-8-azabicyclo[3.2.1]oct-3-endo-yl}-2-(propylamino)benzene-1,4-dicarboxamide. Prepared as the hydrochloride salt according to the method of example 20 by using 4-(aminocarbonyl)-3-(propylamino)benzoic acid (synthesized according to reagent preparation 39) in step 5. $^1$H NMR (400 MHz, $d_6$-DMSO): 8.83 (d, 1H), 8.24 (d, 1H), 8.12 (dd, 1H), 7.94 (br s, 1H), 7.68 (d, 1H), 7.31 (br s, 1H), 6.98 (d, 1H), 6.95 (br s, 2H), 6.88 (dd, 1H), 4.71 (br s, 2H), 3.90-3.84 (m, 1H), 3.13 (s, 1H), 2.88-2.80 (m, 2H), 2.30-2.23 (m, 2H), 2.12-1.99 (m, 6H), 1.66-1.56 (m, 2H), 1.00-0.93 (m, 2H); MS (EI) for $C_{27}H_{33}N_5O_3$: 476 ($MH^+$).

(20BB): 5-amino-N-{8-[5-(cyclopropylcarbonyl)pyridin-2-yl]-8-azabicyclo[3.2.1]oct-3-endo-yl}-2-methylbenzene-1,4-dicarboxamide. Prepared according to the method of example 20 by using 5-amino-4-(aminocarbonyl)-2-methylbenzoic acid (synthesized according to reagent preparation 48) in step 5. $^1$H NMR (400 MHz, $d_6$-DMSO): 8.89 (d, 1H), 8.32 (d, 1H), 8.04 (dd, 1H), 7.75 (br s, 1H), 7.40 (s, 1H), 7.11 (br s, 1H), 7.79 (d, 1H), 6.64 (s, 1H), 6.52 (s, 2H), 4.63 (br s, 2H), 3.87-3.80 (m, 1H), 2.84-2.76 (m, 1H), 2.16 (s, 3H), 2.12-1.97 (m, 4H), 1.93-1.85 (m, 2H), 0.98-0.89 (m, 4H); MS (EI) for $C_{24}H_{29}N_5O_3$: 448 ($MH^+$).

(20BC): N-{8-[5-(cyclopropylcarbonyl)pyridin-2-yl]-8-azabicyclo[3.2.1]oct-3-endo-yl}-2-methyl-5-[(1-methylethyl)amino]benzene-1,4-dicarboxamide. Prepared according to the method of example 20 by using 4-(aminocarbonyl)-5-[(1-methylethyl)amino]-2-methylbenzoic acid (synthesized according to reagent preparation 42) in step 5. $^1$H NMR (400 MHz, $d_6$-DMSO): 8.90 (d, 1H), 8.29 (d, 1H), 8.04 (dd, 1H), 7.92 (d, 1H), 7.84 (br s, 1H), 7.48 (s, 1H), 7.18 (br s, 1H), 6.80 (d, 1H), 6.59 (s, 1H), 4.63 (br s, 2H), 3.89-3.82 (m, 1H), 3.64-3.56 (m, 1H), 2.84-2.76 (m, 1H), 2.30-2.23 (m, 2H), 2.19 (s, 3H), 2.12-1.98 (m, 4H), 1.98-1.89 (m, 2H), 1.18 (s, 1H), 1.17 (s, 1H), 1.00-0.91 (m, 4H); MS (EI) for $C_{28}H_{35}N_5O_3$: 490 ($MH^+$).

(20BD): 5-(cyclopentylamino)-N-{8-[5-(cyclopropylcarbonyl)pyridin-2-yl]-8-azabicyclo[3.2.1]oct-3-endo-yl}-2-methylbenzene-1,4-dicarboxamide. Prepared according to the method of example 20 by using 4-(aminocarbonyl)-5-(cyclopentylamino)-2-methylbenzoic acid (synthesized according to reagent preparation 42) in step 5. $^1$H NMR (400 MHz, $d_6$-DMSO): 8.89 (d, 1H), 8.29 (d, 1H), 8.05-8.02 (m, 2H), 7.85 (br s, 1H), 7.48 (s, 1H), 7.18 (br s, 1H), 6.79 (d, 1H), 6.62 (s, 1H), 4.63 (br s, 2H), 3.88-3.83 (m, 1H), 3.78-3.71 (m, 1H), 2.84-2.24 (m, 1H), 2.32-2.24 (m, 2H), 2.19 (s, 3H), 2.11-1.90 (m, 8H), 1.73-1.53 (m, 4H), 1.50-1.41 (m, 2H), 0.99-0.92 (m, 4H); MS (EI) for $C_{30}H_{37}N_5O_3$: 516 ($MH^+$).

(20BE): N-{8-[5-(cyclopropylcarbonyl)pyridin-2-yl]-8-azabicyclo[3.2.1]oct-3-endo-yl}-5-[(2,2-dimethylpropyl)amino]-2-methylbenzene-1,4-dicarboxamide. Prepared according to the method of example 20 by using 4-(aminocarbonyl)-5-[(2,2-dimethylpropyl)amino]-2-methylbenzoic acid (synthesized according to reagent preparation 42) in step 5. $^1$H NMR (400 MHz, $d_6$-DMSO): 8.89 (d, 1H), 8.29 (t, 1H), 8.24 (d, 1H), 8.04 (dd, 1H), 7.87 (br s, 1H), 7.49 (s, 1H), 7.18 (br s, 1H), 6.79 (d, 1H), 6.59 (s, 1H), 4.63 (br s, 2H), 3.88-3.82 (m, 1H), 2.89 (d, 2H), 2.84-2.77 (m, 1H), 2.29-2.22 (m, 2H), 2.18 (s, 3H), 2.14-1.97 (m, 4H), 1.95-1.88 (m, 2H), 1.98-0.90 (m, 13H); MS (EI) for $C_{30}H_{39}N_5O_3$: 518 ($MH^+$).

(20BF): N-{8-[5-(cyclopropylcarbonyl)pyridin-2-yl]-8-azabicyclo[3.2.1]oct-3-endo-yl}-5-[(cyclopropylmethyl)amino]-2-methylbenzene-1,4-dicarboxamide. Prepared according to the method of example 20 by using 4-(aminocarbonyl)-5-(cyclopropylmethylamino)-2-methylbenzoic acid (synthesized according to reagent preparation 42) in step 5. $^1$H NMR (400 MHz, $d_6$-DMSO): 8.89 (d, 1H), 8.24 (d, 1H), 8.05-8.03 (m, 2H), 7.85 (br s, 1H), 7.48 (s, 1H), 7.19 (br s, 1H), 6.78 (d, 1H), 6.57 (s, 1H), 4.63 (br s, 2H), 3.88-3.82 (m, 1H), 2.89 (t, 2H), 2.84-2.74 (m, 1H), 2.28-2.21 (m, 2H), 2.19 (s, 3H), 2.13-1.98 (m, 4H), 1.95-1.87 (m, 2H), 1.15-1.06 (m, 1H), 0.98-0.90 (m, 4H), 0.52-0.46 (m, 4H), 0.24-0.19 (m, 2H); MS (EI) for $C_{29}H_{35}N_5O_3$: 502 ($MH^+$).

(20BG): N-{8-[5-(cyclopropylcarbonyl)pyridin-2-yl]-8-azabicyclo[3.2.1]oct-3-endo-yl}-5-[(2,2-difluoro-1-methylethyl)amino]-2-methylbenzene-1,4-dicarboxamide. Prepared according to the method of example 20 by using 4-(aminocarbonyl)-5-[(2,2-difluoro-1-methylethyl)amino]-2-methylbenzoic acid (synthesized according to reagent preparation 42) in step 5. $^1$H-NMR (400 MHz, DMSO-$d_6$): 8.90 (s, 1H), 8.24 (m, 2H), 8.06 (m, 1H), 7.94 (s, 1H), 7.52 (s, 1H), 7.30 (s, 1H), 6.81 (d, 1H), 6.73 (s, 1H), 6.11 (t, 1H), 4.63 (bs, 2H), 4.01 (m, 1H), 3.86 (s, 1H), 2.79 (m, 1H), 2.25 (m, 1H), 2.20 (s, 3H), 2.08 (m, 2H), 2.00 (m, 2H), 1.92 (m, 2H), 1.21 (m, 3H), 0.96 (m, 5H); MS (EI) for $C_{28}H_{33}F_2N_5O_3$: 526.3 ($MH^+$).

(20BH): 2-bromo-N-{8-[5-(cyclopropylcarbonyl)pyridin-2-yl]-8-azabicyclo[3.2.1]oct-3-endo-yl}-5-[(1,1-dimethylethyl)amino]benzene-1,4-dicarboxamide. Prepared according to the method of example 20 by using 4-(aminocarbonyl)-2-bromo-5-[(1,1-dimethylethyl)amino]benzoic acid (synthesized according to reagent preparation 50) in step 5. $^1$H-NMR (400 MHz, DMSO-$d_6$): 8.90 (d, 1H), 8.52 (d, 1H), 8.48 (s, 1H), 8.03-8.06 (m, 2H), 7.82 (s, 1H), 7.36 (s, 1H), 6.78-6.80 (m, 2H), 4.63 (broad s, 2H), 3.82-3.85 (m, 1H), 3.34 (s, 3H), 2.77-2.83 (m, 1H), 2.31 (d, 2H), 1.92-2.09 (m, 6H), 1.35 (s, 9H), 0.94-0.97 (m, 3H). MS (EI) for $C_{28}H_{34}BrN_5O_3$: 569 ($MH^+$).

(20BI): 5-amino-2-bromo-N-{8-[5-(cyclopropylcarbonyl)pyridin-2-yl]-8-azabicyclo[3.2.1]oct-3-endo-yl}benzene-1,4-dicarboxamide. Prepared according to the method of example 20 by using 5-amino-4-(aminocarbonyl)-2-bromobenzoic acid (synthesized according to reagent preparation 50) in step 5. $^1$H NMR (400 MHz, DMSO-$d_6$): 8.85 (d, 1H), 8.42 (d, 1H), 8.04 (dd, 1H), 7.79 (s, 1H), 7.26 (bs, 1H), 6.85 (bs, 2H), 6.79 (d, 1H), 6.69 (s, 1H), 4.62 (bs, 2H), 3.86 (m, 1H), 2.82 (m, 1H) 2.30 (m, 2H), 2.10 (m, 2H), 2.00 (m 2H), 1.88 (m, 2H), 0.96 (m, 4H). MS (EI) for $C_{24}H_{26}BrN_5O_3$: 514 ($MH^+$).

(20BJ): 2-bromo-N-{8-[5-(cyclopropylcarbonyl)pyridin-2-yl]-8-azabicyclo[3.2.1]oct-3-endo-yl}-5-{[(1S)-1,2-dimethylpropyl]amino}benzene-1,4-dicarboxamide. Prepared according to the method of example 20 by using 4-(aminocarbonyl)-2-bromo-5-{[(1S)-1,2-dimethylpropyl]amino}benzoic acid (synthesized according to reagent preparation 50) in step 5. $^1$H NMR (400 MHz, DMSO-$d_6$): 8.85 (d, 1H), 8.42 (m, 2H), 8.02 (2d, 2H), 7.81 (s, 1H), 7.30 (bs, 1H), 6.78 (d, 1H), 6.61 (s, 1H), 4.60 (bs, 2H), 3.87 (m, 1H), 3.40 (m, 1H), 2.80 (m, 1H), 2.31 (m, 2H), 2.08 (m, 2H), 1.98 (m, 2H), 1.90 (m, 2H), 1.82 (m, 1H), 1.06 (d, 3H), 0.94 (m, 7H), 0.87 (d, 3H). MS (EI) for $C_{29}H_{36}BrN_5O_3$: 584 ($MH^+$).

(20BK): 2-bromo-N-{8-[5-(cyclopropylcarbonyl)pyridin-2-yl]-8-azabicyclo[3.2.1]oct-3-endo-yl}-5-[(cyclopropylmethyl)amino]benzene-1,4-dicarboxamide. Prepared according to the method of example 20 by using 4-(aminocarbonyl)-2-bromo-5-[(cyclopropylmethyl)amino]benzoic acid (synthesized according to reagent preparation 50) in step 5. $^1$H-NMR (400 MHz, DMSO-$d_6$): 8.95-8.88 (s, 1H), 8.45-8.38 (d, 1H), 8.35-8.28 (m, 1H), 8.12-8.00 (d, 1H), 7.88-7.81 (s, 1H), 7.40-7.31 (s, 1H), 6.83-6.77 (d, 1H), 6.63-6.58 (s, 1H), 4.77-4.53 (br. s, 2H), 3.93-3.83 (m, 1H), 3.05-2.95 (m, 2H), 2.85-2.76 (m, 1H), 2.38-2.26 (d, 2H), 2.20-1.84 (m, 6H), 1.18-1.04 (m, 1H), 1.03-0.91 (m, 4H), 0.57-0.46 (m, 2H), 0.29-0.19 (m, 2H). MS (EI) for $C_{28}H_{32}BrN_5O_3$: 567 ($MH^+$).

(20BL): N-{8-[5-(cyclopropylcarbonyl)pyridin-2-yl]-8-azabicyclo[3.2.1]oct-3-endo-yl}-5-[(1,1-dimethylethyl)amino]-2-methylbenzene-1,4-dicarboxamide. Prepared according to the method of example 20 by using 4-(aminocarbonyl)-5-[(1,1-dimethylethyl)amino]-2-methylbenzoic acid (synthesized according to reagent preparation 41) in step 5. $^1$H-NMR (400 MHz, DMSO-$d_6$): 8.88-8.83 (s, 1H), 8.17-8.08 (d, 1H), 7.47-7.44 (s, 1H), 6.98-6.95 (s, 1H), 6.83-6.76 (d, 1H), 4.66-4.59 (m, 2H), 4.07-4.00 (m, 1H), 2.77-2.70 (m, 1H), 2.34-2.24 (m, 5H), 2.22-2.09 (m, 2H), 2.07-1.86 (m, 4H), 2.85-2.76 (m, 4H), 1.43-1.37 (s, 9H), 1.30-1.00 (m, 4H). MS (EI) for $C_{29}H_{37}N_5O_3$: 504 ($MH^+$).

(20BM): N-{8-[5-(cyclopropylcarbonyl)pyridin-2-yl]-8-azabicyclo[3.2.1]oct-3-endo-yl}-2-methyl-5-(2-methylpropyl)benzene-1,4-dicarboxamide. Prepared according to the method of example 20 by using 4-(aminocarbonyl)-2-methyl-5-(2-methylpropyl)benzoic acid (synthesized according to reagent preparation 41) in step 5. $^1$H-NMR (400 MHz, DMSO-$d_6$): 8.89 (s, 1H), 8.26-8.25 (d, 1H), 8.06-8.03 (m, 1H), 7.73 (s, 1H), 7.38 (s, 1H), 7.21 (s, 1H), 7.08 (s, 1H), 6.80 (d, 1H), 4.62 (br. s, 2H), 3.87-3.82 (m, 1H), 3.32-3.33 (m, 3H), 2.85-2.77 (m, 1H), 2.63-2.62 (d, 2H), 2.31 (s, 3H), 2.23-2.21 (m, 2H), 2.15-1.89 (m, 7H), 0.97-0.94 (m, 4H), 0.86-0.82 (d, 2H). MS (EI) for $C_{29}H_{36}N_4O_3$: 489 ($MH^+$).

(20BN): 2-chloro-N-{8-[5-(cyclopropylcarbonyl)pyridin-2-yl]-8-azabicyclo[3.2.1]oct-3-endo-yl}-3-[(1-cyclopropylethyl)amino]benzene-1,4-dicarboxamide. Prepared according to the method of example 20 by using 4-(aminocarbonyl)-2-chloro-3-[(1-cyclopropylethyl)amino]benzoic acid (synthesized according to reagent preparation 46) in step 5. $^1$H-NMR (400 MHz, DMSO-$d_6$): 8.87 (d, 1H), 8.44 (d, 1H), 8.04-8.01 (m, 2H), 7.58 (s, 1H), 7.45 (d, 1H), 6.82 (d, 1H), 6.78 (d, 1H), 6.40 (d, 1H), 4.59 (s, 2H), 3.84 (s, 1H), 2.75-2.70 (m, 1H), 2.42 (d, 2H), 2.01-1.91 (m, 4), 1.80 (d, 2H), 1.06 (d, 3H), 0.93-0.91 (m, 4H), 0.79-0.74 (m, 2H), 0.28-0.25 (m, 2H), 0.03-0.02 (m, 2H); MS (EI) for $C_{29}H_{34}ClN_5O_3$: 537 ($MH^+$).

(20BO): N-{8-[5-(cyclopropylcarbonyl)pyridin-2-yl]-8-azabicyclo[3.2.1]oct-3-endo-yl}-2-methyl-5-(methyloxy)benzene-1,4-dicarboxamide. Prepared according to the method of example 20 by using 4-(aminocarbonyl)-2-methyl-5-(methyloxy)benzoic acid (synthesized according to reagent preparation 41) in step 5. $^1$H-NMR (400 MHz, DMSO-$d_6$): 8.62 (s, 1H), 8.32 (s, 1H), 8.03-8.02 (d, 1H), 7.64 (s, 1H), 7.62 (s, 1H), 7.59 (s, 1H), 6.98 (s, 1H), 7.80-6.76 (d, 1H), 4.63 (b, 2H), 4.04 (s, 2H), 3.88 (b, 4H), 3.80-2.75 (m, 1H), 2.26 (s, 3H), 2.24-2.20 (q, 1H), 2.15-1.95 (m, 3H), 2.26 (s, 3H), 1.89 (s, 1H), 1.86 (s, 1H), 0.96-0.89 (m, 4H); MS (EI) for $C_{26}H_{30}N_4O_4$: 463 ($MH^+$).

(20BP): 5-bromo-3-chloro-N4-{8-[5-(cyclopropylcarbonyl)pyridin-2-yl]-8-azabicyclo[3.2.1]oct-3-endo-yl}-2-{[(1R)-1-methylpropyl]amino}benzene-1,4-dicarboxamide. Prepared according to the method of example 20 by using 4-(aminocarbonyl)-6-bromo-2-chloro-3-{[(1R)-1-methylpropyl]amino}benzoic acid (synthesized according to the method of reagent preparation 50) in step 5. $^1$H-NMR (400 MHz, $CD_3OD$): 8.96 (s, 1H), 8.64 (s, 1H), 8.40 (dd, 1H), 7.69 (s, 1H), 7.31 (d, 1H), 4.77 (s, 2H), 4.16 (t, 1H), 3.57-3.37 (m, 1H), 2.74-2.67 (m, 1H), 2.54-2.34 (m, 3H), 2.19-2.09 (m, 6H), 1.66-1.57 (m, 1H), 1.54-1.44 (m, 1H), 1.32-1.21 (m, 1H), 1.26-1.11 (m, 6H), 1.00 (t, 2H); MS (EI) for $C_{28}H_{33}BrClN_5O_3$: 603 ($MH^+$).

(20BQ): N-{8-[5-(cyclopropylcarbonyl)pyridin-2-yl]-8-azabicyclo[3.2.1]oct-3-endo-yl}-2-(methyloxy)-5-{[(1R)-1-methylpropyl]amino}benzene-1,4-dicarboxamide. Prepared according to the method of example 20 by using 4-(aminocarbonyl)-2-(methyloxy)-5-{[(1R)-1-methylpropyl] amino}benzoic acid (synthesized according to the method of reagent preparation 50) in step 5. $^1$H-NMR (400 MHz, DMSO-$d_6$): 8.92-8.89 (s, 1H), 8.68-8.63 (d, 1H), 8.08-8.02 (m, 2H), 7.67-7.62 (d, 1H), 7.38-7.33 (s, 2H), 7.13-7.10 (s, 1H), 6.82-6.77 (d, 1H), 4.77-4.55 (br. s, 2H), 4.08-4.01 (m, 1H), 3.91-3.88 (s, 3H), 3.42-3.32 (m, 1H), 2.84-2.77 (m, 1H), 2.22-2.06 (m, 6H), 1.87-1.78 (d, 2H), 1.55-1.42 (m, 2H), 1.13-1.09 (d, 3H), 0.98-0.93 (m, 4H), 0.91-0.86 (m, 3H). MS (EI) for $C_{29}H_{37}N_5O_4$: 520 ($MH^+$).

(20BR): 3-chloro-N4-{8-[5-(cyclopropylcarbonyl)pyridin-2-yl]-8-azabicyclo[3.2.1]oct-3-endo-yl}-5-methyl-2-{[(1R)-1-methylpropyl]amino}benzene-1,4-dicarboxamide. Prepared according to the method of example 20 by using 4-(aminocarbonyl)-2-chloro-6-methyl-3-{[(1R)-1-methylpropyl]amino}benzoic acid (synthesized according to reagent preparation 41) in step 5. $^1$H-NMR (400 MHz, $CD_3OD$): 8.49 (d, 1H), 8.62 (d, 1H), 8.42 (dd, 1H), 7.58 (s, 1H), 7.32 (dd, 1H), 4.78 (s, 2H), 4.22 (t, 1H), 3.62 (q, 1H), 2.71-2.60 (m, 1H), 2.50-2.37 (m, 4H), 2.27 (s, 3H), 2.25-2.08 (m, 6H), 1.75-1.61 (m, 2H), 1.57-1.47 (m, 1H), 1.22-1.08 (m, 6H), 1.00-0.9 (m, 2H); MS (EI) for $C_{29}H_{36}ClN_{53}$: 539 ($MH^+$).

(20BS): N-{8-[5-(cyclopropylcarbonyl)pyridin-2-yl]-8-azabicyclo[3.2.1]oct-3-endo-yl}thiophene-2,5-dicarboxamide. Prepared according to the method of example 20 by using 5-(aminocarbonyl)thiophene-2-carboxylic acid in step 5. $^1$H-NMR (400 MHz, $CD_3OD$): 8.83 (s, 1H), 8.31 (d, 1H), 8.22-8.12 (m, 2H), 7.73-7.69 (m, 2H), 7.61 (s, 1H), 6.99 (d, 1H), 4.72 (s, 2H), 3.88 (s, 1H), 2.82-2.78 (m, 1H), 2.31-1.97 (m, 8H), 1.00-0.95 (m, 4H); MS (EI) for $C_{22}H_{24}N_4O_3S$: 425 ($MH^+$).

(20BT): N-{8-[5-(cyclopropylcarbonyl)pyridin-2-yl]-8-azabicyclo[3.2.1]oct-3-endo-yl}-2-(ethylamino)-5-{[(1R)-1-methylpropyl]amino}benzene-1,4-dicarboxamide. Prepared according to the method of example 20 by using 4-(aminocarbonyl)-2-(ethylamino)-5-{[(1R)-1-methylpropyl]amino}benzoic acid (synthesized according to reagent preparation 50) in step 5. $^1$H-NMR (400 MHz, DMSO-$d_6$): 8.92-8.89 (s, 1H), 8.45-8.41 (s, 1H), 8.08-8.02 (d, 2H), 7.95-7.90 (s, 1H), 7.26-7.15 (m, 2H), 6.91-6.90 (s, 1H), 6.82-6.77 (d, 1H), 6.76-6.75 (s, 1H), 6.70-6.66 (s, 1H), 5.98-5.92 (m, 1H), 4.72-4.57 (m, 2H), 3.92-3.84 (m, 1H), 3.09-3.01 (m, 2H), 2.85-2.77 (m, 1H), 2.30-2.24 (m, 1H), 2.09-1.99 (m, 2H), 1.97-1.90 (m, 2H), 1.77-1.71 (m, 2H), 1.63-1.53 (m, 2H), 1.48-1.39 (m, 2H), 1.18-1.11 (m, 6H), 0.98-0.87 (m, 5H). MS (EI) for $C_{30}H_{40}N_6O_3$: 533 ($MH^+$).

(20BU): N-{8-[5-(cyclopropylcarbonyl)pyridin-2-yl]-8-azabicyclo[3.2.1]oct-3-endo-yl}-2-methyl-5-[(1-methylpropyl)oxy]benzene-1,4-dicarboxamide. Prepared according to the method of example 20 by using 4-(aminocarbonyl)-2-methyl-5-[(1-methylpropyl)oxy]benzoic acid (synthesized according to reagent preparation 41) in step 5. $^1$H-NMR (400 MHz, DMSO-$d_6$): 8.89-8.87 (s, 1H), 8.36-8.33 (s, 1H), 8.04-8.00 (d, 1H), 7.69-7.67 (s, 1H), 7.66-7.54 (d, 2H), 6.98-6.96 (s, 1H), 6.80-6.76 (d, 1H), 4.69-4.49 (m, 3H), 3.91-3.84 (m, 1H), 2.81-2.74 (m, 1H), 2.28-2.20 (m, 5H), 2.13-1.95 (m, 4H), 1.92-1.85 (d, 2H), 1.79-1.60 (m, 4H), 1.32-1.27 (d, 3H), 0.96-0.88 (m, 5H). MS (EI) for $C_{29}H_{36}N_4O_4$: 505 ($MH^+$).

(20BV): N-{8-[5-(cyclopropylcarbonyl)pyridin-2-yl]-8-azabicyclo[3.2.1]oct-3-endo-yl}-2-ethyl-5-{[(1R)-1-methylpropyl]amino}benzene-1,4-dicarboxamide. Prepared according to the method of example 20 by using 4-(aminocarbonyl)-2-ethyl-5-{[(1R)-1-methylpropyl]amino}benzoic acid (synthesized according to reagent preparation 50) in step 5. $^1$H-NMR (400 MHz, DMSO-$d_6$): $^1$H NMR (400 MHz, DMSO-$d_6$): 8.90 (d, 1H), 8.32 (d, 1H), 8.01-8.06 (m, 2H), 7.88 (s, 1H), 7.49 (s, 1H), 7.17 (s, 1H), 6.79 (d, 1H), 6.53 (s, 1H), 4.63 (broad s, 2H), 3.86 (s, 1H), 3.39-3.42 (m, 1H), 2.77-2.83 (m, 1H), 2.55 (d, 2H), 2.27 (d, 2H), 2.02-2.09 (m, 4H), 1.93 (d, 2H), 1.46-1.61 (m, 2H), 1.09-1.16 (m, 6H), 0.88-0.97 (m, 7H). MS (EI) for $C_{30}H_{39}N_5O_3$: 518 ($MH^+$).

(20BW): N-{8-[5-(cyclopropylcarbonyl)pyridin-2-yl]-8-azabicyclo[3.2.1]oct-3-endo-yl}-5-ethyl-2-methylbenzene-1,4-dicarboxamide. Prepared according to the method of example 20 by using 4-(aminocarbonyl)-5-ethyl-2-methylbenzoic acid (synthesized according to reagent preparation 41) in step 5. $^1$H-NMR (400 MHz, DMSO-$d_6$): 8.90 (d, 1H), 8.32 (d, 1H), 8.03 (dd, 1H), 7.88 (s, 1H), 7.49 (s, 1H), 7.20 (s, 1H), 7.17 (s, 1H), 6.81 (d, 1H), 4.63 (broad s, 2H), 3.85-3.91 (m, 1H), 3.35 (s, 5H), 2.77-2.84 (m, 1H), 2.73 (q, 2H), 2.31 (s, 3H), 2.24 (d, 2H), 2.08-2.14 (m, 2H), 2.00-2.04 (m, 2H), 1.91 (d, 2), 1.16 (t, 3H), 0.93-0.98 (m, 4H). MS (EI) for $C_{27}H_{32}N_4O_3$: 461 ($MH^+$).

(20BX): N-{8-[5-(cyclopropylcarbonyl)pyridin-2-yl]-8-azabicyclo[3.2.1]oct-3-endo-yl}-2-methyl-5-{[2-(methyloxy)ethyl]oxy}benzene-1,4-dicarboxamide. Prepared according to the method of example 20 by using 4-(aminocarbonyl)-2-methyl-5-{[2-(methyloxy)ethyl]oxy}benzoic acid (synthesized according to reagent preparation 41) in step 5. $^1$H-NMR (400 MHz, DMSO-$d_6$): 8.90 (d, 1H), 8.34 (d, 1H), 8.03 (dd, 1H), 7.72 (s, 1H), 7.71 (s, 1H), 7.65 (s, 1H), 7.04 (s, 1H), 6.80 (d, 1H), 4.63 (broad s, 2H), 4.26-4.28 (m, 2H), 3.89-3.91 (m, 1H), 3.72-3.74 (m, 2H), 3.33 (d, 10H), 2.77-2.84 (m, 1H), 2.29 (s, 3H), 2.21-2.27 (m, 2H), 2.10-2.16 (m, 2H), 2.00-2.02 (m, 2H), 1.91 (s, 1H), 1.87 (s, 1H), 0.93-0.98 (m, 4H). MS (EI) for $C_{28}H_{34}N_4O_5$: 507 ($MH^+$).

SYNTHETIC SCHEME 21:
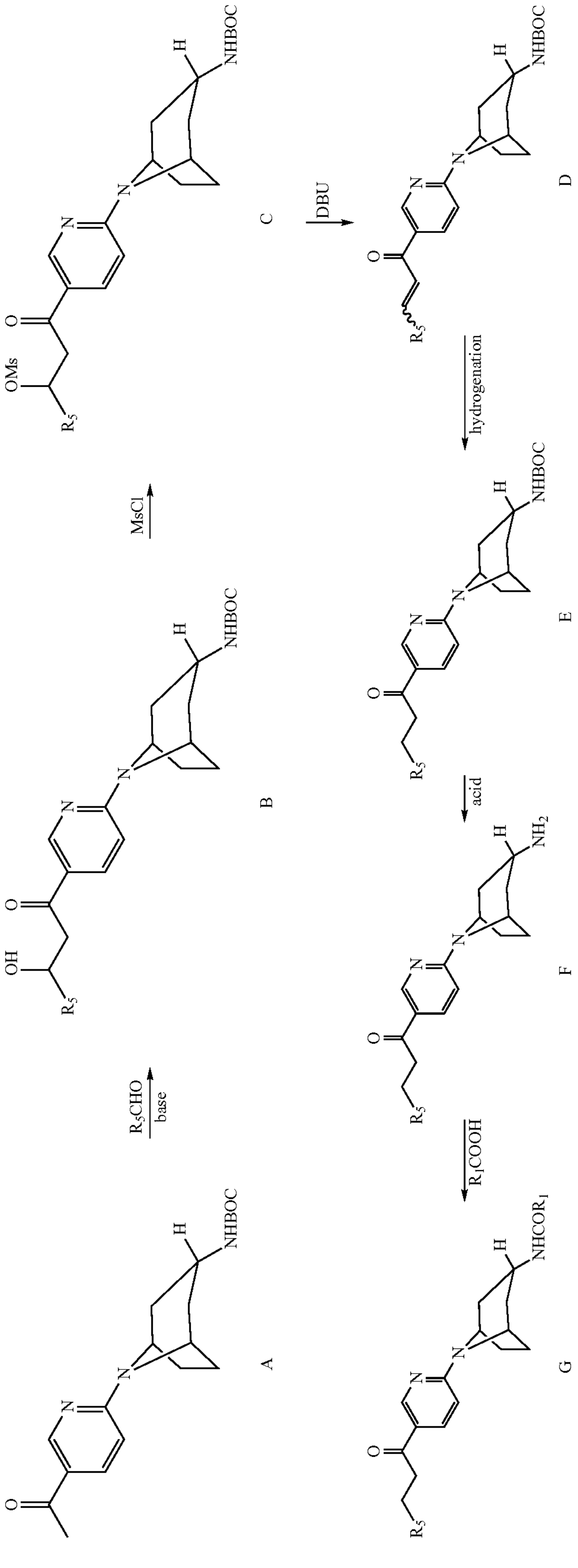

Scheme 21 generally describes the synthesis of all of the compound(s) listed in Example 21, wherein $R_5$ and $R_1$ are as defined in the specification.

In Scheme 21, $R_5CHO$ and a strong base, such as lithium diisopropylamide, is added to compound (A) under appropriate reaction conditions to form compound (B). To compound (B) is added MsCl under appropriate reaction conditions to arrive at compound (C). To compound (C) is added DBU under appropriate reaction conditions to arrive at compound (D). Compound (D) is reduced with an appropriate reducing agent, such as 10% palladium on charcoal, and under appropriate reaction conditions, to arrive at compound (E). Compound (E) is deprotected under acidic conditions, such as with HCl, to remove BOC and arrive at compound (F). $R_1COOH$ is added to compound (F) under appropriate reaction conditions and with a suitable coupling reagent, such as HATU, to condense and form the amide bond in compound (G).

Example 21

2-[(cyclopropylmethyl)amino]-N4-(8-{5-[3-(1-methylpiperidin-4-yl)propanoyl]pyridin-2-yl}-8-azabicyclo[3.2.1]oct-3-endo-yl)benzene-1,4-dicarboxamide acetate STEP 1: A solution of lithium diisopropylamide (0.87 mL, 2.0 M in tetrahydrofuran, 1.74 mmol) was added drop-wise to a mixture of 1,1-dimethylethyl [8-(5-acetylpyridin-2-yl)-8-azabicyclo[3.2.1]oct-3-endo-yl]carbamate (300 mg, 0.87 mmol) in tetrahydrofuran at −78° C. After stirring for 10 minutes, a solution of phenylmethyl 4-formylpiperidine-1-carboxylate (322 mg, 1.30 mmol) in tetrahydrofuran was added drop-wise and stirred for 2 hours at −78° C. The reaction mixture was poured into saturated aqueous ammonium chloride solution (50 mL), extracted with ethyl acetate (3×20 mL), and the combined extract was washed with water (50 mL), then brine (20 mL), dried over sodium sulfate, filtered then concentrated. The residue was purified by flash chromatography (55% to 75% ethyl acetate in hexanes) to give phenylmethyl 4-(3-{6-[3-endo-({[(1,1-dimethylethyl)oxy]carbonyl}amino)-8-azabicyclo[3.2.1]oct-8-yl]pyridin-3-yl}-1-hydroxy-3-oxopropyl)piperidine-1-carboxylate (360 mg, 70% yield). $^1H$ NMR (400 MHz, $CDCl_3$): 8.75 (d, 1H), 7.99 (dd, 1H), 7.37-7.30 (m, 5H), 6.49 (dd, 1H), 5.13 (s, 2H), 4.97 (br, 1H), 4.63 (br, 1H), 4.26 (br, 2H), 3.96 (br, 1H), 3.79 (br, 1H), 3.56 (br, 1H), 3.08 (d, 1H), 2.89 (dd, 1H), 2.77 (2H), 2.26-2.02 (m, 6H), 1.93 (m, 1H), 1.79 (br, 1H), 1.76 (br, 1H), 1.73-1.59 (m, 3H), 1.45 (s, 9H), 1.34 (m, 2H); MS (EI) for $C_{33}H_{44}N_4O_6$: 593 ($MH^+$).

STEP 2: Methanesulfonyl chloride (29 uL, 0.72 mmol) was added to a mixture of phenylmethyl 4-(3-{6-[3-endo-({[(1,1-dimethylethyl)oxy]carbonyl}amino)-8-azabicyclo[3.2.1]oct-8-yl]pyridin-3-yl}-1-hydroxy-3-oxopropyl)piperidine-1-carboxylate (213 mg, 0.36 mmol) and triethylamine (51 uL, 0.72 mmol) in dichloromethane (20 mL) at 0° C. The reaction mixture was slowly warmed to room temperature. After stirring for 18 hours, it was washed with water (20 mL), then saturated aqueous sodium bicarbonate solution (20 mL), dried over sodium sulfate then filtered and concentrated. The residue was purified by flash chromatography (25% to 55% ethyl acetate in hexanes) to give phenylmethyl 4-(3-{6-[3-endo-({[(1,1-dimethylethyl)oxy]carbonyl}amino)-8-azabicyclo[3.2.1]oct-8-yl]pyridin-3-yl}-1-[(methylsulfonyl)oxy]-3-oxopropyl)piperidine-1-carboxylate (212 mg, 89% yield). $^1H$ NMR (400 MHz, $CDCl_3$): 8.75 (d, 1H), 7.97 (dd, 1H), 7.37-7.33 (m, 5H), 6.49 (dd, 1H), 5.22 (s, 1H), 5.13 (br, 2H), 4.97 (br, 1H), 4.26 (br, 2H), 3.79 (br, 1H), 3.36 (dd, 1H), 3.04 (d, 1H), 3.00 (s, 3H), 2.77 (br, 2H), 2.25-2.04 (m, 9H), 1.78 (m, 2H), 1.73-1.59 (m, 3H), 1.69 (br, 1H), 1.45 (s, 9H), 1.34 (m, 2H); MS (EI) for $C_{34}H_{46}N_4O_8S$: 671 ($MH^+$).

STEP 3: 1,8-Diazabicyclo[5.4.0]undec-7-ene (82 uL, 0.27 mmol) was added to a solution of phenylmethyl 4-(3-{6-[3-endo-({[(1,1-dimethylethyl)oxy]carbonyl}amino)-8-azabicyclo[3.2.1]oct-8-yl]pyridin-3-yl}-1-[(methylsulfonyl)oxy]-3-oxopropyl)piperidine-1-carboxylate (183 mg, 0.27 mmol) in dichloromethane (20 mL) and the resulting mixture was stirred for one hour at room temperature. The mixture was washed with saturated aqueous ammonium chloride solution (2×20 mL), brine (20 mL), dried over sodium sulfate, filtered then concentrated. The residue was purified by flash chromatography (25% to 55% ethyl acetate in hexanes) to give phenylmethyl 4-[(1E,Z)-3-{6-[3-endo-({[(1,1-dimethylethyl)oxy]carbonyl}-amino)-8-azabicyclo[3.2.1]oct-8-yl]pyridin-3-yl}-3-oxoprop-1-en-1-yl]piperidine-1-carboxylate (147 mg, 94% yield). MS (EI) for $C_{33}H_{42}N_4O_5$: 575 ($MH^+$).

STEP 4: A mixture of phenylmethyl 4-[(1E,Z)-3-{6-[3-endo-({[(1,1-dimethylethyl)oxy]carbonyl}amino)-8-azabicyclo[3.2.1]oct-8-yl]pyridin-3-yl}-3-oxoprop-1-en-1-yl]piperidine-1-carboxylate (107 mg, 0.19 mmol), 10% palladium on charcoal (Degussa type, 110 mg), and acetic acid (23 uL, 0.37 mmol) in ethyl acetate (50 mL) was hydrogenated at 1 atm for 18 hours. The mixture was filtered and concentrated to give the 1,1-dimethylethyl {8-[5-(3-piperidin-4-ylpropanoyl)pyridin-2-yl]-8-azabicyclo[3.2.1]oct-3-endo-yl}carbamate as the acetate salt (91 mg, 97% yield). MS (EI) for $C_{25}H_{38}N_4O_3$: 443 ($MH^+$).

STEP 5: Sodium triacetoxyborohydride (96 mg, 0.45 mmol) was added to a mixture of 1,1-dimethylethyl {8-[5-(3-piperidin-4-ylpropanoyl)pyridin-2-yl]-8-azabicyclo[3.2.1]oct-3-endoyl}carbamate acetate salt (91 mg, 0.18 mmol), formaldehyde (73 uL, 37% aq. solution, 0.91 mmol) and acetic acid (55 uL, 0.92 mmol) in tetrahydrofuran (5 mL) at room temperature. After stirring for one hour, a saturated aqueous ammonium chloride solution (5 mL) was added and stirred for 5 minutes. The reaction mixture was diluted with water (15 mL), extracted with ethyl acetate (3×20 mL) and the combined extract was washed with water (50 mL), then brine (20 mL), dried over sodium sulfate, filtered, then concentrated to give 1,1-dimethylethyl (8-{5-[3-(1-methylpiperidin-4-yl)propanoyl]pyridin-2-yl}-8-azabicyclo[3.2.1]oct-3-endo-yl)carbamate (68 mg, 82% yield). $^1H$ NMR (400 MHz, $CDCl_3$): 8.76 (d, 1H), 8.01 (dd, 1H), 6.49 (d, 1H), 4.99 (br, 1H), 4.63 (br, 2H), 3.78 (br, 1H), 3.53 (d, 2H), 2.89 (t, 2H), 2.76 (s, 3H), 2.66 (tr, 2H), 2.25-2.04 (m, 6H), 2.00-1.87 (m, 4H), 1.83-1.71 (m, 3H), 1.45 (s, 9H), 1.28 (m, 2H); MS (EI) for $C_{26}H_{40}N_4O_3$: 457 ($MH^+$).

STEP 6: A mixture of 1,1-dimethylethyl (8-{5-[3-(1-methylpiperidin-4-yl)propanoyl]pyridin-2-yl}-8-azabicyclo[3.2.1]oct-3-endo-yl)carbamate (60 mg, 0.13 mmol), methanol (1 mL) and hydrogen chloride in dioxane (4 M, 1 mL) was stirred at 60° C. for 20 minutes. The reaction mixture was concentrated to give a white solid, which was washed with hexane and dried to give 1-[6-(3-endo-amino-8-azabicyclo[3.2.1]oct-8-yl)pyridin-3-yl]-3-(1-methylpiperidin-4-yl)propan-1-one hydrochloride salt (51 mg, 39% yield). MS (EI) for $C_{21}H_{32}N_4O$: 357 ($MH^+$).

STEP 7: N,N-Diisopropylethylamine (101 uL, 0.66 mmol) was added to a mixture of O-(7-azabenzotriazol-1-yl)-N,N,N',N'-tetramethyluronium hexafluorophosphate (53 mg, 0.14 mmol), and 4-(aminocarbonyl)-3-[(cyclopropylmethyl)amino]-benzoic acid (synthesized according to reagent preparation 39) (31 mg, 0.13 mmol) and the resulting mixture was stirred at room temperature for 30 minutes. A solution of 1-[6-(3-endo-amino-8-azabicyclo[3.2.1]oct-8-yl)pyridin-3-yl]-3-(1-methylpiperidin-4-yl)propan-1-one hydrochloride salt (51 mg, 0.13 mmol) in N,N-dimethylformamide (0.5 mL) was added and stirring was continued for 18 hours. The reaction mixture was diluted with methanol (1.5 mL), and purified by preparatory reverse phase HPLC (ammonium acetate buffered aqueous acetonitrile eluent) to give 2-[(cyclopropylmethyl)amino]-N4-(8-{5-[3-(1-methylpiperidin-4-yl)propanoyl]pyridin-2-yl}-8-azabicyclo[3.2.1]oct-3-endo-yl) benzene-1,4-dicarboxamide as the acetate salt, (54 mg, 66% yield). $^1$H NMR (400 MHz, $d_4$-Methanol): 8.65 (d, 1H), 7.97 (dd, 1H), 7.54 (d, 1H), 6.96 (d, 1H), 6.82 (dd, 1H), 6.67 (d, 1H), 4.57, (Br, 2H), 3.89 (tr, 1H), 3.04 (m, 2H), 2.95 (d, 2H), 2.87 (tr, 2H), 2.44 (s, 3H), 2.37 (tr, 2H), 2.21-2.01 (m, 6H), 1.91 (br, 1H), 1.88 (br, 1H), 1.80 (s, 3H), 1.78 (m, 1H), 1.58 (q, 4H), 1.38 (br, 1H), 1.22 (m, 2H), 1.02 (m, 1H), 0.47 (m, 2H), 0.20 (m, 2H); MS (EI) for $C_{33}H_{44}N_6O_3$: 573 ($MH^+$).

Using analogous synthetic techniques and substituting with alternative starting reagents, the following compounds [(21B)-(2H)] were prepared. Alternative starting materials were obtained commercially unless otherwise indicated.

(21B): 2-[(cyclopropylmethyl)amino]-N4-{8-[5-(3-hydroxy-4-methylpentanoyl)pyridin-2-yl]-8-azabicyclo[3.2.1]oct-3-endo-yl}benzene-1,4-dicarboxamide. Prepared according to the method of example 21 by using 2-methylpropanal in step 1 and omitting steps 2 through 5. $^1$H NMR (400 MHz, $d_4$-Methanol): 8.67 (d, 1H), 8.00 (dd, 1H), 7.55 (d, 1H), 6.97 (d, 1H), 6.84 (dd, 1H), 6.68 (d, 1H), 4.60, (Br, 2H), 3.90 (m, 1H), 3.83 (m, 1H), 2.95 (d, 2H), 2.93 (m, 1H), 2.82 (dd, 1H), 2.21-2.01 (m, 6H), 1.93 (br, 1H), 1.89 (br, 1H), 1.66 (m, 1H), 1.07 (m, 1H), 0.90 (d, 6H), 0.49 (m, 2H), 0.20 (m, 2H). MS (EI) for $C_{30}H_{39}N_5O_4$: 534 ($MH^+$).

(21C): 2-[(cyclopropylmethyl)amino]-N4-{8-[5-(3-phenylpropanoyl)pyridin-2-yl]-8-azabicyclo[3.2.1]oct-3-endo-yl}benzene-1,4-dicarboxamide. Prepared according to the method of example 21 by using benzaldehyde in step 1 and omitting step 5. $^1$H NMR (400 MHz, $d_4$-Methanol): 8.67 (d, 1H), 7.97 (dd, 1H), 7.56 (d, 1H), 7.08 (m, 5H), 6.98 (d, 1H), 6.84 (dd, 1H), 6.67 (d, 1H), 4.59, (Br, 2H), 3.90 (m, 1H), 3.93 (tr, 1H), 3.15 (tr, 2H), 3.00 (d, 2H), 2.92 (tr, 2H), 2.18-2.11 (m, 6H), 1.93 (br, 1H), 1.90 (br, 1H), 1.66 (m, 1H), 1.07 (m, 1H), 0.51 (m, 2H), 0.22 (m, 2H); MS (EI) for $C_{33}H_{37}N_5O_3$: 552 ($MH^+$).

(21D): 2-[(cyclopropylmethyl)amino]-N4-{8-[5-(3-hydroxy-3-phenylpropanoyl)pyridin-2-yl]-8-azabicyclo[3.2.1]oct-3-endo-yl}benzene-1,4-dicarboxamide. Prepared according to the method of example 21 by using benzaldehyde in step 1 and omitting steps 2 through 5. $^1$H NMR (400 MHz, $d_4$-Methanol): 8.64 (d, 1H), 7.97 (dd, 1H), 7.55 (d, 1H), 7.34 (m, 2H), 7.25 (m, 2H), 7.17 (m 1H), 6.96 (d, 1H), 6.84 (dd, 1H), 6.65 (d, 1H), 5.18 (dd, 1H), 4.60, (br, 2H), 3.92 (m, 1H), 3.31 (dd, 1H), 3.06 (dd, 1H), 3.00 (d, 2H), 2.18-2.09 (m, 6H), 1.93 (br, 1H), 1.90 (br, 1H), 1.86 (br, 1H), 1.66 (m, 1H), 1.04 (m, 1H), 0.48 (m, 2H), 0.19 (m, 2H); MS (EI) for $C_{33}H_{37}N_5O_4$: 568 ($MH^+$).

(21E): 2-[(cyclopropylmethyl)amino]-N4-{8-[5-(4-methylpentanoyl)pyridin-2-yl]-8-azabicyclo[3.2.1]oct-3-endo-yl}benzene-1,4-dicarboxamide. Prepared according to the method of example 21 by using 2-methylpropanal in step 1 and omitting step 5. $^1$H NMR (400 MHz, $d_4$-Methanol): 8.67 (d, 1H), 8.01 (dd, 1H), 7.55 (d, 1H), 6.98 (d, 1H), 6.83 (dd, 1H), 6.68 (d, 1H), 4.60, (br, 2H), 3.93 (m, 1H), 3.00 (d, 2H), 2.83 (dd, 1H), 2.18-2.05 (m, 7H), 1.93 (br, 1H), 1.90 (br, 1H), 1.59-1.46 (m, 3H), 1.05 (m, 1H), 0.87 (d, 6H), 0.49 (m, 2H), 0.20 (m, 2H); MS (EI) for $C_{30}H_{39}N_5O_3$: 518 ($MH^+$).

(21F): N4-{8-[5-(3-cyclohexylpropanoyl)pyridin-2-yl]-8-azabicyclo[3.2.1]oct-3-endo-yl}-2-[(cyclopropylmethyl)amino]benzene-1,4-dicarboxamide. Prepared according to the method of example 21 by using cyclohexanecarbaldehyde in step 1 and omitting step 5. $^1$H NMR (400 MHz, $d_4$-Methanol): 8.67 (d, 1H), 7.99 (dd, 1H), 7.57 (d, 1H), 6.99 (d, 1H), 6.86 (dd, 1H), 6.68 (d, 1H), 4.61, (br, 2H), 3.91 (m, 1H), 3.01 (d, 2H), 2.83 (dd, 1H), 2.12-2.10 (m, 6H), 1.95 (br, 1H), 1.91 (br, 1H), 1.76-1.59 (m, 5H), 1.51 (q, 2H), 1.05 (m, 5H), 0.87 (d, 2H), 0.51 (m, 2H), 0.23 (m, 2H); MS (EI) for $C_{33}H_{43}N_5O_3$: 558 ($MH^+$).

(21G): 5-[(1-ethylpropyl)amino]-2-methyl-N-(8-{5-[3-(1-methylpiperidin-4-yl)propanoyl]pyridin-2-yl}-8-azabicyclo[3.2.1]oct-3-endo-yl)benzene-1,4-dicarboxamide. Prepared as the hydrochloride salt according to the method of example 21 by using 4-aminocarbonyl-2-methyl-5-(pentan-3-ylamino)benzoic acid (prepared according to reagent preparation 42) in step 7. $^1$H NMR (400 MHz, Methanol-$d_4$): 8.56 (d, 1H), 8.42 (dd, 1H), 7.93 (s, 1H), 7.48 (s, 1H), 7.39 (d, 1H), 4.88-4.81 (m, 2H), 4.21-4.12 (m, 1H), 3.60-3.48 (m, 3H), 3.15-2.93 (m, 4H), 2.86 (s, 3H), 2.53-2.16 (m, 9H), 2.06 (d, 2H), 1.88-1.61 (m, 7H), 1.55-1.39 (m, 2H), 1.01 (t, 6H); MS (EI) for $C_{35}H_{50}N_6O_3$: 604 ($MH^+$).

(21H): 2-[(cyclopropylmethyl)amino]-N4-{8-[5-(3-piperidin-4-ylpropanoyl)pyridin-2-yl]-8-azabicyclo[3.2.1]oct-3-endo-yl}benzene-1,4-dicarboxamide. Prepared according to the method of example 21 by using phenylmethyl 4-formylpiperidine-1-carboxylate in step 1 and omitting step 5. $^1$H NMR (400 MHz, $CD_3OD$): 8.65 (s, 1H), 8.33-8.29 (s, 1H), 8.26-8.19 (d, 1H), 7.68-7.63 (d, 1H), 7.10-7.03 (d, 1H), 6.97-6.92 (d, 1H), 4.77-4.70 (m, 2H), 4.08-4.02 (m, 1H), 3.45-3.35 (m, 2H), 3.11-3.07 (d, 2H), 3.05-2.92 (m, 4H), 2.35-2.19 (m, 6H), 2.14-2.07 (d, 2H), 2.05-1.96 (d, 2H), 1.75-1.66 (m, 2H), 1.45-1.32 (m, 2H), 1.21-1.09 (m, 1H), 0.62-0.55 (m, 2H), 0.32-0.26 (m, 2H), 0.11-0.08 (m, 1H). MS (EI) for $C_{32}H_{42}N_6O_3$: 559 ($MH^+$).

SYNTHETIC SCHEME 22:

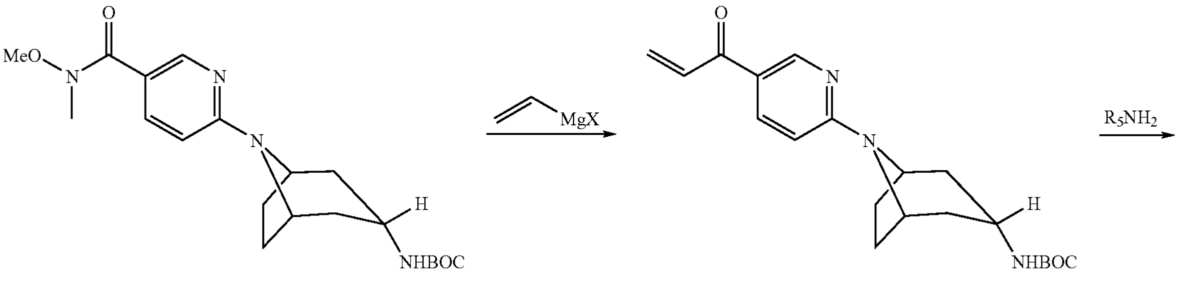

A B

-continued

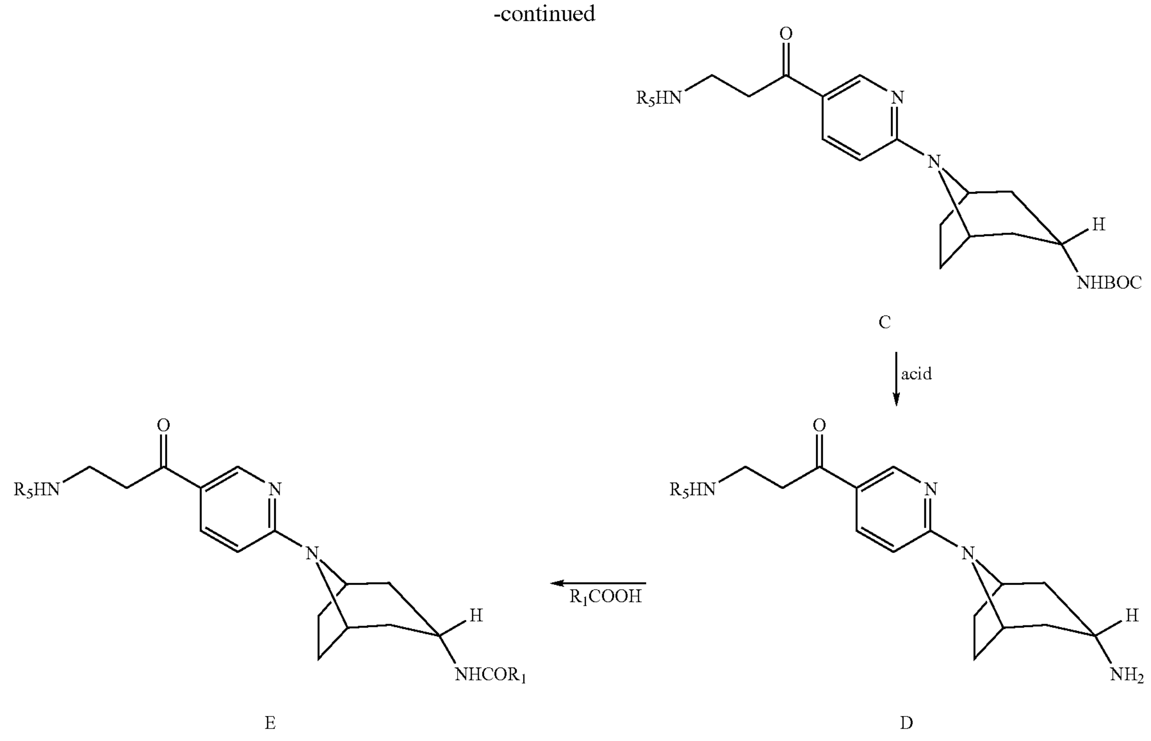

C D E

Scheme 22 generally describes the synthesis of all of the compound(s) listed in Example 22, wherein $R_5$ and $R_1$ are as defined in the specification.

In Scheme 22, an appropriate Grignard reagent, such as vinyl magnesium bromide, is added to compound (A) under appropriate reaction conditions to form compound (B). To compound (B) is added $R_5NH_2$ under appropriate reaction conditions to form compound (C). Compound (C) is deprotected with an acid, such as trifluoroacetic acid in dichloromethane, to form compound (D). To compound (D) is added $R_1COOH$ under appropriate reaction conditions and with a suitable coupling reagent, such as HATU, to condense and form the amide bond in compound (E).

Example 22

2-[(cyclopropylmethyl)amino]-N4-{8-[5-(3-piperidin-1-ylpropanoyl)pyridin-2-yl]-8-azabicyclo[3.2.1]oct-3-endo-yl}benzene-1,4-dicarboxamide STEP 1: A solution of vinyl magnesium bromide (1.0 M in tetrahydrofuran, 6.5 mL) is added to a solution of 1,1-dimethylethyl [8-(5-{[methyl(methyloxy)amino]carbonyl}pyridin-2-yl)-8-azabicyclo[3.2.1]oct-3-endo-yl]carbamate (synthesized according to example 19 step 1) (0.5 g, 1.3 mmol) in tetrahydrofuran (20 mL) at 0° C. and the resulting mixture was stirred at 0° C. for one hour. The mixture was poured into saturated aqueous ammonium chloride solution (50 mL), extracted with ethyl acetate (3×20 mL) and the combined extract was washed with water (50 mL), brine (20 mL) then dried over sodium sulfate, filtered and concentrated. The residue was purified by flash chromatography (50% to 65% ethyl acetate in hexanes) to give 1,1-dimethylethyl [8-(5-acryloylpyridin-2-yl)-8-azabicyclo[3.2.1]oct-3-endo-yl]carbamate (180 mg, 39% yield). $^1H$ NMR (400 MHz, $CDCl_3$): 8.81 (d, 1H), 8.09 (dd, 1H), 7.13 (dd, 1H), 6.55 (d, 1H), 6.43 (d, 1H), 5.85 (dd, 1H), 4.97 (br, 1H), 4.63 (b, 2H), 3.93 (m, 1H), 2.28-2.05 (m, 6H), 1.78 (d, 2H), 1.45 (s, 9H); MS (EI) for $C_{20}H_{27}N_3O_3$: 358 ($MH^+$).

STEP 2: To a solution of 1,1-dimethylethyl [8-(5-acryloylpyridin-2-yl)-8-azabicyclo[3.2.1]oct-3-endo-yl]carbamate (45 mg, 13 mmol) in tetrahydrofuran (2 mL) was added piperidine (13 uL, 13 mmol) and the resulting mixture was stirred at room temperature for 18 hours. The reaction mixture was concentrated and the residue was purified by flash chromatography (10% methanol in dichloromethane) to give 1,1-dimethylethyl {8-[5-(3-piperidin-1-ylpropanoyl)pyridin-2-yl]-8-azabicyclo[3.2.1]oct-3-endo-yl}carbamate (41 mg, 74% yield). MS (EI) for $C_{25}H_{38}N_4O_3$: 443 ($MH^+$).

STEP 3: A solution of 1,1-dimethylethyl {8-[5-(3-piperidin-1-ylpropanoyl)pyridin-2-yl]-8-azabicyclo[3.2.1]oct-3-endo-yl}carbamate (41 mg, 0.093 mmol) in 1:1 trifluoroacetic acid dichloromethane (1 mL) was stirred at room temperature for 15 min. The reaction mixture was concentrated and the residue was triturated with hexanes (3×2 mL) and dried in vacuo to give the 1-[6-(3-endo-amino-8-azabicyclo[3.2.1]oct-8-yl)pyridin-3-yl]-3-piperidin-1-ylpropan-1-one as the trifluoroacetate salt (42 mg, 100% yield). MS (EI) for $C_{20}H_{30}N_4O$: 343 ($MH^+$).

STEP 4: N,N-Diisopropylethylamine (192 uL, 0.46 mmol) was added to a mixture of O-(7-azabenzotriazol-1-yl)-N,N,N',N'-tetramethyluronium hexafluorophosphate (38 mg, 0.10 mmol), and 4-(aminocarbonyl)-3-[(cyclopropylmethyl)amino]benzoic acid (synthesized according to reagent preparation 39) (22 mg, 0.093 mmol) and the resulting mixture was stirred at room temperature for 30 minutes. A solution of 1-[6-(3-endo-amino-8-azabicyclo[3.2.1]oct-8-yl)pyridin-3-yl]-3-piperidin-1-ylpropan-1-one trifluoroacetate salt (42 mg, 0.093 mmol) in N,N-dimethylformamide (0.5 mL) was added and stirring was continued for 18 hours. The reaction mixture was diluted with methanol (1.5 mL) and purified by preparatory reverse phase HPLC (ammonium acetate buffered aqueous acetonitrile eluent) to afford 2-[(cyclopropylmethyl)amino]-N4-{8-[5-(3-piperidin-1-ylpropanoyl)pyridin-2-yl]-8-azabicyclo[3.2.1]oct-3-endo-yl}benzene-1,4-dicarboxamide as the acetate salt (4.6 mg, 12% yield). $^1$H NMR (400 MHz, $D_4$-Methanol): 8.67 (d, 1H), 7.97 (dd, 1H), 7.54 (d, 1H), 6.96 (d, 1H), 6.82 (dd, 1H), 6.67 (d, 1H), 4.60 (br, 2H), 3.89 (tr, 1H), 3.07 (tr, 3H), 2.98 (d, 2H), 2.84 (br, 3), 2.16-2.10 (m, 6H), 1.84 (m, 3H), 1.67 (m, 4H), 1.50 (m, 2H), 1.07 (m, 1H), 0.48 (m, 2H), 0.18 (m, 2H); MS (EI) for $C_{32}H_{42}N_6O_3$: 559 ($MH^+$).

Using analogous synthetic techniques and substituting with alternative starting reagents, the following compounds [(22B)-(221)] were prepared. Alternative starting materials were obtained commercially unless otherwise indicated.

(22B): 2-[(cyclopropylmethyl)amino]-N4-{8-[5-(N,N-dimethyl-beta-alanyl)pyridin-2-yl]-8-azabicyclo[3.2.1]oct-3-endo-yl}benzene-1,4-dicarboxamide. Prepared according to the method of example 22 by using dimethylamine in step 2. $^1$H NMR (400 MHz, $D_4$-Methanol): 8.67 (d, 1H), 7.99 (dd, 1H), 7.54 (d, 1H), 6.95 (d, 1H), 6.82 (dd, 1H), 6.68 (d, 1H), 4.61 (br, 2H), 3.90 (tr, 1H), 3.43-3.38 (m, 4H), 2.98 (d, 2H), 2.84 (s, 6H), 2.17-2.10 (m, 6H), 1.92 (m, 3H), 1.09 (m, 1H), 0.47 (m, 2H), 0.19 (m, 2H); MS (EI) for $C_{29}H_{38}N_6O_3$: 519 ($MH^+$).

(22C): 2-[(cyclopropylmethyl)amino]-N4-(8-{5-[3-(methyloxy)propanoyl]pyridin-2-yl}-8-azabicyclo[3.2.1]oct-3-endo-yl)benzene-1,4-dicarboxamide. Prepared according to the method of example 22 by using methanol in step 2. $^1$H NMR (400 MHz, $D_4$-Methanol): 8.67 (d, 1H), 7.98 (dd, 1H), 7.55 (d, 1H), 6.97 (d, 1H), 6.83 (dd, 1H), 6.68 (d, 1H), 4.61 (br, 2H), 3.90 (tr, 1H), 3.69 (tr, 2H), 3.25 (s, 3H), 3.06 (tr, 2H), 3.00 (d, 2H), 2.21-2.02 (m, 6H), 1.91 (m, 2H), 1.04 (m, 1H), 0.49 (m, 2H), 0.20 (m, 2H); MS (EI) for $C_{28}H_{35}N_5O_4$: 506 ($MH^+$).

(22D): 2-[(cyclopropylmethyl)amino]-N4-(8-{5-[3-(ethyloxy)propanoyl]pyridin-2-yl}-8-azabicyclo[3.2.1]oct-3-endo-yl)benzene-1,4-dicarboxamide. Prepared according to the method of example 22 by using ethanol in step 2. $^1$H NMR (400 MHz, $CDCl_3$): 8.81 (d, 1H), 8.06 (dd, 1H), 7.93 (b, 1H), 7.45 (d, 1H), 7.09 (d, 1H), 6.75 (dd, 1H), 6.58 (d, 1H), 6.54 (d, 1H), 5.70 (br, 1H), 4.70 (br, 2H), 4.23 (q, 1H), 3.86 (tr, 1H), 3.54 (q, 2H), 3.14 (tr, 2H), 3.07 (tr, 2H), 2.39-2.23 (m, 4H), 2.09 (m, 2H), 1.89 (d, 2H), 1.20 (tr, 3H), 1.13 (m, 1H), 0.59 (m, 2H), 0.28 (m, 2H); MS (EI) for $C_{29}H_{37}N_5O_4$: 520 ($MH^+$).

(22E): 2-[(cyclopropylmethyl)amino]-N4-(8-{5-[N-(4-fluorophenyl)-beta-alanyl]pyridin-2-yl}-8-azabicyclo[3.2.1]oct-3-endo-yl)benzene-1,4-dicarboxamide Prepared according to the method of example 22 by using 4-fluoroaniline in step 2. $^1$H NMR (400 MHz, $D_4$-Methanol): 8.74 (d, 1H), 8.06 (dd, 1H), 7.63 (b, 1H), 7.06 (d, 1H), 6.92 (dd, 1H), 6.86 (m, 21H), 6.75 (d, 1H), 6.65 (m, 2H), 4.57 (br, 2H), 3.90 (tr, 1H), 3.34 (m, 2H), 3.07 (tr, 2H), 3.02 (m 2H), 2.98 (d, 2H), 2.21-2.02 (m, 5H), 1.91 (m, 3H), 1.03 (m, 1H), 0.57 (m, 2H), 0.29 (m, 2H); MS (EI) for $C_{33}H_{37}FN_6O_3$: 585 ($MH^+$).

(22F): 2-[(cyclopropylmethyl)amino]-N4-{8-[5-(3-morpholin-4-ylpropanoyl)pyridin-2-yl]-8-azabicyclo[3.2.1]oct-3-endo-yl}benzene-1,4-dicarboxamide. Prepared according to the method of example 22 by using morpholine in step 2. $^1$H NMR (400 MHz, $D_4$-Methanol): 8.67 (d, 1H), 7.98 (dd, 1H), 7.54 (d, 1H), 6.96 (d, 1H), 6.82 (dd, 1H), 6.68 (d, 1H), 4.60 (br, 2H), 3.90 (tr, 1H), 3.61 (tr, 4H), 3.05 (tr, 2H), 3.00 (d, 2H), 2.71 (tr, 2H), 2.47 (br, 4H), 2.22-2.04 (m, 6H), 1.91 (d, 2H), 1.06 (m, 1H), 0.48 (m, 2H), 0.19 (m, 2H); MS (EI) for $C_{31}H_{40}N_6O_4$: 561 ($MH^+$).

(22G): 2-[(cyclopropylmethyl)amino]-N4-(8-{5-[3-(4-methylpiperazin-1-yl)propanoyl]pyridin-2-yl}-8-azabicyclo[3.2.1]oct-3-endo-yl)benzene-1,4-dicarboxamide. Prepared according to the method of example 22 by using 1-methylpiperazine in step 2. $^1$H NMR (400 MHz, $D_4$-Methanol): 8.69 (d, 1H), 7.99 (dd, 1H), 7.57 (d, 1H), 6.99 (d, 1H), 6.85 (dd, 1H), 6.70 (d, 1H), 4.63 (br, 2H), 3.93 (tr, 1H), 3.21 (m, 1H), 3.09 (tr, 2H), 3.02 (d, 2H), 2.71 (tr, 2H), 2.47 (br, 4H), 2.42 (s, 3H), 2.26-2.04 (m, 7H), 1.98-1.84 (m, 4H), 1.08 (m, 1H), 0.51 (m, 2H), 0.22 (m, 2H); MS (EI) for $C_{32}H_{43}N_7O_3$: 574 ($MH^+$).

(22H): 2-[(cyclopropylmethyl)amino]-N4-{8-[5-(3-pyrrolidin-1-ylpropanoyl)pyridin-2-yl]-8-azabicyclo[3.2.1]oct-3-endo-yl}benzene-1,4-dicarboxamide. Prepared according to the method of example 22 by using pyrrolidine in step 2. $^1$H NMR (400 MHz, $D_4$-Methanol): 8.69 (d, 1H), 8.00 (dd, 1H), 7.54 (d, 1H), 6.96 (d, 1H), 6.82 (dd, 1H), 6.70 (d, 1H), 4.61 (br, 2H), 3.90 (tr, 1H), 3.06-2.97 (m, 6H), 2.71 (tr, 2H), 2.47 (br, 4H), 2.42 (s, 3H), 2.19-2.08 (m, 6H), 1.82 (br, 2H), 1.06 (m, 1H), 0.48 (m, 2H), 0.20 (m, 2H); MS (EI) for $C_{31}H_{40}N_6O_3$: 545 ($MH^+$).

(22I): 2-[(cyclopropylmethyl)amino]-N4-(8-{5-[3-(4-phenylpiperazin-1-yl)propanoyl]pyridin-2-yl}-8-azabicyclo[3.2.1]oct-3-endo-yl)benzene-1,4-dicarboxamide. Prepared according to the method of example 22 by using 1-phenylpiperazine in step 2. $^1$H NMR (400 MHz, $D_4$-Methanol): 8.80 (d, 1H), 8.10 (dd, 1H), 7.63 (d, 1H), 7.27 (m, 2H), 7.06 (d, 1H), 7.02 (d, 2H), 6.91 (m, 2H), 6.79 (d, 1H), 4.72 (br, 2H), 4.00 (tr, 1H), 3.47-3.32 (m, 1H), 3.08 (d, 2H), 2.32-2.15 (m, 6H), 2.02 (m, 3H), 1.14 (m, 1H), 0.58 (m, 2H), 0.29 (m, 2H); MS (EI) for $C_{37}H_{45}N_7O_3$: 636 ($MH^+$).

SYNTHETIC SCHEME 23:

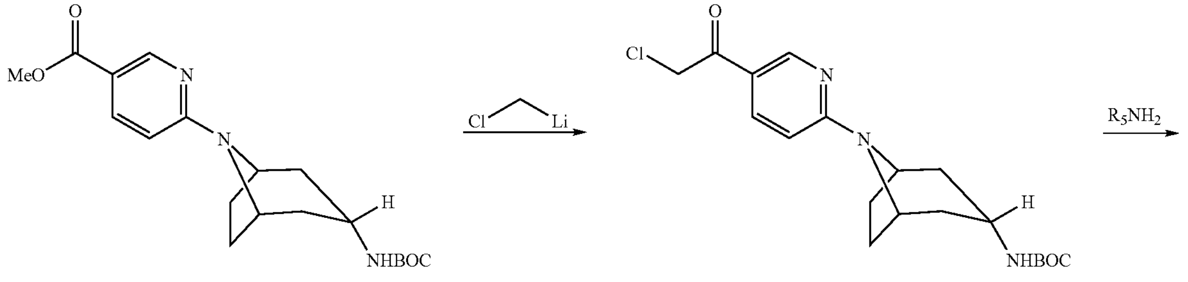

A

B

-continued

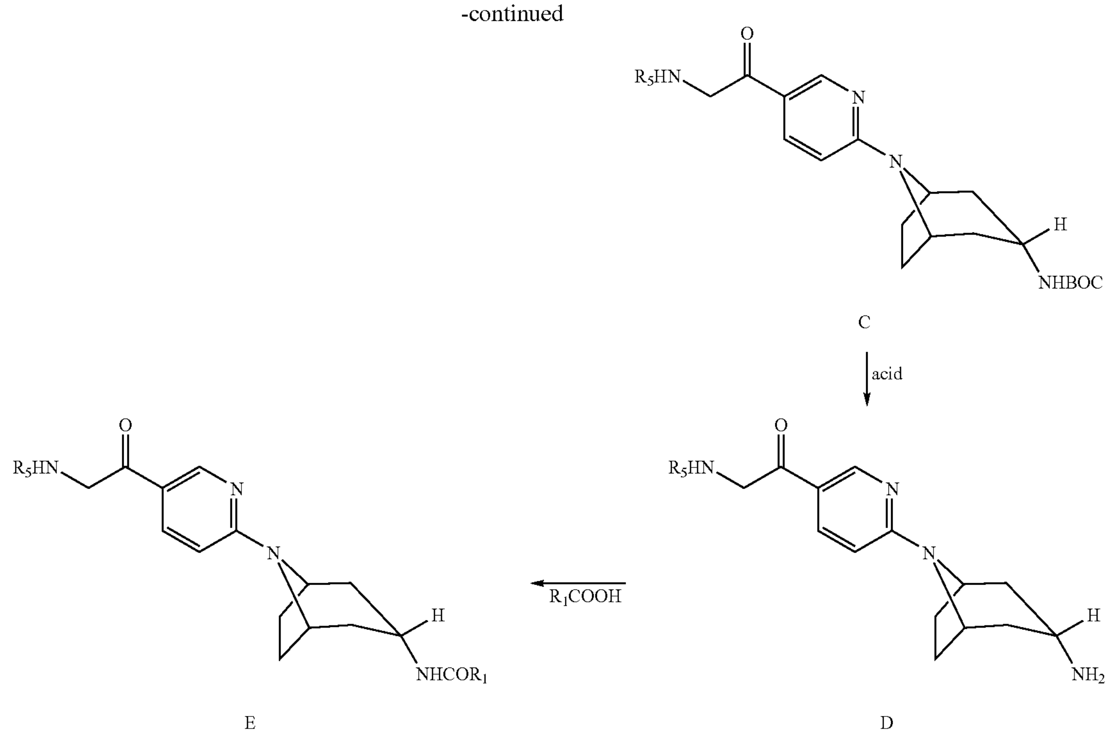

Scheme 23 generally describes the synthesis of all of the compound(s) listed in Example 23, wherein $R_5$ and $R_1$ are as defined in the specification.

In Scheme 23, chloroiodomethane is added to compound (A) with a base, such as lithium diisopropylamide, under appropriate reaction conditions to form compound (B). To compound B is added $R_5NH_2$ under appropriate reaction conditions to form compound (C). Compound (C) is deprotected with an acid, such as trifluoroacetic acid in dichloromethane, to form compound (D). To compound (D) is added $R_1COOH$ under appropriate reaction conditions and with a suitable coupling reagent, such as HATU, to condense and form the amide bond in compound (E).

Example 23

2-[(cyclopropylmethyl)amino]-N4-{8-[5-(piperidin-1-ylacetyl)pyridin-2-yl]-8-azabicyclo[3.2.1]oct-3-endo-yl}benzene-1,4-dicarboxamide STEP 1: A solution of lithium diisopropylamide (0.36 mL, 2.0 M in tetrahydrofuran, 0.72 mmol) was added drop-wise to a mixture of methyl 6-[3-endo-({[(1,1-dimethylethyl)oxy]carbonyl}amino)-8-azabicyclo[3.2.1]oct-8-yl]pyridine-3-carboxylate (synthesized according to the method of example 1) (52 mg, 0.14 mmol) and chloroiodomethane (42 uL, 0.56 mmol) in tetrahydrofuran (2 mL) at −78° C. After stirring for 10 minutes, the reaction mixture was quenched with water (10 mL), extracted with ethyl acetate (3×10 mL), and the combined extract was washed with water (15 mL), then brine (15 mL), dried over sodium sulfate, filtered and concentrated. The residue was purified by flash chromatography (25% to 65% ethyl acetate in hexanes) to give the 1,1-dimethylethyl {8-[5-(chloroacetyl)pyridin-2-yl]-8-azabicyclo[3.2.1]oct-3-endo-yl}carbamate (45 mg, 82% yield). $^1H$ NMR (400 MHz, $CDCl_3$): 8.78 (d, 1H), 8.01 (dd, 1H), 6.53 (d, 1H), 4.95 (br, 1H), 4.85 (br, 1H), 4.55 (s, 2H), 3.80 (br, 1H), 2.27-2.04 (m, 6H), 1.85-1.75 (m, 2H), 1.43 (s, 9H); MS (EI) for $C_{19}H_{26}ClNO_3$: 380 ($MH^+$).

STEP 2: To a solution of {8-[5-(chloroacetyl)pyridin-2-yl]-8-azabicyclo[3.2.1]oct-3-endo-yl}carbamate (44 mg, 0.12 mmol) in tetrahydrofuran (2 mL) was added piperidine (13 uL, 13 mmol), and the resulting mixture was stirred at room temperature for 18 hours. The mixture was diluted with ethyl acetate (10 mL), washed with water (10 mL), then brine (10 mL) and dried over sodium sulfate. The organic solution was filtered and concentrated then dried in vacuo to afford 1,1-dimethylethyl {8-[5-(piperidin-1-ylacetyl)pyridin-2-yl]-8-azabicyclo[3.2.1]oct-3-endo-yl}carbamate (50 mg, 100% yield); MS (EI) for $C_{24}H_{36}N_4O_3$: 429 ($MH^+$).

STEP 3: A solution of 1,1-dimethylethyl {8-[5-(piperidin-1-ylacetyl)pyridin-2-yl]-8-azabicyclo[3.2.1]oct-3-endo-yl}carbamate (50 mg, 0.12 mmol) in 1:1 trifluoroacetic acid dichloromethane (1 mL) was stirred at room temperature for 15 min. The reaction mixture was concentrated, and the residue was triturated with hexanes (3×2 mL) then dried in vacuo to give 1-[6-(3-endo-amino-8-azabicyclo[3.2.1]oct-8-yl)pyridin-3-yl]-2-piperidin-1-ylethanone as the trifluoroacetate salt (51 mg, 99% yield). MS (EI) for $C_{19}H_{28}N_4O$: 329 ($MH^+$).

STEP 4: N,N-Diisopropylethylamine (78 uL, 0.58 mmol) was added to a mixture of O-(7-azabenzotriazol-1-yl)-N,N,N',N'-tetramethyluronium hexafluorophosphate (47 mg, 0.12 mmol), and 4-(aminocarbonyl)-3-[(cyclopropylmethyl)amino]benzoic acid (synthesized according to reagent preparation 39) (22 mg, 0.093 mmol) and the resulting mixture was stirred at room temperature for 30 minutes. A solution of 1-[6-(3-endo-amino-8-azabicyclo[3.2.1]oct-8-yl)pyridin-3-yl]-2-piperidin-1-ylethanone trifluoroacetate salt (42 mg, 0.093 mmol) in N,N-dimethylformamide (0.5 mL) was added and stirring was continued for 18 hours. The reaction mixture was diluted with methanol (1.5 mL) and purified by preparatory reverse phase HPLC (ammonium acetate buffered aqueous acetonitrile eluent) to give 2-[(cyclopropylmethyl) amino]-N4-{8-[5-(piperidin-1-ylacetyl)pyridin-2-yl]-8-azabicyclo[3.2.1]oct-3-endo-yl}benzene-1,4-dicarboxamide as the acetate salt (24.4 mg, 39% yield). $^{1}$H NMR (400 MHz, $d_4$-Methanol): 8.69 (d, 1H), 7.98 (dd, 1H), 7.54 (d, 1H), 6.96 (d, 1H), 6.83 (dd, 1H), 6.67 (d, 1H), 4.55 (br, 2H), 3.90 (br, 3H), 2.98 (d, 2H), 2.62 (m, 4H), 2.20-2.07 (m, 6H), 1.92 (m, 2H), 1.61 (m, 4H), 1.45.

Scheme 24 generally describes the synthesis of all of the compound(s) listed in Example 24, wherein $R_1$ is as defined in the specification.

In Scheme 24, $LiAlH_4$ is added to compound (A) under appropriate reaction conditions to form compound (B). Compound (B) undergoes oxidation of the primary alcohol into an aldehyde to form compound (C) by treatment with an appropriate oxidizing agent such as Dess-Martin periodinane.

SYNTHETIC SCHEME 24:

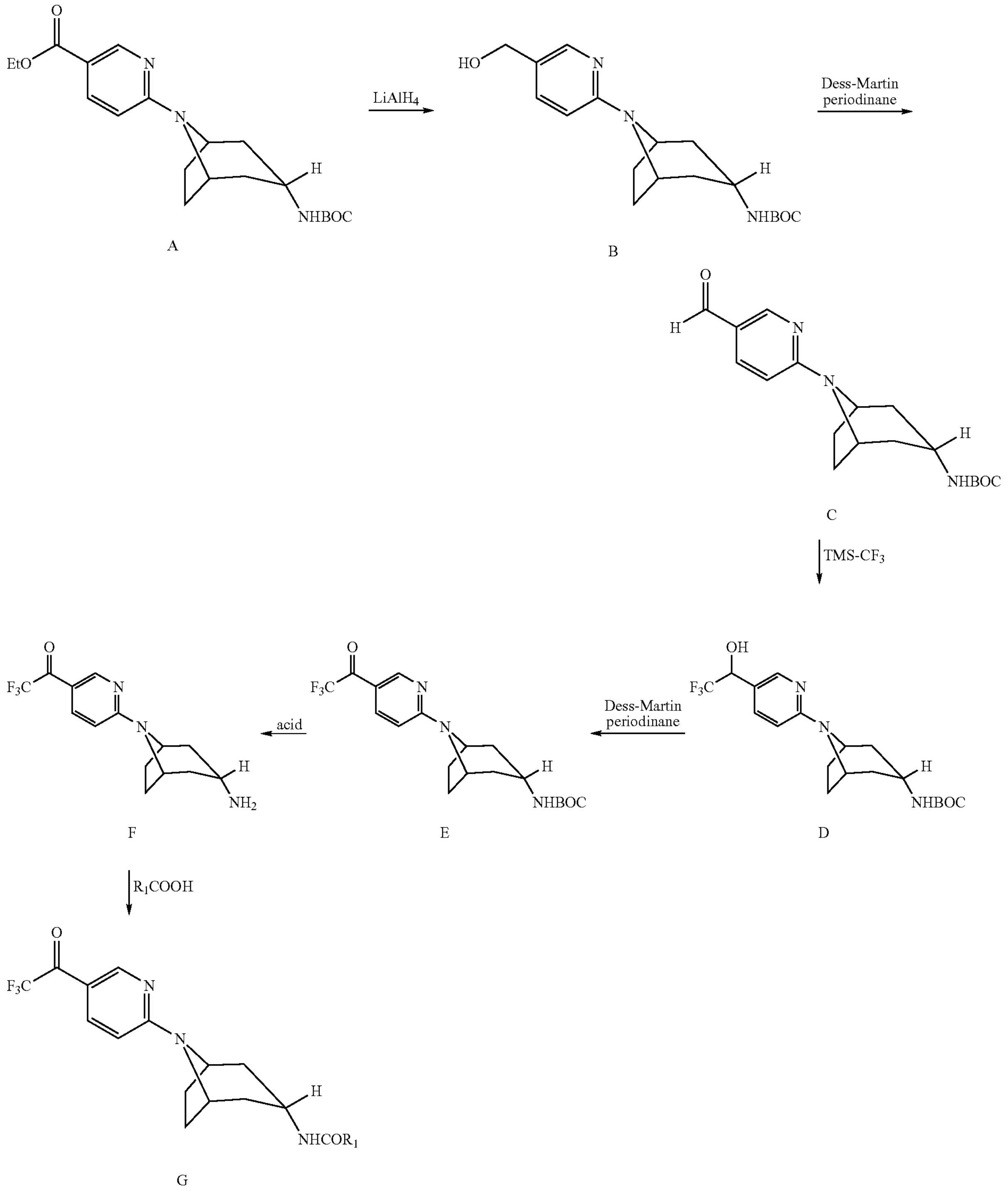

$TMS-CF_3$ is then added to compound (C) under appropriate reaction conditions to form compound (D). Compound (D) undergoes oxidation of the secondary alcohol into a ketone to form compound (E) by treatment with an appropriate oxidizing agent such as Dess-Martin periodinane. Compound (E) is deprotected with an acid, such as HCl, to form compound (F). To compound (F) is added $R_1COOH$ under appropriate reaction conditions and with a suitable coupling reagent, such as HATU, to condense and form the amide bond in compound (G).

Example 24

2-[(cyclopropylmethyl)amino]-N4-{8-[5-(trifluoroacetyl)pyridin-2-yl]-8-azabicyclo[3.2.1]oct-3-endo-yl}benzene-1,4-dicarboxamide STEP 1: To a suspension of ethyl 6-[3-endo-({[(1,1-dimethylethyl)oxy]carbonyl}amino)-8-azabicyclo[3.2.1]oct-8-yl]pyridine-3-carboxylate (synthesized in example 1) (1.47 g, 3.92 mmol) in THF (25 ml) was slowly added lithium aluminum hydride (1.96 ml, 2M solution in THF, 3.92 mmol) at 0° C. The reaction mixture was stirred at 0° C. for 4 hours and then quenched by addition of water (0.15 ml), followed by 15% aqueous sodium hydroxide (0.15 ml) and then water (0.45 ml). After being stirred for 0.5 h at room temperature the mixture was diluted with ethyl acetate, filtered through Celite, washed with ethyl acetate and concentrated. Column chromatography on silica (dichloromethane:methanol 30:1 to 15:1) afforded 1,1-dimethylethyl {8-[5-(hydroxymethyl)pyridin-2-yl]-8-azabicyclo[3.2.1]oct-3-endo-yl}carbamate (0.72 g, 55% yield). MS (EI) for $C_{18}H_{27}N_3O_3$: 334 ($MH^+$).

STEP 2: A suspension of 1,1-dimethylethyl {8-[5-(hydroxymethyl)pyridin-2-yl]-8-azabicyclo[3.2.1]oct-3-endo-yl}carbamate (105 mg, 0.31 mmol) and Dess-Martin periodinane (147 mg, 0.35 mmol) in dichloromethane (5 mL) was stirred at room temperature for 90 min. A 10% solution of sodium thiosulfate (5 mL) and then saturated sodium bicarbonate (5 mL) were added and stirring was continued for 30 min. The layers were separated and the aqueous layer was extracted with dichloromethane (2×20 mL). The combined organic layers were washed with saturated sodium bicarbonate (20 mL) and brine (20 mL), dried over sodium sulfate, and concentrated to give crude 1,1-dimethylethyl [8-(5-formylpyridin-2-yl)-8-azabicyclo[3.2.1]oct-3-endo-yl]carbamate (100 mg, 96% yield) as a colorless foam. $^1H$ NMR (400 MHz, $CDCl_3$): 9.76 (s, 1H), 8.55 (d, 1H), 7.92 (dd, 1H), 6.54 (d, 1H), 4.97 (d, 1H), 4.60 (br s, 2H), 3.81 (m, 1H), 2.20 (m, 4H), 2.08 (d, 2H), 1.80 (d, 2H).

STEP 3: To a solution of 1,1-dimethylethyl [8-(5-formylpyridin-2-yl)-8-azabicyclo[3.2.1]oct-3-endo-yl]carbamate (72 mg, 0.22 mmol) in DMF (1.5 mL) was added trimethyl(trifluoromethyl)silane (154 mg, 1.09 mmol) and cesium carbonate (85 mg, 0.26 mol), and the reaction mixture was stirred at room temperature for 1 h. Ethyl acetate (30 mL) was added, and the mixture was washed with water (3×10 mL) and brine (10 mL), dried over sodium sulfate, and concentrated. Column chromatography on silica (dichloromethane:methanol 95:5) afforded 1,1-dimethylethyl {8-[5-(2,2,2-trifluoro-1-hydroxyethyl)pyridin-2-yl]-8-azabicyclo[3.2.1]oct-3-endo-yl}carbamate (45 mg, 52% yield). $^1H$ NMR (400 MHz, $CDCl_3$): 8.17 (d, 1H), 7.59 (dd, 1H), 6.55 (d, 1H), 4.98 (br s, 1H), 4.91 (m, 1H), 4.51 (br s, 2H), 3.78 (m, 1H), 2.51 (d, 1H), 2.24 (m, 2H), 2.16 (m, 2H), 2.03 (m, 2H), 1.70 (d, 2H), 1.45 (s, 9H); MS (EI) for $C_{19}H_{26}F_3N_3O_3$: 402 ($MH^+$).

STEP 4: A suspension of 1,1-dimethylethyl {8-[5-(2,2,2-trifluoro-1-hydroxyethyl)pyridin-2-yl]-8-azabicyclo[3.2.1]oct-3-endo-yl}carbamate (41 mg, 0.10 mmol) and Dess-Martin periodinane (52 mg, 0.12 mmol) in dichloromethane (2 mL) was stirred at room temperature for 3.5 h. A 10% solution of sodium thiosulfate (2 mL) and then saturated sodium bicarbonate (2 mL) were added and stirring was continued for 30 min. The layers were separated and the aqueous layer was extracted with dichloromethane (2×10 mL). The combined organic layers were washed with brine (50 mL), dried over sodium sulfate, and concentrated to give crude 1,1-dimethylethyl {8-[5-(trifluoroacetyl)pyridin-2-yl]-8-azabicyclo[3.2.1]oct-3-endo-yl}carbamate (40 mg, 98% yield) as a colorless. MS (EI) for $C_{19}H_{24}F_3N_3O_3$: 400 ($MH^+$).

STEP 5: To a solution of 1,1-dimethylethyl {8-[5-(trifluoroacetyl)pyridin-2-yl]-8-azabicyclo[3.2.1]oct-3-endo-yl}carbamate (38 g, 0.10 mmol) in methanol (2 mL) was added a solution of 4N hydrogen chloride in dioxane (2 mL), and the reaction mixture was refluxed for 2 min. After cooling to room temperature the mixture was concentrated and dried in vacuo. To the residue was added 4-(aminocarbonyl)-3-[(cyclopropylmethyl)amino]benzoic acid (synthesized according to reagent prep 39) (23 mg, 0.10 mmol), HATU (38 mg, 0.10 mmol), DMF (1 mL), and diisopropylethylamine (76 mg, 0.58 mmol), and the mixture was stirred at room temperature for 16 h. Purification by preparatory HPLC (0.1% ammonium acetate buffered aqueous acetonitrile mobile phase) provided 2-[(cyclopropylmethyl)amino]-N4-{8-[5-(trifluoroacetyl)pyridin-2-yl]-8-azabicyclo[3.2.1]oct-3-endo-yl}benzene-1,4-dicarboxamide (18 mg, 37% yield). $^1H$ NMR (400 MHz, DMSO-$d_6$): 8.77 (s, 1H), 8.26 (t, 1H), 8.23 (d, 1H), 7.99 (dd, 1H), 7.94 (br s, 1H), 7.67 (d, 1H), 7.30 (br s, 1H), 6.99 (d, 1H), 6.91 (m, 2H), 4.96 (br s, 1H), 4.56 (br s, 1H), 3.89 (m, 1H), 3.03 (t, 2H), 2.26 (m, 2H), 2.06 (m, 6H), 1.11 (m, 1H), 0.52 (m, 2H), 0.25 (m, 2H); MS (EI) for $C_{26}H_{28}F_3N_5O_3$: 516 ($MH^+$).

SYNTHETIC SCHEME 25:

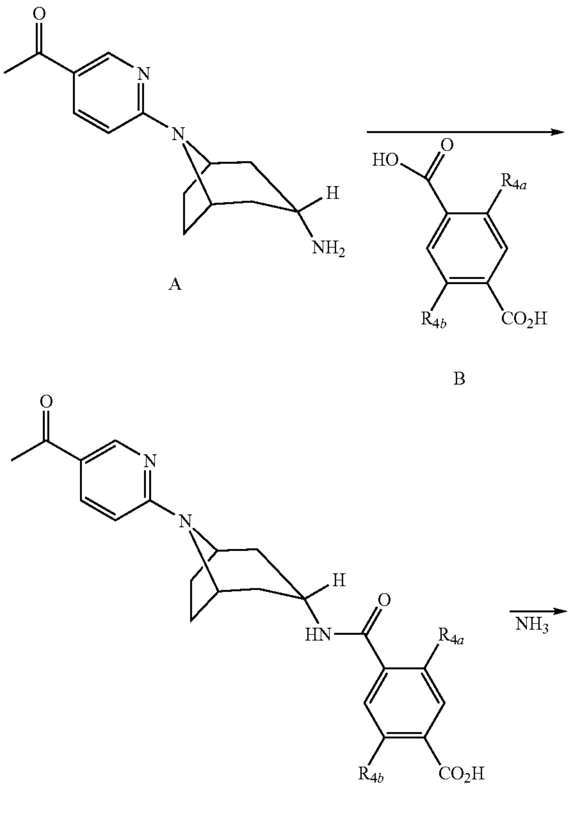

A

B

C

-continued

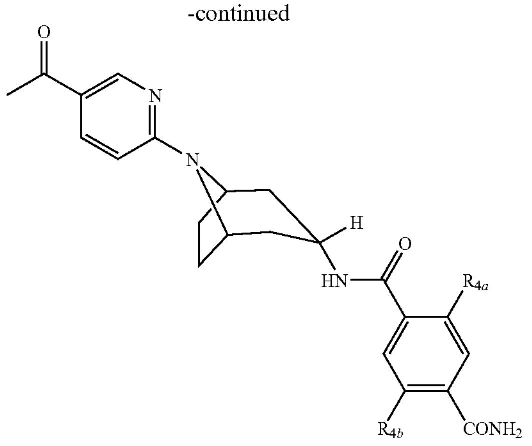

D

Scheme 25 generally describes the synthesis of all of the compound(s) listed in Example 25, wherein $R_{4a}$ and $R_{4b}$ are as defined in the specification.

In Scheme 25, compound (B) is added to compound (A), with a suitable coupling reagent, such as HATU, to condense and form the amide bond in compound (C). This scheme is applicable when $R_{4a}$ and $R_{4b}$ are the same. To compound (C) is added $NH_3$ (g) under appropriate reaction conditions to form compound (D).

Example 25

N-[8-(5-Acetylpyridin-2-yl)-8-azabicyclo[3.2.1]oct-3-endo-yl]-2,5-dimethylbenzene-1,4-dicarboxamide STEP 1: 2,5-Dimethylterephthalic acid (200 mg, 1.03 mmol) was dissolved in DMF (5 mL) and HATU (392 mg, 1.03 mmol) was added and the mixture was stirred at ambient for 15 minutes. N,N-Diisopropylethylamine (0.7 mL, 3.99 mmol) was added and after 5 minutes 1-[6-(3-endo-amino-8-azabicyclo[3.2.1]oct-8-yl)pyridine-3-yl]ethanone (prepared in Example 19 Step 3) (250 mg, 1.02 mmol) was added and the mixture was stirred at 50° C. for 15 h. The mixture was cooled to ambient temperature and HATU (392 mg, 1.03 mmol) and N,N-diisopropylethylamine (0.2 mL, 1.14 mmol) were added and the mixture was stirred at ambient for 15 minutes. Ammonia gas was bubbled into the solution and a thick precipitate formed. The mixture was stirred at 50° C. for 0.5 h and then was cooled to ambient temperature and was concentrated. The residue was treated with 1N aqueous hydrochloric acid (2 mL) and DMSO. Water was added and the precipitate was collected by filtration then further purified by reverse phase HPLC. The pure fractions were combined and concentrated to an aqueous residue. The aqueous residue was basified with sodium bicarbonate and extracted with ethyl acetate (2×). The combined organic portion was dried over magnesium sulfate then filtered and was concentrated to afford N-[8-(5-acetylpyridin-2-yl)-8-azabicyclo[3.2.1]oct-3-endo-yl]-2,5-dimethylbenzene-1,4-dicarboxamide (77 mg, 0.183 mmol, 18% yield). $^1H$ NMR (400 MHz, $d_6$-DMSO): δ 8.74 (d, 1H), 8.28 (d, 1H), 7.97 (dd, 1H), 7.71 (br s, 1H), 7.41 (br s, 1H), 7.24 (s, 1H), 7.12 (s, 1H), 6.79 (d, 1H), 4.62 (br s, 2H), 3.87 (br s, 1H), 2.45 (s, 3H), 2.35 (s, 3H), 2.30 (s, 3H), 2.27-2.18 (m, 2H), 2.15-1.94 (m, 4H), 1.89 (d, 2H); MS (EI) for $C_{24}H_{28}N_4O_3$: 421 ($MH^+$).

Reagent Preparations:

The following reagents referred to in the above examples were made as follows. The reagent numbers below correspond to the reagent numbers referred to in the above examples.

Reagent Preparation 1: tert-butyl 8-azabicyclo[3.2.1]octan-3-endo-ylcarbamate

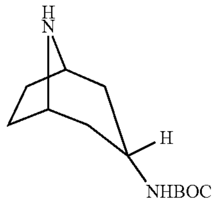

STEP 1: To a 5 L round-bottom flask was added 8-methyl-8-azabicyclo[3.2.1]octan-3-endo-amine (432 g, 3.1 mol), 2 L of dry 1,4-dioxane, 675 mL of deionized water and 468 g of dry triethylamine. Di-tert-butyl dicarbonate (solution in 1.2 L of dioxane) was added dropwise to the stirring solution at room temperature over 16 h. The reaction mixture was concentrated and the resulting residue suspended in 2.5 L of methylene chloride. then washed twice with 1 L of water, dried with anhydrous magnesium sulfate, filtered, and volatile organics removed by rotary evaporation to yield 617 g (83%) of tert-butyl 8-methyl-8-azabicyclo[3.2.1]octan-3-ylcarbamate (mp 79-81° C.).

STEP 2: To a 5 L round-bottom flask was added 480 g (2.0 mol) of tert-butyl 8-methyl-8-azabicyclo[3.2.1]octan-3-endo-ylcarbamate, 2 L of toluene, and 69 g (0.5 mol) of potassium carbonate. 2,2,2-Trichloroethyl chloroformate (347 mL, 2.4 mol) was added dropwise at room temperature over 6 h and the reaction heated at reflux temperature for 8 h. After the solution was cooled to room temperature, 1.2 L of water was added to the reaction solution and stirred 0.5 h. The organic layer was separated and washed with 1 L of brine, dried with anhydrous magnesium sulfate, filtered, and concentrated to yield a cloudy oil. The oil was titurated with 700 mL of a 3:2 ethyl ether/hexanes solution to yield 280 g (mp 131-135° C.) of 2,2,2-trichloroethyl 3-endo-(tert-butoxycarbonylamino)-8-azabicyclo[3.2.1]octane-8-carboxylate that was collected by filtration. The mother liquor was concentrated and titurated further to yield a less pure sample of the Troc protected diamine (129 g, mp 116-118° C.).

STEP 3: To a 5 L round-bottom flask was added 360 g (0.9 mol) of 2,2,2-trichloroethyl 3-endo-(tert-butoxycarbonylamino)-8-azabicyclo[3.2.1]octane-8-carboxylate, 2.8 L of methanol and 675 g (12.6 mol) of ammonium chloride. The solution was heated to reflux and 387 g (7.5 mol) of zinc dust was carefully added in small portions over 0.5 h. Upon complete addition of the zinc dust, the reaction was heated at reflux temperature for 2 h then cooled to room temperature. The reaction filtered through a thin pad a Celite 545, and the methanol removed by rotary evaporation. The resulting solid was dissolved in 800 mL of methylene chloride and stirred with 600 mL of concentrated ammonium hydroxide for 0.5 h. The organic layer was separated, washed with 600 mL of water, dried with anhydrous magnesium sulfate, filtered, and concentrated to yield an oil. The residue was dissolved in 200 mL of methylene chloride and 1 L of ethyl ether then filtered. The resulting solution was chilled to 0° C. and 215 mL of 4N hydrogen chloride in dioxane were added slowly, dropwise over 0.5 h, being sure to maintain the reaction solution temperature close to 0° C. After the addition was complete, 200 mL of methylene chloride and 1.4 L of ethyl ether were added to the cooled solution and a pale white precipitate formed. The resulting solid was collected by filtration to yield 173 g (85%) of tert-butyl 8-azabicyclo[3.2.1]octan-3-endo-ylcarbamate hydrochloride salt.

Reagent Preparation 2: 4-(1-methylpiperidin-4-yl)benzylamine

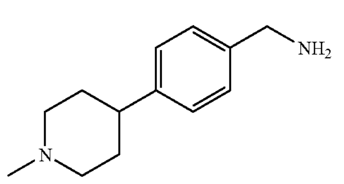

STEP 1: To a solution of 4-piperidin-4-ylbenzamide (200 mg, 1.00 mmol), 37% aqueous formaldehyde (162 μL, 2.00 mmol), and acetic acid (86 uL, 1.5 mmol) in a mixture of dichloromethane and methanol (2:1, 6 mL) was added sodium triacetoxylborohydride (318 mg, 1.5 mmol) in portions over fifteen minutes and stirring was continued for 2 hr at room temperature. The reaction was then quenched with water and adjusted to pH 9 with 2N aqueous sodium hydroxide then extracted with dichloromethane (2×50 ml). The organic extracts were combined and dried over sodium sulfate, filtered and concentrated to give 4-(1-methylpiperidin-4-yl)benzamide (190 mg, 87%). MS (EI) for $C_{13}H_{18}N_2O$: 218 ($MH^+$).

STEP 2: To an ice cold solution of 4-(1-methylpiperidin-4-yl)benzamide (190 mg, 0.87 mmol) in tetrahydrofuran (5 mL) was added 1.0M lithium aluminum hydride in tetrahydrofuran (1.79 mL, 1.79 mmol) and stirring continued overnight at room temperature. The reaction mixture was quenched by adding sodium sulfate decahydrate until gas evolution ceased. The suspension was filtered through Celite and the filter cake washed with a mixture of ethyl acetate and chloroform (2:1, 50 mL). The filtrate was concentrated to give 4-(1-methylpiperidin-4-yl)benzylamine (130 mg, 71%) as an oil. $^1$H NMR (400 MHz, $CDCl_3$): 7.23 (dd, 4H), 3.86 (s, 3H), 2.98 (m, 2H), 2.49 (m, 1H), 2.11 (m, 2H), 1.83 (m, 4H).

Reagent Preparation 3: (S)-1-[4-(4-methylpiperazin-1-yl)phenyl]ethylamine

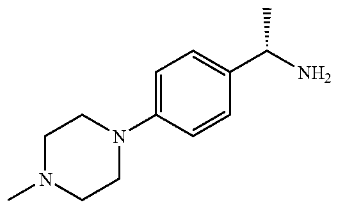

STEP 1: A solution of (1S)-1-(4-bromophenyl)ethylamine (10 g, 50 mmol) and di-tert-butyl dicarbonate (13 g, 60 mmol) in dichloromethane (80 mL) was stirred at room temperature for 15 hours. Concentration of the reaction mixture afforded a solid residue that was then suspended in diethyl ether (100 mL). The mixture was diluted with hexane (100 mL) and the solid was isolated by filtration, then washed with hexane and dried to afford 14.4 g, 48 mmol (96%) of 1,1-dimethylethyl [(1S)-1-(4-bromophenyl)ethyl]carbamate. $^1$H NMR (400 MHz, $CDCl_3$): 7.46-7.42 (m, 2H), 7.19-1.76 (m, 2H), 5.29 (s, 1H), 4.71 (br s, 1H), 1.43-1.39 (m, 12H). MS (EI) for $C_{13}H_{18}BrNO_2$: 301 ($MH^+$).

STEP 2: A mixture of 1,1-dimethylethyl [(1S)-1-(4-bromophenyl)-ethyl]carbamate (14.4 g, 48 mmol), tris(dibenzylideneacetone)dipalladium(0) (4.6 g, 4.8 mmol), N-methylpiperazine (22 mL, 200 mmol), BINAP (1.4 g, 4.8 mmol) and tribasic potassium phosphate in ethylene glycol dimethylether (120 mL) was refluxed for 15 hours. On cooling to room temperature, the mixture was diluted with ethyl acetate (100 mL). The organic mixture was extracted using 1N aqueous hydrochloric acid (3×100 mL). The pH of the combined aqueous portions was adjusted to 10 and was then extracted using ethyl acetate (3×100 mL). The combined organic portion was washed with brine then dried over anhydrous sodium sulfate. Filtration and concentration afforded a brown residue which was purified by silica gel column chromatography. Eluting with 0-20% methanol in ethyl acetate, purified fractions were pooled and concentrated to afford 12.9 g, 40.5 mmol (84%) of 1,1-dimethylethyl {(1S)-1-[4-(4-methylpiperazin-1-yl)phenyl]ethyl}carbamate. $^1$H NMR (400 MHz, $d_6$-DMSO): 7.16 (d, 2H), 6.84 (d, 2H), 4.54 (m, 1H), 3.07 (m, 4H), 2.42 (m, 4H) 2.21 (s, 3H), 1.38 (s, 9H), 1.25 (d, 3H). MS (EI) for $C_{18}H_{29}N_3O_2$: 320 ($MH^+$).

STEP 3: A solution of 1,1-dimethylethyl {(1S)-1-[4-(4-methylpiperazin-1-yl)phenyl]ethyl}carbamate (2 g, 6.3 mmol) and 4N hydrogen chloride in dioxane (5 mL) in methanol (5 mL) was refluxed for 2 min. After cooling to room temperature the mixture was concentrated and rotary evaporated from benzene, and further dried in vacuo to afford 1.7 g, 5.9 mmol (95%) of (S)-1-[4-(4-methylpiperazin-1-yl)phenyl]ethylamine dihydrochloride. MS (EI) for $C_{13}H_{21}N_3$: 220 ($MH^+$).

Reagent Preparation 4: (S)-2-[4-(1-aminoethyl)phenoxy]-N,N-diethylethylamine

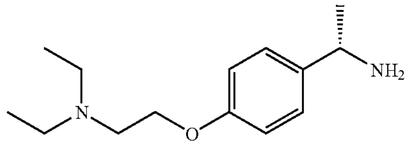

STEP 1: A solution of(S)-1-(4-methoxyphenyl)ethanamine (3.10 g, 20.5 mmol) in dichloromethane (30 ml) was cooled to −78° C. and a solution of boron tribromide (3.88 ml, 41 mmol) in dichloromethane (15 ml) was added dropwise. The reaction mixture was stirred at −78° C. for two hours and then at room temperature for 2 h. The solution was then cooled to 0° C. and water (15 ml) was added followed by saturated aqueous sodium carbonate to pH 8. The mixture was partially concentrated by rotary evaporation, tetrahydrofuran (50 ml) was then added followed by di-tert-butyl dicarbonate (4.47 g, 20.5 mmol) and the reaction mixture was stirred at room temperature overnight. The water layer was extracted with ethyl acetate (2×150 ml) and the combined organic layers were washed with brine, dried over sodium sulfate then filtered and concentrated. The residue was purified by silica gel column chromatography using hexanes: ethyl acetate 4:1 to 3:1 as eluent to afford 1,1-dimethylethyl [(1S)-1-(4-hydroxyphenyl)ethyl]carbamate (2.90 g, 60% yield). $^1$H NMR (400 MHz, $CDCl_3$): 7.10 (br s, 2H), 6.73 (d, 2H), 6.07 (br s, 1H), 4.91-4.51 (m, 2H), 1.56-1.25 (m, 12H).

STEP 2: To a solution of 1,1-dimethylethyl [(1S)-1-(4-hydroxyphenyl)ethyl]carbamate (2.90 g, 12.2 mmol) in dimethylformamide (25 ml) were added cesium carbonate (11.9 g, 36.6 mmol) and 2-bromo-N,N-diethylamine hydrobromide (3.18 g, 12.2 mmol) and the reaction mixture was stirred at 60° C. for 24 h. The mixture was partitioned between ethyl acetate (150 ml) and water (75 ml) and the organic phase was washed with 1 M aqueous sodium hydroxide (50 ml), 5% aqueous lithium chloride (50 ml), dried over sodium sulfate then filtered and concentrated to give 1,1-dimethylethyl [(1S)-1-(4-{[2-(diethylamino)ethyl]oxy}phenyl)ethyl]carbamate (0.920 g, 22% yield) as a yellow oil. MS (EI) for $C_{19}H_{32}N_2O_3$: 337 ($MH^+$).

STEP 3: A solution of 1,1-dimethylethyl [(1S)-1-(4-{[2-(diethylamino)ethyl]oxy}phenyl)ethyl]carbamate (0.912 g, 2.7 mmol) in 4N hydrogen chloride in dioxane (5 mL) and methanol (5 mL) was refluxed for 2 min. After cooling to room temperature the mixture was concentrated to afford (S)-2-[4-(1-aminoethyl)phenoxy]-N,N-diethylethylamine as the hydrochloride salt (0.830 g, 99% yield). MS (EI) for $C_{14}H_{24}N_2O$: 237 ($MH^+$).

Using analogous synthetic techniques and substituting with alternative starting reagents, the following reagents were prepared. Alternative starting materials were obtained commercially unless otherwise indicated.

2-[4-(aminomethyl)phenoxy]-N,N-diethylethylamine

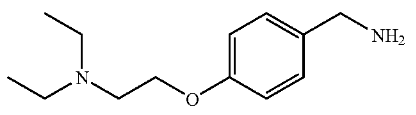

Synthesized according to the method of reagent preparation 4 using 4-(aminomethyl)phenol in step 1. $^1H$ NMR ($CD_3OD$): 7.45 (d, 2H), 7.10 (d, 2H), 4.40 (t, 2H), 4.06 (s, 2H), 3.70 (s, 2H), 3.65 (t, 2H), 3.32 (t, 2H), 1.39-1.36 (m, 6H). MS (EI) for $C_{13}H_{22}N_2O$: 223.

(S)-2-[4-(1-aminoethyl)-3-fluorophenoxy]-N,N-diethylethylamine

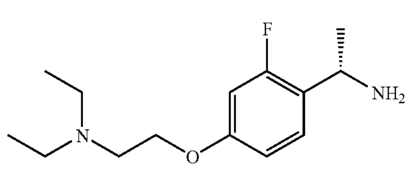

Synthesized according to the method of reagent preparation 4 using (S)-4-(1-aminoethyl)-3-fluorophenol in step 1. MS (EI) for $C_{14}H_{23}FN_2O$: 255 ($MH^+$).

2-[3-(aminomethyl)phenoxy]-N,N-diethylethylamine

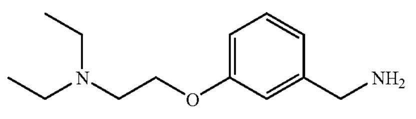

Synthesized according to the method of reagent preparation 4 using 3-(aminomethyl)phenol in step 1. $^1H$ NMR (DMSO-$d_6$): 6.05 (t, 2H), 5.85 (s, 2H), 5.75-5.72 (m, 2H), 3.05-3.03 (m, 2H), 2.28 (s, 2H), 2.28-2.01 (m, 2H), 1.95-1.93 (m, 10H). MS (EI) for $C_{13}H_{22}N_2O$: 223.

Reagent Preparation 5: [3-fluoro-4-(4-methylpiperazin-1-yl)phenyl]benzylamine

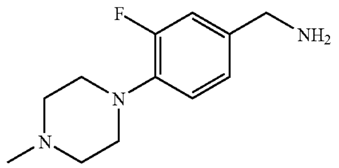

STEP 1: To 4-bromo-3-fluorobenzoic acid (2.00 g, 9.13 mmol) in methanol (12 ml) was added sulfuric acid (500 μl) and heated to 80° C. for 18 h then cooled to room temperature and concentrated. The residue was diluted with saturated sodium bicarbonate and extracted with ethyl acetate. The organic layer was dried over sodium sulfate, filtered, and then concentrated to afford (2.07 g, 97%) of methyl 4-bromo-3-fluorobenzoate, which was used without further purification. $^1H$ NMR (400 MHz, $CD_3OD$): 7.80-7.73 (m, 3H), 3.91 (s, 3H). MS (EI) for $C_8H_6BrFO_2$: 234 ($MH^+$).

STEP 2: To 1-methylpiperazine (980 μl, 8.80 mmol) in toluene (15 ml) was added tris(dibenzylidene acetone)dipalladium (201 mg, 0.22 mmol), BINAP (550 mg, 0.88 mmol), and cesium carbonate (4.30 g, 13.2 mmol). The mixture was stirred for 30 minutes before the addition of methyl 4-bromo-3-fluorobenzoate (2.05 g, 8.80 mmol), after which, the temperature was increased to 105° C. and stirred for an additional 18 h. The mixture was cooled and filtered through Celite, washed with ethyl acetate, and the resultant filtrate concentrated in vacuo to afford an orange oil. The residue was purified by column chromatography eluting with 5% methanol in dichloromethane. Pure fractions were concentrated to afford (1.80 g, 81%) of methyl 3-fluoro-4-(4-methylpiperazin-1-yl)benzoate as a colorless oil. $^1H$ NMR (400 MHz, $CD_3OD$): 7.78-7.73 (d, 1H), 7.64-7.59 (d, 1H), 7.09-7.03 (m, 1H), 3.86 (s, 3H), 3.26-3.20 (m, 4H), 2.65-2.59 (m, 4H), 2.35 (s, 3H). MS (EI) for $C_{13}H_{17}FN_2O_2$: 253 ($MH^+$).

STEP 3: To methyl 3-fluoro-4-(4-methylpiperazin-1-yl)benzoate (1.80 g, 7.13 mmol) in methanol (40 ml) was added 1 M sodium hydroxide (25 ml, 25.0 mmol). The solution was stirred at 50° C. for 3 h, at which point the mixture was concentrated. The residue was diluted with water (10 ml) and the pH adjusted to 6 with 1 N hydrochloric acid. The resultant precipitate was collected by filtration and dried in vacuo to afford (733 mg, 43%) of 3-fluoro-4-(4-methylpiperazin-1-yl)benzoic acid. $^1H$ NMR (400 MHz, $CD_3OD$): 7.73-7.68 (d, 1H), 7.62-7.57 (d, 1H), 7.03-6.97 (m, 1H), 3.26-3.20 (m, 4H), 2.83-2.76 (m, 4H), 2.47 (s, 3H). MS (EI) for $C_{12}H_{15}FN_2O_2$: 239 ($MH^+$).

STEP 4: To 3-fluoro-4-(4-methylpiperazin-1-yl)benzoic acid (250 mg, 1.05 mmol) in THF (10 ml) was added triethylamine (221 μl, 1.58 mmol) and isobutyl chloroformate (145 μl, 1.10 mmol). The mixture was stirred at 0° C. for 1 hour, at which time concentrated aqueous ammonia (3 ml) was added. The reaction mixture was stirred for 3 hours then the volume was reduced in vacuo. The residue was diluted with water and extracted with ethyl acetate. The organic layer was washed with brine, dried over anhydrous sodium sulfate, filtered, and then concentrated to afford (30.0 mg, 12%) of 3-fluoro-4-(4-methylpiperazin-1-yl)benzamide, which was used without further purification. MS (EI) for $C_{12}H_{16}FN_3O$: 238 ($MH^+$).

STEP 5: To 3-fluoro-4-(4-methylpiperazin-1-yl)benzamide (300 mg, 1.33 mmol) in THF (10 ml) was added sodium borohydride (252 mg, 6.67 mmol), followed by dropwise addition of boron trifluoride etherate (2.28 ml, 8.65 mmol) over 5 minutes. The mixture was stirred at 70° C. for 16 h, at which point the mixture was cooled and quenched with 1N aqueous hydrochloric acid then THF was removed by rotary evaporation. The mixture was diluted with water (10 ml) and the pH adjusted to 10 with 1 N sodium hydroxide, extracted with ethyl acetate and the organic phase dried over sodium sulfate, filtered, and concentrated to afford (221 mg, 75%) of [3-fluoro-4-(4-methylpiperazin-1-yl)phenyl]benzylamine. $^1H$ NMR (400 MHz, $CD_3OD$): 7.23-7.11 (m, 3H), 4.05 (s, 2H), 3.49-3.40 (m, 2H), 3.26-3.20 (m, 2H), 3.17-3.08 (m, 2H), 2.99-2.91 (m, 2H), 2.68 (s, 3H). MS (EI) for $C_{12}H_{18}FN_3$: 224 ($MH^+$).

Reagent Preparation 6: 3-fluoro-4-methoxybenzylamine

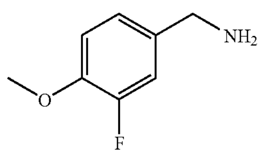

STEP 1: A mixture of 3-fluoro-4-hydroxybenzoic acid (500 mg, 3.2 mmol), cesium carbonate (3.1 g, 9.6 mmol) and iodomethane (440 μl, 7.0 mmol) in dimethylformamide (7 mL) was stirred at room temperature for 4 hours. The mixture was diluted with ethyl acetate and washed with 5% aqueous lithium chloride, 1N aqueous sodium hydroxide, brine, then dried over anhydrous sodium sulfate. Filtration and concentration afforded 534 mg, 2.9 mmol (92%) of methyl 3-fluoro-4-(methyloxy)benzoate. MS (EI) for $C_9H_9FO_3$: 185 ($MH^+$).

STEP 2: A solution of methyl 3-fluoro-4-(methyloxy)benzoate (534 mg, 2.9 mmol) in 35% aqueous potassium hydroxide:methanol (1:4, 10 mL) was stirred at reflux for 1 hour. The solution was cooled to room temperature and the methanol was evaporated. The pH of the aqueous portion was brought to 2 using concentrated hydrochloric acid. The precipitate which formed was collected by filtration and washed with water to afford 400 mg, 2.4 mmol (83%) of 3-fluoro-4-methoxybenzoic acid. MS (EI) for $C_8H_7FO_3$: 169 (M−H).

STEP 3: To a solution of 3-fluoro-4-methoxybenzoic acid (400 mg, 2.4 mmol) and triethylamine (560 μl, 3.5 mmol) in tetrahydrofuran (10 mL) cooled to 0° C. was added isobutylchloroformate (320 μl, 2.4 mmol), and the mixture was stirred at 0° C. for 1 hour. The solution was warmed to room temperature and was saturated with ammonia gas, then stirred for 15 hours at room temperature. The mixture was diluted with ethyl acetate, then washed with 20% aqueous citric acid, saturated aqueous sodium bicarbonate, and brine, then dried over anhydrous sodium sulfate. Filtration and concentration afforded 280 mg, 1.7 mmol (70%) of 3-fluoro-4-(methyloxy) benzamide. MS (EI) for $C_8H_8FNO_2$: 170 ($MH^+$).

STEP 4: To a solution of 3-fluoro-4-(methyloxy)benzamide (100 mg, 0.60 mmol) in tetrahydrofuran (5 mL) was added sodium borohydride (115 mg, 3.0 mmol) followed by the drop-wise addition of a solution of borontrifluoride etherate (48% $BF_3$ ca., 475 μl, 3.8 mmol) in tetrahydrofuran (3 mL). The mixture was stirred at reflux for 15 hours, then was cooled to room temperature and diluted with ethyl acetate. The organic portion was extracted with 20% aqueous citric acid. The aqueous portion was brought to pH 8 using solid sodium bicarbonate, then was extracted several times using ethyl acetate. The combined organic portion was washed with brine then dried over anhydrous sodium sulfate. Filtration and concentration afforded a yellow residue, which was purified by silica gel column chromatography using 10% methanol in dichloromethane as eluent. Purified fractions were pooled and concentrated to afford 56 mg, 0.36 mmol (61%) of 3-fluoro-4-methoxybenzylamine as a colorless residue. MS (EI) for $C_8H_{10}FNO$: 156 ($MH^+$).

Using analogous synthetic techniques and substituting with alternative starting reagents, the following intermediate reagents were prepared. Alternative starting reagents were obtained commercially.

4-fluoro-3-methoxybenzylamine

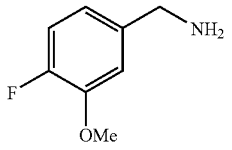

Prepared according to the method of reagent preparation 6 by omission of step 1 and 2 and using 2-fluoro-6-methoxybenzoic acid in step 3. MS (EI) for $C_8H_{10}FNO$: 156 ($MH^+$).

2-chloro-6-fluoro-3-methylbenzylamine

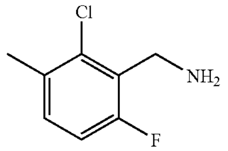

Prepared according to the method of reagent preparation 6 by omission of step 1 and 2 and using 2-chloro-6-fluoro-3-methylbenzoic acid in step 3. MS (EI) for $C_8H_9ClFN$: 178 ($MH^+$).

2-fluoro-6-methoxybenzylamine

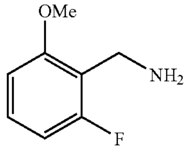

Prepared according to the method of reagent preparation 6 by omission of step 1 and 2 and using 2-fluoro-6-methoxybenzoic acid in step 3. MS (EI) for $C_8H_{10}FNO$: 156 ($MH^+$).

2,6-difluoro-4-methoxybenzylamine

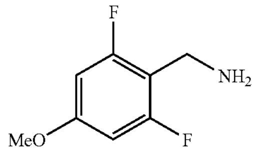

Prepared according to the method of reagent preparation 6 by omission of step 1 and 2 and using 2,6-difluoro-4-methoxybenzoic acid in step 3. MS (EI) for $C_8H_9F_2NO$: 174 ($MH^+$).

2-chloro-4-methoxybenzylamine

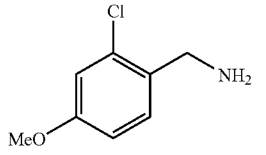

Prepared according to the method of reagent preparation 6 by using 2-chloro-4-hydroxybenzoic acid in step 1. MS (EI) for $C_8H_{10}ClNO$: 173 ($MH^+$).

4-fluoro-2-methoxybenzylamine

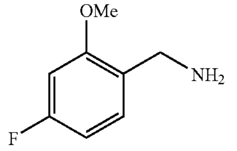

Prepared according to the method of reagent preparation 6 by using 4-fluoro-2-hydroxybenzoic acid in step 1. MS (EI) for $C_8H_{10}FNO$: 156 ($MH^+$).

Reagent Preparation 7: tert-butyl 4-(5-(1-aminoethyl)pyridin-2-yl)piperazine-1-carboxylate

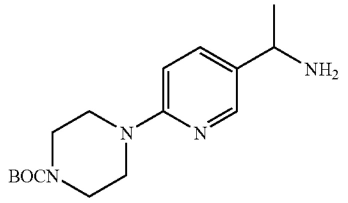

STEP 1: A mixture of ethyl 6-chloronicotinate (2.67 g, 14.4 mmol), tert-butyl piperazine-1-carboxylate (2.5 g, 13.4 mmol) and N,N-diisopropylethylamine (3.5 mL, 20 mmol) in DME (15 mL) was heated at 120° C. for 12 hours. The mixture was then cooled to room temperature and partitioned with ethyl acetate and 10% aqueous citric acid. The organic layer was washed twice with 10% aqueous citric acid then brine and dried over anhydrous sodium sulfate. Filtration and concentration followed by silica gel flash chromatography of the residue using 3:1 hexanes:ethyl acetate to 100% ethyl acetate afforded tert-butyl 4-(5-(ethoxycarbonyl)pyridin-2-yl)piperazine-1-carboxylate (3.65 g). $^1H$ NMR (400 MHz, $CDCl_3$): 8.81 (s, 1H), 8.04 (d, 1H), 6.58 (d, 1H), 4.33 (q, 2H), 3.70-3.67 (m, 4H), 3.56-3.53 (m, 4H), 1.49 (s, 9H), 1.37 (tr, 3H).

STEP 2: tert-Butyl 4-(5-(ethoxycarbonyl)pyridin-2-yl) piperazine-1-carboxylate (3.65 g, 10.9 mmol) was taken into methanol (40 mL) followed by addition of 1M aqueous sodium hydroxide (15 mL) and THF (15 mL), and the mixture was heated at 50° C. for one hour. An additional portion of 1 M aqueous sodium hydroxide (10 mL) was then added and heating was continued an additional two hours. The mixture was then cooled to room temperature and concentrated to remove organic solvents. The aqueous residue was partitioned with ethyl ether and the organic layer was discarded. The aqueous phase has carefully brought to pH 5-6 by addition of 1M aqueous hydrochloric acid to give a thick white suspension. The solid was collected by filtration and dried to give 6-(4-(tert-butoxycarbonyl)piperazin-1-yl)nicotinic acid (2.0 g). $^1H$ NMR (400 MHz, DMSO-$d_6$): 12.57 (br s, 1H), 8.64 (s, 1H), 7.95 (d, 1H), 6.86 (d, 1H), 3.67-3.62 (m, 4H), 3.45-3.40 (m, 4H), 1.43 (s, 9H).

STEP 3: 6-(4-(tert-Butoxycarbonyl)piperazin-1-yl)nicotinic acid (2.0 g, 6.5 mmol) was taken into DMF (10 mL) followed by addition of HATU (2.48 g, 6.5 mmol), N,N-diisopropylethylamine (2.5 mL, 14.1 mmol) and N,O-dimethylhydroxylamine hydrochloride (652 mg, 6.7 mmol), and the mixture was stirred at room temperature over 12 hours. The resulting solution was partitioned with ethyl acetate and water then the organic phase washed with water (3×), 10% aqueous citric acid (2×) then 0.5M aqueous sodium hydroxide and brine. The organic solution was dried over anhydrous sodium sulfate, filtered and concentrated, then purified by silica gel flash chromatography with ethyl ether as eluent to provide tert-butyl 4-(5-(methoxy(methyl)carbamoyl)pyridin-2-yl)piperazine-1-carboxylate (1.45 g). MS (EI) for $C_{17}H_{26}N_4O_4$: 351 ($MH^+$).

STEP 4: tert-Butyl 4-(5-(methoxy(methyl)carbamoyl)pyridin-2-yl)piperazine-1-carboxylate (1.45 g, 4.1 mmol) was taken into THF (20 mL) and the solution cooled to 0° C. under a nitrogen atmosphere. Methyl magnesium bromide (3.0M in ethyl ether, 3.5 mL) was added in portions and the mixture was allowed to stir 10 minutes followed by addition of another 1.5 mL aliquot then the mixture was warmed to room temperature. The solution was then partitioned with ethyl ether and water and the organic phase washed with brine then dried over anhydrous sodium sulfate, filtered and concentrated. The residue was taken into methanol (25 mL) followed by portion-wise addition of sodium borohydride solid (250 mg) over 10 minutes. The mixture was allowed to stir at room temperature another 10 minutes then concentrated. The residue was partitioned with ethyl ether and water and the aqueous phase extracted ethyl ethyl ether (2×). The combined organic layers were dried over anhydrous sodium sulfate, filtered and concentrated to give tert-butyl 4-(5-(1-hydroxyethyl)pyridin-2-yl)piperazine-1-carboxylate (1.48 g) which was carried forward without further purification.

STEP 5: tert-Butyl 4-(5-(1-hydroxyethyl)pyridin-2-yl) piperazine-1-carboxylate (1.48 g) as obtained in step 4 was taken into DMF (10 mL) followed by addition of sodium azide (580 mg, 8.9 mmol), DPPA (1.6 g, 5.7 mmol) and N,N-diisopropylethylamine (0.72 mL, 4.2 mmol) and the mixture was heated to 60° C. for 12 hours. Additional aliquots of sodium azide and DPPA were then added to the reaction mixture and the temperature was raised to 75° C. for an additional 12 hours. The mixture was then cooled to room temperature and partitioned with ethyl ether and water. The organic layer was washed with water (2×), 0.5M aqueous sodium hydroxide (2×) then with 10% aqueous citric acid brought to pH 1 with 1 M aqueous hydrochloric acid. The organic phase was discarded and the acidic aqueous phase was quickly basified to pH 7 by portion-wise addition of solid sodium bicarbonate and 50% aqueous sodium hydroxide. The neutralized aqueous phase was extracted once with ethyl ether and the organic layer dried over anhydrous sodium sulfate, filtered, and concentrated to provide tert-butyl 4-(5-(1-azidoethyl)pyridin-2-yl)piperazine-1-carboxylate (1.21 g).

STEP 6: tert-Butyl 4-(5-(1-azidoethyl)pyridin-2-yl)piperazine-1-carboxylate (1.21 g), as obtained in step 5, was hydrogenated in methanol (50 mL) in the presence of 10% palladium on carbon (390 mg) at one atmosphere of hydrogen for 6 hours. The mixture was then filtered and concentrated to afford tert-butyl 4-(5-(1-aminoethyl)pyridin-2-yl)piperazine-1-carboxylate (1.1 g).

Reagent Preparation 8:
1-(4-bromophenyl)ethylamine

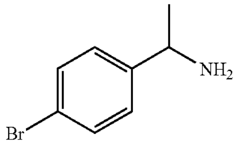

Synthesized according to the method of example 12 step 1 by using 1-(4-bromo-2-fluorophenyl)ethanone. MS (EI) for $C_8H_9BrFN$: 219 ($MH^+$).

Reagent Preparation 9:
(3S)-1-(1-methylethyl)pyrrolidin-3-yl-amine

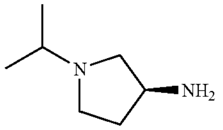

To a solution of 1,1-dimethylethyl (3S)-pyrrolidin-3-yl carbamate (500 mg, 2.68 mmol) in acetone (0.5 mL, 6.80 mmol) was added sodium triacetoxyborohydride (1.50 g, 7.07 mmol). After 15 minutes stirring, additional sodium triacetoxyborohydride (750 mg, 3.53 mmol) was added and the mixture was stirred overnight at room temperature. Ethyl acetate (15 mL) was added to reaction mixture and the organic layer was washed with 0.5 M aqueous sodium hydroxide solution (10 mL) and brine, dried with anhydrous sodium sulfate then filtered and concentrated. The residue was diluted with acetonitrile (15 mL) and 4 M hydrogen chloride in dioxane (5 mL) was added. The mixture was stirred for 2 hr at 40° C. then concentrated and dried in vacuo to give the title compound hydrochloride salt (384 mg, 72.0%). $^1H$ NMR (400 MHz, $d_4$-methanol): 4.00-4.30 (m, 1H), 3.50-3.90 (m, 4H), 3.30 (m, 1H), 2.50-2.70 (m, 1H), 2.15 (m, 1H), 1.45 (d, 6H).

Using analogous synthetic techniques and substituting with alternative starting reagents, the following reagents were prepared. Alternative starting materials were obtained commercially unless otherwise indicated.

(3R)-1-(1-methylethyl)pyrrolidin-3-amine

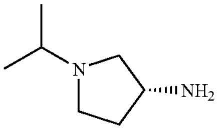

Synthesized according to the method of reagent preparation 9 by using 1,1-dimethylethyl (3R)-pyrrolidine-3-yl carbamate. MS (EI) for $C_7H_{16}N_2$: 129 ($MH^+$).

(3S)-1-ethylpyrrolidin-3-amine

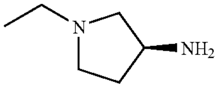

Synthesized according to the method of reagent preparation 9 by using acetaldehyde. MS (EI) for $C_6H_{14}N_2$: 115 ($MH^+$).

(3R)-1-ethylpyrrolidin-3-amine

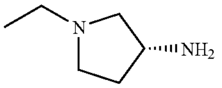

Synthesized according to the method of reagent preparation 9 by using acetaldehyde and 1,1-dimethylethyl (3R)-pyrrolidin-3-yl carbamate. MS (EI) for $C_6H_{14}N_2$: 115 ($MH^+$).

(3R)-1-methylpiperidin-3-amine

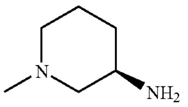

Synthesized according to the method of reagent preparation 9 by using aqueous formaldehyde and 1,1-dimethylethyl (3R)-piperidin-3-yl carbamate. MS (EI) for $C_6H_{14}N_2$: 115 ($MH^+$).

(3R)-1-ethylpiperidin-3-amine

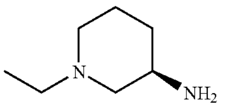

Synthesized according to the method of reagent preparation 9 by using acetaldehyde and 1,1-dimethylethyl (3R)-piperidin-3-yl carbamate. MS (EI) for $C_7H_{16}N_2$: 129 ($MH^+$).

(3R)-1-(1-methylethyl)piperidin-3-amine

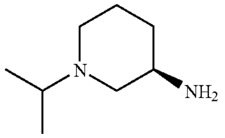

Synthesized according to the method of reagent preparation 9 by using 1,1-dimethylethyl (3R)-piperidin-3-yl carbamate. MS (EI) for $C_8H_{18}N_2$: 143 ($MH^+$).

(3S)-1-methylpiperidin-3-amine

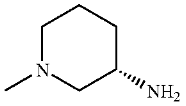

Synthesized according to the method of reagent preparation 9 by using aqueous formaldehyde and 1,1-dimethylethyl (3S)-piperidin-3-yl carbamate. MS (EI) for $C_6H_{14}N_2$: 113 (M–H).

(3S)-1-ethylpiperidin-3-amine

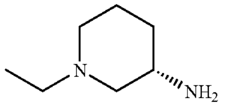

Synthesized according to the method of reagent preparation 9 by using acetaldehyde and 1,1-dimethylethyl (3S)-piperidin-3-yl carbamate. MS (EI) for $C_7H_{16}N_2$: 131 ($MH^+$).

(3S)-1-(1-methylethyl)piperidin-3-amine

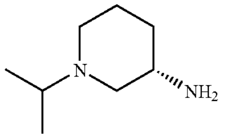

Synthesized according to the method of reagent preparation 9 by using 1,1-dimethylethyl (3S)-piperidin-3-yl carbamate. MS (EI) for $C_8H_{18}N_2$: 143 ($MH^+$).

1-methylazetidin-3-amine

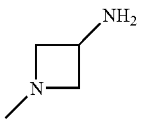

Synthesized according to the method of reagent preparation 9 by using formaldehyde and 1,1-dimethylethyl azetidin-3-ylcarbamate.

1-(1-methylethyl)piperidin-4-amine

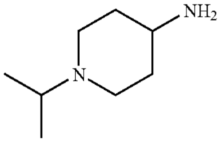

Synthesized according to the method of reagent preparation 9 by using acetone and 1,1-dimethylethyl piperidin-4-ylcarbamate. MS (EI) for $C_8H_{18}N_2$: 143 ($MH^+$).

1-ethylpiperidin-4-amine

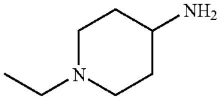

Synthesized according to the method of reagent preparation 9 by using acetaldehyde and 1,1-dimethylethyl piperidin-4-ylcarbamate. MS (EI) for $C_7H_{16}N_2$: 131 ($MH^+$).

Reagent Preparation 10: 3-(aminocarbonyl)-2-methylbenzoic Acid

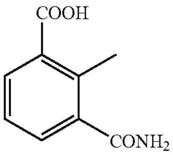

STEP 1: To a solution of methyl 3-bromo-2-methylbenzoate (0.646 g, 2.8 mmol) in 4 ml of dimethylamine was added $Pd(OAc)_2$ (0.5 mol %), sodium carbonate (0.3 g, 2.8 mmol), $K_4[Fe(CN)_6].3H_2O$ (0.262 g, 0.62 mmol). The mixture was heated to 120° C. and stirred at this temperature for 4 hours then at RT for 18 hours. The reaction mixture was diluted with 30 ml of ethyl acetate and the resulting slurry was filtered through Celite. The filtrate was washed with water (2×15 ml) then 5% aqueous ammonium hydroxide (1×15 ml). The organic layer was dried over anhydrous sodium sulfate then filtered and concentrated to provide methyl 3-cyano-2-methylbenzoate (0.248 g, 50% yield) (S. Weissman, D. Zewge, C. Chen, *J. Org. Chem.* 2005, 70, 1508-1510). $^1H$-NMR (400 MHz, DMSO-$d_6$): 8.09 (d, 1H), 8.04 (d, 1H), 7.53 (t, 1H), 3.87 (s, 3H), 2.66 (s, 3H).

STEP 2: To a solution of methyl 3-cyano-2-methylbenzoate (0.111 g, 0.63 mmol) in 3 ml of t-butanol was added potassium hydroxide (0.29 g, 5.1 mmol). The mixture was refluxed for 6 hours and stirred at room temperature for 48 hours. The mixture was rotary evaporated to dryness and the residue dissolved in water then extracted with ethyl acetate (2×20 ml). The water layer was acidified with concentrated aqueous hydrochloric acid to pH 1-2 and extracted with ethyl acetate (3×20 ml). The ethyl acetate layer was dried over anhydrous sodium sulfate, then filtered and concentrated to yield 3-(aminocarbonyl)-2-methylbenzoic acid (86 mg).

Reagent Preparation 11: 4-(aminocarbonyl)-2-methylbenzoic Acid

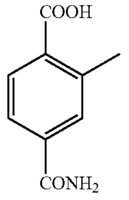

STEP 1: To a solution of 4-bromo-3-methylbenzonitrile (0.48 g, 2.43 mmol) in 1 ml of toluene at −78° C. was added 1 ml of 2.6M n-BuLi in toluene followed by quenching with dry ice (0.5 g, 12.5 mmol). The reaction mixture was warmed to room temperature, then taken into water and extracted with ethyl acetate (2×15 ml). The water layer was acidified to pH 1-2 by addition of concentrated aqueous hydrochloric acid and extracted with ethyl acetate (3×15 ml). The organic layer was dried over anhydrous sodium sulfate, then filtered and concentrated to give 4-cyano-2-methylbenzoic acid (0.08 g, 20% yield). $^{1}$H-NMR (400 MHz, DMSO-$d_6$): 13.10 (br s, 1H), 7.92 (d, 1H), 7.84 (m, 1H), 7.76 (d, 1H), 2.53 (s, 3H).

STEP 2: To 4-cyano-2-methylbenzoic acid (0.071 g, 0.44 mmol) in 2 ml of t-butanol was added potassium hydroxide (0.13 g, 2.15 mmol). The reaction mixture was refluxed for 30 min and cooled to room temperature. To the reaction mixture was added 10 ml of brine and the reaction mixture was extracted with ethyl acetate (2×15 ml). The water layer was acidified to pH 1-2 with concentrated aqueous hydrochloric acid to give a white precipitate. The solid was collected by filtration, washed several times with water (3×15 ml) and dried in vacuo to provide 4-(aminocarbonyl)-2-methylbenzoic acid (0.038 g, 49% yield). $^{1}$H-NMR (400 MHz, DMSO-$d_6$): 13.10 (br s, 1H), 8.07 (s, 1H), 7.87 (d, 1H), 7.78-7.72 (m, 2H), 7.50 (s, 1H), 2.54 (s, 3H).

Reagent Preparation 12: 4-[(aminocarbonyl)oxy]-2-methylbenzoic Acid

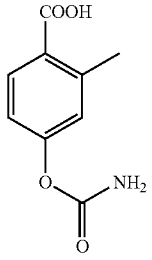

STEP 1: A solution of 4-hydroxy-2-methylbenzoic acid (550 mg, 3.60 mmol), benzyl chloride (458 mg, 3.60 mmol) and N,N-diisopropylethylamine (465 mg, 3.6 mmol) was stirred at 70° C. for 22 h. A solution of saturated sodium bicarbonate was added and the mixture was extracted with ethyl acetate. The organic layer was separated, dried over anhydrous sodium sulfate, filtered and concentrated in vacuo. The residue was purified by column chromatography ($SiO_2$, hexanes/ethyl acetate) to afford phenylmethyl 4-hydroxy-2-methylbenzoate (687 mg, 79%). $^{1}$H NMR (400 MHz, DMSO): 10.21-10.18 (br. s, 1H), 7.84-7.77 (d, 1H), 7.48-7.31 (m, 5H), 6.71-6.64 (br. s, 2H), 5.26 (s, 2H), 2.47 (s, 3H). MS (EI) for $C_{15}H_{14}O_3$: 243 ($MH^+$).

STEP 2: To a solution of phenylmethyl 4-hydroxy-2-methylbenzoate (687 mg, 2.82 mmol) in dichloromethane (8 ml) at 0° C., was added chlorosulfonyl isocyanate (1.20 g, 8.50 mmol). The reaction was allowed to warm to 25° C. and stirred for 20 h. The reaction mixture was concentrated then taken into ethyl acetate and washed with water. The organic layer was separated, dried over anhydrous sodium sulfate, filtered and concentrated in vacuo. The residue was purified by column chromatography ($SiO_2$, hexanes/ethyl acetate) to afford phenylmethyl 4-[(aminocarbonyl)oxy]-2-methylbenzoate (356 mg, 89%). $^{1}$H NMR (400 MHz, DMSO): 7.91-7.87 (d, 1H), 7.49-7.29 (m, 5H), 7.11-7.00 (m, 4H), 5.31 (s, 2H), 2.52 (s, 3H). MS (EI) for $C_{16}H_{15}NO_4$: 286 ($MH^+$).

STEP 3: A mixture of phenylmethyl 4-[(aminocarbonyl)oxy]-2-methylbenzoate (356 mg, 1.25 mmol), 5% palladium on carbon (50 mg) and ethanol (10 ml) was hydrogenated at 10 psi using a Parr apparatus. After completion of the hydrogenation, the mixture was filtered and the filtrate concentrated in vacuo. The resulting crude 4-[(aminocarbonyl)oxy]-2-methylbenzoic acid (14 mg, 6%) was used without further purification. $^{1}$H NMR (400 MHz, DMSO): 12.86-12.69 (br. s, 1H), 7.87-7.81 (d, 1H), 7.34-7.27 (br. s, 1H), 7.07-6.98 (m, 3H), 2.52 (s, 3H). MS (EI) for $C_9H_9NO_4$: 196 ($MH^+$).

Using analogous synthetic techniques and substituting with alternative starting reagents, the following reagents were prepared. Alternative starting materials were obtained commercially unless otherwise indicated.

3-[(aminocarbonyl)oxy]-2-methylbenzoic acid

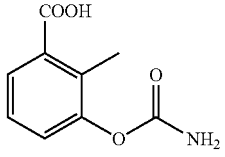

Synthesized according to the method of reagent preparation 12 starting with 3-hydroxy-2-methylbenzoic acid. $^{1}$H NMR (400 MHz, DMSO): 12.87-12.70 (br. s, 1H), 7.65-7.60 (d, 1H), 7.35-7.19 (m, 3H), 7.00-6.93 (br. s, 1H), 2.30 (s, 3H). MS (EI) for $C_9H_9NO_4$: 196 ($MH^+$).

Reagent Preparation 13: 4-(hydroxymethyl)-2-methylbenzoic Acid

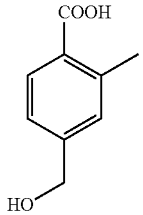

STEP 1: To 4-bromo-2-methyl benzoic acid (2.50 g, 11.6 mmol) suspended in anhydrous THF (90 ml) at −78° C. was added n-butyl lithium (9.8 ml, 2.5 M in hexane) and dimethylformamide (2.0 ml). The reaction was stirred at −78° C. for 1 h and then warmed to 25° C. and allowed to react for an additional hour. The reaction was quenched with 1 N aqueous hydrochloric acid and extracted with ethyl acetate. The organic layer was extracted with 1 N aqueous sodium hydroxide and the aqueous layer was separated and the pH adjusted with 1 N aqueous hydrochloric acid. The aqueous phase was extracted with ethyl acetate, then washed with brine, dried over sodium sulfate, filtered and concentrated. The resulting crude 4-formyl-2-methylbenzoic acid (900 mg, 47%) was obtained and was used without further purification. $^1$H NMR (400 MHz, $CD_3OD$): 10.02-10.00 (s, 1H), 8.04-8.01 (d, 1H), 7.81-7.76 (m, 2H), 2.66-2.63 (s, 3H). MS (EI) for $C_9H_8O_3$: 163 ($M^-$).

STEP 2: To 4-formyl-2-methylbenzoic acid (75 mg, 0.46 mmol), in methanol (5 ml), was added sodium borohydride (26 mg, 0.69 mmol). The solution was stirred at 25° C. for 1 h. The reaction was quenched with saturated aqueous ammonium chloride and the pH adjusted to 2 with 2 N aqueous hydrochloric acid, then extracted with dichloromethane. The organic layer was separated, dried over anhydrous sodium sulfate, filtered and concentrated. The resulting crude 4-(hydroxymethyl)-2-methylbenzoic acid (37 mg, 76%) was obtained and was used without further purification. $^1$H NMR (400 MHz, DMSO): 12.73-12.68 (s, 1H), 7.82-7.77 (d, 1H), 7.24-7.19 (m, 2H), 5.32-5.27 (m, 1H), 4.53-4.48 (d, 2H), 2.53-2.49 (s, 3H). MS (EI) for $C_9H_{10}O_3$: 167 ($MH^+$).

Reagent Preparation 14:
2-[3-(aminocarbonyl)phenyl]acetic Acid

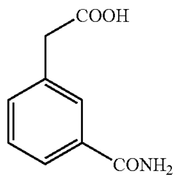

A solution of 3-cyanophenylacetic acid (0.2 g, 1.24 mmol) in a mixture of trifluoroacetic acid (1 ml) and concentrated sulfuric acid (0.5 ml) was stirred at room temperature for 16 h. The reaction mixture was then poured into ice-cold water and the resulting solid was filtered, washed with water and dried under vacuum to give 2-[3-(aminocarbonyl)phenyl] acetic acid (0.167 g, 75% yield). MS (EI) for $C_9H_9NO_3$: 178 (M−H).

Reagent Preparation 15:
7-methyl-1-benzofuran-6-carboxylic Acid

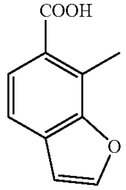

STEP 1: A solution of 3-hydroxy-2-methylbenzoic acid (5 g, 33 mmol) and sulfuric acid (500 µl) in methanol (20 mL) was stirred at reflux for 15 hours. The reaction mixture was allowed to cool to room temperature and partitioned between water and ethyl acetate. The aqueous portion was extracted with ethyl acetate and the combined organic portion was washed with saturated sodium bicarbonate, brine, and then was dried over sodium sulfate, filtered and concentrated under reduced pressure to afford (5.46 g, 100%) of methyl 3-hydroxy-2-methylbenzoate. $^1$H NMR (400 MHz, DMSO-$d_6$): 9.71 (s, 1H), 7.20-7.17 (m, 1H), 7.11-7.07 (m, 1H), 7.01-6.97 (m, 1H), 3.79 (s, 3H), 2.28 (s, 3H). MS (EI) for $C_9H_{10}O_3$: 166 ($MH^+$).

STEP 2: A mixture of 3-hydroxy-2-methylbenzoate (5.46 g, 33 mmol), allyl bromide (4.33 mL, 50 mmol) and cesium carbonate (21.5 g, 66 mmol) in dimethylformamide (60 mL) was stirred at 60° C. for 2.5 hours. The reaction mixture was allowed to cool to room temperature and was then partitioned between water and ethyl acetate. The aqueous portion was extracted twice using ethyl acetate, and the combined organic portion was washed with 5% aqueous lithium chloride, 1N aqueous sodium hydroxide, brine, and then was dried over sodium sulfate, filtered and concentrated in vacuo to afford (6.85 g, 100%) of methyl 2-methyl-3-(prop-2-en-1-yloxy) benzoate as a colorless oil. $^1$H NMR (400 MHz, DMSO-$d_6$): 7.33-7.30 (m, 1H), 7.27-7.23 (m, 1H), 7.18-7.15 (m, 1H), 6.13-6.02 (m, 1H), 5.35 (dd, 2H), 4.61 (d, 2H), 3.82 (s, 3H), 2.35 (s, 3H). MS (EI) for $C_{12}H_{14}O_3$: 207 ($MH^+$).

STEP 3: The above methyl 2-methyl-3-(prop-2-en-1-yloxy)benzoate was heated at 180° C. for 1 hour. The reaction mixture was allowed to cool to room temperature then purified by column chromatography using 10-20% ethyl acetate in hexanes as eluent. Combined pure fractions were concentrated and dried in vacuo to afford (1.64 g, 24%) of methyl 3-hydroxy-2-methyl-4-prop-2-en-1-ylbenzoate. $^1$H NMR (400 MHz, DMSO-$d_6$): 8.62 (br s, 1H), 7.22 (d, 1H), 6.99 (d, 1H), 6.00-5.89 (m, 1H), 5.07-5.02 (m, 2H), 3.79 (s, 3H), 3.40-3.35 (m, 2H), 2.35 (3H). MS (EI) for $C_{12}H_{14}O_3$: 207 ($MH^+$).

STEP 4: A solution of methyl 3-hydroxy-2-methyl-4-prop-2-en-1-ylbenzoate (1.64 g, 8.0 mmol) in methanol (20 mL) was cooled to −78° C. While maintaining the reaction temperature at −78° C., ozone was bubbled into the reaction mixture for 30 minutes, followed by the addition of dimethyl sulfide (5 mL). The reaction mixture was allowed to warm to room temperature and was then stirred for an additional 15 hours. The reaction mixture was concentrated in vacuo and diluted with diethyl ether. The organic portion was washed with water, brine, dried over sodium sulfate and concentrated to afford (1.59 g, 90%) of methyl 7-methyl-2-(methyloxy)-2,3-dihydro-1-benzofuran-6-carboxylate as a yellow oil. MS (EI) for $C_{12}H_{14}O_4$: 223 ($MH^+$).

STEP 5: A solution of methyl 7-methyl-2-(methyloxy)-2,3-dihydro-1-benzofuran-6-carboxylate in phosphoric acid (3 mL) was stirred at room temperature for 10 minutes and then was stirred at 100° C. for 15 minutes. The reaction mixture was cooled to room temperature and then was partitioned between water and diethyl ether. The aqueous portion was extracted three times with diethyl ether. The combined organic portion was washed three times with water and twice with 10% aqueous potassium carbonate. The basic portion was extracted three times with diethyl ether and the combined organic portions were washed with brine, dried over sodium sulfate, filtered and concentrated in vacuo to afford a brown residue which was purified by column chromatography eluting with 5% ethyl acetate in hexanes. Pure fractions were concentrated in vacuo to afford (371 mg, 54%) of methyl 7-methyl-1-benzofuran-6-carboxylate as a colorless oil.

$^1$H NMR (400 MHz, DMSO-$d_6$): 8.21-8.18 (m, 1H), 7.80-7.77 (m, 1H), 7.60-7.56 (m, 1H), 7.07-7.04 (m, 1H), 3.86 (s, 3H), 2.72 (s, 3H). MS (EI) for $C_{11}H_{10}O_3$: 191 ($MH^+$).

STEP 6: A solution of methyl 7-methyl-1-benzofuran-6-carboxylate (370 mg, 1.95 mmol) in 35% aqueous potassium hydroxide/methanol (1:3, 4 mL) was stirred at reflux for 30 minutes. The methanol was removed under reduced pressure and resultant aqueous portion was brought to pH 2 using 6N aqueous hydrochloric acid. The precipitate which formed was collected by filtration and dried in vacuo to afford (258 mg, 75%) of 7-methyl-1-benzofuran-6-carboxylic acid. $^1$H NMR (400 MHz, DMSO-$d_6$): 8.17 (d, 1H), 7.78 (d, 1H), 7.54 (d, 1H), 7.03 (d, 1H), 2.72 (s, 3H). MS (EI) for $C_{10}H_8O_3$: 177 ($MH^+$).

Reagent Preparation 16:
7-methyl-2,3-dihydrobenzofuran-6-carboxylic Acid

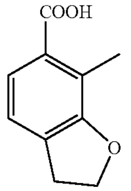

7-Methyl-1-benzofuran-6-carboxylic acid (synthesized in reagent preparation 15) (0.050 g, 0.28 mmol) was solubilized in anhydrous ethanol (2.0 mL) and 0.050 g of palladium (II) hydroxide (20%) was added. This mixture was shaken for 3 hours under 35 psi hydrogen gas using a Parr hydrogenator apparatus. The mixture was filtered through celite and concentrated in vacuo to give crude 7-methyl-2,3-dihydro-1-benzofuran-6-carboxylic acid (0.049 g, 97% yield) which was used without further purification. $^1$H NMR (400 MHz, $d_6$-DMSO): 12.67 (broad s, 1H), 7.33 (d, 1H), 7.11 (d, 1H), 4.55 (t, 2H), 3.23 (t, 2H), 2.32 (s, 3H).

Reagent Preparation 17:
3,4-dimethoxy-2-methylbenzoic Acid

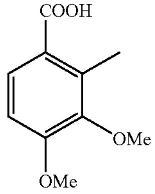

To a mixture of magnesium turnings (0.059 g, 2.40 mmol) in tetrahydrofuran (1 ml) was added a solution of 6-bromo-2,3-dimethoxy toluene (0.660 g, 2.3 mmol) in tetrahydrofuran (1 ml). The reaction was initiated by addition of methylmagnesium bromide and the solution was stirred at room temperature overnight under nitrogen. To the mixture was then added an excess of dry ice. When the addition was complete, water was added (2 ml) followed by 1.5 M hydrochloric acid to pH 2. The water phase was extracted with ethyl acetate (2×5 ml) and the combined organic layers were dried over sodium sulfate, filtered and concentrated to give 3,4-dimethoxy-2-methylbenzoic acid (0.315 g, 70% yield). MS (EI) for $C_{10}H_{12}O_4$: 195 (M−H).

Reagent Preparation 18:
3-(methyloxy)-2-propylbenzoic Acid

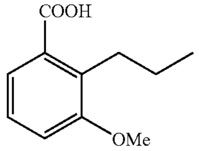

STEP 1: To methyl 3-hydroxy-2-prop-2-en-1-ylbenzoate (10.3 g, 53.6 mmol, M. A. Eissenstat et al., *J. Med. Chem.* 1995, 38, 3094-3105) and cesium carbonate (26.2 g, 80.4 mmol) in DMF (100 ml) was added methyl iodide (15.2 g, 102.2 mmol). The reaction mixture was stirred at room temperature for 18 h, then filtered and concentrated. The residue was partitioned between ethyl acetate (250 mL) and water (100 mL). The layers were separated, the organic layer was washed with 5% lithium chloride (2×100 mL) and brine (100 mL), dried over sodium sulfate, and concentrated to provide methyl 3-(methyloxy)-2-prop-2-en-1-ylbenzoate (10.3 g, 93% yield) as a pale yellow oil. $^1$H NMR (400 MHz, $CDCl_3$): δ 7.41 (m, 1H), 7.24 (m, 1H), 7.02 (m, 1H), 6.97 (m, 1H), 4.97 (m, 2H), 3.88 (s, 3H), 3.85 (s, 3H), 3.73 (m, 2H).

STEP 2: Methyl 3-(methyloxy)-2-prop-2-en-1-ylbenzoate (100 mg, 0.48 mmol) in methanol (2 mL) was hydrogenated over 5% palladium on carbon for 15 h under atmospheric pressure. The reaction mixture was filtered and 35% aqueous potassium hydroxide (1 mL) was added. The mixture was refluxed for 1 h and then concentrated. The pH was adjusted to 2 with 6N HCl. The precipitate was filtered, washed with water and dried to give 3-(methyloxy)-2-propylbenzoic acid (35 mg, 38% yield). MS (EI) for $C_{11}H_{14}O_3$: 193 (M−H)

Reagent Preparation 19:
3-(methyloxy)-2-prop-2-en-1-ylbenzoic Acid

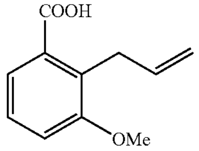

Proceeding as in reagent preparation 18 and omitting hydrogenation step 2, 3-(methyloxy)-2-prop-2-en-1-ylbenzoic acid was prepared.

Reagent Preparation 20:
2-bromo-3-(methyloxy)benzoic Acid

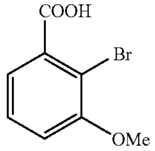

To 2-amino-3-(methyloxy)benzoic acid (4.00 g, 23.9 mmol) in 10% aqueous hydrobromic acid (54 ml) at 0° C. was added sodium nitrite (1.65 g, 23.9 mmol) in water (17 ml). To this solution was added dropwise a solution of copper (I) bromide (3.78 g, 26.3 mmol) in 48% hydrobromic acid (22 ml) and heated to 60° C. for 2 h. The mixture was cooled to 0° C., and the resultant precipitate was collected by filtration, washed with cold water and recrystallized from water to give pure 2-bromo-3-(methyloxy)benzoic acid (4.07 g, 74%). MS (EI) for $C_8H_7BrO_3$: 232 ($MH^+$).

Reagent Preparation 21: 2-iodo-3-(methyloxy)benzoic Acid

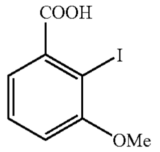

To 2-amino-3-methoxybenzoic acid (1.00 g, 5.98 mmol) in 25% aqueous hydrochloric acid (8 ml) at 0° C. was added sodium nitrite (0.45 g, 6.50 mmol) in water (3 ml). This solution was added drop-wise to a solution of potassium iodide (15.8 g, 59.3 mmol) in water (60 ml) and allowed to warm to 25° C. then stirred for 16 h. The reaction mixture was quenched with 1 N aqueous sodium bicarbonate until the pH became basic. The solution was extracted with methylene chloride and the organic dried over sodium sulfate, filtered, and concentrated to give a purple oil. The residue was purified by column chromatography, eluting with 10% methanol in dichloromethane. Pure fractions were concentrated to afford (0.623 g, 38%) of 2-iodo-3-methoxybenzoic acid. MS (EI) for $C_8H_7IO_3$: 279 ($MH^+$).

Reagent Preparation 22: 7-methyl-1H-benzotriazole-6-carboxylic Acid

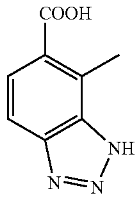

Step 1: 4-(Acetylamino)-2-methylbenzoic acid (3.93 g, 20.3 mmol) was taken up in concentrated sulfuric acid (20 mL) and warmed to solubilize. The solution was then cooled with an ice bath. Fuming nitric acid (0.86 mL) in sulfuric acid (2.0 mL) was added dropwise and the resultant solution was stirred one hour. The solution was then diluted with water and a yellow solid was collected by filtration and discarded. Upon standing, an orange solid formed in the filtrate, which was collected by filtration to give (0.61 g) of 4-amino-2-methyl-3-nitrobenzoic acid. The aqueous filtrate was then extracted (3×100 mL of 10% methanol in ethyl acetate), and the combined organic layers were dried (magnesium sulfate), filtered and concentrated to yield additional 4-amino-2-methyl-3-nitrobenzoic acid (0.90 g). $^1H$ NMR (400 MHz, $d_6$-DMSO): 7.75 (d, 1H), 6.75 (d, 1H), 2.41 (s, 3H). MS (EI) for $C_8H_8N_2O_4$: 195 ($MH^+$).

Step 2: 4-Amino-2-methyl-3-nitrobenzoic acid (1.87 g, 9.54 mmol) was solubilized in methanol (100 mL) and tetrahydrofuran (100 mL) and was treated with (trimethylsilyl) diazomethane solution (5.3 mL, 10.5 mmol, 2.0M in diethyl ether). After the reaction was shown to be complete, the mixture was concentrated and the residue was purified via column chromatography (silica gel, 5:1 hexanes/ethyl acetate) to give 1.10 g (55% yield) of methyl 4-amino-2-methyl-3-nitrobenzoate. $^1H$ NMR (400 MHz, $d_6$-DMSO): 7.73 (d, 1H), 6.75 (d, 1H), 6.51 (broad s, 2H), 3.75 (s, 3H), 2.37 (s, 3H). MS (EI) for $C_9H_{10}N_2O_4$: 210 ($MH^+$).

Step 3: To a solution of methyl 4-amino-2-methyl-3-nitrobenzoate (1.10 g, 5.22 mmol) in tetrahydrofuran (75 mL) and water (25 mL) was added ammonium formate (6.6 g, 104 mmol) and iron powder (2.92 g, 52.2 mmol). This mixture was refluxed for 12 hours then filtered and the filter cake rinsed with ethyl acetate. The filtrate layers were separated and the organic layer was dried (magnesium sulfate), filtered and concentrated to give 0.92 g (98% yield) of crude methyl 3,4-diamino-2-methylbenzoate, which was used without further purification. $^1H$ NMR (400 MHz, $d_6$-DMSO): 7.05 (d; 1H), 6.40 (d, 1H), 3.69 (s, 3H), 2.29 (s, 3H). MS (EI) for $C_9H_{12}N_2O_2$: 181 ($MH^+$).

Step 4: Methyl 3,4-diamino-2-methylbenzoate (0.27 g, 1.5 mmol) was taken up in concentrated sulfuric acid (30 mL) and heated to solubilize, then cooled with an ice bath. Concurrently, sodium nitrite (0.14 g, 2.1 mmol) was solubilized in concentrated sulfuric acid (8.4 mL) using heating. This sodium nitrite solution was then cooled and added dropwise to the cooled solution of diamine. The mixture was stirred at 0° C. for 30 minutes then warmed to 60° C. for 15 minutes. The solution was then poured onto ice and extracted with 10% methanol in ethyl acetate (2×100 mL). The combined organic layers were dried (magnesium sulfate), filtered and concentrated to give 0.3 g of crude methyl 7-methyl-1H-benzotriazole-6-carboxylate, which was taken up in methanol (5 mL) and tetrahydrofuran (10 mL) and treated with 2M aqueous lithium hydroxide (5 mL), then heated to 70° C. for one hour. This solution was made acidic using concentrated aqueous hydrochloric acid, then extracted with 10% methanol in ethyl acetate (2×50 mL). The combined organic layers were dried (magnesium sulfate), filtered and concentrated to give 0.26 g of 7-methyl-1H-benzotriazole-6-carboxylic acid. $^1H$ NMR (400 MHz, $d_6$-DMSO): 7.94 (d, 1H), 7.72 (m, 1H), 2.95 (s, 3H). MS (EI) for $C_8H_7N_3O_2$: 178 ($MH^+$).

Reagent Preparation 23: 7-methyl-1H-benzimidazole-6-carboxylic Acid

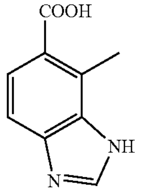

Methyl 3,4-diamino-2-methylbenzoate (synthesized in reagent preparation 22) (0.18 g, 1.0 mmol) was taken up in formic acid (8.0 mL) and refluxed for 4 hours. The solution was then concentrated in vacuo. The material was taken up in methanol (2.5 mL) and tetrahydrofuran (5.0 mL) and treated with 2M aqueous lithium hydroxide (2.5 mL) and heated to 70° C. for 12 hours. This solution was made acidic using concentrated aqueous hydrochloric acid, then extracted with 10% methanol in ethyl acetate (2×50 mL). The combined organic layers were dried (magnesium sulfate), filtered and concentrated to give 0.055 g of 7-methyl-1H-benzimidazole-6-carboxylic acid. $^1H$ NMR (400 MHz, $d_6$-DMSO): 9.34 (s, 1H), 7.94 (d, 1H), 7.64 (d, 1H), 2.85 (s, 3H). MS (EI) for $C_9H_8N_2O_2$: 177 ($MH^+$).

Reagent Preparation 24: 4-(hydroxymethyl)-3-(methyloxy)benzoic Acid

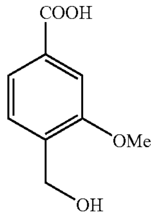

STEP 1: A mixture of methyl 4-methyl-3-(methyloxy)benzoate (1.00 g, 5.55 mmol), N-bromosuccinimide (1.09 g, 6.10 mmol) and a catalytic amount of 2,2'-azobis(isobutyronitrile) (AIBN) was refluxed in carbon tetrachloride (40 ml) for 16 h. The reaction mixture was filtered and the solution was washed with brine (25 ml), dried over sodium sulfate and concentrated to give methyl 4-(bromomethyl)-3-(methyloxy) benzoate (1.4 g, 97% yield).

STEP 2: methyl 4-(bromomethyl)-3-(methyloxy)benzoate (300 mg, 1.15 mmol) was suspended in water (3 ml) and concentrated aqueous hydrochloric acid (380 μl) was added. The reaction mixture was refluxed for 16 h, then cooled to room temperature and partitioned with ethyl acetate (10 ml). The organic phase was separated, washed with brine, dried over sodium sulfate and concentrated. The residue was purified by flash chromatography on silica gel (dichloromethane: methanol 95:5) to provide 4-(hydroxymethyl)-3-(methyloxy) benzoic acid (74 mg, 35% yield). MS (EI) for $C_9H_{10}O_4$: 181(M−H).

Reagent Preparation 25: 4-(aminocarbonyl)-3-(cyclobutyloxy)benzoic Acid

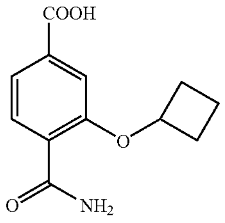

STEP 1: To a solution of methyl 4-bromo-3-hydroxybenzoate (1.01 g, 4.4 mmol) in 7 ml of dimethylamine was added $Pd(OAc)_2$ (15 mg, 0.5 mol %), sodium carbonate (0.47 g, 4.4 mmol) and potassium ferricyanide (0.41 g, 0.97 mmol). The mixture was heated to 120° C. and stirred at this temperature for 4 hours and at RT for 18 hours. The reaction mixture was diluted with 30 ml of ethyl acetate and the resulting slurry was filtered through Celite. The filtrate was washed with water (2×15 ml) and 5% aqueous ammonium hydroxide (1×15 ml). The organic layer was dried over sodium sulfate, filtered and concentrated to provide methyl 4-cyano-3-hydroxybenzoate (0.26 g, 33.5% yield) (S. Weissman, D. Zewge, C. Chen; *J. Org. Chem.* 2005, 70, 1508-1510). $^1H$ NMR (400 MHz, $CD_3OD$): 7.65 (d, 1H), 7.56-7.54 (m, 2H), 3.91 (s, 3H). MS (EI) for $C_9H_7NO_3$: 178 ($MH^+$).

STEP 2: To a solution of methyl 4-cyano-3-hydroxybenzoate (0.067 g, 0.38 mmol) in 2 ml of DMF was added cesium carbonate (0.2 g, 0.62 mmol), bromocyclobutane (0.051 g, 0.38 mmol), and the reaction mixture was heated at 60° C. and stirred at this temperature for 3 hrs. The reaction mixture was cooled to RT, poured into ice water, and extracted several times with ethyl acetate (3×20 ml). The organic solution was dried over $Na_2SO_4$, filtered, rotary evaporated to dryness then dried in vacuo to provide methyl 4-cyano-3-(cyclobutyloxy) benzoate (0.055 g, 63%). $^1H$ NMR (400 MHz, $CD_3OD$): 7.74 (d, 1H), 7.67 (d, 1H), 7.54 (s, 1H), 3.93 (s, 3H), 2.57-2.52 (m, 2H), 2.26-2.21 (m, 2H), 1.94-1.90 (m, 1H), 1.94-1.78 (m, 2H). MS (EI) for $C_{13}H_{13}NO_3$: 232 ($MH^+$).

STEP 3: To a solution of methyl 4-cyano-3-(cyclobutyloxy)benzoate (0.051 g, 0.23 mmol) in 2 ml of ethanol was added 0.5 ml of DMSO, 1 ml of 1N aqueous sodium hydroxide, 1 ml of 30% aqueous hydrogen peroxide, and the reaction mixture was stirred at RT for 18 hrs. The reaction mixture was diluted with 10 ml of water and the aqueous solution extracted three times with ethyl acetate (20 ml). The aqueous layer was acidified to pH 3-4 by portion-wise addition of aqueous hydrochloric acid, then extracted with ethyl acetate (3×20 mL). The organic solution was rotary evaporated to dryness and dried in vacuo to provide 4-(aminocarbonyl)-3-(cyclobutyloxy)benzoic acid (0.026 g, 50%). $^1H$ NMR (400 MHz, DMSO-$d_6$): 13.25 (s, 1H), 7.80 (d, 1H), 7.68 (s, 1H), 7.63 (s, 1H), 7.55 (d, 1H), 7.41 (s, 1H), 4.88-4.85 (m, 1H), 2.44-2.43 (m, 2H), 2.18-2.14 (m, 2H), 1.99-1.73 (m, 2H). MS (EI) for $C_{12}H_{13}NO_4$: 236 ($MH^+$).

Reagent Preparation 26: 4-(aminocarbonyl)-3-(methoxy)benzoic Acid

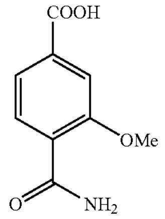

Synthesized according to the method of reagent preparation 25 using iodomethane in step 2. $^1H$NMR (400 MHz, $CD_3OD$): 13.21 (s, 1H), 7.81 (d, 1H), 7.67 (d, 1H), 7.59 (d, 1H), 2.49 (s, 3H). MS (EI) for $C_9H_9NO_4$: 196 ($MH^+$).

Reagent Preparation 27: 4-(aminocarbonyl)-3-[(2-morpholin-4-ylethyl)oxy]benzoic Acid

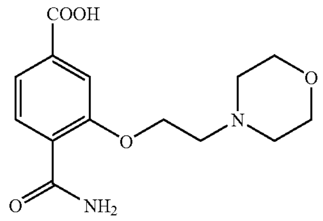

Synthesized according to the method of reagent preparation 25 using 4-(2-chloroethyl)morpholine hydrochloride in step 2. MS (EI) for $C_{14}H_{18}N_2O_5$: 295 ($MH^+$).

Reagent Preparation 28: 4-(aminocarbonyl)-2-(4-hydroxybut-1-ynyl)-3-methoxybenzoic Acid

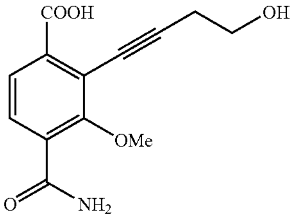

STEP 1: To a solution of 2-bromo-3-methoxybenzoic acid (718 mg, 3.11 mmol) in methanol (20 mL) was added a catalytic amount of concentrated sulfuric acid and the mixture was brought to reflux for 20 h. On cooling to room temperature, the solution was concentrated and the residue was taken into ethyl acetate and washed with water, saturated aqueous sodium bicarbonate (2×) and brine then dried over sodium sulfate. The solution was then filtered and concentrated to give methyl 2-bromo-3-methoxybenzoate (610 mg, 80%). MS (EI) for $C_9H_9BrO_3$: 245 ($MH^+$).

STEP 2: A mixture of methyl 2-bromo-3-methoxybenzoate (0.4 g, 1.63 mmol), $Pd(PPh_3)_2Cl_2$ (0.057 g, 0.082 mmol), copper (I) iodide (0.031 g, 0.16 mmol) and 3-butyn-1-ol (0.173 ml, 2.28 mmol) were stirred in trietylamine (5 ml) at 80° C. for 20 h. The solvent was concentrated under vacuum, and the residue was partitioned between ethyl acetate (15 ml) and water (5 ml). The organic layer was dried over sodium sulfate, filtered and concentrated. The residue was purified by silica gel column chromatography using hexanes:ethyl acetate 2:1 as eluent to afford methyl 2-(4-hydroxybut-1-yn-1-yl)-3-(methyloxy)benzoate (0.056 g; 15% yield). MS (EI) for $C_{13}H_{14}O_4$: 235 ($MH^+$).

STEP 3: Methyl 2-(4-hydroxybut-1-yn-1-yl)-3-(methyloxy)benzoate (0.056 g, 0.24 mmol) was dissolved in methanol (2 ml), and a solution of potassium hydroxide (0.027 g, 0.48 mmol) in water (0.5 ml) was added. The reaction mixture was stirred at 60° C. for 1 h, cooled to room temperature, and 1.5M hydrochloric acid was added to pH 4. The aqueous mixture was extracted with ethyl acetate, and the organic layer was washed with brine then dried over sodium sulfate. The mixture was then filtered and concentrated to give 2-(4-hydroxybut-1-yn-1-yl)-3-(methyloxy)benzoic acid (0.052 g, 99% yield). MS (EI) for $C_{12}H_{12}O_4$: 219 (M−H).

Reagent Preparation 29: 3-(acetylamino)-4-(aminocarbonyl)benzoic Acid

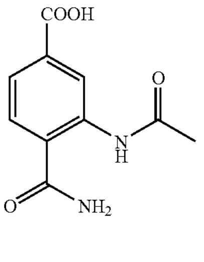

STEP 1: N,N-Diisopropylethylamine (0.41 mL, 2.30 mmol) was added to a mixture of O-(7-azabenzotriazol-1-yl)-N,N,N',N'-tetramethyluronium hexafluorophosphate (321 mg, 0.84 mmol) and 4-{[(1,1-dimethylethyl)oxy]carbonyl}-2-nitrobenzoic acid (prepared according to Gao, Y. et. al WO2001070737) (205 mg, 0.77 mmol) in N,N-dimethylformamide (2 mL), and the reaction mixture was stirred at room temperature for 30 minutes. Ammonia was bubbled into the reaction mixture and stirring was continued for 45 minutes. The reaction mixture was quenched with 0.5M aqueous hydrochloric acid solution (20 mL) and extracted with ethyl acetate (3×20 mL), and the combined extract was washed with water (20 mL), then brine (20 mL), dried over sodium sulfate, filtered and concentrated. The residue was purified by silica gel flash chromatography (25 to 75% ethyl acetate in hexanes) to give the 1,1-dimethylethyl 4-(aminocarbonyl)-3-nitrobenzoate (160 mg, 78% yield). $^1H$ NMR (400 MHz, $CDCl_3$): 8.55 (s, 1H), 8.25 (d, 1H), 7.64 (d, 1H), 6.51 (br, 1H), 6.26 (br, 1H), 1.61 (s 9H); MS (EI) for $C_{12}H_{14}N_2O_5$: 267 ($MH^+$).

STEP 2: A mixture of 1,1-dimethylethyl 4-(aminocarbonyl)-3-nitrobenzoate (213 mg, 0.80 mmol), 10% palladium on charcoal (Degussa type, 200 mg) in ethyl acetate (20 mL) was shaken in a Parr hydrogenation apparatus at 35 psi for 4 hours. The reaction mixture was filtered and concentrated to give 1,1-dimethylethyl 3-amino-4-(aminocarbonyl)benzoate (180 mg, 95% yield). MS (EI) for $C_{12}H_{16}N_2O_3$: 237 ($MH^+$).

STEP 3: Acetyl chloride (50 uL, 0.32 mmol) was added to a solution of 1,1-dimethylethyl 3-amino-4-(aminocarbonyl) benzoate (126 mg, 0.53 mmol) and pyridine (52 uL, 0.64 mmol) in tetrahydrofuran (3 mL) at 0° C., and the resulting mixture was stirred at 0° C. for one hour. The mixture was quenched with ice-water (10 mL) and extracted ethyl acetate (3×10 mL). The combined extract was washed with 15 mL, each of 5% aqueous citric acid, saturated aqueous sodium bicarbonate, and brine solutions then dried over sodium sulfate, filtered and concentrated to give the 1,1-dimethylethyl 3-(acetylamino)-4-(aminocarbonyl)benzoate (140 mg, 94% yield). MS (EI) for $C_{14}H_{18}N_2O_4$: 279 ($MH^+$).

STEP 4: A solution of 1,1-dimethylethyl 3-(acetylamino)-4-(aminocarbonyl)benzoate (110 mg, 0.47 mmol) in trifluoroacetic acid (2 mL) was stirred at room temperature for 15 minutes, concentrated, and the residue was rinsed with hexane (3×3 mL) and dried in vacuo to give 3-(acetylamino)-4-(aminocarbonyl)benzoic acid (100 mg, 97% yield), MS (EI) for $C_{10}H_{10}N_2O_4$: 223 ($MH^+$).

Reagent Preparation 30: 7-(aminocarbonyl)-1H-indole-4-carboxylic Acid

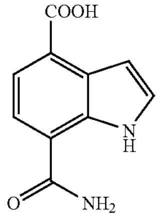

STEP 1: To a solution of 4-tert-butyl 1-methyl 2-nitroterephthalate (prepared according to Gao, Y. et. al WO2001070737) (2.15 g, 7.64 mmol) in tetrahydrofuran (30 mL) was added a 1M solution of vinylmagnesium bromide in tetrahydrofuran (23.0 mL) at −40° C., followed by stirring at room temperature for 18 hours. The reaction mixture was quenched by the addition of a solution of 1 M aqueous ammonium chloride, and the organic portion of the solvent was evaporated. The resulting material was partitioned with ethyl acetate (300 mL), and the organic layer was separated then washed with 10% aqueous citric acid (100 mL) and brine, dried over sodium sulfate, filtered and the solvent was concentrated. The resulting crude material was purified by column chromatography (hexane:ethyl acetate 9:1 to 7:3 eluent) to give 4-tert-butyl 7-methyl 1H-indole-4,7-dicarboxylate (0.58 g, 27%). $^1$H NMR (400 MHz, $CDCl_3$): 10.00 (bs, 1H), 7.88 (dd, 2H), 7.43 (m, 1H), 7.19 (m, 1H), 4.00 (s, 3H), 1.66 (s, 9H). MS (EI) for $C_{15}H_{17}NO_4$: 274 (M−H).

STEP 2: To a solution of 4-tert-butyl 7-methyl 1H-indole-4,7-dicarboxylate (0.58 g, 2.10 mmol) in a mixture of methanol (20 mL), terahydrofuran (10 mL) and water (10 mL) was added a 2M aqueous solution of lithium hydroxide (2.1 mL, 4.20 mmol), and the reaction mixture was stirred at 40° C. until full consumption of starting material. The organic portion of the solvent was evaporated and the pH of the aqueous solution was adjusted to 3-4 by the addition of 1 M aqueous hydrochloric acid. The acidic aqueous phase was partitioned with ethyl acetate (150 mL), and the organic layer was separated and washed with brine, dried over sodium sulfate, filtered and concentrated to give 4-(tert-butoxycarbonyl)-1H-indole-7-carboxylic acid (0.36 g, 67%). MS (EI) for $C_{14}H_{15}NO_4$: 260 (M−H).

STEP 3: A solution of 4-(tert-butoxycarbonyl)-1H-indole-7-carboxylic acid (0.36 g, 1.38 mmol), HATU (0.30 g, 1.60 mmol), 4-methylmorpholine (0.75 mL, 6.89 mmol) and a 2M solution of ammonia in methanol (1.80 mL, 3.45 mmol) in dimethylformamide (5 mL) was stirred at room temperature for 18 hours. The reaction mixture was diluted with ethyl acetate (150 mL) and the organic layer was washed with brine, dried over sodium sulfate, filtered and concentrated. Purification by column chromatography chloroform: (10% ammonium hydroxide in methanol) 9:1 as eluent afforded tert-butyl 7-carbamoyl-1H-indole-4-carboxylate (0.18 g, 50%). $^1$H NMR (400 MHz, $CDCl_3$): 10.50 (bs, 1H), 7.83 (d, 1H), 7.43 (m, 2H), 7.15 (m, 1H), 6.30 (bd, 2H), 1.62 (s, 9H). MS (EI) for $C_{14}H_{16}N_2O_3$: 259 (M−H).

STEP: 4: To a solution of tert-butyl 7-carbamoyl-1H-indole-4-carboxylate (0.15 g, 0.58 mmol) in dichloromethane (10 mL) was added trifluoroacetic acid (10 mL), and the mixture was heated to reflux until the starting material was fully consumed. The solvent was evaporated followed by rotary evaporation of the residue from a mixture of ethyl acetate (50 mL) and toluene (50 mL). The procedure was repeated three times and the residue dried in vacuo to obtain 7-(aminocarbonyl)-1H-indole-4-carboxylic acid (0.16 g, 89%). MS (EI) for $C_{10}H_8N_2O_3$: 205 ($MH^+$).

Reagent Preparation 31:
2-methyl-3-(methylamino)benzoic Acid

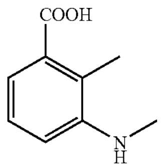

STEP 1: To 3-amino-2-methylbenzoic acid (500 mg, 3.3 mmol) in methanol (20 ml) was added sulfuric acid (500 µl) and heated to 70° C. for 22 h, at which point the volume was reduced by rotary evaporation. The residue was diluted with saturated sodium bicarbonate and extracted with ethyl acetate. The resultant organic layer was dried over sodium sulfate, filtered, and then concentrated to afford a tan oil (125 mg, 23%) of methyl 3-amino-2-methylbenzoate, which was used without further purification. $^1$H NMR (400 MHz, DMSO-$d_6$): 6.99-6.93 (m, 1H), 6.89-6.86 (d, 1H), 6.81-6.78 (d, 1H), 5.12-5.07 (br. s, 2H), 3.78 (s, 3H), 2.16 (s, 3H). MS (EI) for $C_9H_{11}NO_2$: 166 ($MH^+$).

STEP 2: To methyl 3-amino-2-methylbenzoate (125 mg, 0.758 mmol) in DMF (2 ml) was added DIPEA (291 µl, 1.67 mmol) and methyl iodide (104 µl, 1.67 mmol) and heated to 70° C. for 6 h in a sealed vessel. The mixture was diluted with 1N aqueous potassium hydroxide (3 ml) and immediately extracted with ethyl acetate. The resultant organic layer was dried over sodium sulfate, filtered and concentrated to afford a brown residue which was purified by column chromatography eluting with 15% ethyl acetate in hexanes. Pure fractions were concentrated to afford (30 mg) of a faster eluting fraction consisting of methyl 3-(dimethylamino)-2-methylbenzoate and (125 mg) of a slower eluting fraction consisting of methyl 2-methyl-3-(methylamino)benzoate. $^1$H NMR methyl 2-methyl-3-(methylamino)benzoate (400 MHz, DMSO-$d_6$): 7.14-7.08 (m, 1H), 6.91-6.87 (d, 1H), 6.67-6.62 (d, 1H), 5.34-5.27 (br. s, 1H), 3.78 (s, 3H), 2.76-2.71 (d, 3H), 2.17 (s, 3H). MS (EI) for $C_{10}H_{13}NO_2$: 180 ($MH^+$). $^1$H NMR methyl 3-(dimethylamino)-2-methylbenzoate (400 MHz, DMSO-$d_6$): 7.40-7.36 (d, 1H), 7.28-7.22 (m, 2H), 3.81 (s, 3H), 2.63 (s, 6H), 2.39 (s, 3H). MS (EI) for $C_{11}H_5NO_2$: 194 ($MH^+$).

STEP 3: To methyl 2-methyl-3-(methylamino)benzoate (125 mg, 0.698 mmol) in methanol (7 ml) was added 2M aqueous lithium hydroxide (1.8 ml, 3.63 mmol), and the solution was stirred at 25° C. for 3 h, at which point the volume was reduced by rotary evaporation. The aqueous mixture was diluted with water (3 ml) and the pH adjusted to 5 with 1 N hydrochloric acid. The resultant precipitate was collected by filtration and dried in vacuo to afford (50 mg, 42%) of 2-methyl-3-(methylamino)benzoic acid. MS (EI) for $C_9H_{11}NO_2$: 166 ($MH^+$).

Reagent Preparation 32:
3-(dimethylamino)-2-methylbenzoic Acid

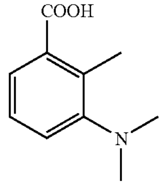

Synthesized according to the method of reagent preparation 31 by using methyl 3-(dimethylamino)-2-methylbenzoate (reagent preparation 31 step 2) in step 3. MS (EI) for $C_{10}H_{13}NO_2$: 180 ($MH^+$).

Reagent Preparation 33:
2-methyl-3-(methylthio)benzoic Acid

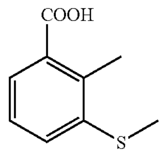

STEP 1: To a solution of 3-amino-2-methylbenzoic acid (500 mg, 3.3 mmol) in methanol (5 mL) cooled to 0° C. was added concentrated hydrochloric acid (1 mL), followed by a solution of sodium nitrite (275 mg, 4.0 mmol) in water (2 mL). The mixture was stirred at 0° C. for 30 minutes, then warmed to room temperature and stirred for an additional 30 minutes. The solution was diluted with diethyl ether to afford a solid residue that was collected by filtration, then washed with additional diethyl ether to afford 700 mg of the intermediate diazonium salt. The diazonium salt was then transferred to a warm (55° C.) solution of potassium ethylxanthogenate (635 mg, 4.0 mmol) in water (5 mL) while maintaining the pH at 8 by portion-wise addition of solid sodium carbonate. The solution was stirred at 55° C. for 30 minutes, then cooled to room temperature and poured into a 6N aqueous hydrochloric acid solution (30 mL). The precipitate which formed was collected by filtration, washed with water, then diethyl ether to afford 270 mg, 1.05 mmol (32%) of 3-{[(ethyloxy)carbonothioyl]thio}-2-methylbenzoic acid. MS (EI) for $C_{11}H_{12}S_2O_3$: 257 ($MH^+$).

STEP 2: 3-{[(ethyloxy)carbonothioyl]thio}-2-methylbenzoic acid (270 mg, 1.05 mmol) in a 1N aqueous sodium hydroxide solution (3 mL) was stirred at reflux for 15 hours. The mixture was cooled to room temperature and the pH was adjusted to 2 using concentrated aqueous hydrochloric acid. The aqueous mixture was extracted twice using dichloromethane and the combined organic solutions were washed with brine, then dried over anhydrous sodium sulfate. Filtration and concentration afforded 180 mg, 1.05 mmol (99%) of 3-mercapto-2-methylbenzoic acid. $^1H$ NMR (400 MHz, $CDCl_3$): 7.87 (d, 1H), 7.47 (d, 1H), 7.16-7.11 (m, 1H), 3.43 (s, 1H), 2.62 (s, 3H).

STEP 3: A mixture of 3-mercapto-2-methylbenzoic acid (180 mg, 1.05 mmol), cesium carbonate (690 mg, 2.1 mmol) and iodomethane (132 $L_1$, 2.10 mmol) in dimethylformamide (3 mL) was stirred at room temperature for 2 hours. The mixture was diluted with ethyl acetate then washed with 5% aqueous lithium chloride, 1N aqueous sodium hydroxide, and brine then dried over anhydrous sodium sulfate. Filtration and concentration afforded 138 mg, 0.62 mmol (58%) of methyl 2-methyl-3-(methylthio)benzoate. $^1H$ NMR (400 MHz, $CDCl_3$): 7.58 (d, 1H), 7.41 (d, 1H), 7.21-7.16 (m, 1H), 4.09 (s, 3H), 2.83 (s, 3H), 2.58 (s, 3H). MS (EI) for $C_{10}H_{12}SO_2$: 197 ($MH^+$).

STEP 4: A solution of methyl 2-methyl-3-(methylthio)benzoate (138 mg, 0.62 mmol) in 35% aqueous potassium hydroxide:methanol (1:3, 4 mL) was stirred at 80° C. for 1 hour. After cooling to room temperature the methanol was evaporated. Water (4 mL) was added and the pH of the resulting mixture was adjusted to 2 using concentrated aqueous hydrochloric acid. The precipitate which formed was collected by filtration, washed with water, then diethyl ether to afford, 85 mg, 0.43 mmol (70%) of 2-methyl-3-(methylthio)benzoic acid. $^1H$ NMR (400 MHz, $CDCl_3$): 7.76 (d, 1H), 7.37 (d, 1H), 7.29-7.25 (m, 1H), 2.65 (s, 3H), 2.49 (s, 3H). MS (EI) for $C_9H_{10}SO_2$: 181 (M−H).

Reagent Preparation 34: 4-(aminocarbonyl)-2-methyl-3-(methyloxy)benzoic Acid

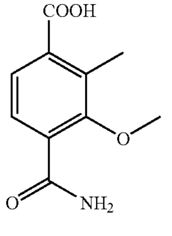

STEP 1: A solution of 3-hydroxy-2-methylbenzoic acid (5 g, 33 mmol) and concentrated sulfuric acid (3 mL) in methanol (300 mL) was stirred at reflux for 48 hours. The mixture was cooled to room temperature and the pH was adjusted to 7 using solid sodium bicarbonate. Some methanol was evaporated and residue was partitioned between saturated aqueous sodium bicarbonate and ethyl acetate. The organic portion was washed with brine then dried over anhydrous sodium sulfate. Filtration and concentration afforded 5.3 g, 32 mmol (97%) of methyl 3-hydroxy-2-methylbenzoate. $^1H$ NMR (400 MHz, $CDCl_3$): 7.41 (d, 1H), 7.13-7.09 (m, 1H), 6.94 (d, 1H), 3.89 (s, 3H), 2.46 (s, 3H). MS (EI) for $C_9H_{10}O_3$: 167 ($MH^+$).

STEP 2: To a solution of tert-butylamine (1.6 mL, 15 mmol) in dichloromethane (100 mL) at −78° C. was added drop-wise over 30 minutes a solution of bromine (773 µl, 15 mmol in 15 mL of dichloromethane). The solution was stirred at −78° C. for 30 minutes. While maintaining the temperature at −78° C., a solution of methyl 3-hydroxy-2-methylbenzoate (2.5 g, 15 mmol in 15 mL of dichloromethane) was added to the reaction mixture drop-wise over 30 minutes. The mixture was allowed to warm to room temperature and was stirred for 15 hours. The mixture was washed with 20% aqueous citric acid then brine and dried over anhydrous sodium sulfate. Filtration and concentration afforded a brown residue that was purified by silica gel column chromatography. Eluting with 10% diethyl ether in hexane, purified fractions were pooled and concentrated to afford 612 mg, 2.5 mmol (17%) of methyl 4-bromo-3-hydroxy-2-methylbenzoate as a colorless oil. $^1H$ NMR (400 MHz, $CDCl_3$): 7.37-7.29 (m, 2H), 5.71 (s, 1H), 3.81 (s, 3H), 2.53 (s, 3H). MS (EI) for $C_9H_9BrO_3$: 245 ($MH^+$).

STEP 3: A solution of methyl 4-bromo-3-hydroxy-2-methylbenzoate (610 mg, 2.5 mmol), cesium carbonate (1.22 g, 3.7 mmol) and iodomethane (162 µl, 2.6 mmol) in dimethylformamide (5 mL) was stirred at room temperature for 15 hours. The mixture was diluted with ethyl acetate, then washed with 5% aqueous lithium chloride then brine and dried over anhydrous sodium sulfate. Filtration and concentration afforded an orange residue, which was purified by silica gel column chromatography. Eluting with 15% diethyl ether in hexane, purified fractions were pooled and concentrated to afford 455 mg, 1.76 mmol (71%) of methyl 4-bromo-2-methyl-3-(methyloxy)benzoate as a colorless residue. $^1H$ NMR (400 MHz, $CDCl_3$): 7.52 (d, 1H), 7.43 (d, 1H), 3.88 (s, 3H), 3.80 (s, 3H), 2.55 (s, 3H). MS (EI) for $C_{10}H_1BrO_3$: 260 ($MH^+$).

STEP 4: To a sealed tube vessel was added methyl 4-bromo-2-methyl-3-(methyloxy)benzoate (280 mg, 1.08 mmol), copper (I) cyanide (97 mg, 1.08 mmol) and dimethylformamide (2 mL). The mixture was heated at 150° C. for 24 hours, then was cooled to room temperature and filtered through a pad of Celite. After washing the Celite with ethyl acetate, the combined filtrate was washed with 5% aqueous lithium chloride, and brine, then dried over anhydrous sodium sulfate. Filtration and concentration afforded a brown residue that was purified by silica gel column chromatography. Eluting with 10% ethyl acetate in hexane, purified fractions were pooled and concentrated to afford 150 mg, 0.73 mmol (68%) of methyl 4-cyano-2-methyl-3-(methyloxy)benzoate. $^1H$ NMR (400 MHz, $CDCl_3$): 7.61 (d, 1H), 7.47 (d, 1H), 3.99 (s, 3H), 3.93 (s, 3H), 2.49 (s, 3H). MS (EI) for $C_{11}H_{11}NO_3$: 206 ($MH^+$).

STEP 5: Methyl 4-cyano-2-methyl-3-(methyloxy)benzoate (150 mg, 0.73 mmol) in a solution of 35% aqueous potassium hydroxide:methanol (1:3, 4 mL) was stirred at 60° C. for 1 hour. The mixture was cooled to room temperature, and the methanol was removed by rotary evaporation. Water (4 mL) was added to the mixture and the pH was adjusted to 2 using concentrated aqueous hydrochloric acid. The precipitate which formed was collected by filtration and was washed with water, then hexanes to afford 86 mg, 0.45 mmol (62%) of 4-cyano-2-methyl-3-(methyloxy)benzoic acid. $^1$H NMR (400 MHz, $d_6$-DMSO): 7.72 (d, 1H), 7.60 (d, 1H), 3.90 (s, 3H), 2.40 (s, 3H). MS (EI) for $C_{10}H_9NO_3$: 190 (M−H).

STEP 6: To a solution of 4-cyano-2-methyl-3-(methyloxy) benzoic acid (80 mg, 0.42 mmol) in DMSO:ethanol (1:4, 1 mL) was added 1N aqueous sodium hydroxide (1 mL), and hydrogen peroxide (30% wt. in water, 1 mL). The mixture was stirred at room temperature for 72 hours, then partitioned between 1N aqueous sodium hydroxide and ethyl acetate and the organic layer discarded. The pH of the aqueous portion was adjusted to 7 using 1N aqueous hydrochloric acid. The aqueous portion was extracted several times using ethyl acetate, and the combined organic portion was washed with brine then dried over anhydrous sodium sulfate. Filtration and concentration afforded 55 mg, 0.26 mmol (63%) of 4-(aminocarbonyl)-2-methyl-3-(methyloxy)benzoic acid. $^1$H NMR (400 MHz, $d_6$-DMSO): 7.77 (br s, 1H), 7.60 (br s, 1H), 7.54 (d, 1H), 7.41 (d, 1H), 3.72 (s, 3H), 2.41 (s, 3H). MS (EI) for $C_{10}H_9NO_3$: 190 (M−H).

Reagent Preparation 35: 1,4-dimethyl-1H-benzoimidazole-5-carboxylic Acid

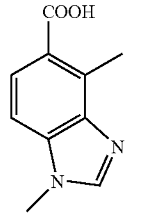

STEP 1: A mixture of 4-amino-2-methyl-3-nitrobenzoic acid (synthesized in reagent preparation 22, step 1) (500 mg, 2.6 mmol) methanol (25 mL) and concentrated sulfuric acid (1.25 mL) was stirred at 60° C. for 18 hours. The reaction mixture was cooled concentrated, diluted with ethyl acetate (50 mL), washed with water (50 mL), saturated aqueous sodium bicarbonate solution (2×30 mL), brine (30 mL), dried over sodium sulfate, filtered and concentrated to give the methyl 4-amino-2-methyl-3-nitrobenzoate (400 mg, 75% yield), MS (EI) for $C_9H_{10}N_2O_4$: 211 (MH$^+$).

STEP 2: Iodomethane (125 uL, 2.0 mmol) was added to a mixture of the methyl 4-amino-2-methyl-3-nitrobenzoate (400 mg, 1.9 mmol) and sodium hydride (60% oil dispersion, 84 mg, 2.1 mmol) in tetrahydrofuran (10 mL) at 0° C. The reaction mixture was slowly warmed to room temperature and stirred for 18 hours. The reaction mixture was quenched with saturated aqueous ammonium chloride solution and extracted with ethyl acetate. The combined extract was washed with water (2×30 mL), brine (30 mL), dried over sodium sulfate, filtered and concentrated, then purified by flash chromatography (25% ethyl acetate in hexanes) to give methyl 2-methyl-4-(methylamino)-3-nitrobenzoate (308 mg, 72% yield). $^1$H NMR (400 MHz, $CDCl_3$): 7.94 (d, 1H), 6.63 (d, 1H), 5.68 (br, 1H), 3.86 (d, 2H), 2.58 (s, 3H); MS (EI) for $C_{10}H_{12}N_2O_4$: 225 (MH$^+$).

STEP 3: A mixture of methyl 2-methyl-4-(methylamino)-3-nitrobenzoate (90 mg, 0.4 mmol), 10% palladium on charcoal (Degussa type, 90 mg), acetic acid (124 uL, 1.5 mmol), and ethyl acetate (20 mL) was shaken in a Parr hydrogenation apparatus at 40 psi for 18 hours. The reaction mixture was then filtered and concentrated. The residue was dissolved in formic acid was stirred at 100° C. for 1.5 hour. The reaction mixture was concentrated, quenched with ice-water (15 mL) and the pH was adjusted to basic by portion-wise sodium bicarbonate addition then extracted with ethyl acetate. The combined extract was washed with water (2×30 mL), brine (30 mL), dried over sodium sulfate, filtered and concentrated to give methyl 1,4-dimethyl-1H-benzimidazole-5-carboxylate (78 mg, 95% yield). MS (EI) for C $1H_{12}N_2O_2$: 205 (MH$^+$).

STEP 4: A mixture of the methyl 1,4-dimethyl-1H-benzimidazole-5-carboxylate (78 mg, 0.38 mmol) in methanol (2 mL) and 5% aqueous sodium hydroxide solution (2 mL) was stirred at 60° C. for one hour. The reaction mixture was concentrated, diluted with water (10 mL) and the pH adjusted to 4 then saturated with solid sodium chloride. The aqueous mixture was extracted ethyl acetate (3×10 mL) and the combined extract was washed with water (15 mL), brine (15 mL), dried over sodium sulfate, filtered and concentrated to give 1,4-dimethyl-1H-benzimidazole-5-carboxylic acid (46 mg, 63% yield), MS (EI) for $C_{10}H_{10}N_2O_2$: 191 (MH$^+$).

Reagent Preparation 36: 4-(aminocarbonyl)-3-(ethylamino)-2,5-dimethylbenzoic Acid

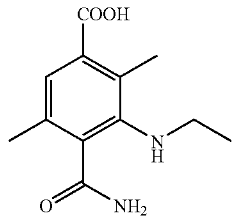

STEP 1: 2,5-Dimethylterephthalic acid (3 g, 15.5 mmol) was suspended in ether (30 mL) and methanol (10 mL) and was cooled in an ice bath. (Trimethylsilyl)diazomethane (2 M solution in hexanes; 16 mL) was added drop-wise. The mixture was stirred at ambient temperature for 0.5 h and then was quenched with acetic acid (2 mL) and was concentrated. The residue was partitioned between ethyl acetate and saturated aqueous sodium bicarbonate. The organic portion was washed with brine, dried over sodium sulfate, then filtered and was concentrated to afford dimethyl 2,5-dimethylterephthalate (3.18 g, 14.3 mmol, 93% yield). $^1$H NMR (400 MHz, $CDCl_3$): δ 7.76 (s, 2H), 3.91 (s, 6H), 2.57 (s, 6H); MS (EI) for $C_{12}H_{14}O_4$: 223 (MH$^+$).

STEP 2: Dimethyl 2,5-dimethylterephthalate (3.14 g, 14.1 mmol) was dissolved in dichloromethane (30 mL) and was cooled in an ice bath. Fuming nitric acid (7.6 mL) and concentrated sulfuric acid (0.92 mL) were added carefully, and the mixture was stirred for 1.75 h. The mixture was then quenched with water and diluted with dichloromethane. The aqueous portion was extracted with dichloromethane. The combined organic portion was dried over sodium sulfate, then filtered and concentrated to afford a yellow oil which was purified by column chromatography (silica gel, 10-20% ethyl acetate in hexanes) to afford dimethyl 2,5-dimethyl-3-nitroterephthalate (2.78 g, 10.4 mmol, 74% yield). $^1$H NMR (400 MHz, $CDCl_3$): δ 7.85 (s, 1H), 3.94 (s, 3H), 3.89 (s, 3H), 2.49 (s, 3H), 2.46 (s, 3H); GCMS for $C_{12}H_{13}NO_6$: 267 (M$^+$).

STEP 3: Dimethyl 2,5-dimethyl-3-nitroterephthalate (2.27 g, 8.50 mmol) was dissolved in 1,4-dioxane (20 mL) and was cooled in an ice bath. 1N Sodium hydroxide (8.5 mL) was added dropwise, and the mixture was stirred at ambient temperature for 2.25 h. Additional 1N sodium hydroxide (0.5 mL) was added drop-wise and the mixture was stirred at ambient temperature for a further 1 h at which point another 0.5 mL aliquot of 1N aqueous sodium hydroxide was added and stirring was continued for an additional 1 h. The reaction mixture was diluted with water and was washed with ether. The aqueous portion was acidified with 1N hydrochloric acid to pH ~2 and then was extracted with ethyl acetate (2×). The combined ethyl acetate portion was dried over sodium sulfate, then filtered and concentrated to provide 4-(methoxycarbonyl)-2,5-dimethyl-3-nitrobenzoic acid (quantitative yield). $^1H$ NMR (400 MHz, $d_6$-DMSO): δ 13.8 (br s, 1H), 7.93 (d, 1H), 3.81 (s, 3H), 2.38 (s, 3H), 2.37 (s, 3H); MS (EI) for $C_{11}H_{11}NO_6$: 252 (M−H).

STEP 4: 4-(Methoxycarbonyl)-2,5-dimethyl-3-nitrobenzoic acid (9.5 mmol) was suspended in dichloromethane (30 mL) and N-(3-dimethylaminopropyl)-N'-ethylcarbodiimide hydrochloride (1.82 g, 9.5 mmol) and 4-dimethylaminopyridine (1.16 g, 9.5 mmol) were added. The mixture was stirred at ambient temperature for 0.5 h. tert-Butanol (6 mL, 64 mmol) was added and the mixture was stirred for 15.5 h. tert-Butanol (20 mL, 213 mmol) was added and the mixture was stirred at reflux for 1 h. The dichloromethane was removed and the mixture was stirred at 75° C. for 21 h. Triethylamine (1.3 mL, 9.3 mmol) and diphenylphosphoryl chloride (1.96 mL, 9.5 mmol) were added and the mixture was stirred at 75° C. for 6 h. The mixture was cooled to ambient temperature and then was concentrated. The residue was partitioned between ethyl acetate and 1N hydrochloric acid. The organic portion was washed with 1N sodium hydroxide, brine, dried over sodium sulfate, then filtered and concentrated to afford an orange semi-solid which was purified by column chromatography (silica gel, 5-15% ethyl acetate in hexanes) to afford crude 1-tert-butyl 4-methyl 2,5-dimethyl-3-nitroterephthalate (1.98 g, 6.4 mmol, 68% yield) as a colorless oil. $^1H$ NMR (400 MHz, $CDCl_3$): δ 7.69 (s, 1H), 3.88 (s, 3H), 2.45 (s, 3H), 2.44 (s, 3H), 1.60 (s, 9H); GCMS for $C_{15}H_{19}NO_6$: 309 ($M^+$).

STEP 5: 1-tert-Butyl 4-methyl 2,5-dimethyl-3-nitroterephthalate (0.5 g, 1.62 mmol) was dissolved in tetrahydrofuran (4 mL). 10 wt % Palladium on carbon (Degussa type, 50 mg) was added to the solution and the mixture was treated with hydrogen at ambient temperature for 3 h. 10 wt % Palladium on carbon (Degussa type, 50 mg) was added to the solution, and the mixture was treated with hydrogen at ambient temperature for a further 2 h. 10 wt % Palladium on carbon (Degussa type, 100 mg) was added to the solution, and the mixture was treated with hydrogen at ambient temperature for a further 5 h. The mixture was filtered and the filtrate was concentrated to afford 1-tert-butyl 4-methyl 3-amino-2,5-dimethylterephthalate (0.444 g, 1.59 mmol, 98% yield) as a brown oil. $^1H$ NMR (400 MHz, $CDCl_3$): δ 6.78 (s, 1H), 5.20 (br s, 2H), 3.90 (s, 3H), 2.40 (s, 3H), 2.24 (s, 3H), 1.59 (s, 9H); MS (EI) for $C_{15}H_{21}NO_4$: 280 ($MH^+$).

STEP 6: 1-tert-Butyl 4-methyl 3-amino-2,5-dimethylterephthalate (0.444 g, 1.59 mmol) was dissolved in THF (10 mL), and the mixture was sparged with nitrogen for 10 minutes. Copper (I) iodide (302 mg, 1.59 mmol) and diiodomethane (0.64 mL, 7.93 mmol) were added followed by isoamyl nitrite (0.63 mL, 4.74 mmol), and the mixture was stirred at reflux for 20 h. The mixture was cooled to ambient temperature and then was partitioned between ethyl acetate and 1N hydrochloric acid. The aqueous portion was extracted with ethyl acetate (2×). The combined organic portion was washed with brine, dried over sodium sulfate, then filtered and concentrated to provide an oil which was purified by column chromatography (silica gel, 2-10% ethyl acetate in hexanes). The clean fractions were combined and concentrated, and the residue was partitioned between ethyl acetate and 1: I saturated sodium bicarbonate solution: 1 M sodium thiosulfate. The aqueous portion was extracted with ethyl acetate. The combined organic portion was washed with brine, dried over sodium sulfate, then filtered and concentrated to afford 1-tert-butyl 4-methyl 3-iodo-2,5-dimethylterephthalate (300 mg, 0.769 mmol, 48% yield) as a yellow oil. $^1H$ NMR (400 MHz, $CDCl_3$): δ 7.42 (s, 1H), 3.96 (s, 3H), 2.60 (s, 3H), 2.31 (s, 3H), 1.59 (s, 9H); GCMS for $C_{15}H_{19}IO_4$: 359 ($[M-OCH_3]^+$).

STEP 7: 1-tert-Butyl 4-methyl 3-iodo-2,5-dimethylterephthalate (300 mg, 0.769 mmol) was dissolved in dioxane (3 mL) and sparged with nitrogen for 15 minutes. XANTPHOS (18 mg, 0.031 mmol), cesium carbonate (326 mg, 1.00 mmol), ethylamine (0.1 mL) and tris(dibenzylideneacetone) dipalladium (14 mg, 0.015 mmol) were added, and the mixture was stirred in a sealed tube at 95° C. for 19 h. XANTPHOS (36 mg, 0.062 mmol), ethylamine (0.1 mL) and tris (dibenzylideneacetone)dipalladium (28 mg, 0.030 mmol) were added and the mixture was stirred in a sealed tube at 95° C. for a further 20 h. The reaction mixture was cooled to ambient temperature and was filtered through celite. The filter cake was washed with ethyl acetate, and the filtrate was concentrated to afford an orange oil which was purified by column chromatography (silica gel, 2-10% ethyl acetate in hexanes) to afford 1-tert-butyl 4-methyl 3-(ethylamino)-2,5-dimethylterephthalate (158 mg, 0.515 mmol, 67% yield) as a yellow oil. $^1H$ NMR (400 MHz, $CDCl_3$): δ 7.08 (s, 1H), 3.91 (s, 3H), 3.83 (br s, 1H), 3.00 (q, 2H), 2.36 (s, 3H), 2.29 (s, 3H), 1.59 (s, 9H), 1.14 (t, 3H); MS (EI) for $C_{17}H_{25}NO_4$: 308 ($MH^+$).

STEP 8: 1-tert-Butyl 4-methyl 3-(ethylamino)-2,5-dimethylterephthalate (142 mg, 0.463 mmol) was dissolved in dioxane (2 mL) and was cooled in an ice bath. 2N Lithium hydroxide (0.25 mL) was added and the mixture was stirred for 16 h and then methanol (0.5 mL) and 2N lithium hydroxide (0.25 mL) were added, and the mixture was stirred at ambient temperature for 1.5 h. The mixture was cooled in an ice bath and 1N sodium hydroxide (0.5 mL) was added and the mixture was stirred for 1 h and then was warmed to ambient temperature and was stirred for a further 1 h. The mixture was stirred at 50-55° C. for a further 16 h and then was cooled to ambient temperature and acidified with 1N hydrochloric acid to pH ~4.5. The mixture was diluted with water and extracted with ethyl acetate (2×). The organic portion was dried over sodium sulfate, then filtered and concentrated to provide 4-(tert-butoxycarbonyl)-2-(ethylamino)-3,6-dimethylbenzoic acid (115 mg, 0.392 mmol, 85% yield) as a brown oil. $^1H$ NMR (400 MHz, $CDCl_3$): δ 7.45 (s, 1H), 2.97 (q, 2H), 2.67 (s, 3H), 2.46 (s, 3H), 1.61 (s, 9H), 1.34 (t, 3H); MS (EI) for $C_{16}H_{23}NO_4$: 294 ($MH^+$).

STEP 9: 4-(tert-Butoxycarbonyl)-2-(ethylamino)-3,6-dimethylbenzoic acid (115 mg, 0.392 mmol) was dissolved in tetrahydrofuran (1 mL) and then cooled in an ice bath. N,N-Diisopropylethylamine (0.07 mL, 0.403 mmol) and triphosgene (40 mg, 0.135 mmol) were added, and the mixture was stirred at ambient temperature for 0.5 h. The mixture was quenched with water and extracted with dichloromethane (2×). The combined organic portion was dried over sodium sulfate, then filtered and concentrated to provide tert-butyl 1-ethyl-5,8-dimethyl-2,4-dioxo-2,4-dihydro-1H-benzo[d][1,3]oxazine-7-carboxylate (109 mg, 0.342 mmol, 87% yield). $^1H$ NMR (400 MHz, $CDCl_3$): δ 7.35 (s, 1H), 4.06 (q, 2H), 2.70 (s, 3H), 2.46 (s, 3H), 1.62 (s, 9H), 1.28 (t, 3H); MS (EI) for $C_{17}H_{21}NO_5$: 320 ($MH^+$).

STEP 10: tert-Butyl 1-ethyl-5,8-dimethyl-2,4-dioxo-2,4-dihydro-1H-benzo[d][1,3]oxazine-7-carboxylate (90 mg, 0.282 mmol) was dissolved in tetrahydrofuran (6 mL), treated with ammonia for 15 min and then stirred at ambient temperature for 1 h. The mixture was concentrated, and the residue was stirred for 15 min as a suspension in 20% citric acid (3 mL) and tetrahydrofuran (1 mL). The mixture was extracted with ethyl acetate. The aqueous portion was basified with sodium bicarbonate and then extracted with ethyl acetate. The combined organic portion was washed with water, brine, was dried over sodium sulfate, then filtered and concentrated to afford an orange film which was treated with trifluoroacetic acid (1 mL) at ambient temperature for 2 h. The mixture was concentrated and the residue was treated with 1N hydrochloric acid and concentrated. The residue was dissolved in a mixture of 1N hydrochloric acid and acetonitrile and then lyophilized to afford 4-aminocarbonyl-3-(ethylamino)-2,5-dimethylbenzoic acid hydrochloride salt (quantitative yield). MS (EI) for $C_{12}H_{16}N_2O_3$: 237 ($MH^+$).

Reagent Preparation 37: 3-[(trans-4-hydroxycyclohexyl)-amino]benzoic Acid

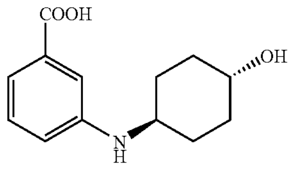

STEP 1: A suspension of methyl 3-bromobenzoate (0.43 g, 2.00 mmol), trans-4-aminocyclohexanol (0.35 g, 3.00 mmol), cesium carbonate (1.63 g, 5.00 mmol), Xantphos (0.024 g, 0.02 mmol) and tris(dibenzylideneacetone)dipalladium(0) (0.010 g, 0.01 mmol) in 1,4-dioxane (25 mL) was stirred at 80° C. under $N_2$ atmosphere for 18 hours. After cooling to room temperature the reaction mixture was filtered through a pad of Celite and was washed with ethyl acetate (200 mL), and the combined filtrate was partitioned with water. The organic layer was separated and washed with 1 M aqueous hydrochloric acid and brine, dried over sodium sulfate, filtered, and the solution was concentrated. The residue was purified by column chromatography (hexane:ethyl acetate 4:1 to 3:2) to give methyl 3-[(trans-4-hydroxycyclohexyl) amino]benzoate. (0.28 g, 56%). $^1H$ NMR (400 MHz, DMSO-$d_6$): 7.18 (m, 2H), 7.08 (m, 1H), 6.82 (m, 1H), 5.82 (d, 1H), 3.84 (s, 3H), 3.34 (m, 1H), 2.57 (m, 1H), 1.85 (m, 2H), 1.71 (m, 2H), 1.58 (m, 2H), 1.46 (m, 2H). MS (EI) for $C_{14}H_{19}NO_3$: 250 ($MH^+$).

STEP 2: To a solution of methyl 3-[(trans-4-hydroxycyclohexyl)amino]benzoate (0.25 g, 1.00 mmol) in a mixture of methanol (20 mL), terahydrofuran (10 mL) and water (10 mL) was added a 4M aqueous solution of potassium hydroxide (0.5 mL, 2.00 mmol), and the reaction mixture was heated to reflux for five minutes. The organic portion of the solvent was evaporated, and the pH of the aqueous solution was adjusted to 2 by the addition of 2M aqueous hydrochloric acid. The aqueous mixture was partitioned with ethyl acetate, the organic layer was separated and washed with brine, dried over sodium sulfate, filtered, and the solution was concentrated to give 3-[(trans-4-hydroxycyclohexyl)amino]benzoic acid (40 mg, 17%). MS (EI) for $C_{13}H_{17}NO_3$: 234 (M−H).

Reagent Preparation 38: (S)-methyl 2-amino-2-(4-methoxyphenyl)-acetate

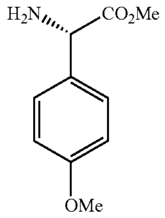

STEP 1: To a solution of L-4-hydroxyphenylglycine (1.00 g, 5.98 mmol) and sodium hydrogencarbonate (2.50 g, 29.11 mmol) in a mixture of 1,4-dioxane (20 mL) and water (20 mL) was added di-tert-butyl dicarbonate (1.40 g, 6.58 mmol) at 0° C., followed by stirring at room temperature for 18 hours. The organic portion of the solvent was evaporated, and the reaction mixture was partitioned between ethyl acetate (300 mL) and 0.5M aqueous hydrochloric acid (50 mL). The organic layer was separated and washed with 0.5M aqueous hydrochloric acid, water and brine, dried over sodium sulfate, filtered and the solvent concentrated to give (S)-2-(tert-butoxycarbonylamino)-2-(4-hydroxyphenyl)acetic acid (1.6 g, quantitative). $^1H$ NMR (400 MHz, $CDCl_3$): 8.80 (bs, 1H), 7.12 (d, 2H), 6.62 (d, 2H), 5.80 (d, 1H), 5.00 (d, 1H), 1.22 (s, 9H). MS (EI) for $C_{13}H_{17}NO_5$: 266 (M−H).

STEP 2: To a solution of (S)-2-(tert-butoxycarbonylamino)-2-(4-hydroxyphenyl)acetic acid (1.60 g, 5.98 mmol) in dimethylformamide (20 mL) was added potassium carbonate (1.85 g, 13.42 mmol), and the mixture was stirred at room temperature for thirty minutes, followed by the addition of methyl iodide (0.76 mL, 12.20 mmol). The reaction mixture was then stirred at room temperature for 18 hours. The solvent was evaporated and the residue was partitioned between ethyl acetate (250 mL) and water (50 mL). The organic layer was separated and washed with saturated aqueous sodium hydrogencarbonate, water and brine, dried over sodium sulfate, filtered and the solvent was concentrated to give (S)-methyl 2-(tert-butoxycarbonylamino)-2-(4-methoxyphenyl)acetate (1.8 g, quantitative). $^1H$ NMR (400 MHz, $CDCl_3$): 7.16 (d, 2H), 6.72 (d, 2H), 5.68 (d, 1H), 5.14 (d, 1H), 3.62 (s, 3H), 3.56 (s, 3H), 1.24 (s, 9H). MS (EI) for $C_{15}H_{21}NO_5$: 294 ($MH^-$).

STEP 3: To a solution of (S)-methyl 2-(tert-butoxycarbonylamino)-2-(4-methoxyphenyl)acetate (0.30 g, 1.00 mmol) in dichloromethane (10 mL) was added trifluoroacetic acid (2 mL) and the mixture was heated to 40° C. for thirty minutes. The solvent was evaporated followed by rotary evaporation of the residue from toluene and drying in vacuo to obtain (S)-methyl 2-amino-2-(4-methoxyphenyl)acetate as the trifluoroacetate salt (0.30 g, quantitative). $^1H$ NMR (400 MHz, DMSO-$d_6$): 7.18 (d, 2H), 6.82 (d, 2H), 5.68 (d, 1H), 4.82 (d, 1H), 3.78 (s, 3H), 3.64 (s, 3H). MS (EI) for $C_{10}H_{13}NO_3$: 196 ($MH^+$).

Reagent Preparation 39: 4-(aminocarbonyl)-3-(cyclopentylamino)-benzoic Acid

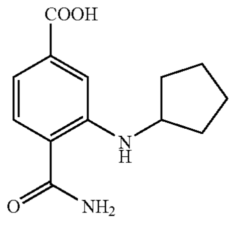

STEP 1: A mixture of ethyl 3-bromo-4-cyanobenzoate (500 mg, 1.97 mmol), XANTPHOS (228 mg, 0.39 mmol), cesium carbonate (1.282 g, 3.94 mmol), cyclopentylamine (233 mg, 2.75 mmol), and tris(dibenzylideneacetone)dipalladium (180 mg, 0.20 mmol) in dioxane (5 mL) was stirred at 100° C. for 17 h. The reaction mixture was partitioned between ethyl acetate (100 mL) and water (50 mL), the organic layer washed with brine (50 mL), dried over sodium sulfate, filtered and concentrated. Column chromatography on silica (hexanes:ethyl acetate 9:1) afforded ethyl 4-cyano-3-(cyclopentylamino)benzoate (366 mg, 72% yield) as a brown oil. $^1$H NMR (400 MHz, $CDCl_3$): 7.43 (m, 2H), 7.35 (m, 1H), 7.27 (m, 1H), 4.62 (d, 1H), 4.38 (q, 2H), 3.93 (m, 1H), 2.10 (m, 2H), 1.78 (m, 2H), 1.67 (m, 2H), 1.53 (m, 2H), 1.39 (t, 3H). MS (EI) for $C_{15}H_{18}N_2O_2$: 259 ($MH^+$).

STEP 2: A solution of ethyl 4-cyano-3-(cyclopentylamino) benzoate (363 mg, 1.41 mmol), potassium carbonate (50 mg, 0.36 mmol), and 30% aqueous hydrogen peroxide (0.25 mL) in DMSO (1.5 mL) was stirred at 60° C. for 1 h. After cooling to room temperature, water was added and the resulting mixture was extracted with ethyl acetate (50 mL). The organic layer was washed with water (10 mL) and brine (10 mL), dried over sodium sulfate, filtered and concentrated to give ethyl 4-(aminocarbonyl)-3-(cyclopentylamino)benzoate (333 mg, 86% yield). MS (EI) for $C_{15}H_{20}N_2O_3$: 277 ($MH^+$).

STEP 3: A suspension of ethyl 4-(aminocarbonyl)-3-(cyclopentylamino)-benzoate (333 mg, 1.21 mmol) and potassium hydroxide (135 mg, 2.41 mmol) in methanol (6 mL) and water (2 mL) was stirred at 55° C. for 1 h. After cooling to room temperature, water was added and the pH adjusted to 4 with 1N aqueous hydrochloric acid. The resulting precipitate was collected by filtration, washed with water and dried to provide 4-(aminocarbonyl)-3-(cyclopentylamino) benzoic acid (260 mg, 87% yield). $^1$H NMR (400 MHz, DMSO-$d_6$): 13.02 (br s, 1H), 8.17 (d, 1H), 7.97 (br s, 1H), 7.66 (d, 1H), 7.34 (br s, 1H), 7.21 (d, 1H), 7.04 (dd, 1H), 3.81 (m, 1H), 1.99 (m, 2H), 1.64 (m, 4H), 1.42 (m, 2H). MS (EI) for $C_{13}H_{16}N_2O_3$: 249 ($MH^+$).

Using analogous synthetic techniques and substituting with alternative starting reagents, the following compounds were prepared. Alternative starting materials were obtained commercially unless otherwise indicated.

4-(Aminocarbonyl)-3-[(trans-4-hydroxycyclohexyl)amino]benzoic acid

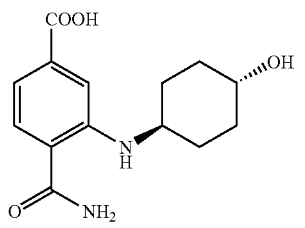

Prepared according to the method of reagent preparation 39 by using trans 4-aminocyclohexanol in step 1. MS (EI) for $C_{14}H_{18}N_2O_4$: 279 ($MH^+$).

4-(Aminocarbonyl)-3-{[2-(methylsulfonyl)ethyl]amino}benzoic acid

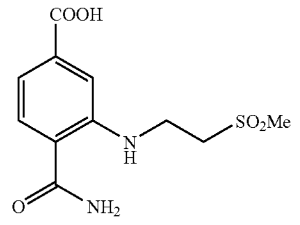

Prepared according to the method of reagent preparation 39 by using 2-aminoethylmethylsulfone hydrochloride in step 1. MS (EI) for $C_{11}H_{14}N_2O_5S$: 287 ($MH^+$).

4-(Aminocarbonyl)-3-[(cyclopropylmethyl)amino]benzoic acid

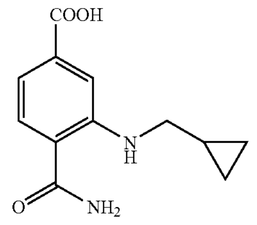

Prepared according to the method of reagent preparation 39 by using aminomethylcyclopropane in step 1. MS (EI) for $C_{12}H_{14}N_2O_3$: 235 ($MH^+$).

4-(Aminocarbonyl)-3-(pyridin-4-ylamino)benzoic acid

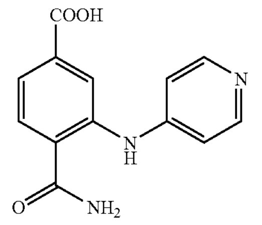

Prepared according to the method of reagent preparation 39 by using 4-aminopyridine in step 1. $^1$H NMR (400 MHz, DMSO-$d_6$): 9.82 (s, 1H), 8.30 (d, 2H), 8.23 (s, 1H), 7.97 (d, 1H), 7.79 (d, 1H), 7.76 (s, 1H), 7.57 (dd, 1H), 7.03 (d, 2H). MS (EI) for $C_{13}H_{11}N_3O_3$: 258 ($MH^+$).

4-(Aminocarbonyl)-3-[(cis-4-hydroxy-4-methylcyclohexyl)amino]benzoic acid

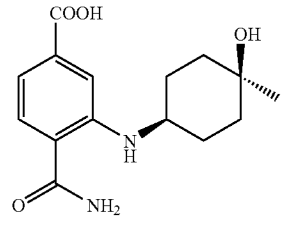

Prepared according to the method of reagent preparation 39 by using cis-4-hydroxy-4-methylcyclohexylamine (synthesized according to WO2005009966) in step 1. MS (EI) for $C_{15}H_{20}N_2O_4$: 293 ($MH^+$).

4-(Aminocarbonyl)-3-{[(1R)-1-methylpropyl] amino}benzoic acid

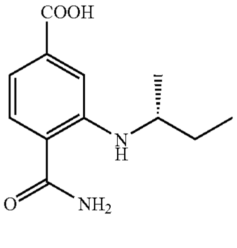

Prepared according to the method of reagent preparation 39 by using (R)-(−)-3-methyl-2-butylamine in step 1. $^1H$ NMR (400 MHz, DMSO-$d_6$): 13.03 (br s, 1H), 8.26 (d, 1H), 7.97 (br s, 1H), 7.67 (d, 1H), 7.33 (br s, 1H), 7.20 (d, 1H), 7.00 (dd, 1H), 3.42 (m, 1H), 1.79 (m, 1H), 1.07 (d, 3H), 0.94 (d, 3H), 0.88 (d, 3H). MS (EI) for $C_{13}H_{18}N_2O_3$: 249 (M−H).

4-(Aminocarbonyl)-3-({2-[(1-methylethyl)oxy] ethyl}amino)benzoic acid

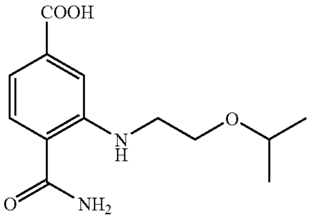

Prepared according to the method of reagent preparation 39 by using 2-{(1-methylethyl)oxy}ethanamine in step 1. MS (EI) for $C_{13}H_{18}N_2O_4$: 267 ($MH^+$).

4-(Aminocarbonyl)-3-(tetrahydrofuran-3-ylamino) benzoic acid

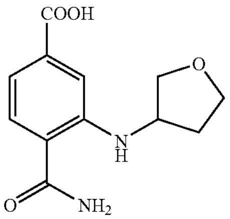

Prepared according to the method of reagent preparation 39 by using (±)-tetrahydrofuran-3-amine hydrochloride in step 1. MS (EI) for $C_{12}H_{14}N_2O_4$: 251 ($MH^+$).

4-(Aminocarbonyl)-3-(2,2,3,3,3-pentafluoropropylamino)benzoic acid

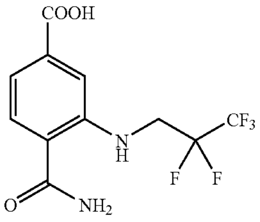

Prepared according to the method of reagent preparation 39 by using 2,2,3,3,3-pentafluoropropylamine in step 1. $^1H$ NMR (400 MHz, $d_6$-DMSO): 13.1 (br s, 1H), 8.54 (t, 1H), 8.11 (br s, 1H), 7.73 (d, 1H), 7.54 (br s, 1H), 7.42 (s, 1H), 7.19 (dd, 1H), 4.23 (td, 2H). MS (EI) for $C_{11}H_9F_5N_2O_3$: 311 (M−H).

4-(Aminocarbonyl)-3-(2,2,3,3,4,4,4-heptafluorobutylamino)benzoic acid

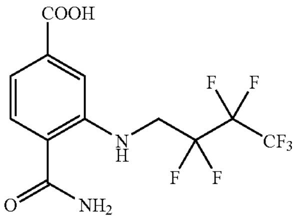

Prepared according to the method of reagent preparation 39 by using 2,2,3,3,4,4,4-heptafluorobutylamine in step 1. MS (EI) for $C_{12}H_9F_7N_2O_3$: 363 ($MH^+$).

4-(Aminocarbonyl)-3-(piperidin-1-ylamino)benzoic acid

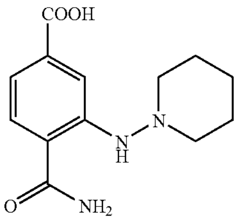

Prepared according to the method of reagent preparation 39 using piperidin-1-amine in step 1. $^1H$ NMR (400 MHz, $CD_3OD$): 8.00 (d, 1H), 7.58 (d, 1H), 724 (dd, 1H), 2.71 (br s, 4H), 1.75-1.69 (m, 4H), 1.47 (br s, 2H). MS (EI) for $C_{13}H_{17}N_3O_3$: 264 ($MH^+$).

4-(Aminocarbonyl)-3-[(1-{[(1,1-dimethylethyl)oxy]carbonyl}piperidin-4-yl)amino]benzoic acid

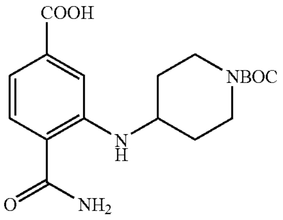

Prepared according to the method of reagent preparation 39 by using 1-tert-butoxycarbonyl-4-aminopiperidine in step 1. $^1$HNMR (400 MHz, methanol-$d_4$): 7.63 (d, J=8.0 Hz, 1H), 7.40 (s, 1H), 7.20 (d, J=8.0 Hz, 1H), 3.93 (m, 2H), 3.67 (m, 1H), 3.05 (m, 2H), 2.03 (m, 2H), 1.46 (s, 9H), 1.40 (m, 2H). MS (EI) for $C_{18}H_{25}N_3O_5$: 364 ($MH^+$).

4-(Aminocarbonyl)-3-[(1-{[(1,1-dimethylethyl)oxy]carbonyl}pyrrolidin-3-yl)amino]benzoic acid

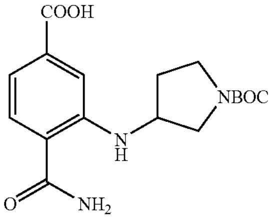

Prepared according to the method of reagent preparation 39 by using 1-tert-butoxy-carbonyl-3-aminopyrrolidine in step 1. $^1$HNMR (400 MHz, methanol-$d_4$): 7.65 (d, J=8.0 Hz, 1H), 7.38 (s, 1H), 7.25 (d, J=8.0 Hz, 1H), 4.20 (m, 1H), 3.70 (m, 1H), 3.50 (m, 2H), 2.26 (m, 1H), 2.28 (m, 1H), 1.95 (m, 1H), 1.44 (s, 9H). MS (EI) for $C_{17}H_{23}N_3O_5$ 250 ($MH^+$-Boc).

4-(Aminocarbonyl)-3-{(1-{[(1,1-dimethylethyl)oxy]carbonyl}piperidin-3-yl)methyl]amino}benzoic acid:

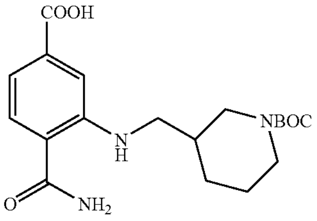

Prepared according to the method of reagent preparation 39 by using 4-aminomethyl-1-N-(tert-butoxycarbonyl)piperidine in step 1. $^1$HNMR (400 MHz, methanol-$d_4$): 7.63 (d, J=8.0 Hz, 1H), 7.34 (s, 1H), 7.20 (d, J=8.0 Hz, 1H), 3.80 (br, s, 1H), 3.14 (m, 2H), 2.95 (m, 2H), 1.95-1.60 (m, 3H), 1.44 (m, 3H), 1.40 (s, 9H). MS (EI) for $C_{19}H_{27}N_3O_5$ 378 ($MH^+$).

4-(Aminocarbonyl)-3-{(1-{[(1,1-dimethylethyl)oxy]carbonyl}pyrrolidin-3-yl)methyl]amino}benzoic acid:

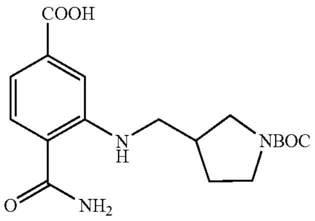

Prepared according to the method of reagent preparation 39 by using tert-butyl 3-(aminomethyl)pyrrolidine-1-carboxylate in step 1. $^1$HNMR (400 MHz, methanol-$d_4$): 7.63 (d, J=8.0 Hz, 1H), 7.36 (s, 1H), 7.21 (d, J=8.0 Hz, 1H), 3.56 (m, 1H), 3.47 (m, 1H), 3.30 (m, 1H), 3.12 (m, 1H), 3.09 (m, 1H), 2.56 (m, 1H), 2.11 (m, 1H), 1.74 (m, 1H), 1.45 (s, 9H). MS (EI) for $C_{18}H_{25}N_3O_5$ 364 ($MH^+$).

4-(Aminocarbonyl)-3-[(3-{[(2-dimethylamino)ethyl]oxy}phenyl)-amino]benzoic acid

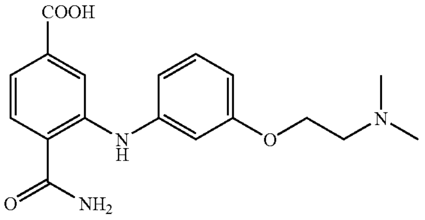

Prepared according to the method of reagent preparation 39 by using 3-[2-(dimethylamino)ethoxy]aniline (*Bioorg. & Med. Chem. Lett.* 2005, 15(22), 4989-4993) in step 1. $^1$HNMR (400 MHz, DMSO-$d_6$): 13.18 (br, s, 1H), 9.96 (s, 1H), 8.23 (s, 1H), 7.83 (s, 1H), 7.79 (d, J=8.0 Hz, 1H), 7.69 (s, 1H), 7.31 (m, 2H), 6.82 (m, 2H), 6.69 (d, J=8.0 Hz, 1H), 4.34 (m, 2H), 3.50 (m, 2H), 2.84 (s, 6H). MS (EI) for $C_{18}H_{21}N_3O_4$ 344 ($MH^+$).

4-(Aminocarbonyl)-3-(tetrahydro-2H-pyran-4-ylamino)benzoic acid

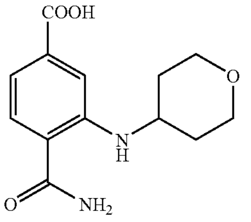

Prepared according to the method of reagent preparation 39 by using 4-aminotetrahydropyran in step 1. $^1$H NMR (400 MHz, methanol-$d_4$): 7.64 (d, 1H), 7.41 (d, 1H), 7.21 (dd, 1H), 3.96 (dt, 2H), 3.73-3.65 (m, 1H), 3.60 (td, 2H), 2.08-2.00 (m, 2H), 1.58-1.48 (m, 2H). MS (EI) for $C_{13}H_{16}N_2O_4$: 265 ($MH^+$).

4-(Aminocarbonyl)-3-(phenylamino)benzoic acid

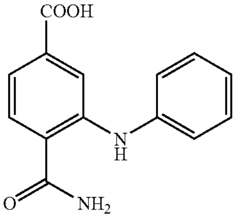

Prepared according to the method of reagent preparation 39 by using aniline in step 1. $^1$H NMR (400 MHz, methanol-$d_4$): 7.91 (d, 1H), 7.71 (d, 1H), 7.39-7.32 (m, 3H), 3.19 (d, 2H), 7.04 (t, 1H). MS (EI) for $C_{14}H_{12}N_2O_3$: 257 ($MH^+$).

4-(Aminocarbonyl)-3-(benzylamino)benzoic acid

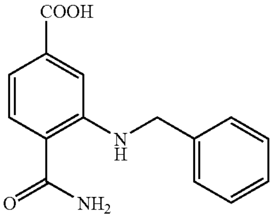

Prepared according to the method of reagent preparation 39 by using benzylamine in step 1. $^1$H NMR (400 MHz, methanol-$d_4$): 7.63 (d, 1H), 7.40-7.36 (m, 2H), 7.34-7.30 (m, 3H), 7.24 (d, 1H), 7.21 (dd, 1H), 4.43 (s, 2H). MS (EI) for $C_{15}H_{14}N_2O_3$: 271 ($MH^+$).

(S)-4-(Aminocarbonyl)-3-(tetrahydrofuran-3-ylamino)benzoic acid

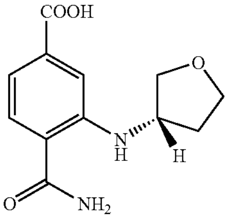

Prepared according to the method of reagent preparation 39 by using (S)-tetrahydrofuran-3-amine in step 1. $^1$H NMR (400 MHz, methanol-$d_4$): 7.69-7.63 (m, 1H), 7.40-7.36 (m, 1H), 7.30-7.25 (m, 1H), 7.30-7.25 (m, 1H), 4.24-4.18 (m, 1H), 4.04-3.91 (m, 2H), 3.90-3.83 (m, 1H), 3.73-3.67 (m, 1H), 2.38-2.27 (m, 1H), 1.94-1.85 (m, 1H). MS (EI) for $C_{12}H_{14}N_2O_4$: 251 ($MH^+$).

4-(Aminocarbonyl)-3-(2,2,2-trifluoroethylamino)benzoic acid

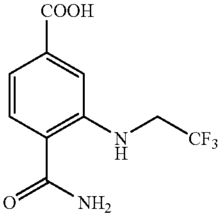

Prepared according to the method of reagent preparation 39 by using 2,2,2-trifluoroethylamine in step 1. MS (EI) for $C_{10}H_9F_3N_2O_3$: 261 (M−H).

(R)-4-(Aminocarbonyl)-3-(tetrahydrofuran-3-ylamino)benzoic acid

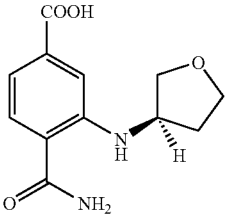

Prepared according to the method of reagent preparation 39 by using (R)-tetrahydrofuran-3-amine in step 1. $^1$H NMR (400 MHz, $d_6$-DMSO): 13.04 (br s, 1H), 8.27 (br s, 1H), 8.02 (s, 1H), 7.69 (d, 1H), 7.41 (s, 1H), 7.19 (s, 1H), 7.09 (d, 1H), 4.16-4.09 (br s, 1H), 3.92-3.86 (m, 1H), 3.84-3.72 (m, 2H), 3.56-3.49 (m, 1H), 2.32-2.20 (m, 1H), 1.77-1.68 (m, 1H). MS (EI) for $C_{12}H_{14}N_2O_4$: 251 ($MH^+$).

4-(Aminocarbonyl)-3-(propylamino)benzoic acid

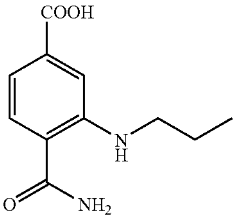

Prepared according to the method of reagent preparation 39 by using n-propylamine in step 1. $^1$H NMR (400 MHz, $d_6$-DMSO): 13.01 (br s, 1H), 8.12 (t, 1H), 7.98 (br s, 1H), 7.67

(d, 1H), 7.36 (br s, 1H), 7.17 (s, 1H), 7.05 (dd, 1H), 3.12-3.07 (m, 2H), 1.64-1.56 (m, 2H), 0.96 (t, 3H). MS (EI) for $C_{11}H_{14}N_2O_3$: 221 (M−H).

4-(Aminocarbonyl)-3-(azetidin-1-yl)benzoic acid

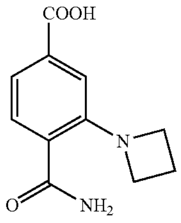

Prepared according to the method of reagent preparation 39 by using azetidine in step 1. MS (EI) for $C_{11}H_{12}N_2O_3$: 221 ($MH^+$).

4-(Aminocarbonyl)-3-(3,3,3-trifluoropropylamino)benzoic acid:

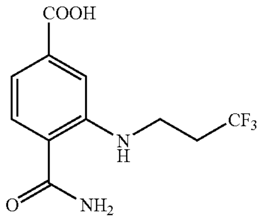

Prepared according to the method of reagent preparation 39 by using 3,3,3-trifluoropropylamine in step 1. $^1H$ NMR (400 MHz, $d_6$-DMSO): 13.06 (br s, 1H), 8.23 (t, 1H), 8.01 (br s, 1H), 7.69 (d, 1H), 7.41 (br s, 1H), 7.20 (dd, 1H), 3.46-3.41 (m, 2H), 2.66-2.54 (m, 3H). MS (EI) for $C_{11}H_{11}F_3N_2O_3$: 277 ($MH^+$).

4-(Aminocarbonyl)-3-(butylamino)benzoic

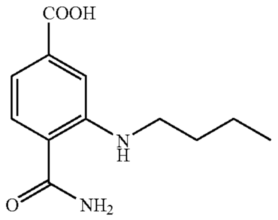

Prepared according to the method of reagent preparation 39 by using n-butylamine in step 1. $^1H$ NMR (400 MHz, $d_6$-DMSO): 13.02 (br s, 1H), 8.09 (t, 1H), 7.98 (br s, 1H), 7.67 (d, 1H), 7.35 (br s, 1H), 7.17 (d, 1H), 7.05 (dd, 1H), 3.15-3.10 (m, 2H), 1.059-1.54 (m, 2H), 1.42-1.37 (m, 2H), 0.95-0.91 (m, 3H). MS (EI) for $C_{12}H_{16}N_2O_3$: 237 ($MH^+$).

4-(aminocarbonyl)-3-[(1-methylethyl)amino]benzoic acid

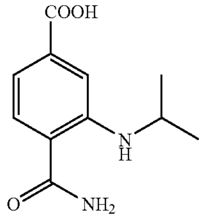

Prepared according to the method of reagent preparation 39 by using isopropylamine in step 1. MS (EI) for $C_{11}H_{14}N_2O_3$: 223 ($MH^+$).

4-(aminocarbonyl)-3-[(2-methylpropyl)amino]benzoic acid

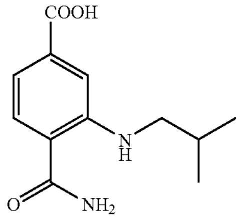

Prepared according to the method of reagent preparation 39 by using isobutylamine in step 1. MS (EI) for $C_{12}H_{16}N_2O_3$: 237 ($MH^+$).

4-(aminocarbonyl)-3-[(tetrahydrofuran-2-ylmethyl)amino]benzoic acid

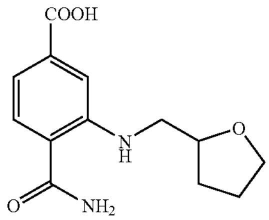

Prepared according to the method of reagent preparation 39 by using 2-tetrahydrofurfurylamine in step 1. MS (EI) for $C_{13}H_{16}N_2O_4$: 265 ($MH^+$)

4-(aminocarbonyl)-3-{[2-({[(1,1-dimethylethyl)oxy]carbonyl}amino)-ethyl]amino}benzoic acid

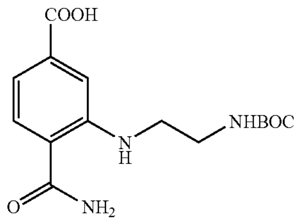

Prepared according to the method of reagent preparation 39 by using N-Boc-ethylenediamine in step 1. MS (EI) for $C_{15}H_{21}N_3O_5$: 324 ($MH^+$).

4-(aminocarbonyl)-3-[(1-propylbutyl)amino]benzoic acid

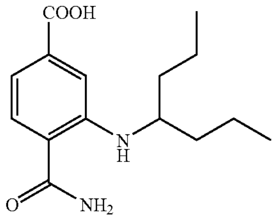

Prepared according to the method of reagent preparation 39 by using 4-heptylamine in step 1. MS (EI) for $C_{15}H_{22}N_2O_3$: 279 ($MH^+$).

4-(aminocarbonyl)-3-[(1,2-dimethylpropyl)amino]benzoic acid

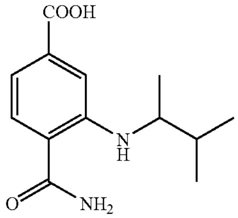

Prepared according to the method of reagent preparation 39 by using 1,2-dimethylpropylamine in step 1. MS (EI) for $C_{13}H_{18}N_2O_3$: 251 ($MH^+$).

4-(aminocarbonyl)-3-[(1,2,2-trimethylpropyl)amino]benzoic acid

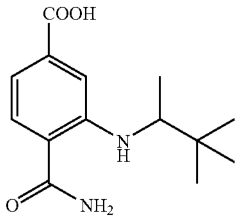

Prepared according to the method of reagent preparation 39 by using 1,2,2-trimethylpropylamine in step 1. MS (EI) for $C_{14}H_{20}N_2O_3$: 265 ($MH^+$).

4-(aminocarbonyl)-3-({1-[(methyloxy)methyl]propyl)amino}benzoic acid

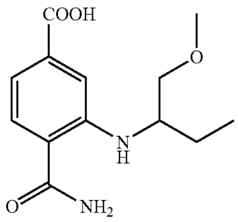

Prepared according to the method of reagent preparation 39 by using 2-amino-1-methyoxybutane in step 1. MS (EI) for $C_{13}H_{18}N_2O_4$: 267 ($MH^+$).

4-(aminocarbonyl)-3-{[(1S)-1-methylpropyl]amino}benzoic acid

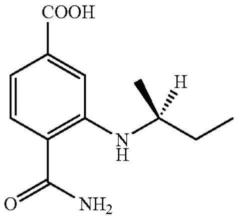

Prepared according to the method of reagent preparation 39 by using (S)-(+)-2-butylamine in step 1. MS (EI) for $C_{12}H_{16}N_2O_3$: 237 ($MH^+$).

4-(aminocarbonyl)-3-{[(1R)-1-methylpropyl]amino}benzoic acid

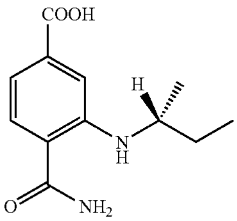

Prepared according to the method of reagent preparation 39 by using (R)-(−)-2-butylamine in step 1. MS (EI) for $C_{12}H_{16}N_2O_3$: 237 ($MH^+$).

4-(aminocarbonyl)-3-({3-[(1-methylethyl)amino]propyl}amino)benzoic acid

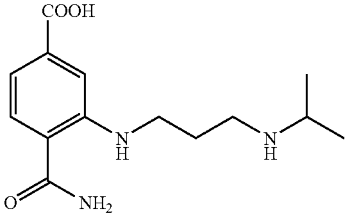

Prepared according to the method of reagent preparation 39 by using N-isopropyl-1,3-propanediamine in step 1. MS (EI) for $C_{14}H_{21}N_3O_3$: 507.2 ($MH^+$).

4-(aminocarbonyl)-3-[(2,2-dimethylpropyl)amino]benzoic acid

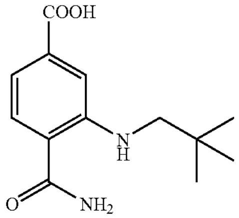

Prepared according to the method of reagent preparation 39 by using neopentylamine in step 1. MS (EI) for $C_{13}H_{18}N_2O_3$: 251 ($MH^+$).

4-(aminocarbonyl)-3-[(1-ethylpropyl)amino]benzoic acid:

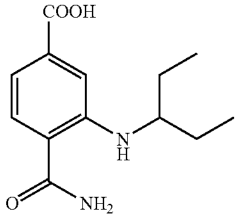

Prepared according to the method of reagent preparation 39 by using 3-aminopentane in step 1. MS (EI) for $C_{13}H_{18}N_2O_3$: 251 ($MH^+$).

4-(aminocarbonyl)-3-[(1-methylpropyl)amino]benzoic acid

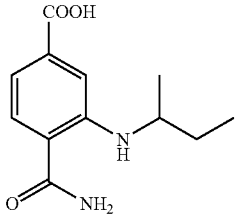

Prepared according to the method of reagent preparation 39 by using 2-aminobutane in step 1. MS (EI) for $C_{12}H_{16}N_2O_3$: 251 ($MH^+$).

4-(aminocarbonyl)-3-{[(1R)-1,2-dimethylpropyl]amino}benzoic acid

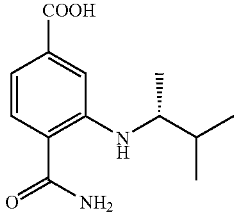

Prepared according to the method of reagent preparation 39 by using (2R)-3-methylbutan-2-amine in step 1. $^1H$ NMR (400 MHz, DMSO-$d_6$): 13.02 (s, 1H), 8.30-8.24 (d, 1H), 7.98 (s, 1H), 7.69-7.64 (d, 1H), 7.33 (s, 1H), 7.20 (s, 1H), 7.03-6.98 (d, 1H), 3.46-3.39 (m, 1H), 1.85-1.75 (m, 1H), 1.09-1.04 (d, 3H), 0.97-0.93 (d, 3H), 0.91-0.87 (d, 3H). MS (EI) for $C_{13}H_{18}N_2O_3$: 251 ($MH^+$).

4-(aminocarbonyl)-3-[(1-cyclopropylethyl)amino]benzoic acid

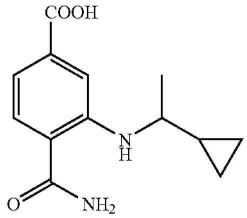

Prepared according to the method of reagent preparation 39 by using 1-cyclopropylethanamine in step 1. $^1H$ NMR (400 MHz, DMSO-$d_6$): 13.02 (br s, 1H), 8.14 (d, 1H), 7.96 (s, 1H), 7.65 (d, 1H), 7.33 (s, 1H), 7.18 (d, 1H), 7.01 (dd, 1H), 3.14 (m, 1H), 1.18 (d, 3H), 0.95 (m, 1H), 0.44 (m, 2H), 0.24 (m, 2H). MS (EI) for $C_{13}H_{16}N_2O_3$: 247 (M−H).

4-(aminocarbonyl)-3-{[3,4,5-tris(methyloxy)phenyl]amino}benzoic acid

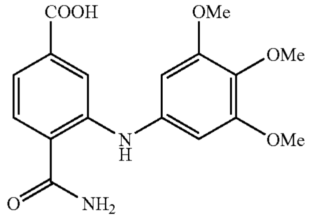

Prepared according to the method of reagent preparation 39 by using 3,4,5-trimethoxyaniline in step 1. MS (EI) for $C_{17}H_{18}N_2O_6$: 345 (M−H).

4-(aminocarbonyl)-3-(cyclobutylamino) benzoic acid

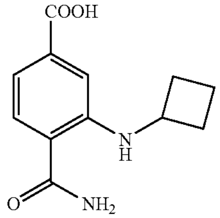

Prepared according to the method of reagent preparation 39 by using cyclobutylamine in step 1. MS (EI) for $C_{12}H_{14}N_2O_3$: 233 (M−H).

4-(aminocarbonyl)-3-{[1-(methylsulfonyl)piperidin-4-yl]amino}benzoic acid

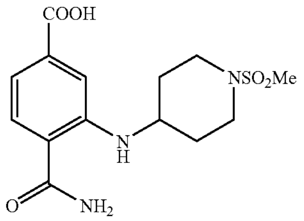

Prepared according to the method of reagent preparation 39 by using methylsulfonylpiperidin-4-ylamine hydrochloride in step 1. MS (EI) for $C_{14}H_{19}N_3O_5S$: 340 (M−H).

Reagent Preparation 40: 4-(aminocarbonyl)-3-(cyclohexylamino)benzoic Acid

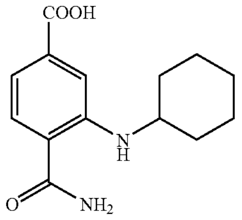

STEP 1: To a pressure vessel were added benzyl 3-bromo-4-cyanobenzoate (150 mg, 0.47 mmol) prepared as described in example 11 (steps 1, 2), cesium carbonate (310 mg, 0.95 mmol), cyclohexylamine (108 uL, 0.95 mmol), XANTPHOS (27 mg, 0.047 mmol), tris(dibenzylideneacetone)dipalladium(0) (21 mg, 0.023 mmol), and dioxane (3 mL). The vessel was sealed and heated to 95° C. for 4 h. After cooling to room temperature, the mixture was diluted with ethyl acetate and was washed with water. The aqueous phase was extracted with ethyl acetate. The combined organic extracts were dried over magnesium sulfate, filtered, and concentrated. The residue was purified by column chromatography (10% ethyl acetate in hexanes) to provide benzyl 4-cyano-3-(cyclohexylamino)benzoate (118 mg, 0.35 mmol, 75% yield) as a yellow syrup. $^1$H NMR (400 MHz, $CDCl_3$): 7.45-7.30 (m, 7H), 7.27 (dd, 1H), 5.36 (s, 2H), 4.56 (d, 1H), 3.48-3.38 (m, 1H), 2.08-2.01 (m, 2H), 1.83-1.75 (m, 2H), 1.71-1.64 (m, 1H), 1.46-1.35 (m, 2H), 1.31-1.20 (m, 3H); MS (EI) for $C_{21}H_{22}N_2O_2$: 333 (M−H).

STEP 2: To a solution of benzyl 4-cyano-3-(cyclohexylamino)benzoate (66.2 mg, 0.198 mmol) in DMSO (2 mL) was added potassium carbonate (27.4 mg, 0.198 mmol) followed by 30% aqueous hydrogen peroxide (5 drops). The mixture was stirred at room temperature for 45 min, and was then diluted with ethyl acetate. Water was added and then the layers were separated. The aqueous phase was then extracted with ethyl acetate. The combined organic extracts were dried over magnesium sulfate, filtered, and concentrated. The residue was purified by column chromatography (40% ethyl acetate in hexanes) to provide benzyl 4-(aminocarbonyl)-3-(cyclohexylamino)benzoate (45.0 mg, 0.128 mmol, 64% yield) as a yellow film. $^1$H NMR (400 MHz, $CDCl_3$): 7.81 (d, 1H), 7.46-7.32 (m, 7H), 7.16 (dd, 1H), 5.77 (br s, 2H), 5.36 (s, 2H), 3.48-3.38 (m, 1H), 2.05-1.98 (m, 2H), 1.80-1.72 (m, 2H), 1.66-1.59 (m, 1H), 1.45-1.23 (m, 4H); MS (EI) for $C_{21}H_{24}N_2O_3$: 353 ($MH^+$).

STEP 3: To a solution of benzyl 4-(aminocarbonyl)-3-(cyclohexylamino)benzoate (45 mg, 0.128 mmol) in methanol (2 mL) was added palladium on carbon (10W %, Degussa type, 45 mg). The mixture was vigorously stirred under 1 atm of hydrogen for 50 minutes. The catalyst was removed by filtration through celite, and the filtrate was concentrated to provide 4-(aminocarbonyl)-3-(cyclohexylamino)benzoic acid (25 mg, 0.095 mmol, 74% yield) as a yellow powder. $^1$H NMR (400 MHz, $CD_3OD$): 7.59 (d, 1H), 7.35 (s, 1H), 7.14 (dd, 1H), 3.47-3.39 (m, 1H), 2.05-1.98 (m, 2H), 1.81-1.73 (m, 2H), 1.68-1.60 (m, 1H), 1.52-1.41 (m, 2H), 1.38-1.25 (m, 3H).

Using analogous synthetic techniques and substituting with alternative starting reagents, the following reagents were prepared. Alternative starting materials were obtained commercially unless otherwise indicated.

4-(aminocarbonyl)-3-(ethylamino)benzoic acid

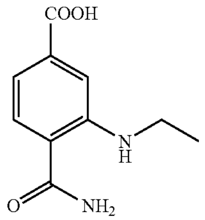

Prepared according to the method reagent preparation 40 using ethylamine in step 1. $^1$H NMR (400 MHz, DMSO-$d_6$): 7.99-7.95 (m, 2H), 7.66 (d, 1H), 7.34 (br s, 1H), 7.17 (d, 1H), 7.06 (dd, 1H), 3.19-3.12 (m, 2H), 1.20 (t, 3H); MS (EI) for $C_{10}H_{12}N_2O_3$: 209 ($MH^+$).

4-(aminocarbonyl)-3-{[3-{[2-(dimethylamino)ethyl]oxy}-4-(methyloxy)phenyl]amino}benzoic acid

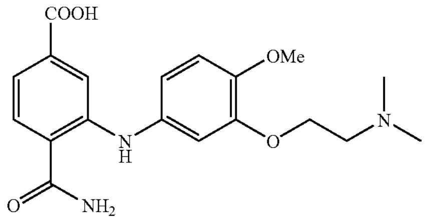

Prepared according to the method of reagent preparation 40 using 3-{[2-(dimethylamino)ethyl]oxy}-4-(methyloxy)phenylamine (Gaster et al. *J. Med. Chem.* 1998, 41(8), 1218-1235) in step 1. $^1$H NMR (400 MHz, $CD_3OD$): 7.74 (s, 1H), 7.66 (d, 1H), 7.29 (d, 1H), 7.02-6.97 (m, 2H), 6.87 (dd, 1H), 4.34-4.30 (m, 2H), 3.86 (s, 3H), 3.55-3.51 (m, 2H), 2.99 (s, 6H).

4-(aminocarbonyl)-3-(cyclopropylamino)benzoic acid

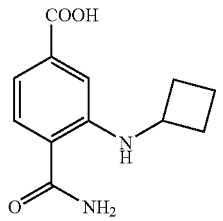

Prepared according to the method of reagent preparation 40 by using cyclopropylamine in step 1. MS (EI) for $C_{11}H_{12}N_2O_3$: 221 ($MH^+$).

4-(aminocarbonyl-3-[4-methoxy-3-(2-morpholinoethoxy)phenylamino]-benzoic acid

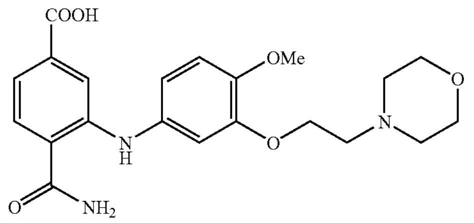

Prepared according to the method of reagent preparation 40 by using 4-methoxy-3-(2-morpholinoethoxy)aniline (Witty et al. *Bioorg. Med. Chem. Lett.* 2006, 16, 4865-4871) in step 1. MS (EI) for $C_{21}H_{25}N_3O_6$: 414 (M–H).

Reagent Preparation 41: (R)-5-(sec-butylamino)-4-(aminocarbonyl)-2-methylbenzoic Acid

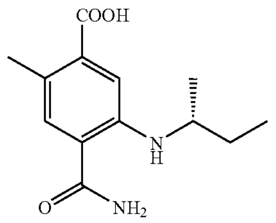

STEP 1: To a cooled (0° C.) solution of 4-bromo-2-methylbenzoic acid (15.1 g, 0.070 mol) in tetrahydrofuran (180 mL) and methanol (45 mL) was slowly added (trimethylsilyl) diazomethane (2.0M in hexanes, 42 mL, 0.084 mol). The reaction mixture was allowed to warm to room temperature and stirred for 1 h, at which time it was concentrated in vacuo to afford methyl 4-bromo-2-methylbenzoate (16 g, 100%) as a yellow oil. The residue was taken to the next step without further purification. $^1$H NMR (400 MHz, $CDCl_3$): 7.78 (d, 1H), 7.42 (s, 1H), 7.38 (d, 1H), 3.88 (s, 3H), 2.58 (s, 3H). MS (EI) for $C_9H_9BrO_2$: 230 ($MH^+$).

STEP 2: To a solution of methyl 4-bromo-2-methylbenzoate (26.6 g, 0.116 mol) in DMF (300 mL) was added zinc cyanide (8.1 g, 0.07 mol) followed by tetrakis(triphenylphosphine)palladium(0) (6.7 g, 0.0058 mol). The reaction mixture was placed in a 100° C. oil bath and stirred for 2 h, at which time it was filtered through a bed of celite and the filter cake rinsed with ethyl acetate. The filtrate was concentrated in vacuo and the residue was purified by flash chromatography (10% ethyl acetate in hexanes) to afford methyl 4-cyano-2-methylbenzoate (18.1 g, 89%) as a white powder. $^1$H NMR (400 MHz, $CDCl_3$): 7.97 (d, 1H), 7.55 (s, 1H), 7.53 (br m, 1H), 3.93 (s, 3H), 2.62 (s, 3H).

STEP 3: A solution of methyl 4-cyano-2-methylbenzoate (18.1 g, 0.103 mol) in concentrated sulfuric acid (130 mL) was cooled to −10° C. While maintaining this internal temperature, fuming nitric acid (15.6 mL) was slowly added over a period of 30 min. The reaction mixture was stirred an additional 2.5 h at 0° C., at which time it was poured over 1.0 L of ice and then partitioned with ethyl acetate. The organic layer was washed with saturated sodium bicarbonate, brine, dried over anhydrous magnesium sulfate, and then concentrated in vacuo. The residue was triturated with 10% ethyl acetate/hexanes to afford methyl 4-cyano-2-methyl-5-nitrobenzoate (14.8 g, 65%) as a white powder. The title product was isolated as the major isomer in a 9:1 regioisomeric mixture. $^1$H NMR (400 MHz, $CDCl_3$), Major: 8.85 (s, 1H), 7.81 (s, 1H), 4.00 (s, 3H), 2.77 (s, 3H); Minor: 8.07 (d, 1H), 7.72 (d, 1H), 3.98 (s, 3H), 2.57 (s, 3H). MS (EI) for $C_{10}H_8N_2O_4$: 238 ($M+H_2O$).

STEP 4: To a solution of methyl 4-cyano-2-methyl-5-nitrobenzoate (14.8 g, 0.0672 mol) in acetic acid (250 mL) was added iron powder (22.5 g, 0.40 mol). The reaction mixture was heated to 45° C. and stirred for 1 h, at which time it was cooled to room temperature. The reaction mixture was filtered through a bed of celite, and the filter cake rinsed with ethyl acetate. The volume of the filtrate was reduced by half and then partitioned between water and ethyl acetate. The organic layer was washed with 10% lithium chloride followed by saturated aqueous sodium bicarbonate. The organic layer was further washed with brine, dried over anhydrous magnesium sulfate, filtered and concentrated. The residue was triturated with hexanes to afford methyl 5-amino-4-cyano-2-methylbenzoate (11.7 g, 91%) as a bright yellow powder. $^1$H NMR (400 MHz, $CDCl_3$): 7.28 (s, 1H), 7.26 (s, 1H), 4.35 (br s, 2H), 3.89 (s, 3H), 2.43 (s, 3H). MS (EI) for $C_{10}H_{10}N_2O_2$: 191 ($MH^+$).

STEP 5: To a solution of methyl 5-amino-4-cyano-2-methylbenzoate (5.0 g, 0.0262 mol) in THF (100 mL) was added copper iodide (5.0 g, 0.0262 mol), diiodomethane (10.5 mL, 0.131 mol) and isoamyl nitrite (10.5 mL, 0.0786 mol). The reaction mixture was heated to 85° C. and stirred for 3 h, at which time it was cooled to room temperature. The heterogeneous mixture was filtered through a bed of celite, and the filter cake rinsed with ethyl acetate. The filtrate was concentrated and the residue was purified by flash chromatography (100% hexanes to 2% diethyl ether in hexanes), then triturated with hexanes to afford methyl 4-cyano-5-iodo-2-methylbenzoate (3.7 g, 76%) as a white powder. $^1$H NMR (400 MHz, $CDCl_3$): 8.39 (s, 1H), 7.50 (s, 1H), 3.94 (s, 3H), 2.56 (s, 3H).

STEP 6: To a solution of methyl 4-cyano-5-iodo-2-methylbenzoate (500 mg, 1.66 mmol) in 1,4-dioxane (25 mL) was added 9,9-dimethyl-4,5-(bis(diphenylphosphino)xanthene (96 mg, 0.166 mmol), tris(dibenzylideneacetone)-dipalladium (76 mg, 0.083 mmol), cesium carbonate (1.08 g, 3.32 mmol) and (R)-butan-2-amine (506 μL, 4.98 mmol). The reaction mixture was heated to 95° C. and stirred for 16 h, at which time it was cooled to room temperature. The heterogeneous mixture was filtered through a bed of celite, and the filter cake rinsed with ethyl acetate. The filtrate was concentrated, and the residue was purified by flash chromatography (100% hexanes to 5% ethyl acetate in hexanes) to afford (R)-methyl 5-(sec-butylamino)-4-cyano-2-methylbenzoate (300 mg, 73%) as a bright yellow oil. MS (EI) for $C_{14}H_{18}N_2O_2$: 247 ($MH^+$).

STEP 7: To a cooled (0° C.) solution of (R)-methyl 5-(sec-butylamino)-4-cyano-2-methylbenzoate (300 mg, 1.22 mmol) in DMSO (1.5 mL) was added 30% hydrogen peroxide solution (258 μL, 8.96 mmol) and potassium carbonate (56 mg, 0.402 mmol). The reaction mixture was allowed to warm to room temperature and stirred for 4 h, at which time it was concentrated in vacuo. The residue was purified by flash chromatography (100% hexanes to 10% ethyl acetate in hexanes) to afford (R)-methyl 5-(sec-butylamino)-4-(aminocarbonyl)-2-methylbenzoate (300 mg, 93%) as yellow crystals. MS (EI) for $C_{14}H_{20}N_2O_3$: 265 ($MH^+$).

STEP 8: To a solution of (R)-methyl 5-(sec-butylamino)-4-(aminocarbonyl)-2-methylbenzoate (300 mg, 1.13 mmol) in methanol (2.0 mL) and dichloromethane (1.0 mL) was added 2.0M aqueous sodium hydroxide solution (2.0 mL, 4.0 mmol). The reaction mixture was heated to 45° C. and stirred for 2 h, at which time it was cooled to room temperature and all volatiles were removed by rotary evaporation. To the residual solution was slowly added 1.0M aqueous hydrochloric acid until pH<2. The yellow precipitate was collected by filtration and washed with water to afford (R)-5-(sec-butylamino)-4-(aminocarbonyl)-2-methylbenzoic acid (210 mg, 65%). MS (EI) for $C_{13}H_{18}N_2O_3$: 251 ($MH^+$).

Using analogous synthetic techniques and substituting with alternative starting reagents, the following reagents were prepared. Alternative starting materials were obtained commercially unless otherwise indicated.

(R)-4-(aminocarbonyl)-5-(3,3-dimethylbutan-2-ylamino)-2-methylbenzoic acid

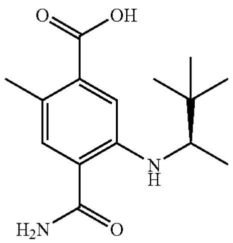

Synthesized according to the method of reagent preparation 41 using (R)-3,3-dimethylbutan-2-amine in step 6. MS (EI) for $C_{15}H_{22}N_2O_3$: 279 ($MH^+$).

(S)-5-(sec-butylamino)-4-(aminocarbonyl)-2-methylbenzoic acid

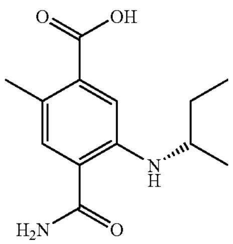

Synthesized according to the method of reagent preparation 41 using (S)-butan-2-amine in step 6. MS (EI) for $C_{13}H_{18}N_2O_3$: 251 ($MH^+$).

4-(aminocarbonyl)-5-(1-cyclopropylethylamino)-2-methylbenzoic acid

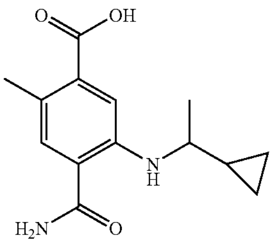

Synthesized according to the method of reagent preparation 41 using 1-cyclopropylethanamine in step 6. MS (EI) for $C_{14}H_{18}N_2O_3$: 263 ($MH^+$).

4-(aminocarbonyl)-2-methyl-5-(1,1,1-trifluoro-3-methylbutan-2-ylamino)benzoic acid

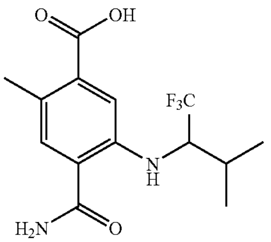

Synthesized according to the method of reagent preparation 41 using 1,1,1-trifluoro-3-methylbutan-2-amine in step 6. $^1H$ NMR (400 MHz, $CD_3OD$): 7.53 (s, 1H), 7.37 (s, 1H), 4.12-4.05 (m, 1H), 2.45 (s, 3H), 2.30-2.22 (m, 1H), 1.07 (d, 3H), 1.02 (d, 3H); MS (EI) for $C_{14}H_{17}F_3N_2O_3$: 319 ($MH^+$).

(S)-4-(aminocarbonyl)-2-methyl-5-(tetrahydrofuran-3-ylamino)benzoic acid

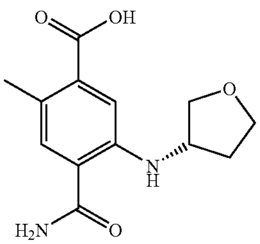

Synthesized according to the method of reagent preparation 41 using (S)-tetrahydrofuran-3-amine in step 6. $^1H$ NMR (400 MHz, $d_6$-DMSO): 12.95 (br s, 1H), 7.99 (d, 1H), 7.94 (br s, 1H), 7.53 (s, 1H), 7.36 (br s, 1H), 7.06 (br s, 1H), 4.11-4.04 (m, 1H), 3.90-3.70 (m, 1H), 3.50 (dd, 1H), 2.35 (s, 3H), 2.27-2.17 (m, 1H), 1.75-1.66 (m, 1H); MS (EI) for $C_{13}H_{16}N_2O_4$: 265 ($MH^+$).

4-(aminocarbonyl)-2-methyl-5-(propylamino)benzoic acid

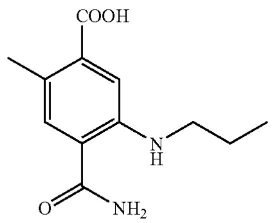

Synthesized according to the method of reagent preparation 41 using propan-1-amine in step 6. $^1$HNMR (400 MHz, $CD_3OD$): 7.45 (s, 1H), 7.21 (s, 1H), 3.12 (t, 2H), 2.42 (s, 3H), 1.69 (q, 2H), 1.03 (t, 3H). MS (EI) for $C_{12}H_{16}N_2O_3$: 237 ($MH^+$).

4-(aminocarbonyl)-5-(cyclobutylamino)-2-methylbenzoic acid

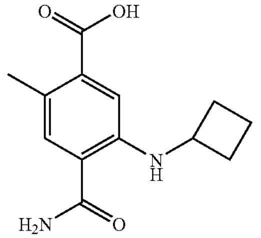

Synthesized according to the method of reagent preparation 41 using cyclobutanamine in step 6. $^1$HNMR (400 MHz, $CD_3OD$): 7.43 (s, 1H), 7.04 (s, 1H), 3.95 (m, 1H), 2.46 (m, 2H), 2.40 (s, 3H), 1.85 (m, 4H). MS (EI) for $C_{13}H_{16}N_2O_3$: 249 ($MH^+$).

4-(aminocarbonyl)-2-methyl-5-(3,3,3-trifluoropropylamino)benzoic acid

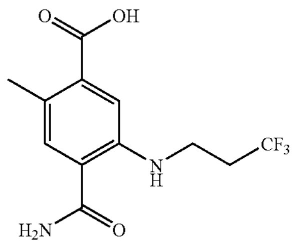

Synthesized according to the method of reagent preparation 41 using 3,3,3-trifluoropropan-1-amine in step 6. MS (EI) for $C_{12}H_{13}F_3N_2O_3$: 291 ($MH^+$).

(R)-4-(aminocarbonyl)-2-methyl-5-(3-methylbutan-2-ylamino)benzoic acid

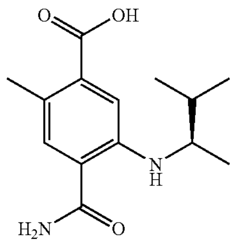

Synthesized according to the method of reagent preparation 41 using (R)-3-methylbutan-2-amine in step 6. MS (EI) for $C_{14}H_{20}N_2O_3$: 265 ($MH^+$).

4-(aminocarbonyl)-2-methyl-5-(1,1,1-trifluorobutan-2-ylamino)benzoic acid

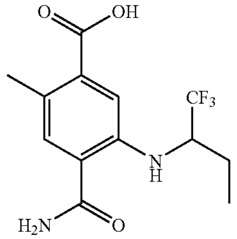

Synthesized according to the method of reagent preparation 41 using 1,1,1 trifluorobutane-2-amine hydrochloride salt (synthesized in reagent preparation 53) in step 6. MS (EI) for $C_{13}H_{15}F_3N_2O_3$: 305 ($MH^+$).

4-cyano-5-(trans-4-hydroxycyclohexylamino)-2-methylbenzoic acid

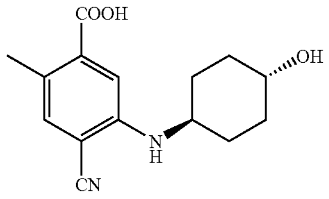

Synthesized according to the method of reagent preparation 41 using trans-4-(tert-butyldimethylsilyloxy)cyclohexanamine in step 6 followed by deprotection of the silyl protecting group as described by Greene, T. W. and Wuts, P. G. M, *Protective Groups in Organic Synthesis* 1999, John Wiley and Sons, Inc., New York, N.Y., then omission of step 7. MS (EI) for $C_{15}H_{18}N_2O_3$: 273 (M−H).

4-(aminocarbonyl)-5-[(1,1-dimethylethyl)amino]-2-methylbenzoic acid

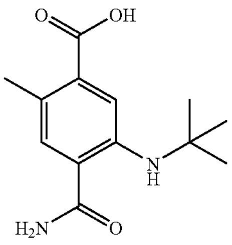

Synthesized according to the method of reagent preparation 41 using 1,1-dimethylethylamine in step 6. MS (EI) for $C_{13}H_{18}N_2O_3$: 251 ($MH^+$).

4-(aminocarbonyl)-2-methyl-5-(2-methylpropyl)benzoic acid

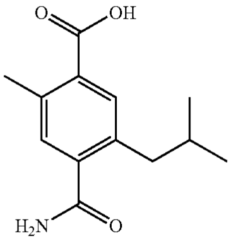

Synthesized according to the method of reagent preparation 41 using isobutylboronic acid in step 6. $^1H$ NMR (400 MHz, $CD_3OD$): 7.84 (s, 1H), 7.39 (s, 1H), 2.80-2.78 (d, 2H), 2.66 (s, 3H), 2.03-1.99 (m, 1H), 1.00-0.99 (d, 6H). MS (EI) for $C_{13}H_{17}NO_3$: 236 (M–H).

4-(aminocarbonyl)-2-methyl-5-(methyloxy)benzoic acid

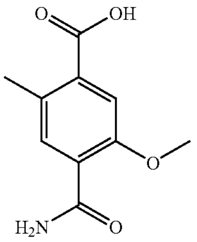

Synthesized according to the method of reagent preparation 41 by replacement of step 6 with the conversion of methyl 4-cyano-5-iodo-2-methylbenzoate to methyl 4-cyano-5-hydroxy-2-methylbenzoate according to the method described in Chemical & Pharmaceutical Bulletin (2007), 55(9), 1361-1364 followed by phenol alkylation with iodomethane then proceeding with steps 7 and 8. $^1H$ NMR (400 MHz, DMSO-$d_6$): 7.69 (b, 1H), 7.63 (b, 2H), 7.45 (s, 1H), 3.88 (s, 3H), 2.44 (s, 3H); MS (EI) for $C_{10}H_{11}NO_4$: 210 ($MH^+$).

4-(aminocarbonyl)-2-chloro-6-methyl-3-{[(1R)-1-methylpropyl]amino}benzoic acid

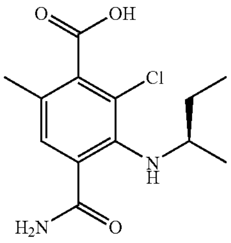

Synthesized according to the method of reagent preparation 41 using (R)-1-methylpropylamine in step 6 followed by chlorination of the resulting aniline using N-chlorosuccinimide then proceeding with steps 7 and 8. MS (EI) for $C_{13}H_{17}N_2O_3Cl$: 285 ($MH^+$).

4-(aminocarbonyl)-2-methyl-5-[(1-methylpropyl)oxy]benzoic acid

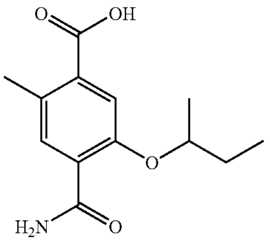

Synthesized according to the method of reagent preparation 41 by replacement of step 6 with the conversion of methyl 4-cyano-5-iodo-2-methylbenzoate to methyl 4-cyano-5-hydroxy-2-methylbenzoate according to the method described in Chemical & Pharmaceutical Bulletin (2007), 55(9), 1361-1364 followed by phenol alkylation with 2-bromobutane then proceeding with steps 7 and 8. MS (EI) for $C_{13}H_{17}NO_4$: 252 ($MH^+$).

4-(aminocarbonyl)-5-ethyl-2-methylbenzoic acid

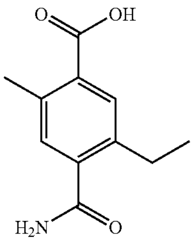

Synthesized according to the method of reagent preparation 41 by using ethylmagnesium chloride in step 6 according to the method described in Synlett 1996, 5, 473-474 then proceeding with steps 7 and 8. $^1H$ NMR (400 MHz, DMSO-$d_6$):

7.84 (s, 1H), 7.69 (s, 1H), 7.59 (s, 1H), 7.23 (s, 1H), 3.00 (s, 3H), 2.71 (q, 2H), 1.14 (t, 3H). MS (EI) for $C_{11}H_{13}NO_3$: 208 ($MH^+$).

4-(aminocarbonyl)-2-methyl-5-{[2-(methyloxy) ethyl]oxy}benzoic acid

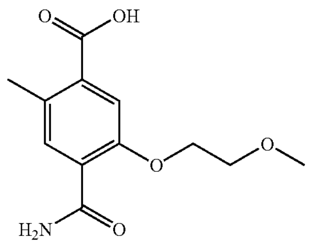

Synthesized according to the method of reagent preparation 41 by replacement of step 6 with the conversion of methyl 4-cyano-5-iodo-2-methylbenzoate to methyl 4-cyano-5-hydroxy-2-methylbenzoate according to the method described in Chemical & Pharmaceutical Bulletin (2007), 55(9), 1361-1364 followed by phenol alkylation with 2-bromoethyl methyl ether then proceeding with steps 7 and 8. MS (EI) for $C_{12}H_{15}NO_5$: 254 ($MH^+$).

Reagent Preparation 42: 4-(aminocarbonyl)-5-(isopropylamino)-2-methylbenzoic Acid

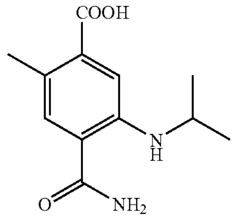

STEP 1: Methyl 5-amino-4-cyano-2-methylbenzoate (synthesized in reagent preparation 41, step 4) (240 mg, 1.26 mmol) was dissolved in 1,2-dichloroethane (7 mL) and was treated with trifluoroacetic acid (0.6 mL, 7.57 mmol), acetone (0.28 mL, 3.79 mmol), and sodium triacetoxyborohydride (802 mg, 3.78 mmol) at 45° C. for 20 min. The reaction mixture was cooled to ambient temperature and quenched with saturated aqueous sodium bicarbonate and was partitioned with dichloromethane. The aqueous portion was extracted with dichloromethane. The combined organic portion was washed with brine, dried over sodium sulfate, then filtered and concentrated to afford a yellow oil which was purified by column chromatography (silica gel, 10% dichloromethane in hexanes) to afford methyl 4-cyano-5-(isopropylamino)-2-methylbenzoate (224 mg, 0.96 mmol, 76% yield) as a pale yellow oil. $^1H$ NMR (400 MHz, $CDCl_3$): δ 7.25 (s, 1H), 7.16 (s, 1H), 4.28 (d, 1H), 3.91 (s, 3H), 3.77-3.74 (m, 1H), 2.40 (s, 3H), 1.27 (s, 3H), 1.26 (s, 3H); MS (EI) for $C_{14}H_{16}N_2O_2$: 233 ($MH^+$).

STEP 2: Methyl 4-cyano-5-(isopropylamino)-2-methylbenzoate (224 mg, 0.96 mmol) was dissolved in DMSO (2 mL) and cooled in a cold water bath. 30% Aqueous hydrogen peroxide (0.2 mL) and potassium carbonate (42.6 mg, 0.31 mmol) was added, and the mixture was stirred at ambient temperature for 1 h. The reaction mixture was partitioned between ethyl acetate and 10% aqueous lithium chloride. The aqueous portion was extracted with ethyl acetate. The combined organic portion was dried over sodium sulfate, then filtered and concentrated to a yellow oil which was purified by column chromatography (silica gel, 15-30% ethyl acetate in hexanes to afford methyl 4-aminocarbonyl-5-(isopropylamino)-2-methylbenzoate (202 mg, 0.81 mmol, 83% yield) as a yellow oil. $^1H$ NMR (400 MHz, $CDCl_3$): δ 7.35 (d, 1H), 7.26 (d, 1H), 7.24-7.22 (m, 2H), 5.70 (br s, 1H), 3.90 (s, 3H), 3.75-3.68 (m, 1H), 2.42 (s, 3H), 1.26-1.24 (m, 6H); MS (EI) for $C_{13}H_{18}N_2O_3$: 251 ($MH^+$).

STEP 3: Methyl 4-aminocarbonyl-5-(isopropylamino)-2-methylbenzoate (202 mg, 0.81 mmol) was dissolved in methanol (3 mL) and was treated with 1M sodium hydroxide (3 mL, 3 mmol) at 45° C. for 1.5 h. The reaction mixture was cooled to ambient temperature and was concentrated to afford an aqueous residue that was acidified with 1N hydrochloric acid to pH 3. The precipitate was collected by filtration, washed with water and dried to afford 4-aminocarbonyl-5-(isopropylamino)-2-methylbenzoic acid (99.5 mg, 0.42 mmol, 52% yield). $^1H$ NMR (400 MHz, $d_6$-DMSO): δ 12.95 (br s, 1H), 7.90 (br s, 1H), 7.72 (d, 1H), 7.49 (s, 1H), 7.28 (br s, 1H), 7.06 (s, 1H), 3.64-3.54 (m, 1H), 2.33 (s, 3H), 1.15 (s, 3H), 1.14 (s, 3H); MS (EI) for $C_{12}H_{16}N_2O_3$: 237 ($MH^+$).

Using analogous synthetic techniques and substituting with alternative starting reagents, the following starting reagents were prepared. In cases where an aldehyde was used as the substrate for (step 1) acetic acid was generally used instead of trifluoroacetic acid. Alternative starting materials were obtained commercially unless otherwise indicated.

4-(aminocarbonyl)-5-(cyclopentylamino)-2-methylbenzoic acid

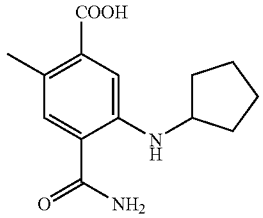

Synthesized according to the method of reagent preparation 42 using cyclopentanone in step 1. $^1H$ NMR (400 MHz, $d_6$-DMSO): δ 12.90 (br s, 1H), 7.92 (br s, 1H), 7.87 (d, 1H), 7.49 (s, 1H), 7.28 (br s, 1H), 7.08 (s, 1H), 3.78-3.73 (m, 1H), 2.34 (s, 3H), 2.02-1.90 (m, 2H), 1.70-1.53 (m, 4H), 1.43-1.33 (m, 2H); MS (EI) for $C_{14}H_{18}N_2O_3$: 263 ($MH^+$).

4-(aminocarbonyl)-2-methyl-5-(neopentylamino) benzoic acid

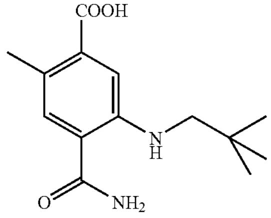

Synthesized according to the method of reagent preparation 42 using pivalaldehyde in step 1. $^1$H NMR (400 MHz, $d_6$-DMSO): δ 12.94 (br s, 1H), 8.12 (t, 1H), 7.93 (br s, 1H), 7.51 (s, 1H), 7.28 (br s, 1H), 7.04 (s, 1H), 2.87 (d, 2H), 2.34 (s, 3H), 0.97 (m, 9H); MS (EI) for $C_{14}H_{20}N_2O_3$: 265 ($MH^+$).

4-(aminocarbonyl)-5-(cyclopropylmethylamino)-2-methylbenzoic acid

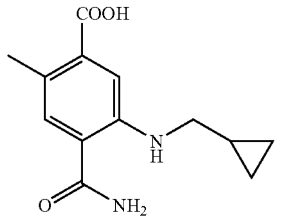

Synthesized according to the method of reagent preparation 42 using cyclopropanecarbaldehyde in step 1. $^1$H NMR (400 MHz, $d_6$-DMSO): δ 12.89 (br s, 1H), 7.92 (br s, 1H), 7.85 (t, 1H), 7.50 (s, 1H), 7.29 (br s, 1H), 7.07 (s, 1H), 2.95 (t, 2H), 2.35 (t, 3H), 1.07-1.04 (m, 1H), 0.52-0.47 (m, 2H), 0.25-0.21 (m, 2H); MS (EI) for $C_{13}H_{16}N_2O_3$: 249 ($MH^+$).

4-aminocarbonyl-2-methyl-5-[4-(trifluoromethyl) cyclohexylamino]benzoic acid

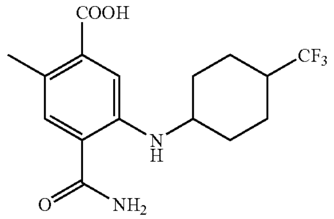

Synthesized according to the method of reagent preparation 42 using 4-(trifluoromethyl)cyclohexanone in step 1. MS (EI) for $C_{16}H_{19}F_3N_2O_3$: 345 ($MH^+$).

4-aminocarbonyl-2-methyl-5-(pentan-3-ylamino) benzoic acid

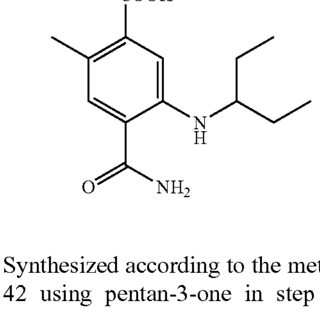

Synthesized according to the method of reagent preparation 42 using pentan-3-one in step 1. $^1$H NMR (400 MHz, $CD_3OD$): 7.44 (s, 1H), 7.22 (s, 1H), 3.35-3.29 (m, 1H buried), 2.41 (s, 3H), 1.68-1.46 (m, 4H), 0.94 (t, 6H); MS (EI) for $C_{14}H_{20}N_2O_3$: 265 ($MH^+$).

4-aminocarbonyl-2-methyl-5-(pentylamino)benzoic acid

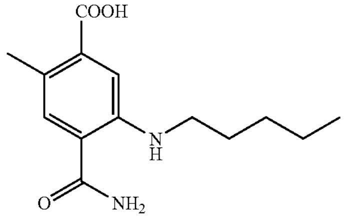

Synthesized according to the method of reagent preparation 42 using n-pentanal in step 1. $^1$H NMR (400 MHz, $CD_3OD$): 7.45 (s, 1H), 7.20 (s, 1H), 3.15 (t, 2H), 2.42 (s, 3H), 1.70-1.62 (m, 2H), 1.47-1.34 (m, 4H), 0.94 (t, 6H).

4-aminocarbonyl-5-(1,3-difluoropropan-2-ylamino)-2-methylbenzoic acid

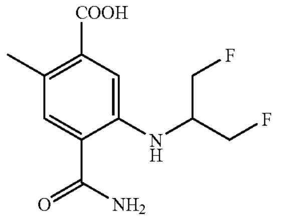

Synthesized according to the method of reagent preparation 42 using 1,3-difluoropropanone in step 1. $^1$H NMR (400 MHz, $CD_3OD$): 7.50 (s, 1H), 7.34 (s, 1H), 4.67-4.58 (m, 2H), 4.56-4.46 (m, 2H), 4.11-3.97 (m, 1H), 2.42 (s, 3H); MS (EI) for $C_{12}H_{14}F_2N_2O_3$: 265 ($MH^+$).

4-(aminocarbonyl)-2-methyl-5-[(3,3,3-trifluoro-1-methylpropyl)amino]-benzoic acid

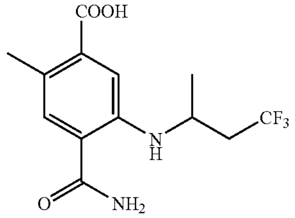

Synthesized according to the method of reagent preparation 42 using 4,4,4-trifluorobutan-2-one in step 1. MS (EI) for $C_{13}H_{15}F_3N_2O_3$: 305 ($MH^+$).

4-(aminocarbonyl)-2-methyl-5-{[2-methyl-1-(1-methylethyl)propyl]amino}-benzoic acid

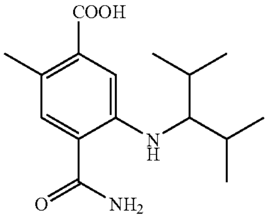

Synthesized according to the method of reagent preparation 42 using 2,4-dimethylpentan-3-one in step 1. $^1$H NMR (400 MHz, $d_6$-DMSO): δ 12.85 (br s, 1H), 8.05-7.99 (d, 1H), 7.90 (br. s, 1H), 7.47 (s, 1H), 7.26 (br s, 1H), 7.18 (s, 1H), 3.09-3.00 (m, 1H), 2.31 (s, 3H), 1.89-1.77 (m, 2H), 0.91-0.79 (m, 12H); MS (EI) for $C_{16}H_{24}N_2O_3$: 293 ($MH^+$).

4-(aminocarbonyl)-5-[(dicyclopropylmethyl)amino]-2-methylbenzoic acid

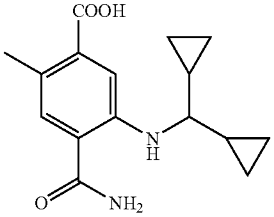

Synthesized according to the method of reagent preparation 42 using dicyclopropylmethanone in step 1. MS (EI) for $C_{16}H_{20}N_2O_3$: 293 ($MH^+$).

4-(aminocarbonyl)-2-methyl-5-[(2-methylpropyl)amino]benzoic acid

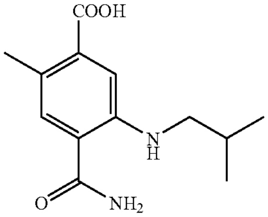

Synthesized according to the method of reagent preparation 42 using isobutyraldehyde in step 1. MS (EI) for $C_{13}H_{18}N_2O_3$: 251 ($MH^+$).

4-(aminocarbonyl)-5-[(cyclopentylmethyl)amino]-2-methylbenzoic acid

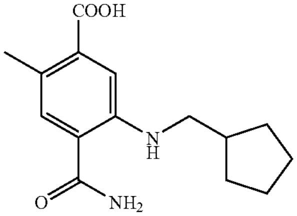

Synthesized according to the method of reagent preparation 42 using cyclopentanecarboxaldehyde in step 1. MS (EI) for $C_{15}H_{20}N_2O_3$: 277 ($MH^+$).

4-(aminocarbonyl)-2-methyl-5-{[1-(1-methylcyclopropyl)-ethyl]amino}benzoic acid

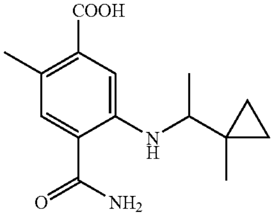

Synthesized according to the method of reagent preparation 42 using methyl 1-methylcyclopropyl ketone in step 1. MS (EI) for $C_{15}H_{20}N_2O_3$: 277 ($MH^+$).

4-aminocarbonyl-2-methyl-5-(2-methylpentan-3-ylamino)benzoic acid

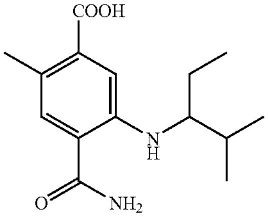

Prepared according to the method of reagent preparation 42 by using 2-methylpentan-3-one in step 1.

4-aminocarbonyl-5-(1-cyclopropylpropylamino)-2-methylbenzoic acid

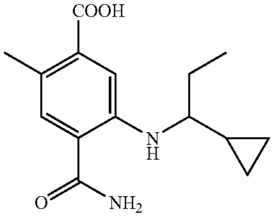

Prepared according to the method of reagent preparation 42 by using 1-cyclopropylpropan-1-one in step 1.

Reagent Preparation 43: 3-amino-4-(aminocarbonyl)benzoic Acid

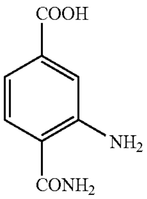

STEP 1: 4-(Methoxycarbonyl)-3-nitrobenzoic acid (100 g, 0.44 mol) was taken into concentrated aqueous ammonia (37w %, 500 mL), and the resulting yellow solution was allowed to stir at room temperature over 12 hours. The solution was then reduced in volume to approximately 300 mL by rotary evaporation, and the solution was acidified to pH 2 by portion-wise addition of concentrated aqueous hydrochloric acid. The thick precipitate was collected by filtration and dried in vacuo to afford 4-(aminocarbonyl)-3-nitrobenzoic acid (51 g, 60% yield). $^1$H-NMR ($d_6$-DMSO): 8.42 (d, 1H), 8.27 (dd, 1H), 8.26 (br s, 1H), 7.86 (br s, 1H), 7.76 (d, 1H).

STEP 2: 4-(aminocarbonyl)-3-nitrobenzoic acid (2.00 g, 9.52 mmol) was suspended in water (50 ml) and sodium bicarbonate (0.80 g, 9.52 mmol) was added. The resulting solution was hydrogenated in the presence of 10% palladium on carbon (300 mg) at 30 psi for 16 hours. The mixture was then filtered through Celite. The filtrate was acidified by addition of concentrated hydrochloric acid and the resulting solid was collected by filtration and dried in vacuo to afford 3-amino-4-(aminocarbonyl)benzoic acid (1.70 g, 99% yield). MS (EI) for $C_8H_8N_2O_3$: 179 (M−H).

Reagent Preparation 44: 3-bromo-4-(aminocarbonyl)benzoic Acid

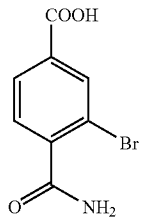

STEP 1: Methyl 3-bromo-4-cyanobenzoate (prepared as described in Wang, G. T. et al. *Bioorg. Med. Chem. Lett.* 2005, 15(1), 153(1) (130 mg, 0.54 mmol) was dissolved in DMSO (1.5 mL) and was cooled in a cold water bath. 30% aqueous hydrogen peroxide (0.1 mL) and potassium carbonate (23.9.0 mg, 0.17 mmol) were added and the mixture was stirred at room temperature for 18.5 h. The reaction mixture was partitioned between ethyl acetate and 10% aqueous lithium chloride. The aqueous portion was extracted with ethyl acetate. The combined organic portions were dried over sodium sulfate, filtered and concentrated to afford methyl 3-bromo-4-(aminocarbonyl)benzoate (quantitative yield) as a yellow oil. GCMS for $C_9H_8BrNO_3$: 257, 259 ($M^+$).

STEP 2: Methyl 3-bromo-4-(aminocarbonyl)benzoate (0.54 mmol) was dissolved in methanol (1 mL) and was treated with 1M aqueous sodium hydroxide (1 mL) at 45° C. for 3 h. The reaction mixture was cooled to room temperature and concentrated to afford an aqueous residue that was acidified with 1N aqueous hydrochloric acid to pH ~3. The precipitate was collected by filtration, washed with water, and dried to afford 3-bromo-4-(aminocarbonyl)benzoic acid (69.4 mg, 0.28 mmol, 53% overall). $^1$H NMR (400 MHz, $d_6$-DMSO): 13.47 (br s, 1H), 8.08 (dd, 1H), 8.00 (br s, 1H), 7.94 (dd, 1H), 7.73 (br s, 1H), 7.51 (d, 1H); MS (EI) for $C_8H_6BrNO_3$: 242, 244(M−H).

Reagent Preparation 45: 4-(aminocarbonyl)-2-fluoro-5-(pentan-3-ylamino)benzoic Acid

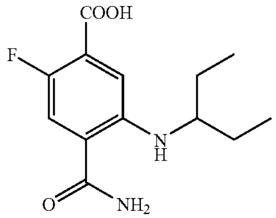

STEP 1: To a solution of 4-bromo-2-fluorobenzoic acid (2.0 g, 9.1 mmol) in THF (24 mL) and methanol (6 mL) at 0° C. was added a solution of (trimethylsilyl)diazomethane in hexanes (2.0 M, 5.46 mL, 10.9 mmol). The yellow solution was allowed to gradually warm to room temperature over 1 h. The volatile materials were removed and the residue was treated with aqueous hydrochloric acid (1 M). The aqueous mixture was extracted with ethyl acetate. The organic extract was dried over magnesium sulfate, filtered, and concentrated to provide crude methyl 4-bromo-2-fluorobenzoate (2.7 g, quantitative yield). This material was used in the subsequent step without further purification. $^1$H NMR (400 MHz, $CDCl_3$): 7.85-7.81 (m, 1H), 7.38-7.33 (m, 2H), 3.93 (s, 3H); MS (EI) for $C_8H_6BrFO_2$: 232, 234 ($MH^+$).

STEP 2: To a solution of methyl 4-bromo-2-fluorobenzoate (9.1 mmol) in DMF (50 mL) was added zinc cyanide (641 mg, 5.5 mmol) followed by tetrakis(triphenyphosphine)palladium(0) (1.05 g, 0.91 mmol). The mixture was heated to 100° C. and stirred for 3 h. At that point, additional tetrakis(triphenyphosphine)-palladium(0) (500 mg, 0.43 mmol) was added. The mixture was stirred a further 30 min and was then cooled to room temperature. Water and ethyl acetate were added, and insoluble solids were removed by filtration through celite. The layers were then separated. The aqueous phase was extracted with ethyl acetate. The organic extracts were combined, washed with 10% aqueous lithium chloride, dried over magnesium sulfate, filtered and concentrated. The residue was purified by column chromatography (10% ethyl acetate in hexanes) to provide methyl 4-cyano-2-fluorobenzoate (1.36 g, 7.6 mmol, 84% yield).

$^1$H NMR (400 MHz, $CDCl_3$): 8.06 (dd, 1H), 7.53 (dd, 1H), 7.47 (dd, 1H), 3.98 (s, 3H); MS (EI) for $C_9H_6FNO_2$: 179 ($M^+$).

STEP 3: To a flask containing methyl 4-cyano-2-fluorobenzoate (1.61 g, 9.0 mmol) was added fuming nitric acid (15 mL) followed by concentrated sulfuric acid (4 mL). The mixture was heated to 45° C. for 15 h before cooling to room temperature. The solution was then poured into ice water and the resulting mixture was extracted twice with ethyl acetate. The combined organic extracts were washed with saturated sodium bicarbonate solution, dried over magnesium sulfate, filtered, and concentrated to provide methyl 4-cyano-2-fluoro-5-nitrobenzoate (859 mg, 3.83 mmol, 43% yield).

$^1$H NMR (400 MHz, $CDCl_3$): 8.95 (d, 1H), 7.72 (d, 1H), 4.04 (s, 3H); MS (EI) for $C_9H_5FN_2O_4$: 224 ($M^+$).

STEP 4: To a solution of methyl 4-cyano-2-fluoro-5-nitrobenzoate (785 mg, 3.5 mmol) in acetic acid (15 mL) was added iron powder (1.17 g, 21.0 mmol). The mixture was stirred vigorously at room temperature for 2 h. Insoluble solids were then removed by filtration through celite. Water was added to the filtrate and the aqueous mixture was extracted with ethyl acetate. The organic extract was washed with saturated aqueous sodium bicarbonate, dried over magnesium sulfate, filtered, and concentrated. The residue was purified by column chromatography (30% ethyl acetate in hexanes) to provide methyl 5-amino-4-cyano-2-fluorobenzoate (463 mg, 2.38 mmol, 68% yield). $^{1}$H NMR (400 MHz, $CDCl_3$): 7.30 (d, 1H), 7.19 (d, 1H), 4.41 (br s, 2H), 3.94 (s, 3H); MS (EI) for $C_9H_7FN_2O_2$: 193 (M−H).

STEP 5: To a solution of methyl 5-amino-4-cyano-2-fluorobenzoate (437 mg, 2.2 mmol) in THF (13 mL) was added copper(I) iodide (419 mg, 2.2 mmol), diiodomethane (890 uL, 11 mmol), and isoamyl nitrite (890 uL, 6.6 mmol). The solution was heated to reflux for 4 h and was then allowed to cool to room temperature. After dilution with ethyl acetate, water was added and the mixture was filtered through celite. The biphasic filtrate was partitioned. The organic phase was dried over magnesium sulfate, filtered, and concentrated. The residue was then subject to column chromatography to provide impure methyl 4-cyano-2-fluoro-5-iodobenzoate (452 mg, ~63% purity, ~0.93 mmol). The remainder of the material consisted primarily of methyl 4-cyano-2-fluorobenzoate and was carried forward into the subsequent reaction without further purification. $^{1}$H NMR (400 MHz, $CDCl_3$): 8.44 (d, 1H), 7.43 (d, 1H), 3.97 (s, 3H); MS (EI) for $C_9H_5FINO_2$: 305 ($M^+$).

STEP 6: To a pressure vessel were added the above methyl 4-cyano-2-fluoro-5-iodobenzoate (~0.93 mmol), cesium carbonate (606 mg, 1.86 mmol), pentan-3-amine (325 uL, 2.79 mmol), XANTPHOS (54 mg, 0.093 mmol), tris(dibenzylideneacetone)dipalladium(0) (43 mg, 0.047 mmol), and dioxane (4 mL). The vessel was sealed and heated to 95° C. for ~17 h. After cooling to room temperature, the mixture was filtered through celite, and the filter cake rinsed with ethyl acetate. The filtrate was then concentrated. The residue was subject to column chromatography (10% ethyl acetate in hexanes). Eluent containing the desired project was collected and concentrated to afford an impure residue. This residue was dissolved in DMSO (6 mL) and was treated with potassium carbonate (111 mg, 0.8 mmol) and 30% aqueous hydrogen peroxide (150 uL). After stirring at room temperature for 30 min, the mixture was diluted with ethyl acetate. The organic solution was washed with a mixture of water and 10% aqueous lithium chloride. The aqueous wash was extracted with ethyl acetate. The combined organic extracts were washed with 10% aqueous lithium chloride, dried over magnesium sulfate, filtered, and concentrated. The residue was purified by gradient column chromatography (30% ethyl acetate in hexanes to 50% ethyl acetate in hexanes) to provide methyl 4-(aminocarbonyl)-2-fluoro-5-(pentan-3-ylamino)benzoate (73.7 mg, 0.26 mmol, 28% yield). $^{1}$H NMR (400 MHz, $CDCl_3$): 7.42 (d, 1H), 7.18-7.15 (m, 2H), 5.86 (br s, 2H), 3.94 (s, 3H), 3.37-3.29 (m, 1H), 1.67-1.47 (m, 4H), 0.93 (t, 6H).

STEP 7: To a solution of methyl 4-(aminocarbonyl)-2-fluoro-5-(pentan-3-ylamino)benzoate (73.7 mg, 0.26 mmol) in methanol (1 mL) at 0° C. was added 1 N sodium hydroxide (520 uL, 0.52 mmol). The mixture was stirred 30 min at 0° C., and was then warmed to room temperature. Dichloromethane (500 uL) was added to improve solubility, and the homogeneous solution was stirred 3.5 h at room temperature. After acidification with 1 N hydrochloric acid (500 uL), the volatile solvents were removed by rotary evaporation. An insoluble solid material was then isolated from the aqueous residue by filtration. The solid was dried to give 4-(aminocarbonyl)-2-fluoro-5-(pentan-3-ylamino)benzoic acid (61.7 mg, 0.23 mmol, 88% yield). $^{1}$H NMR (400 MHz, $CD_3OD$): 7.41 (d, 1H), 7.16 (d, 1H), 3.43-3.28 (m, 1H buried), 1.68-1.46 (m, 4H), 0.95 (t, 6H).

Reagent Preparation 46: 4-(aminocarbonyl)-2-chloro-5-(pentan-3-ylamino)benzoic Acid

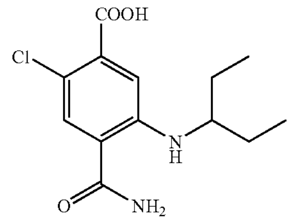

STEP 1: To a pressure vessel were added ethyl 3-bromo-4-cyanobenzoate (500 mg, 1.97 mmol), cesium carbonate (1.28 g, 3.94 mmol), pentan-3-amine (688 uL, 5.90 mmol), XANTPHOS (114 mg, 0.20 mmol), tris(dibenzylideneacetone)dipalladium(0) (90 mg, 0.10 mmol), and dioxane (3 mL). The vessel was sealed and heated to 95° C. for 15 h. After cooling to room temperature, the mixture was filtered through celite and the filter cake rinsed with ethyl acetate. The filtrate was then concentrated and the residue was purified by column chromatography (10% ethyl acetate in hexanes) to provide ethyl 4-cyano-3-(pentan-3-ylamino)benzoate (315 mg, 1.21 mmol, 61% yield) as a yellow syrup. $^{1}$H NMR (400 MHz, $CDCl_3$): 7.43 (d, 1H), 7.33 (s, 1H), 7.25 (dd, 1H), 4.44-4.35 (m, 3H), 3.48-3.40 (m, 1H), 1.72-1.48 (m, 4H), 1.40 (t, 3H), 0.96 (t, 6H); MS (EI) for $C_{15}H_{20}N_2O_2$: 261 ($MH^+$).

STEP 2: To a solution of ethyl 4-cyano-3-(pentan-3-ylamino)benzoate (315 mg, 1.21 mmol) in DMF was added N-chlorosuccinimide (162 mg, 1.21 mmol), and the solution was heated to 45° C. for 24 h. After cooling to room temperature, the mixture was diluted with ethyl acetate. The organic solution was then washed with a mixture of water and 10% aqueous lithium chloride. The aqueous wash was extracted with ethyl acetate and the organic extracts were combined, dried over magnesium sulfate, filtered, and concentrated.

STEP 3: The above residue was then dissolved in DMSO (6 mL) and was treated with potassium carbonate (167 mg, 1.21 mmol) and 30% aqueous hydrogen peroxide (150 uL) at room temperature for 5.5 h. After dilution with ethyl acetate, water was added to the reaction mixture. The layers were separated and the aqueous phase was extracted with ethyl acetate. The combined organic extracts were washed with 10% aqueous lithium chloride, dried over magnesium sulfate, filtered, and concentrated. The residue was purified by column chromatography (30% ethyl acetate in hexanes) to provide ethyl 4-(aminocarbonyl)-2-chloro-5-(pentan-3-ylamino)benzoate (126.5 mg, 0.40 mmol, 33% yield) as a yellow film. $^{1}$H NMR (400 MHz, $CDCl_3$): 7.73 (d, 1H), 7.41 (s, 1H), 7.04 (s, 1H), 5.86 (br s, 2H), 4.40 (q, 2H), 3.34-3.26 (m, 1H), 1.68-1.47 (m, 4H), 1.41 (t, 3H), 0.93 (t, 6H); MS (EI) for $C_{15}H_{21}ClN_2O_3$: 313 ($MH^+$).

STEP 4: To a solution of ethyl 4-(aminocarbonyl)-2-chloro-5-(pentan-3-ylamino)benzoate (126.5 mg, 0.40 mmol) in methanol (2 mL) was added 2 N aqueous sodium hydroxide (400 uL, 0.80 mmol). The mixture was stirred 4.5 h at room temperature. After acidification with 1 N hydrochloric acid (800 uL), the volatile solvent were removed. An insoluble solid material was then isolated from the aqueous residue by filtration. The solid was dried to give 4-(aminocarbonyl)-2-chloro-5-(pentan-3-ylamino)benzoic acid (73 mg, 0.26 mmol, 64% yield). $^1$H NMR (400 MHz, $CD_3OD$): 7.65 (s, 1H), 7.07 (s, 1H), 3.35-3.29 (m, 1H buried), 1.69-1.47 (m, 4H), 0.94 (t, 6H).

Using analogous synthetic techniques and substituting with alternative starting reagents the following reagents were prepared. Alternative starting materials were obtained commercially unless otherwise indicated.

4-(aminocarbonyl)-2-chloro-3-[(1-cyclopropylethyl) amino]benzoic acid

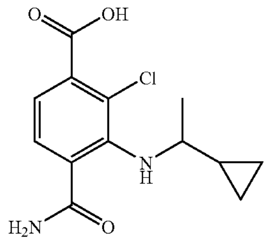

Synthesized according to the method of reagent preparation 46 by first conducting step 2 to give a mixture of ethyl 3-bromo-2-chloro-4-cyanobenzoate and ethyl 5-bromo-2-chloro-4-cyanobenzoate then proceeding with step 1 using 1-cyclopropylethylamine followed by steps 3 and 4. $^1$HNMR (400 MHz, $CD_3OD$): 7.49 (d, 1H), 7.22 (d, 1H), 2.84 (q, 2H), 1.17 (d, 3H), 0.9-0.76 (m, 1H), 0.3-0.26 (m, 2H), 0.04-0.00 (m, 2H). MS (EI) for $C_{13}H_{15}ClN_2O_3$: 284 ($MH^+$).

Reagent Preparation 47: 4-(aminocarbonyl)-3-[trans-4-(piperidin-1-yl)cyclohexylamino]benzoic Acid

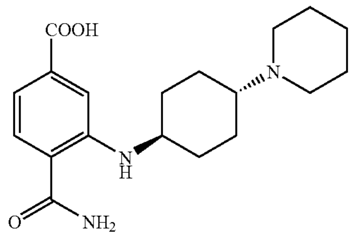

STEP 1: A mixture of ethyl 3-bromo-4-cyanobenzoate (0.82 g, 3.24 mmol), 1,1-dimethylethyl(trans-4-aminocyclohexyl)carbamate (0.69 g, 3.24 mmol), tris(dibenzylideneacetone)dipalladium(0) (0.148 g, 0.16 mmol), XANTPHOS (0.19 g, 0.32 mmol) and cesium carbonate (1.48 g, 4.54 mmol) in dioxane (13 mL) was refluxed for 15 hours. On cooling to room temperature, the mixture was filtered through Celite, concentrated, and purified by silica gel column chromatography using hexanes:ethyl acetate from 5:1 to 4:1 to afford ethyl 4-cyano-3-{[trans-4-({[(1,1-dimethylethyl)oxy]carbonyl}amino)cyclohexyl]amino}benzoate (0.370 g, 30% yield). $^1$H NMR (400 MHz, $d_6$-DMSO): 7.59 (d, 1H), 7.28 (s, 1H), 7.13 (dd, 1H), 6.82 (d, 1H), 6.05 (d, 1H), 4.31 (q, 2H), 3.46-3.37 (m, 1H), 3.28-3.17 (m, 1H), 1.95-1.85 (m, 2H), 1.84-1.76 (m, 2H), 1.46, 1.22 (m, 16H).

STEP 2: ethyl 4-cyano-3-{[trans-4-({[(1,1-dimethylethyl)oxy]carbonyl}-amino)cyclohexyl]amino}benzoate (0.37 g, 0.97 mmol) was stirred in a mixture of dichloromethane (2 mL) and trifluoroacetic acid (2 mL) at room temperature for 1 hour. The solvent was rotary evaporated, and the residue was dried in vacuo to give ethyl 3-[(trans-4-aminocyclohexyl)amino]-4-cyanobenzoate (0.490 g, 99% yield) as trifluoroacetic acid salt. MS (EI) for $C_{16}H_{21}N_3O_2$: 288 ($MH^+$).

STEP 3: A mixture of ethyl 3-[(trans-4-aminocyclohexyl) amino]-4-cyanobenzoate (0.490 g, 0.96 mmol), potassium carbonate (0.66 g, 4.78 mmol) and 1,5 dibromopentane (0.130 mL, 0.96 mmol) was stirred in dimethylformamide (10 mL) at room temperature for 48 h. Water (20 mL) was then added to the mixture, and the water phase was extracted with dichloromethane (2×30 mL). The combined organic layers were dried over sodium sulfate, filtered and concentrated. The residue was purified by silica gel column chromatography using methanol in dichloromethane (5% to 10%) to afford ethyl 4-cyano-3-[(trans-4-piperidin-1-ylcyclohexyl)amino] benzoate (0.145 g, 43% yield). MS (EI) for $C_{21}H_{29}N_3O_2$: 356 ($MH^+$).

STEP 4: To a solution of ethyl 4-cyano-3-[(trans-4-piperidin-1-ylcyclohexyl)amino]benzoate (0.145 g, 0.41 mmol) in DMSO (0.5 mL) was added a 30% hydrogen peroxide solution (0.078 mL, 0.81 mmol) and potassium carbonate (0.014 g, 0.10 mmol). The reaction mixture was stirred at 50° C. for 3 h. A mixture of methanol (1.5 mL) and water (0.5 mL) was then added followed by potassium hydroxide (0.046 g, 0.81 mmol), and the solution was stirred at 55° C. for 2 h. The mixture was acidified to pH 5 by addition of 1N aqueous hydrochloric acid and lyophilized to afford crude 4-(aminocarbonyl)-3-(trans-4-(piperidin-1-yl)cyclohexylamino] benzoic acid which was used without further purification. MS (EI) for $C_{19}H_{27}N_3O_3$: 346 ($MH^+$).

Reagent Preparation 48: 5-amino-4-(aminocarbonyl)-2-methylbenzoic Acid

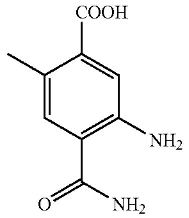

STEP 1: Methyl 5-amino-4-cyano-2-methylbenzoate (151 mg, 0.79 mmol) (synthesized according to reagent preparation 41) was dissolved in DMSO (1.5 mL). 30% Aqueous hydrogen peroxide (0.3 mL) and potassium carbonate (35 mg, 0.25 mmol) were added, and the mixture was stirred at ambient temperature for 1.5 h. The reaction mixture was partitioned between ethyl acetate and water. The aqueous portion was extracted (2×) with ethyl acetate. The combined organic portion was dried over sodium sulfate, filtered and concentrated to a yellow oil which was purified by preparative reverse phase HPLC to afford methyl 5-amino-4-(aminocarbonyl)-2-methylbenzoate (108 mg, 0.52 mmol, 66% yield). NMR (400 MHz, $CDCl_3$): δ 7.85 (s, 1H), 7.45 (br s, 1H), 7.26 (s, 1H), 7.19 (br s, 1H), 6.48 (s, 2H), 3.80 (s, 3H), 2.32 (s, 3H); MS (EI) for $C_{10}H_{12}N_2O_3$: 209 ($MH^+$).

STEP 2: Methyl 5-amino-4-(aminocarbonyl)-2-methylbenzoate (108 mg, 0.52 mmol) was dissolved in methanol (1.5 mL) and was treated with 1 M sodium hydroxide (1.5 mL, 1.5 mmol) for 1 h. The reaction mixture was concentrated to afford an aqueous residue that was acidified with 1N hydrochloric acid to pH ~3. The precipitate was collected by filtration, washed with water, and dried in vacuo to afford 5-amino-4-carbamoyl-2-methylbenzoic acid (60.8 mg, 0.31 mmol, 61% yield). $^1$H NMR (400 MHz, $d_6$-DMSO): δ 12.95 (br s, 1H), 7.99 (br s, 1H), 7.52 (s, 1H), 7.42 (br s, 1H), 7.35 (s, 1H), 4.75 (br s, 2H), 2.33 (s, 3H).

Reagent Preparation 49: 6-(aminocarbonyl)-2-methyl-5-(pentan-3-ylamino)nicotinic Acid

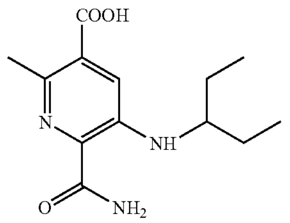

STEP 1: To a solution of ethyl 5-amino-2-methylnicotinate (Fanta, P. E. *J. Am. Chem. Soc.* 1953, 75, 737) (4.1 g, 22.78 mmol) in DMF (50 ml) was added NBS (4.46 g, 25.06 mmol), and the reaction mixture was stirred at room temperature overnight. The reaction mixture was diluted with water (100 ml) and then extracted with ethyl acetate (3×100 ml). The organic layer was washed with saturated aqueous sodium bicarbonate and brine. After evaporation of solvent, the residue was triturated with ethanol to give ethyl 5-amino-6-bromo-2-methylnicotinate. (5.2 g, 88% yield). $^1$H NMR (400 MHz, $CDCl_3$): 7.56 (s, 1H), 4.40 (q, J=6.8 Hz, 2H), 4.05 (br, s, 2H), 2.75 (s, 3H), 1.39 (t, J=6.8 Hz, 3H). MS (EI) for $C_9H_1BrN_2O_2$: 259.1 ($MH^+$).

STEP 2: To a solution of ethyl 5-amino-6-bromo-2-methylnicotinate (1.267 g, 4.89 mmol) in ethyl acetate (30 ml) were added 3-pentanone (0.463 g, 5.38 mmol), sodium triacetoxyborohydride (1.244 g, 5.868 mmol) and trifluoroacetic acid (1.15 g, 9.78 mmol) at room temperature. After stirring overnight at room temperature, another portion of sodium triacetoxyborohydride (0.6 g, 2.83 mmol) was added. The reaction mixture was stirred for another 6 hours. The reaction mixture was quenched with water (20 ml). The organic layer was washed with saturated sodium bicarbonate and brine. After evaporation of solvent, ethyl 6-bromo-2-methyl-5-(pentan-3-ylamino)nicotinate (1.20 g, 74.6% yield) was purified by column chromatography with 7% ethyl acetate/Hexane as eluent. $^1$H NMR (400 MHz, $CDCl_3$): 7.35 (s, 1H), 4.40 (q, J=6.8 Hz, 2H), 4.10 (br, s, 1H), 3.30 (m, 1H), 2.68 (s, 3H), 1.8-1.5 (m, 4H), 1.42 (t, J=6.8 Hz, 3H), 1.0 (t, J=7.2 Hz, 6H). MS (EI) for $C_{14}H_{21}BrN_2O_2$: 329.1 ($MH^+$).

STEP 3: To a solution of ethyl 6-bromo-2-methyl-5-(pentan-3-ylamino)nicotinate (1.202 g, 3.65 mmol) in acetonitrile (30 ml) was added sodium cyanide (0.357 g, 7.3 mmol), tributyltin chloride (1.306 g, 4.015 mmol) and Pd(dpppf)$_3$ (0.298 g, 0.365 mmol). The reaction mixture was stirred at 88° C. overnight. The reaction mixture was diluted with water (100 ml), then extracted with ethyl acetate (3×100 ml). The organic layer was washed with saturated aqueous sodium bicarbonate and brine. After evaporation of solvent, ethyl 6-cyano-2-methyl-5-(pentan-3-ylamino)nicotinate (0.59 g, 59% yield) was obtained by column chromatography. $^1$H NMR (400 MHz, $CDCl_3$): 7.56 (s, 1H), 4.50 (q, J=6.8 Hz, 2H), 4.35 (br, s, 1H), 3.40 a9m, 1H), 2.64 (s, 3H), 1.80-1.50 (m, 4H), 1.42 (t, J=6.8 Hz, 3H), 1.0 (t, 6H). MS (EI) for $C_{15}H_{21}N_3O_2$: 276.2 ($MH^+$).

STEP 4: To a solution of 6-cyano-2-methyl-5-(pentan-3-ylamino)nicotinate (0.543 g, 1.97 mmol) in DMSO (10 ml) were added 50% aqueous hydrogen peroxide (0.2441 g, 3.55 mmol) and potassium carbonate (0.068 g, 0.49 mmol) at 10° C. The reaction mixture was stirred at room temperature for two hours then a solution of potassium hydroxide (0.22 g, 3.94 mmol) in water (2 ml) and methanol (10 ml) were added to above reaction mixture. After being stirred for another two hours at 45° C., the reaction mixture was cooled to room temperature and neutralized to PH 7. 6-(Aminocarbonyl)-2-methyl-5-(pentan-3-ylamino)nicotinic acid (0.453 g, 87%) was obtained by filtration and drying. $^1$HNMR (400 MHz, MeOH-$D_4$): 7.62 (s, 1H), 3.35 (m, 1H), 2.60 (s, 3H), 1.65 (m, 2H), 1.52 (m, 2H), 0.95 (t, J=7.20 Hz, 6H). MS (EI) for $C_{13}H_{20}N_3O_3$: 267.2 ($MH^+$).

Reagent Preparation 50:1:4-(aminocarbonyl)-2-bromo-5-[(2-methylpropyl)amino]benzoic Acid

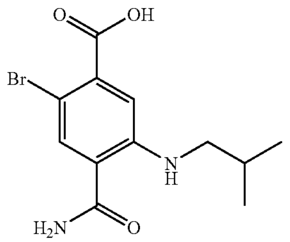

STEP 1: A mixture of ethyl 3-bromo-4-cyanobenzoate (500 mg, 2.08 mmol), 2-methylpropan-1-amine (250 μL, 4.16 mmol), $Pd_2(dba)_3$ (96 mg, 5 mol %), Xantphos (120 mg, 10 mol %) and potassium phosphate (959 mg, 4.16 mmol) in dioxane (10 mL) was stirred for overnight at 95° C. After cooling to room temperature the mixture was diluted with water and extracted with ethyl acetate. The organic layer was dried over anhydrous sodium sulfate, filtered, and concentrated followed by column chromatography (10% ethyl acetate in hexanes) to give ethyl 4-cyano-3-[(2-methylpropylamino)]benzoate (393 mg, 76.7%) as a yellow solid. $^1$MS (EI) for $C_{14}H_{18}N_2O_2$: 247.1 ($MH^+$).

STEP 2: To a solution of ethyl 4-cyano-3-[(2-methylpropylamino)]benzoate (393 mg, 1.60 mmol) in DMF (10 mL) was added N-bromsuccinimide (284 mg, 1.60 mmol). The mixture was stirred overnight at 45° C. then cooled to room temperature and diluted with water then extracted with ethyl acetate. The organic layer was dried over anhydrous sodium sulfate, filtered and concentrated. The residue was purified by column chromatography (10% ethyl acetate in hexanes) to give ethyl 2-bromo-4-cyano-5-[(2-methylpropyl)amino]benzoate (374 mg, 72.0%) as a yellow solid. MS (EI) for $C_{14}H_17BrN_2O_2$: 324 ($M^+$).

STEP 3: To a solution of ethyl 2-bromo 4-cyano-5-[(2-methylpropyl)amino]benzoate (374 mg, 1.15 mmol) in DMSO (10 mL), potassium carbonate (51 mg, 0.37 mmol) and aqueous hydrogen peroxide (645 μl, 6.31 mmol) were added successively. The mixture was stirred for 3 hr at room temperature then diluted with water, extracted with ethyl acetate, dried over anhydrous sodium sulfate, filtered and concentrated. The residue was purified by column chromatography to give ethyl 4-(amino)-2-bromo-5-[(2-methylpropyl)amino]benzoate (315 mg, 85.0%) as a crystalline solid. MS (EI) for $C_{14}H_{19}BrN_2O_3$: 342.1 ($M^+$).

STEP 4: To a solution of ethyl 2-bromo-4-(aminocarbonyl)-5-[(2-methylpropyl)amino]benzoate (315 mg, 0.91 mmol) in methanol (20 mL) was added 1N aqueous sodium hydroxide (15 mL) and the mixture was stirred for 2 hr at 45° C. The mixture was then concentrated by rotary evaporation and diluted with water then adjusted to pH 2 by 1N aqueous hydrochloric acid addition and the mixture was allowed to stand for 1 hr at room temperature. The crystalline solid was collected by filtration and washed with water then dried to give 4-(aminocarbonyl)-2-bromo-5-[(2-methylpropyl)amino]benzoic acid (250 mg, 87.1%). MS (EI) for $C_{12}H_{15}BrN_2O_3$: 315.1 ($MH^+$)

Using analogous synthetic techniques and substituting with alternative starting reagents the following reagents were prepared. Alternative starting materials were obtained commercially unless otherwise indicated.

4-(Aminocarbonyl)-2-bromo-5-[(1-ethylpropyl)amino]benzoic acid

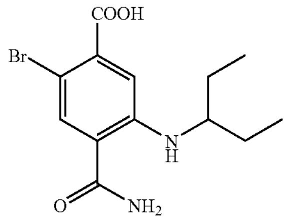

Prepared according to the method of reagent preparation 50 by using pentan-3-amine in step 1. $^1H$ NMR (400 MHz, $d_6$-DMSO): 13.40 (broad s, 1H), 8.20 (d, 1H), 8.06 (broad s, 1H), 7.85 (s, 1H), 7.40 (broad s, 1H), 6.94 (s, 1H), 1.55 (m, 2H), 1.44 (m, 2H), 0.86 (t, 3H). MS (EI) for $C_{13}H_{17}BrN_2O_3$: 330 ($MH^+$).

4-(Aminocarbonyl)-2-bromo-5-{[(1R)-1-methylpropyl]amino}benzoic acid

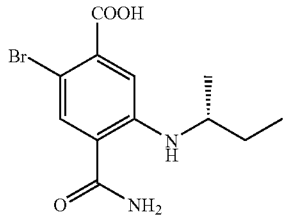

Prepared according to the method of reagent preparation 50 by using (2R)-butan-2-amine in step 1. $^1H$ NMR (400 MHz, $d_6$-DMSO): 13.42 (broad s, 1H), 8.16 (d, 1H), 8.06 (broad s, 1H), 7.84 (s, 1H), 7.40 (broad s, 1H), 6.92 (s, 1H), 3.47 (m, 1H), 1.49 (m, 2H), 1.10 (d, 3H), 0.87 (t, 3H). MS (EI) for $C_{12}H_{15}BrN_2O_3$: 317 ($MH^+$).

4-(Aminocarbonyl)-2-bromo-5-[(2,2-dimethylpropyl)amino]benzoic acid

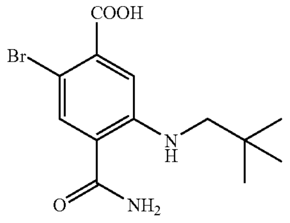

Prepared according to the method of reagent preparation 50 by using 2,2-dimethylpropan-1-amine in step 1. $^1H$ NMR (400 MHz, $CD_3OD$): 7.83 (s, 1H), 7.04 (s, 1H), 2.94 (s, 2H), 1.03 (s, 9H); MS (EI) for $C_{13}H_{17}BrN_2O_3$: 329, 331 ($MH^+$, Br isotopes).

4-(Aminocarbonyl)-2-bromo-5-{[(1R)-1,2-dimethylpropyl]amino}benzoic acid

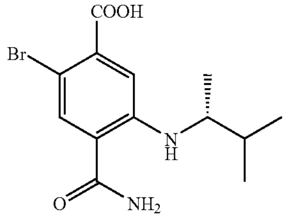

Prepared according to the method reagent preparation 50 by using (2R)-3-methylbutane-2-amine in step 1. $^1H$ NMR (400 MHz, DMSO-$d_6$): 13.36 (s, 1H), 8.32 (d, 1H), 8.04 (bs, 1H), 7.84 (s, 1H), 7.38 (bs, 1H), 7.73 (s, 1H), 3.43 (m, 1H), 1.76 (m, 1H), 1.05 (d, 3H), 0.92 (d, 3H), 0.87 (d, 3H). MS (EI) for $C_{13}H_{17}BrN_2O_3$: 330 ($MH^+$).

4-(Aminocarbonyl)-2-bromo-5-[(1-methylethyl)amino]benzoic acid

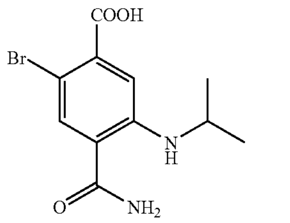

Prepared according to the method of reagent preparation 50 by using propan-2-amine in step 1. $^1H$ NMR (400 MHz, $d_6$-DMSO): 8.07 (d, 2H), 7.85 (s, 1H), 7.40 (s, 1H), 6.93 (s, 1H), 3.61-3.69 (m, 1H), 1.15 (d, 6H). MS (EI) for $C_{11}H_{13}BrN_2O_3$: 303 ($MH^+$).

4-(Aminocarbonyl)-2-bromo-5-(butylamino)benzoic acid

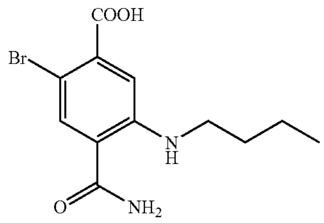

Prepared according to the method of reagent preparation 50 by using propan-1-amine in step 1. $^1H$ NMR (400 MHz, $d_6$-DMSO): δ 13.43 (br s, 1H), 8.18 (m, 1H), 8.07 (br s, 1H), 7.86 (s, 1H), 7.42 (br s, 1H), 6.90 (s, 1H), 3.09-3.05 (m, 2H), 1.60-1.54 (m, 3H), 0.94 (t, 2H); MS (EI) for C, $1H_{13}BrN_2O_3$: 299, 301 ($MH^+$) (bromine isotope pattern).

4-(Aminocarbonyl)-2-bromo-5-(cyclopentylamino) benzoic acid

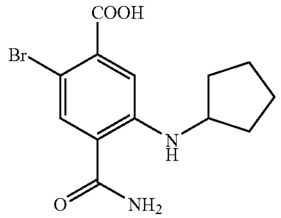

Prepared according to the method of reagent preparation 50 by using cyclopentanamine in step 1. $^1H$ NMR (400 MHz, $CD_3OD$): 7.81 (s, 1H), 7.06 (s, 1H), 3.83-3.82 (m, 1H), 2.06-2.01 (m, 2H), 1.77-1.65 (m, 4H), 1.54-1.50 (m, 2H). MS (EI) for $C_{13}H_{15}BrN_2O_3$: 328 ($MH^+$).

4-(Aminocarbonyl)-2-bromo-5-[(3,3,3-trifluoropropyl)amino]benzoic acid

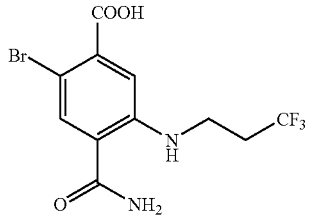

Prepared according to the method of reagent preparation 50 by using 3,3,3-trifluoropropan-1-amine in step 1. $^1H$ NMR (400 MHz, $d_6$-DMSO): 13.47 (br. s, 1H), 8.28 (s, 1H), 8.10 (s, 1H), 7.88 (d, 1H), 7.47 (d, 1H), 6.97 (s, 1H), 3.47-3.39 (m, 2H), 2.66-2.53 (m, 2H). MS (EI) for $C_{11}H_{10}BrF_3N_2O_3$: 356 ($MH^+$).

4-(Aminocarbonyl)-2-bromo-5-(cyclobutylamino) benzoic acid

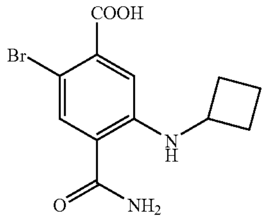

Prepared according to the method of reagent preparation 50 by using cyclobutanamine in step 1. $^1H$ NMR (400 MHz, $CD_3OD$): 7.82 (s, 1H), 6.92 (s, 1H), 4.00-3.89 (m, 1H), 2.50-2.41 (m, 2H), 1.95-1.80 (m, 4H). MS (EI) for $C_{12}H_{13}BrN_2O_3$: 314 ($MH^+$).

4-(aminocarbonyl)-2-bromo-5-[(1,1-dimethylethyl) amino]benzoic acid

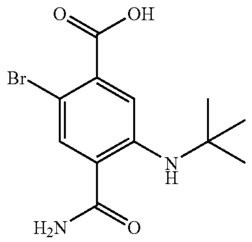

Synthesized according to the method of reagent preparation 50 by using 1,1-dimethylethylamine in step 1. MS (EI) for $C_{12}H_{15}BrN_2O_3$: 315 ($MH^+$).

5-amino-4-(aminocarbonyl)-2-bromobenzoic acid

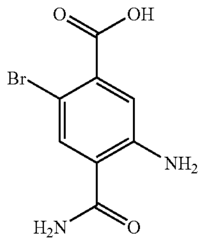

Synthesized according to the method of reagent preparation 50 by conducting only step 2 using 1,1-dimethylethyl 3-amino-4-(aminocarbonyl)benzoate (reagent preparation 29 step 2) followed by acid catalyzed tert-butyl ester hydrolysis under standard conditions, see Green and Wutts in Protective Groups in Organic Synthesis, Wiley-Interscience Ed. $^1H$ NMR (400 MHz, DMSO-$d_6$): 13.14 (s, 1H), 8.28 (s, 1H), 8.00 (bs, 2H), 7.80 (s, 1H), 7.28 (bs, 2H). MS (EI) for $C_8H_7BrN_2O_3$: 260 ($MH^+$).

4-(aminocarbonyl)-2-bromo-5-{[(1S)-1,2-dimethylpropyl]amino}benzoic acid

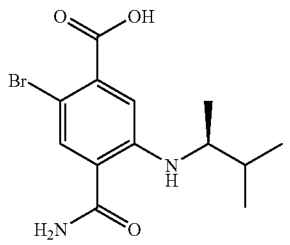

Synthesized according to the method of reagent preparation 50 by using (1S)-1,2-dimethylpropylamine in step 1. $^1$H NMR (400 MHz, DMSO-$d_6$): 13.36 (s, 1H), 8.33 (d, 1H), 8.04 (bs, 1H), 7.82 (s, 1H), 7.38 (bs, 1H), 7.72 (s, 1H), 3.42 (m, 1H), 1.74 (m, 1H), 1.05 (d, 3H), 0.93 (d, 3H), 0.88 (d, 3H). MS (EI) for $C_{13}H_{17}BrN_2O_3$: 330 ($MH^+$).

4-(aminocarbonyl)-2-bromo-5-[(cyclopropylmethyl)amino]benzoic acid

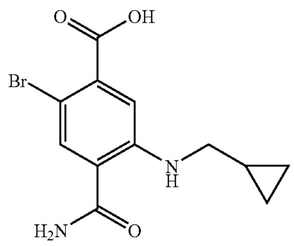

Synthesized according to the method of reagent preparation 50 by using cyclopropylmethylamine in step 1. MS (EI) for $C_{12}H_{13}BrN_2O_3$: 314 ($MH^+$).

4-(aminocarbonyl)-6-bromo-2-chloro-3-{[(1R)-1-methylpropyl]amino}benzoic acid

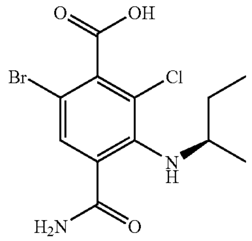

Synthesized according to the method of reagent preparation 50 by using (1R)-1-methylpropylamine in step 1 then repetition of step 2 first using N-bromosuccinimide then using N-chlorosuccinimide and proceeding with steps 3 and 4. MS (EI) for $C_{12}H_{14}BrClN_2O_3$: 350 ($MH^+$).

4-(aminocarbonyl)-2-(methyloxy)-5-{[(1R)-1-methylpropyl]amino}benzoic acid

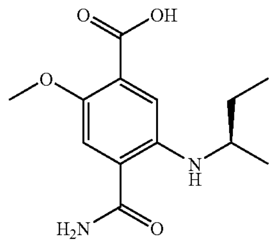

Synthesized according to the method of reagent preparation 50 by using (1R)-1-methylpropylamine in step 1 then following step 2 with the conversion of ethyl 2-bromo-4-cyano-5-{[(1R)-1-methylpropyl]amino}benzoate to ethyl 4-cyano-2-hydroxy-5-{[(1R)-1-methylpropyl]amino}benzoate according to the method described in Chemical & Pharmaceutical Bulletin (2007), 55(9), 1361-1364 and subsequent methylation using iodomethane under standard conditions then proceeding through steps 3 and 4. $^1$H NMR (400 MHz, d6-DMSO): 12.79-12.74 (s, 1H), 8.03-7.95 (s, 1H), 7.60-7.52 (d, 1H), 7.35-7.28 (s, 1H), 7.26-7.24 (s, 1H), 6.85-6.81 (s, 1H), 3.72-3.70 (s, 3H), 3.31-3.29 (s, 1H), 1.49-1.40 (m, 2H), 1.08-1.05 (d, 3H), 0.89-0.83 (m, 3H). MS (EI) for $C_{13}H_{18}N_2O_4$: 267 ($MH^+$).

4-(aminocarbonyl)-2-(ethylamino)-5-{[(1R)-1-methylpropyl]amino}benzoic acid

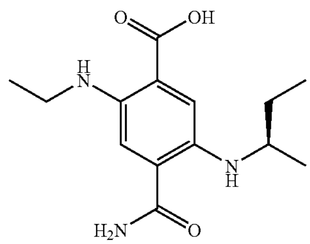

Synthesized according to the method of reagent preparation 50 by using (1R)-1-methylpropylamine in step 1 then following step 2 with the conversion of ethyl 2-bromo-4-cyano-5-{[(1R)-1-methylpropyl]amino}benzoate to ethyl 4-cyano-2-(ethylamino)-5-{[(1R)-1-methylpropyl]amino}benzoate according to the method described in step 1 then proceeding through steps 3 and 4. MS (EI) for $C_{14}H_{21}N_3O_3$: 280 ($MH^+$).

4-(aminocarbonyl)-2-ethyl-5-{[(1R)-1-methylpropyl]amino}benzoic acid

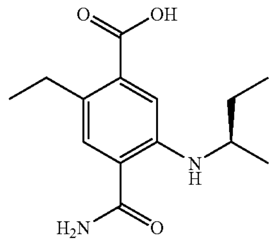

Synthesized according to the method of reagent preparation 50 by using (1R)-1-methylpropylamine in step 1 then following step 2 with the conversion of ethyl 2-bromo-4-cyano-5-{[(1R)-1-methylpropyl]amino}benzoate to ethyl 4-cyano-2-ethyl-5-{[(1R)-1-methylpropyl]amino}benzoate by treatment with ethylmagnesium chloride according to the method described in Synlett 1996, 5, 473-474 then proceeding through steps 3 and 4. $^1H$ NMR (400 MHz, DMSO-$d_6$): 7.94 (s, 1H), 7.81 (d, 1H), 7.49 (s, 1H), 7.27 (s, 1H), 6.98 (s, 1H), 2.67-2.75 (m, 2H), 1.44-1.53 (m, 2H), 1.06-1.15 (m, 6H), 0.89 (t, 3H).

MS (EI) for $C_{14}H_{20}N_2O_3$: 265 ($MH^+$).

Reagent Preparation 51: 4-(aminocarbonyl)-5-[(1-ethylpropyl)amino]-2-(trifluoromethyl)benzoic Acid

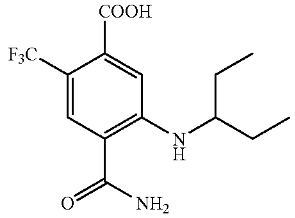

STEP 1: 4-Amino-2-(trifluoromethyl)benzoic acid (10 g, 48.8 mmol) was suspended in THF (100 mL) and methanol (30 mL) and was cooled in an ice bath. (Trimethylsilyl)diazomethane (2 M solution in hexanes; 32 mL) was added drop-wise. The mixture was stirred for 5 minutes and then concentrated to afford methyl 4-amino-2-(trifluoromethyl)benzoate (quantitative yield) as a brown oil. $^1H$ NMR (400 MHz, $CDCl_3$): δ 7.78 (d, 1H), 6.99 (d, 1H), 6.77 (d, 1H), 4.18 (br s, 2H), 3.88 (s, 3H); GCMS for $C_9H_8F_3NO_2$: 219 ($M^+$).

STEP 2: Methyl 4-amino-2-(trifluoromethyl)benzoate (~22 mmol), was dissolved in THF (100 mL) and the mixture was sparged with nitrogen for 15 minutes. Copper (I) iodide (4.14 g, 21.8 mmol) and diiodomethane (8.8 mL, 109 mmol) were added followed by isoamyl nitrite (8.8 mL, 66.2 mmol) and the mixture was stirred at reflux for 4 h. The mixture was cooled to ambient temperature and then was partitioned between ethyl acetate and 1N hydrochloric acid. The aqueous portion was extracted with ethyl acetate (2×). The combined organic portion was washed sequentially with 1:1 saturated sodium bicarbonate solution: 1 M sodium thiosulfate (2×) and brine, dried over sodium sulfate, then filtered and concentrated to provide a brown oil which was purified by column chromatography (silica gel, 2-40% dichloromethane in hexanes) to afford methyl 4-iodo-2-(trifluoromethyl)benzoate (5.42 g, 16.4 mmol, ~75% yield over 2 steps) as a pale yellow oil. $^1H$ NMR (400 MHz, $CDCl_3$): δ 8.08 (s, 1H), 7.97 (dd, 1H), 7.52 (d, 1H), 3.93 (s, 3H); GCMS for $C_9H_6F_3IO_2$: 330 ($M^+$).

STEP 3: Methyl 4-iodo-2-(trifluoromethyl)benzoate (1.65 g, 5.0 mmol) was dissolved in concentrated sulfuric acid (6 mL) and was cooled in an ice bath. Fuming nitric acid (4 mL) was added drop-wise and the mixture was stirred at 70° C. for 1.5 h. The mixture was cooled to ambient temperature and then poured into ice (~100 mL). The aqueous mixture was extracted with ethyl acetate (2×). The combined organic portion was washed with saturated sodium bicarbonate (2×), brine, dried over sodium sulfate then filtered and concentrated to afford (1.7 g, 4.53 mmol, 91% yield) composed of the two regioisomers methyl 4-iodo-5-nitro-2-(trifluoromethyl)benzoate (major) and methyl 4-iodo-3-nitro-2-(trifluoromethyl)benzoate (minor) in a 4:1 ratio. $^1H$ NMR for desired (major) isomer (400 MHz, $CDCl_3$): δ 8.42 (s, 1H), 8.26 (s, 1H), 3.98 (s, 3H); GCMS for $C_9H_5F_{31}NO_4$: 375 ($M^+$).

STEP 4: A mixture of methyl 4-iodo-5-nitro-2-(trifluoromethyl)benzoate (desired) and methyl 4-iodo-3-nitro-2-(trifluoromethyl)benzoate as obtained in step 3 (1.7 g, 4.53 mmol) in acetic acid (20 mL) was treated with iron powder (1.5 g, 26.8 mmol) at 45° C. for 2 h. The reaction mixture was cooled to ambient temperature and was filtered through celite. The filter cake was washed with ethyl acetate and the filtrate was concentrated. The residue was diluted with ethyl acetate, washed with saturated sodium bicarbonate and brine, dried over sodium sulfate, then filtered and concentrated to afford a brown oil which was purified by column chromatography (silica gel, 10-30% ethyl acetate in hexanes) to afford the two regioisomers methyl 5-amino-4-iodo-2-(trifluoromethyl) benzoate (major) and methyl 3-amino-4-iodo-2-(trifluoromethyl)benzoate (minor) in a 4:1 ratio (1.484 g, 4.30 mmol, 95% yield). $^1H$ NMR for desired (major) isomer (400 MHz, $CDCl_3$): δ 7.96 (s, 1H), 7.06 (s, 1H), 4.55 (br s, 2H), 3.90 (s, 3H); GCMS for $C_9H_7F_31NO_2$: 345 ($M^+$).

STEP 5: A mixture of methyl 5-amino-4-iodo-2-(trifluoromethyl)benzoate (desired) and methyl 3-amino-4-iodo-2-(trifluoromethyl)benzoate as obtained in step 4 (392 mg, 1.14 mmol) was dissolved in 1,2-dichloroethane (12 mL) and was treated with trifluoroacetic acid (0.5 mL, 6.73 mmol), 3-pentanone (0.36 mL, 3.40 mmol) and sodium triacetoxyborohydride (724 mg, 3.42 mmol) at 45° C. for 0.5 h. GCMS indicated complete conversion of desired isomer to required product. After a further 0.5 h at 45° C., the reaction mixture was cooled to ambient temperature and was quenched with 1N sodium hydroxide (5 mL) and saturated sodium bicarbonate and was partitioned with dichloromethane. The aqueous portion was extracted with dichloromethane. The combined organic portion was washed with brine, dried over magnesium sulfate, then filtered and concentrated to afford a yellow oil which was purified by column chromatography (silica gel, 10-40% dichloromethane in hexanes) to afford pure methyl 4-iodo-5-(pentan-3-ylamino)-2-(trifluoromethyl)benzoate (330 mg, 0.795 mmol, 70% yield) as a pale yellow oil. $^1H$ NMR (400 MHz, $CDCl_3$): δ 7.95 (s, 1H), 6.79 (s, 1H), 4.44 (d, 1H), 3.92 (s, 3H), 3.44-3.34 (m, 1H), 1.73-1.48 (m, 4H), 0.95 (t, 6H); GCMS for $C_{14}H_{17}F_{31}NO_2$: 415 ($M^+$).

STEP 6: Methyl 4-iodo-5-(pentan-3-ylamino)-2-(trifluoromethyl)benzoate (401 mg, 0.966 mmol) was dissolved in DMF (9 mL) and the mixture was sparged with nitrogen for 15 minutes. Zinc cyanide (79 mg, 0.673 mmol) and tetrakis (triphenylphosphine)palladium(0) (100 mg, 0.086 mmol) were added and the mixture was stirred at 100° C. for 15 h. The reaction mixture was cooled to ambient temperature and was filtered through celite. The filter cake was washed with ethyl acetate and the filtrate was washed with 5% lithium chloride (2×). The combined aqueous wash was back-extracted with ethyl acetate. The combined organic portion was washed with brine, dried over sodium sulfate, then filtered and concentrated to afford a brown semi-solid which was purified by column chromatography (silica gel, 30-50% dichloromethane in hexanes) to afford methyl 4-cyano-5-(pentan-3-ylamino)-2-(trifluoromethyl)benzoate (262 mg, 0.834 mmol, 86% yield) as colorless crystals. $^1H$ NMR (400 MHz, $CDCl_3$): δ 7.71 (s, 1H), 6.96 (s, 1H), 4.76 (d, 1H), 3.94 (s, 3H), 3.49-3.38 (m, 1H), 1.75-1.63 (m, 2H), 1.61-1.49 (m, 2H), 0.96 (t, 6H); GCMS for $C_{15}H_{17}F_3N_2O_2$: 314 ($M^+$).

STEP 7: Methyl 4-cyano-5-(pentan-3-ylamino)-2-(trifluoromethyl)benzoate (257 mg, 0.818 mmol) was dissolved in DMSO (2 mL) and was cooled in a cold water bath. 30%

Aqueous hydrogen peroxide (0.2 mL) and potassium carbonate (38 mg, 0.275 mmol) was added and the mixture was stirred at ambient temperature for 1.5 h. The reaction mixture was partitioned between ethyl acetate and water. The aqueous portion was extracted with ethyl acetate. The combined organic portion was dried over sodium sulfate then filtered and concentrated to afford methyl 4-aminocarbonyl-5-(pentan-3-ylamino)-2-(trifluoromethyl)benzoate (quantitative yield) as a yellow oil. MS (EI) for $C_{15}H_{19}F_3N_2O_3$: 333 ($MH^+$).

STEP 8: Methyl 4-aminocarbonyl-5-(pentan-3-ylamino)-2-(trifluoromethyl)benzoate (0.818 mmol) was dissolved in methanol (2 mL) and was treated with 2M sodium hydroxide (1 mL, 2 mmol) at 45° C. for 1.5 h. The reaction mixture was cooled to ambient temperature and was concentrated to afford an aqueous residue that was washed with ether, then cooled in an ice bath and acidified with 1N hydrochloric acid to pH ~3. The precipitate was collected by filtration, washed with water, then dried to afford 4-aminocarbonyl-5-(pentan-3-ylamino)-2-(trifluoromethyl)benzoic acid (233 mg, 0.733 mmol, 90% yield over 2 steps). $^1H$ NMR (400 MHz, $d_6$-DMSO): δ 13.5 (br s, 1H), 8.74 (d, 1H), 8.21 (br s, 1H), 7.95 (s, 1H), 7.46 (br s, 1H), 6.94 (s, 1H), 3.51-3.43 (m, 1H), 1.63-1.51 (m, 2H), 1.51-1.39 (m, 2H), 0.87 (t, 6H); MS (EI) for $C_{14}H_{17}F_3N_2O_3$: 319 ($MH^+$).

Reagent Preparation 52: 4-(aminocarbonyl)-5-{[(1R)-1-methylpropyl]amino}-2-(trifluoromethyl) benzoic Acid

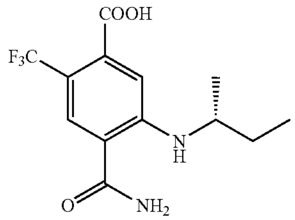

STEP 1: A mixture of methyl 5-amino-4-iodo-2-(trifluoromethyl)benzoate (major) and methyl 3-amino-4-iodo-2-(trifluoromethyl)benzoate (minor) in a 4:1 ratio (prepared in Example 51 Step 4) (1.08 g, 3.13 mmol) was dissolved in DMF (17 mL), and the mixture was sparged with nitrogen for 15 minutes. Zinc cyanide (257 mg, 2.19 mmol) and tetrakis (triphenylphosphine)palladium(0) (362 mg, 0.313 mmol) were added and the mixture was stirred at 100° C. for 15 h. The reaction mixture was cooled to ambient temperature and was filtered through celite. The filter cake was washed with ethyl acetate and the filtrate was washed with 5% lithium chloride. The aqueous wash was back-extracted with ethyl acetate (2×). The combined organic portion was washed with 10% lithium chloride and brine, was dried over sodium sulfate then filtered and concentrated to afford a residue which was purified by column chromatography (silica gel, 30-50% ethyl acetate in hexanes) to afford pure methyl 5-amino-4-cyano-2-(trifluoromethyl)benzoate (556 mg, 2.28 mmol, 73% yield). $^1H$ NMR (400 MHz, $CDCl_3$): δ 7.76 (s, 1H), 7.10 (s, 1H), 4.88 (br s, 2H), 3.93 (s, 3H); GCMS for $C_{10}H_7F_3N_2O_2$: 244 ($M^+$).

STEP 2: Methyl 5-amino-4-cyano-2-(trifluoromethyl) benzoate (250 mg, 1.02 mmol) was dissolved in THF (6 mL), and the mixture was sparged with nitrogen for 15 minutes. Copper (I) iodide (195 mg, 1.02 mmol) and diiodomethane (0.4 mL, 4.95 mmol) were added followed by isoamyl nitrite (0.4 mL, 3.01 mmol), and the mixture was stirred at reflux for 2.5 h. The mixture was cooled to ambient temperature and then was partitioned between ethyl acetate and 1N hydrochloric acid. The aqueous portion was extracted with ethyl acetate (2×). The combined organic portion was washed sequentially with 1:1 saturated sodium bicarbonate solution: 1 M sodium thiosulfate (2×) and brine, was dried over sodium sulfate, then filtered and concentrated to provide a semi-solid which was purified by column chromatography (silica gel, 20-50% dichloromethane in hexanes) to afford methyl 4-cyano-5-iodo-2-(trifluoromethyl)benzoate (174 mg, 0.49 mmol, 48% yield). $^1H$ NMR (400 MHz, $CDCl_3$): δ 8.33 (s, 1H), 7.93 (s, 1H), 3.98 (s, 3H); GCMS for $C_{10}H_5F_3INO_2$: 355 ($M^+$).

STEP 3: Methyl 4-cyano-5-iodo-2-(trifluoromethyl)benzoate (174 mg, 0.49 mmol) was dissolved in dioxane (2 mL) and was sparged with nitrogen for 15 minutes. XANTPHOS (57 mg, 0.098 mmol), cesium carbonate (350 mg, 1.07 mmol), (R)-sec-butylamine (0.1 mL, 0.986 mmol), and tris (dibenzylideneacetone)dipalladium (45 mg, 0.049 mmol) were added, and the mixture was stirred in a sealed tube at 95° C. for 20 h. The reaction mixture was cooled to ambient temperature and was filtered through celite. The filter cake was washed with ethyl acetate and the filtrate was concentrated to afford an orange oil which was purified by column chromatography (silica gel, 5-15% ethyl acetate in hexanes) to afford (R)-methyl 5-(sec-butylamino)-4-cyano-2-(trifluoromethyl)benzoate (45 mg, 0.150 mmol, 31% yield) as a yellow oil. GCMS for $C_{14}H_{15}F_3N_2O_2$: 300 ($M^+$).

STEP 4: (R)-Methyl 5-(sec-butylamino)-4-cyano-2-(trifluoromethyl)benzoate (45 mg, 0.150 mmol) was dissolved in DMSO (1 mL) and was treated with 30% aqueous hydrogen peroxide (0.05 mL) and potassium carbonate (6 mg, 0.043 mmol) at ambient temperature for 2 h. The reaction mixture was partitioned between ethyl acetate and water. The aqueous portion was extracted with ethyl acetate. The combined organic portion was dried over sodium sulfate, then filtered and concentrated to afford a yellow oil which was purified by column chromatography (silica gel, 10-40% ethyl acetate in hexanes) to afford (R)-methyl 5-(sec-butylamino)-4-aminocarbonyl-2-(trifluoromethyl)benzoate (27 mg, 0.085 mmol, 57% yield). (R)-M ethyl 5-(sec-butylamino)-4-aminocarbonyl-2-(trifluoromethyl)benzoate (27 mg, 0.085 mmol) was suspended in methanol (1 mL) and was treated with 1 M sodium hydroxide (0.2 mL, 0.2 mmol) at 45° C. for 1 h. Dichloromethane (0.5 mL) and 1M sodium hydroxide (0.2 mL, 0.2 mmol) was added and the mixture was stirred at 45° C. for a further 1.5 h. Dichloromethane (0.5 mL) and 1M sodium hydroxide (0.2 mL, 0.2 mmol) were added, and the mixture was stirred at 45° C. for a further 1 h and then at ambient temperature for 15 h. The reaction mixture was concentrated to afford an aqueous residue that was cooled in an ice bath, was acidified with 1N hydrochloric acid to pH ~2, then extracted with ethyl acetate (2×). The organic portion was dried over sodium sulfate, then filtered and concentrated to provide 4-(aminocarbonyl)-5-{[(1R)-1-methylpropyl] amino}-2-(trifluoromethyl)benzoic acid (23 mg, 0.076 mmol, 89% yield). MS (EI) for $C_{13}H_{15}F_3N_2O_3$: 305 ($MH^+$).

Reagent Preparation 53: 1,1,1-trifluorobutan-2-amine

STEP 1: To a solution of 1,1,1-trifluorobutan-2-one (5.0 g, 39.9 mmol) and hydroxylamine hydrochloride (3.22 g, 46.3 mmol) in water (28 mL) was added a solution of sodium hydroxide (1.84 g, 46.0 mmol) in water (14 mL), then the mixture was brought to reflux for 4 hr. After cooling to room temperature, the mixture was extracted with dichloromethane (3×50 mL) and the combined organic layers were washed with water, brine, then dried over anhydrous sodium sulfate. Filtration and concentration then distillation using a 10 cm Vigreux column (b.p. 123-124° C.) afforded (E)-1,1,1-trifluorobutan-2-one oxime (2.50 g, 44.5% yield) as a clear liquid. $^1$H NMR (400 MHz, $CDCl_3$): 9.18 (br s, 1H), 2.52 (q, 2H), 1.21 (t, 3H).

STEP 2: To a solution of IM lithium aluminum hydride in ethyl ether (40 ml) was added (E)-1,1,1-trifluorobutan-2-one oxime (2.50 g, 17.7 mmol) dissolved in ethyl ether (25 mL) at room temperature. The reaction mixture was stirred for 3 hr, then carefully quenched by addition of water and the aqueous solution was extracted with ethyl acetate (3×50 mL) and dried over anhydrous sodium sulfate. After filtration, 4.0 M hydrogen chloride in dioxane was added (10 mL). The solution was then rotary evaporated nearly 80% in volume, and ethyl ether (30 mL) was added to give a precipitate. The solid was collected by filtration and dried to give 1,1,1-trifluorobutan-2-amine hydrochloride salt (2.46 g, 85.6% yield). $^1$H NMR (400 MHz, d6-DMSO): 9.30 (br s, 2H), 4.18 (m, 1H), 1.81 (q, 2H), 1.02 (t, 3H).

Hsp90 Assays

Hsp90 Time-Resolved Fluorescence Resonance Energy Transfer (TR-FRET) Assay Protocol The determination of IC50 values of HSP90 inhibitors was conducted using a time-resolved fluorescence resonance energy transfer (TR-FRET) displacement binding assay. The assay employs a biotinylated geldanamycin probe (biotin-GM) and His6-tagged human Hsp90 N-terminal ATP-binding domain (Hsp90N). Test compounds are serially diluted in DMSO and 0.5 μL aliquots are transferred to 384-well black, medium binding microtiter assay plates (Greiner). Reagent 1 is prepared by mixing 80 nM biotin-GM, 1 nM anti-His-Eu chelate, and 100 nM streptavidin allophycocyanin (SA-APC) in binding buffer (50 mM Tris-HCl, pH 7.5, 1 mM EDTA, 150 mM NaCl, 0.1% Triton X-100, 0.05% BSA, and 1 mM DTT) and 10 μL is transferred to the assay plate. Reagent 2 is prepared by mixing 80 nM HSP90N in binding buffer and 10 μL is transferred to columns 3-24 of the assay plate. Binding buffer (10 μL) is added to columns 1-2 as 100% inhibition control. The plate is incubated for 180 minutes at room temperature. TR-FRET signals are measured on an Envision plate reader (Perkin Elemer) using the LANCE assay detection protocol. IC(50) values are calculated as a percentage of the displacement of biotin-GM from HSP90N by compounds at variable molar concentrations.

The compounds in both Table I and II have been tested for their HSP90 inhibitory activity ($IC_{50}$ values), and these compounds have HSP90 $IC_{50}$ values of less than 10,000 nM. A preferred group of compounds of Table I have HSP90 $IC_{50}$ values of less than 5,000 nM. Another preferred group of compounds of Table I have HSP90 $IC_{50}$ values of less than 2,000 nM. Another preferred group of compounds of Table I have HSP90 $IC_{50}$ values of less than 1,000 nM. Another preferred group of compounds of Table I have HSP90 $IC_{50}$ values of less than 500 nM. Another preferred group of compounds of Table I have HSP90 $IC_{50}$ values of less than 200 nM. Another preferred group of compounds of Table I have HSP90 $IC_{50}$ values of less than 100 nM. Another preferred group of compounds of Table I have HSP90 $IC_{50}$ values of less than 50 nM. Another preferred group of compounds of Table I have HSP90 $IC_{50}$ values of less than 25 nM.

Pharmaceutical Composition Examples

The following are representative pharmaceutical formulations containing a compound of Formula I, II or III.

Tablet Formulation

The following ingredients are mixed intimately and pressed into single scored tablets.

| Ingredient | Quantity per tablet, mg |
|---|---|
| Formula I, II or III | 400 |
| Cornstarch | 50 |
| croscarmellose sodium | 25 |
| Lactose | 120 |
| magnesium stearate | 5 |

Capsule Formulation

The following ingredients are mixed intimately and loaded into a hard-shell gelatin capsule.

| Ingredient | Quantity per tablet, mg |
|---|---|
| Formula I, II or III | 200 |
| lactose, spray-dried | 148 |
| magnesium stearate | 2 |

Suspension Formulation

The following ingredients are mixed to form a suspension for oral administration.

| Ingredient | Amount |
|---|---|
| Formula I, II or III | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| Flavoring | 0.035 mL |
| Colorings | 0.5 mg |
| distilled water | q.s. to 100 mL |

Injectable Formulation

The following ingredients are mixed to form an injectable formulation.

| Ingredient | Amount |
|---|---|
| Formula I, II or III | 1.2 g |
| sodium acetate buffer solution | 0.4 M 2.0 mL |
| HCl (1 N) or NaOH (1 M) | q.s. to suitable pH |
| water (distilled, sterile) | q.s. to 20 mL |

All of the above ingredients, except water, are combined and heated to 60°-70° with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of disclosed herein (compounds of Formula I, II or III) with Witepsol® H-15 (triglycerides of saturated vegetable fatty acid; Riches-Nelson, Inc., New York), and has the following composition:

| Ingredient | Quantity per tablet, mg |
|---|---|
| Formula I, II or III | 500 |
| Witepsol ® H-15 | Balance |

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

We claim:

1. A compound according to Formula I:

I

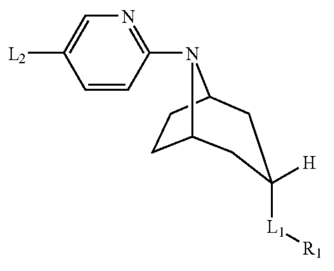

or a pharmaceutically acceptable salt thereof, wherein:

$R_1$ is selected from (C)

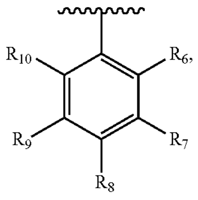

-continued (D2)

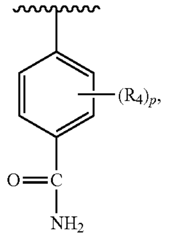

and (E)

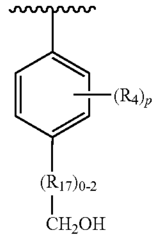

$R_3$ is selected from hydrogen, —$CF_3$, —$NH_2$, OH; alkyl optionally substituted with 1, 2, or 3 $R_5$; alkoxy, dialkylaminoalkyl; cycloalkyl optionally substituted with arylalkoxy; aryl optionally substituted with 1, 2, or 3 groups selected from halogen, alkyl, alkoxy, dialkylaminoalkoxy, and heterocycloalkyl optionally substituted with alkyl or aryl; alkenyl, alkynyl; heterocycloalkyl optionally substituted with a group selected from alkyl, —C(O)O-alkyl, and arylalkyl; arylalkyl optionally substituted with alkylheterocycloalkyl at any ring position of the aryl group; and heteroaryl;

$R_4$, $R_7$, $R_8$, and $R_9$ are each independently selected from hydrogen, —$OR_{16}$, —$SR_{16}$, —$N(H)R_{16}$, hydroxy, alkenyl, alkynyl, hydroxyalkynyl, halogen, hydroxyalkyl, dihydroxyalkyl, —O—C(O)—$NH_2$, amino(imino) alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl; alkyl optionally substituted with 1-8 halogen; dialkylamino, —N(H)alkylheterocycloalkyl, alkylsulfonylheterocycloalkylamino, cycloalkylalkylamino, cycloalkoxy, —$NH_2$, —O-alkyl-heterocycloalkyl, dialkylaminoalkoxy, alkylsulfonylalkylamino; and —N(H)heterocycloalkyl optionally substituted with 1, 2, or 3 groups selected from alkyl, alkoxy, and halogen;

$R_5$ is selected from halogen, cycloalkyl, cycloalkylalkylamino; heteroaryl optionally substituted with 1, 2, or 3 groups selected from halogen, alkyl, and alkoxy; alkylthio; heterocycloalkyl optionally substituted with 1, 2, or 3 groups selected from alkyl, halogen, phenyl, and oxo; aryl optionally substituted with 1, 2, or 3 groups selected from halogen, alkyl, alkoxy, dialkylaminoalkoxy, and heterocycloalkyl optionally substituted with alkyl; alkoxy, dialkylamino, —OH, —C(O)—$NH_2$, —C(O)—O—$CH_3$, —C(O)—N(H)($C_1$-$C_3$)alkyl; heteroarylamino optionally substituted with halogen; and —$OCF_3$;

$R_6$ and $R_{10}$ are each selected from hydrogen; alkyl optionally substituted with 1-8 halogens; alkylthio, alkenyl, alkynyl, hydroxyalkynyl, halogen, hydroxyalkyl, dihydroxyalkyl, amino(imino)alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl; alkylamino optionally substituted with 1-8 halogens; dialkylamino, alkoxyalkylamino, —N(H)alkylheterocycloalkyl, cycloalkylalkylamino, alkylsulfonylheterocycloalkylamino, cycloalkylalkylamino; cycloalkylamino optionally substituted with a group selected from —OH, alkyl, —$CF_3$, and heterocycloalkyl; —N(H)cycloalkyl optionally substituted with —OH or —$NH_2$, —$NH_2$, —N(H)-heteroaryl; —N(H)-aryl optionally substituted with 1, 2, or 3 groups selected from alkoxy, heterocycloalkylalkoxy, and dialkylaminoalkoxy; alkylsulfonylalkylamino and —N(H)heterocycloalkyl;

$R_{16}$ is selected from hydrogen; alkyl optionally substituted with 1-8 halogens; cycloalkyl optionally substituted with 1 or 2 groups selected from —OH, —$NH_2$, alkyl, heterocycloalkyl, and —$CF_3$; cycloalkylalkyl; heterocycloalkyl optionally substituted with —OH or —$NH_2$; alkoxyalkyl; aryl optionally substituted with 1, 2, or 3 alkoxy; heterocycloalkylalkyl, heteroaryl, gem-dicycloalkylalkyl, and dialkylaminoalkyl;

$R_{17}$, when present, is —$CH_2$— or —CH(OH)—;

$L_1$ is selected from —C(O)O—, —C(O)NH—, —C(O)NH$SO_2$—, —$(CH_2)_n$C(O)NH—, —$(CH_2)_n$NHC(O)—, —$(CH_2)_m$NH—, —$(CH_2)_n$$SO_2$NH—, —$(CH_2)_n$NH$SO_2$—, —$(CH_2)_m$C(O)—, —$(CH_2)_m$O—, and —$(CH_2)_m$NH—$(CH_2)_n$—;

$L_2$ is —C(O)—NH—$R_3$, —CN, —C(O)—N($CH_3$)—O$CH_3$, or —C(O)—$R_3$;

n is 0 or 1;

m is 0, 1 or 2; and each p is independently 0, 1, 2, 3 or 4.

2. The compound according to claim 1, wherein $R_1$ is selected from (C)

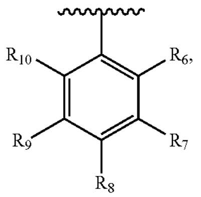

(D2)

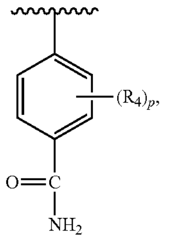

and (E)

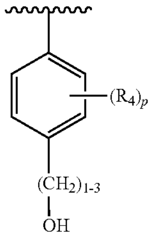

$L_1$ is selected from —NHC(O)—, —NH$SO_2$—, —C(O)O—, —C(O)NH—, —C(O)NH$SO_2$—, —C(O)—, —$(CH_2)_n$C(O)NH—, —$(CH_2)_n$NHC(O)—, —$(CH_2)_n$$SO_2$NH—, —$(CH_2)_n$NH$SO_2$—, —$(CH_2)_m$C(O)—, —$(CH_2)_m$O—, and —$(CH_2)_m$NH—;

and $L_2$ is —C(O)—NH—$R_3$, —CN or —C(O)—$R_3$.

3. The compound according to claim 1 selected from:

IB

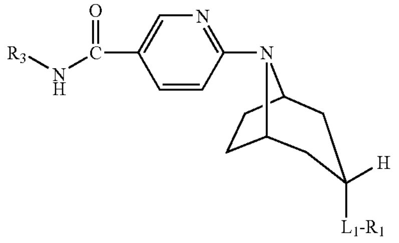

or a pharmaceutically acceptable salt thereof, wherein $L_1$, $R_1$ and $R_3$ are as defined in claim 1,

IC

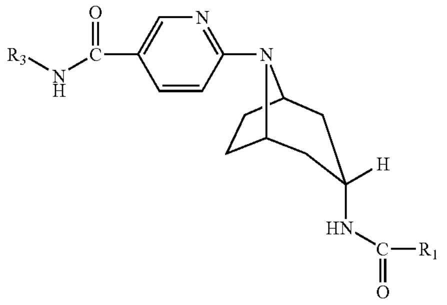

or a pharmaceutically acceptable salt thereof, wherein $R_1$ and $R_3$ are as defined in claim 1,

ID

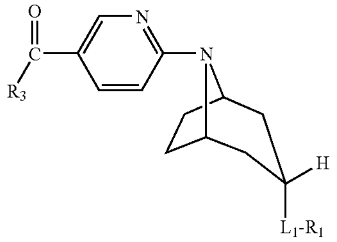

or a pharmaceutically acceptable salt thereof, wherein $R_1$, $R_3$ and $L_1$ are as defined in claim 1, and

IE

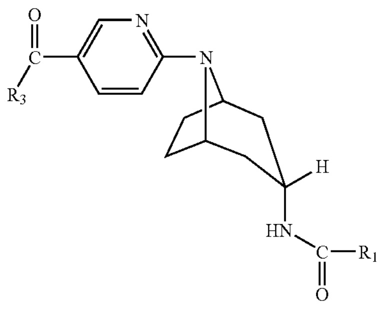

or a pharmaceutically acceptable salt thereof, wherein $R_1$ and $R_3$ are as defined in claim 1.

4. A compound or a pharmaceutically acceptable salt thereof, of formula I:

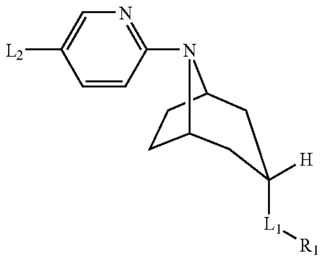

I wherein, $R_1$ is selected from

C2

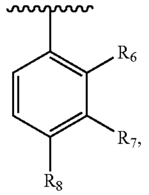

D2

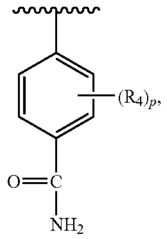

and

E2

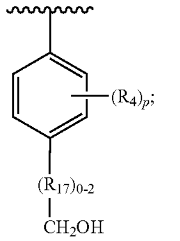

$R_3$ is selected from $CF_3$, cyclopropyl, cyclobutyl; cyclohexyl optionally substituted with hydroxyl; cyclopropylmethyl, N-propyl, 3-methylbutyl, (1S)-2-hydroxy-1-methylethyl, (2S)-2-hydroxypropyl, methoxyethyl, ethoxyethyl, methylphenyl, phenyl, dimethylphenyl, methoxyphenyl, dimethylaminoethyl, dimethylaminopropyl, diethylaminoethyl, diethylaminopropyl, cyclopentyl, halophenyl, phenylmethyl; phenylethyl optionally substituted with hydroxyl at the ethyl position of phenylethyl; phenylpropyl, phenylpiperidinyl, diethylaminoethyloxyphenylmethyl, diethylaminoethyloxyphenylethyl, pyrrolidinylphenylmethyl, diethylaminoethyloxy-2-fluorophenylethyl; phenyl($C_1$-$C_3$)alkyl optionally substituted at the phenyl position of phenyl ($C_1$-$C_3$)alkyl with 1-3 groups selected from methoxy, halo, and methyl; methylphenyl($C_1$-$C_4$)alkyl wherein the ($C_1$-$C_4$)alkyl portion of methylphenyl($C_1$-$C_4$)alkyl is optionally substituted with —C(O)$NH_2$, —C(O)$NHCH_3$, or —C(O)$NHCH_2CH_3$; thienylmethyl, furanylmethyl, pyridinylethyl, pyridinylmethyl, methylpyrazinylmethyl, methyl, ethyl, methylpropyl, 2-methylpropyl, 2,3-dihydroxypropyl, (1S)-1-methylpropyl, (1S)-1,2-dimethylpropyl, (1R)-1,2-dimethylpropyl, methyloxypropyl, ethyloxypropyl, (1S)-1-methyl-2-(methyloxy)ethyl, 1,3-benzodioxolyl, 1,3-benzodioxolylmethyl, N-prop-2-yn-1-yl, N-[3-(4-methylpiperazin-1-yl)propyl, N-[2-(ethylthio)ethyl], (1S,2S)-2-[(phenylmethyl)oxy]cyclopentyl, 6-chloropyridinylmethyl, 2-chloro-6-fluorophenylmethyl, methylthioethyl, N-butyl, 1-methylethyloxyethyl, 1-methylethyloxypropyl, 4,4-bismethyloxybutyl, methylpyrazinylmethyl, propyloxypropyl, trifluoromethyloxyphenylmethyl, methyloxyphenylethyl, (2,2-dimethyl-1,3-dioxolan-4-yl)methyl, phenylmethylpyrrolidinyl, oxopyrrolidinylpropyl, pyrrolidinylethyl, methylpyrrolidinylethyl, ethylpyrrolidinylmethyl, N-(1R,2R,4S)-bicyclo[2.2.1]hept-2-yl, 3,3-dimethylbutyl, ethyloxyphenylmethyl, phenylmethylpiperidinyl, ethoxycarbonylpiperidinyl, trifluoromethylphenylmethyl, imidazolylpropyl, (3R)-pyrrolidin-3-yl, morpholinylethyl, morpholinylpropyl, piperidinylethyl, pyrrolidinyl, piperidinyl, pyrrolidinylmethyl, 1-methylethylpyrrolidinyl, ethylpyrrolidinyl, methylpyrrolidinyl, methylethylpiperidinyl, methylpiperidinyl, ethylpiperidinyl, ethylazetidinyl, azetidinyl, methylazetidinyl, 1-methylethylazetidinyl, methylpiperazinylphenylmethyl, piperazinylphenylmethyl, methylpiperazinylphenyl, methylpiperidinylphenyl; piperidinylphenyl($C_1$-$C_3$)alkyl optionally substituted with 1-4 halo; methylpiperazinylphenyl(halo)methyl, methylpiperidinylphenylmethyl, methylpiperazinylphenylethyl, 2-methylpropylpiperazinylphenylmethyl, morpholinylphenylmethyl, piperazinylpyridinylethyl, —CH($CH_3$)C(O)—$NH_2$, dimethylaminoethyloxyphenyl, isopropyl; ($C_1$-$C_5$)alkyl optionally substituted with 1-7 halo; —OH, —$NH_2$; cyclohexyl($C_1$-$C_5$)alkyl optionally substituted with 1-2 hydroxyl groups; phenylaminoethyl optionally substituted with halo; morpholinylethyl, phenylpiperazinylethyl, and methylpiperazinylethyl;

each $R_4$, when present, is independently selected from halo, 1-ethylpropylamino, methyl, ethyl; cyclohexylamino optionally substituted with hydroxyl, cyclobutylamino, 1-methylpropyloxy, methoxyethoxy, —$CF_3$, piperidinyl or amino; mopholinylamino, dimethylaminobutyl, methylethylaminopropyl, methylethylaminopropylamino, cyclopentylamino, piperidinylamino, methylethylamino, ethylamino, 2-methylpropylamino, tetrahydropyranylamino, ethylpiperidinylamino, 2,2-dimethylpropylamino, pyrrolidinylamino, 1-methylpropylamino, 2-methylpropylamino, amino, 1,1 dimethylethylamino, tetrahydropyranylmethylamino; piperidinylamino optionally substituted with methylsulfonyl; phenylamino optionally substituted with 1-3 groups selected from methoxy and dimethylaminoethyloxy; methylsulfonylethylamino, methoxyethylamino, morpholinylethyloxy, —N(H)C(O)$CH_3$, cyclobutylamino, methoxy, cyclobutyloxy, cyclobutylamino, pyridinylamino, ethylamino, 1-methylcyclopropylethylamino, methylethyloxyethylamino, butylamino, piperidinyl, pentylamino, azetinyl, 1,2-dimethylpropylamino, 1-methylethylpropylamino, propylamino, 1-cyclopropylpropylamino, 1-propylbutylamino, 1-cyclopropylethylamino, dicyclopropylmethylamino, 1,2,2-trimethylpropylamino, tetrahydrofuranylamino; ($C_1$-

$C_5$)alkylamino substituted with 1-7 halo; morpholinylethyloxy, and cyclopropylmethylamino;

$R_5$ is selected from halogen, cycloalkyl, cycloalkylalkylamino; heteroaryl optionally substituted with 1, 2, or 3 groups selected from halogen, alkyl, and alkoxy; alkylthio; heterocycloalkyl optionally substituted with 1, 2, or 3 groups selected from alkyl, halogen, phenyl, and oxo; aryl optionally substituted with 1, 2, or 3 groups selected from halogen, alkyl, alkoxy, dialkylaminoalkoxy, and heterocycloalkyl optionally substituted with alkyl; alkoxy, dialkylamino, —OH, —C(O)—$NH_2$, —C(O)—O—$CH_3$, —C(O)—N(H)($C_1$-$C_3$)alkyl; heteroarylamino optionally substituted with halogen; and —$OCF_3$;

$R_6$ is selected from hydrogen; ($C_1$-$C_4$)alkyl optionally substituted with hydroxy, ($C_1$-$C_3$)alkylamino, or dimethylamino; ($C_1$-$C_4$)alkynyl optionally substituted with hydroxyl; and halo;

$R_7$ is selected from hydrogen, —OH, —O($C_1$-$C_3$)alkyl, —S($C_1$-$C_3$)alkyl, —N(H)($C_1$-$C_3$)alkyl; —($C_5$-$C_6$)cycloalkylamino optionally substituted with hydroxyl, ($C_1$-$C_3$)alkylamino, or dimethylamino; —C(O)$NH_2$, and —O—C(O)$NH_2$;

$R_8$ is selected from hydrogen, —O($C_1$-$C_3$)alkyl, —O—C(O)$NH_2$, and —C(=NH)—$NH_2$;

$L_1$ is —N(H)C(O)—;

$L_2$ is —C(O)—NH—$R_3$ or —C(O)—$R_3$; and each p is independently 0, 1, 2, or 3.

5. A compound, or a pharmaceutically acceptable salt thereof, of formula I:

I

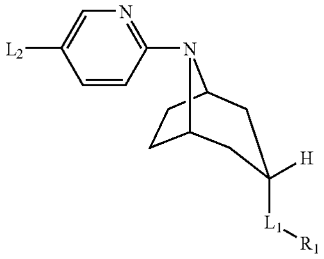

wherein, $R_1$ is selected from

C2

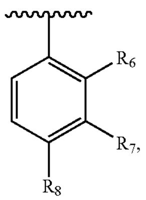

D2

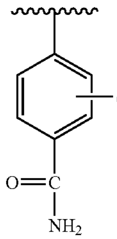 and

-continued

E2

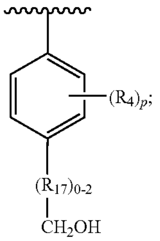

$R_3$ is selected from hydrogen, —$CF_3$, —$NH_2$, —OH; alkyl optionally substituted with 1, 2, or 3 $R_5$; alkoxy, diethylaminoethoxy, ethylmethylaminoethoxy, dimethylaminoethoxy; cyclopentyl optionally substituted with arylalkoxy; cyclobutyl optionally substituted with arylalkoxy; cyclopropyl optionally substituted with arylalkoxy; aryl optionally substituted with 1, 2, or 3 groups selected from halogen, alkyl, alkoxy, dialkylaminoalkoxy, piperazinyl optionally substituted with alkyl or phenyl, morpholinyl optionally substituted with alkyl or phenyl, azetidinyl, and piperidinyl optionally substituted with alkyl or phenyl; alkenyl, alkynyl; heterocycloalkyl selected from piperidinyl, pyrrolidinyl, morpholinyl, and piperizinyl, wherein the heterocycloalkyl is optionally substituted with a group selected from alkyl, —C(O)O-alkyl, and arylalkyl; arylalkyl optionally substituted with alkylheterocycloalkyl at any ring position of the aryl group; and heteroaryl;

each $R_4$, when present, is independently selected from methyl, 1-methylethylamino, ethylamino, 1-ethylpropylamino, 2-methylpropylamino, (2,2-dimethylpropyl)amino, (2-aminoethyl)amino, (2,2,3,3,3-pentafluoropropyl)amino, 1-methylpropylamino, (1S)-1-methylpropylamino, (2,2,2-trifluoroethyl)amino, 1-propylbutylamino, propylamino, 1,2-dimethylpropylamino, (3,3,3-trifluoropropyl)amino, (2,2,3,3,4,4,4-heptafluorobutyl)amino, butylamino, 1,2,2-trimethylpropylamino, 1-[(methyloxy)methyl]propylamino, 1-methylethyloxyethylamino, 1-methylpropylamino, pentylamino, (2,2,3,3,3-pentafluoropropyl)amino, butylamino, 2-[(1-methylethyl)oxy]ethylamino, (1S)-1-methylpropylamino, (1R)-1-methylpropylamino, (1S)-1,2-dimethylpropylamino, 1-cyclopropylethylamino, (1R)-1,2-dimethylpropylamino, 1-ethyl-2-methylpropylamino, and 3-[(1-methylethyl)amino]propylamino;

$R_5$ is selected from halogen, cycloalkyl, cycloalkylalkylamino; heteroaryl optionally substituted with 1, 2, or 3 groups selected from halogen, alkyl, and alkoxy; alkylthio; heterocycloalkyl optionally substituted with 1, 2, or 3 groups selected from alkyl, halogen, phenyl, and oxo; aryl optionally substituted with 1, 2, or 3 groups selected from halogen, alkyl, alkoxy, dialkylaminoalkoxy, and heterocycloalkyl optionally substituted with alkyl; alkoxy, dialkylamino, —OH, —C(O)—$NH_2$, —C(O)—O—$CH_3$, —C(O)—N(H)($C_1$-$C_3$)alkyl; heteroarylamino optionally substituted with halogen; and —$OCF_3$;

$R_6$ is selected from hydrogen; ($C_1$-$C_4$)alkyl optionally substituted with hydroxy, ($C_1$-$C_3$)alkylamino or dimethylamino; ($C_1$-$C_4$)alkynyl optionally substituted with hydroxyl; and halo;

$R_7$ is selected from hydrogen, —OH, —O($C_1$-$C_3$)alkyl, —S($C_1$-$C_3$)alkyl, —N(H)($C_1$-$C_3$)alkyl; —($C_5$-$C_6$)cycloalkylamino optionally substituted with hydroxyl, $(C_1-C_3)$alkylamino, or dimethylamino; —C(O)$NH_2$, and —O—C(O)$NH_2$;

$R_8$ is selected from hydrogen, —O$(C_1-C_3)$alkyl, —O—C(O)$NH_2$, and —C(=NH)—$NH_2$;

$L_1$ is —N(H)C(O)—;

$L_2$ is —C(O)—NH—$R_3$ or —C(O)—$R_3$; and each p is independently 0, 1, 2, or 3.

6. The compound according to claim 1 having Formula I:

I

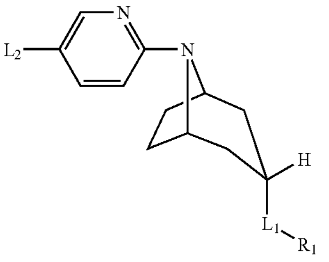

or a pharmaceutically acceptable salt thereof, wherein:

$R_1$ is selected from:

(G)

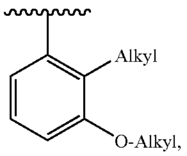

(H)

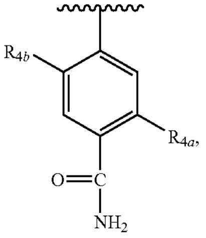

and (I)

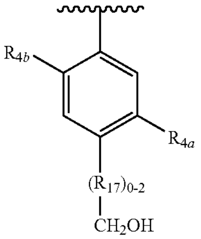

wherein $R_{4a}$ is selected from hydrogen, —$OR_{16}$, —$SR_{16}$, —N(H)$R_{16}$, hydroxy, alkenyl, alkynyl, hydroxyalkynyl, halogen, hydroxyalkyl, dihydroxyalkyl, —O—C(O)—$NH_2$, amino(imino)alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl; alkyl optionally substituted with 1-8 halogens; dialkylamino, —N(H)alkylheterocycloalkyl, alkylsulfonylheterocycloalkylamino, cycloalkylalkylamino, cycloalkoxy, —$NH_2$, —O-alkyl-heterocycloalkyl, dialkylaminoalkoxy, alkylsulfonylalkylamino; and —N(H)heterocycloalkyl optionally substituted with 1, 2, or 3 groups selected from alkyl, alkoxy, and halogen;

$R_{4b}$ is selected from H, halogen, and methyl optionally substituted with 1-3 halogens;

$R_{16}$ is selected from hydrogen; alkyl optionally substituted with 1-8 halogens; cycloalkyl optionally substituted with 1 or 2 groups selected from —OH, —$NH_2$, alkyl, heterocycloalkyl, and —$CF_3$; cycloalkylalkyl; heterocycloalkyl optionally substituted with —OH or —$NH_2$; alkoxyalkyl; aryl optionally substituted with 1, 2, or 3 alkoxy; heterocycloalkylalkyl, heteroaryl, gem-dicycloalkylalkyl, and dialkylaminoalkyl;

$R_{17}$, when present, is —$CH_2$— or —CH(OH)—;

$L_1$ is selected from —NHC(O)—, —$NHSO_{2-5}$—C(O)O—, —C(O)NH—, —C(O)$NHSO_2$—; —C(O)—, —$(CH_2)$C(O)NH—, —$(CH_2)$NHC(O)—, —$(CH_2)$NH—, —$(CH_2)_n SO_2$NH—, —$(CH_2)NHSO_2$—, —$(CH_2)$C(O)—, —$(CH_2)$O—, and —NH—$(CH_2)$—; and $L_2$ is —C(O)—NH-cyclopropyl.

7. The compound according to claim 6, or a pharmaceutically acceptable salt thereof, wherein $R_1$ is selected from:

(G)

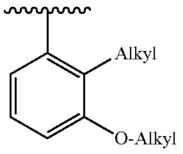

and (H)

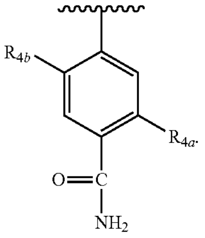

8. The compound according to claim 1, or a pharmaceutically acceptable salt thereof, wherein $R_1$ is selected from (G)

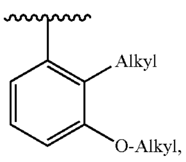

(H)

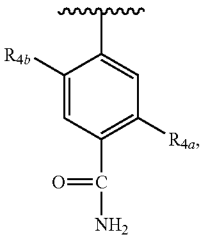

and

-continued (I)

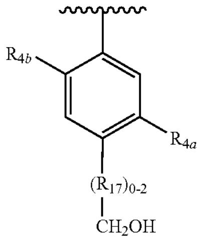

wherein $R_{4a}$ is selected from hydrogen, —$OR_{16}$, —$SR_{16}$, —$N(H)R_{16}$, hydroxy, alkenyl, alkynyl, hydroxyalkynyl, halogen, hydroxyalkyl, dihydroxyalkyl, —O—C(O)—$NH_2$, amino(imino)alkyl, —C(O)—$NH_2$, —N(H)C(O)alkyl, alkylaminoalkyl, alkylaminoalkylamino, aminoalkylamino, arylalkylamino, heterocycloalkyl, dialkylaminoalkyl; alkyl optionally substituted with 1-8 halogens; dialkylamino, —N(H)alkylheterocycloalkyl, alkylsulfonylheterocycloalkylamino, cycloalkylalkylamino, cycloalkoxy, —$NH_2$, —O-alkyl-heterocycloalkyl, dialkylaminoalkoxy, alkylsulfonylalkylamino; and —N(H)heterocycloalkyl optionally substituted with 1, 2, or 3 groups selected from alkyl, alkoxy, and halogen;

$R_{4b}$ is selected from H, halogen, and methyl optionally substituted with 1-3 halogens;

$R_{16}$ is selected from hydrogen; alkyl optionally substituted with 1-8 halogens; cycloalkyl optionally substituted with 1 or 2 groups selected from —OH, —$NH_2$, alkyl, heterocycloalkyl, and —$CF_3$; cycloalkylalkyl; heterocycloalkyl optionally substituted with —OH or —$NH_2$; alkoxyalkyl; aryl optionally substituted with 1, 2, or 3 alkoxy; heterocycloalkylalkyl, heteroaryl, gem-dicycloalkylalkyl, and dialkylaminoalkyl; and $R_{17}$, when present, is —$CH_2$— or —CH(OH)—.

9. The compound according to claim 1, or a pharmaceutically acceptable salt thereof, wherein $R_1$ is (K)

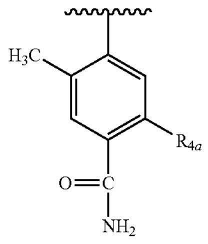

wherein $R_{4a}$ is selected from —$N(H)R_{16}$, —$OR_{16}$, and —$SR_{16}$; and $R_{16}$ is selected from hydrogen; alkyl optionally substituted with 1-8 halogens; cycloalkyl optionally substituted with 1 or 2 groups selected from —OH, —$NH_2$, —$CH_3$ and —$CF_3$; cycloalkylalkyl; heterocycloalkyl optionally substituted with —OH or —$NH_2$; alkoxyalkyl; aryl optionally substituted with 1, 2, or 3 alkoxy; heteroaryl, gem-dicycloalkylalkyl, and dialkylaminoalkyl.

10. The compound according to claim 1, or a pharmaceutically acceptable salt thereof, wherein $R_1$ is

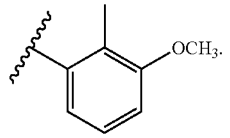

11. The compound according to claim 1, or a pharmaceutically acceptable salt thereof, wherein $R_1$ is (H)

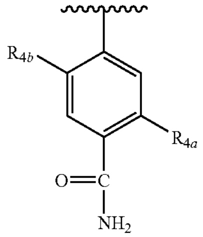

or (I)

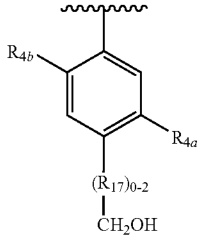

wherein $R_{4a}$ is alkylamino optionally substituted with 1-8 halogens;

$R_{4b}$ is selected from H, halogen, and methyl optionally substituted with 1-3 halogens;

$R_{17}$, when present, is —$CH_2$— or —CH(OH)—; and $L_1$ is —N(H)C(O)—.

12. The compound according to claim 1, or a pharmaceutically acceptable salt thereof, wherein $R_1$ is (H)

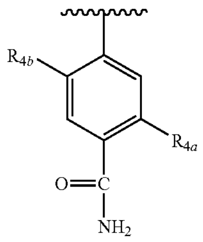

or (I)

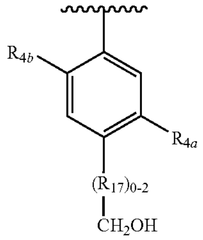

$R_{4a}$ is 1-methylethylamino, ethylamino, 1-ethylpropylamino, 2-methylpropylamino, (2,2-dimethylpropyl)amino, (2-aminoethyl)amino, (2,2,3,3,3-pentafluoropropyl)amino, 1-methylpropylamino, (1S)-1-methylpropylamino, (2,2,2-trifluoroethyl)amino, 1-propylbutylamino, propylamino, 1,2-dimethylpropylamino, (3,3,3-trifluoropropyl)amino, (2,2,3,3,4,4,4-heptafluorobutyl)amino, butylamino, 1,2,2-trimethylpropylamino, 1-[(methyloxy)methyl]propylamino, 1-methylethyloxyethylamino, 1-methylpropylamino, pentylamino, (2,2,3,3,3-pentafluoropropyl)amino, butylamino, 2-[(1-methylethyl)oxy]ethylamino, (1S)-1-methylpropylamino, (1R)-1-methylpropylamino, (1S)-1,2-dimethylpropylamino, 1-cyclopropylethylamino, (1R)-1,2-dimethylpropylamino, 1-ethyl-2-methylpropylamino, or 3-[(1-methylethyl)amino]propylamino;

$R_{4b}$ is selected from H, halogen, and methyl optionally substituted with 1-3 halogens;

$R_{17}$, when present, is $—CH_2—$ or —CH(OH)—; and $L_1$ is —N(H)C(O)—.

13. The compound according to claim 1, or a pharmaceutically acceptable salt thereof, wherein $R_1$ is (H)

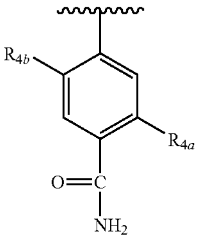

or (I)

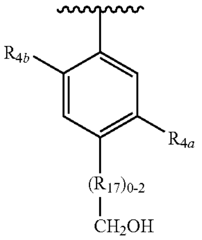

wherein $R_{4a}$ is heterocycloalkylamino optionally substituted with alkyl;

$R_{4b}$ is selected from H, halogen, and methyl optionally substituted with 1-3 halogens;

$R_{17}$, when present, is $—CH_2—$ or —CH(OH)—; and $L_1$ is —N(H)C(O)—.

14. The compound according to claim 1, or a pharmaceutically acceptable salt thereof, wherein $R_1$ is (H)

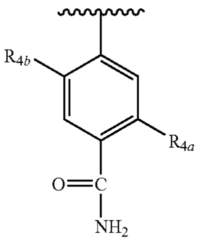

or (I)

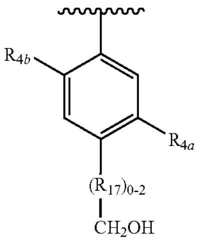

wherein $R_{4a}$ is tetrahydrofuran-3-ylamino, piperidin-4-ylamino, tetrahydro-2H-pyran-4-ylamino, (1-ethylpiperidin-4-yl)amino, (tetrahydrofuran-2-ylmethyl)amino, pyrrolidin-3-ylamino, (piperidin-3-ylmethyl)amino, (pyrrolidin-3-ylmethyl)amino, (3R)-tetrahydrofuran-3-ylamino, azetidin-1-yl, piperidin-1-ylamino, or (3S)-tetrahydrofuran-3-ylamino; and $R_{4b}$ is selected from H, halogen, and methyl optionally substituted with 1-3 halogens;

$R_{17}$, when present, is $—CH_2—$ or —CH(OH)—; and $L_1$ is —N(H)C(O)—.

15. The compound according to claim 1, wherein the compound of Formula I is selected from one of the following compounds:

| NAME |
| --- |
| N-cyclopropyl-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[2-(methyloxy)ethyl]pyridine-3-carboxamide; |
| N-[2-(dimethylamino)ethyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-(2-morpholin-4-ylethyl)pyridine-3-carboxamide; |
| 6-[3-endo-({[2-methyl-3-(methyloxy)phenyl]carbonyl}amino)-8-azabicyclo[3.2.1]oct-8-yl]-N-(pyridin-3-ylmethyl)pyridine-3-carboxamide; |
| N-cyclopentyl-6-[3-endo-({[2-methyl-3-(methyloxy)phenyl]carbonyl}amino)-8-azabicyclo[3.2.1]oct-8-yl]pyridine-3-carboxamide |
| N-[(2-chlorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[(4-chlorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-{2-[3,4-bis(methyloxy)phenyl]ethyl}-6-[3-endo-({[2-methyl-3-(methyloxy)phenyl]carbonyl}amino)-8-azabicyclo[3.2.1]oct-8-yl]pyridine-3-carboxamide; |
| N-(furan-2-ylmethyl)-6-[3-endo-({[2-methyl-3-(methyloxy)phenyl]carbonyl}amino)-8-azabicyclo[3.2.1]oct-8-yl]pyridine-3-carboxamide; |

-continued

| NAME |
| --- |
| 6-[3-endo-({[2-methyl-3-(methyloxy)phenyl]carbonyl}amino)-8-azabicyclo[3.2.1]oct-8-yl]-N-(2-methylpropyl)pyridine-3-carboxamide; |
| 6-[3-endo-({[2-methyl-3-(methyloxy)phenyl]carbonyl}amino)-8-azabicyclo[3.2.1]oct-8-yl]-N-{[4-(methyloxy)phenyl]methyl}pyridine-3-carboxamide; |
| 6-[3-endo-({[2-methyl-3-(methyloxy)phenyl]carbonyl}amino)-8-azabicyclo[3.2.1]oct-8-yl]-N-[3-(methyloxy)propyl]pyridine-3-carboxamide; |
| 6-[3-endo-({[2-methyl-3-(methyloxy)phenyl]carbonyl}amino)-8-azabicyclo[3.2.1]oct-8-yl]-N-[(4-methylphenyl)methyl]pyridine-3-carboxamide; |
| N-(1,3-benzodioxol-5-ylmethyl)-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-prop-2-yn-1-ylpyridine-3-carboxamide; |
| N-{[3,4-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[3-(4-methylpiperazin-1-yl)propyl]pyridine-3-carboxamide; |
| N-[2-(ethylthio)ethyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-{(1S,2S)-2-<br>[(phenylmethyl)oxy]cyclopentyl}pyridine-3-carboxamide; |
| N-[(6-chloropyridin-3-yl)methyl]-6-[3-endo-({[2-methyl-3-(methyloxy)phenyl]carbonyl}amino)-8-azabicyclo[3.2.1]oct-8-yl]pyridine-3-carboxamide; |
| N-[(2-chloro-6-fluorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[2-(methylthio)ethyl]pyridine-3-carboxamide; |
| N-butyl-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-(3-morpholin-4-ylpropyl)pyridine-3-carboxamide; |
| 6-[3-endo-({[2-methyl-3-(methyloxy)phenyl]carbonyl}amino)-8-azabicyclo[3.2.1]oct-8-yl]-N-(2-pyridin-4-ylethyl)pyridine-3-carboxamide; |
| N-{2-[(1-methylethyl)oxy]ethyl}-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-(2-pyridin-3-ylethyl)pyridine-3-carboxamide; |
| N-[4,4-bis(methyloxy)butyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[(5-methylpyrazin-2-yl)methyl]pyridine-3-carboxamide; |
| 6-[3-endo-({[2-methyl-3-(methyloxy)phenyl]carbonyl}amino)-8-azabicyclo[3.2.1]oct-8-yl]-N-[3-endo-(propyloxy)propyl]pyridine-3-carboxamide; |
| 6-[3-endo-({[2-methyl-3-(methyloxy)phenyl]carbonyl}amino)-8-azabicyclo[3.2.1]oct-8-yl]-N-{[3,4,5-<br>tris(methyloxy)phenyl]methyl}pyridine-3-carboxamide; |
| N-{[3,5-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| N-(cyclopropylmethyl)-6-[3-endo-({[2-methyl-3-(methyloxy)phenyl]carbonyl}amino)-8-azabicyclo[3.2.1]oct-8-yl]pyridine-3-carboxamide; |
| N-{[2,4-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| N-[(4-bromophenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[(2,2-dimethyl-1,3-dioxolan-4-yl)methyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[(3S)-1-(phenylmethyl)pyrrolidin-3-yl]pyridine-3-carboxamide; |
| 6-[3-endo-({[2-methyl-3-(methyloxy)phenyl]carbonyl}amino)-8-azabicyclo[3.2.1]oct-8-yl]-N-[(3R)-1-(phenylmethyl)pyrrolidin-3-yl]pyridine-3-carboxamide; |
| N-[3-(diethylamino)propyl]-6-[3-endo-({[2-methyl-3-(methyloxy)phenyl]carbonyl}amino)-8-azabicyclo[3.2.1]oct-8-yl]pyridine-3-carboxamide; |
| N-{3-[(1-methylethyl)oxy]propyl}-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-propylpyridine-3-carboxamide |
| N-[2-(diethylamino)ethyl]-6-[3-endo-({[2-methyl-3-(methyloxy)phenyl]carbonyl}amino)-8-azabicyclo[3.2.1]oct-8-yl]pyridine-3-carboxamide |
| N-(3-methylbutyl)-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[(3-methylphenyl)methyl]pyridine-3-carboxamide; |
| N-[(3-fluorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[(2-methylphenyl)methyl]pyridine-3-carboxamide; |
| N-[(3-(chlorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-(tetrahydrofuran-2-ylmethyl)pyridine-3-carboxamide; |
| 6-[3-endo-({[2-methyl-3-(methyloxy)phenyl]carbonyl}amino)-8-azabicyclo[3.2.1]oct-8-yl]-N-[3-(2-oxopyrrolidin-1-yl)propyl]pyridine-3-carboxamide; |
| 6-[3-endo-({[2-methyl-3-(methyloxy)phenyl]carbonyl}amino)-8-azabicyclo[3.2.1]oct-8-yl]-N-[2-(1-methylpyrrolidin-2-yl)ethyl]pyridine-3-carboxamide; |

-continued

| NAME |
|---|
| 6-[3-endo-({[2-methyl-3-(methyloxy)phenyl]carbonyl}amino)-8-azabicyclo[3.2.1]oct-8-yl]-N-(2-piperidin-1-ylethyl)pyridine-3-carboxamide; |
| 6-[3-endo-({[2-methyl-3-(methyloxy)phenyl]carbonyl}amino)-8-azabicyclo[3.2.1]oct-8-yl]-N-{[2-(methyloxy)phenyl]methyl}pyridine-3-carboxamide; |
| 6-[3-endo-({[2-methyl-3-(methyloxy)phenyl]carbonyl}amino)-8-azabicyclo[3.2.1]oct-8-yl]-N-{[3-(methyloxy)phenyl]methyl}pyridine-3-carboxamide; |
| N-[(2-fluorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[(4-fluorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[(1R,2R,4S)-bicyclo[2.2.1]hept-2-yl]-6-[3-endo-({[2-methyl-3-(methyloxy)phenyl]carbonyl}amino)-8-azabicyclo[3.2.1]oct-8-yl]pyridine-3-carboxamide; |
| N-(3,3-dimethylbutyl)-6-[3-endo-({[2-methyl-3-(methyloxy)phenyl]carbonyl}amino)-8-azabicyclo[3.2.1]oct-8-yl]pyridine-3-carboxamide; |
| N-{[2,3-bis(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| N-{[2-(ethyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[1-(phenylmethyl)piperidine-4-yl]pyridine-3-carboxamide; |
| ethyl 4-[({6-[3-endo-({[2-methyl-3-(methyloxy)phenyl]carbonyl}amino)-8-azabicyclo[3.2.1]oct-8-yl]pyridin-3-yl}carbonyl)amino]piperidine-1-carboxylate; |
| 6-[3-endo-({[2-methyl-3-(methyloxy)phenyl]carbonyl}amino)-8-azabicyclo[3.2.1]oct-8-yl]-N-(2-(thienylmethyl)pyridine-3-carboxamide; |
| N-cyclobutyl-6-[3-endo-({[2-methyl-3-(methyloxy)phenyl]carbonyl}amino)-8-azabicyclo[3.2.1]oct-8-yl]pyridine-3-carboxamide; |
| N-[3-(ethyloxy)propyl]-6-[3-endo-({[2-methyl-3-(methyloxy)phenyl]carbonyl}amino)-8-azabicyclo[3.2.1]oct-8-yl]pyridine-3-carboxamide; |
| N-[3-(dimethylamino)propyl]-6-[3-endo-({[2-methyl-3-(methyloxy)phenyl]carbonyl}amino)-8-azabicyclo[3.2.1]oct-8-yl]pyridine-3-carboxamide; |
| N-[(2,4-difluorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[(2,5-difluorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[(2,6-difluorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[(3,4-difluorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[3-(1H-imidazol-1-yl)propyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-(2-methylphenyl)pyridine-3-carboxamide; |
| N-(3,5-dimethylphenyl)-6-[3-endo-({[2-methyl-3-(methyloxy)phenyl]carbonyl}amino)-8-azabicyclo[3.2.1]oct-8-yl]pyridine-3-carboxamide; |
| N-1,3-benzodioxol-5-yl-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-(4-methylphenyl)pyridine-3-carboxamide; |
| 6-[3-endo-({[2-methyl-3-(methyloxy)phenyl]carbonyl}amino)-8-azabicyclo[3.2.1]oct-8-yl]-N-(3-methylphenyl)pyridine-3-carboxamide; |
| 6-[3-endo-({[2-methyl-3-(methyloxy)phenyl]carbonyl}amino)-8-azabicyclo[3.2.1]oct-8-yl]-N-[2-(methyloxy)phenyl]pyridine-3-carboxamide; |
| 6-[3-endo-({[2-methyl-3-(methyloxy)phenyl]carbonyl}amino)-8-azabicyclo[3.2.1]oct-8-yl]-N-[3-(methyloxy)phenyl]pyridine-3-carboxamide; |
| 6-[3-endo-({[2-methyl-3-(methyloxy)phenyl]carbonyl}amino)-8-azabicyclo[3.2.1]oct-8-yl]-N-[4-(methyloxy)phenyl]pyridine-3-carboxamide; |
| N-(3-chlorophenyl)-6-[3-endo-({[2-methyl-3-(methyloxy)phenyl]carbonyl}amino)-8-azabicyclo[3.2.1]oct-8-yl]pyridine-3-carboxamide; |
| N-(4-fluorophenyl)-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-{(1S)-1-[3-(methyloxy)phenyl]ethyl}pyridine-3-carboxamide; |
| 6-[3-endo-({[2-methyl-3-(methyloxy)phenyl]carbonyl}amino)-8-azabicyclo[3.2.1]oct-8-yl]-N-[(4-morpholin-4-ylphenyl)methyl]pyridine-3-carboxamide; |
| 6-[3-endo-({[2-methyl-3-(methyloxy)phenyl]carbonyl}amino)-8-azabicyclo[3.2.1]oct-8-yl]-N-[(3R)-pyrrolidin-3-yl]pyridine-3-carboxamide; |
| 6-[3-endo-({[2-methyl-3-(methyloxy)phenyl]carbonyl}amino)-8-azabicyclo[3.2.1]oct-8-yl]-N-piperidin-3-ylpyridine-3-carboxamide; |
| 6-[3-endo-({[2-methyl-3-(methyloxy)phenyl]carbonyl}amino)-8-azabicyclo[3.2.1]oct-8-yl]-N-piperidin-4-ylpyridine-3-carboxamide; |
| 6-[3-endo-({[2-methyl-3-(methyloxy)phenyl]carbonyl}amino)-8-azabicyclo[3.2.1]oct-8-yl]-N-(pyrrolidin-3-ylmethyl)pyridine-3-carboxamide; |
| 6-[3-endo-({[2-methyl-3-(methyloxy)phenyl]carbonyl}amino)-8-azabicyclo[3.2.1]oct-8-yl]-N-(1-methylpiperidin-4-yl)pyridine-3-carboxamide; |
| 6-[3-endo-({[2-methyl-3-(methyloxy)phenyl]carbonyl}amino)-8-azabicyclo[3.2.1]oct-8-yl]-N-{[4-(4-methylpiperazin-1-yl)phenyl]methyl}pyridine-3-carboxamide; |
| N-(1-methylethyl)-6-[3-endo-({[2-methyl-3-(methyloxy)phenyl]carbonyl}amino)-8-azabicyclo[3.2.1]oct-8-yl]pyridine-3-carboxamide; |
| N-cyclohexyl-6-[3-endo-({[2-methyl-3-(methyloxy)phenyl]carbonyl}amino)-8-azabicyclo[3.2.1]oct-8-yl]pyridine-3-carboxamide; |
| N-methyl-6-[3-endo-({[2-methyl-3-(methyloxy)phenyl]carbonyl}amino)-8-azabicyclo[3.2.1]oct-8-yl]pyridine-3-carboxamide; |
| N-ethyl-6-[3-endo-({[2-methyl-3-(methyloxy)phenyl]carbonyl}amino)-8-azabicyclo[3.2.1]oct-8-yl]pyridine-3-carboxamide; |
| N-[(1S)-1,2-dimethylpropyl]-6-[3-endo-({[2-methyl-3-(methyloxy)phenyl]carbonyl}amino)-8-azabicyclo[3.2.1]oct-8-yl]pyridine-3-carboxamide; |
| N-[(1R)-1,2-dimethylpropyl]-6-[3-endo-({[2-methyl-3-(methyloxy)phenyl]carbonyl}amino)-8-azabicyclo[3.2.1]oct-8-yl]pyridine-3-carboxamide; |
| N-[(1S)-1-methyl-2-(methyloxy)ethyl]-6-[3-endo-({[2-methyl-3-(methyloxy)phenyl]carbonyl}amino)-8-azabicyclo[3.2.1]oct-8-yl]pyridine-3-carboxamide; |

-continued

| NAME |
|---|
| N-azetidin-3-yl-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-{[4-(1-methylpiperidin-4-yl)phenyl]methyl}pyridine-3-carboxamide; |
| 6-[3-endo-({[2-methyl-3-(methyloxy)phenyl]carbonyl}amino)-8-azabicyclo[3.2.1]oct-8-yl]-N-{(1S)-1-[4-(methyloxy)phenyl]ethyl}pyridine-3-carboxamide; |
| 6-[3-endo-({[2-methyl-3-(methyloxy)phenyl]carbonyl}amino)-8-azabicyclo[3.2.1]oct-8-yl]-N-{(1R)-1-[4-(methyloxy)phenyl]ethyl}pyridine-3-carboxamide; |
| 6-[3-endo-({[2-methyl-3-(methyloxy)phenyl]carbonyl}amino)-8-azabicyclo[3.2.1]oct-8-yl]-N-[(1R)-1-phenylethyl]pyridine-3-carboxamide; |
| 6-[3-endo-({[2-methyl-3-(methyloxy)phenyl]carbonyl}amino)-8-azabicyclo[3.2.1]oct-8-yl]-N-[(1S)-1-phenylethyl]pyridine-3-carboxamide; |
| 6-[3-endo-({[2-methyl-3-(methyloxy)phenyl]carbonyl}amino)-8-azabicyclo[3.2.1]oct-8-yl]-N-[(1S)-1-phenylpropyl]pyridine-3-carboxamide; |
| 6-[3-endo-({[2-methyl-3-(methyloxy)phenyl]carbonyl}amino)-8-azabicyclo[3.2.1]oct-8-yl]-N-((1-phenylethyl)pyridine-3-carboxamide; |
| 6-[3-endo-({[2-methyl-3-(methyloxy)phenyl]carbonyl}amino)-8-azabicyclo[3.2.1]oct-8-yl]-N-{(1S)-1-[4-(4-methylpiperazin-1-yl)phenyl]ethyl}pyridine-3-carboxamide; |
| N-[(1S)-1-(4-chlorophenyl)ethyl]-6-[3-endo-({[2-methyl-3-(methyloxy)phenyl]carbonyl}amino)-8-azabicyclo[3.2.1]oct-8-yl]pyridine-3-carboxamide; |
| N-{(1S)-1-[2-fluoro-4-(methyloxy)phenyl]ethyl}-6-[3-endo-({[2-methyl-3-(methyloxy)phenyl]carbonyl}amino)-8-azabicyclo[3.2.1]oct-8-yl]pyridine-3-carboxamide; |
| N-{[2-fluoro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| N-[(2-chloro-3,6-difluorophenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[(4-{[(2-(diethylamino)ethyl]oxy}phenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[(1S)-2-amino-1-methyl-2-oxoethyl]-6-[3-endo-({[2-methyl-3-(methyloxy)phenyl]carbonyl}amino)-8-azabicyclo[3.2.1]oct-8-yl]pyridine-3-carboxamide; |
| N-[(3-{[(2-(diethylamino)ethyl]oxy}phenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-{[4-fluoro-3-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| N-{[3-fluoro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| N-{[2-chloro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[(2,4,6-trifluorophenyl)methyl]pyridine-3-carboxamide; |
| 6-[3-endo-({[2-methyl-3-(methyloxy)phenyl]carbonyl}amino)-8-azabicyclo[3.2.1]oct-8-yl]-N-{[3-(4-methylpiperazin-1-yl)phenyl]methyl}pyridine-3-carboxamide; |
| N-{[2,6-difluoro-4-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| N-[(2-chloro-6-fluoro-3-methylphenyl)methyl]-6-[3-endo-({[2-methyl-3-(methyloxy)phenyl]carbonyl}amino)-8-azabicyclo[3.2.1]oct-8-yl]pyridine-3-carboxamide; |
| N-[1-(4-chlorophenyl)ethyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[(4-pyrrolidin-1-ylphenyl)methyl]pyridine-3-carboxamide; |
| 6-[3-endo-({[2-methyl-3-(methyloxy)phenyl]carbonyl}amino)-8-azabicyclo[3.2.1]oct-8-yl]-N-[(2,3,6-trifluorophenyl)methyl]pyridine-3-carboxamide; |
| N-{[2-fluoro-6-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| N-{[4-fluoro-2-(methyloxy)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-{[2-(4-methylpiperazin-1-yl)phenyl]methyl}pyridine-3-carboxamide; |
| 6-[3-endo-({[2-methyl-3-(methyloxy)phenyl]carbonyl}amino)-8-azabicyclo[3.2.1]oct-8-yl]-N-[(2,4,5-trifluorophenyl)methyl]pyridine-3-carboxamide; |
| N-{[3-fluoro-4-(4-methylpiperazin-1-yl)phenyl]methyl}-6-[3-endo-({[2-methyl-3-(methyloxy)phenyl]carbonyl}amino)-8-azabicyclo[3.2.1]oct-8-yl]pyridine-3-carboxamide; |
| N-(8-{5-[({[4-(4-methylpiperazin-1-yl)phenyl]methyl}amino)carbonyl]pyridin-2-yl}-8-azabicyclo[3.2.1]oct-3-endo-yl)benzene-1,4-dicarboxamide; |
| N-[(1S)-1-(4-{[2-(diethylamino)ethyl]oxy}-2-fluorophenyl)ethyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[4-(4-methylpiperazin-1-yl)phenyl]pyridine-3-carboxamide; |
| 6-[3-endo-({[2-methyl-3-(methyloxy)phenyl]carbonyl}amino)-8-azabicyclo[3.2.1]oct-8-yl]-N-[4-(1-methylpiperidin-4-yl)phenyl]pyridine-3-carboxamide; |
| N-(4-{[2-(dimethylamino)ethyl]oxy}phenyl)-6-[3-endo-({[2-methyl-3-(methyloxy)phenyl]carbonyl}amino)-8-azabicyclo[3.2.1]oct-8-yl]pyridine-3-carboxamide; |
| N-hydroxy-6-[3-endo-({[2-methyl-3-(methyloxy)phenyl]carbonyl}amino)-8-azabicyclo[3.2.1]oct-8-yl]pyridine-3-carboxamide; |
| N-{8-[5-(hydrazinocarbonyl)pyridin-2-yl]-8-azabicyclo[3.2.1]oct-3-endo-yl}-2-methyl-3-(methyloxy)benzamide; |
| N-[(1S)-1-(4-{[2-(diethylamino)ethyl]oxy}phenyl)ethyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[(4-piperazin-1-ylphenyl)methyl]pyridine-3-carboxamide; |
| 6-[3-endo-({[2-methyl-3-(methyloxy)phenyl]carbonyl}amino)-8-azabicyclo[3.2.1]oct-8-yl]-N-({4-[4-(2-methylpropyl)piperazin-1-yl]phenyl}methyl)pyridine-3-carboxamide; |

-continued

| NAME |
|---|
| N-[1-(4-bromo-2-fluorophenyl)ethyl]-6-[3-endo-({[2-methyl-3-(methyloxy)phenyl]carbonyl}amino)-8-azabicyclo[3.2.1]oct-8-yl]pyridine-3-carboxamide; |
| N-{1-[3,4-bis(methyloxy)phenyl]ethyl}-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-methyl-3-(methyloxy)phenyl]carbonyl}amino)-8-azabicyclo[3.2.1]oct-8-yl]-N-[(1S)-1-methylpropyl]pyridine-3-carboxamide; |
| 6-[3-endo-({[2-methyl-3-(methyloxy)phenyl]carbonyl}amino)-8-azabicyclo[3.2.1]oct-8-yl]-N-[(3R)-1-methylpyrrolidin-3-yl]pyridine-3-carboxamide; |
| 6-[3-endo-({[2-methyl-3-(methyloxy)phenyl]carbonyl}amino)-8-azabicyclo[3.2.1]oct-8-yl]-N-[(3S)-1-methylpyrrolidin-3-yl]pyridine-3-carboxamide; |
| N-(2,3-dihydroxypropyl)-6-[3-endo-({[2-methyl-3-(methyloxy)phenyl]carbonyl}amino)-8-azabicyclo[3.2.1]oct-8-yl]pyridine-3-carboxamide; |
| N-[(1S)-2-hydroxy-1-methylethyl]-6-[3-endo-({[2-methyl-3-(methyloxy)phenyl]carbonyl}amino)-8-azabicyclo[3.2.1]oct-8-yl]pyridine-3-carboxamide; |
| N-[(2S)-2-hydroxypropyl]-6-[3-endo-({[2-methyl-3-(methyloxy)phenyl]carbonyl}amino)-8-azabicyclo[3.2.1]oct-8-yl]pyridine-3-carboxamide; |
| N-(2-hydroxyethyl)-6-[3-endo-({[2-methyl-3-(methyloxy)phenyl]carbonyl}amino)-8-azabicyclo[3.2.1]oct-8-yl]pyridine-3-carboxamide; |
| 2-[(1-ethylpropyl)amino]-N4-[8-(5-{[(3R)-pyrrolidin-3-ylamino]carbonyl}pyridin-2-yl)-8-azabicyclo[3.2.1]oct-3-endo-yl]benzene-1,4-dicarboxamide; |
| 2-[(1-ethylpropyl)amino]-N4-{8-[5-({[(3R)-1-(1-methylethyl)pyrrolidin-3-yl]amino}carbonyl)pyridin-2-yl]-8-azabicyclo[3.2.1]oct-3-endo-yl}benzene-1,4-dicarboxamide; |
| 2-[(1-ethylpropyl)amino]-N4-{8-[5-({[(3S)-1-(1-methylethyl)pyrrolidin-3-yl]amino}carbonyl)pyridin-2-yl]-8-azabicyclo[3.2.1]oct-3-endo-yl}benzene-1,4-dicarboxamide; |
| 2-[(1-ethylpropyl)amino]-N4-{8-[5-({[(3R)-1-ethylpyrrolidin-3-yl]amino}carbonyl)pyridin-2-yl]-8-azabicyclo[3.2.1]oct-3-endo-yl}benzene-1,4-dicarboxamide; |
| 5-[(1-ethylpropyl)amino]-2-methyl-N-{8-[5-({[(3R)-1-(1-methylethyl)pyrrolidin-3-yl]amino}carbonyl)pyridin-2-yl]-8-azabicyclo[3.2.1]oct-3-endo-yl}benzene-1,4-dicarboxamide; |
| 2-[(1-ethylpropyl)amino]-N4-[8-(5-{[(3S)-piperidin-3-ylamino]carbonyl}pyridin-2-yl)-8-azabicyclo[3.2.1]oct-3-endo-yl]benzene-1,4-dicarboxamide; |
| 5-[(1-ethylpropyl)amino]-2-methyl-N-{8-[5-({[(3R)-1-(1-methylethyl)piperidin-3-yl]amino}carbonyl)pyridin-2-yl]-8-azabicyclo[3.2.1]oct-3-endo-yl}benzene-1,4-dicarboxamide; |
| 6-(3-endo-{[(2,3-dimethylphenyl)carbonyl]amino}-8-azabicyclo[3.2.1]oct-8-yl)-N-(phenylmethyl)pyridine-3-carboxamide; |
| 6-[3-endo-({[2-methyl-3-(methyloxy)phenyl]carbonyl}amino)-8-azabicyclo[3.2.1]oct-8-yl]-N-(phenylmethyl)pyridine-3-carboxamide; |
| 6-(3-endo-{[(3-hydroxy-2-methylphenyl)carbonyl]amino}-8-azabicyclo[3.2.1]oct-8-yl)-N-(phenylmethyl)pyridine-3-carboxamide; |
| 6-(3-endo-{[(3-amino-2-methylphenyl)carbonyl]amino}-8-azabicyclo[3.2.1]oct-8-yl)-N-(phenylmethyl)pyridine-3-carboxamide; |
| N-[8-(5-{[(phenylmethyl)amino]carbonyl}pyridin-2-yl)-8-azabicyclo[3.2.1]oct-3-endo-yl]benzene-1,4-dicarboxamide; |
| 2-methyl-N1-[8-(5-{[(phenylmethyl)amino]carbonyl}pyridin-2-yl)-8-azabicyclo[3.2.1]oct-3-endo-yl]benzene-1,4-dicarboxamide; |
| 6-[3-endo-({[4-(hydroxymethyl)phenyl]carbonyl}amino)-8-azabicyclo[3.2.1]oct-8-yl]-N-(phenylmethyl)pyridine-3-carboxamide; |
| 2-methyl-N-[8-(5-{[(phenylmethyl)amino]carbonyl}pyridin-2-yl)-8-azabicyclo[3.2.1]oct-3-endo-yl]benzene-1,3-dicarboxamide; |
| 3-methyl-4-({[8-(5-{[(phenylmethyl)amino]carbonyl}pyridin-2-yl)-8-azabicyclo[3.2.1]oct-3-endo-yl]amino}carbonyl)phenyl carbamate; |
| 2-methyl-3-({[8-(5-{[(phenylmethyl)amino]carbonyl}pyridin-2-yl)-8-azabicyclo[3.2.1]oct-3-endo-yl]amino}carbonyl)phenyl carbamate; |
| 6-[3-endo-({[4-(hydroxymethyl)-2-methylphenyl]carbonyl}amino)-8-azabicyclo[3.2.1]oct-8-yl]-N-(phenylmethyl)pyridine-3-carboxamide; |
| 6-[3-endo-({[4-(hydroxymethyl)phenyl]carbonyl}amino)-8-azabicyclo[3.2.1]oct-8-yl]-N-(pyridin-3-ylmethyl)pyridine-3-carboxamide; |
| N-[8-(5-{[(pyridin-3-ylmethyl)amino]carbonyl}pyridin-2-yl)-8-azabicyclo[3.2.1]oct-3-endo-yl]benzene-1,4-dicarboxamide; |
| 6-[3-endo-({[4-(hydroxymethyl)phenyl]carbonyl}amino)-8-azabicyclo[3.2.1]oct-8-yl]-N-[(5-methylpyrazin-2-yl)methyl]pyridine-3-carboxamide; |
| N-{8-[5-({[(5-methylpyrazin-2-yl)methyl]amino}carbonyl)pyridin-2-yl]-8-azabicyclo[3.2.1]oct-3-endo-yl}benzene-1,4-dicarboxamide; |
| 6-[3-endo-({[4-(hydroxymethyl)-2-methylphenyl]carbonyl}amino)-8-azabicyclo[3.2.1]oct-8-yl]-N-(pyridin-3-ylmethyl)pyridine-3-carboxamide; |
| 6-{3-endo-[({4-[amino(imino)methyl]phenyl}carbonyl)amino]-8-azabicyclo[3.2.1]oct-8-yl}-N-(phenylmethyl)pyridine-3-carboxamide; |
| 6-[3-endo-({[2-methyl-3,4-bis(methyloxy)phenyl]carbonyl}amino)-8-azabicyclo[3.2.1]oct-8-yl]-N-(phenylmethyl)pyridine-3-carboxamide; |
| 6-[3-endo-({[3-(methyloxy)-2-propylphenyl]carbonyl}amino)-8-azabicyclo[3.2.1]oct-8-yl]-N-(phenylmethyl)pyridine-3-carboxamide; |
| 6-[3-endo-({[3-(methyloxy)-2-prop-2-en-1-ylphenyl]carbonyl}amino)-8-azabicyclo[3.2.1]oct-8-yl]-N-(phenylmethyl)pyridine-3-carboxamide; |
| 6-[3-endo-({[2-bromo-3-(methyloxy)propyl]carbonyl}amino)-8-azabicyclo[3.2.1]oct-8-yl]-N-(phenylmethyl)pyridine-3-carboxamide; |
| 6-[3-endo-({[2-iodo-3-(methyloxy)phenyl]carbonyl}amino)-8-azabicyclo[3.2.1]oct-8-yl]-N-(phenylmethyl)pyridine-3-carboxamide; |
| 2,6-dimethyl-N1-[8-(5-{[(phenylmethyl)amino]carbonyl}pyridin-2-yl)-8-azabicyclo[3.2.1]oct-3-endo-yl]benzene-1,4-dicarboxamide; |
| N4-(8-{5-[(cyclopentylamino)carbonyl]pyridin-2-yl}-8-azabicyclo[3.2.1]oct-3-endo-yl)-2-{[3-{[2-(dimethylamino)ethyl]oxy}-4-(methyloxy)phenyl]amino}benzene-1,4-dicarboxamide; |
| N4-(8-{5-[(cyclopentylamino)carbonyl]pyridin-2-yl}-8-azabicyclo[3.2.1]oct-3-endo-yl)-2-{[2-(methylsulfonyl)ethyl]amino}benzene-1,4-dicarboxamide; |
| N4-(8-{5-[(cyclopentylamino)carbonyl]pyridin-2-yl}-8-azabicyclo[3.2.1]oct-3-endo-yl)-2-[(4-trans-hydroxycyclohexyl)amino]benzene-1,4-dicarboxamide; |
| 2-[(4-trans-hydroxycyclohexyl)amino]-N4-{8-[5-({[1-(1-methylethyl)pyrrolidin-3-yl]amino}carbonyl)pyridin-2-yl]-8-azabicyclo[3.2.1]oct-3-endo-yl}benzene-1,4-dicarboxamide; |
| 2-[(cyclopropylmethyl)amino]-N4-[8-(5-{[methyl(methyloxy)amino]carbonyl}pyridin-2-yl)-8-azabicyclo[3.2.1]oct-3-endo-yl]benzene-1,4-dicarboxamide; |
| N4-(8-{5-[(cyclopentylamino)carbonyl]pyridin-2-yl}-8-azabicyclo[3.2.1]oct-3-endo-yl)-2-[(cyclopropylmethyl)amino]benzene-1,4-dicarboxamide; |
| 2-[(cyclopropylmethyl)amino]-N4-{8-[5-({[(3R)-1-(1-methylethyl)pyrrolidin-3-yl]amino}carbonyl)pyridin-2-yl]-8-azabicyclo[3.2.1]oct-3-endo-yl}benzene-1,4-dicarboxamide; |
| 5-[(1-ethylpropyl)amino]-N-{8-[5-({[(1-ethylpyrrolidin-2-yl)methyl]amino}carbonyl)pyridin-2-yl]-8-azabicyclo[3.2.1]oct-3-endo-yl}-2-methylbenzene-1,4-dicarboxamide; |
| 6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-fluoro-3-(methyloxy)phenyl]carbonyl}amino)-8-azabicyclo[3.2.1]oct-8-yl]pyridine-3-carboxamide; |
| 6-[3-endo-({[2-chloro-3-(methyloxy)phenyl]carbonyl}amino)-8-azabicyclo[3.2.1]oct-8-yl]pyridine-3-carboxamide; |

-continued

| NAME |
| --- |
| 6-(3-endo-{[(4-amino-2-methylphenyl)carbonyl]amino}-8-azabicyclo[3.2.1]oct-8-yl)pyridine-3-carboxamide; |
| 6-[3-endo-({[4-(hydroxymethyl)phenyl]carbonyl}amino)-8-azabicyclo[3.2.1]oct-8-yl]pyridine-3-carboxamide; |
| N-{8-[5-(aminocarbonyl)pyridin-2-yl]-8-azabicyclo[3.2.1]oct-3-endo-yl}benzene-1,4-dicarboxamide; |
| 6-[3-endo-({[4-(hydroxymethyl)-3-(methyloxy)phenyl]carbonyl}amino)-8-azabicyclo[3.2.1]oct-8-yl]pyridine-3-carboxamide; |
| 6-[3-endo-({[2-(4-hydroxybut-1-yn-1-yl)-3-(methyloxy)phenyl]carbonyl}amino)-8-azabicyclo[3.2.1]oct-8-yl]pyridine-3-carboxamide; |
| N4-{8-[5-(aminocarbonyl)pyridin-2-yl]-8-azabicyclo[3.2.1]oct-3-endo-yl}-2-{[2-(methyloxy)ethyl]amino}benzene-1,4-dicarboxamide; |
| N4-{8-[5-(aminocarbonyl)pyridin-2-yl]-8-azabicyclo[3.2.1]oct-3-endo-yl}-2-[(2-morpholin-4-ylethyl)oxybenzene-1,4-dicarboxylate; |
| N4-{8-[5-(aminocarbonyl)pyridin-2-yl]-8-azabicyclo[3.2.1]oct-3-endo-yl}-2-[(4-hydroxycyclohexyl)amino]benzene-1,4-dicarboxamide; |
| 2-(acetylamino)-N4-{8-[5-(aminocarbonyl)pyridin-2-yl]-8-azabicyclo[3.2.1]oct-3-endo-yl}benzene-1,4-dicarboxamide; |
| N4-{8-[5-(aminocarbonyl)pyridin-2-yl]-8-azabicyclo[3.2.1]oct-3-endo-yl}-2-{[2-(methylsulfonyl)ethyl]amino}benzene-1,4-dicarboxamide; |
| N4-{8-[5-(aminocarbonyl)pyridin-2-yl]-8-azabicyclo[3.2.1]oct-3-endo-yl}-2-(cyclobutylamino)benzene-1,4-dicarboxamide; |
| 2,5-dimethyl-N-{8-[5-({[(3S)-1-(1-methylethyl)pyrrolidin-3-yl]amino}carbonyl)pyridin-2-yl]-8-azabicyclo[3.2.1]oct-3-endo-yl}benzene-1,4-dicarboxamide; |
| 6-(3-endo-{[(3-hydroxy-2-methylphenyl)carbonyl]amino}-8-azabicyclo[3.2.1]oct-8-yl)-N-{(1S)-1-[4-(4-methylpiperazin-1-yl)phenyl]ethyl}pyridine-3-carboxamide; |
| 2-(methyloxy)-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide; |
| 6-[3-endo-({[2-methyl-3-(methylamino)phenyl]carbonyl}amino)-8-azabicyclo[3.2.1]oct-8-yl]-N-{(1S)-1-[4-(4-methylpiperazin-1-yl)phenyl]ethyl}pyridine-3-carboxamide; |
| 6-[3-endo-({[3-(dimethylamino)-2-methylphenyl]carbonyl}amino)-8-azabicyclo[3.2.1]oct-8-yl]-N-{(1S)-1-[4-(4-methylpiperazin-1-yl)phenyl]ethyl}pyridine-3-carboxamide; |
| 6-[3-endo-({[2-methyl-3-(methylthio)phenyl]carbonyl}amino)-8-azabicyclo[3.2.1]oct-8-yl]-N-{(1S)-1-[4-(4-methylpiperazin-1-yl)phenyl]ethyl}pyridine-3-carboxamide; |
| 2-(cyclobutyloxy)-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide; |
| 2-methyl-3-(methyloxy)-N-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide; |
| 2-(cyclobutylamino)-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide; |
| N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-{[3,4,5-tris(methyloxy)phenyl]amino}benzene-1,4-dicarboxamide; |
| N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-(phenylamino)benzene-1,4-dicarboxamide; |
| 2-[(cyclopropylmethyl)amino]-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide; |
| N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-(pyridin-4-ylamino)benzene-1,4-dicarboxylate; |
| N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-{[1-(methylsulfonyl)piperidin-4-yl]amino}benzene-1,4-dicarboxamide; |
| 3-(ethylamino)-2,5-dimethyl-N1-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide; |
| 2-[(4-hydroxycyclohexyl)amino]-N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide; |
| N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-{[2-(methylsulfonyl)ethyl]amino}benzene-1,4-dicarboxamide; |
| 6-{3-endo-[({3-[(4-hydroxycyclohexyl)amino]phenyl}carbonyl)amino]-8-azabicyclo[3.2.1]oct-8-yl}-N-{(1S)-1-[4-(4-methylpiperazin-1-yl)phenyl]ethyl}pyridine-3-carboxamide; |
| 2,5-dimethyl-N-[8-(5-{[(phenylmethyl)amino]carbonyl}pyridin-2-yl)-8-azabicyclo[3.2.1]oct-3-endo-yl]benzene-1,4-dicarboxamide; |
| 2,5-dichloro-N-[8-(5-{[(phenylmethyl)amino]carbonyl}pyridin-2-yl)-8-azabicyclo[3.2.1]oct-3-endo-yl]benzene-1,4-dicarboxamide; |
| 2,5-dimethyl-N-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)benzene-1,4-dicarboxamide; |
| N-{8-[5-(aminocarbonyl)pyridin-2-yl]-8-azabicyclo[3.2.1]oct-3-endo-yl}-2,5-dimethylbenzene-1,4-dicarboxamide; |
| 2,5-dimethyl-N-{8-[5-({[(3R)-1-(1-methylethyl)pyrrolidin-3-yl]amino}carbonyl)pyridin-2-yl]-8-azabicyclo[3.2.1]oct-3-endo-yl}benzene-1,4-dicarboxamide; |
| 2,5-dimethyl-N-{8-[5-({[(3S)-1-methylpiperidin-3-yl]amino}carbonyl)pyridin-2-yl]-8-azabicyclo[3.2.1]oct-3-endo-yl}benzene-1,4-dicarboxamide; |
| N-{8-[5-({[(3R)-1-ethylpiperidin-3-yl]amino}carbonyl)pyridin-2-yl]-8-azabicyclo[3.2.1]oct-3-endo-yl}-2,5-dimethylbenzene-1,4-dicarboxamide; |
| 2,5-dimethyl-N-{8-[5-({[(3R)-1-methylpiperidin-3-yl]amino}carbonyl)pyridin-2-yl]-8-azabicyclo[3.2.1]oct-3-endo-yl}benzene-1,4-dicarboxamide; |
| 2,5-dimethyl-N-{8-[5-({[(3R)-1-methylpyrrolidin-3-yl]amino}carbonyl)pyridin-2-yl]-8-azabicyclo[3.2.1]oct-3-endo-yl}benzene-1,4-dicarboxamide; |
| 2,5-dimethyl-N-[8-(5-{[(1-methylpiperidin-4-yl)amino]carbonyl}pyridin-2-yl)-8-azabicyclo[3.2.1]oct-3-endo-yl]benzene-1,4-dicarboxamide; |
| N-[8-(5-{[(1-ethylpiperidin-4-yl)amino]carbonyl}pyridin-2-yl)-8-azabicyclo[3.2.1]oct-3-endo-yl]-2,5-dimethylbenzene-1,4-dicarboxamide; |
| 2,5-dimethyl-N-{8-[5-({[1-(1-methylethyl)piperidin-4-yl]amino}carbonyl)pyridin-2-yl]-8-azabicyclo[3.2.1]oct-3-endo-yl}benzene-1,4-dicarboxamide; |
| N-{8-[5-({[(3S)-1-ethylpyrrolidin-3-yl]amino}carbonyl)pyridin-2-yl]-8-azabicyclo[3.2.1]oct-3-endo-yl}-2,5-dimethylbenzene-1,4-dicarboxamide; |
| 2,5-dimethyl-N-{8-[5-({[(3R)-1-(1-methylethyl)piperidin-3-yl]amino}carbonyl)pyridin-2-yl]-8-azabicyclo[3.2.1]oct-3-endo-yl}benzene-1,4-dicarboxamide; |
| N-{8-[5-({[(3S)-1-ethylpiperidin-3-yl]amino}carbonyl)pyridin-2-yl]-8-azabicyclo[3.2.1]oct-3-endo-yl}-2,5-dimethylbenzene-1,4-dicarboxamide; |
| 2,5-dimethyl-N-{8-[5-({[(3S)-1-(1-methylethyl)piperidin-3-yl]amino}carbonyl)pyridin-2-yl]-8-azabicyclo[3.2.1]oct-3-endo-yl}benzene-1,4-dicarboxamide; |

-continued

| NAME |
| --- |
| 2,5-dimethyl-N-{8-[5-({[(3S)-1-methylpyrrolidin-3-yl]amino}carbonyl)pyridin-2-yl]-8-azabicyclo[3.2.1]oct-3-endo-yl}benzene-1,4-dicarboxamide; |
| N-{8-[5-({[(3R)-1-ethylpyrrolidin-3-yl]amino}carbonyl)pyridin-2-yl]-8-azabicyclo[3.2.1]oct-3-endo-yl}-2,5-dimethylbenzene-1,4-dicarboxamide; |
| N-[8-(5-{[(1-ethylazetidin-3-yl)amino]carbonyl}pyridin-2-yl)-8-azabicyclo[3.2.1]oct-3-endo-yl]-2,5-dimethylbenzene-1,4-dicarboxamide; |
| 2,5-dimethyl-N-{8-[5-({[1-(1-methylethyl)azetidin-3-yl]amino}carbonyl)pyridin-2-yl]-8-azabicyclo[3.2.1]oct-3-endo-yl}benzene-1,4-dicarboxamide; |
| 2,5-dimethyl-N-[8-(5-{[(1-methylazetidin-3-yl)amino]carbonyl}pyridin-2-yl)-8-azabicyclo[3.2.1]oct-3-endo-yl]benzene-1,4-dicarboxamide; |
| methyl (2S)-[({6-[3-endo-({[2-methyl-3-(methyloxy)phenyl]carbonyl}amino)-8-azabicyclo[3.2.1]oct-8-yl]pyridin-3-yl}carbonyl)amino][4-(methyloxy)phenyl]ethanoate; |
| N-{(1S)-2-amino-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide; |
| N-{(1S)-2-(methylamino)-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide; |
| N-{(1S)-2-(ethylamino)-1-[4-(methyloxy)phenyl]-2-oxoethyl}-6-[3-endo-({[2-methyl-3-(methyloxy)phenyl]carbonyl}amino)-8-azabicyclo[3.2.1]oct-8-yl]pyridine-3-carboxamide; |
| N4-(8-{5-[({(1S)-1-[4-(4-methylpiperazin-1-yl)phenyl]ethyl}amino)carbonyl]pyridin-2-yl}-8-azabicyclo[3.2.1]oct-3-endo-yl)-2-[(2-morpholin-4-ylethyl)amino]benzene-1,4-dicarboxamide; |
| N4-{8-[5-(aminocarbonyl)pyridin-2-yl]-8-azabicyclo[3.2.1]oct-3-endo-yl}-2-{[3-{[2-(dimethylamino)ethyl]oxy}-4-(methyloxy)phenyl]amino}benzene-1,4-dicarboxamide; |
| N4-{8-[5-(aminocarbonyl)pyridin-2-yl]-8-azabicyclo[3.2.1]oct-3-endo-yl}-2-[(trans-4-aminocyclohexyl)amino]benzene-1,4-dicarboxamide; |
| N-[1-(2-fluoro-4-piperidin-4-ylphenyl)ethyl]-6-[3-endo-({[2-methyl-3-(methyloxy)phenyl]carbonyl}amino)-8-azabicyclo[3.2.1]oct-8-yl]pyridine-3-carboxamide; |
| N-[1-(2,6-difluoro-4-piperidin-4-ylphenyl)ethyl]-6-[3-endo-({[2-methyl-3-(methyloxy)phenyl]carbonyl}amino)-8-azabicyclo[3.2.1]oct-8-yl]pyridine-3-carboxamide; |
| 6-[3-endo-({[2-(3-hydroxypropyl)-3-(methyloxy)phenyl]carbonyl}amino)-8-azabicyclo[3.2.1]oct-8-yl]-N-(phenylmethyl)pyridine-3-carboxamide; |
| 6-[3-endo-({[2-(3-hydroxypropyl)-3-(methyloxy)phenyl]carbonyl}amino)-8-azabicyclo[3.2.1]oct-8-yl]pyridine-3-carboxamide; |
| 6-[3-endo-({[2-{3-[(1-methylethyl)amino]propyl}-3-(methyloxy)phenyl]carbonyl}amino)-8-azabicyclo[3.2.1]oct-8-yl]-N-(phenylmethyl)pyridine-3-carboxamide; |
| 6-[3-endo-({[2-(4-hydroxybutyl)-3-(methyloxy)phenyl]carbonyl}amino)-8-azabicyclo[3.2.1]oct-8-yl]pyridine-3-carboxamide; |
| 6-{3-endo-[({2-[4-(dimethylamino)butyl]-3-(methyloxy)phenyl}carbonyl)amino]-8-azabicyclo[3.2.1]oct-8-yl}pyridine-3-carboxamide; |
| 6-[3-endo-({[2-(2,3-dihydroxypropyl)-3-(methyloxy)phenyl]carbonyl}amino)-8-azabicyclo[3.2.1]oct-8-yl]pyridine-3-carboxamide; |
| 6-[3-endo-({[4-(1,2-dihydroxyethyl)phenyl]carbonyl}amino)-8-azabicyclo[3.2.1]oct-8-yl]-N-(phenylmethyl)pyridine-3-carboxamide; |
| N4-[8-(5-acetylpyridin-2-yl)-8-azabicyclo[3.2.1]oct-3-endo-yl]-2-[(trans-4-hydroxycyclohexyl)amino]benzene-1,4-dicarboxamide; |
| N-[8-(5-acetylpyridin-2-yl)-8-azabicyclo[3.2.1]oct-3-endo-yl]-2-methyl-3-(methyloxy)benzamide; |
| N4-[8-(5-acetylpyridin-2-yl)-8-azabicyclo[3.2.1]oct-3-endo-yl]-2-[(cyclopropylmethyl)amino]benzene-1,4-dicarboxamide; |
| N4-[8-(5-acetylpyridin-2-yl)-8-azabicyclo[3.2.1]oct-3-endo-yl]-2-(cyclohexylamino)benzene-1,4-dicarboxamide; |
| N4-[8-(5-acetylpyridin-2-yl)-8-azabicyclo[3.2.1]oct-3-endo-yl]-2-(cyclopentylamino)benzene-1,4-dicarboxamide; |
| N4-[8-(5-acetylpyridin-2-yl)-8-azabicyclo[3.2.1]oct-3-endo-yl]-2-(piperidin-4-ylamino)benzene-1,4-dicarboxamide; |
| N4-[8-(5-acetylpyridin-2-yl)-8-azabicyclo[3.2.1]oct-3-endo-yl]-2-[(1-methylethyl)amino]benzene-1,4-dicarboxamide; |
| N-[8-(5-acetylpyridin-2-yl)-8-azabicyclo[3.2.1]oct-3-endo-yl]-5-[(trans-4-hydroxycyclohexyl)amino]-2-methylbenzene-1,4-dicarboxamide; |
| N4-[8-(5-acetylpyridin-2-yl)-8-azabicyclo[3.2.1]oct-3-endo-yl]-2-(ethylamino)benzene-1,4-dicarboxamide; |
| N4-[8-(5-acetylpyridin-2-yl)-8-azabicyclo[3.2.1]oct-3-endo-yl]-2-[(1-ethylpropyl)amino]benzene-1,4-dicarboxamide; |
| N4-[8-(5-acetylpyridin-2-yl)-8-azabicyclo[3.2.1]oct-3-endo-yl]-2-(cyclopropylamino)benzene-1,4-dicarboxamide; |
| N4-[8-(5-acetylpyridin-2-yl)-8-azabicyclo[3.2.1]oct-3-endo-yl]-2-[(2-methylpropyl)amino]benzene-1,4-dicarboxamide; |
| N4-[8-(5-acetylpyridin-2-yl)-8-azabicyclo[3.2.1]oct-3-endo-yl]-2-(tetrahydrofuran-3-ylamino)benzene-1,4-dicarboxamide; |
| 2-[(cyclopropylmethyl)amino]-N4-{8-[5-(3-methylbutanoyl)pyridin-2-yl]-8-azabicyclo[3.2.1]oct-3-endo-yl}benzene-1,4-dicarboxamide; |
| 2-[(cyclopropylmethyl)amino]-N4-[8-(5-propanoylpyridin-2-yl)-8-azabicyclo[3.2.1]oct-3-endo-yl]benzene-1,4-dicarboxamide; |
| N4-[8-(5-acetylpyridin-2-yl)-8-azabicyclo[3.2.1]oct-3-endo-yl]-2-(tetrahydro-2H-pyran-4-ylamino)benzene-1,4-dicarboxamide; |
| N4-[8-(5-acetylpyridin-2-yl)-8-azabicyclo[3.2.1]oct-3-endo-yl]-2-[(1-ethylpiperidin-4-yl)amino]benzene-1,4-dicarboxamide; |
| N4-[8-(5-acetylpyridin-2-yl)-8-azabicyclo[3.2.1]oct-3-endo-yl]-2-[(2,2-dimethylpropyl)amino]benzene-1,4-dicarboxamide; |
| N4-[8-(5-acetylpyridin-2-yl)-8-azabicyclo[3.2.1]oct-3-endo-yl]-2-[(tetrahydrofuran-2-ylmethyl)amino]benzene-1,4-dicarboxamide; |
| N4-[8-(5-acetylpyridin-2-yl)-8-azabicyclo[3.2.1]oct-3-endo-yl]-2-(pyrrolidin-3-ylamino)benzene-1,4-dicarboxamide; |
| 2-[(cyclopropylmethyl)amino]-N4-{8-[5-(4,4,4-trifluorobutanoyl)pyridin-2-yl]-8-azabicyclo[3.2.1]oct-3-endo-yl}benzene-1,4-dicarboxamide; |
| N4-[8-(5-acetylpyridin-2-yl)-8-azabicyclo[3.2.1]oct-3-endo-yl]-2-(phenylamino)benzene-1,4-dicarboxamide; |
| N4-[8-(5-acetylpyridin-2-yl)-8-azabicyclo[3.2.1]oct-3-endo-yl]-2-[(2-aminoethyl)amino]benzene-1,4-dicarboxamide; |
| N4-[8-(5-acetylpyridin-2-yl)-8-azabicyclo[3.2.1]oct-3-endo-yl]-2-[(2,2,3,3,3-pentafluoropropyl)amino]benzene-1,4-dicarboxamide; |
| 2-[(cyclopropylmethyl)amino]-N4-{8-[5-(2-methylpropanoyl)pyridin-2-yl]-8-azabicyclo[3.2.1]oct-3-endo-yl}benzene-1,4-dicarboxamide; |
| N4-[8-(5-acetylpyridin-2-yl)-8-azabicyclo[3.2.1]oct-3-endo-yl]-2-[(piperidin-3-ylmethyl)amino]benzene-1,4-dicarboxamide; |
| N4-[8-(5-acetylpyridin-2-yl)-8-azabicyclo[3.2.1]oct-3-endo-yl]-2-[(pyrrolidin-3-ylmethyl)amino]benzene-1,4-dicarboxamide; |
| N4-[8-(5-butanoylpyridin-2-yl)-8-azabicyclo[3.2.1]oct-3-endo-yl]-2-[(cyclopropylmethyl)amino]benzene-1,4-dicarboxamide; |
| N4-[8-(5-acetylpyridin-2-yl)-8-azabicyclo[3.2.1]oct-3-endo-yl]-2-[(phenylmethyl)amino]benzene-1,4-dicarboxamide; |
| N4-[8-(5-acetylpyridin-2-yl)-8-azabicyclo[3.2.1]oct-3-endo-yl]-2-[(3S)-tetrahydrofuran-3-ylamino]benzene-1,4-dicarboxamide; |
| N4-[8-(5-acetylpyridin-2-yl)-8-azabicyclo[3.2.1]oct-3-endo-yl]-2-[(1-methylpropyl)amino]benzene-1,4-dicarboxamide; |
| N-[8-(5-acetylpyridin-2-yl)-8-azabicyclo[3.2.1]oct-3-endo-yl]-5-[(1-ethylpropyl)amino]-2-methylbenzene-1,4-dicarboxamide; |
| N4-[8-(5-acetylpyridin-2-yl)-8-azabicyclo[3.2.1]oct-3-endo-yl]-2-[(2,2,2-trifluoroethyl)amino]benzene-1,4-dicarboxamide; |
| N4-[8-(5-acetylpyridin-2-yl)-8-azabicyclo[3.2.1]oct-3-endo-yl]-2-[(3R)-tetrahydrofuran-3-ylamino]benzene-1,4-dicarboxamide; |
| ;N4-[8-(5-acetylpyridin-2-yl)-8-azabicyclo[3.2.1]oct-3-endo-yl]-2-{[3-{[2-(dimethylamino)ethyl]oxy}-4-(methyloxy)phenyl]amino}benzene-1,4-dicarboxamide; |
| N4-{8-[5-(cyclopentylcarbonyl)pyridin-2-yl]-8-azabicyclo[3.2.1]oct-3-endo-yl}-2-[(cyclopropylmethyl)amino]benzene-1,4-dicarboxamide; |

-continued

| NAME |
| --- |
| N4-{8-[5-(cyclobutylcarbonyl)pyridin-2-yl]-8-azabicyclo[3.2.1]oct-3-endo-yl}-2-[(cyclopropylmethyl)amino]benzene-1,4-dicarboxamide; |
| N4-[8-(5-acetylpyridin-2-yl)-8-azabicyclo[3.2.1]oct-3-endo-yl]-2-aminobenzene-1,4-dicarboxamide; |
| N4-[8-(5-acetylpyridin-2-yl)-8-azabicyclo[3.2.1]oct-3-endo-yl]-2-[(1-propylbutyl)amino]benzene-1,4-dicarboxamide; |
| N4-[8-(5-acetylpyridin-2-yl)-8-azabicyclo[3.2.1]oct-3-endo-yl]-2-(propylamino)benzene-1,4-dicarboxamide; |
| N4-[8-(5-acetylpyridin-2-yl)-8-azabicyclo[3.2.1]oct-3-endo-yl]-2-azetidin-1-ylbenzene-1,4-dicarboxamide; |
| N4-[8-(5-acetylpyridin-2-yl)-8-azabicyclo[3.2.1]oct-3-endo-yl]-2-bromobenzene-1,4-dicarboxamide; |
| N4-[8-(5-acetylpyridin-2-yl)-8-azabicyclo[3.2.1]oct-3-endo-yl]-2-[(1,2-dimethylpropyl)amino]benzene-1,4-dicarboxamide; |
| N-[8-(5-acetylpyridin-2-yl)-8-azabicyclo[3.2.1]oct-3-endo-yl]-5-[(1-ethylpropyl)amino]-2-fluorobenzene-1,4-dicarboxamide; |
| N-[8-(5-acetylpyridin-2-yl)-8-azabicyclo[3.2.1]oct-3-endo-yl]-2-methyl-5-{[4-(trifluoromethyl)cyclohexyl]amino}benzene-1,4-dicarboxamide; |
| N4-[8-(5-acetylpyridin-2-yl)-8-azabicyclo[3.2.1]oct-3-endo-yl]-2-[(2,2,3,3,4,4,4-heptafluorobutyl)amino]benzene-1,4-dicarboxamide; |
| N4-[8-(5-acetylpyridin-2-yl)-8-azabicyclo[3.2.1]oct-3-endo-yl]-2-[(3,3,3-trifluoropropyl)amino]benzene-1,4-dicarboxamide; |
| N4-[8-(5-acetylpyridin-2-yl)-8-azabicyclo[3.2.1]oct-3-endo-yl]-2-(butylamino)benzene-1,4-dicarboxamide; |
| N4-[8-(5-acetylpyridin-2-yl)-8-azabicyclo[3.2.1]oct-3-endo-yl]-2-[(1,2,2-trimethylpropyl)amino]benzene-1,4-dicarboxamide; |
| N4-[8-(5-acetylpyridin-2-yl)-8-azabicyclo[3.2.1]oct-3-endo-yl]-2-(piperidin-1-ylamino)benzene-1,4-dicarboxamide; |
| N4-[8-(5-acetylpyridin-2-yl)-8-azabicyclo[3.2.1]oct-3-endo-yl]-2-({1-[(methyloxy)methyl]propyl}amino)benzene-1,4-dicarboxamide; |
| N4-[8-(5-acetylpyridin-2-yl)-8-azabicyclo[3.2.1]oct-3-endo-yl]-2-({2-[(1-methylethyl)oxy]ethyl}amino)benzene-1,4-dicarboxamide; |
| N4-[8-(5-acetylpyridin-2-yl)-8-azabicyclo[3.2.1]oct-3-endo-yl]-2-{[(1S)-1-methylpropyl]amino}benzene-1,4-dicarboxamide; |
| N-[8-(5-acetylpyridin-2-yl)-8-azabicyclo[3.2.1]oct-3-endo-yl]-2-methyl-5-(pentylamino)benzene-1,4-dicarboxamide; |
| N4-[8-(5-acetylpyridin-2-yl)-8-azabicyclo[3.2.1]oct-3-endo-yl]-2-({3-[(1-methylethyl)amino]propyl}amino)benzene-1,4-dicarboxamide; |
| N4-{8-[5-(cyclopropylcarbonyl)pyridin-2-yl]-8-azabicyclo[3.2.1]oct-3-endo-yl}-2-[(cyclopropylmethyl)amino]benzene-1,4-dicarboxamide; |
| N4-{8-[5-(cyclopropylcarbonyl)pyridin-2-yl]-8-azabicyclo[3.2.1]oct-3-endo-yl}-2-[(1-ethylpropyl)amino]benzene-1,4-dicarboxamide; |
| N-{8-[5-(cyclopropylcarbonyl)pyridin-2-yl]-8-azabicyclo[3.2.1]oct-3-endo-yl}-5-[(1-ethylpropyl)amino]-2-methylbenzene-1,4-dicarboxamide; |
| N4-{8-[5-(cyclopropylcarbonyl)pyridin-2-yl]-8-azabicyclo[3.2.1]oct-3-endo-yl}-2-(pyridin-4-ylamino)benzene-1,4-dicarboxamide; |
| N4-{8-[5-(cyclopropylcarbonyl)pyridin-2-yl]-8-azabicyclo[3.2.1]oct-3-endo-yl}-2-[(2,2,3,3,3-pentafluoropropyl)amino]benzene-1,4-dicarboxamide; |
| 2-chloro-N-{8-[5-(cyclopropylcarbonyl)pyridin-2-yl]-8-azabicyclo[3.2.1]oct-3-endo-yl}-5-[(1-ethylpropyl)amino]benzene-1,4-dicarboxamide; |
| 2-(cyclopentylamino)-N4-{8-[5-(cyclopropylcarbonyl)pyridin-2-yl]-8-azabicyclo[3.2.1]oct-3-endo-yl}benzene-1,4-dicarboxamide; |
| N-{8-[5-(cyclopropylcarbonyl)pyridin-2-yl]-8-azabicyclo[3.2.1]oct-3-endo-yl}-2-methyl-5-[(3S)-tetrahydrofuran-3-ylamino]benzene-1,4-dicarboxamide; |
| 2-(butylamino)-N4-{8-[5-(cyclopropylcarbonyl)pyridin-2-yl]-8-azabicyclo[3.2.1]oct-3-endo-yl}benzene-1,4-dicarboxamide; |
| N4-{8-[5-(cyclopropylcarbonyl)pyridin-2-yl]-8-azabicyclo[3.2.1]oct-3-endo-yl}-2-({2-[(1-methylethyl)oxy]ethyl}amino)benzene-1,4-dicarboxamide; |
| N4-{8-[5-(cyclopropylcarbonyl)pyridin-2-yl]-8-azabicyclo[3.2.1]oct-3-endo-yl}-2-[(cis-4-hydroxy-4-methylcyclohexyl)amino]benzene-1,4-dicarboxamide; |
| N4-{8-[5-(cyclopropylcarbonyl)pyridin-2-yl]-8-azabicyclo[3.2.1]oct-3-endo-yl}-2-{[(1S)-1-methylpropyl]amino}benzene-1,4-dicarboxamide; |
| N4-{8-[5-(cyclopropylcarbonyl)pyridin-2-yl]-8-azabicyclo[3.2.1]oct-3-endo-yl}-2-[(1-methylpropyl)amino]benzene-1,4-dicarboxamide; |
| N4-{8-[5-(cyclopropylcarbonyl)pyridin-2-yl]-8-azabicyclo[3.2.1]oct-3-endo-yl}-2-(propylamino)benzene-1,4-dicarboxamide; |
| N-{8-[5-(cyclopropylcarbonyl)pyridin-2-yl]-8-azabicyclo[3.2.1]oct-3-endo-yl}-5-[(1-ethylpropyl)amino]-2-fluorobenzene-1,4-dicarboxamide; |
| N4-{8-[5-(cyclopropylcarbonyl)pyridin-2-yl]-8-azabicyclo[3.2.1]oct-3-endo-yl}-2-[(trans-4-piperidin-1-ylcyclohexyl)amino]benzene-1,4-dicarboxamide; |
| N4-{8-[5-(cyclopropylcarbonyl)pyridin-2-yl]-8-azabicyclo[3.2.1]oct-3-endo-yl}-2-{[(1R)-1-methylpropyl]amino}benzene-1,4-dicarboxamide; |
| N4-{8-[5-(cyclopropylcarbonyl)pyridin-2-yl]-8-azabicyclo[3.2.1]oct-3-endo-yl}-2-{[(1S)-1,2-dimethylpropyl]amino}benzene-1,4-dicarboxamide; |
| N4-{8-[5-(cyclopropylcarbonyl)pyridin-2-yl]-8-azabicyclo[3.2.1]oct-3-endo-yl}-2-[(1-cyclopropylethyl)amino]benzene-1,4-dicarboxamide; |
| N4-{8-[5-(cyclopropylcarbonyl)pyridin-2-yl]-8-azabicyclo[3.2.1]oct-3-endo-yl}-2-{[(1R)-1,2-dimethylpropyl]amino}benzene-1,4-dicarboxamide; |
| N-{8-[5-(cyclopropylcarbonyl)pyridin-2-yl]-8-azabicyclo[3.2.1]oct-3-endo-yl}-5-[(1-ethyl-2-methylpropyl)amino]-2-methylbenzene-1,4-dicarboxamide; |
| N-{8-[5-(cyclopropylcarbonyl)pyridin-2-yl]-8-azabicyclo[3.2.1]oct-3-endo-yl}-2-methyl-5-{[(1R)-1-methylpropyl]amino}benzene-1,4-dicarboxamide; |
| N-{8-[5-(cyclopropylcarbonyl)pyridin-2-yl]-8-azabicyclo[3.2.1]oct-3-endo-yl}-5-[(1-cyclopropylethyl)amino]-2-methylbenzene-1,4-dicarboxamide; |
| N-{8-[5-(cyclopropylcarbonyl)pyridin-2-yl]-8-azabicyclo[3.2.1]oct-3-endo-yl}-5-[(1-cyclopropylpropyl)amino]-2-methylbenzene-1,4-dicarboxamide; |
| N-{8-[5-(cyclopropylcarbonyl)pyridin-2-yl]-8-azabicyclo[3.2.1]oct-3-endo-yl}-2-methyl-5-{[(1R)-1,2,2-trimethylpropyl]amino}benzene-1,4-dicarboxamide; |
| N-{8-[5-(cyclopropylcarbonyl)pyridin-2-yl]-8-azabicyclo[3.2.1]oct-3-endo-yl}-5-{[(1R)-1,2-dimethylpropyl]amino}-2-methylbenzene-1,4-dicarboxamide; |
| N-{8-[5-(cyclopropylcarbonyl)pyridin-2-yl]-8-azabicyclo[3.2.1]oct-3-endo-yl}-2-methyl-5-[(3,3,3-trifluoro-1-methylpropyl)amino]benzene-1,4-dicarboxamide; |
| N-{8-[5-(cyclopropylcarbonyl)pyridin-2-yl]-8-azabicyclo[3.2.1]oct-3-endo-yl}-2-methyl-5-{[2-methyl-1-(trifluoromethyl)propyl]amino}benzene-1,4-dicarboxamide; |
| N-{8-[5-(cyclopropylcarbonyl)pyridin-2-yl]-8-azabicyclo[3.2.1]oct-3-endo-yl}-2-methyl-5-{[2-methyl-1-(1-methylethyl)propyl]amino}benzene-1,4-dicarboxamide; |
| 2-bromo-N-{8-[5-(cyclopropylcarbonyl)pyridin-2-yl]-8-azabicyclo[3.2.1]oct-3-endo-yl}-5-[(1-ethylpropyl)amino]benzene-1,4-dicarboxamide; |
| N-{8-[5-(cyclopropylcarbonyl)pyridin-2-yl]-8-azabicyclo[3.2.1]oct-3-endo-yl}-2-methyl-5-[(1-methylethyl)amino]benzene-1,4-dicarboxamide; |

-continued

| NAME |
|---|
| N-{8-[5-(cyclopropylcarbonyl)pyridin-2-yl]-8-azabicyclo[3.2.1]oct-3-endo-yl}-5-[(dicyclopropylmethyl)amino]-2-methylbenzene-1,4-dicarboxamide; |
| 5-(cyclopentylamino)-N-{8-[5-(cyclopropylcarbonyl)pyridin-2-yl]-8-azabicyclo[3.2.1]oct-3-endo-yl}-2-methylbenzene-1,4-dicarboxamide; |
| N-{8-[5-(cyclopropylcarbonyl)pyridin-2-yl]-8-azabicyclo[3.2.1]oct-3-endo-yl}-2-methyl-5-{[1-(trifluoromethyl)propyl]amino}benzene-1,4-dicarbaxamide; |
| N-{8-[5-(cyclopropylcarbonyl)pyridin-2-yl]-8-azabicyclo[3.2.1]oct-3-endo-yl}-2-methyl-5-[(2-methylpropyl)amino]benzene-1,4-dicarboxamide; |
| 5-[(cyclopentylmethyl)amino]-N-{8-[5-(cyclopropylcarbonyl)pyridin-2-yl]-8-azabicyclo[3.2.1]oct-3-endo-yl}-2-methylbenzene-1,4-dicarboxamide; |
| 5-(cyclobutylamino)-N-{8-[5-(cyclopropylcarbonyl)pyridin-2-yl]-8-azabicyclo[3.2.1]oct-3-endo-yl}-2-methylbenzene-1,4-dicarboxamide; |
| N-{8-[5-(cyclopropylcarbonyl)pyridin-2-yl]-8-azabicyclo[3.2.1]oct-3-endo-yl}-2-methyl-5-{[(1S)-1-methylpropyl]amino}benzene-1,4-dicarboxamide; |
| N-{8-[5-(cyclopropylcarbonyl)pyridin-2-yl]-8-azabicyclo[3.2.1]oct-3-endo-yl}-5-[(1-ethylpropyl)amino]-2-(trifluoromethyl)benzene-1,4-dicarboxamide; |
| 2-bromo-N-{8-[5-(cyclopropylcarbonyl)pyridin-2-yl]-8-azabicyclo[3.2.1]oct-3-endo-yl}-5-{[(1R)-1-methylpropyl]amino}benzene-1,4-dicarboxamide; |
| 2-bromo-N-{8-[5-(cyclopropylcarbonyl)pyridin-2-yl]-8-azabicyclo[3.2.1]oct-3-endo-yl}-5-[(1-methylethyl)amino]benzene-1,4-dicarboxamide; |
| N-{8-[5-(cyclopropylcarbonyl)pyridin-2-yl]-8-azabicyclo[3.2.1]oct-3-endo-yl}-5-[(2,2-dimethylpropyl)amino]-2-methylbenzene-1,4-dicarboxamide; |
| N-{8-[5-(cyclopropylcarbonyl)pyridin-2-yl]-8-azabicyclo[3.2.1]oct-3-endo-yl-}-5-[(cyclopropylmethyl)amino]-2-methylbenzene-1,4-dicarboxamide; |
| 2-bromo-5-(cyclopentylamino)-N-{8-[5-(cyclopropylcarbonyl)pyridin-2-yl]-8-azabicyclo[3.2.1]oct-3-endo-yl}benzene-1,4-dicarboxamide; |
| 2-bromo-N-{8-[5-(cycloprapylcarbonyl)pyridin-2-yl]-8-azabicyclo[3.2.1]oct-3-endo-yl}-5-[(2-methylpropyl)amino]benzene-1,4-dicarboxamide; |
| N-{8-[5-(cyclopropylcarbonyl)pyridin-2-yl]-8-azabicyclo[3.2.1]oct-3-endo-yl}-2-methyl-5-[(3,3,3-trifluoropropyl)amino]benzene-1,4-dicarboxamide; |
| N-{8-[5-(cyclopropylcarbonyl)pyridin-2-yl]-8-azabicyclo[3.2.1]oct-3-endo-yl}-2-methyl-5-(propylamino)benzene-1,4-dicarboxamide; |
| N-{8-[5-(cyclopropylcarbonyl)pyndin-2-yl]-8-azabicyclo[3.2.1]oct-3-endo-yl}-2-methyl-5-{[1-(1-methylcyclopropyl)ethyl]amino}benzene-1,4-dicarboxamide; |
| 2-bromo-N-{8-[5-(cyclopropylcarbonyl)pyridin-2-yl]-8-azabicyclo[3.2.1]oct-3-endo-yl}-5-[(2,2-dimethylpropyl)amino]benzene-1,4-dicarboxamide; |
| 2-bromo-N-{8-[5-(cyclopropylcarbonyl)pyridin-2-yl]-8-azabicyclo[3.2.1]oct-3-endo-yl}-5-{[(1R)-1,2-dimethylpropyl]amino}benzene-1,4-dicarboxamide; |
| N-{8-[5-(cyclopropylcarbonyl)pyridin-2-yl]-8-azabicyclo[3.2.1]oct-3-endo-yl}-5-{[2-fluoro-1-(fluoromethyl)ethyl]amino}-2-methylbenzene-1,4-dicarboxamide; |
| 2-bromo-N-{8-[5-(cyclopropylcarbonyl)pyridin-2-yl]-8-azabicyclo[3.2.1]oct-3-endo-yl}-5-(propylamino)benzene-1,4-dicarboxamide; |
| N-{8-[5-(cyclopropylcarbonyl)pyridin-2-yl]-8-azabicyclo[3.2.1]oct-3-endo-yl}-5-{[(1R)-1-methylpropyl]amino}-2-(trifluoromethyl)benzene-1,4-dicarboxamide; |
| 2-bromo-N-{8-[5-(cyclopropylcarbonyl)pyridin-2-yl]-8-azabicyclo[3.2.1]oct-3-endo-yl}-5-[(3,3,3-trifluoropropyl)amino]benzene-1,4-dicarboxamide; |
| 2-bromo-5-(cyclobutylamino)-N-{8-[5-(cyclopropylcarbonyl)pyridin-2-yl]-8-azabicyclo[3.2.1]oct-3-endo-yl}benzene-1,4-dicarboxamide; |
| 2-[(cyclopropylmethyl)amino]-N4-(8-{5-[3-(1-methylpiperidin-4-yl)propanoyl]pyridin-2-yl}-8-azabicyclo[3.2.1]oct-3-endo-yl)benzene-1,4-dicarboxamide; |
| 2-[(cyclopropylmethyl)amino]-N4-{8-[5-(3-hydroxy-4-methylpentanoyl)pyridin-2-yl]-azabicyclo[3.2.1]oct-3-endo-yl}benzene-1,4-dicarboxamide; |
| 2-[(cyclopropylmethyl)amino]-N4-{8-[5-(3-phenylpropanoyl)pyridin-2-yl]-8-azabicyclo[3.2.1]oct-3-endo-yl}benzene-1,4-dicarboxamide; |
| 2-[(cyclopropylmethyl)amino]-N4-{8-[5-(3-hydroxy-3-phenylpropanoyl)pyridin-2-yl]-8-azabicyclo[3.2.1]oct-3-endo-yl}benzene-1,4-dicarboxamide; |
| 2-[(cyclopropylmethyl)amino]-N4-{8-[5-(4-methylpentanoyl)pyridin-2-yl]-8-azabicyclo[3.2.1]oct-3-endo-yl}benzene-1,4-dicarboxamide; |
| N4-{8-[5-(3-cyclohexylpropanoyl)pyridin-2-yl]-8-azabicyclo[3.2.1]oct-3-endo-yl}-2-[(cyclopropylmethyl)amino]benzene-1,4-dicarboxamide; |
| 5-[(1-ethylpropyl)amino]-2-methyl-N-(8-{5-[3-(1-methylpiperidin-4-yl)propanoyl]pyridin-2-yl}-8-azabicyclo[3.2.1]oct-3-endo-yl)benzene-1,4-dicarboxamide; |
| 2-[(cyclopropylmethyl)amino]-N4-{8-[5-(3-piperidin-4-ylpropanoyl)pyridin-2-yl]-8-azabicyclo[3.2.1]oct-3-endo-yl}benzene-1,4-dicarboxamide; |
| 2-[(cyclopropylmethyl)amino]-N4-{8-[5-(N,N-dimethyl-beta-alanyl)pyridin-2-yl]-8-azabicyclo[3.2.1]oct-3-endo-yl}benzene-1,4-dicarboxamide; |
| 2-[(cyclopropylmethyl)amino]-N4-(8-{5-[3-(methyloxy)propanoyl]pyridin-2-yl}-8-azabicyclo[3.2.1]oct-3-endo-yl)benzene-1,4-dicarboxamide; |
| 2-[(cyclopropylmethyl)amino]-N4-{8-[5-(3-piperidin-1-ylpropanoyl)pyridin-2-yl]-8-azabicyclo[3.2.1]oct-3-endo-yl}benzene-1,4-dicarboxamide; |
| 2-[(cyclopropylmethyl)amino]-N4-(8-{5-[3-(ethyloxy)propanoyl]pyridin-2-yl}-8-azabicyclo[3.2.1]oct-3-endo-yl)}benzene-1,4-dicarboxamide; |
| 2-[(cyclopropylmethyl)amino]-N4-(8-{5-[N-(4-fluorphenyl)-beta-alanyl]pyridin-2-yl}-8-azabicyclo[3.2.1]oct-3-endo-yl)benzene-1,4-dicarboxamide; |
| 2-[(cyclopropylmethyl)amino]-N4-{8-[5-(3-morpholin-4-ylpropanoyl)pyridin-2-yl]-8-azabicyclo[3.2.1]oct-3-endo-yl}benzene-1,4-dicarboxamide; |
| 2-[(cyclopropylmethyl)amino]-N4-(8-{5-[3-(4-methylpiperazin-1-yl)propanoyl]pyridin-2-yl}-8-azabicyclo[3.2.1]oct-3-endo-yl)benzene-1,4-dicarboxamide; |
| 2-[(cyclopropylmethyl)amino]-N4-{8-[5-(3-pyrrolidin-1-ylpropanoyl)pyridin-2-yl]-8-azabicyclo[3.2.1]oct-3-endo-yl}benzene-1,4-dicarboxamide; |

-continued

| NAME |
| --- |
| 2-[(cyclopropylmethyl)amino]-N4-(8-{5-[3-(4-phenylpiperazin-1-yl)propanoyl]pyridin-2-yl}-8-azabicyclo[3.2.1]oct-3-endo-yl)benzene-1,4-dicarboxamide; |
| 2-[(1-ethylpropyl)amino]-N4-{8-[5-(3-piperidin-1-ylpropanoyl)pyridin-2-yl]-8-azabicyclo[3.2.1]oct-3-endo-yl}benzene-1,4-dicarboxamide; |
| 2-[(cyclopropylmethyl)amino]-N4-{8-[5-(piperidin-1-ylacetyl)pyridin-2-yl]-8-azabicyclo[3.2.1]oct-3-endo-yl}benzene-1,4-dicarboxamide; |
| N-[8-(5-acetylpyridin-2-yl)-8-azabicyclo[3.2.1]oct-3-endo-yl]-2,5-dimethylbenzene-1,4-dicarboxamide; and |
| 2-[(cyclopropylmethyl)amino]-N4-{8-[5-(trifluoroacetyl)pyridin-2-yl]-8-azabicyclo[3.2.1]oct-3-endo-yl}benzene-1,4-dicarboxamide; |
| and a pharmaceutically acceptable salts of any of the above compounds. |

16. A pharmaceutical composition comprising the compound according to claim 1, or a pharmaceutically acceptable salt thereof, and a pharmaceutically acceptable carrier, excipient, or diluent.

17. A compound that is

6-[3-endo-({[2-methyl-3-(methyloxy)phenyl]carbonyl}amino)-8-azabicyclo [3.2.1]oct-8-yl]-N-({4-[(trifluoromethyl)oxy]phenyl}methyl)pyridine-3-carboxamide;

6-[3-endo-({[2-methyl-3-(methyloxy)phenyl]carbonyl}amino)-8-azabicyclo [3.2.1]oct-8-yl]-N-{[4-(trifluoromethyl)phenyl]methyl}pyridine-3-carboxamide;

6-[3-endo-({[2-methyl-3-(methyloxy)phenyl]carbonyl}amino)-8-azabicyclo [3.2.1]oct-8-yl]-N-(1-phenylpiperidin-4-yl)pyridine-3-carboxamide;

6-[3-endo-({[2-methyl-3-(methyloxy)phenyl]carbonyl}amino)-8-azabicyclo [3.2.1]oct-8-yl]-N-[1-(6-piperazin-1-ylpyridin-3-yl)ethyl]pyridine-3-carboxamide;

N-[(1S,2S)-2-hydroxycyclopentyl]-6-[3-endo-({[2-methyl-3-(methyloxy)phenyl]carbonyl}amino)-8-azabicyclo [3.2.1]oct-8-yl]pyridine-3-carboxamide;

N-[(1S,2S)-2-hydroxycyclohexyl]-6-[3-endo-({[2-methyl-3-(methyloxy)phenyl]carbonyl}amino)-8-azabicyclo [3.2.1]oct-8-yl]pyridine-3-carboxamide;

(2S)-[({6-[3-endo-({[2-methyl-3-(methyloxy)phenyl]carbonyl}amino)-8-azabicyclo [3.2.1]oct-8-yl]pyridin-3-yl}carbonyl)amino][4-(methyloxy)phenyl]ethanoic acid;

N4-[8-(5-acetylpyridin-2-yl)-8-azabicyclo[3.2.1]oct-3-endo-yl]-2-[(3-{[2-(dimethylamino)ethyl]oxy}phenyl)amino]benzene-1,4-dicarboxamide;

N4-[8-(5-acetylpyridin-2-yl)-8-azabicyclo [3.2.1]oct-3-endo-yl]-2-({4-(methyloxy)-3-[(2-morpholin-4-ylethyl)oxy]phenyl}amino)benzene-1,4-dicarboxamide;

or a pharmaceutically acceptable salt of any of the above compounds.

18. The compound according to claim 1, wherein the compound of Formula I is selected from one of the following compounds:

5-amino-N-{8-[5-(cyclopropylcarbonyl)pyridin-2-yl]-8-azabicyclo[3.2.1]oct-3-endo-yl}-2-methylbenzene-1,4-dicarboxamide;

N-{8-[5-(cyclopropylcarbonyl)pyridin-2-yl]-8-azabicyclo [3.2.1]oct-3-endo-yl}-5-[(2,2-difluoro-1-methylethyl)amino]-2-methylbenzene-1,4-dicarboxamide;

2-bromo-N-{8-(5-(cyclopropylcarbonyl)pyridin-2-yl]-8-azabicyclo[3.2.1]oct-3-endo-yl}-5-[(1,1-dimethylethyl)amino]benzene-1,4-dicarboxamide;

5-amino-2-bromo-N-{8-[5-(cyclopropylcarbonyl)pyridin-2-yl]-8-azabicyclo[3.2.1]oct-3-endo-yl}benzene-1,4-dicarboxamide;

2-bromo-N-{8-[5-(cyclopropylcarbonyl)pyridin-2-yl]-8-azabicyclo[3.2.1]oct-3-endo-yl}-5-{[(1S)-1,2-dimethylpropyl]amino}benzene-1,4-dicarboxamide;

2-bromo-N-{8-[5-(cyclopropylcarbonyl)pyridin-2-yl]-8-azabicyclo[3.2.1]oct-3-endo-yl}-5-[(cyclopropylmethyl)amino]benzene-1,4-dicarboxamide;

N-{8-[5-(cyclopropylcarbonyl)pyridin-2-yl]-8-azabicyclo [3.2.1]oct-3-endo-yl}-5-[(1,1-dimethylethyl)amino]-2-methylbenzene-1,4-dicarboxamide;

N-{8-[5-(cyclopropylcarbonyl)pyridin-2-yl]-8-azabicyclo [3.2.1]oct-3-endo-yl}-2-methyl-5-(2-methylpropyl)benzene-1,4-dicarboxamide;

2-chloro-N-{8-[5-(cyclopropylcarbonyl)pyridin-2-yl]-8-azabicyclo[3.2.1]oct-3-endo-yl}-3-[(1-cyclopropylethyl)amino]benzene-1,4-dicarboxamide;

N-{8-[5-(cyclopropylcarbonyl)pyridin-2-yl]-8-azabicyclo [3.2.1]oct-3-endo-yl}-2-methyl-5-(methyloxy)benzene-1,4-dicarboxamide;

5-bromo-3-chloro-N-4-{8-[5-(cyclopropylcarbonyl)pyridin-2-yl]-8-azabicyclo [3.2.1]oct-3-endo-yl}-2-{[(1R)-1-methylpropyl]amino}benzene-1,4-dicarboxamide;

N-{8-[5-(cyclopropylcarbonyl)pyridin-2-yl]-8-azabicyclo [3.2.1]oct-3-endo-yl}-2-(methyloxy)-5-{[(1R)-1-methylpropyl]amino}benzene-1,4-dicarboxamide;

3-chloro-N-4-{8-[5-(cyclopropylcarbonyl)pyridin-2-yl]-8-azabicyclo [3.2.1]oct-3-endo-yl}-5-methyl-2-{[(1R)-1-methylpropyl]amino}benzene-1,4-dicarboxamide;

N-{8-[5-(cyclopropylcarbonyl)pyridin-2-yl]-8-azabicyclo [3.2.1]oct-3-endo-yl}thiophene-2,5-dicarboxamide;

N-{8-[5-(cyclopropylcarbonyl)pyridin-2-yl]-8-azabicyclo [3.2.1]oct-3-endo-yl}-2-(ethylamino)-5-{[(1R)-1-methylpropyl]amino}benzene-1,4-dicarboxamide;

N-{8-[5-(cyclopropylcarbonyl)pyridin-2-yl]-8-azabicyclo [3.2.1]oct-3-endo-yl}-2-methyl-5-[(1-methylpropyl)oxy]benzene-1,4-dicarboxamide;

N-{8-[5-(cyclopropylcarbonyl)pyridin-2-yl]-8-azabicyclo [3.2.1]oct-3-endo-yl}-2-ethyl-5-{[(1R)-1-methylpropyl]amino}benzene-1,4-dicarboxamide;

N-{8-[5-(cyclopropylcarbonyl)pyridin-2-yl]-8-azabicyclo [3.2.1]oct-3-endo-yl}-5-ethyl-2-methylbenzene-1,4-dicarboxamide;

N-{8-[5-(cyclopropylcarbonyl)pyridin-2-yl]-8-azabicyclo [3.2.1]oct-3-endo-yl}-2-methyl-5-{[2-(methyloxy)ethyl]oxy}benzene-1,4-dicarboxamide;

and pharmaceutically acceptable salts thereof.

* * * * *